US010934302B1

(12) United States Patent
Taylor et al.

(10) Patent No.: US 10,934,302 B1
(45) Date of Patent: Mar. 2, 2021

(54) SHP2 PHOSPHATASE INHIBITORS AND METHODS OF USE THEREOF

(71) Applicant: Relay Therapeutics, Inc., Cambridge, MA (US)

(72) Inventors: Alexander M. Taylor, Cambridge, MA (US); André Lescarbeau, Somerville, MA (US); Elizabeth H. Kelley, Cambridge, MA (US); Kelley C. Shortsleeves, Maynard, MA (US); W. Patrick Walters, Westborough, MA (US); Mark Andrew Murcko, Holliston, MA (US); Fabrizio Giordanetto, New York, NY (US); Eric Therrien, Bronx, NY (US)

(73) Assignee: Relay Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/886,105

(22) Filed: May 28, 2020

Related U.S. Application Data

(63) Continuation of application No. PCT/US2019/023389, filed on Mar. 21, 2019.

(60) Provisional application No. 62/646,083, filed on Mar. 21, 2018, provisional application No. 62/646,099, filed on Mar. 21, 2018, provisional application No. 62/649,834, filed on Mar. 29, 2018, provisional application No. 62/661,902, filed on Apr. 24, 2018, provisional application No. 62/737,819, filed on Sep. 27, 2018.

(51) Int. Cl.
*C07D 487/04* (2006.01)
*C07D 401/14* (2006.01)
*C07D 401/04* (2006.01)
*C07D 519/00* (2006.01)

(52) U.S. Cl.
CPC ......... *C07D 487/04* (2013.01); *C07D 401/04* (2013.01); *C07D 401/14* (2013.01); *C07D 519/00* (2013.01)

(58) Field of Classification Search
None
See application file for complete search history.

(56) References Cited

U.S. PATENT DOCUMENTS

| 10,280,171 | B2 | 5/2019 | Jones et al. |
|---|---|---|---|
| 2017/0001975 | A1 | 1/2017 | Chen et al. |
| 2017/0015680 | A1 | 1/2017 | Chen et al. |
| 2017/0204080 | A1 | 7/2017 | Chen et al. |
| 2017/0342078 | A1 | 11/2017 | Jones et al. |
| 2018/0186770 | A1 | 7/2018 | Chen et al. |
| 2018/0251471 | A1 | 9/2018 | Chen et al. |
| 2019/0077792 | A1 | 3/2019 | Volkmann et al. |
| 2019/0127378 | A1 | 5/2019 | Ma et al. |
| 2019/0185475 | A1 | 6/2019 | Bagdanoff et al. |
| 2019/0210977 | A1 | 7/2019 | Jogalekar et al. |
| 2019/0290649 | A1 | 9/2019 | Xie et al. |
| 2019/0307745 | A1 | 10/2019 | Albrecht et al. |
| 2019/0389867 | A1 | 12/2019 | Jones et al. |
| 2020/0002330 | A1 | 1/2020 | Chen et al. |
| 2020/0017511 | A1 | 1/2020 | Blank et al. |
| 2020/0017517 | A1 | 1/2020 | Gill et al. |
| 2020/0048249 | A1 | 2/2020 | Jones et al. |
| 2020/0062760 | A1 | 2/2020 | Giordanetto et al. |
| 2020/0108071 | A1 | 4/2020 | Chin et al. |
| 2020/0115389 | A1 | 4/2020 | Fu et al. |

FOREIGN PATENT DOCUMENTS

| CN | 107286150 A | 10/2017 |
|---|---|---|
| CN | 110143949 A | 8/2019 |
| CN | 111153899 A | 5/2020 |
| TW | 201925186 A | 7/2019 |
| WO | WO-2004/111060 A1 | 12/2004 |
| WO | WO-2020076723 A1 | 1/2007 |
| WO | WO-2010/011666 A2 | 1/2010 |
| WO | WO-2010/097798 A1 | 9/2010 |
| WO | WO-2010/121212 A2 | 10/2010 |
| WO | WO-2011/130396 A1 | 10/2011 |
| WO | WO-2015/107494 A1 | 7/2015 |
| WO | WO-2015/107495 A1 | 7/2015 |
| WO | WO-2016/203404 A1 | 12/2016 |
| WO | WO-2016/203406 A1 | 12/2016 |
| WO | WO-2017156397 A1 | 9/2017 |
| WO | WO-2017/210134 A1 | 12/2017 |
| WO | WO-2017/211303 A1 | 12/2017 |
| WO | WO-2018/013597 A1 | 1/2018 |
| WO | WO-2018/057884 A1 | 3/2018 |
| WO | WO-2018/081091 A1 | 5/2018 |
| WO | WO-2018/172984 A1 | 9/2018 |

(Continued)

OTHER PUBLICATIONS

Chloe, Copin et al. "Snar Versus Buchwald-Hartwig Amination/Amidation in the Imidazo[2,1-b] [1,3,4]thiadiazole Series," European Journal of Organic Chemistry, vol. 2015, No. 31, Sep. 29, 2015, pp. 6932-6942.

Larochelle, Jonathan et al. "Identification of an Allosteric Benzothiazolopyrimidone Inhibitor of the Oncogenic Protein Tyrosine Phosphatase SHP2," Bioorganic & Medicinal Chemistry, vol. 25, No. 24, Oct. 20, 2017, pp. 6479-6485.

Temple, Kayla et al. "Identification of the Minimum PAR4 Inhibitor Pharmacophore and Optimization of a Series of 2-Methoxy-6-Arylimidazo[2,1-b][1,3,4]Thiadiazoles," Bioorganic & Medicinal Chemistry Letters, Pergamon, Amsterdam, NL, vol. 26, No. 22, 11 Oct. 11, 2016, pp. 5481-5486.

(Continued)

*Primary Examiner* — Jeffrey S Lundgren
*Assistant Examiner* — Michael J Schmitt
(74) *Attorney, Agent, or Firm* — Goodwin Procter LLP

(57) ABSTRACT

The present disclosure relates to novel compounds and pharmaceutical compositions thereof, and methods for inhibiting the activity of SHP2 phosphatase with the compounds and compositions of the disclosure. The present disclosure further relates to, but is not limited to, methods for treating disorders associated with SHP2 deregulation with the compounds and compositions of the disclosure.

7 Claims, 3 Drawing Sheets

(56) References Cited

FOREIGN PATENT DOCUMENTS

| WO | WO-2018/218133 A1 | 11/2018 |
|---|---|---|
| WO | WO-2019051084 A1 | 3/2019 |
| WO | WO-2019/067843 A1 | 4/2019 |
| WO | WO-2019075265 A1 | 4/2019 |
| WO | WO-2019118909 A1 | 6/2019 |
| WO | WO-2019/165073 A1 | 8/2019 |
| WO | WO-2019158019 A1 | 8/2019 |
| WO | WO-2019/183364 A1 | 9/2019 |
| WO | WO-2019/183367 A1 | 9/2019 |
| WO | WO-2019167000 A1 | 9/2019 |
| WO | WO-2019199792 A1 | 10/2019 |
| WO | WO-2019233810 A1 | 12/2019 |
| WO | WO-2020022323 A1 | 1/2020 |
| WO | WO-2020063760 A1 | 4/2020 |
| WO | WO-2020065452 A1 | 4/2020 |
| WO | WO-2020065453 A1 | 4/2020 |
| WO | WO-2020073945 A1 | 4/2020 |
| WO | WO-2020073949 A1 | 4/2020 |
| WO | WO-2020081848 A1 | 4/2020 |
| WO | WO-2020094018 A1 | 5/2020 |
| WO | WO-2020094104 A1 | 5/2020 |

OTHER PUBLICATIONS

Yokoi, Taiyo et al. "Quantitative Structure-Activity Relationship of Substituted Imidazothiadiazoles for Their Binding Against the Ecdysone Receptor of Sf-9 Cells," Bioorganic & Medicinal Chemistry Letters, vol. 27, No. 23, Oct. 13, 2017, pp. 5305-5309.

Saifidin, Safarov et al. "Preparation of 5-Bromo-6-phenylimidazo(2,1-b)(1,3,4)thiadiazol-2-ylamines," Journal of Heterocyclic Chemistry, Wiley-Blackwell Publishing, Inc, US, vol. 45, No. 1, Jan. 1, 2008, pp. 299-302.

Krasavin M et al. "Tert-Butyl Isocyanide Revisited as a Convertible Reagent in the Groebke-Blackburn Reaction," Tetrahedron Letters, Elsevier, Amsterdam, NL, vol. 49, No. 51, Dec. 15, 2008, pp. 7318-7321.

Shen, Jiayi et al. "3-Aminopyrazolopyrazine Derivatives as Spleen Tyrosine Kinase Inhibitors," Hemical Biology & Drug Design, vol. 88, No. 5, 2016, pp. 690-698.

Jorge, Fortanet et al. "Allosteric Inhibition of SHP2: Identification of a Potent, Selective, and Orally Efficacious Phosphatase Inhibitor," J. Med. Chem. 2016, 59, 17, pp. 7773-7782.

Bollu et al. Clin Cancer Res. May 1, 2017; 23(9): 2136-2142. (Year: 2017).

Lazo et al. SLAS Discovery 2017, vol. 22(9) 1071-1083 (Year: 2017).

Jones et al. U.S. Appl. No. 62/343,455, filed May 31, 2016. (Year: 2016).

International Search Report and Written Opinion for International Patent Application PCT/US2019/023389 dated May 10, 2019 (12 pages).

U.S. Appl. No. 16/616,361, dated Nov. 22, 2019.
U.S. Appl. No. 16/651,733, dated Mar. 27, 2020.

SHP2 PHOSPHATASE INHIBITORS AND METHODS OF USE THEREOF

CROSS REFERENCE TO RELATED APPLICATIONS

This application is a continuation of International Patent Application No. PCT/US2019/023389, filed Mar. 21, 2019, which claims the benefit of, and priority to, U.S. provisional application Ser. No. 62/646,099, filed Mar. 21, 2018; 62/649,834, filed Mar. 29, 2018; 62/646,083, filed Mar. 21, 2018; 62/661,902, filed Apr. 24, 2018; and 62/737,819, filed Sep. 27, 2018; the contents of each of which are hereby incorporated by reference herein in their entirety.

JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are 1) RELAY THERAPEUTICS, INC. and 2) D.E. SHAW RESEARCH, LLC.

BACKGROUND

Src homology region 2 (SH2)-containing protein tyrosine phosphatase 2 (SHP2) is a protein tyrosine phosphatase encoded by the PTPN11 gene. SHP2 contains two Src homology 2 (SH2) NH2-terminal domains and a C-terminal protein-tyrosine phosphatase domain. It is ubiquitously expressed in various tissues and cell types. SHP2 plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles in intracellular signaling processes. SHP2 is believed to function by dephosphorylating its associated signaling molecules, thereby attenuating the local signaling flow. However, the main effect of SHP2 action in most signaling pathways (e.g., growth factor, cytokine, and extracellular matrix receptors) is to enhance signal transduction. For example, SHP2 is a positive regulator of the ERK/MAPK signaling pathway, playing a key role in regulating cellular proliferation and survival. (For a review of SHP2 phosphatase, see, e.g, K. S. Grossman et al., Adv. Cancer Res. 2010, 106, 53-89; and references cited therein.)

In the basal state, SHP2 is normally auto-inhibited due to intramolecular interactions between its N-terminal SH2 (N—SH2) domain and its catalytic (PTP) domain, which blocks access to the catalytic site. Activating proteins that interact with the SH2 domains induce a conformational change that reverses this inhibition and allows substrate access to the catalytic site. Mutations in the PTPN11 gene that affect the N—SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Thus, there is a need for SHP2 phosphatase inhibitor compounds and methods for treating cancer and other disorders with these compounds.

SUMMARY

In some embodiments, the present disclosure provides a compound of Formula Ia or Ib, or a pharmaceutically acceptable salt or stereoisomer thereof, represented by:

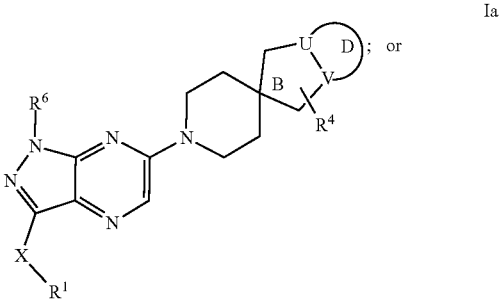

Ia

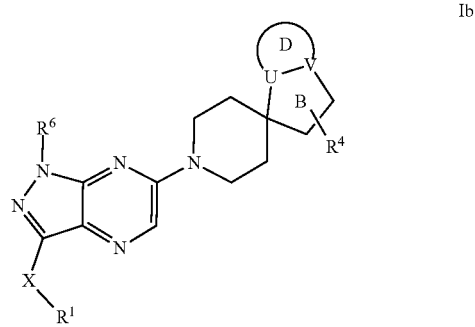

Ib wherein

D is selected from the group consisting of: phenyl, a 5- or 6-membered heteroaryl having one or two heteroatoms each independently selected from the group consisting of S, O or N, and $C_{3-6}$cycloalkyl, wherein D is optionally substituted on an available carbon with one or two substituents each independently selected from $R^m$, and, optionally substituted, on nitrogen, if present, with one or two substituents each independently selected from $R^{D2}$;

U is C, $CR^4$ or N;

V is C, $CR^4$ or N; wherein at least one of U or V must be C, $CR^4$ or N;

B is fused to D such that the two atoms shared by D and B are both carbon or one carbon and one nitrogen;

$R^4$ is independently selected from the group consisting of hydrogen, —C(O)N($R^6$)$_2$, —N($R^6$)$_2$, and —$C_{1-3}$alkyl-N($R^6$)$_2$;

$R^6$ is independently for each occurrence selected from the group consisting of H, —($C_1$-$C_6$)alkyl, —C(O)O$C_{1-4}$alkyl, and phenyl;

$R^{D1}$ is selected from the group consisting of hydroxyl, cyano, halogen, and —N($R^6$)$_2$;

$R^{D2}$ is selected from —($C_1$-$C_6$)alkyl and phenyl; X is selected from the group consisting of a bond, —O—, —$NR^{X1}$—, and —S(O)$_w$-(wherein w is 0, 1 or 2);

$R^1$ is a ring moiety selected from the group consisting of a 8-12 membered bicyclic heteroaryl, phenyl, a 5-7 membered monocyclic heteroaryl, and a 4-7 membered heterocyclyl, wherein the ring moiety may optionally be substituted with one, two or more substituents each independently selected from the group consisting of $R^{10}$, —$OR^{10}$, —S(O)$_w$$R^{10}$ (wherein w is 0, 1 or 2), —$C_{1-6}$alkyl-S(O)$_w$—$C_{1-3}$alkyl, —N($R^{10}$)$_2$, —N(CO)$R^{10}$, —N—S(O)$_w$—$R^{10}$ (where w is 0, 1 or 2), —OS(O)$_w$—$R^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, OXO, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$ alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);

R$^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl may optionally be substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;

R$^{20}$ is selected from the group consisting of hydrogen, hydroxyl, halogen, —NR$^a$R$^b$, C$_{1-6}$alkyl and C$_{1-6}$alkoxy;

R$^{X1}$ is selected from the group consisting of hydrogen, —(C$_1$-C$_6$)alkyl and phenyl; and R$^a$ and R$^b$ are each independently selected from the group consisting of hydrogen and C$_{1-3}$alkyl.

The present disclosure also provides, for example, pharmaceutical compositions containing the compounds described herein. Further, the disclosure provides a method of inhibiting SHP2 phosphatase activity in a subject by administering a therapeutically effective amount of a compound or composition described herein, to a subject, e.g., a human, in need.

The present disclosure further provides, for example, a method of treating a disorder in a subject by administering a therapeutically effective amount of a compound or composition described herein, to a subject in need thereof. Examples of disorders include Noonan syndrome, neutropenia, diabetes, neuroblastoma, melanoma, acute myeloid leukemia, juvenile leukemia, juvenile myelomonocytic leukemia, breast cancer, lung cancer, and colorectal cancer. In addition to the compound or composition described herein, such method may include administration of a therapeutically effective amount of an antibody, an antibody-drug conjugate, an immunomodulator, or a histone deacetylase inhibitor.

The present disclosure is based, in part, on certain discoveries which are described more fully in the Examples section of the present application. For example, the present disclosure is based, in part, on the discovery of compounds disclosed herein, and the SHP2 phosphatase inhibition exhibited by such compounds.

These and other embodiments of the disclosure are further described in the following sections of the application, including the Detailed Description, Examples, and Claims. Still other objects and advantages of the disclosure will become apparent by those of skill in the art from the disclosure herein, which are simply illustrative and not restrictive. Thus, other embodiments will be recognized by the ordinarily skilled artisan without departing from the spirit and scope of the disclosure.

DETAILED DESCRIPTION

Figure 1A:
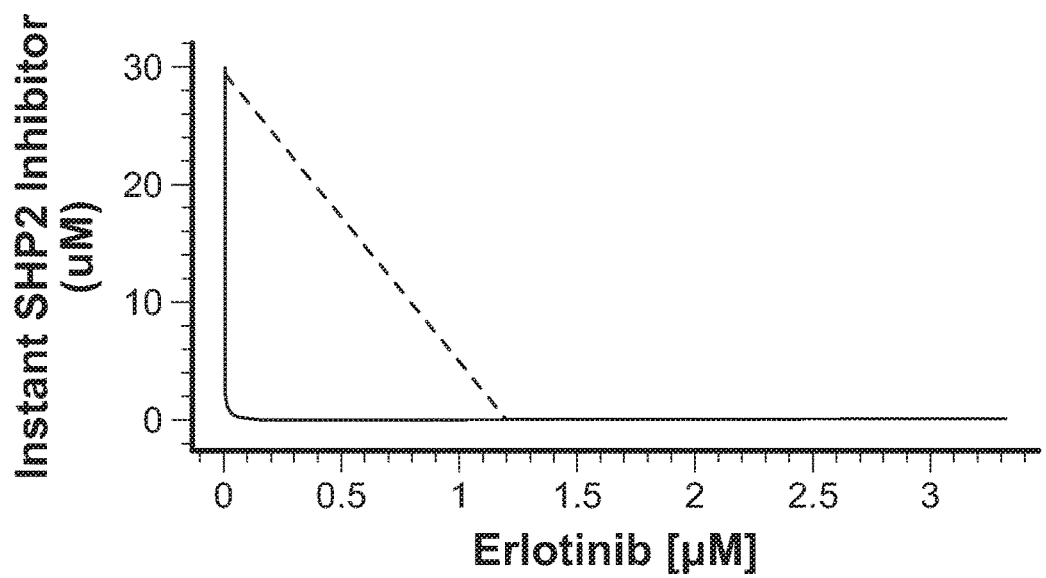
FIG. 1A depicts an isobologram illustrating synergistic growth inhibition of KYSE520 (squamous-cell carcinoma of the head and neck cells) using erlotinib (EGFR inhibitor) and a SHP2 inhibitor of the instant disclosure.
Figure 1B:
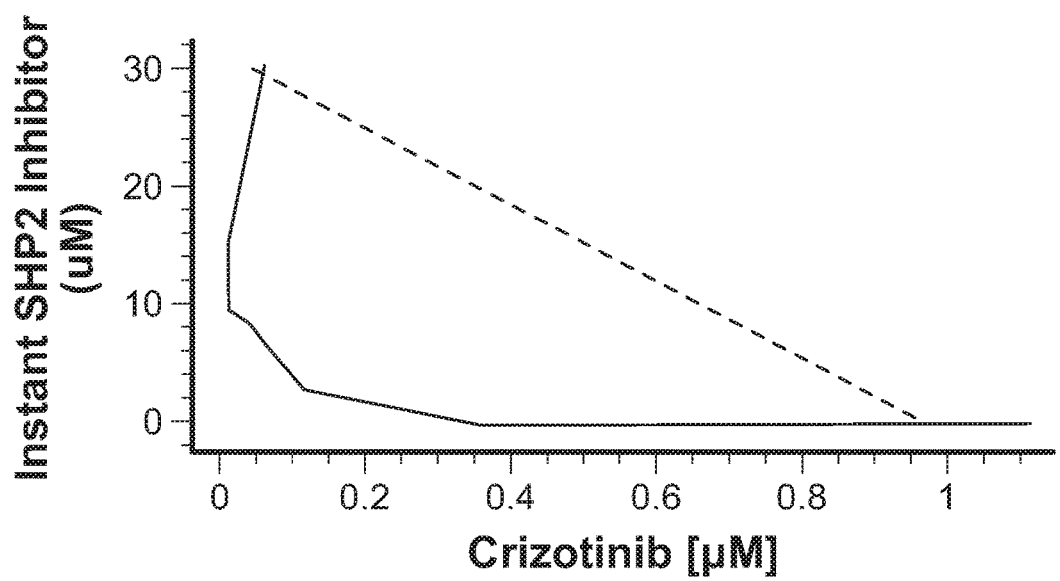
FIG. 1B. depicts an isobologram illustrating synergistic growth inhibition of NCI—H3122 (non-small cell lung cancer cells) using crizotinib (ALK inhibitor) and a SHP2 inhibitor of the instant disclosure.
Figure 2A:
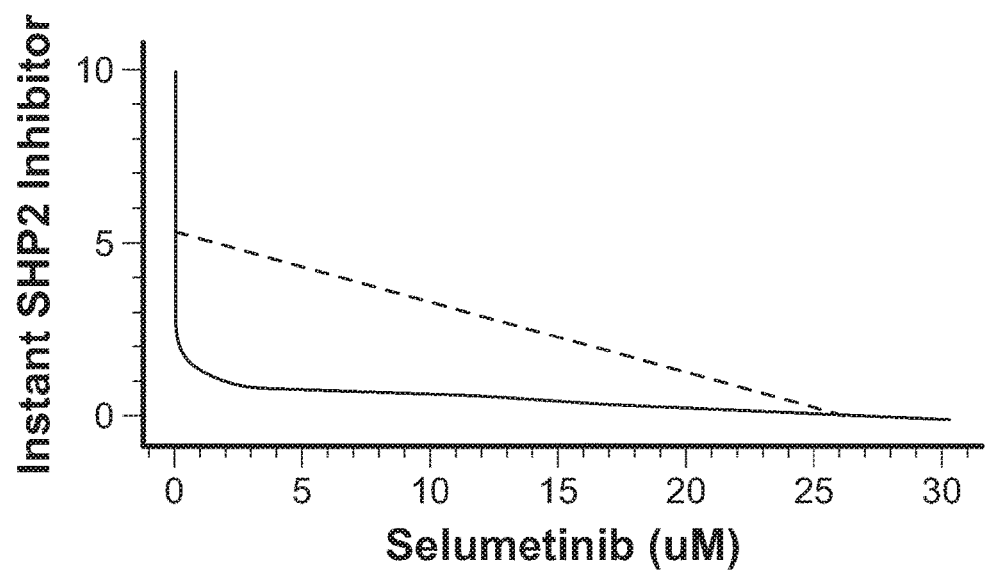
FIG. 2A. Depicts an isobologram illustrating synergistic growth inhibition of NCI—N87 (gastric cancer cells) using selumetinib (MEK inhibitor) and a SHP2 inhibitor of the instant disclosure.
Figure 2B:
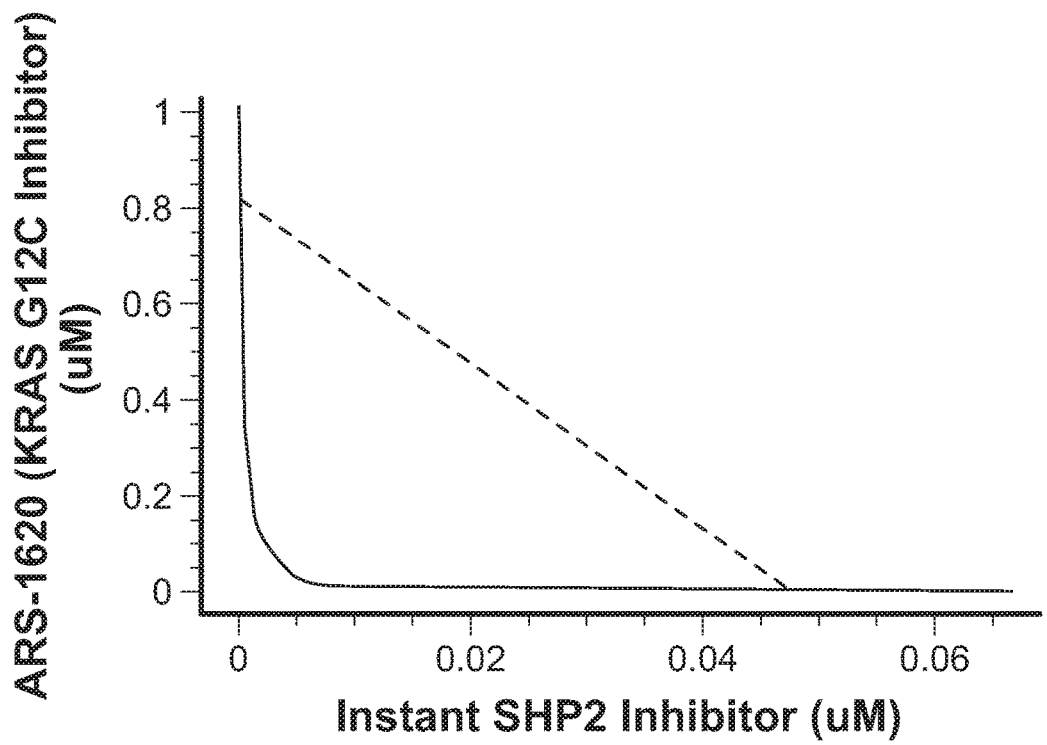
FIG. 2B. Depicts an isobologram illustrating synergistic growth inhibition of NCI—H23 (KRAS G12C mutant non-small cell lung cancer cells) using ARS-1620 (KRAS G12C inhibitor) and a SHP2 inhibitor of the instant disclosure.
Figure 3:
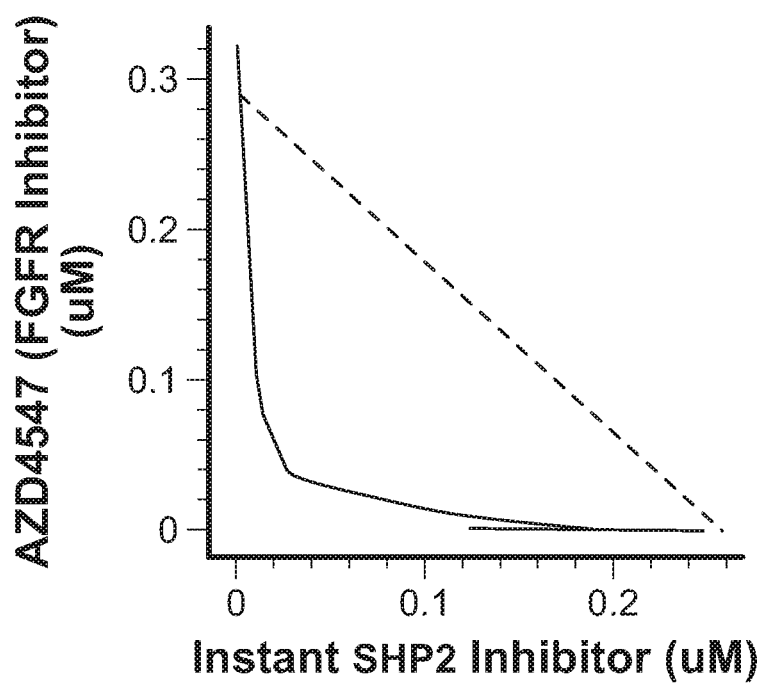
FIG. 3. an isobologram illustrating synergistic growth inhibition of HuH-7 (hepatocellular carcinoma cells) using AZD-4547 (FGFR inhibitor) and a SHP2 inhibitor of the instant disclosure.

Activating SHP2 mutations have been detected in juvenile myelomonocytic leukemia (e.g., Q506P), chronic myelomonocytic leukemia (e.g, Y63C), neuroblastoma (e.g., T507K), melanoma (e.g., R138Q), acute myeloid leukemia (e.g., G503V), breast cancer, lung cancer (e.g., E76V), colorectal cancer (e.g., E76G). (M. Bentires-Alj et al., in Cancer Res. 2004, 64, 8816-8820; and references cited therein.

SHP2 phosphatase inhibitors are disclosed, e.g., in WO 2015/107493; WO 2015/107494; WO 2015/107495; and J. G. Fortanet et al., in J. Med. Chem. 2016, DOI: 10.1021/acs.jmedchem.6b00680; and references cited therein. The effects of SHP2 phsophatase inhibition are described, e.g., Y.-N. P. Chen et al., in Nature, 2016, doi:10.1038/nature18621; J. Wang et al., in J. Clin. Invest. 2016, 126, 2077-2092; and references cited therein.

The compounds and/or compositions of the disclosure, alone or in combination with other treatments, may be effective in treating, reducing, and/or suppressing disorders related to SHP2 phosphatase activity such as, e.g., Noonan syndrome, Leopard Syndrome, diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer, esophageal cancer, gastric cancer, squamous-cell carcinoma of the head and neck (SCCHN), neutropenia (Kostmann's syndrome), and systemic lupus erythematosus. See, e.g, N. Aceto et al. Nature Medicine, 2012, 28,529-538; C M. Furcht et al. Oncogene, 2013, 32, 2346-2355; V. E. Schneeberger et al. Oncotarget, 2015, 6, 6191-6202; P. Cai et al., Biomedicine & Pharmacotherapy 2014, 68, 285-290; and references cited therein.

The methods described herein may also include additionally administering a therapeutically effective amount of an antibody, an antibody-drug conjugate, an immunomodulator, or a histone deacetylase inhibitor.

Abbreviations and Definitions

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)(OR°)R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph. —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$). —OH, —OR$^\bullet$, —O(haloR$^\bullet$), —CN, —C(O)OH, —C(O)OR$^\bullet$, —NH$_2$, NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this disclosure.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2H$ (also represented as D) and $^3H$. Examples of the isotope of a carbon atom include $^{13}C$ and $^{14}C$. Examples of the isotope of an oxygen atom include $^{18}O$.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently $C_1$-$C_{10}$ alkyl. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur, or a 8-10 membered bicyclic unsaturated or partially unsaturated ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine, tetrahydroquinoline, etc.

The terms "heterocyclyl" or "heterocyclic group" are art-recognized and refer to saturated 4-10 membered monocyclic and bicyclic ring structures, including bridged or fused rings, and whose ring structures include one to three heteroatoms, such as nitrogen, oxygen, and sulfur. Where possible, heterocyclyl rings may be linked to the adjacent radical through carbon or nitrogen.

The term "pharmaceutically acceptable salt" is intended to include salts derived from inorganic or organic acids including, e.g., hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, e.g., sodium, potassium, calcium, magnesium, zinc, ammonia, lysine, arginine, histidine, polyhydroxylated amines or tetrafluoroborate. Exemplary pharmaceutically acceptable salts are found, e.g, in Berge, et al. (*J. Pharm. Sci.* 1977, 66(1), 1; and Gould, P. L., *Int. J. Pharmaceutics* 1986, 33, 201-217; (each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to SHP2 phosphatase, or one or more symptoms thereof, prevent the advancement of conditions or symptoms related to afflictions related to SHP2 phosphatase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to SHP2 phosphatase activity or that may otherwise be relieved by the compounds and/or compositions of the disclosure.

In some embodiments, the present disclosure provides a compound of Formula Ia or Ib, or a pharmaceutically acceptable salt or stereoisomer thereof, represented by:

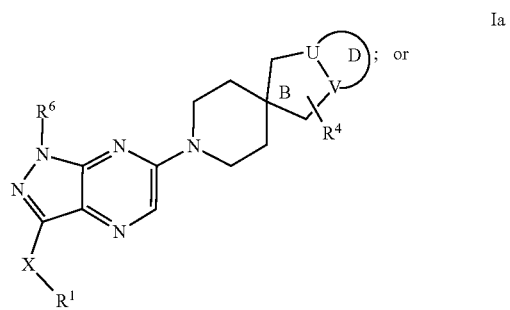

-continued

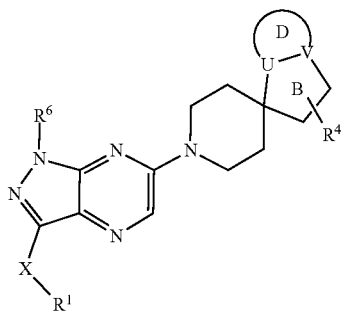

Ib wherein

D (also described in Formulas X and XI herein as Cy$^C$) is selected from the group consisting of: phenyl, a 5- or 6-membered heteroaryl having one or two heteroatoms each independently selected from the group consisting of S, O or N, and C$_{3-6}$cycloalkyl, wherein D is optionally substituted on an available carbon with one or two substituents each independently selected from R$^{D1}$, and, optionally substituted, on nitrogen, if present, with one or two substituents each independently selected from R$^{D2}$;

U is C, CR$^4$ or N;

V is C, CR$^4$ or N;

wherein at least one of U or V must be C or CR$^4$;

B is fused to D such that the two atoms shared by D and B are both carbon or one carbon and one nitrogen;

R$^4$ is independently selected from the group consisting of hydrogen, —C(O)N(R$^6$)$_2$, —N(R$^6$)$_2$, and —C$_{1-3}$alkyl-N(R$^6$)$_2$;

R$^6$ is independently for each occurrence selected from the group consisting of H, —(C$_1$-C$_6$)alkyl, —C(O)OC$_{1-4}$alkyl, and phenyl;

R$^{D1}$ is selected from the group consisting of hydroxyl, cyano, halogen, and —N(R$^6$)$_2$;

R$^{D2}$ is selected from —(C$_1$-C$_6$)alkyl and phenyl;

X (also described in Formulas X and XI herein as L$^2$) is selected from the group consisting of a bond, —O—, —NR$^{X1}$—, and —S(O)$_w$— (wherein w is 0, 1 or 2);

R$^1$ (also described in Formulas X and XI herein as R$^2$) is a ring moiety selected from the group consisting of a 8-12 membered bicyclic heteroaryl, phenyl, a 5-7 membered monocyclic heteroaryl, and a 4-7 membered heterocyclyl, wherein the ring moiety may optionally be substituted with one, two or more substituents each independently selected from the group consisting of R$^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)$_w$—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);

R$^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl may optionally be substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;

R$^{20}$ is selected from the group consisting of hydrogen, hydroxyl, halogen, —NR$^a$R$^b$, C$_{1-6}$alkyl and C$_{1-6}$alkoxy;

R$^{X1}$ is selected from the group consisting of hydrogen, —(C$_1$-C$_6$)alkyl and phenyl; and R$^a$ and R$^b$ are each independently selected from the group consisting of hydrogen and C$_{1-3}$alkyl.

In some embodiments, D is selected from the group consisting of:

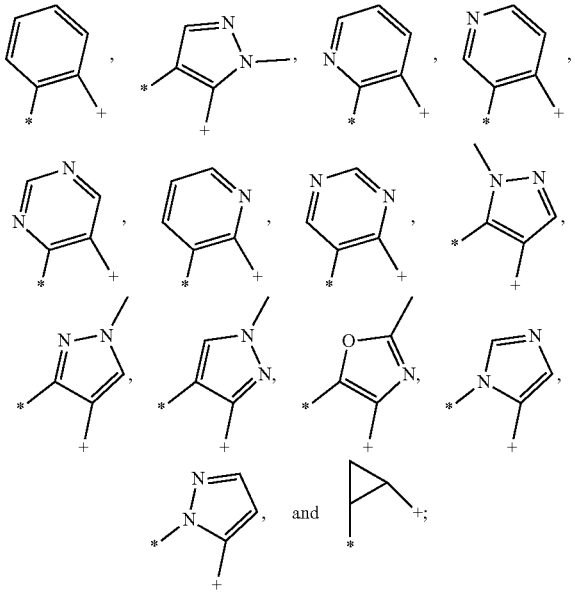

wherein * and + represent fusion points of attachment to ring B.

In some embodiments, X is a bond, R$^1$ is a nitrogen containing ring moiety and R$^1$ is bound through the nitrogen.

In some embodiments, R$^1$ is selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[ ][1,4]oxazepin-4-yl, 2-(3,4-dihydroisoquinolin-1(2H)-one), 2-(3,4-dihydroisoquinolin-1(2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4(1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 1 1-dioxide, 1,2,3,4-tetrahydropyrazino[2,3-d]pyridazin-1-yl, 1,4-dihydropyrido[3,4-b]pyrazin-1-yl-3(2H)-one, 5,6,7,8-tetrahydro-1,6-naphthyridin-6-yl, 5,6,7,8-tetrahydro-1,7-naphthyridin-7-yl, 1,2,3,4-tetrahydropyrido[3,4-b]pyrazin-1-yl, 5,8-dihydropteridin-5-yl-7(6H)-one, 4,5,6,7-tetrahydrothieno[3,2-b]pyridin-4-yl, or 5,6,7,8-tetrahydropyrazino[2,3-c]pyridazin-5-yl wherein the nitrogen ring moiety may be optionally substituted with one or two substituents each independently selected from the group consisting of Cl, F, —CN, $C_{1-4}$alkyl, —$OC_{1-4}$alkyl, $C_{2-6}$alkenyl, $C_{2-4}$alkynyl, $C_{3-6}$cycloalkyl, $C_{5-6}$cycloalkenyl, —C(H)=N—OCH$_3$, —C(H)=N—OH, —C(CH$_3$)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —S(O)$_2$C$_{1-4}$alkyl, —(CH$_2$)$_{0-1}$NH$_2$, —(CH$_2$)$_{0-1}$NHC$_{1-4}$alkyl, —(CH$_2$)$_{0-1}$(C$_{1-4}$alkyl)$_2$, —(CH$_2$)$_{0-1}$ NH(CO)C$_{1-4}$alkyl, phenyl, optionally substituted heteroaryl and optionally substituted heterocyclyl, wherein $C_{1-4}$alkyl or $C_{3-6}$cycloalkyl may be optionally substituted with one, two or three fluorine atoms, one or two hydroxyl groups, or one or two —OC$_{1-2}$alkyl groups.

In some embodiments, heteroaryl is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, and 1,2,4-oxadiazol-3-yl, 1,3,4-oxadiazol-2-yl, 1,2,4-triazol-2-yl, 1,3,4-triazol-2-yl; wherein heteroaryl may be optionally substituted with $C_{1-2}$alkyl (optionally substituted with one, two or three fluorine atoms, one or two 2 hydroxyl groups, or one or two —OC$_{1-2}$alkyl groups).

In some embodiments, heterocyclyl is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, or 1,2,4-oxadiazo-3-yl-5-one, wherein heterocyclyl may be optionally substituted with hydroxyl or $C_{1-2}$alkyl (optionally substituted with one, two or three fluorine atoms, one or two 2 hydroxyl groups, or one or two —OC$_{1-2}$alkyl groups).

In some embodiments, $R^1$ is a 1,2,3,4-tetrahydroquinoline moiety optionally substituted with one, two or three halo, $C_{1-3}$alkyl or $C_{1-3}$haloalkyl), $C_{1-3}$alkyl, $C_{1-3}$haloalkyl, and heteroaryl (optionally substituted with one, two or three halogens, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is a 1,2,3,4-tetrahydro-1,5-naphthyridine moiety optionally substituted with one, two or three halo, $C_{1-3}$alkyl, $C_{1-3}$haloalkyl, and heteroaryl (optionally substituted with one, two or three halogens, —C(O)N(R$^{10}$)$_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is phenyl; wherein phenyl may optionally be substituted by one, two, or three substituents each independently selected from the group consisting of —OR$^{10}$, halogen, and cyano.

In some embodiments, $R^1$ is pyridyl; wherein pyridyl may optionally be substituted by one, two, or three substituents each independently selected from the group consisting of —OR$^{10}$, halogen, and cyano.

In some embodiments, $R^1$ is indolyl or indolinyl, wherein indolyl or indolinyl may optionally be substituted with one, two or three substituents each independently selected from the group consisting of —OR$^{10}$, halogen, and cyano; and wherein indolyl or indolinyl is bound through carbon.

Also disclosed herein, for example, is a compound of Formula II, or a pharmaceutically acceptable salt or stereoisomer thereof, wherein Formula II is represented by:

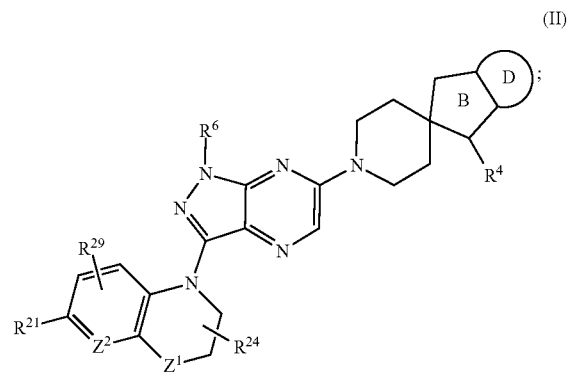

(II)

wherein:

D is selected from the group consisting of: phenyl, a 5- or 6-membered heteroaryl having one or two heteroatoms independently selected from the group consisting of S, O or N, and $C_{3-6}$cycloalkyl, wherein D is optionally substituted on a carbon with one or two substituents each independently selected from $R^{D1}$, and, optionally substituted, on nitrogen, if present, with one or two substituents each independently selected from $R^{D2}$;

B is fused to D such that the two atoms shared by D and B are both carbon;

$Z^2$ is selected from the group consisting of $CR^{22}$ and N;

$Z^1$ is selected from the group consisting of: $NR^{61}$, $C(R^{23})_2$; $C(O)$, and O;

$R^{21}$ is selected from the group consisting of hydrogen, halogen, cyano, hydroxyl, $N(R^6)_2$, $C_1$-$C_6$alkyl, $C_3$-$C_6$cycloalkyl, $C_1$-$C_6$alkyoxy, —C(O)N(R$^6$)$_2$, heterocycloalkyl, phenyl, and heteroaryl, wherein $C_1$-$C_6$alkyl, $C_3$-$C_6$cycloalkyl, $C_1$-$C_6$alkyoxy, heterocycloalkyl, phenyl, and heteroaryl may each be substituted by one, two or three or more substituents each selected from the group consisting of halo, —C(O)—OR$^{26}$, —C(O)R$^{26}$, —C(O)N(R$^6$)$_2$, —N(R$^6$)$_2$, $C_{1-3}$alkyl (optionally substituted by hydroxyl or methoxy), $C_1$-$C_3$alkyoxy, and $C_{1-3}$haloalkyl;

$R^{29}$ is selected from the group consisting of hydrogen, halogen, cyano, $N(R^6)_2$, $C_1$-$C_6$alkyl, $C_3$-$C_6$cycloalkyl, $C_1$-$C_6$alkyoxy, —C(O)N(R$^6$)$_2$, heterocycloalkyl, phenyl, and heteroaryl, wherein $C_1$-$C_6$alkyl, $C_3$-$C_6$cycloalkyl, $C_1$-$C_6$alkyoxy, heterocycloalkyl, phenyl, and heteroaryl may each be substituted by one, two or three or more substituents each selected from the group consisting of halo, —C(O)R$^{26}$, C(O)—OR$^{26}$, —C(O)N(R$^6$)$_2$, N(R$^6$)$_2$, $C_{1-3}$alkyl (optionally substituted with hydroxyl or methoxy) and $C_{1-3}$haloalkyl;

$R^{22}$, for each occurrence, is independently selected from the group consisting of hydrogen, halogen, cyano, hydroxyl, $N(R^6)_2$, $C_1$-$C_6$alkyl, $C_3$-$C_6$cycloalkyl, $C_1$-$C_6$alkyoxy, —C(O)N(R$^6$)$_2$, heterocycloalkyl, phenyl, and heteroaryl, wherein $C_1$-$C_6$alkyl, $C_3$-$C_6$cycloalkyl, $C_1$-$C_6$alkyoxy, heterocycloalkyl, phenyl, and heteroaryl may each be substituted by one, two or three or more substituents each selected from the group consisting of halo, —C(O)—OR$^{26}$, C(O)R$^{26}$, —C(O)N(R$^6$)$_2$, N(R$^6$)$_2$, $C_{1-3}$alkyl (optionally substituted with hydroxyl or methoxy), $C_1$-$C_2$alkyoxy, and $C_{1-2}$haloalkyl;

$R^{23}$ independently, for each occurrence, is selected from the group consisting of H, halogen, and $C_1$-$C_6$alkyl;

$R^{24}$ is selected from the group consisting of H, halogen, and $C_1$-$C_6$alkyl:

$R^{26}$ is selected from the group consisting of hydrogen and $C_{1-3}$alkyl;

$R^4$ is independently selected from the group consisting of hydrogen, —C(O)N($R^6$)$_2$, and —N($R^6$)$_2$;

$R^6$ is selected, independently for each occurrence, from the group consisting of hydrogen, —($C_1$-$C_6$)alkyl and phenyl;

$R^{61}$ is selected from the group consisting of hydrogen, —($C_1$-$C_6$)alkyl, —C(O)—($C_1$-$C_6$)alkyl, $C_{3-6}$ cycloalkyl (optionally substituted with one or two hydroxyl, $C_{1-2}$alkyl, and $C_{1-2}$alkoxy), and phenyl;

$R^{D1}$ is selected from the group consisting of hydroxyl, cyano, halogen, and, —N($R^6$)$_2$; and $R^{D2}$ is selected from —($C_1$-$C_6$)alkyl and phenyl.

In some embodiments, D is selected from the group consisting of:

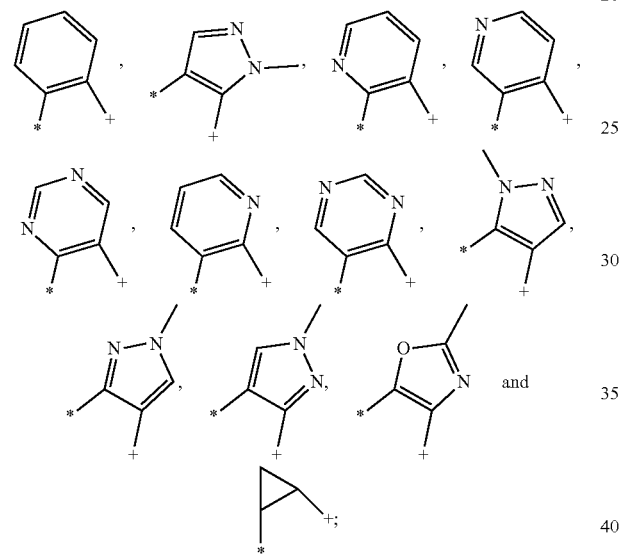

wherein * and + represent fusion points of attachment to ring B.

In some embodiments, $Z^2$ is N. In some embodiments, $Z^2$ is CH. In some embodiments, $Z^1$ is C($R^{23}$)$_2$.

In some embodiments, $R^{23}$ for each occurrence is hydrogen. In some embodiments, $R^{23}$ for each occurrence is methyl.

In some embodiments, $R^{22}$ and $R^{24}$, for each occurrence, is hydrogen.

In some embodiments, $R^{21}$ is selected from the group consisting of hydrogen, halogen, $CF_3$, N($R^6$)$_2$, C(O)N($R^6$)$_2$, heteroaryl, and phenyl. In some embodiments, $R^{21}$ is C(O)NHCH$_3$.

In some embodiments, $R^{21}$ is heteroaryl. In some embodiments, $R^{21}$ is selected from the group consisting of selected from the group consisting of:

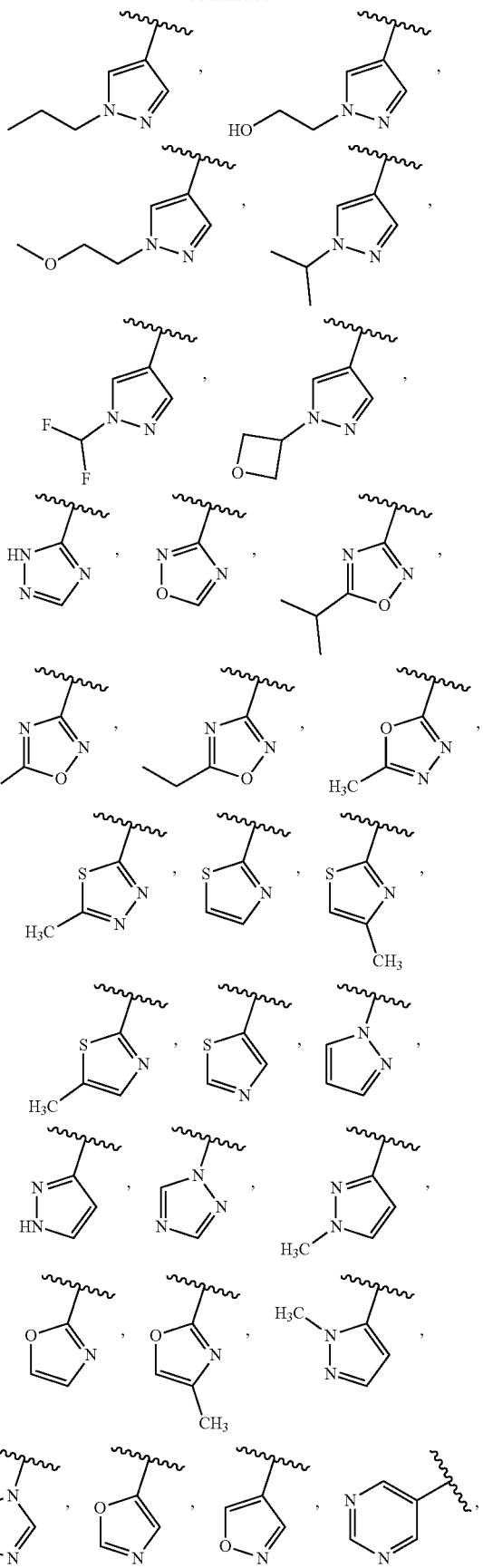

-continued

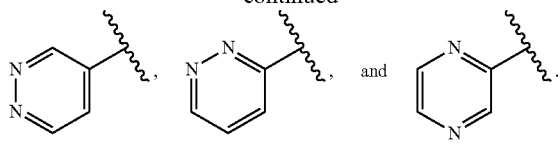

In some embodiments, $R^{21}$ is hydrogen.

Also disclosed herein, for example, is a compound of Formula III, or a pharmaceutically acceptable salt or stereoisomer thereof, represented by:

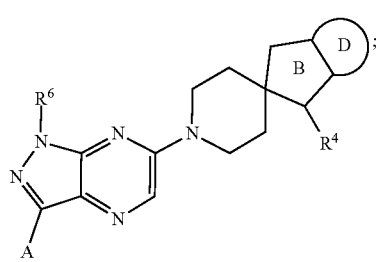

wherein:

A (also described herein for Formulas X and XI as $R^2$ where $L^2$ of Formulas X and XI is a covalent bond) is selected from the group consisting of:

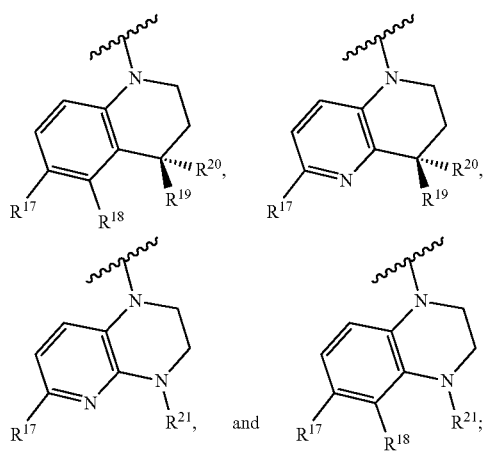

wherein:

$R^{17}$ is selected from the group consisting of H, Cl, F, $CHF_2$, $CF_3$, —CN, $C_{1-4}$alkyl, $C_{3-6}$cycloalkyl, $C_{5-6}$cycloalkenyl, —$OC_{1-4}$alkyl, —O-heteroaryl, $C_{2-4}$alkenyl, $C_{2-4}$alkynyl, —C=N—$OC_{1-4}$alkyl, —C=N—OH, —C($C_{1-4}$alkyl)=N—OH, —$(CH_2)_{0-1}$C(O)$NH_2$, —$(CH_2)_{0-1}$C(O)$NHC_{1-4}$alkyl, —$(CH_2)_{0-1}$C(O)$NHC_{1-4}$alkyl-heteroaryl, —$(CH_2)_{0-1}$C(O)N($C_{1-4}$alkyl)$_2$, —$(CH_2)_{0-1}$C(O)$OC_{1-4}$alkyl, —$(CH_2)_{0-1}$C(O)OH, —$(CH_2)_{0-1}$S(O)$_2C_{1-4}$alkyl, —$(CH_2)_{0-1}NH_2$, —$(CH_2)_{0-1}NHC_{1-4}$alkyl, —$(CH_2)_{0-1}N(C_{1-4}$alkyl)$_2$, —$(CH_2)_{0-1}NH(CO)C_{1-4}$alkyl, phenyl, heteroaryl, and heterocyclyl,
wherein heteroaryl and O-heteroaryl may optionally be substituted with one or more $C_{1-2}$alkyl (optionally substituted with one, two or three fluorine atoms, one or two hydroxyl groups, or one or two —$OC_{1-2}$alkyl groups); and
wherein heterocyclyl may optionally be substituted with one or more hydroxyl or $C_{1-2}$alkyl (optionally substituted with one, two or three fluorine atoms, one or two hydroxyl groups, or one or two —$OC_{1-2}$alkyl groups);

$R^{18}$ is selected from the group consisting of H, Cl, F, —CN, $NO_2$, $C_{1-4}$alkyl, $C_{3-4}$cycloalkyl, $C_{2-4}$alkenyl, $C_{2-4}$alkynyl, —$OC_{1-4}$alkyl, —$(CH_2)_{0-1}$C(O)$NH_2$, —$(CH_2)_{0-1}$C(O)$NHC_{1-4}$alkyl, —$(CH_2)_{0-1}$C(O)N($C_{1-4}$alkyl)$_2$, —$(CH_2)_{0-1}$C(O)$OC_{1-4}$alkyl, —$(CH_2)_{0-1}$C(O)OH, $NH_2$, —$NHC(O)C_{1-4}$alkyl, —$NHS(O)_2C_{1-4}$alkyl, —$N(S(O)_2C_{1-4}$alkyl)$_2$, —$N(C_{1-4}$alkyl)$S(O)_2C_{1-4}$alkyl, —N=S(O)($C_{1-4}$alkyl)$_2$, —$(CH_2)_{0-1}S(O)_{1-4}$alkyl, —$(CH_2)_{0-1}S(O)C_{1-4}$alkyl, —$(CH_2)_{0-1}S(O)_2C_{1-4}$alkyl, —$S(O)_2C_{3-4}$cycloalkyl, —$S(O)_2$heteroaryl, —S(O)(=NH)$C_{1-4}$alkyl, —S(O)(=N$C_{1-4}$alkyl)$C_{1-4}$alkyl, phenyl, heteroaryl, and heterocyclyl;
wherein phenyl, heteroaryl and heterocyclyl may optionally be substituted with one or more groups independently selected from the group consisting of F, C1alky1 (optionally substituted with one, two or three fluorine atoms, one or two hydroxyl groups, or one or two —$OC_{1-2}$alkyl groups), cyclopropyl, —C(O)$NH_2$, —C(O)$NHC_{1-4}$alkyl, —C(O)N($C_{1-4}$alkyl)$_2$, —C(O)$OC_{1-4}$alkyl, and —C(O)OH;

each of $R^{19}$ and $R^{20}$ is independently selected from the group consisting of H and —$C_{1-4}$alkyl; or $R^{19}$ and $R^{20}$ together with the carbon atom to which they are attached form a €2-4 alkenyl moiety which may optionally be substituted with one or two fluorine atoms;

$R^{21}$ is selected from the group consisting of H, $C_{1-4}$alkyl, —$C_{3-4}$cycloalkyl, —$(CH_2)_{0-4}$C(O)$C_{1-4}$alkyl, —$(CH_2)_{0-4}$C(O)$OC_{1-4}$alkyl, —$(CH_2)_{0-4}$C(O)NH2, —$(CH_2)_{0-4}$C(O)$NHC_{1-4}$alkyl, —$(CH_2)_{0-4}$C(O)N($C_{1-4}$alkyl)$_2$, —$(CH_2)_{0-4}$S(O)$_2C_{1-4}$alkyl, and heterocyclyl;
wherein each $C_{1-4}$alkyl, $C_{2-4}$alkenyl, $C_{2-4}$alkynyl, $C_{3-4}$cycloalkyl, $C_{3-6}$cycloalkyl, or $C_{5-6}$cycloalkenyl of $R^{17}$, $R^{18}$, $R^{19}$, $R^{20}$, or $R^{21}$ may optionally be substituted with one, two or three fluorine atoms, one or two hydroxyl groups, or one or two —$OC_{1-2}$alkyl groups;

$R^6$ is independently for each occurrence selected from the group consisting of H, —($C_1$-$C_6$)alkyl, —C(O)$OC_{1-4}$alkyl, and phenyl;

$R^4$ is independently selected from the group consisting of hydrogen, —C(O)N($R^6$)$_2$, and —N($R^6$)$_2$;

D is selected from the group consisting of: phenyl, a 5- or 6-membered heteroaryl having one or two heteroatoms independently selected from the group consisting of S, O or N, and $C_{3-6}$cycloalkyl, wherein D is optionally substituted on a carbon with one or two substituents each independently selected from $R^m$, and, optionally substituted, on nitrogen, if present, with one or two substituents each independently selected from $R^m$;

B is fused to D such that the two atoms shared by D and B are both carbon;

$R^{D1}$ is selected from the group consisting of hydroxyl, cyano, halogen, and, —N($R^6$)$_2$; and $R^{D2}$ is selected from —($C_1$-$C_6$)alkyl and phenyl.

In some embodiments, $R^{17}$ is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, 1,2,4-oxadiazol-3-yl, 1,3,4-oxadiazol-2-yl, 1,2,4-triazol-2-yl, and 1,3,4-triazol-2-yl; wherein $R^{17}$ may optionally be substituted with one, two or three fluorine atoms, one or two hydroxyl groups, or one or two —$OC_{1-2}$alkyl groups.

In some embodiments, $R^{17}$ is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, and 1,2,4-oxadiazo-3-yl-5-one; wherein $R^{17}$ may optionally be substituted with one or more hydroxyl or $C_{1-2}$alkyl (optionally substituted with one, two or three fluorine atoms, one or two hydroxyl groups, or one or two —$OC_{1-2}$alkyl groups).

In some embodiments, $R^{18}$ is selected from the group consisting of phenyl, 2-pyridyl, 3-pyridyl, 4-pyridyl, pyrazol-3-yl, pyrazol-4-yl, thiazol-2-yl, 1,2,4-oxadiazol-3-yl, and 1,3,4-oxadiazol-2-yl; wherein $R^{18}$ may optionally be substituted with one or more groups independently selected from the group consisting of F, $C_{1-2}$alkyl (optionally substituted with one, two or three fluorine atoms, one or two hydroxyl groups, or one or two —$OC_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, $R^{18}$ is selected from the group consisting of —(CH$_2$)$_{0-1}$-morpholine, tetrahydropyranyl, tetrahydrofuranyl, oxiranyl, isothiazolidin-2-yl-1,1-dioxide, and —(CH$_2$)$_{0-1}$-oxazolidin-3-yl-2-one; wherein $R^{18}$ $R^{18}$ may optionally be substituted with one or more groups independently selected from the group consisting of F, $C_{1-2}$alkyl (optionally substituted with one, two or three fluorine atoms, one or two hydroxyl groups, or one or two —$OC_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, $R^{19}$ is —CH$_3$ or —CHF$_2$, $R^{20}$ is H, and the carbon to which $R^{19}$ and $R^{20}$ are attached has an (R)-configuration. In some embodiments, $R^{19}$ is H, $R^{20}$ is —CH$_3$ or —CHF$_2$, and the carbon to which $R^{19}$ and $R^{20}$ are attached has an (S)-configuration.

In some embodiments, D is selected from the group consisting of:

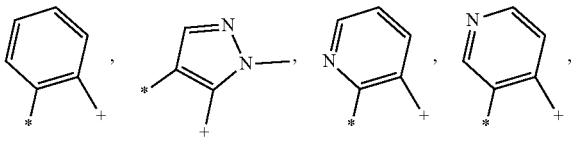

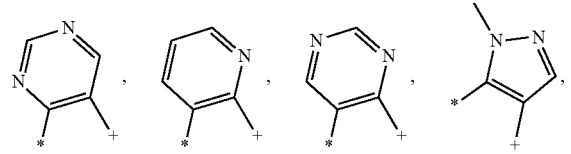

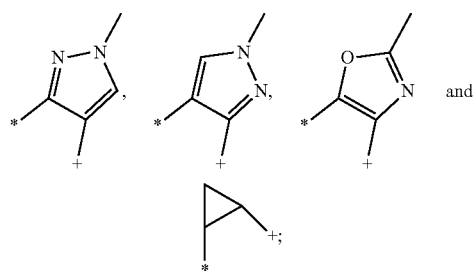

wherein * and + represent fusion points of attachment to ring B.

In some embodiments, the present disclosure provides a compound of formula X:

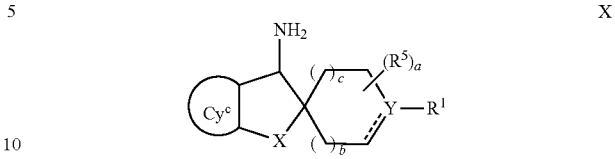

or a pharmaceutically acceptable salt thereof, wherein;
X is —CH$_2$—, —CH(R$^X$)—, —C(R$^X$)$_2$—, —C(O)—, —NH—, —N(R$^X$)—, or —O—;
Y is C, CH, C(R$^Y$), or N;
⚌ is a single bond when Y is CH, C(R$^Y$), or N; or ⚌ is a double bond when Y is C;
R$^1$ is L$^1$-Cy$^B$-L$^2$-R$^2$;
Cy$^B$ is phenyl, a monocyclic 5-6 membered heteroaryl having 1-4 heteroatoms independently selected from nitrogen, oxygen, and sulfur; or a bicyclic 8-10 membered heteroaryl having 1-5 heteroatoms independently selected from nitrogen, oxygen, and sulfur; wherein Cy$^B$ is substituted by m instances of R$^3$;
Cy$^C$ is benzo; 5-6 membered heteroarylo having 1-4 heteroatoms independently selected from nitrogen, oxygen, and sulfur; 3-7 membered saturated or partially unsaturated cycloaliphatic-fused; or 3-7 membered saturated of partially unsaturated heterocyclo having 1-2 heteroatoms independently selected from nitrogen, oxygen, and sulfur; wherein when Cy$^C$ is heterocyclo or heteroarylo, said heteroatoms may occur at any position within Cy$^C$; and wherein in each case Cy$^C$ is substituted by n instances of R$^4$;
L$^1$ is a covalent bond or —C(O)—;
L$^2$ is a covalent bond, or a CM bivalent saturated or unsaturated, straight or branched hydrocarbon chain wherein one or two methylene units of the chain are optionally and independently replaced by —CH(R$^L$), —C(R$^L$)$_2$—, C$_{3-5}$ cycloalkylene, —N(R>, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;
R$^2$ is hydrogen, R$^A$, or R$^B$, and when R$^2$ is R$^B$, R$^2$ is substituted by q instances of R$^C$;
each instance of R$^3$, R$^4$, R$^X$, R$^Y$, and R$^L$ is independently R$^A$ or R$^B$, and is substituted by r instances of R$^C$;
each instance of R$^5$ is independently R$^A$ or R$^B$, and is substituted by r instances of R$^C$; or two instances of R$^5$ are taken together with their intervening atoms to form a 3-6 membered carbocyclic fused ring or a 3-6 membered heterocyclic fused ring having 1-2 heteroatoms independently selected from nitrogen, oxygen, and sulfur;
each instance of R$^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —O C(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;
each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —OS(O)$_2$F, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each of b and c is independently 0 or 1; and each of a, m, n, q, and r is independently 0, 1, 2, 3, or 4;

wherein the compound is not

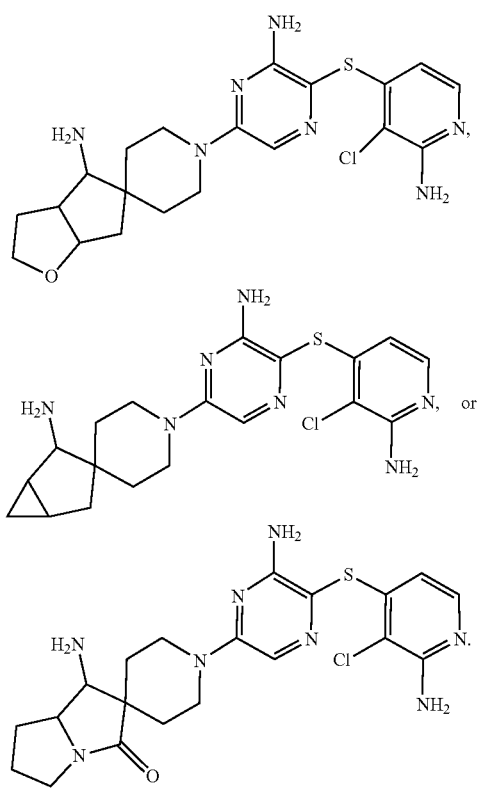

In some embodiments, a compound disclosed herein is of the one of formulas:

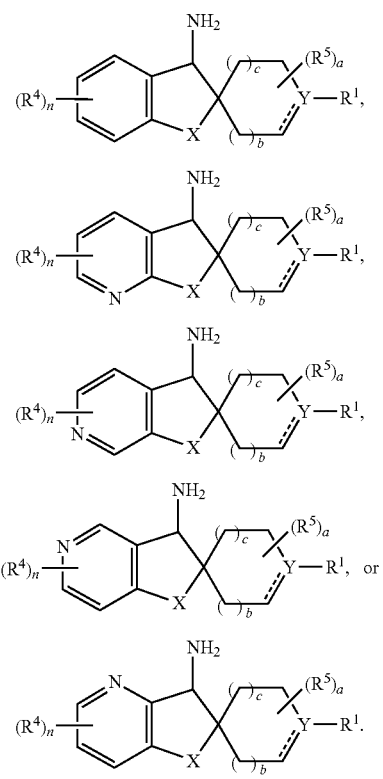

or a pharmaceutically acceptable salt thereof, wherein each of X, Y, $R^1$, $R^4$, $R^5$, a, b, c, and n are as defined in embodiments and classes and subclasses herein.

In some embodiments, $Cy^B$ is selected from the group consisting of:

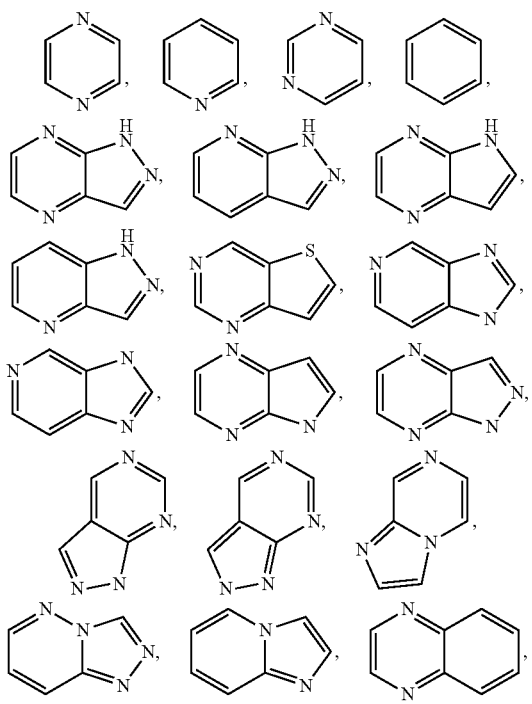

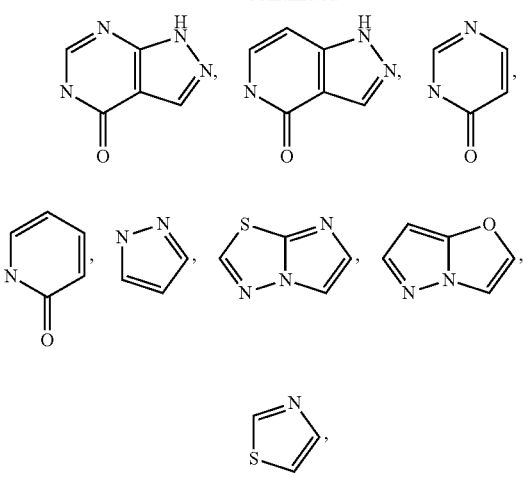

wherein $Cy^B$ is substituted by m instances of $R^3$.

In some embodiments, a compound disclosed herein is of one of formulas:

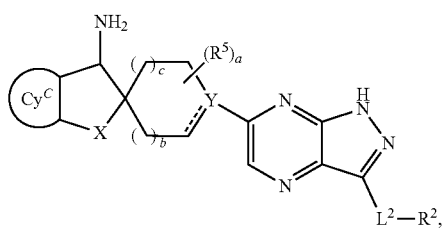

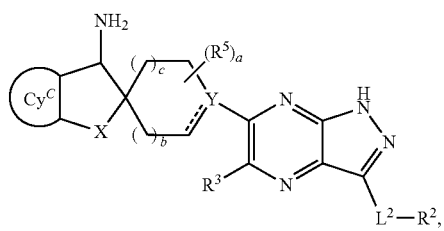

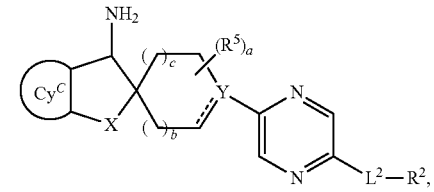

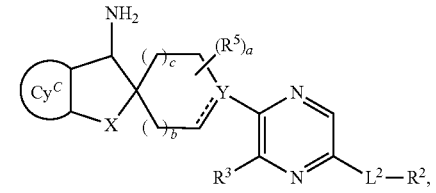

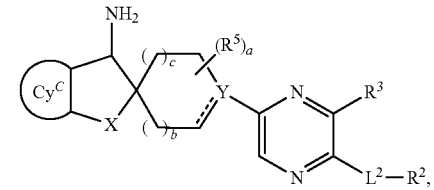

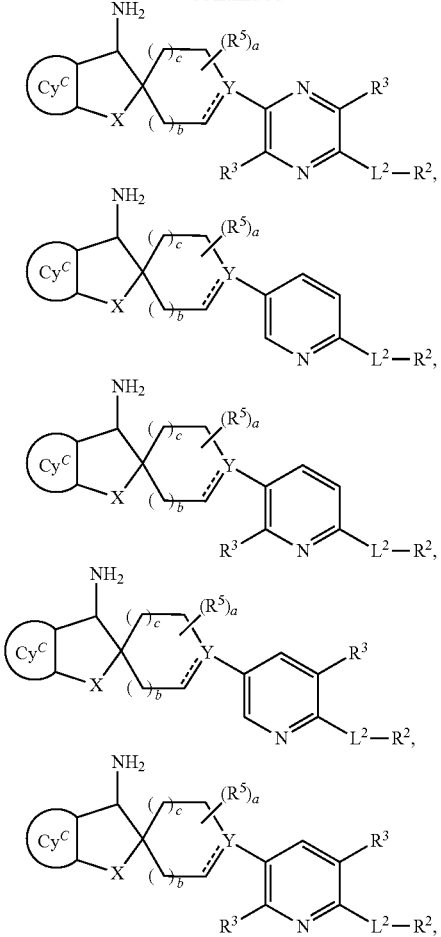

or a pharmaceutically acceptable salt thereof, wherein each of $Cy^C$, X, Y, $L^2$, $R^2$, $R^3$, $R^5$, a, b, and c, are as defined in embodiments and classes and subclasses herein.

In some embodiments, a compound disclosed herein is of one of formulas:

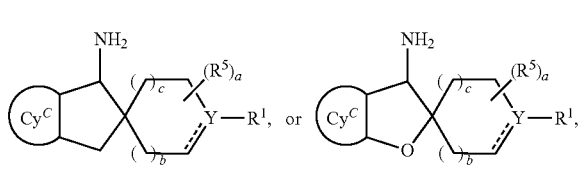

or a pharmaceutically acceptable salt thereof, wherein each of $Cy^C$, Y, $R^1$, $R^5$, a, b, and c, are as defined in embodiments and classes and subclasses herein.

In some embodiments, a compound disclosed herein is of one of formulas:

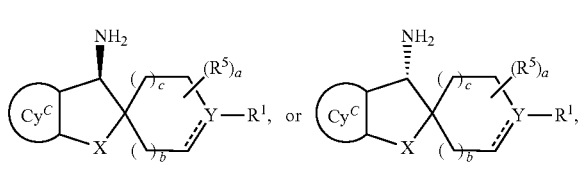

or a pharmaceutically acceptable salt thereof, wherein each of $Cy^C$, X, Y, $R^1$, $R^5$, a, b, and c, are as defined in embodiments and classes and subclasses herein.

In some embodiments, a compound disclosed herein is of one of formulas:

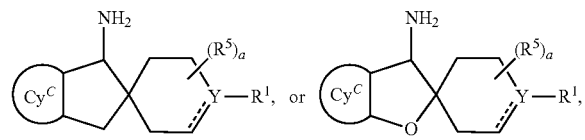

or a pharmaceutically acceptable salt thereof, wherein each of $Cy^C$, Y, $R^1$, $R^5$, and a are as defined in embodiments and classes and subclasses herein.

In some embodiments, a compound disclosed herein is of one of formulas:

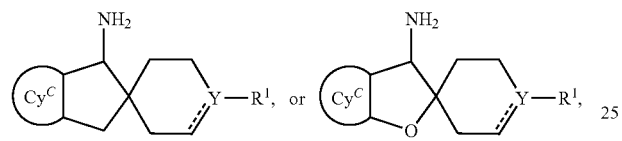

or a pharmaceutically acceptable salt thereof, wherein each of $Cy^C$, Y, and $R^1$ are as defined in embodiments and classes and subclasses herein.

In some embodiments, a compound disclosed herein is of one of formulas:

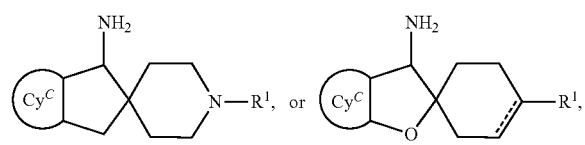

or a pharmaceutically acceptable salt thereof, wherein each of $Cy^C$ and $R^1$ are as defined in embodiments and classes and subclasses herein.

In some embodiments, variable a is 2, or a pharmaceutically acceptable salt thereof.

In some embodiments, two instances of $R^5$ are taken together with their intervening atoms to form a 3-6 membered carbocyclic fused ring or a 3-6 membered heterocyclic fused ring having 1-2 heteroatoms independently selected from nitrogen, oxygen, and sulfur, or a pharmaceutically acceptable salt thereof.

In some embodiments, the present disclosure provides a compound of the formula:

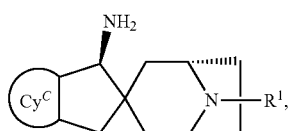

or a pharmaceutically acceptable salt thereof, wherein each of $Cy^C$ and $R^1$ are as defined in embodiments and classes and subclasses herein.

In some embodiments, the present disclosure provides a compound of the formula:

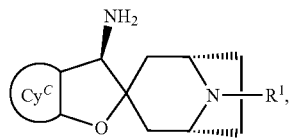

or a pharmaceutically acceptable salt thereof, wherein each of $Cy^C$ and $R^1$ are as defined in embodiments and classes and subclasses herein.

In some embodiments, the present disclosure provides a compound of one of formulas:

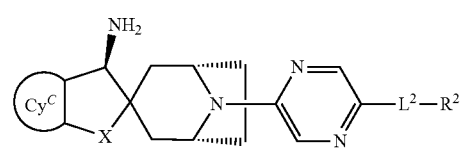

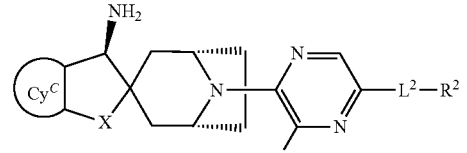

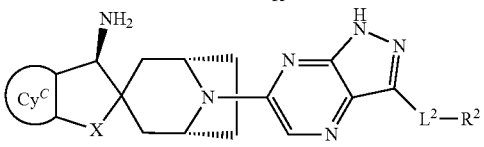

or a pharmaceutically acceptable salt thereof, wherein each of $Cy^C$, X, $L^2$ and $R^2$ are as defined in embodiments and classes and subclasses herein.

In some embodiments, a compound disclosed herein is of one of formulas:

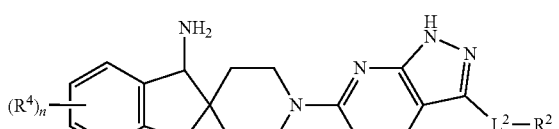

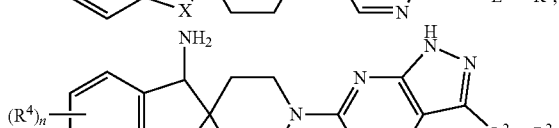

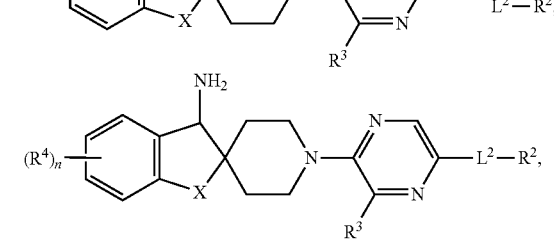

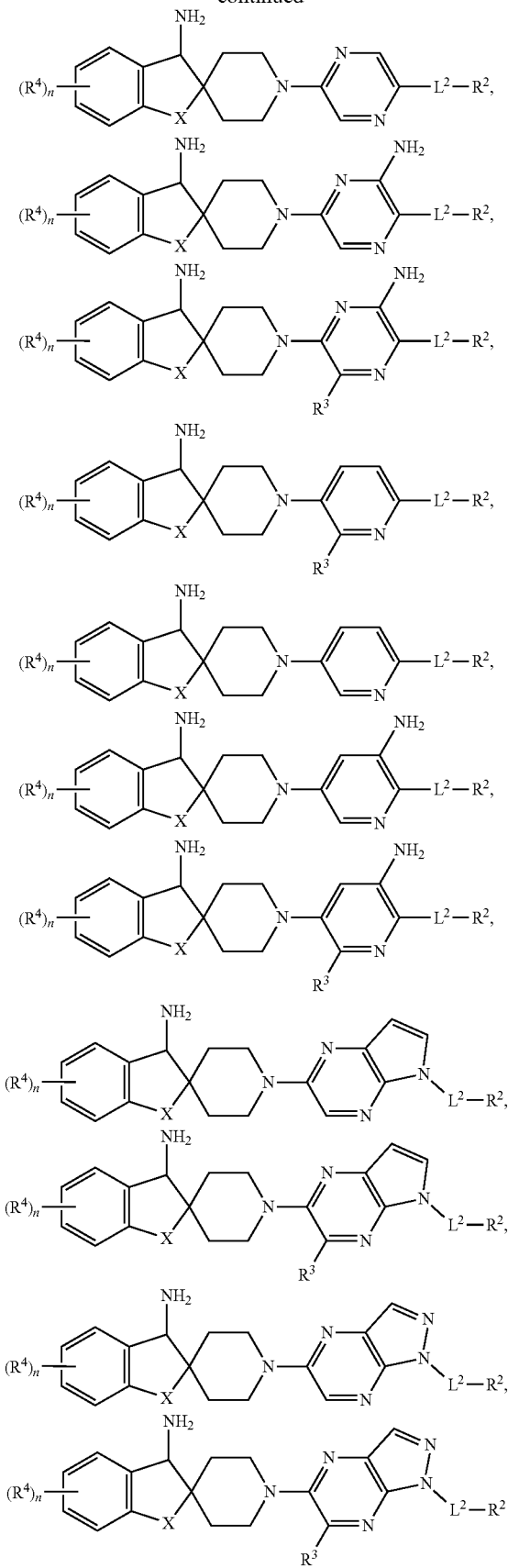
or a pharmaceutically acceptable salt thereof, wherein each of X, $L^2$, $R^2$, $R^3$, $R^4$, and n are as defined in embodiments and classes and subclasses herein.
In some embodiments, a compound disclosed herein is of one of formulas:
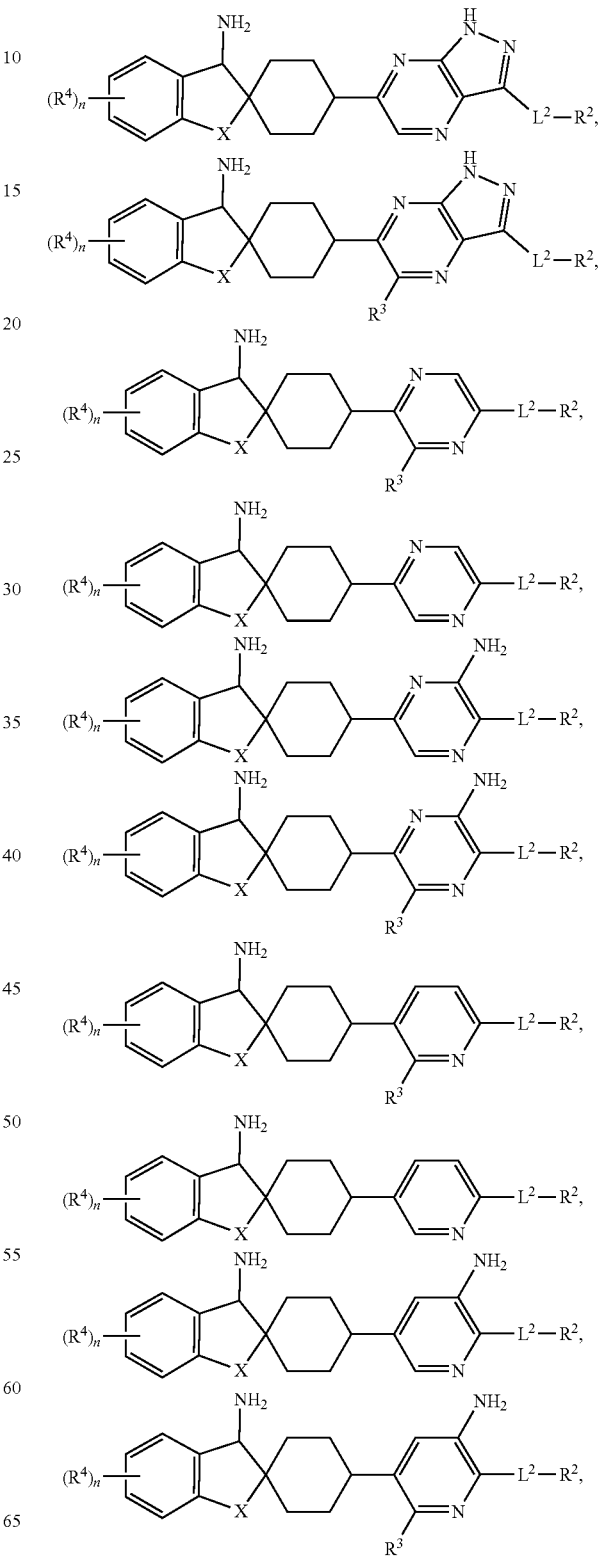

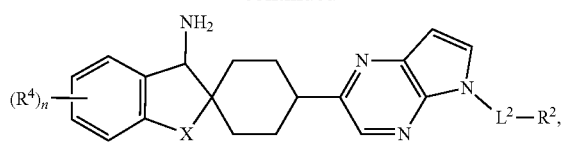

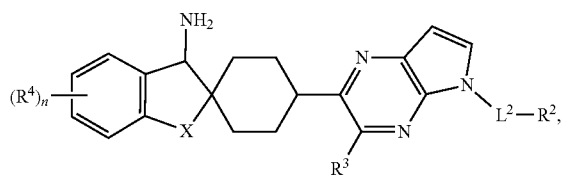

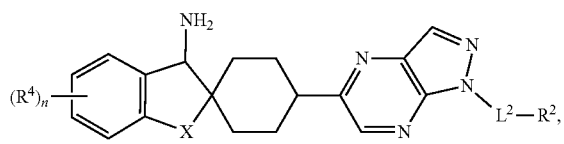

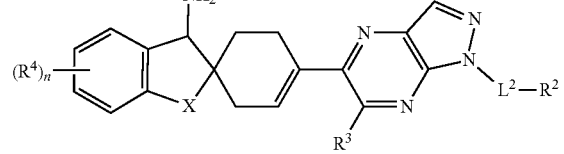

or a pharmaceutically acceptable salt thereof, wherein each of X, $L^2$, $R^2$, $R^3$, $R^4$, and n are as defined in embodiments and classes and subclasses herein.

In some embodiments, a compound disclosed herein is of one of formulas:

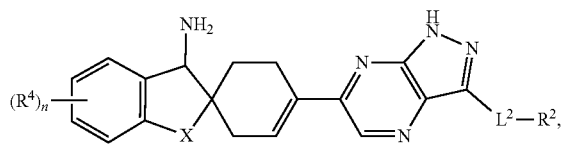

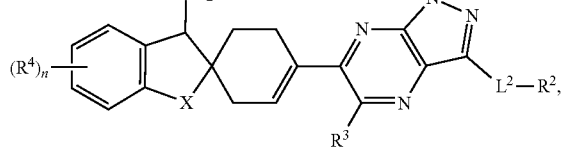

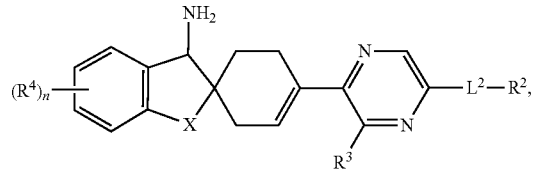

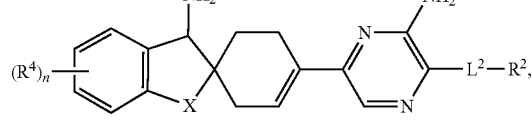

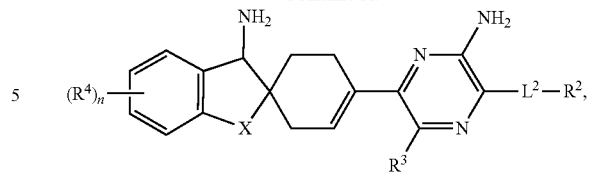

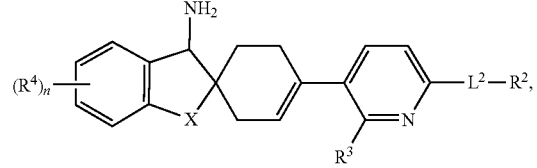

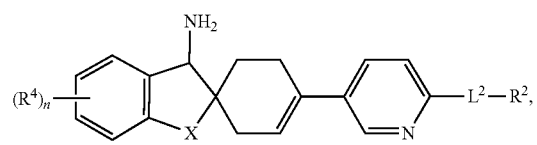

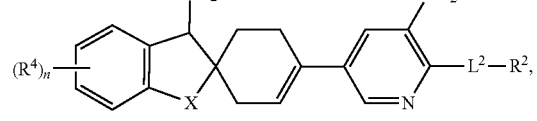

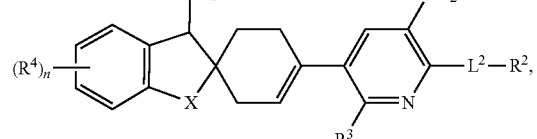

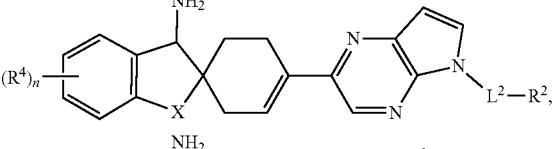

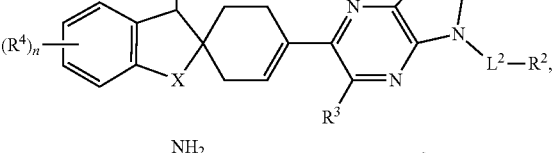

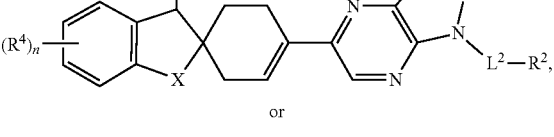

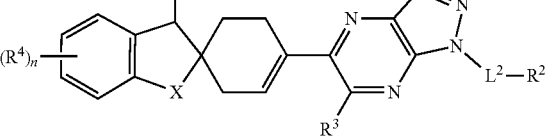

or

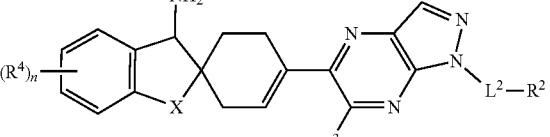

or a pharmaceutically acceptable salt thereof, wherein each of X, $L^2$, $R^2$, $R^3$, $R^4$, and n are as defined in embodiments and classes and subclasses herein.

In some embodiments, a compound disclosed herein is of one of formulas:

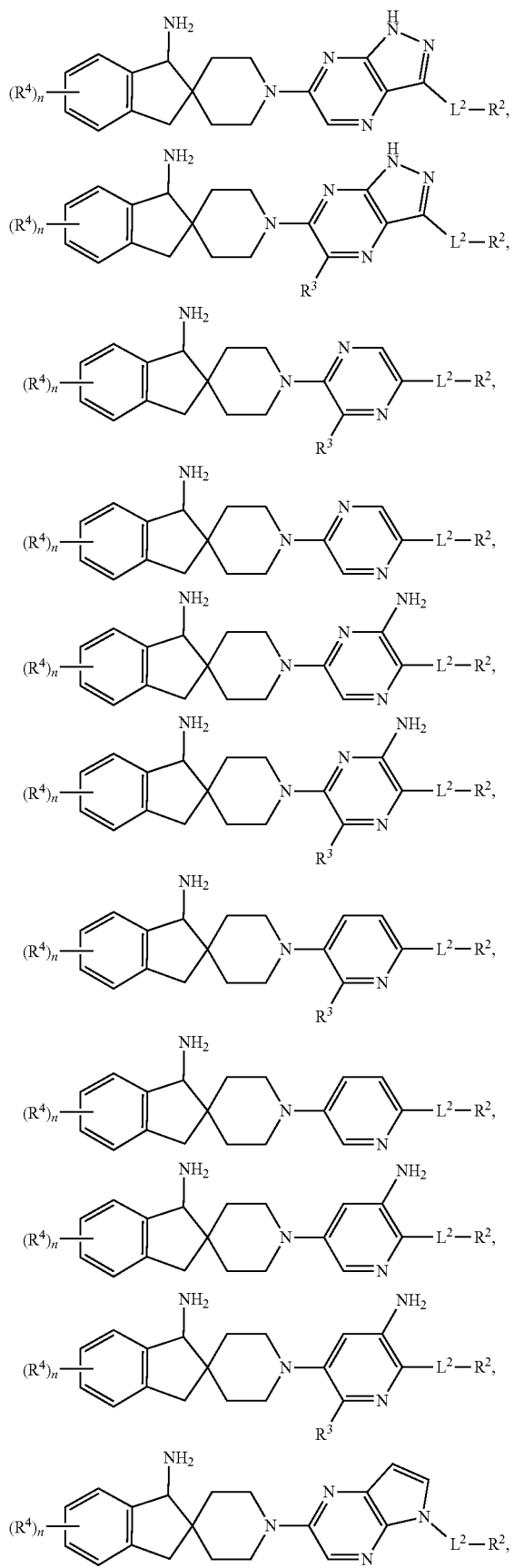
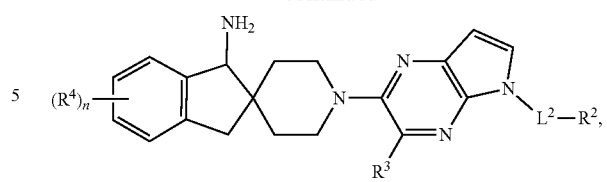
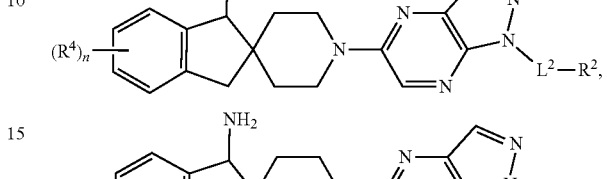
or a pharmaceutically acceptable salt thereof, wherein each of L², R², R³, R⁴, and n are as defined in embodiments and classes and subclasses herein.
In some embodiments, a compound disclosed herein is of one of formulas:
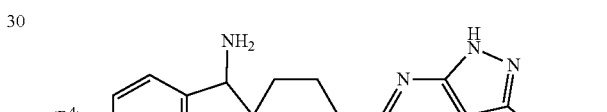
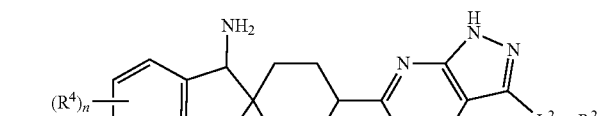

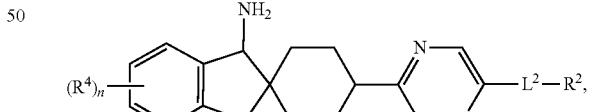
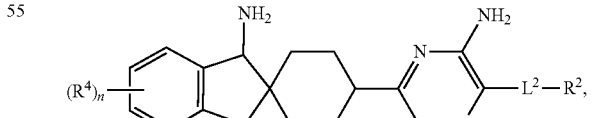
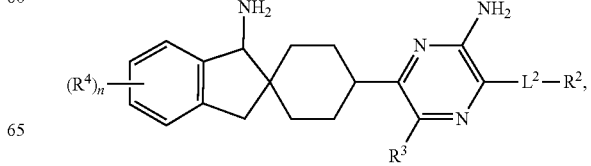

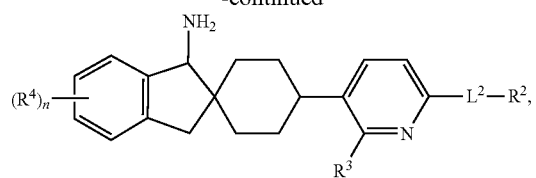
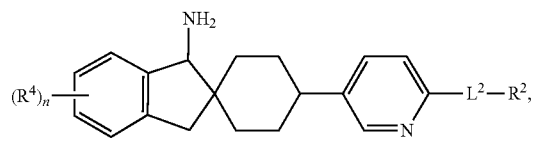
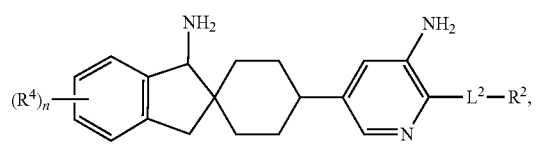
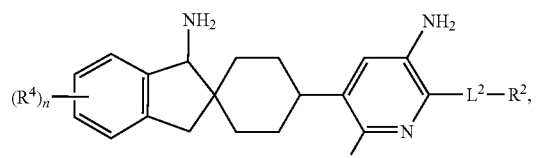
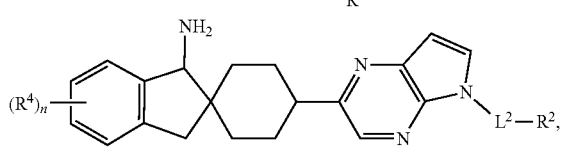
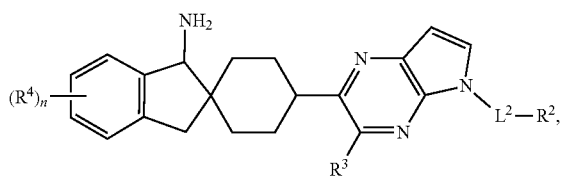
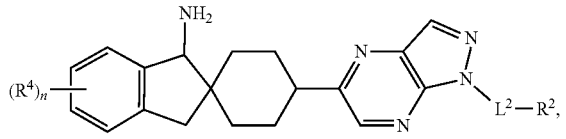
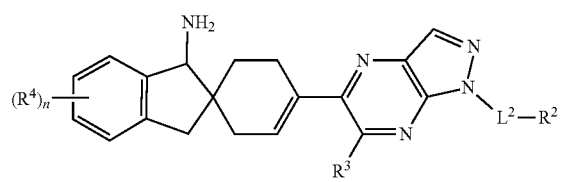
or a pharmaceutically acceptable salt thereof, wherein each of $L^2$, $R^2$, $R^3$, $R^4$, and n are as defined in embodiments and classes and subclasses herein.
In some embodiments, a compound disclosed herein is of one of formulas:
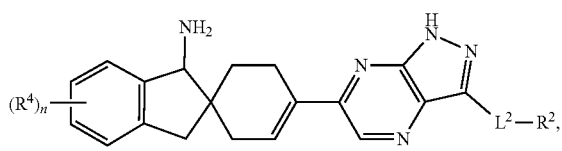
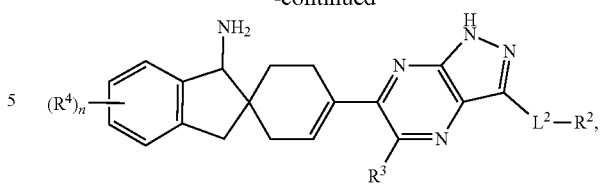
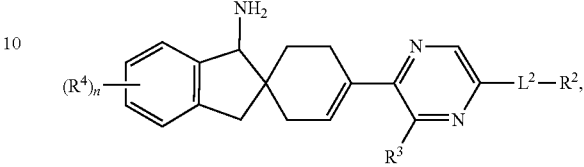
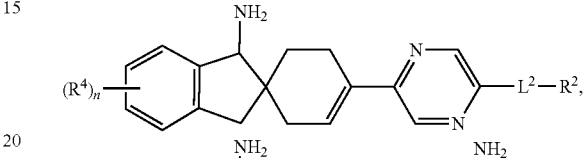
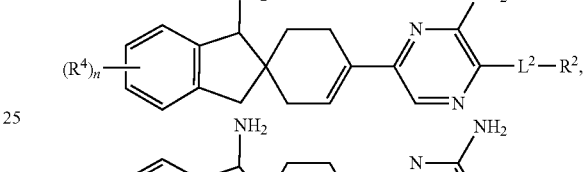
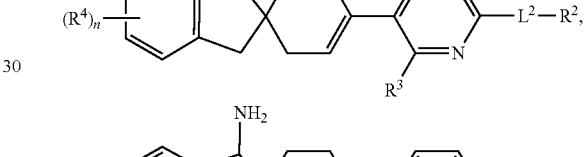
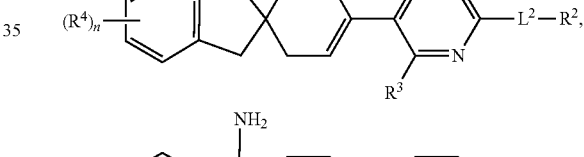
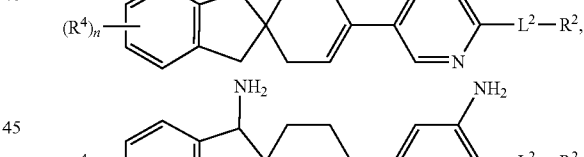
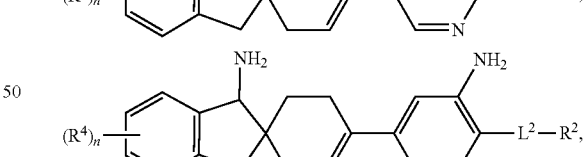
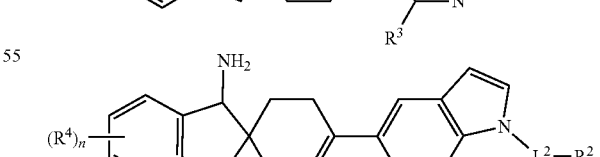
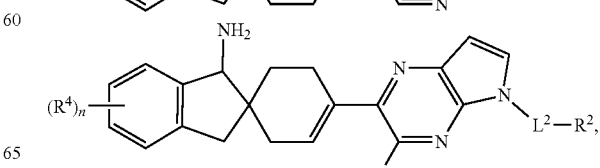

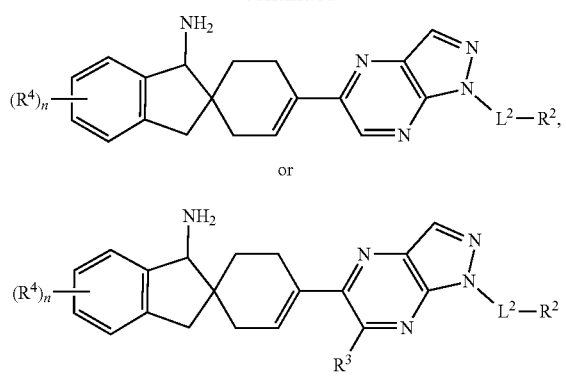

or a pharmaceutically acceptable salt thereof, wherein each of $L^2$, $R^2$, $R^3$, $R^4$, and n are as defined in embodiments and classes and subclasses herein.

In some embodiments, a compound disclosed herein is of one of formulas:

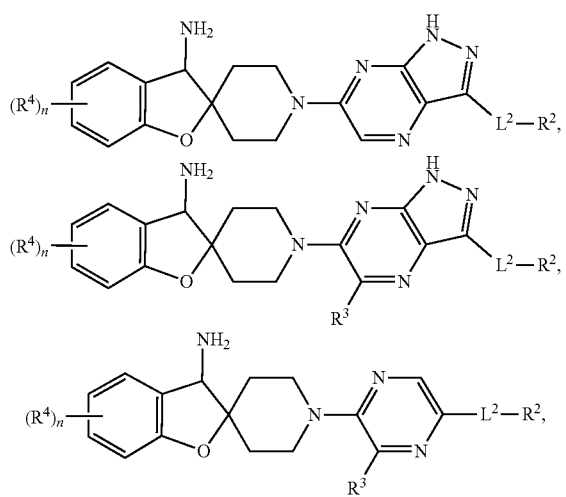

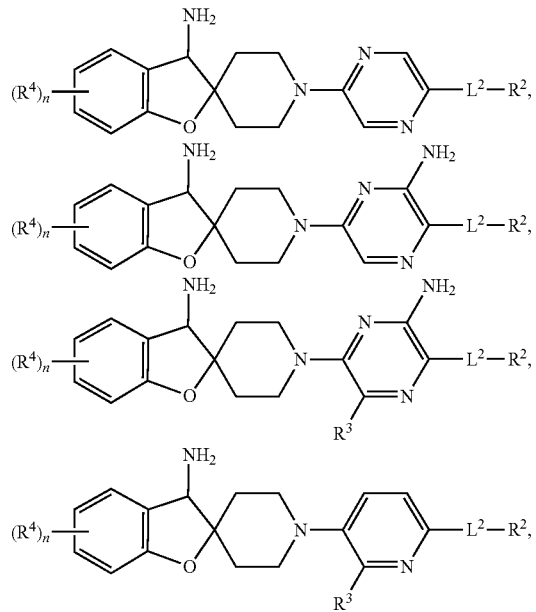

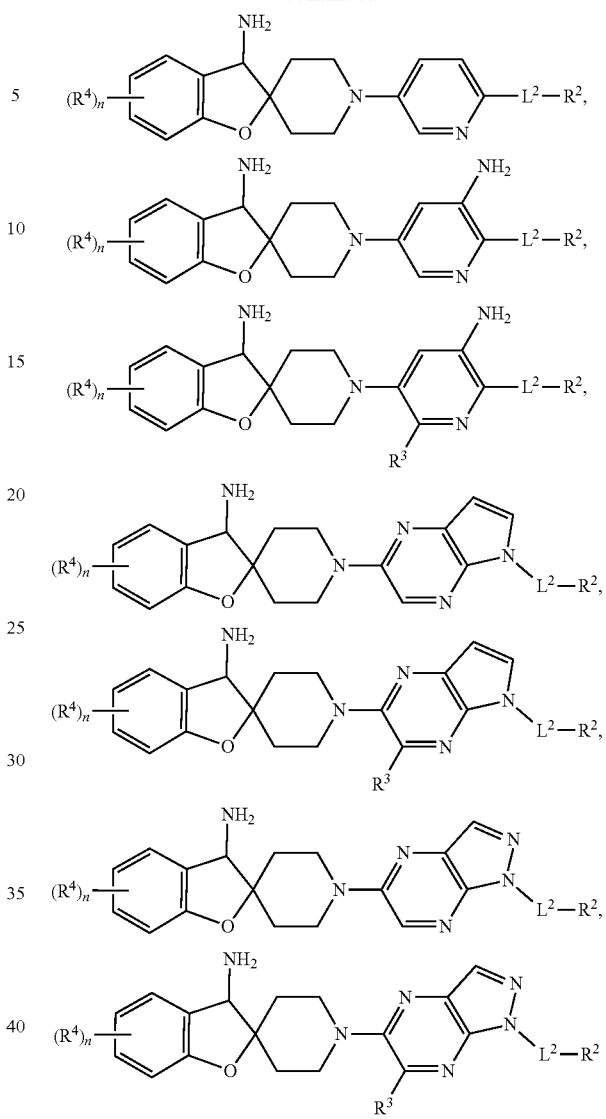

or a pharmaceutically acceptable salt thereof, wherein each of $L^2$, $R^2$, $R^3$, $R^4$, and n are as defined in embodiments and classes and subclasses herein.

In some embodiments, a compound disclosed herein is of one of formulas:

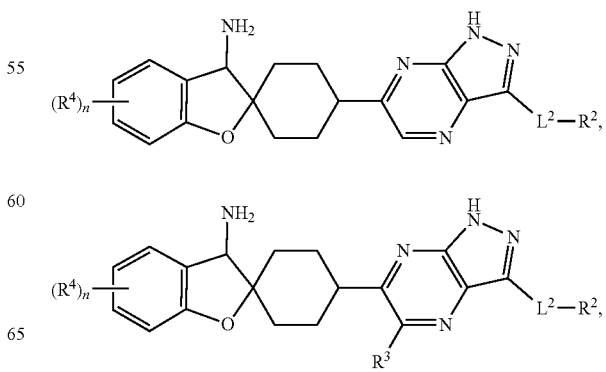

-continued
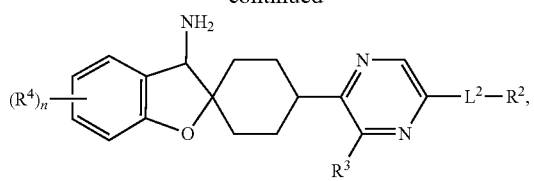
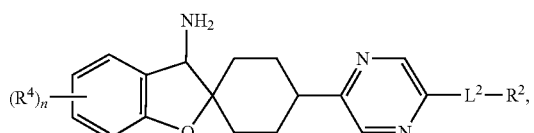
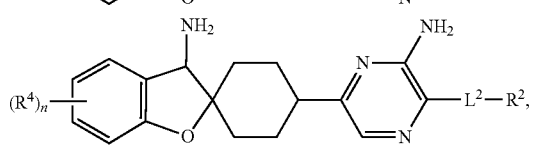
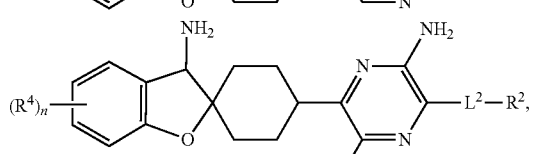
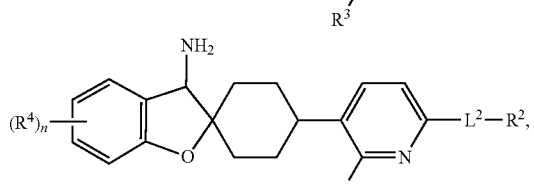
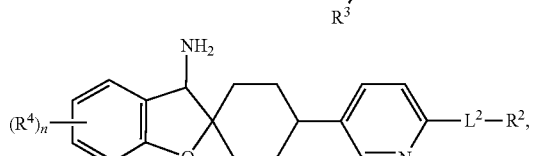
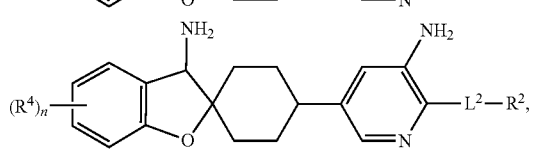
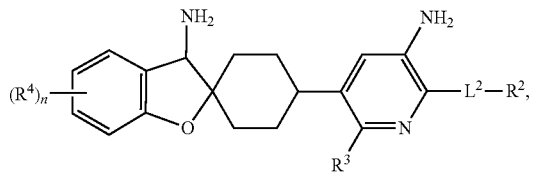
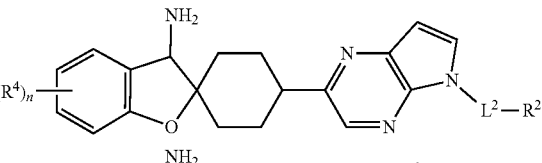
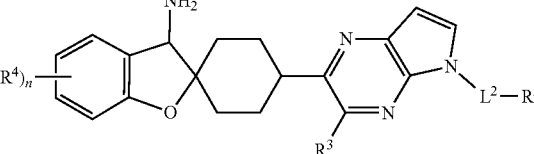
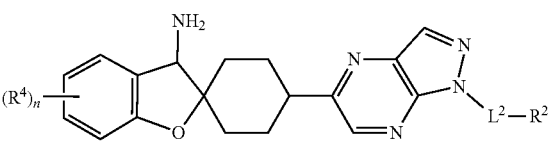
-continued
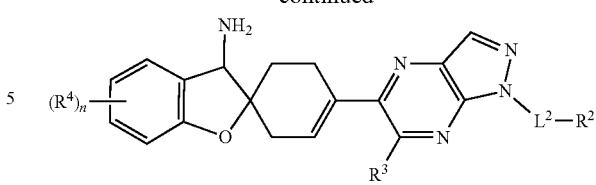
or a pharmaceutically acceptable salt thereof, wherein each of $L^2$, $R^2$, $R^3$, $R^4$, and n are as defined in embodiments and classes and subclasses herein.
In some embodiments, a compound disclosed herein is of one of formulas:
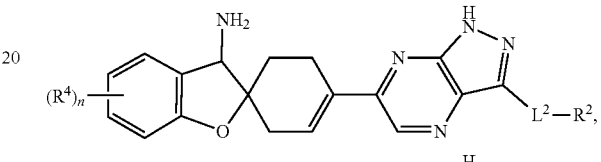
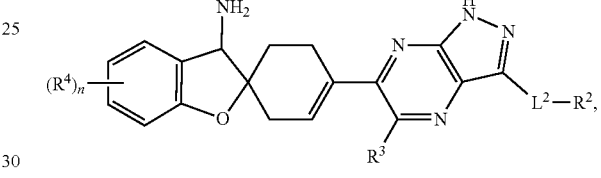
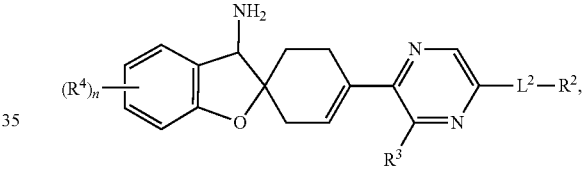
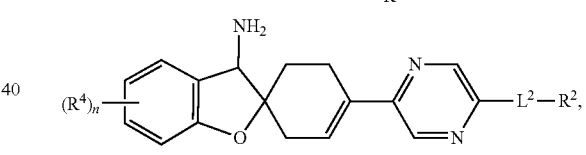
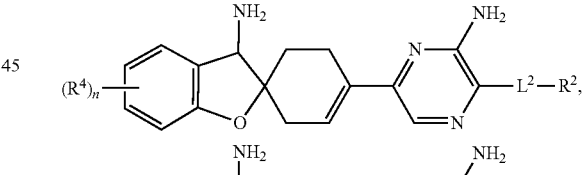
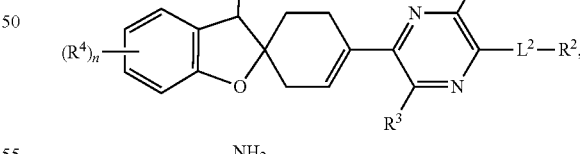
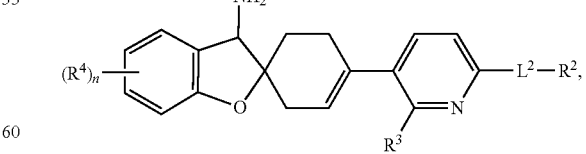
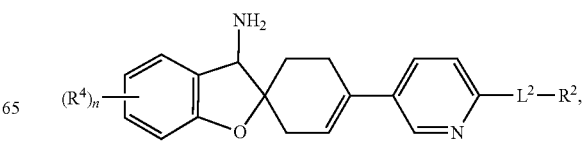

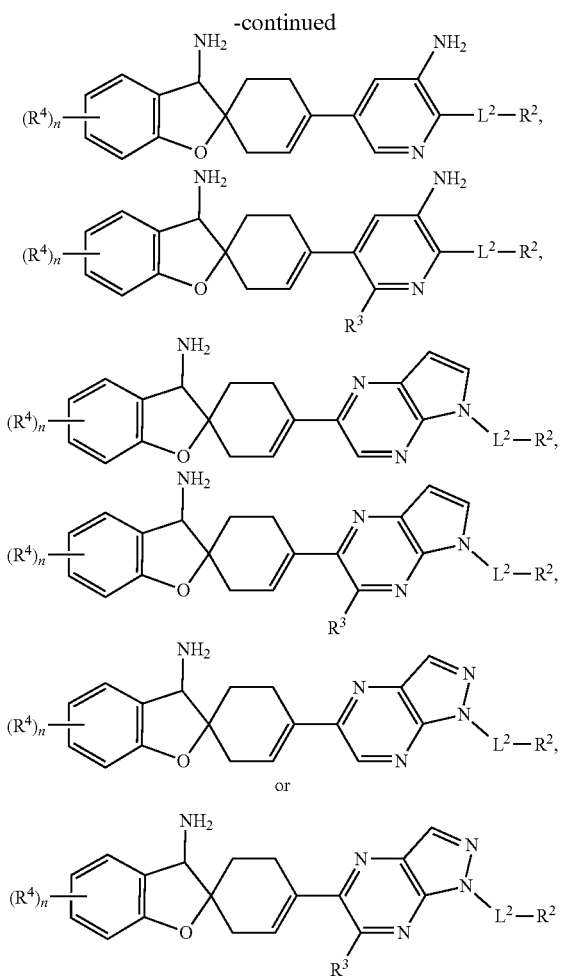

or a pharmaceutically acceptable salt thereof, wherein each of $L^2$, $R^2$, $R^3$, $R^4$, and n are as defined in embodiments and classes and subclasses herein.

In some embodiments, at least one instance of $R^3$ is —CH$_3$, —CHF$_2$, —CH$_2$OH, —CH(CH$_3$)OH, or cyclopropyl.

In some embodiments, X is —CH$_2$—, or a pharmaceutically acceptable salt thereof.

In some embodiments, X is —O—, or a pharmaceutically acceptable salt thereof.

In some embodiments, Cy$^C$ is benzo, or a pharmaceutically acceptable salt thereof.

In some embodiments, Cy$^C$ is 5-6 membered heteroarylo having 1-4 heteroatoms independently selected from nitrogen, oxygen, and sulfur, or a pharmaceutically acceptable salt thereof.

In some embodiments, Y is —N—, or a pharmaceutically acceptable salt thereof.

In some embodiments, Y is —CH$_2$—, or a pharmaceutically acceptable salt thereof.

In some embodiments, $L^1$ is a covalent bond, or a pharmaceutically acceptable salt thereof.

In some embodiments, $L^1$ is —C(O)—, or a pharmaceutically acceptable salt thereof.

In some embodiments, $L^2$ is a covalent bond, or a pharmaceutically acceptable salt thereof.

In some embodiments, $L^2$ is —S—, or a pharmaceutically acceptable salt thereof.

In some embodiments, $L^2$ is —O—, or a pharmaceutically acceptable salt thereof.

In some embodiments, $L^2$ is —C(O)—, or a pharmaceutically acceptable salt thereof.

In some embodiments, $L^2$ is C$_{1-3}$ aliphatic, or a pharmaceutically acceptable salt thereof.

In some embodiments, n is 1, 2, 3, or 4, or a pharmaceutically acceptable salt thereof.

In some embodiments, n is 0, or a pharmaceutically acceptable salt thereof.

In some embodiments, at least one instance of $R^4$ is fluoro, or a pharmaceutically acceptable salt thereof.

In some embodiments, $R^2$ is C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^2$ is substituted by q instances of $R^C$, or a pharmaceutically acceptable salt thereof.

In some embodiments, $R^2$ is C$_{1-6}$ aliphatic substituted with q instances of $R^C$, or a pharmaceutically acceptable salt thereof.

In some embodiments, $R^2$ is phenyl substituted with q instances of $R^C$, or a pharmaceutically acceptable salt thereof.

In some embodiments, $R^2$ is an 8-10 membered bicyclic heteroaryl ring having 1-4 heteroatoms independently selected from nitrogen, oxygen, and sulfur substituted with q instances of $R^C$, or a pharmaceutically acceptable salt thereof; a 5-6 membered monocyclic heteroaryl ring having 1-4 heteroatoms independently selected from nitrogen, oxygen, and sulfur In some embodiments, $R^2$ is a 3-7 membered saturated or partially unsaturated carbocyclic ring substituted with q instances of $R^C$, or a pharmaceutically acceptable salt thereof.

In some embodiments, $R^2$ is a 3-7 membered saturated or partially unsaturated monocyclic heterocyclic ring having 1-2 heteroatoms independently selected from nitrogen, oxygen, and sulfur, substituted with q instances of $R^C$, or a pharmaceutically acceptable salt thereof.

In some embodiments, $R^2$ is 7-12 membered saturated or partially unsaturated bicyclic heterocyclic ring having 1-4 heteroatoms independently selected from nitrogen, oxygen, and sulfur, substituted with q instances of $R^C$, or a pharmaceutically acceptable salt thereof.

In some embodiments, $R^2$ is:

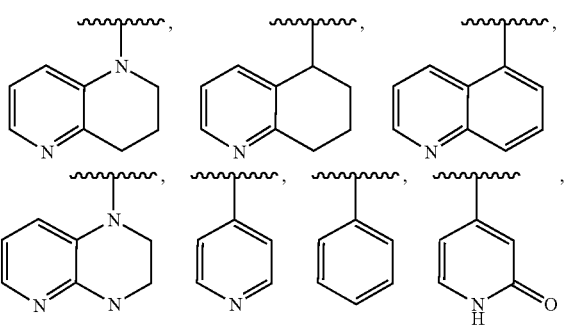

-continued

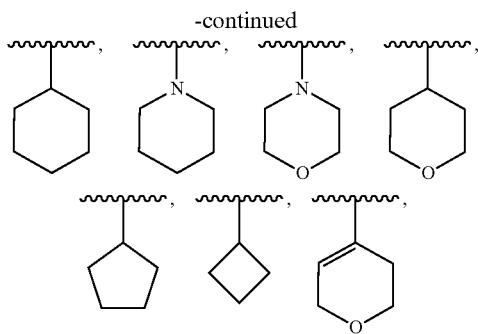

isopropyl, ethyl, or methyl, each of which is substituted with q instances of $R^C$, or a pharmaceutically acceptable salt thereof.

In some embodiments, $R^2$ is:

each of which is substituted with q instances of $R^C$, or a pharmaceutically acceptable salt thereof.

In some embodiments, $R^2$ is:

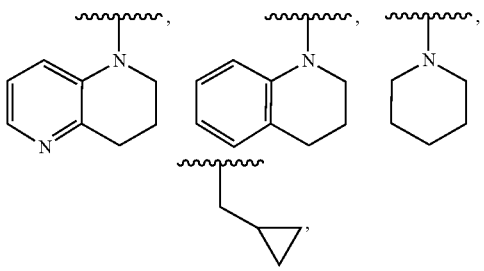

each of which is substituted with q instances of $R^C$, or a pharmaceutically acceptable salt thereof.

In some embodiments, $R^2$ is:

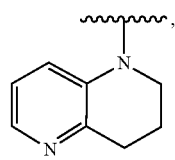 [SMILES: *N1CCCc2ncccc21]

or a pharmaceutically acceptable salt thereof.

In some embodiments, the present disclosure provides a compound of formula XI:

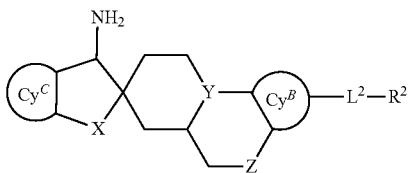

XI or a pharmaceutically acceptable salt thereof, wherein;

X is —CH$_2$—, —CH(R$^X$)—, —C(R$^X$)$_2$—, —C(O)—, —NH—, —N(R$^X$)—, or —O—;

Y is CH, C(R$^Y$), or N;

Z is —CH$_2$—, —CH(R$^Z$)—, —C(R$^Z$)$_2$—, —NH—, —N(R$^Z$)—, or —O—;

Cy$^B$ is phenyl, a monocyclic 5-6 membered heteroaryl having 1-4 heteroatoms independently selected from nitrogen, oxygen, and sulfur; or a bicyclic 8-10 membered heteroaryl having 1-5 heteroatoms independently selected from nitrogen, oxygen, and sulfur; wherein Cy$^B$ is substituted by m instances of R$^3$;

Cy$^C$ is benzo; 5-6 membered heteroarylo having 1-4 heteroatoms independently selected from nitrogen, oxygen, and sulfur; 3-7 membered saturated or partially unsaturated cycloaliphatic-fused; or 3-7 membered saturated of partially unsaturated heterocyclo having 1-2 heteroatoms independently selected from nitrogen, oxygen, and sulfur; wherein when Cy$^C$ is heterocyclo or heteroarylo, said heteroatoms may occur at any position within Cy$^C$; and wherein in each case Cy$^C$ is substituted by n instances of R$^4$;

L$^2$ is a covalent bond, or a CM bivalent saturated or unsaturated, straight or branched hydrocarbon chain wherein one or two methylene units of the chain are optionally and independently replaced by —CH(R$^L$)—, —C(R$^L$)$_2$—, C$_{3-5}$ cycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O), or —S(O)$_2$—;

R$^2$ is hydrogen, R$^A$, or R$^B$, and when R$^2$ is R$^B$, R$^2$ is substituted by q instances of R$^C$;

each instance of R$^3$, R$^4$, R$^X$, R$^Y$, R$^Z$, and R$^L$ is independently R$^A$ or R$^B$, and is substituted by r instances of R$^C$;

each instance of R$^5$ is independently R$^A$ or R$^B$, and is substituted by r instances of R$^C$; or two instances of R$^5$ are taken together with their intervening atoms to form a 3-6 membered carbocyclic fused ring or a 3-6 membered heterocyclic fused ring having 1-2 heteroatoms independently selected from nitrogen, oxygen, and sulfur;

each instance of R$^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from C$_{ue}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each of b and c is independently 0 or 1; and each of a, m, n, q, and r is independently 0, 1, 2, 3, or 4

In some embodiments, the present disclosure provides a compound of formula XI of one of formulas:

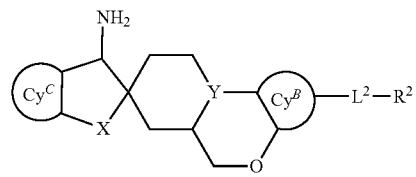

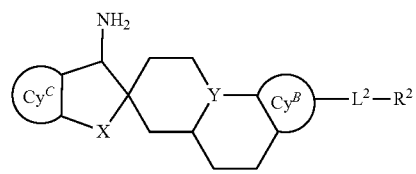

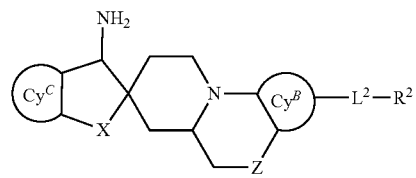

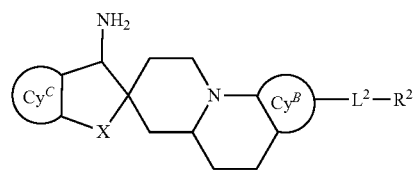

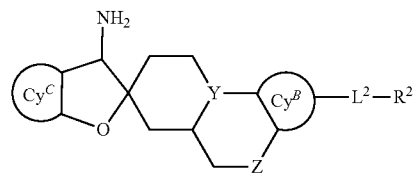

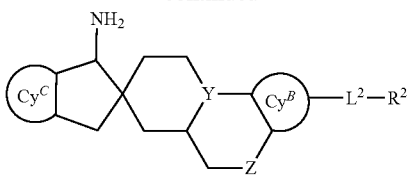

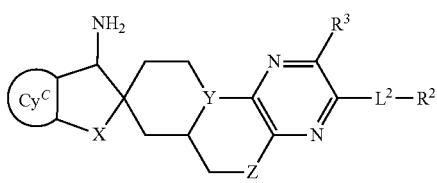

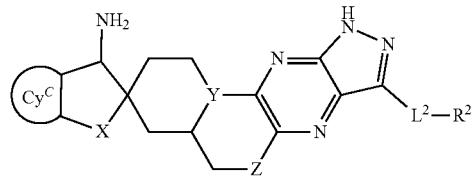

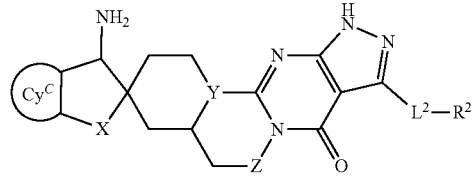

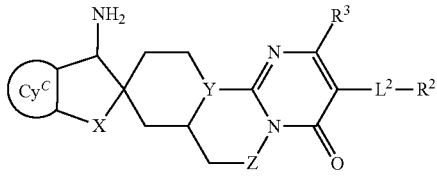

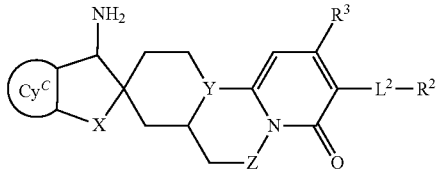

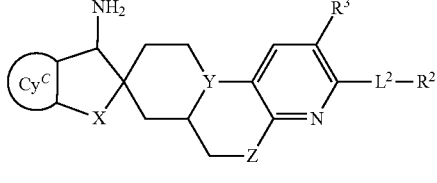

or a pharmaceutically acceptable salt thereof, wherein each of $Cy^C$, $Cy^B$, X, Y, Z, $R^3$, $L^2$, and $R^2$ are as defined in embodiments and classes and subclasses herein.

In some embodiments, the present disclosure provides a compound of formula XI of one of formulas:

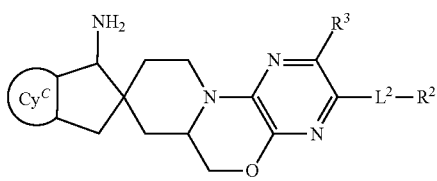

43

-continued

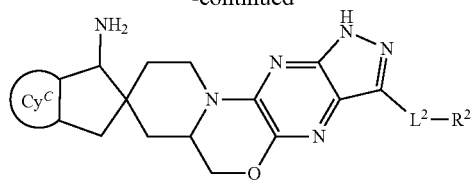

5

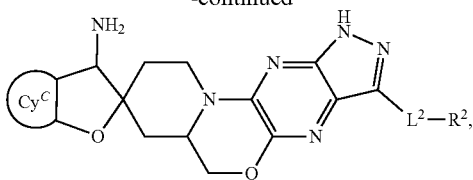

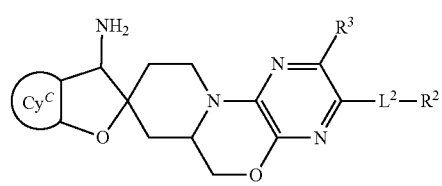

or a pharmaceutically acceptable salt thereof, wherein each of $Cy^C$, $R^3$, $L^2$, and $R^2$ are as defined in embodiments and classes and subclasses herein.

Examples of compounds of the present disclosure include those listed in the Tables and exemplification herein, or a pharmaceutically acceptable salt, stereoisomer, or mixture of stereoisomers thereof. In some embodiments, the present disclosure comprises a compound selected from those depicted in Table 1, or a pharmaceutically acceptable salt, stereoisomer, or mixture of stereoisomers thereof:

TABLE 1

Representative Compounds of the disclosure.

| Example | Structure |
|---|---|
| 1 | $C_{28}H_{30}N_8O$ |
| 2 | $C_{28}H_{30}N_8O$ |

TABLE 1-continued
Representative Compounds of the disclosure.
| Example | Structure |
|---|---|
| 3 | 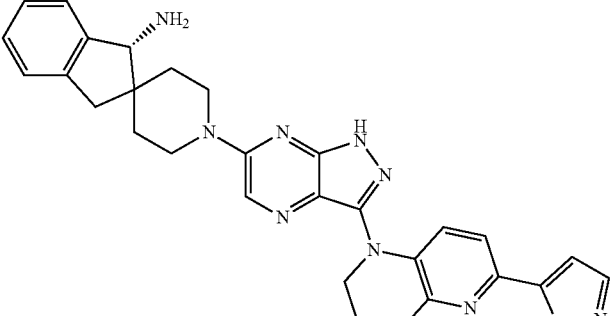<br>C$_{29}$H$_{30}$N$_{10}$ |
| 4 | 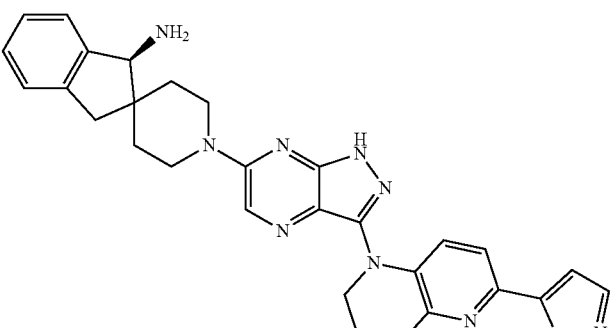<br>C$_{29}$H$_{30}$N$_{10}$ |
| 5 | 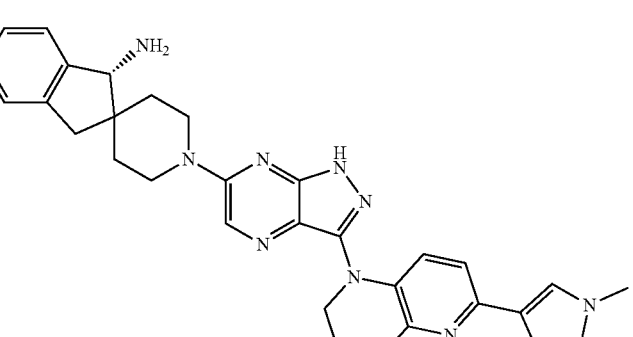<br>C$_{30}$H$_{32}$N$_{10}$ |
| 6 | 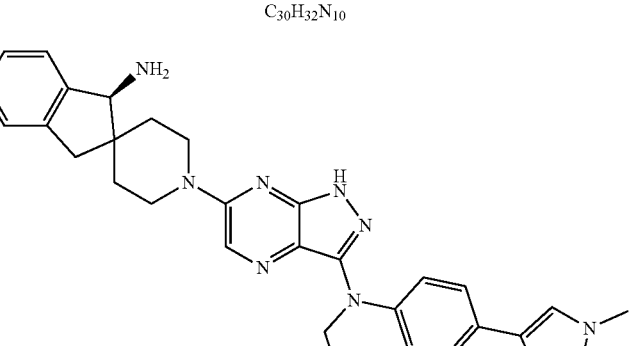<br>C$_{30}$H$_{32}$N$_{10}$ |
| 7 | C$_{27}$H$_{28}$N$_{8}$O |
| 8 | C$_{24}$H$_{29}$N$_{7}$O |

TABLE 1-continued
Representative Compounds of the disclosure.
| Example | Structure |
|---|---|
| 9 | $C_{25}H_{31}N_7$ |
| 10 | $C_{25}H_{31}N_7O$ |
| 11 | $C_{22}H_{26}N_4OS$ |
| 12 | 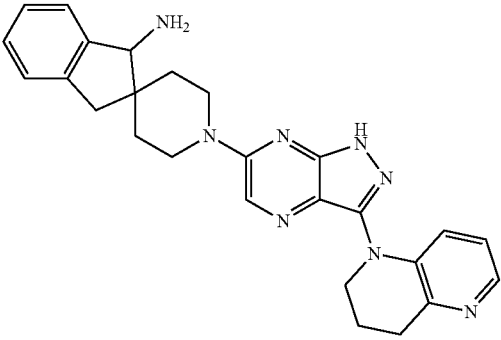<br>$C_{26}H_{28}N_8$ |
| 13 | 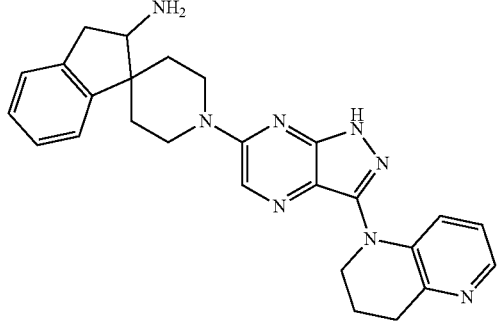<br>$C_{26}H_{28}N_8$ |
| 14 | 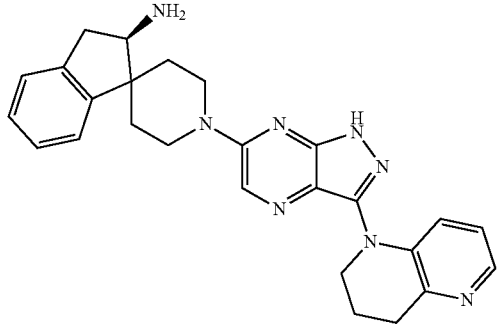<br>$C_{26}H_{28}N_8$ |
| 15 | 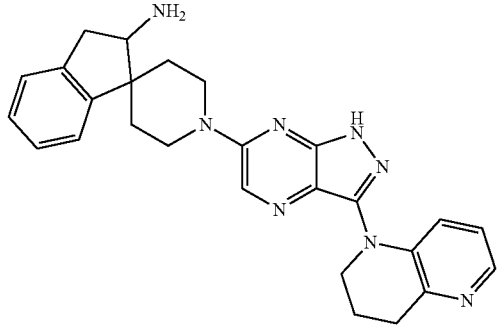<br>$C_{26}H_{28}N_8$ |

TABLE 1-continued
Representative Compounds of the disclosure.
| Example | Structure |
|---|---|
| 16 | 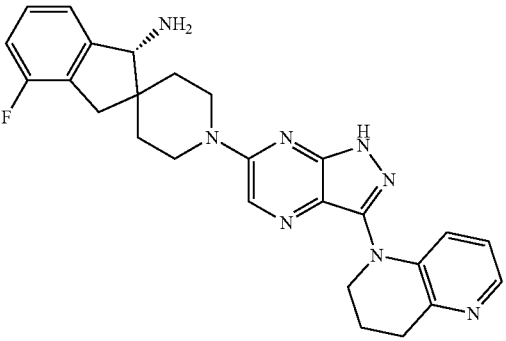$C_{26}H_{27}FN_8$ |
| 17 | 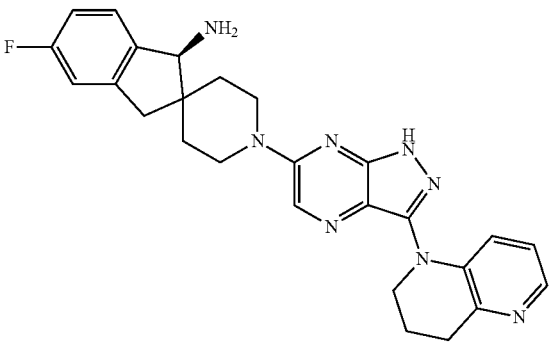$C_{26}H_{27}FN_8$ |
| 18 | 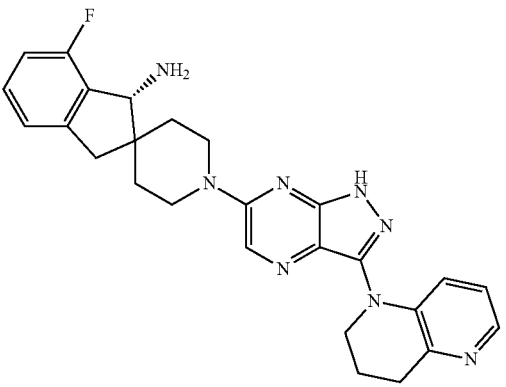$C_{26}H_{27}FN_8$ |
| 19 | 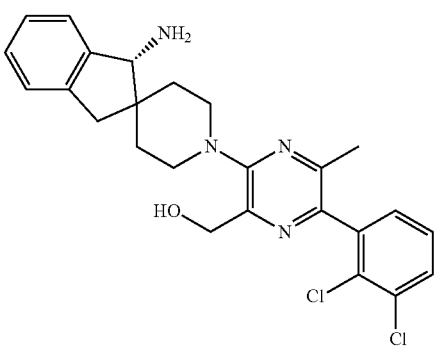$C_{25}H_{26}Cl_2N_4O$ |

TABLE 1-continued
Representative Compounds of the disclosure.
| Example | Structure |
|---|---|
| 20 | 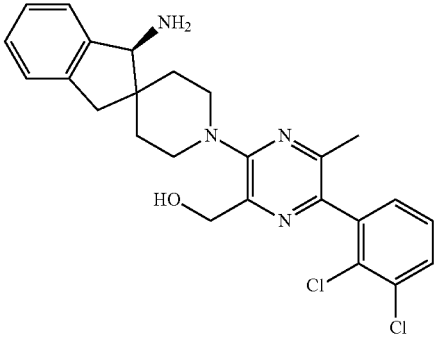<br>$C_{25}H_{26}Cl_2N_4O$ |
| 21 | 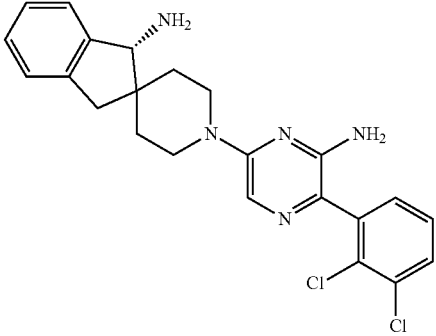<br>$C_{23}H_{23}Cl_2N_5$ |
| 22 | 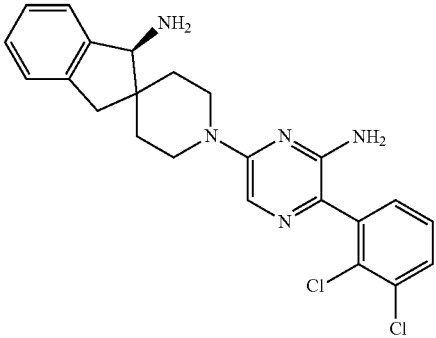<br>$C_{23}H_{23}Cl_2N_5$ |
| 23 | 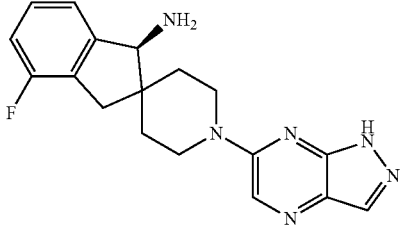<br>$C_{18}H_{19}FN_6$ |

TABLE 1-continued
Representative Compounds of the disclosure.
| Example | Structure |
|---|---|
| 24 | 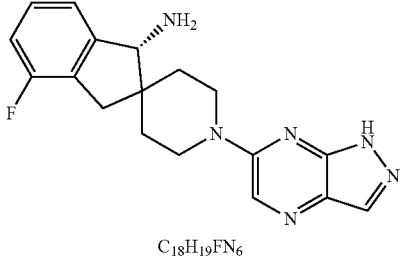 [SMILES: N[C@H]1c2cccc(F)c2CC12CCN(c1cnc3cn[nH]c3n1)CC2 ; "C18H19FN6"]<br>C$_{18}$H$_{19}$FN$_6$ |
| 25 | 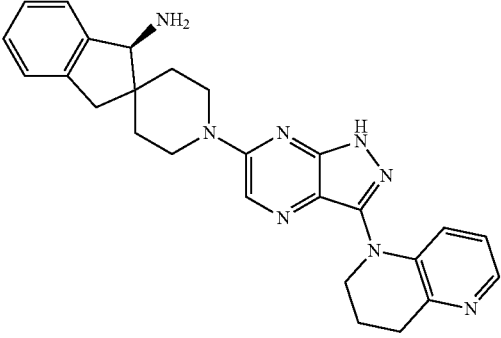<br>C$_{26}$H$_{28}$N$_8$ |
| 26 | 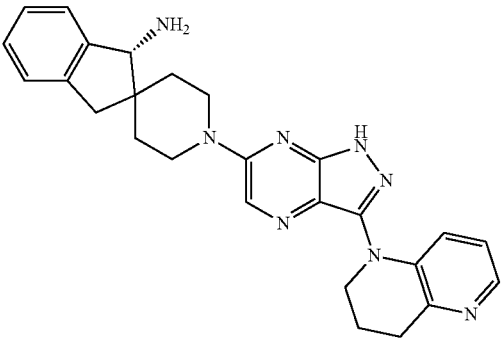<br>C$_{26}$H$_{28}$N$_8$ |
| 27 | 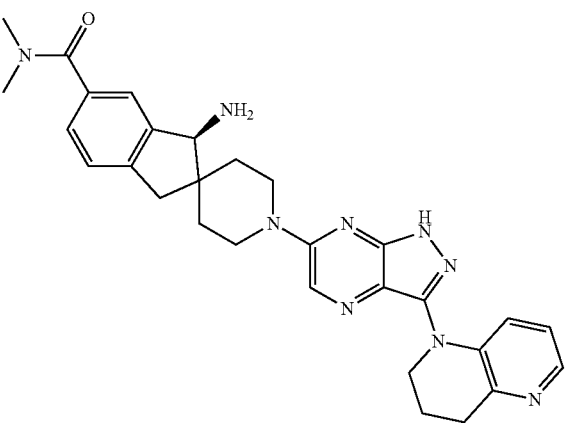<br>C$_{29}$H$_{33}$N$_9$O |

TABLE 1-continued
Representative Compounds of the disclosure.
| Example | Structure |
|---|---|
| 28 | 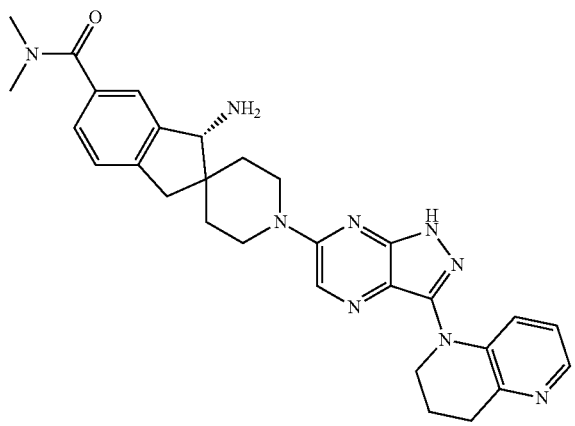
$C_{29}H_{33}N_9O$ |
| 29 | 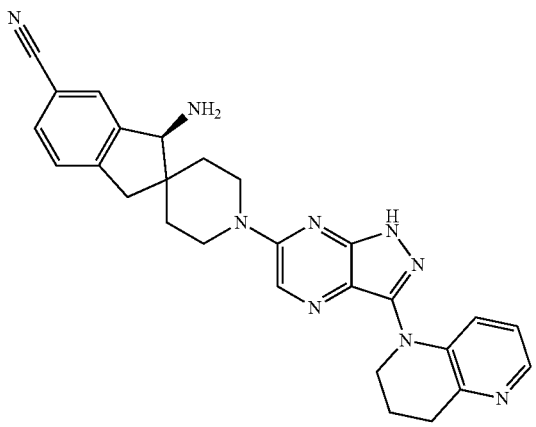
$C_{27}H_{27}N_9$ |
| 30 | 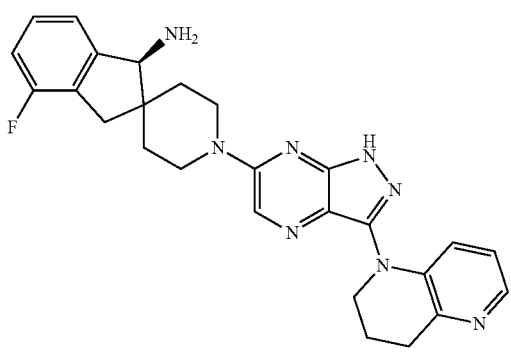
$C_{26}H_{27}FN_8$ |

TABLE 1-continued
Representative Compounds of the disclosure.
| Example | Structure |
|---|---|
| 31 | 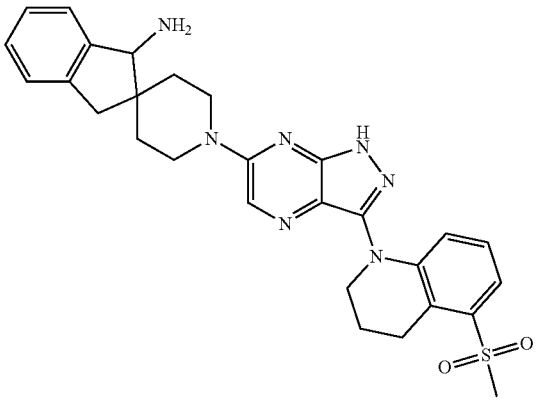<br>$C_{28}H_{31}N_7O_2S$ |
| 32 | 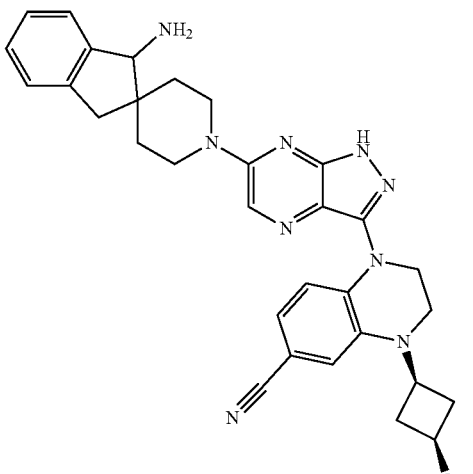<br>$C_{32}H_{35}N_9O$ |
| 33 | 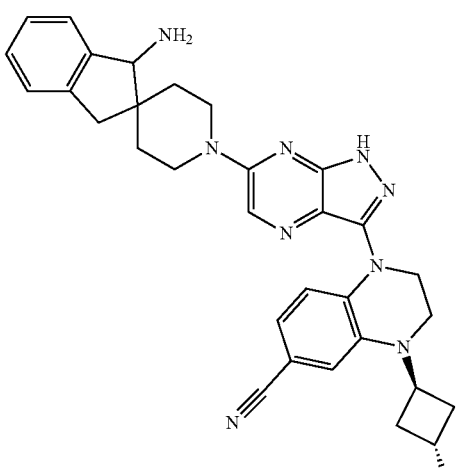<br>$C_{32}H_{35}N_9O$ |

TABLE 1-continued
Representative Compounds of the disclosure.
| Example | Structure |
|---|---|
| 34 | 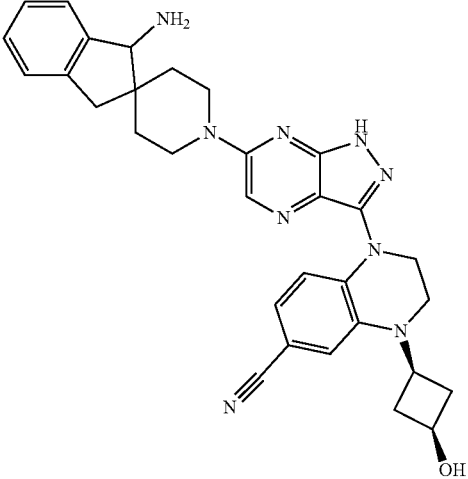<br>$C_{31}H_{33}N_9O$ |
| 35 | 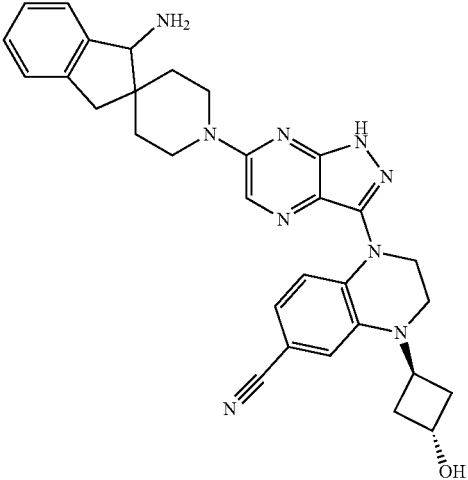<br>$C_{31}H_{33}N_9O$ |
| 36 | 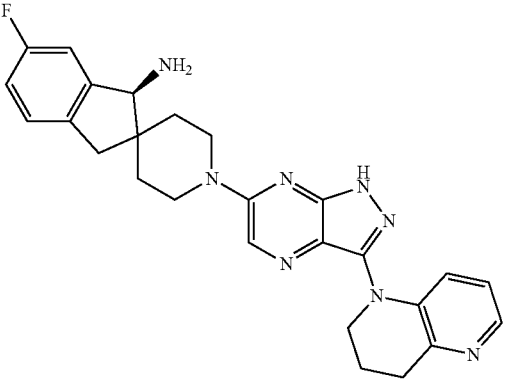<br>$C_{26}H_{27}FN_8$ |

US 10,934,302 B1
TABLE 1-continued
Representative Compounds of the disclosure.
| Example | Structure |
|---|---|
| 37 | 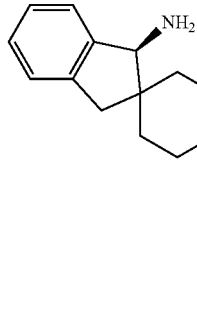<br>C29H29N9O |
| 38 | <br>C28H31N7O2S |
| 39 | <br>C31H30N10 |

TABLE 1-continued
Representative Compounds of the disclosure.
| Example | Structure |
|---|---|
| 40 | 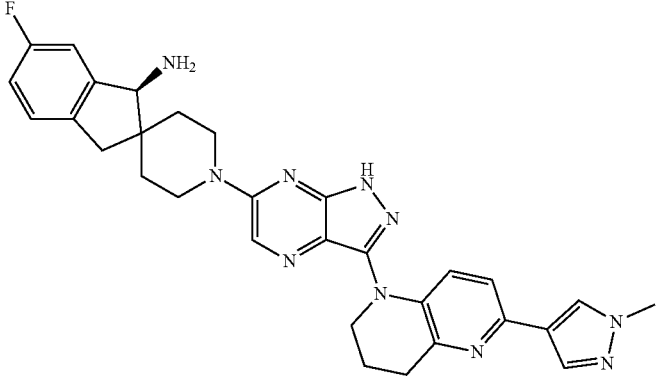<br>$C_{30}H_{31}FN_{10}$ |
| 41 | 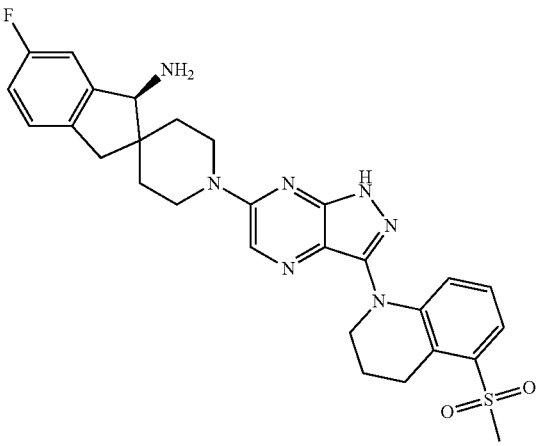<br>$C_{28}H_{30}FN_7O_2S$ |
| 42 | 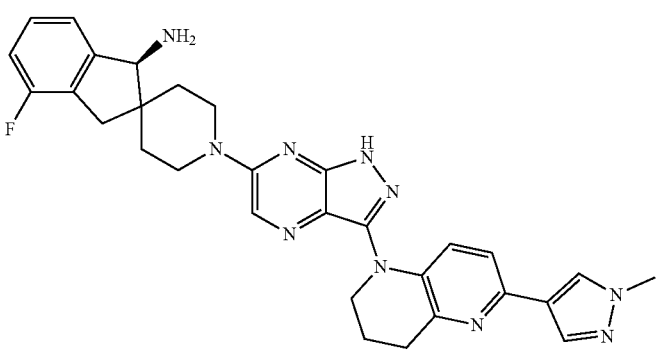<br>$C_{30}H_{31}FN_{10}$ |

TABLE 1-continued
Representative Compounds of the disclosure.
| Example | Structure |
|---------|-----------|
| 43 | 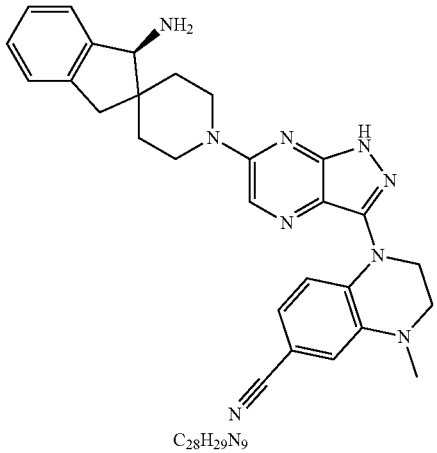 [SMILES: CN1CCN(c2n[nH]c3nc(N4CCC5(CC4)Cc4ccccc4[C@H]5N)cnc23)c2ccc(C#N)cc21 ; "C28H29N9"]<br>C$_{28}$H$_{29}$N$_9$ |
| 44 | 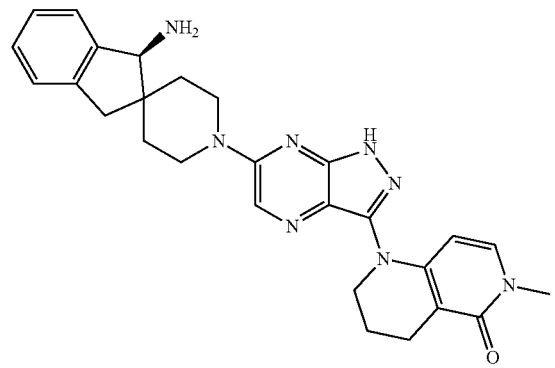<br>C$_{27}$H$_{30}$N$_8$O |
| 45 | 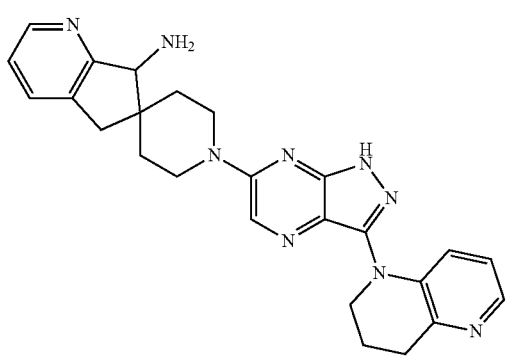<br>C$_{25}$H$_{27}$N$_9$ |

TABLE 1-continued
Representative Compounds of the disclosure.
| Example | Structure |
|---|---|
| 46 | 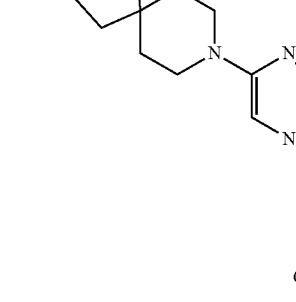<br>C$_{29}$H$_{31}$N$_{11}$ |
| 47 | 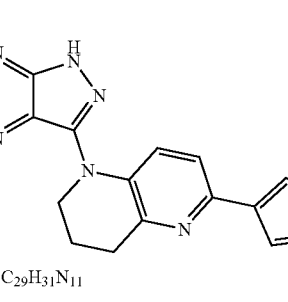<br>C$_{26}$H$_{27}$FN$_8$ |
| 48 | <br>C$_{30}$H$_{31}$FN$_{10}$ |

TABLE 1-continued
Representative Compounds of the disclosure.
| Example | Structure |
|---|---|
| 49 | 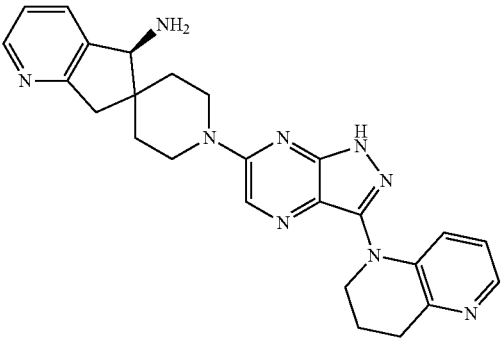<br>C<sub>25</sub>H<sub>27</sub>N<sub>9</sub> |
| 50 | 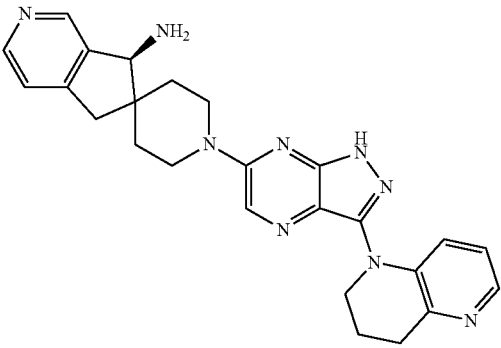<br>C<sub>25</sub>H<sub>27</sub>N<sub>9</sub> |
| 51 | 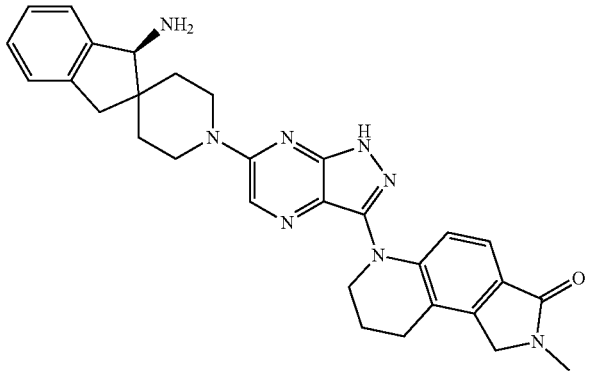<br>C<sub>30</sub>H<sub>32</sub>N<sub>8</sub>O |
| 52 | 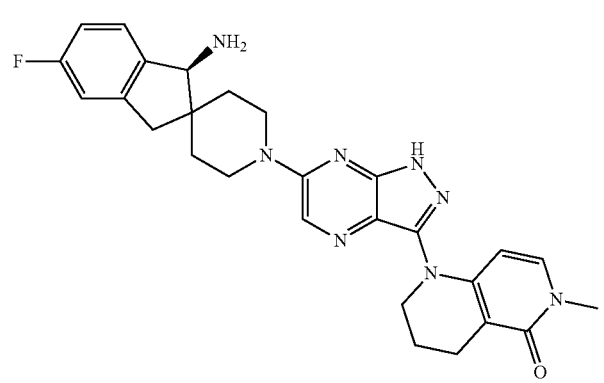<br>C<sub>27</sub>H<sub>29</sub>FN<sub>8</sub>O |

TABLE 1-continued
Representative Compounds of the disclosure.
| Example | Structure |
|---|---|
| 53 | 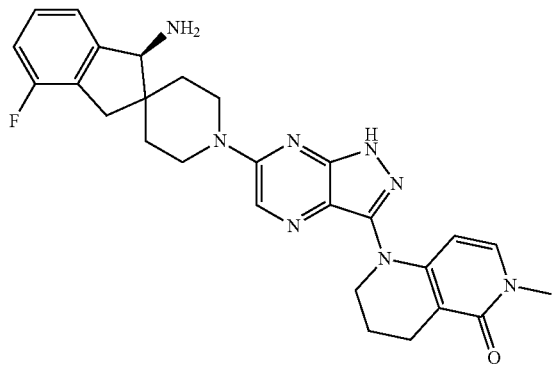… C27H29FN8O |
| 54 | 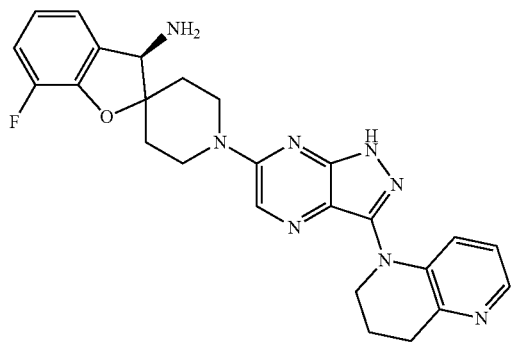… C25H25FN8O |
| 55 | 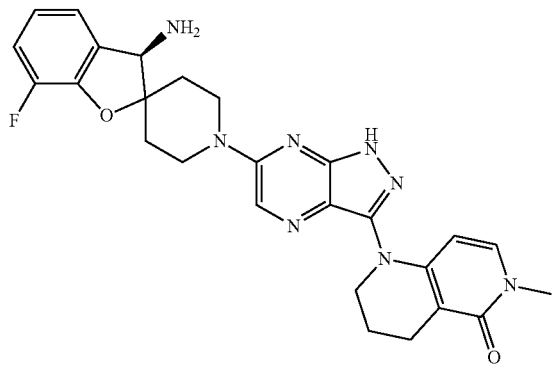… C26H27FN8O2 |

TABLE 1-continued
Representative Compounds of the disclosure.
| Example | Structure |
|---|---|
| 56 | 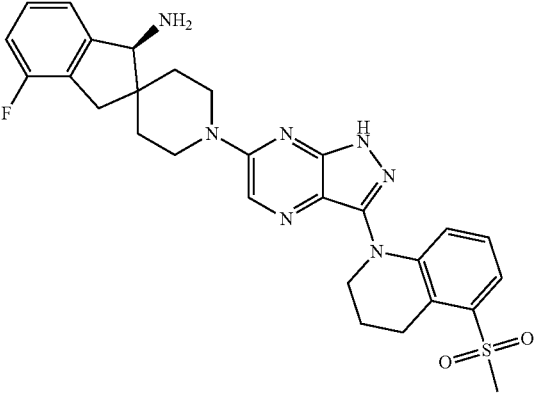<br>$C_{28}H_{30}FN_7O_2S$ |
| 57 | 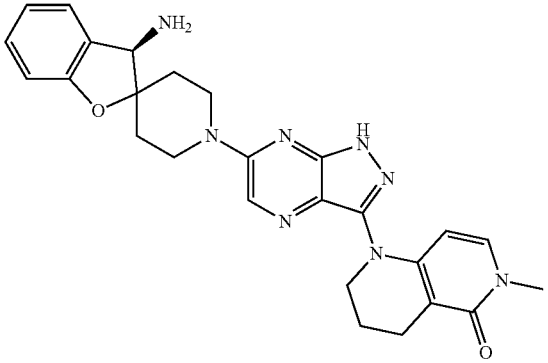<br>$C_{26}H_{28}N_8O_2$ |
| 58 | 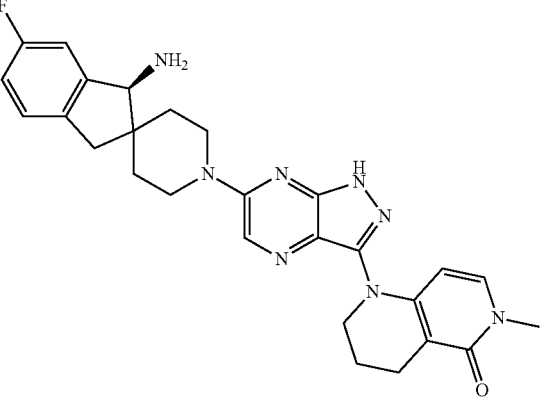<br>$C_{27}H_{29}FN_8O$ |

TABLE 1-continued
Representative Compounds of the disclosure.
| Example | Structure |
|---|---|
| 59 | 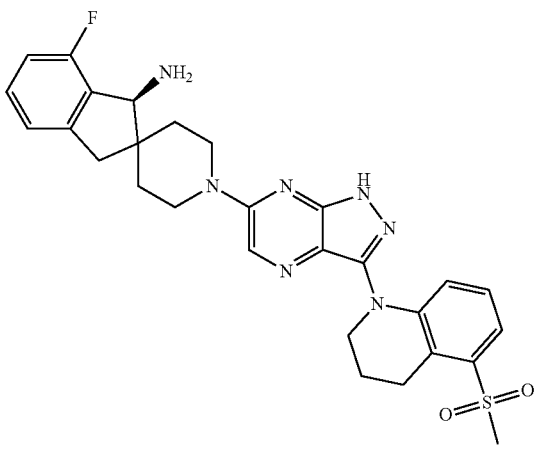
$C_{28}H_{30}FN_7O_2S$ |
| 60 | 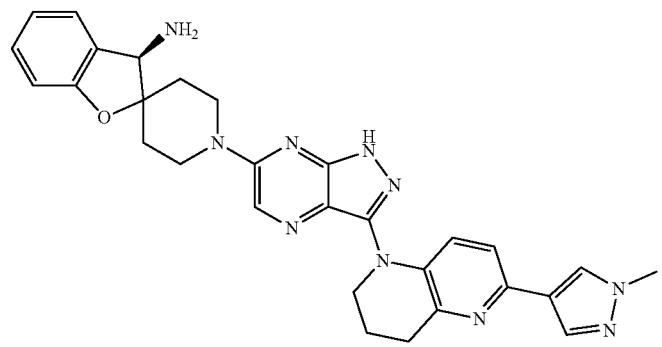
$C_{29}H_{30}N_{10}O$ |
| 61 | 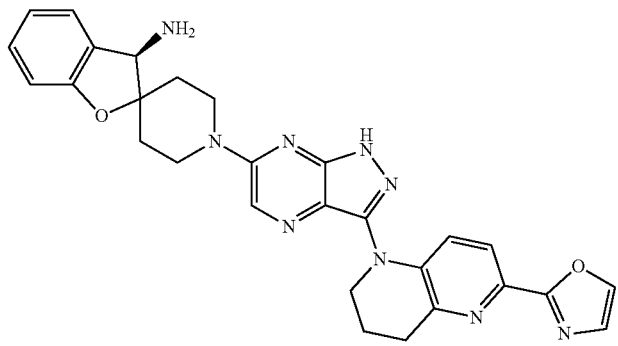
$C_{28}H_{27}N_9O_2$ |

TABLE 1-continued
Representative Compounds of the disclosure.
| Example | Structure |
|---------|-----------|
| 62 | 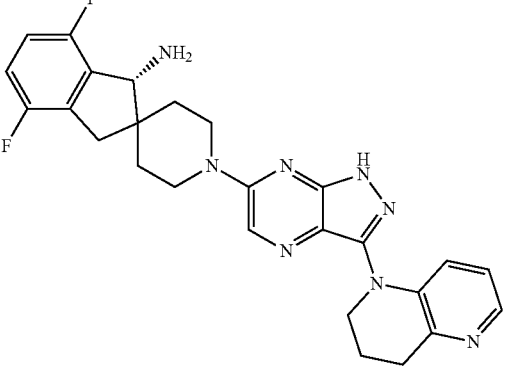<br>C₂₆H₂₆F₂N₈ |
| 63 | 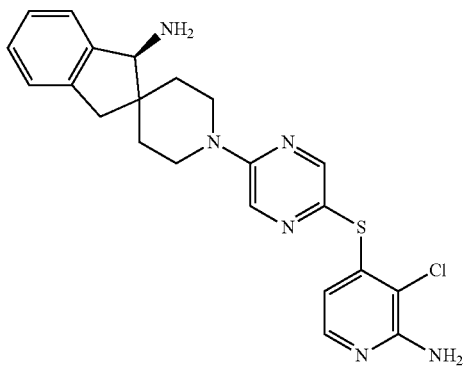<br>C₂₂H₂₃ClN₆S |
| 64 | 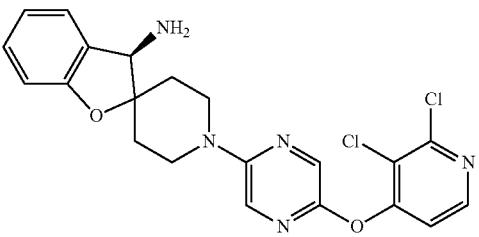<br>C₂₁H₂₉Cl₂N₅O₂ |
| 65 | 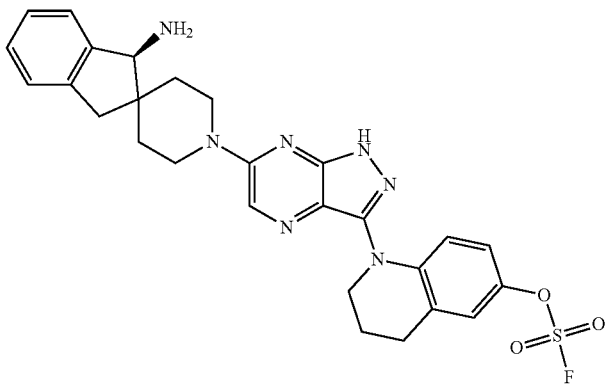<br>C₂₇H₂₈FNO₃S |

TABLE 1-continued
Representative Compounds of the disclosure.
| Example | Structure |
|---|---|
| 66 | 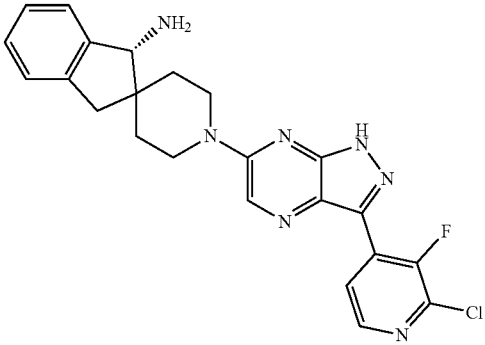<br>C$_{23}$H$_{21}$ClFN$_7$ |
| 67 | 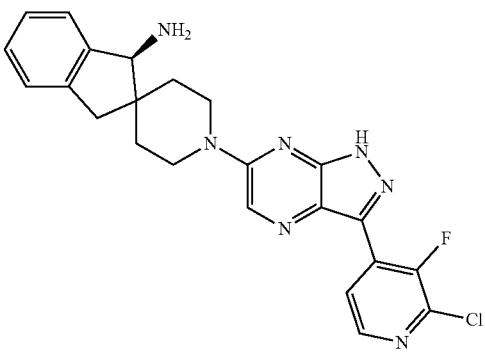<br>C$_{23}$H$_{21}$ClFN$_7$ |
| 68 | 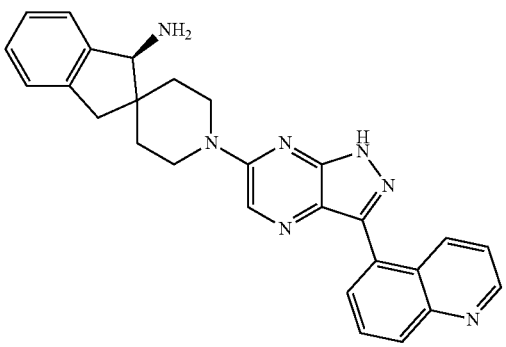<br>C$_{27}$H$_{25}$N$_7$ |
| 69 | 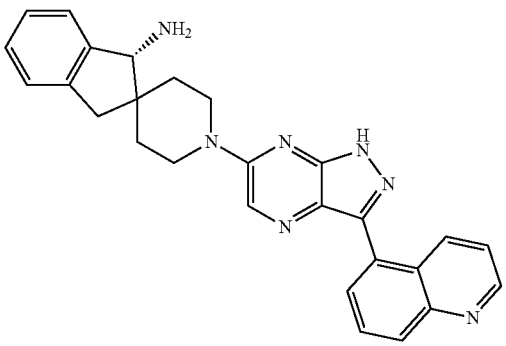<br>C$_{27}$H$_{25}$N$_7$ |

TABLE 1-continued
Representative Compounds of the disclosure.
| Example | Structure |
|---|---|
| 70 | 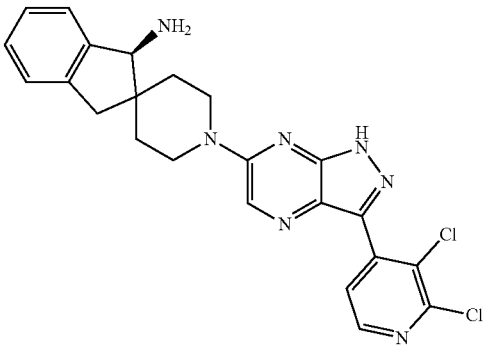<br>$C_{23}H_{21}Cl_2N_7$ |
| 71 | 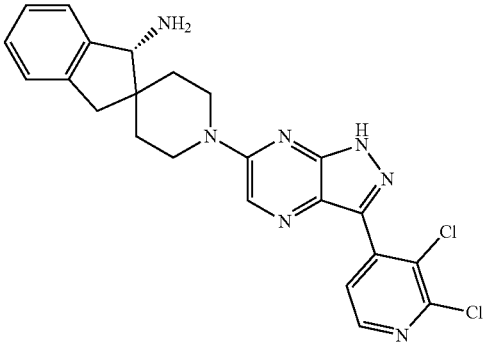<br>$C_{23}H_{21}Cl_2N_7$ |
| 72 | 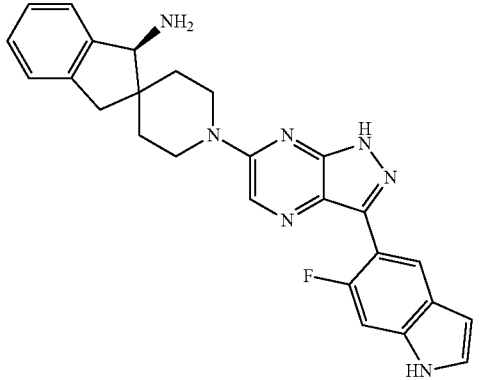<br>$C_{26}H_{24}FN_7$ |

TABLE 1-continued
Representative Compounds of the disclosure.
| Example | Structure |
|---|---|
| 73 | 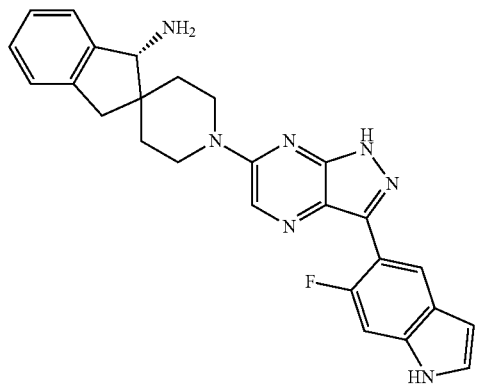<br> |
| 74 | 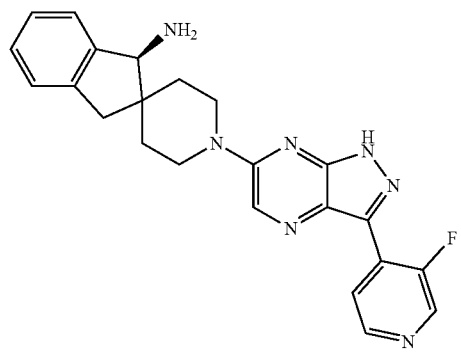<br> |
| 75 | 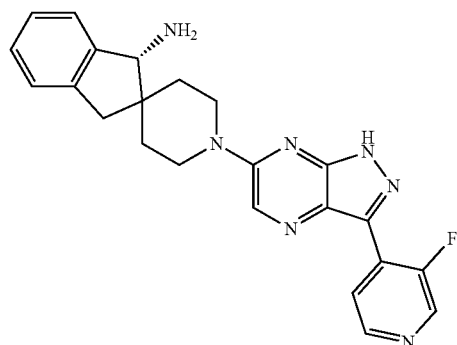<br>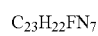 |

TABLE 1-continued
Representative Compounds of the disclosure.
| Example | Structure |
|---|---|
| 76 | 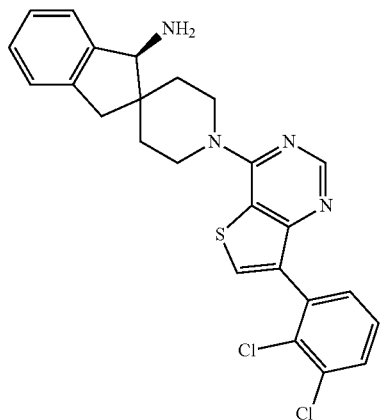$C_{25}H_{22}Cl_2N_4S$ |
| 77 | 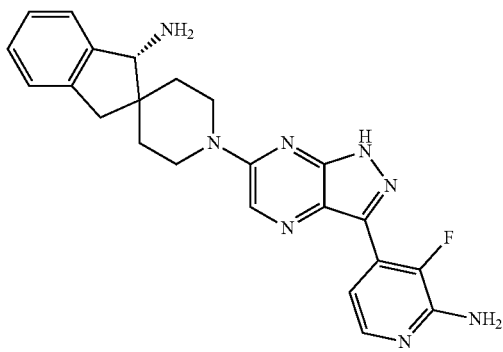$C_{23}H_{23}FN_8$ |
| 78 | 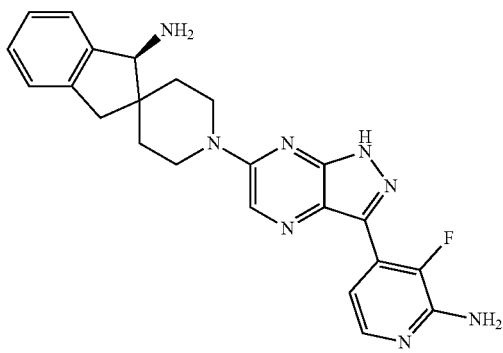$C_{23}H_{23}FN_8$ |

TABLE 1-continued
Representative Compounds of the disclosure.
| Example | Structure |
|---------|-----------|
| 79 | 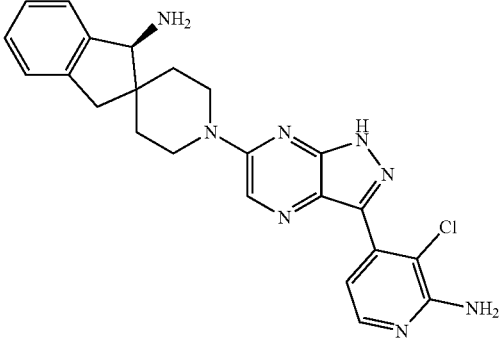<br>C$_{22}$H$_{23}$ClN$_6$S |
| 80 | 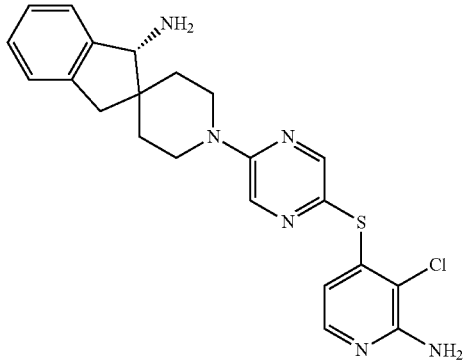<br>C$_{22}$H$_{23}$ClN$_6$S |
| 81 | 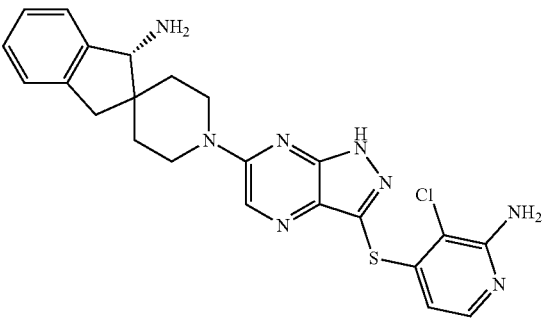<br>C$_{23}$H$_{23}$ClN$_8$S |
| 82 | 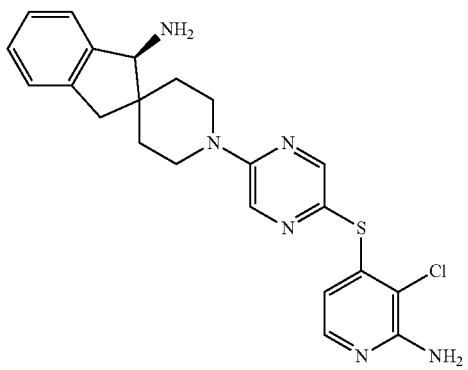<br>C$_{22}$H$_{23}$ClN$_6$S |

TABLE 1-continued
Representative Compounds of the disclosure.
| Example | Structure |
|---|---|
| 83 | 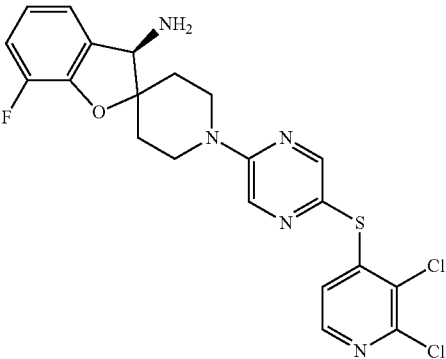<br>C$_{21}$H$_{18}$Cl$_2$FN$_5$OS |
| 84 | 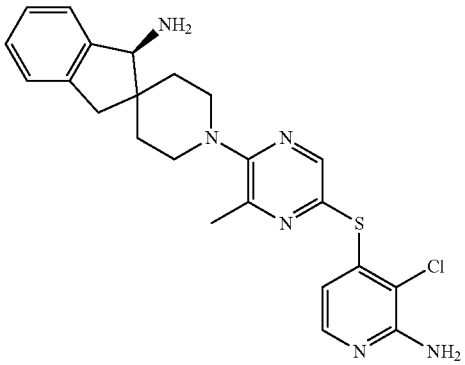<br>C$_{23}$H$_{25}$ClN$_6$S |
| 85 | 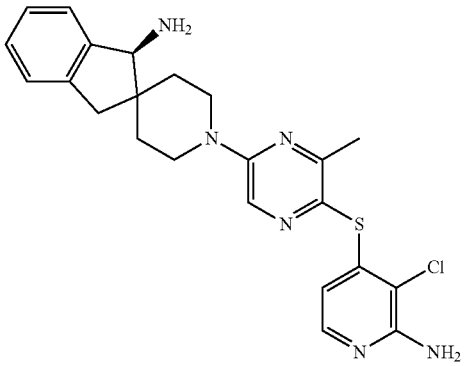<br>C$_{23}$H$_{25}$ClN$_6$S |
| 86 | 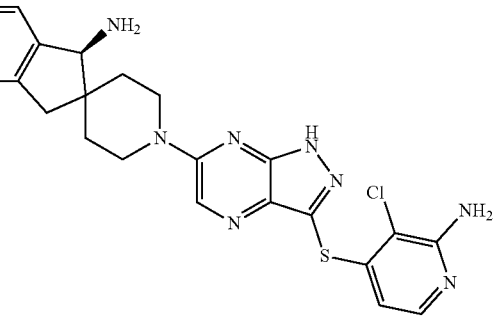<br>C$_{23}$H$_{23}$ClN$_8$S |

TABLE 1-continued
Representative Compounds of the disclosure.
| Example | Structure |
|---|---|
| 87 | 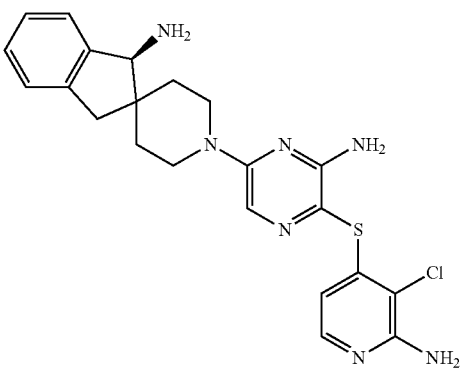<br>$C_{22}H_{24}ClN_7S$ |
| 88 | 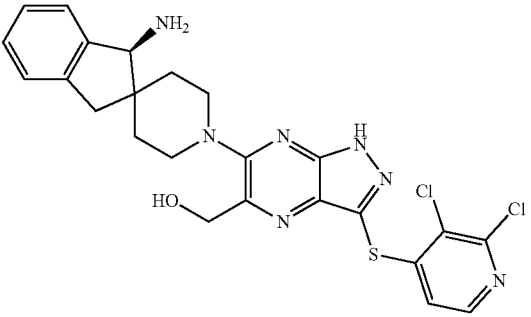<br>$C_{24}H_{23}Cl_2N_7OS$ |
| 89 | 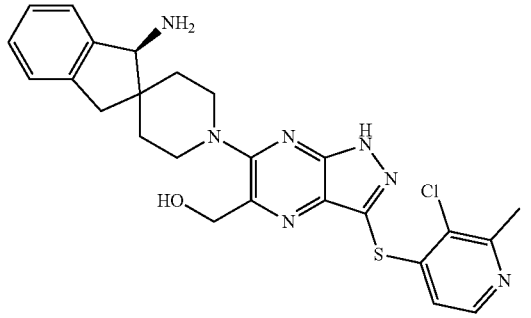<br>$C_{25}H_{26}ClN_7OS$ |
| 90 | 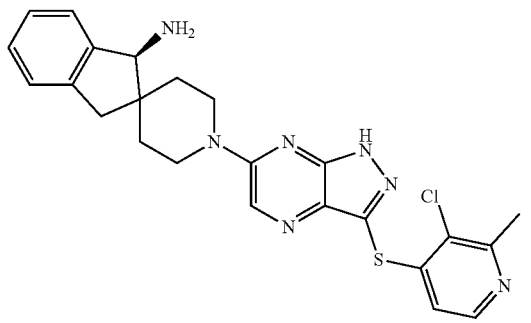<br>$C_{24}H_{24}ClN_7S$ |

TABLE 1-continued
Representative Compounds of the disclosure.
| Example | Structure |
|---|---|
| 91 | 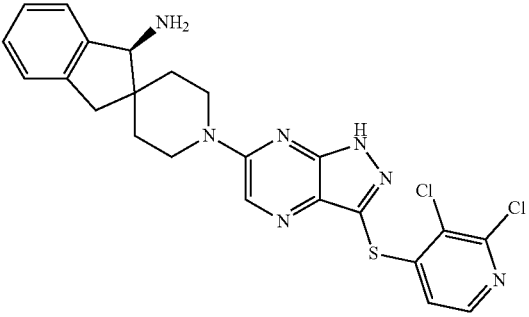<br>C<sub>23</sub>H<sub>21</sub>Cl<sub>2</sub>N<sub>7</sub>S |
| 92 | 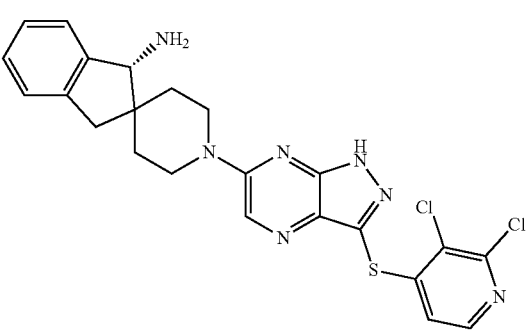<br>C<sub>23</sub>H<sub>21</sub>Cl<sub>2</sub>N<sub>7</sub>S |
| 93 | 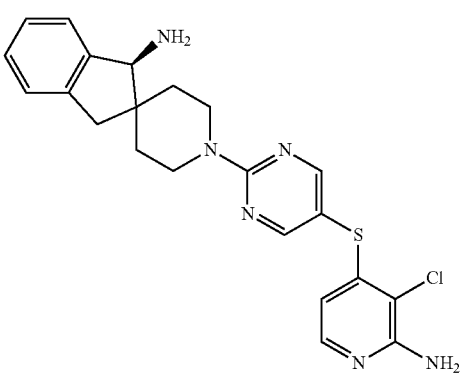<br>C<sub>22</sub>H<sub>23</sub>ClN<sub>6</sub>S |
| 94 | 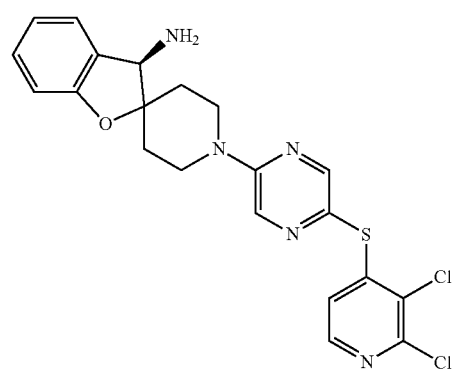<br>C<sub>21</sub>H<sub>19</sub>Cl<sub>2</sub>N<sub>5</sub>OS |

TABLE 1-continued
Representative Compounds of the disclosure.
| Example | Structure |
|---|---|
| 95 | 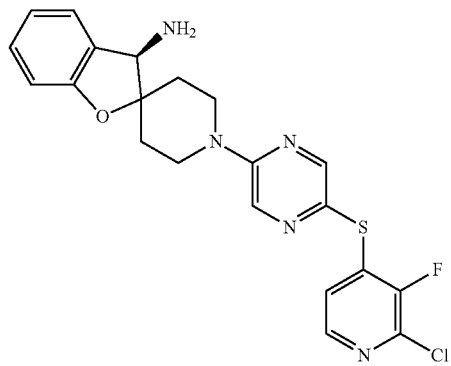<br>$C_{21}H_{19}ClFN_5OS$ |
| 96 | 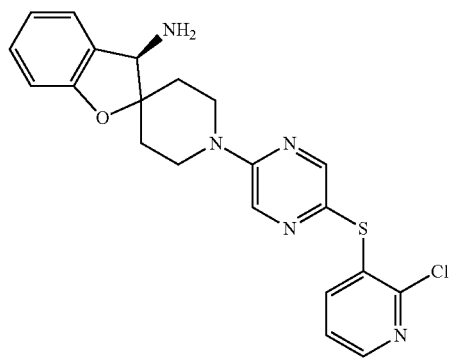<br>$C_{21}H_{20}ClN_5OS$ |
| 97 | 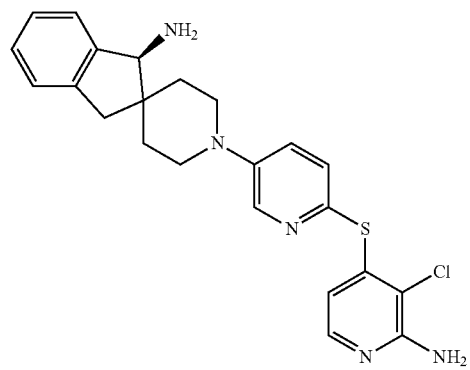<br>$C_{23}H_{24}ClN_5S$ |

TABLE 1-continued
Representative Compounds of the disclosure.
| Example | Structure |
|---------|-----------|
| 98 | 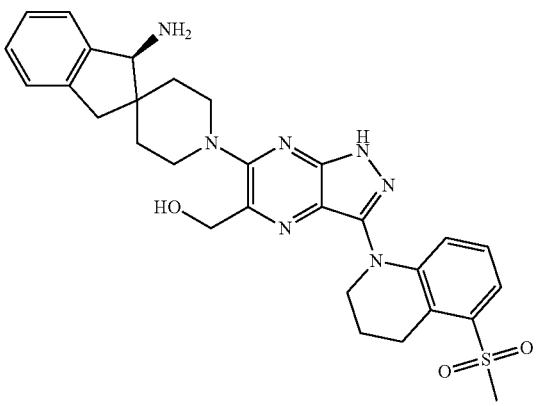<br>$C_{29}H_{33}N_7O_3S$ |
| 99 | 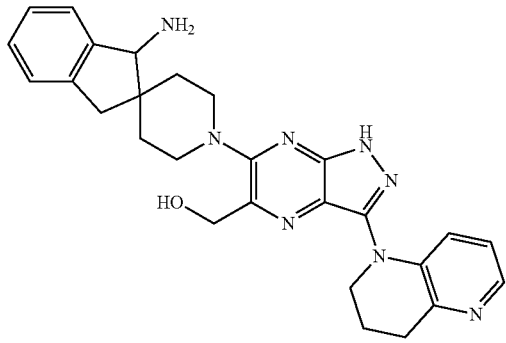<br>$C_{27}H_{30}N_8O$ |
| 100 | 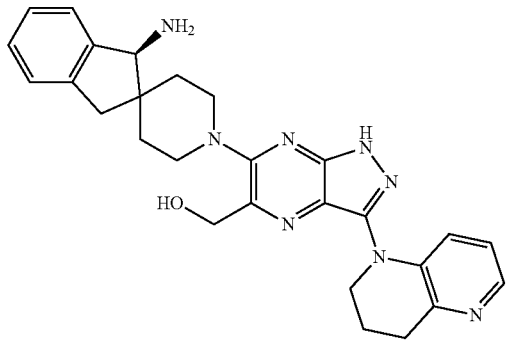<br>$C_{27}H_{30}N_8O$ |
| 101 | 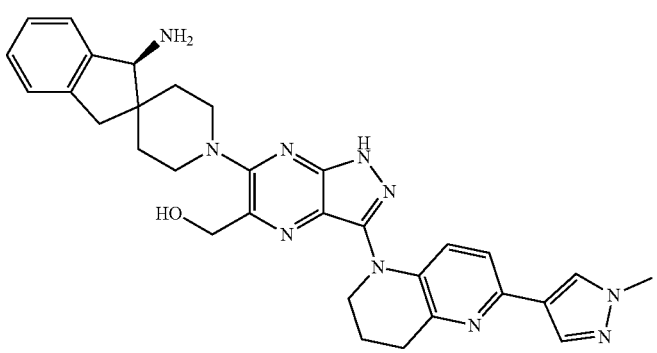<br>$C_{31}H_{34}N_{10}O$ |

TABLE 1-continued
Representative Compounds of the disclosure.
| Example | Structure |
|---|---|
| 102 | 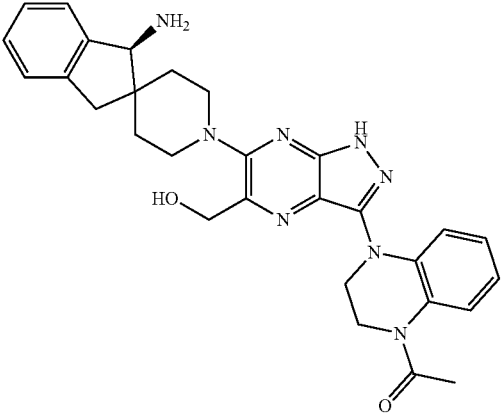<br>$C_{29}H_{32}N_8O_2$ |
| 103 | 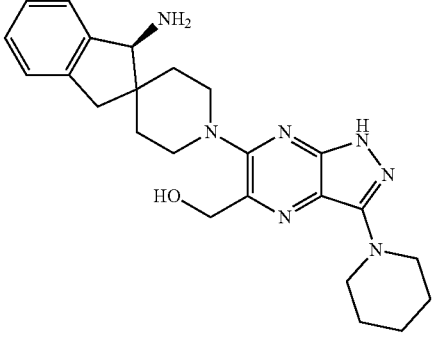<br>$C_{24}H_{31}N_7O$ |
| 104 | 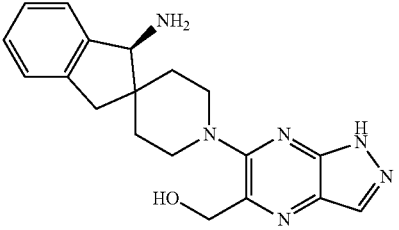<br>$C_{19}H_{22}N_6O$ |
| 105 | 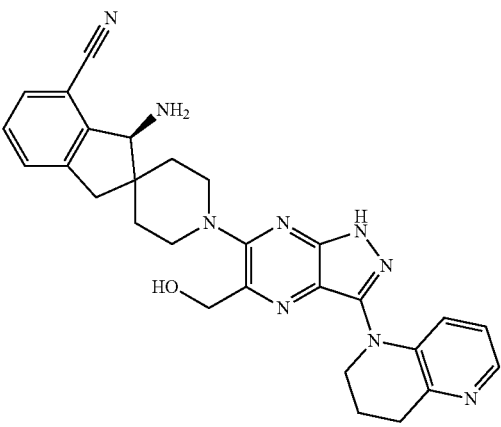<br>$C_{27}H_{27}N_9$ |

TABLE 1-continued
Representative Compounds of the disclosure.
| Example | Structure |
|---|---|
| 106 | 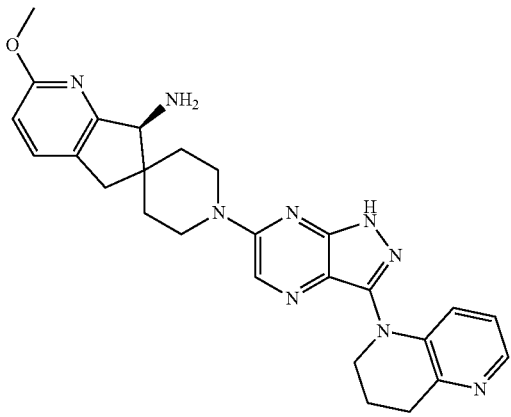
$C_{26}H_{29}N_9O$ |
| 107 | 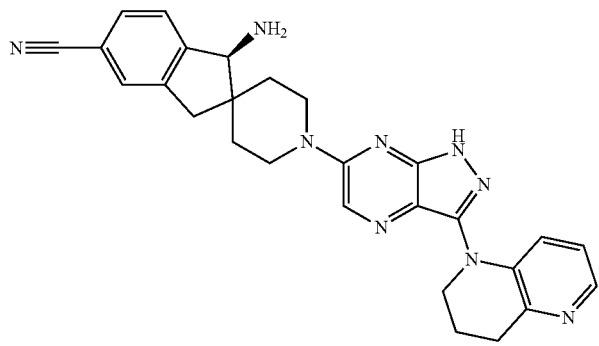
$C_{27}H_{27}N_9$ |
| 108 | 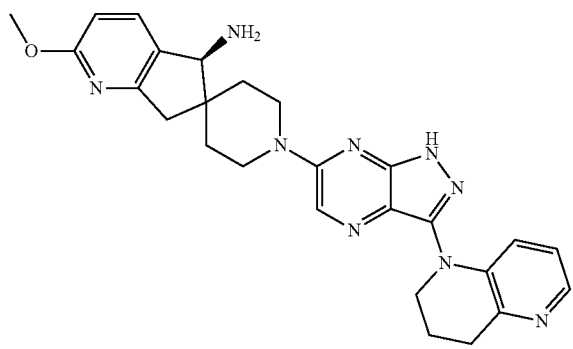
$C_{26}H_{29}N_9O$ |

103 104
TABLE 1-continued
Representative Compounds of the disclosure.
| Example | Structure |
|---|---|
| 109 | 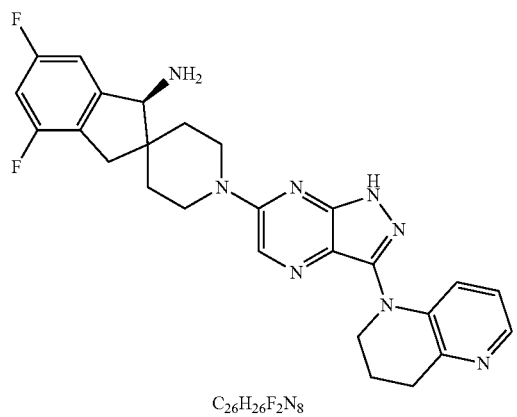 [SMILES: N[C@@H]1c2cc(F)cc(F)c2CC12CCN(c1cnc3c(N4CCCc5ncccc54)n[nH]c3n1)CC2 ; "C26H26F2N8"]<br>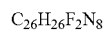 |
| 110 | 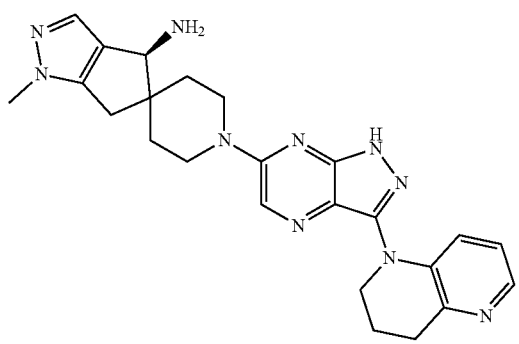<br> |
| 111 | 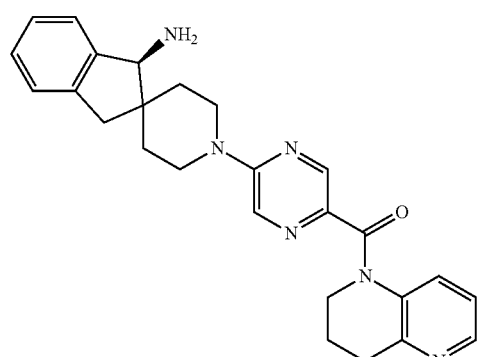<br>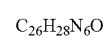 |

TABLE 1-continued
Representative Compounds of the disclosure.
| Example | Structure |
|---------|-----------|
| 112 | 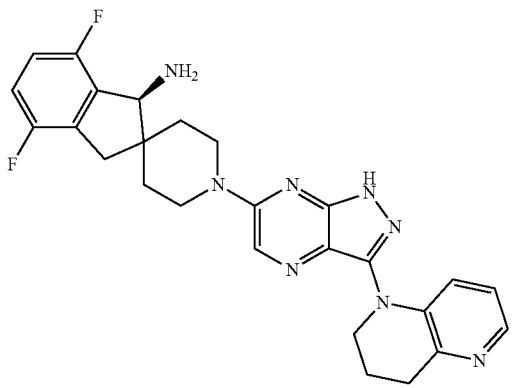<br>$C_{26}H_{26}F_2N_8$ |
| 113 | 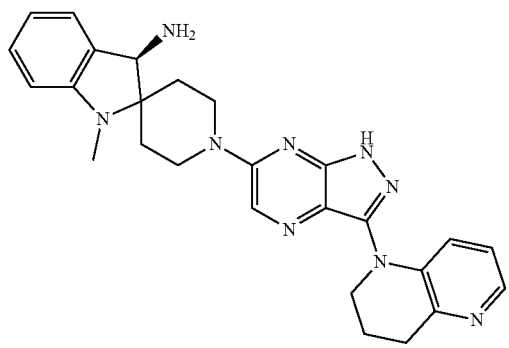<br>$C_{26}H_{29}N_9$ |
| 114 | 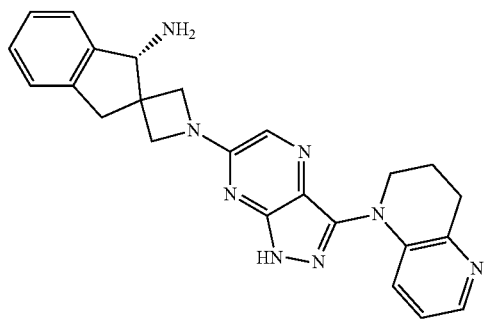<br>$C_{24}H_{24}N_8$ |
| 115 | 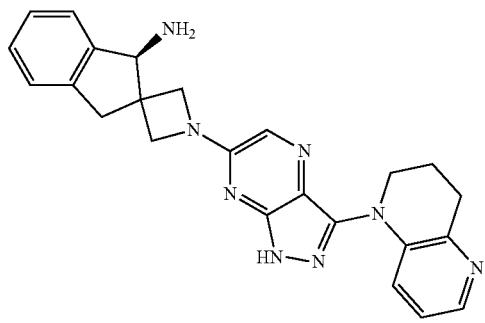<br>$C_{24}H_{24}N_8$ |

TABLE 1-continued
Representative Compounds of the disclosure.
| Example | Structure |
|---|---|
| 116 | 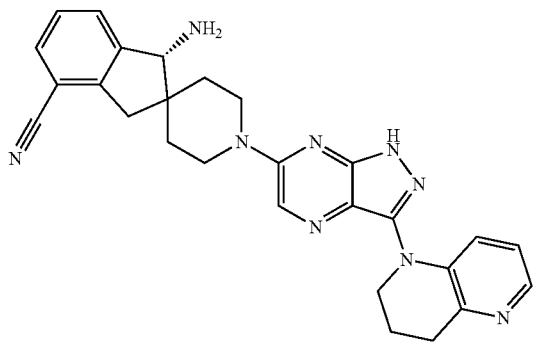
$C_{27}H_{27}N_9$ |
| 117 | 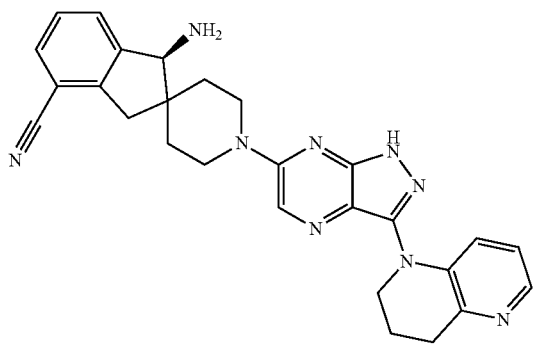
$C_{27}H_{27}N_9$ |
| 118 | 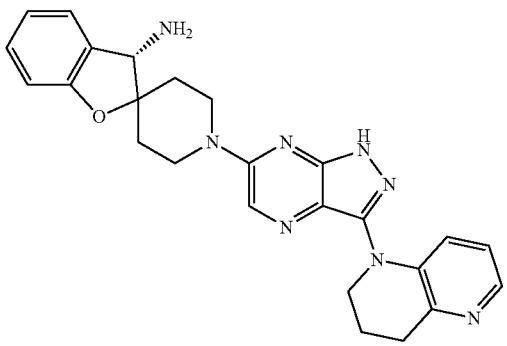
$C_{25}H_{26}N_8O$ |
| 119 | 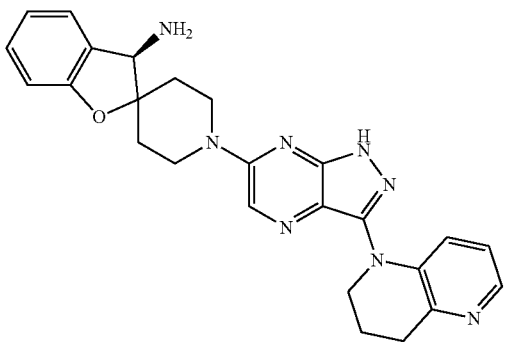
$C_{25}H_{26}N_8O$ |

TABLE 1-continued
Representative Compounds of the disclosure.
| Example | Structure |
|---|---|
| 120 | 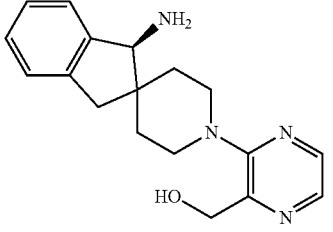<br>$C_{18}H_{22}N_4O$ |
| 121 | 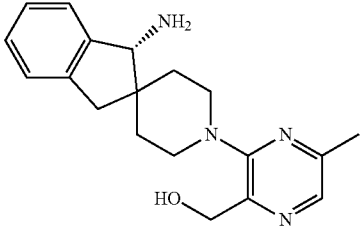<br>$C_{19}H_{24}N_4O$ |
| 122 | 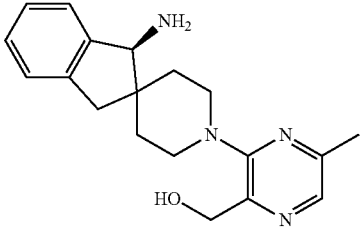<br>$C_{19}H_{24}N_4O$ |
| 123 | 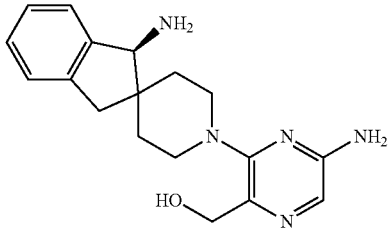<br>$C_{18}H_{23}N_5O$ |
| 124 | 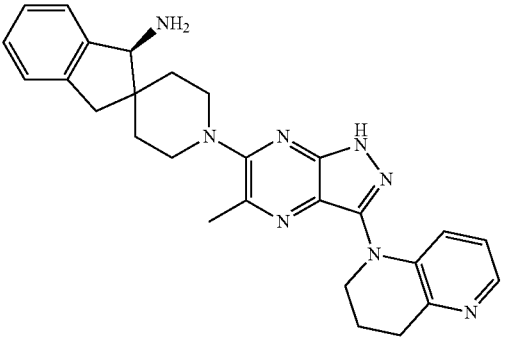<br>$C_{27}H_{30}N_8$ |

TABLE 1-continued
Representative Compounds of the disclosure.
| Example | Structure |
|---------|-----------|
| 125 | 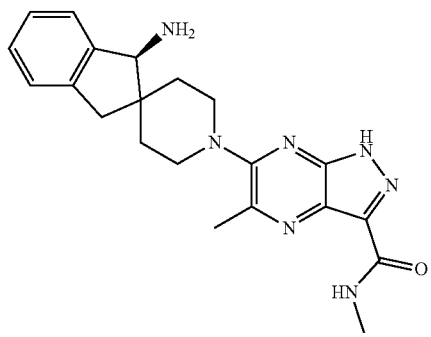
$C_{21}H_{25}N_7O$ |
| 126 | 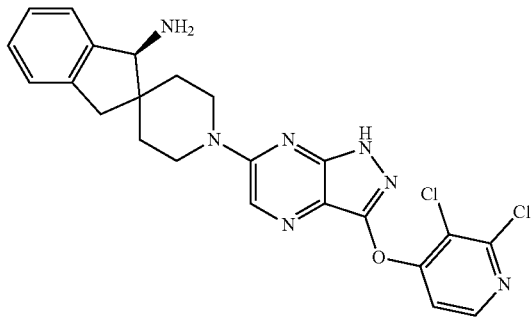
$C_{23}H_{21}Cl_2N_7O$ |
| 127 | 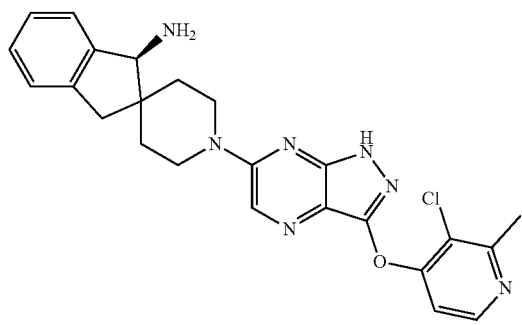
$C_{23}H_{21}ClN_7O$ |
| 128 | 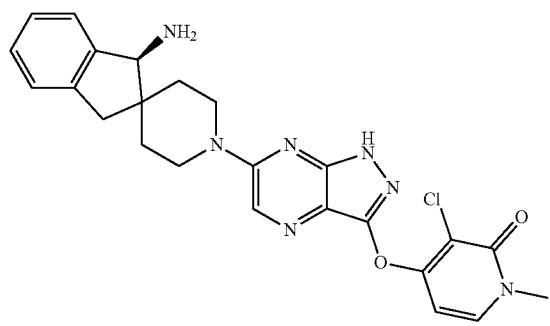
$C_{24}H_{24}ClN_7O_2$ |

TABLE 1-continued
Representative Compounds of the disclosure.
| Example | Structure |
|---|---|
| 129 | 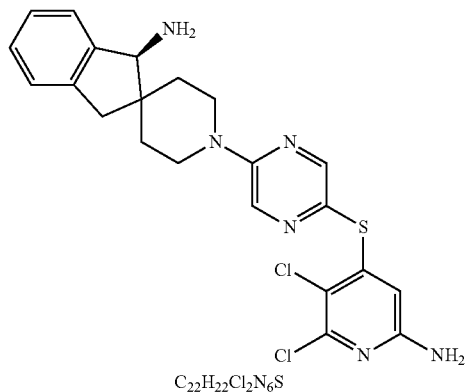 [SMILES: Nc1cc(Sc2cnc(N3CCC4(CC3)Cc3ccccc3[C@H]4N)cn2)c(Cl)c(Cl)n1 ; "C22H22Cl2N6S"]<br>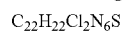 |
| 130 | 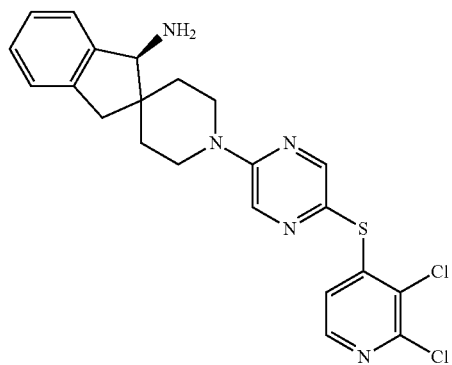<br>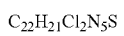 |
| 131 | 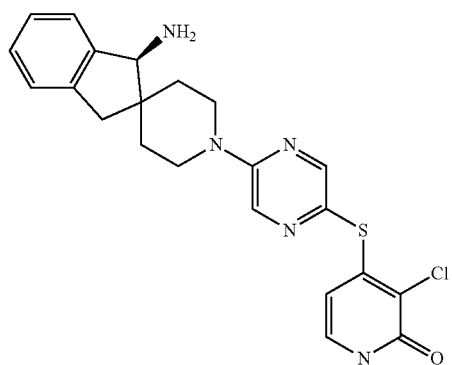<br>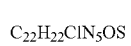 |

115
116
TABLE 1-continued
Representative Compounds of the disclosure.
| Example | Structure |
|---|---|
| 132 | 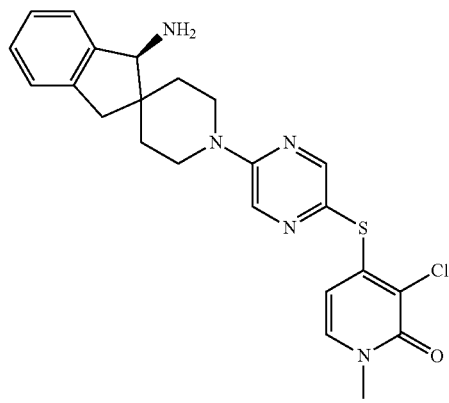
$C_{23}H_{24}ClN_5OS$ |
| 133 | 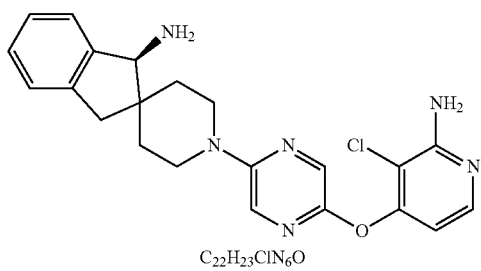 [SMILES: Nc1nccc(Oc2cnc(N3CCC4(CC3)Cc3ccccc3[C@H]4N)cn2)c1Cl ; "C22H23ClN6O"]
$C_{22}H_{23}ClN_6O$ |
| 134 | 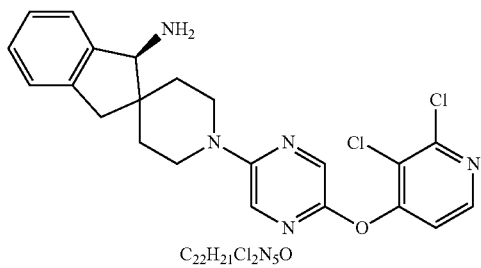 [SMILES: N[C@@H]1c2ccccc2CC12CCN(c1cnc(Oc3ccnc(Cl)c3Cl)cn1)CC2 ; "C22H21Cl2N5O"]
$C_{22}H_{21}Cl_2N_5O$ |
| 135 | 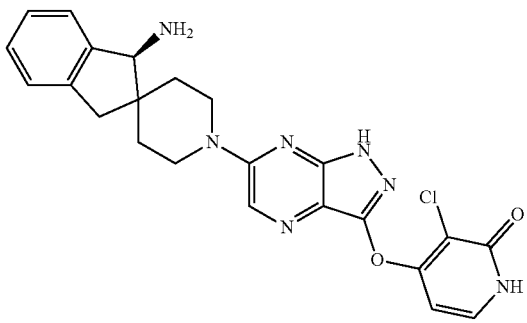
$C_{23}H_{22}ClN_7O_2$ |

TABLE 1-continued
Representative Compounds of the disclosure.
| Example | Structure |
|---|---|
| 136 | 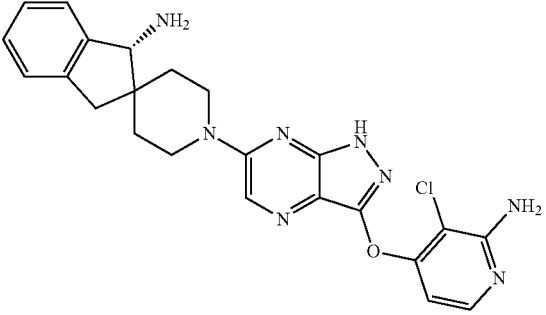<br>C<sub>23</sub>H<sub>23</sub>ClN<sub>8</sub>O |
| 137 | 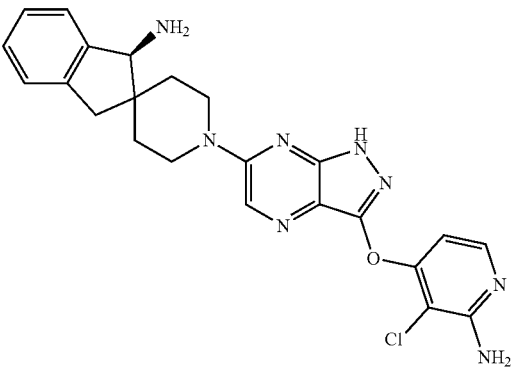<br>C<sub>23</sub>H<sub>23</sub>ClN<sub>8</sub>O |
| 138 | 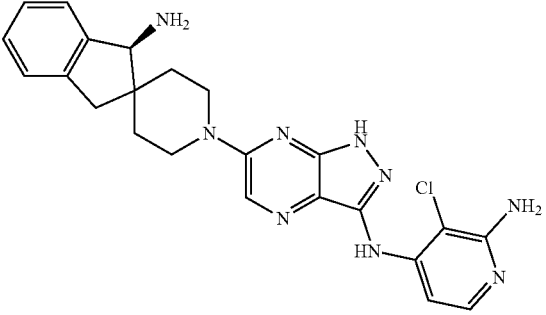<br>C<sub>23</sub>H<sub>24</sub>ClN<sub>9</sub> |
| 139 | 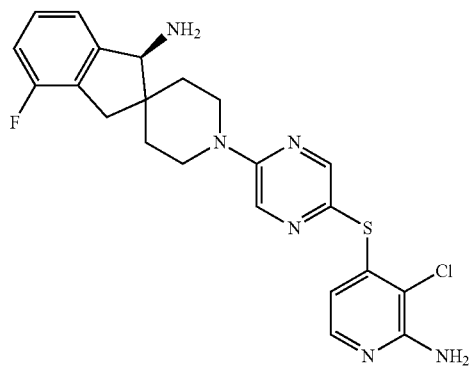<br>C<sub>22</sub>H<sub>22</sub>ClFN<sub>6</sub>S |

TABLE 1-continued
Representative Compounds of the disclosure.
| Example | Structure |
|---|---|
| 140 | 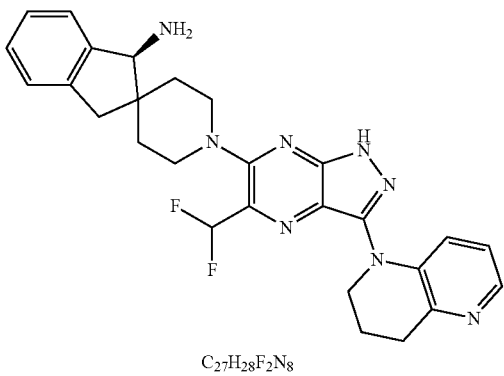 [SMILES: N[C@@H]1c2ccccc2CC12CCN(c1nc3[nH]nc(N4CCCc5ncccc54)c3nc1C(F)F)CC2 ; "C27H28F2N8"]<br>$C_{27}H_{28}F_2N_8$ |
| 141 | 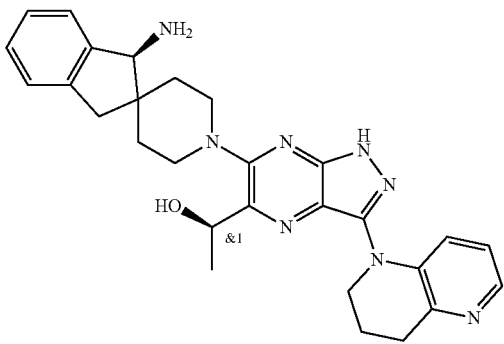<br>$C_{28}H_{32}N_8O$ |
| 142 | 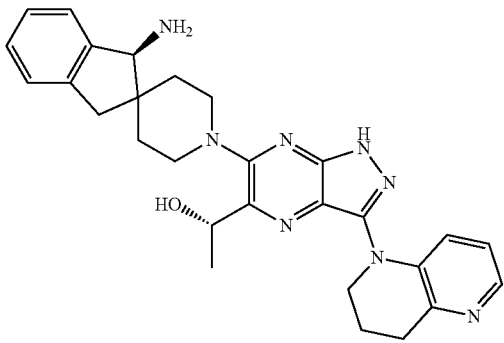<br>$C_{28}H_{32}N_8O$ |
| 143 | 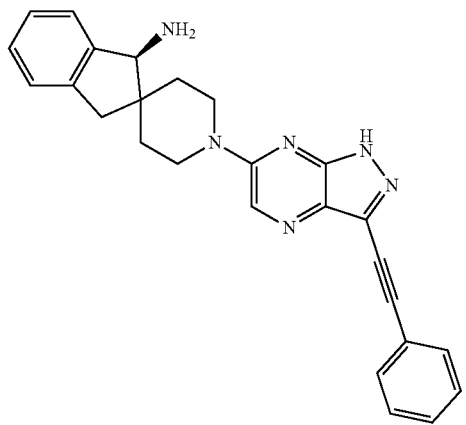<br>$C_{26}H_{24}N_6$ |

TABLE 1-continued
Representative Compounds of the disclosure.
| Example | Structure |
|---|---|
| 144 | 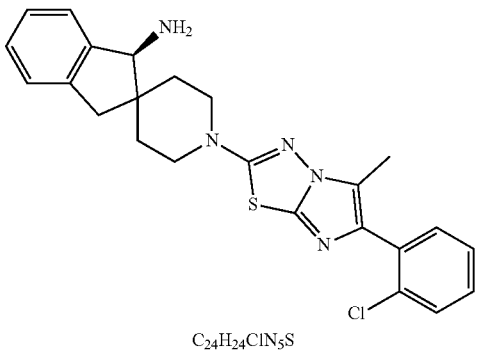 [SMILES: Cc1c(-c2ccccc2Cl)nc2sc(N3CCC4(CC3)Cc3ccccc3[C@H]4N)nn12 ; "C24H24ClN5S"]<br>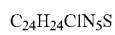<br>$C_{24}H_{24}ClN_5S$ |
| 145 | 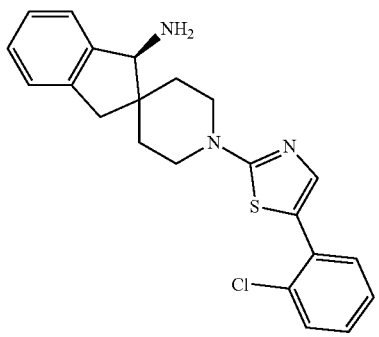<br><br>$C_{22}H_{22}ClN_3S$ |
| 146 | 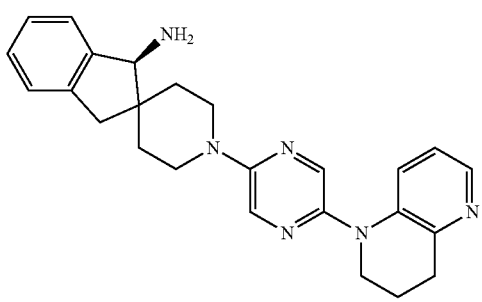<br><br>$C_{25}H_{28}N_6$ |
| 147 | 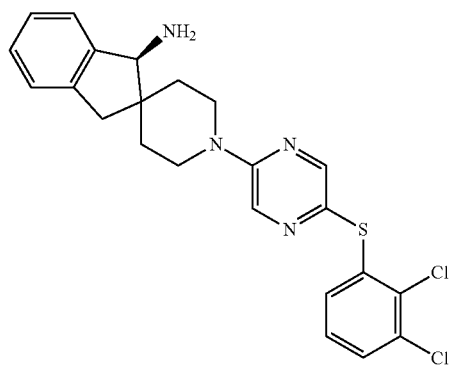<br><br>$C_{23}H_{22}Cl_2N_4S$ |

TABLE 1-continued
Representative Compounds of the disclosure.
| Example | Structure |
|---|---|
| 148 | 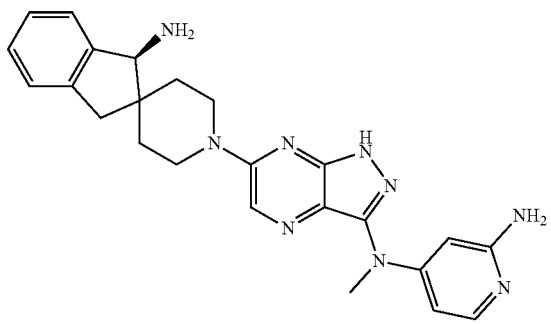<br>$C_{24}H_{27}N_9$ |
| 149 | 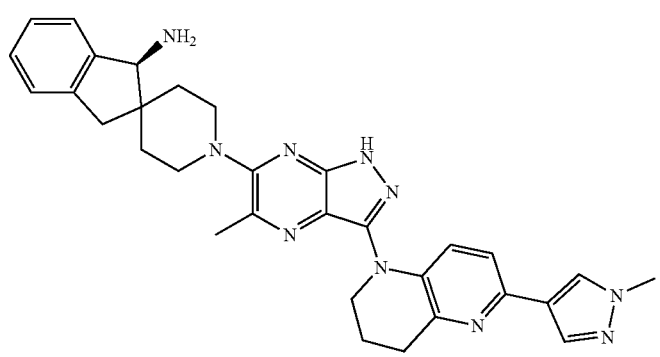<br>$C_{31}H_{34}N_{10}$ |
| 150 | 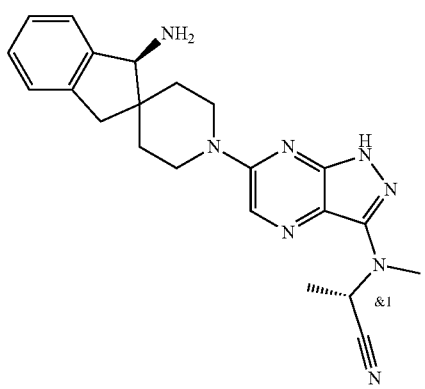<br>$C_{22}H_{26}N_8$ |
| 151 | 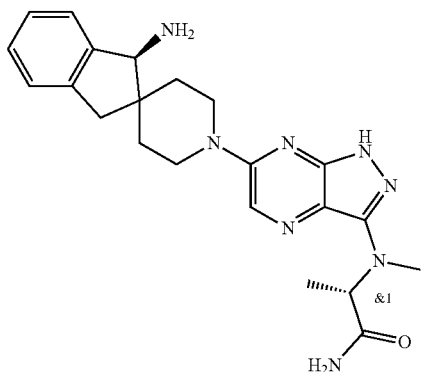<br>$C_{22}H_{28}N_8O$ |

TABLE 1-continued
Representative Compounds of the disclosure.
| Example | Structure |
|---|---|
| 152 | 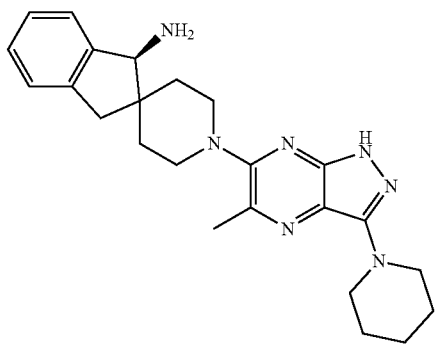<br>$C_{24}H_{31}N_7$ |
| 153 | 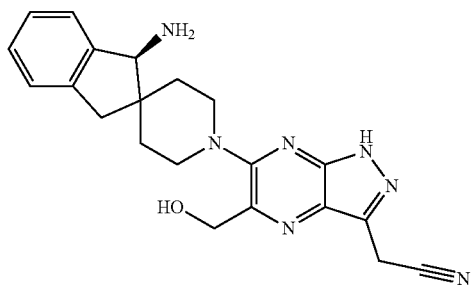<br>$C_{21}H_{23}N_7O$ |
| 154 | 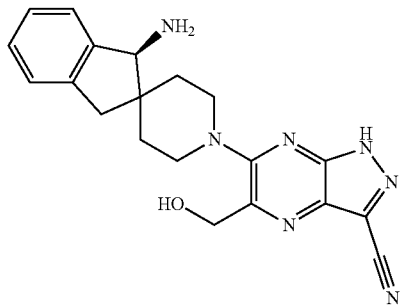<br>$C_{20}H_{21}N_7O$ |
| 155 | 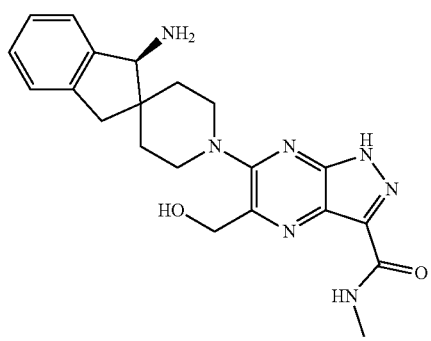<br>$C_{21}H_{25}N_7O_2$ |

TABLE 1-continued
Representative Compounds of the disclosure.
| Example | Structure |
|---|---|
| 156 | 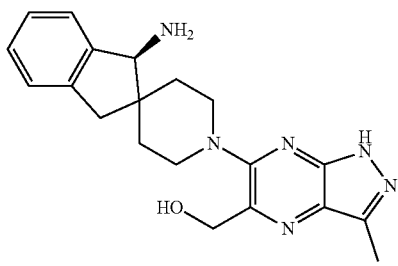<br>$C_{20}H_{24}N_6O$ |
| 157 | 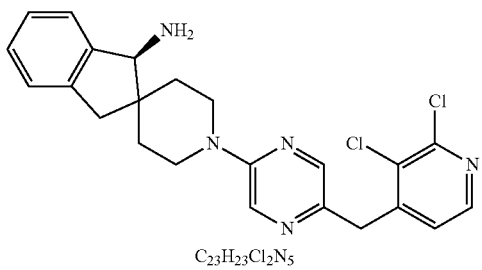 [SMILES: N[C@@H]1c2ccccc2CC12CCN(c1cnc(Cc3ccnc(Cl)c3Cl)cn1)CC2 ; "C23H23Cl2N5"]<br>$C_{23}H_{23}Cl_2N_5$ |
| 158 | 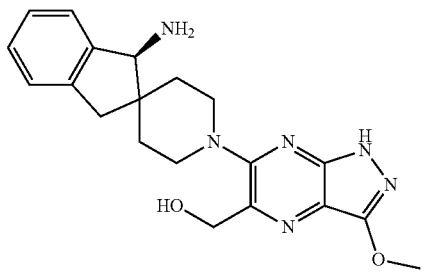<br>$C_{20}H_{24}N_6O_2$ |
| 159 | 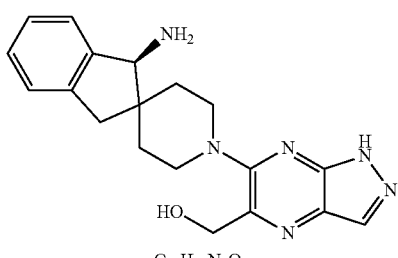<br>$C_{18}H_{20}N_6O_2$ |
| 160 | 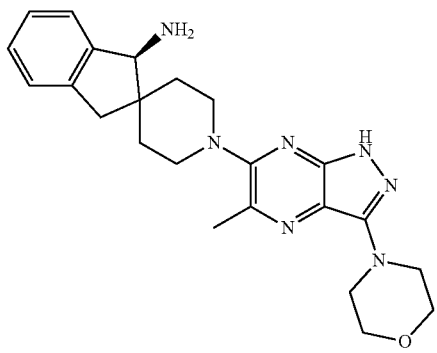<br>$C_{22}H_{29}N_7O$ |

129
130
TABLE 1-continued
Representative Compounds of the disclosure.
| Example | Structure |
|---|---|
| 161 | 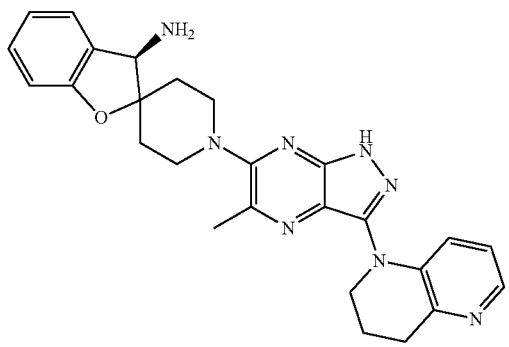<br>C$_{26}$H$_{28}$N$_8$O |
| 162 | 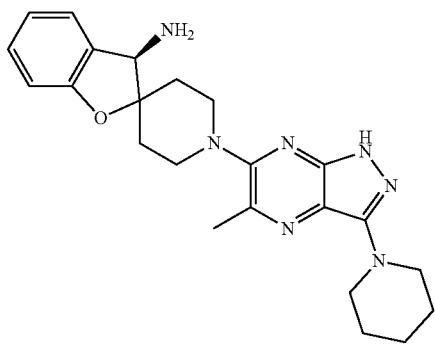<br>C$_{23}$H$_{29}$N$_7$O |
| 163 | 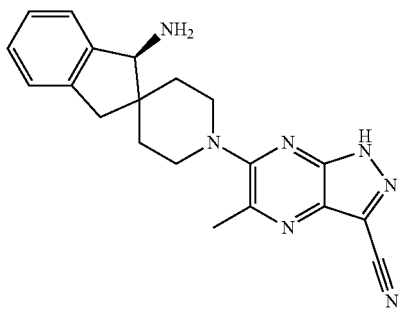<br>C$_{20}$H$_{21}$N$_7$ |
| 164 | 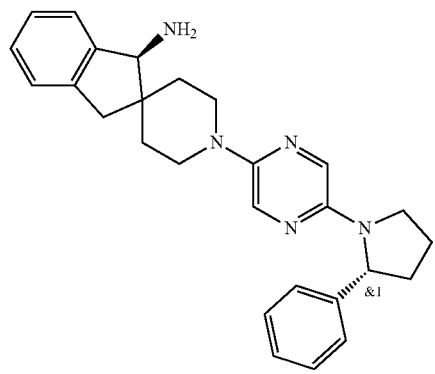<br>C$_{27}$H$_{31}$N$_5$ |

TABLE 1-continued
Representative Compounds of the disclosure.
| Example | Structure |
|---|---|
| 165 | 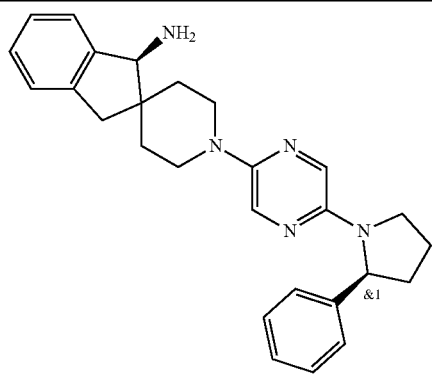<br>C<sub>27</sub>H<sub>31</sub>N<sub>5</sub> |
| 166 | 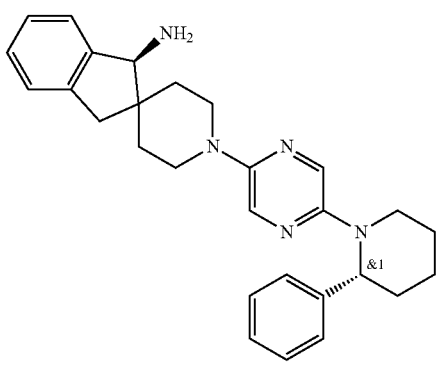<br>C<sub>28</sub>H<sub>33</sub>N<sub>5</sub> |
| 167 | 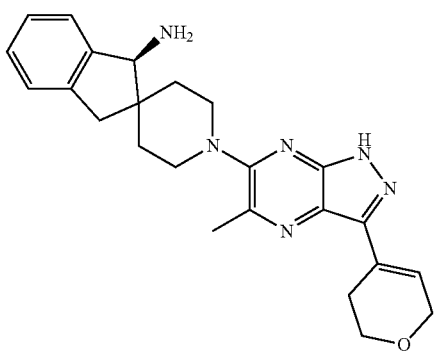<br>C<sub>24</sub>H<sub>28</sub>N<sub>6</sub>O |
| 168 | 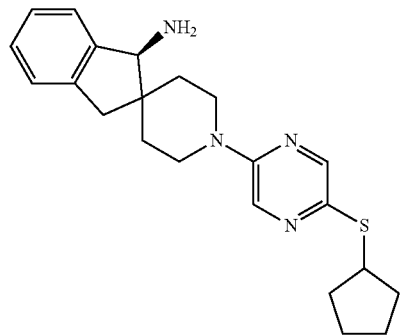<br>C<sub>22</sub>H<sub>28</sub>N<sub>4</sub>S |

TABLE 1-continued
Representative Compounds of the disclosure.
| Example | Structure |
|---|---|
| 169 | 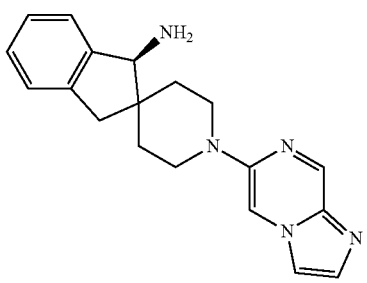<br>$C_{19}H_{21}N_5$ |
| 170 | 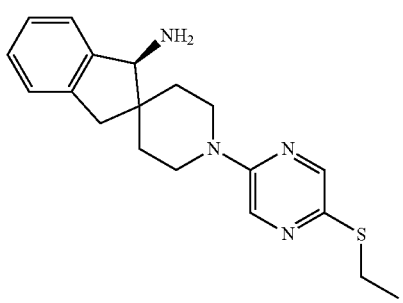<br>$C_{19}H_{24}N_4S$ |
| 171 | 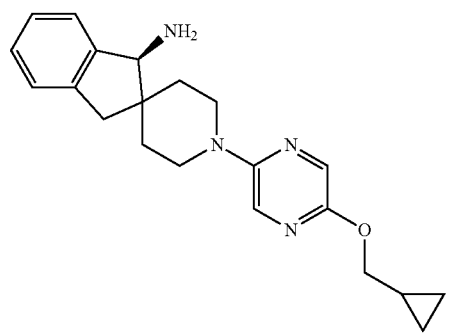<br>$C_{21}H_{26}N_4O$ |
| 172 | 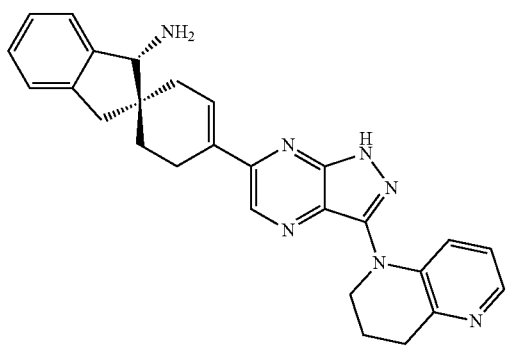<br>$C_{27}H_{27}N_7$ |

TABLE 1-continued
Representative Compounds of the disclosure.
| Example | Structure |
|---|---|
| 173 | 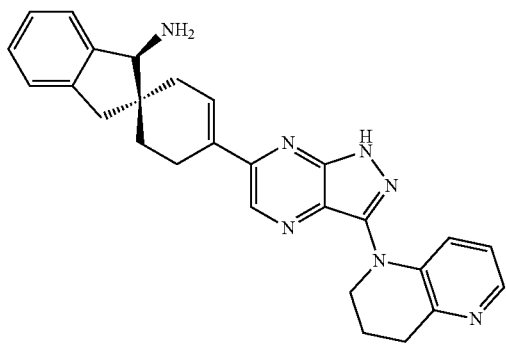<br>$C_{27}H_{27}N_7$ |
| 174 | 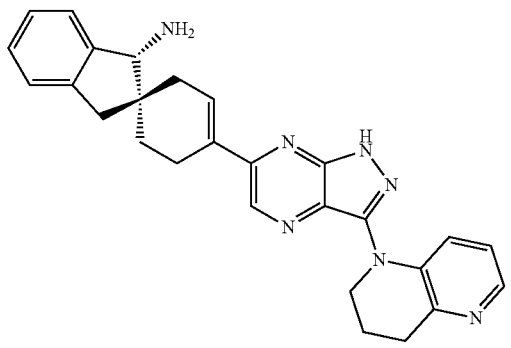<br>$C_{27}H_{27}N_7$ |
| 175 | 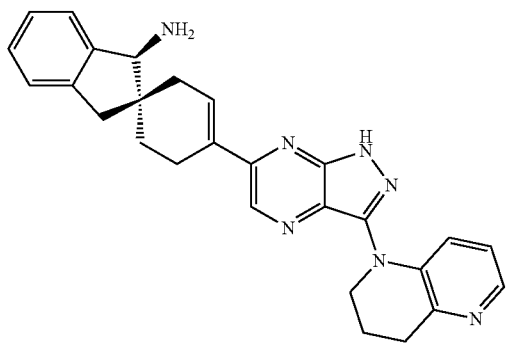<br>$C_{27}H_{27}N_7$ |
| 176 | 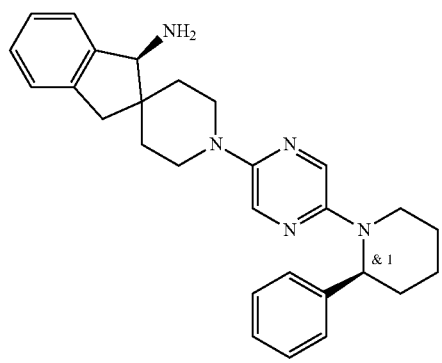<br>$C_{28}H_{33}N_5$ |

TABLE 1-continued
Representative Compounds of the disclosure.
| Example | Structure |
|---|---|
| 177 | 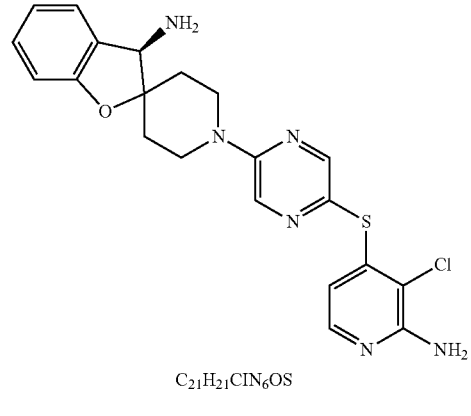 [SMILES: Nc1nccc(Sc2cnc(N3CCC4(CC3)Oc3ccccc3[C@H]4N)cn2)c1Cl ; "C21H21CIN6OS"]<br>$C_{21}H_{21}ClN_6OS$ |
| 178 | 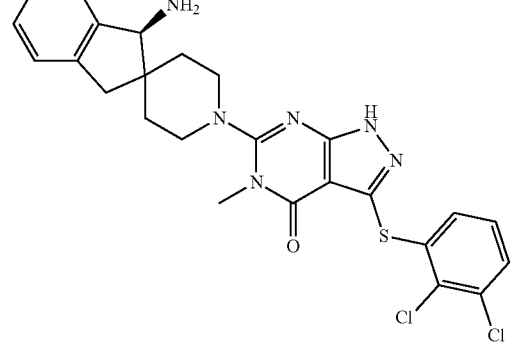<br>$C_{25}H_{24}Cl_2N_6OS$ |
| 179 | 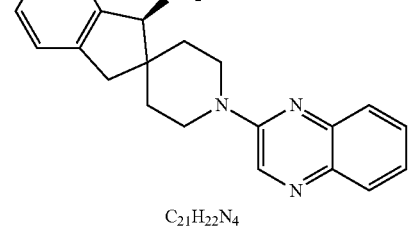<br>$C_{21}H_{22}N_4$ |
| 180 | 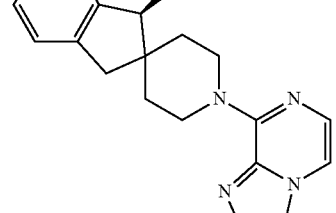<br>$C_{19}H_{21}N_5$ |

TABLE 1-continued
Representative Compounds of the disclosure.
| Example | Structure |
|---------|-----------|
| 181 | 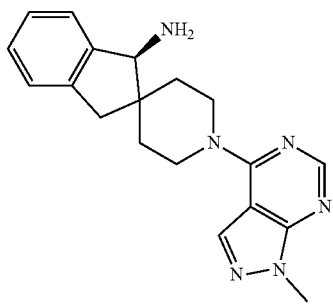<br>$C_{19}H_{22}N_6$ |
| 182 | 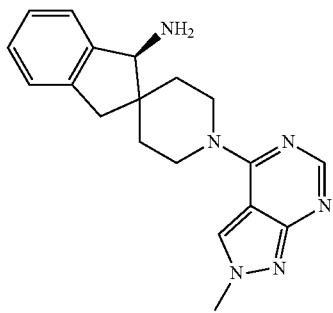<br>$C_{19}H_{22}N_6$ |
| 183 | 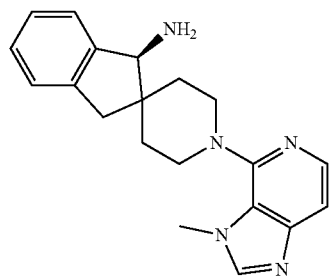<br>$C_{20}H_{23}N_5$ |
| 184 | 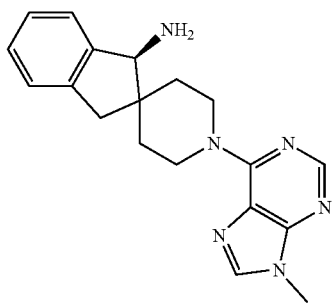<br>$C_{20}H_{23}N_5$ |

141
142
TABLE 1-continued
Representative Compounds of the disclosure.
| Example | Structure |
|---------|-----------|
| 185 | 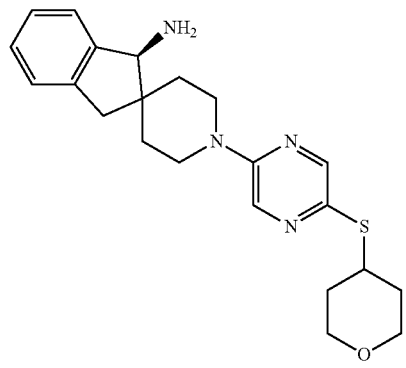<br>$C_{22}H_{28}N_4OS$ |
| 186 | 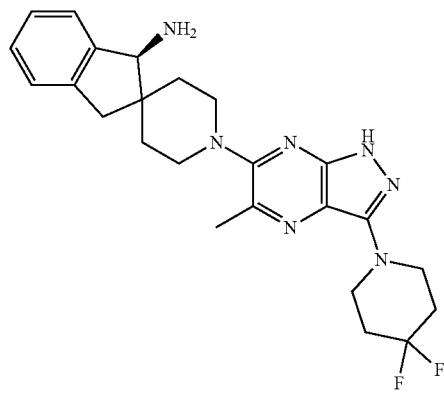<br>$C_{24}H_{29}F_2N_7$ |
| 187 | 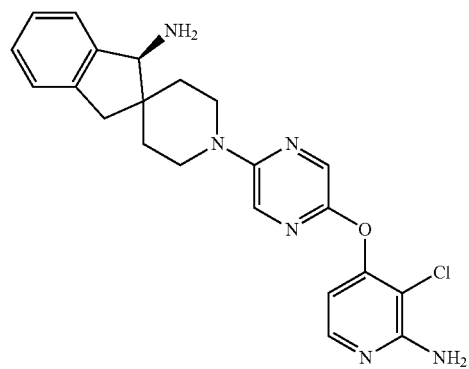<br>$C_{21}H_{21}ClN_6O_2$ |

TABLE 1-continued
Representative Compounds of the disclosure.
| Example | Structure |
|---------|-----------|
| 188 | 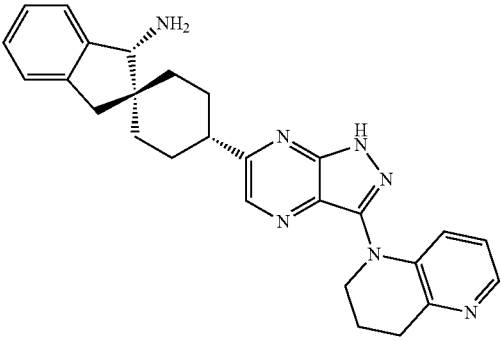<br>C₂₇H₂₉N₇ |
| 189 | 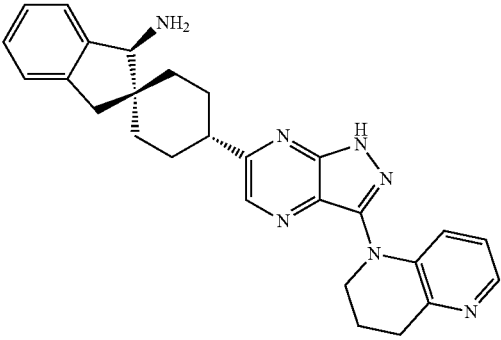<br>C₂₇H₂₉N₇ |
| 190 | 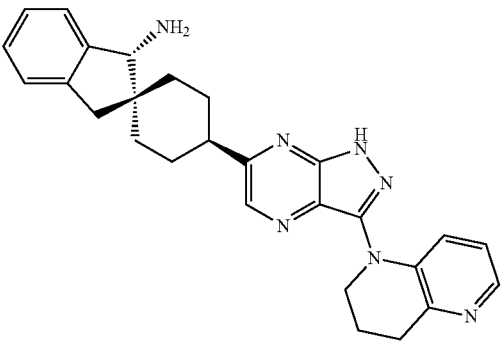<br>C₂₇H₂₉N₇ |
| 191 | 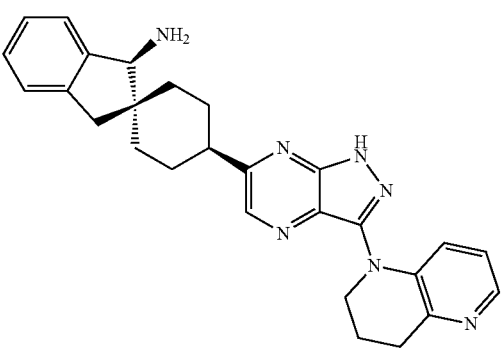<br>C₂₇H₂₉N₇ |

TABLE 1-continued
Representative Compounds of the disclosure.
| Example | Structure |
|---|---|
| 192 | 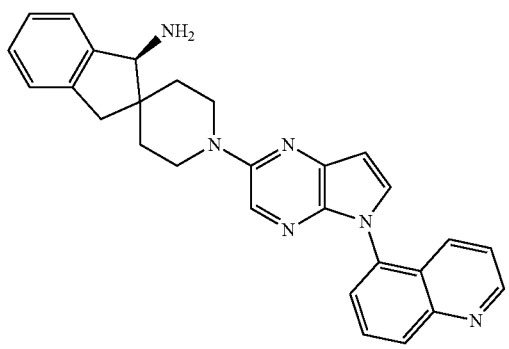
$C_{28}H_{26}N_6$ |
| 193 | 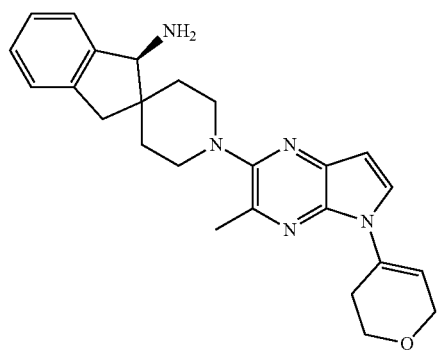
$C_{25}H_{29}N_5O$ |
| 194 | 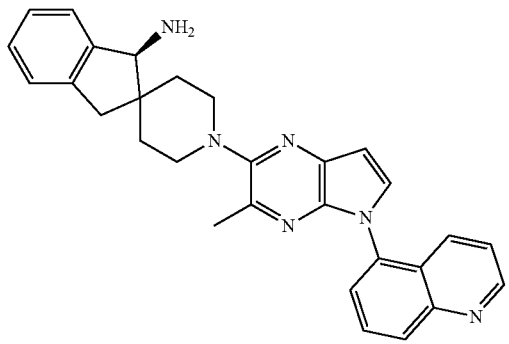
$C_{29}H_{28}N_6$ |
| 195 | 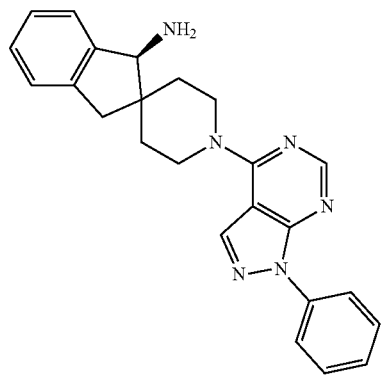
$C_{24}H_{24}N_6$ |

TABLE 1-continued
Representative Compounds of the disclosure.
| Example | Structure |
|---|---|
| 196 | 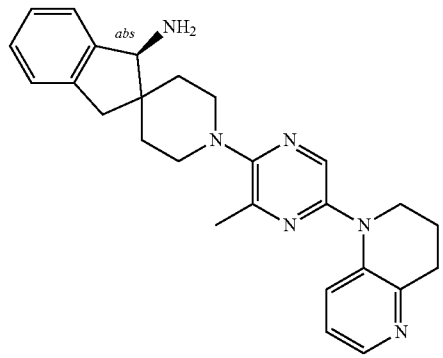<br>C<sub>26</sub>H<sub>30</sub>N<sub>6</sub> |
| 197 | 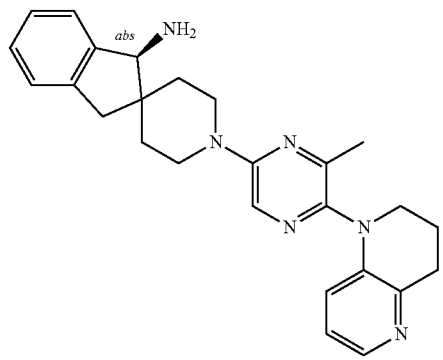<br>C<sub>26</sub>H<sub>30</sub>N<sub>6</sub> |
| 198 | 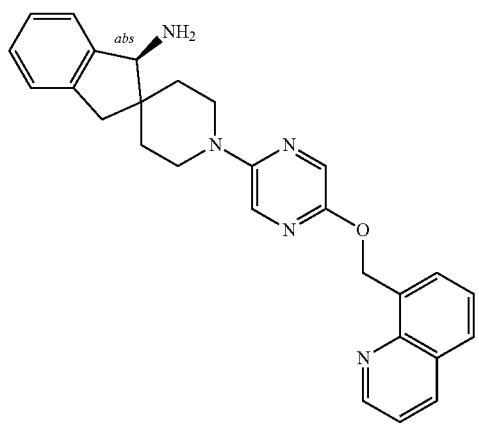<br>C<sub>27</sub>H<sub>27</sub>N<sub>5</sub>O |

149
150
TABLE 1-continued
Representative Compounds of the disclosure.
| Example | Structure |
|---|---|
| 199 | 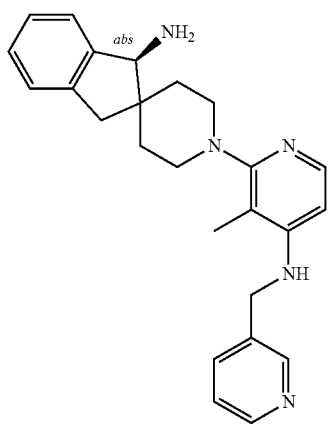<br>C$_{25}$H$_{29}$N$_5$ |
| 200 | 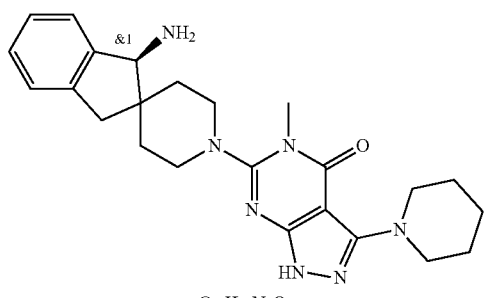<br>C$_{24}$H$_{31}$N$_7$O |
| 201 | 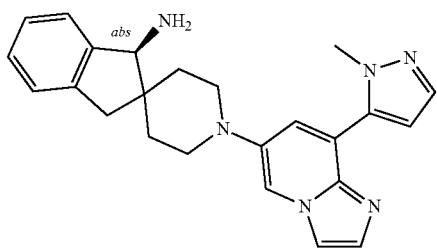<br>C$_{24}$H$_{26}$N$_6$ |
| 202 | 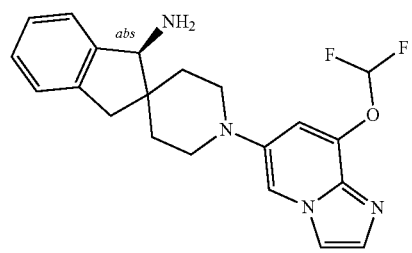<br>C$_{21}$H$_{22}$F$_2$N$_4$O |

151
TABLE 1-continued
Representative Compounds of the disclosure.
| Example | Structure |
|---|---|
| 203 | 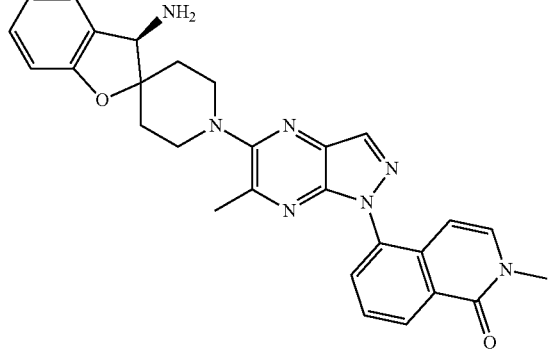<br>$C_{28}H_{27}N_7O_2$ |
| 204 | 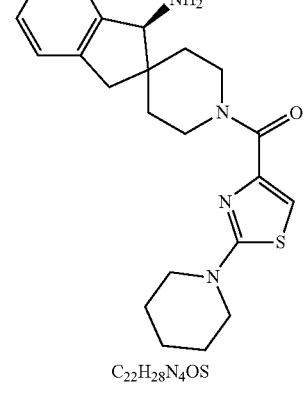<br>$C_{22}H_{28}N_4OS$ |
| 205 | 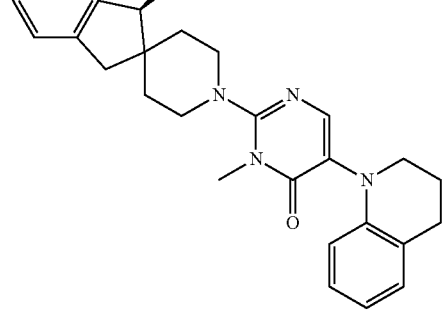<br>$C_{27}H_{31}N_5O$ |

US 10,934,302 B1
153 154
TABLE 1-continued
Representative Compounds of the disclosure.
| Example | Structure |
|---------|-----------|
| 206 | 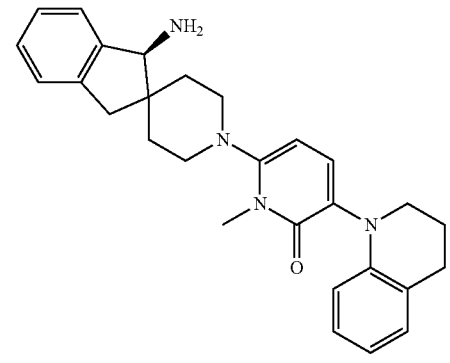 C<sub>28</sub>H<sub>32</sub>N<sub>4</sub>O |
| 207 | 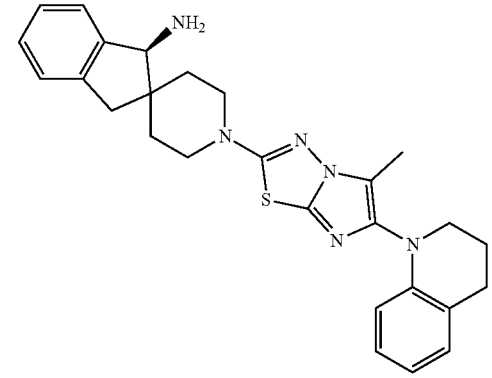 C<sub>27</sub>H<sub>30</sub>N<sub>6</sub>S |
| 208 | 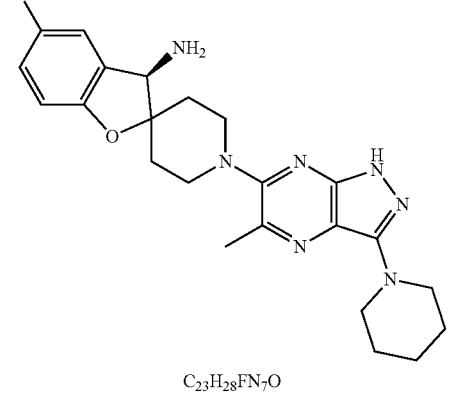 C<sub>23</sub>H<sub>28</sub>FN<sub>7</sub>O |

TABLE 1-continued
Representative Compounds of the disclosure.
| Example | Structure |
|---|---|
| 209 | 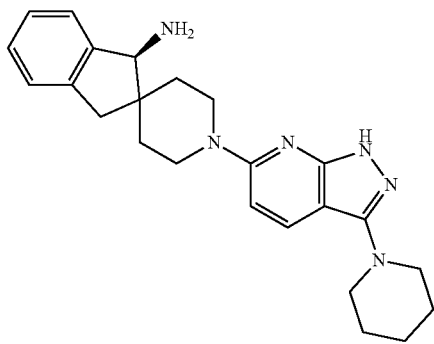
C₂₄H₃₀N₆ |
| 210 | 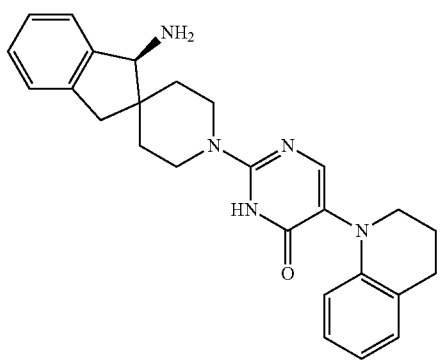
C₂₆H₂₉N₅O |
| 211 | 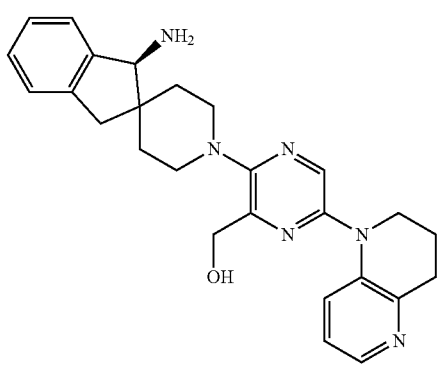
C₂₆H₃₀N₆O |
| 212 | 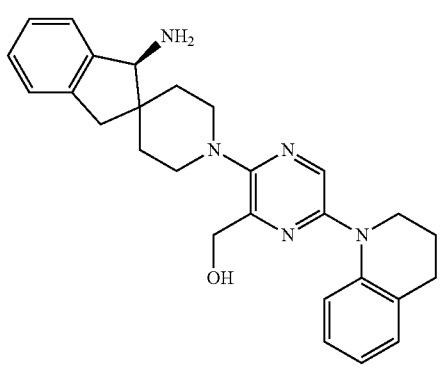
C₂₇H₃₁N₅O |

157
158
TABLE 1-continued
Representative Compounds of the disclosure.
| Example | Structure |
|---|---|
| 213 | 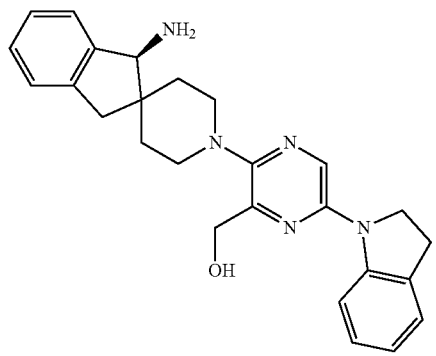<br>C26H29N5O |
| 214 | 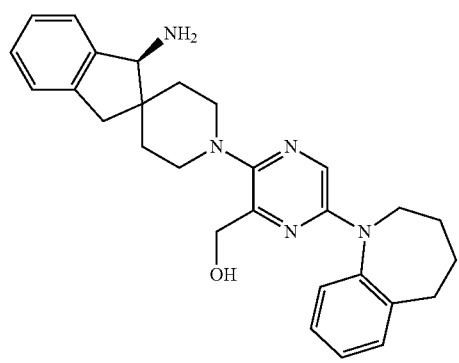<br>C28H33N5O |
| 215 | 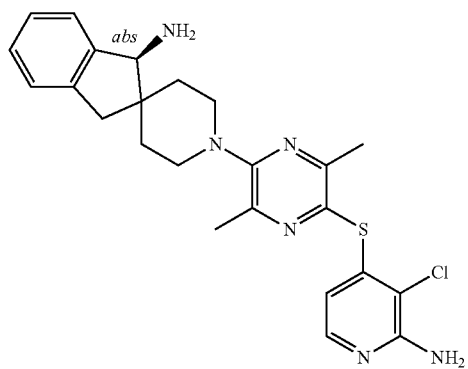<br>C24H27ClN6S |
| 216 | 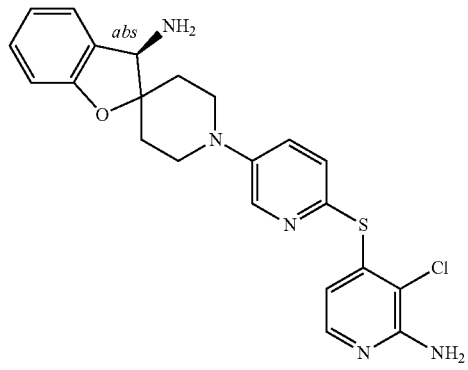<br>C22H22ClN5OS |

159
TABLE 1-continued
Representative Compounds of the disclosure.
| Example | Structure |
|---|---|
| 217 | 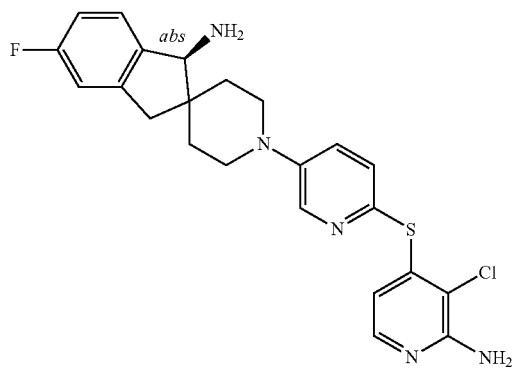<br>C₂₃H₂₃ClFN₅S |
| 218 | 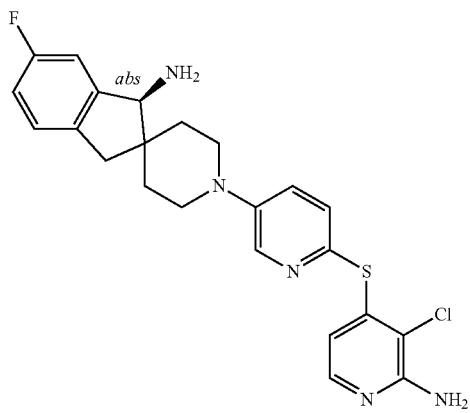<br>C₂₃H₂₃ClFN₅S |
| 219 | 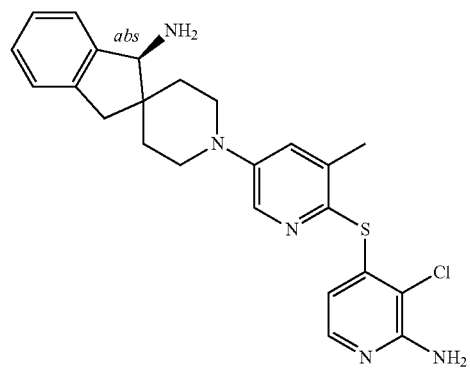<br>C₂₃H₂₃ClFN₅S |

TABLE 1-continued
Representative Compounds of the disclosure.
| Example | Structure |
|---|---|
| 220 | 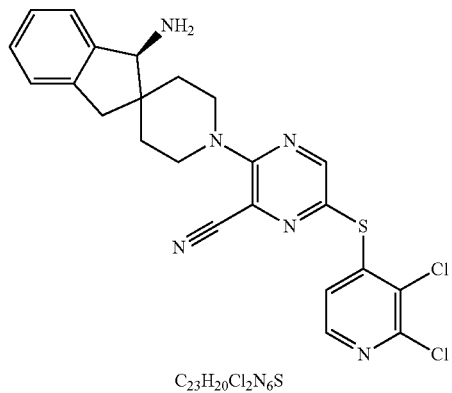 [SMILES: N#Cc1nc(Sc2ccnc(Cl)c2Cl)cnc1N1CCC2(CC1)Cc1ccccc1[C@H]2N ; "C23H20Cl2N6S"]
$C_{23}H_{20}Cl_2N_6S$ |
| 221 | 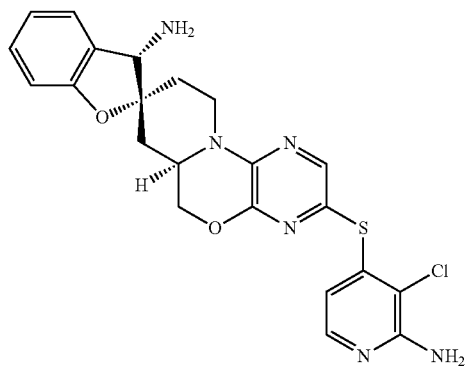
$C_{22}H_{21}ClN_6O_2S$ |
| 222 | 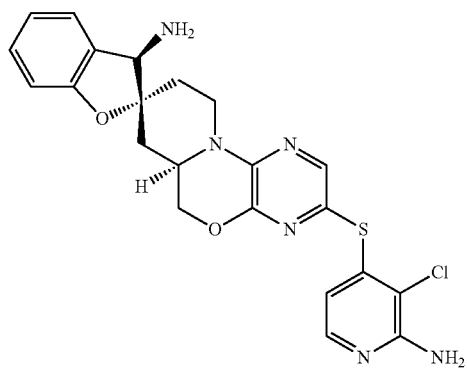
$C_{22}H_{21}ClN_6O_2S$ |

163
TABLE 1-continued
Representative Compounds of the disclosure.
| Example | Structure |
|---|---|
| 223 | 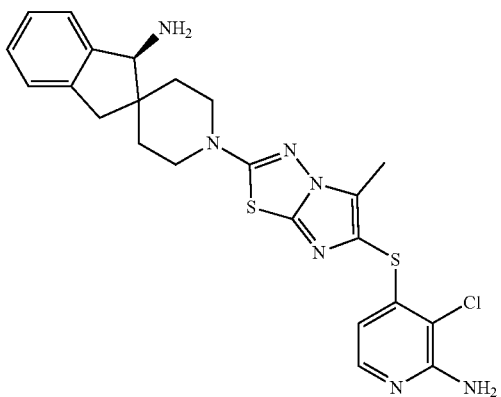 $C_{23}H_{24}ClN_7S_2$ |
| 224 | 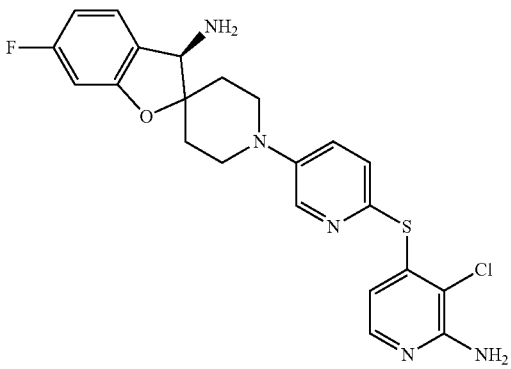 $C_{22}H_{21}ClFN_5OS$ |
| 225 | 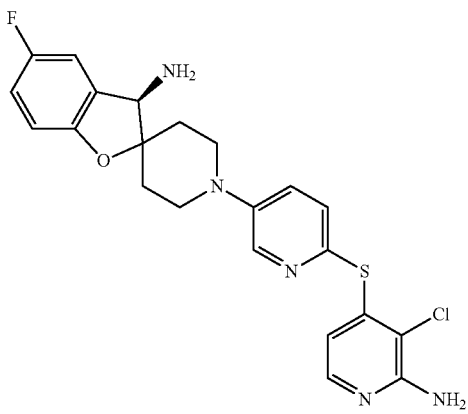 $C_{22}H_{21}ClFN_5OS$ |

TABLE 1-continued
Representative Compounds of the disclosure.
| Example | Structure |
|---|---|
| 226 | 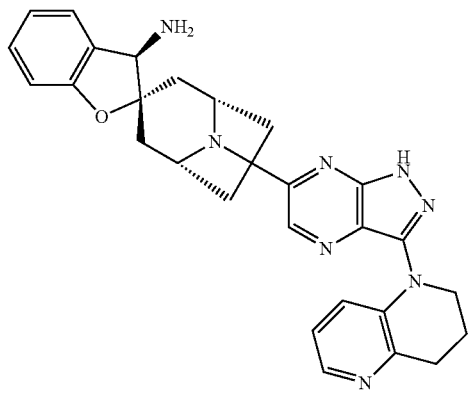<br>$C_{27}H_{28}N_8O$ |
| 227 | 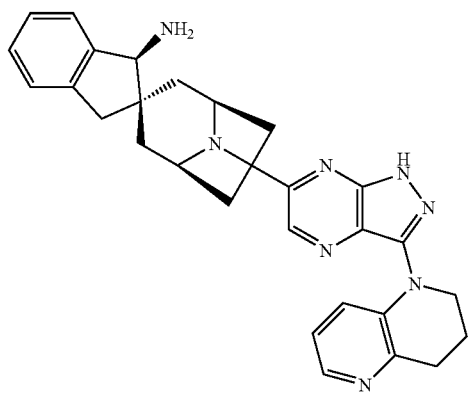<br>$C_{28}H_{30}N_8$ |
| 228 | 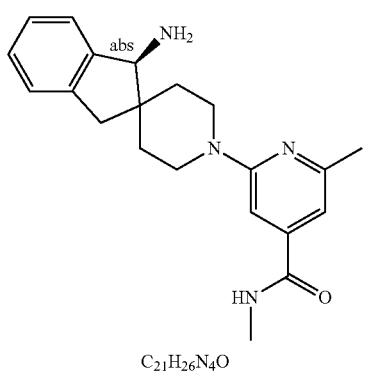 [SMILES: CNC(=O)c1cc(C)nc(N2CCC3(CC2)Cc2ccccc2[C@H]3N)c1 ; "C21H26N4O"]<br>$C_{21}H_{26}N_4O$ |
| 229 | 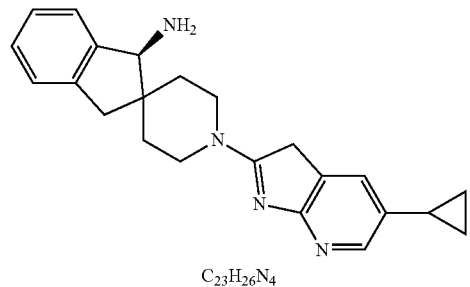 [SMILES: N[C@@H]1c2ccccc2CC12CCN(C1=Nc3ncc(C4CC4)cc3C1)CC2 ; "C23H26N4"]<br>$C_{23}H_{26}N_4$ |

167
168
TABLE 1-continued
Representative Compounds of the disclosure.
| Example | Structure |
|---|---|
| 230 | 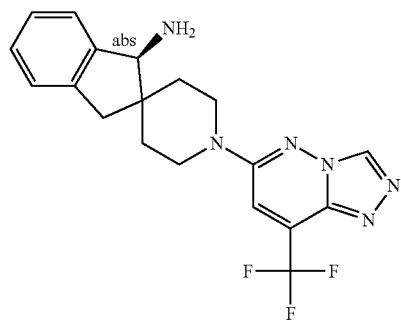<br>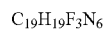 $C_{19}H_{19}F_3N_6$ |
| 231 | 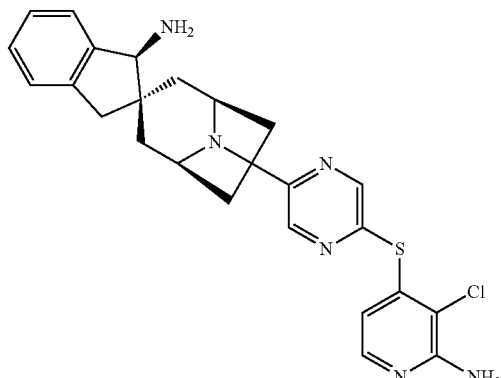<br>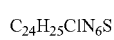 $C_{24}H_{25}ClN_6S$ |
| 232 | 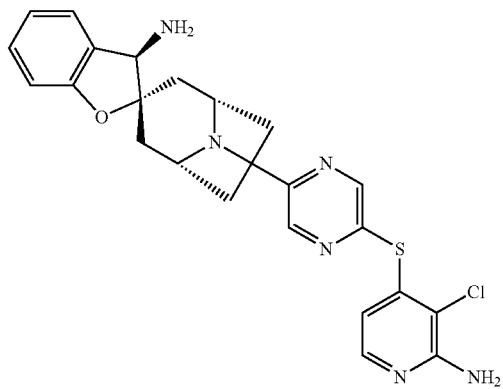<br> $C_{23}H_{23}ClN_6OS$ |

TABLE 1-continued
Representative Compounds of the disclosure.
| Example | Structure |
|---|---|
| 233 | 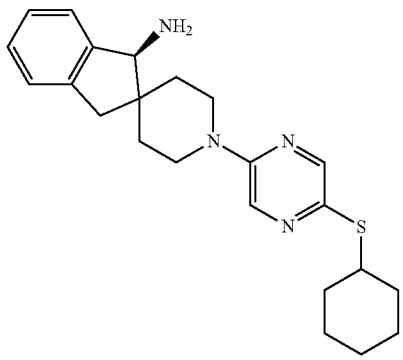<br>C$_{23}$H$_{30}$N$_4$S |
| 234 | 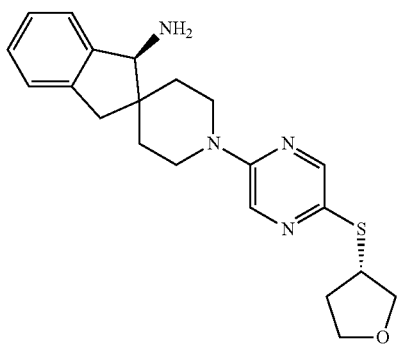<br>C$_{21}$H$_{26}$N$_4$OS |
| 235 | 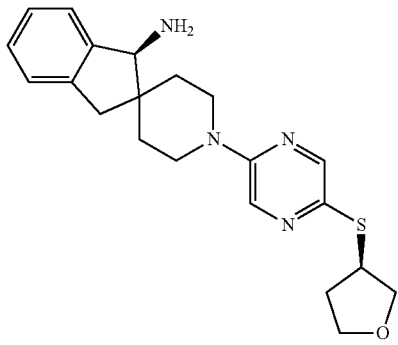<br>C$_{21}$H$_{26}$N$_4$OS |
| 236 | 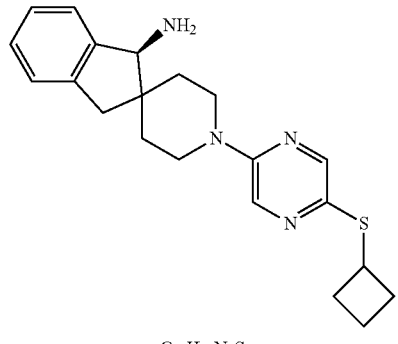<br>C$_{21}$H$_{26}$N$_4$S |

US 10,934,302 B1
TABLE 1-continued
Representative Compounds of the disclosure.
| Example | Structure |
|---|---|
| 237 | 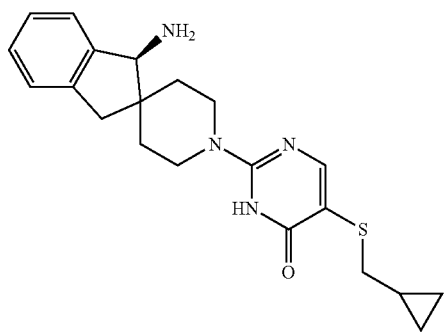
$C_{21}H_{26}N_4OS$ |
| 238 | 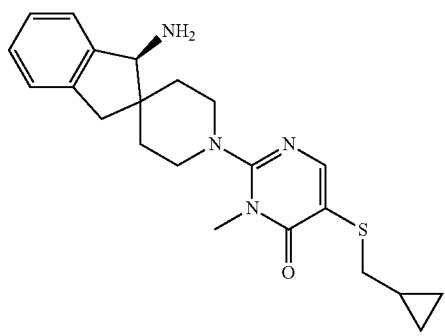
$C_{22}H_{28}N_4OS$ |
| 239 | 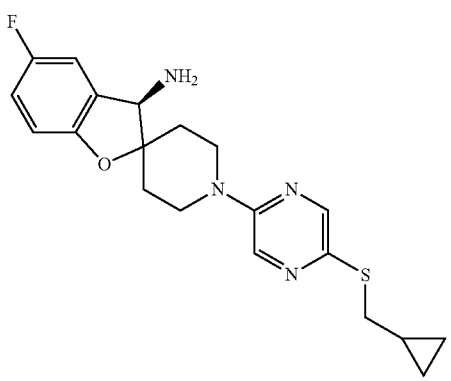
$C_{20}H_{23}FN_4OS$ |
| 240 | 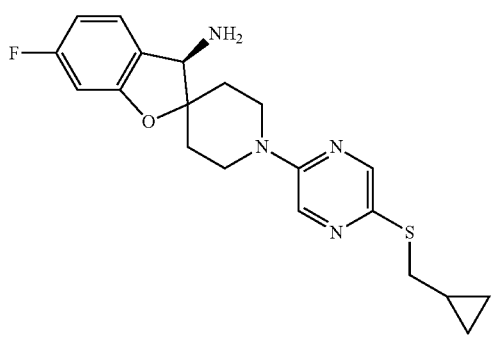
$C_{20}H_{23}FN_4OS$ |

US 10,934,302 B1
173
174
TABLE 1-continued
Representative Compounds of the disclosure.
| Example | Structure |
|---|---|
| 241 | 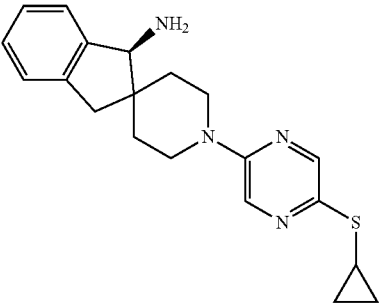<br>C$_{20}$H$_{24}$N$_4$S |
| 242 | 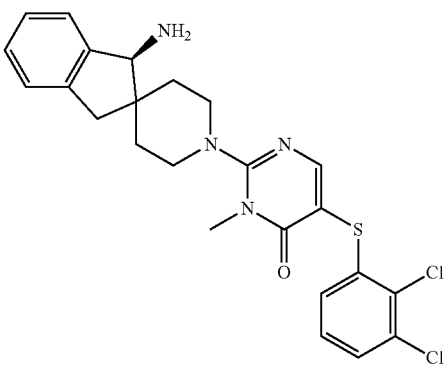<br>C$_{24}$H$_{24}$N$_4$OS |
| 243 | 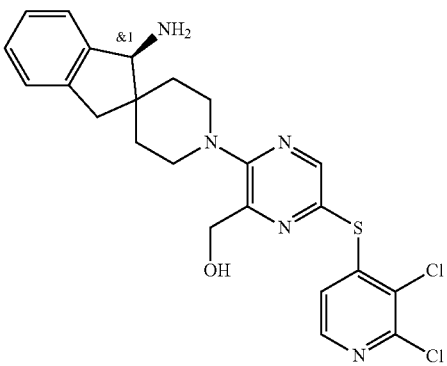<br>C$_{23}$H$_{23}$Cl$_2$N$_5$OS |
| 244 | 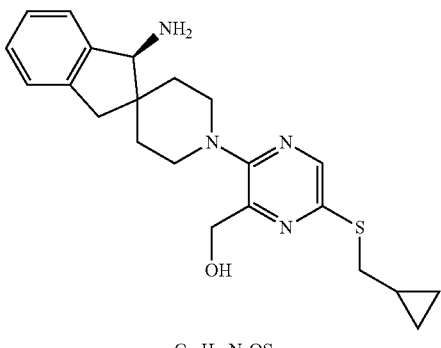<br>C$_{22}$H$_{28}$N$_4$OS |

TABLE 1-continued
Representative Compounds of the disclosure.
| Example | Structure |
|---|---|
| 245 | 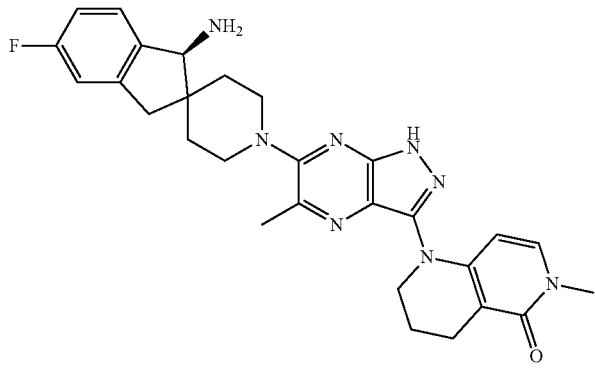<br>C₂₈H₃₁FN₈O |
| 246 | 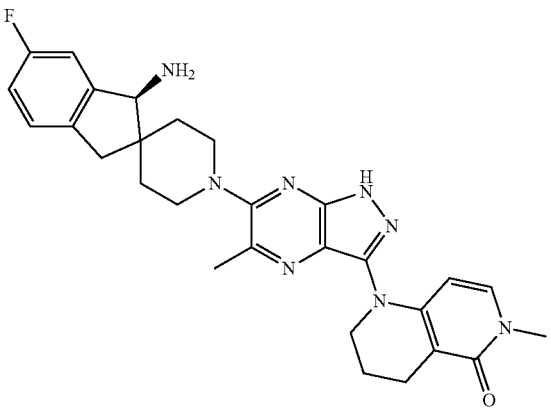<br>C₂₈H₃₁FN₈O |
| 247 | 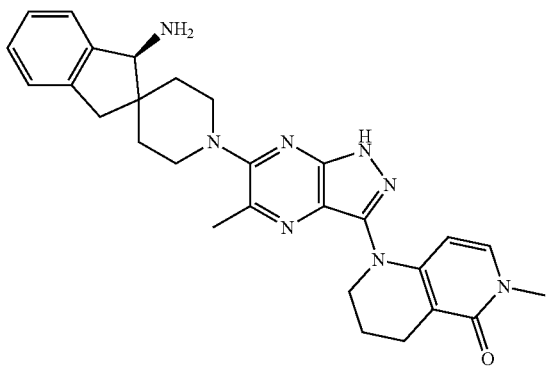<br>C₂₈H₃₂N₈O |
| 248 | 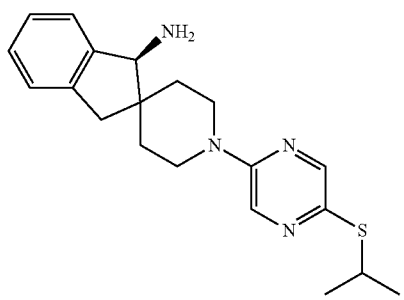<br>C₂₀H₂₆N₄S |

US 10,934,302 B1
177      178
TABLE 1-continued
Representative Compounds of the disclosure.
| Example | Structure |
|---|---|
| 249 | 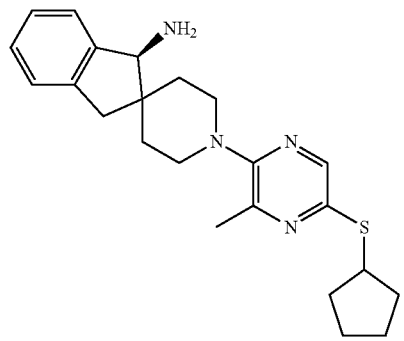<br>C$_{23}$H$_{30}$N$_4$S |
| 250 | 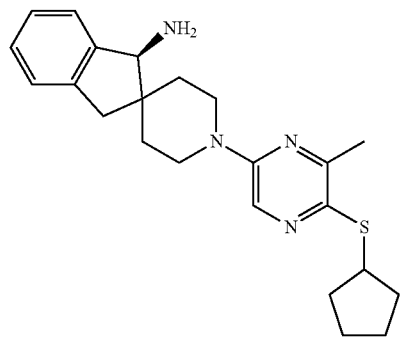<br>C$_{23}$H$_{30}$N$_4$S |
| 251 | 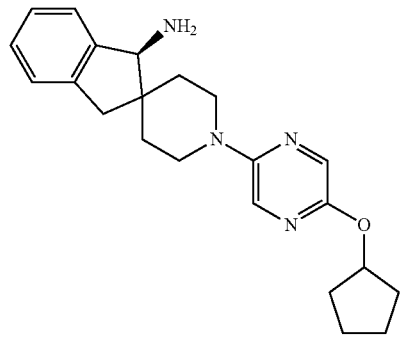<br>C$_{22}$H$_{28}$N$_4$O |
| 252 | 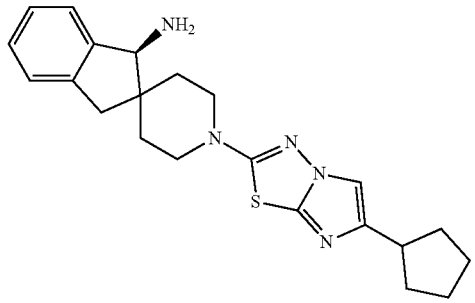<br>C$_{22}$H$_{27}$N$_5$S |

TABLE 1-continued
Representative Compounds of the disclosure.
| Example | Structure |
|---|---|
| 253 | 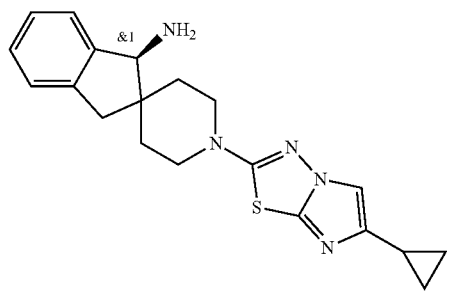
$C_{20}H_{23}N_5S$ |
| 254 | 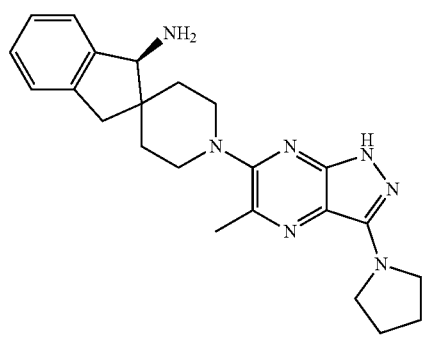
$C_{23}H_{29}N_7$ |
| 255 | 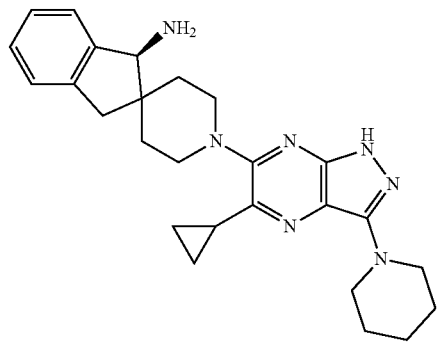
$C_{26}H_{33}N_7$ |
| 256 | 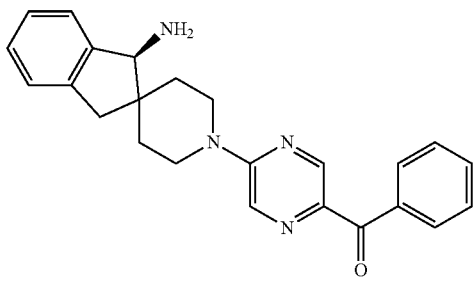
$C_{24}H_{24}N_4O$ |

181
182
TABLE 1-continued
Representative Compounds of the disclosure.
| Example | Structure |
| --- | --- |
| 257 | 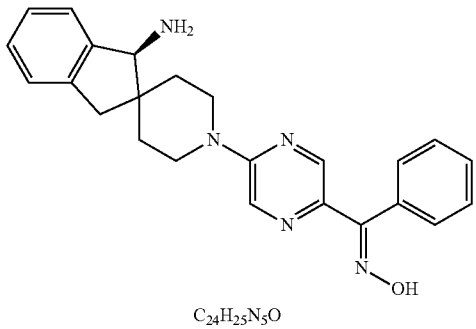 [SMILES: N[C@@H]1c2ccccc2CC12CCN(c1cnc(/C(=N/O)c3ccccc3)cn1)CC2 ; "C24H25N5O"]<br>$C_{24}H_{25}N_5O$ |
| 258 | 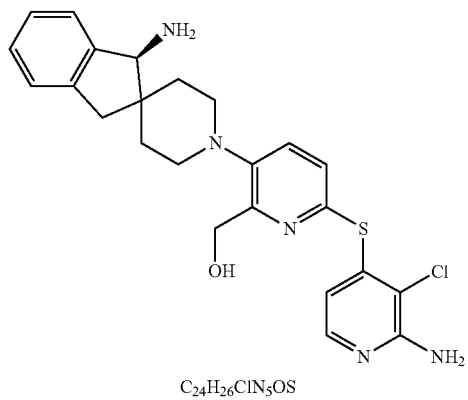 [SMILES: Nc1nccc(Sc2ccc(N3CCC4(CC3)Cc3ccccc3[C@H]4N)c(CO)n2)c1Cl ; "C24H26ClN5OS"]<br>$C_{24}H_{26}ClN_5OS$ |
| 259 | 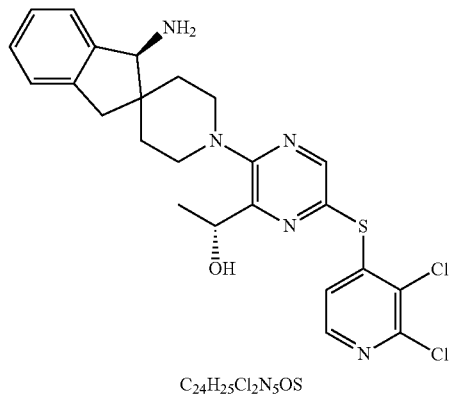 [SMILES: C[C@@H](O)c1nc(Sc2ccnc(Cl)c2Cl)cnc1N1CCC2(CC1)Cc1ccccc1[C@H]2N ; "C24H25Cl2N5OS"]<br>$C_{24}H_{25}Cl_2N_5OS$ |
| 260 | 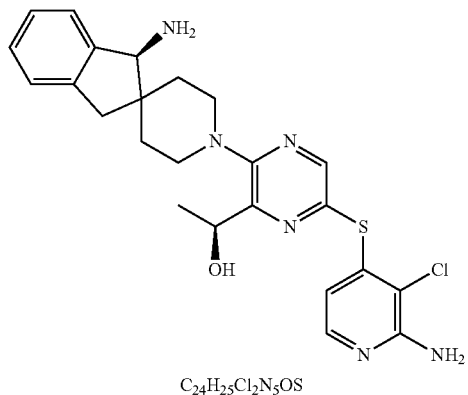 [SMILES: C[C@H](O)c1nc(Sc2ccnc(N)c2Cl)cnc1N1CCC2(CC1)Cc1ccccc1[C@H]2N ; "C24H25Cl2N5OS"]<br>$C_{24}H_{25}Cl_2N_5OS$ |

TABLE 1-continued
Representative Compounds of the disclosure.
| Example | Structure |
|---------|-----------|
| 261 | 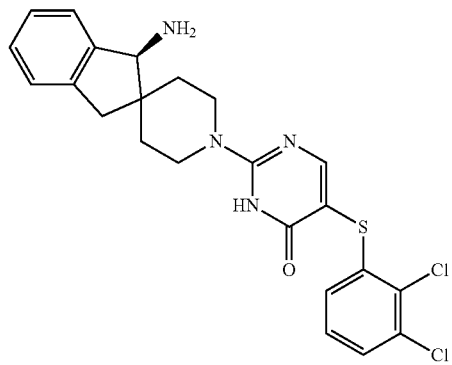<br>C₂₃H₂₂Cl₂N₄OS |
| 262 | 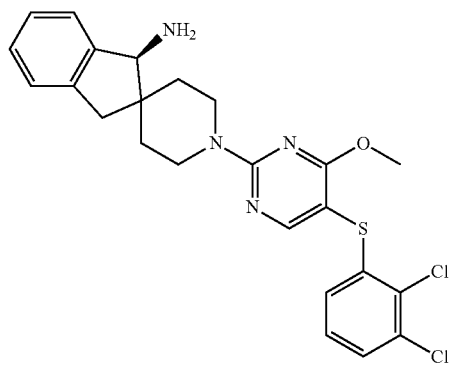<br>C₂₄H₂₄Cl₂N₄OS |
| 263 | 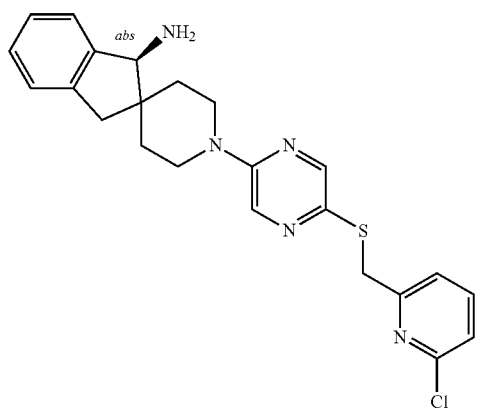<br>C₂₃H₂₄ClN₅S |

TABLE 1-continued
Representative Compounds of the disclosure.
| Example | Structure |
|---|---|
| 264 | 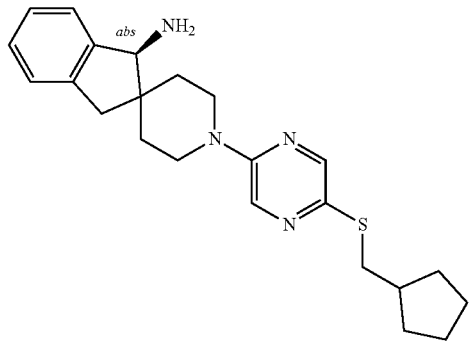<br>$C_{23}H_{30}N_4S$ |
| 265 | 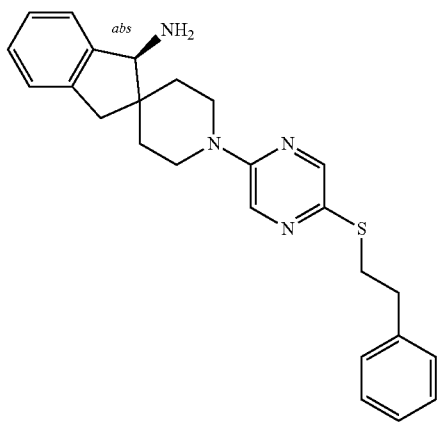<br>$C_{25}H_{28}N_4S$ |
| 266 | 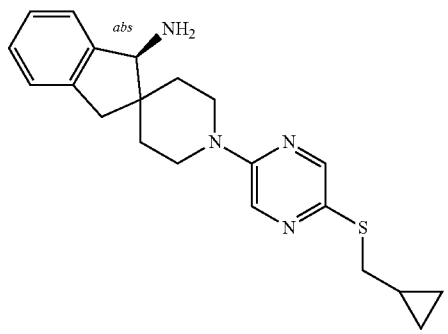<br>$C_{21}H_{26}N_4S$ |

TABLE 1-continued
Representative Compounds of the disclosure.
| Example | Structure |
|---|---|
| 267 | 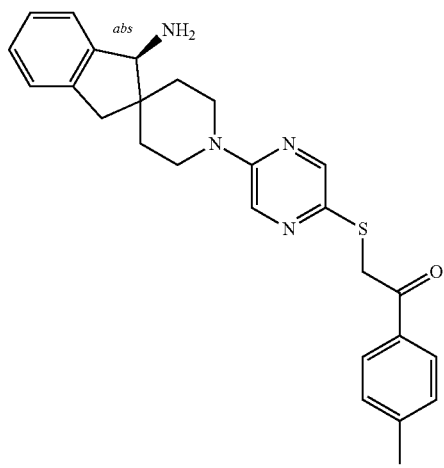<br>$C_{26}H_{28}N_4OS$ |
| 268 | 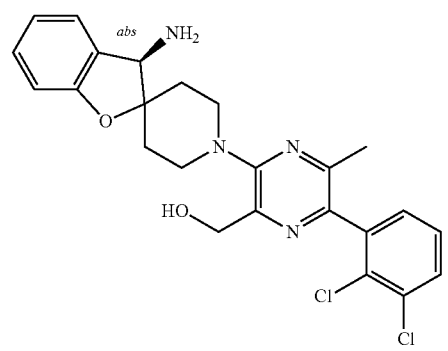<br>$C_{24}H_{24}Cl_2N_4O_2$ |
| 269 | 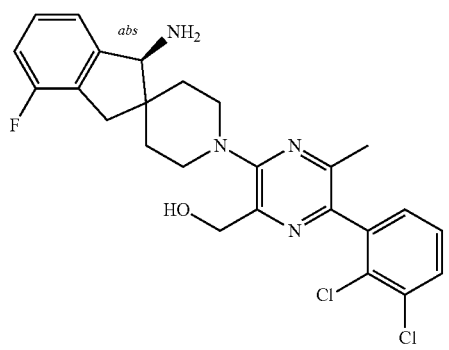<br>$C_{25}H_{25}Cl_2FN_4O$ |

US 10,934,302 B1
189
190
TABLE 1-continued
Representative Compounds of the disclosure.
| Example | Structure |
|---|---|
| 270 | 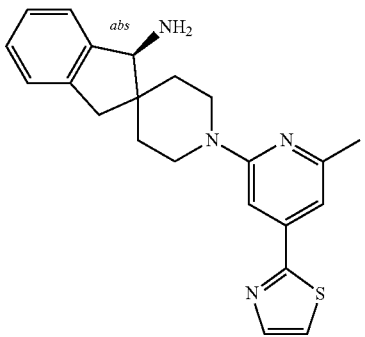<br>C₂₂H₂₄N₄S |
| 271 | 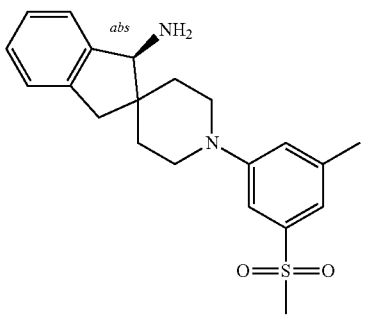<br>C₂₁H₂₆N₂O₂S |
| 272 | 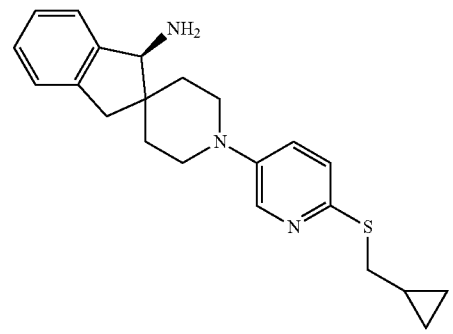<br>C₂₂H₂₇N₃S |
| 273 | 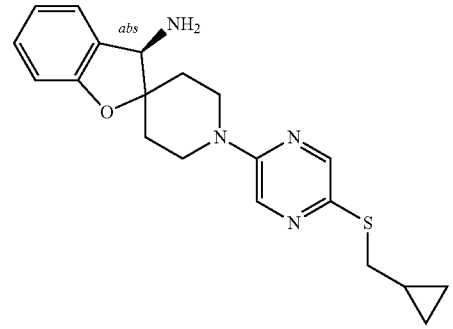<br>C₂₀H₂₄N₄OS |

TABLE 1-continued
Representative Compounds of the disclosure.
| Example | Structure |
|---|---|
| 274 | 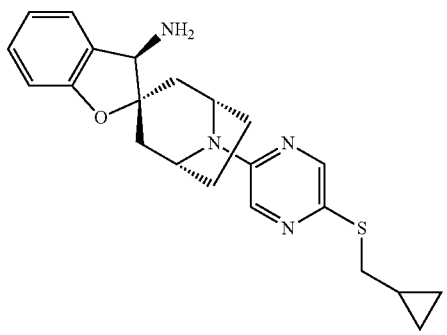<br>$C_{22}H_{26}N_4OS$ |
| 275 | 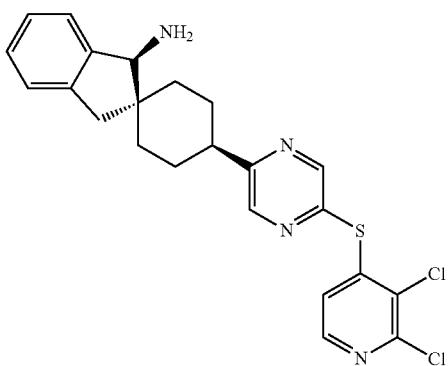<br>$C_{23}H_{22}Cl_2N_4S$ |
| 276 | 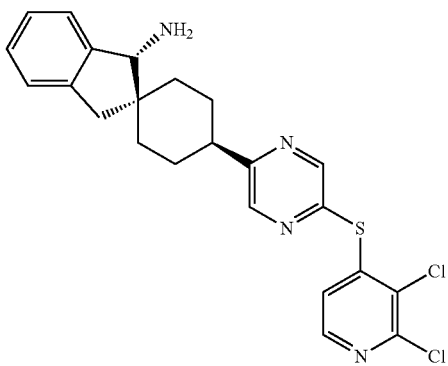<br>$C_{23}H_{22}Cl_2N_4S$ |
| 277 | 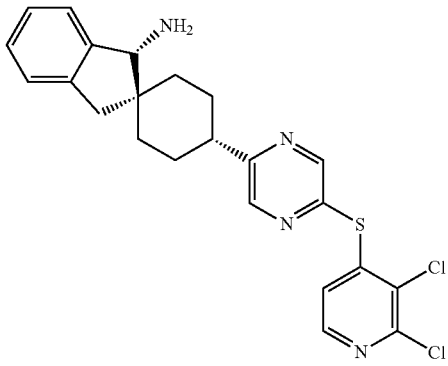<br>$C_{23}H_{22}Cl_2N_4S$ |

TABLE 1-continued
Representative Compounds of the disclosure.
| Example | Structure |
|---|---|
| 278 | 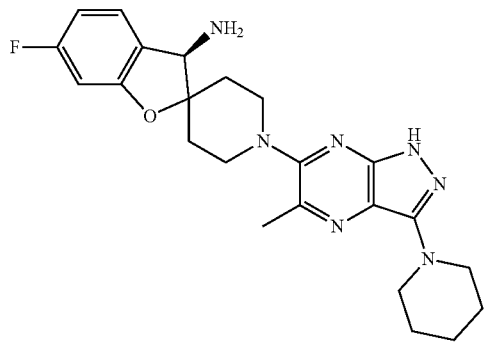<br>$C_{23}H_{28}FN_7O$ |
| 279 | 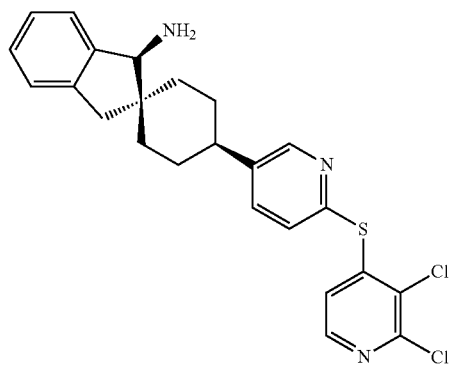<br>$C_{24}H_{23}Cl_2N_3S$ |
| 280 | 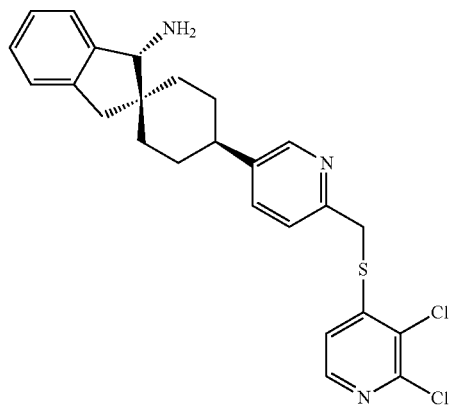<br>$C_{24}H_{23}Cl_2N_3S$ |

TABLE 1-continued
Representative Compounds of the disclosure.
| Example | Structure |
|---|---|
| 281 | 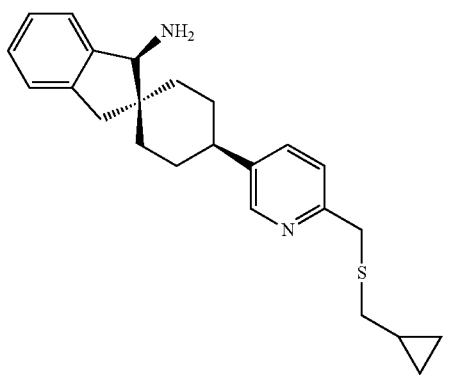<br>$C_{23}H_{28}N_2S$ |
| 282 | 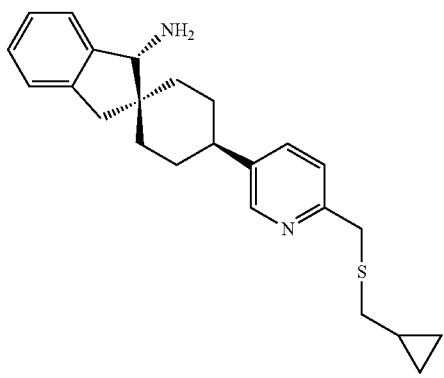<br>$C_{23}H_{28}N_2S$ |
| 283 | 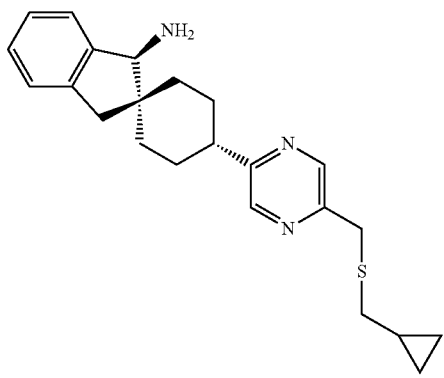<br>$C_{22}H_{27}N_3S$ |
| 284 | 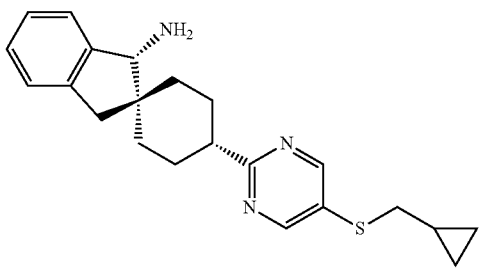<br>$C_{22}H_{27}N_3S$ |

TABLE 1-continued
Representative Compounds of the disclosure.
| Example | Structure |
|---|---|
| 285 | 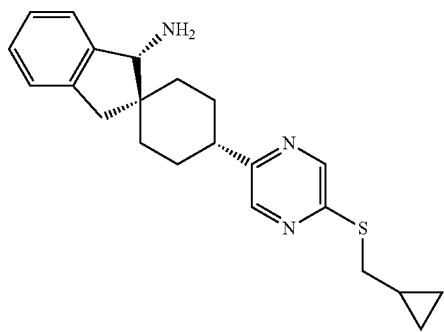
$C_{22}H_{27}N_3S$ |
| 286 | 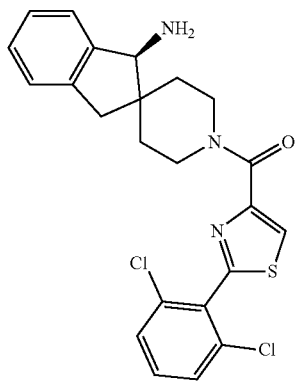
$C_{23}H_{21}Cl_2N_3OsS$ |
| 287 | 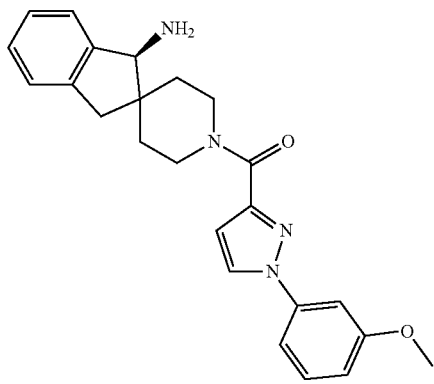
$C_{24}H_{26}N_4O_2$ |
| 288 | 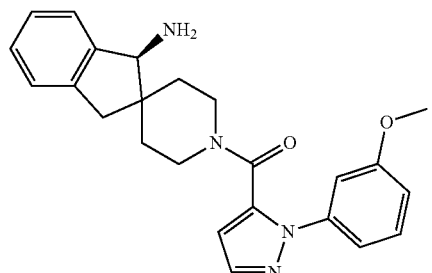
$C_{24}H_{26}N_4O_2$ |

TABLE 1-continued
Representative Compounds of the disclosure.
| Example | Structure |
|---|---|
| 289 | 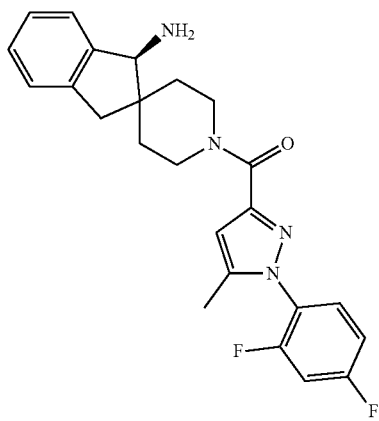<br>H24H24F2N4O |
| 290 | 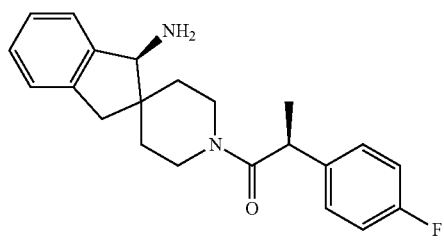<br>C22H25FN2O |
| 291 | 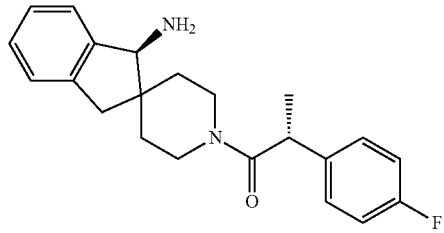<br>C22H25FN2O |
| 292 | 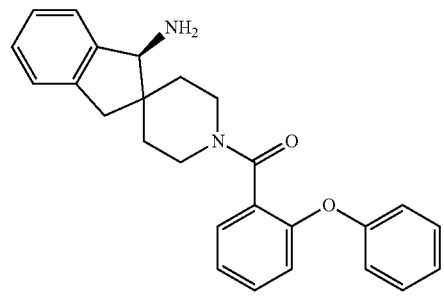<br>C26H26N2O2 |

TABLE 1-continued

Representative Compounds of the disclosure.

| Example | Structure |
|---|---|
| 293 | 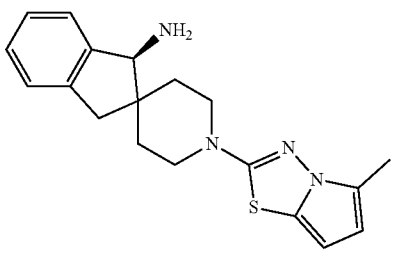<br>C$_{18}$H$_{21}$N$_5$S |
| 294 | 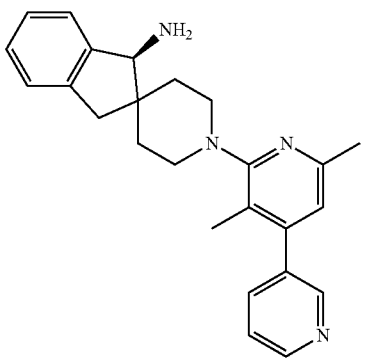<br>C$_{25}$H$_{28}$N$_4$ |

Compounds or compositions of the disclosure can be useful in applications that benefit from inhibition of SHP2 phosphatase enzymes. For example, inhibition of SHP2 phosphatase may offer a therapeutic approach for the treatment of cancer. (See, e.g., Y.-N. P. Chen et al., in *Nature*, 2016, doi:10.1038/nature18621; and references cited therein; each of which hereby incorporated by reference in its entirety.) Inhibition of SHP2 phosphatase also has been found to ameliorate the pathogensis of systemic lupus erythematosus. (See, e.g, J. Wang et al., in *J. Clin. Invest.* 2016, 126, 2077-2092; and references cited therein; each of which hereby incorporated by reference in its entirety.)

In some embodiments, compounds or compositions of the disclosure can be useful in suppressing tumor cell growth. In some embodiments, compounds or compositions of the disclosure can be useful in ameliorating the pathogenesis of systemic lupus erythematosus. In some embodiments, compounds or compositions of the disclosure can be useful in the treatment of various other disorders, including neurofibromatosis (e.g. neurofibromatosis type 1 (NF1), Noonan syndrome (NS)), diabetes, neuroblastoma, melanoma (see. Hill et al, Mol. Cancer Res. 2019, 77, 583-593), juvenile leukemia, juvenile myelomonocytic leukemia (JMML, see Yu et al, Mol. Cancer Ther. 2013, 12, 1738-1748), chronic myelomonocytic leukemia, acute myeloid leukemia, HER2-positive breast cancer (see Hu et al, Oncol Rep. 2014; 32(1): 205-12; and Zhao et al, Oncogene, doi: 10.1038/s41388-018-0574-8), triple-negative breast cancer (see Sausgruber et al, Oncogene, 2015, 34, 2272-2278), ductal carcinoma of the breast, invasive ductal carcinoma of the breast, non-small cell lung cancer (including adenocarcinoma of the lung, see Nichols et al, 2018, Nat. Cell Biol. 20, 1064-1073; and Mainardi et al, 2018, Nat Med. 24(4): 512-517), colorectal cancer, esophageal cancer (Qi et al, 2017, Int. J. Mol. Sci. 18, 134), gastric cancer, squamous-cell carcinoma of the head and neck (SCCHN), neutropenia (Kostmann's syndrome), ovarian cancer (see Sun et al, 2019, Am J Cancer Res.; 9(1): 145-159), an FGFR1-amplified/mutant cancer (e.g. FGFR1-amplified or mutant breast cancer, lung cancer, or prostate cancer), an FGFR2-amplified cancer (e.g. FGFR2-amplified gastric cancer), an FGFR2-fusion/mutant cancer (e.g. FGFR2-fusion/mutant cholangiocarcinoma), or an FGFR3-fusion/mutant cancer (e.g. FGFR3-fusion or mutant bladder cancer). In some embodiments, the disorder treated is a proliferative disorder. In some embodiments, the disorder treated is a solid tumor. In some embodiments, the disorder treated is a neurofibromatosis (e.g. neurofibromatosis type 1 (NF1), Noonan syndrome (NS)). In some embodiments, the disorder treated is diabetes. In some embodiments, the disorder treated is a neuroblastoma. In some embodiments, the disorder treated is melanoma. In some embodiments, the disorder treated is a hematological cancer. In some embodiments, the disorder treated is a juvenile leukemia. In some embodiments, the disorder treated is a juvenile myelomonocytic leukemia (JMML). In some embodiments, the disorder treated is a chronic myelomonocytic leukemia. In some embodiments, the disorder treated is an acute myeloid leukemia. In some embodiments, the disorder treated is a breast cancer. In some embodiments, the disorder treated is a HER2-positive breast cancer. In some embodiments, the disorder treated is a triple-negative breast cancer. In some embodiments, the disorder treated is a ductal carcinoma of the breast. In some embodiments, the disorder treated is an invasive ductal carcinoma of the breast. In some embodiments, the disorder treated is a non-small cell lung cancer (including adenocarcinoma of the lung). In some embodiments, the disorder treated is a colorectal cancer. In some embodiments, the disorder treated is an esophageal cancer. In some embodiments, the disorder treated is a gastric cancer. In some embodiments, the disorder treated is a squamous-cell carcinoma of the head and neck (SCCHN). In some embodiments, the disorder treated is a neutropenia (e.g. Kostmann's syndrome). In some embodiments, the disorder treated is an ovarian cancer. In some embodiments, the disorder treated is an FGFR1-amplified/mutant cancer (e.g. FGFR1-amplified or mutant breast cancer, lung cancer, or prostate cancer). In some embodiments, the disorder treated is an FGFR2-amplified cancer (e.g. FGFR2-amplified gastric cancer). In some embodiments, the disorder treated is an FGFR2-fusion/mutant cancer (e.g. FGFR2-fusion/mutant cholangiocarcinoma). In some embodiments, the disorder treated is or an FGFR3-fusion/mutant cancer (e.g. FGFR3-fusion or mutant bladder cancer).

In some embodiments, compounds or compositions of the disclosure can be used in combination with other treatments and/or cancer therapies. For example, compounds or compositions of the disclosure can be used in combination with, but are not limited to, antibodies, antibody-drug conjugates, kinase inhibitors, immunomodulators, and histone deacetylase inhibitors. The compounds or compositions of the disclosure can also be used in combination with other treatments and/or cancer therapies as disclosed in WO 2015/107495; and references cited therein; each of which is hereby incorporated by reference in its entirety.

For example, the compounds disclosed herein (or pharmaceutical compositions containing them) can be used in the treatment of one or more of the diseases mentioned herein, alone or in combination with another therapeutic agent. For example, in some embodiments, a provided compound can be used in combination with one or more of the following agents, or a pharmaceutically acceptable salt thereof: BCR-ABL inhibitors: e.g. imatinib, inilotinib, nilotinib, dasatinib, bosutinib, ponatinib, bafetinib, danusertib, saracatinib, PF03814735; ALK inhibitors (see Dardaei et al, 2018, Nat Med.; 24(4):512-517): e.g. crizotinib, NVP-TAE684, ceritinib, alectinib, brigatinib, entrecinib, lorlatinib; BRAF inhibitors (see Prahallad et al, 2015, Cell Rep. 12, 1978-1985): e.g. vemurafenib, dabrafenib; FGFR inhibitors: e.g. infigratinib, dovitinib, erdafitinib, BLU-554, AZD4547; FLT3 inhibitors: e.g. sunitinib, midostaurin, tanutinib, sorafenib, lestaurtinib, quizartinib, and crenolanib; MEK Inhibitors (see Fedele et al, 2018, BioRxiv 307876; Torres-Ayuso et al, 2018, Cancer Discov. 8, 1210-1212; and Wong et al, 2016, Oncotarget. 2016 Oct. 4; 7(40): 65676-65695): e.g. trametinib, cobimetinib, binimetinib, selumetinib; ERK inhibitors: e.g. ulixertinib, MK-8353, LY-3214996; VEGF receptor inhibitors: e.g. bevacizumab, axitinib, aflibercept, brivanib, motesanib, pasireotide, sorafenib; Tyrosine kinase inhibitors: e.g. erlotinib, linifanib, sunitinib, pazopanib; Epidermal growth factor receptor (EGFR) inhibitors: gefitnib, osimertinib, cetuximab, panitumumab; HER2 receptor inhibitors: e.g. trastuzumab, neratinib, lapatinib, lapatinib; MET inhibitors: e.g. crizotinib, cabozantinib; CD20 antibodies: e.g. rituximab, tositumomab, ofatumumab; DNA Synthesis inhibitors: e.g. capecitabine, gemcitabine, nelarabine, hydroxy carbamide; Antineoplastic agents: e.g. oxaliplatin, cisplatin; HER dimerization inhibitors: e.g. pertuzumab; Human Granulocyte colony-stimulating factor (G-CSF) modulators: e.g. filgrastim; Immunomodulators: e.g. afutuzumab, lenalidomide, thalidomide, pomalidomide; CD40 inhibitors: e.g. dacetuzumab; Pro-apoptotic receptor agonists (PARAs): e.g. dulanermin; Heat Shock Protein (HSP) inhibitors: e.g. tanespimycin (17-allylamino-17-desmethoxygeldanamycin); Hedgehog antagonists: e.g. vismodegib; Proteasome inhibitors: e.g. bortezomib; PI3K inhibitors: e.g. pictibsib, dactobsib, buparbsib, tasebsib, idelabsib, duvebsib, umbralisib; Phospholipase A2 inhibitors: e.g. anagrelide; BCL-2 inhibitors: e.g. venetoclax; Aromatase inhibitors: exemestane, letrozole, anastrozole, faslodex, tamoxifen; Topoisomerase I inhibitors: e.g. irinotecan, topotecan; Topoisomerase II inhibitors: e.g. etoposide, teniposide; mTOR inhibitors: e.g. temsirolimus, ridaforolimus, everolimus, sirolimus; Osteoclastic bone resorption inhibitors: e.g. zoledronic acid; CD33 Antibody Drug Conjugates: e.g. gemtuzumab ozogamicin; CD22 Antibody Drug Conjugates: e.g. inotuzumab ozogamicin; CD20 Antibody Drug Conjugates: e.g. ibritumomab tiuxetan; Somatostain analogs: e.g. octreotide; Interleukin-11 (IL-11): e.g. oprelvekin; Synthetic erythropoietin: e.g. darbepoetin alfa; Receptor Activator for Nuclear Factor K B (RANK) inhibitors: e.g. denosumab; Thrombopoietin mimetic peptides: e.g. romiplostim; Cell growth stimulators: e.g. palifermin; Anti-Insulin-like Growth Factor-1 receptor (IGF-1R) antibodies: e.g. figitumumab; Anti-CS1 antibodies: e.g. elotuzumab; CD52 antibodies: e.g. alemtuzumab; CTLA-4 inhibitors: e.g. tremelimumab. ipilimumab; PD1 inhibitors: e.g. nivolumab, pembrolizumab; an immunoadhesin; e.g. pidilizumab, AMP-224; PDL1 inhibitors: e.g. MSB0010718C; YW243.55.S70, MPDL3280A; MEDI-4736, MSB-0010718C, or MDX-1105; LAG-3 inhibitors: e.g. BMS-986016; GITR agonists; GITR fusion proteins and anti-GITR antibodies; Histone deacetylase inhibitors (HDI): e.g. voninostat; Anti-CTLA4 antibodies: e.g. tremelimumab, ipilimumab; Alkylating agents: e.g. temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine, streptozocin, thiotepa; Biologic response modifiers: e.g. *bacillus* calmette-guerin, denileukin diftitox; Anti-tumor antibiotics: e.g. doxorubicin, bleomycin, daunorubicin, daunorubicin liposomal, mitoxantrone, epirubicin, idarubicin, mitomycin C; Anti-microtubule agents: e.g. estramustine; Cathepsin K inhibitors: e.g. odanacatib; Epothilone analogs: e.g. ixabepilone; TpoR agonists: e.g. eltrombopag; Anti-mitotic agents: e.g. docetaxel; Adrenal steroid inhibitors: e.g. aminoglutethimide; Anti-androgens: e.g. nilutamide; Androgen Receptor inhibitors: e.g. enzalutamide, abiraterone acetate, orteronel, galeterone, and seviteronel, bicalutamide, flutamide; Androgens: e.g. fluoxymesterone; CDK1 inhibitors: e.g. alvocidib, palbociclib, ribociclib, trilaciclib, abemaciclib; Gonadotropin-releasing hormone (GnRH) receptor agonists: e.g. leuprolide or leuprolide acetate; Taxane anti-neoplastic agents: e.g. cabazitaxel, larotaxel; 5-HT1a receptor agonists: e.g. xaliproden; HPV vaccines: e.g. Cervarix® sold by GlaxoSmithKline, Gardasil® sold by Merck; Iron Chelating agents: e.g. deferasirox; Anti-metabolites: e.g. claribine, 5-fluorouracil, 6-thioguanine, pemetrexed, cytarabine, cytarabine liposomal, decitabine, hydroxyurea, fludarabine, floxuridine, cladribine, methotrexate, pentostatin; Bisphosphonates: e.g. pamidronate; Demethylating agents: e.g. 5-azacitidine, decitabine; Anti-tumor Plant Alkaloids: e.g. paclitaxel protein-bound; vinblastine, vincristine, vinorelbine, paclitaxel; Retinoids: e.g. alitretinoin, tretinoin, isotretinoin, bexarotene; Glucocorticosteroids: e.g. hydrocortisone, dexamethasone, prednisolone, prednisone, methylprednisolone; Cytokines: e.g. interleukin-2, interleukin-11 (oprevelkin), alpha interferon alfa (IFN-alpha); estrogen receptor downregulators: fulvestrant; Anti-estrogens: e.g. tamoxifen, toremifene; Selective estrogen receptor modulators (SERMs): e.g. raloxifene;

Luteinizing hormone releasing hormone (LHRH) agonists: e.g. goserelin; Progesterones: e.g. megestrol; cytotoxic agents: arsenic trioxide, asparaginase (also known as L-asparaginase, Erwinia L-asparaginase; Anti-nausea drugs: e.g. NK-1 receptor antagonists (e.g. casopitant); Cytoprotective agents: e.g. amifostine, leucovorin; and Immune checkpoint inhibitors. The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAGS. Immunotherapeutic agents which can act as immune checkpoint inhibitors useful in the methods of the present disclosure, include, but are not limited to, inhibitors of PD-L1, PD-L2, CTLA4, TIMS, LAGS, VISTA, BTLA, TIGIT, LAIR1, CD 160, 2B4 and/or TGFR beta.

The compounds described herein can function as allosteric inhibitors and block the activation of SHP2 by targeting the auto-inhibited conformation of SHP2.

The compounds described herein can also inhibit SHP2 function through incorporation into agents that catalyze the destruction of SHP2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of SHP2 to the E3 ligase will thus result in the destruction of the SHP2 protein. The variable chain of atoms can include, for example, rings, heteroatoms, and/or repeating polymeric units. It can be rigid or flexible. It can be attached to the two portions described above using standard techniques.

The compounds described herein can be linked to one end of a variable chain, while the other end of the variable chain can be bound to the E3 ligase. Recruitment of SHP2 to the ligase will thus result in the destruction of the SHP2 protein.

In some embodiments, compounds or compositions of the disclosure can be used in combination with an antibody. In some embodiments, compounds or compositions of the disclosure can be used in combination with an antibody-drug conjugate. In some embodiments, compounds or compositions of the disclosure can be used in combination with a kinase inhibitor. In some embodiments, compounds or compositions of the disclosure can be used in combination with an immunomodulator. In some embodiments, compounds or compositions of the disclosure can be used in combination with a histone deacetyl as e inhibitor.

In some embodiments, the present disclosure provides a method of treating a SHP2-mediated disorder comprising administering to a subject in need thereof a compound described herein, wherein the disorder is selected from those described in WO2019051084A1, hereby incorporated by reference in its entirety.

In some embodiments, the present disclosure provides a method of treating a SHP2-mediated disorder comprising administering to a subject in need thereof a compound described herein together with an additional therapeutic agent, wherein the additional therapeutic agent is not a SHP2 inhibitor, and is selected from those described in WO2019051084A1, hereby incorporated by reference in its entirety.

In some embodiments, a disclosed compound can be administered to a subject in need of treatment at dosages ranging from about 0.0001 mg to about 100 mg/kg body weight of the subject to be treated per day, such as from about 1.0 to 10 mg/kg. However, additional variations are within the scope of the disclosure.

A disclosed compound can be administered alone or in combination with pharmaceutically acceptable carriers, such as diluents, fillers, aqueous solution, and even organic solvents. The compound and/or compositions of the disclosure can be administered as a tablet, powder, lozenge, syrup, injectable solution, and the like. Additional ingredients, such as flavoring, binder, excipients, and the like are within the scope of the disclosure.

In some embodiments, pharmaceutically acceptable compositions can contain a disclosed compound and/or a pharmaceutically acceptable salt thereof at a concentration ranging from about 0.01 to about 90 wt %, about 0.01 to about 80 wt %, about 0.01 to about 70 wt %, about 0.01 to about 60 wt %, about 0.01 to about 50 wt %, about 0.01 to about 40 wt %, about 0.01 to about 30 wt %, about 0.01 to about 20 wt %, about 0.01 to about 2.0 wt %, about 0.01 to about 1 wt %, about 0.05 to about 0.5 wt %, about 1 to about 30 wt %, or about 1 to about 20 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

In some embodiments, the present disclosure provides for the use of pharmaceutical compositions and/or medicaments comprised of a disclosed compound or a pharmaceutically acceptable salt thereof, in a method of treating a disease state, and/or condition caused by or related to SHP2 phosphatase. For example, provided herein are methods of treating subjects in need thereof (e.g., subjects suffering from cancer (e.g., leukemia, breast, lung and/or colorectal cancer) an effective amount of a disclosed compound, and optionally an effective amount of an additional compound (e.g., therapeutic agent) such as disclosed herein.

In some embodiments, the method of treatment comprises the steps of: i) identifying a subject in need of such treatment; (ii) providing a disclosed compound, e.g., of Formula Ia, Formula Ib, Formula II, Formula III, Formula X, or Formula XI, or a pharmaceutically acceptable salt thereof; and (iii) administering said disclosed compound, e.g., of Formula Ia, Formula Ib, Formula II, Formula III, Formula X, or Formula XI in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a disclosed compound, e.g., of Formula Ia, Formula Ib, Formula II, Formula III, Formula X, or Formula XI, or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, a compound or composition of the disclosure is administered orally, intravenously, by inhalation, intranasally, intraocularly, topically, subcutaneously, rectally, intravaginally, or intrathecally. In some embodiments, the compound or composition is administered orally. In some embodiments, the compound or composition is administered intravenously.

In some embodiments, the methods comprise administering to the subject an effective amount of a disclosed compound, e.g., of Formula Ia, Formula Ib, Formula II, Formula III, Formula X, or Formula XI, or a pharmaceutically acceptable salt thereof; or a composition comprising a disclosed compound, e.g., of Formula Ia, Formula Ib, Formula II, Formula III, Formula X, or Formula XI, or a pharmaceutically acceptable salt thereof, and a pharmaceutically acceptable carrier.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g, water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modem Pharmaceutics, 5$^{th}$ Ed. (Alexander T. Florence, Juergen Siepmann, CRC Press (2009)); Handbook of Pharmaceutical Excipients, 7$^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the method of treatment, prevention and/or suppression of a condition related to SHP2 phosphatase comprises the steps of: i) identifying a subject in need of such treatment; (ii) providing a disclosed compound, e.g., of Formula Ia, Formula Ib, Formula II, Formula III, Formula X, or Formula XI, or a pharmaceutically acceptable salt thereof; or a composition comprising a disclosed compound, e.g., of Formula Ia, Formula Ib, Formula II, Formula III, Formula X, or Formula XI, or a pharmaceutically acceptable salt thereof, and a pharmaceutically acceptable carrier; and (iii) administering said compound or composition in a therapeutically effective amount to treat, prevent and/or suppress the disease state or condition related to SHP2 phosphatase in a subject in need of such treatment.

In some embodiments, the compounds of the disclosure are formulated into pharmaceutical compositions for administration to subjects in a biologically compatible form suitable for administration in vivo. According to another aspect, the present disclosure provides a pharmaceutical composition comprising a disclosed compound, e.g., of Formula Ia, Formula Ib, Formula II, Formula III, Formula X, or Formula XI, in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula N$^+$R'R"R'"R""Y$^-$, in which the R radicals are identical or different optionally hydroxylated hydrocarbon radicals and Y$^-$ is an anion of a strong acid, such as halide, sulfate and sulfonate anions; cetyltrimethylammonium bromide is one of the cationic surfactants which can be used, amine salts of formula N$^+$R'R"R'", in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, poly glycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, a disclosed compound, e.g., of Formula Ia, Formula Ib, Formula II, Formula III, Formula X, or Formula XI, and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present disclosure are administered to a human or animal subject by known procedures including oral administration, sublingual or buccal administration. In some embodiments, the compound and/or composition is administered orally.

For oral administration, a formulation of the compounds of the disclosure may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present disclosure, the compounds of the disclosure are administered to the subject in a therapeutically effective amount, e.g, to reduce or ameliorate symptoms related to SHP2 phosphatase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the disclosure may be provided in a kit comprising the compounds and/or compositions. Thus, in some embodiments, the compound and/or composition of the disclosure is provided in a kit.

Those skilled in the art will recognize, or be able to ascertain using no more than routine experimentation, many equivalents to the specific embodiments of the disclosure described herein. Such equivalents are intended to be within the scope of the present disclosure.

The disclosure is further described by the following non-limiting Examples.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the disclosure.

Examples are provided herein to facilitate a more complete understanding of the disclosure. The following examples serve to illustrate the exemplary modes of making and practicing the subject matter of the disclosure. However, the scope of the disclosure is not to be construed as limited to specific embodiments disclosed in these examples, which are illustrative only. The compounds of Formula (I), for example, can generally be prepared according to exemplary Scheme 1:

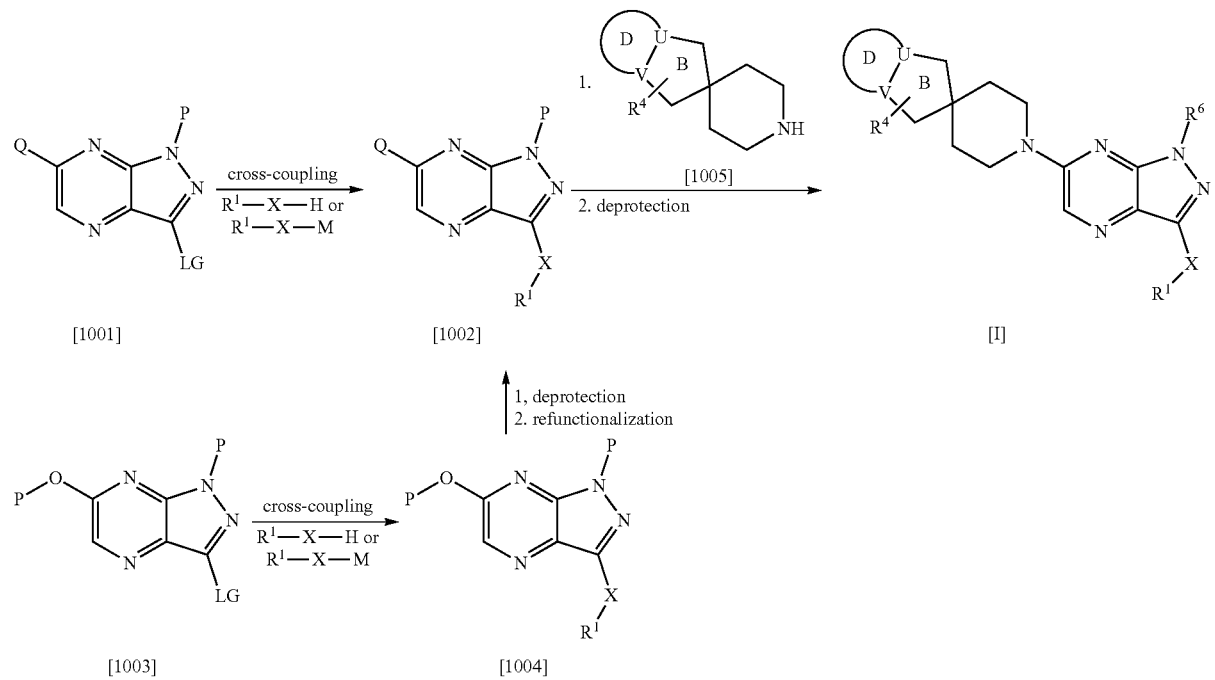

where X, $R^1$, $R^6$, $R^4$, U, V, B and D are as defined as elsewhere herein, Q is independently a halogen, such as Cl, Br, I, and the like, or any other leaving group, such as OSChMe, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene el al., Protective Groups in Organic Synthesis ($4^{th}$ ed. 2006).

As shown in Scheme 1, an aryl compound such as a compound of Formula 1001 undergoes a cross-coupling reaction with a metalated or otherwise activated moiety to provide a compound of Formula 1002. The compound of Formula 1002 then undergoes a substitution reaction with an amine such as Compound 1005, followed by removal of the protecting group to provide a compound of Formula (I). In some embodiments, LG is I. In some embodiments, LG is Cl. In some embodiments, LG is OTf or OTs. Alternatively, a protected heteroaryl ether, such as a compound of Formula 1003, undergoes a cross-coupling reaction to provide a compound of Formula 1004. The ether protecting group is subsequently removed and the resulting hydroxyl group activated to form a Q group, such as OSChMe, OMs, OTs, OTf, and the like, to form a compound of Formula 1002, which can then be carried forward to prepare compounds having the Formula (I).

Alternatively, compounds of the disclosure can generally be prepared according to exemplary Scheme 2:

stitution reaction with an amine such as 1005 to provide a compound of Formula 1006. The compound of Formula 1006 then undergoes a cross-coupling reaction with a metalated or otherwise activated moiety to provide a compound of Formula 1007. In some embodiments, the compound of Formula 1007 can be deprotected to produce a compound of Formula (I). In other embodiments, the compound of Formula 1007 can be left protected and functional groups on the $R^1$ moiety refunctionalized by methods known to those of ordinary skill in the art.

In some embodiments, the cross-coupling reaction is a Buchwald-Hartwig reaction. In some embodiments, the cross-coupling reaction is a Chan-Lam coupling reaction. In

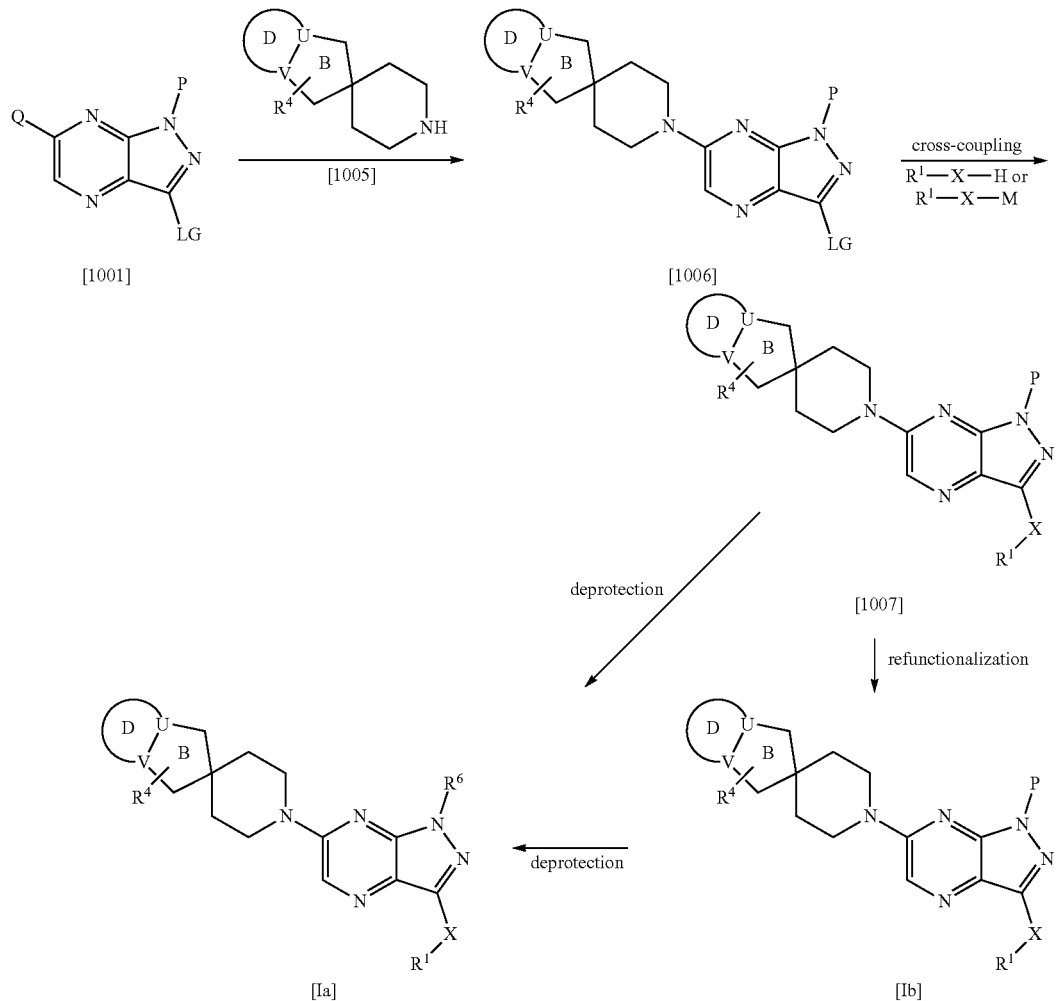

wherein X, $R^1$, $R^6$, $R^4$, U, V, B and D are as defined as elsewhere herein, Q is independently a halogen, such as Cl, Br, I, and the like, or any other leaving group, such as OSChMe, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene el al., Protective Groups in Organic Synthesis (4$^{th}$ ed. 2006).

As shown in Scheme 2, an aryl compound such as a compound of Formula 1001 undergoes a undergoes a sub-some embodiments, the cross-coupling reaction is an Ullmann reaction. In some embodiments, the cross-coupling reaction is a Suzuki reaction. In some embodiments, the cross-coupling reaction is a Stille reaction. In some embodiments, the cross-coupling reaction is a Negishi reaction. In some embodiments, the cross-coupling reaction is a Hiyama reaction. Other cross-coupling reactions may be employed as would be apparent to one of ordinary skill in the art.

In some embodiments, the protecting group is removed under acidic conditions, such as HBr in AcOH. Conditions for removal of the protecting group will depend on the nature of the protecting group. Conditions for the removal of various protecting groups can be found, e.g., in Greene el al. Protective Groups in Organic Synthesis (4<sup>th</sup> ed. 2006).

Reactions were monitored and final products were characterized using one of the following methods. LCMS standard conditions were: Waters HPLC system equipped with an Alliance 2695 main module, Waters 996 diode array detector and ZQ micromass ESI-MS detector. Mobile phase A: H$_2$O (10.0 mM NH4HCO$_2$), mobile phase B: CH$_3$CN. HPLC conditions were: XBridge C18 column, 4.6×30 mm, 3.5 µm, 0.0-0.2 min. isocratic (5% B), 0.2-2.0 min. gradient (5-100% B), 3.0-3.0 min. isocratic (100% B); flow rate: 3.0 mL/min; UV channel: 254 nm.

Purification of some racemic products was performed using semi preparative HPLC A, semi preparative HPLC B, or semi preparative SFC. Semi preparative HPLC A: Gilson 215 system equipped with a Waters 996 diode array detector and a Waters 2525 pump. Semi preparative HPLC B: Waters 2767 system equipped with a Waters 996 diode array detector, 2×Waters 515 pumps, a Waters 2525 pump and a ZQ micromass ESI-MS detector. Semi preparative SFC: Mettler Toledo Minigram SFC equipped with a Knauer K-2501 UV detector and an Alcott Model 1719 Autosampler.

Product homogeneity and enantiomeric excess determination were performed using Analytical HPLC A: Agilent 1100 HPLC system equipped with an Agilent G1315A diode array detector.

Abbreviations:
Ac: acetyl
AcOH or HO Ac: acetic acid
ACN or MeCN: acetonitrile
Anhyd: anhydrous
Aq: aqueous
BINAP: 2,2'-bis(diphenylphosphino)-1,1'-binaphthyl
Bn: benzyl
Boc: fert-butoxycarbonyl
BOC$_2$O: di-tert-butyl dicarbonate
BPO: benzoyl peroxide
BOP: (benzotriazol-1-yloxytris(dimethylamino)phosphonium hexatluorophosphate
CSA: camphorsulfonic acid
d: days
DAST: diethylaminosulfur trifluoride
dba: dibenzylideneacetone
DBU: 1,8-diazobicy clo[5.4.0]undec-7-ene
DCE: 1,2-dichloroethane
DCM: dichloromethane
DBA: diethylamine
DHP: dihydropyran
DIBAL-H: diisobutylaluminum hydride
DIPEA: N,N-diisopropylethylamine
DMA: N,N-dimethylacetamide
DME: 1,2-dimethoxy ethane
DMAP: 4-dimethylaminopyridine
DMF: N,N-dimethylformamide
DMS O-dimethyl sulfoxide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uroniumhexafluorophosphate
HCl: hydrochloric acid
HPLC: high performance liquid chromatography
IPA: isopropyl alcohol
K$_2$CO$_3$: potassium carbonate
LAH: lithium aluminum hydride
LDA: lithium diisopropylamide
M: molar
MeOH: methanol
Me$_2$S: dimethyl sulfide
MeONa: sodium methylate
Mel: iodomethane
min: minutes
mL: milliliters
mM: millimolar
mmol: millimoles
MTBE: methyl tert-butyl ether
nBuLi: n-butyllithium
NaOH: sodium hydroxide
Na$_2$SO$_4$: sodium sulfate
NBS: N-bromosuccinimide
NCS: N-chlorosuccinimide
NMP: N-methylpyrrolidine
NMR: Nuclear Magnetic Resonance
° C.: degrees Celsius
PE: petroleum ether
POCl$_3$: phosphorus oxychloride
PPh$_3$: triphenylphosphine
Rel: relative
R.T. or rt: room temperature
RuPhos: 2-Dicyclohexylphosphino-2',6'-diisopropoxybiphenyl
sat: saturated
SFC: supercritical fluid chromatography
SOCl$_2$: sulfur dichloride
TBAB: tetrabutylammonium bromide
TEA: triethylamine
Tf: trifluoromethanesulfonate
TfAA, TFMSA or Tf$_2$O: trifluoromethanesulfonic anhydride
TFA: trifluoracetic acid
TIPS: triisopropylsilyl
THF: tetrahydrofuran
THP: tetrahydropyran
TEC: thin layer chromatography
wt: weight
Xantphos: 4,5-bis(diphenylphosphino)-9,9-dimethylxanthene Syntheses of Intermediates 6-chloro-3-iodo-1-(oxan-2-yl)-1H-pyrazolo[3,4-b]pyrazine, Intermediate A

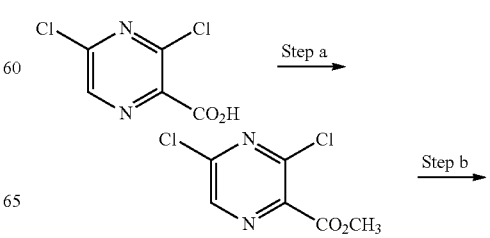

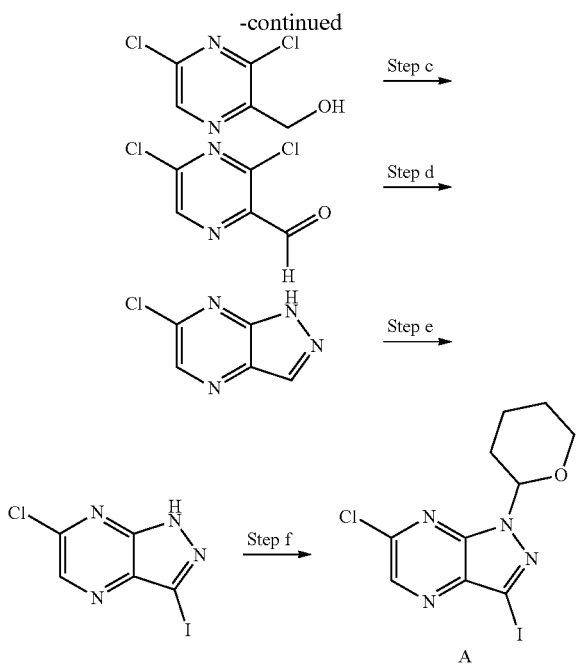

Step a: In a 100 mL round-bottomed flask, 3,5-dichloropyrazine-2-carboxylic acid (3.65 g, 18.9 mmol) and NaHCO$_3$ (4.70 g, 22.7 mmol) were dissolved in dimethylformamide (38 mL). Iodomethane (7.14 mL, 113 mmol) was added dropwise and the resulting mixture stirred overnight at rt. The mixture was diluted with water (50 mL) and extracted with ethyl acetate (3×15 mL). The combined organics were washed with brine (4×10 mL), dried over anhydrous Na$_2$SO$_4$, filtered, and concentrated under reduced pressure. Methyl 3,5-dichloropyrazine-2-carboxylate (3.77 g, 96%) was obtained as a yellowish solid after drying under high vacuum for 2-3 h. $^1$H-NMR (500 MHz, CDCl$_3$) δ 8.57 (s, 1H), 4.03 (s, 3H).

Step b: Methyl 3,5-dichloropyrazine-2-carboxylate (5.0 g, 24.2 mmol) was dissolved in a 9:1 mixture of dry tetrahydrofuran (242 mL) and methanol (27 mL). The mixture was cooled to 1.5-2° C. with an ice/water bath and stirred at this temperature for 10 min. A 2 M solution of lithium borohydride in THF (13.3 mL, 26.6 mmol) was then added carefully keeping the temperature below 4-5° C. After addition, the reaction mixture was stirred for an additional 10-15 min at 0-4° C. Methanol (120 mL) was added to the flask and the mixture stirred for 15 min at rt. The reaction was slowly poured into a mixture of 1 M HCl solution (100 mL) and ethyl acetate (200 mL). The resulting mixture was stirred at rt for 15 min. The aqueous layer was extracted with ethyl acetate (3×150 mL) and the combined organics washed with brine (2×100 mL), dried over anhydrous MgSO$_4$, filtered, and concentrated under reduced pressure. (3,5-Dichloropyrazin-2-yl)methanol (4.3 g, 99% yield) was obtained as a yellow oil after drying under high vacuum for 2 h. $^1$H-NMR (500 MHz, CDCl$_3$) δ 8.52 (s, 1H), 4.85 (s, 2H).

Step c: (3,5-Dichloropyrazin-2-yl)methanol (4.3 g, 24 mmol) was dissolved in dichloromethane (100 mL) and MnO$_2$ (20.2 g, 240 mmol) was then added in one portion. The resulting dark heterogeneous mixture was stirred for 16 h at rt. After this time, the reaction mixture was sonicated for 5 min. and additional MnO$_2$ (4 g) was added to the reaction mixture. The resulting suspension was stirred for 2 h at rt. Then the mixture was filtered over a pad of celite, and the cake washed with dichloromethane. The filtrate was concentrated under reduced pressure, affording 3,5-dichloropyrazine-2-carbaldehyde (2.36 g, 56% yield) as pale yellow oil after drying under high vacuum for 30 min. $^1$H-NMR (500 MHz, CDCl$_3$) δ 10.29 (s, 1H), 8.71 (s, 1H).

Step d: 3,5-Dichloropyrazine-2-carbaldehyde (2.9 g, 16.4 mmol) was dissolved in N-methyl-2-pyrrolidone (16 mL), then hydrazine hydrate (0.78 mL, 49.2 mmol) was added dropwise. The resulting brown suspension was stirred at 65° C. for 40 min. After this time, additional hydrazine hydrate (0.4 mL) was added and the mixture stirred at 65° C. for 2 h. The mixture was cooled to rt, poured into 1 M HCl solution (100 mL), and ethyl acetate (400 mL) was added. The aqueous layer was extracted with ethyl acetate (2×100 mL) and the combined organics washed with brine (300 mL), dried over anhydrous MgSO$_4$, filtered, and concentrated under reduced pressure. The yellow crude residue was purified by reversed phase chromatography (0 to 50% gradient of acetonitrile/10 mM aqueous ammonium formate) affording 6-chloro-1H-pyrazolo[3,4-b]pyrazine (800 mg, 32% yield) as a light brown solid after lyophilization. $^1$H-NMR (500 MHz, CD$_3$OD) δ 8.58 (s, 1H), 8.34 (s, 1H).

Step e: 6-Chloro-1H-pyrazolo[3,4-b]pyrazine was dissolved in acetonitrile (24 mL). N-iodosuccinimide (3.43 g, 14.5 mmol) and tetrafluoroboric acid solution (2.8 mL, 21.7 mmol, 48% in water) were successively added. The resulting brown/orange mixture was then stirred at reflux for 2 h. A beige/brown precipitate formed and the mixture cooled to room temperature, then placed into an ice/water bath for 5 min. The resulting solid was collected by filtration and washed with cold acetonitrile to give 6-chloro-3-iodo-1H-pyrazolo[3,4-b]pyrazine (1.81 g, 89% yield) as a yellow solid after drying under high vacuum. LCMS [M+H]$^+$=280.9; $^1$H-NMR (500 MHz, CDCl$_3$) δ 8.59 (s, 1H).

Step f: 6-Chloro-3-iodo-1H-pyrazolo[3,4-b]pyrazine (850 mg, 3 mmol) was dissolved in dichloromethane (15 mL). 3,4-Dihydro-2H-pyran (0.85 mL, 9.1 mmol) and p-toluenesulfonic acid monohydrate (176 mg, 0.91 mmol) were successively added to the flask. The resulting mixture was stirred at room temperature for 10 min. The mixture became homogeneous and darkish overtime. After this time, a saturated aqueous solution of NaHCO$_3$ (20 mL) was added to the flask and the biphasic mixture stirred for 10 min. The layers were separated, and organic layer washed with brine (20 mL), dried over anhydrous Na$_2$SO$_4$, filtered, and concentrated under reduced pressure. The crude residue was purified by flash chromatography (0 to 50% gradient of ethyl acetate/hexanes) to give 6-chloro-3-iodo-1-(tetrahydro-2H-pyran-2-yl)-1H-pyrazolo[3,4-b]pyrazine (1.02 g, 93% yield) as an off-white solid after drying under high vacuum overnight. LCMS [M+H]$^+$=364.9, [M−THP+H]$^+$=281.0; $^1$H NMR (500 MHz, CDCl$_3$) δ 8.56 (s, 1H), 5.96 (dd, J=10.4, 2.6 Hz, 1H), 4.16-4.06 (m, 1H), 3.82-3.74 (m, 1H), 2.72-2.58 (m, 1H), 2.21-2.11 (m, 1H), 2.01-1.94 (m, 1H), 1.89-1.70 (m, 2H), 1.69-1.59 (m, 1H).

Methyl 6-chloro-3-iodo-1H-pyrazolo[3,4-b]pyrazine-1-carboxylate, Intermediate B

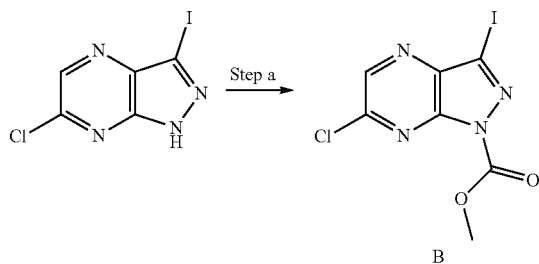

Step a: A solution of sodium hydride (213 mg, 5.34 mmol) in DMF (10 mL) was cooled to 0° C., then 6-chloro-3-iodo-1H-pyrazolo[3,4-b]pyrazine (1 g, 3.56 mmol, synthesized via Steps a-e of Intermediate B) was added. The reaction mixture was allowed to warm to rt and the reaction was stirred for 2.25 hr. The reaction mixture was then cooled to 0-10° C. and methyl carbonochloridate (817 µL, 10.6 mmol) was added and the reaction mixture was stirred for 20 min. On completion, water was added (20 mL), then the mixture was poured in water (60 mL). The reaction mixture was filtered, and the solid washed with water to give methyl 6-chloro-3-iodo-1H-pyrazolo[3,4-b]pyrazine-1-carboxylate as a white solid (1.71 g, crude). LCMS m/z [M+H]$^+$=338.9.

[6-chloro-3-iodo-1-(oxan-2-yl)-1H-pyrazolo[3,4-b]pyrazin-5-yl]methyl acetate, Intermediate C

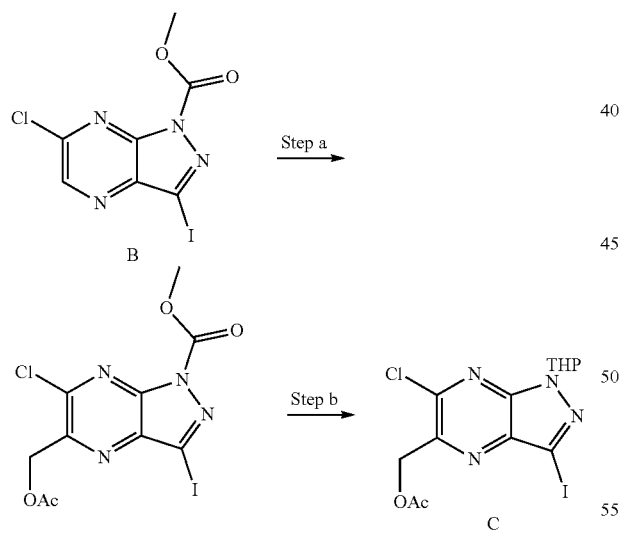

Step a: A round bottomed flask was charged with methyl 6-chloro-3-iodo-1H-pyrazolo[3,4-b]pyrazine-1-carboxylate (525 mg, 1.55 mmol, Intermediate B), 2-(acetyloxy)acetic acid (1.46 g, 12.4 mmol), silver nitrate (52.6 mg, 0.31 mmol), and acetonitrile (15 mL) and water (9 mL). To the mixture was added ammonium persulfate (2.82 g, 12.4 mmol), and the reaction was heated to 85° C. After 2 h, the reaction was cooled to room temperature and poured into ethyl acetate and brine. The organic layer was pre-absorbed onto silica gel and purified by column chromatography (eluting with ethyl acetate and heptanes) to afford methyl 5-[(acetyloxy)methyl]-6-chloro-3-iodo-1H-pyrazolo[3,4-b]pyrazine-1-carboxylate (225 mg, 35% yield) as a white solid. LCMS m/z [M+H]$^+$=410.9.

Step b: A reaction tube containing methyl 5-[(acetyloxy)methyl]-6-chloro-3-iodo-1H-pyrazolo[3,4-b]pyrazine-1-carboxylate (220 mg, 0.5358 mmol) in dichloromethane (4 mL) was charged with piperidine (52.9 µL, 0.5358 mmol) at room temperature. After 15 min, further piperidine (0.2 equiv) was added. After 15 min, 3,4-dihydro-2H-pyran (145 µL, 1.60 mmol) and 4-methylbenzene-1-sulfonic acid (92.2 mg, 0.5358 mmol) were added. After 30 min, the reaction mixture was pre-absorbed onto silica gel and purified by column chromatography (eluting with ethyl acetate and heptanes) to afford [6-chloro-3-iodo-1-(oxan-2-yl)-1H-pyrazolo[3,4-b]pyrazin-5-yl]methyl acetate as a white solid. LCMS m/z [M+H]$^+$=437.0.

tert-butyl 3-oxo-1,3-dihydrospiro[indene-2,4'-piperidine]-1'-carboxylate, Intermediate D

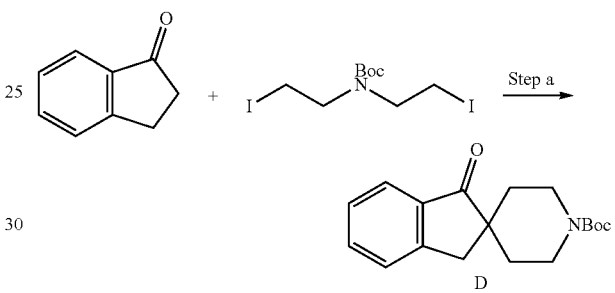

To a solution of NaH (486 mg, 60%) in DMF (20 mL) was added 2,3-dihydro-1H-inden-1-one (541 mg, 4.10 mmol) in DMF (10 mL). The reaction was stirred at 10° C. for 30 min. Then tert-butyl N-(2-chloroethyl)-N-(2-iodoethyl)carbamate (1.37 g, 4.10 mmol) in DMF (10 mL) was added and the reaction was stirred and heated to 50° C. for 12 hours. The reaction mixture was diluted with water (100.0 mL) and extracted ethyl acetate (100.0 mL×2). The combined organic layers were washed with water (100.0 mL) and brine (100.0 mL), dried over anhydrous Na$_2$SO$_4$, filtered and concentrated under reduced pressure to give a residue. The residue was purified by column chromatography (petroleum ether/ethyl acetate=100:0 to 100:10) to give tert-butyl 3-oxo-1,3-dihydrospiro[indene-2,4'-piperidine]-1'-carboxylate (220 mg, 18% yield) as a brown oil. LCMS m/z [M+H−100]$^+$=202.1.

1,3-dihydrospiro[indene-2,4'-piperidin]-3-amine, Intermediate E

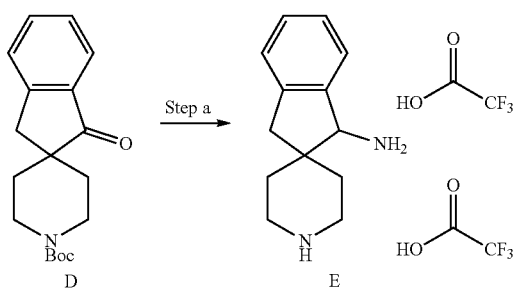

In a microwave vial was added tert-butyl 5-chloro-1-oxo-1,3-dihydrospiro[indene-2,4'-piperidine]-1'-carboxylate (500 mg, 1.65 mmol, Intermediate D) and MeOH (2.5 mL). Then acetic acid amine (1.90 g, 24.7 mmol) and sodium iminomethanide triboran-1-ylium trihydride (175 mg, 1.98 mmol) were added to the reaction mixture, which was heated at 110° C. under microwave for 1 h. Then, another 15 eq. of ammonium acetate and 1.2 eq. of sodium cyanoborohydride were added and the reaction mixture was heated under microwave at 110° C. for 1.5 h. The reaction mixture was then concentrated and then 2N NaOH (5 mL) was added. The mixture was then extracted with EtOAc (2×5 mL) and the organic layer was dried over Na$_2$SO$_4$. The mixture was filtered and concentrated give the crude product as a colorless oil. The oil was purified by column chromatography (0-10% MeOH in DCM w/1% NH40H) to give tert-butyl 3-amino-1,3-dihydrospiro[indene-2,4 (185 mg, 0.612 mmol). This intermediate was then dissolved in DCM (4 mL) and TFA (1 mL) was added and the reaction mixture was stirred at rt for 16 h. The reaction mixture was concentrated in vacuo, and the residue was azeotroped 3× with toluene. 1,3-dihydrospiro[indene-2,4'-piperidin]-3-amine (307 mg, 43% yield, 2 TFA salt) was isolated as a foamy solid. LCMS m/z [M+H]$^+$=203.1.

tert-butyl (1'-(3-iodo-1-(tetrahydro-2H-pyran-2-yl)-1H-pyrazolo[3,4-b]pyrazin-6-yl)-1,3-dihydrospiro [indene-2,4'-piperidin]-1-yl)carbamate, Intermediate F

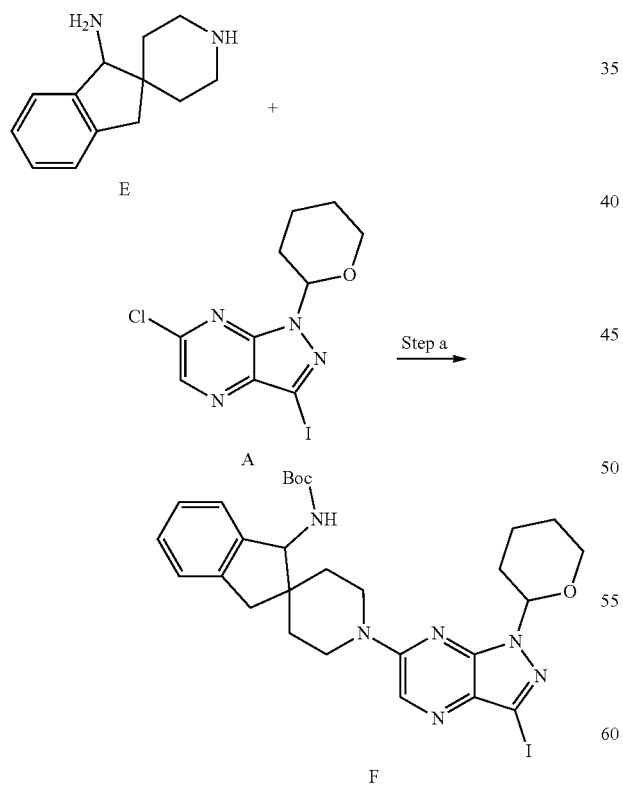

Step a: A mixture of 1,3-dihydrospiro[indene-2,4'-piperidin]-3-amine dihydrochloride (800.0 mg, 2.9 mmol, Intermediate E), 6-chloro-3-iodo-1-(oxan-2-yl)-1H-pyrazolo[3,4-b]pyrazine (1.05 g, 2.9 mmol, Intermediate A) and Et$_3$N (2.0 mL, 14.4 mmol) in DMF (20 mL) was stirred at 60° C. for 1 hour. To the reaction mixture was added Boc$_2$O (757.0 mg, 3.5 mmol) and the reaction was stirred at 60° C. for another 2 hours. The reaction mixture was diluted with EtOAc (150 mL), and washed with water (100 mL×3). The organic layer was concentrated and purified by silica gel column (EtOAc in petroleum ether=0~20%) to give tert-butyl N-{1'-[3-iodo-1-(oxan-2-yl)-1H-pyrazolo[3,4-b] pyrazin-6-yl]-1,3-dihydrospiro[indene-2,4'-piperidin]-3-yl}carbamate (1.50 g, 82% yield) as a white solid. LCMS m/z [M+H]$^+$=653.1.

(6-(1-(((tert-butoxycarbonyl)amino)-1,3-dihydrospiro [indene-2,4'-piperidin]-1'-yl)-3-iodo-1-(tetrahydro-2H-pyran-2-yl)-1H-pyrazolo[3,4-b]pyrazin-5-yl) methyl acetate, Intermediate G

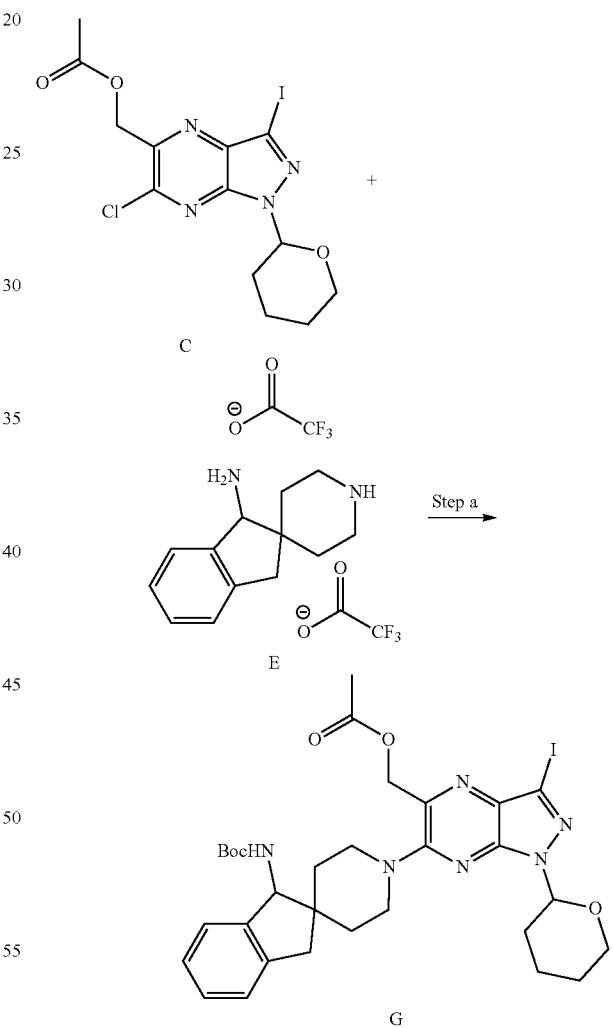

Step a: To a vial with [6-chloro-3-iodo-1-(oxan-2-yl)-1H-pyrazolo[3,4-b]pyrazin-5-yl]methyl acetate (76 mg, 0.1740 mmol, Intermediate C) in DMF (0.13 mL, 1 mL) was added 1,3-dihydrospiro[indene-2,4'-piperidin]-3-amine ditrifluoroacetate (89.4 mg, 0.2088 mmol, Intermediate E) in 1 mL DMF and ethylbis(propan-2-yl)amine (121 µL, 0.696 mmol, Hunig's base). The vial was sealed and the mixture heated to 75° C. After 1 hr, more dihydrospiro[indene-2,4'-piperidin]-3-amine ditrifluoroacetate was added with Hunig's base (240 uL). Upon formation of (6-(1-amino-1,3-dihydrospiro [indene-2,4'-piperidin]-1'-yl)-3-iodo-1-(tetrahydro-2H-pyran-2-yl)-1H-pyrazolo[3,4-b]pyrazin-5-yl)methyl acetate, tert-butyl dicarbonate (56.9 mg, 0.261 mmol) was added and the reaction mixture was stirred at rt for 48 h. To complete the conversion, another 35 mg of Boc$_2$O was added and the reaction mixture was heated to 75° C. for 20 min. The reaction mixture was cooled to rt, then 5% w/w LiCl solution was added and the mixture was extracted with EtOAc. The organic layer was concentrated in vacuo and the residue was purified by column chromatography (10 g column, 10-50% EtOAc in hexanes) to give (6-(1-((tert-butoxycarbonyl)amino)-1,3-dihydrospiro[indene-2,4'-piperidin]-1'-yl)-3-iodo-1-(tetrahydro-2H-pyran-2-yl)-1H-pyrazolo[3,4-b]pyrazin-5-yl)methyl acetate (85 mg, 71% yield). LCMS m/z [M+H]$^+$=703.3.

tert-butyl (S)-1-(((R)-tert-butylsulfinyl)amino)-1,3-dihydrospiro[indene-2,4'-piperidine]-1'-carboxylate, Intermediate H

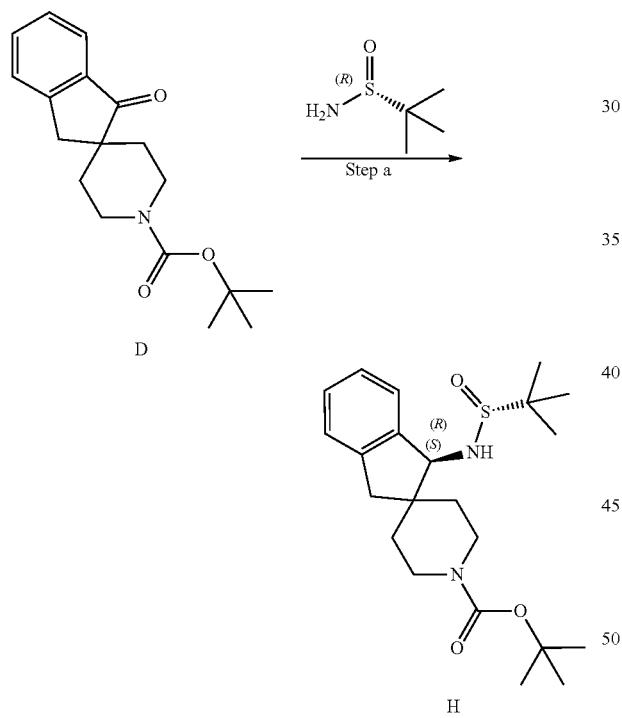

Step a: Dissolved tert-butyl 3-oxo-1,3-dihydrospiro[indene-2,4'-piperidine]-1'-carboxylate (1 g, 3.31 mmol, Intermediate D) in 2-Me-THF (20 mL). Then tetratitanium-1-ylium tetraethanolate (4.50 mL, 13.2 mmol) was added followed by (R)-2-methylpropane-2-sulfinamide (721 mg, 5.95 mmol) and the reaction mixture was stirred at 90° C. for 16 h. The reaction mixture was then cooled to 0° C. and lithium(1+) borohydride (79.2 mg, 3.64 mmol) was added portion-wise and the mixture was stirred for 0.5 h. The reaction was then quenched with methanol and concentrated in vacuo. EtOAc and water were added and the mixture was extracted with EtOAc, and the organic layer was dried over Na$_2$SO$_4$, filtered and concentrated. The residue was purified by column chromatography (24 g column, 0-100% EtOAc in heptanes) to give tert-butyl (3S)-3-{[(R)-2-methylpropane-2-sulfinyl]amino}-1,3-dihydrospiro[indene-2,4'-piperidine]-1'-carboxylate (500 mg, 21% yield) as a white solid. LCMS m/z [M+H-100]$^+$=307.0.

(S)-1,3-dihydrospiro[indene-2,4'-piperidin]-1-amine, Intermediate I

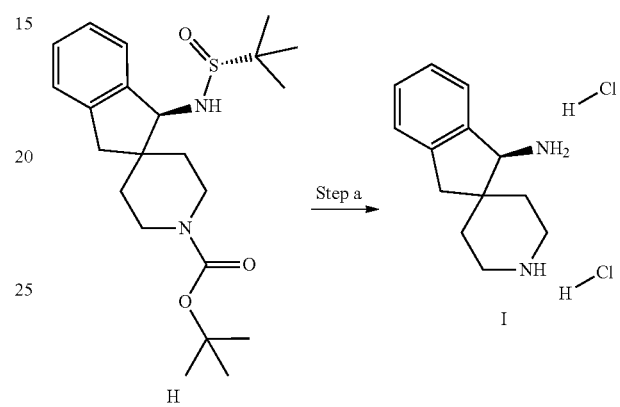

Step a: Dissolved tert-butyl (3S)-3-{[(R)-2-methylpropane-2-sulfinyl]amino}-1,3-dihydrospiro[indene-2,4'-piperidine]-1'-carboxylate (500 mg, 1.22 mmol, Intermediate H) in MeOH (15 mL) and added hydrogen chloride (3.05 mL, 12.2 mmol), and the reaction mixture was stirred at rt for 16 h. Then 1 mL more 4N HCl was added and the reaction mixture was stirred at rt for 1 h, then heated to 60° C. for 2 h. The reaction mixture was then concentrated. MBTE was added to the residue which was then filtered to give (S)-1,3-dihydrospiro[indene-2,4'-piperidin]-1-amine (335 mg, 99% yield) as a white solid. LCMS m/z [M+H]$^+$= 203.1.

tert-butyl ((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate, Intermediate J

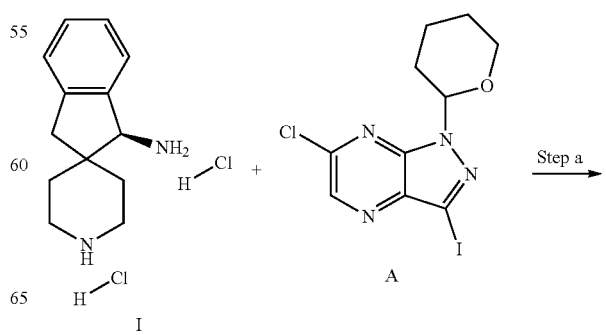

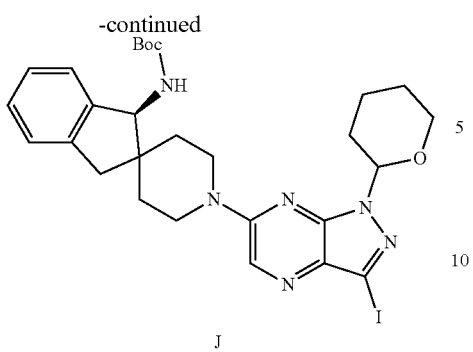

J

Step a: Dissolved (3S)-1,3-dihydrospiro[indene-2,4'-piperidin]-3-amine dihydrochloride (1.37 g, 5.01 mmol, Intermediate I) in DMF (15 mL), then added 6-chloro-3-iodo-1-(tetrahydro-2H-pyran-2-yl)-1H-pyrazolo[3,4-b]pyrazine (2 g, 7.13 mmol, Intermediate A) followed by ethylbis(propan-2-yl)amine (4.97 mL, 28.5 mmol). The reaction was stirred at 75° C. for 3 h to form (1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-amine. The reaction mixture was cooled to rt then divided in half. To ~10 mL reaction mixture was added di-tert-butyl dicarbonate (1.79 mL, 7.84 mmol) and the reaction mixture was stirred at rt for 16 h. To the reaction mixture was added EtOAc and water, and the reaction was extracted with EtOAc 3 times. The combined organic layer was dried over MgSO$_4$, filtered and concentrated onto silica gel. The mixture was purified by column chromatography (0-45% EtOAc in heptanes) to give tert-butyl ((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (955 mg, 1.51 mmol). LCMS m/z [M+H]$^+$=631.1.

(6-((S)-1-((tert-butoxycarbonyl)amino)-1,3-dihydrospiro[indene-2,4'-piperidin]-1'-yl)-3-iodo-1-(tetrahydro-2H-pyran-2-yl)-1H-pyrazolo[3,4-b]pyrazin-5-yl)methyl acetate, Intermediate K

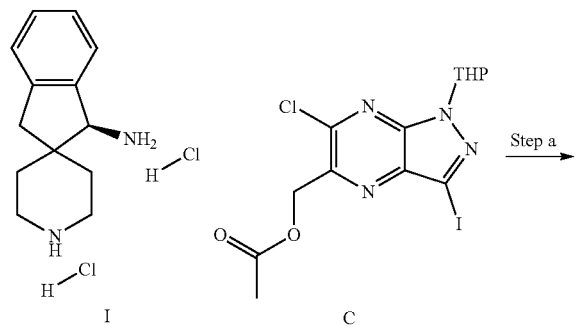

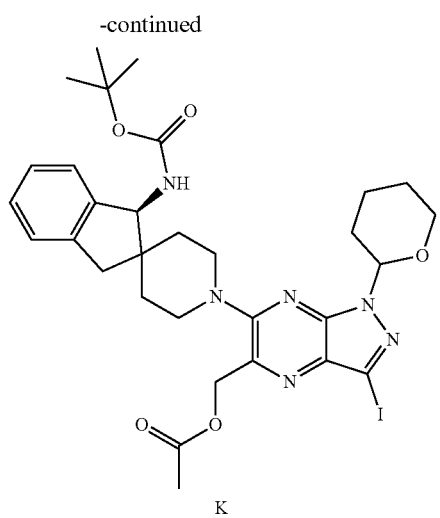

K

Step a: Dissolved [6-chloro-3-iodo-1-(oxan-2-yl)-1H-pyrazolo[3,4-b]pyrazin-5-yl]methyl acetate (528 mg, 1.21 mmol, Intermediate C) in DMF (10 mL). Then added (3S)-1,3-dihydrospiro[indene-2,4'-piperidin]-3-amine dihydrochloride (335 mg, 1.21 mmol, Intermediate I) followed by ethylbis(propan-2-yl)amine (844 µL, 4.84 mmol) to the reaction and the mixture was stirred at 75° C. for 16 h. The reaction mixture was then cooled to rt and di-tert-butyl dicarbonate (305 µL, 1.33 mmol) was added and the reaction was stirred at rt for 3 h. The reaction was then diluted with EtOAc and water. The layers were separated, then the organic layer was washed with brine, dried over Na$_2$SO$_4$, filtered and concentrated directly onto SiO$_2$. The mixture was purified by column chromatography (0-50% EtOAc in heptanes) to give (6-((S)-1-((tert-butoxycarbonyl)amino)-1,3-dihydrospiro[indene-2,4'-piperidin]-1'-yl)-3-iodo-1-(tetrahydro-2H-pyran-2-yl)-1H-pyrazolo[3,4-b]pyrazin-5-yl) methyl acetate (500 mg, 54% yield) as an off-white solid. LCMS m/z [M+H]$^+$=703.3.

1-(1,2,3,4-tetrahydroquinoxalin-1-yl)ethan-1-one, Intermediate L

Step a: To a solution of 1,2,3,4-tetrahydroquinoxaline (500.0 mg, 3.7 mmol, CAS #3476-89-9) and Et$_3$N (770.0 uL, 5.6 mmol) in DCM (20 mL) at 0° C. was added AcCl (289.0 uL, 4.1 mmol) in DCM (5 mL) and the reaction was stirred at 0° C. for 0.5 hour. The reaction was concentrated and purified by silica gel column (EtOAc in Petroleum ether=50%) to give 1-(1,2,3,4-tetrahydroquinoxalin-1-yl)ethan-1-one (530.0 mg, 80.9% yield) as a yellow solid. LCMS m/z [M+H]$^+$=177.1.

227

1-(Oxan-2-yl)-3-(1,2,3,4-tetrahydro-1,5-naphthyridin-1-yl)-1H-pyrazolo[3,4-b]pyrazin-6-yl 4-methylbenzene-1-sulfonate, Intermediate M

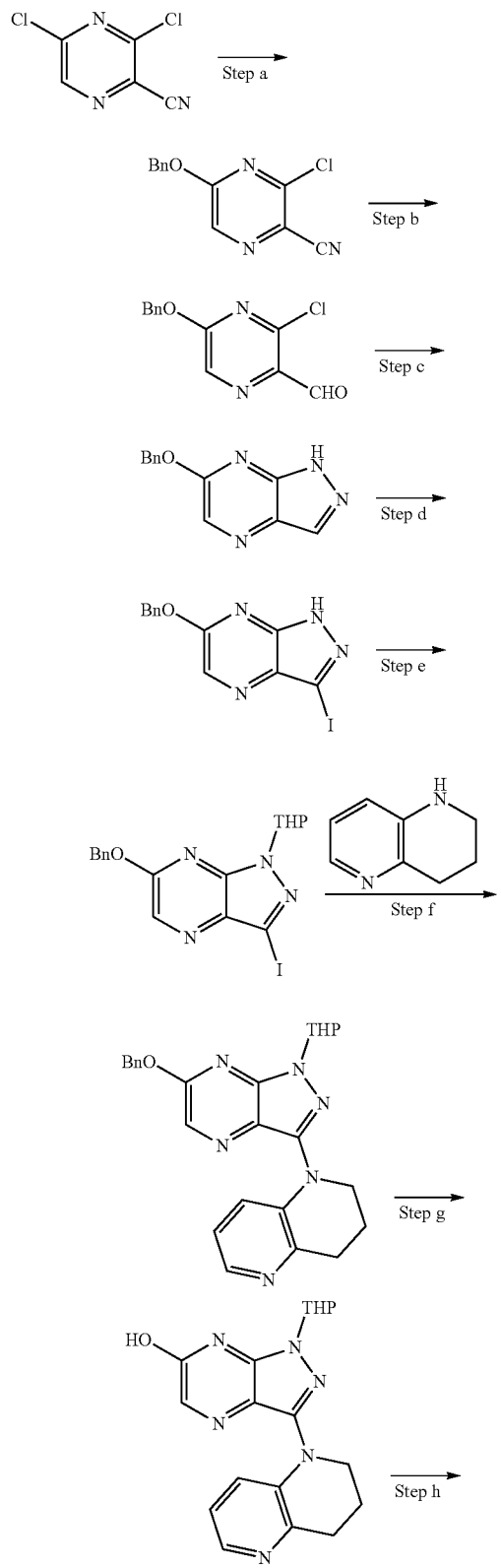

-continued

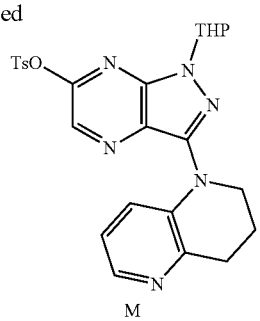

M

Step a: A solution of BnOH (30.8 g, 0.285 mol, 29.6 mL, 1.1 eq) in THF (450 mL) was cooled to 0° C. NaH (12.4 g, 0.311 mol, 60% oil dispersion, 1.2 eq) was added slowly to the mixture at 0° C. After addition, the mixture was stirred at 25° C. for 1 hr. The resultant solution was added a solution of 3,5-dichloropyrazine-2-carbonitrile (45.0 g, 258.64 mmol, 1.0 eq) in THF (450 mL) at −78° C. and the mixture was stirred at −78° C. for 0.5 hr. The reaction was then poured into water (1.00 L) and extracted with EtOAc (1.00 L*3). The combined organic layer was washed with brine (500 mL), dried over Na$_2$SO$_4$, filtered and concentrated. The residue was slurryed in petroleum ether/EtOAc=10:1 (1.50 L) at 25° C. for 0.5 hr. The mixture was filtered and the filter cake was washed with petroleum ether (200 mL). The filter cake was dried under reduced pressure to give 5-(benzyloxy)-3-chloropyrazine-2-carbonitrile (79.3 g, 300 mmol, 58% yield, 93% purity) as a white solid. LCMS m/z [M+H]$^+$= 245.9. $^1$H NMR (400 MHz CDCl$_3$) δ 8.23 (s, 1H), 7.51-7.39 (m, 5H), 5.48 (s, 2H).

Step b: To a solution of 5-(benzyloxy)-3-chloropyrazine-2-carbonitrile (20.0 g, 75.6 mmol, 1.0 eq) in THF (200 mL) was added DIBAL-H (1.0 M, 227 mL, 3.0 eq) at −78° C. under N2. The mixture was stirred at −78° C. for 1 hr. The reaction was quenched by a solution of 10% aqueous HOAc (2.00 L) at −78° C. and extracted with EtOAc (1.50 L*3). The combined organic layer was adjusted pH to 8~9 with saturated aqueous of NaHCO$_3$ and separated. The organic layer was washed with brine (1.00 L), dried over Na$_2$SO$_4$, filtered and concentrated. The residue was slurryed in mix solution of EtOAc (300 mL) and petroleum ether (6.00 L). The precipitate was collected by filtration to give 5-(benzyloxy)-3-chloropyrazine-2-carbaldehyde (11.3 g) as a brown oil. LCMS m/z [2M+H]$^+$=497.9; $^1$H NMR (400 MHz CDCl$_3$) δ 10.27 (s, 1H), 8.33 (s, 1H), 7.50-7.40 (m, 5H), 5.51 (s, 2H).

Step c: To a mixture of 5-(benzyloxy)-3-chloropyrazine-2-carbaldehyde (11.3 g, 45.4 mmol, 1.0 eq) and NH2NH2.H$_2$O (6.96 g, 137 mmol, 6.76 mL, 3.0 eq) in EtOH (113 mL) was stirred at 25° C. Then Et$_3$N (23.0 g, 228 mmol, 31.6 mL, 5.00 eq) was added to the mixture at 25° C. The mixture was heated to 80° C. and stirred at 80° C. for 16 hrs. Then the reaction was concentrated to give a residue. The residue was dissolved with EtOAc (500 mL) and washed with sat.aq.NH4Cl (500 mL). The organic layer was dried over Na$_2$SO$_4$, filtered and concentrated to give 6-(benzyloxy)-1H-pyrazolo[3,4-b]pyrazine (9.5 g, 84% purity, 47% yield over Step b-c) as a brown solid. LCMS m/z [M+H]$^+$=227.0; $^1$H NMR (400 MHz CDCl$_3$) δ 11.07 (br s, 1H), 8.29 (s, 1H), 8.25 (s, 1H), 7.50-7.47 (m, 2H), 7.44-7.36 (m, 3H), 5.46 (s, 2H).

Step d: To a solution of 6-(benzyloxy)-1H-pyrazolo[3,4-b]pyrazine (9.50 g, 35.4 mmol, 1.0 eq) in DMF (190 mL) was added NIS (10.4 g, 46.0 mmol, 1.3 eq) at 25° C. Then the mixture was heated to 80° C. and stirred for 1 h. The reaction was then cooled to 25° C. and then poured into ice-water (2.00 L). The mixture was extracted with EtOAc (2.00 L). The organic layer was washed with 10% aq.Na$_2$SO$_3$ (500 mL*2) and brine (500 mL), dried over Na$_2$SO$_4$, filtered and concentrated to give 6-(benzyloxy)-3-iodo-1H-pyrazolo[3,4-b]pyrazine (24.7 g, 97% yield) as a yellow solid. LCMS m/z [M+H]$^+$=352.8; $^1$H NMR (400 MHz CDCl$_3$) δ 10.73 (br s, 1H), 8.27 (s, 1H), 8.03 (s, 1H), 7.50-7.47 (m, 2H), 7.44-7.38 (m, 3H), 5.46 (s, 2H).

Step e: To a solution of 6-(benzyloxy)-3-iodo-1H-pyrazolo[3,4-b]pyrazine (12.1 g, 34.3 mmol, 1.0 eq) in DCM (20.0 mL) was added DHP (8.65 g, 103 mmol, 9.40 mL, 3.0 eq) and TsOH.H$_2$O (1.96 g, 10.3 mmol, 0.3 eq). The mixture was stirred at 25° C. for 0.5 hr. Three batched in parallel were combined for work-up. The mixture was poured into saturated NaHCO$_3$ solution (250 mL) and then extracted with EtOAc (250 mL*2). The organic layers were combined and washed with brine (500 mL), dried over Na$_2$SO$_4$, filtered and then concentrated under vacuum. The residue was purified by silica gel chromatography (petroleum ether: EtOAc=30:1) to give 6-(benzyloxy)-3-iodo-1-(tetrahydro-2H-pyran-2-yl)-1H-pyrazolo[3,4-b]pyrazine (34.0 g, 72% yield) as a yellow solid. LCMS m/z [M+H]$^+$=436.8; $^1$H NMR (400 MHz CDCl$_3$) δ 8.24 (s, 1H), 7.51 (br d, J=6.8 Hz, 2H), 7.45-7.37 (m, 3H), 5.87 (dd, J=2.6, 10.2 Hz, 1H), 5.50 (d, J=1.6 Hz, 2H), 4.19-4.11 (m, 1H), 3.84-3.75 (m, 1H), 2.74-2.61 (m, 1H), 2.23-2.14 (m, 1H), 1.99 (br dd, J=2.4, 12.8 Hz, 1H), 1.86-1.75 (m, 2H), 1.69-1.63 (m, 1H).

Step f: To a mixture of 6-(benzyloxy)-3-iodo-1-(tetrahydro-2H-pyran-2-yl)-1H-pyrazolo[3,4-b]pyrazine (12.9 g, 27.9 mmol, 1.00 eq) and 1,2,3,4-tetrahydro-1,5-naphthyridine (3.74 g, 27.9 mmol, 1.00 eq) in toluene (130 mL) was added RuPhos (2.60 g, 5.57 mmol, 0.2 eq), Pd$_2$(dba)$_3$ (766 mg, 836 umol, 0.03 eq) and Cs$_2$CO$_3$ (27.3 g, 83.6 mmol, 3.0 eq) at 25° C. under N2. The mixture was heated to 100° C. and stirred at 100° C. for 20 hrs. The mixture was filtered and to the filtrate was added water (500 mL) and extracted with EtOAc (500 mL). The combined organic layer was washed with 0.5 M aq.HCl (200 mL). The aqueous layer was further extracted with DCM (200 mL*2). The combined organic layers (EtOAc and DCM) were washed with sat. NaHCO$_3$ (200 mL), brine (200 mL), dried over Na$_2$SO$_4$, filtered and concentrated. The residue was purified by flash silica gel chromatography (330 g silica column, eluent of 10~30% ethyl acetate/petroleum ether) to give 1-(6-(benzyloxy)-1-(tetrahydro-2H-pyran-2-yl)-1H-pyrazolo[3,4-b]pyrazin-3-yl)-1,2,3,4-tetrahydro-1,5-naphthyridine (17.6 g, 64% yield) as a yellow solid. LCMS m/z [M+H]$^+$=443.1; $^1$H NMR (400 MHz CDCl$_3$) δ 8.12 (s, 1H), 8.05 (dd, J=1.2, 4.6 Hz, 1H), 7.70 (dd, J=1.2, 8.4 Hz, 1H), 7.52 (br d, J=6.8 Hz, 2H), 7.45-7.35 (m, 3H), 6.97 (dd, J=4.6, 8.4 Hz, 1H), 5.86 (dd, J=2.4, 10.2 Hz, 1H), 5.50 (d, J=2.2 Hz, 2H), 4.19-4.12 (m, 2H), 3.86-3.76 (m, 1H), 3.07 (t, J=6.6 Hz, 2H), 2.73-2.58 (m, 1H), 2.25-2.13 (m, 3H), 1.98 (br d, J=12.8 Hz, 1H), 1.80 (br t, J=9.7 Hz, 2H), 1.74-1.63 (m, 2H).

Step g: To a solution of 1-(6-(benzyloxy)-1-(tetrahydro-2H-pyran-2-yl)-1H-pyrazolo[3,4-b]pyrazin-3-yl)-1,2,3,4-tetrahydro-1,5-naphthyridine (9.00 g, 20.4 mmol, 1.00 eq) in MeOH (950 mL) was added Pd(OH)$_2$/C (1.14 g, 4.07 mmol, 50% purity, 0.20 eq) under N2. The suspension was degassed under vacuum and purged with H2 several times. The mixture was stirred under H2 (50 psi) at 25° C. for 30 hrs. 2 batches in parallel were combined for work-up. The mixture was filtered and the filter cake was dried under reduced pressure to give 3-(3,4-dihydro-1,5-naphthyridin-1(2H)-yl)-1-(tetrahydro-2H-pyran-2-yl)-1H-pyrazolo[3,4-b]pyrazin-6-ol (13.7 g) which contained Pd(OH)$_2$/C as a blackish solid. $^1$H NMR (400 MHz CDCl$_3$) δ 12.60 (br s, 1H), 8.05-7.91 (m, 2H), 7.64 (br d, J=8.4 Hz, 1H), 7.02 (dd, J=4.4, 8.2 Hz, 1H), 5.68 (br d, J=8.7 Hz, 1H), 4.02 (br s, 2H), 3.94 (br d, J=11.2 Hz, 1H), 3.67-3.58 (m, 1H), 2.94 (br t, J=6.4 Hz, 2H), 2.40-2.30 (m, 1H), 2.11-1.98 (m, 3H), 1.89 (br d, J=10.8 Hz, 1H), 1.71 (br s, 1H), 1.55 (br s, 2H).

Step h: To a mixture of 3-(3,4-dihydro-1,5-naphthyridin-1(2H)-yl)-1-(tetrahydro-2H-pyran-2-yl)-1H-pyrazolo[3,4-b]pyrazin-6-ol (7.00 g, 19.9 mmol, 1.0 eq) in DCM (70.0 mL) was added DIPEA (2.82 g, 21.9 mmol, 3.81 mL, 1.1 eq) at 25° C. Then the mixture was cooled to 0° C. and added a solution of p-TsCl (4.54 g, 23.9 mmol, 1.20 eq) in DCM (70.0 mL) at 0° C. The mixture was stirred at 0~10° C. for 1 hr. 2 batches in parallel were combined for work-up. The reaction was poured into ice-water (250 mL) and extracted with EtOAc (250 mL*3). The combined organic layer was washed with brine (200 mL), dried over Na$_2$SO$_4$, filtered and concentrated. The residue was purified by silica gel chromatography (petroleum ether:EtOAc=5:1 to 1:1) to give 3-(3,4-dihydro-1,5-naphthyridin-1(2H)-yl)-1-(tetrahydro-2H-pyran-2-yl)-1H-pyrazolo[3,4-b]pyrazin-6-yl 4-methylbenzenesulfonate (16.4 g, 76% yield) as a red foam. LCMS m/z [M+H]$^+$=507.1; $^1$H NMR (400 MHz CDCl$_3$) δ 8.23 (s, 1H), 8.10 (dd, J=1.4, 4.6 Hz, 1H), 8.00 (d, J=8.4 Hz, 2H), 7.76 (dd, J=1.4, 8.4 Hz, 1H), 7.41 (d, J=8.2 Hz, 2H), 7.00 (dd, J=4.6, 8.4 Hz, 1H), 5.68 (dd, J=2.4, 10.5 Hz, 1H), 4.19-4.13 (m, 2H), 4.10 (br s, 1H), 3.72 (dt, J=2.4, 11.2 Hz, 1H), 3.06 (t, J=6.6 Hz, 2H), 2.59-2.51 (m, 1H), 2.49 (s, 3H), 2.22-2.11 (m, 3H), 1.91 (br dd, J=2.2, 12.9 Hz, 1H), 1.79-1.71 (m, 2H), 1.64 (br d, J=6.8 Hz, 1H).

2,3-dihydrospiro[indene-1,4'-piperidin]-2-amine, Intermediate N

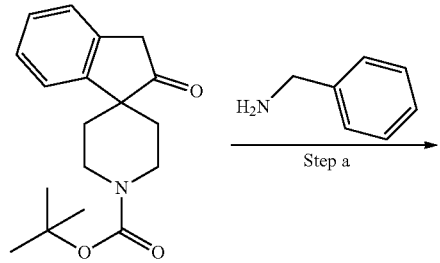

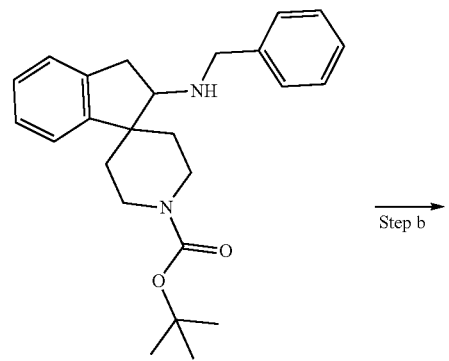

232

4-[cis-3-[(tert-butyldimethylsilyl)oxy]cyclobutyl]-1,2,3,4-tetrahydroquinoxaline-6-carbonitrile, Intermediate O

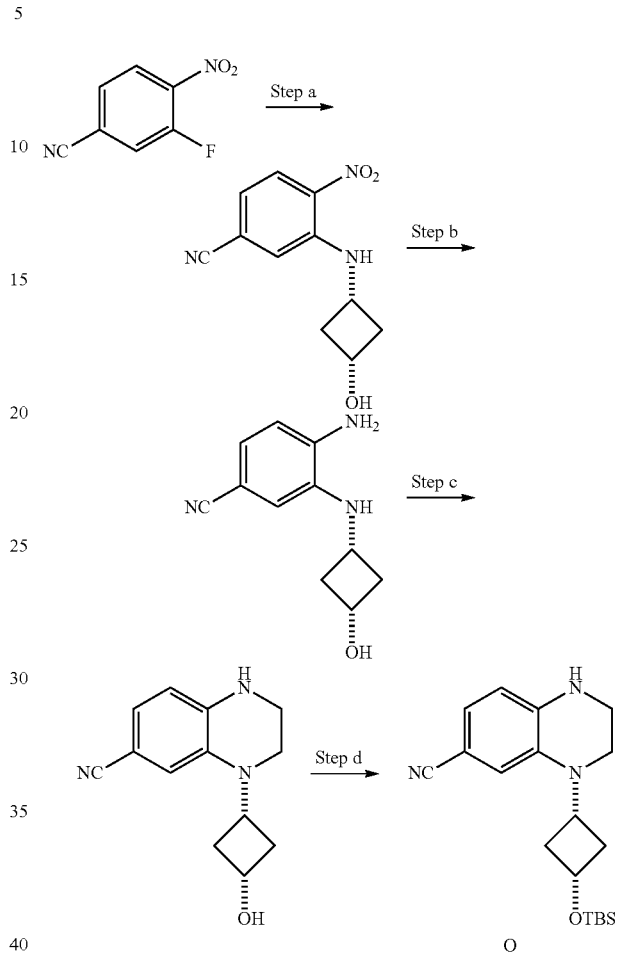

Step a: To a solution of cis-3-aminocyclobutan-1-ol hydrochloride (3.04 g, 24.6 mmol) and Et₃N (10.3 mL, 73.8 mmol) in EtOH (100.0 mL) was added 3-fluoro-4-nitrobenzonitrile (4.10 g, 24.6 mmol) at 40° C. The mixture was stirred at 40° C. for 0.5 hour. The mixture was then concentrated in vacuo to give crude product. The solid was triturated with EtOAc:Petroleum ether=1:4 and stirred for 20 min. The mixture was filtered and filtrate cake was dried in vacuo to give 3-[(3-hydroxycyclobutyl)amino]-4-nitrobenzonitrile (5.60 g, 98% yield) as an orange solid. LCMS m/z [M+H]⁺=234.0.

Step b: A solution of 3-[(3-hydroxycyclobutyl)amino]-4-nitrobenzonitrile (5.60 g, 24.0 mmol) and Pd/C (1.00 g, 10%) in MeOH (100.0 mL) was stirred at 10° C. for 12 hours under H2 (15 psi). The reaction mixture was then filtered and the filtrate was concentrated in vacuo to give 4-amino-3-[(3-hydroxycyclobutyl)amino]benzonitrile (5.00 g, quant. crude yield) as a yellow gum. LCMS m/z [M+H]⁺=203.9.

Step c: A solution of 4-amino-3-[(3-hydroxycyclobutyl)amino]benzonitrile (5.00 g, 24.6 mmol), 1,2-dibromoethane (18.40 g, 98.4 mmol), TBAB (31.70 g, 98.4 mmol) and TEA (13.7 mL, 98.4 mmol) was stirred at 60° C. for 12 hours. The solution was added into H₂O (500.0 mL) and then extracted with EtOAc (500.0 mL×2). The combined organic layers were washed with brine (500.0 mL), dried over anhydrous

231

-continued

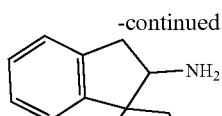

Step c →

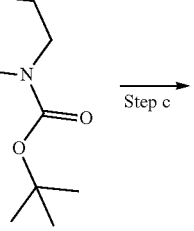

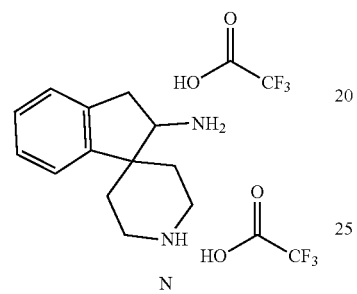

N

Step a: Dissolved tert-butyl 2-oxo-2,3-dihydrospiro[indene-1,4'-piperidine]-1'-carboxylate (500 mg, 1.65 mmol, CAS #241819-85-2) and 1-phenylmethanamine (264 mg, 2.47 mmol) in DCE (10 mL). Then acetic acid (9.42 µL, 0.165 mmol) was added and the reaction mixture was stirred at rt for 1 hr. Next, sodium cyanoboranuide (155 mg, 2.47 mmol) was added and the reaction was stirred at rt for 48 h. The reaction was then heated to 50° C. for 2.5 h, then AcOH (90 uL) was added and the reaction was stirred at 50° C. for an additional 48 h. The reaction was then diluted with saturated aqueous sodium bicarbonate solution (5 mL) and extracted with EtOAc (3×10 mL). The combined organic phases were washed with brine and concentrated. The residue was purified by column chromatography (0-100% EtOAc in heptanes) to give tert-butyl 2-(benzylamino)-2,3-dihydrospiro[indene-1,4'-piperidine]-1'-carboxylate (242 mg, 37% yield) as a yellow oil. LCMS m/z [M+H]⁺=393.5.

Step b: Dissolved tert-butyl 2-(benzylamino)-2,3-dihydrospiro[indene-1,4'-piperidine]-1'-carboxylate (242 mg, 0.616 mmol) and trifluoroacetic acid (70.2 mg, 0.616 mmol) in MeOH (5 mL). The reaction mixture was then cycled through a H-Cube at 3 bar hydrogen gas with a 10% Pd/C cartridge for 2 hr at rt. The reaction mixture was then concentrated and purified by column chromatography (0-100% EtOAc in heptanes, followed by 0-10% MeOH in DCM w/1% NH40H) to give tert-butyl 2-amino-2,3-dihydrospiro[indene-1,4'-piperidine]-1'-carboxylate (68 mg, 37% yield).

Step c: Dissolved tert-butyl 2-amino-2,3-dihydrospiro[indene-1,4'-piperidine]-1'-carboxylate (68 mg, 0.23 mmol) in MeOH (2 mL), then added TFA (1 mL) and stirred the reaction mixture at rt for 1 h. The reaction mixture was concentrated, chased with toluene and dried under high vacuum for 1 h to give 2,3-dihydrospiro[indene-1,4'-piperidin]-2-amine (40.0 mg, 41% yield, 2TFA). LCMS m/z [M+H]⁺=203.3.

Na₂SO₄, filtered and concentrated in vacuo to give crude product as orange gum. The residue was purified by flash silica gel chromatography (80 g column, ethyl acetate in petroleum ether from 0% to 65%) to give 4-[cis-3-hydroxy-cyclobutyl]-1,2,3,4-tetrahydroquinoxaline-6-carbonitrile (3.50 g, 62% yield) as an orange oil. LCMS m/z [M+H]⁺= 230.1

Step d: A solution of cis-3-hydroxycyclobutyl]-1,2,3,4-tetrahydroquinoxaline-6-carbonitrile (3.50 g, 15.2 mmol), TBSCl (2.96 g, 19.7 mmol) and imidazole (2.06 g, 30.4 mmol) in CH₂Cl₂ (30.0 mL) was stirred at 40° C. for 0.5 hour. The mixture was concentrated in vacuo. The residue was purified by flash silica gel chromatography (40 g column, ethyl acetate in petroleum ether from 0% to 15%) to give 4-[cis-3-[(tert-butyldimethylsilyl)oxy]cyclobutyl]-1,2,3,4-tetrahydroquinoxaline-6-carbonitrile (2.50 g, 48% yield) as an orange oil. LCMS m/z [M+H]⁺=343.9. HPLC: 93.5% purity at 254 nm. ¹HNMR (400 MHz, CDCl₃): 6.83-6.86 (m, 1H), 6.57 (s, 1H), 6.30-6.33 (m, 1H), 4.36 (s, 1H), 4.01-4.05 (m, 1H), 3.45-3.49 (m, 2H), 3.17-3.23 (m, 1H), 3.01-3.06 (m, 2H), 2.65-2.70 (m, 2H), 1.89-1.95 (m, 2H), 0.82 (s, 9H), 0.00 (s, 6H).

4-(trans-3-((tert-butyldimethylsilyl)oxy)cyclobutyl)-1,2,3,4-tetrahydroquinoxaline-6-carbonitrile, Intermediate P

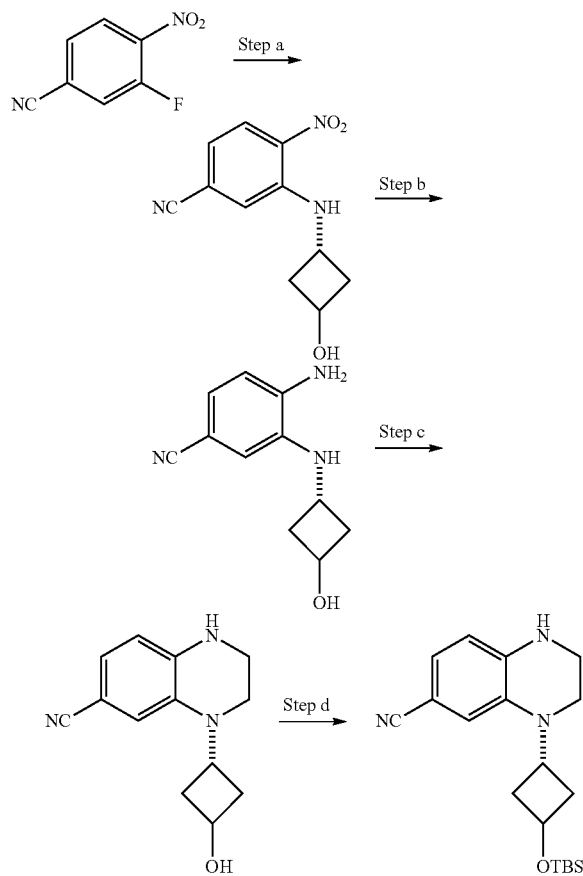

4-(trans-3-((tert-butyldimethylsilyl)oxy)cyclobutyl)-1,2,3,4-tetrahydroquinoxaline-6-carbonitrile was synthesized as described for Intermediate O, coupling trans-3-aminocyclobutan-1-ol hydrochloride in Step a. Characterization of the final intermediate: LCMS m/z [M+H]⁺=344.2. ¹HNMR (400 MHz, CDCl₃): 6.81-6.88 (m, 1H), 6.50-6.51 (m, 1H), 6.31-6.34 (m, 1H), 4.29-4.36 (m, 1H), 3.90-3.97 (m, 1H), 3.49-3.50 (m, 2H), 3.01-3.04 (m, 2H), 2.24-2.34 (m, 4H), 0.85 (s, 9H), 0.01 (s, 6H).

4-(trans-3-methoxycyclobutyl)-1,2,3,4-tetrahydroquinoxaline-6-carbonitrile, Intermediate Q

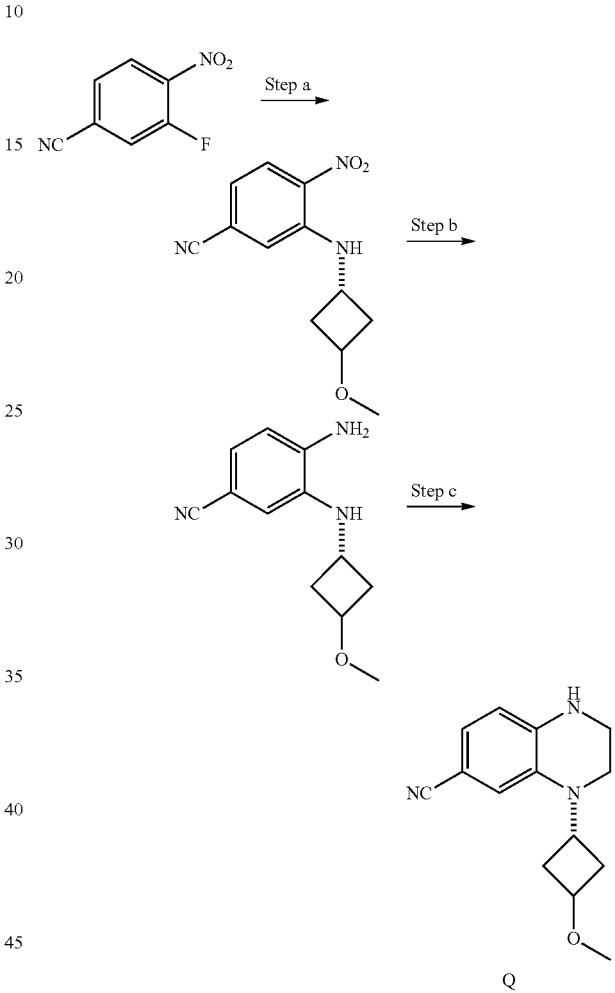

4-(trans-3-methoxycyclobutyl)-1,2,3,4-tetrahydroquinoxaline-6-carbonitrile was synthesized as described in Steps a-c of Intermediate O, coupling trans-3-methoxycyclobutan-1-amine hydrochloride in Step a. Characterization of the final intermediate: LCMS m/z [M+H]⁺=243.9; ¹H NMR (400 MHz, CDCl₃): δ=7.02-6.95 (m, 2H), 6.64 (s, 1H), 6.42 (d, J=8.0 Hz, 1H), 4.09-3.98 (m, 2H), 3.59 (t, J=5.0 Hz, 2H), 3.32 (s, 3H), 3.12 (t, J=5.0 Hz, 2H), 2.46-2.32 (m, 4H).

4-(cis-3-methoxycyclobutyl)-1,2,3,4-tetrahydroquinoxaline-6-carbonitrile, Intermediate R

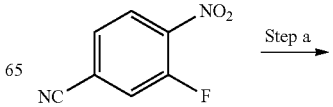

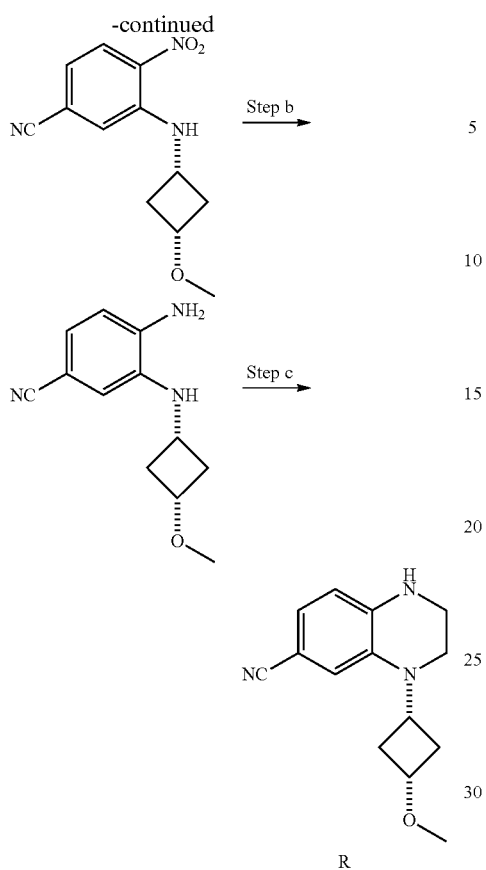

4-(cis-3-methoxycyclobutyl)-1,2,3,4-tetrahydroquinoxaline-6-carbonitrile was synthesized as described in Steps a-c of Intermediate 0, coupling cis-3-methoxycyclobutan-1-amine hydrochloride in Step a. Characterization of the final intermediate: LCMS m/z [M+H]$^+$=244.1; $^1$HNMR (400 MHz, CDCl$_3$): 6.94 (d, J=8.0 Hz, 1H), 6.67 (s, 1H), 6.41 (d, J=8.0 Hz, 1H), 4.37 (br, 1H), 3.70-3.78 (m, 1H), 3.56 (t, J=4.8 Hz, 2H), 3.38-3.48 (m, 1H), 3.30 (s, 3H), 3.13 (t, J=4.8 Hz, 2H), 2.73-2.83 (m, 2H), 1.93-2.03 (m, 2H).

6-chloro-3-(2,3-dichlorophenylpyrazin-2-amine, Intermediate S

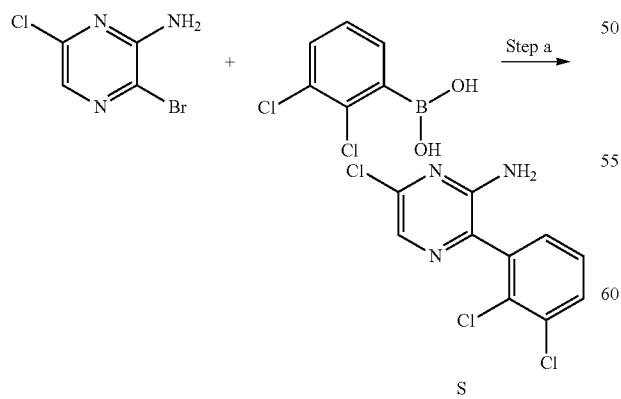

Step a: The mixture of 3-bromo-6-chloropyrazin-2-amine (600 mg, 2.87 mmol, 1.0 eq, CAS #212779-21-0), (2,3-dichlorophenyl)boronic acid (547 mg, 2.87 mmol, 1.0 eq), Pd(dppf)Cl$_2$ (210 mg, 287 μmol, 0.1 eq) and K$_3$PO$_4$ (1.82 g, 8.61 mmol, 3.0 eq) in dioxane (15 mL) and H$_2$O (3 mL) was evacuated and refilled 3 times with N2 gas, then stirred at 70° C. for 12 hours. The mixture was concentrated under reduced pressure to afford a residue, which was purified by column chromatography (petroleum ether/ethyl acetate=1: 0~10:1) to afford 6-chloro-3-(2,3-dichlorophenyl)pyrazin-2-amine (630 mg, 80% yield) as a yellow solid. LCMS m/z [M+H]$^+$=273.9/275.9.

(S)-4-fluoro-1,3-dihydrospiro[indene-2,4'-piperidin]-1-amine dihydrochloride, Intermediate T

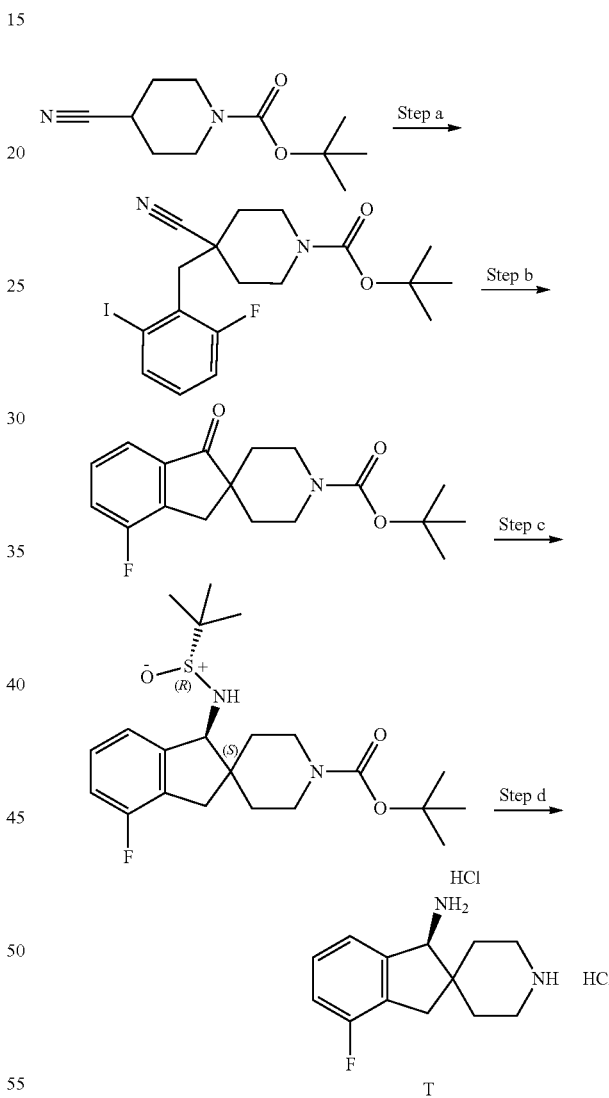

Step a: A round bottomed flask was charged with tert-butyl 4-cyanopiperidine-1-carboxylate (533 mg, 2.53 mmol) and THF (10 mL) before being cooled to −78° C. for the addition of lithiobis(propan-2-yl)amine (2.90 mL, 2.90 mmol). After 45 min, a solution of 2-(bromomethyl)-1-fluoro-3-iodobenzene (954 mg, 3.03 mmol) in THF (2 mL) was added, and the reaction warmed to rt. After 45 min, the reaction was diluted with water and ethyl acetate. The organic layer was pre-absorbed on silica gel (4 g) and was purified by column chromatography (eluting with ethyl acetate/heptanes) to yield tert-butyl 4-cyano-4-[(2-fluoro-6-iodophenyl)methyl]piperidine-1-carboxylate (860 mg, 76% yield) as a colorless oil. LCMS m/z [M+H]$^+$=445.1.

Step b: A round bottomed flask was charged with tert-butyl 4-cyano-4-[(2-fluoro-6-iodophenyl)methyl]piperidine-1-carboxylate (860 mg, 1.93 mmol), Pd/P(tBu)$_3$ G2 (98.8 mg, 0.1930 mmol), DMF (15 mL), water (1.5 mL), and triethylamine (320 µL, 2.31 mmol). Nitrogen was bubbled through the mixture for 5 min, before the vial was sealed and heated to 130° C. After 3 h, additional Pd/P(tBu)$_3$ G2 (98.8 mg, 0.1930 mmol) and triethylamine (233 mg, 2.31 mmol) was added, and the mixture was stirred at 130° C. overnight. The reaction was cooled to rt and partitioned between ethyl acetate, water, and brine. The organic layer was pre-absorbed on silica gel (4 g) and purified by column chromatography (eluting with ethyl acetate and heptanes) to afford tert-butyl 4-fluoro-1-oxo-1,3-dihydrospiro[indene-2,4'-piperidine]-1'-carboxylate (280 mg, 0.8767 mmol). LCMS m/z [M+H]$^+$=320.7.

Step c: A reaction tube was charged with tert-butyl 4-fluoro-1-oxo-1,3-dihydrospiro[indene-2,4'-piperidine]-1'-carboxylate (280 mg, 0.8767 mmol), (R)-2-methylpropane-2-sulfinamide (158 mg, 1.31 mmol), 2-MeTHF, and tetratitanium-1-ylium tetraethanolate (1.19 mL, 3.50 mmol). The vial was sealed and heated to 80° C. overnight. The mixture was cooled to rt and charged with boranium lithiumuide (28.5 mg, 1.31 mmol). After 2 h, the reaction was quenched with methanol and concentrated in vacuo. The residue was taken up in ethyl acetate and water. The aqueous layer was charged with celite, filtered and back-extracted with ethyl acetate. The combined organic fractions were pre-absorbed on silica gel (4 g), and purified by column chromatography (eluting with ethyl acetate and heptanes) to afford tert-butyl (3S)-7-fluoro-3-{[(R)-2-methylpropane-2-sulfinyl]amino}-1,3-dihydrospiro[indene-2,4'-piperidine]-1-carboxylate (175 mg, 0.412 mmol) as a colorless oil. LCMS m/z [M+H]$^+$=425.2.

Step d: A reaction tube was charged with tert-butyl (3S)-7-fluoro-3-{[(R)-2-methylpropane-2-sulfinyl]amino}-1,3-dihydrospiro[indene-2,4'-piperidine]-1'-carboxylate (170 mg, 0.40 mmol) and methanol (3 mL), followed by hydrogen chloride (1 mL, 4.00 mmol). The reaction mixture was stirred at rt for 16 h. The solvent was then removed in vacuo, and the residue was triturated with methyl tertbutyl ether. (S)-4-fluoro-1,3-dihydrospiro[indene-2,4'-piperidin]-1-amine dihydrochloride (150 mg) was isolated as a white solid following filtration and air drying to a constant weight. LCMS m/z [M+H]$^+$=221.1.

tert-butyl ((1S)-4-fluoro-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate, Intermediate U

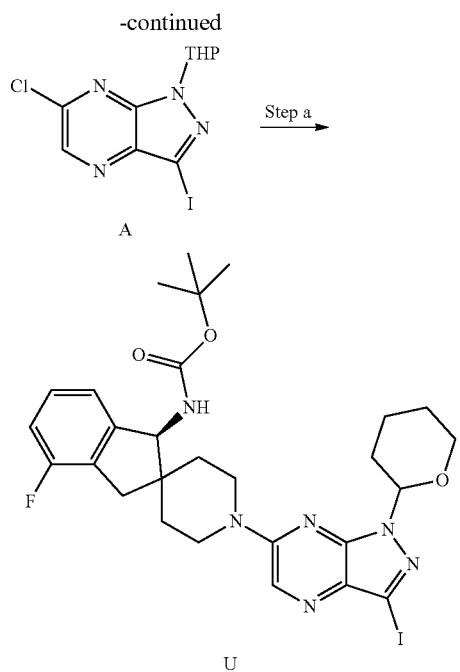

Step a: Dissolved (3S)-4-fluoro-1,3-dihydrospiro[indene-2,4'-piperidin]-3-amine dihydrochloride (1.38 g, 4.70 mmol, Intermediate T) in DMF (12 mL). 6-chloro-3-iodo-1-(oxan-2-yl)-1H-pyrazolo[3,4-b]pyrazine (1.71 g, 4.70 mmol, Intermediate A) was then added followed by ethylbis(propan-2-yl)amine (3.27 mL, 18.8 mmol) and the reaction mixture was stirred at 75° C. for 2 h. The reaction mixture was then cooled to rt and di-tert-butyl dicarbonate (1.17 mL, 5.17 mmol) was added and the reaction mixture was stirred at rt for 2 h. The reaction mixture was then diluted with EtOAc and water. The layers were separated, then the organic layer was washed with brine, dried over Na$_2$SO$_4$, filtered and concentrated onto SiO$_2$. The mixture was purified via column chromatography (0-100% EtOAc in heptanes) to give tert-butyl N-[(3S)-7-fluoro-1'-[3-iodo-1-(oxan-2-yl)-1H-pyrazolo[3,4-b]pyrazin-6-yl]-1,3-dihydrospiro[indene-2,4'-piperidin]-3-yl]carbamate (392 mg, 13% yield). LCMS m/z [M+H]$^+$=649.5.

(R)-4-fluoro-1,3-dihydrospiro[indene-2,4'-piperidin]-1-amine dihydrochloride, Intermediate V

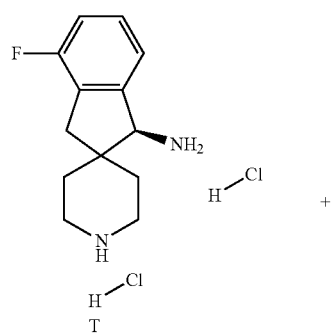

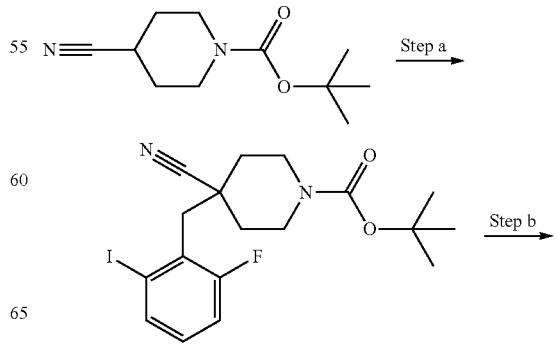

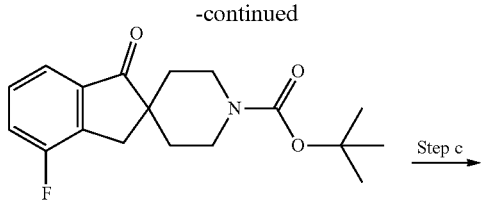

Step c

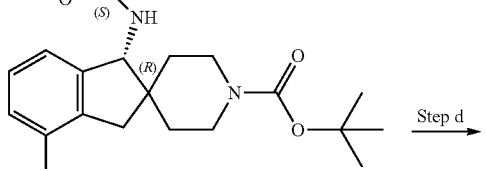

Step d

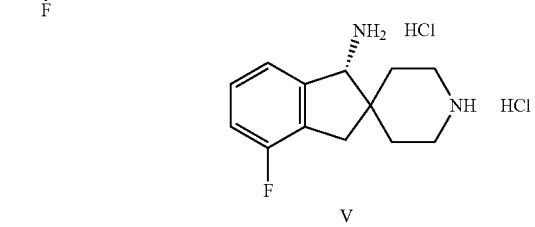

V (R)-4-fluoro-1,3-dihydrospiro[indene-2,4'-piperidin]-1-amine dihydrochloride was synthesized as described for Intermediate T, using (S)-2-methylpropane-2-sulfinamide in Step c to form tert-butyl (3R)-7-fluoro-3-{[(S)-2-methylpropane-2-sulfinyl]amino}-1,3-dihydrospiro[indene-2,4'-piperidine]-1'-carboxylate. (R)-4-fluoro-1,3-dihydrospiro[indene-2,4'-piperidin]-1-amine dihydrochloride was isolated as a white solid. LCMS m/z [M+H]⁺=221.2.

6-[1-(oxan-2-yl)-1H-pyrazol-5-yl]-1,2,3,4-tetrahydro-1,5-naphthyridine, Intermediate W

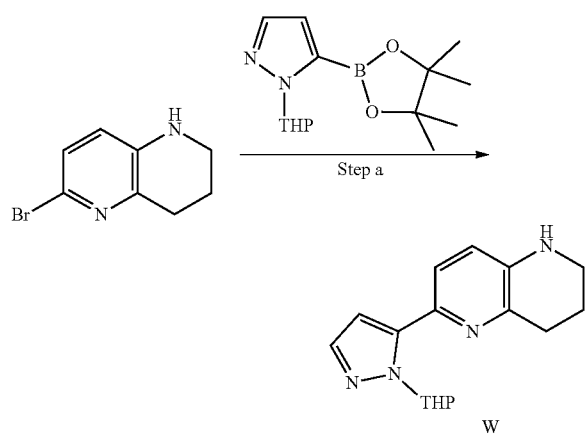

Step a: To a solution of 6-bromo-1,2,3,4-tetrahydro-1,5-naphthyridine (4.0 g, 18.7 mmol) in dioxane (50 mL) and H₂O (5 mL) were added Cs₂CO₃ (12.1 g, 37.4 mmol), 1-(oxan-2-yl)-5-(4,4,5,5-tetramethyl-1,3,2-dioxaborolan-2-yl)-1H-pyrazole (7.8 g, 28.0 mmol, CAS #903550-26-5) and Pd(dppf)Cl₂ (684 mg, 935 mmol). The mixture was stirred at 100° C. for 12 hours under N2 atmosphere. The reaction mixture was then concentrated in vacuo and purified by silica gel column (elution:petroleum ether:ethyl acetate=1:0 to 1:3) to give 6-[1-(oxan-2-yl)-1H-pyrazol-5-yl]-1,2,3,4-tetrahydro-1,5-naphthyridine (3.7 g, 70% yield) as a yellow solid. LCMS m/z [M+H]⁺=284.9. ¹HNMR (400 MHz, CD₃OD): δ 7.55~7.54 (m, 1H), 7.25 (d, J=6.4 Hz, 1H), 6.92 (d, J=6.4 Hz, 1H), 6.48 (s, 1H), 5.94~5.90 (m, 1H), 4.04~4.00 (m, 1H), 3.61~3.60 (m, 1H), 3.34~3.32 (m, 2H), 2.94~2.92 (m, 2H), 2.48-2.41 (m, 1H), 2.12~2.08 (m, 3H), 1.92~1.90 (m, 1H), 1.78~1.48 (m, 3H).

6-(1-methyl-1H-pyrazol-4-yl)-1,2,3,4-tetrahydro-1,5-naphthyridine, Intermediate X

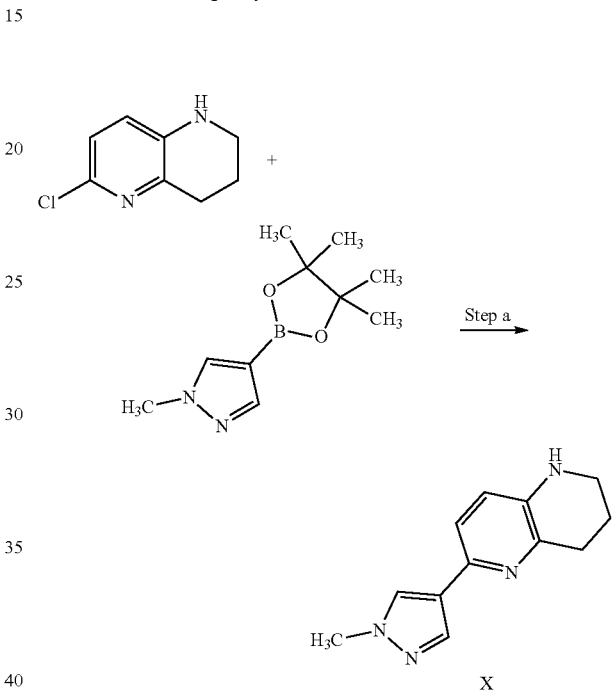

X

Step a: To the mixture of 6-chloro-1,2,3,4-tetrahydro-1,5-naphthyridine (2 g, 11.8 mmol) and 1-methyl-4-(4,4,5,5-tetramethyl-1,3,2-dioxaborolan-2-yl)-1H-pyrazole (2.93 g, 14.1 mmol) in dioxane (35.0 mL) and H₂O (5.0 mL) were added Pd(dppf)Cl₂ (1.29 g, 1.77 mmol) and K₃PO₄ (5.49 g, 25.9 mmol) under N2. The mixture was stirred at 100° C. under N2 for 3 hrs. The mixture was then concentrated in vacuo and purified by flash silica gel chromatography (petroleum ether/EtOAc=1/0 to 0/1) to give the product of 6-(1-methyl-1H-pyrazol-4-yl)-1,2,3,4-tetrahydro-1,5-naphthyridine (1.30 g, 52% yield) as a brown solid. LCMS m/z [M]⁺=214.9.

(S)-6-fluoro-1,3-dihydrospiro[indene-2,4'-piperidin]-1-amine dihydrochloride, Intermediate Y

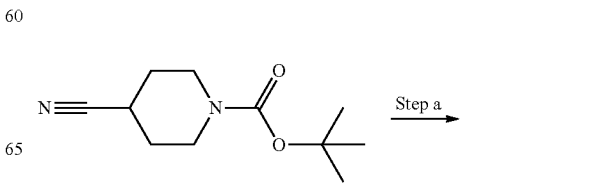

Step a

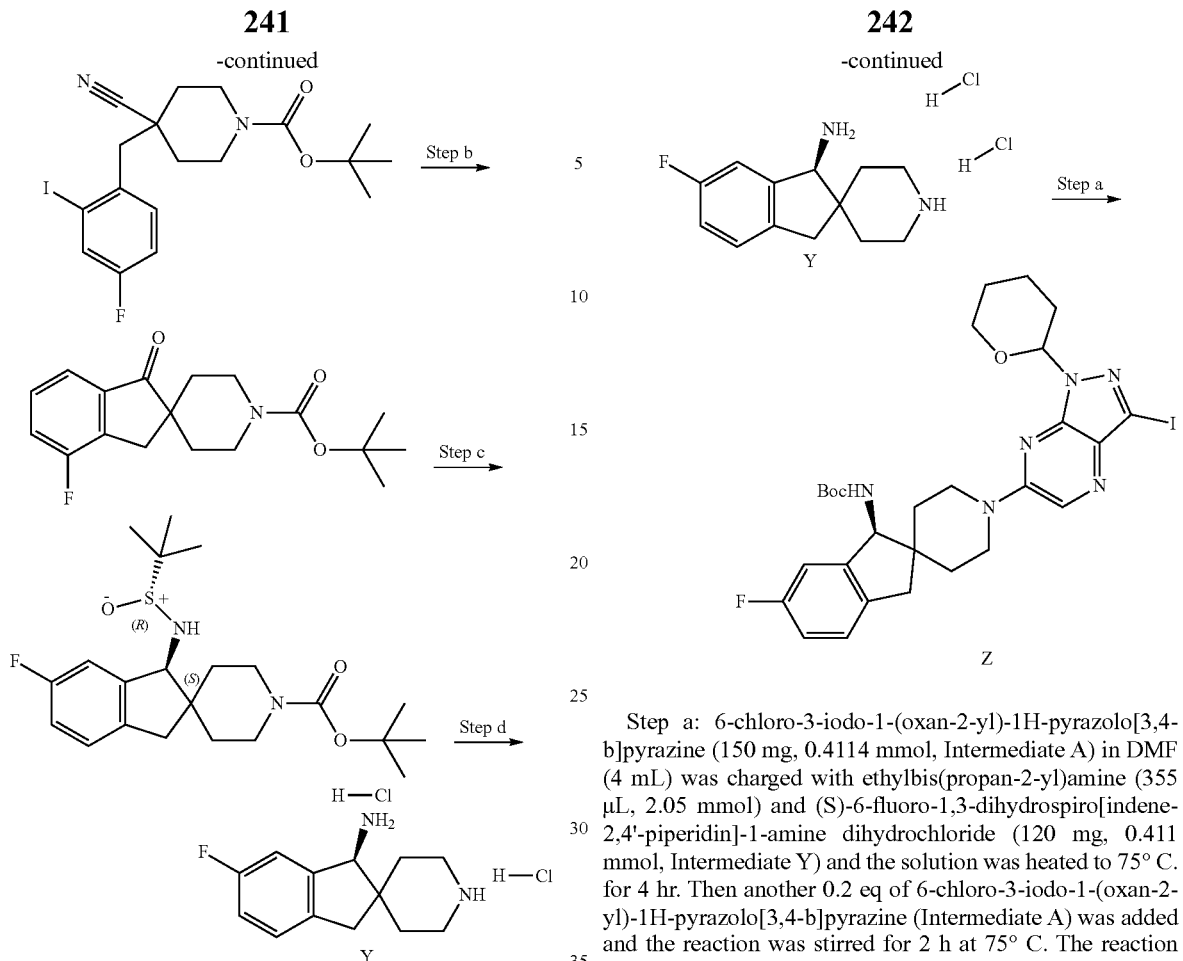

(S)-6-fluoro-1,3-dihydrospiro[indene-2,4'-piperidin]-1-amine was synthesized as described above for Intermediate T, using 1-(bromomethyl)-4-fluoro-2-iodobenzene for the coupling in Step a. $^1$H NMR (400 MHz, DMSO-d6) δ 8.80-9.04 (m, 2H), 8.65 (br s, 3H), 7.42 (dd, J=2.44, 9.03 Hz, 1H), 7.32 (dd, J=5.37, 8.30 Hz, 1H), 7.19 (dt, J=2.44, 8.79 Hz, 1H), 4.41 (br d, J=4.64 Hz, 1H), 3.69-3.74 (m, 1H), 3.31 (br d, J=13.18 Hz, 1H), 2.89-3.20 (m, 5H), 1.94-2.10 (m, 1H), 1.68-1.84 (m, 2H), 1.47-1.61 (m, 1H), 0.99-1.18 (m, 4H).

tert-butyl ((3S)-5-fluoro-1'-(3-iodo-1-(tetrahydro-2H-pyran-2-yl)-1H-pyrazolo[3,4-b]pyrazin-6-yl)-1,3-dihydrospiro[indene-2,4'-piperidin]-3-yl)carbamate, Intermediate Z Step a: 6-chloro-3-iodo-1-(oxan-2-yl)-1H-pyrazolo[3,4-b]pyrazine (150 mg, 0.4114 mmol, Intermediate A) in DMF (4 mL) was charged with ethylbis(propan-2-yl)amine (355 µL, 2.05 mmol) and (S)-6-fluoro-1,3-dihydrospiro[indene-2,4'-piperidin]-1-amine dihydrochloride (120 mg, 0.411 mmol, Intermediate Y) and the solution was heated to 75° C. for 4 hr. Then another 0.2 eq of 6-chloro-3-iodo-1-(oxan-2-yl)-1H-pyrazolo[3,4-b]pyrazine (Intermediate A) was added and the reaction was stirred for 2 h at 75° C. The reaction was then cooled to rt and di-tert-butyl dicarbonate (107 mg, 0.4936 mmol) was added and the reaction was stirred at rt for 16 h. The mixture was then partitioned between brine and EA. The org layer was pre-absorbed on SiO$_2$ (2 g) and purified on by column chromatography (12 g column, 20-70% EA/hep) to give tert-butyl ((3S)-5-fluoro-1'-(3-iodo-1-(tetrahydro-2H-pyran-2-yl)-1H-pyrazolo[3,4-b]pyrazin-6-yl)-1,3-dihydrospiro[indene-2,4'-piperidin]-3-yl)carbamate (175 mg, 66% yield) as a white solid. LCMS m/z [M+H]$^+$=649.2.

1-(6-chloro-1-(tetrahydro-2H-pyran-2-yl)-1H-pyrazolo[3,4-b]pyrazin-3-yl)-1,2,3,4-tetrahydro-1,5-naphthyridine, Intermediate AA

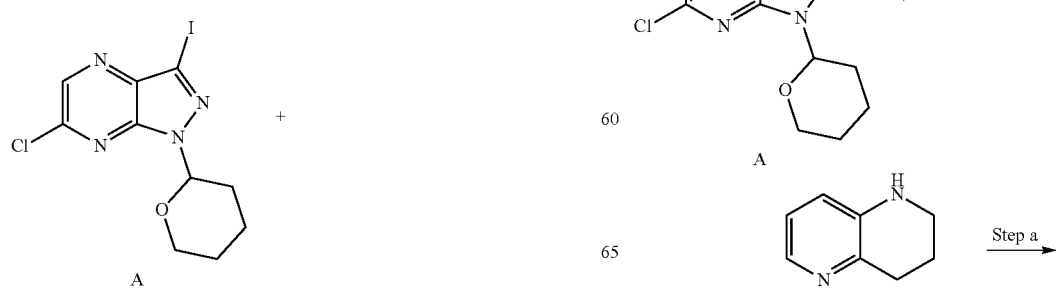

-continued

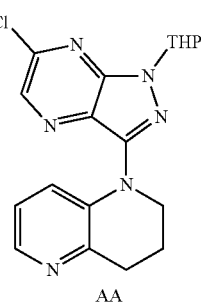

AA

Step a: A vial was charged with 6-chloro-3-iodo-1-(oxan-2-yl)-1H-pyrazolo[3,4-b]pyrazine (2 g, 5.48 mmol, Intermediate A), XantPhos-Pd-G4 (263 mg, 0.274 mmol), 1,2,3,4-tetrahydro-1,5-naphthyridine (720 mg, 5.37 mmol), and Cs$_2$CO$_3$ (3.54 g, 10.9 mmol) in PhMe (20 mL). The mixture was bubbled with nitrogen for 10 min, then the vial was sealed and heated to 60° C. for 48 h. The reaction mixture was cooled water and EA were added. The organic layer was washed with brine, dried, and concentrated. The residue was purified by column chromatography (Si-40 g column, 50-90% EA/hep) to afford 1-(6-chloro-1-(tetrahydro-2H-pyran-2-yl)-1H-pyrazolo[3,4-b]pyrazin-3-yl)-1,2,3,4-tetrahydro-1,5-naphthyridine (1.48 g, 73% yield) as an orange solid. LCMS m/z [M+H]$^+$=371.3.

Ethyl 6-(2,3-dichlorophenyl)-5-methyl-3-(tosyloxy)pyrazine-2-carboxylate, Intermediate AB

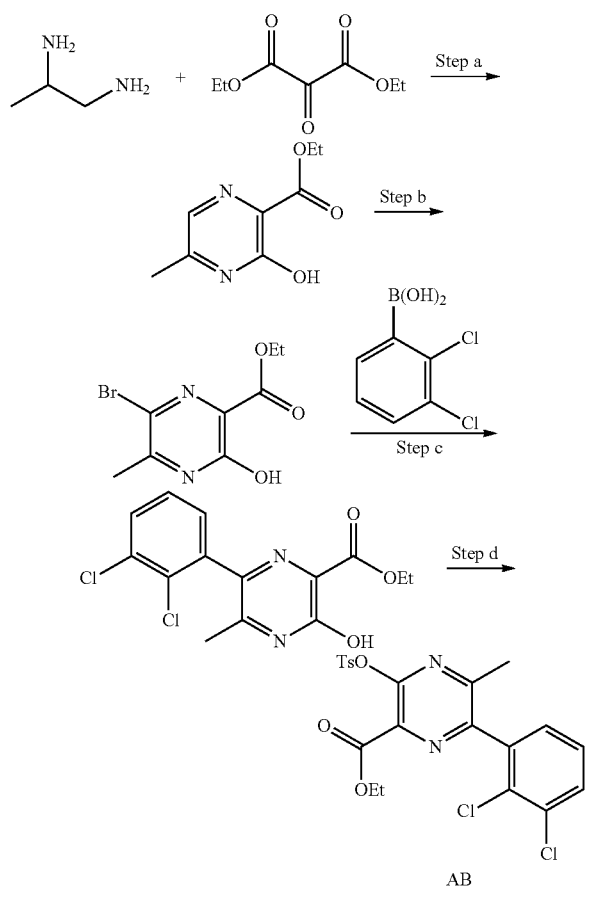

AB

Step a: To the stirred mixture of propane-1,2-diamine (5.00 g, 67.4 mmol, 5.76 mL, 1.00 eq) in EtOH (25.0 mL) was added diethyl 2-oxomalonate (11.7 g, 67.4 mmol, 10.4 mL, 1.00 eq) dropwise at 0° C. The mixture was warmed to 25° C. The reaction was stirred at 25° C. for 2 h, then the reaction was stirred at 95° C. for 18 h. The reaction mixture was concentrated then the residue was purified by column chromatography (SiO$_2$, petroleum ether/ethyl acetate=20:1~0:1 then petroleum ethyl/ethyl acetate/EtOH=8:3:1) to give ethyl 3-hydroxy-5-methylpyrazine-2-carboxylate (2.24 g, 18% yield) as a yellow solid. $^1$H NMR (400 MHz DMSO-d$_6$) 12.8 (br s, 1H), 7.35 (br s, 1H), 4.25 (q, J=7.2 Hz, 2H), 2.24 (s, 3H), 1.26 (t, J=7.2 Hz, 3H).

Step b: To the stirred solution of ethyl 3-hydroxy-5-methylpyrazine-2-carboxylate (2.24 g, 12.3 mmol, 1.00 eq) in DMF (11.2 mL) was added NBS (2.30 g, 12.9 mmol, 1.05 eq) in one portion at 0° C. under N2, then the mixture was stirred at 20° C. for 2 h. The reaction mixture was poured into H$_2$O (60.0 mL) where solid precipitate formed. The suspension was filtered and the solid filtrate was dried under reduced pressure to give ethyl 6-bromo-3-hydroxy-5-methylpyrazine-2-carboxylate (1.90 g, 59% yield) as a light yellow solid. LCMS m/z [M+H]$^+$=262.9; $^1$H NMR (400 MHz DMSO-d6) 12.8 (br s, 1H), 4.30 (q, J=7.2 Hz, 2H), 2.45 (s, 3H), 1.29 (t, J=7.2 Hz, 3H).

Step c: To the stirred mixture of ethyl 6-bromo-3-hydroxy-5-methylpyrazine-2-carboxylate (1.90 g, 7.28 mmol, 1.00 eq) and K$_2$CO$_3$ (4.02 g, 29.1 mmol, 4 eq) in ACN (9.50 mL) and H$_2$O (1.90 mL) was added (2,3-dichlorophenyl)boronic acid (1.39 g, 7.28 mmol, 1.00 eq) and Pd(dppf)Cl$_2$.CH$_2$Cl$_2$ (594 mg, 728 umol, 0.10 eq) under N2 at 20° C. The mixture was stirred at 90° C. for 1 h. To the mixture was then added H$_2$O (20.0 mL) and acidified with 0.5 N HCl to pH=7. The mixture was then extracted with ethyl acetate (40.0 mL×3). The combined organic layers were washed with brine (30.0 mL×2), dried over Na$_2$SO$_4$, filtered and concentrated. The residue was purified by flash silica gel chromatography (petroleum ether/ethyl acetate=50/1~1/1, R$_f$=0.6) to give ethyl 6-(2,3-dichlorophenyl)-3-hydroxy-5-methylpyrazine-2-carboxylate (700 mg, 29% yield) as a yellow solid. LCMS m/z [M+H]$^+$=327.1; $^1$H NMR (400 MHz CDCl$_3$) 11.47 (br s, 1H), 7.57 (d, J=7.6 Hz, 1H), 7.34 (t, J=7.6 Hz, 1H), 7.27-7.25 (m, 1H), 4.56 (q, J=6.8 Hz, 2H), 2.42 (s, 3H), 1.45 (td, J=7.2 Hz, 0.8 Hz, 3H).

Step d: A solution of ethyl-6-(2,3-dichlorophenyl)-3-hydroxy-5-methylpyrazine-2-carboxylate (150.0 mg, 458.0 μmol), TsCl (130.0 mg, 686.0 umol) and DIPEA (241.0 uL, 1.37 mmol) in CH$_2$Cl$_2$ (3.0 mL) was stirred at 20° C. for 1 hour. The solution was poured into H$_2$O (10.0 mL) and extracted with CH$_2$Cl$_2$ (10.0 mL×2). The combined organic layers were washed with brine (20.0 mL), dried over anhydrous Na$_2$SO$_4$, filtered and concentrated to give ethyl 6-(2,3-dichlorophenyl)-5-methyl-3-[(4-methylbenzenesulfonyl)oxy]pyrazine-2-carboxylate (240.0 mg, quant. crude yield) as an orange oil, which was used in the next step without further purification. LCMS m/z [M+H]$^+$=481.0/483.0.

Sodium 2-amino-3-chloropyridine-4-thiolate, Intermediate AC

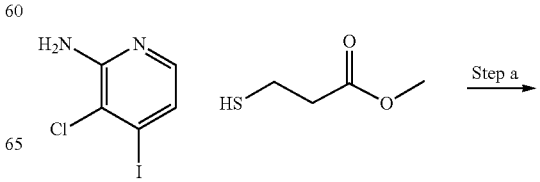

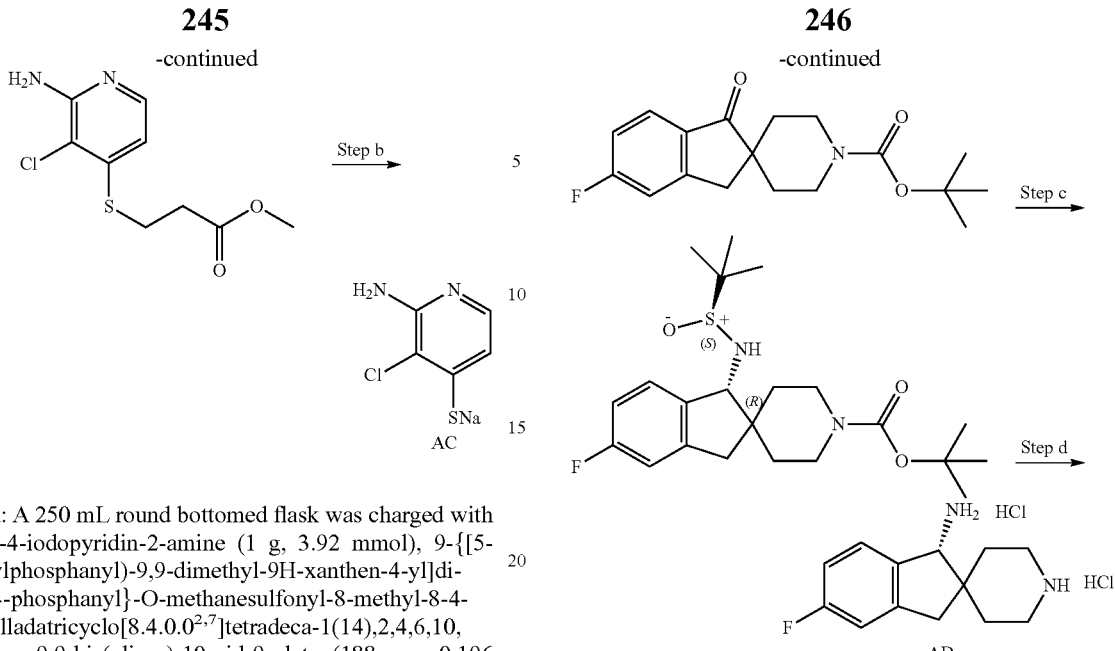

Step a: A 250 mL round bottomed flask was charged with 3-chloro-4-iodopyridin-2-amine (1 g, 3.92 mmol), 9-{[5-(diphenylphosphanyl)-9,9-dimethyl-9H-xanthen-4-yl]diphenyl-4-phosphanyl}-O-methanesulfonyl-8-methyl-8-4-aza-9-palladatricyclo[8.4.0.0$^{2,7}$]tetradeca-1(14),2,4,6,10,12-hexaene-9,9-bis(ylium)-10-uid-9-olate (188 mg, 0.196 mmol), dioxane (30 mL), methyl 3-sulfanylpropanoate (476 μL, 4.31 mmol) and ethylbis(propan-2-yl)amine (1.36 mL, 7.84 mmol). The mixture was bubbled with nitrogen for 5 min then the mixture was stirred at 100° C. for 1 h. The reaction mixture was diluted with EA, filtered through celite and washed with EA. The filtrate was pre-absorbed on SiO$_2$ (8 g) and purified by column chromatography (40 g column, 0-50% EA/Hex) to give methyl 3-((2-amino-3-chloropyridin-4-yl)thio)propanoate (890 mg, 92% yield). LCMS m/z [M]$^+$=246.9.

Step b: Methyl 3-[(2-amino-3-chloropyridin-4-yl)sulfanyl]propanoate (890 mg, 3.60 mmol), and ethoxysodium (1.40 mL, 3.78 mmol) were dissolved in THF (10 mL). The mixture was stirred at 25° C. for 10 min. The mixture was diluted with DCM (10-15 mL) and stirred until nucleation occurred; after 5 min, large amount of solid formed in suspension. Additional DCM (86 mL) was added, the reaction was filtered and the filter cake washed with DCM and was air dried. Sodium 2-amino-3-chloropyridine-4-thiolate (473 mg, 71% yield) was isolated as a red/brown solid, which was stored in the freezer until use. LCMS m/z [M+H-Na]$^+$=160.9.

(S)-5-fluoro-1,3-dihydrospiro[indene-2,4'-piperidin]-1-amine, Intermediate AD

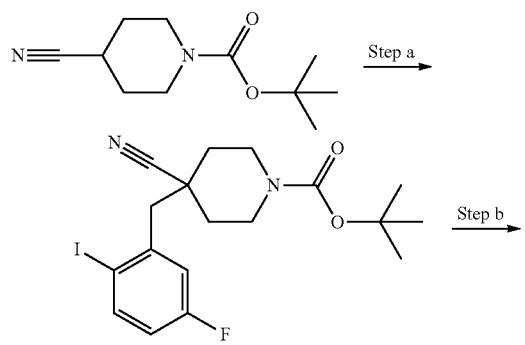

(S)-5-fluoro-1,3-dihydrospiro[indene-2,4'-piperidin]-1-amine was synthesized as described above for Intermediate T, using 2-(bromomethyl)-4-fluoro-1-iodobenzene for the coupling in Step a and using (S)-2-methylpropane-2-sulfinamide in Step c. $^1$H NMR (400 MHz, DMSO-d6) δ ppm 8.94 (br s, 2H) 8.58 (br s, 3H) 7.61 (br dd, J=7.81, 5.86 Hz, 1H) 7.07-7.18 (m, 2H) 4.37 (br d, J=4.39 Hz, 1H) 3.71 (s, 1H) 3.31 (br d, J=13.43 Hz, 1H) 3.13-3.22 (m, 2H) 2.87-3.10 (m, 3H) 1.95-2.11 (m, 1H) 1.64-1.85 (m, 2H) 1.50 (br d, J=14.40 Hz, 1H) 1.09 (s, 4H).

6-(1,3-oxazol-2-yl)-1,2,3,4-tetrahydro-1,5-naphthyridine, Intermediate AE

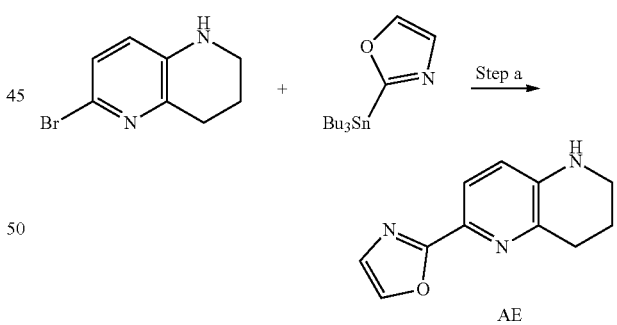

Step a: A mixture of 6-bromo-1,2,3,4-tetrahydro-1,5-naphthyridine (1 g, 4.69 mmol, CAS #1219022-46-4), 2-(tributylstannyl)-1,3-oxazole (2.51 g, 7.03 mmol), Pd$_2$(dba)$_3$ (429 mg, 469 μmol) and XPhos (447 mg, 938 μmol) in dioxane (30 mL) was stirred at 100° C. for 12 hours under N$_2$ atmosphere. After cooling to room temperature, KF (2 g) was added and the reaction mixture was stirred at 20° C. for 0.5 hour. The reaction mixture was diluted with ethyl acetate (60 mL), and washed with H$_2$O (30 mL×2). The organic phase was washed with brine (15 mL), dried over anhydrous Na$_2$SO$_4$, filtered and concentrated in vacuo to give a residue. The residue was purified by silica gel chromatography (ethyl acetate as eluent) to afford 6-(1,3-oxazol-2-yl)-1,2,3,4-tetrahydro-1,5-naphthyridine (260 mg, 28% yield) as a yellow oil. LCMS m/z [M]+=201.9.

4-(1-cyanocyclopropyl)-1,2,3,4-tetrahydroquinoxaline-6-carbonitrile, Intermediate AF

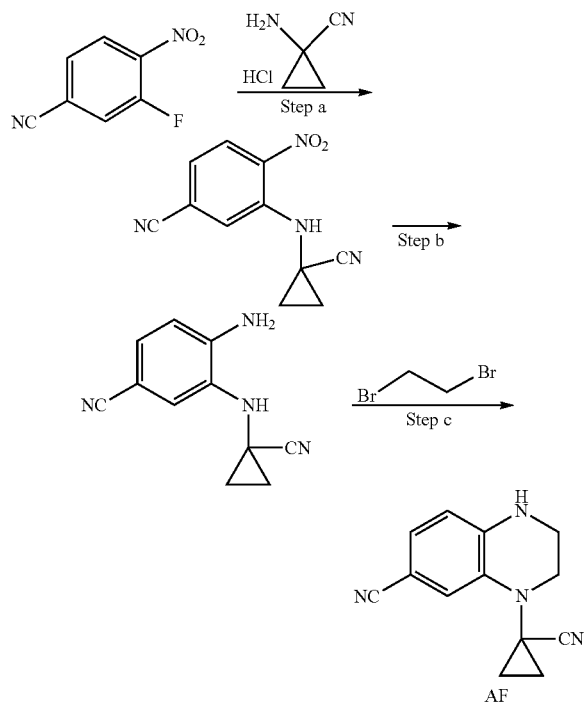

Step a: To the mixture of 1-aminocyclopropane-1-carbonitrile hydrochloride (4.0 g, 33.7 mmol) and TEA (13.9 mL, 101 mmol) in EtOH (60.0 mL) was added 3-fluoro-4-nitrobenzonitrile (5.6 g, 33.7 mmol). The mixture was stirred at 90° C. for 12 hours. The mixture was concentrated in vacuo and purified by flash silica gel chromatography (petroleum ether/EtOAc=I/O to 3/1) to give the product 3-[(1-cyanocyclopropyl)amino]-4-nitrobenzonitrile (2.8 g, 36% yield) as a yellow solid. $^1$HNMR (400 MHz, CDCl$_3$) δ 8.34-8.24 (m, 2H), 7.64 (s, 1H), 7.20-7.18 (m, 1H), 1.82-1.79 (m, 2H), 1.45-1.42 (m, 2H).

Step b: To the mixture of 3-[(1-cyanocyclopropyl)amino]-4-nitrobenzonitrile (2.5 g, 10.9 mmol) in MeOH (40.0 mL) was added 10% wet Pd/C (300.0 mg). The mixture was stirred at 15° C. under H2 (15 psi) for 2 hours. The mixture was filtered and the filtrate was concentrated in vacuo to give a residue. The residue was purified by flash silica gel chromatography (petroleum ether/EtOAc=I/O to 1/1) to give the product of 4-amino-3-[(1-cyanocyclopropyl)amino]benzonitrile (1.1 g, 51% yield) as a brown solid. $^1$HNMR (400 MHz, CDCl$_3$) δ 7.22-7.20 (m, 1H), 7.11-7.05 (m, 1H), 6.68 (d, J=12.0 Hz, 1H), 4.29 (s, 1H), 3.70 (s, 2H), 1.58-1.51 (m, 2H), 1.23-1.19 (m, 2H).

Step c: A mixture of 4-amino-3-[(1-cyanocyclopropyl)amino]benzonitrile (500.0 mg, 2.5 mmol), TBAB (3.2 g, 10.0 mmol), TEA (1.1 mL, 8.6 mmol) and 1,2-dibromoethane (1.5 mL, 17.4 mmol) was stirred at 60° C. for 24 hours. The mixture was poured into water (50 mL) and extracted with DCM (50 mL×3). The organic layers were washed with brine and dried over anhydrous Na$_2$SO$_4$, filtered and the filtrate was concentrated in vacuo to give a residue. The residue was purified by flash silica gel chromatography (petroleum ether/EtOAc=I/O to 1/1) to give the product of 4-(1-cyanocyclopropyl)-1,2,3,4-tetrahydroquinoxaline-6-carbonitrile (175.0 mg, combined product) as an off-white solid. LCMS m/z [M+H]+=224.9; $^1$H NMR (400 MHz, CDCl$_3$): δ=7.10 (s, 1H), 6.96 (d, J=8.0 Hz, 1H), 6.38 (d, J=8.0 Hz, 1H), 4.32 (s, 1H), 3.46 (t, J=4.6 Hz, 2H), 3.46 (t, J=4.6 Hz, 2H), 1.55 (s, 2H), 1.21 (s, 2H).

Tert-butyl 3-{[(tert-butoxy)carbonyl]amino}-1,3-dihydrospiro[indene-2,4'-piperidine]-1'-carboxylate, Intermediate AG

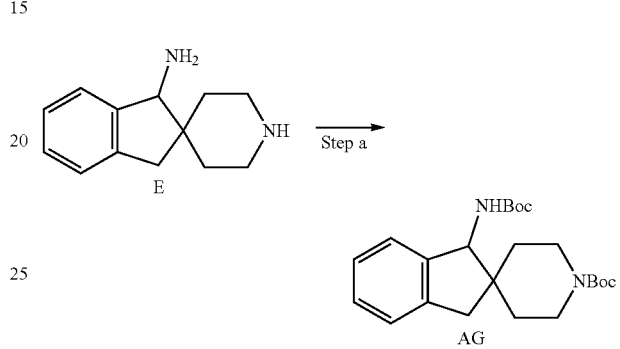

Step a: The mixture of 1,3-dihydrospiro[indene-2,4'-piperidin]-3-amine (100 mg, 494 µmol, Intermediate E), Boc$_2$O (322 mg, 1.48 mmol) and TEA (149 mg, 1.48 mmol) in DCM (3 mL) was stirred at 30° C. for 2 hours. Then the mixture was concentrated under reduced pressure. The residue was purified by column chromatography (petroleum ether/ethyl acetate=1:0~10:1) to afford tert-butyl 3-{[(tert-butoxy)carbonyl]amino}-1,3-dihydrospiro[indene-2,4'-piperidine]-1'-carboxylate (30 mg, 62% purity, 15% yield) as a colorless oil. LCMS m/z [M+Na]+=425.1.

Tert-butyl 6-bromo-1-((tert-butoxycarbonyl)amino)-1,3-dihydrospiro[indene-2,4'-piperidine]-1'-carboxylate, Intermediate AH

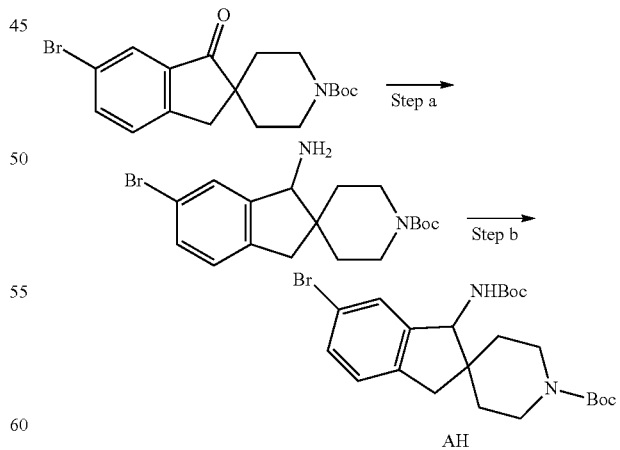

Step a: A solution of tert-butyl 6-bromo-1-oxo-1,3-dihydrospiro[indene-2,4'-piperidine]-1'-carboxylate (1.5 g, 3.94 mmol, synthesized via Steps a-c of Intermediate AL), AcONH$_4$ (3.03 g, 39.4 mmol) and NaBH$_3$CN (297 mg, 4.72 mmol) in EtOH (30 mL) was stirred at 80° C. for 1 h. Then to the mixture was added additional AcONH₄ (3.03 g, 39.4 mmol) and NaBH₃CN (297 mg, 4.72 mmol) 3 times every hour and the mixture was stirred at 80° C., then the mixture was stirred at 80° C. for 9 h. The solution was added into 10% NaOH (150 mL) and then extracted with EtOAc (200 mL×2). The combined organic layers were washed with brine (200 mL), dried over anhydrous Na₂SO₄, filtered and concentrated in vacuo to give tert-butyl 1-amino-6-bromo-1,3-dihydrospiro[indene-2,4'-piperidine]-1'-carboxylate (1.5 g, quant. crude yield) as a yellow gum. LCMS m/z [M+H]⁺= 381.0/383.0.

Step b: A solution of tert-butyl 1-amino-6-bromo-1,3-dihydrospiro[indene-2,4'-piperidine]-1-carboxylate (1.5 g, 3.93 mmol), Boc₂O (1.02 g, 4.71 mmol) and Et₃N (1.61 mL, 11.7 mmol) in DCM (30 mL) was stirred at 20° C. for 1 h. The solution was added into H₂O (100 mL) and then extracted with CH₂Cl₂ (50 mL×2). The combined organic layers were washed with brine (100 mL), dried over anhydrous Na₂SO₄, filtered and concentrated in vacuo to give crude product as yellow gum. The residue was purified by flash silica gel chromatography (40 g, Ethyl acetate in Petroleum ether from 0% to 10%) to give tert-butyl 6-bromo-1-((tert-butoxycarbonyl)amino)-1,3-dihydrospiro[indene-2,4'-piperidine]-1'-carboxylate (1.4 g, 74%) as a yellow gum. LCMS m/z [M+H−100]⁺=381.0/383.0.

1-amino-N,N-dimethyl-1,3-dihydrospiro[indene-2,4'-piperidine]-6-carboxamide, Intermediate AI

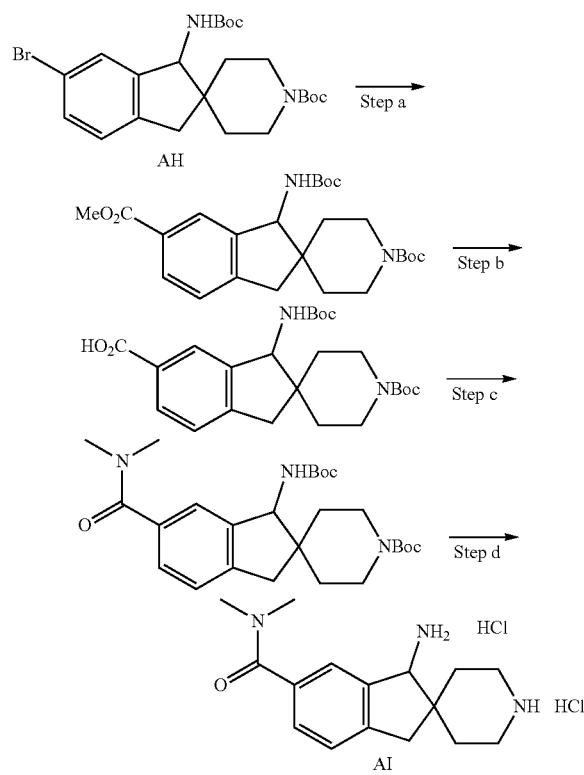

Step a: A solution of tert-butyl 6-bromo-1-((tert-butoxycarbonyl)amino)-1,3-dihydrospiro[indene-2,4'-piperidine]-1'-carboxylate (300.0 mg, 623.0 μmol), Pd(dppf)Cl₂ (45.6 mg, 62.3 umol) and TEA (256.0 uL, 1.86 mmol) in MeOH (20.0 mL) was stirred at 80° C. for 12 hours under CO (50 psi). The mixture was concentrated to give a residue, which was purified by flash silica gel chromatography (12 g, ethyl acetate in petroleum ether from 0% to 15%) to give 1'-tert-butyl 5-methyl (3S)-3-{[(tert-butoxy)carbonyl]amino}-1,3-dihydrospiro[indene-2,4'-piperidine]-1',5-dicarboxylate (200.0 mg, 70% yield) as a white solid. LCMS m/z [M+H]⁺= 461.2.

Step b: A solution of 1'-tert-butyl 5-methyl (3)-3-{[(tert-butoxy)carbonyl]amino}-1,3-dihydrospiro[indene-2,4'-piperidine]-1',5-dicarboxylate (200.0 mg, 434.0 μmol) and LiOH H₂O (91.1 mg, 2.17 mmol) in MeOH/H₂O (3.0 mL/3.0 mL) was stirred at 50° C. for 0.5 hour. The reaction mixture was adjusted pH=4 with 2 N HC and extracted with CH₂Cl₂ (10.0 mL×2). The combined organic layers were concentrated under reduced pressure to give the product of 1'-[(tert-butoxy)carbonyl]-3-{[(tert-butoxy)carbonyl]amino}-1,3-dihydrospiro[indene-2,4'-piperidine]-5-carboxylic acid (150.0 mg, 78% yield) as a yellow oil. LCMS m/z [M+H]⁺=447.2.

Step c: A solution of 1'-[(tert-butoxy)carbonyl]-1-{[(tert-butoxy)carbonyl]amino}-1,3-dihydrospiro[indene-2,4'-piperidine]-6-carboxylic acid (200.0 mg, 447.0 μmol), dimethylamine hydrochloride (109.0 mg, 1.34 mmol), HATU (254.0 mg, 670.0 umol) and TEA (245.0 uL, 1.78 mmol) in DMF (5.0 mL) was stirred at 50° C. for 0.5 hour. The reaction mixture was poured into H₂O (20.0 mL) and extracted with EtOAc (20.0 mL×2). The combined organic layers were washed with brine (20.0 mL), dried over anhydrous Na₂SO₄, filtered and concentrated under reduced pressure to give the product of tert-butyl 1-{[(tert-butoxy)carbonyl]amino}-6-(dimethylcarbamoyl)-1,3-dihydrospiro[indene-2,4'-piperidine]-1'-carboxylate (200.0 mg, 95% yield) as a yellow oil. LCMS m/z [M+H]⁺=474.2.

Step d: A solution of tert-butyl 1-{[(tert-butoxy)carbonyl]amino}-6-(dimethylcarbamoyl)-1,3-dihydrospiro[indene-2,4'-piperidine]-1'-carboxylate (200.0 mg, 422.0 μmol) in HCl/MeOH (5.0 mL, 4 M) was stirred at 20° C. for 0.5 hour. The reaction mixture was concentrated under reduced pressure to give the product of 1-amino-N,N-dimethyl-1,3-dihydrospiro[indene-2,4'-piperidine]-6-carboxamide dihydrochloride (150.0 mg, quant. crude yield) as a yellow oil. LCMS m/z [M+H]⁺=274.1.

Sodium 2-chloro-3-fluoropyridine-4-thiolate, Intermediate AJ

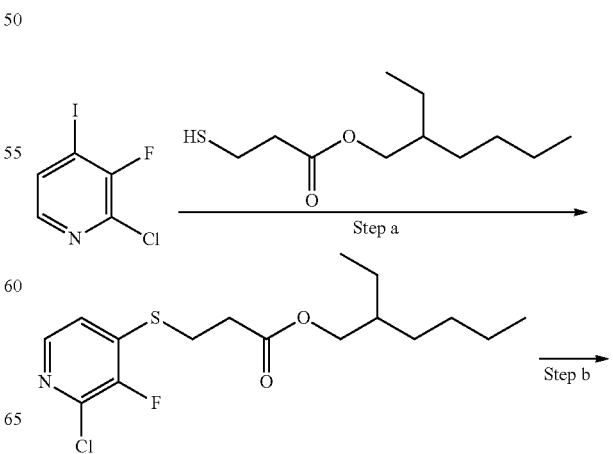

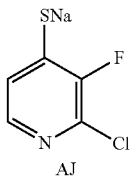

AJ

Step a: To a mixture of 2-chloro-3-fluoro-4-iodopyridine (900 mg, 3.5 mmol) and 2-ethylhexyl 3-sulfanylpropanoate (912 mg, 4.2 mmol) in dioxane (10 mL) were added Pd$_2$(dba)$_3$ (319 mg, 0.3 mmol), XantPhos (403 mg, 0.7 mmol) and DIPEA (1.8 mL, 10.4 mmol). The reaction mixture was purged with N2 for 3 min and stirred at 100° C. for 12 hours under N2. The reaction mixture was concentrated under reduced pressure to give the residue, which was purified by column chromatography (petroleum ether:ethyl acetate=100:0 to 100:10) to give 2-ethylhexyl 3-[(2-chloro-3-fluoropyridin-4-yl)sulfanyl]propanoate (410 mg, 34% yield) as a yellow solid. LCMS m/z [M+H]$^+$=348.1.

Step b: A mixture of 2-ethylhexyl 3-[(2-chloro-3-fluoropyridin-4-yl)sulfanyl]propanoate (200 mg, 0.6 mmol) and MeONa (37.1 mg, 0.7 mmol) in THF (1.0 mL) was stirred at 20° C. for 1 hour. The mixture was diluted with DCM (0.5 mL) and stirred at 0° C. for 30 min. The reaction mixture was filtered and the cake washed with DCM and air dried to give sodium 2-chloro-3-fluoropyridine-4-thiolate as a light yellow solid (80 mg, 75% yield). LCMS m/z [M+H]$^+$=164.0.

Methyl 3-chloro-5-methylpyrazine-2-carboxylate, Intermediate AK

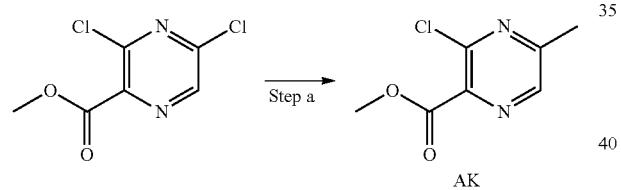

AK

Step a: A mixture of methyl 3,5-dichloropyrazine-2-carboxylate (2.0 g, 9.7 mmol, synthesized via Step a of Intermediate A), trimethyl-1,3,5,2,4,6-trioxatriborinane (2.4 g, 19.3 mmol), Pd(PPh$_3$)$_4$ (558 mg, 483 μmol) and Cs$_2$CO$_3$ (6.3 g, 19.3 mmol) in dioxane (70 mL) was stirred at 110° C. for 12 hours under N2 atmosphere. The reaction mixture was concentrated in vacuo to give a residue, which was purified by silica gel chromatography (ethyl acetate in petroleum ether=0% to 50%) to afford methyl 3-chloro-5-methylpyrazine-2-carboxylate (250 mg, 14% yield) as a yellow solid. LCMS m/z [M+H]$^+$=187.0.

tert-butyl (1S)-6-bromo-1-{[(R)-2-methylpropane-2-sulfinyl]amino}-1,3-dihydrospiro[indene-2,4'-piperidine]-1'-carboxylate, Intermediate AL

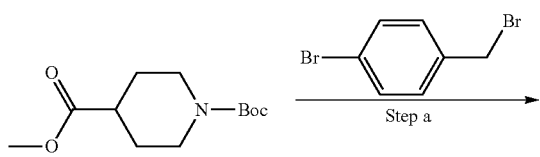

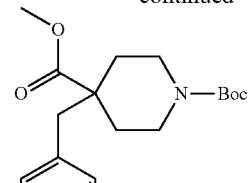

Step a: To a solution of 1-tert-butyl-4-methyl piperidine-1,4-dicarboxylate (10.00 g, 41.10 mmol) in THF (150.0 mL) was added LDA (24.6 mL, 49.3 mmol, 2 M) at −78° C. under N2. The mixture was stirred at −78° C. for 1 hour. To the mixture was added 1-bromo-4-(bromomethyl)benzene (10.70 g, 43.10 mmol) in THF (50.0 mL) at −78° C. The mixture was then stirred at 20° C. for 11 hours under N2. The reaction mixture was quenched with H$_2$O (400.0 mL) and extracted with EtOAc (400.0 mL×2). The combined organic layers were washed with brine (300.0 mL), dried over anhydrous Na$_2$SO$_4$, filtered and concentrated to give a yellow residue. The residue was purified by flash silica gel chromatography (120 g column, ethyl acetate in petroleum ether from 0% to 5%) to give 1-tert-butyl 4-methyl 4-[(4-bromophenyl)methyl]piperidine-1,4-dicarboxylate (11.40 g, 67% yield) as a yellow oil. LCMS m/z [M+H−100]$^+$=312.0/314.0.

Step b: A solution of 1-tert-butyl 4-methyl 4-[(4-bromophenyl)methyl]piperidine-1,4-dicarboxylate (11.40 g, 27.6 mmol) and KOH (7.74 g, 138.0 mmol) in MeOH/H$_2$O (50.0 mL/50.0 mL) was stirred at 60° C. for 16 hours. The mixture was adjusted to pH=5 with 2 N HCl and extracted with CH$_2$Cl$_2$ (150.0 mL×2). The combined organic layers were washed with brine (200.0 mL), dried over anhydrous Na$_2$SO$_4$, filtered and concentrated to give 4-[(4-bromophenyl)methyl]-1-[(tert-butoxy)carbonyl]piperidine-4-carboxylic acid (10.8 g, 99% yield) as a white solid. LCMS m/z [M+H−100]$^+$=298.0/300.0.

Step c: To a solution of 4-[(4-bromophenyl)methyl]-1-[(tert-butoxy)carbonyl]piperidine-4-carboxylic acid (10.00 g, 25.1 mmol) in DCM (150.0 mL) was added SOCl$_2$ (3.64 mL, 50.2 mmol) at 20° C. under N2. The mixture was stirred at 20° C. for 1 hour, where a white suspension was observed. To the mixture was added AlCl$_3$ (5.01 g, 37.6 mmol) in portions at 0° C. The mixture was stirred at 20° C. for 2 h under N2. The reaction mixture was then quenched by 2 N NaOH and adjusted pH=10. Next, to the mixture was added Boc$_2$O (10.90 g, 50.2 mmol) at 20° C. The mixture was stirred at 20° C. for 1 hour. The reaction mixture was filtered and the filtrate was extracted with CH$_2$Cl$_2$ (100.0 mL×2). The combined organic layers were washed with brine (200.0 mL), dried over anhydrous Na$_2$SO$_4$, filtered and concentrated to give a yellow residue. The residue was purified by flash silica gel chromatography (80 g column, ethyl acetate in petroleum ether from 0% to 10%) to give tert-butyl 6-bromo-1-oxo-1,3-dihydrospiro[indene-2,4'-piperidine]-1'-carboxylate (6.00 g, 63% yield) as an orange solid. LCMS m/z [M+H−100]$^+$=280.0/282.0.

Step d: To a solution of tert-butyl 6-bromo-1-oxo-1,3-dihydrospiro[indene-2,4'-piperidine]-1-carboxylate (1.00 g, 2.62 mmol) and Ti(OEt)$_4$ (2.17 mL, 10.4 mmol) in 2-Me-THF (20.0 mL) was added (R)-2-methylpropane-2-sulfinamide (635.0 mg, 5.24 mmol). The reaction mixture was stirred at 90° C. for 12 hours under N2. Tert-butyl (1E)-6-bromo-1-{[(R)-2-methylpropane-2-sulfinyl]imino}-1,3-dihydrospiro[indene-2,4'-piperidine]-1'-carboxylate (1.30 g, crude) in 2-Me-THF (20.0 mL) was used directly in the next step without further purification.

Step e: To a solution of tert-butyl (1E)-6-bromo-1-{[(R)-2-methylpropane-2-sulfinyl]imino}-1,3-dihydrospiro[indene-2,4'-piperidine]-1'-carboxylate (1.30 g, 2.68 mmol) in 2-Me-THF (20.0 mL) was added LiBH$_4$ (2.68 mL, 5.36 mmol) at 0° C. The mixture was stirred at 20° C. for 1 hour. The reaction mixture was quenched with MeOH, then triturated with H$_2$O (200.0 mL) and extracted with EtOAc (200.0 mL×2). The combined organic layers were washed with brine (200.0 mL), dried over anhydrous Na$_2$SO$_4$, filtered and concentrated to give an orange residue. The residue was purified by flash silica gel chromatography (40 g column, ethyl acetate in petroleum ether from 0% to 30%) to give tert-butyl (1S)-6-bromo-1-{[(R)-2-methylpropane-2-sulfinyl]amino}-1,3-dihydrospiro[indene-2,4'-piperidine]-1'-carboxylate (550.0 mg, 42% yield) as a white solid. LCMS m/z [M+H]$^+$=485.1/487.1.

(S)-1-amino-1,3-dihydrospiro[indene-2,4'-piperidine]-6-carbonitrile, Intermediate AM

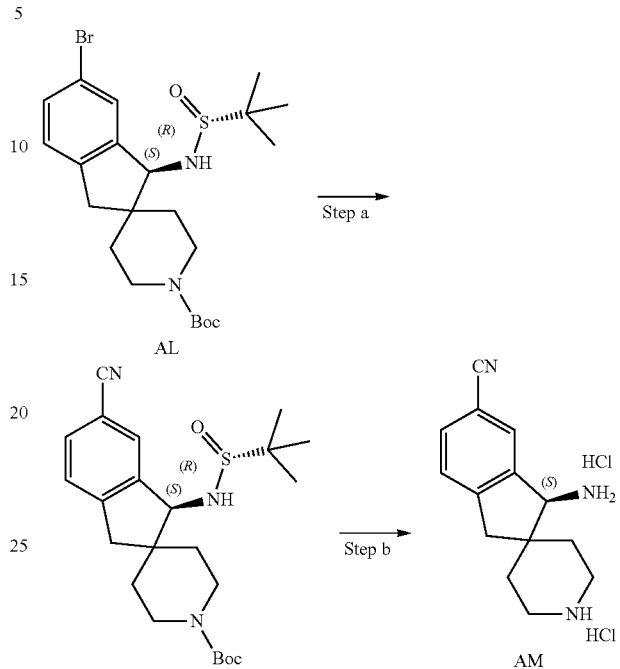

Step a: A solution of tert-butyl (1S)-6-bromo-1-{[(R)-2-methylpropane-2-sulfinyl]amino}-1,3-dihydrospiro[indene-2,4'-piperidine]-1'-carboxylate (550.0 mg, 1.13 mmol, Intermediate AL), Zn(CN)$_2$ (265.0 mg, 2.26 mmol) and XantPhos-Pd-G4 (108.0 mg, 113.0 umol) in DMF (20.0 mL) was stirred at 100° C. for 12 hours under N2. The reaction mixture was poured into H$_2$O (100.0 mL) and extracted with EtOAc (100.0 mL×2). The combined organic layers were washed with brine (200.0 mL), dried over anhydrous Na$_2$SO$_4$, filtered and concentrated to give an orange residue. The residue was purified by flash silica gel chromatography (12 g column, ethyl acetate in petroleum ether from 0% to 50%) to give tert-butyl (1S)-6-cyano-1-{[(R)-2-methylpropane-2-sulfinyl]amino}-1,3-dihydrospiro[indene-2,4'-piperidine]-1'-carboxylate (490.0 mg, 100% yield) as a white solid. LCMS m/z [M+H]$^+$=432.2.

Step b: A solution of tert-butyl (1S)-6-cyano-1-{[(R)-2-methylpropane-2-sulfinyl]amino}-1,3-dihydrospiro[indene-2,4'-piperidine]-1'-carboxylate (450.0 mg, 1.04 mmol) in HCl/MeOH (15.0 mL, 4 M) was stirred at 20° C. for 0.5 hour. The reaction mixture was concentrated to give the product of (S)-1-amino-1,3-dihydrospiro[indene-2,4'-piperidine]-6-carbonitrile dihydrochloride (450.0 mg, 70% purity, quant. crude yield) as a white solid. LCMS m/z [M+H]$^+$= 228.1.

7-bromo-1-methyl-1,2,3,4-tetrahydroquinoxaline, Intermediate AN

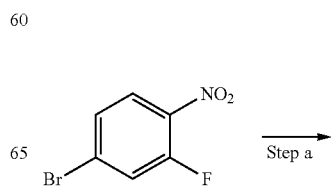

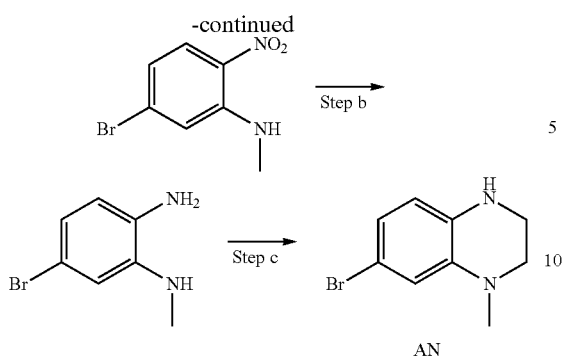

Step a: To the mixture of 4-bromo-2-fluoro-1-nitrobenzene (25.0 g, 113.0 mmol) in MeOH (100.0 mL) and THF (50.0 mL) was added MeNH$_2$ (67.5 mL, 135.0 mmol, 2 M in THF) dropwise. The mixture was stirred at 10° C. for 12 hours. Then more MeNH$_2$ (60.0 mL, 2 M in THF) was added to the mixture and the mixture was stirred at 45° C. for 12 hours. The mixture was concentrated in vacuo to give residue. Water (200.0 mL) added to the mixture and the mixture was extracted with EtOAc (200.0 mL×2). The organic layers were washed with brine and dried over anhydrous Na$_2$SO$_4$, filtered and the filtrate was concentrated in vacuo to give 5-bromo-N-methyl-2-nitroaniline (25.5 g, 98% yield) as a yellow solid. $^1$HNMR (400 MHz, CDCl$_3$) 7.95 (d, J=9.2 Hz, 2H), 6.93 (d, J=1.6 Hz, 1H), 6.71-6.68 (m, 1H), 7.48 (s, 1H), 2.94 (d, J=5.2 Hz, 3H).

Step b: To the mixture of 5-bromo-N-methyl-2-nitroaniline (10.0 g, 43.2 mmol) in MeOH (150.0 mL) was added sodium dithionite (67.5 g, 388.0 mmol) in H$_2$O (60.0 mL) dropwise. The mixture was stirred at 60° C. for 12 hours. The mixture was then filtered and the filtrate was concentrated in vacuo. The residue was extracted with EtOAc (200.0 mL×3), the organic layers were washed with H$_2$O (100.0 mL) and brine (100.0 mL), then dried over anhydrous Na$_2$SO$_4$. The mixture was filtered and the filtrate was concentrated in vacuo to give the product of 5-bromo-N1-methylbenzene-1,2-diamine (8.60 g, crude) as a brown oil.

Step c: A mixture of 5-bromo-N-methylbenzene-1,2-diamine (1.0 g, 4.97 mmol), 1,2-dibromoethane (2.13 mL, 24.8 mmol) and TBAB (4.80 g, 14.9 mmol) was stirred at 60° C. for 12 hours. The mixture was concentrated in vacuo and purified by flash silica gel chromatography (petroleum ether/EtOAc=I/O to 2/1) to give 7-bromo-1-methyl-1,2,3,4-tetrahydroquinoxaline (233.0 mg, 21% yield) as a brown solid. LCMS m/z [M+H]$^+$=226.9/228.9.

4-methyl-1,2,3,4-tetrahydroquinoxaline-6-carbonitrile, Intermediate AO

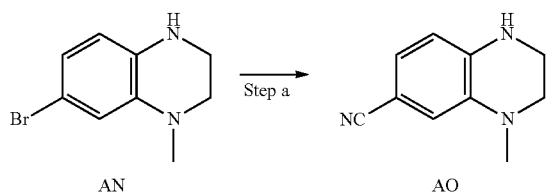

Step a: To the mixture of 7-bromo-1-methyl-1,2,3,4-tetrahydroquinoxaline (500.0 mg, 2.20 mmol) and Zn(CN)$_2$ (516.0 mg, 4.40 mmol) in DMF (10.0 mL) was added [(t-Bu)$_3$P]2Pd (224.0 mg, 440.0 µmol) under N2. The mixture was stirred at 120° C. under N2 for 12 hours. TLC (petroleum ether/EtOAc=2/1) showed a new spot formed and no starting material remained. The combined mixture was poured into water (50.0 mL) and extracted with EtOAc (50.0 mL×3). The combined organic layers were washed with brine (50.0 mL), dried over anhydrous Na$_2$SO$_4$, filtered and concentrated under reduce pressure to give a brown residue. The residue was purified by flash silica gel chromatography (petroleum ether/EtOAc=I/O to 2/1) to give the product of 4-methyl-1,2,3,4-tetrahydroquinoxaline-6-carbonitrile (370.0 mg, 95.0% purity) as a brown solid. LCMS m/z [M]$^+$=173.8.

3H-spiro[1-benzofuran-2,4'-piperidin]-3-one, Intermediate AP

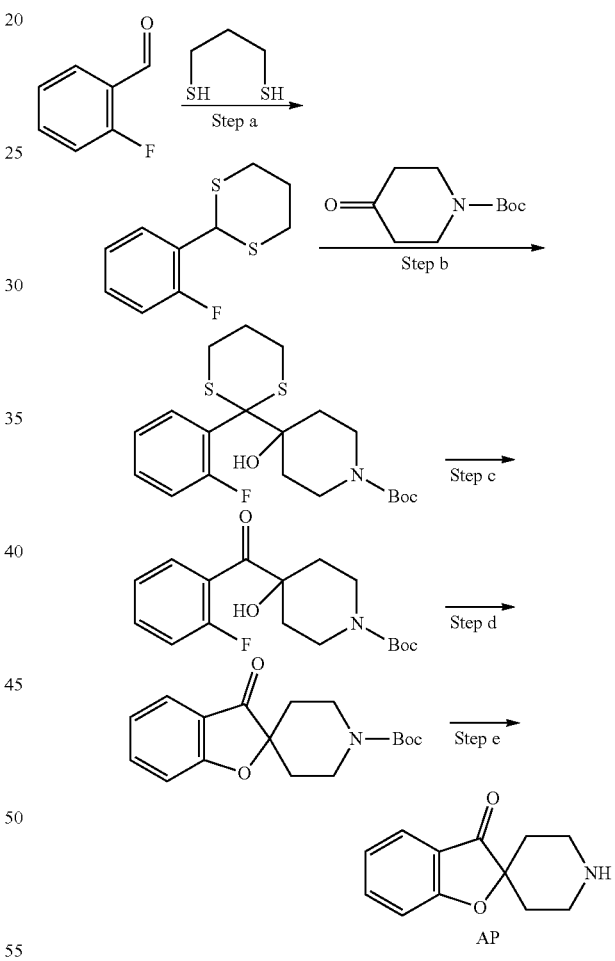

Step a: To a solution of 2-fluorobenzaldehyde (4 g, 32.2 mmol) in DCM (20 mL) were added propane-1, 3-dithiol (3.5 mg, 32.2 mmol) and 12 (244 mg, 966 umol). The mixture was stirred at 25° C. for 12 hours. The reaction mixture was poured into the solution of Na$_2$S2O3 (0.4 M, 180 mL) and 150 mL of NaOH solution was added. The organic phase was separated and the aqueous phase was extracted with CH$_2$Cl$_2$ (200 mL). The combined organic fractions were washed with water (150 mL), brine (150 mL), dried over anhydrous Na$_2$SO$_4$, then filtered and evaporated under reduced pressure to give a yellow solid. Recrystallisation from CH$_2$Cl$_2$: petroleum ether (1:1) afforded 2-(2-fluorophenyl)-1,3-dithiane (5.00 g, 72% yield) as a white solid. LCMS m/z [M+H]$^+$=215.0.

Step b: To a mixture of 2-(2-fluorophenyl)-1,3-dithiane (4 g, 18.6 mmol) in THF (50 mL) was added LDA (18.6 mL, 37.2 mmol) at −78° C. slowly. The resulting mixture was stirred at −20° C. for 0.5 hour, then tert-butyl 4-oxopiperidine-1-carboxylate (3.7 g, 18.6 mmol) was added at −78° C. The reaction mixture was stirred at −78° C. for 2 hours. The reaction mixture was then poured into saturated NH4Cl (50 mL) and extracted with EtOAc (80 mL×3). The combined organic fractions were washed with water (100 mL), brine (100 mL), dried over Na$_2$SO$_4$, then filtered and evaporated under reduced pressure to give a yellow oil. The oil was purified by silica gel column (elution:petroleum ether:ethyl acetate=5:1~2:1) to give the product of tert-butyl 4-[2-(2-fluorophenyl)-1,3-dithian-2-yl]-4-hydroxypiperidine-1-carboxylate (3.20 g, 42% yield) as a white solid. LCMS m/z [M−100]$^+$=313.9.

Step c: A mixture of tert-butyl 4-[2-(2-fluorophenyl)-1,3-dithian-2-yl]-4-hydroxypiperidine-1-carboxylate (2 g, 4.83 mmol) in DCM (20 mL) and H$_2$O (5 mL) were added pyridine (2 mL), pyridine HBr$_3$ (1.82 g, 5.79 mmol) and TBAB (158 mg, 483 umol). The mixture was stirred at 25° C. for 12 hours. The solution was poured into water (30 mL) and extracted with DCM (50 mL×3). The combined organic layers were washed with brine (50 mL), dried over anhydrous Na$_2$SO$_4$, then filtered and evaporated under reduced pressure. The crude product was purified by silica gel column (elution:petroleum ether:ethyl acetate=5:1~1:1) to give tert-butyl 4-(2-fluorobenzoyl)-4-hydroxypiperidine-1-carboxylate (1.20 g, 77% yield) as a yellow solid. LCMS m/z [M−100]$^+$=223.9.

Step d: To a solution of tert-butyl 4-(2-fluorobenzoyl)-4-hydroxypiperidine-1-carboxylate (600 mg, 1.85 mmol) in dioxane (5 mL) was added t-BuOK (207 mg, 1.85 mmol). The mixture was stirred at 70° C. for 2 hours. The mixture was concentrated under reduced pressure and diluted with water (20 mL), extracted by EtOAc (30 mL×3). The combined organic layers were washed with brine (30.0 mL), dried over anhydrous Na$_2$SO$_4$, filtered and concentrated under reduced pressure to give a residue. The residue was purified by column chromatography (petroleum ether:ethyl acetate=100:0 to 100:10) to give tert-butyl 3-oxo-3H-spiro[1-benzofuran-2,4 (210 mg, 75% yield) as a white solid. LCMS m/z [M−100]+=203.9.

Step e: To a solution of tert-butyl 3-oxo-3H-spiro[1-benzofuran-2,4'-piperidine]-1'-carboxylate (300 mg, 988 µmol) in dioxane (2 mL) was added HCl/dioxane (2.46 mL, 4M). The mixture was stirred at 20° C. for 12 hours. The reaction mixture was concentrated to dryness, MeOH (2 mL) and K$_2$CO$_3$ (100 mg) were added. The mixture was filtered and the filtrate was concentrated to dryness to give 3H-spiro[1-benzofuran-2,4'-piperidin]-3-one (150 mg, 75% yield) as a white solid. LCMS m/z [M+H]$^+$=204.9.

6-methyl-2,3,4,6-tetrahydro-1,6-naphthyridin-5(1H)-one, Intermediate AQ

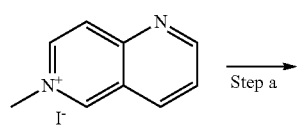

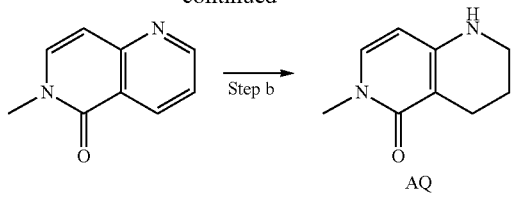

Step a: 6-methyl-1,6-naphthyridin-6-ium iodide (1.56 g, 5.73 mmol, CAS #37960-58-0) was suspended in water (10 mL) and cooled to 0° C. The reaction was charged with sodium hydroxide (1.25 g, 31.5 mmol) in water (10 mL) and tripotassium hexakis(iminomethanide) iron (4.04 g, 12.3 mmol) in water (10 mL). The solution was stirred for 1 hr at 0° C., then 16 hr at rt. The mixture was extracted with CHCl$_3$, dried and pre-absorbed on SiO$_2$ (3 g). The residue was purified by column chromatography (Si-40 g column, 0-10% MeOH/DCM) to give 6-methyl-1,6-naphthyridin-5(6H)-one (540 mg, 59% yield) as a light yellow solid. LCMS m/z [M+H]$^+$=161.1; $^1$H NMR (400 MHz, CHLOROFORM-d) δ 8.90 (dd, J=1.89, 4.67 Hz, 1H), 8.71 (dd, J=1.26, 8.08 Hz, 1H), 7.42 (dd, J=4.55, 8.08 Hz, 1H), 7.32 (d, J=7.58 Hz, 1H), 6.79 (d, J=7.58 Hz, 1H), 3.63 (s, 3H).

Step b: 6-methyl-5,6-dihydro-1,6-naphthyridin-5-one (109 mg, 0.6805 mmol) was dissolved in MeOH (10 mL). The solution was cycled through the H-Cube, 1 mL/min, 10% Pd/C, 70 bar, 70° C. After 1 h, the solvent was removed and residue chased with DCM to give 6-methyl-2,3,4,6-tetrahydro-1,6-naphthyridin-5(1H)-one (105 mg, 94% yield) as a white solid. LCMS m/z [M+H]$^+$=165.0.

(R)-7-fluoro-1,3-dihydrospiro[indene-2,4'-piperidin]-1-amine, Intermediate AR, and (S)-7-fluoro-1,3-dihydrospiro[indene-2,4'-piperidin]-1-amine, Intermediate AS

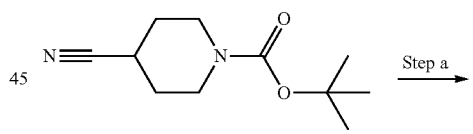

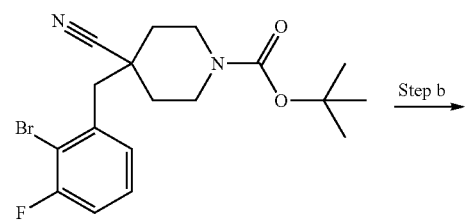

259

-continued

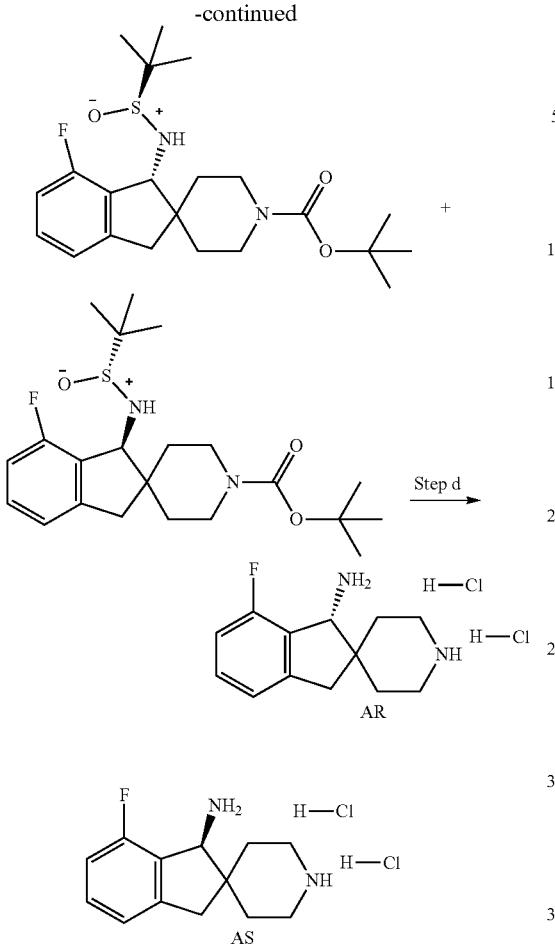

260

5,7-dihydrospiro[cyclopenta[b]pyridine-6,4'-piperidin]-7-amine, Intermediate AT

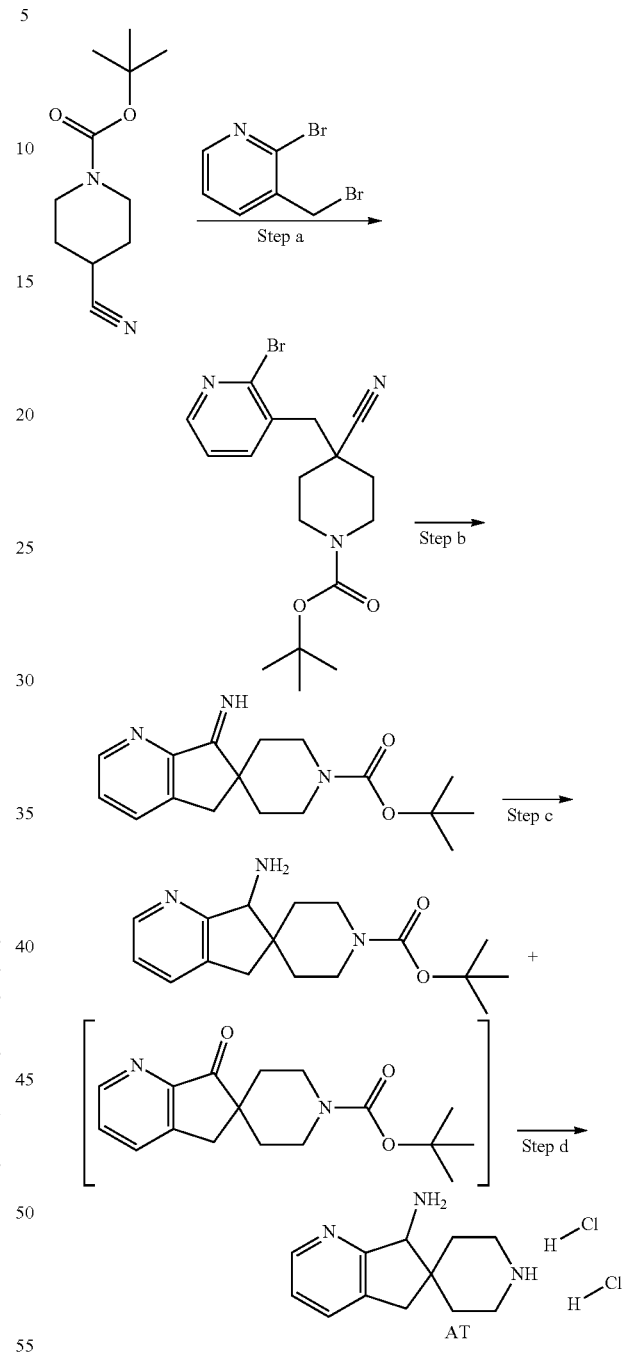

(R)-7-fluoro-1,3-dihydrospiro[indene-2,4'-piperidin]-1-amine and (S)-7-fluoro-1,3-dihydrospiro[indene-2,4'-piperidin]-1-amine was synthesized as described above for Intermediate T, using 2-bromo-1-(bromomethyl)-3-fluorobenzene as the coupling partner in Step a. In Step c, (R)-2-methylpropane-2-sulfinamide was utilized and a mixture of diastereomers was formed during the reduction, which were separable by prep-HPLC to give tert-butyl (R)-1-(((S)-tert-butylsulfinyl)amino)-7-fluoro-1,3-dihydrospiro[indene-2,4'-piperidine]-1'-carboxylate (earlier eluting isomer, $^1$H NMR (400 MHz, DMSO-d6) δ 7.26 (dt, J=5.25, 7.75 Hz, 1H), 7.04 (d, J=7.57 Hz, 1H), 6.95 (t, J=8.79 Hz, 1H), 5.68 (d, J=9.77 Hz, 1H), 4.44 (d, J=10.01 Hz, 1H), 3.78 (br d, J=11.96 Hz, 1H), 3.59-3.72 (m, 1H), 3.00 (br d, J=16.11 Hz, 3H), 2.77 (br d, J=16.11 Hz, 1H), 1.71 (br t, J=10.25 Hz, 1H), 1.34-1.56 (m, 11H), 1.21-1.31 (m, 1H), 1.10 (s, 9H)) and tert-butyl (S)-1-(((R)-tert-butylsulfinyl)amino)-7-fluoro-1,3-dihydrospiro[indene-2,4'-piperidine]-1'-carboxylate (later eluting isomer, $^1$H NMR (400 MHz, DMSO-d6) δ 7.27 (dt, J=5.25, 7.75 Hz, 1H), 7.05 (d, J=7.32 Hz, 1H), 6.95 (t, J=8.67 Hz, 1H), 5.51 (d, J=7.57 Hz, 1H), 4.38 (d, J=7.57 Hz, 1H), 3.52-3.72 (m, 2H), 2.95-3.19 (m, 3H), 2.80 (br d, J=15.87 Hz, 1H), 1.59-1.74 (m, 2H), 1.38 (s, 9H), 1.18-1.33 (m, 2H), 1.08 (s, 9H)). Characterization of (R)-7-fluoro-1,3-dihydrospiro[indene-2,4'-piperidin]-1-amine & (S)-7-fluoro-1,3-dihydrospiro[indene-2,4'-piperidin]-1-amine: LCMS m/z [M+H]+ for both enantiomers=221.1.

Step a: tert-butyl 4-cyanopiperidine-1-carboxylate (1.65 g, 7.84 mmol) in THF (10 mL) was cooled to −78° C. and charged with lithiobis(propan-2-yl)amine (9.01 mL, 9.01 mmol) (max temperature −65° C. on addition) and the reaction was stirred at −78° C. for 1.5 hr. Then a solution of 2-bromo-3-(bromomethyl)pyridine (1.93 g, 7.72 mmol) (caution, material is very irritant) in THF (2 mL) with a few drops of DMF to improve solubility, was added and the reaction stirred at −78° C. for 2 h. Then the reaction was allowed to warm to 0° C. then to rt and the reaction was stirred for 16 hr. The reaction was diluted with water and EA. The org layer pre-absorbed on SiO$_2$ (7 g) and purified by column chromatography (Si-80 g column, 25-50% EA/Hep) to give tert-butyl 4-((2-bromopyridin-3-yl)methyl)-4-cyanopiperidine-1-carboxylate (910 mg, 31% yield) as a colorless oil that solidified to a waxy solid upon standing. LCMS m/z [M-tBu]$^+$=324.0/326.0.

Step b: tert-butyl 4-[(2-bromopyridin-3-yl)methyl]-4-cyanopiperidine-1-carboxylate (910 mg, 2.39 mmol) in 2-MeTHF (15 mL) was cooled to 0° C. and charged with chloro(propan-2-yl)magnesium; chlorolithium (3.67 mL, 4.78 mmol) and the reaction was stirred at 0° C. for 30 min. Next, the reaction was cooled to −78° C. and charged with butyllithium (1.04 mL, 2.62 mmol) and the reaction was stirred for 1 hr at −78° C. Then an additional 0.25 eq. of nBuLi was added and the reaction was stirred for 45 min more. The reaction mixture was then quenched with water and extracted with EA (2×). The organic layer was dried and concentrated to give tert-butyl 7-imino-5,7-dihydrospiro[cyclopenta[b]pyridine-6,4'-piperidine]-1'-carboxylate (700 mg, 97% yield). LCMS m/z [M+H]$^+$=246.0/302.0.

Step c: tert-butyl 7-imino-5,7-dihydrospiro[cyclopenta[b]pyridine-6,4'-piperidine]-1'-carboxylate (720 mg, 2.38 mmol) was dissolved in EA (15 mL) and run in a H-Cube for 90 min (5 bar, 40 C). The solvent was then removed by rotary evaporation and the crude residue was purified by prep-HPLC (5-40% ACN/water/FA). tert-butyl 7-amino-5,7-dihydrospiro[cyclopenta[b]pyridine-6,4'-piperidine]-1'-carboxylate (208 mg, 29% yield). $^1$H NMR (400 MHz, DMSO-d6) δ 8.32-8.43 (m, 1H), 8.21 (s, 1H), 7.56-7.69 (m, 1H), 7.13-7.27 (m, 1H), 3.94 (s, 1H), 3.74 (br d, J=12.94 Hz, 2H), 2.99 (br d, J=16.11 Hz, 3H), 2.62 (br d, J=16.11 Hz, 1H), 2.45-2.51 (m, 3H), 1.49-1.71 (m, 2H), 1.31-1.48 (m, 8H), 1.04 (br d, J=13.43 Hz, 1H). Side product tert-butyl 7-oxo-5,7-dihydrospiro[cyclopenta[b]pyridine-6,4'-piperidine]-1'-carboxylate (100 mg) was also isolated. $^1$H NMR (400 MHz, DMSO-d6) δ 8.75 (d, J=3.66 Hz, 1H), 8.07 (d, J=7.81 Hz, 1H), 7.62 (dd, J=4.64, 7.81 Hz, 1H), 3.93 (br d, J=12.94 Hz, 2H), 3.11 (s, 2H), 2.99 (br s, 2H), 1.59 (dt, J=4.27, 12.63 Hz, 2H), 1.30-1.52 (m, 10H).

Step d: tert-butyl 7-amino-5,7-dihydrospiro[cyclopenta[b]pyridine-6,4'-piperidine]-1'-carboxylate (208 mg, 0.6855 mmol) in MeOH (5 mL) was charged with hydrogen chloride (1.71 mL, 6.85 mmol) and the reaction was stirred at rt for 2.5 h. Then the reaction was heated to 50° C. for 5 h. The reaction was cooled to rt and stirred for 16 h. The solvent was then removed by rotary evaporation and chased with MTBE to yield 5,7-dihydrospiro[cyclopenta[b]pyridine-6,4'-piperidin]-7-amine dihydrochloride (188 mg, 99% yield) as a white solid. LCMS m/z [M+H]$^+$=204.0.

tert-butyl (1'-(3-iodo-1-(tetrahydro-2H-pyran-2-yl)-1H-pyrazolo[3,4-b]pyrazin-6-yl)-5,7-dihydrospiro[cyclopenta[b]pyridine-6,4'-piperidin]-7-yl)carbamate, Intermediate AU

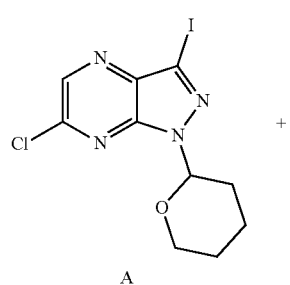

A

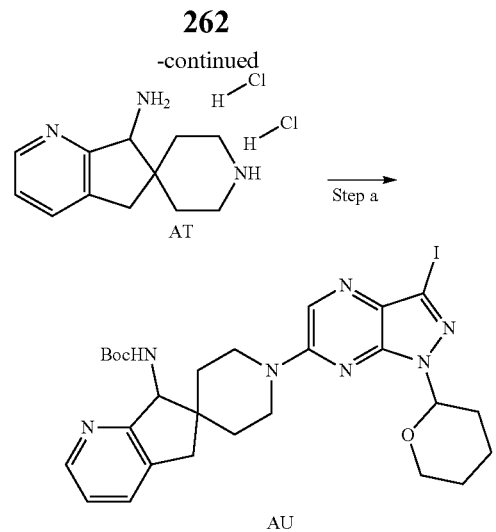

Step a: 6-chloro-3-iodo-1-(oxan-2-yl)-1H-pyrazolo[3,4-b]pyrazine (244 mg, 0.6697 mmol, Intermediate A) in DMF (4 mL) was charged with ethylbis(propan-2-yl)amine (580 µL, 3.34 mmol) and 5,7-dihydrospiro[cyclopenta[b]pyridine-6,4'-piperidin]-7-amine dihydrochloride (185 mg, 0.6697 mmol, Intermediate AT) and the solution was heated to 80° C. for 4 h. Then the reaction was cooled to rt and and di-tert-butyl dicarbonate (175 mg, 0.8036 mmol) was added and the reaction was stirred at rt for 16 h. Then an additional 0.25 eq of di-tert-butyl dicarbonate was added and the reaction was stirred for an additional 2.5 hr at rt. The reaction mixture was then partitioned between brine and EA. The organic layer was pre-absorbed on SiO$_2$ (2 g) and the mixture was purified by column chromatography (Si 12 g column, 70-100% EA/hep) to give tert-butyl (1'-(3-iodo-1-(tetrahydro-2H-pyran-2-yl)-1H-pyrazolo[3,4-b]pyrazin-6-yl)-5,7-dihydrospiro[cyclopenta[b]pyridine-6,4'-piperidin]-7-yl)carbamate (260 mg, 73% yield) as a yellow solid. LCMS m/z [M+H]$^+$=632.1.

Sodium 2,3-dichloropyridine-4-thiolate, Intermediate AV

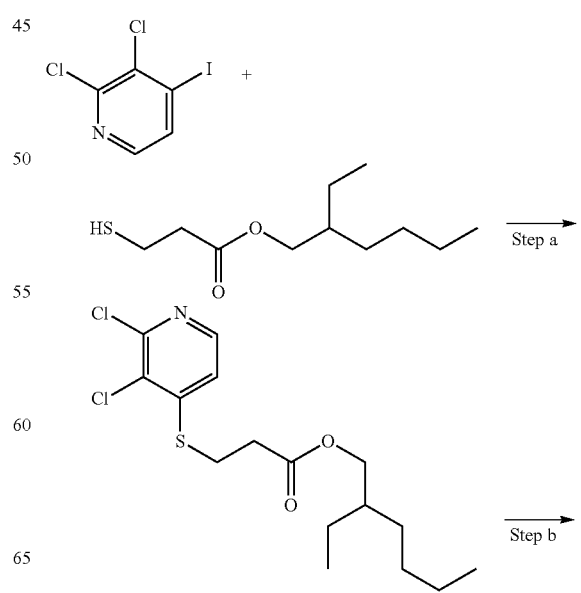

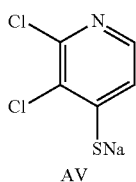

AV

Step a: To a solution of 2,3-dichloro-4-iodopyridine (2 g, 7.30 mmol) and 2-ethylhexyl 3-sulfanylpropanoate (1.75 g, 8.01 mmol) in dioxane (20 mL) was added XantPhos (844 mg, 1.46 mmol), $Pd_2dba_3$ (668 mg, 0.7300 mmol) and DIPEA (3.81 mL, 21.9 mmol). Then the mixture was stirred at 100° C. for 12 h under N2. Brine and EtOAc were then added to the reaction mixture, which was then extracted with EtOAc (3×). The combined organic layer was dried over $Na_2SO_4$, filtered and evaporated down with $SiO_2$. The mixture was purified by column chromatography (6-50% EtOAc in hexanes) to give 2-ethylhexyl 3-((2,3-dichloropyridin-4-yl)thio)propanoate (1.6 g, 60% yield). LCMS m/z $[M+H]^+$=363.9/365.9.

Step b: 2-ethylhexyl 3-[(2,3-dichloropyridin-4-yl)sulfanyl]propanoate (307 mg, 0.8426 mmol) was dissolved in THF (0.3M, 2.8 mL) and ethoxysodium (329 μL, 0.8847 mmol, 21% in EtOH) was added and the reaction was stirred at rt for 10 min. The mixture was diluted with DCM (10-15 mL) and stirred until nucleation occurred; after 5 min a large amount of solid formed in suspension. The mixture was filtered to give (2,3-dichloropyridin-4-yl)sulfanide (79 mg, 46% yield). LCMS m/z $[M+H-Na]^+$=179.9/181.9.

Sodium 3-chloro-2-methylpyridine-4-thiolate, Intermediate AW

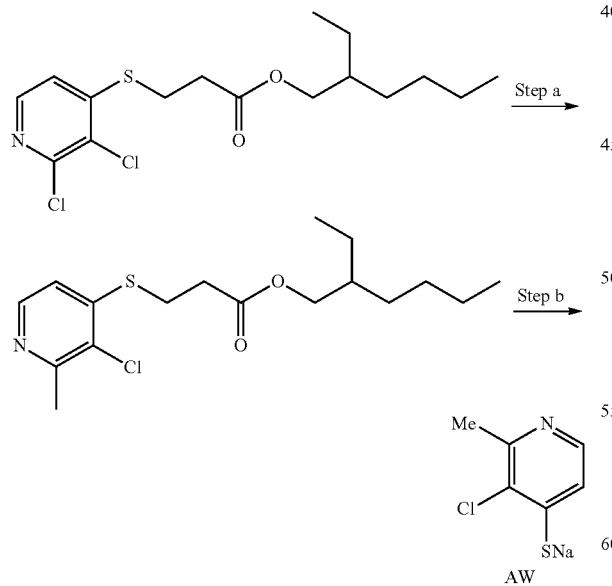

Step a: To a solution of 2-ethylhexyl 3-[(2,3-dichloropyridin-4-yl)sulfanyl]propanoate (800 mg, 2.19 mmol, synthesized via Step a of Intermediate AV) and trimethylboroxine (411 mg, 3.28 mmol) in dioxane (0.3M, 7 mL) and water (4M, 0.5 mL) was added XphosG4 (376 mg, 0.438 mmol) and $Pd_2dba_3$ (376 mg, 0.438 mmol). The mixture was degassed for 3 min then heated to 110° C. for 2 h. The mixture was then cooled to rt, and EtOAc and brine were added. The mixture was extract with EtOAc, and the organic layer was dried over $Na_2SO$, filtered and concentrated in vacuo. The residue was purified via column chromatography (40 g column, 0-60% EtOAc) to give 2-ethylhexyl 3-((3-chloro-2-methylpyridin-4-yl)thio)propanoate (317 mg. 42% yield). LCMS m/z $[M]^+$=343.9.

Step b: 2-ethylhexyl 3-[(3-chloro-2-methylpyridin-4-yl)sulfanyl]propanoate (317 mg, 0.922 mmol) was dissolved in THF (0.3M, 3 mL) and ethoxysodium (360 μL, 0.968 mmol) [21% in EtOH] was added and the mixture was stirred at rt for 10 min. The mixture was diluted with DCM (10-15 mL) and stirred until nucleation occurred. After 5 min, large amount of solid formed in the suspension. The mixture was filtered to yield (3-chloro-2-methylpyridin-4-yl)sulfanide (146 mg, quan. yield). LCMS m/z $[M+H-Na]^+$=159.9/161.9.

tert-butyl ((3S)-4-fluoro-1'-(3-iodo-1-(tetrahydro-2H-pyran-2-yl)-1H-pyrazolo[3,4-b]pyrazin-6-yl)-1, 3-dihydrospiro[indene-2,4'-piperidin]-3-yl)carbamate, Intermediate AX

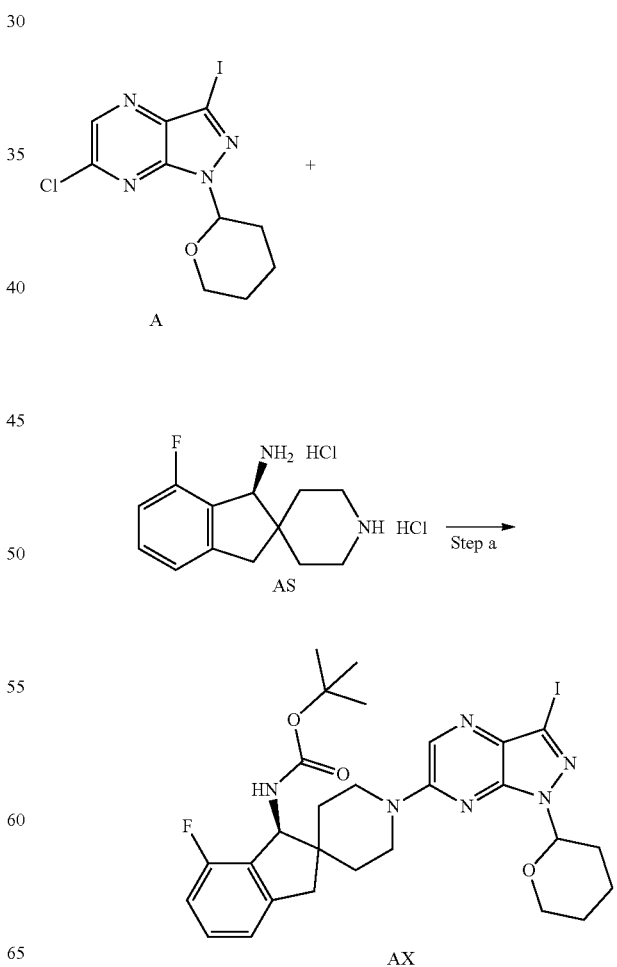

Step a: 6-chloro-3-iodo-1-(oxan-2-yl)-1H-pyrazolo[3,4-b]pyrazine (91.9 mg, 0.252 mmol, Intermediate A) in DMF (4 mL) was charged with ethylbis(propan-2-yl)amine (218 µL, 1.26 mmol) and (S)-7-fluoro-1,3-dihydrospiro[indene-2,4'-piperidin]-1-amine dihydrochloride (74 mg, 0.252 mmol, Intermediate AS) and the solution was heated to 80° C. for 3 hr. The reaction was cooled to rt and di-tert-butyl dicarbonate (66.0 mg, 0.303 mmol) was added and the reaction was stirred for 16 hr at rt. Then 0.25 eq more of di-tert-butyl dicarbonate was added and the reaction was stirred for an additional 2.5 h. The reaction was then partitioned between brine and EA. The organic layer was pre-absorbed on SiO₂ (2 g) and purified by column chromatography (Si-12 g column, 20-70% EA/hep) to give tert-butyl ((3S)-4-fluoro-1'-(3-iodo-1-(tetrahydro-2H-pyran-2-yl)-1H-pyrazolo[3,4-b]pyrazin-6-yl)-1,3-dihydrospiro[indene-2,4'-piperidin]-3-yl)carbamate (90 mg, 55% yield) as a white solid. LCMS m/z [M+Na]⁺=671.1.

(S)-5,7-dihydrospiro[cyclopenta[b]pyridine-6,4'-piperidin]-5-amine, Intermediate AY

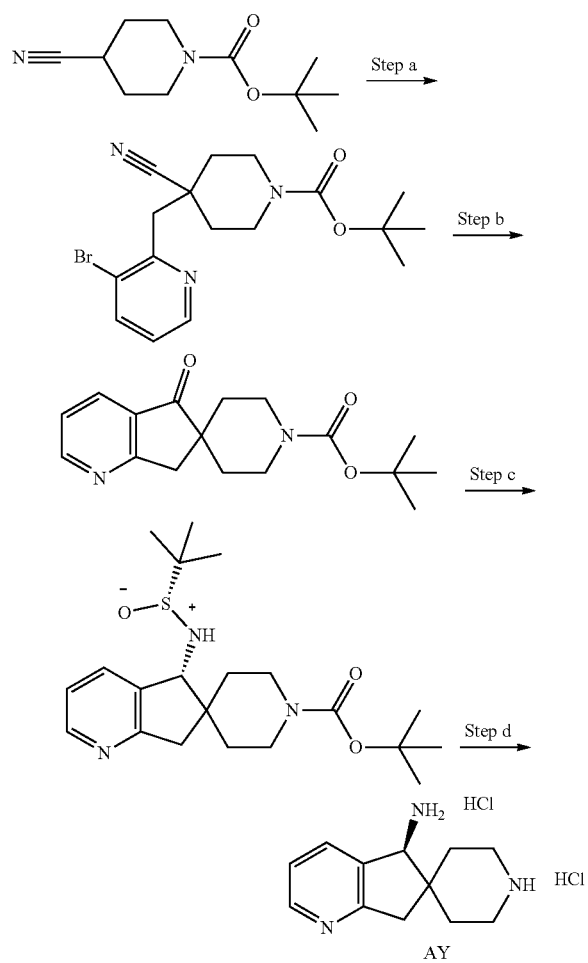

(S)-5,7-dihydrospiro[cyclopenta[b]pyridine-6,4'-piperidin]-5-amine was synthesized as described for Intermediate T, using 3-bromo-2-(bromomethyl)pyridine as the coupling partner in Step a. LCMS m/z [M+H]⁺=204.1.

tert-butyl N-[(5S)-1'-[3-iodo-1-(oxan-2-yl)-1H-pyrazolo[3,4-b]pyrazin-6-yl]-5,7-dihydrospiro[cyclopenta[b]pyridine-6,4'-piperidin]-5-yl]carbamate, Intermediate AZ

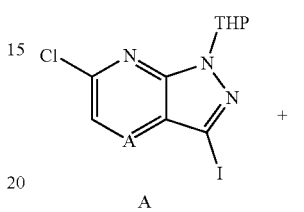

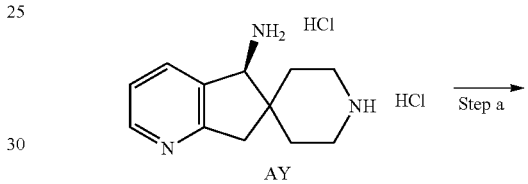

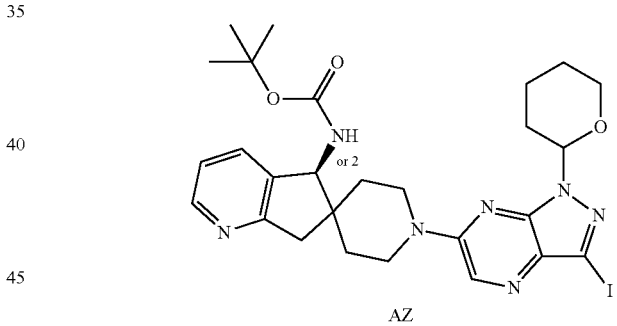

Step a: Dissolved 6-chloro-3-iodo-1-(oxan-2-yl)-1H-pyrazolo[3,4-b]pyrazine (223 mg, 0.6118 mmol, Intermediate A) in DMF (5 mL). Next, (5S)-5,7-dihydrospiro[cyclopenta[b]pyridine-6,4'-piperidin]-5-amine dihydrochloride (169 mg, 0.6118 mmol, Intermediate AY) was added followed by ethylbis(propan-2-yl)amine (425 µL, 2.44 mmol) and the reaction was stirred at 75° C. for 2 h. Next, di-tert-butyl dicarbonate (153 µL, 0.6729 mmol) was added and the reaction was stirred at rt for 1.5 hr. The reaction mixture was then diluted with EtOAc and extracted with water. The layers were separated, and the organic layer was washed with brine, dried over Na₂SO₄, filtered and concentrated onto SiO₂. The mixture was purified by column chromatography (0-100% EtOAc in heptanes) to give tert-butyl N-[(5S)-1'-[3-iodo-1-(oxan-2-yl)-1H-pyrazolo[3,4-b]pyrazin-6-yl]-5,7-dihydrospiro[cyclopenta[b]pyridine-6,4'-piperidin]-5-yl]carbamate (167 mg, 43% yield). LCMS m/z [M+H]⁺=632.1.

Spiro[bicyclo[3.1.0]hexane-3,4'-piperidin]-2-amine, Intermediate AB

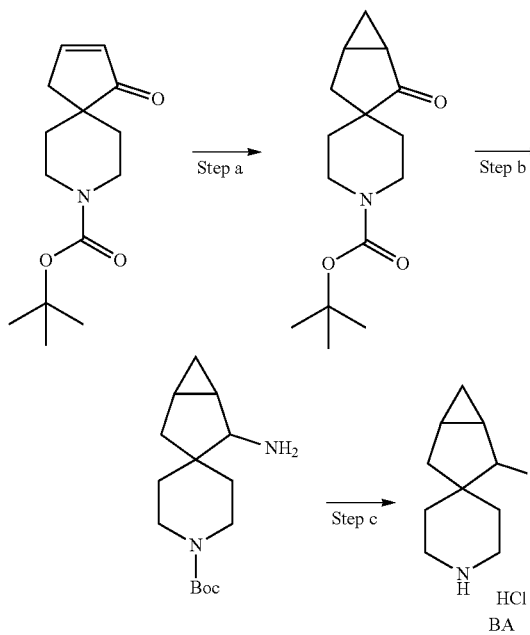

Step a: Dry DMSO (5 mL) was added to a 50 mL flask, which was then bubbled with N2 gas and equipped with a thermocouple. To the solution was added sodium hydride (173 mg, 4.36 mmol, 60% in oil) in small portions while the temperature was monitored so as not to exceed 35° C. Then trimethyl(oxo)-$\lambda^6$-sulfanylium iodide (959 mg, 4.36 mmol) was added in small portions while monitoring temperature. The suspension was then stirred at rt for 45 min. Meanwhile, tert-butyl 1-oxo-8-azaspiro[4.5]dec-2-ene-8-carboxylate (1 g, 3.97 mmol, synthesized as described in PCT Int. Appl., 2016203406) was dissolved in 2.5 mL dry DMSO. This solution was then added dropwise to reaction mixture while stirring vigorously and monitoring temperature so as not to exceed 27° C. The reaction mixture was then stirred at rt for 16 h. Then 10 mL of water was added dropwise and the solution was extracted with diethyl ether (2×30 mL). The combined organic layer was dried over $Na_2SO_4$, filtered and concentrated in vacuo. The residue was purified by column chromatography (0-100% EtOAc in heptanes) to give tert-butyl 4-oxospiro[bicyclo[3.1.0]hexane-3,4'-piperidine]-1'-carboxylate (422 mg, 40% yield) as a colorless oil. LCMS m/z $[M+H-100]^+$=166.0.

Step b: Dissolved hydrogen chloride (288 mg, 7.91 mmol) in EtOH (15 mL), then added tert-butyl 4-oxospiro[bicyclo[3.1.0]hexane-3,4 (210 mg, 0.791 mmol) followed by acetic acid amine (909 mg, 11.8 mmol) and $NaCNBH_3$ (54.6 mg, 0.870 mmol). The reaction mixture was then heated in a microwave at 130° C. for 1 h. Additional $NaCNBH_3$ (54.6 mg, 0.870 mmol) was added and the mixture was stirred in a microwave at 130° C. for 1 h more. The reaction mixture was then concentrated in vacuo and the residue was treated with NaOH (2N, 15 mL). The mixture was extracted with EtOAc (2×5 mL), and the combined organic layer was dried over $Na_2SO_4$. The solution was concentrated in vacuo and purified by column chromatography (0-100% EtOAc in heptanes, followed by 0-10% MeOH in DCM w/0.1% NH40H, where product eluted at 7% MeOH) give tert-butyl 4-aminospiro[bicyclo[3.1.0]hexane-3,4 (70.0 mg, 33% yield). LCMS m/z $[M+H-56]+$=211.1.

Step c: Dissolved tert-butyl 4-aminospiro[bicyclo[3.1.0] hexane-3,4 (70.0 mg, 0.26 mmol) in 3 mL MeOH. Then HCl (4N in dioxanes, 1 mL) was added and the reaction mixture was stirred at rt for 16 h. The reaction mixture was then concentrated in vacuo and chased with MeOH to give spiro[bicyclo[3.1.0]hexane-3,4'-piperidin]-4-amine dihydrochloride (76.0 mg, quant. crude yield). LCMS m/z $[M+H]^+$=167.0.

tert-butyl (1'-(3-iodo-1-(tetrahydro-2H-pyran-2-yl)-1H-pyrazolo[3,4-b]pyrazin-6-yl)spiro[bicyclo[3.1.0] hexane-3,4'-piperidin]-2-yl)carbamate, Intermediate BB

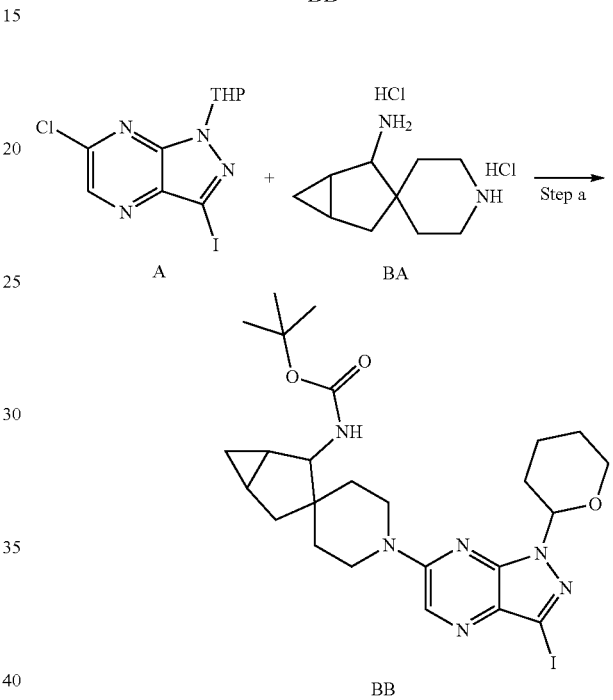

Step a: Spiro[bicyclo[3.1.0]hexane-3,4 (120 mg, 0.502 mmol, Intermediate BA) and 6-chloro-3-iodo-1-(oxan-2-yl)-1H-pyrazolo[3,4-b]pyrazine (182 mg, 0.502 mmol, Intermediate A) were placed into a round bottom flask and dissolved in DMF (2 mL). Then ethylbis(propan-2-yl)amine (435 µL, 2.50 mmol) was added and the reaction mixture was stirred at rt for 2 h. Next, di-tert-butyl dicarbonate (114 µL, 0.502 mmol) was added and the reaction mixture was stirred at rt from 2.5 h. The reaction mixture was then concentrated in vacuo and purified by column chromatography (0-100% EtOAc in heptanes) to give tert-butyl (1'-(3-iodo-1-(tetrahydro-2H-pyran-2-yl)-1H-pyrazolo[3,4-b]pyrazin-6-yl) spiro[bicyclo[3.1.0]hexane-3,4'-piperidin]-2-yl)carbamate (185 mg, 62% yield). LCMS m/z $[M]^+$=594.3.

(S)-5,7-dihydrospiro[cyclopenta[c]pyridine-6,4'-piperidin]-7-amine, Intermediate BC

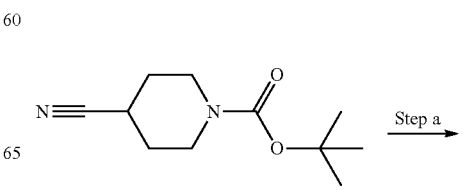

269
-continued

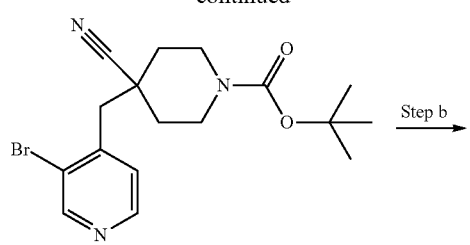

Step b

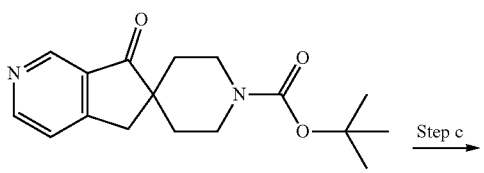

Step c

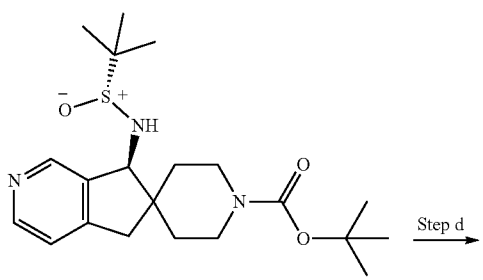

Step d

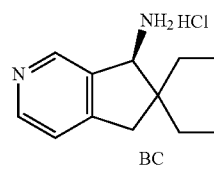

BC (S)-5,7-dihydrospiro[cyclopenta[c]pyridine-6,4'-piperidin]-7-amine was synthesized as described for Intermediate T and Intermediate AY, coupling (3-bromopyridin-4-yl)methyl methanesulfonate in Step a. LCMS m/z [M+H]⁺= 204.1.

tert-butyl N-[(7R)-1'-[3-iodo-1-(oxan-2-yl)-1H-pyrazolo[3,4-b]pyrazin-6-yl]-5,7-dihydrospiro[cyclopenta[c]pyridine-6,4'-piperidin]-7-yl]carbamate, Intermediate BD

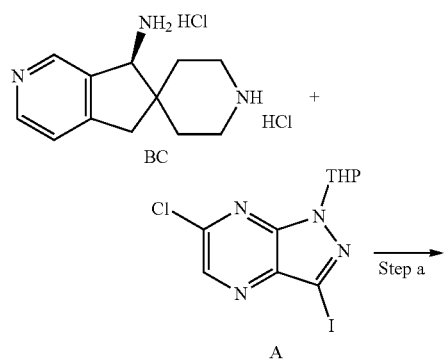

270
-continued

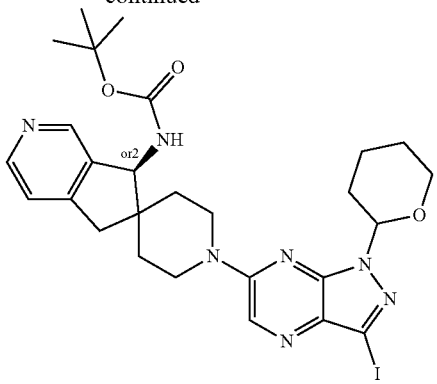

BD tert-butyl N-[(7R)-1'-[3-iodo-1-(oxan-2-yl)-1H-pyrazolo[3,4-b]pyrazin-6-yl]-5,7-dihydrospiro [cyclopenta[c]pyridine-6,4'-piperidin]-7-yl]carbamate was synthesized as described for Intermediate AZ, coupling 6-chloro-3-iodo-1-(oxan-2-yl)-1H-pyrazolo[3,4-b]pyrazine (Intermediate A) and (S)-5,7-dihydrospiro[cyclopenta[c]pyridine-6,4'-piperidin]-7-amine dihydrochloride (Intermediate BC) in Step a. LCMS m/z [M+H]⁺=632.1.

tert-butyl N-[(3S)-1'-{3-hydroxy-1-[(4-methoxyphenyl)methyl]-1H-pyrazolo[3,4-b]pyrazin-6-yl}-1,3-dihydrospiro[indene-2,4'-piperidin]-3-yl]carbamate, Intermediate BE

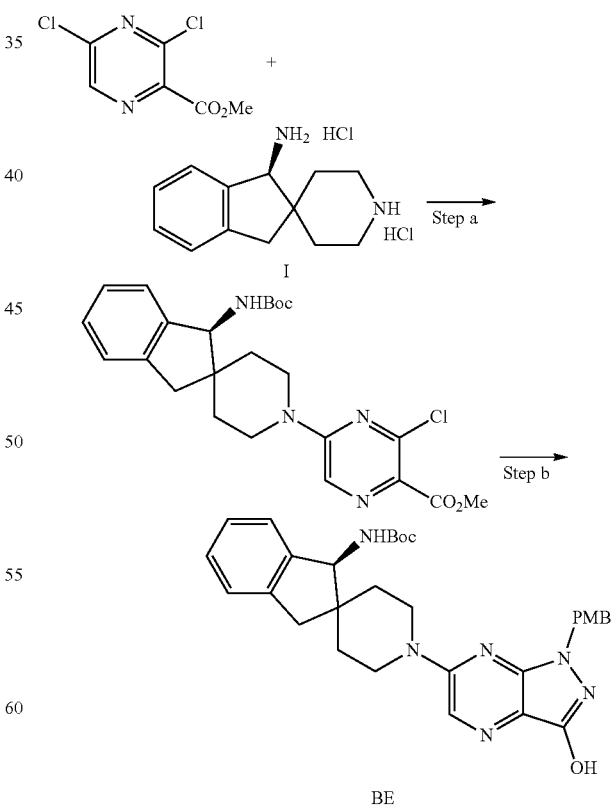

BE

Step a: The mixture of methyl 3,5-dichloropyrazine-2-carboxylate (1.0 g, 4.83 mmol, CAS #330786-09-9), (3S)-

1,3-dihydrospiro[indene-2,4'-piperidin]-3-amine dihydrochloride (1.65 g, 4.83 mmol, Intermediate I) and CsF (3.66 g, 24.1 mmol) in DMF (15 mL) was stirred at 70° C. for 2 hours. Boc$_2$O (1.57 g, 7.24 mmol) and TEA (1 mL) were then added to the mixture and the mixture was stirred at 20° C. for 1 hour. The mixture was diluted with H$_2$O (50 mL), and extracted with EtOAc (50 mL×2). The organic layer was washed with brine (50 mL), dried over anhydrous Na$_2$SO$_4$, filtered and concentrated under reduced pressure. The residue was purified by column chromatography (petroleum ether/ethyl acetate=1:0~5:1) to afford methyl 5-[(3S)-3-{[(tert-butoxy)carbonyl]amino}-1,3-dihydrospiro[indene-2,4'-piperidin]-1'-yl]-3-chloropyrazine-2-carboxylate (1.58 g, 69% yield) as a yellow solid. LCMS m/z [M+H]$^+$=473.1.

Step b: The mixture of methyl 5-[(3S)-3-{[(tert-butoxy)carbonyl]amino}-1,3-dihydrospiro[indene-2,4'-piperidin]-1'-yl]-3-chloropyrazine-2-carboxylate (1.5 g, 3.17 mmol), PMBNHNH$_2$ 2HCl (927 mg, 4.12 mmol) and TEA (2.01 mL, 15.8 mmol) in EtOH (20 mL) was stirred at 80° C. for 10 hours. The mixture was concentrated under reduced pressure and the residue was purified by column chromatography (DCM/MeOH=1:0~10:1) to afford tert-butyl N-[(3S)-1'-{3-hydroxy-1-[(4-methoxyphenyl)methyl]-1H-pyrazolo[3,4-b]pyrazin-6-yl}-1,3-dihydrospiro[indene-2,4'-piperidin]-3-yl]carbamate (2.6 g, quant. crude yield) as a yellow solid. LCMS m/z [M+H]$^+$=557.2.

tert-butyl (S)-(6-(1-amino-1,3-dihydrospiro[indene-2,4'-piperidin]-1'-yl)-3-bromopyrazin-2-yl)carbamate and tert-butyl (S)-(6-(1-amino-1,3-dihydrospiro[indene-2,4'-piperidin]-1'-yl)-3-bromopyrazin-2-yl)(tert-butoxycarbonyl)carbamate (mixture), Intermediate BF

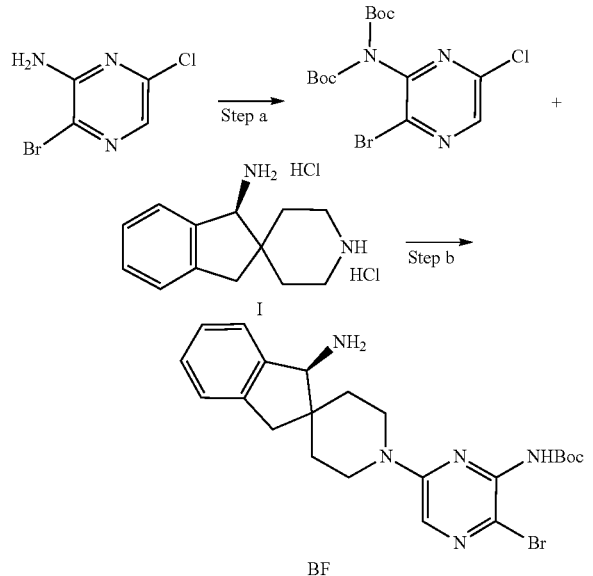

Step a: A mixture of 3-bromo-6-chloropyrazin-2-amine (300 mg, 1.4 mmol, CAS #212779-21-0), DMAP (87 mg, 0.7 mmol) and (Boc)$_2$O (936 mg, 4.3 mmol) in DCM (15 mL) was stirred at 25° C. for 16 h. The reaction mixture was then washed with H$_2$O (15 mL×2) and brine (15 mL). The organic phase was dried over anhydrous Na$_2$SO$_4$, filtered and concentrated to give a residue. The residue was purified by flash silica gel chromatography (petroleum ether:ethyl acetate=100:0 to 100:10) to afford tert-butyl N-(3-bromo-6-chloropyrazin-2-yl)-N-[(tert-butoxy)carbonyl]carbamate (580 mg, 99% yield) as a white solid. LCMS m/z [M+Na]$^+$=429.8/431.8.

Step b: tert-butyl N-(3-bromo-6-chloropyrazin-2-yl)-N-[(tert-butoxy)carbonyl]carbamate (270 mg, 0.7 mmol), (3S)-1,3-dihydrospiro[indene-2,4'-piperidin]-3-amine (200 mg, 1.0 mmol, Intermediate I) and DIPEA (0.3 mL, 2.0 mmol) were added into DMF (2 mL). The mixture was stirred at 85° C. for 12 h. The reaction mixture was then diluted with EtOAc (50 mL). The mixture was washed with H$_2$O (15 mL×3) and brine (15 mL×3), dried over anhydrous Na$_2$SO$_4$, filtered and concentrated to give a residue. The residue was purified by flash silica gel chromatography (DCM:MeOH=100:5) to afford the mixture of tert-butyl (S)-(6-(1-amino-1,3-dihydrospiro[indene-2,4'-piperidin]-1'-yl)-3-bromopyrazin-2-yl)carbamate and tert-butyl (S)-(6-(1-amino-1,3-dihydrospiro[indene-2,4'-piperidin]-1'-yl)-3-bromopyrazin-2-yl)(tert-butoxycarbonyl)carbamate (200 mg) as a yellow oil. LCMS m/z [M+H]$^+$=474.4/476.1; 574.1/576.1.

2-methyl-6,7,8,9-tetrahydro-1H-pyrrolo[3,4-f]quinolin-3-one, Intermediate BG

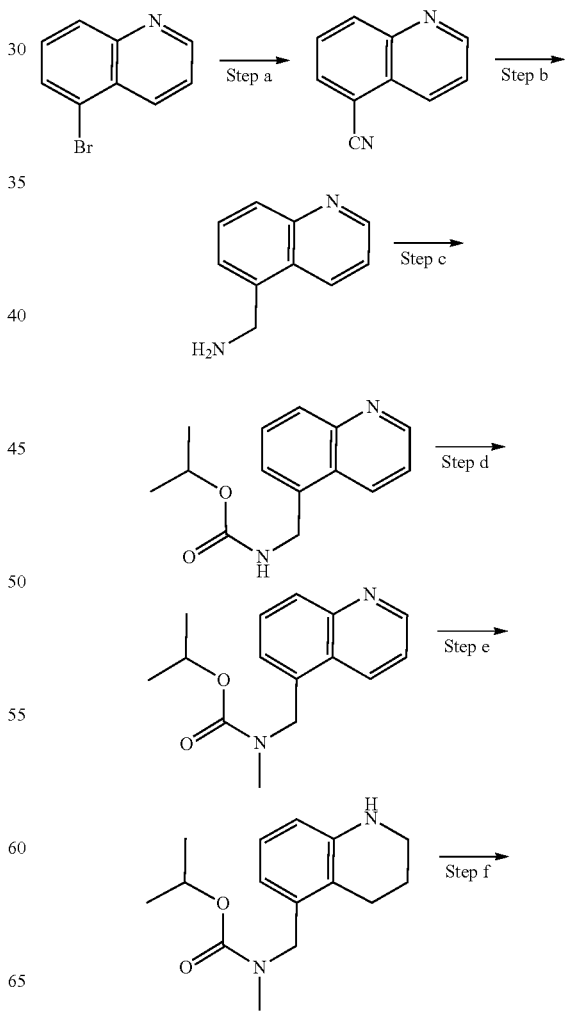

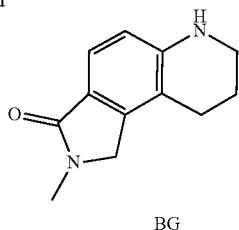

BG

Step a: A mixture of 5-bromoquinoline (2.0 g, 9.61 mmol, 1.0 eq), Zn(CN)$_2$ (2.26 g, 19.23 mmol, 2.0 eq) and Xant-Phos-Pd-G4 (924.8 mg, 961.3 umol, 0.1 eq) in dioxane (20.0 mL) and H$_2$O (2.0 mL) was stirred at 80° C. for 16 hours under N2. The reaction mixture was concentrated under reduced pressure. The residue was purified by silica gel column chromatography (petroleum ether/ethyl acetate=1:1) to afford quinoline-5-carbonitrile (1.28 g, 84.6% yield) as a white solid. LCMS m/z [M+H]$^+$=155.1.

Step b: To a solution of quinoline-5-carbonitrile (780.0 mg, 5.06 mmol, 1.0 eq) in MeOH (10.0 mL) were added Raney-Ni (300.0 mg, 5.11 mmol, 1.0 eq) and NH3.H$_2$O (1.91 g, 2.10 mL, 28% solution). The reaction mixture was degassed and refilled with H2 for three times. The reaction mixture was stirred at 15° C. for 16 hours under H2 (15 psi). The reaction mixture was filtered through a pad of celite and washed with MeOH (5.0 mL×4). The filtrate was concentrated under reduced pressure to give a green residue. The residue was purified by silica gel column chromatography (DCM:MeOH=10:1) to afford 5-quinolylmethanamine (550.0 mg, 69% yield) as a green oil. LCMS m/z [M]$^+$=158.1.

Step c: To a solution of 5-quinolylmethanamine (550.0 mg, 3.48 mmol, 1.0 eq) in DCM (7.0 mL) were added isopropyl carbonochloridate (852.1 mg, 6.95 mmol, 965.0 uL, 2.0 eq) and TEA (1.06 g, 10.43 mmol, 1.45 mL, 3.0 eq). The reaction mixture was stirred at 15° C. for 16 hours under N2. The reaction mixture was concentrated under reduced pressure to give a yellow residue. The residue was purified by silica gel column chromatography (petroleum ether/ethyl acetate=0:1) to afford isopropyl N-(5-quinolylmethyl)carbamate (670.0 mg, 79% yield) as a white solid. LCMS m/z [M+H]$^+$=245.1.

Step d: To a solution of isopropyl-N-(5-quinolylmethyl)carbamate (830.0 mg, 3.40 mmol, 1.0 eq) and Cs$_2$CO$_3$ (3.32 g, 10.19 mmol, 3.0 eq) in DMF (10.0 mL) was added a solution of MeI (578.7 mg, 4.08 mmol, 253.8 uL, 1.2 eq) in DMF (2.0 mL). The reaction mixture was stirred at 15° C. for 16 hours under N2. The reaction mixture was concentrated under reduced pressure. The residue was washed with water (70.0 mL) and extracted with EtOAc (50.0 mL×3). The combined organic layer was concentrated under reduced pressure to give a red residue. The residue was purified by silica gel column chromatography (DCM:MeOH=10:1) to afford isopropyl-N-methyl-N-(5-quinolylmethyl)carbamate (610.0 mg) as a red oil. The crude product was purified again by silica gel column chromatography (petroleum ether/rthyl acetate=0:1) to afford isopropyl-N-methyl-N-(5-quinolylmethyl)carbamate (210.0 mg, 24% yield) as a yellow oil. LCMS m/z [M+H]$^+$=259.1.

Step e: To a solution of isopropyl-N-methyl-N-(5-quinolylmethyl)carbamate (130.0 mg, 503.3 umol, 1.0 eq) in MeOH (3.0 mL) was added PtO$_2$ (20.0 mg, 88.08 umol, 1.75 eq). The reaction mixture was degassed and refilled with H2 for three times. The reaction mixture was stirred at 30° C. for 16 hours under H2 (15 psi). The reaction mixture was filtered through a pad of celite and washed with MeOH (5.0 mL×3). The filtrate was concentrated under reduced pressure to give the product of isopropyl N-methyl-N-(1,2,3,4-tetrahydroquinolin-5-ylmethyl)carbamate (115.0 mg, 87% yield) as a green oil. LCMS m/z [M+H]$^+$=262.9; $^1$HNMR (400 MHz, Methanol-d4): δ 6.95-6.91 (m, 1H), 6.51 (d, J=8.0 Hz, 1H), 6.43 (d, J=7.2 Hz, 1H), 4.98-4.92 (m, 1H), 4.43 (s, 2H), 3.26-3.23 (m, 2H), 2.84 (s, 3H), 2.68-2.65 (m, 2H), 2.00-1.94 (m, 2H), 1.31-1.29 (m, 6H).

Step f: To a solution of isopropyl N-methyl-N-(1,2,3,4-tetrahydroquinolin-5-ylmethyl)carbamate (60.0 mg, 228.7 umol, 1.0 eq) in DCM (3.8 mL) was added P$_2$O$_5$ (324.6 mg, 2.29 mmol, 10.0 eq). The reaction mixture was stirred at 40° C. for 16 hours under N2. The reaction mixture was adjusted to pH=8 by adding saturated NaHCO$_3$ aqueous solution and extracted with DCM (30.0 mL×2). The combined organic layer was dried over anhydrous Na$_2$SO$_4$ and concentrated under reduced pressure to give a yellow residue. The crude product was purified by prep-HPLC (NH$_4$HCO$_3$) (column: Waters Xbridge 150×25 5 u; mobile phase: [water (10 mM NH$_4$HCO$_3$)-ACN]; B %: 15%-45%, 7 min) to afford 2-methyl-6,7,8,9-tetrahydro-1H-pyrrolo[3,4-f]quinolin-3-one (20.0 mg, 43% yield) as a white solid. LCMS m/z [M+H]$^+$=202.9.

(R)—N-[(1S)-7-cyano-1,3-dihydrospiro[indene-2,4'-piperidin]-1-yl]-2-methylpropane-2-sulfinamide, Intermediate BH

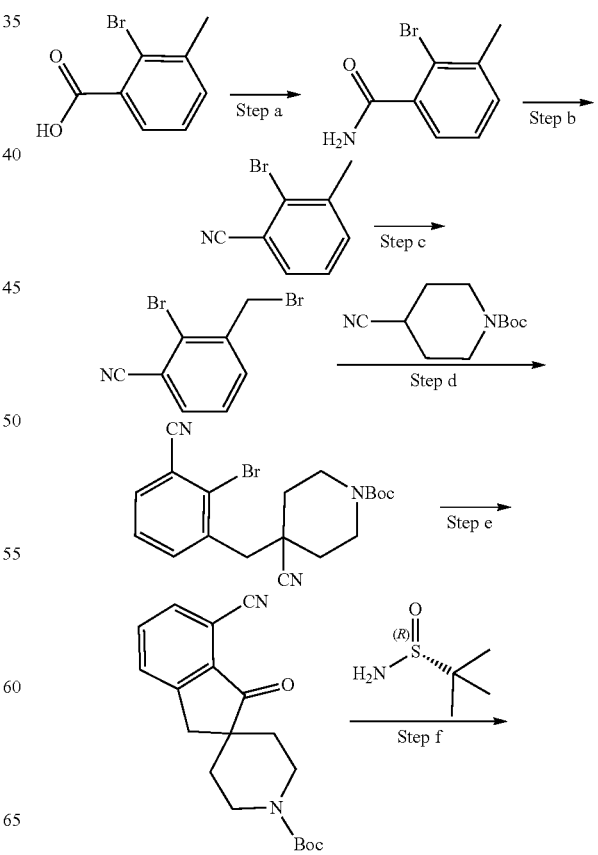

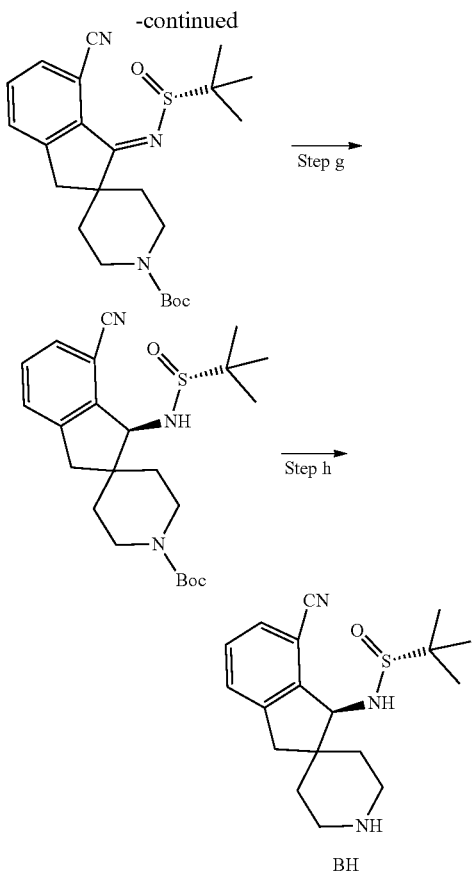

Step a: A mixture of 2-bromo-3-methylbenzoic acid (10.0 g, 46.5 mmol, CAS #53663-39-1), DIPEA (38.2 mL, 232.0 mmol), HATU (22.9 g, 60.4 mmol) and DMF (80.0 mL) was stirred at 25° C. for 1 hour. Then NH₄Cl (7.4 g, 139.0 mmol) was added, and the resulting mixture was stirred at 25° C. for 12 hours. The reaction mixture was concentrated to remove DMF. Then water (200.0 mL) was added into the residue. The mixture was filtered and the filtered cake was washed with water (100.0 mL×2) to give 2-bromo-3-methylbenzamide (8.7 g, 87% yield) as a brown solid. LCMS m/z [M+H]⁺=214.0/216.0.

Step b: To the reaction mixture of 2-bromo-3-methylbenzamide (8.5 g, 39.7 mmol) and TEA (8.2 mL, 59.5 mmol) in DCM (100.0 mL) was added TFAA (8.3 mL, 59.5 mmol) slowly at 0° C. The reaction mixture was stirred at 0° C. for 15 min. The reaction mixture was then quenched with H₂O (20.0 mL) and extracted with DCM (50.0 mL). The combined organic layers were washed with brine (20.0 mL), dried over anhydrous Na₂SO₄, filtered and concentrated under reduced pressure to give a residue. The residue was purified by flash silica gel chromatography (12 g column, EtOAc in petroleum ether from 0% to 30%) to give 2-bromo-3-methylbenzonitrile (8.3 g, quant yield) as a light yellow solid. LCMS m/z [M+H]⁺=197.9/199.9.

Step c: The mixture of 2-bromo-3-methylbenzonitrile (4.0 g, 20.4 mmol), NBS (4.3 g, 24.4 mmol) and BPO (491.0 mg, 2.0 mmol) in CCl₄ (30.0 mL) was stirred at 85° C. for 12 hours under N2 atmosphere. The reaction mixture was filtered and concentrated. The residue was purified by column chromatography (petroleum ether/EtOAc=1:0-3:1) to give 2-bromo-3-(bromomethyl)benzonitrile (2.3 g, 42% yield) was obtained as a white solid.

Step d: To a solution of tert-butyl 4-cyanopiperidine-1-carboxylate (1.9 g, 9.2 mmol) in THF (20.0 mL) at −78° C. was added LDA (6.9 mL, 13.8 mmol, 2 M in THF) dropwise and stirred at −78° C. for 1 hour. 2-bromo-3-(bromomethyl)benzonitrile (2.1 g, 7.7 mmol) was then added into the reaction and the reaction mixture was allowed stirring at −78° C. for 0.5 hour. The reaction mixture was then warmed to 20° C. The reaction mixture was quenched with sat. NH₄Cl solution (30.0 mL), and extracted with EtOAc (50.0 mL×2). The combined organic layers were dried over anhydrous Na₂SO₄, filtered and concentrated to give a residue. The residue was purified by flash silica gel chromatography (20 g column, petroleum ether in EtOAc from 0% to 25%) to give tert-butyl 4-[(2-bromo-3-cyanophenyl)methyl]-4-cyanopiperidine-1-carboxylate (1.8 g, 57% yield) as a yellow oil. LCMS m/z [M+H]⁺=304.0/306.0.

Step e: The mixture of tert-butyl 4-[(2-bromo-3-cyanophenyl)methyl]-4-cyanopiperidine-1-carboxylate (1.3 g, 3.3 mmol), P(t-Bu)₃-Pd-G4 (387.0 mg, 0.7 mmol) and TEA (915.0 μL, 6.6 mmol) in DMF (13.5 mL) and H2 (1.5 mL) was stirred at 130° C. for 12 hours under N2 atmosphere. The reaction mixture was quenched with water (80.0 mL), and extracted with EtOAc (100.0 mL×2). The combined organic layers were dried over anhydrous Na₂SO₄, filtered and concentrated to give a residue. The residue was purified by flash silica gel chromatography (20 g column, EtOAc in petroleum ether from 0% to 25%) to give tert-butyl 7-cyano-1-oxo-1,3-dihydrospiro[indene-2,4'-piperidine]-1'-carboxylate (400.0 mg, 1.2 mmol, 37% yield) as a yellow oil. LCMS m/z [M+Na]⁺=349.1.

Step f: A reaction mixture of tert-butyl 7-cyano-1-oxo-1,3-dihydrospiro[indene-2,4 (400.0 mg, 1.2 mmol), (R)-2-methylpropane-2-sulfinamide (591.0 mg, 4.9 mmol), Ti(OEt)₄ (1.7 g, 7.3 mmol) and 2-Me-THF (10.0 mL) was stirred at 90° C. for 12 hours under N2 atmosphere. The addition of (R)-2-methylpropane-2-sulfinamide (591.0 mg, 4.9 mmol) and Ti(OEt)₄ (1.7 g, 7.3 mmol) at 90° C. was repeated for 2 times in 24 hours. The crude solution was used directly in the next step.

Step g: NaBH₄ (13.7 mg, 0.4 mmol) was added into the crude solution of tert-butyl (1Z)-7-cyano-1-{[(R)-2-methylpropane-2-sulfinyl]imino}-1,3-dihydrospiro[indene-2,4 (524.0 mg, 1.2 mmol) in 2-Me-THF (10.0 mL) at 0° C. The reaction mixture was stirred at 0° C. for 0.5 hour. Then NaBH₄ (13.7 mg, 0.4 mmol) was added again, and the resulting mixture was stirred at 0° C. for 0.5 hour. The reaction mixture was quenched with MeOH (1.0 mL), EtOAc (80.0 mL) and H₂O (50.0 mL). The reaction mixture was filtered, and the filtered cake was washed with EtOAc (80.0 mL×2). The filtrate was extracted with EtOAc (80.0 mL×2). The combined organic layers were washed with brine (20.0 mL), dried over anhydrous Na₂SO₄, filtered and concentrated under reduced pressure to give a residue. The residue was purified by flash silica gel chromatography (20 g column, EtOAc in petroleum ether from 0% to 50%) to give tert-butyl (1S)-7-cyano-1-{[(R)-2-methylpropane-2-sulfinyl]amino}-1,3-dihydrospiro[indene-2,4 (250.0 mg, 48% yield) as a yellow solid. LCMS m/z [M+Na]+=454.2.

Step h: To a reaction mixture of tert-butyl (1S)-7-cyano-1-{[(R)-2-methylpropane-2-sulfinyl]amino}-1,3-dihydrospiro[indene-2,4'-piperidine]-1'-carboxylate (200.0 mg, 0.5 mmol) in DCM (8.0 mL) was added TFA (0.8 mL). The reaction mixture was stirred at 25° C. for 0.5 hour. Then the reaction mixture was adjusted to pH=7-8 with TEA. The mixture was concentrated to give (R)—N-[(1S)-7-cyano-1, 3-dihydrospiro[indene-2,4'-piperidin]-1-yl]-2-methylpropane-2-sulfinamide (153.0 mg, 92% yield) as a yellow oil. LCMS m/z [M+H]$^+$=332.1.

1,2,3,4-tetrahydroquinolin-6-yl acetate, Intermediate BI

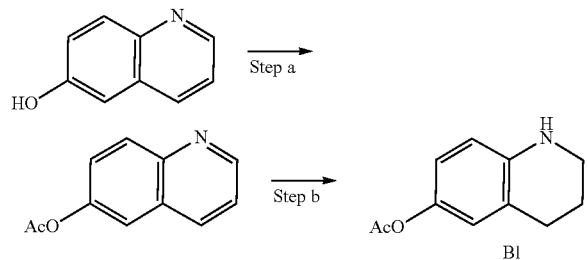

Step a: To a solution of quinolin-6-ol (1.00 g, 6.88 mmol) and TEA (2.84 mL, 20.6 mmol) in DCM (50.0 mL) was added acetyl chloride (1.07 g, 13.7 mmol) dropwise at 0° C. The reaction mixture was stirred at 20° C. for 1 hour. The reaction mixture was poured into H$_2$O (100.0 mL) and extracted with DCM (50.0 mL×2). The combined organic layers were washed with brine (50.0 mL), dried over anhydrous Na$_2$SO$_4$, filtered and concentrated under reduced pressure to give an orange residue. The residue was purified by flash silica gel chromatography (20 g column, ethyl acetate in petroleum ether from 0% to 30%) to give the product of quinolin-6-yl acetate (1.20 g, 94% yield) as a yellow oil. LCMS m/z [M+H]$^+$=188.0.

Step b: A solution of quinolin-6-yl acetate (1.20 g, 6.41 mmol) and PtO$_2$ (218.0 mg, 961.0 umol) in THF (50.0 mL) was stirred at 20° C. for 12 hours under H2 (15 psi). The reaction mixture was filtered and the filtrate was concentrated under reduced pressure to give a residue, which was purified by flash silica gel chromatography (20 g column, ethyl acetate in petroleum ether from 0% to 20%) to give 1,2,3,4-tetrahydroquinolin-6-yl acetate (1.00 g, 82% yield) as a yellow oil. LCMS m/z [M+H]$^+$=192.1.

[(4-acetamidophenyl)(fluorosulfonyl)amino]sulfonyl fluoride, Intermediate BJ

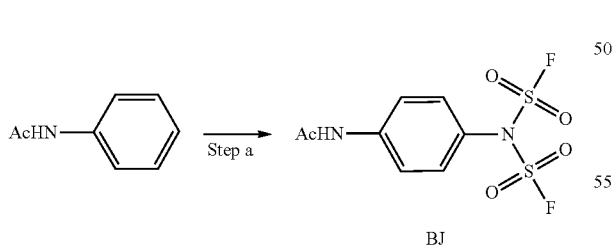

Step a: To a solution of LiN(SO$_2$F)$_2$ (2.74 g, 14.7 mmol) and PhI(OAc)$_2$ (3.54 g, 11.0 mmol) in DCE (30.0 mL) was added N-phenylacetamide (1.00 g, 7.39 mmol) in DCE (20.0 mL) dropwise under N2 at 20° C. The reaction mixture was stirred at 90° C. for 20 min. The reaction mixture was concentrated under reduced pressure to give a residue, which was purified by flash silica gel chromatography (40 g column, ethyl acetate in petroleum ether from 0% to 35%) to give [(4-acetamidophenyl)(fluorosulfonyl)amino]sulfonyl fluoride (1.35 g, 58% yield) as a yellow solid. LCMS m/z [M+H]$^+$=314.9.

2-bromo-3-(bromomethyl)-6-methoxypyridine, Intermediate BK

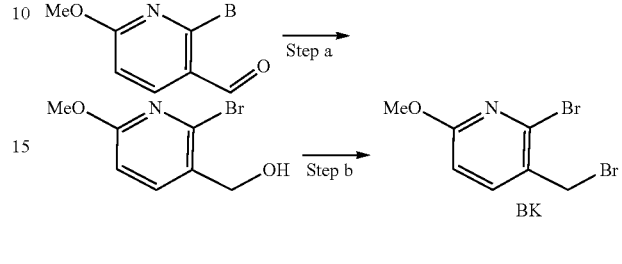

Step a: NaBH$_4$ (327.0 mg, 8.6 mmol) was added in portions to the mixture of 2-bromo-6-methoxypyridine-3-carbaldehyde (3.75 g, 17.3 mmol, CAS #1060810-41-4) in MeOH (120 mL) at 25° C. The mixture was stirred at 25° C. for 5 min. The reaction was quenched with H$_2$O (150 mL). The MeOH was removed under reduced pressure. The combined mixture was extracted with ethyl acetate (100 mL×3). The combined organic layers were washed with brine (150 mL), dried over anhydrous Na$_2$SO$_4$, filtered and concentrated to give a residue. The residue was purified by flash silica gel chromatography (petroleum ether:ethyl acetate=100:0 to 100:20) to afford (2-bromo-6-methoxypyridin-3-yl)methanol (4.7 g, combined product) as a yellow oil. LCMS m/z [M+H]$^+$=218.0/220.0.

Step b: The compound of (2-bromo-6-methoxypyridin-3-yl)methanol (4.50 g, 20.6 mmol) and CBr$_4$ (8.19 g, 24.7 mmol) were added in DCM (200 mL). PPh$_3$ (6.47 g, 24.7 mmol) in DCM (50 mL) was then added dropwise at 0° C. The mixture was stirred at 0° C. for 0.5 h. The reaction was then quenched with brine (100 mL) and the partitioned layers were separated. The aqueous phase was extracted with DCM (100 mL×2). The combined organic layers were washed with brine (150 mL), dried over anhydrous Na$_2$SO$_4$, filtered and concentrated to give a residue. The residue was purified by flash silica gel chromatography (petroleum ether: ethyl acetate=100:10) to afford 2-bromo-3-(bromomethyl)-6-methoxypyridine (5.7 g, 99% yield) as a white solid. LCMS m/z [M+H]$^+$=281.8.

(R)—N-[(7S)-2-methoxy-5,7-dihydrospiro[cyclopenta[b]pyridine-6,4'-piperidin]-7-yl]-2-methylpropane-2-sulfinamide, Intermediate BL

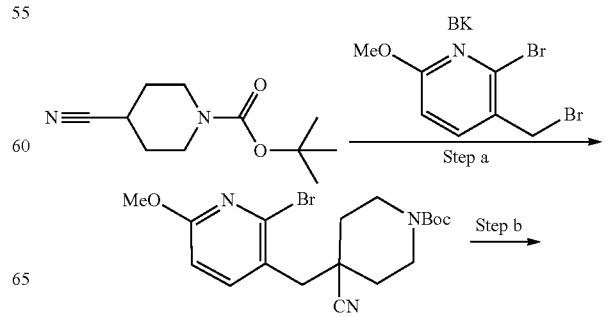

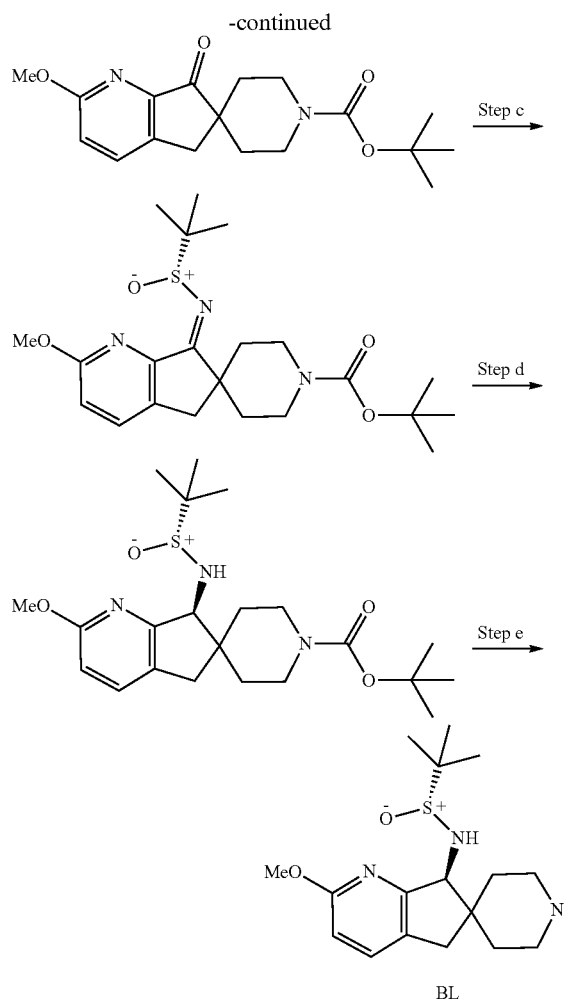

Step a: The compound of tert-butyl 4-cyanopiperidine-1-carboxylate (2.43 g, 11.6 mmol) was placed in THF (100 mL). The LDA (10.6 mL, 21.2 mmol, 2M in THF) was added dropwise into the mixture at 0° C. The mixture was stirred at 0° C. for 0.5 hour. The 2-bromo-3-(bromomethyl)-6-methoxypyridine (3.0 g, 10.6 mmol, Intermediate BK) in THF (50 mL) was added dropwise into the mixture at 0° C. The mixture was allowed to warm to 25° C. and stirred for 2 hours. The reaction was quenched by addition of saturated NH$_4$Cl (100 mL). The mixture was extracted with ethyl acetate (100 mL×2). The combined organic layers were washed with brine (100 mL), dried over anhydrous Na$_2$SO$_4$, filtered and concentrated to give a residue. The residue was purified by flash silica gel chromatography (petroleum ether:ethyl acetate=100:0 to 100:20) to afford tert-butyl 4-[(2-bromo-6-methoxypyridin-3-yl)methyl]-4-cyanopiperidine-1-carboxylate (2.7 g, 62% yield) as a yellow oil. LCMS m/z [M+H]$^+$=410.0/412.0.

Step b: The compound of tert-butyl 4-[(2-bromo-6-methoxypyridin-3-yl)methyl]-4-cyanopiperidine-1-carboxylate (1.7 g, 4.1 mmol) was added in the 2-Me-THF (20 mL) and PhMe (20 mL). i-PrMgCl.LiCl (6.4 mL, 8.3 mmol, 1.3 M in THF) and n-BuLi (1.7 mL, 4.1 mmol, 2.5 M in hexane) were added at −78° C. The reaction mixture was stirred at −78° C. for 1 hour. The mixture was slowly warmed to 25° C. and stirred for 15 h. The reaction was quenched with saturated NH$_4$Cl (20 mL). The mixture was adjusted to pH=5-6 with HCl (2 N). The mixture was extracted with ethyl acetate (50 mL×3). The combined organic phases were washed with brine (50 mL), dried over anhydrous Na$_2$SO$_4$, filtered and concentrated to give a residue. The residue was purified by flash silica gel chromatography (petroleum ether:ethyl acetate=100:0 to 100:30) to afford tert-butyl 2-methoxy-7-oxo-5,7-dihydrospiro[cyclopenta[b]pyridine-6,4'-piperidine]-1'-carboxylate (160 mg, 12% yield) as a white solid. LCMS m/z [M+H]$^+$=333.1

Step c: To a solution of tert-butyl 2-methoxy-7-oxo-5,7-dihydrospiro[cyclopenta[b]pyridine-6,4'-piperidine]-1'-carboxylate (160 mg, 0.5 mmol) and Ti(OEt)$_4$ (0.5 mL, 2.4 mmol) in 2-Me-THF (10 mL) was added (R)-2-methylpropane-2-sulfinamide (116 mg, 1.0 mmol). The reaction mixture was stirred at 90° C. for 12 h under N2. Additional (R)-2-methylpropane-2-sulfinamide (116 mg, 1.0 mmol) and Ti(OEt)$_4$ (0.5 mL, 2.4 mmol) were added. The reaction mixture was stirred at 90° C. for another 12 h under N2. The reaction was diluted with EtOAc (20 mL) and H$_2$O (10 mL) was added where a lot of white solid formed. The mixture was filtered and the filtrate was extracted with ethyl acetate (10 mL×3). The combined organic layers were washed with brine (30 mL), dried over anhydrous Na$_2$SO$_4$, filtered and concentrated to give a residue. The residue was purified by prep-TLC (ethyl acetate/petroleum ether=1/1) to afford tert-butyl (7Z)-2-methoxy-7-{[(R)-2-methylpropane-2-sulfinyl]imino}-5,7-dihydrospiro[cyclopenta[b]pyridine-6,4'-piperidine]-1'-carboxylate (70.0 mg, 33% yield) as a yellow oil. LCMS m/z [M+H]$^+$=436.1.

Step d: The compound of tert-butyl (7Z)-2-methoxy-7-{[(R)-2-methylpropane-2-sulfinyl]imino}-5,7-dihydrospiro[cyclopenta[b]pyridine-6,4'-piperidine]-1'-carboxylate (70 mg, 160 μmol) in THF (2 mL) was added NaBH$_4$ (18 mg, 480 μmol) at 0° C. The mixture was stirred at 25° C. for 1 h. The reaction mixture was quenched with MeOH. The solution was added into H$_2$O (10 mL) and EtOAc (10 mL). The mixture was filtered and extracted with EtOAc (10 mL×2). The combined organic layers were washed with brine (10 mL), dried over anhydrous Na$_2$SO$_4$, filtered and concentrated to give a residue. The residue was purified by prep-TLC (ethyl acetate:petroleum ether=1:1) to afford tert-butyl (7S)-2-methoxy-7-{[(R)-2-methylpropane-2-sulfinyl]amino}-5,7-dihydrospiro[cyclopenta[b]pyridine-6,4'-piperidine]-1'-carboxylate (70 mg, quant. crude yield) as a colorless oil. LCMS m/z [M+H]$^+$=438.1.

Step e: tert-butyl (7S)-2-methoxy-7-{[(R)-2-methylpropane-2-sulfinyl]amino}-5,7-dihydrospiro[cyclopenta[b]pyridine-6,4'-piperidine]-1'-carboxylate (70 mg, 0.2 mmol) was added in the solution of TFA (0.2 mL) and DCM (2 mL). The mixture was stirred at 25° C. for 0.5 h. The mixture was adjusted to pH=8-9 with TEA. The mixture was concentrated to give (R)—N-[(7S)-2-methoxy-5,7-dihydrospiro[cyclopenta[b]pyridine-6,4'-piperidin-7-yl]-2-methylpropane-2-sulfinamide (60 mg, crude product) as a colorless oil. LCMS m/z [M+H]+=338.1.

3-bromo-2-(bromomethyl-6-methoxypyridine, Intermediate BM

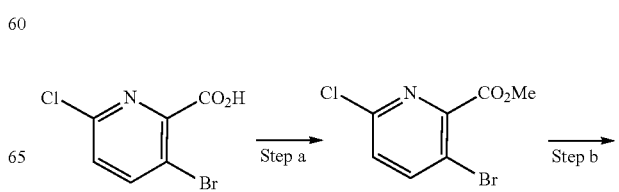

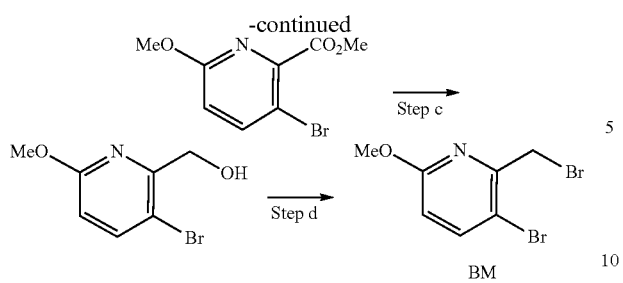

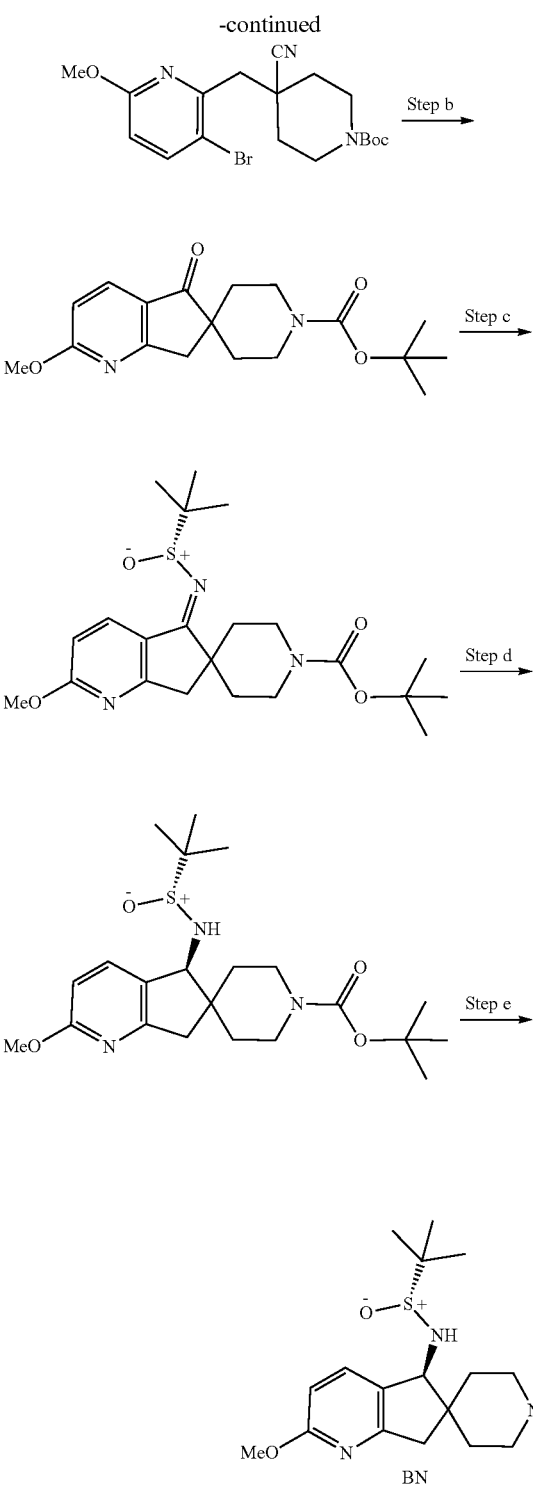

Step a: A mixture of 3-bromo-6-chloropyridine-2-carboxylic acid (10.0 g, 42.2 mmol, CAS #929000-66-8) in MeOH (100.0 mL)/SOCl$_2$ (10.0 mL) was stirred at 80° C. for 3 hours. The reaction mixture was concentrated in vacuo to give methyl 3-bromo-6-chloropyridine-2-carboxylate (10.4 g, 99% yield) as a yellow solid.

Step b: To the solution of methyl 3-bromo-6-chloropyridine-2-carboxylate (5.0 g, 19.9 mmol) and MeOH (1.0 mL, 25.8 mmol) in THF (15.0 mL, freshly dried over NaH) was added t-BuOK (29.8 mL, 29.8 mmol, 1 M in THF) slowly over 20 min at 0° C. under N$_2$ atmosphere. The reaction mixture was stirred at 0° C. for 5 min. The reaction mixture was quenched with ice-cold sat. NH$_4$Cl solution (30.0 mL), and extracted with EtOAc (50.0 mL×2) rapidly. The combined organic layers were dried over anhydrous Na$_2$SO$_4$, filtered and concentrated. The residue was purified by flash silica gel chromatography (40 g column, EtOAc in petroleum ether from 0% 10%) to give methyl-3-bromo-6-methoxypyridine-2-carboxylate (4.5 g, 92.0% yield) as a colorless oil.

Step c: To the mixture of methyl-3-bromo-6-methoxypyridine-2-carboxylate (9.0 g, 36.5 mmol) in MeOH (30 mL) was added NaBH$_4$ (1.38 g, 36.5 mmol). The mixture was stirred at 25° C. for 0.5 hour. The addition of NaBH$_4$ (1.38 g, 36.5 mmol) at 25° C. was repeated for 2 times each 0.5 hour. The reaction mixture was concentrated. The residue was purified by flash silica gel chromatography (40 g column, EtOAc in petroleum ether from 0% to 15%) to give (3-bromo-6-methoxypyridin-2-yl)methanol (6.40 g, 81% yield) as a colorless oil. LCMS m/z [M+H]$^+$=217.7/219.7.

Step d: (3-bromo-6-methoxypyridin-2-yl)methanol (2.5 g, 11.4 mmol) and CBr$_4$ (4.5 g, 13.6 mmol) were added into DCM (30 mL). PPh$_3$ (3.6 g, 13.6 mmol) in DCM (10 mL) was added dropwise into the reaction mixture at 0° C. The mixture was stirred at 0° C. for 0.5 hour. The reaction was concentrated to give a residue. The residue was purified by flash silica gel chromatography (40 g column, EtOAc in petroleum ether from 0% to 10%) to afford 3-bromo-2-(bromomethyl)-6-methoxypyridine (2.69 g, 84% yield) as a colorless oil. LCMS m/z [M+H]$^+$=281.8.

(R)—N-[(5S)-2-methoxy-5,7-dihydrospiro[cyclonenta[b]pyridine-6,4'-piperidin]-5-yl]-2-methylpropane-2-sulfinamide, Intermediate BN

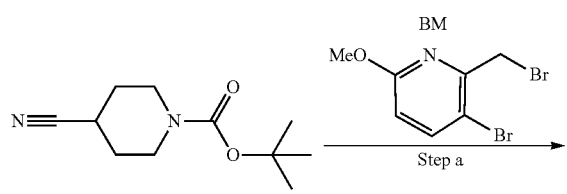

(R)—N-[(5S)-2-methoxy-5,7-dihydrospiro[cyclopenta[b]pyridine-6,4'-piperidin]-5-yl]-2-methylpropane-2-sulfinamide was synthesized as described for Intermediate BL, coupling tert-butyl 4-cyanopiperidine-1-carboxylate with 3-bromo-2-(bromomethyl)-6-methoxypyridine (Intermediate BM) in Step a. In Step b, the conditions P(t-Bu)$_3$-Pd-G4 and TEA in DMF and H$_2$O at 130° C. for 12 hours were used for the cyclization. LCMS of final Intermediate BN: LCMS m/z [M+H]$^+$=338.1.

3-(bromomethyl)-4-iodobenzonitrile, Intermediate BO

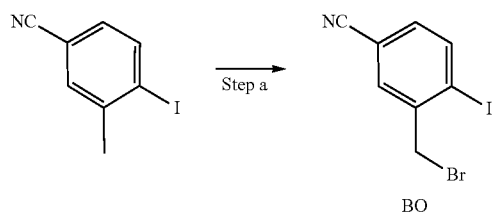

Step a: 4-Iodo-3-methylbenzonitrile (2.00 g, 8.20 mmol), BPO (199.0 mg, 822.0 µmol) and NBS (2.20 g, 12.30 mmol) were added in DCE (30.0 mL), and the reaction mixture was evacuated and refilled for 3 times with N2 and stirred at 80° C. for 2 hours. Another batch of NBS (1.50 g, 8.44 mmol) was added and the mixture was stirred at 80° C. for another 12 hours. The reaction mixture was concentrated under reduced pressure and purified by flash silica gel chromatography (petroleum ether:EtOAc=100:0 to 100:5) to afford 3-(bromomethyl)-4-iodobenzonitrile (1.60 g, 61% yield) as a white solid. $^1$HNMR (400 MHz, CDCl$_3$) 8.03-8.00 (m, 1H), 7.77-7.72 (m, 1H), 7.28-7.24 (m, 1H), 4.58 (s, 2H).

(R)—N-[(1S)-5-cyano-1,3-dihydrospiro[indene-2,4'-piperidin]-1-yl]-2-methylpropane-2-sulfinamide, Intermediate BP

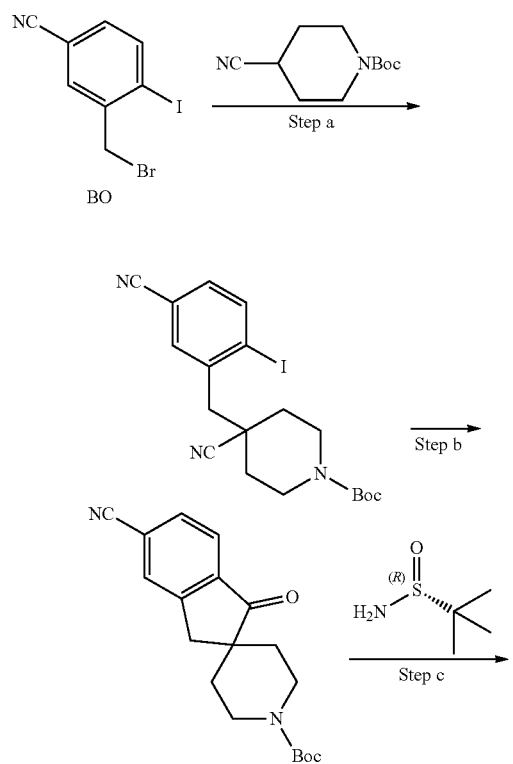

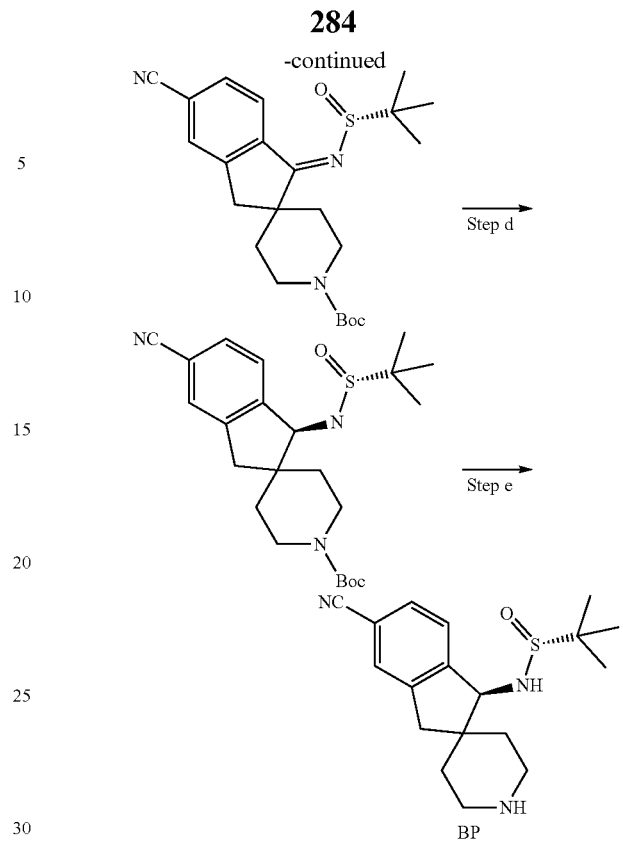

(R)—N-[(1S)-5-cyano-1,3-dihydrospiro[indene-2,4'-piperidin]-1-yl]-2-methylpropane-2-sulfinamide was synthesized as described via Steps d-h of Intermediate BH, starting with tert-butyl 4-cyanopiperidine-1-carboxylate and 3-(bromomethyl)-4-iodobenzonitrile (Intermediate BO) in Step a. Characterization of the final product: LCMS m/z [M]$^+$= 331.9.

tert-butyl (4,5,6-trichloropyridin-2-yl)carbamate, Intermediate BQ

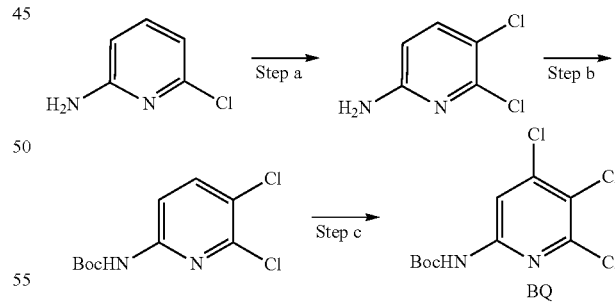

Step a: A mixture of 6-chloropyridin-2-amine (2.5 g, 19.4 mmol) and NCS (2.8 g, 21.3 mmol) in MeCN (40 mL) was stirred at 80° C. for 18 hours. The reaction mixture was concentrated in vacuo to give a residue, which was purified by silica gel chromatography (ethyl acetate in petroleum ether=0% to 30%) to afford 5,6-dichloropyridin-2-amine (2.1 g, 66% yield) as a white solid. LCMS m/z [M+H]$^+$= 162.8.

Step b: To a solution of 5,6-dichloropyridin-2-amine (2.1 g, 12.8 mmol) in anhydrous THF (20 mL) was added NaHMDS (25.6 mL, 25.6 mmol) at 0° C. The reaction mixture was stirred at this temperature for 30 mins, then the solution of (Boc)₂O (2.9 g, 13.4 mmol) in anhydrous THF (10 mL) was added. The resulting mixture was stirred at 0° C. for 1.5 hours. The mixture was quenched with saturated NH₄Cl and extracted with ethyl acetate (50 mL×2). The organic phases were washed with brine (20 mL), dried over anhydrous Na₂SO₄, filtered and concentrated in vacuo to give a residue, which was purified by silica gel chromatography (ethyl acetate in petroleum ether=0% to 10%) to afford tert-butyl (5,6-dichloropyridin-2-yl)carbamate (2.5 g, 74% yield) as a colorless oil.

Step c: To a mixture of tert-butyl (5,6-dichloropyridin-2-yl)carbamate (1.2 g, 4.6 mmol) in anhydrous THF (15 mL) at −70° C. was added LDA (5.7 mL, 11.4 mmol) under N2 atmosphere. After stirring at this temperature for 2 hours, NCS (1.1 g, 8.2 mmol) in THF (5 mL) was added. The resulting mixture was stirred at −70° C. for 2 hours and 10 hours at 20° C. The reaction mixture was diluted with H₂O (40 mL) and extracted with ethyl acetate (45 mL×2). The combined organic phases were washed with brine (20 mL), dried over anhydrous Na₂SO₄, filtered and concentrated in vacuo to give a residue, which was purified by silica gel chromatography (ethyl acetate in petroleum ether=0% to 5%) to afford tert-butyl (4,5,6-trichloropyridin-2-yl)carbamate (1.3 g, purity: 30%) as a colorless oil.

(R)-2-methyl-N-[(3S)-1'-[5-(sodiosulfanyl)pyrazin-2-yl]-1,3-dihydrospiro[indene-2,4'-piperidin]-3-yl]propane-2-sulfinamide, Intermediate BR

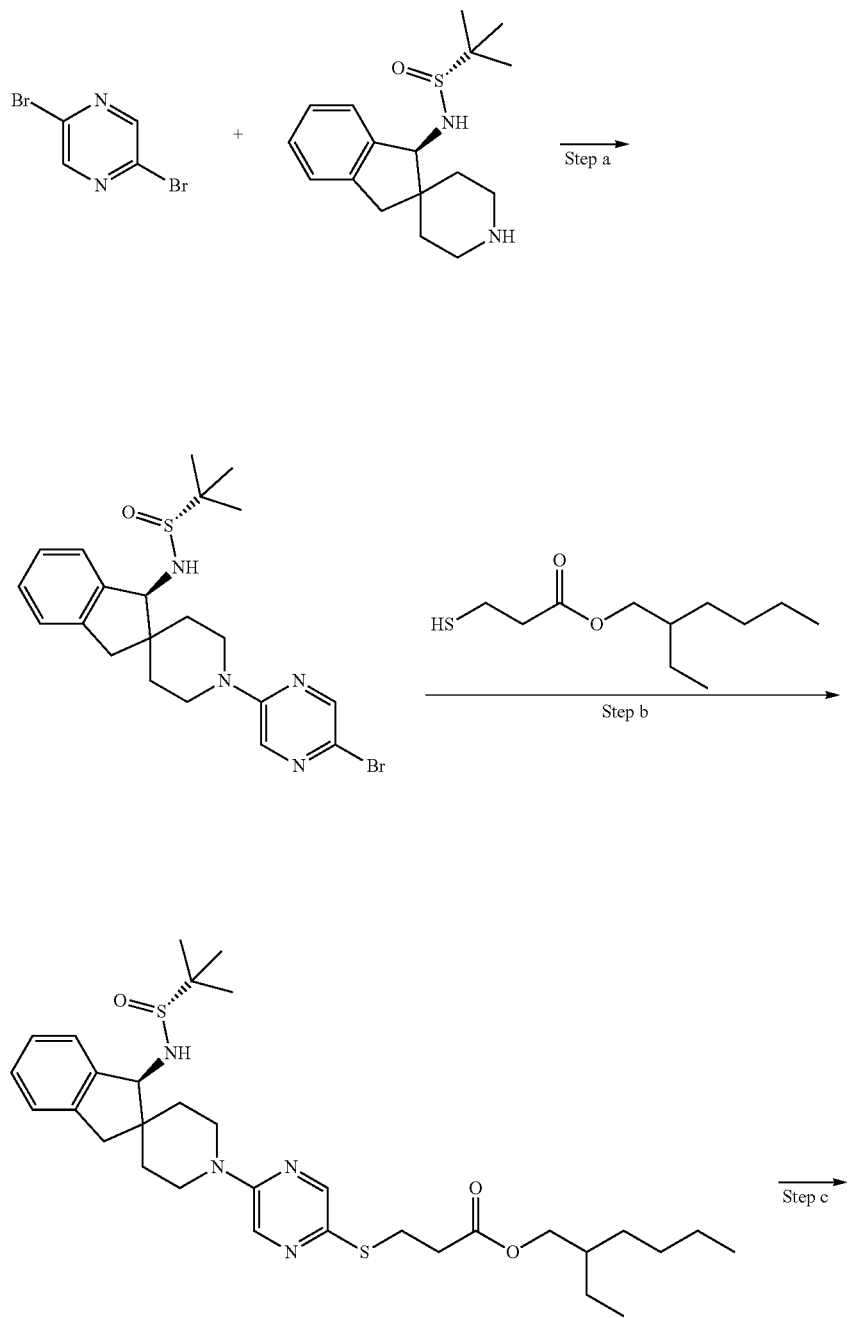

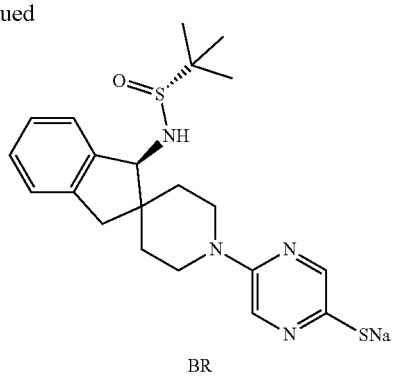

BR

Step a: A mixture of (R)—N-[(3S)-1,3-dihydrospiro[indene-2,4'-piperidin]-3-yl]-2-methylpropane-2-sulfinamide (450 mg, 1.5 mmol, synthesized via Step a of Example 120), 2,5-dibromopyrazine (416 mg, 1.8 mmol) and TEA (1.0 mL, 7.3 mmol) in DMF (10 mL) was stirred at 80° C. for 2 hours. The reaction mixture was then diluted with ethyl acetate (30 mL), and washed with H$_2$O (20 mL×2). The organic phase was washed with brine (10 mL), dried over anhydrous Na$_2$SO$_4$, filtered and concentrated in vacuo to give a residue. The residue was purified by silica gel chromatography (ethyl acetate in petroleum ether=0% to 70%) to afford (R)—N-[(3S)-1'-(5-bromopyrazin-2-yl)-1,3-dihydrospiro[indene-2,4'-piperidin]-3-yl]-2-methylpropane-2-sulfinamide (580 mg, 86% yield) as a brown solid. LCMS m/z [M+H]$^+$=463.0/465.0.

Step b: A mixture of (R)—N-[(3S)-1'-(5-bromopyrazin-2-yl)-1,3-dihydrospiro[indene-2,4'-piperidin]-3-yl]-2-methylpropane-2-sulfinamide (550 mg, 1.2 mmol), 2-ethylhexyl 3-mercaptopropanoate (307 mg, 1.4 mmol), Pd$_2$(dba)$_3$ (108 mg, 118 μmol), XantPhos (136 mg, 236 μmol) and TEA (0.5 mL, 3.5 mmol) in toluene (30 mL) was stirred at 100° C. for 12 hours under N2 atmosphere. The reaction mixture was concentrated in vacuo to give a residue, which was purified by silica gel chromatography (ethyl acetate in petroleum ether=0% to 55%) to afford 2-ethylhexyl 3-((5-((S)-1-((R)-1,1-dimethylethylsulfinamido)-1,3-dihydrospiro[indene-2,4'-piperidin]-1'-yl)pyrazin-2-yl)thio)propanoate (650 mg, 92% yield) as a yellow oil. LCMS m/z [M+H]$^+$=601.6.

Step c: To a mixture of 2-ethylhexyl 3-((5-((S)-1-((R)-1,1-dimethylethylsulfinamido)-1,3-dihydrospiro[indene-2,4'-piperidin]-1'-yl)pyrazin-2-yl)thio)propanoate (650 mg, 1.1 mmol) in anhydrous THF (3.0 mL) was added MeONa (116 mg, 2.2 mmol), the resulting mixture was stirred at 20° C. for 12 hours under N2 atmosphere. The reaction mixture was then concentrated in vacuo to give the crude product, which triturated with petroleum ether:ethyl acetate=10:1 (15 mL) and filtered. The solid was collected and dried in vacuo to afford (R)-2-methyl-N-[(3S)-1'-[5-(sodiosulfanyl)pyrazin-2-yl]-1,3-dihydrospiro[indene-2,4'-piperidin]-3-yl]propane-2-sulfinamide (650 mg, purity: 70%) as a yellow solid. LCMS m/z [M+H−Na]$^+$=417.0.

2-bromo-5-((2,3-dichloropyridin-4-yl)oxy)pyrazine, Intermediate BS

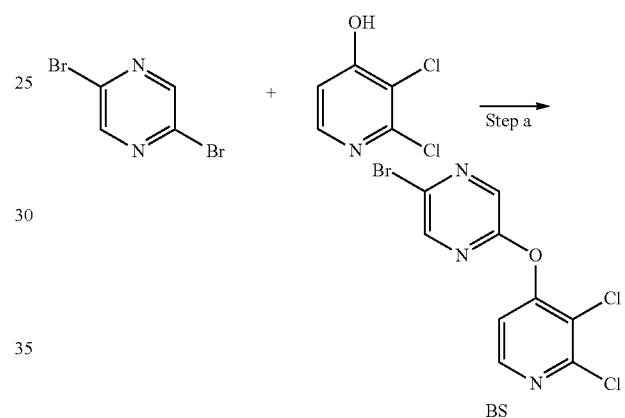

Step a: A mixture of 2,5-dibromopyrazine (287 mg, 1.2 mmol), 2,3-dichloropyridin-4-ol (300 mg, 1.8 mmol) and Cs$_2$CO$_3$ (593 mg, 1.8 mmol) in DMF (5.0 mL) was stirred at 85° C. for 24 hours. The reaction mixture was concentrated under reduced pressure. The residue was diluted with water (30.0 mL) and extracted ethyl acetate (50.0 mL×2). The combined organic layers were washed with H$_2$O (30.0 mL) and brine (30.0 mL), dried over anhydrous Na$_2$SO$_4$, filtered and concentrated under reduced pressure to give a residue. The residue was purified by column chromatography (petroleum ether:ethyl acetate=100:0 to 100:15) to give 2-bromo-5-((2,3-dichloropyridin-4-yl)oxy)pyrazine (530 mg) as a light yellow oil. LCMS m/z [M+H]$^+$=321.8.

tert-butyl 7-bromo-3-oxo-1,3-dihydrospiro[indene-2,4'-piperidine]-1'-carboxylate, Intermediate BT

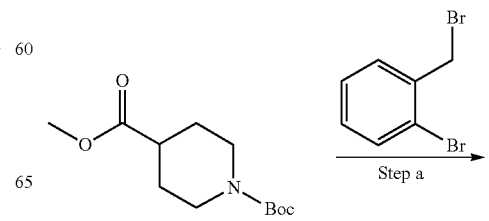

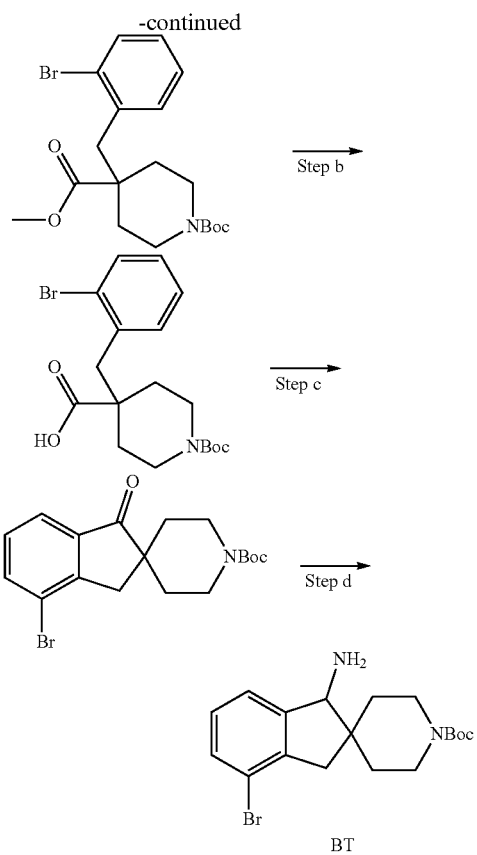

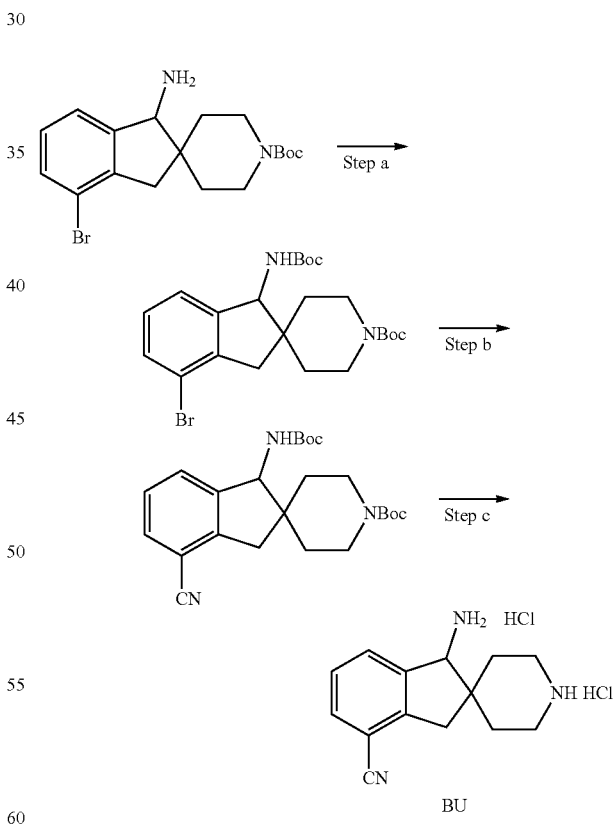

mixture was stirred at 20° C. for 2 hours under N2. The mixture was adjusted to pH=9 with 2N NaOH. To the mixture was added (Boc)$_2$O (7.6 mL, 33.5 mmol) and stirred at 20° C. for 12 hours. The mixture was extracted with DCM (100.0 mL×2). The combined organic phases were dried over anhydrous Na$_2$SO$_4$, filtered and concentrated under reduced pressure to give a residue. The residue was purified by flash silica gel chromatography (ethyl acetate in petroleum ether=0-10%) to afford tert-butyl 7-bromo-3-oxo-1,3-dihydrospiro[indene-2,4'-piperidine]-1'-carboxylate (1.6 g, 4.2 mmol) as a yellow solid.

Step d: To a solution of tert-butyl 7-bromo-3-oxo-1,3-dihydrospiro[indene-2,4'-piperidine]-1-carboxylate (1.1 g, 2.9 mmol) in EtOH (20.0 mL) were added NH$_{40}$Ac (8.9 g, 115.0 mmol) and NaBH$_3$CN (907.0 mg, 14.4 mmol) in portions (4 times). The mixture was stirred at 80° C. for 12 hours. The mixture was concentrated under reduced pressure to give a residue. The residue was extracted with EtOAc (100.0 mL×2), and the combined organic phases were washed with 2N aqueous NaOH (50.0 mL×2). The separated organic phase was dried over anhydrous Na$_2$SO$_4$, filtered and concentrated under reduced pressure to give tert-butyl 1-amino-4-bromo-1,3-dihydrospiro[indene-2,4'-piperidine]-1'-carboxylate (1.1 g, quant. crude yield). LCMS m/z [M+H]$^+$=381.0/383.0.

1-amino-1,3-dihydrospiro[indene-2,4'-piperidine]-4-carbonitrile, Intermediate BU Step a: To a solution of 1-tert-butyl 4-methyl piperidine-1,4-dicarboxylate (10.0 g, 41.1 mmol) in THF (150.0 mL) was added LDA (24.6 mL, 49.3 mmol, 2 M) at −78° C. under N2. The mixture was stirred at −78° C. for 1 hour. Then the solution of 1-bromo-2-(bromomethyl)benzene (12.3 g, 49.3 mmol) in THF (50.0 mL) was added at −78° C. The mixture was stirred at 20° C. for 11 hours under N2. The mixture was poured into H$_2$O (300.0 mL) and extracted with EtOAc (300.0 mL×2). The combined organic phases were washed with brine (300.0 mL), dried over anhydrous Na$_2$SO$_4$, filtered and concentrated in vacuo to give 1-(tert-butyl) 4-methyl 4-(2-bromobenzyl)piperidine-1,4-dicarboxylate (20 g, 50% purity) as a yellow oil.

Step b: A solution of 1-tert-butyl 4-methyl 4-[(2-bromophenyl)methyl]piperidine-1,4-dicarboxylate (20.0 g, 50% purity) and KOH (13.5 g, 242.0 mmol) in MeOH/H$_2$O (50.0 mL/50.0 mL) was stirred at 60° C. for 12 hours. The mixture was concentrated under reduced pressure to about 50.0 mL. The residue was diluted with H$_2$O (300.0 mL), extracted with EtOAc/Petroleum ether (1/10, 220.0 mL). The organic phase was discarded. The aqueous phase was acidified with 6 N HCl to pH=5~6, then extracted with EtOAc (250.0 mL×2). The combined organic phase were washed by brine (100.0 mL), dried over anhydrous Na$_2$SO$_4$, filtered and concentrated to give 4-[(2-bromophenyl)methyl]-1-[(tert-butoxy)carbonyl]piperidine-4-carboxylic acid (5.98 g, 15.0 mmol) as a white solid. LCMS m/z [M+H]$^+$=298.0.

Step c: To a solution of 4-[(2-bromophenyl)methyl]-1-[(tert-butoxy)carbonyl]piperidine-4-carboxylic acid (6.2 g, 14.7 mmol) in DCM (100.0 mL) was added SOCl$_2$ (2.1 mL, 29.4 mmol) at 20° C. under N2. The mixture was stirred at 20° C. for 1 hour. White suspension was observed, then AlCl$_3$ (2.9 g, 22.0 mmol) was added in portions at 0° C. The Step a: To a solution of tert-butyl 3-amino-7-bromo-1,3-dihydrospiro[indene-2,4'-piperidine]-1'-carboxylate (1.1 g, Intermediate BT) in DCM (10.0 mL) were added (Boc)$_{20}$ (1.3 g, 5.8 mmol) and Et$_3$N (1.2 mL, 8.6 mmol). The mixture was stirred at 20° C. for 1 hour. The reaction mixture was concentrated under reduced pressure and purified by flash silica gel chromatography (ethyl acetate in petroleum ether=0-10%) to afford tert-butyl 7-bromo-3-{[(tert-butoxy)carbonyl]amino}-1,3-dihydrospiro[indene-2,4'-piperidine]-1'-carboxylate (840.0 mg, 1.7 mmol) as a white solid. LCMS m/z [M+H]$^+$=481.1/483.1.

Step b: To a solution of tert-butyl 7-bromo-3-{[(tert-butoxy)carbonyl]amino}-1,3-dihydrospiro[indene-2,4'-piperidine]-1'-carboxylate (600.0 mg, 1.2 mmol) in DMF (20.0 mL) were added Zn(CN)$_2$ (1.2 g, 9.9 mmol) and XantPhos-Pd-G4 (119.0 mg, 124.0 μmol). The mixture was stirred at 100° C. for 12 hours under N2. The combined mixture was filtered, extracted with EtOAc (50.0 mL×3) and washed with brine (50.0 mL). The organic phase was dried over anhydrous Na$_2$SO$_4$, filtered and concentrated under reduced pressure to give a residue. The residue was purified by flash silica gel chromatography (ethyl acetate in petroleum ether=0~15%) to afford tert-butyl 3-{[(tert-butoxy)carbonyl]amino}-7-cyano-1,3-dihydrospiro[indene-2,4'-piperidine]-1'-carboxylate (500.0 mg, 67% yield) as a white solid. LCMS m/z [M+Na]$^+$=450.1.

Step c: To a solution of tert-butyl 3-{[(tert-butoxy)carbonyl]amino}-7-cyano-1,3-dihydrospiro[indene-2,4'-piperidine]-1'-carboxylate (250.0 mg, 584.0 μmol) in MeOH (5.0 mL) was added HCl/MeOH (5.0 mL, 4M), and the mixture was stirred at 20° C. for 12 hours. The mixture was concentrated under reduced pressure to give 1-amino-1,3-dihydrospiro[indene-2,4'-piperidine]-4-carbonitrile dihydrochloride (150 mg, 86% crude yield) as a white solid. LCMS m/z [M+H]$^+$=228.1.

tert-butyl N-[(tert-butoxy)carbonyl]-N-(1'-{3-hydroxy-1-[(4-methoxyphenyl)methyl]-1H-pyrazolo[3,4-b]pyrazin-6-yl}-1,3-dihydrospiro[indene-2,4'-piperidin]-3-yl)carbamate, Intermediate BV

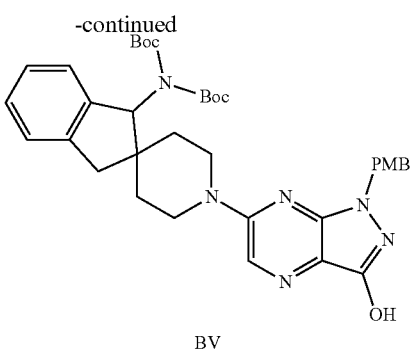

BV

6-{3-amino-1,3-dihydrospiro[indene-2,4'-piperidin]-1'-yl}-1-[(4-methoxyphenyl)methyl]-1H-pyrazolo[3,4-b]pyrazin-3-ol was synthesized as described for Intermediate BE above, coupling methyl 3,5-dichloropyrazine-2-carboxylate and 1,3-dihydrospiro[indene-2,4'-piperidin]-3-amine (Intermediate E) in Step a. 6-{3-amino-1,3-dihydrospiro[indene-2,4'-piperidin]-1'-yl}-1-[(4-methoxyphenyl)methyl]-1H-pyrazolo[3,4-b]pyrazin-3-ol (300 mg, 657 μmol) was then protected in Step c under the following conditions: Boc$_2$O (285 mg, 1.31 mmol) and TEA (250 μL, 1.97 mmol) in DCM (5 mL) was stirred at 20° C. for 5 hours. The mixture was concentrated under reduced pressure to afford tert-butyl N-[(tert-butoxy)carbonyl]-N-(1'-{3-hydroxy-1-[(4-methoxyphenyl)methyl]-1H-pyrazolo[3,4-b]pyrazin-6-yl}-1,3-dihydrospiro[indene-2,4'-piperidin]-3-yl)carbamate (500 mg, 80% purity, 93% yield) as a yellow oil. LCMS m/z [M+H]$^+$=657.2.

6-methyl-1,2,3,4,5,6-hexahydro-1,6-naphthyridin-5-one, Intermediate BW

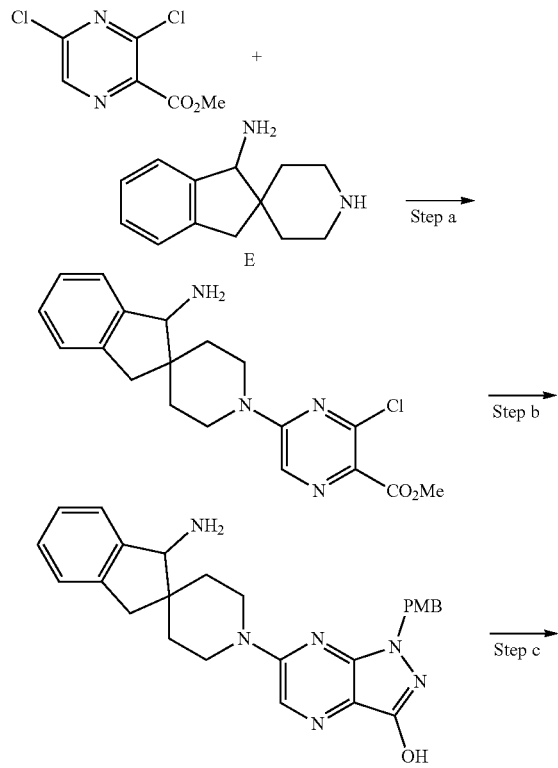

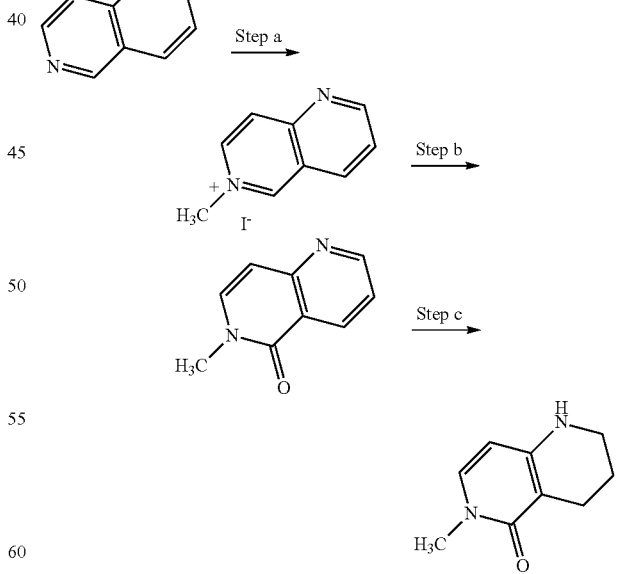

Step a: 1,6-naphthyridine (0.965 g, 7.41 mmol) was dissolved in MeOH (8.5 mL) and charged with iodomethane (921 μL, 14.8 mmol). The vial was sealed and heated to 65° C. and stirred for 16 hrs. The solvent was removed, the residue taken up in a small amount of MeOH (1-2 mL) and ethyla acetate was charged. The mixture was filtered, washed with EA and air dried to constant weight to afford 6-methyl-1,6-naphthyridin-6-ium iodide (1.56 g).

Step b: 6-methyl-1,6-naphthyridin-6-ium iodide (1.56 g, 5.73 mmol) was suspended in water (10 mL) and cooled to 0° C. The reaction was charged with NaOH (1.25 g, 31.5 mmol) in water (10 mL) and tripotassium hexakis(iminomethanide) iron (4.04 g, 12.3 mmol) in water (10 mL). The solution was stirred for 1 hr at 0° C. then overnight at rt. The mixture was extracted with $CHCl_3$, dried and concentrated. The residue was purified by flash silica gel chromatography (eluting with MeOH:DCM=0:100 to 10:90) to afford 6-methyl-5,6-dihydro-1,6-naphthyridin-5-one (540 mg) as alight yellow solid. LCMS: $[M+H]^+=161$.

Step c: 6-methyl-5,6-dihydro-1,6-naphthyridin-5-one (109 mg, 0.6805 mmol) was dissolved in MeOH (10 mL). The solution was pumped a 10% Pd/C cartridge at 1 mL/min under 70 bars of H2 at 70° C. for 90 min. Solvent was removed to afford 6-methyl-1,2,3,4,5,6-hexahydro-1,6-naphthyridin-5-one (90 mg) as a white solid. LCMS m/z $[M+H]^+=165$.

(S)-5-fluoro-1,3-dihydrospiro[indene-2,4'-piperidin]-1-amine, Intermediate BX (S)-5-fluoro-1,3-dihydrospiro[indene-2,4'-piperidin]-1-amine was synthesized as described for Intermediate T, using 2-(bromomethyl)-4-fluoro-1-iodobenzene for the coupling in Step a. Characterization of the final intermediate: $^1$H NMR (400 MHz, DMSO-d6) δ ppm 8.94 (br s, 2H) 8.58 (br s, 3H) 7.61 (br dd, J=7.81, 5.86 Hz, 1H) 7.07-7.18 (m, 2H) 4.37 (br d, J=4.39 Hz, 1H) 3.71 (s, 1H) 3.31 (br d, J=13.43 Hz, 1H) 3.13-3.22 (m, 2H) 2.87-3.10 (m, 3H) 1.95-2.11 (m, 1H) 1.64-1.85 (m, 2H) 1.50 (br d, J=14.40 Hz, 1H) 1.09 (s, 4H).

tert-butyl ((1S)-5-fluoro-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate, Intermediate BY

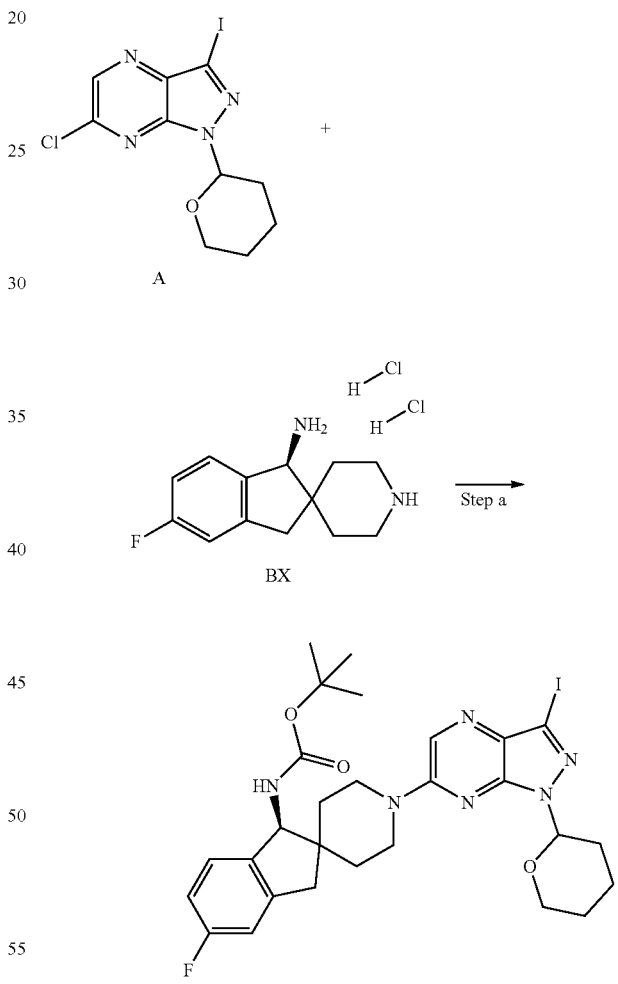

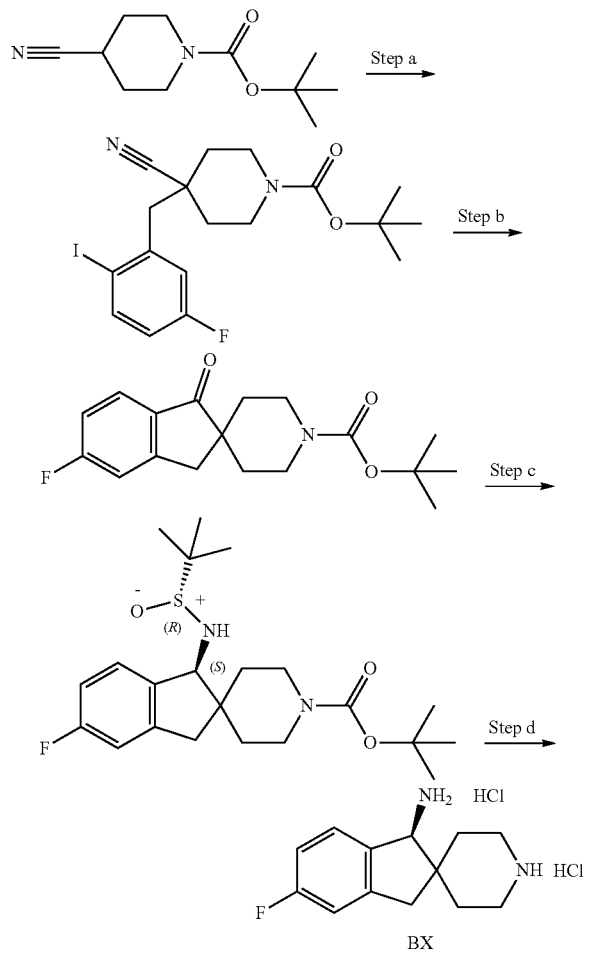

tert-butyl ((1S)-5-fluoro-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate was synthesized as described for Intermediate J, coupling 6-chloro-3-iodo-1-(oxan-2-yl)-1H-pyrazolo[3,4-b]pyrazine (Intermediate A) with (S)-5-fluoro-1,3-dihydrospiro[indene-2,4'-piperidin]-1-amine (Intermediate BX). Characterization of final intermediate BY: LCMS m/z $[M+H]^+=649.2$.

(R)-7-fluoro-3H-spiro[benzofuran-2,4'-piperidin]-3-amine, Intermediate BZ

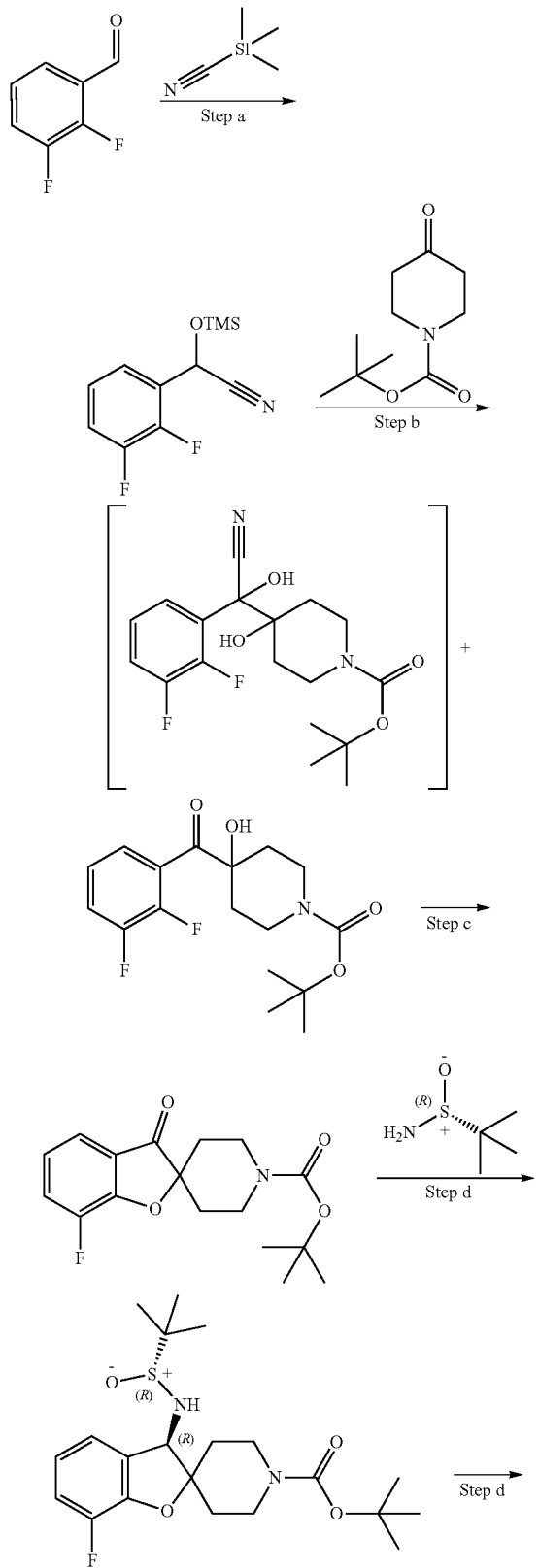

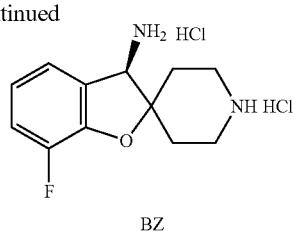

BZ

Step a: To a mixture of 2,3-difluorobenzaldehyde (10 g, 70.3 mmol) and N,N-dimethylpyridin-4-amine (103 mg, 0.8436 mmol) in ACN (100 mL) was added trimethylsilanecarbonitrile (7.87 g, 79.4 mmol), where a cold bath was used to offset the small exotherm during addition. The reaction was stirred at rt for 5 h. The reaction was concentrated to give 2-(2,3-difluorophenyl)-2-((trimethylsilyl)oxy)acetonitrile as a yellow oil.

Step b: 2-(2,3-difluorophenyl)-2-[(trimethylsilyl)oxy]acetonitrile (8.45 g, 35.0 mmol) in THF (65 mL) was cooled to −78° C. and charged with 1M LHMDS (38.5 mL, 38.5 mmol) not allowing the temperature to rise above −65° C. during the addition. The reaction mixture was stirred at −78° C. for 1.5 h, then tert-butyl 4-oxopiperidine-1-carboxylate (7.67 g, 38.5 mmol) in THF (10 mL) was added, again not allowing the temperature to rise above −65° C. during the addition, and the reaction was stirred at −78° C. for 3 h. Hydrogen chloride (84.0 mL, 84.0 mmol) was then added to the reaction mixture and the solution was allowed to warm to rt and stirred 16 h. The organic layer was separated and the aqueous layer was back extracted with EA. The organic layer was dried, concentrated and purified by column chromatography (330 g column, 0-40% EA/hep) to give tert-butyl 4-(cyano(2,3-difluorophenyl)(hydroxy)methyl)-4-hydroxypiperidine-1-carboxylate (4.5 g) as a colorless oil and tert-butyl 4-(2,3-difluorobenzoyl)-4-hydroxypiperidine-1-carboxylate (4.3 g) as a white solid. LCMS m/z [M+H−100]$^+$=241.9.

Step c: Tert-butyl 4-(2,3-difluorobenzoyl)-4-hydroxypiperidine-1-carboxylate (2.25 g, 6.59 mmol) and (tert-butoxy)potassium (7.24 mL, 7.24 mmol) were dissolved in THF (3 mL) and heated in a microwave at 70° C. for 1 hr. Water was then added and the mixture was extracted with EA. The combined organic layer was dried and concentrated to afford tert-butyl 7-fluoro-3-oxo-3H-spiro[benzofuran-2,4'-piperidine]-1'-carboxylate as a light yellow oil. LCMS m/z [M+H−100]$^+$=222.2.

Step d: To a mixture of tert-butyl 7-fluoro-3-oxo-3H-spiro[1-benzofuran-2,4'-piperidine]-1-carboxylate (4.2 g, 13.0 mmol) and (R)-2-methylpropane-2-sulfinamide (2.36 g, 19.5 mmol) in 2-MeTHF (5 mL) was added tetratitanium-1-ylium tetraethanolate (17.7 mL, 52.0 mmol). The vial was then sealed and heated to 95° C. for 16 h. The reaction mixture was then cooled and was diluted with 2-MeTHF (20 mL) and further cooled to −10° C. To the solution was then added boranium lithiumuide (283 mg, 13.0 mmol) and the reaction mixture was stirred for 20 min. Ethyl acetate was then added to the reaction mixture and stirred for 10 min. The reaction mixture was then added dropwise to a vigorously stirred brine solution. The resulting suspension was stirred for 15 min, charged with celite, then filtered. The layers were separated and the organic layer was pre-absorbed on SiO$_2$ (8 g). The mixture was purified by column chromatography (25 g column, 25-75EA/hep) to afford tert-butyl (R)-3-(((R)-tert-butylsulfinyl)amino)-7-fluoro-3H-spiro[benzofuran-2,4'-piperidine]-1'-carboxylate (1.6 g, 29% yield) as a white foam. ¹HNMR (400 MHz, Methanol-d4) δ 7.44 (d, J=7.6 Hz, 1H), 7.30-7.26 (m, 1H), 7.13-7.08 (m, 1H), 4.92 (s, 1H), 3.67-3.62 (m, 1H), 3.50-3.36 (m, 3H), 2.59-2.47 (m, 1H), 2.31-2.10 (m, 3H).

Step e: tert-butyl (3R)-7-fluoro-3-{[(R)-2-methylpropane-2-sulfinyl]amino}-3H-spiro[1-benzofuran-2,4'-piperidine]-1'-carboxylate (1.54 g, 3.61 mmol) in MeOH (25 mL) was charged with hydrogen chloride (9.02 mL, 36.1 mmol) and the reaction mixture was stirred at rt for 5 h. The solvent was then removed and chased with MTBE to yield (R)-7-fluoro-3H-spiro[benzofuran-2,4'-piperidin]-3-amine dihydrochloride as a white solid. LCMS m/z [M+H]⁺=649.2.

tert-butyl ((3R)-7-fluoro-1'-(3-iodo-1-(tetrahydro-2H-pyran-2-yl)-1H-pyrazolo[3,4-b]pyrazin-6-yl)-3H-spiro[benzofuran-2,4'-piperidin]-3-yl)carbamate, Intermediate CA

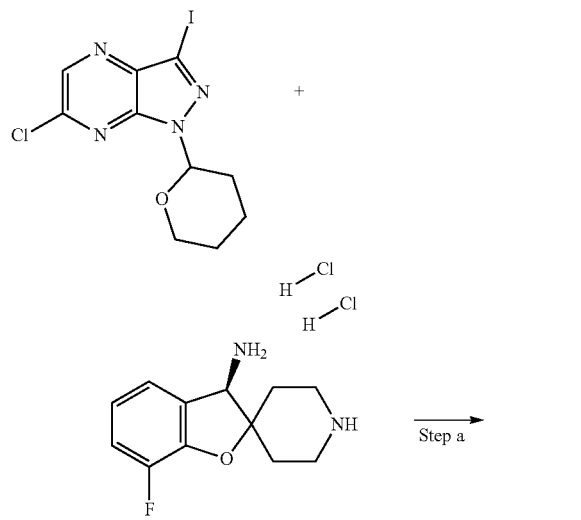

tert-butyl ((3R)-7-fluoro-1'-(3-iodo-1-(tetrahydro-2H-pyran-2-yl)-1H-pyrazolo[3,4-b]pyrazin-6-yl)-3H-spiro[benzofuran-2,4'-piperidin]-3-yl)carbamate was synthesized as described for Intermediate J, coupling 6-chloro-3-iodo-1-(oxan-2-yl)-1H-pyrazolo[3,4-b]pyrazine (Intermediate A) with (3R)-7-fluoro-3H-spiro[1-benzofuran-2,4'-piperidin]-3-amine dihydrochloride (Intermediate BZ). LCMS m/z [M+H]⁺=651.2.

(R)-3H-spiro[benzofuran-2,4'-piperidin]-3-amine, Intermediate CB

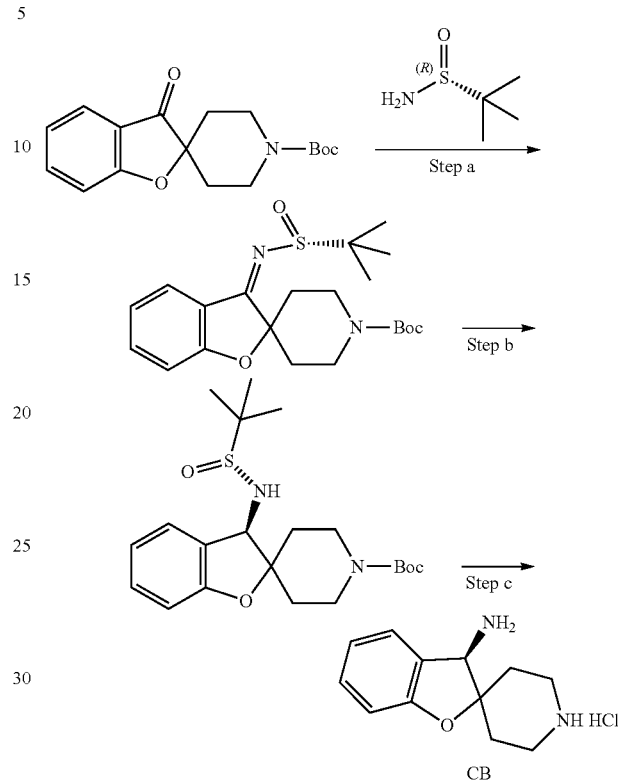

Step a: A mixture of tert-butyl 3-oxo-3H-spiro[benzofuran-2,4'-piperidine]-1'-carboxylate (200 mg, 659 µmol, synthesized via Steps a-d of Intermediate AP), Ti(OEt)₄ (599 mg, 2.63 mmol) and (R)-2-methylpropane-2-sulfinamide (119 mg, 988 umol) in 2-Me-THF (10 mL) was stirred at 80° C. for 12 hours under N2 atmosphere. The reaction mixture was then concentrated to give tert-butyl (R,Z)-3-((tert-butylsulfinyl)imino)-3H-spiro[benzofuran-2,4'-piperidine]-1'-carboxylate (600 mg, quant. crude yield). LCMS m/z [M+Na]⁺=429.0.

Step b: To a mixture of tert-butyl (3Z)-3-{[(R)-2-methylpropane-2-sulfinyl]imino}-3H-spiro[1-benzofuran-2,4'-piperidine]-1'-carboxylate (5.5 g, crude) in THF (50 mL) was added borane lithium hydride (331 mg, 15.1 mmol) at 0° C., then the resulting mixture was stirred at 25° C. for 2 hours. The reaction mixture was quenched with sat.NH₄Cl, diluted with H₂O (200 mL), then extracted with ethyl acetate (200 mL×2). The organic phases were washed with brine (200 mL), dried over anhydrous Na₂SO₄, filtered and concentrated in vacuo to give a residue. The residue was purified by silica gel column (elution: petroleum ether:ethyl acetate=1:0-1:3) to give tert-butyl (3R)-3-{[(R)-2-methylpropane-2-sulfinyl]amino}-3H-spiro[1-benzofuran-2,4'-piperidine]-1'-carboxylate (4.1 g, 74% yield) as a white solid. LCMS m/z [M+Na]⁺=431.0.

Step c: Dissolved tert-butyl (3R)-3-{[(R)-2-methylpropane-2-sulfinyl]amino}-3H-spiro[1-benzofuran-2,4'-piperidine]-1'-carboxylate (1.15 g, 2.81 mmol) in 20 mL MeOH then added hydrogen chloride (7.00 mL, 28.0 mmol). The reaction mixture was stirred at 60° C. for 30 min. The reaction mixture was then concentrated to an oil. MTBE was added and the product precipitated. The mixture was filtered and the solid was washed with MTBE and dried to give (3R)-3H-spiro[1-benzofuran-2,4'-piperidin]-3-amine dihydrochloride (750 mg, 96% yield).

Tert-butyl ((3R)-1'-(3-iodo-1-(tetrahydro-2H-pyran-2-yl)-1H-pyrazolo[3,4-b]pyrazin-6-yl)-3H-spiro[benzofuran-2,4'-piperidin]-3-yl)carbamate, Intermediate CC

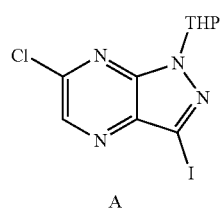

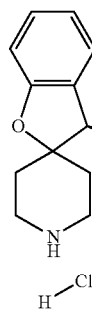

Tert-butyl ((3R)-1'-(3-iodo-1-(tetrahydro-2H-pyran-2-yl)-1H-pyrazolo[3,4-b]pyrazin-6-yl)-3H-spiro[benzofuran-2,4'-piperidin]-3-yl)carbamate was synthesized as described for Intermediate J, coupling 6-chloro-3-iodo-1-(oxan-2-yl)-1H-pyrazolo[3,4-b]pyrazine (Intermediate A) with (R)-3H-spiro[benzofuran-2,4'-piperidin]-3-amine dihydrochloride (Intermediate CB). LCMS m/z [M+H−100]⁺=533.3.

(R)—N-[(1S)-4,6-difluoro-1,3-dihydrospiro[indene-2,4'-piperidin]-1-yl]-2-methylpropane-2-sulfinamide, Intermediate CD

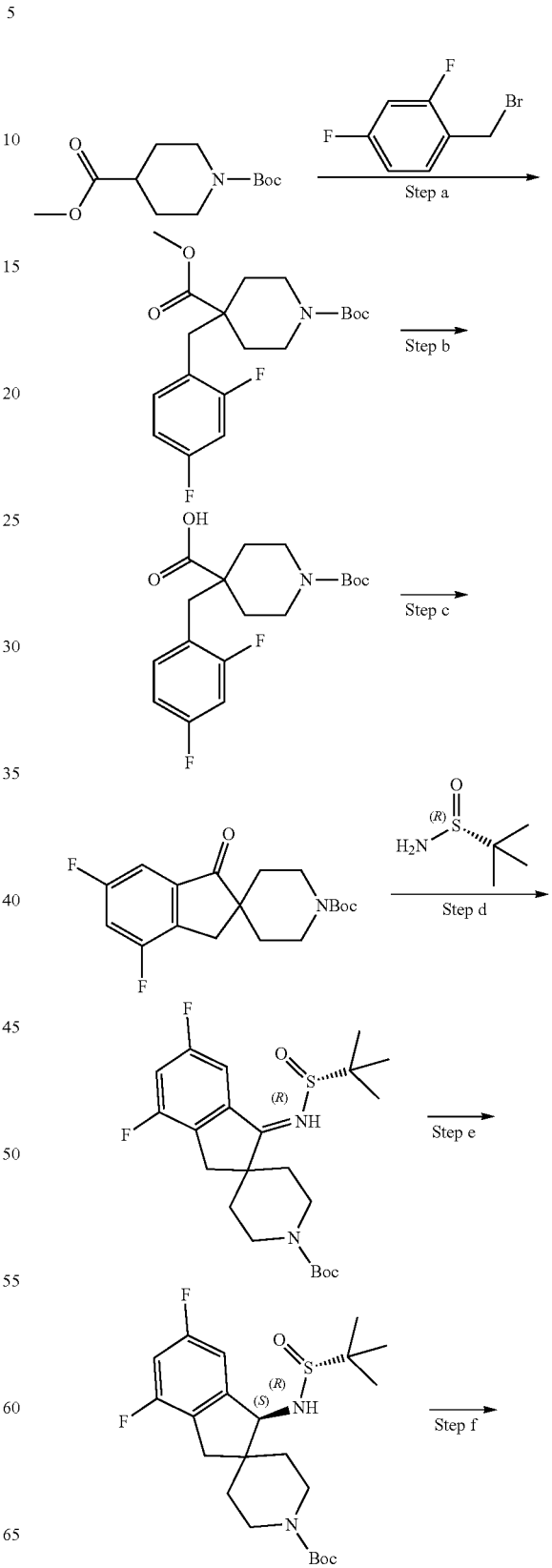

-continued

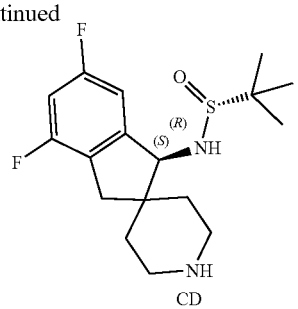

CD (R)—N-[(1S)-4,6-difluoro-1,3-dihydrospiro[indene-2,4'-piperidin]-1-yl]-2-methylpropane-2-sulfinamide was synthesized as described for Intermediate AL, coupling 1-tert-butyl 4-methyl piperidine-1,4-dicarboxylate and 1-(bromomethyl)-2,4-difluorobenzene in Step a. tert-butyl (1S)-4,6-difluoro-1-{[(R)-2-methylpropane-2-sulfinyl]amino}-1,3-dihydrospiro[indene-2,4'-piperidine]-1'-carboxylate was then deprotected as follows: the mixture of tert-butyl (1S)-4,6-difluoro-1-{[(R)-2-methylpropane-2-sulfinyl]amino}-1,3-dihydrospiro[indene-2,4'-piperidine]-1'-carboxylate (190 mg, 429 μmol) in DCM (5 mL) and TFA (1 mL) was stirred at 20° C. for 2 hours. The mixture was concentrated under reduced pressure and the residue was diluted with MeOH. The mixture was adjusted with $Na_2CO_3$ to pH=8. The mixture was filtered and the filtrate was concentrated under reduced pressure to afford (R)—N-[(1S)-4,6-difluoro-1,3-dihydrospiro[indene-2,4'-piperidin]-1-yl]-2-methylpropane-2-sulfinamide (140 mg, 96% yield) as a yellow oil. LCMS m/z $[M+H]^+$=343.0.

(5-chloropyrazin-2-yl)(3,4-dihydro-1,5-naphthyridin-1(2H)-yl)methanone, Intermediate CE

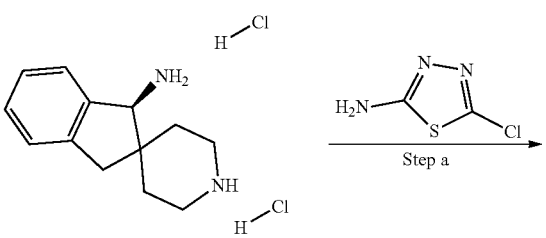

CE

Step a: A resealable reaction vial was charged with 5-chloropyrazine-2-carboxylic acid (500 mg, 3.15 mmol) and sulfurooyl dichloride (5.73 mL, 78.7 mmol). The mixture was charged with DMF (3 drops) and heated to 80° C. for 3.5 h. The solvent was removed in vacuo and chased with toluene to give a yellow crystalline solid. The solid was suspended in DCM (4 mL), cooled to 0-5° C. and charged with triethylamine (1.74 mL, 12.6 mmol) and 1,2,3,4-tetrahydro-1,5-naphthyridine (422 mg, 3.15 mmol) and the reaction mixture was stirred for 1 h. The reaction mixture was then charged with bicarbonate, and extracted with DCM. The organic layer was dried, concentrated and purified by column chromatography (Si-25 g column, 70-100% EA/hep) to afford (5-chloropyrazin-2-yl)(3,4-dihydro-1,5-naphthyridin-1(2H)-yl)methanone (748 mg, 86% yield). LCMS m/z $[M+H]^+$=275.1.

tert-butyl (S)-(1'-(5-amino-1,3,4-thiadiazol-2-yl)-1,3-dihydrospiro[indene-2,4'-piperidin]-1-yl)carbamate, Intermediate CF

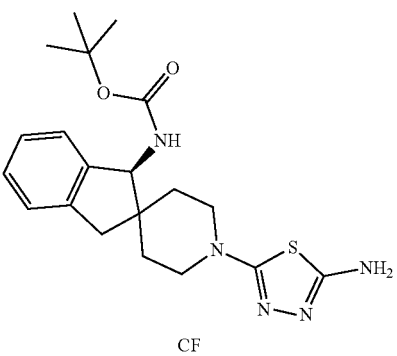

I

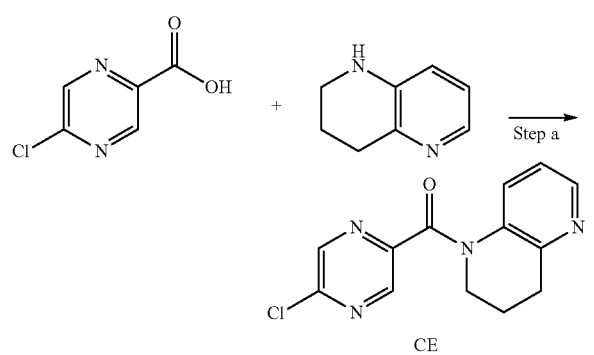

CF

Step a: A disposable tube was charged with (S)-1,3-dihydrospiro[indene-2,4'-piperidin]-1-amine (203 mg, 0.738 mmol, Intermediate I) triethylamine (148 mg, 1.47 mmol), 5-chloro-1,3,4-thiadiazol-2-amine (100 mg, 0.738 mmol, CAS #37566-40-8) and a stir bar. DMF (2 mL) was added and the solution was stirred at 80° C. for 2 hr where the intermediate (S)-5-(1-amino-1,3-dihydrospiro[indene-2,4'-piperidin]-1'-yl)-1,3,4-thiadiazol-2-amine was formed. The reaction mixture was then partitioned between EtOAc and water. The layers were separated, and the aqueous layer was concentrated and dried under high vacuum. The residue was then resuspended in DCM (2 mL) and triethylamine (200 uL) and di-tert-butyl dicarbonate (186 μL, 0.8113 mmol) were added. The reaction mixture was stirred at rt for 2 hr. The mixture was concentrated in vacuo then purified by column chromatography (0-10% MeOH in DCM w/1% $NH_4OH$) to give tert-butyl N-[(3S)-1'-(5-amino-1,3,4-thiadiazol-2-yl)-1,3-dihydrospiro[indene-2,4'-piperidin]-3-yl]carbamate (101 mg, 34% yield). LCMS m/z $[M+H]^+$=402.6.

303 tert-butyl N-[(3S)-1'-(5-bromo-1,3-thiazol-2-yl)-1,3-dihydrospiro[indene-2,4'-piperidin]-3-yl]carbamate, Intermediate CG

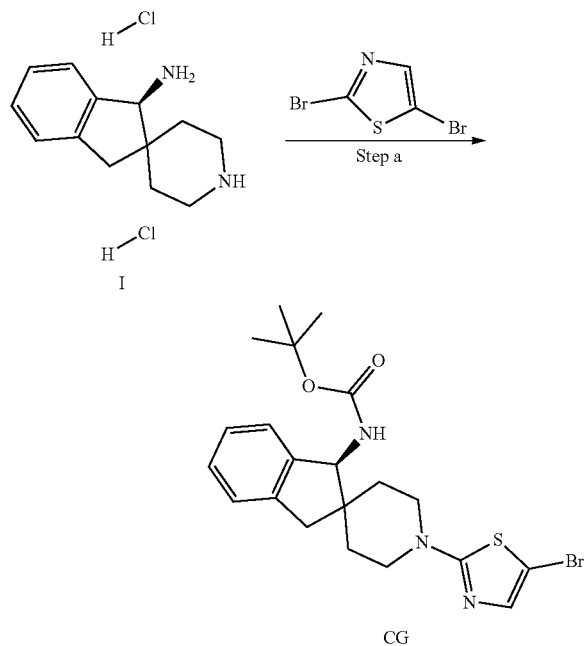

Step a: A mixture of 2,5-dibromo-1,3-thiazole (106 mg, 0.436 mmol), (S)-1,3-dihydrospiro[indene-2,4'-piperidin]-1-amine dihydrochloride (120 mg, 0.436 mmol, Intermediate I) and triethylamine (121 µL, 0.873 mmol) in 2 mL DMF was heated at 100° C. for 20 hr. The reaction mixture was cooled to rt and di-tert-butyl dicarbonate (109 µL, 0.480 mmol) was added and the mixture was stirred at rt for 48 hr. The reaction mixture was then partitioned between EtOAc and water. The aqueous layer was extracted 3× with EtOAc. The combined organic layer was dried over Na$_2$SO$_4$, filtered and concentrated in vacuo. The residue was purified by column chromatography (0-100% ethyl acetate in heptanes) to give tert-butyl N-[(3S)-1'-(5-bromo-1,3-thiazol-2-yl)-1,3-dihydrospiro[indene-2,4'-piperidin]-3-yl]carbamate (47.0 mg, 23% yield). LCMS m/z [M+H]$^+$=464.5/466.5.

(S)-1'-(5-chloropyrazin-2-yl)-1,3-dihydrospiro[indene-2,4'-piperidin]-1-amine, Intermediate CH

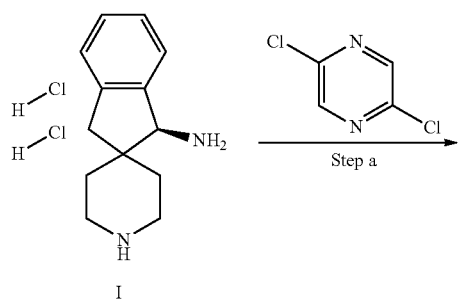

304

-continued

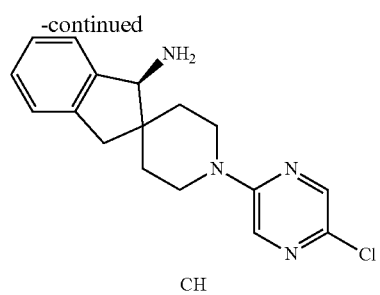

Step a: Dissolved 2,5-dichloropyrazine (50 mg, 0.336 mmol), dicaesium(1+) carbonate (436 mg, 1.34 mmol), and (3S)-1,3-dihydrospiro[indene-2,4'-piperidin]-3-amine dihydrochloride (92.3 mg, 0.336 mmol, Intermediate I) in DMF (2 mL). The reaction mixture was stirred at 80° C. for 3 h. The reaction mixture was then partitioned between EtOAc and water, and the aqueous layer was extracted 3× with EtOAc. The organic layers were combined, dried over Na$_2$SO$_4$, filtered and concentrated in vacuo. The residue was purified by column chromatography (0-10% MeOH in DCM w/1% NH$_4$OH) to give (3S)-1'-(5-chloropyrazin-2-yl)-1,3-dihydrospiro[indene-2,4'-piperidin]-3-amine (52.0 mg, 49% yield). LCMS m/z [M+H]$^+$=315.4.

(S)-1'-(5-bromopyrazin-2-yl)-1,3-dihydrospiro[indene-2,4'-piperidin]-1-amine, Intermediate CI

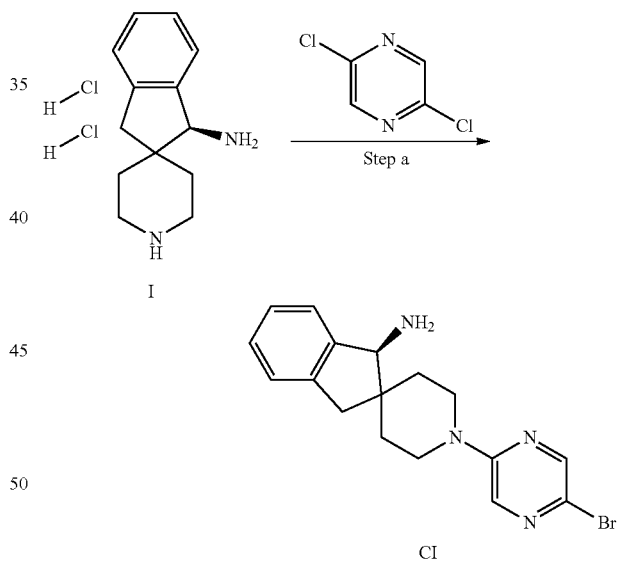

Step a: 2,5-dibromopyrazine (1.23 g, 5.19 mmol), (S)-1,3-dihydrospiro[indene-2,4'-piperidin]-1-amine dihydrochloride (1.3 g, 4.72 mmol, Intermediate I) and TEA (3.26 mL, 23.6 mmol) were added in DMF (20 mL). The reaction mixture was stirred at 85° C. for 12 hr. The mixture was then diluted with ethyl acetate (100 mL), the organic layer separated and washed with H$_2$O (20 mL×3), brine (30 mL×3), dried over anhydrous Na$_2$SO$_4$, filtered and concentrated to give a residue. The residue was purified by flash silica gel chromatography (DCM:MeOH=100:0 to 100:5) to afford (S)-1'-(5-bromopyrazin-2-yl)-1,3-dihydrospiro[indene-2,4'-piperidin]-1-amine (1.2 g, 71% yield) as a yellow oil. LCMS m/z [M+H]$^+$=360.0/362.0.

305 tert-butyl N-{4-[(5-bromopyrimidin-2-yl)sulfanyl]-3-chloropyridin-2-yl}-N-[(tert-butoxy)carbonyl]carbamate, Intermediate CJ

306

(R)—N-[(3S)-1'-(5-bromopyrimidin-2-yl)-1,3-dihydrospiro[indene-2,4'-piperidin]-3-yl]-2-methylpropane-2-sulfinamide, Intermediate CK

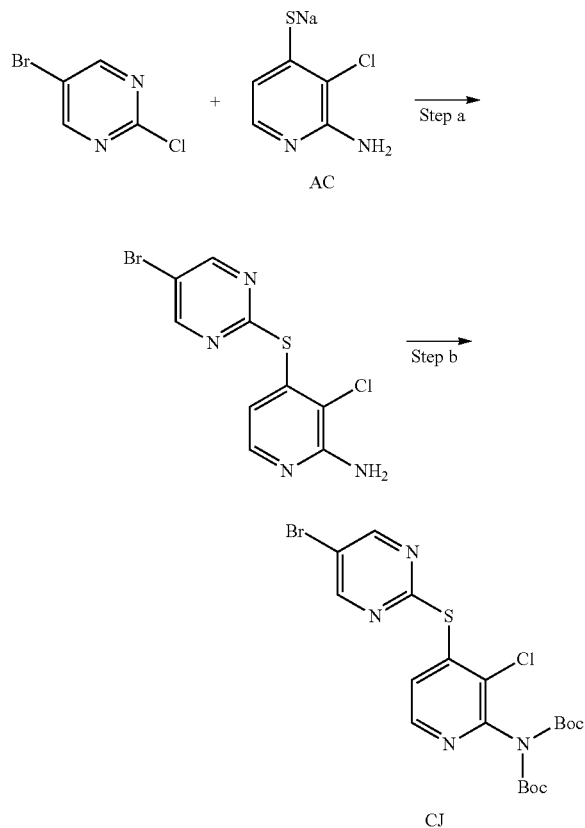

Step a: The mixture of 5-bromo-2-chloropyrimidine (550 mg, 2.84 mmol), 3-chloro-4-(sodiosulfanyl)pyridin-2-amine (491 mg, 2.69 mmol, Intermediate AC) and Cs$_2$CO$_3$ (1.85 g, 5.68 mmol) in DMF (5 mL) was stirred at 80° C. for 1 hour. The mixture was diluted with H$_2$O (20 mL), then extracted with EtOAc (20 mL×2). The organic layer was washed with brine (20 mL), dried over anhydrous Na$_2$SO$_4$, filtered and concentrated under reduced pressure. The residue was purified by column chromatography (petroleum ether/ethyl acetate=1:0~3:1) to afford 4-[(5-bromopyrimidin-2-yl)sulfanyl]-3-chloropyridin-2-amine (530 mg, 59% yield) as a yellow solid. LCMS m/z [M+H]$^+$=318.8.

Step b: The mixture of 4-[(5-bromopyrimidin-2-yl)sulfanyl]-3-chloropyridin-2-amine (200 mg, 629 µmol), Boc$_2$O (164 mg, 754 µmol) and DMAP (115 mg, 943 µmol) in DCM (10 mL) was stirred at 25° C. for 12 hours. The mixture was concentrated under reduced pressure. The residue was purified by column chromatography (petroleum ether/ethyl acetate=1:0~10:1) to afford tert-butyl N-{4-[(5-bromopyrimidin-2-yl)sulfanyl]-3-chloropyridin-2-yl}-N-[(tert-butoxy)carbonyl]carbamate (300 mg, 92% yield) as a yellow solid. LCMS m/z [M+H]+=518.9; $^1$HNMR (400 MHz, DMSO-d6): δ 8.87 (s, 2H), 8.51-8.49 (d, J=5.2 Hz, 1H), 7.94-7.92 (d, J=5.2 Hz, 1H), 1.36 (s, 18H).

Step a: The mixture of (R)—N—((S)-1,3-dihydrospiro[indene-2,4'-piperidin]-1-yl)-2-methylpropane-2-sulfinamide (200 mg, 652 µmol, synthesized via Step a of Example 120), 5-bromo-2-chloropyrimidine (126 mg, 652 µmol), XantPhos-Pd-G4 (62.7 mg, 65.2 µmol) and Cs$_2$CO$_3$ (423 mg, 1.30 mmol) in DMF (10 mL) was stirred at 80° C. for 10 hours under N2 atmosphere. The mixture was diluted with H$_2$O (20 mL), then extracted with EtOAc (20 mL×2). The combined organic layer was washed with brine (20 mL), dried over anhydrous Na$_2$SO$_4$, filtered and concentrated under reduced pressure. The residue was purified by column chromatography (petroleum ether/ethyl acetate=1:0~3:1) to afford (R)—N-[(3S)-1'-(5-bromopyrimidin-2-yl)-1,3-dihydrospiro[indene-2,4'-piperidin]-3-yl]-2-methylpropane-2-sulfinamide (140 mg, 46% yield) as a white solid. LCMS m/z [M+H]$^+$=465.0.

tert-butyl N-[(3R)-1'-(5-bromopyrazin-2-yl)-3H-spiro[1-benzofuran-2,4'-piperidin]-3-yl]carbamate, Intermediate CL

307

-continued

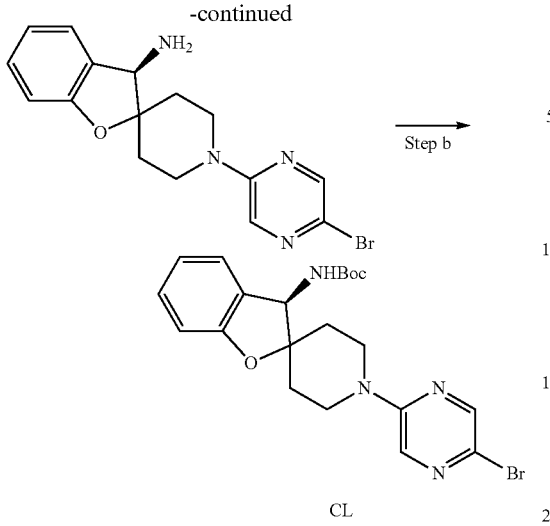

Step a: A mixture of (3R)-3H-spiro[1-benzofuran-2,4'-piperidin]-3-amine hydrochloride (100 mg, 0.4 mmol, Intermediate CB), 2,5-dibromopyrazine (108 mg, 0.5 mmol) and TEA (230 μL, 1.7 mmol) in DMF (2.0 mL) was stirred at 85° C. for 12 hours. This reaction mixture was used for the next step directly. LCMS m/z [M+H]$^+$=361.9.

Step b: To the reaction mixture was added (Boc)$_2$O (134 mg, 0.6 mmol). The reaction mixture was stirred at 70° C. for 2 hours. The reaction mixture was concentrated under reduced pressure to give the residue which was purified by column chromatography (petroleum ether:ethyl acetate=100:0 to 100:100, ethyl acetate:methanol=100:0 to 100:10) to give tert-butyl N-[(3R)-1'-(5-bromopyrazin-2-yl)-3H-spiro[1-benzofuran-2,4'-piperidin]-3-yl]carbamate (110 mg, 58% yield) as a white solid. LCMS m/z [M+H]$^+$=460.9.

2-chloro-N-methylpyridin-4-amine (Intermediate CM)

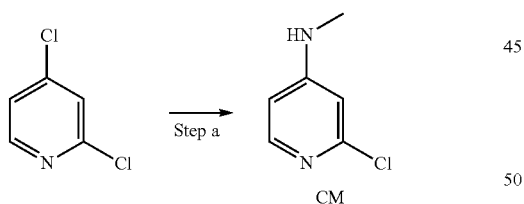

Step a: A mixture of 2,4-dichloropyridine (1.00 g, 6.75 mmol) and aq. MeNH$_2$ (30.0 mL) in MeOH (10.0 mL) was stirred in sealed tube at 85° C. for 12 hours. The reaction mixture was poured into H$_2$O (100.0 mL) and extracted with EtOAc (100.0 mL×2). The combined organic layers were washed with brine (200.0 mL), dried over anhydrous Na$_2$SO$_4$, filtered and the filtrate was concentrated under reduced pressure to give a residue. The residue was purified by flash silica gel chromatography (20 g, ethyl acetate in petroleum ether from 0% to 30%) to give 2-chloro-N-methylpyridin-4-amine (600.0 mg, 62% yield) as a white solid. LCMS m/z [M+H]$^+$=143.0; $^1$HNMR (400 MHz, CD$_3$OD): 7.78-7.80 (m, 1H), 6.47-6.52 (m, 2H), 2.80-2.83 (m, 3H).

308

(1'S)-1',3'-dihydrospiro[azetidine-3,2'-inden]-1'-amine, Intermediate CN, and (1'R)-1',3'-dihydrospiro[azetidine-3,2'-inden]-1'-amine, Intermediate CO

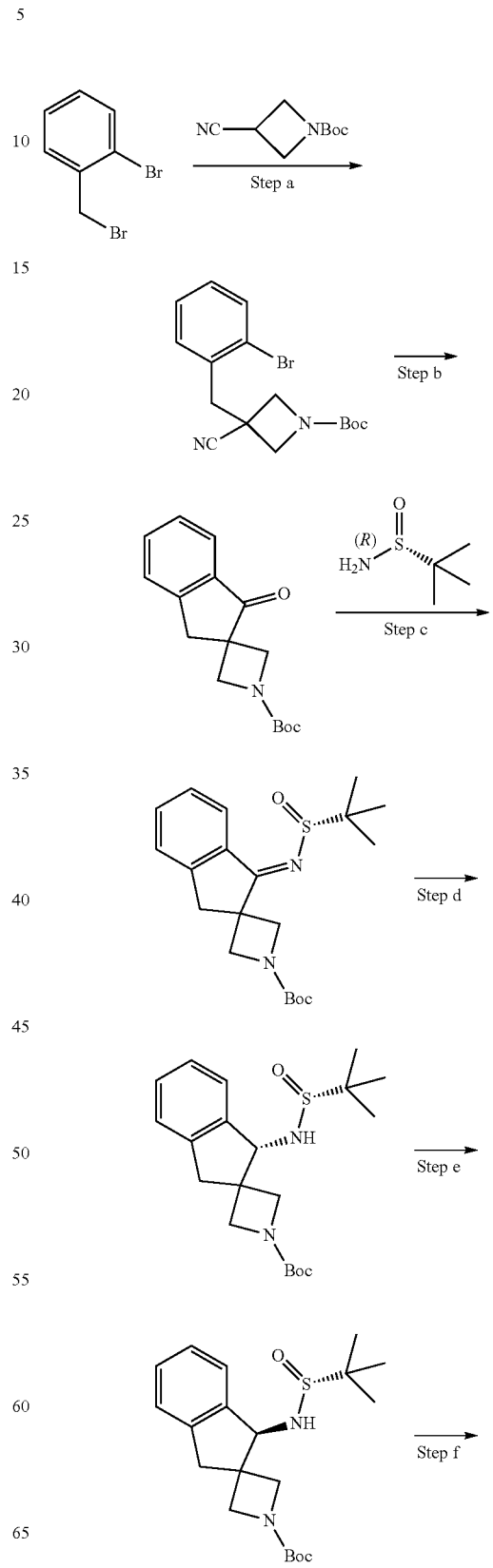

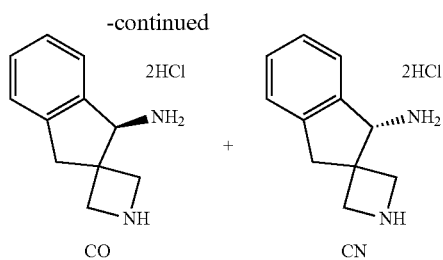

Step a: To a solution of tert-butyl 3-cyanoazetidine-1-carboxylate (3.60 g, 19.70 mmol, CAS #142253-54-1) in THF (40 mL) was added LDA (11.8 mL, 23.60 mmol, 2.0 M) dropwise at −78° C. under N2. The mixture was stirred at 0° C. for 15 min. Then to the mixture was added 1-bromo-2-(bromomethyl)benzene (5.40 g, 21.60 mmol) in THF (20 mL) at −78° C. The mixture was stirred at 0-25° C. for 12 hours under N2. The reaction mixture was then quenched by $H_2O$ (150 mL) and extracted with EtOAc (150 mL×2). The combined organic layers were washed with brine (150 mL), dried over anhydrous $Na_2SO_4$, filtered and concentrated under reduced pressure to give a residue. The residue was purified by flash silica gel chromatography (ethyl acetate in petroleum ether=0~10%) to afford tert-butyl 3-[(2-bromophenyl)methyl]-3-cyanoazetidine-1-carboxylate (1.00 g, 14% yield) as a light yellow oil. $^1$HNMR (400 MHz, CDCl$_3$): δ 7.10-7.57 (m, 4H), 4.20 (d, J=8.8 Hz, 2H), 4.03 (d, J=8.8 Hz, 2H), 3.34 (s, 2H), 1.37 (s, 9H).

Step b: A mixture of tert-butyl 3-[(2-bromophenyl)methyl]-3-cyanoazetidine-1-carboxylate (800.0 mg, 2.27 mmol), PdCl$_2$(Amphos) (160.0 mg, 227.0 μmol, CAS #887919-35-9) and TEA (918.0 mg, 9.08 mmol) in DMA/$H_2O$ (10 mL, 10/1) was stirred at 120° C. under N2 for 12 hours. The reaction mixture was then poured into EtOAc (50 mL) and washed with water (30 mL×3). The organic layer was dried over anhydrous $Na_2SO_4$, filtered, concentrated and purified by silica gel chromatography (ethyl acetate in petroleum ether=0~20%) to afford tert-butyl 1'-oxo-1',3'-dihydrospiro[azetidine-3,2'-indene]-1-carboxylate (520.0 mg, 84% yield) as a yellow solid. $^1$HNMR (400 MHz, CDCl$_3$): δ 7.40-7.83 (m, 4H), 4.26 (d, J=8.4 Hz, 2H), 3.90 (d, J=8.4 Hz, 2H), 3.49 (s, 2H), 1.49 (s, 9H).

Step c: A mixture of tert-butyl 1'-oxo-1',3'-dihydrospiro[azetidine-3,2'-indene]-1-carboxylate (520.0 mg, 1.90 mmol), (R)-2-methylpropane-2-sulfinamide (460.0 mg, 3.80 mmol, CAS #196929-78-9) and Ti(OEt)$_4$ (3.50 g, 15.20 mmol) in 2-Me-THF (10 mL) was stirred at 100° C. for 12 hours. The reaction mixture was used for next step directly.

Step d: To a mixture of (R)-tert-butyl 1'-((tert-butylsulfinyl)imino)-1',3'-dihydrospiro[azetidine-3,2'-indene]-1-carboxylate (1.90 mmol from Step c) in 2-Me-THF (10 mL) was added L-selectride (2.85 mmol, 2.85 mL, 1.0 M in THF, CAS #38721-52-7) slowly at −78° C. After addition, the mixture was stirred at 0° C. for 1 hour. The reaction mixture was then quenched with MeOH (10 mL), poured into EtOAc (500 mL) and $H_2O$ (5 mL), and stirred for 0.5 hour. The mixture was filtered through celite and washed with EtOAc (300 mL×2). The filtrate was concentrated and purified by silica gel column (EtOAc in petroleum ether=30~50%) to give tert-butyl (1'S)-1'-{[(R)-2-methylpropane-2-sulfinyl]amino}-1',3'-dihydrospiro[azetidine-3,2'-indene]-1-carboxylate (300.0 mg, 42% yield, the faster eluting isomer) as a light yellow solid and tert-butyl (1'R)-1'-{[(R)-2-methylpropane-2-sulfinyl]amino}-1',3'-dihydrospiro[azetidine-3,2'-indene]-1-carboxylate (280.0 mg, 39% yield, the slower eluting isomer) as a light yellow solid. Absolute configuration of the enantiomers was arbitrarily assigned. Characterization of tert-butyl (1'S)-1'-{[(R)-2-methylpropane-2-sulfinyl]amino}-1',3'-dihydrospiro[azetidine-3,2'-indene]-1-carboxylate: $^1$HNMR (400 MHz, DMSO_d6): δ 7.21-7.45 (m, 4H), 5.91 (br, 1H), 4.63 (d, J=9.6 Hz, 1H), 4.15 (br, 1H), 3.84 (br, 2H), 3.50 (br, 1H), 3.21 (d, J=15.6 Hz, 1H), 3.06 (d, J=15.6 Hz, 1H), 1.35 (s, 9H), 1.18 (s, 9H). LCMS m/z [M+H]$^+$=323.1. Characterization of tert-butyl (1'R)-1'-{[(R)-2-methylpropane-2-sulfinyl]amino}-1',3'-dihydrospiro[azetidine-3,2'-indene]-1-carboxylate: $^1$H NMR (400 MHz, DMSO_d6): δ 7.19-7.30 (m, 4H), 5.92 (d, J=8.4 Hz, 1H), 4.63 (d, J=9.6 Hz, 1H), 4.23 (br, 1H), 3.84-4.10 (m, 2H), 3.66 (br, 1H), 3.27 (d, J=15.6 Hz, 1H), 3.07 (d, J=15.6 Hz, 1H), 1.38 (s, 9H), 1.19 (s, 9H). LCMS m/z [M+H]$^+$=323.1.

Step e: A solution of tert-butyl (1'S)-1'-{[(R)-2-methylpropane-2-sulfinyl]amino}-1',3'-dihydrospiro[azetidine-3,2'-indene]-1-carboxylate (300.0 mg, 792.0 μmol) in 2M HCl/MeOH (20 mL) was stirred at 25° C. for 1 hour. The reaction mixture was concentrated to give (1'S)-1',3'-dihydrospiro[azetidine-3,2'-inden]-1'-amine dihydrochloride (240.0 mg, 123% crude yield) as a light yellow solid.

Step f: A solution of tert-butyl (1'R)-1'-{[(R)-2-methylpropane-2-sulfinyl]amino}-1',3'-dihydrospiro[azetidine-3,2'-indene]-1-carboxylate (280.0 mg, 739.0 μmol) in 2M HCl/MeOH (20 mL) was stirred at 25° C. for 1 hour. The reaction mixture was concentrated to give (1'R)-1',3'-dihydrospiro[azetidine-3,2'-inden]-1'-amine dihydrochloride (220.0 mg, 120% crude yield) as a light yellow solid.

(R)-2-methyl-N-[(4S)-1-methyl-4,6-dihydro-1H-spiro[cyclopenta[c]pyrazole-5,4'-piperidin]-4-yl]propane-2-sulfinamide, Intermediate CP

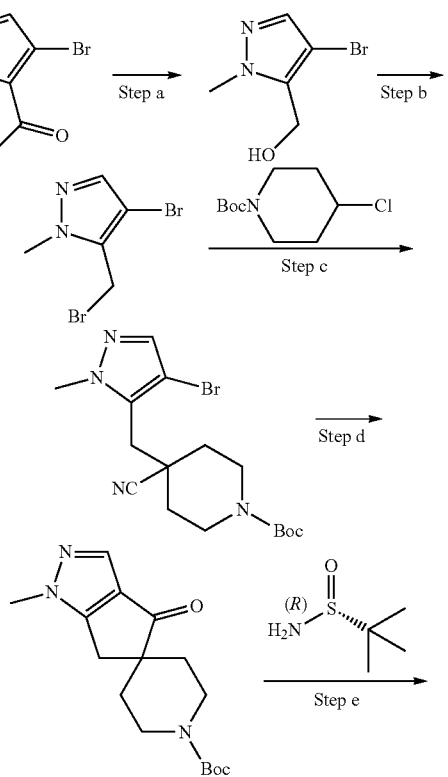

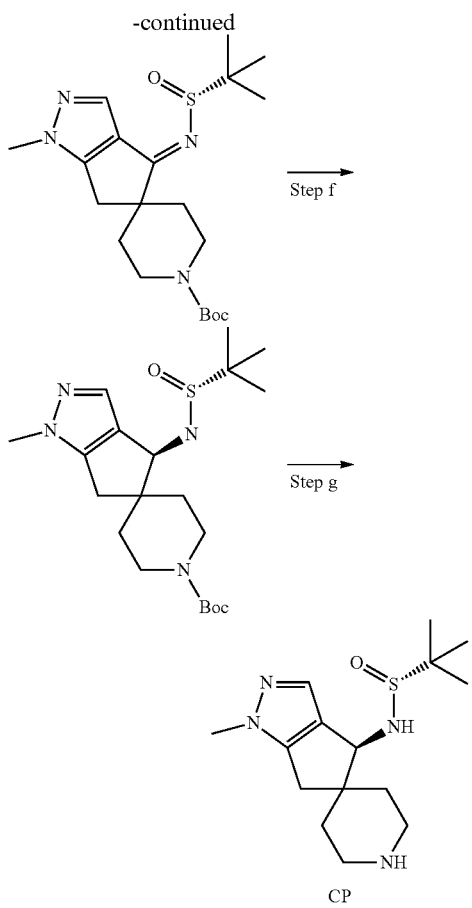

Step a: A mixture of 4-bromo-1-methyl-1H-pyrazole-5-carboxylic acid (4.80 g, 23.4 mmol, CAS #84547-84-2) in THF (40.00 mL) was added BH$_3$/THF (93.60 mL, 1 M). The mixture was stirred at 80° C. for 12 hours under N2 atmosphere. To the mixture was added EtOAc (200 mL). The mixture was washed with saturated NaHCO$_3$ (200 mL×3). The organic layer was dried over anhydrous Na$_2$SO$_4$, filtered and concentrated to give a residue. The residue was purified by column chromatography (petroleum ether:ethyl acetate=100:0 to 100:10) to give (4-bromo-1-methyl-1H-pyrazol-5-yl)methanol (4.10 g, 92% yield) as a white solid. $^1$HNMR (400 MHz, DMSO-d6): δ 7.26 (s, 1H), 4.62 (s, 2H), 3.86 (s, 3H).

Step b: The compound of (4-bromo-1-methyl-1H-pyrazol-5-yl)methanol (3.00 g, 15.7 mmol) and CBr$_4$ (6.23 g, 18.8 mmol) was added in DCM (100 mL). Then PPh$_3$ (4.93 g, 18.8 mmol) in DCM (50 mL) was added dropwise at 0° C. and the mixture was stirred at 0° C. for 0.5 h. The reaction was quenched with brine (100 mL) and the partitioned layers were separated. The aqueous phase was extracted with DCM (100 mL×2). The combined organic layers were washed with brine (150 mL), dried over anhydrous Na$_2$SO$_4$, filtered and concentrated to give a residue. The residue was purified by flash silica gel chromatography (petroleum ether:ethyl acetate=100:0 to 100:10) to afford 4-bromo-5-(bromomethyl)-1-methyl-1H-pyrazole (3.20 g, 81% yield) as a colorless oil. LCMS m/z [M+H]$^+$=252.8, 254.8, 256.8.

Step c: The compound of tert-butyl 4-cyanopiperidine-1-carboxylate (2.96 g, 14.1 mmol) was placed in THF (100 mL). LDA (8.85 mL, 17.7 mmol, 2M in THF) was added dropwise into the mixture at 0° C. and the mixture was stirred at 0° C. for 0.5 h. The mixture was then cooled to −78° C. Then 4-bromo-5-(bromomethyl)-1-methyl-1H-pyrazole (3 g, 11.8 mmol) in THF (50 mL) was added dropwise into the mixture at −78° C. and the mixture was stirred at −78° C. for 1 h. The reaction was quenched by addition of sat. NH$_4$Cl (100 mL) and the mixture was extracted with ethyl acetate (100 mL×2). The combined organic layers were washed with brine (100 mL), dried over anhydrous Na$_2$SO$_4$, filtered and concentrated to give a residue. The residue was purified by flash silica gel chromatography (petroleum ether ethyl acetate=100:0 to 100:50) to afford tert-butyl 4-[(4-bromo-1-methyl-H-pyrazol-5-yl)methyl]-4-cyanopiperidine-1-carboxylate (3.30 g, 73% yield) as a white solid. LCMS m/z [M−56+MeCN+H]$^+$=368.0, 370.0.

Step d: The compound of tert-butyl 4-[(4-bromo-1-methyl-1H-pyrazol-5-yl)methyl]-4-cyanopiperidine-1-carboxylate (1.00 g, 2.6 mmol), PdCl$_2$(AmPhos) (92.0 mg, 130 μmol) and TEA (1.43 mL, 10.4 mmol) were placed into DMA (50.00 mL) and H$_2$O (1.00 mL). The reaction mixture was evacuated and refilled 3 times using N2. The reaction mixture was stirred at 120° C. for 12 hours. The mixture was diluted with ethyl acetate (150 mL), washed with H$_2$O (50 mL×5), brine (100 mL×2), dried over anhydrous Na$_2$SO$_4$, filtered and concentrated to give a residue. The residue was purified by flash silica gel chromatography (petroleum ether: ethyl acetate=100:50) to afford tert-butyl 1-methyl-4-oxo-4,6-dihydro-1H-spiro[cyclopenta[c]pyrazole-5,4'-piperidine]-1'-carboxylate (560 mg, 71% yield) as a yellow solid. LCMS m/z [M+H]$^+$=306.0.

Step e: To a solution of tert-butyl 1-methyl-4-oxo-4,6-dihydro-1H-spiro[cyclopenta[c]pyrazole-5,4 (200.0 mg, 654 μmol) and Ti(OEt)$_4$ (1.34 mL, 6.54 mmol) in 2-Me-THF (5.00 mL) was added (R)-2-methylpropane-2-sulfinamide (316 mg, 2.61 mmol). The reaction mixture was stirred at 90° C. for 12 h under N2. The reaction mixture was stirred at 100° C. for another 24 h under N2. The mixture was used in next step without directly. LCMS m/z [M+H]$^+$=409.1.

Step f: NaBH$_4$ (48.0 mg, 1.27 mmol) was added in the mixture of tert-butyl (4Z)-1-methyl-4-{[(R)-2-methylpropane-2-sulfinyl]imino}-4,6-dihydro-1H-spiro[cyclopenta[c]pyrazole-5,4'-piperidine]-1'-carboxylate (260.0 mg, 636 μmol) in 2-Me-THF (5.00 ml) at 0° C. The mixture was stirred at 25° C. for 12 h. The mixture was diluted with ethyl acetate (50 mL). H$_2$O (20 mL) was added with stirring, a lot of white solid formed. The mixture was filtered. The filtrate was separated, and the aqueous phase was extracted with ethyl acetate (20 mL×2). The combined organic phases were washed with brine (50 mL), dried over anhydrous Na$_2$SO$_4$, filtered and concentrated to give a residue. The residue was purified by flash silica gel chromatography (petroleum ether: ethyl acetate=100:20 to 100:80) to afford tert-butyl (4S)-1-methyl-4-{[(R)-2-methylpropane-2-sulfinyl]amino}-4,6-dihydro-1H-spiro[cyclopenta[c]pyrazole-5,4'-piperidine]-1'-carboxylate (150.0 mg, 57% yield) as a yellow oil. LCMS m/z [M+H]$^+$=411.1. $^1$HNMR (400 MHz, CD$_3$OD): δ 7.53 (s, 1H), 4.35 (s, 1H), 3.90-4.00 (m, 2H), 3.85 (s, 3H), 3.00-3.30 (m, 2H), 2.86 (s, 2H), 1.60-2.10 (m, 4H), 1.27 (s, 9H), 1.22 (s, 9H).

Step g: The compound of tert-butyl (4S)-1-methyl-4-{[(R)-2-methylpropane-2-sulfinyl]amino}-4,6-dihydro-1H-spiro[cyclopenta[c]pyrazole-5,4'-piperidine]-1'-carboxylate (150.0 mg, 365 μmol) was added into a solution of TFA (1.00 mL) and DCM (10.00 mL). The mixture was stirred at 25° C. for 1 h. The mixture was then adjusted to pH=8-9 with TEA. The mixture was concentrated to give (R)-2-methyl-N-[(4S)-1-methyl-4,6-dihydro-1H-spiro[cyclopenta

[c]pyrazole-5,4'-piperidin]-4-yl]propane-2-sulfinamide (200.0 mg, 177% crude yield). LCMS m/z [M+H]⁺=311.1.

(1R)-4,7-difluoro-1,3-dihydrospiro[indene-2,4'-piperidin]-1-amine, Intermediate CO and (1S)-4,7-difluoro-1,3-dihydrospiro[indene-2,4'-piperidin]-1-amine, Intermediate CR

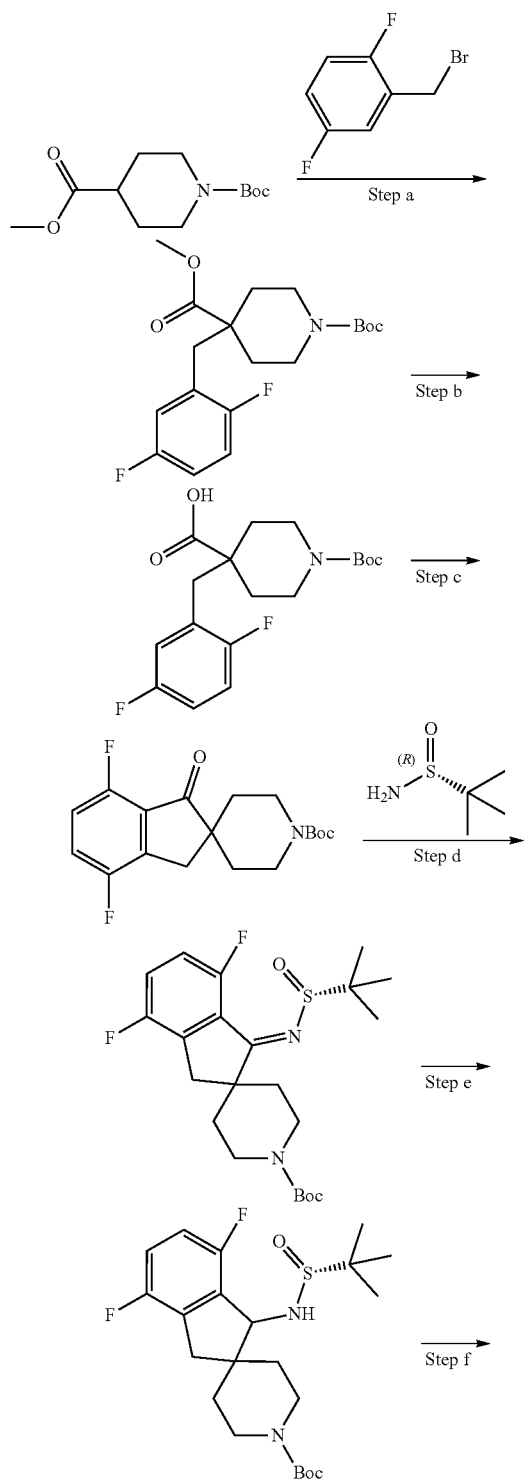

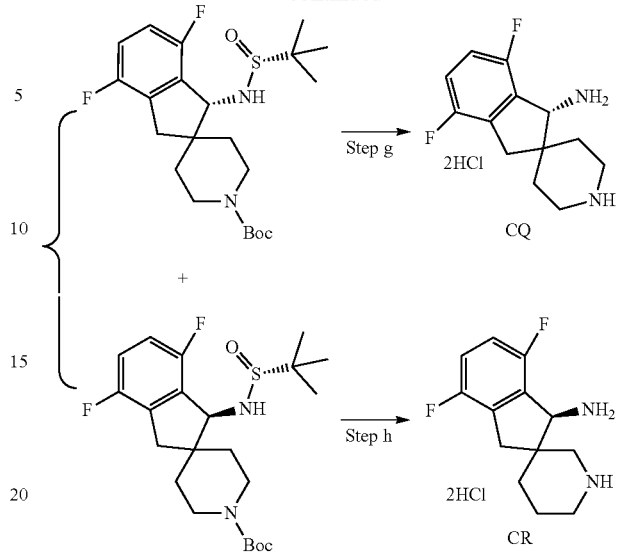

Step a: 1-tert-butyl 4-methyl piperidine-1,4-dicarboxylate (25.70 g, 106.0 mmol, CAS #124443-68-1) was dissolved in THF (200 mL), and the reaction mixture was cooled to −78° C. Then LDA (57.5 mL, 115.0 mmol) was added, and the reaction mixture was stirred at −78° C. for 2 hours. Then a solution of 2-(bromomethyl)-1,4-difluorobenzene (20.00 g, 96.6 mmol, CAS #85117-99-3) in THF (100 mL) was added, and the reaction mixture was warmed to 20° C. and stirred for 2 hours. The reaction mixture was quenched with brine (300 mL), extracted with EtOAc (300 mL×2), the organic phase was dried over anhydrous $Na_2SO_4$, filtered and concentrated under reduced pressure. The residue was purified by flash silica gel chromatography (petroleum ether:ethyl acetate=100:0 to 100:10) to afford 1-tert-butyl 4-methyl 4-[(2,5-difluorophenyl)methyl]piperidine-1,4-dicarboxylate (25.00 g, 70% yield) as a yellow oil. LCMS m/z [M+H-Boc]⁺=269.9.

Step b: 1-tert-butyl 4-methyl 4-[(2,5-difluorophenyl)methyl]piperidine-1,4-dicarboxylate (25.00 g, 67.6 mmol) and KOH (30.20 g, 540 mmol) were added in the mixture of MeOH (150 mL) and $H_2O$ (150 mL), the reaction mixture was stirred at 60° C. for 12 hours. The reaction mixture was concentrated under reduced pressure to about 200 mL, then extracted with petroleum ether (200 mL×3). The aqueous phase was adjusted to pH=4 by adding 6N HCl, then extracted with ethyl acetate (300 mL×3). The combined organic phases were washed with brine (200 mL), dried over anhydrous $Na_2SO_4$, filtered and concentrated under reduced pressure to afford 1-[(tert-butoxy)carbonyl]-4-[(2,5-difluorophenyl)methyl]piperidine-4-carboxylic acid (20.00 g, 83% yield) as a white solid. LCMS m/z [M+H-Boc]⁺=256.0.

Step c: 1-[(tert-butoxy)carbonyl]-4-[(2,5-difluorophenyl)methyl]piperidine-4-carboxylic acid (10.00 g, 28.1 mmol) was dissolved in 1,2-dichloroethane (200 mL) and the reaction mixture was cooled to 0° C. Then $SOCl_2$ (4.1 mL, 56.2 mmol) was added, and the reaction mixture was warmed to 20° C. and stirred for 4 hours. $AlCl_3$ (5.60 g, 42.1 mmol) was then added, and the reaction mixture was stirred at 75° C. for 12 hours. The reaction mixture was adjusted to pH=12 by adding 2N NaOH, then $(Boc)_2O$ (9.8 mL, 42.1 mmol) was added, and the reaction mixture was stirred at 25° C. for 2 hours. The reaction mixture was concentrated under reduced pressure, diluted with EtOAc (500 mL), washed with H₂O (300 mL×3), brine (300 mL), dried over anhydrous Na₂SO₄, filtered and concentrated under reduced pressure. The residue was purified by flash silica gel chromatography (petroleum ether:ethyl acetate=100:0 to 100:20) to afford tert-butyl 4,7-difluoro-1-oxo-1,3-dihydrospiro[indene-2,4 (6.50 g, 69% yield) as a brown solid. LCMS m/z [M+H-Boc]⁺=237.8.

Step d: Tert-butyl 4,7-difluoro-1-oxo-1,3-dihydrospiro[indene-2,4 (2.50 g, 7.4 mmol), (R)-2-methylpropane-2-sulfinamide (3.58 g, 29.6 mmol), Ti(OEt)₄ (9.3 mL, 44.4 mmol) were added in 2-Me-THF (40 mL), and the reaction mixture was stirred at 90° C. for 48 hours. The reaction mixture was used in next step without further purification (3.26 g crude product, calculated as theoretical yield). LCMS m/z [M+H]⁺=441.0.

Step e: Tert-butyl (1Z)-4,7-difluoro-1-{[(R)-2-methylpropane-2-sulfinyl]imino}-1,3-dihydrospiro[indene-2,4'-piperidine]-1'-carboxylate (3.26 g, crude) in 2-Me-THF (40 mL) was cooled to 0° C., then NaBH₄ (136.0 mg, 3.7 mmol) was added. The reaction mixture was warmed to 20° C. and stirred for 2 hours. The reaction mixture was then quenched with H₂O (50 mL) and EtOAc (100 mL), filtered and the filter cake was washed with EtOAc (50 mL×2). The filtrate was washed with H₂O (100 mL×2) and brine (100 mL), dried over anhydrous Na₂SO₄, filtered and concentrated under reduced pressure and purified by flash silica gel chromatography (petroleum ether:ethyl acetate=100:0 to 100:50) to afford tert-butyl 4,7-difluoro-1-{[(R)-2-methylpropane-2-sulfinyl]amino}-1,3-dihydrospiro[indene-2,4'-piperidine]-1'-carboxylate (2.70 g, 83% yield) as a yellow solid. LCMS m/z [M+H]⁺=443.0. ¹HNMR (400 MHz, CDCl₃): δ 6.89-6.74 (m, 2H), 4.57-4.51 (m, 1H), 3.79-3.72 (m, 1H), 3.42-3.40 (m, 1H), 3.10-3.01 (m, 4H), 1.86-1.69 (m, 2H), 1.55-1.45 (m, 1H), 1.40-1.38 (m, 9H), 1.20-1.16 (m, 1H), 1.13-1.12 (m, 9H). SFC: e.e. =51.36%, Acq. Method Set: AD-3-EtOH-DEA-5-40-25 mL, Vial: 1:E,5, Channel Name: PDA Ch1 220 nm@4.8 nm.

Step f: Tert-butyl 4,7-difluoro-1-{[(R)-2-methylpropane-2-sulfinyl]amino}-1,3-dihydrospiro[indene-2,4 (2.50 g, 5.6 mmol) was purified by prep-HPLC (NH₃.H₂O) to afford the product of tert-butyl (1R)-4,7-difluoro-1-{[(R)-2-methylpropane-2-sulfinyl]amino}-1,3-dihydrospiro[indene-2,4 (900.0 mg, 36% yield) as a yellow solid (LCMS m/z [M+H]⁺=443.1; ¹HNMR (400 MHz, DMSO-d6): δ 7.14-7.04 (m, 2H), 5.63-5.60 (m, 1H), 4.44-4.41 (m, 1H), 3.65-3.56 (m, 2H), 3.18-2.85 (m, 3H), 1.71-1.69 (m, 2H), 1.41-1.38 (m, 9H), 1.32-1.26 (m, 2H), 1.13-1.12 (m, 9H)) and tert-butyl (1S)-4,7-difluoro-1-{[(R)-2-methylpropane-2-sulfinyl]amino}-1,3-dihydrospiro[indene-2,4 (900.0 mg, 36% yield) as a yellow solid (LCMS m/z [M+H]⁺=443.1; ¹HNMR (400 MHz, DMSO-d6): δ 7.14-7.04 (m, 2H), 5.79-5.76 (m, 1H), 4.55-4.43 (m, 1H), 3.80-3.67 (m, 2H), 3.08-2.82 (m, 4H), 1.76-1.71 (m, 1H), 1.56-1.30 (m, 11H), 1.11 (s, 9H)).

Step g: Tert-butyl (1R)-4,7-difluoro-1-{[(R)-2-methylpropane-2-sulfinyl]amino}-1,3-dihydrospiro[indene-2,4'-piperidine]-1'-carboxylate (900.0 mg, 2.0 mmol) was added in 4N HCl/MeOH (20 mL), the reaction mixture was stirred at 25° C. for 2 hours. The white precipitate was collected by filtration and dried to afford (1R)-4,7-difluoro-1,3-dihydrospiro[indene-2,4'-piperidin]-1-amine dihydrochloride (500.0 mg, 79% yield) as a white solid. LCMS m/z [M+H]⁺= 239.0; ¹HNMR (400 MHz, DMSO-d6): δ 9.33-9.23 (m, 2H), 8.87 (s, 3H), 7.30-7.18 (m, 2H), 4.60 (s, 1H), 3.42-3.33 (m, 2H), 3.12-2.97 (m, 4H), 2.24-2.04 (m, 2H), 1.71-1.49 (m, 2H).

Step h: Tert-butyl (1S)-4,7-difluoro-1-{[(R)-2-methylpropane-2-sulfinyl]amino}-1,3-dihydrospiro[indene-2,4'-piperidine]-1'-carboxylate (300.0 mg, 677.0 μmol) was added in 4N HCl/MeOH (6 mL), the reaction mixture was stirred at 25° C. for 1 hour. The precipitate was collected by filtration and dried to give (1S)-4,7-difluoro-1,3-dihydrospiro[indene-2,4'-piperidin]-1-amine dihydrochloride (150.0 mg, 71% yield) as a white solid. LCMS m/z [M+H]⁺=239.0; ¹HNMR (400 MHz, DMSO-d6): δ 9.21-9.15 (m, 2H), 8.81 (s, 3H), 7.31-7.19 (m, 2H), 4.62 (s, 1H), 3.38-3.33 (m, 2H), 3.17-2.98 (m, 4H), 2.22-2.01 (m, 2H), 1.72-1.50 (m, 2H).

tert-butyl N-[(3R)-4,7-difluoro-1'-[3-iodo-1-(oxan-2-yl)-1H-pyrazolo[3,4-b]]pyrazin-6-yl-1,3-dihydrospiro[indene-2,4'-piperidin]-3-yl]carbamate, Intermediate CS

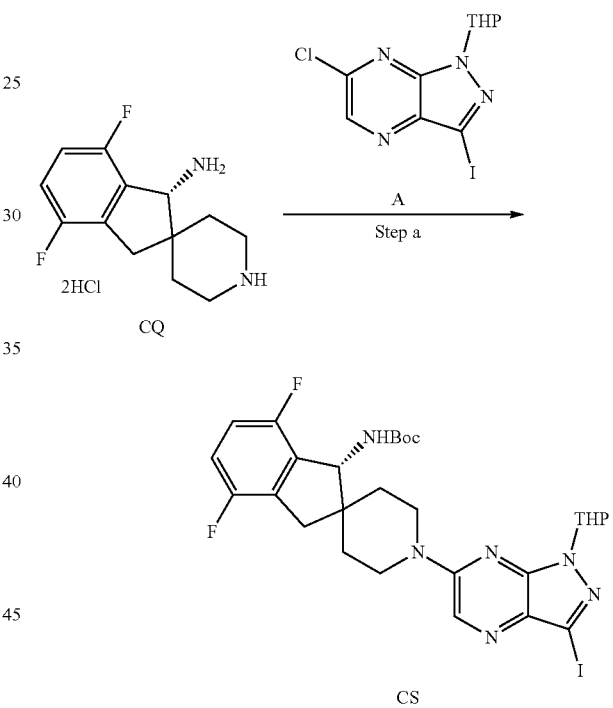

Step a: 6-chloro-3-iodo-1-(oxan-2-yl)-1H-pyrazolo[3,4-b]pyrazine (150.0 mg, 411.0 μmol, Intermediate A), (1R)-4,7-difluoro-1,3-dihydrospiro[indene-2,4'-piperidin]-1-amine dihydrochloride (127.0 mg, 411.0 μmol, Intermediate CQ), TEA (283.0 μL, 2.1 mmol) were added in DMF (6 mL), and the reaction mixture was stirred at 80° C. for 12 hours. (Boc)₂O (94.3 μL, 411.0 μmol) was added, and the reaction mixture was stirred at 25° C. for 2 hours. The reaction mixture was concentrated under reduced pressure and purified by flash silica gel chromatography (petroleum ether:ethyl acetate=100:0 to 100:20) to afford tert-butyl N-[(3R)-4,7-difluoro-1'-[3-iodo-1-(oxan-2-yl)-1H-pyrazolo[3,4-b]pyrazin-6-yl]-1,3-dihydrospiro[indene-2,4'-piperidin]-3-yl]carbamate (200.0 mg, 73% yield) as a yellow solid. LCMS m/z [M+H]⁺=667.1.

317

Sodium 2-chloropyridine-3-thiolate, Intermediate CT

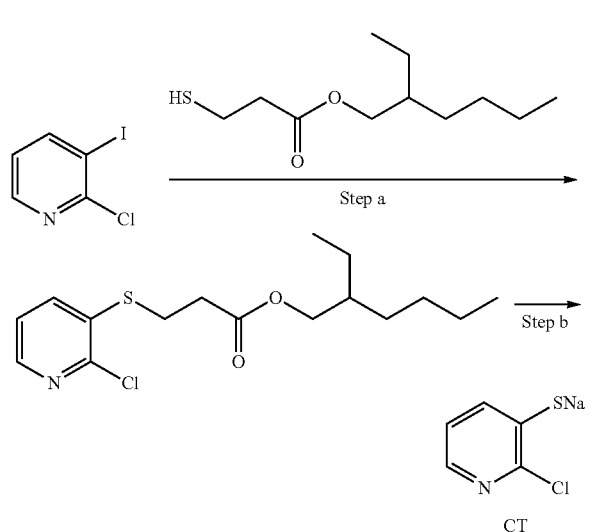

Step a: To a mixture of 2-chloro-3-iodopyridine (1.00 g, 4.17 mmol, CAS #78607-36-0) and 2-ethylhexyl 3-mercaptopropanoate (1.13 g, 5.21 mmol, CAS #50448-95-8) in dioxane (30 mL) were added $Pd_2(dba)_3$ (317 mg, 347 µmol), XantPhos (401.0 mg, 695 µmol) and DIPEA (1.80 mL, 10.4 mmol). The reaction mixture was purged with N2 for 3 min and stirred at 100° C. for 12 hours under N2 protection. The reaction mixture was concentrated under reduced pressure. The residue was purified by column chromatography (petroleum ether:ethyl acetate=100:0 to 100:20) to give 2-ethylhexyl 3-[(2-chloropyridin-3-yl)sulfanyl]propanoate (1.00 g, 88% yield) was as a light yellow solid. LCMS m/z [M+H]$^+$= 330.1.

Step b: A mixture of 2-ethylhexyl 3-[(2-chloropyridin-3-yl)sulfanyl]propanoate (500.0 mg, 1.51 mmol) and MeONa (122.0 mg, 2.26 mmol) in THF (5 mL) was stirred at 0° C. for 1 hour. Then the mixture solution was stirred at 20° C. for 1 hour. The mixture was diluted with DCM (5 mL) and stirred for 0.5 hour, where large amount of solid precipitated. Additional DCM was added and the solid was collected by filtration to give sodium 2-chloropyridine-3-thiolate as a yellow solid (111.0 mg, 44% yield). LCMS m/z [M+H]$^+$= 218.0.

(R)—N-[(3S)-1'-(6-bromopyridin-3-yl)-1,3-dihydrospiro[indene-2,4'-piperidin]-3-yl]-2-methylpropane-2-sulfinamide, Intermediate CU

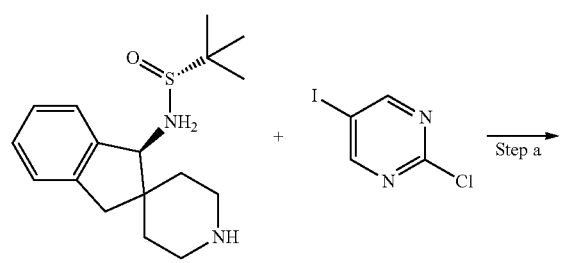

318

-continued

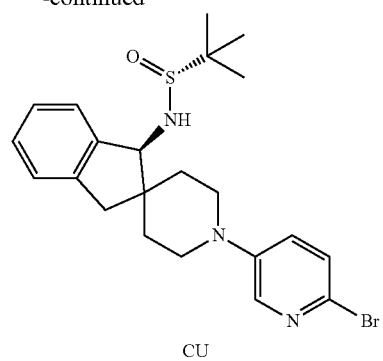

Step a: To the mixture of (R)—N-[(3S)-1,3-dihydrospiro[indene-2,4'-piperidin]-3-yl]-2-methylpropane-2-sulfinamide (50.0 mg, 163.0 µmol, synthesized via Step a of Example 120) and 2-bromo-5-iodopyridine (46.2 mg, 163 µmol, CAS #73290-22-9) in toluene (3.0 mL) were added XantPhos-Pd-G4 (15.6 mg, 16.3 µmol) and $Cs_2CO_3$ (116.0 mg, 358.0 µmol) under N2. The mixture was stirred at 80° C. under N2 for 12 hours. The mixture was then concentrated under reduced pressure and the residue was purified by flash silica gel chromatography (DCM/MeOH=1/0 to 10/1) to give (R)—N-[(3S)-1'-(6-bromopyridin-3-yl)-1,3-dihydrospiro[indene-2,4'-piperidin]-3-yl]-2-methylpropane-2-sulfinamide (60.0 mg, 80% yield) as a brown oil. LCMS m/z [M+H]$^+$=462.0.

(R)-2-methyl-N—((R)-1-methylspiro[indoline-2,4'-piperidin]-3-yl)propane-2-sulfinamide, Intermediate CV

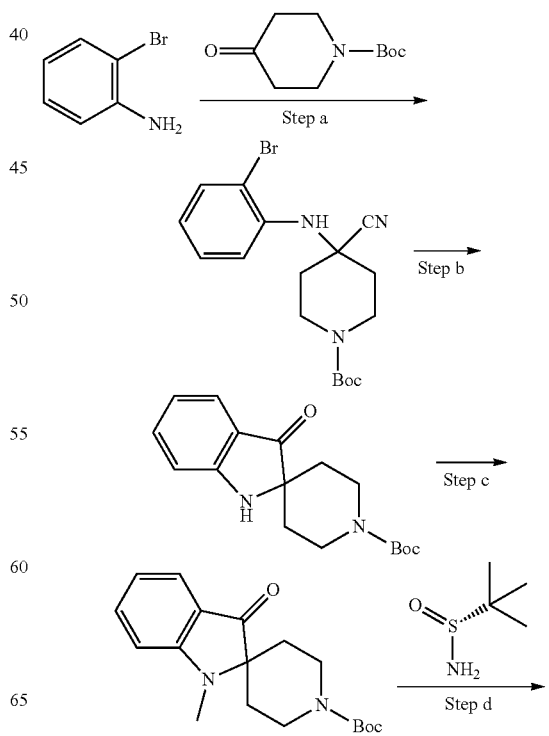

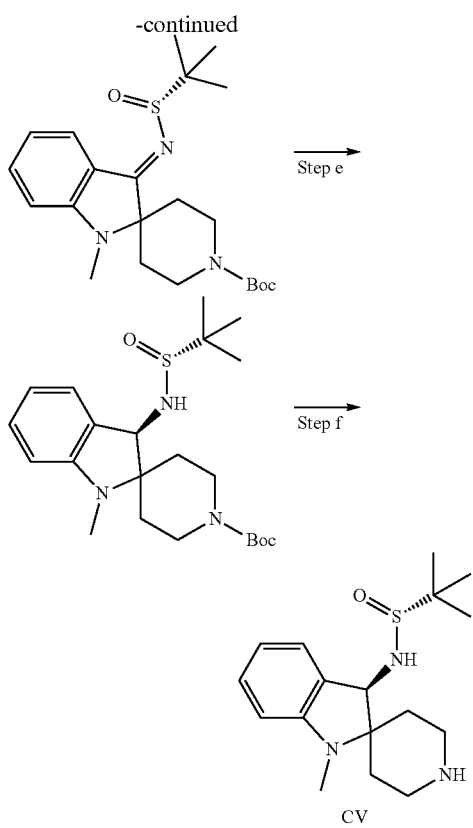

Step a: To the reaction mixture of 2-bromoaniline (10.00 g, 58.1 mmol, CAS #615-36-1) and tert-butyl 4-oxopiperidine-1-carboxylate (11.50 g, 58.1 mmol, CAS #79099-07-3) in HOAc (80 mL) was added Me$_3$SiCN (7.98 mL, 63.9 mmol, CAS #7677-24-9) at 25° C. under N2 atmosphere. The reaction mixture was stirred at 25° C. for 12 hours. The combined reaction mixture was poured into ice-cold NH$_4$OH solution (500 mL, 28% solution), then extracted with EtOAc (300 mL×2). The combined organic layers were washed with brine (100 mL), dried over anhydrous Na$_2$SO$_4$, filtered and concentrated under reduced pressure to give a residue. The residue was triturated with petroleum ether (100 mL), then filtered to give tert-butyl 4-[(2-bromophenyl)amino]-4-cyanopiperidine-1-carboxylate (19.00 g, 86% yield) as a white solid. $^1$HNMR (400 MHz, CDCl$_3$) δ 7.52-7.50 (m, 1H), 7.27-7.24 (m, 1H), 7.20-7.18 (m, 1H), 6.80-6.77 (m, 1H), 4.40 (s, 1H), 3.90 (br s, 2H), 3.42-3.35 (m, 2H), 2.37 (br d, J=13.6 Hz, 2H), 1.93-1.86 (m, 2H), 1.47 (s, 9H).

Step b: The mixture of tert-butyl 4-[(2-bromophenyl)amino]-4-cyanopiperidine-1-carboxylate (6.00 g, 15.7 mmol), PdCl$_2$(Amphos)$_2$ (1.11 g, 1.57 mmol, CAS #887919-35-9) and TEA (8.67 mL, 62.7 mmol) in DMA (120 mL) and H$_2$O (2.4 mL) was stirred at 120° C. for 12 hours under N2 atmosphere. The reaction mixture was diluted with water (120 mL), then extracted with EtOAc (100 mL×3). The organic layers were washed with water (80 mL×2), dried over anhydrous Na$_2$SO$_4$, filtered and concentrated. The residue was purified by flash silica gel chromatography (220 g, EtOAc in petroleum ether from 0% to 20%) to give tert-butyl 3-oxospiro[indoline-2,4'-piperidine]-1'-carboxylate (1.95 g, 41% yield) as a yellow solid. LCMS m/z [M+Na]$^+$=324.9.

Step c: To the reaction mixture of tert-butyl 3-oxospiro[indoline-2,4'-piperidine]-1'-carboxylate (450.0 mg, 1.5 mmol) in THF (9 mL) was added NaHMDS (2.21 mL, 2.2 mmol, 1 M in THF) under N2 atmosphere. The reaction mixture was stirred at 0° C. for 0.5 hour. Then (MeO)$_2$SO$_2$ (1.86 g, 14.8 mmol) was added and the resulting mixture was stirred at 0° C. for 0.5 hour. The combined reaction mixture was poured into saturated NaHCO$_3$ (40 mL) and extracted with EtOAc (50 mL×2). The combined organic layers were washed with brine (20 mL), dried over anhydrous Na$_2$SO$_4$, filtered and concentrated under reduced pressure to give a residue. The residue was purified by flash silica gel chromatography (40 g, EtOAc in petroleum ether from 0% to 15%) to give the product (1.4 g) as a yellow oil. Then NaOH solution (20 mL, 4 M in water) was added into the residue, and the mixture was stirred at 25° C. for 1 hour. The mixture was then extracted with EtOAc (50 mL×2). The combined organic layers were dried over anhydrous Na$_2$SO$_4$, filtered and concentrated under reduced pressure to give tert-butyl 1-methyl-3-oxospiro[indoline-2,4'-piperidine]-1'-carboxylate (500.0 mg, quant. crude yield) as a green oil. LCMS m/z [M+Na]$^+$=338.9; $^1$HNMR (400 MHz, CDCl$_3$) δ 7.57 (d, J=7.6 Hz, 1H), 7.49-7.45 (m, 1H), 6.74-6.66 (m, 2H), 4.14-3.97 (m, 2H), 3.67-3.65 (m, 2H), 2.89 (s, 3H), 1.88 (br s, 2H), 1.53-1.38 (m, 12H).

Step d: The reaction mixture of tert-butyl 1-methyl-3-oxo-1,3-dihydrospiro[indole-2,4'-piperidine]-1'-carboxylate (600.0 mg, 1.9 mmol), (R)-2-methylpropane-2-sulfinamide (916.0 mg, 7.6 mmol) and Ti(OEt)$_4$ (6 mL) was stirred at 100° C. for 12 hours under N2 atmosphere. The addition of (R)-2-methylpropane-2-sulfinamide (916.0 mg, 7.6 mmol) at 100° C. was repeated one time. The resulting mixture was stirred at 100° C. for 20 hours. The combined reaction mixture was quenched with EtOAc (50 mL) and H$_2$O (50 mL). The reaction mixture was filtered, and the filter cake was washed with EtOAc (50 mL×2). The filtrate was separated and the aqueous was extracted with EtOAc (50 mL×2). The combined organic layers were washed with brine (20 mL), dried over anhydrous Na$_2$SO$_4$, filtered and concentrated under reduced pressure to give a residue. The residue was purified by flash silica gel chromatography (40 g, EtOAc in petroleum ether from 0% to 33%) to give tert-butyl (3E)-1-methyl-3-{[(R)-2-methylpropane-2-sulfinyl]imino}-1,3-dihydrospiro[indole-2,4'-piperidine]-1'-carboxylate (190.0 mg, 20% yield) as a yellow solid. LCMS m/z [M+H]$^+$=420.1.

Step e: To a mixture of tert-butyl (3E)-1-methyl-3-{[(R)-2-methylpropane-2-sulfinyl]imino}-1,3-dihydrospiro[indole-2,4'-piperidine]-1'-carboxylate (190.0 mg, 0.4 mmol) in 2-Me-THF (4 mL) was added NaBH$_4$ (170.0 mg, 4.5 mmol) and MeOH (1 mL) at 25° C. The mixture was stirred at 40° C. for 0.5 hour. The reaction mixture was quenched with MeOH (1 mL) and poured into the mixture of H$_2$O (50 mL) and EtOAc (60 mL). The mixture was separated and the aqueous was extracted with EtOAc (60 mL×2). The combined organic layers were washed with brine (20 mL), dried over anhydrous Na$_2$SO$_4$, filtered and concentrated in vacuo to give a residue. The residue was purified by prep-TLC (petroleum ether/EtOAc=1/1) to afford tert-butyl (3R)-1-methyl-3-{[(R)-2-methylpropane-2-sulfinyl]amino}-1,3-dihydrospiro[indole-2,4'-piperidine]-1'-carboxylate (157.0 mg, 83% yield) as a yellow solid. LCMS m/z [M+Na]$^+$=444.1; $^1$H NMR (400 MHz, CDCl$_3$) δ 7.22-7.17 (m, 2H), 6.71 (t, J=7.6 Hz, 1H), 6.46 (d, J=8.0 Hz, 1H), 4.61 (d, J=9.2 Hz, 1H), 4.36-4.20 (m, 2H), 3.61 (br d, J=9.2 Hz, 1H), 3.18-2.92 (m, 2H), 2.01-1.88 (m, 1H), 1.47-1.46 (m, 11H), 1.28-1.23 (m, 1H), 1.17 (s, 9H).

Step f: To the reaction mixture of tert-butyl (3R)-1-methyl-3-{[(R)-2-methylpropane-2-sulfinyl]amino}-1,3-dihydrospiro[indole-2,4'-piperidine]-1'-carboxylate (157.0 mg, 0.4 mmol) in DCM (4 mL) was added TFA (0.4 mL). The reaction mixture was stirred at 25° C. for 0.5 hour, and then stirred at 40° C. for 0.5 hour. The reaction mixture was adjusted to pH=7-8 with TEA. The mixture was then concentrated to give (R)-2-methyl-N—((R)-1-methylspiro[indoline-2,4'-piperidin]-3-yl)propane-2-sulfinamide (119.0 mg, quant. crude yield) as a yellow oil. LCMS m/z [M+H]$^+$= 321.9.

tert-butyl (S)-(1'-(7-bromothieno[3,2-d]pyrimidin-4-yl)-1,3-dihydrospiro[indene-2,4'-piperidin]-1-yl) carbamate, Intermediate CW

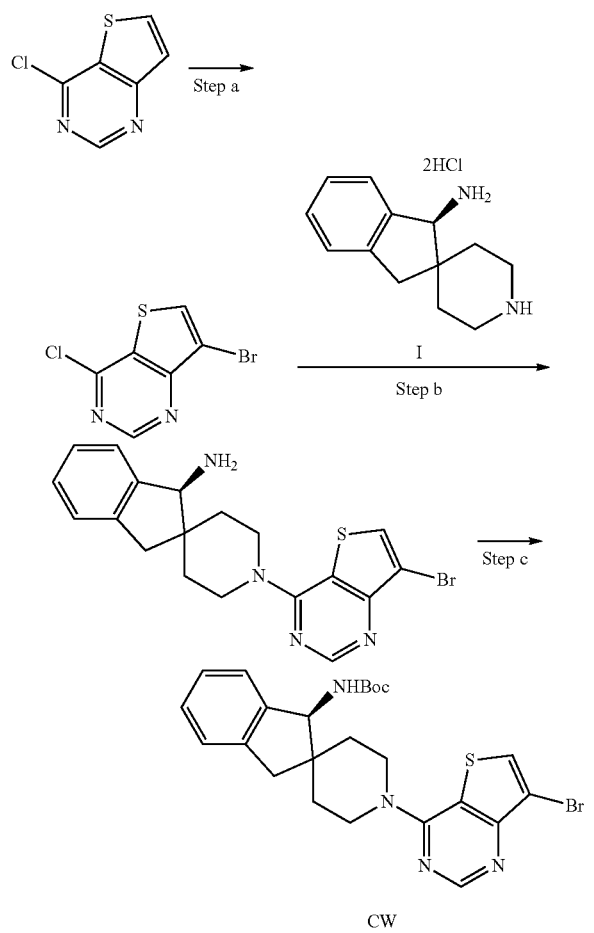

Step a: The compound of 4-chlorothieno[3,2-d]pyrimidine (800 mg, 4.68 mmol, CAS #16269-66-2), NBS (1.05 g, 4.68 mmol) and HOAc (0.2 mL) were added in MeCN (20 mL). The mixture was stirred at 85° C. for 18 h. The mixture was then extracted with ethyl acetate (30 mL×3). The combined organic layers were washed with brine (20 mL×2), dried over anhydrous Na$_2$SO$_4$, filtered and concentrated to give a residue. The residue was purified by flash silica gel chromatography (ethyl acetate/petroleum ether=0/100 to 15/100) to afford 7-bromo-4-chlorothieno[3,2-d]pyrimidine (229 mg, 20% yield) as a white solid. LCMS m/z [M+H]$^+$=250.8; $^1$HNMR 2 (400 MHz, CDCl$_3$) δ 9.14 (s, 1H), 8.09 (s, 1H).

Step b: The compound of 7-bromo-4-chlorothieno[3,2-d]pyrimidine (210 mg, 841 μmol), (S)-1,3-dihydrospiro[indene-2,4'-piperidin]-1-amine dihydrochloride (254 mg, 925 μmol, Intermediate I) and TEA (582 μL, 4.20 mmol) were placed into DMF (10 mL). The reaction mixture was evacuated and refilled 3 times using N2. The reaction mixture was stirred at 85° C. for 12 hours. The reaction mixture was concentrated and H$_2$O (30 mL) was added and the mixture was extracted with ethyl acetate (100 mL). The combined organic layers were washed with H$_2$O (20 mL×5) and brine (30 mL), dried over anhydrous Na$_2$SO$_4$, filtered and concentrated to give a residue as a yellow solid (330 mg, 94% yield). LCMS m/z [M+H]$^+$=415.0.

Step c: The compound of (3S)-1(S)-1'-(7-bromothieno[3,2-d]pyrimidin-4-yl)-1,3-dihydrospiro[indene-2,4'-piperidin]-1-amine (330 mg, 794 μmol), TEA (400 mg, 4.0 mmol) and (Boc)$_2$O (519 mg, 2.4 mmol) were placed into DMF (10 mL). The reaction mixture was stirred at 25° C. for 2 hours. The reaction mixture was concentrated and H$_2$O (20 mL) was added, then extracted with ethyl acetate (30 mL×3). The combined organic layers were washed with brine (50 mL), dried over anhydrous Na$_2$SO$_4$, filtered and concentrated to give a residue. The residue was purified by flash silica gel chromatography (petroleum ether:ethyl acetate=100:0 to 100:40) to afford tert-butyl (S)-(1'-(7-bromothieno[3,2-d]pyrimidin-4-yl)-1,3-dihydrospiro[indene-2,4'-piperidin]-1-yl)carbamate (240.0 mg, 59% yield) as a white solid. LCMS m/z [M+H]$^+$=517.0.

(6-((R)-3-((tert-butoxycarbonyl)amino)-3H-spiro[benzofuran-2,4'-piperidin]-1'-yl)-3-iodo-1-(tetrahydro-2H-pyran-2-yl)-1H-pyrazolo[3,4-b]pyrazin-5-yl)methyl acetate, Intermediate

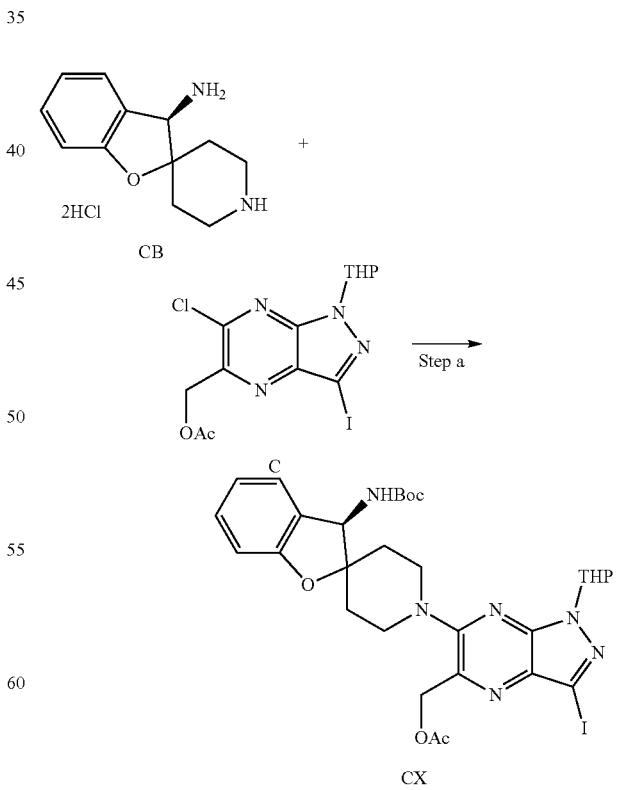

Step a: To a solution of (R)-3H-spiro[benzofuran-2,4'-piperidin]-3-amine dihydrochloride (230 mg, 0.8 mmol, Intermediate CB) and [6-chloro-3-iodo-1-(oxan-2-yl)-1H-pyrazolo[3,4-b]pyrazin-5-yl]methyl acetate (361 mg, 0.8 mmol, Intermediate C) in DMF (5.0 mL) was added TEA (573 µL, 4.1 mmol). The reaction was stirred at 70° C. for 12 hours. Then to the solution was added (Boc)₂O (379 uL, 1.7 mmol) and the reaction was stirred at 70° C. for another 2 hours. The reaction mixture was concentrated under reduced pressure to give a residue which was purified by column chromatography (petroleum ether:ethyl acetate= 100:0 to 100:20). (6-((R)-3-((tert-butoxycarbonyl)amino)-3H-spiro[benzofuran-2,4'-piperidin]-1'-yl)-3-iodo-1-(tetrahydro-2H-pyran-2-yl)-1H-pyrazolo[3,4-b]pyrazin-5-yl) methyl acetate (550 mg, 94% yield) was obtained as a white solid. LCMS m/z [M+H]⁺=705.0.

(R)—N-((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)-2-methylpropane-2-sulfinamide, Intermediate CY

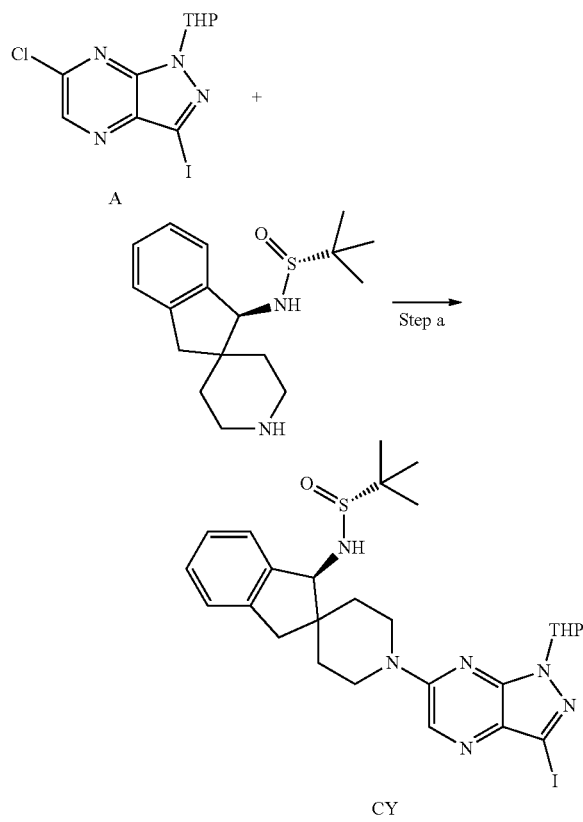

Step a: A solution of 6-chloro-3-iodo-1-(oxan-2-yl)-1H-pyrazolo[3,4-b]pyrazine (12 g, 32.9 mmol, Intermediate A), (R)—N—((S)-1,3-dihydrospiro[indene-2,4'-piperidin]-1-yl)-2-methylpropane-2-sulfinamide (10.0 g, 32.9 mmol, synthesized via Step a of Example 120) and CsF (14.9 g, 98.6 mmol) in DMSO (150 mL) was stirred at 60° C. for 2 h. The reaction mixture was poured into H₂O (700 mL) and extracted with EtOAc (700 mL×2). The combined organic layers were washed with brine (800 mL), dried over anhydrous Na₂SO₄, filtered and filtrate concentrated under reduced pressure to give an orange residue. The residue was purified by flash silica gel chromatography (220 g, ethyl acetate in petroleum ether from 0% to 50%) to give (R)—N-((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)-2-methylpropane-2-sulfinamide (12.5 g, 60% yield) as a yellow solid. LCMS m/z [M+H]⁺=635.0; ¹HNMR (400 MHz, CD₃OD): 8.31 (s, 1H), 7.33-7.36 (m, 1H), 7.22-7.27 (m, 3H), 5.78-5.83 (m, 1H), 4.62 (s, 1H), 4.46-4.55 (m, 3H), 4.03-4.06 (m, 1H), 3.72-3.77 (m, 1H), 3.34-3.37 (m, 1H), 3.23-3.27 (m, 1H), 2.82-2.87 (m, 1H), 2.54-2.58 (m, 1H), 2.10-2.19 (m, 2H), 1.90-1.93 (m, 2H), 1.68-1.80 (m, 4H), 1.52-1.64 (m, 1H), 1.31 (s, 9H).

tert-butyl N-[(3S)-1'-(5-bromopyrazin-2-yl)-1,3-dihydrospiro[indene-2,4'-piperidin]-3-yl]carbamate, Intermediate CZ

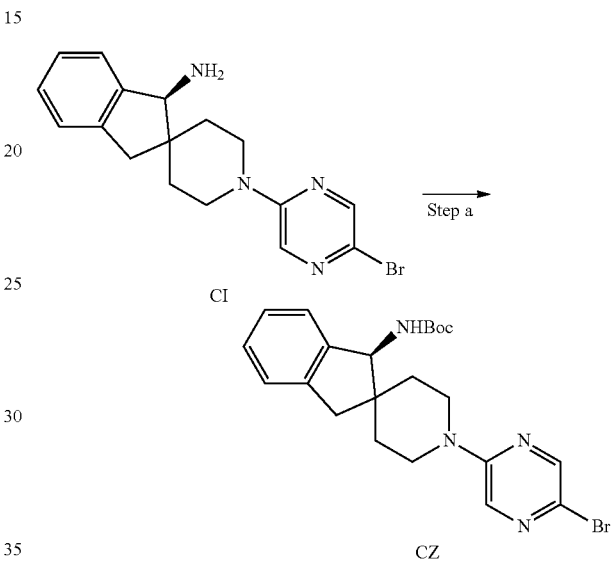

Step a: To a solution of (3S)-1'-(5-bromopyrazin-2-yl)-1,3-dihydrospiro[indene-2,4'-piperidin]-3-amine (1.30 g, 3.6 mmol, Intermediate CI) in DMF (15 mL) was added Boc₂O (1.65 mL, 7.22 mmol). The resulting mixture was stirred at 25° C. for 12 hours. The reaction mixture was diluted with water (30 mL), then extracted with EtOAc (50 mL×2). The organic layers were dried over anhydrous Na₂SO₄, filtered and concentrated to give a residue. The residue was purified by flash silica gel chromatography (40 g column, EtOAc in petroleum ether from 0% to 15%) to give tert-butyl N-[(3S)-1'-(5-bromopyrazin-2-yl)-1,3-dihydrospiro[indene-2,4'-piperidin]-3-yl]carbamate (815 mg, 50% yield) as a yellow solid. LC-MS (M+H)⁺ m/z=459.0.

1-benzyl-6-chloro-3-[(2,3-dichlorophenyl)sulfanyl]-5-methyl-1H,4H,5H-pyrazolo[3,4-d]pyrimidin-4-one, Intermediate DA

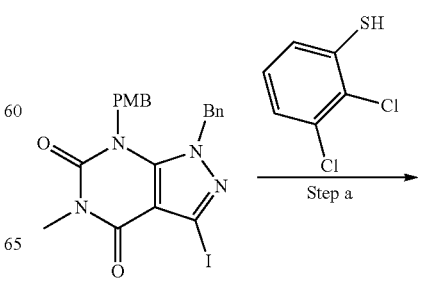

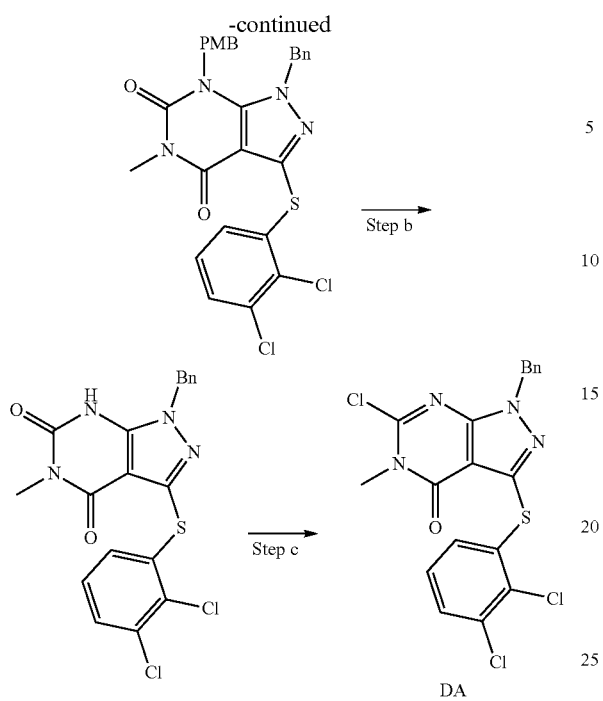

Step a: To a mixture of 1-benzyl-3-iodo-7-[(4-methoxyphenyl)methyl]-5-methyl-1H,4H,5H,6H,7H-pyrazolo[3,4-d]pyrimidine-4,6-dione (2.00 g, 4.0 mmol, CAS #2055938-41-3) and 2,3-dichlorobenzene-1-thiol (1.06 g, 6.0 mmol) in dioxane (20 mL) were added $Pd_2(dba)_3$ (291 mg, 0.4 mmol), XantPhos (370.0 mg, 0.8 mmol) and DIPEA (1.4 mL, 8.0 mmol). The mixture was evacuated and refilled 3 times using N2 and stirred at 120° C. for 10 hours. The mixture was then concentrated under reduced pressure to give a residue and purified by flash silica gel chromatography (petroleum ether:ethyl acetate=100:0 to 100:30) to afford 1-benzyl-3-[(2,3-dichlorophenyl)sulfanyl]-7-[(4-methoxyphenyl)methyl]-5-methyl-1H,4H,5H,6H,7H-pyrazolo[3,4-d]pyrimidine-4,6-dione (1.00 g, 45% yield) as a light red solid. LC-MS (M+H)+m/z=552.9.

Step b: A solution of 1-benzyl-3-[(2,3-dichlorophenyl)sulfanyl]-7-[(4-methoxyphenyl)methyl]-5-methyl-1H,4H,5H,6H,7H-pyrazolo[3,4-d]pyrimidine-4,6-dione (950.0 mg, 1.7 mmol) in TfOH (0.2 mL) and TFA (20 mL) was stirred at 70° C. for 1 hour. The reaction mixture was diluted with DCM (30 mL), concentrated under reduced pressure to give a residue. The residue was diluted with $H_2O$ (10 mL), adjusted to pH=9~10 by adding aq. NaOH (1N) and extracted with ethyl acetate (50 mL×3). The combined organic layers were washed with brine (30 mL), dried over anhydrous $Na_2SO_4$, filtered and concentrated to give a residue. The residue was triturated with petroleum ether and ethyl acetate (10:1) where a lot of precipitate formed. The solid was collected by filtration, and the filter cake was washed with petroleum ether:ethyl acetate=(10:1, 20 mL), then dried to give 1-benzyl-3-[(2,3-dichlorophenyl)sulfanyl]-5-methyl-1H,4H,5H,6H,7H-pyrazolo[3,4-d]pyrimidine-4,6-dione (740.0 mg, 100% yield) as a light brown solid. $^1$HNMR (400 MHz, $CDCl_3$): 8.75 (s, 1H), 7.11-7.18 (m, 5H), 6.87-6.92 (m, 1H), 6.62-6.65 (m, 1H), 5.41 (s, 2H), 3.25 (s, 3H).

Step c: To a mixture of 1-benzyl-3-[(2,3-dichlorophenyl)sulfanyl]-5-methyl-1H,4H,5H,6H,7H-pyrazolo[3,4-d]pyrimidine-4,6-dione (300.0 mg, 0.7 mmol) and DIPEA (1.2 mL, 6.9 mmol) was added $POCl_3$ (1.7 mL, 18.5 mmol). The reaction mixture was stirred at 120° C. for 12 hours. The reaction mixture was concentrated under reduced pressure to give a residue which was diluted with ethyl acetate (50 mL). The mixture was added slowly into ice-cooled sat. $NaHCO_3$ (30 mL) and the partitioned layers were separated. The aqueous phase was extracted with ethyl acetate (50 mL×3). The combined organic layers were washed with brine (50 mL), dried over anhydrous $Na_2SO_4$, filtered and concentrated under reduced pressure to give a residue. The residue was purified by flash silica gel chromatography (petroleum ether:ethyl acetate=100:0 to 100:50) to afford 1-benzyl-6-chloro-3-[(2,3-dichlorophenyl)sulfanyl]-5-methyl-1H,4H,5H-pyrazolo[3,4-d]pyrimidin-4-one (220.0 mg, 71% yield) as a yellow solid. LC-MS (M+H)+m/z=450.9.

(3S)-1'-{3-iodo-5-methyl-1H-pyrazolo[3,4-b]pyrazin-6-yl}-1,3-dihydrospiro[indene-2,4'-piperidin]-3-amine, Intermediate DB

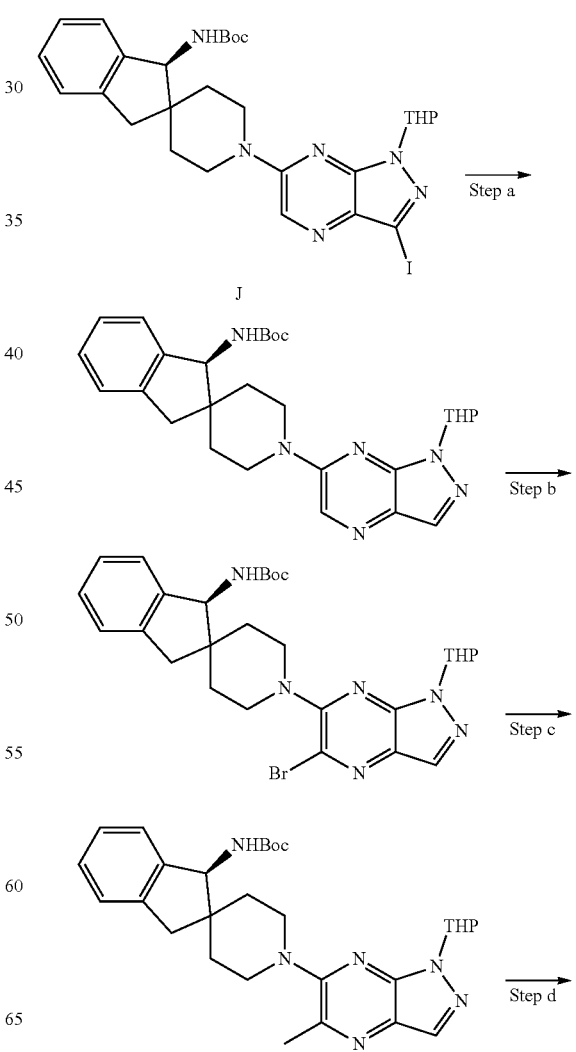

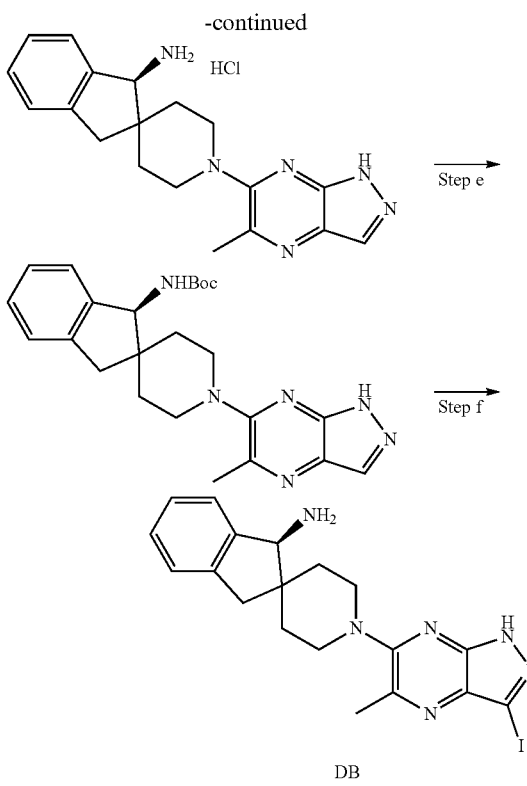

Step a: A solution of tert-butyl ((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (500.0 mg, 792.0 μmol, Intermediate J), 10% Pd/C (100.0 mg) and TEA (220.0 μL, 1.58 mmol) in THF (15.0 ml) was stirred at 20° C. for 12 hours under H2 (15 psi). The reaction mixture was filtered and the filtrate was concentrated to give tert-butyl N-[(3S)-1'-[1-(oxan-2-yl)-1H-pyrazolo[3,4-b]pyrazin-6-yl]-1,3-dihydrospiro[indene-2,4'-piperidin]-3-yl]carbamate (380.0 mg, 95% yield) as a yellow solid. LCMS (ESI$^+$) m/z: 505.1 (M+H)$^+$.

Step b: To a solution of tert-butyl N-[(3S)-1'-[1-(oxan-2-yl)-1H-pyrazolo[3,4-b]pyrazin-6-yl]-1,3-dihydrospiro[indene-2,4'-piperidin]-3-yl]carbamate (380.0 mg, 753.0 μmol) in AcOH/ACN (10.0 mL/10.0 mL) was added NBS (134.0 mg, 753.0 μmol). The reaction mixture was stirred at 20° C. for 0.5 hour. The reaction mixture was then concentrated under reduced pressure. The residue was triturated with H$_2$O (100.0 mL) and extracted with EtOAc (100.0 mL×2). The combined organic layers were washed with sat. NaHCO$_3$ (100.0 mL), dried over anhydrous Na$_2$SO$_4$, filtered and the filtrate was concentrated under reduced pressure to give a residue. The residue was purified by flash silica gel chromatography (12 g column, ethyl acetate in petroleum ether from 0% to 20%) to give tert-butyl N-[(3S)-1'-[5-bromo-1-(oxan-2-yl)-1H-pyrazolo[3,4-b]pyrazin-6-yl]-1,3-dihydrospiro[indene-2,4'-piperidin]-3-yl]carbamate (330.0 mg, 75% yield) as a white solid. LCMS (ESI$^+$) m/z: 583.0 (M+H)$^+$.

Step c: A solution of tert-butyl N-[(3S)-1'-[5-bromo-1-(oxan-2-yl)-1H-pyrazolo[3,4-b]pyrazin-6-yl]-1,3-dihydrospiro[indene-2,4'-piperidin]-3-yl]carbamate (330.0 mg, 565.0 μmol), trimethyl-1,3,5,2,4,6-trioxatriborinane (141.0 mg, 1.13 mmol, CAS #823-96-1), Pd(dppf)Cl$_2$ (82.7 mg, 113.0 umol, CAS #72287-26-4) and K$_2$CO$_3$ (233.0 mg, 1.69 mmol) in dioxane/H$_2$O (10.0 mL/2.0 mL) was stirred at 90° C. for 12 hours under N2. The reaction mixture was poured into H$_2$O (100.0 mL) and extracted with EtOAc (100.0 mL×2). The combined organic layers were washed with brine (200.0 mL), dried over anhydrous Na$_2$SO$_4$, filtered and the filtrate was concentrated under reduced pressure to give a residue. The residue was purified by flash silica gel chromatography (12 g column, ethyl acetate in petroleum ether from 0% to 30%) to give tert-butyl N-[(3S)-1'-[5-methyl-1-(oxan-2-yl)-1H-pyrazolo[3,4-b]pyrazin-6-yl]-1,3-dihydrospiro[indene-2,4'-piperidin]-3-yl]carbamate (250.0 mg, 85% yield) as a yellow oil. LCMS (ESI$^+$) m/z: 519.2 (M+H)$^+$.

Step d: A solution of tert-butyl N-[(3S)-1'-[5-methyl-1-(oxan-2-yl)-1H-pyrazolo[3,4-b]pyrazin-6-yl]-1,3-dihydrospiro[indene-2,4'-piperidin]-3-yl]carbamate (250.0 mg, 482.0 μmol) in HCl/MeOH (15.0 mL, 4 M) was stirred at 20° C. for 1 hour. The reaction mixture was then concentrated, triturated with EtOAc and stirred for 20 min. The mixture was filtered and the filter cake was concentrated to give (S)-1'-(5-methyl-1H-pyrazolo[3,4-b]pyrazin-6-yl)-1,3-dihydrospiro[indene-2,4'-piperidin]-1-amine hydrochloride (180.0 mg, 101% crude yield) as a yellow solid. LCMS (ESI$^+$) m/z: 335.1 (M+H)$^+$.

Step e: The compound of (3S)-1'-{5-methyl-1H-pyrazolo[3,4-b]pyrazin-6-yl}-1,3-dihydrospiro[indene-2,4'-piperidin]-3-amine hydrochloride (100.0 mg, 269.0 μmol) and TEA (111 μL, 807.0 μmol) was dissolved in DCM (10 ml). Then (Boc)$_2$O (73.8 μL, 322.0 μmol) in DCM (0.13 mL) was added. The mixture was stirred at 25° C. for 2 hours. The mixture was washed with H$_2$O (10 mL×2), brine (10 mL), dried over anhydrous Na$_2$SO$_4$, filtered and concentrated to give a residue. The residue was purified by flash silica gel chromatography (petroleum ether:ethyl acetate=100:0 to 100:30) to give tert-butyl N-[(3S)-1'-{5-methyl-1H-pyrazolo[3,4-b]pyrazin-6-yl}-1,3-dihydrospiro[indene-2,4'-piperidin]-3-yl]carbamate (70.0 mg, 60% yield) as a yellow oil. LCMS (ESI$^+$) m/z: 435.1 (M+H)$^+$.

Step f: Tert-butyl N-[(3S)-1'-{5-methyl-1H-pyrazolo[3,4-b]pyrazin-6-yl}-1,3-dihydrospiro[indene-2,4'-piperidin]-3-yl]carbamate (70.0 mg, 161.0 μmol) and NIS (54.2 mg, 241.0 μmol) were added in DMF (2 mL). The reaction mixture was stirred at 110° C. for 16 hours. The mixture was quenched with the mixture of sat. Na$_2$SO$_3$ (10 mL) and sat. NaHCO$_3$ (10 mL) and stirred for 10 min where a lot of precipitate formed. Then H$_2$O (10 mL) was added and the mixture was stirred for 1 min, then extracted with ethyl acetate (10 mL×3). The combined organic layers were washed with brine (20 mL), dried over anhydrous Na$_2$SO$_4$, filtered and concentrated to give (3S)-1'-{3-iodo-5-methyl-1H-pyrazolo[3,4-b]pyrazin-6-yl}-1,3-dihydrospiro[indene-2,4'-piperidin]-3-amine (60.0 mg, 81% yield) as a brown solid. LCMS (ESI$^+$) m/z: 461.0 (M+H)$^+$.

4-chloro-1-methyl-1H-pyrazolo[3,4-d]pyrimidine, Intermediate DC and 4-chloro-2-methyl-2H-pyrazolo[3,4-d]pyrimidine, Intermediate DD

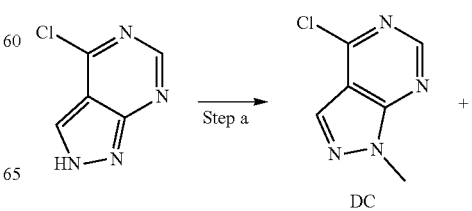

-continued

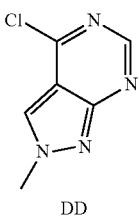

DD

Step a: 4-Chloro-2H-pyrazolo[3,4-d]pyrimidine (1.00 g, 6.5 mmol, CAS #5399-92-8) was dissolved in THF (33.0 mL). Then NaHMDS (10 mL, 1.0 M in THF) was added at 0° C. and the mixture was stirred for 5 min. Me (1.03 mL, 16.7 mmol) was added slowly over 5 min at 0° C. under N2 gas protection. The reaction mixture was warmed to 25° C. and stirred for 1 h. The mixture was diluted with $H_2O$ (200 mL) and $CH_2Cl_2$ (200 mL), then the partitioned layers were separated. The aqueous phase was extracted with $CH_2Cl_2$ (50 mL×3). The combined organic layers were washed with brine (200 mL), dried over anhydrous $Na_2SO_4$, filtered and concentrated to give a residue. The residue was purified by flash silica gel chromatography (ethyl acetate:petroleum ether=0:100 to 100:100) to afford 4-chloro-1-methyl-1H-pyrazolo[3,4-d]pyrimidine (98.3 m, 9.1% yield) as a yellow solid (LCMS (ESI$^+$) m/z: 169 (M+H)$^+$; $^1$HNMR (400 MHz, DMSO-d6) δ 8.87 (s, 1H), 8.47 (s, 1H), 4.09 (s, 3H)) and 4-chloro-2-methyl-2H-pyrazolo[3,4-d]pyrimidine (242 mg, 22° yield) as a yellow solid (LCMS (ESI$^+$) m/z: 169 (M+H)$^+$; $^1$HNMR (400 MHz, DMSO-d6) δ 8.91 (s, 1H), 8.80 (s, 1H), 4.25 (s, 3H)).

Sodium (S)-5-(1-((tert-butoxycarbonyl)amino)-1,3-dihydrospiro[indene-2,4'-piperidin]-1'-yl)pyrazine-2-thiolate, Intermediate DE Step a: A mixture of (S)-tert-butyl (1'-(5-bromopyrazin-2-yl)-1,3-dihydrospiro[indene-2,4'-piperidin]-1-yl)carbamate (590.0 mg, 1.3 mmol, Intermediate CZ), 2-ethylhexyl 3-mercaptopropanoate (334.0 mg, 1.5 mmol, CAS #50448-95-8), $Pd_2(dba)_3$ (117.0 mg, 0.13 mmol), XantPhos (148.0 mg, 0.26 mmol, CAS #161265-03-8) and TEA (522 μL, 3.8 mmol) in toluene (15 mL) was stirred at 100° C. for 12 hours under N2 atmosphere. The reaction mixture was then concentrated to give a residue. The residue was purified by silica gel chromatography (ethyl acetate in petroleum ether=0% to 15%) to afford 2-ethylhexyl 3-((5-((S)-1-((tert-butoxycarbonyl)amino)-1,3-dihydrospiro[indene-2,4'-piperidin]-1'-yl)pyrazin-2-yl)thio)propanoate (690 mg, 90% yield) as a yellow oil. LCMS (ESI$^+$) m/z: 597.2 (M+H)$^+$.

Step b: To a mixture of 2-ethylhexyl 3-((5-((S)-1-((tert-butoxycarbonyl)amino)-1,3-dihydrospiro[indene-2,4'-piperidin]-1'-yl)pyrazin-2-yl)thio)propanoate (690.0 mg, 1.2 mmol) in anhydrous THF (10 mL) was added MeONa (124.0 mg, 2.3 mmol). The resulting mixture was stirred at 20° C. for 3 hours under $N_2$ atmosphere. The reaction mixture was then concentrated to give the crude product, which was triturated with petroleum ether:ethyl acetate=10:1 (50 mL). The solid was collected and dried in vacuo to afford sodium ( )-5-(1-((tert-butoxycarbonyl)amino)-1,3-dihydrospiro[indene-2,4'-piperidin]-1'-yl)pyrazine-2-thiolate (500.0 mg, 100% yield) as a red solid. LCMS (ESI$^+$) m/z: 413.1 (M-Na+H)$^+$.

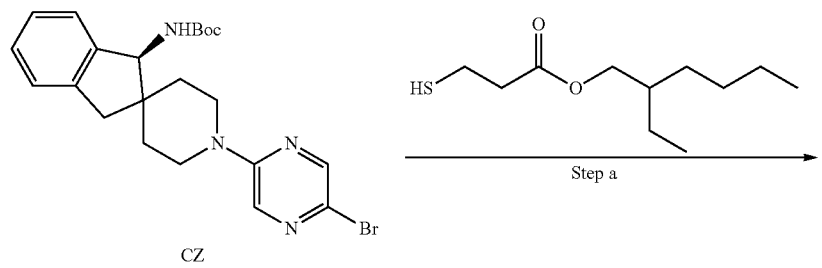

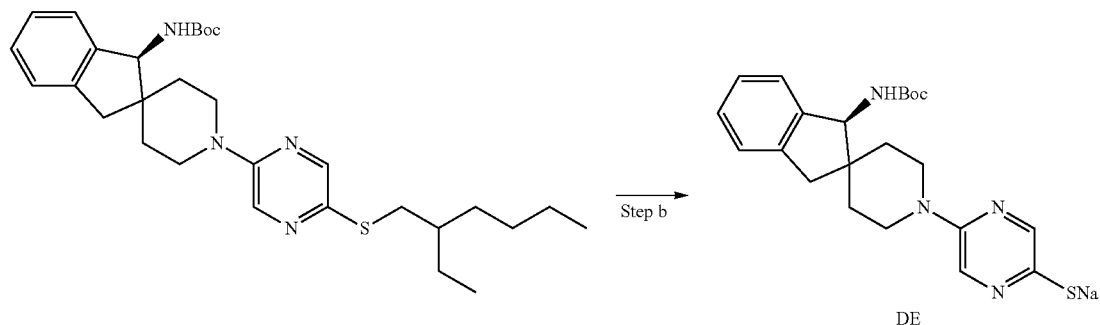

4-[1-(oxan-2-yl)-3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3-en-3'-one, Intermediate DF

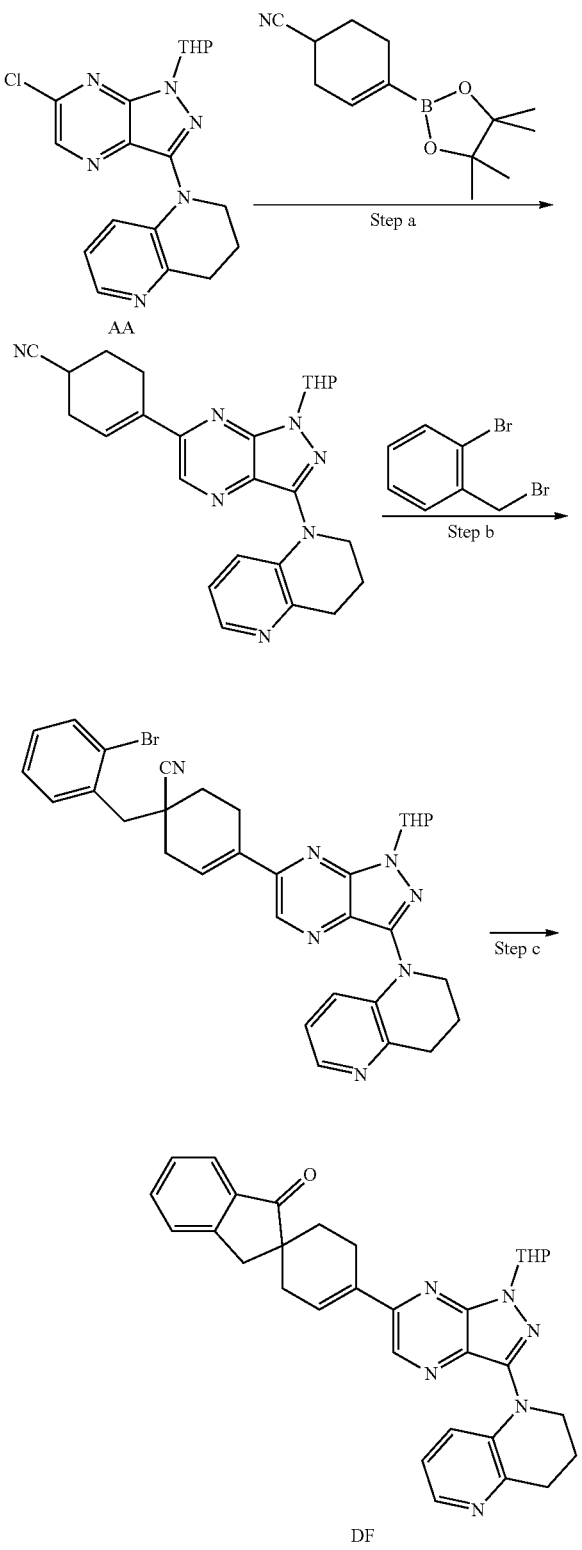

Step a: The compound of 1-[6-chloro-1-(oxan-2-yl)-1H-pyrazolo[3,4-b]pyrazin-3-yl]-1,2,3,4-tetrahydro-1,5-naphthyridine (4.00 g, 10.7 mmol, Intermediate AA), 4-(4,4,5,5-tetramethyl-1,3,2-dioxaborolan-2-yl)cyclohex-3-ene-1-carbonitrile (2.72 g, 11.7 mmol, CAS #1310384-20-3), Pd(dppf)Cl$_2$ (782.0 mg, 1.1 mmol) and Cs$_2$CO$_3$ (6.97 g, 21.4 mmol) were placed into the solvent of dioxane (250 mL) and H$_2$O (25 mL). The reaction mixture was evacuated and refilled for 3 times using N2; then the reaction mixture was stirred at 90° C. for 12 hours. The reaction mixture was then concentrated and H$_2$O (200 mL) was added, then the mixture was extracted with ethyl acetate (300 mL×3). The combined organic layers were washed with brine (500 mL), dried over anhydrous Na$_2$SO$_4$, filtered and concentrated to give a residue. The residue was purified by flash silica gel chromatography (petroleum ether ethyl acetate=100:50 to 100:90) to afford 4-[1-(oxan-2-yl)-3-(1,2,3,4-tetrahydro-1,5-naphthyridin-1-yl)-1H-pyrazolo[3,4-b]pyrazin-6-yl]cyclohex-3-ene-1-carbonitrile (4.70 g, 99.5% yield) as a yellow solid. LCMS (ESI$^+$) m/z: 442.1 (M+H)$^+$.

Step b: 4-[1-(Oxan-2-yl)-3-(1,2,3,4-tetrahydro-1,5-naphthyridin-1-yl)-1H-pyrazolo[3,4-b]pyrazin-6-yl]cyclohex-3-ene-1-carbonitrile (2.70 g, 6.1 mmol) and 1-bromo-2-(bromomethyl)benzene (1.67 g, 6.7 mmol) were dissolved in THF (150 mL). Then LDA (3.66 mL, 7.3 mmol, 2 M in THF) was added dropwise into the mixture at −10° C. The mixture was stirred at 0° C. for 0.5 hour, then warmed to 25° C. for 1 hour. Next, another LDA (3.66 mL, 7.3 mmol), 2 M in THF) was added dropwise into the mixture at 0° C. The mixture was stirred at 0° C. for 0.5 hour, then warmed to 25° C. for 1 hour. The reaction mixture was quenched by addition of saturated NH$_4$Cl (200 mL), then the mixture was extracted with ethyl acetate (200 mL×3). The combined organic layers were washed with brine (300 mL), dried over anhydrous Na$_2$SO$_4$, filtered and concentrated to give a residue. The residue was purified by flash silica gel chromatography (petroleum ether:ethyl acetate=100:20 to 100:80) to afford 1-[(2-bromophenyl)methyl]-4-[1-(oxan-2-yl)-3-(1,2,3,4-tetrahydro-1,5-naphthyridin-1-yl)-1H-pyrazolo[3,4-b]pyrazin-6-yl]cyclohex-3-ene-1-carbonitrile (1.70 g, 26% yield) as a yellow solid. LCMS (ESI$^+$) m/z: 610.0, 612.0 (M+H)$^+$.

Step c: 1-[(2-Bromophenyl)methyl]-4-[1-(oxan-2-yl)-3-(1,2,3,4-tetrahydro-1,5-naphthyridin-1-yl)-1H-pyrazolo[3,4-b]pyrazin-6-yl]cyclohex-3-ene-1-carbonitrile (700.0 mg, 1.1 mmol), PdCl$_2$(AmPhos)$_2$ (23.1 mg, 32.6 μmol) and TEA (631 μL, 4.6 mmol) were placed into DMA (25 mL) and H$_2$O (0.5 mL). The reaction mixture was evacuated and refilled 3 times using N2. The reaction mixture was stirred at 120° C. for 12 hours. The mixture was then diluted with ethyl acetate (100 mL). The mixture was washed with H$_2$O (30 mL×5), brine (50 mL×2), dried over anhydrous Na$_2$SO$_4$, filtered and concentrated to give a residue. The residue was purified by flash silica gel chromatography (petroleum ether:ethyl acetate=100:50 to 100:80) to afford 4-[1-(oxan-2-yl)-3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3-en-3'-one (520 mg, 86% yield) as a yellow oil. LCMS (ESI$^+$) m/z: 533.1 (M+H)$^+$.

4-chloro-1-methyl-1H-imidazo[4,5-c]pyridine, Intermediate DG and 4-chloro-3-methyl-3H-imidazo[4,5-c]pyridine, Intermediate DH

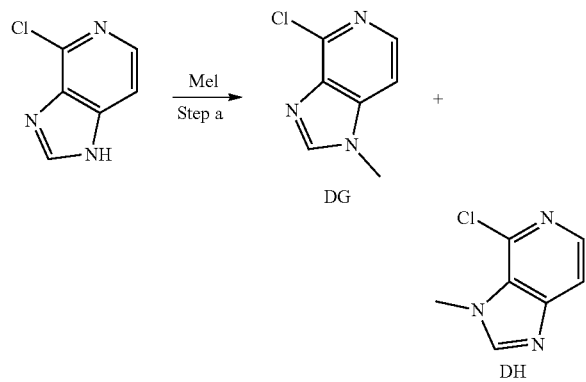

Step a: To a solution of 4-chloro-3H-imidazo[4,5-c]pyridine (1 g, 6.51 mmol, CAS #81053-66-9) in DMSO/THF (2.5 mL/25 mL) was added NaHMDS (9.76 mL, 9.76 mmol) at 20° C. under N2. The reaction mixture was stirred at 20° C. for 1 h. Then, to the reaction mixture was added MeI (1.21 mL, 19.5 mmol) at 20° C. The reaction mixture was then stirred at 20° C. for 11 h. The reaction mixture was filtered and the filtrate was concentrated to give a residue. The residue was purified by prep-HPLC (NH$_3$.H$_2$O) to give 4-chloro-1-methyl-1H-imidazo[4,5-c]pyridine (Intermediate DG) (257.2 mg, 24% yield) as a white solid, LCMS (ESI$^+$) m/z: 167.8 (M+H)$^+$; $^1$HNMR (400 MHz, DMSO-d6) δ 8.16-8.14 (m, 1H), 7.92 (s, 1H), 7.27-7.25 (m, 1H), 3.71 (s, 3H), and 4-chloro-3-methyl-3H-imidazo[4,5-c]pyridine (Intermediate DH) (201.8 mg, 19% yield) as a white solid, LC-MS (ESI$^+$) m/z: 167.8 (M+H), 11HNMR (400 MHz, DMSO-d6) δ 8.34~8.13 (m, 1H), 7.98 (m, 1H), 7.79~7.54 (m, 1H), 7.29 (m, 1H), 4.34-4.09 (m, 3H).

2-chloro-5-cyclopropyl-1H-pyrrolo[2,3-b]pyridine, Intermediate DI

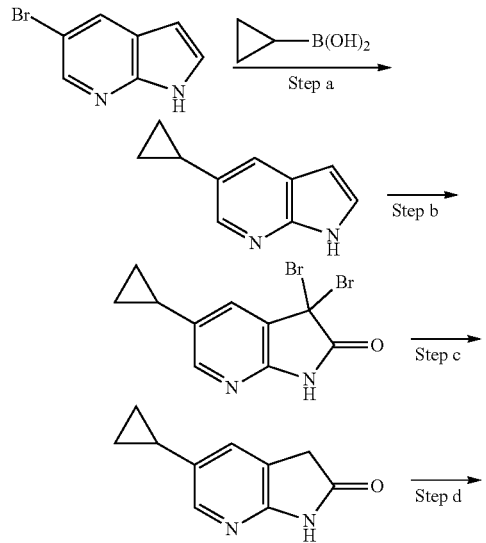

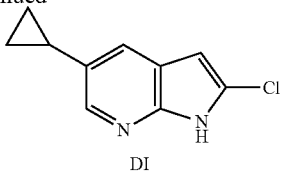

Step a: A mixture of 5-bromo-1H-pyrrolo[2,3-b]pyridine (8.00 g, 40.6 mmol, CAS #183208-35-7), cyclopropylboronic acid (8.01 g, 93.3 mmol) and K$_2$CO$_3$ (16.60 g, 121.0 mmol) in toluene (100.0 mL) was stirred at 25° C. for 0.5 hours under N2 atmosphere. Then, Pd$_2$(dba)$_3$ (1.85 g, 2.0 mmol) and SPhos (1.66 g, 4.1 mmol) were added, and the resulting mixture was stirred at 100° C. for 11.5 hours under N2 atmosphere. The reaction mixture was then concentrated in vacuo to give a residue, which was then dissolved in ethyl acetate (200.0 mL), and washed with H$_2$O (150.0 mL×3). The organic phase was washed with brine (50 mL), dried over anhydrous Na$_2$SO$_4$, filtered and concentrated in vacuo to give a residue. The residue was purified by silica gel chromatography (ethyl acetate in petroleum ether=0% to 35%) to afford 5-cyclopropyl-1H-pyrrolo[2,3-b]pyridine (2.70 g, 42% yield) as a yellow solid. LC-MS (ESI$^+$) m/z 159.0 (M+H)$^+$.

Step b: To a stirring solution of 5-cyclopropyl-1H-pyrrolo[2,3-b]pyridine (2.10 g, 13.2 mmol) in t-BuOH (120.0 mL) was added pyridium tribromide (12.50 g, 39.5 mmol) portion-wise, then the resulting mixture was stirred at 25° C. for 12 hours. The reaction mixture was concentrated in vacuo to give a residue, which was then dissolved in ethyl acetate (200.0 mL) and washed with H$_2$O (150.0 mL×2). The organic phase was washed with brine (50.0 mL), dried over anhydrous Na$_2$SO$_4$, filtered and concentrated in vacuo to afford 3,3-dibromo-5-cyclopropyl-1H,2H,3H-pyrrolo[2,3-b]pyridin-2-one (4.3 g, crude product) as a yellow solid. LC-MS (ESI$^+$) m/z 330.9 (M+H)$^+$.

Step c: To a mixture of 3,3-dibromo-5-cyclopropyl-1H,2H,3H-pyrrolo[2,3-b]pyridin-2-one (4.30 g, 12.9 mmol) in AcOH (20.0 mL) and MeOH (20.0 mL) was added Zn (4.21 g, 64.5 mmol), and the resulting mixture was stirred at 25° C. for 2 hours. The reaction mixture was then filtered and concentrated in vacuo to give a residue, which was then dissolved in ethyl acetate (100.0 mL), and washed with H$_2$O (80.0 mL×2). The organic phase was washed with brine (25.0 mL), dried over anhydrous Na$_2$SO$_4$, filtered and concentrated in vacuo to give a residue, which was triturated with EtOH (20 mL) to afford 5-cyclopropyl-1H,2H,3H-pyrrolo[2,3-b]pyridin-2-one (1.50 g, 67% yield) as a brown solid. LC-MS (ESI$^+$) m/z 174.9 (M+H)$^+$.

Step d: A mixture of 5-cyclopropyl-1H,2H,3H-pyrrolo[2,3-b]pyridin-2-one (700.0 mg, 4.0 mmol) in POCl$_3$ (6.50 mL, 69.9 mmol) was stirred at 110° C. for 4 hours. The reaction mixture was then concentrated in vacuo to give a residue, which was dissolved in DCM (20.0 mL) and adjusted to pH=8 with saturated Na$_2$CO$_3$, then extracted with DCM (25.0 mL×3). The organic phases were washed with brine (25.0 mL), dried over anhydrous Na$_2$SO$_4$, filtered and concentrated in vacuo to give a residue. The residue was purified by silica gel chromatography (ethyl acetate in petroleum ether=0% to 35%) to afford 2-chloro-5-cyclopropyl-1H-pyrrolo[2,3-b]pyridine (410.0 mg, 34% yield) as a yellow solid. LC-MS (ESI$^+$) m/z 193.0 (M+H)$^+$.

tert-butyl N-[(3S)-1'-(5-sulfanylpyrazin-2-yl)-1,3-dihydrospiro[indene-2,4'-piperidin]-3-yl]carbamate, Intermediate DJ

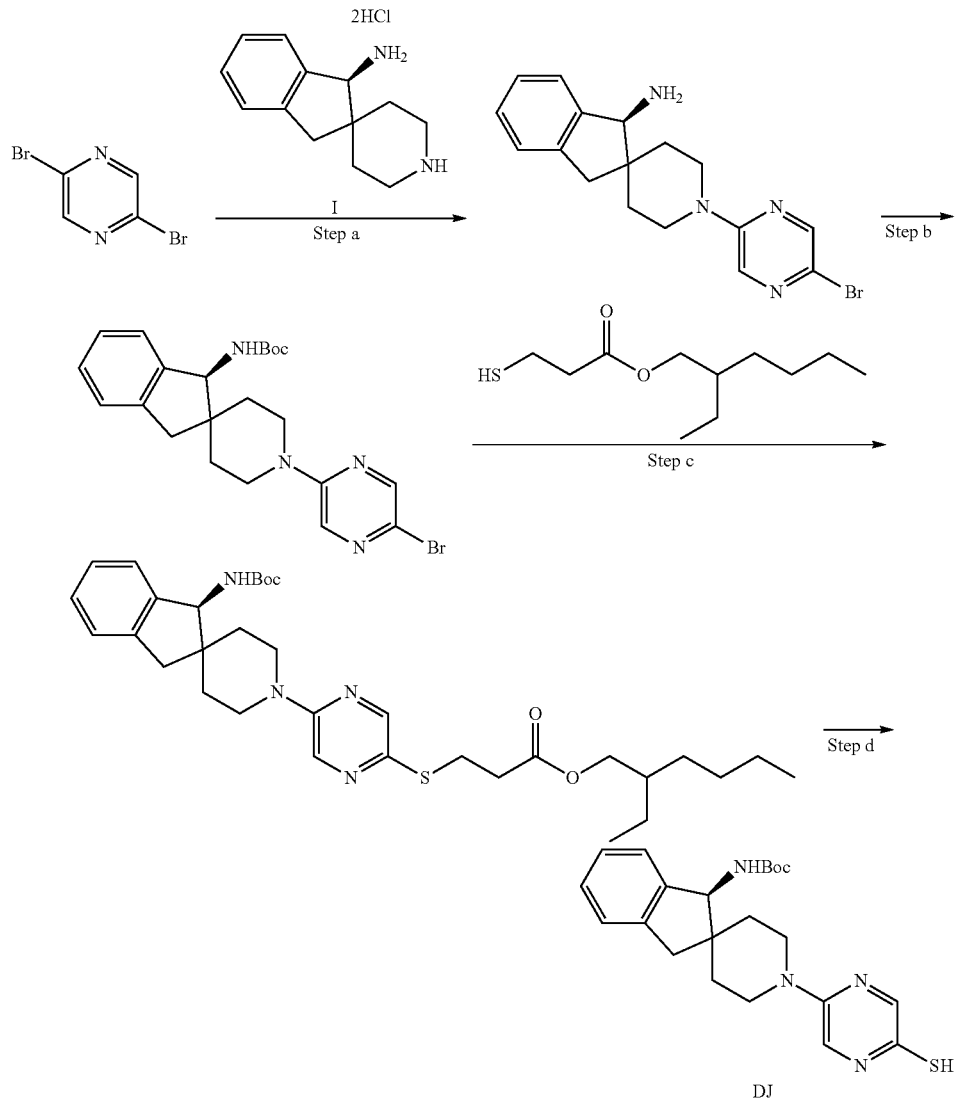

Step a: A mixture of 2,5-dibromopyrazine (4.00 g, 16.8 mmol, CAS #23229-26-7), (3S)-1,3-dihydrospiro[indene-2,4'-piperidin]-3-amine dihydrochloride (5.06 g, 18.4 mmol, Intermediate I) and TEA (11.6 mL, 84.0 mmol) in DMF (50 mL) was stirred at 80° C. for 3 hours. The crude solution was then cooled to rt and used directly in the next step. LC-MS (ESI$^+$) m/z: 341.9, 343.9 (M-NH$_2$)+.

Step b: To the crude solution of (S)-1'-(5-bromopyrazin-2-yl)-1,3-dihydrospiro[indene-2,4'-piperidin]-1-amine (6.03 g, 16.7 mmol) in DMF (50 mL) was added (Boc)$_2$O (5.73 mL, 25.0 mmol). The resulting mixture was stirred at 25° C. for 12 hours. Then the mixture was diluted with EtOAc (500 mL). The mixture was next washed with H$_2$O (100 mL×5), brine (500 mL), dried over anhydrous Na$_2$SO$_4$, filtered and concentrated to give a residue. The residue was purified by silica gel chromatography (ethyl acetate in petroleum ether=0% to 15% to afford (S)-tert-butyl (1'-(5-bromopyrazin-2-yl)-1,3-dihydrospiro[indene-2,4'-piperidin]-1-yl) carbamate (7.60 g, 99% yield) as a yellow solid. LC-MS (ESI$^+$) m/z: 459.2, 461.2 (M+H)$^+$.

Step c: (S)-tert-butyl (1'-(5-bromopyrazin-2-yl)-1,3-dihydrospiro[indene-2,4'-piperidin]-1-yl)carbamate (3.00 g, 6.53 mmol), 2-ethylhexyl 3-sulfanylpropanoate (1.56 g, 7.18 mmol, CAS #50448-95-8), XantPhos (752 g, 1.30 mmol), Pd$_2$(dba)$_3$ (597.0 mg, 0.65 mmol), and DIPEA (3.40 mL, 19.5 mmol) were added into dioxane (60 mL). The reaction mixture was evacuated and refilled 3 times with N2. The solution was stirred at 100° C. for 12 h. The solvent was then removed under reduced pressure. The residue was triturated with DCM (100 mL) and H$_2$O (100 mL), and the yellow solid was filtered off. The organic layer was separated and the aqueous layer was extracted with DCM (100 mL×2). The combined organic layers were washed with brine (100 mL), dried over anhydrous Na$_2$SO$_4$, filtered and concentrated to give a brown residue. The residue was purified by flash column chromatography (petroleum ether/EtOAc=100:0 to 100:15) to afford 2-ethylhexyl 3-({5-[(3S)-3-{[(tert-butoxy)

carbonyl]amino}-1,3-dihydrospiro[indene-2,4 (3.0 g, 77% yield) as a yellow oil. LC-MS (ESI+) m/z: 597.2 (M+H)+.

Step d: The compound of 2-ethylhexyl 3-({5-[(3S)-3-{[(tert-butoxy)carbonyl]amino}-1,3-dihydrospiro[indene-2,4'-piperidin]-1'-yl]pyrazin-2-yl}sulfanyl)propanoate (200.0 mg, 335 μmol) was dissolved in THF (1.00 mL). The reaction mixture was cooled to −78° C. and t-BuOK (1.00 mL, 1 M in THF) was added dropwise over 10 min under N2. The reaction mixture was stirred at −78° C. for 20 min. The reaction mixture was diluted with DCM (30 mL) and acidified with HCl/MeOH (2 N) to pH=6 at −78° C. The mixture was washed with H2O (20 mL) and brine (20 ml).

The organic layer were dried over anhydrous Na2SO4, filtered and concentrated to give tert-butyl N-[(3S)-1'-(5-sulfanylpyrazin-2-yl)-1,3-dihydrospiro[indene-2,4'-piperidin]-3-yl]carbamate (138.0 mg, 100% yield, crude) as a yellow oil.

Sodium 5-((S)-1-(((R)-tert-butylsulfinyl)amino)-1,3-dihydrospiro[indene-2,4'-piperidin]-1'-yl)-6-methylpyrazine-2-thiolate, Intermediate DK, and sodium 5-((S)-1-(((R)-tert-butylsulfinyl)amino)-1,3-dihydrospiro[indene-2,4'-piperidin]-1'-yl)-3-methylpyrazine-2-thiolate, Intermediate DL

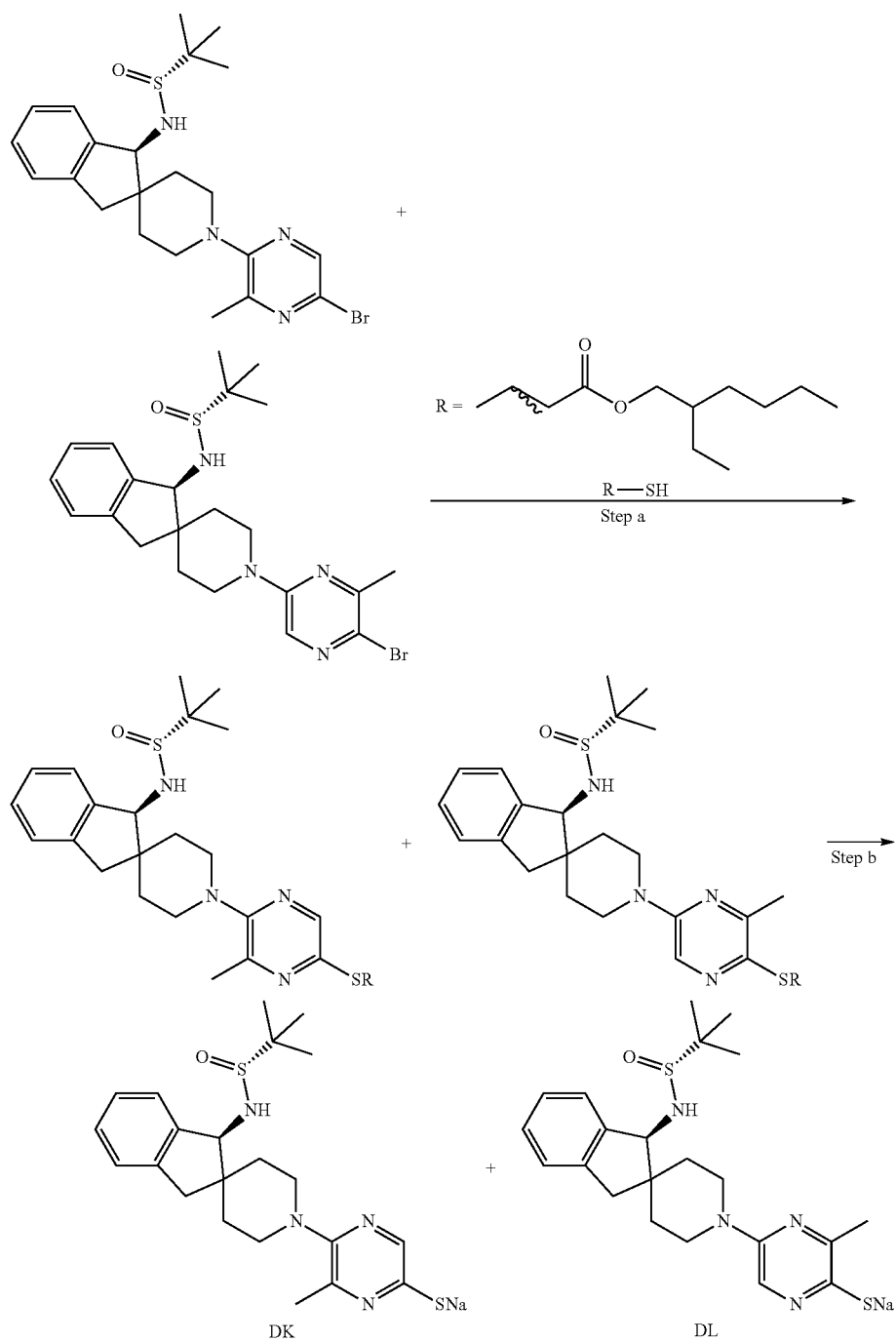

Step a: A mixture of (R)—N—((S)-1'-(5-bromo-3-methylpyrazin-2-yl)-1,3-dihydrospiro[indene-2,4'-piperidin]-1-yl)-2-methylpropane-2-sulfinamide and (R)—N—((S)-1'-(5-bromo-6-methylpyrazin-2-yl)-1,3-dihydrospiro[indene-2,4'-piperidin]-1-yl)-2-methylpropane-2-sulfinamide (320.0 mg, 670.0 μmol, synthesized via Step a of Examples 83 and 84), 2-ethylhexyl 3-sulfanylpropanoate (292.0 mg, 1.3 mmol, CAS #50448-95-8), XantPhos (77.5 mg, 134.0 μmol), DIPEA (344.0 μL, 2.0 mmol) and Pd$_2$(dba)$_3$ (61.3 mg, 67.0 μmol) in 1,4-dioxane (15.0 mL) was stirred at 110° C. for 12 hours under N2 atmosphere. The reaction mixture was concentrated in vacuo to give a residue, which was purified by silica gel chromatography (ethyl acetate in petroleum ether=0% to 55%) to afford 2-ethylhexyl 3-((5-((S)-1-(((R)-tert-butylsulfinyl)amino)-1,3-dihydrospiro[indene-2,4'-piperidin]-1'-yl)-6-methylpyrazin-2-yl)thio)propanoate and 2-ethylhexyl 3-((5-((S)-1-(((R)-tert-butylsulfinyl)amino)-1,3-dihydrospiro[indene-2,4'-piperidin]-1'-yl)-3-methylpyrazin-2-yl)thio)propanoate (400.0 mg) as a yellow oil. LC-MS (ESI$^+$) m/z 615.2 (M+H)$^+$.

Step b: To a mixture of 2-ethylhexyl 3-((5-((S)-1-(((R)-tert-butylsulfinyl)amino)-1,3-dihydrospiro[indene-2,4'-piperidin]-1'-yl)-6-methylpyrazin-2-yl)thio)propanoate and 2-ethylhexyl 3-((5-((S)-1-(((R)-tert-butylsulfinyl)amino)-1,3-dihydrospiro[indene-2,4'-piperidin]-1'-yl)-3-methylpyrazin-2-yl)thio)propanoate (390.0 mg, 634.0 μmol) in anhydrous THF (10.0 mL) was added MeONa (68.0 mg, 1.3 mmol), and the resulting mixture was stirred at 20° C. for 1 hour under N2 atmosphere. The reaction mixture was concentrated in vacuo to give a residue, which was triturated with petroleum ether:ethyl acetate=10:1 (20 mL) and filtered. The solids were combined and dried under vacuum to afford sodium 5-((S)-1-(((R)-tert-butylsulfinyl)amino)-1,3-dihydrospiro[indene-2,4'-piperidin]-1'-yl)-6-methylpyrazine-2-thiolate and sodium 5-((S)-1-(((R)-tert-butylsulfinyl)amino)-1,3-dihydrospiro[indene-2,4'-piperidin]-1'-yl)-3-methylpyrazine-2-thiolate (260 mg, 91% yield) as a yellow solid. LC-MS (ESI$^+$) m/z 431.1 (M+H-Na)+.

2-Chloro-1-cyclopentylethan-1-one, Intermediate DM

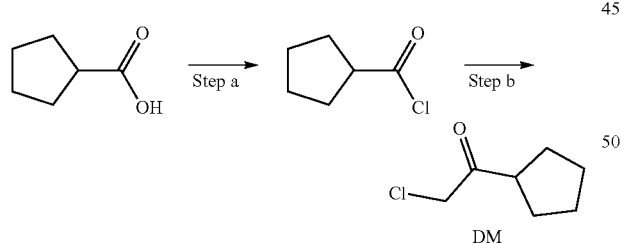

Step a: To a mixture of cyclopentanecarboxylic acid (3.00 g, 26.2 mmol) in SOCl$_2$ (10.0 mL) was added DMF (2 drops), and the resulting mixture was stirred at 50° C. for 3 hours under N2 atmosphere. The mixture was concentrated in vacuo to give a residue, which was dissolved in DCM (30.0 mL) and then re-concentrated in vacuo to give cyclopentanecarbonyl chloride (3.40 g, 98% crude yield) as a colorless oil.

Step b: To a mixture of cyclopentanecarbonyl chloride (3.40 g, 25.6 mmol) in anhydrous THF (60.0 mL) at 0° C. was added TMSCHN$_2$ (38.4 mL, 76.8 mmol) slowly, then the mixture was stirred at this temperature for 0.5 hours. Then the resulting mixture was warmed to 20° C. and stirred for 11.5 hours. The mixture was concentrated in vacuo to give a residue, which was then dissolved in THF (60.0 mL) and HCl/1,4-dioxane (4 M, 19.2 mL) was added slowly at 0° C. The resulting mixture was warmed to 20° C. and stirred for 2 hours. The mixture was then concentrated in vacuo to give a residue, which was dissolved in ethyl acetate (50.0 mL), and washed with sat.NaHCO$_3$ (30.0 mL). The organic phase was washed with brine (20.0 mL), dried over anhydrous Na$_2$SO$_4$, filtered and concentrated in vacuo to give a residue. The residue was purified by silica gel chromatography (ethyl acetate in petroleum ether=0% to 5%) to afford 2-chloro-1-cyclopentylethan-1-one (2.50 g, 67% yield) as a yellow oil. $^1$HNMR (400 MHz, CDCl$_3$): δ 4.16 (s, 2H), 3.14-3.06 (m, 1H), 1.87-1.59 (m, 8H).

Methyl 6-bromo-3-[(3S)-3-{[(tert-butoxy)carbonyl]amino}-1,3-dihydrospiro[indene-2,4'-piperidin-1'-yl] pyrazine-2-carboxylate, Intermediate DN

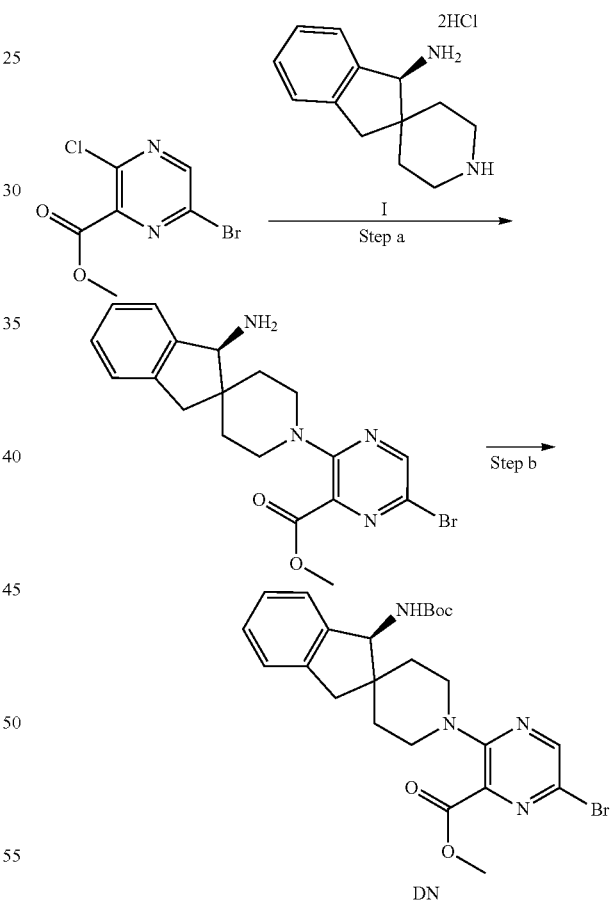

Step a: Methyl 6-bromo-3-chloropyrazine-2-carboxylate (3 g, 11.9 mmol, CAS #1256921-67-1), TEA (8.26 mL, 59.5 mmol) and (S)-1,3-dihydrospiro[indene-2,4'-piperidin]-1-amine dihydrochloride (3.27 g, 11.9 mmol, Intermediate I) were placed into DMF (80 mL). The reaction mixture was evacuated and refilled 3 times using N2. The reaction mixture was then stirred at 50° C. for 2 hours. The mixture was used for the next step without further purification. LC-MS (ESI$^+$) m/z: 440.8 (M+Na)+.

Step b: Methyl 3-[(3S)-3-amino-1,3-dihydrospiro[indene-2,4'-piperidin]-1'-yl]-6-bromopyrazine-2-carboxylate (4.96 g, 11.8 mmol), TEA (8.20 mL, 59.0 mmol) and (Boc)$_2$O (7.72 g, 35.4 mmol) were placed into DMF (80 mL). The reaction mixture was stirred at 25° C. for 2 hours. Then the combined mixture was diluted with EtOAc (1 L), washed with H$_2$O (300 mL×5), brine (800 mL), dried over anhydrous Na$_2$SO$_4$, filtered and concentrated to give a residue. The residue was purified by flash silica gel chromatography (ethyl acetate/petroleum ether=0/100 to 20/100) to afford methyl 6-bromo-3-[(3S)-3-{[(tert-butoxy)carbonyl]amino}-1,3-dihydrospiro[indene-2,4'-piperidin]-1'-yl]pyrazine-2-carboxylate (7.67 g, combined product) as a yellow oil. LC-MS (ESI$^+$) m/z: 425.2 (M−NHBoc+Na)+.

Tert-butyl N-[(3S)-1'-(5-bromo-3-cyanopyrazin-2-yl)-1,3-dihydrospiro[indene-2,4'-piperidin]-3-yl]carbamate, Intermediate DO

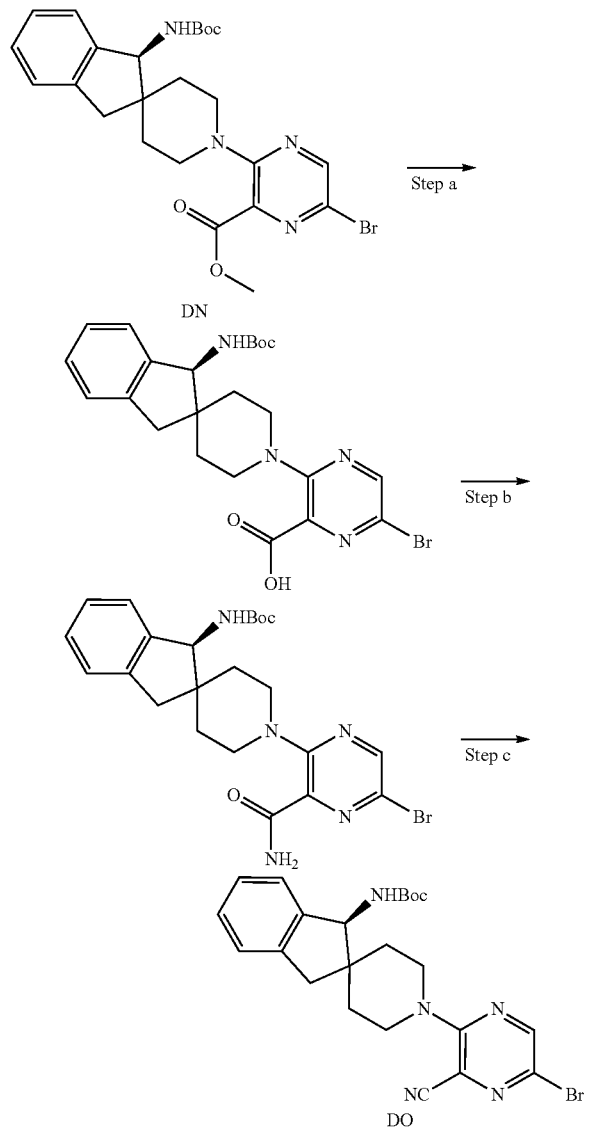

Step a: Methyl 6-bromo-3-[(3S)-3-{[(tert-butoxy)carbonyl]amino}-1,3-dihydrospiro[indene-2,4'-piperidin]-1'-yl]pyrazine-2-carboxylate (500.0 mg, 966 μmol, Intermediate DN) and NaOH (386 mg, 9.66 mmol) were placed into MeOH/H$_2$O=5 mL/5 mL. The reaction mixture was stirred at 25° C. for 12 hours. The reaction mixture was concentrated and extracted with ethyl acetate (40 mL×2) and the partitioned layers were separated. The combined organic layers were washed with brine (50 mL), dried over anhydrous Na$_2$SO$_4$, filtered and concentrated to give 6-bromo-3-[(3S)-3-{[(tert-butoxy)carbonyl]amino}-1,3-dihydrospiro[indene-2,4'-piperidin]-1'-yl]pyrazine-2-carboxylic acid (600 mg, 1.19 mmol, quant. crude yield) as a yellow solid. LC-MS (ESI$^+$) m/z: 503.0 (M+H)$^+$.

Step b: A mixture of 6-bromo-3-[(3S)-3-{[(tert-butoxy)carbonyl]amino}-1,3-dihydrospiro[indene-2,4'-piperidin]-1'-yl]pyrazine-2-carboxylic acid (600.0 mg, 1.19 mmol), DIPEA (1.83 g, 14.2 mmol), HATU (676 mg, 1.78 mmol) and DMF (10 mL) was stirred at 25° C. for 1 h. Then NH$_4$C (631 mg, 11.8 mmol) was added, and the resulting mixture was stirred at 25° C. for 12 h. The mixture was then diluted with EtOAc (200 mL). The mixture was washed with H$_2$O (60 mL×5), brine (200 mL), dried over anhydrous Na$_2$SO$_4$, filtered and concentrated to give tert-butyl N-[(3S)-1'-(5-bromo-3-carbamoylpyrazin-2-yl)-1,3-dihydrospiro[indene-2,4'-piperidin]-3-yl]carbamate (480 mg, 80% yield) as a yellow solid. LC-MS (ESI$^+$) m/z: 504.0 (M+H)$^+$.

Step c: To a reaction mixture of tert-butyl N-[(3S)-1'-(5-bromo-3-carbamoylpyrazin-2-yl)-1,3-dihydrospiro[indene-2,4'-piperidin]-3-yl]carbamate (480 mg, 955 μmol) and TEA (197 μL, 1.43 mmol) in DCM (10.0 mL) was added TFFA (201 μL, 1.43 mmol) slowly at 0° C. The reaction mixture was stirred at 0° C. for 15 min. Then the reaction mixture was quenched with H$_2$O (20.0 mL) and extracted with DCM (50.0 mL). The combined organic layers were washed with brine (20.0 mL), dried over anhydrous Na$_2$SO$_4$, filtered and concentrated under reduced pressure to give a residue. The residue was purified by flash silica gel chromatography (12 g column, EtOAc in petroleum ether from 0% to 10%) to give tert-butyl N-[(3S)-1'-(5-bromo-3-cyanopyrazin-2-yl)-1,3-dihydrospiro[indene-2,4'-piperidin]-3-yl]carbamate (361 mg, 78% yield) as a light yellow oil. LC-MS (ESI$^+$) m/z: 506.0 (M+Na)+.

2-chloro-5-iodo-3-methyl-3,4-dihydropyrimidin-4-one, Intermediate DP

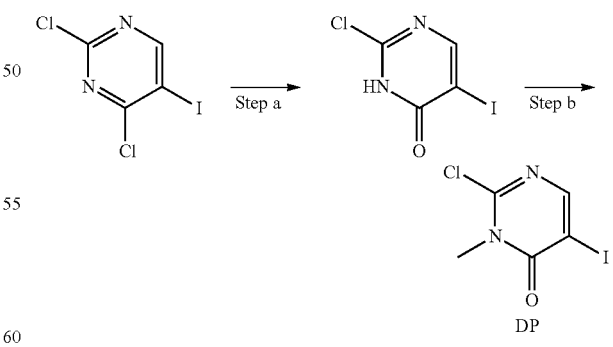

Step a: To a solution of 2,4-dichloro-5-iodopyrimidine (3.5 g, 12.7 mmol, CAS #13544-44-0) in THF (60 ml) was added sodium hydroxide (1 N, 45 mL). The reaction mixture was stirred at 15° C. for 12 hours. The mixture was then extracted with ethyl acetate (50 mL×1). The aqueous layer was adjusted to pH=5-6 with aqueous HCl (2 N) and extracted with ethyl acetate (50 mL×4). The combined organic layers were washed with brine (50 mL), dried over anhydrous Na₂SO₄, filtered and concentrated to give a residue. The residue was purified by flash silica gel chromatography (petroleum ether:ethyl acetate=100:20 to 100:60) to afford 2-chloro-5-iodo-3,4-dihydropyrimidin-4-one (620 mg, 19% yield) as a yellow solid. LC-MS (ESI⁺) m/z: 256.8 (M+H)⁺.

Step b: To a solution of 2-chloro-5-iodo-3,4-dihydropyrimidin-4-one (400 mg, 1.55 mmol) in DMF (10 mL) was added LDA (1.55 mL, 2.0 M in THF) dropwise at 0° C. The mixture was stirred at 0° C. for 5 min, then MeI (212.0 µL, 3.41 mmol) was added. The mixture was allowed to warm up to 15° C. and stirred at this temperature for 18 h. The mixture was then diluted with H₂O (20 mL), and extracted with ethyl acetate (200 mL×3). The combined organic layers were washed with saturated NH₄C (60 mL×2), brine (100 mL×2), dried over anhydrous Na₂SO₄, filtered and concentrated to give a residue. The residue was purified by flash silica gel chromatography (ethyl acetate/petroleum ether=0/100 to 30/100) to afford 2-chloro-5-iodo-3-methyl-3,4-dihydropyrimidin-4-one (234.0 mg, 56% yield) as a white solid. LC-MS (ESI⁺) m/z: 270.7 (M+H)⁺.

(S)-tert-butyl (1'-(5-iodo-1-methyl-6-oxo-1,6-dihydropyrimidin-2-yl)-1,3-dihydrospiro[indene-2,4'-piperidin]-1-yl)carbamate, Intermediate DO

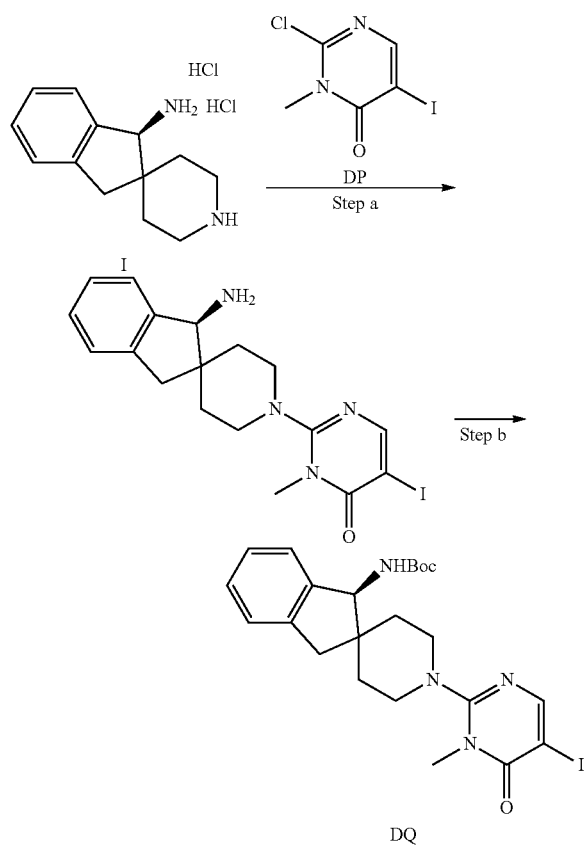

Step a: 2-Chloro-5-iodo-3-methyl-3,4-dihydropyrimidin-4-one (234.0 mg, 865 µmol, Intermediate DP), DIPEA (766 µL, 4.32 mmol), and (S)-1,3-dihydrospiro[indene-2,4'-piperidin]-1-amine dihydrochloride (283 mg, 1.03 mmol, Intermediate I) were placed into DMF (10 mL). The reaction mixture was evacuated and refilled 3 times using N2. The reaction mixture was stirred at 100° C. for 2 hours. The mixture cooled to rt and was used in the next step without further purification. LC-MS (ESI⁺) m/z: 458.9 (M+H)⁺.

Step b: A mixture of 2-[(3S)-3-amino-1,3-dihydrospiro[indene-2,4 (377.0 mg, 864 µmol), TEA (362 µL, 2.59 mmol) and (Boc)₂O (295 µL, 1.29 mmol) in DMF (10 mL) was stirred at 15° C. for 2 hours. The mixture was then concentrated and purified by flash silica gel chromatography (petroleum ether:EtOAc=100:0 to 100:60) to afford (S)-tert-butyl (1'-(5-iodo-1-methyl-6-oxo-1,6-dihydropyrimidin-2-yl)-1,3-dihydrospiro[indene-2,4'-piperidin]-1-yl)carbamate (150.0 mg, 32% yield) as a colorless oil. LC-MS (ESI⁺) m/z: 537.1 (M+Na)+.

1-benzyl-6-chloro-3-iodo-5-methyl-1H,4H,5H-pyrazolo[3,4-d]pyrimidin-4-one, Intermediate DR

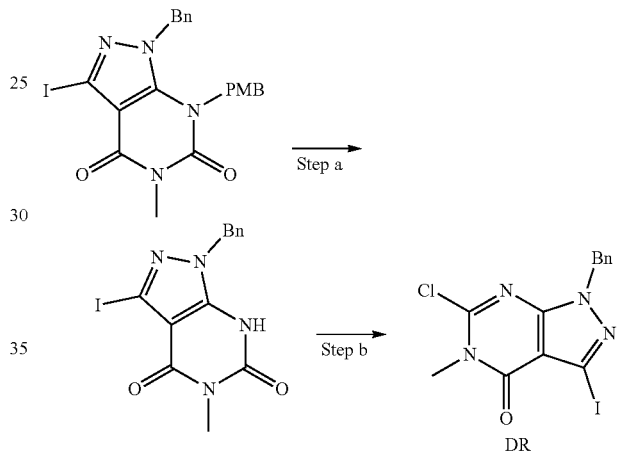

Step a: A mixture of 1-benzyl-3-iodo-7-(4-methoxybenzyl)-5-methyl-1H-pyrazolo[3,4-d]pyrimidine-4,6(5H,7H)-dione (1.0 g, 2.0 mmol, CAS #2055938-41-3, synthesis described in PCT Int. Appl. 2016203404) in TFA (10 mL) and TfOH (0.1 mL) was stirred at 70° C. for 15 hours. The mixture was then concentrated to give a residue which was triturated with saturated aqueous NH₄Cl (100 mL), then extracted with EtOAc (100 mL×2). The combined organic layer was concentrated to give a residue which triturated with EtOAc (3 mL), where precipitate formed. The solid was collected by filtration to afford 1-benzyl-3-iodo-5-methyl-1H-pyrazolo[3,4-d]pyrimidine-4,6(5H,7H)-dione (600 mg, 79% yield) as a green solid. LC-MS (ESI⁺) m/z: 383.0 (M+H)⁺.

Step b: 1-benzyl-3-iodo-5-methyl-1H,4H,5H,6H,7H-pyrazolo[3,4-d]pyrimidine-4,6-dione (500 mg, 1.30 mmol) and DIPEA (681 µL, 3.90 mmol) were added in the POCl₃ (5 mL). The mixture was stirred at 120° C. for 12 h. The reaction mixture was then concentrated to give a residue which was diluted with EtOAc (20 mL). The mixture was added slowly into an ice and sat. aq. NaHCO₃ (30 mL). The partitioned layers were separated and the aqueous phase was extracted with ethyl acetate (20 mL×3). The combined organic layers were washed with brine (50 mL), dried over anhydrous Na₂SO₄, filtered and concentrated to give a redisue. The residue was purified by flash silica gel chromatography (ethyl acetate/petroleum ether=0/100 to 30/100)

to give 1-benzyl-6-chloro-3-iodo-5-methyl-1H,4H,5H-pyrazolo[3,4-d]pyrimidin-4-one (400 mg, 998 µmol) as a gray solid. LC-MS (ESI+) m/z: 401.2 (M+H)+.

(S)-tert-butyl (1'-(1-benzyl-3-iodo-5-methyl-4-oxo-4,5-dihydro-1H-pyrazolo[3,4-d]pyrimidin-6-yl)-1,3-dihydrospiro[indene-2,4'-piperidin]-1-yl)carbamate, Intermediate DS

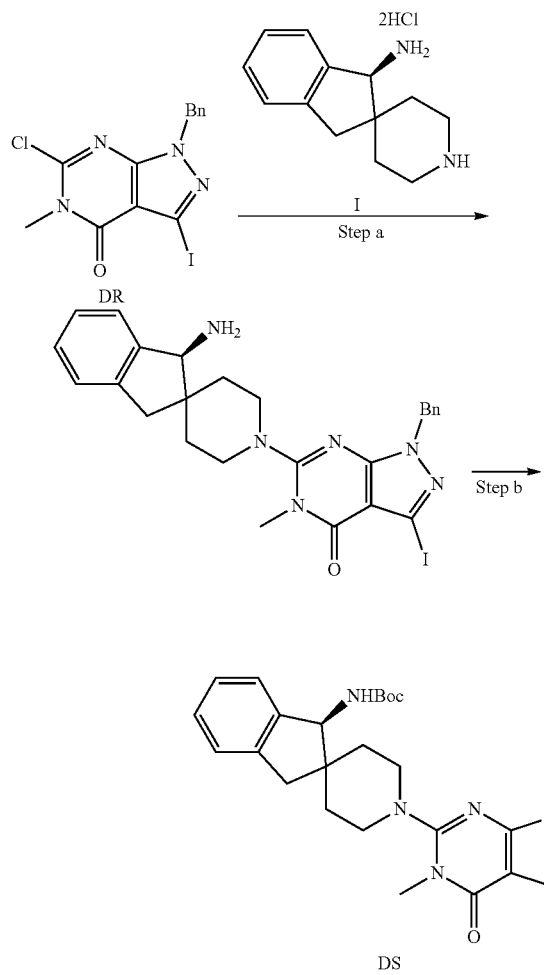

Step a: 1-Benzyl-6-chloro-3-iodo-5-methyl-1H, 4H, 5H-pyrazolo[3,4-d]pyrimidin-4-one (210.0 mg, 524 µmol, Intermediate DR), (3S)-1,3-dihydrospiro[indene-2,4'-piperidin]-3-amine dihydrochloride (172.0 mg, 628 µmol, Intermediate I) and DIPEA (455 µL, 2.61 mmol) were added in DMSO (2.00 mL). The reaction mixture was stirred at 120° C. for 12 hours. The reaction mixture was cooled to rt and the crude solution was used into the next step without further purification. LC-MS (ESI+) m/z: 550.0 (M-NH$_2$)+.

Step b: The (Boc)$_2$O (178 µL, 783 µmol) was added into a mixture of (S)-6-(1-amino-1,3-dihydrospiro[indene-2,4'-piperidin]-1'-yl)-1-benzyl-3-iodo-5-methyl-1H-pyrazolo[3,4-d]pyrimidin-4(5H)-one (296.0 mg, 522 µmol) in DMSO (3 mL). The mixture was stirred at 30° C. for 2 hours. Then the mixture was diluted with EtOAc (30 mL). The mixture was washed with H$_2$O (20 mL×3), brine (30 mL), dried over anhydrous Na$_2$SO$_4$, filtered and concentrated to give a residue. The residue was purified by flash silica gel chromatography (ethyl acetate/petroleum ether=0/100 to 50/100) to give (S)-tert-butyl (1'-(1-benzyl-3-iodo-5-methyl-4-oxo-4,5-dihydro-1H-pyrazolo[3,4-d]pyrimidin-6-yl)-1,3-dihydrospiro[indene-2,4'-piperidin]-1-yl)carbamate (200.0 mg, 58% yield) as a yellow solid. LC-MS (ESI+) m/z: 667.1 (M+H)+.

(R)—N—((S)-1'-(5-bromo-3,6-dimethylpyrazin-2-yl)-1,3-dihydrospiro[indene-2,4'-piperidin]-1-yl)-2-methylpropane-2-sulfinamide, Intermediate DT

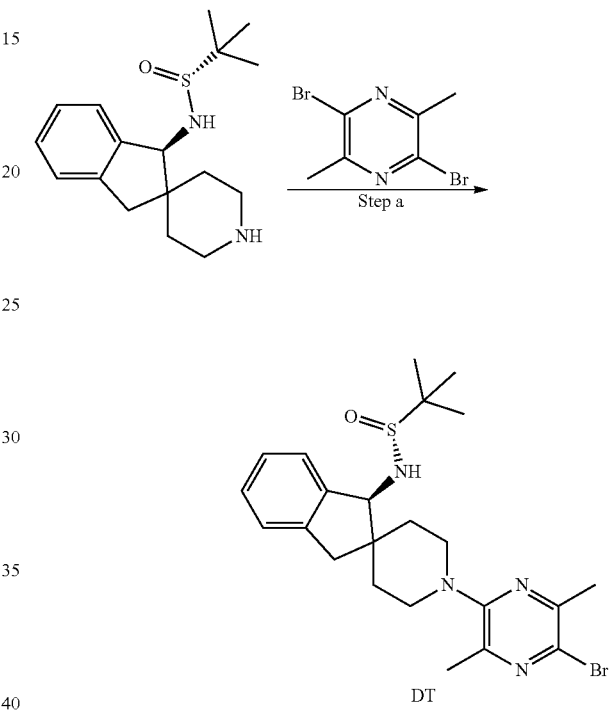

Step a: To a solution of (R)—N—((S)-1,3-dihydrospiro[indene-2,4'-piperidin]-1-yl)-2-methylpropane-2-sulfinamide (1.00 g, 3.76 mmol, synthesized via Step a of Example 120) in DMF (10.0 mL) was added 2,5-dibromo-3,6-dimethylpyrazine (1.33 g 3.76 mmol, CAS #121594-49-8) and TEA (1.90 g, 18.8 mmol, 2.62 mL), and the resulting mixture was stirred at 80° C. for 12 hrs. The mixture was then diluted with H$_2$O (50 mL) and extracted with ethyl acetate 90 mL (30 mL×3). The combined organic layers were washed with brine (50 mL×2), dried over Na$_2$SO$_4$, filtered and concentrated under reduced pressure to give a residue. The residue was purified by column chromatography (SiO$_2$, petroleum ether/ethyl acetate=10/1 to 1/1) to give (R)—N—((S)-1'-(5-bromo-3,6-dimethylpyrazin-2-yl)-1,3-dihydrospiro[indene-2,4'-piperidin]-1-yl)-2-methylpropane-2-sulfinamide (1.12 g, 2.07 mmol, 55% yield) as a yellow oil. LC-MS (ESI+) m/z: 493.2 (M+H)+; $^1$HNMR (400 MHz, CDCl$_3$): δ 7.33 (d, J=6.8 Hz 1H), 7.25-7.20 (m, 3H), 4.58 (d, J=10 Hz, 1H), 3.66 (d, J=10 Hz 1H), 3.46-3.40 (m, 2H), 3.15 (d, J=16 Hz 1H), 3.07-3.01 (m, 1H), 2.96-2.91 (m, 1H), 2.75 (d, J=16 Hz 1H), 2.50 (d, J=12.4 Hz 6H), 2.41-2.34 (m, 1H), 2.00-1.94 (m, 1H), 1.67 (d, J=13.6 1H), 1.40-1.37 (m, 1H), 1.30 (s, 9H).

347

(R)—N—((S)-1'-(6-bromo-5-methylpyridin-3-yl)-1,3-dihydrospiro[indene-2,4'-piperidin]-1-yl)-2-methylpropane-2-sulfinamide, Intermediate DU

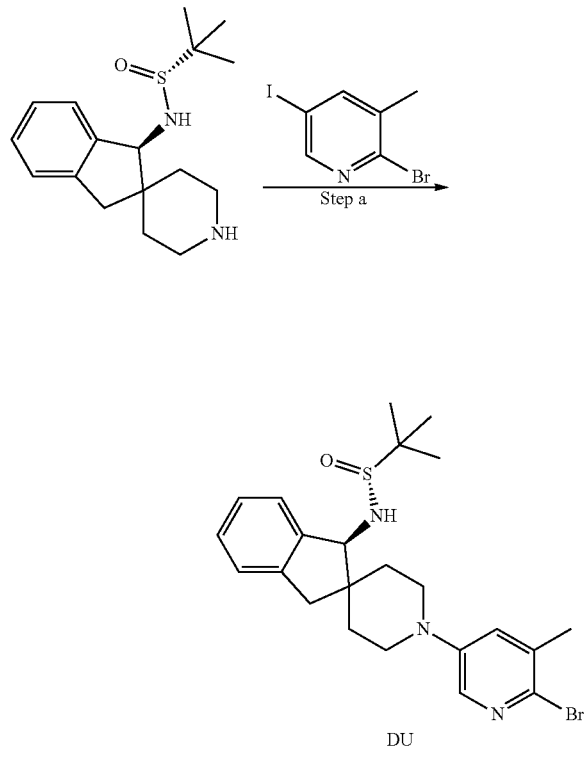

Step a: To a solution of 2-bromo-5-iodo-3-methylpyridine (500 mg, 167.8 umol, CAS #65550-78-9) in toluene (1.00 mL) was added (R)—N—((S)-1,3-dihydrospiro[indene-2,4'-piperidin]-1-yl)-2-methylpropane-2-sulfinamide (594.8 mg, 1.68 mmol, synthesized via Step a of Example 120), $Cs_2CO_3$ (1.64 g, 5.03 mmol, 3.00 eq) and Xantphos-Pd-G4 (161.5 mg, 167.8 umol, 0.10 eq), and the resulting mixture was stirred at 80° C. for 12 hrs. The mixture was then diluted with $H_2O$ (20 mL), and the mixture was extracted with ethyl acetate (20.0 mL×3). The organic extracts were combined and washed with brine (50.0 mL), dried over $Na_2SO_4$, filtered and concentrated to give a yellow residue. The yellow residue was purified by prep-HPLC (column: Phenomenex luna C18 250*50 mm*10 um; mobile phase: [water (0.225% FA)-ACN]; B %: 55%-85%, 10 min) to give (R)—N—((S)-1'-(6-bromo-5-methylpyridin-3-yl)-1,3-dihydrospiro[indene-2,4'-piperidin]-1-yl)-2-methylpropane-2-sulfinamide (330 mg, 678 umol, 40% yield) as a yellow solid. LC-MS (ESI$^+$) m/z: 478.1 (M+H)$^+$; $^1$HNMR (400 MHz, CDCl$_3$) δ 7.87 (d, J=2.8 Hz, 1H), 7.34-7.32 (m, 1H), 7.26-7.21 (m, 3H), 7.09 (d, J=2.8 Hz, 1H), 4.59 (d, J=10 Hz, 2H), 3.62-3.50 (m, 3H), 3.1 (d, J=16 Hz, 1H), 2.98-2.87 (m, 2H), 2.75 (d, J=16 Hz, 1H), 2.43 (m, 1H), 2.33 (s, 3H), 2.01-1.94 (m, 1H), 1.72-1.71 (m, 1H), 1.44-1.40 (m, 1H), 1.31 (s, 9H).

348

(R)—N—((S)-1'-(5-bromo-6-methylpyrazin-2-yl)-1,3-dihydrospiro[indene-2,4'-piperidin]-1-yl)-2-methylpropane-2-sulfinamide, Intermediate DV and (R)—N—((S)-1'-(5-chloro-3-methylpyrazin-2-yl)-1,3-dihydrospiro[indene-2,4'-piperidin]-1-yl)-2-methylpropane-2-sulfinamide, Intermediate DW

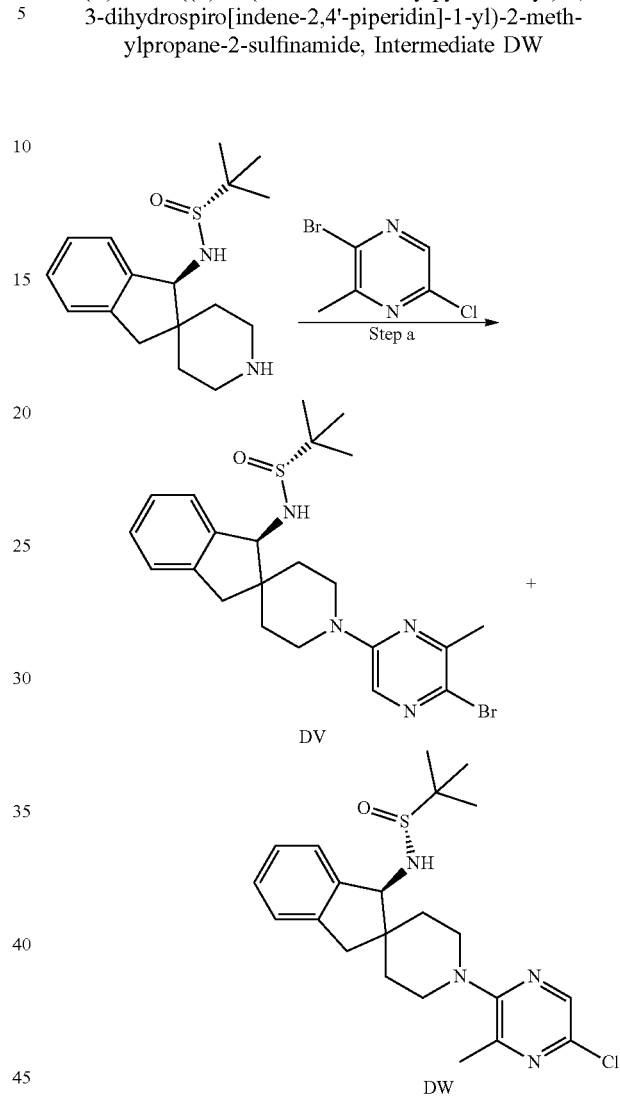

Step a: To a solution of 2-bromo-5-chloro-3-methylpyrazine (400 mg, 1.93 mmol, CAS #1260664-82-1) in DMF (2.00 mL) was added (R)—N—((S)-1,3-dihydrospiro[indene-2,4'-piperidin]-1-yl)-2-methylpropane-2-sulfinamide (683.36 mg, 1.93 mmol, synthesized via Step a of Example 120) and TEA (975.53 mg, 9.64 mmol, 1.34 mL), and the mixture was stirred at 80° C. for 3 h. The mixture was then adjusted to pH to 6-7 with FA. The mixture was then purified by pre-HPLC (column: Phenomenex Synergi Max-RP 150*50 mm*10 μm; mobile phase: [water (0.225% FA)-ACN]; B %: 48%-78%, 10 min) to give (R)—N—((S)-1'-(5-bromo-6-methylpyrazin-2-yl)-1,3-dihydrospiro[indene-2,4'-piperidin]-1-yl)-2-methylpropane-2-sulfinamide (290 mg, 607.38 μmol, 32% yield) as a white solid (LC-MS (ESI$^+$) m/z: 479.2 (M+H)+) and (R)—N—((S)-1'-(5-chloro-3-methylpyrazin-2-yl)-1,3-dihydrospiro[indene-2,4'-piperidin]-1-yl)-2-methylpropane-2-sulfinamide (135 mg, 312 μmol, 16% yield) as a white solid (LC-MS (ESI$^+$) m/z: 433.2 (M+H)+).

349

Tert-butyl (S)-(5-fluoro-1,3-dihydrospiro[indene-2,4'-piperidin]-1-yl)carbamate, Intermediate DX

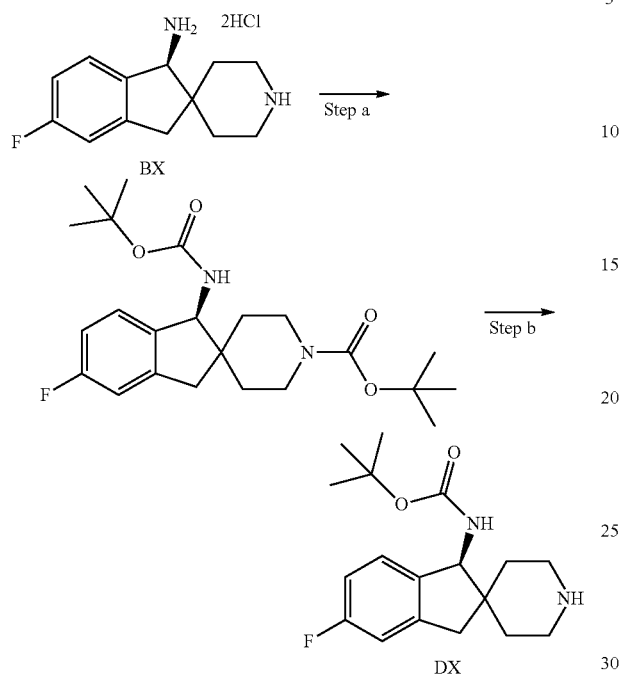

Step a: To a solution of (S)-5-fluoro-1,3-dihydrospiro[indene-2,4'-piperidin]-1-amine (3.00 g, 10.2 mmol, Intermediate BX) in DMF (30.0 mL) was added NaOH (2.29 g, 57.3 mmol). The mixture was stirred at 25° C. for 5 min, then to the mixture was added Boc$_2$O (6.70 g, 30.7 mmol). The mixture was stirred at 25° C. for 5 hr. The mixture was then poured into water (50.0 mL), and extracted with ethyl acetate (40.0 mL×3). The combined organic layer was washed with brine (40.0 mL×3), dried over Na$_2$SO$_4$, filtered and concentrated under reduced pressure to give a residue. The residue was purified by Pre-HPLC (column: Phenomenex Gemini C18 250*50 mm*10 um; mobile phase: [water (0.05% ammonia hydroxide v/v)-ACN]; B %: 65%-90%, 28 min) to give tert-butyl (S)-1-((tert-butoxycarbonyl)amino)-5-fluoro-1,3-dihydrospiro[indene-2,4'-piperidine]-1'-carboxylate (3.21 g, 7.59 mmol, 74% yield) as a white solid. LC-MS (ESI$^+$) m/z: 421.2 (M+H)$^+$.

Step b: To a solution of tert-butyl (S)-1-((tert-butoxycarbonyl)amino)-5-fluoro-1,3-dihydrospiro[indene-2,4'-piperidine]-1'-carboxylate (3.21 g, 7.59 mmol) in DCM (30.0 mL) was added ZnBr$_2$ (3.42 g, 15.2 mmol, 759 uL) and the mixture was stirred at 25° C. for 12 h. The mixture was then concentrated under reduced pressure to give the residue. The mixture was purified by Pre-HPLC (column: Phenomenex luna C18 250*50 mm*10 um; mobile phase: [water (0.225% FA)-ACN]; B %: 10%-25%, 13 min) to give tert-butyl (S)-(5-fluoro-1,3-dihydrospiro[indene-2,4'-piperidin]-1-yl)carbamate (1.5 g, 4.68 mmol, 62% yield) as a white oil. LC-MS (ESI$^+$) m/z: 321.2 (M+H)$^+$.

350

Tert-butyl (S)-(1'-(6-bromopyridin-3-yl)-5-fluoro-1,3-dihydrospiro[indene-2,4'-piperidin]-1-yl)carbamate, Intermediate DY

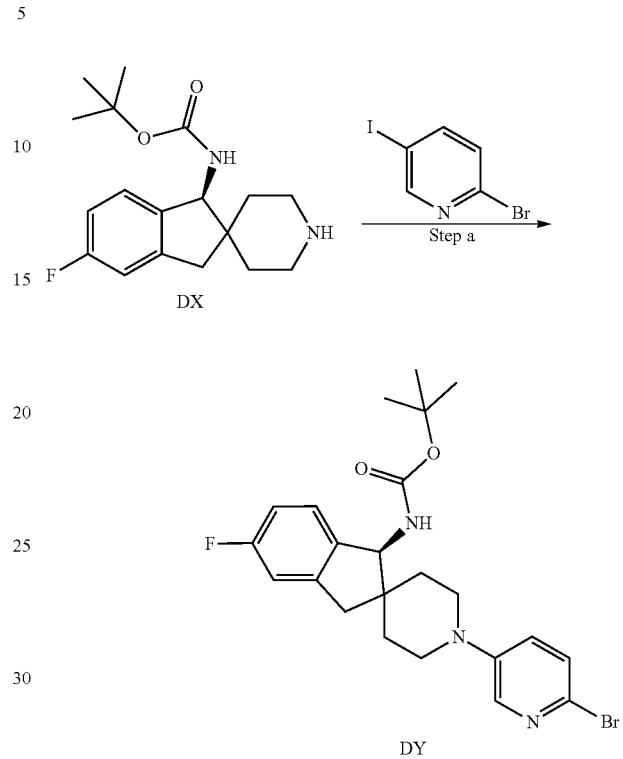

Step a: To a solution of 2-bromo-5-iodopyridine (1.33 g, 4.68 mmol), tert-butyl (S)-(5-fluoro-1,3-dihydrospiro[indene-2,4'-piperidin]-1-yl)carbamate (1.50 g, 4.68 mmol, Intermediate DX) and Cs$_2$CO$_3$ (4.58 g, 14.04 mmol) in toluene (15.0 mL) was added XantPhos-Pd-G4 (451 mg, 468 umol), and the mixture was stirred at 80° C. for 12 h. The mixture was then filtered and the filtrate was concentrated under reduced pressure to give a residue. The residue was purified by Pre-HPLC (column: Phenomenex Gemini C18 250*50 mm*10 um; mobile phase: [water (0.05% ammonia hydroxide v/v)-ACN]; B %: 58%-83%, 28 min) to give tert-butyl (S)-(1'-(6-bromopyridin-3-yl)-5-fluoro-1,3-dihydrospiro[indene-2,4'-piperidin]-1-yl)carbamate (645 mg, 1.34 mmol, 29% yield,) as a yellow solid. LC-MS (ESI$^+$) m/z: 478.3 (M+H)$^+$.

Tert-butyl (S)-(5-fluoro-1,3-dihydrospiro[indene-2,4'-piperidin]-3-yl)carbamate, Intermediate DZ

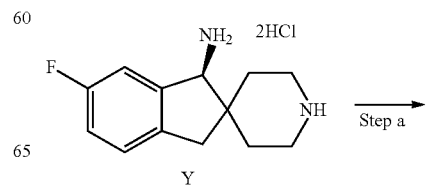

351
-continued

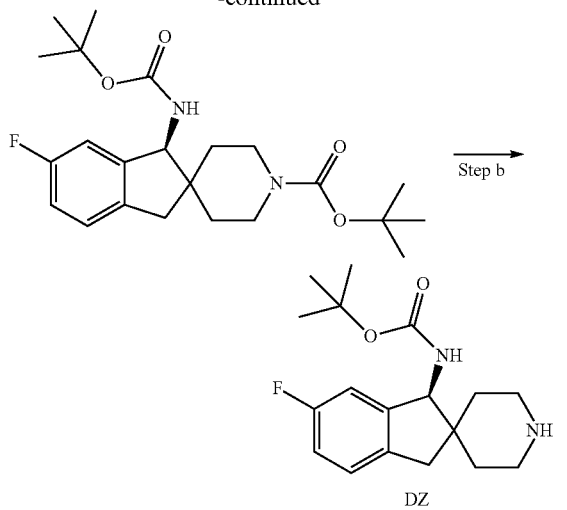

Step a: To a solution of (S)-6-fluoro-1,3-dihydrospiro[indene-2,4'-piperidin]-1-amine (2.00 g, 6.82 mmol, Intermediate Y) in DMF (20.0 mL) was added Boc$_2$O (4.47 g, 20.5 mmol, 4.70 mL) and NaOH (1.53 g, 38.2 mmol), and the mixture was stirred at 25° C. for 5 h. The mixture was poured into water (40.0 mL), and extracted with ethyl acetate (30.0 mL×3). The combined organic layer was washed with brine (30.0 mL×3), dried over Na$_2$SO$_4$, filtered and concentrated under reduced pressure to give a residue. The residue was purified by Pre-HPLC (column: Phenomenex Gemini C18 250*50 mm*10 um; mobile phase: [water (0.05% ammonia hydroxide v/v)-ACN]; B %: 64%-89%, 28 min) to give tert-butyl (S)-1-((tert-butoxycarbonyl)amino)-6-fluoro-1,3-dihydrospiro[indene-2,4'-piperidine]-1'-carboxylate (1.78 g, 4.23 mmol, 62% yield) as a white solid. LC-MS (ESI$^+$) m/z: 421.1 (M+H)$^+$.

Step b: To a solution of tert-butyl (S)-1-((tert-butoxycarbonyl)amino)-6-fluoro-1,3-dihydrospiro[indene-2,4'-piperidine]-1'-carboxylate (1.78 g, 4.23 mmol) in DCM (20.0 mL) was added ZnBr$_2$ (1.91 g, 8.47 mmol, 424 uL), and the mixture was stirred at 25° C. for 12 h. The mixture was concentrated under reduced pressure to give the residue. The mixture was purified by Pre-HPLC (column: Phenomenex luna C18 250*50 mm*10 um; mobile phase: [water (0.225% FA)-ACN]; B %: 10%-25%, 13 min) to give tert-butyl (S)-(5-fluoro-1,3-dihydrospiro[indene-2,4'-piperidin]-3-yl)carbamate (1.1 g, 3.43 mmol, 81% yield) was obtained as a white oil. LC-MS (ESI$^+$) m/z: 321.1 (M+H)$^+$.

Tert-butyl (S)-(1'-(6-bromopyridin-3-yl)-5-fluoro-1,3-dihydrospiro[indene-2,4'-piperidin]-1-yl)carbamate, Intermediate EA

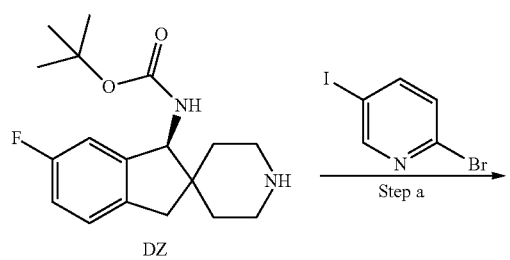

352
-continued

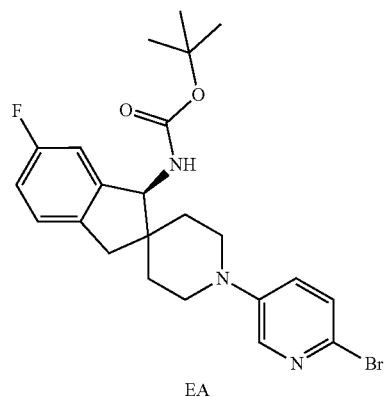

Step a: To a solution of 2-bromo-5-iodopyridine (975 mg, 3.43 mmol), tert-butyl (S)-(5-fluoro-1,3-dihydrospiro[indene-2,4'-piperidin]-3-yl)carbamate (1.10 g, 3.43 mmol, Intermediate DZ) and Cs$_2$CO$_3$ (3.36 g, 10.3 mmol) in toluene (15.0 mL) was added XantPhos-Pd-G4 (330 mg, 343 umol,). The mixture was stirred at 80° C. for 12 h. Then the mixture was filtered with diatomaceous earth and the filtrate was concentrated under reduced pressure to give a residue. The mixture was purified by Pre-HPLC (column: Phenomenex Gemini C18 250*50 mm*10 um; mobile phase: [water (0.05% ammonia hydroxide v/v)-ACN]; B %: 57%-82%, 35 min) to give tert-butyl (S)-(1'-(6-bromopyridin-3-yl)-5-fluoro-1,3-dihydrospiro[indene-2,4'-piperidin]-1-yl)carbamate (596 mg, 1.25 mmol, 36% yield) as a white solid. LC-MS (ESI$^+$) m/z: 500.1 (M+23)$^+$; $^1$HNMR (400 MHz, CDCl$_3$): δ 8.04 (d, J=3.20 Hz, 1H), 7.31-7.14 (m, 1H), 7.14-7.10 (m, 1H), 7.56-7.53 (m, 2H), 6.98-6.93 (m, 2H), 5.02 (d, J=10.0 Hz, 1H), 4.68 (d, J=10.0 Hz, 1H), 3.57-3.50 (m, 2H), 3.02-2.92 (m, 3H), 2.72 (d, J=15.6 Hz, 1H), 2.04-2.01 (m, 1H), 1.84-1.78 (m, 2H), 1.49 (s, 9H), 1.44-1.40 (m, 1H).

Tert-butyl (R)-(3H-spiro[benzofuran-2,4'-piperidin]-3-yl)carbamate, Intermediate EB

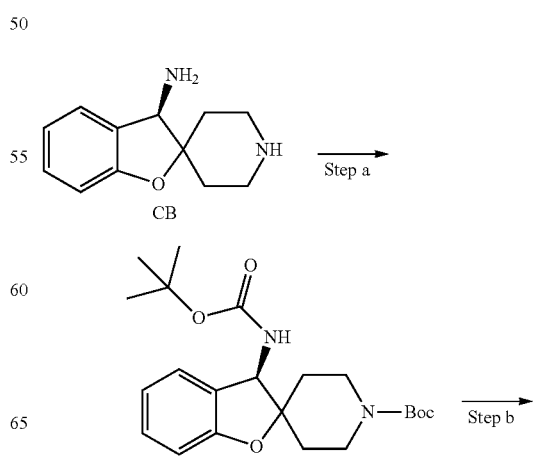

-continued

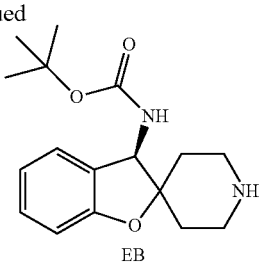

Step a: Tert-butyl (R)-3-((tert-butoxycarbonyl)amino)-3H-spiro[benzofuran-2,4'-piperidine]-1'-carboxylate, synthesized via Boc protection of (R)-3H-spiro[benzofuran-2,4'-piperidin]-3-amine, Intermediate CB (under standard conditions with Boc₂O) was mono-deprotected using ZnBr₂, as described in Step b of Intermediate DZ to give tert-butyl (R)-(3H-spiro[benzofuran-2,4'-piperidin]-3-yl)carbamate.

(R)—N—((R)-1'-(6-bromopyridin-3-yl)-3H-spiro[benzofuran-2,4'-piperidin]-3-yl)-2-methylpropane-2-sulfinamide, Intermediate EC

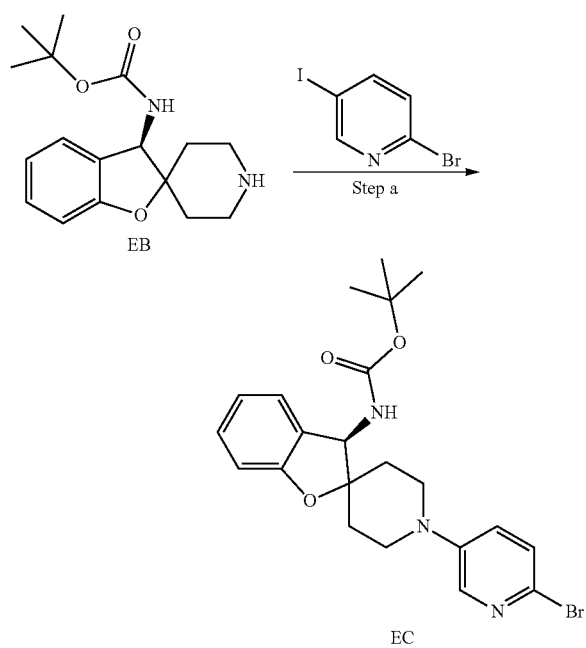

Step a: To a solution of 2-bromo-5-iodopyridine (1.00 g, 3.52 mmol), tert-butyl (R)-(3H-spiro[benzofuran-2,4'-piperidin]-3-yl)carbamate (1.09 g, 3.52 mmol, Intermediate EB) and Cs₂CO₃ (3.44 g, 10.6 mmol) in toluene (10.0 mL) was added XantPhos-Pd-G4 (339 mg, 352 umol). The mixture was stirred at 80° C. for 12 h. The mixture was then filtered and the filtrate was concentrated under reduced pressure to give a residue. The residue was purified by Pre-HPLC (column: Phenomenex Synergi C18 250*50*10 um; mobile phase: [water (0.05% ammonia hydroxide v/v)-ACN]; B %: 46%-71%, 36 min, 80% min) to give (R)—N—((R)-1'-(6-bromopyridin-3-yl)-3H-spiro[benzofuran-2,4'-piperidin]-3-yl)-2-methylpropane-2-sulfinamide (570 mg, 1.23 mmol, 35% yield) as a white solid. LC-MS (ESI⁺) m/z: 466.1 (M+H)⁺; ¹HNMR (400 MHz, CDCl₃): δ 8.04 (d, J=3.20 Hz, 1H), 7.31-7.29 (m, 3H), 7.14-7.11 (m, 1H), 7.56-7.53 (m, 2H), 6.96-6.95 (m, 1H), 6.85 (d, J=8.00 Hz, 1H), 4.73 (d, J=10.8 Hz, 1H), 3.72 (d, J=10.8 Hz, 1H), 3.66-3.53 (m, 2H), 3.26-3.22 (m, 2H), 2.28-2.16 (m, 1H), 2.16-2.13 (m, 1H), 1.96-1.83 (m, 2H), 1.28 (s, 9H).

Ethyl (S)-3-((5-(1-((tert-butoxycarbonyl)amino)-1,3-dihydrospiro[indene-2,4'-piperidin]-1'-yl)pyrazin-2-yl)thio)propanoate, Intermediate ED

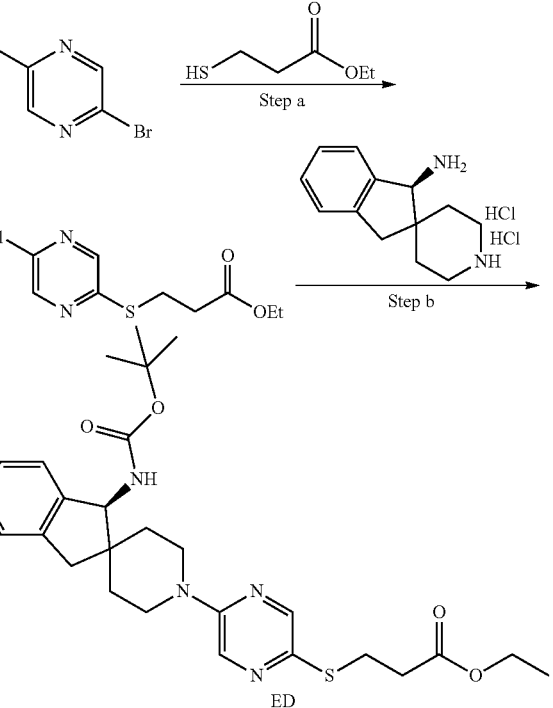

Step a: To a mixture of 2-bromo-5-chloropyrazine (46.0 g, 237 mmol) and ethyl 3-mercaptopropanoate (31.9 g, 237 mmol) in dioxane (460 mL) was added DIPEA (61.4 g, 475 mmol, 82.8 mL), Xantphos (13.7 g, 23.8 mmol) and Pd₂(dba)₃ (10.8 g, 11.8 mmol) in one portion under N₂. The mixture was stirred at 80° C. for 2 hours under N2. The mixture was then filtered and the filtrate was concentrated in vacuo. The residue was purified by column chromatography (SiO₂, petroleum ether/ethyl acetate=1:0 to 5:1, petroleum ether:ethyl acetate=10:1) to afford ethyl 3-((5-chloropyrazin-2-yl)thio)propanoate (52.0 g, 192 mmol, 81% yield) as a light yellow oil. LC-MS (ESI⁺) m/z: 247.1 (M+H)⁺; ¹HNMR (400 MHz, CDCl₃): δ 8.37 (s, 1H), 8.20 (s, 1H), 4.18-4.13 (m, 2H), 3.40 (t, J=7.0 Hz, 2H), 2.73 (t, J=7.2 Hz, 2H), 1.25 (t, J=7.2 Hz, 3H).

Step b: To a solution of ethyl 3-((5-chloropyrazin-2-yl)thio)propanoate (18.0 g, 72.9 mmol) and (S)-1,3-dihydrospiro[indene-2,4'-piperidin]-1-amine, (20.1 g, 72.9 mmol, Intermediate I, 2HCl) in NMP (180 mL) was added Na₂CO₃ (30.9 g, 291 mmol) at 25° C. Then the mixture was heated to 130° C. and stirred for 1 h. The mixture was then cooled to 25° C. To the reaction mixture was next added (Boc)₂O (7.00 g, 32.1 mmol, 7.37 mL) and DIPEA (4.15 g, 32.1 mmol, 5.59 mL) and the mixture was stirred at 25° C. for 1 h. Then to the mixture was added additional (Boc)₂O (10.5 g, 48.2 mmol, 11.1 mL) and DIPEA (5.28 g, 40.9 mmol, 7.12 mL) at 25° C. and the mixture was stirred for another 1 h. The reaction mixture was then poured into water (600 mL) where precipitate formed, and the mixture was extracted with EtOAc (200 mL×2). The combined organic layer was washed with 0.500 N HCl (250 mL×2), brine (200 mL), dried over Na$_2$SO$_4$, filtered and concentrated. The residue was purified by column chromatography on silica gel (eluted with petroleum ether:ethyl acetate=1:0 to 3:1) to afford ethyl (S)-3-((5-(1-((tert-butoxycarbonyl)amino)-1,3-dihydrospiro[indene-2,4'-piperidin]-1'-yl)pyrazin-2-yl)thio)propanoate (7.50 g, 14.3 mmol, 20% yield) as yellow oil. LC-MS (ESI$^+$) m/z: 513.3 (M+H)$^+$; $^1$HNMR (400 MHz, CDCl$_3$): δ 8.071 (d, J=2.80 Hz, 2H), 7.29-7.27 (m, 1H), 7.25-7.20 (m, 3H), 5.01 (d, J=10.0 Hz, 1H), 4.67 (s, 1H), 4.18-4.11 (m, 4H), 3.29-3.26 (m, 2H), 3.19-3.16 (m, 2H), 3.05 (d, J=16.0 Hz 1H), 2.79 (d, J=15.6 Hz 1H), 2.69-2.65 (m, 2H), 1.94-1.93 (m, 1H), 1.74-1.71 (m, 2H), 1.46 (s, 9H), 1.28-1.24 (m, 3H).

8-(((5-bromopyrazin-2-yl)oxy)methyl)quinoline, Intermediate EE

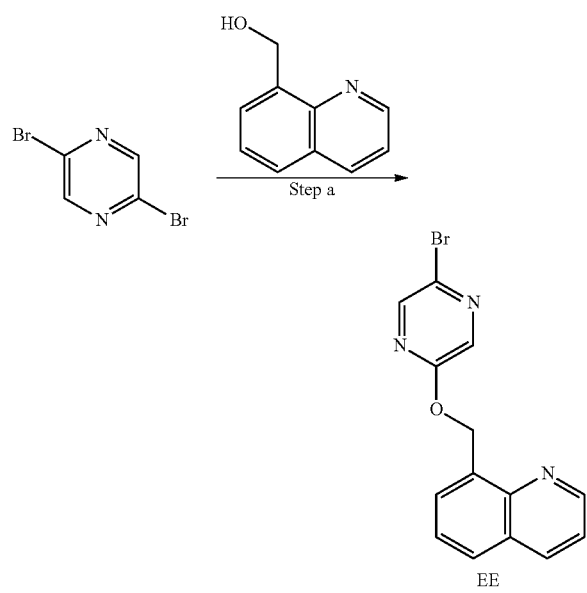

Step a: To a solution of quinolin-8-ylmethanol (1.70 g, 10.7 mmol) in DMF (65.0 mL) was added NaH (428 mg, 10.7 mmol, 60% dispersion in mineral oil) at 0° C. Then the mixture was stirred at 0° C. for 1 h. Next, 2,5-dibromopyrazine (2.12 g, 8.91 mmol) was added to the mixture. Then the reaction mixture was stirred at 0 to 25° C. for 6 h. The mixture was then poured into water (200 mL) and extracted with ethyl acetate (150 mL×3). The organic layer was washed with brine (100 mL×2), dried over Na$_2$SO$_4$, filtered and concentrated. The residue was purified by column chromatography (SiO$_2$, petroleum ether/ethyl acetate=1/0~10/1, R$_f$=0.40) to give 8-(((5-bromopyrazin-2-yl)oxy)methyl)quinoline (1.80 g, 5.68 mmol, 64% yield) as a yellow solid. LC-MS (ESI$^+$) m/z: 318.0 (M+H)$^+$; $^1$HNMR (400 MHz, CDCl$_3$): δ 8.98-8.97 (m, 1H), 8.24-8.14 (m, 3H), 7.87-7.82 (m, 2H), 7.57 (t, J=7.6 Hz, 1H), 7.48-7.45 (m, 1H), 6.13 (s, 2H).

Tert-butyl (S)-(1,3-dihydrospiro[indene-2,4'-piperidin]-1-yl)carbamate, Intermediate EF

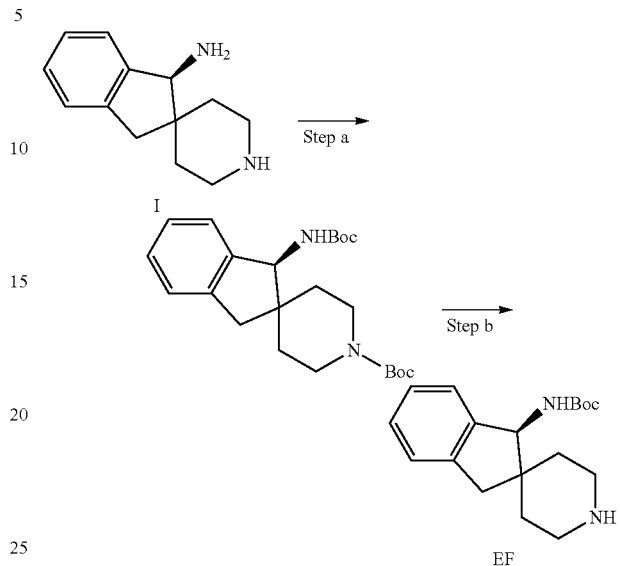

Step a: To a solution of (S)-1,3-dihydrospiro[indene-2,4'-piperidin]-1-amine (3.00 g, 10.9 mmol, Intermediate I, 2HCl) in DMF (30.0 mL) was added NaOH (2.44 g, 61.0 mmol). The mixture was stirred at 25° C. for 5 min, then to the mixture was added Boc$_2$O (7.14 g, 32.7 mmol, 7.51 mL). The mixture was stirred at 25° C. for another 16 h. The mixture was then poured into water (100 mL) and extracted with ethyl acetate (50.0 mL×3). The combined organic layer was washed with saturated NH$_4$Cl solution (50.0 mL×2), brine (50.0 mL×2), dried over Na$_2$SO$_4$, filtered and concentrated under reduced pressure to give tert-butyl (S)-1-((tert-butoxycarbonyl)amino)-1,3-dihydrospiro[indene-2,4'-piperidine]-1'-carboxylate (5.07 g, quant. crude yield) as a white solid. LC-MS (ESI$^+$) m/z: 495.4 (M−172)$^+$; $^1$HNMR (400 MHz, CDCl$_3$): δ 7.25-7.19 (m, 4H), 4.96 (br d, J=10.0 Hz, 1H), 4.63 (br d, J=9.2 Hz, 1H), 3.93 (br d, J=12.4 Hz, 2H), 3.05-2.96 (m, 3H), 2.73 (br d, J=15.6 Hz, 1H), 1.83-1.76 (m, 1H), 1.63-1.59 (m, 3H), 1.49-1.47 (m, 18H).

Step b: To a solution of tert-butyl (S)-1-((tert-butoxycarbonyl)amino)-1,3-dihydrospiro[indene-2,4'-piperidine]-1'-carboxylate (4.00 g, 9.94 mmol) in DCM (40.0 mL) was added ZnBr$_2$ (4.48 g, 19.9 mmol, 995 uL) and the mixture was stirred at 25° C. for 12 h. Then, additional ZnBr$_2$ (2.24 g, 9.94 mmol, 497 uL) was added to the mixture and the mixture was stirred at 25° C. for another 4 h. The mixture was then concentrated under reduced pressure to remove DCM. The residue was dissolved with MeOH (50.0 mL) and adjusted pH to 8~9 with ammonium hydroxide (25.0 mL, 28% solution). The mixture was then filtered and the filtrate was concentrated to give a residue. The residue was purified by reversed-phase HPLC (FA condition) to give tert-butyl (S)-(1,3-dihydrospiro[indene-2,4'-piperidin]-1-yl)carbamate (1.50 g, 50% yield) as a red solid. LC-MS (ESI$^+$) m/z: 303.2 (M+H)$^+$; $^1$HNMR (400 MHz, CDCl$_3$): δ 7.24-7.19 (m, 4H), 4.95 (br d, J=9.6 Hz, 1H), 4.71 (br d, J=10.0 Hz, 1H), 4.33 (br s, 2H), 3.14-2.87 (m, 5H), 2.73 (br d, J=15.6 Hz, 1H), 1.91-1.84 (m, 1H), 1.69 (br d, J=14.0 Hz, 1H), 1.49 (s, 9H), 1.35 (br d, J=14.0 Hz, 1H).

(3R)-3H-8'-azaspiro[benzofuran-2,3'-bicyclo[3.2.1]octan]-3-amine, Intermediate EG

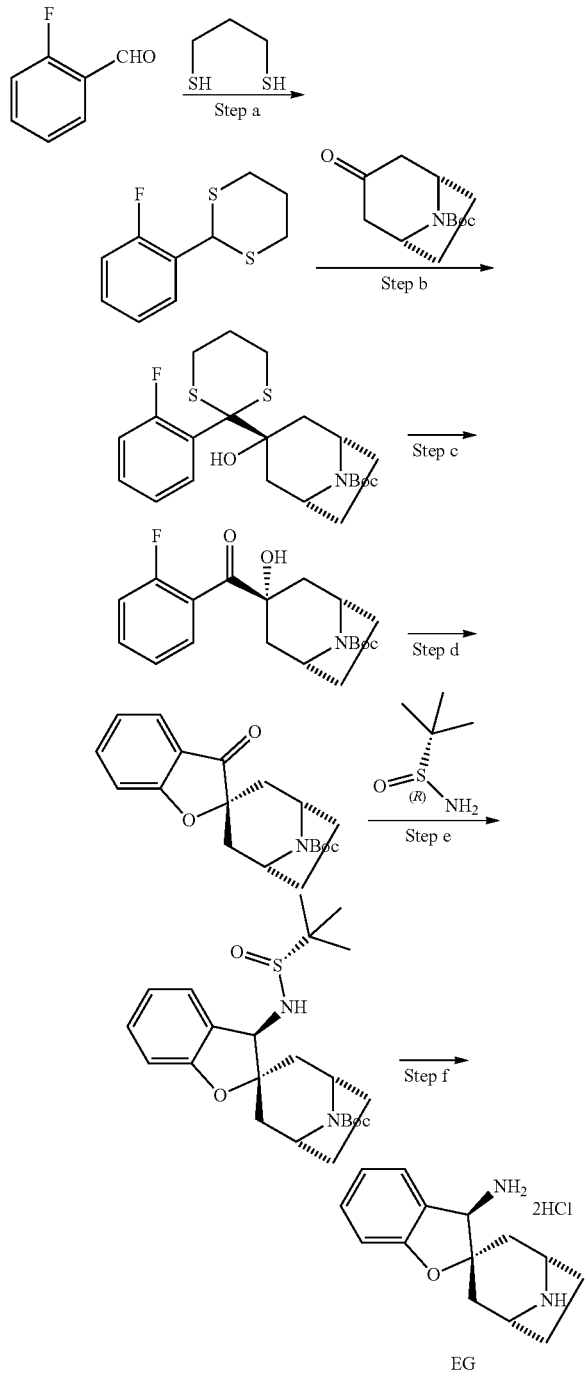

Step a: Boron trifluoride-Et₂O (103 mL, 402 mmol, 48% solution) was added dropwise to a solution of 2-fluorobenzaldehyde (200 g, 168 mL, 1.61 mol) and propane-1,3-dithiol (176 g, 163 mL, 1.63 mol) in DCM (1.00 L) at 0° C. The reaction was then stirred at 25° C. for 1 h. The reaction mixture was then poured into water (200 mL) and the organic phase was separated and the aqueous phase was extracted with dichloromethane (200 mL×2). The combined organic fractions were washed with brine (200 mL), dried over anhydrous Na₂SO₄, then filtered and evaporated under reduced pressure. The crude product was triturated with petroleum ether (1.00 L) at 25° C. for 1 h, and then filtered. The residue was dried in vacuo to give 2-(2-fluorophenyl)-1,3-dithiane (302 g, 1.40 mol, 87% yield) as a white solid. ¹HNMR (400 MHz, CDCl₃): δ 7.64-7.62 (m, 1H), 7.31-7.25 (m, 1H), 7.18-7.16 (m, 1H), 7.08-7.06 (m, 1H), 5.57 (s, 1H), 3.15-3.09 (m, 2H), 2.94-2.90 (m, 2H), 2.20-2.16 (m, 1H), 1.97-1.93 (m, 2H).

Step b: A mixture of 2-(2-fluorophenyl)-1,3-dithiane (100 g, 464 mmol) in THF (500 mL) was cooled to −50~−40° C. for 30 min with stirring under N2 atmosphere. To the mixture was added LDA (2.00 M, 278 mL) dropwise at −50-40° C. for 30 min. Then the mixture was warmed to −30~20° C. for 1 hr. Next the mixture was cooled to −50~40° C. again and to the mixture was added a solution of tert-butyl (1R,5S)-3-oxo-8-azabicyclo[3.2.1]octane-8-carboxylate (109 g, 487 mmol, CAS #185099-67-6) dropwise in THF (200 mL) for 1 hr. After addition, the mixture was stirred at −50~−40° C. for another 1 hr. The mixture was warmed to 0° C. and it was quenched with sat. NH₄Cl (500 mL) at 25° C. and extracted with ethyl acetate (500 mL×2) at 25° C. The organic phase was dried with Na₂SO₄, filtered and the filtrate was concentrated in vacuo to give a crude product. The crude product was triturated with petroleum ether (500 mL) at 25° C. for 1 hr, and then filtered. The residue was dried in vacuo to give tert-butyl (1R,3r,5S)-3-(2-(2-fluorophenyl)-1,3-dithian-2-yl)-3-hydroxy-8-azabicyclo[3.2.1]octane-8-carboxylate (182 g, 414 mmol, 89% yield) as a white solid. LC-MS (ESI⁺) m/z: 340.1 (M−99)⁺; ¹HNMR (400 MHz, CDCl₃): δ 8.03 (t, J=7.6 Hz, 1H), 7.32-7.31 (m, 1H), 7.18 (t, J=7.2 Hz, 1H), 7.10-7.05 (m, 1H), 4.21 (s, 1H), 4.13 (s, 1H), 2.82-2.76 (m, 2H), 2.62-2.55 (m, 4H), 2.42 (s, 1H), 2.06-2.01 (m, 2H), 1.84-1.81 (m, 4H), 1.89-1.55 (m, 1H), 1.46 (s, 9H).

Step c: A mixture of tert-butyl (1R,3r,5S)-3-(2-(2-fluorophenyl)-1,3-dithian-2-yl)-3-hydroxy-8-azabicyclo[3.2.1]octane-8-carboxylate (180 g, 409 mmol), Pyridine (66.1 mL, 818. mmol), Py.HBr₃ (26.4 g, 81.8 mmol) in water (90.0 mL) and DCM (900 mL) was added TBAB (261 g, 818 mmol) at 0° C. The mixture was stirred at 25° C. for 2 hrs. The reaction mixture was then poured into water (2.00 L) and extracted with DCM (1.00 L×3). The combined organic layers were washed with brine (1.00 L), dried over anhydrous Na₂SO₄, then filtered and evaporated under reduced pressure to give a residue. Tert-butyl (1R,3r,5S)-3-(2-fluorobenzoyl)-3-hydroxy-8-azabicyclo[3.2.1]octane-8-carboxylate (140 g, 98% crude yield) was obtained as a yellow gum and was used into the next step without further purification.

Step d: A mixture of tert-butyl (1R,3r,5S)-3-(2-fluorobenzoyl)-3-hydroxy-8-azabicyclo[3.2.1]octane-8-carboxylate (140 g, 400 mmol) in dioxane (700 mL) was added t-BuOK (67.4 g, 601 mmol) at 20° C. The mixture was then stirred at 70° C. for 2 hrs. The reaction mixture was poured into water (1.50 L) and extracted with ethyl acetate (1.00 L×2). The combined organic layers were washed with brine (1.00 L), dried over anhydrous Na₂SO₄, then filtered and evaporated under reduced pressure. The residue was purified by column chromatography (SiO₂, petroleum ether/ethyl acetate=50/1 to 20/1) to give tert-butyl (1'R,2r,5'S)-3-oxo-3H-8'-azaspiro[benzofuran-2,3'-bicyclo[3.2.1]octane]-8'-carboxylate (45.0 g, 135 mmol, 34% yield) as a yellow solid. LC-MS (ESI⁺) m/z: 352.1 (M+Na)⁺; ¹HNMR (400 MHz, CDCl₃): δ 7.63 (t, J=8 Hz, 2H), 7.12-7.00 (m, 2H), 4.40-4.29 (m, 2H), 2.33-2.23 (m, 4H), 2.04 (d, J=4.8 Hz, 2H), 1.55 (d, J=13.6 Hz, 2H), 1.51 (s, 9H).

Step e: To a solution of tert-butyl (1'R,2r,5'S)-3-oxo-3H-8'-azaspiro[benzofuran-2,3'-bicyclo[3.2.1]octane]-8'-carboxylate (45.0 g, 135 mmol) in 2-Me-THF (90.0 mL) were added Ti(OEt)$_4$ (92.7 g, 406 mmol, 84.3 mL) and (R)-2-methylpropane-2-sulfinamide (32.8 g, 271 mmol) at 25° C. Then the mixture was stirred at 90° C. for 96 hrs. The reaction mixture was then cooled to −5~0° C., and LiBH$_4$ (3.25 g, 149 mmol, 1.10 eq) was added carefully portionwise keeping the temperature at −5-0° C. over 1 hr, then the mixture was stirred at −5-0° C. for 2 hours. The solution was quenched by addition methanol (2.00 mL) at 0~10° C. and 2-[2-[bis(2-hydroxyethyl)amino]ethyl-(2-hydroxyethyl)amino]ethanol (50.0 g) was added, and the mixture was stirred for 1 hr at 20° C. Then, to the mixture was added 0.5 N HCl to adjust the pH=1.00, and the mixture was extracted with ethyl acetate (2.00 L×3). The combined organic layers were washed with brine (1.00 L), dried over anhydrous Na$_2$SO$_4$, then filtered through SiO$_2$ using petroleum ether/ethyl acetate=1:1 (2 L×3) and evaporated under reduced pressure. Then, to the crude residue was added methyl tert-butyl ether (100 mL) and the mixture was stirred at 20° C. for 2 hrs, then filtered and the cake was dried to give tert-butyl (1'R,2r,3R,5'S)-3-(((R)-tert-butylsulfinyl)amino)-3H-8'-azaspiro[benzofuran-2,3'-bicyclo[3.2.]octane]-8'-carboxylate (28.0 g, 64.1 mmol, 47% yield) as a white solid. LC-MS (ESI$^+$) m/z: 335.0 (M−99)$^+$; $^1$HNMR (400 MHz, DMSO): δ 7.27 (d, J=7.6 Hz, 1H), 7.20 (t, J=7.2 Hz, 1H), 6.91-6.87 (m, 1H), 6.80 (d, J=8 Hz, 1H), 6.03 (d, J=10 Hz, 1H), 4.47 (d, J=10 Hz, 1H), 4.21 (s, 1H), 4.14 (s, 1H), 2.33-2.31 (m, 1H), 2.16 (d, J=7.2 Hz, 2H), 1.97-1.76 (m, 5H), 1.43 (s, 9H), 1.15 (s, 9H).

Step f: To a solution of tert-butyl (1'R,2r,3R,5'S)-3-(((R)-tert-butylsulfinyl)amino)-3H-8'-azaspiro[benzofuran-2,3'-bicyclo[3.2.1]octane]-8'-carboxylate (10.0 g, 22.9 mmol) in MeOH (20.0 mL) was added HCl/MeOH (4.00 M, 50.0 mL). The mixture was stirred at 20° C. for 2 hrs. The reaction mixture was concentrated under reduced pressure to remove methanol to give a residue. The residue was triturated with ethyl acetate (50.0 mL) at 20° C. for 30 min. Then the mixture was filtered and the filtrate cake was concentrated under reduced pressure to give (1'R,2r,3R,5'S)-3H-8'-azaspiro[benzofuran-2,3'-bicyclo[3.2.1]octan]-3-amine (6.5 g, 21.4 mmol, 94% yield, 2HCl) as a white solid. LC-MS (ESI$^+$) m/z: 231.1 (M+H)$^+$; $^1$HNMR (400 MHz, DMSO): δ 9.74 (s, 1H), 9.36 (s, 1H), 8.98 (s, 3H), 7.71 (d, J=7.6 Hz, 1H), 7.36-7.33 (m, 1H), 7.02-6.95 (m, 2H), 4.53 (s, 1H), 4.19 (s, 1H), 4.00 (s, 1H), 3.16 (s, 2H), 2.82-2.77 (m, 1H), 2.41-2.40 (m, 1H), 2.27-2.23 (m, 2H), 2.14-2.02 (m, 3H), 1.87 (d, J=15.2 Hz, 1H).

3-chloro-4-((5-chloropyrazin-2-yl)thio)pyridin-2-amine, Intermediate EH

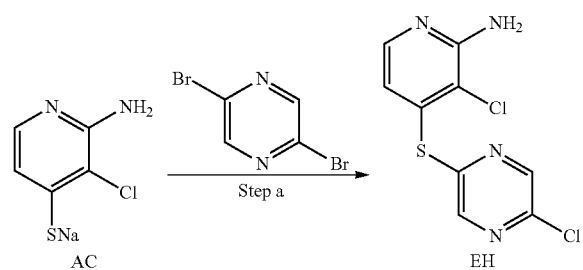

Step a: To a solution of 2-bromo-5-chloropyrazine (20.0 g, 103 mmol) and sodium 2-amino-3-chloropyridine-4-thiolate (18.9 g 103 mmol, Intermediate AC) in dioxane (80.0 mL) was added Pd$_2$(dba)$_3$ (3.79 g, 4.14 mmol), Xantphos (2.99 g, 5.17 mmol) and DIPEA (26.7 g, 207 mmol, 36.0 mL) at 25° C. Then the mixture was heated to 80° C. and stirred at 80° C. for 3 h. The mixture was then cooled to 25° C. and filtered. The filter cake was washed with ethyl acetate (50.0 mL×3). The combined organic layer was concentrated to give a residue. The residue was purified by column chromatography twice (SiO$_2$, petroleum ether:ethyl acetate=20:1 to 3:1, TLC: petroleum ether:ethyl acetate=3:1, R$_f$=0.25) to afford 3-chloro-4-((5-chloropyrazin-2-yl)thio)pyridin-2-amine (3.00 g, 10.4 mmol, 10% yield) as a yellow solid. LC-MS (ESI$^+$) m/z: 273.0 (M+H)$^+$; $^1$HNMR (400 MHz, CDCl$_3$): δ 8.50 (d, J=1.2 Hz, 1H), 8.34 (d, J=1.2 Hz, 1H), 7.87 (d, J=4.0 Hz, 1H), 8.55 (d, J=4.0 Hz, 1H), 8.52 (s, 2H).

Ethyl 3-chloro-6-(2,3-dichlorophenyl)-5-methylpyrazine-2-carboxylate, Intermediate EI

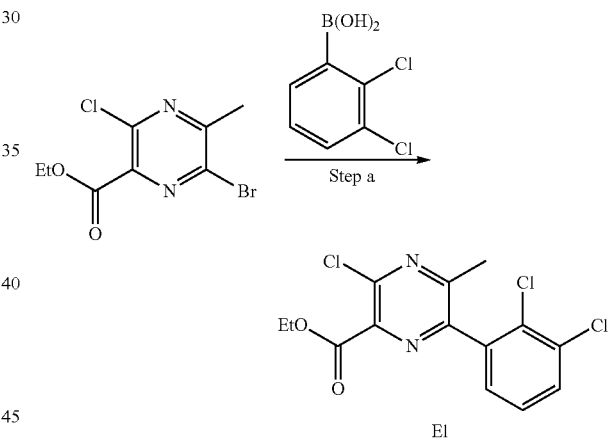

Step a: To a solution of ethyl 6-bromo-3-chloro-5-methylpyrazine-2-carboxylate (1.00 g, 3.58 mmol, CAS #2091009-80-0) and K$_2$CO$_3$ (494 mg, 3.58 mmol) in ACN (10.0 mL) and H$_2$O (2.00 mL) was added (2,3-dichlorophenyl)boronic acid (887 mg, 4.65 mmol) and Pd(dppf)Cl$_2$ (262 mg, 358 umol) at 25° C. The solution was heated to 80° C. and stirred for 2 h. The reaction mixture was then quenched by addition water (20.0 mL) and extracted with ethyl acetate (20.0 mL×3). The combined organic layers were washed with saturated NaCl (20.0 mL), dried over Na$_2$SO$_4$, filtered and concentrated under reduced pressure to give red oil. The residue was purified by silica gel chromatography (SiO$_2$, petroleum ether/ethyl acetate=100/1 to 0/1) to give ethyl 3-chloro-6-(2,3-dichlorophenyl)-5-methylpyrazine-2-carboxylate (683 mg, 1.98 mmol, 55% yield) as a white solid. LC-MS (ESI$^+$) m/z: 345.0/347.0 (M+H)$^+$.

2-Chloro-N,6-dimethylisonicotinamide, Intermediate EJ

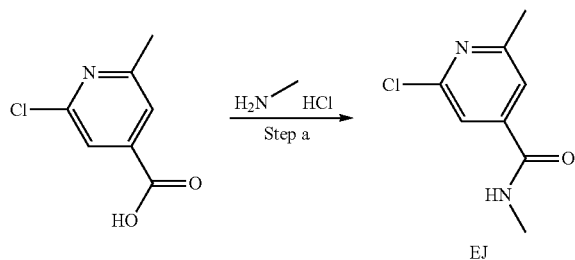

Step a: To the stirred solution of 2-chloro-6-methylisonicotinic acid (500 mg, 2.91 mmol, CAS #25462-85-5), methanamine hydrochloride (984 mg, 14.6 mmol) and TEA (2.03 mL, 14.6 mmol,) in DMF (20.0 mL) was added HATU (2.22 g, 5.83 mmol). The reaction mixture was stirred at 15° C. for 2 h. The reaction mixture was then poured into H$_2$O (50.0 mL) and extracted with ethyl acetate (30.0 mL×3). The combined organic layers were washed with brine (30.0 mL×3), dried over Na$_2$SO$_4$, filtered and concentrated. The residue was purified by column chromatography (petroleum ether/ethyl acetate=50/1~2/1, R$_f$=0.35) to give 2-chloro-N,6-dimethylisonicotinamide (900 mg, crude) as a yellow oil. LC-MS (ESI$^+$) m/z: 185.0 (M+H)$^+$; $^1$HNMR (400 MHz, CDCl$_3$): δ 7.44 (s, 1H), 7.41 (s, 1H), 6.37 (br s, 1H), 3.02 (d, J=4.4 Hz, 3H), 2.59 (s, 3H).

Tert-butyl (S)-(1'-(4-iodo-3-methylpyridin-2-yl)-1,3-dihydrospiro[indene-2,4'-piperidin]-1-yl)carbamate, Intermediate EK

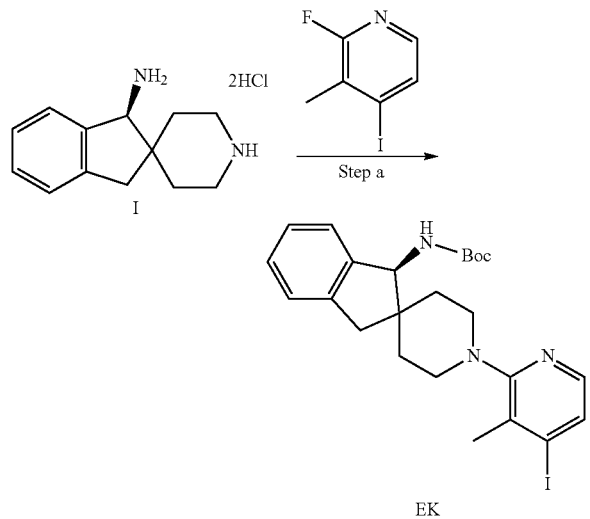

Step a: To the stirred solution of 2-fluoro-4-iodo-3-methylpyridine (1.00 g, 4.22 mmol, CAS #153034-80-1) and DIPEA (2.94 mL, 16.9 mmol) in NMP (5.00 mL) was added (S)-1,3-dihydrospiro[indene-2,4'-piperidin]-1-amine (1.39 g, 5.06 mmol, 2HCl, Intermediate I) at 20° C. The mixture was stirred at 120° C. for 14 h. Then more DIPEA (2.00 mL) was added and the reaction mixture was stirred at 130° C. for 14 h. Next, Boc$_2$O (1.38 g, 6.33 mmol, 1.45 mL) was added at 15° C. and the reaction mixture was stirred at 15° C. for 4 h. The reaction mixture was then diluted with H$_2$O (20.0 mL) and extracted with ethyl acetate (30.0 mL×3). The combined organic layers were washed with brine (20.0 mL×2), dried over Na$_2$SO$_4$, filtered and concentrated under reduced pressure to give a residue. The residue was purified by column chromatography (petroleum ether/ethyl acetate=1/0-5/1, R$_f$=0.50) to give the crude product (600 mg) as a light yellow oil. The oil was purified by reverse MPLC (FA condition) to give tert-butyl (S)-(1'-(4-iodo-3-methylpyridin-2-yl)-1,3-dihydrospiro[indene-2,4'-piperidin]-1-yl)carbamate (110 mg, 212 umol, 5% yield) as a yellow gum. LC-MS (ESI$^+$) m/z: 520.1 (M+H)$^+$; $^1$HNMR (400 MHz, CDCl$_3$): δ 7.73 (d, J=5.2 Hz, 1H), 7.39 (d, J=5.2 Hz, 1H), 7.31-7.29 (m, 1H), 7.24-7.20 (m, 3H), 5.01 (d, J=10.0 Hz, 1H), 4.68 (d, J=10.4 Hz, 1H), 3.31 (d, J=10.8 Hz, 2H), 3.07-2.90 (m, 4H), 2.80 (d, J=16.0 Hz, 1H), 2.41 (s, 3H), 2.12-2.07 (m, 1H), 1.86-1.80 (m, 1H), 1.73-1.67 (m, 1H), 1.51 (s, 9H).

Tert-butyl (S)-(1'-(4-iodo-6-methylpyridin-2-yl)-1,3-dihydrospiro[indene-2,4'-piperidin]-1-yl)carbamate, Intermediate EL

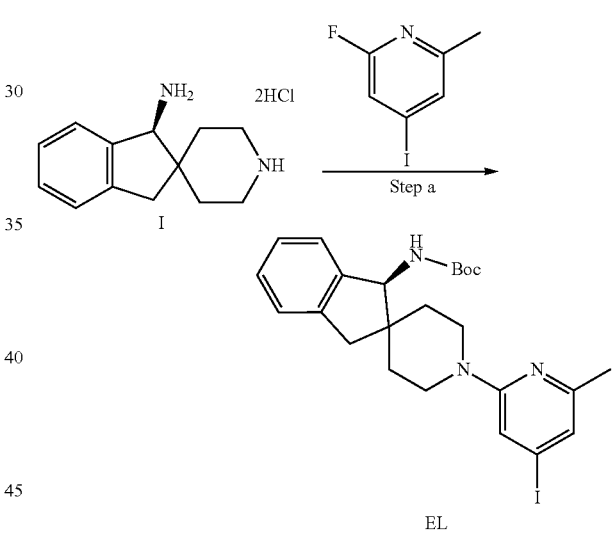

Step a: To a solution of 2-fluoro-4-iodo-6-methylpyridine (800 mg, 3.38 mmol, CAS #884494-45-5) and (S)-1,3-dihydrospiro[indene-2,4'-piperidin]-1-amine (1.11 g, 4.05 mmol, Intermediate I, 2HCl) in NMP (10.0 mL) was added DIPEA (2.35 mL, 13.50 mmol) at 25° C., then the mixture was stirred at 120° C. for 24 h. Then, additional (S)-1,3-dihydrospiro[indene-2,4'-piperidin]-1-amine (464 mg, 1.69 mmol, Intermediate I, 2HCl) and DIPEA (1.18 mL, 6.75 mmol) were added with stirring at 120° C. for 3 h. Next, (Boc)$_2$O (1.10 g, 5.06 mmol, 1.16 mL) was added to the mixture with stirring, then the reaction was stirred at 25° C. for 12 h. The reaction mixture was poured into water (100 mL), and then the aqueous phase was extracted with ethyl acetate (100 mL×2). The combined organic phase was washed with brine (100 mL×3), dried over Na$_2$SO$_4$, filtered and concentrated in vacuo. The crude product was purified by column chromatography (100-200 mesh silica gel, petroleum ether/ethyl acetate=100/1 to 20/1, Product R$_f$=0.48) to afford tert-butyl (S)-(1'-(4-iodo-6-methylpyridin-2-yl)-1,3- dihydrospiro[indene-2,4'-piperidin]-1-yl)carbamate (860 mg, 49% yield) as a yellow solid. LC-MS (ESI⁺) m/z: 520.1 (M+H)⁺.

Tert-butyl (S)-(1'-(3-bromo-5-methylphenyl)-1,3-dihydrospiro[indene-2,4'-piperidin]-1-yl)carbamate, Intermediate EM

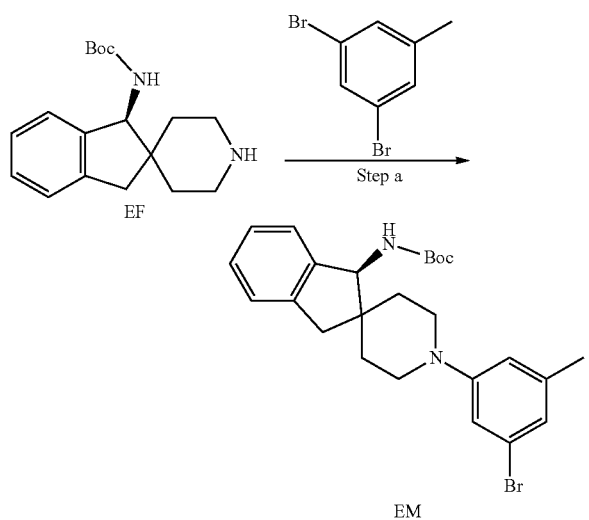

Step a: To a solution of 1,3-dibromo-5-methylbenzene (450 mg, 1.80 mmol, CAS #1611-92-3), tert-butyl (S)-(1,3-dihydrospiro[indene-2,4'-piperidin]-1-yl)carbamate (327 mg, 1.08 mmol, Intermediate EF) and Cs₂CO₃ (1.76 g, 5.40 mmol) in dioxane (2 mL) was added Xantphos (208 mg, 360 umol) and Pd₂(dba)₃ (165 mg, 180 umol) under N2, then the mixture was stirred at 100° C. for 4 h. The reaction mixture was poured into water (100 mL), then the aqueous phase was extracted with ethyl acetate (100 mL×2). The combined organic phase was washed with brine (100 mL×2), dried over Na₂SO₄, filtered and concentrated in vacuo to give a crude product, which was purified by silica gel chromatography (100-200 mesh silica gel, petroleum ether/ethyl acetate=100/1 to 5/1, R$_f$=0.45) to afford tert-butyl (S)-(1'-(3-bromo-5-methylphenyl)-1,3-dihydrospiro[indene-2,4'-piperidin]-1-yl)carbamate (180 mg, 35% yield) as yellow oil. LC-MS (ESI⁺) m/z: 471.1 (M+H)⁺; ¹HNMR (400 MHz, CDCl₃): δ 7.63-7.65 (m, 2H), 7.53-7.58 (m, 2H), 7.12 (s, 1H), 7.08 (s, 1H), 6.86-6.88 (m, 1H), 3.72 (s, 3H), 3.51-3.54 (m, 1H), 3.02 (s, 3H), 2.88-2.90 (m, 2H), 2.72-2.74 (m, 2H), 2.27-2.30 (m, 4H), 1.27-1.55 (m, 9H).

6-Chloro-8-(trifluoromethyl)-[1,2,4]triazolo[4,3-b]pyridazine, Intermediate EN

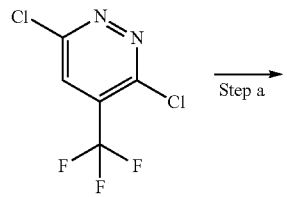

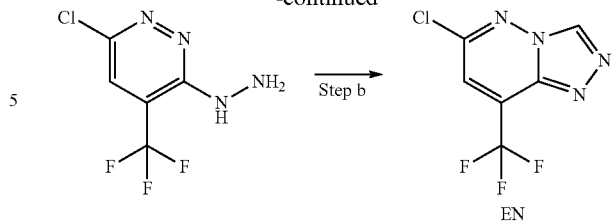

Step a: To a mixture of 3,6-dichloro-4-(trifluoromethyl)pyridazine (4.50 g, 20.7 mmol, CAS #1057672-68-0) in EtOH (45.0 mL) was added TEA (3.18 mL, 22.8 mmol) and NH₂NH₂·H₂O (4.86 g, 97.1 mmol, 4.72 mL), and the mixture was stirred at 85° C. for 3 h. The mixture was concentrated under reduced pressure to give a residue. The residue was purified by prep-HPLC (FA condition) to give 6-chloro-3-hydrazineyl-4-(trifluoromethyl)pyridazine (1.10 g, 5.18 mmol, 25% yield) as a brown solid. LC-MS (ESI⁺) m/z: 213.1 (M+H)⁺; ¹HNMR (400 MHz, MeOD): δ 7.75 (s, 1H).

Step b: To a solution of 6-chloro-3-hydrazineyl-4-(trifluoromethyl)pyridazine (1.10 g, 5.18 mmol, FA) in HCOOH (11.0 mL), and the mixture was stirred at 100° C. for 3 h. The mixture was concentrated under reduced pressure to remove HCOOH, then the residue was poured into aqueous NaHCO₃ (30.0 mL) and extracted with ethyl acetate (20.0 mL×3). The combined organic layers were washed with brine (30.0 mL), and concentrated under reduced pressure to give 6-chloro-8-(trifluoromethyl)-[1,2,4]triazolo[4,3-b]pyridazine (950 mg, 4.27 mmol, 83% yield) as a brown solid. LC-MS (ESI⁺) m/z: 223.0 (M+H)⁺; ¹HNMR (400 MHz, MeOD): δ 9.59 (s, 1H), 7.94 (s, 1H).

6-Bromo-8-(1-methyl-1H-pyrazol-5-yl)imidazo[1,2-a]pyridine, Intermediate EO

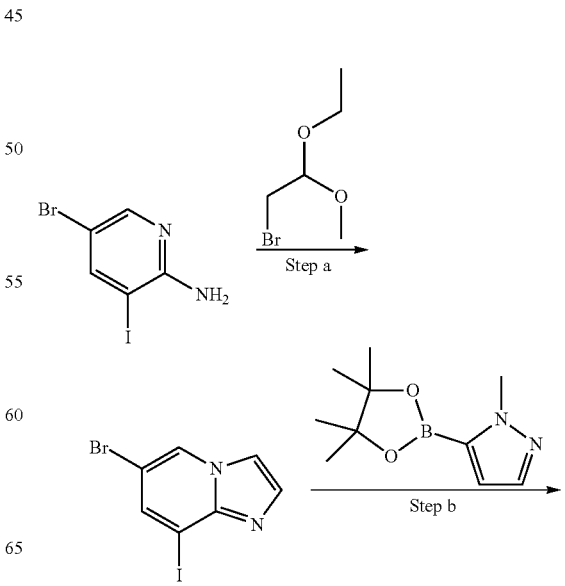

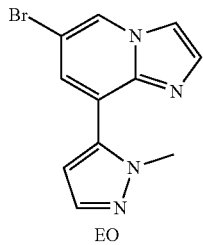

EO

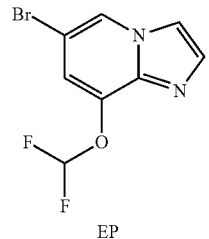

EP

Step a: To a mixture of 5-bromo-3-iodopyridin-2-amine (10.0 g, 33.5 mmol, CAS #381233-96-1) and 2-bromo-1,1-diethoxyethane (7.91 g, 40.1 mmol, 6.04 mL) in EtOH (100 mL) was added HCl (10.0 M, 20.0 mL), and the reaction mixture was stirred at 75° C. for 16 h. The reaction mixture was concentrated under reduced pressure to remove EtOH, the residue was diluted with $H_2O$ (200 mL) and the mixture was adjusted to pH=9 with aqueous $NaHCO_3$. The residue was purified by column chromatography ($SiO_2$, petroleum ether/ethyl acetate=10/1 to 1/1, $R_f$=0.21) to give 6-bromo-8-iodoimidazo[1,2-a]pyridine (3.40 g, 10.5 mmol, 32% yield) as a yellow solid. LC-MS ($ESI^+$) m/z: 322.9 $(M+H)^+$; $^1$HNMR (400 MHz, MeOD): δ 8.72 (d, J=1.6 Hz, 1H), 7.98-7.97 (d, J=1.2 Hz, 1H), 7.88 (s, 1H), 7.61 (d, J=1.2 Hz, 1H).

Step b: A mixture of 6-bromo-8-iodoimidazo[1,2-a]pyridine (1.20 g, 3.72 mmol), 1-methyl-5-(4,4,5,5-tetramethyl-1,3,2-dioxaborolan-2-yl)-1H-pyrazole (773 mg, 3.72 mmol, CAS #847818-74-0), $K_2CO_3$ (770 mg, 5.57 mmol), Pd(dppf)$Cl_2$·$CH_2Cl_2$ (607 mg, 743 umol) in $H_2O$ (1.20 mL) and 1,4-dioxane (12.0 mL) was de-gassed and then heated to 60° C. for 16 h under N2. The mixture was diluted with $H_2O$ (100 mL) and extracted with ethyl acetate (100 mL×2), the combined organic layers were washed with brine (150 mL), concentrated under reduced pressure to give a residue. The residue was purified by column chromatography ($SiO_2$, petroleum ether/ethyl acetate=10/1 to 1/1, $R_f$=0.30) to give 6-bromo-8-(1-methyl-1H-pyrazol-5-yl)imidazo[1,2-a]pyridine (0.70 g, 2.53 mmol, 68% yield) as a yellow solid. LC-MS ($ESI^+$) m/z: 277.1 $(M+H)^+$; $^1$HNMR (400 MHz, MeOD): δ 8.86-8.85 (d, J=1.6 Hz, 1H), 7.96 (s, 1H), 7.63 (d, J=1.2 Hz 1H), 7.60-7.59 (d, J=2.0 Hz, 1H), 7.48 (d, J=2.0 Hz 1H), 6.57 (d, J=2.0 Hz 1H), 3.82 (s, 3H).

6-Bromo-8-(difluoromethoxy)imidazo[1,2-a]pyridine, Intermediate EP

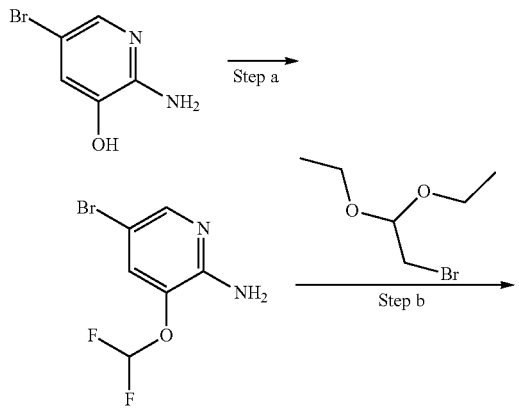

Step a: To a mixture of 2-amino-5-bromopyridin-3-ol (5.00 g, 23.5 mmol, CAS #39903-01-0) in DME (50.0 mL) was added NaOH (3.00 g, 75.0 mmol) in $H_2O$ (30.0 mL) dropwise at 10~20° C. The reaction mixture was degassed under vacuum and chloro(difluoro)methane (15.0 psi) was passed through the reaction mixture at 10~20° C. and the mixture was stirred for 16 h. The reaction mixture poured into $H_2O$ (100 mL), then extracted with ethyl acetate (50.0 mL×4). The combined organic layers were washed with brine (100 mL), dried over $Na_2SO_4$, and concentrated under reduce pressure to get a residue. The residue was purified by column chromatography ($SiO_2$, petroleum ether/ethyl acetate=I/O to 0/1) to give 5-bromo-3-(difluoromethoxy)pyridin-2-amine (1.70 g, 6.20 mmol, 26% yield) as a yellow solid. LC-MS ($ESI^+$) m/z: 238.7 $(M+H)^+$.

Step b: To a mixture of 5-bromo-3-(difluoromethoxy)pyridin-2-amine (1.00 g, 4.18 mmol) in EtOH (10.0 mL) was added 2-bromo-1,1-diethoxyethane (1.07 g, 5.44 mmol, 818 uL) and HBr (7.45 g, 30.4 mmol, 5.00 mL, 33% in HOAc), and the mixture was stirred at 90° C. for 16 h. The mixture was concentrated under reduced pressure to remove EtOH, and the residue was dissolved into ethyl acetate (50.0 mL) and washed with $NaHCO_3$ (50 mL) and brine (50.0 mL). The organic layer was dried with $Na_2SO_4$, then concentrated under reduced pressure to give 6-bromo-8-(difluoromethoxy)imidazo[1,2-a]pyridine (900 mg, 3.42 mmol, 82% yield) as a brown solid. LC-MS ($ESI^+$) m/z: 265.1 $(M+H)^+$; $^1$HNMR (400 MHz, MeOD): δ 8.67 (s, 1H), 7.98 (d, 1H), 7.67 (s, 1H), 7.29 (s, 1H), 7.46-7.10 (m, 1H).

Tert-butyl (S)-(1'-(6-bromopyridin-3-yl)-1,3-dihydrospiro[indene-2,4'-piperidin]-1-yl)carbamate, Intermediate EO

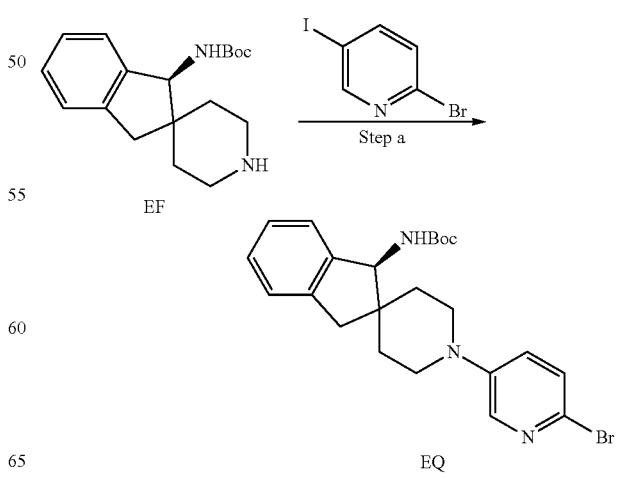

Step a: A mixture of tert-butyl (S)-(1,3-dihydrospiro[indene-2,4'-piperidin]-1-yl)carbamate (1.00 g, 3.31 mmol, Intermediate EF), 2-bromo-5-iodopyridine (1.03 g, 3.64 mmol), Cs$_2$CO$_3$ (3.23 g, 9.92 mmol), Pd$_2$(dba)$_3$ (303 mg, 331 umol) and RuPhos (308 mg, 661 umol) in DMSO (20.0 mL) was degassed and purged with N2 three times, and then the mixture was stirred at 100° C. for 3.5 h under N2 atmosphere. The reaction was poured into H$_2$O, then filtered and the filter cake was collected. The residue was purified by column chromatography (SiO$_2$, petroleum ether:ethyl acetate=1:0 to 0:1, R$_f$=0.45) to give tert-butyl (S)-(1'-(6-bromopyridin-3-yl)-1,3-dihydrospiro[indene-2,4'-piperidin]-1-yl)carbamate (740 mg, 49% yield) as an orange solid. LC-MS (ESI$^+$) m/z: 458.2 (M+H)$^+$; $^1$HNMR (400 MHz, CDCl$_3$): δ 8.04 (d, J=3.2 Hz, 2H), 7.33-7.28 (m, 2H), 7.25-7.19 (m, 3H), 7.12-7.09 (m, 1H), 5.02 (d, J=10 Hz, 1H), 4.66 (d, J=9.6 Hz, 1H), 3.58-3.50 (m, 2H), 3.04-2.93 (m, 3H), 2.76 (d, J=15.6 Hz, 1H), 2.08-2.01 (m, 1H), 1.86-1.75 (m, 2H), 1.49 (s, 9H).

Sodium (S)-5-(1-((tert-butoxycarbonyl)amino)-1,3-dihydrospiro[indene-2,4'-piperidin]-1'-yl)pyridine-2-thiolate, Intermediate ER 2,4'-piperidin]-1'-yl)pyridin-2-yl)thio)propanoate (1.10 g, 1.83 mmol, 93% yield) as a yellow oil. LC-MS (ESI$^+$) m/z: 512.2 (M+H)$^+$; $^1$HNMR (400 MHz, CDCl$_3$): δ 8.19 (s, 1H), 7.29-7.23 (m, 4H), 7.21-7.11 (m, 2H), 5.02 (d, J=10 Hz, 1H), 4.66 (d, J=9.6 Hz, 1H), 4.19-4.13 (m, 2H), 3.74-3.54 (m, 2H), 3.39-3.60 (m, 2H), 3.00-2.77 (m, 3H), 2.75-2.71 (m, 3H), 2.05 (s, 1H), 1.87-1.84 (m, 2H), 1.57 (s, 9H), 1.49-1.24 (m, 3H).

Step b: To a solution of (S)-3-((5-(1-((tert-butoxycarbonyl)amino)-1,3-dihydrospiro[indene-2,4'-piperidin]-1'-yl)pyridin-2-yl)thio)propanoate (0.50 g, 977 umol) in THF (5.00 mL) was added the solution of EtONa (99.7 mg, 1.47 mmol) in EtOH (1.00 mL) at 0° C. The mixture was stirred at 0° C. for 0.5 h, then warmed to 25° C. and stirred at 25° C. for 2 h. The mixture was then concentrated under vacuum to give sodium (S)-5-(1-((tert-butoxycarbonyl)amino)-1,3-dihydrospiro[indene-2,4'-piperidin]-1'-yl)pyridine-2-thiolate (423 mg, quant. crude yield) as a red solid. LC-MS (ESI$^+$) m/z: 412.2 (M−23+2H)$^+$.

Sodium (R)-5-(3-((tert-butoxycarbonyl)amino)-3H-spiro[benzofuran-2,4'-piperidin]-1'-yl)pyrazine-2-thiolate, Intermediate ES

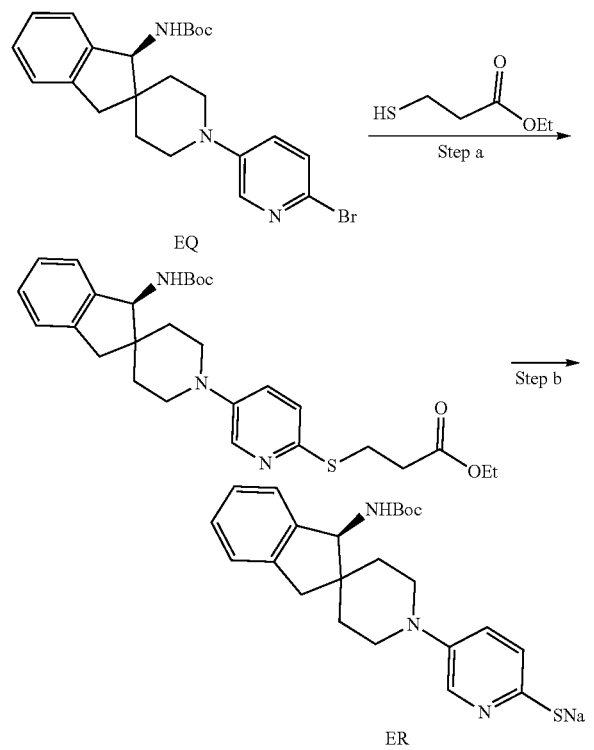

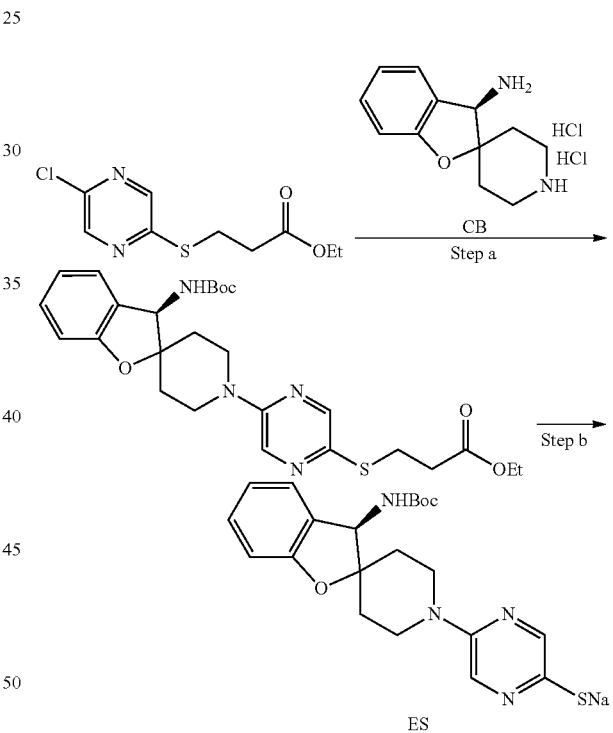

Step a: A mixture of tert-butyl (S)-(1'-(6-bromopyridin-3-yl)-1,3-dihydrospiro[indene-2,4'-piperidin]-1-yl)carbamate (900 mg, 1.96 mmol, Intermediate EQ), ethyl 3-mercaptopropanoate (316 mg, 2.36 mmol), Pd$_2$(dba)$_3$ (89.9 mg, 98.1 umol), Xantphos (113 mg, 196 umol), DIPEA (761 mg, 5.89 mmol, 1.03 mL) and dioxane (10.0 mL) was stirred at 80° C. for 2 h under N2. The mixture was then filtered and the solution was concentrated in vacuo. The residue was purified by column chromatography (SiO$_2$, petroleum ether: ethyl acetate=10:1 to 3:1, R$_f$=0.3) to give ethyl (S)-3-((5-(1-((tert-butoxycarbonyl)amino)-1,3-dihydrospiro[indene- Step a: To a solution of ethyl 3-((5-chloropyrazin-2-yl)thio)propanoate (2.00 g, 8.11 mmol, synthesized via Step a of Intermediate ED) and (R)-3H-spiro[benzofuran-2,4'-piperidin]-3-amine dihydrochloride (2.25 g, 8.11 mmol, Intermediate CB) in NMP (20.0 mL) was added Na$_2$CO$_3$ (3.44 g, 32.4 mmol) at 25° C. Then the mixture was heated to 130° C. and stirred at 130° C. for 1 h. Next, the mixture was cooled to 25° C. and Boc$_2$O (1.95 g, 8.92 mmol, 2.05 mL) and DIPEA (1.15 g, 8.92 mmol, 1.55 mL) were added and the mixture was stirred at 25° C. for 12 h. Then the mixture was poured into water (100 mL), and extracted with ethyl acetate (100 mL×2). The combined organic layer was washed with 0.5 N HCl solution (50.0 mL), saturated NaHCO$_3$ solution (50.0 mL), brine (50.0 mL), then dried over Na₂SO₄, filtered and concentrated. The residue was purified by column chromatography (SiO₂, petroleum ether/ethyl acetate=1/0~3/1, Product $R_f$=0.40) to give ethyl (R)-3-((5-(3-((tert-butoxycarbonyl)amino)-3H-spiro[benzofuran-2,4'-piperidin]-1'-yl)pyrazin-2-yl)thio)propanoate (600 mg, 1.15 mmol, 14% yield) as yellow oil. LC-MS (ESI⁺) m/z: 515.2 (M+H)⁺; ¹HNMR (400 MHz, CDCl₃): δ 8.09 (d, J=10.8 Hz, 2H), 7.32 (d, J=7.6 Hz, 1H), 7.24 (d, J=7.6 Hz, 1H), 6.93 (t, J=7.4 Hz, 1H), 6.83 (d, J=8.0 Hz, 1H), 5.02 (d, J=8.8 Hz, 1H), 4.71 (d, J=8.8 Hz, 1H), 4.22-4.16 (m, 1H), 4.13-4.08 (m, 2H), 3.47-3.42 (m, 2H), 3.28 (t, J=7.2 Hz, 2H), 2.69 (t, J=7.2 Hz, 2H), 1.97-1.92 (m, 4H), 1.45 (s, 9H), 1.40 (s, 1H), 1.27 (t, J=7.2 Hz, 3H).

Step b: To a solution of ethyl (R)-3-((5-(3-((tert-butoxycarbonyl)amino)-3H-spiro[benzofuran-2,4'-piperidin]-1'-yl)pyrazin-2-yl)thio)propanoate (350 mg, 680 umol) in THF (5.00 mL) was added a solution of EtONa (69.4 mg, 1.02 mmol, 8.52 uL) in EtOH (1.00 mL) at 0° C. Then the mixture was stirred at 0° C. for 0.5 h and was allowed to warm to 25° C. and stirred for 1.5 h. The mixture was concentrated under vacuum to give sodium (R)-5-(3-((tert-butoxycarbonyl)amino)-3H-spiro[benzofuran-2,4'-piperidin]-1'-yl)pyrazine-2-thiolate (290 mg, quant. crude yield) as a yellow solid. LC-MS (ESI⁺) m/z: 415.2 (M−23+2H)⁺.

Tert-butyl ((1'R,2r,3R,5'S)-8'-(5-bromopyrazin-2-yl)-3H-8'-azaspiro[benzofuran-2,3'-bicyclo[3.2.1]octan]-3-yl)carbamate, Intermediate ET

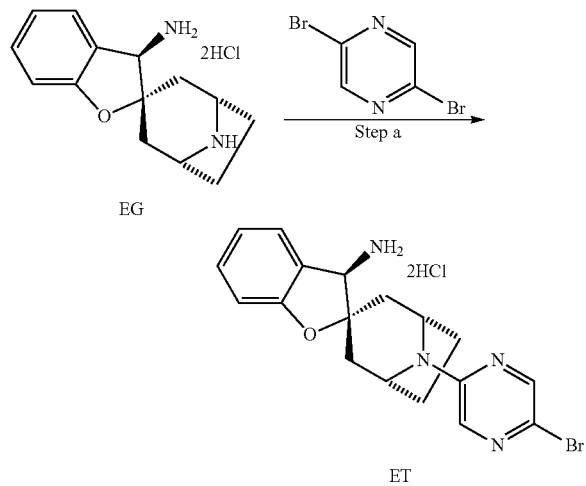

Step a: To a solution of 2,5-dibromopyrazine (1.00 g, 4.20 mmol) and (1'R,2r,3R,5'S)-3H-8'-azaspiro[benzofuran-2,3'-bicyclo[3.2.1]octan]-3-amine (1.53 g, 5.04 mmol, Intermediate EG, 2HCl) in DMSO (10.0 mL) was added diisopropylamine (3.40 g, 33.6 mmol, 4.75 mL) at 25° C. Then the mixture was heated to 100-110° C. and the mixture was stirred at 100-110° C. for 3 h. The mixture was cooled to 25° C. and (Boc)₂O (1.65 g, 7.57 mmol, 1.74 mL) was added to the mixture and the mixture was stirred at 25° C. for 6 h. The mixture was diluted with H₂O (40.0 mL) and extracted with ethyl acetate (40.0 mL×3). The combined organic layers were washed with brine (30.0 mL), dried over Na₂SO₄, filtered and concentrated under reduced pressure to give a residue. The residue was purified by column chromatography (SiO₂, petroleum ether:ethyl acetate=20:1 to 16:1, $R_f$=0.50) to afford tert-butyl ((1'R,2r,3R,5'S)-8'-(5-bromopyrazin-2-yl)-3H-8'-azaspiro[benzofuran-2,3'-bicyclo[3.2.1]octan]-3-yl)carbamate (1.60 g, 3.14 mmol, 75% yield) as a light yellow solid. LC-MS (ESI⁺) m/z: 487.2 (M+H)⁺.

Sodium 5-((1'R,2r,3R,5'S)-3-((tert-butoxycarbonyl)amino)-3H-8'-azaspiro[benzofuran-2,3'-bicyclo[3.2.1]octan]-8'-yl)pyrazine-2-thiolate, Intermediate EU

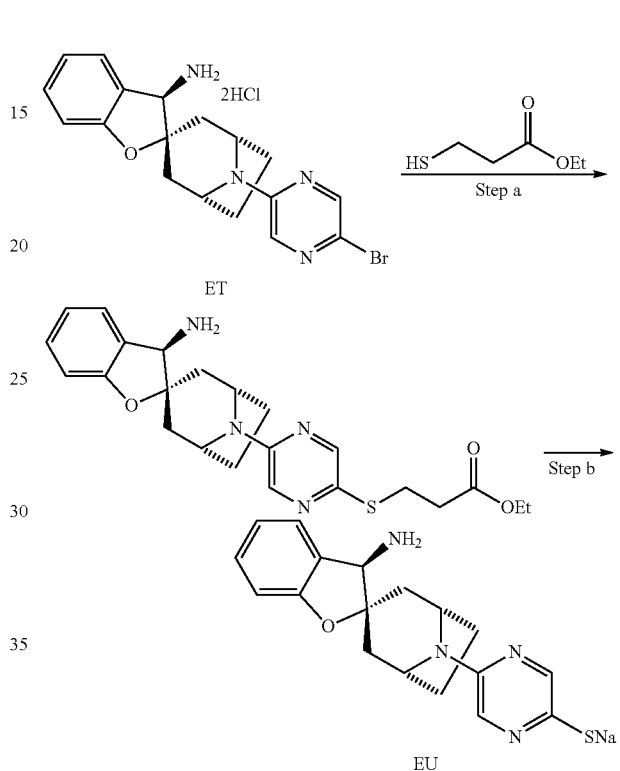

Step a: A mixture of tert-butyl ((1'R,2r,3R,5'S)-8'-(5-bromopyrazin-2-yl)-3H-8'-azaspiro[benzofuran-2,3'-bicyclo[3.2.1]octan]-3-yl)carbamate (1.50 g, 2.92 mmol, Intermediate ET), ethyl 3-mercaptopropanoate (392 mg, 2.92 mmol), Pd₂(dba)₃ (134 mg, 146 umol), XantPhos (169 mg, 292 umol) and DIPEA (756 mg, 5.85 mmol, 1.02 mL) in dioxane (15.0 mL) was degassed and purged with N₂ three times, and the mixture was stirred at 80° C. for 2 h under N₂ atmosphere. The mixture was then filtered through diatomite, and the reaction mixture was concentrated under reduced pressure to remove dioxane. The residue was purified by prep-HPLC (NH₃.H₂O condition) to afford ethyl 3-((5-((1'R,2r,3R,5'S)-3-((tert-butoxycarbonyl)amino)-3H-8'-azaspiro[benzofuran-2,3'-bicyclo[3.2.1]octan]-8'-yl)pyrazin-2-yl)thio)propanoate (1.40 g, 2.59 mmol, 78% yield) as a white solid. LC-MS (ESI⁺) m/z: 541.6 (M+H)⁺; ¹HNMR (400 MHz, CDCl₃): δ 8.06 (s, 1H), 7.98 (s, 1H), 7.23-7.20 (m, 2H), 6.91-6.87 (m, 1H), 6.80-6.78 (m, 1H), 4.84 (d, J=9.2 Hz, 1H), 4.64-4.54 (m, 3H), 4.19-4.12 (m, 2H), 3.29-3.25 (m, 2H), 2.72-2.68 (m, 2H), 2.43-2.42 (m, 2H), 2.21-2.20 (m, 2H), 2.18-2.17 (m, 2H), 2.07-2.06 (m, 1H), 2.06-2.05 (m, 1H), 1.49-1.45 (m, 3H), 1.34 (s, 6H), 1.27 (s, 3H).

Step b: To a solution of ethyl 3-((5-((1'R,2r,3R,5'S)-3-((tert-butoxycarbonyl)amino)-3H-8'-azaspiro[benzofuran-2,3'-bicyclo[3.2.1]octan]-8'-yl)pyrazin-2-yl)thio)propanoate (500 mg, 924 umol) in THF (1.00 mL) was added the solution of EtONa (100 mg, 1.48 mmol) in EtOH (1.00 mL) at 0° C. The mixture was stirred at 0° C. for 0.5 h. Then the mixture was warmed to 25° C. and stirred at 25° C. for 1 h. Next, an additional solution of EtONa (31.4 mg, 462 umol) in EtOH (1.00 mL) was added to the mixture at 25° C. and the mixture was stirred at 25° C. for 1 h. The reaction mixture was concentrated under vacuum at 25° C. to afford sodium 5-((1'R,2r,3R,5'S)-3-((tert-butoxycarbonyl)amino)-3H-8'-azaspiro[benzofuran-2,3'-bicyclo[3.2.1]octan]-8'-yl)pyrazine-2-thiolate (400 mg, 98% crude yield) as a yellow solid. LC-MS (ESI$^+$) m/z: 441.2 (M–Na+2H)$^+$.

5-(5-chloro-6-methyl-1H-pyrazolo[3,4-b]pyrazin-1-yl)-2-methylisoquinolin-1(2H)-one, Intermediate EV

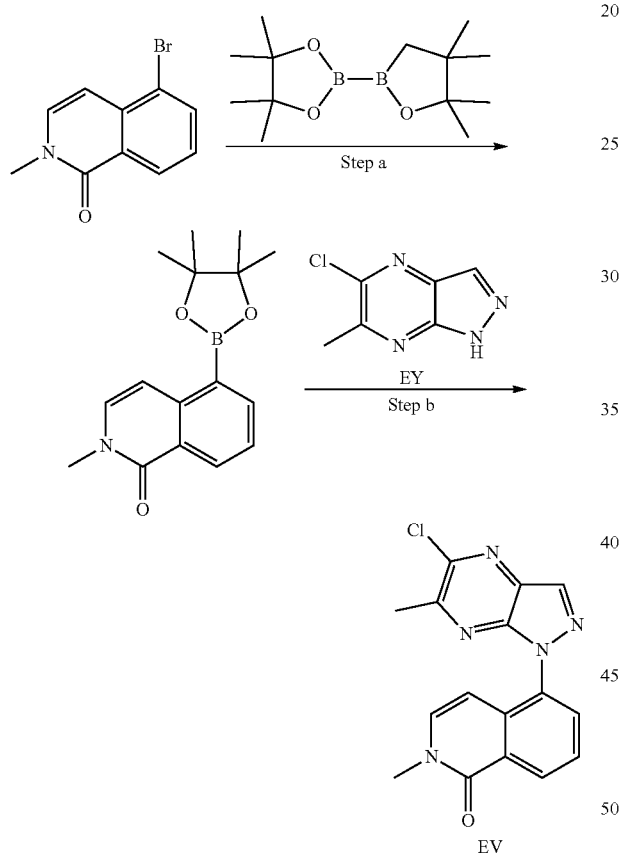

Step a: To a solution of 4,4,4,4,5,5,5',5'-octamethyl-2,2'-bi(1,3,2-dioxaborolane) (478 mg, 1.88 mmol), 5-bromo-2-methylisoquinolin-1(2H)-one (320 mg, 1.34 mmol, CAS #1367905-79-0) in dioxane (6.00 mL) was added KOAc (396 mg, 4.03 mmol) and Pd(dppf)Cl$_2$ (49.2 mg, 67.2 umol) at 25° C. The solution was degassed under vacuum and purged with N2 several times. Then the mixture was heated to 100° C. and stirred at 100° C. for 4 h. The mixture was cooled to 25° C. and concentrated under reduced pressure to give a residue. The residue was diluted with water (10.0 mL) and ethyl acetate (10.0 mL), then extracted with ethyl acetate (10.0 mL×2). The combined organic layer was washed with brine (10.0 mL), dried over Na$_2$SO$_4$, filtered and concentrated. The residue was purified by column chromatography (SiO$_2$, petroleum ether/ethyl acetate=4/1 to 3/1, R$_f$=0.40) to afford 2-methyl-5-(4,4,5,5-tetramethyl-1,3,2-dioxaborolan-2-yl)isoquinolin-1(2H)-one (302 mg, 900 umol, 6700 yield) as a white solid. LC-MS (SI) m/z: 286.1 (M+H).

Step b: To a solution of 2-methyl-5-(4,4,5,5-tetramethyl-1,3,2-dioxaborolan-2-yl)isoquinolin-1(2H)-one (350 mg, 1.04 mmol), 5-chloro-6-methyl-1H-pyrazolo[3,4-b]pyrazine (172 mg, 1.02 mmol, Intermediate EY) in DMF (5.00 mL) was added Cu(OAc)$_2$ (189 mg 1.04 mmol) and pyridine (324 mg, 4.09 mmol, 330 uL) at 25° C. Then the mixture was heated to 100-110° C. and stirred for 6 h. The mixture was cooled to 25° C. and poured in H$_2$O (5.00 mL). The mixture was then extracted with ethyl acetate (10.0 mL×3). The combined organic layers were washed with brine (5 mL), dried over Na$_2$SO$_4$, filtered and concentrated under reduced pressure to give a residue. The residue was purified by prep-HPLC (column: Phenomenex Synergi C18 150*25 * 10 um; mobile phase: [water (0.2% FA)-ACN]; B %: 33%-63%, 11 min) to afford 5-(5-chloro-6-methyl-1H-pyrazolo[3,4-b]pyrazin-1-yl)-2-methylisoquinolin-1(2H)-one (20.0 mg, 61.4 umol, 6% yield) as a yellow solid. LC-MS (ESI$^+$) m/z: 326.1 (M+H)$^+$; $^1$HNMR (400 MHz, CDCl$_3$): δ 8.64 (d, J=8.0 Hz, 1H), 8.43 (s, 1H), 7.84-7.82 (m, 1H), 7.66 (t, J=7.4 Hz, 1H), 7.06 (d, J=7.6 Hz, 1H), 6.27 (d, J=7.6 Hz, 1H), 3.63 (s, 3H), 2.76 (s, 3H).

(R)-2-methyl-N—((R)-3H-spiro[benzofuran-2,4'-piperidin]-3-yl)propane-2-sulfinamide, Intermediate EW

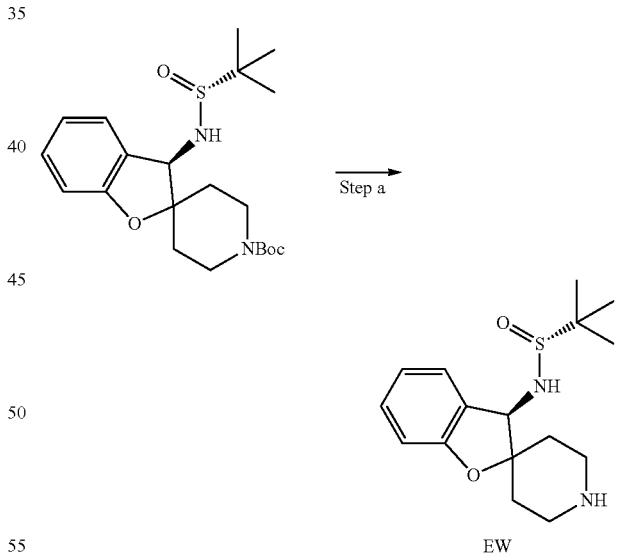

Step a: A solution of tert-butyl (3R)-3-{[(R)-2-methylpropane-2-sulfinyl]amino}-3H-spiro[1-benzofuran-2,4'-piperidine]-1'-carboxylate (500 mg, 1.22 mmol, synthesized via Steps a-b of Intermediate CB) in TFA (2 mL) and DCM (10 mL) was stirred at 30° C. for 2 hours. The reaction mixture was then concentrated under reduced pressure. The residue was diluted with DCM (10 mL) and MeOH (1 mL) and adjusted to pH=8 with solid K$_2$CO$_3$. The solution was filtered and the filtrate was concentrated under reduced pressure to give (R)-2-methyl-N—((R)-3H-spiro[benzofuran-2,4'-piperidin]-3-yl)propane-2-sulfinamide (370 mg, 1.19 mmol) as a light yellow solid. LC-MS (ESI⁺) m/z: 309.1 (M+H)⁺.

(1'S)-1',3'-dihydro-8-azaspiro[bicyclo[3.2.1]octane-3,2'-inden]-1'-amine, Intermediate EX (RTX-1136712)

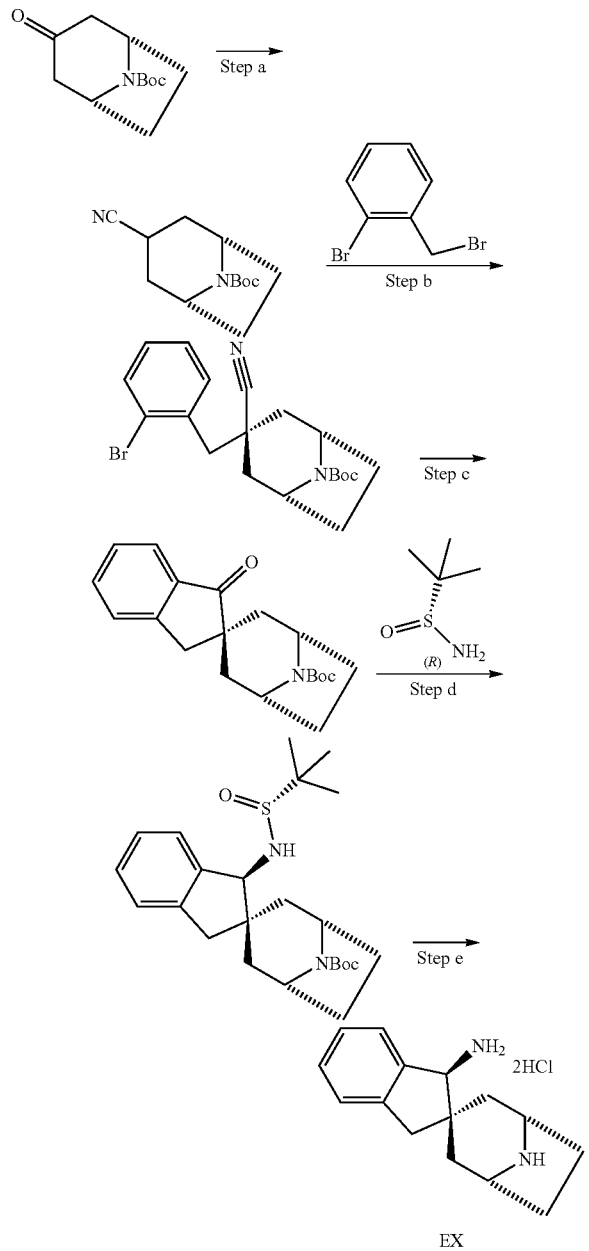

Step a: Potassium t-butoxide (373 g, 3.33 mol,) was suspended at 0° C. in DME (900 mL) under N2 atmosphere. Then tosylmethyl isocyanide (390 g, 2.00 mol) dissolved in DME (900 mL) was added dropwise keeping the temperature below 5° C. over 30 min, and was then stirred for additional 1 h at 0° C. Next, isopropanol (160 g, 2.66 mol, 204 mL) was added dropwise at 0° C. and the reaction mixture was stirred for additional 30 min. Then tert-butyl (1R,5S)-3-oxo-8-azabicyclo[3.2.1]octane-8-carboxylate (300 g, 1.33 mol) dissolved in DME (900 mL) was added dropwise maintaining the reaction temperature below 5° C. over 30 min. After the addition, the reaction mixture was stirred 1 hr at 0° C., then warmed to 20° C. and stirred for 12 hrs. The reaction mixture was then filtered over celite and the residue was washed with ethyl acetate (300 mL×2). The organic layers were combined and evaporated to give the crude product. The crude product was purified by column chromatography (SiO₂, petroleum ether/ethyl acetate=50:1 to 30:1) to give tert-butyl (1R,5S)-3-cyano-8-azabicyclo[3.2.1]octane-8-carboxylate (210 g, 888 mmol, 67% yield) as a white solid. ¹HNMR (400 MHz, CDCl₃): δ 4.22 (m, 2H), 2.99-2.90 (m, 1H), 2.00 (t, J=2.6 Hz, 4H), 1.85-1.81 (m, 2H), 1.59 (d, J=8 Hz, 4H), 1.45 (s, 9H).

Step b: To a solution of tert-butyl (1R,5S)-3-cyano-8-azabicyclo[3.2.1]octane-8-carboxylate (100 g, 423 mmol) in THF (700 mL) was added LDA (2.00 M, 253 mL) at −70° C. and the mixture was stirred at −70° C. for 1 hr. Then to the mixture was added 1-bromo-2-(bromomethyl)benzene (111 g, 444 mmol) in THF (300 mL) and the mixture was stirred at −70° C. for 2 hrs. The reaction mixture was then poured into ice saturated NH₄Cl solution (1.00 L) and extracted with ethyl acetate (1.00 L×2). The organic layer was washed with brine (1.00 L×1), dried over Na₂SO₄, filtered and concentrated under vacuum to give a residue. The residue was triturated with petroleum ether/acetate ethyl (20/1, 500 mL) to afford tert-butyl (1R,3s,5S)-3-(2-bromobenzyl)-3-cyano-8-azabicyclo[3.2.1]octane-8-carboxylate (145 g, 353 mmol, 84% yield) as a white solid. Stereochemistry was assigned arbitrarily. LC-MS (ESI⁺) m/z: 351.1 (M−55)⁺; ¹HNMR (400 MHz, CDCl₃): δ 7.59 (d, J=0.8 Hz, 1H), 7.57-7.51 (m, 1H), 7.30-7.28 (m, 1H), 7.14-7.16 (m, 1H), 4.30 (s, 1H), 4.19 (s, 1H), 3.08 (s, 2H), 2.23 (t, J=4.8 Hz, 2H), 2.05-1.93 (m, 6H), 1.44 (s, 9H).

Step c: To a solution of tert-butyl (1R,3s,5S)-3-(2-bromobenzyl)-3-cyano-8-azabicyclo[3.2.1]octane-8-carboxylate (145 g, 353 mmol) in DMA (1.00 L) and H₂O (100 mL) was added TEA (214 g, 2.12 mol, 295 mL) and PdCl₂(Amphos)₂ (5.01 g, 7.08 mmol, 5.01 mL) at 20° C. under nitrogen atmosphere. Then the mixture was heated to 100° C. and stirred at 100° C. for 18 hrs. The reaction mixture was then further heated to 130° C. and stirred at 130° C. for 24 hrs. The reaction mixture was then poured into saturated NH₄Cl solution (1.00 L) and extracted with ethyl acetate (1.00 L×2). The combined organic layers were washed with 0.50 N HCl (1.00 L), saturated NaHCO₃ solution (1.00 L) and brine (800 mL), dried over Na₂SO₄, filtered and concentrated. The residue was triturated with petroleum ether/ethyl acetate (200/1, 500 mL) and filtered to give tert-butyl (1R,3s,5S)-1'-oxo-1',3'-dihydro-8-azaspiro[bicyclo[3.2.1]octane-3,2'-indene]-8-carboxylate (108 g, 321 mmol, 91% yield) as a yellow solid. LC-MS (ESI⁺) m/z: 272.1 (M−55)⁺; ¹HNMR (400 MHz, CDCl₃): δ 7.71 (d, J=7.6 Hz, 1H), 7.58-7.52 (m, 1H), 7.35 (t, J=6.8 Hz, 2H), 4.37 (s, 1H), 4.28 (s, 1H), 3.13-2.99 (m, 2H), 2.09-1.92 (m, 6H), 1.82-1.55 (m, 2H), 1.51 (s, 9H).

Step d: To a solution of tert-butyl (1R,3s,5S)-1∝-oxo-1',3'-dihydro-8-azaspiro[bicyclo[3.2.1]octane-3,2'-indene]-8-carboxylate (100 g, 297 mmol) in Ti(OEt)₄ (330 g, 1.45 mol, 300 mL) was added (R)-2-methylpropane-2-sulfinamide (108 g, 893 mmol) at 25° C. The reaction mixture was then heated to 90° C. and stirred for 5 days. Then the reaction mixture was cooled to −5-0° C. and 2-Me-THF (200 mL) was added, followed by LiBH₄ (7.13 g, 327 mmol) carefully portionwise keep the temperature at −5-0° C. over 2 hrs, The mixture was stirred at −5-0° C. for an additional 2 hrs. The solution was quenched by addition methyl alcohol (4.00 mL) at 0-10° C. and 2-[2-[bis(2-hydroxyethyl)amino]ethyl-(2-hydroxyethyl)amino]ethanol (500 g) was added, and the mixture was stirred for 1 hr at 20° C. To the mixture was then added to 1.00 N HCl to adjust the pH=1.00, and the mixture was extracted with ethyl acetate (3.00 L× 3). The combined organic layers were washed with brine (2.00 L×1), dried over anhydrous $Na_2SO_4$, then filtered through $SiO_2$ with petroleum ether:ethyl acetate=1:1 (3.00 L×3) and evaporated under reduced pressure. The crude product was purified by column chromatography ($SiO_2$, petroleum ether/ethyl acetate=8/1 to 3/1, petroleum ether/ethyl acetate=3/1, $R_f$=0.20) to give tert-butyl (1R,1'S,3s,5S)-1'-(((R)-tert-butylsulfinyl)amino)-1',3'-dihydro-8-azaspiro[bicyclo[3.2.1]octane-3,2'-indene]-8-carboxylate (52.5 g, 120 mmol, 41% yield) as a brown gum. LC-MS (ESI$^+$) m/z: 433.2 (M+H)$^+$; $^1$HNMR (400 MHz, DMSO): δ 7.30-7.28 (m, 1H), 7.18-7.14 (m, 3H), 5.50 (d, J=4 Hz, 1H), 4.50 (d, J=5.2 Hz, 1H), 4.06-4.00 (m, 2H), 3.09 (d, J=15.2 Hz, 1H), 2.29-2.19 (m, 2H), 2.15-2.06 (m, 1H), 1.83 (s, 3H), 1.69 (s, 2H), 1.42 (s, 9H), 1.10 (s, 9H).

Step e: To a solution of tert-butyl (1R,1'S,3s,5S)-1'-(((R)-tert-butylsulfinyl)amino)-1',3'-dihydro-8-azaspiro[bicyclo[3.2.1]octane-3,2'-indene]-8-carboxylate (10.0 g, 22.9 mmol) in MeOH (25.0 mL) was added HCl/MeOH (4.00 M, 49.7 mL) and the mixture was stirred at 20° C. for 2 hrs. The reaction mixture was then concentrated under reduced pressure to remove MeOH to give a residue. The residue was triturated with dichloromethane/methanol=1/1 (50.0 mL) at 20° C. for 30 min. Then the mixture was filtered and the filtrate cake was concentrated under reduced pressure to give (1R,1'S,3s,5S)-1',3'-dihydro-8-azaspiro[bicyclo[3.2.1]octane-3,2'-inden]-1'-amine (6.50 g, 21.5 mmol, 94% yield, 2HCl) as a white solid. $^1$HNMR (400 MHz, DMSO): δ 9.61 (s, 1H), 9.44 (s, 1H), 8.64 (s, 3H), 7.60 (d, J=7.6 Hz, 1H), 7.33-7.24 (m, 3H), 4.57 (s, 1H), 3.94 (s, 1H), 3.83 (s, 1H), 3.45 (d, J=15.6 Hz, 1H), 2.59 (d, J=15.6 Hz, 1H), 2.34-2.23 (m, 1H), 2.11-2.03 (m, 2H), 2.04-1.98 (m, 4H), 1.47 (d, J=10.8 Hz, 1H).

5-Chloro-6-methyl-1H-pyrazolo[3,4-b]pyrazine, Intermediate EY

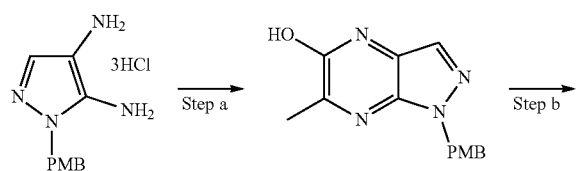

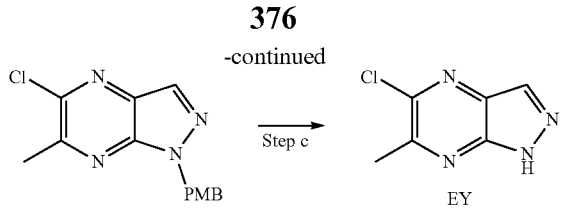

Step a: To a stirred solution of 1-(4-methoxybenzyl)-1H-pyrazole-4,5-diamine (159 g, 485 mmol) in EtOH (1.60 L) was added the solution of 2-oxopropanoic acid (42.7 g, 485 mmol, 34.2 mL) in EtOH (600 mL) dropwise at 75° C., and the reaction mixture was stirred at 75° C. for 1 h. The reaction mixture was then concentrated to give a residue. The residue was purified by column chromatography (petroleum ether/ethyl acetate=5/1-0/1, $R_f$=0.20) to afford crude product (45.0 g) as a yellow solid. The crude product was further purified by reversed-phase HPLC (0.1% FA condition) to afford 1-(4-methoxybenzyl)-6-methyl-1H-pyrazolo[3,4-b]pyrazin-5-ol (12.0 g, 40.9 mmol, 8% yield) as a yellow solid. LC-MS (ESI$^+$) m/z: 271.2 (M+H)$^+$; $^1$HNMR (400 MHz, DMSO): δ 12.14 (s, 1H), 7.46 (s, 1H), 7.18 (d, J=8.8 Hz, 2H), 6.86 (d, J=8.8 Hz 2H), 5.42 (s, 2H), 3.71 (s, 3H), 2.39 (s, 3H).

Step b: To a solution of 1-(4-methoxybenzyl)-6-methyl-1H-pyrazolo[3,4-b]pyrazin-5-ol (12.0 g, 44.4 mmol) in 1,4-dioxane (220 mL) was added $POCl_3$ (37.7 g, 246 mmol, 22.9 mL) dropwise at 0° C. The mixture was then stirred at 80° C. for 12 h. The reaction mixture was then concentrated to give a residue. The residue was purified by flash silica gel chromatography (petroleum ether/ethyl acetate=20/0-5/1, $R_f$=0.50) to afford 5-chloro-1-(4-methoxybenzyl)-6-methyl-1H-pyrazolo[3,4-b]pyrazine (6.00 g, 20.7 mmol, 47% yield) as a yellow solid. LC-MS (ESI$^+$) m/z: 289.2 (M+H)$^+$; $^1$HNMR (400 MHz, CDCl$_3$): δ 8.12 (s, 1H), 7.32 (d, J=8.4 Hz, 2H), 6.85 (d, J=6.8 Hz, 2H), 5.59 (s, 2H), 3.78 (s, 3H), 2.81 (s, 3H).

Step c: A solution of 5-chloro-1-(4-methoxybenzyl)-6-methyl-1H-pyrazolo[3,4-b]pyrazine in CF$_3$COOH (47.4 g, 416 mmol, 30.8 mL) was stirred at 70° C. for 5 h. The reaction mixture was then concentrated in vacuo and the residue was dissolved in water (200 mL). The pH was adjusted to 8 with saturated NaHCO$_3$ (200 mL) and the mixture was extracted with ethyl acetate (500 mL×3). The combined organic layers were washed with brine (200 mL×2), dried over Na$_2$SO$_4$, filtered and concentrated to afford crude product as a yellow solid. The crude product was purified by reversed-phase HPLC (0.1% HCl condition) to afford 5-chloro-6-methyl-1H-pyrazolo[3,4-b]pyrazine (1.40 g, 8.24 mmol, 40% yield) as a light yellow solid. LC-MS (ESI$^+$) m/z: 169.2 (M+H)$^+$; $^1$HNMR (400 MHz, DMSO): δ 14.10 (s, 1H), 8.34 (s, 1H), 2.69 (s, 1H).

4-(5-mercaptopyrazin-2-yl)spiro[cyclohexane-1,2'-inden]-1'(3'H)-one, Intermediate EZ

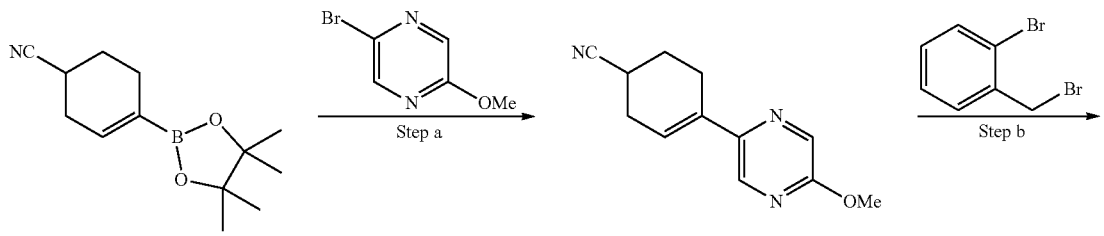

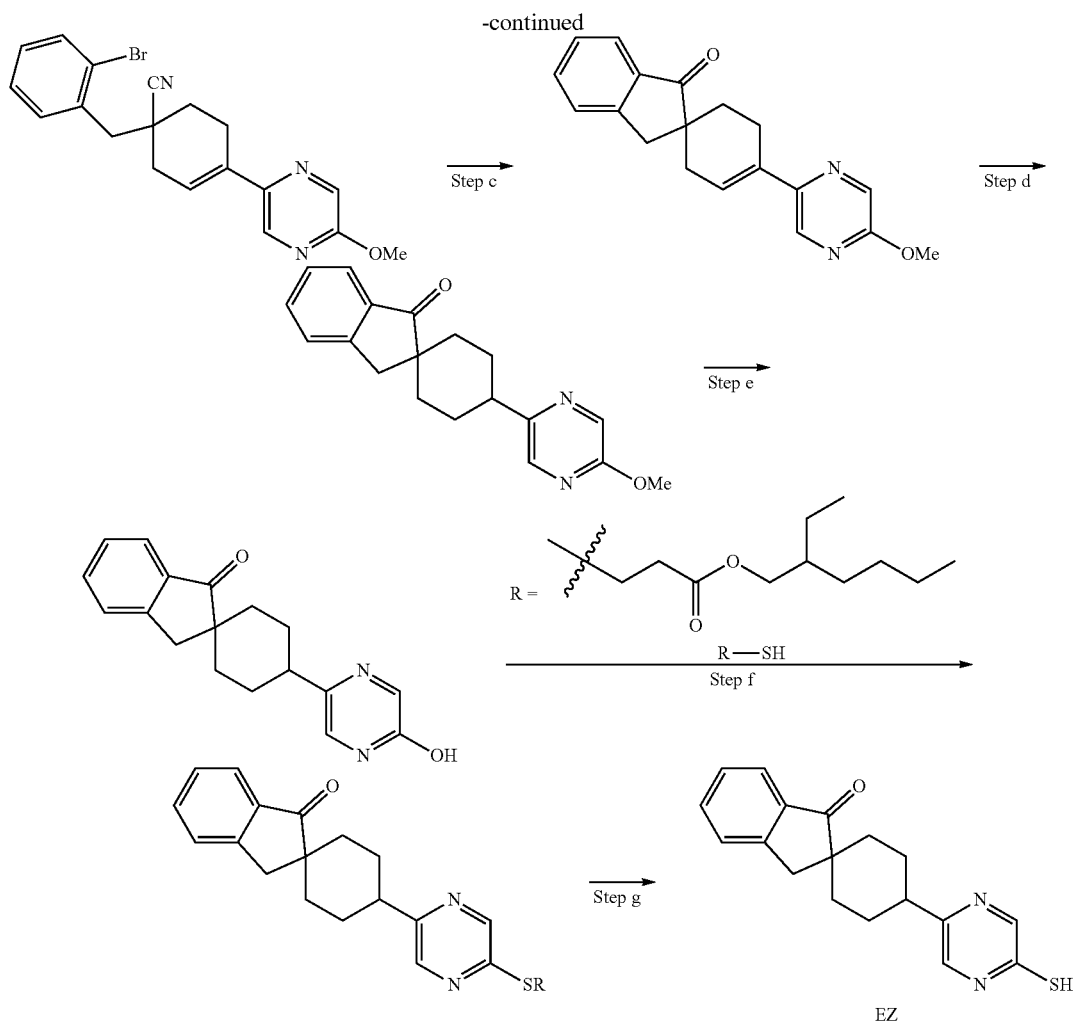

Step a: A mixture of 2-bromo-5-methoxypyrazine (5.08 g, 26.9 mmol), 4-(4,4,5,5-tetramethyl-1,3,2-dioxaborolan-2-yl)cyclohex-3-ene-1-carbonitrile (6.00 g, 25.7 mmol, CAS #1310384-20-3), $K_2CO_3$ (10.6 g, 77.1 mmol) and Pd(dppf)$Cl_2$ (1.88 g, 2.57 mmol, CAS #72287-26-4) in dioxane (150.00 mL) and $H_2O$ (15.00 mL) was stirred at 100° C. for 12 hours under $N_2$ atmosphere. The reaction mixture was then concentrated and $H_2O$ (200 mL) was added. The mixture was extracted with ethyl acetate (300 mL×3) and the combined organic layers were washed with brine (500 mL), dried over anhydrous $Na_2SO_4$, filtered and concentrated to give a residue. The residue was purified by flash silica gel chromatography (petroleum ether:ethyl acetate=100:0 to 100:30) to afford 4-(5-methoxypyrazin-2-yl)cyclohex-3-ene-1-carbonitrile (4.80 g, 87% yield) as a white solid. LC-MS (ESI$^+$) m/z: 216.0 (M+H)$^+$.

Step b: 4-(5-Methoxypyrazin-2-yl)cyclohex-3-ene-1-carbonitrile (1.90 g, 8.82 mmol) and 1-bromo-2-(bromomethyl)benzene (2.42 g, 9.70 mmol, CAS #3433-80-5) were dissolved in THF (200 mL). Then, LDA (4.85 mL, 9.70 mmol, 2M in THF) was added dropwise into the mixture at −10° C. The mixture was stirred at 0° C. for 0.5 hour, then the mixture was then warmed to 25° C. for 1 hour. Another batch of LDA (4.41 mL, 8.82 mmol, 2 M in THF) was added dropwise into the mixture at −10° C. The mixture was stirred at 0° C. for 0.5 hour, then the mixture was then warmed to 25° C. for 1 hour. The combined reaction mixture was quenched by addition of sat. $NH_4Cl$ (200 mL). The mixture was extracted with ethyl acetate (200 mL×3) and the combined organic layers were washed with brine (200 mL), dried over anhydrous $Na_2SO_4$, filtered and concentrated to give a residue. The residue was purified by flash silica gel chromatography (petroleum ether:ethyl acetate=100:0 to 100:20) to afford 1-[(2-bromophenyl)methyl]-4-(5-methoxypyrazin-2-yl)cyclohex-3-ene-1-carbonitrile (3.00 g, 89% yield) as a yellow solid. LC-MS (ESI$^+$) m/z: 383.7, 385.7 (M+H)$^+$.

Step c: 1-[(2-Bromophenyl)methyl]-4-(5-methoxypyrazin-2-yl)cyclohex-3-ene-1-carbonitrile (3.00 g, 7.80 mmol), $PdCl_2(AmPhos)_2$ (276 mg, 390 μmol, CAS #887919-35-9) and TEA (4.31 mL, 31.2 mmol) were placed into DMA (50.00 mL) and $H_2O$ (1.00 mL). The reaction mixture was evacuated and refilled three times using N2. The reaction mixture was stirred at 120° C. for 12 hours. Then the mixture was concentrated to give a residue. The residue was purified by flash silica gel chromatography (petroleum ether:ethyl acetate=100:0 to 100:20) to afford 4-(5-methoxypyrazin-2-yl)-1',3'-dihydrospiro[cyclohexane-1,2'-inden]-3-en-3'-one (2.20 g, 92% yield) as a yellow oil. LC-MS (ESI$^+$) m/z: 307.0 (M+H)$^+$.

Step d: 4-(5-Methoxypyrazin-2-yl)-1',3'-dihydrospiro[cyclohexane-1,2'-inden]-3-en-3'-one (1.60 g, 5.22 mmol) was dissolved in MeOH (90.0 mL) and THF (10.0 mL), then 10% Pd/C (160.0 mg, wet) was added. The reaction mixture was evacuated and refilled three times using $H_2$. The reaction mixture was then stirred at 25° C. for 12 hours under H2 (15 psi). The mixture was then filtered and the filtrate was concentrated to give a residue. The residue was purified by flash silica gel chromatography (petroleum ether:ethyl acetate=100:20) to afford 4-(5-methoxypyrazin-2-yl)-1',3'-dihydrospiro[cyclohexane-1,2'-inden]-3'-one (1.20 g, 75% yield) as a colorless oil. LC-MS (ESI$^+$) m/z: 308.9 (M+H)$^+$.

Step e: 4-(5-Methoxypyrazin-2-yl)-1',3'-dihydrospiro[cyclohexane-1,2'-inden]-3'-one (900.0 mg, 2.91 mmol) was placed into HBr/AcOH (33%, 15.0 mL), and the reaction mixture was stirred at 100° C. for 1 hour. Then the mixture was concentrated to give a residue. The reaction mixture was concentrated and $H_2O$ (10.0 mL) was added, then the solution was extracted with DCM (20.0 mL×3). The combined organic layers were washed with brine (30.0 mL), dried over anhydrous $Na_2SO_4$, filtered and concentrated to give a residue. The residue was purified by flash silica gel chromatography (DCM:MeOH=100:0 to 100:5) to afford 4-(5-hydroxypyrazin-2-yl)-1',3'-dihydrospiro[cyclohexane-1,2'-inden]-3'-one (80.0 mg, 58% yield) as a yellow solid. LC-MS (ESI$^+$) m/z: 295.1 (M+H)$^+$.

Step f: 4-(5-Hydroxypyrazin-2-yl)spiro[cyclohexane-1,2'-inden]-1'(3'H)-one (500 mg, 1.69 mmol) was dissolved in DMF (10 mL). BOP (2.23 g, 5.06 mmol) was added and the reaction mixture was stirred at 20° C. for 5 min. Next, 2-ethylhexyl 3-sulfanylpropanoate (575 µL, 2.53 mmol) and DBU (1.50 mL, 10.1 mmol) were added and the reaction mixture was stirred at 20° C. for 1 hour. Additional 2-ethylhexyl 3-sulfanylpropanoate (1.91 mL, 8.45 mmol) was added and the mixture was stirred at 20° C. for 12 hours. The mixture was then diluted with EtOAc (30 mL) and $H_2O$ (20 mL), and the partitioned layers were separated. The aqueous phase was extracted with ethyl acetate (20 mL×2) and the combined organic layers were washed with brine (30 mL×3), dried over anhydrous $Na_2SO_4$, filtered and concentrated to give a residue. The residue was purified by flash silica gel chromatography (petroleum ether/ethyl acetate= 100:0 to 100:15) to afford 2-ethylhexyl 3-((5-(1'-oxo-1',3'-dihydrospiro[cyclohexane-1,2'-inden]-4-yl)pyrazin-2-yl)thio)propanoate (410 mg, 49% yield) as a colorless oil. LC-MS (ESI$^+$) m/z: 495.2 (M+H)$^+$.

Step g: 2-Ethylhexyl 3-((5-(1'-oxo-1',3'-dihydrospiro[cyclohexane-1,2'-inden]-4-yl)pyrazin-2-yl)thio)propanoate (220.0 mg, 444 µmol) was dissolved in THF (1.00 mL). The reaction mixture was cooled to −78° C. and t-BuOK (1.33 mL, 1.33 mmol, 1 M in THF) was added dropwise over 10 min under N2. The reaction mixture was then stirred at −78° C. for 20 min. The reaction mixture was then diluted with DCM (30 mL) and acidified with HCl/MeOH (2 N) to pH=6 at −78° C. The mixture was washed with $H_2O$ (20 mL) and brine (20 ml). The organic layer was dried over anhydrous $Na_2SO_4$, filtered and concentrated to give 4-(5-mercaptopyrazin-2-yl)spiro[cyclohexane-1,2'-inden]-1'(3'H)-one (137.0 mg, 441 µmol, 100% crude yield) as a yellow solid. LC-MS (ESI$^+$) m/z: 311.0 (M+H)$^+$.

Tert-butyl N-[(3S)-1'-(1-methyl-6-oxo-5-sulfanyl-1,6-dihydropyrimidin-2-yl)-1,3-dihydrospiro[indene-2,4'-piperidin]-3-yl]carbamate, Intermediate FA

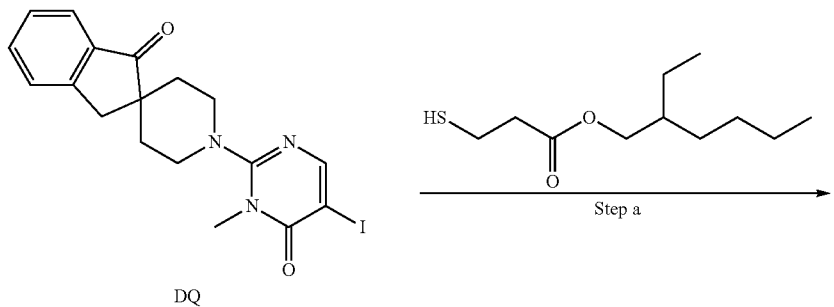

DQ

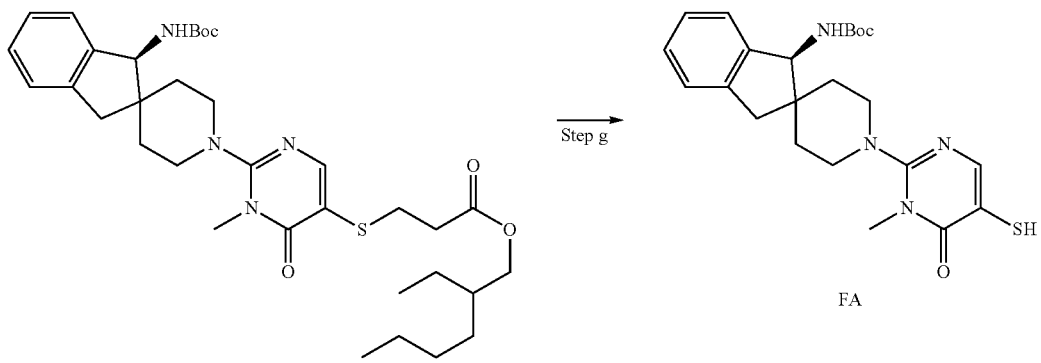

FA

Step a: A mixture of tert-butyl N-[(3S)-1'-(5-iodo-1-methyl-6-oxo-1,6-dihydropyrimidin-2-yl)-1,3-dihydrospiro[indene-2,4'-piperidin]-3-yl]carbamate (400.0 mg, 745 µmol, Intermediate DQ), Pd₂(dba)₃ (68.2 mg, 74 µmol), XantPhos (86.2 mg, 149 µmol), 2-ethylhexyl butyrate (162.0 mg, 745 µmol) and DIPEA (367 µL, 2.2 mmol) in dioxane (10.00 mL) was stirred at 100° C. for 12 hours under N2 atmosphere. The mixture was concentrated and was purified by silica gel chromatography (ethyl acetate in petroleum ether=0% to 60%) to afford 2-ethylhexyl 3-({2-[(3S)-3-{[(tert-butoxy)carbonyl]amino}-1,3-dihydrospiro[indene-2,4'-piperidin]-1'-yl]-1-methyl-6-oxo-1,6-dihydropyrimidin-5-yl}sulfanyl)propanoate (236.0 mg, 51% yield) as a yellow oil. LC-MS (ESI⁺) m/z: 627.3 (M+H)⁺.

Step b: To a mixture of 2-ethylhexyl 3-({2-[(3S)-3-{[(tert-butoxy)carbonyl]amino}-1,3-dihydrospiro[indene-2,4'-piperidin]-1'-yl]-1-methyl-6-oxo-1,6-dihydropyrimidin-5-yl}sulfanyl)propanoate (236.0 mg, 376 µmol) in anhydrous THF (1.50 mL) was added t-BuOK (1.12 mL, 1.1 mmol, 1M in THF) over 10 min at −78° C. The mixture was stirred at −78° C. for 0.5 hour under N2 atmosphere. The reaction mixture was then diluted with DCM (30 mL) and acidified with HCl/EtOAc (2 N, 1.00 mL) to pH=6 at −78° C. The mixture was washed with brine (20 mL), and the organic layer were dried over anhydrous Na₂SO₄, filtered and concentrated to give tert-butyl N-[(3S)-1'-(1-methyl-6-oxo-5-sulfanyl-1,6-dihydropyrimidin-2-yl)-1,3-dihydrospiro[indene-2,4'-piperidin]-3-yl]carbamate (120.0 mg, 72% crude yield) as a red oil. LC-MS (ESI⁺) m/z: 443.1 (M+H)⁺.

Methyl 3-[(3S)-3-{[(tert-butoxy)carbonyl]amino}-1,3-dihydrospiro[indene-2,4'-piperidin]-1'-yl]-6-sulfanylpyrazine-2-carboxylate, Intermediate FB

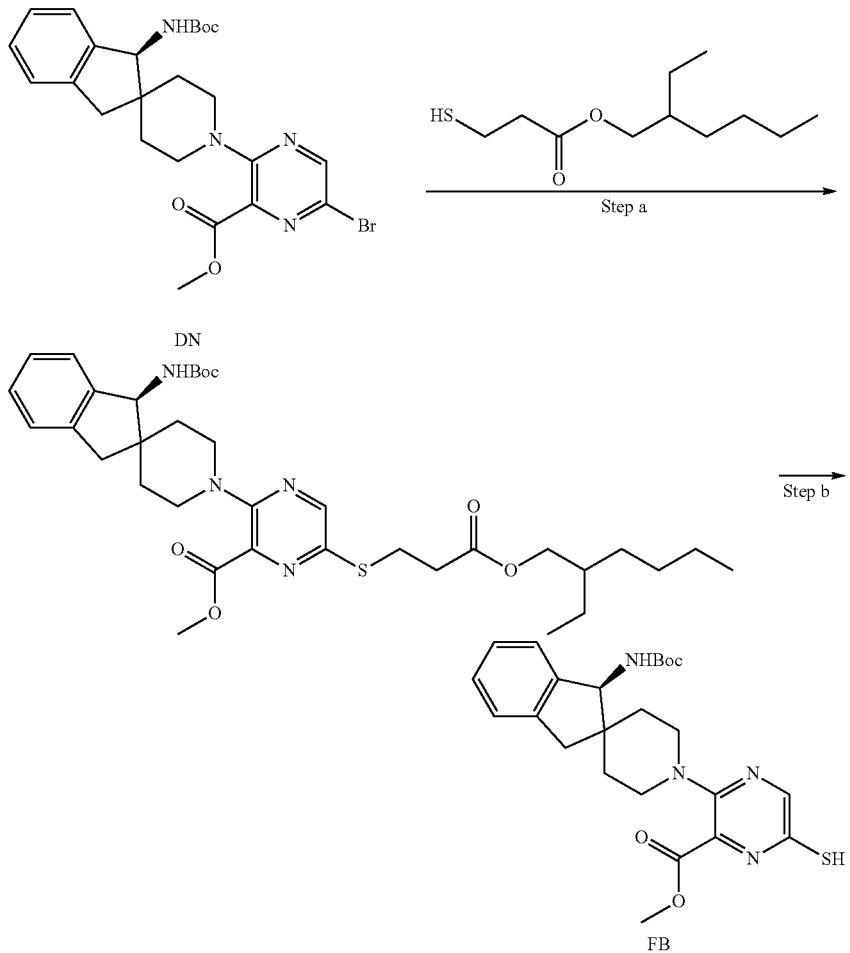

Step a: Methyl 6-bromo-3-[(3S)-3-{[(tert-butoxy)carbonyl]amino}-1,3-dihydrospiro[indene-2,4'-piperidin]-1'-yl]pyrazine-2-carboxylate (500 mg, 966 µmol, Intermediate DN), 2-ethylhexyl 3-sulfanylpropanoate (231 mg, 1.06 mmol), Pd₂(dba)₃ (88.4 mg, 96.6 umol), Xantphos (111 mg, 193 umol), and DIPEA (249 mg, 1.93 mmol) were placed into dioxane (20 mL). The reaction mixture was evacuated and refilled 3 times using N2 and then stirred at 100° C. for 10 hours. The reaction mixture was then concentrated, H₂O (20 mL) was added, and the solution was extracted with ethyl acetate (30 mL×3). The combined organic layers were washed with brine (50 mL), dried over anhydrous Na₂SO₄, filtered and concentrated to give a residue. The residue was purified by flash silica gel chromatography (petroleum ether:ethyl acetate=100:40) to afford methyl 3-[(3S)-3-{[(tert-butoxy)carbonyl]amino}-1,3-dihydrospiro[indene-2,4'-piperidin]-1'-yl]-6-({3-[(2-ethylhexyl)oxy]-3-oxopropyl}sulfanyl)pyrazine-2-carboxylate (450 mg, 71% yield) as a yellow oil. LC-MS (ESI⁺) m/z: 655.3 (M+H)⁺.

Step b: The compound of methyl 3-[(3S)-3-{[(tert-butoxy)carbonyl]amino}-1,3-dihydrospiro[indene-2,4'-piperidin]-1'-yl]-6-({3-[(2-ethylhexyl)oxy]-3-oxopropyl}sulfanyl)pyrazine-2-carboxylate (250.0 mg, 381.0 μmol) was dissolved in THF (1.5 mL). The reaction mixture was cooled to −78° C. and t-BuOK (1.14 mL, 1.1 mmol, 1 M in THF) was added dropwise over 10 min under N2. The reaction mixture was stirred at −78° C. for 0.5 hour. The reaction mixture was diluted with DCM (20 mL) and acidified with HCl/MeOH (4 N) to pH=5-6 at −78° C. The mixture was washed with H₂O (20 mL) and brine (20 ml). The organic layer were dried over anhydrous Na₂SO₄, filtered and concentrated to give 3-[(3S)-3-{[(tert-butoxy)carbonyl]amino}-1,3-dihydrospiro[indene-2,4'-piperidin]-1'-yl]-6-sulfanylpyrazine-2-carboxylate (179.0 mg, 100% crude yield).

tert-butyl N-[(3S)-1'-(1-benzyl-5-iodo-6-oxo-1,6-dihydropyrimidin-2-yl)-1,3-dihydrosniro[indene-2,4'-piperidin]-3-yl]carbamate, Intermediate FC drospiro[indene-2,4'-piperidin]-3-yl]carbamate (783.0 mg, 2.6 mmol, Intermediate EF) and TEA (1.5 mL, 10.8 mmol) were placed into DMF (15 mL). The reaction mixture was evacuated and refilled three times using N2, then the reaction mixture was stirred at 70° C. for 2 hours. The reaction mixture was then diluted with water (40 mL), and extracted with EtOAc (80 mL×2). The organic layers were washed with H₂O (40 mL) and brine (40 mL), dried over anhydrous Na₂SO₄, filtered and concentrated. The residue was purified by flash silica gel chromatography (20 g column, EtOAc in petroleum ether from 0% 30%) to give tert-butyl N-[(3S)-1'-(1-benzyl-5-iodo-6-oxo-1,6-dihydropyrimidin-2-yl)-1,3-dihydrospiro[indene-2,4'-piperidin]-3-yl]carbamate (730.0 mg, 1.2 mmol, 55% yield) as a white solid. LC-MS (ESI⁺) m/z: 613.1 (M+H)⁺.

(R)-5-fluoro-3H-spiro[benzofuran-2,4'-piperidin]-3-amine, Intermediate FD

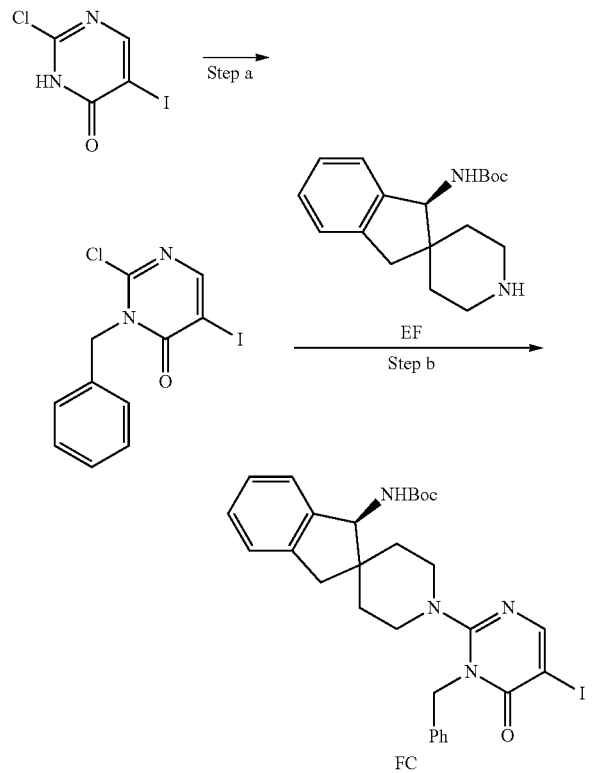

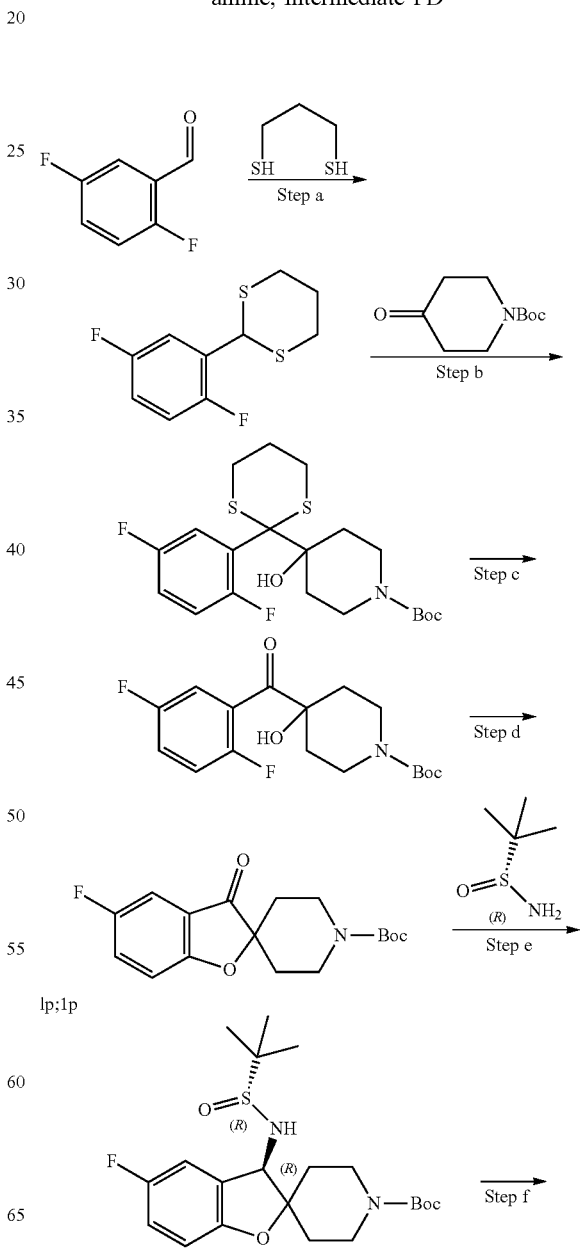

Step a: 2-Chloro-5-iodo-3,4-dihydropyrimidin-4-one (1.5 g, 5.8 mmol, synthesized via Step a of Intermediate DP), K₂CO₃ (2.4 g, 17.5 mmol) and benzyl bromide (2.0 g, 11.6 mmol) were added in DMF (40 mL). The reaction mixture was stirred at 50° C. for 2 hours. The mixture was diluted with EtOAc (100 mL), washed with H₂O (40 mL×2), brine (20 mL), dried over anhydrous Na₂SO₄, filtered and concentrated to give a residue. The residue was purified by flash silica gel chromatography (petroleum ether:ethyl acetate=100:0 to 100:20) to afford 3-benzyl-2-chloro-5-iodo-3,4-dihydropyrimidin-4-one (750.0 mg, 2.2 mmol, 37% yield) as a yellow oil. LC-MS (ESI⁺) m/z: 346.8 (M+H)⁺.

Step b: 3-Benzyl-2-chloro-5-iodo-3,4-dihydropyrimidin-4-one (750.0 mg, 2.2 mmol), tert-butyl N-[(3S)-1,3-dihy- -continued

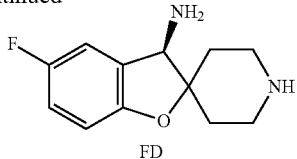

FD

Step a: BF$_3$·Et$_2$O (78.0 g, 263 mmol, 67.8 mL, 48% solution) was added dropwise to a solution of propane-1,3-dithiol (119 g, 1.11 mol, 111 mL) and 2,5-difluorobenzaldehyde (150 g, 1.06 mol, 114 mL) in DCM (750 mL) at 0° C. The reaction was then stirred at 25° C. for 1 hr. The reaction mixture was then diluted with water (500 mL) and extracted with CH$_2$Cl$_2$ (500 mL×3) and the organic layer was concentrated under vacuum. The residue was slurried in petroleum ether (400 mL) and collected with filtration to give 2-(2,5-difluorophenyl)-1,3-dithiane (180 g, 774 mmol, 73% yield) as a white solid. $^1$HNMR (400 MHz, CDCl$_3$): δ 7.36 (dd, J$_{ab}$=2.8 Hz, J$_{ac}$=8.4 Hz, H), 7.02-6.97 (m, 2H), 5.50 (s, 1H), 3.15-3.08 (m, 2H), 2.95-2.91 (m, 2H), 2.21-2.17 (m, H), 1.97-1.93 (m, H).

Step b: A solution of 2-(2,5-difluorophenyl)-1,3-dithiane (100 g, 430 mmol) in THF (400 mL) was cooled to −50~−40° C. To the mixture was then added LDA (2 M, 258 mL) at −50~8−40° C. and the mixture was warmed to −30~−20° C. for 1 hr. Then the mixture was cooled to −50~−40° C. and to the mixture was added a solution of tert-butyl 4-oxopiperidine-1-carboxylate (90.0 g, 451 mmol) in THF (200 mL) dropwise. After the addition, the mixture was stirred at −50~−40° C. for another 1 hr. The mixture was then quenched with sat.NH$_4$Cl (600 mL) and extracted with ethyl acetate (400 mL×2) at 25° C. The organic phase was dried with Na$_2$SO$_4$, filtered and the filtrate was concentrated in vacuo to give the crude product. The crude product was triturated with petroleum ether (400 mL) at 25° C. for 1 hr, and then filtered. The residue was dried in vacuo to give tert-butyl 4-(2-(2,5-difluorophenyl)-1,3-dithian-2-yl)-4-hydroxypiperidine-1-carboxylate (132 g, 286 mmol, 67% yield) as white solid. LC-MS (ESI$^+$) m/z: 332.1 (M−100)$^+$; $^1$HNMR (400 MHz, CDCl$_3$): δ 7.85-7.80 (m, H), 7.05-7.00 (m, 2H), 3.91 (s, 2H), 2.97 (s, 2H), 2.86-2.81 (m, 2H), 2.66-2.61 (m, 2H), 2.55 (s, H), 1.90-1.87 (m, 2H), 1.79 (t, J=16.4 Hz, 3H), 1.41 (s, 9H).

Step c: To a solution of tert-butyl 4-(2-(2,5-difluorophenyl)-1,3-dithian-2-yl)-4-hydroxypiperidine-1-carboxylate (147 g, 318 mmol), pyridine (50.4 g, 637 mmol, 51.4 mL), TBAB (20.56 g, 63.77 mmol) in H$_2$O (73.5 mL) and CH$_2$Cl$_2$ (735 mL) was added pyridine-HBr$_3$ (203 g, 637 mmol) at 0° C. The mixture was then stirred at 25° C. for 2 hrs. The solution was then poured into water (750 mL) and extracted with CH$_2$Cl$_2$ (500 mL×3). The combined organic layers were washed with brine (500 mL), dried over Na$_2$SO$_4$, then filtered. The filtrate was concentrated under vacuum to give tert-butyl 4-(2,5-difluorobenzoyl)-4-hydroxypiperidine-1-carboxylate (109 g, quant. crude yield) as a yellow solid.

Step d: To a mixture of tert-butyl 4-(2,5-difluorobenzoyl)-4-hydroxypiperidine-1-carboxylate (109 g, 319 mmol) in dioxane (440 mL) was added t-BuOK (53.7 g, 478 mmol) at 25° C. The mixture was then stirred at 70° C. for 2 hrs. The solution was then poured into water (1.00 L) and extracted with ethyl acetate (500 mL×3). The combined organic layers were washed with brine (500 mL), dried over Na$_2$SO$_4$, then filtered and evaporated under reduced pressure. The crude product was purified by column chromatography (SiO$_2$, petroleum ether:ethyl acetate=1:0 to 8:1, R$_f$=0.30, petroleum ether:ethyl acetate=3:1). The mixture was further triturated with petroleum ether (50.0 mL) to give tert-butyl 5-fluoro-3-oxo-3H-spiro[benzofuran-2,4'-piperidine]-1'-carboxylate (32.0 g, 93.1 mmol, 29% yield) as a light yellow solid. LC-MS (ESI$^+$) m/z: 265.8 (M−55)$^+$; $^1$HNMR (400 MHz, CDCl$_3$): δ 7.38-7.32 (m, H), 7.32-7.27 (m, H), 7.12 (dd, J$_{ab}$=4.0 Hz, J$_{ac}$=9.2 Hz, H), 4.15 (s, 2H), 3.22 (s, 2H), 1.98-1.90 (m, 2H), 1.61 (d, J=13.6 Hz, 2H), 1.50 (s, 9H).

Step e: To a solution of tert-butyl 5-fluoro-3-oxo-3H-spiro[benzofuran-2,4'-piperidine]-1'-carboxylate (31.0 g, 90.2 mmol) in 2-methyl tetrahydrofuran (217 mL) was added Ti(OEt)$_4$ (61.8 g, 271 mmol, 56.1 mL) and (R)-2-methylpropane-2-sulfinamide (21.9 g, 180 mmol) at 25° C. The mixture was then stirred at 90° C. for 18 hrs. Then the reaction mixture was cooled to 0° C., and LiBH$_4$ (2.94 g, 134.9 mmol) was added at 0-10° C., and the mixture was stirred at 0-10° C. for 2 hrs. The mixture was quenched by addition methyl alcohol (15.0 mL) at 0-10° C. and 2-[2-[bis(2-hydroxyethyl)amino]ethyl-(2-hydroxyethyl)amino]ethanol (50.0 g) was added, and the mixture was stirred for 30 min at 25° C. To the mixture was added to 10% citric acid solution (800 mL) and the solution was extracted with ethyl acetate (400 mL×3). The combined organic layer was washed with brine (80.0 mL), dried over anhydrous Na$_2$SO$_4$, then filtered through SiO$_2$ and evaporated under reduced pressure to give a yellow oil. The yellow oil was purified by column chromatography (SiO$_2$, petroleum ether:ethyl acetate=10:1 to 2:1, R$_f$=0.30, 0.35) to give a yellow solid. The yellow solid was slurred in methyl tertiary butyl ether (120 mL) and filtered to give a white solid. The white solid was purified by column chromatography (SiO$_2$, petroleum ether:ethyl acetate=10:1 to 2:1, R$_f$=0.30) to give tert-butyl (R)-3-(((R)-tert-butylsulfinyl)amino)-5-fluoro-3H-spiro[benzofuran-2,4'-piperidine]-1'-carboxylate (15.0 g, 34.4 mmol, 38% yield) as a white solid. $^1$HNMR (400 MHz, DMSO): δ 7.06-7.01 (m, H), 6.82 (dd, J=4.00 Hz, J=8.40 Hz, H), 6.13 (d, J=10.80 Hz, H), 4.65 (d, J=10.40 Hz, H), 4.01-3.88 (m, H), 3.04 (s, H), 1.85-1.69 (m, 4H), 1.42 (s, 9H), 1.19 (s, 9H).

Step f: A mixture of tert-butyl (R)-3-(((R)-tert-butylsulfinyl)amino)-5-fluoro-3H-spiro[benzofuran-2,4'-piperidine]-1'-carboxylate (16.0 g, 37.5 mmol) in methyl alcohol (32.0 mL) were added HCl/MeOH (4.00 M, 80.0 mL) at 25° C. and the mixture was stirred at 25° C. for 2 hrs. The reaction mixture was then concentrated in vacuo to give a white solid. The white solid was slurred in ethyl acetate (50.0 mL), filtered, and the cake was dried in vacuo to give (R)-5-fluoro-3H-spiro[benzofuran-2,4'-piperidin]-3-amine (10.0 g, 33.3 mmol, 89% yield, 2HCl) as a white solid. $^1$HNMR (400 MHz, DMSO): δ 9.71 (d, J=8.00 Hz, H), 9.39 (d, J=9.20 Hz, H), 9.18 (s, H), 9.39 (dd, J=2.40 Hz, J=8.00 Hz, H), 7.20-7.15 (m, H), 9.39 (d, J=9.20 Hz, H), 9.39 (dd, J=4.00 Hz, J=8.80 Hz, H), 4.75 (s, H), 4.75 (s, H), 3.42 (d, J=12.80 Hz, H), 3.21 (d, J=12.00 Hz, H), 3.03 (s, 2H), 2.43-2.37 (m, H), 2.17 (d, J=13.20 Hz, H), 1.99 (d, J=12.40 Hz, H), 1.87 (d, J=12.40 Hz, H).

387

Tert-butyl N-[(3R)-1'-(5-bromopyrazin-2-yl)-5-fluoro-3H-spiro[1-benzofuran-2,4'-piperidin]-3-yl]carbamate, Intermediate FE

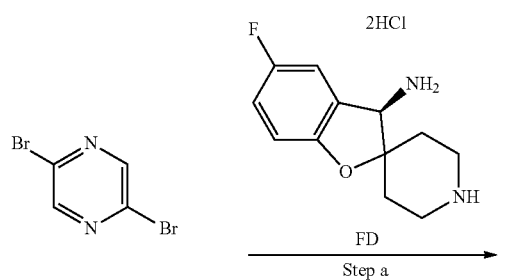

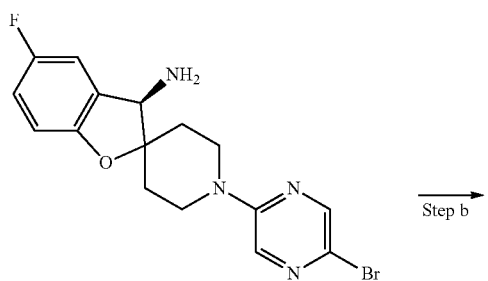

388

-continued

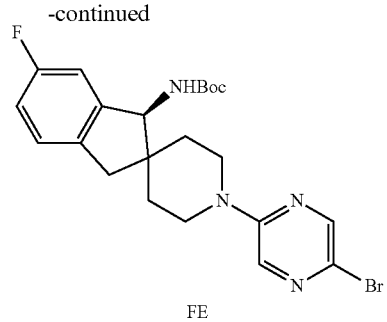

Step a: A mixture of 2,5-dibromopyrazine (200.0 mg, 0.8 mmol, CAS #23229-25-6), (3R)-5-fluoro-3H-spiro[1-benzofuran-2,4'-piperidin]-3-amine dihydrochloride (272.0 mg, 0.9 mmol, Intermediate FD) and TEA (580 μL, 4.2 mmol) in DMF (10 mL) was stirred at 80° C. for 2.5 hours. The crude solution was used directly in the next step. LC-MS (ESI⁺) m/z: 361.6 (M-NH₂)+.

Step b: To the crude solution of (R)-1'-(5-bromopyrazin-2-yl)-5-fluoro-3H-spiro[benzofuran-2,4'-piperidin]-3-amine (318.0 mg, 0.8 mmol) in DMF (10 mL) was added Boc₂O (383 μL, 1.7 mmol) at 15° C. The reaction mixture was stirred at 15° C. for 12 hours. The reaction mixture was then diluted with water (30 mL), and extracted with EtOAc (50 mL×2). The organic layers were washed with H₂O (40 mL), dried over anhydrous Na₂SO₄, filtered and concentrated. The residue was purified by flash silica gel chromatography (20 g column, EtOAc in petroleum ether from 0% 10%) to give tert-butyl N-[(3R)-1'-(5-bromopyrazin-2-yl)-5-fluoro-3H-spiro[1-benzofuran-2,4'-piperidin]-3-yl]carbamate (270.0 mg, 0.6 mmol, 67% yield in two steps) as a yellow solid. LC-MS (ESI⁺) m/z: 479.0 (M+H)⁺.

Tert-butyl N-[(3R)-5-fluoro-1'-(5-sulfanylpyrazin-2-yl)-3H-spiro[1-benzofuran-2,4'-piperidin]-3-yl]carbamate, Intermediate FF

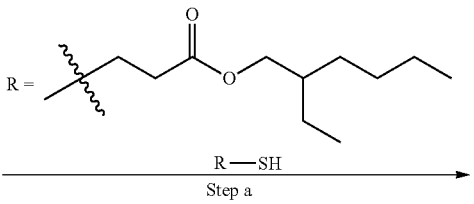

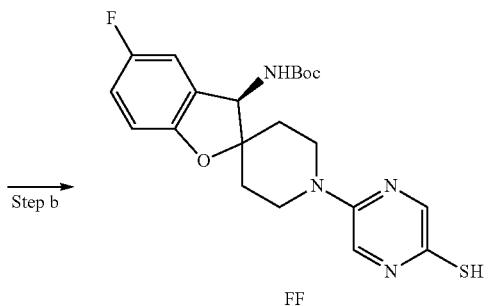

Step a: A mixture of tert-butyl N-[(3R)-1'-(5-bromopy-razin-2-yl)-5-fluoro-3H-spiro[1-benzofuran-2,4'-piperidin]-3-yl]carbamate (270.0 mg, 0.6 mmol, Intermediate FE), 2-ethylhexyl 3-sulfanylpropanoate (135.0 mg, 0.6 mmol, CAS #50448-95-8), $Pd_2(dba)_3$ (51.5 mg, 0.06 mmol), Xant-Phos (65.1 mg, 0.1 mmol) and DIPEA (276 µL, 1.7 mmol) in dioxane (10 mL) was stirred at 100° C. for 12 hours under N2 atmosphere. The reaction mixture was poured into $H_2O$ (20 mL) and extracted with EtOAc (40 mL×2). The combined organic layers were washed with brine (20 mL), dried over anhydrous $Na_2SO_4$, filtered and concentrated under reduced pressure to give a residue. The residue was purified by silica gel chromatography (ethyl acetate in petroleum ether=0% to 15%) to afford 2-ethylhexyl 3-({5-[(3R)-3-{[(tert-butoxy)carbonyl]amino}-5-fluoro-3H-spiro[1-benzofuran-2,4'-piperidin]-1'-yl]pyrazin-2-yl}sulfanyl)propanoate (220.0 mg, 0.4 mmol, 63% yield) as a yellow solid. LC-MS $(ESI^+)$ m/z: 617.2 $(M+H)^+$.

Step b: To the mixture of 2-ethylhexyl 3-({5-[(3R)-3-{[(tert-butoxy)carbonyl]amino}-5-fluoro-3H-spiro[1-benzofuran-2,4'-piperidin]-1'-yl]pyrazin-2-yl}sulfanyl)propanoate (220.0 mg, 0.4 mmol) in anhydrous THF (1.5 mL) was added t-BuOK (1.1 mL, 1.1 mmol, 1 M in THF) over 10 min at −78° C., and the resulting mixture was stirred at −78° C. for 0.5 hour under $N_2$ atmosphere. The reaction mixture was then diluted with DCM (30 mL) and acidified with HCl/EtOAc (2 N, 1 mL) to pH=6 at −78° C. The mixture was washed with $H_2O$ (20 mL) and brine (20 ml). The organic layer was dried over anhydrous $Na_2SO_4$, filtered and concentrated to give tert-butyl N-[(3R)-5-fluoro-1'-(5-sulfanylpyrazin-2-yl)-3H-spiro[1-benzofuran-2,4'-piperidin]-3-yl]carbamate (154.0 mg, 100% crude yield) as a red oil.

6-Chloro-1-methyl-3-(1,2,3,4-tetrahydroquinolin-1-yl)-1,2-dihydropyridin-2-one, Intermediate FG

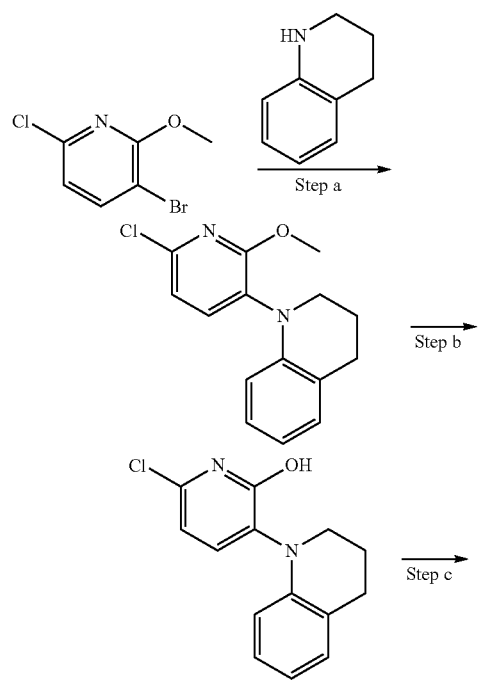

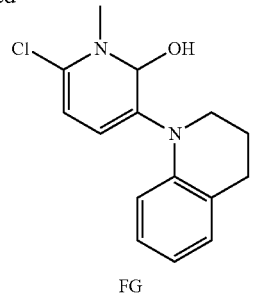

FG

Step a: A mixture of 3-bromo-6-chloro-2-methoxypyridine (1.0 g, 4.5 mmol, CAS #1211526-62-3), 1,2,3,4-tetrahydroquinoline (656.0 mg, 4.9 mmol, CAS #25448-04-8), $Pd_2(dba)_3$ (616.0 mg, 0.7 mmol), t-BuONa (646.0 mg, 6.7 mmol) and XantPhos (1.6 g, 2.7 mmol) were added into toluene (30 mL). The reaction mixture was evacuated and refilled three times using $N_2$ and the reaction mixture was stirred at 100° C. for 12 hours. The reaction mixture was then filtered and washed with EtOAc (80 mL×2). The filtrate was washed with $H_2O$ (30 mL×2) and the organic layer was dried over anhydrous $Na_2SO_4$, filtered and concentrated. The residue was purified by flash silica gel chromatography (40 g column, EtOAc in petroleum ether from 0% 5%) to give 1-(6-chloro-2-methoxypyridin-3-yl)-1,2,3,4-tetrahydroquinoline (1.3 g, 4.5 mmol, 101% crude yield) as a yellow oil. LC-MS $(ESI^+)$ m/z: 274.9 $(M+H)^+$.

Step b: A mixture of 1-(6-chloro-2-methoxypyridin-3-yl)-1,2,3,4-tetrahydroquinoline (1.3 g, 4.5 mmol) and TMSI (6.5 mL, 45.3 mmol) in DCM (20 mL) was stirred at 50° C. for 12 hours. Then additional TMSI (6.5 mL, 45.3 mmol) was added and the resulting mixture was stirred at 50° C. for 50 hours. The reaction mixture was then diluted with DCM (60 mL) and $H_2O$ (40 mL), and extracted with DCM (50 mL×2). The organic layers were washed with brine (20 mL), dried over anhydrous $Na_2SO_4$, filtered and concentrated. The residue was purified by flash silica gel chromatography (20 g column, EtOAc in petroleum ether from 0%-10%) to give 6-chloro-3-(1,2,3,4-tetrahydroquinolin-1-yl)pyridin-2-ol (550.0 mg, 2.1 mmol, 47% yield) as a yellow solid. LC-MS $(ESI^+)$ m/z: 260.9 $(M+H)^+$.

Step c: To a solution of NaH (166.0 mg, 4.2 mmol, 60% dispersion in mineral oil) in DMF (10 mL) was added 6-chloro-3-(1,2,3,4-tetrahydroquinolin-1-yl)pyridin-2-ol (550.0 mg, 2.1 mmol) at 0° C. under $N_2$ atmosphere. The mixture was stirred at 0° C. for 20 min, then iodomethane (326 µL, 5.3 mmol) was added and the mixture was allowed to warm up to 15° C. and stirred at this temperature for 1 hour under $N_2$ atmosphere. The mixture was then quenched with MeOH (1 mL) diluted with $H_2O$ (40 mL), and the aqueous phase was extracted with ethyl acetate (100 mL×3). The combined organic layers were washed with water (30 mL×2), followed by brine (20 mL), dried over anhydrous $Na_2SO_4$, filtered and concentrated to give a residue. The residue was purified by flash silica gel chromatography (20 g column, ethyl acetate/petroleum ether=0/100 to 30/100) to afford 6-chloro-1-methyl-3-(1,2,3,4-tetrahydroquinolin-1-yl)-1,2-dihydropyridin-2-one (400.0 mg, 1.5 mmol, 69% yield) as a yellow oil. LC-MS $(ESI^+)$ m/z: 275.0 $(M+H)^+$.

391 tert-butyl (S)-(1'-(6-iodo-5-methylimidazo[2,1-b][1,3,4]thiadiazol-2-yl)-1,3-dihydrospiro[indene-2,4'-piperidin]-1-yl)carbamate, Intermediate FH

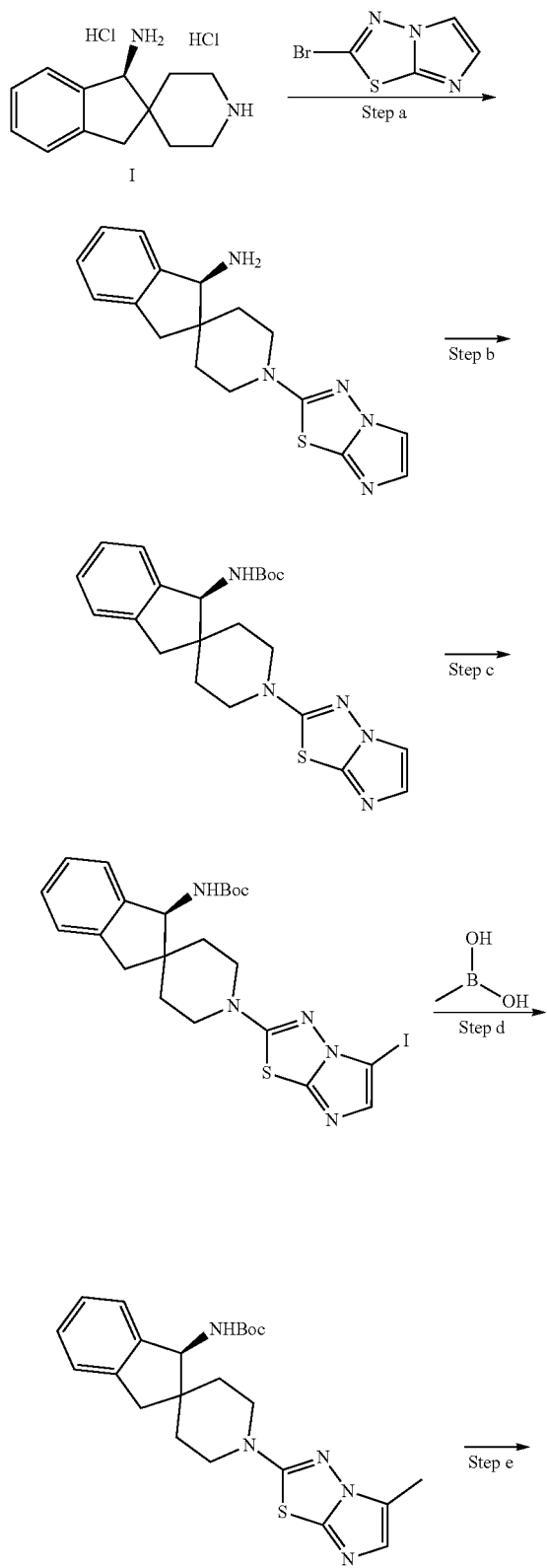

392

-continued

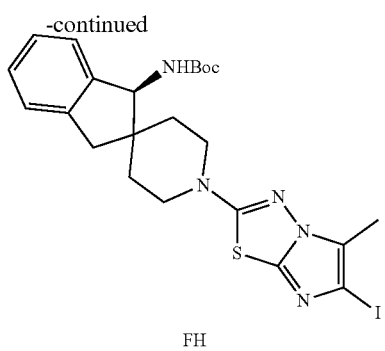

FH

Step a: A mixture of 2-bromoimidazo[2,1-b][1,3,4]thiadiazole (3.0 g, 14.7 mmol, CAS #1137142-58-5), (1S)-1,3-dihydrospiro[indene-2,4'-piperidin]-1-amine dihydrochloride (4.04 g, 14.7 mmol, Intermediate I) and DIPEA (12.8 mL, 73.5 mmol) in DMF (50.0 mL) was stirred at 100° C. for 3 hours. The reaction mixture was used directly in the next step. LC-MS (ESI$^+$) m/z: 326.2 (M+H)$^+$.

Step b: To a mixture of (1S)-1'-{imidazo[2,1-b][1,3,4]thiadiazol-2-yl}-1,3-dihydrospiro[indene-2,4'-piperidin]-1-amine (4.7 g, 14.4 mmol) in DMF (50.0 mL) was added (Boc)$_2$O (4.94 mL, 21.6 mmol), and the resulting mixture was stirred at 20° C. for 1 hour. The mixture was then diluted with ethyl acetate (150.0 mL), and washed with H$_2$O (80.0 mL×3). The organic phase was washed with brine (50.0 mL), dried over anhydrous Na$_2$SO$_4$, filtered and concentrated in vacuo to give a residue. The residue was purified by silica gel chromatography (ethyl acetate in petroleum ether=0% to 75%) to afford tert-butyl N-[(1S)-1'-{imidazo[2,1-b][1,3,4]thiadiazol-2-yl}-1,3-dihydrospiro[indene-2,4'-piperidin]-1-yl]carbamate (4.10 g, 9.63 mmol, 67% yield over 2 steps) as a white solid. LC-MS (ESI$^+$) m/z: 426.0 (M+H)$^+$.

Step c: To a mixture of tert-butyl N-[(1S)-1'-{imidazo[2,1-b][1,3,4]thiadiazol-2-yl}-1,3-dihydrospiro[indene-2,4'-piperidin]-1-yl]carbamate (2.0 g, 4.69 mmol) in DMF (30.0 mL) at 0° C. was added NIS (1.15 g, 5.15 mmol), and the resulting mixture was stirred at 0° C. for 3.5 hours. The mixture was then diluted with ethyl acetate (80.0 mL), and washed with H$_2$O (50.0 mL×2). The organic phase was washed with brine (30.0 mL), dried over anhydrous Na$_2$SO$_4$, filtered and concentrated in vacuo to give a residue. The residue was purified by silica gel chromatography (ethyl acetate in petroleum ether=0% to 45%) to afford tert-butyl N-[(1S)-1'-{5-iodoimidazo[2,1-b][1,3,4]thiadiazol-2-yl}-1,3-dihydrospiro[indene-2,4'-piperidin]-1-yl]carbamate (1.75 g, 3.17 mmol, 68% yield) as a yellow solid. Minor bis-iodination product was also formed during the reaction and removed during purification. LC-MS (ESI$^+$) m/z: 551.9 (M+H)$^+$.

Step d: A mixture of tert-butyl N-[(1S)-1'-{5-iodoimidazo[2,1-b][1,3,4]thiadiazol-2-yl}-1,3-dihydrospiro[indene-2,4'-piperidin]-1-yl]carbamate (1.7 g, 3.08 mmol), methylboronic acid (921 mg, 15.4 mmol), Cs$_2$CO$_3$ (2.00 g, 6.16 mmol) and Pd(PPh$_3$)$_4$ (355 mg, 308 μmol) in 1,4-dioxane (20.0 mL) was stirred under microwave irradiation at 135° C. for 1 hour under N$_2$ atmosphere. The mixture was then concentrated in vacuo to give a residue, which was dissolved in ethyl acetate (30.0 mL), washed with H$_2$O (20.0 mL×2) and brine (15.0 mL). The organic phase was dried over anhydrous Na$_2$SO$_4$, filtered and concentrated in vacuo to give a residue, which was purified by silica gel chromatography (ethyl acetate in petroleum ether=0% to 95%) to afford tert-butyl N-[(1S)-1'-{5-methylimidazo[2,1-b][1,3,4]thiadiazol-2-yl}-1,3-dihydrospiro[indene-2,4'-piperidin]-1-yl]carbamate (780 mg, 1.77 mmol, 57% yield) as a yellow solid. LC-MS (ESI$^+$) m/z: 440.2 (M+H)$^+$.

Step e: A mixture of tert-butyl N-[(1S)-1'-{5-methylimidazo[2,1-b][1,3,4]thiadiazol-2-yl}-1,3-dihydrospiro[indene-2,4'-piperidin]-1-yl]carbamate (1.3 g, 1.77 mmol, purity: 60%) and NIS (595 mg, 2.65 mmol) in DMF (15.0 mL) was stirred at 15° C. for 1.5 hours. The mixture was then diluted with ethyl acetate (50.0 mL), and washed with H$_2$O (25.0 mL×3). The organic phase was washed with brine (20.0 mL), dried over anhydrous Na$_2$SO$_4$, filtered and concentrated in vacuo to give a residue. The residue was purified by silica gel chromatography (ethyl acetate in petroleum ether=0% to 40%) to afford tert-butyl N-[(1S)-1'-{6-iodo-5-methylimidazo[2,1-b][1,3,4]thiadiazol-2-yl}-1,3-dihydrospiro[indene-2,4'-piperidin]-1-yl]carbamate (460 mg, 813 µmol, 46% yield) as a yellow solid. LC-MS (ESI$^+$) m/z: 566.0 (M+H)$^+$.

(R)-6-fluoro-3H-spiro[benzofuran-2,4'-piperidin]-3-amine, Intermediate FI

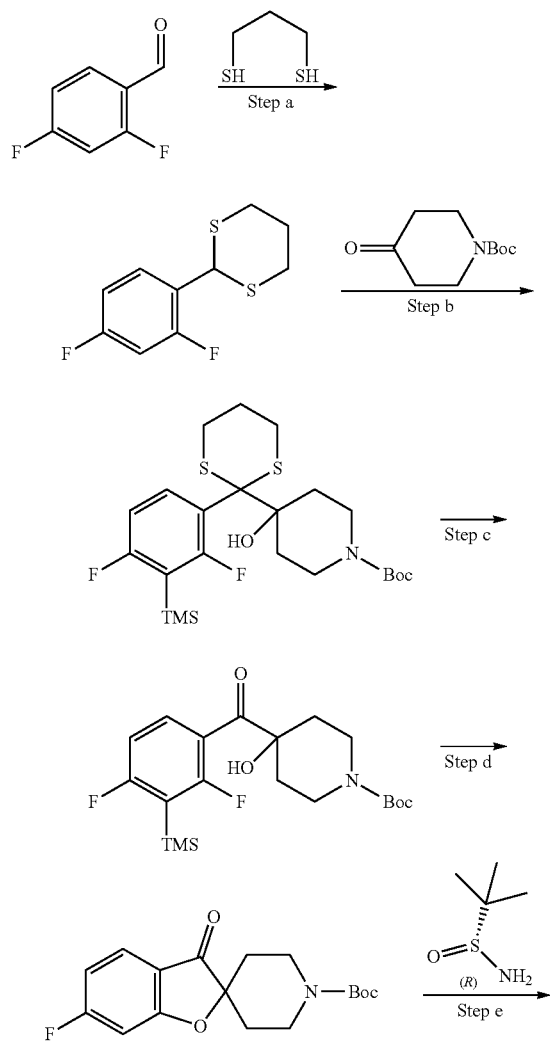

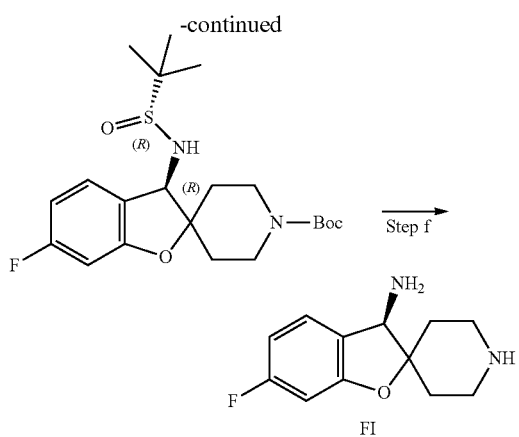

Step a: BF$_3$.Et$_2$O (78.0 g, 263 mmol, 67.8 mL, 48% solution) was added dropwise to a solution of 2,4-difluorobenzaldehyde (150 g, 1.06 mol, 114 mL) and propane-1,3-dithiol (119 g, 1.11 mol, 111 mL) in CH$_2$Cl$_2$ (750 mL) at 0° C. The reaction was then stirred at 25° C. for 1 hr. The reaction mixture was then quenched by water (500 mL) and extracted with CH$_2$Cl$_2$ (300 mL×2). The organic layer was dried over Na$_2$SO$_4$, filtered and the filtrate was concentrated under vacuum. The residue was slurried in petroleum ether (50.0 mL) and collected by filtration to give 2-(2,4-difluorophenyl)-1,3-dithiane (192 g, 826 mmol, 78% yield) as a white solid. LC-MS (ESI$^+$) m/z: 233.0 (M+H)$^+$; $^1$HNMR (400 MHz, CDCl$_3$): δ 7.61-7.55 (m, H), 6.88-6.81 (m, H), 6.80-6.77 (m, H), 5.47 (s, 1H), 3.12-3.05 (m, 2H), 2.91-2.88 (m, 2H), 2.18-2.13 (m, H), 1.92-1.89 (m, H).

Step b: A solution of 2-(2,4-difluorophenyl)-1,3-dithiane (123 g, 529 mmol) in THF (615 mL) was cooled to −50~−40° C. To the mixture was added LDA (2 M, 317 mL) at −50-40° C. Then the mixture was warmed to −30~−20° C. for 1 hr. Next, the mixture was cooled to −50~−40° C. and to the mixture was added TMSCl (60.4 g, 555 mmol, 70.5 mL) dropwise. After the addition, the mixture was stirred at −50~−40° C. for another 1 hr. To the mixture was added additional LDA (2 M, 397 mL) at −50~−40° C. Then the mixture was warmed to −30~−20° C. for 1 hr. Then the mixture was cooled to −50~−40° C. and to the mixture was added a solution of tert-butyl 4-oxopiperidine-1-carboxylate (110 g, 555 mmol) in THF (246 mL) at −50~−40° C. The mixture was stirred at −50~−40° C. for 1 hr. The mixture was then quenched with aqueous NH$_4$Cl solution (1.50 L) and extracted with ethyl acetate (1.00 L×2) at 25° C. The organic phase was dried with Na$_2$SO$_4$, filtered and the filtrate was concentrated in vacuo to give a crude product. The mixture was purified by column chromatography (SiO$_2$, petroleum ether:ethyl acetate=1:0 to 10:1, petroleum ether:ethyl acetate=3:1, R$_f$=0.45) to give tert-butyl 4-(2-(2,4-difluoro-3-(trimethylsilyl)phenyl)-1,3-dithian-2-yl)-4-hydroxypiperidine-1-carboxylate (234 g, 459 mmol, 87% yield) as a yellow oil. LC-MS (ESI$^+$) m/z: 504.2 (M+H)$^+$; $^1$HNMR (400 MHz, CDCl$_3$): δ 7.98-7.92 (m, H), 6.77 (t, J=8.0 Hz, H), 3.81 (s, 2H), 2.88 (s, 2H), 2.74 (t, J=7.2 Hz, 2H), 2.52-2.45 (m, 2H), 1.78-1.75 (m, 2H), 1.64-1.60 (t, J=7.2 Hz, 4H), 1.31 (s, 9H), 0.26 (s, 9H).

Step c: To a solution of tert-butyl 4-(2-(2,4-difluoro-3-(trimethylsilyl)phenyl)-1,3-dithian-2-yl)-4-hydroxypiperidine-1-carboxylate (210 g, 412 mmol), pydirine (65.2 g, 824 mmol, 66.5 mL), and TBAB (26.5 g, 82.4 mmol) in CH$_2$Cl$_2$ (1.05 L) and H$_2$O (105 mL) was pyridine-HBr$_3$ (263 g, 824 mmol) at 0° C. The mixture was then stirred at 25° C. for 2 hrs. The solution was poured into water (1.50 L) and extracted with CH₂Cl₂ (800 mL×3). The combined organic layers were washed with brine (1.50 L), dried over Na₂SO₄, then filtered and the filtrate was concentrated under vacuum to give tert-butyl 4-(2,4-difluoro-3-(trimethylsilyl)benzoyl)-4-hydroxypiperidine-1-carboxylate (171 g, quant. crude yield) as a brown oil. LC-MS (ESI⁺) m/z: 313.9 (M−100)⁺;

Step d: To a solution of tert-butyl 4-(2,4-difluoro-3-(trimethylsilyl)benzoyl)-4-hydroxypiperidine-1-carboxylate (171 g, 413 mmol) in dioxane (650 mL) was added t-BuOK (69.6 g, 620 mmol) at 25° C. The mixture was then stirred at 70° C. for 2 hrs. The solution was poured into water (1.00 L) and extracted with ethyl acetate (800 mL×3). The combined organic layers were washed with brine (1.00 L), dried over Na₂SO₄, then filtered and evaporated under reduced pressure. The crude product was purified by column chromatography (SiO₂, petroleum ether:ethyl acetate=100:1 to 25:1, R$_f$=0.30, petroleum ether:ethyl acetate=3:1) to give tert-butyl 6-fluoro-3-oxo-3H-spiro[benzofuran-2,4'-piperidine]-1'-carboxylate (52.0 g, 160 mmol, 39% yield) as a yellow solid. LC-MS (ESI⁺) m/z: 222.1 (M−100)⁺; ¹HNMR (400 MHz, DMSO): δ 7.78 (dd, J$_{ab}$=2.0 Hz, J$_{ac}$=8.4 Hz, H), 7.27 (dd, J$_{ab}$=2.0 Hz, J$_{ac}$=9.6 Hz, H), 7.07-7.04 (m, H), 4.00 (d, J=13.6 Hz, 2H), 3.14 (s, 2H), 2.88 (s, 2H), 2.74 (t, J=7.2 Hz, 2H), 1.74-1.64 (m, 4H), 1.43 (s, 9H).

Step e: To a solution of tert-butyl 6-fluoro-3-oxo-3H-spiro[benzofuran-2,4'-piperidine]-1'-carboxylate (40.0 g, 123 mmol) in 2-Me-THF (80.0 mL) was added Ti(OEt)₄ (84.5 g, 370 mmol, 76.9 mL) and (R)-2-methylpropane-2-sulfinamide (29.9 g, 247 mmol) at 15° C. The mixture was then stirred at 90° C. for 18 hrs. Next, to the mixture was added LiBH₄ (2.96 g, 135 mmol) at 0° C., and the mixture was stirred at 15° C. for 2 hrs. The solution was quenched by MeOH (20.0 mL) at 0° C. and 2-[2-[bis(2-hydroxyethyl)amino]ethyl-(2-hydroxyethyl)amino]ethanol (40.0 g) was added, and the mixture was stirred for 1 hr at 15° C. The mixture was adjusted to pH=1 with 0.5 N HCl and extracted with ethyl acetate (600 mL×3). The organic layers were washed with brine (800 mL), dried over Na₂SO₄, then filtered through SiO₂ and the filtrate was concentrated under vacuum. The mixture was then triturated with MTBE (100 mL) to give tert-butyl (R)-3-(((R)-tert-butylsulfinyl)amino)-6-fluoro-3H-spiro[benzofuran-2,4'-piperidine]-1'-carboxylate (27.0 g, 62.1 mmol, 50% yield) as a white solid. LC-MS (ESI⁺) m/z: 371.1 (M−55)⁺; ¹HNMR (400 MHz, DMSO): δ 7.26 (t, J=6.4 Hz, H), 6.75 (dd, J$_{ab}$=2.4 Hz, J$_{ac}$=9.6 Hz, 2H), 6.09 (d, J=10.4 Hz, H), 4.61 (d, J=10.4 Hz, H), 3.96 (t, J=16.8 Hz, 2H), 3.04 (s, 2H), 1.89-1.82 (m, 4H), 1.42 (s, 9H), 1.17 (s, 9H).

Step f: To a solution of tert-butyl (R)-3-(((R)-tert-butylsulfinyl)amino)-6-fluoro-3H-spiro[benzofuran-2,4'-piperidine]-1'-carboxylate (15.0 g, 34.5 mmol) in MeOH (30.0 mL) was added HCl/MeOH (4 M, 75.0 mL) at 15° C. and the mixture was stirred at 15° C. for 1 hr. The mixture was concentrated under vacuum. The crude product was triturated with petroleum ether:ethyl acetate=3:1 (40.0 mL) at 15° C. for 1 hr to give (R)-6-fluoro-3H-spiro[benzofuran-2,4'-piperidin]-3-amine (10.08 g, 34.1 mmol, 99% yield, 2HCl) as a white solid. LC-MS (ESI⁺) m/z: 347.8 (M−16)⁺; ¹HNMR (400 MHz, DMSO): δ 9.58 (s, H), 9.36 (s, H), 9.03 (s, 3H), 7.79 (dd, J$_{ab}$=5.6 Hz, J$_{ac}$=8.0 Hz, H), 6.90-6.83 (m, 2H), 4.72 (s, H), 3.43 (s, H), 3.24 (d, J=12.8 Hz, H), 3.06 (s, H), 2.50-2.41 (m, H), 2.19 (d, J=12.4 Hz, H), 2.02-2.00 (m, H), 1.91 (d, J=1.6 Hz, H).

Tert-butyl N-[(3R)-6-fluoro-1'-[3-iodo-1-(oxan-2-yl)-1H-pyrazolo[3,4-b]pyrazin-6-yl]-3H-spiro[1-benzofuran-2,4'-piperidin]-3-yl]carbamate, Intermediate FJ

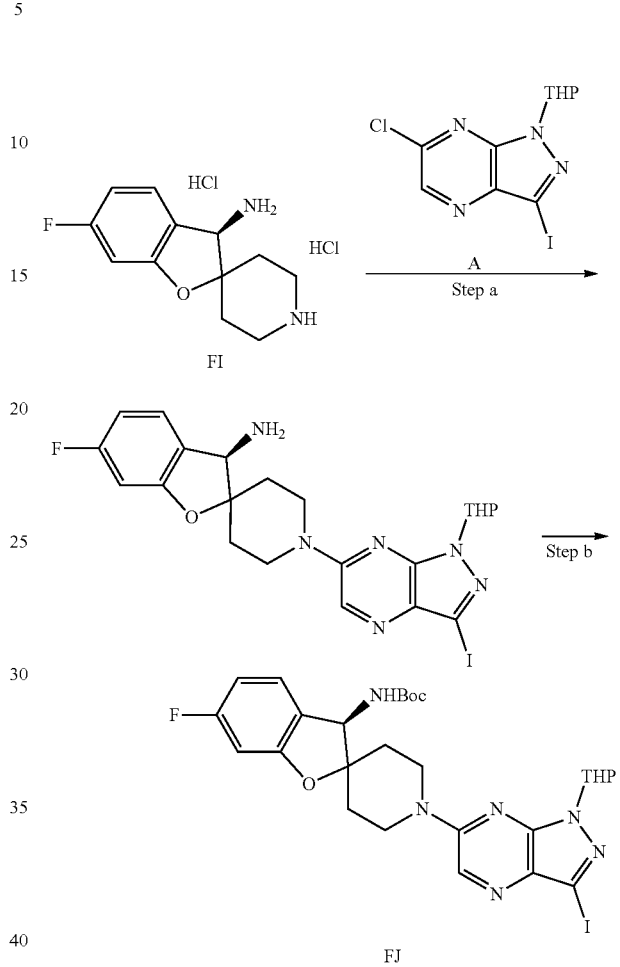

Step a: A mixture of (3R)-6-fluoro-3H-spiro[1-benzofuran-2,4'-piperidin]-3-amine dihydrochloride (800.0 mg, 2.7 mmol, Intermediate FI), 6-chloro-3-iodo-1-(oxan-2-yl)-1H-pyrazolo[3,4-b]pyrazine (1.03 g, 2.8 mmol, Intermediate A) and TEA (1.86 mL, 13.5 mmol) in DMF (25.0 mL) was stirred at 80° C. for 3 hours. The reaction mixture was cooled to rt and used directly in the next step without further purification. LC-MS (ESI⁺) m/z: 551.0 (M+H)⁺.

Step b: To a mixture of (3R)-6-fluoro-1'-[3-iodo-1-(oxan-2-yl)-1H-pyrazolo[3,4-b]pyrazin-6-yl]-3H-spiro[1-benzofuran-2,4'-piperidin]-3-amine (1.45 g, 2.6 mmol) in DMF (25.0 mL) was added (Boc)₂O (1.20 mL, 5.3 mmol), and the mixture was stirred at 15° C. for 2 hours. The mixture was then diluted with ethyl acetate (70.0 mL), and washed with H₂O (30.0 mL×3). The organic phase was washed with brine (20.0 mL), dried over anhydrous Na₂SO₄, filtered and concentrated in vacuo to give a residue. The residue was purified by silica gel chromatography (ethyl acetate in petroleum ether, 0% to 40%) to afford tert-butyl N-[(3R)-6-fluoro-1'-[3-iodo-1-(oxan-2-yl)-1H-pyrazolo[3,4-b]pyrazin-6-yl]-3H-spiro[1-benzofuran-2,4'-piperidin]-3-yl]carbamate (1.30 g, 76% yield) as a white solid. LC-MS (ESI⁺) m/z: 651.1 (M+H)⁺.

6-Chloro-3-iodo-5-methyl-1-(tetrahydro-2H-pyran-2-yl)-1H-pyrazolo[3,4-b]pyrazine, Intermediate FK

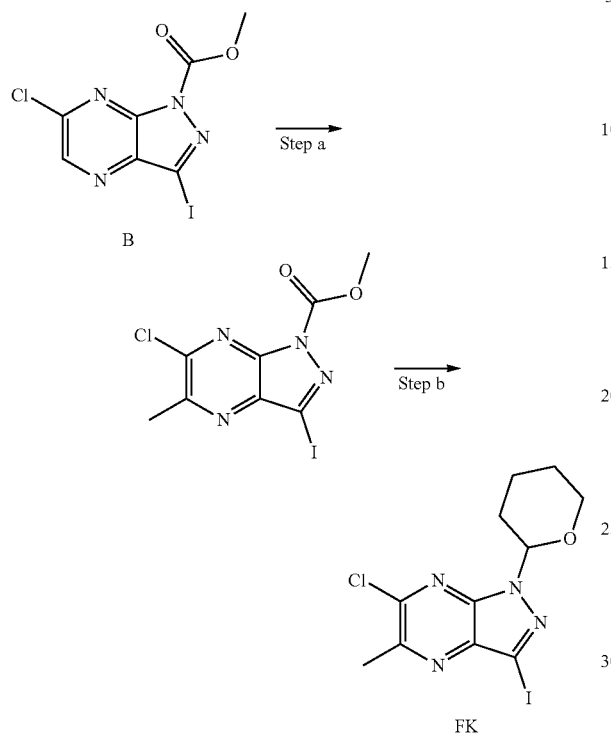

Step a: To a mixture of methyl 6-chloro-3-iodo-H-pyrazolo[3,4-b]pyrazine-1-carboxylate (10.0 g 29.5 mmol, Intermediate B) and ammonium persulfate (20.2 g, 88.6 mmol, 19.3 mL) in $CH_3CN$ (100 mL) and $H_2O$ (50.0 mL) was added a solution of acetic acid (8.87 g, 148 mmol, 8.45 mL) and $AgNO_3$ (50.2 g, 295 mmol) in $CH_3CN$ (40.0 mL) and $H_2O$ (20.0 mL) at 70° C. dropwise, then the mixture was stirred at 70-90° C. for 10 min. Then the mixture was cooled to rt and adjusted to pH=8 with saturated $NaHCO_3$ solution. The mixture was then filtered and the filtrate was extracted with DCM (200 mL×3). The combined organic layers were washed with brine (200 mL), dried over $Na_2SO_4$, filtered and concentrated under reduced pressure to afford methyl 6-chloro-3-iodo-5-methyl-1H-pyrazolo[3,4-b]pyrazine-1-carboxylate (33.0 g, 65.5 mmol, 55.5% yield) as a yellow solid. LC-MS (ESI$^+$) m/z: 352.9 (M+H)$^+$; $^1$HNMR (400 MHz, DMSO): δ 4.07 (s, 3H), 2.75 (s, 3H).

Step b: To a solution of methyl 6-chloro-3-iodo-5-methyl-1H-pyrazolo[3,4-b]pyrazine-1-carboxylate (28.0 g, 55.6 mmol) in DCM (300 mL) was added piperidine (5.21 g, 61.2 mmol, 6.04 mL) at 25° C. and the mixture was stirred at 25° C. for 1 h. Then TsOH—$H_2O$ (13.8 g, 72.3 mmol) and DHP (4.68 g, 55.6 mmol, 5.08 mL) were added to the mixture at 25° C. and the mixture was stirred at 25° C. for 1 h. The mixture was then washed with saturated $NaHCO_3$ solution (10.0 mL×2) and brine (100 mL). The organic layer was dried over $Na_2SO_4$, filtered and concentrated and the residue was purified by column chromatography (SiO$_2$, petroleum ether:ethyl acetate=20:1 to 10:1, R$_f$=0.80) to afford 6-chloro-3-iodo-5-methyl-1-(tetrahydro-2H-pyran-2-yl)-1H-pyrazolo[3,4-b]pyrazine (11.0 g, 27.2 mmol, 48% yield) as a white solid. LC-MS (ESI$^+$) m/z: 379.0 (M+H)$^+$; $^1$HNMR (400 MHz, CDCl$_3$): δ 5.94 (dd, $J_1$=2.4 Hz, $J_2$=10 Hz, 1H), 4.14-4.10 (m, 1H), 3.83-3.76 (m, 1H), 2.82 (s, 3H), 2.70-2.59 (m, 1H), 2.17-2.13 (m, 1H), 1.99-1.96 (m, 1H), 1.83-1.74 (m, 2H), 1.65-1.63 (m, 1H).

Tert-butyl N-[(3R)-5-fluoro-1'-[3-iodo-5-methyl-1-(oxan-2-yl)-1H-pyrazolo[3,4-b]pyrazin-6-yl]-3H-spiro[1-benzofuran-2,4'-piperidin]-3-yl]carbamate, Intermediate FL

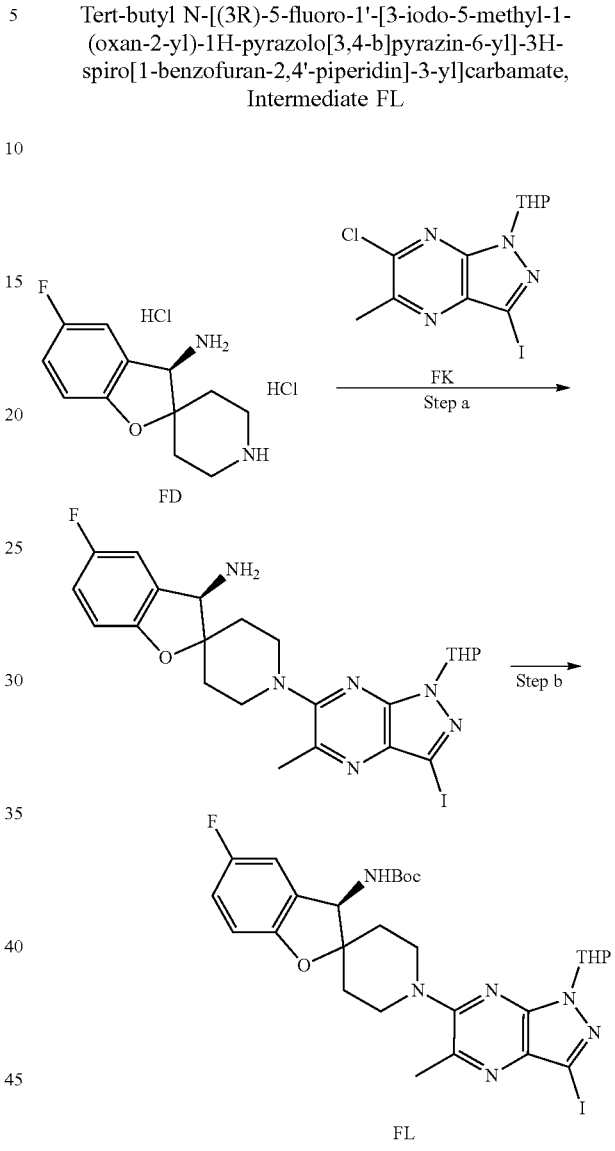

Step a: A mixture of (R)-5-fluoro-3H-spiro[benzofuran-2,4'-piperidin]-3-amine dihydrochloride (350.0 mg, 1.2 mmol, Intermediate FD), 6-chloro-3-iodo-5-methyl-1-(oxan-2-yl)-1H-pyrazolo[3,4-b]pyrazine (446.0 mg, 1.2 mmol, Intermediate FK) and TEA (815.0 µL, 5.9 mmol) in DMF (10.0 mL) was stirred at 80° C. for 4 hours. The reaction mixture was then cooled to rt and used directly without further purification in the next step. LC-MS (ESI$^+$) m/z 565.0 (M+H)$^+$.

Step b: To a mixture of (3R)-5-fluoro-1'-[3-iodo-5-methyl-1-(oxan-2-yl)-1H-pyrazolo[3,4-b]pyrazin-6-yl]-3H-spiro[1-benzofuran-2,4'-piperidin]-3-amine (650.0 mg, 1.2 mmol) in DMF (10.0 mL) was added (Boc)$_{20}$ (527.0 µL, 2.3 mmol), and the mixture was stirred at 15° C. for 1 hour. The mixture was then diluted with ethyl acetate (40.0 mL), and washed with $H_2O$ (25.0 mL×3). The organic phase was washed with brine (15.0 mL), dried over anhydrous $Na_2SO_4$, filtered and concentrated in vacuo to give a residue. The residue was purified by silica gel chromatography (ethyl acetate in petroleum ether=0% to 25%) to afford tert-butyl N-[(3R)-5-fluoro-1'-[3-iodo-5-methyl-1-(oxan-2-yl)-1H-pyrazolo[3,4-b]pyrazin-6-yl]-3H-spiro[1-benzofuran-2,4'-piperidin]-3-yl]carbamate (520.0 mg, 68% yield) as a yellow solid. LC-MS (ESI⁺) m/z: 665.0 (M+H)⁺.

6-chloro-3-iodo-1-(tetrahydro-2H-pyran-2-yl)-1H-pyrazolo[3,4-b]pyridine, Intermediate FM

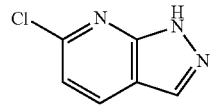

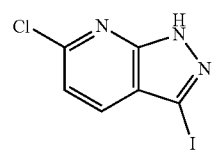

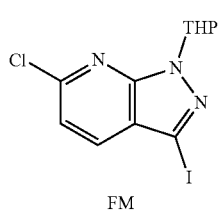

Step a: To a mixture of 6-chloro-H-pyrazolo[3,4-b]pyridine (350.0 mg, 2.3 mmol, CAS #63725-51-9) in DMF (15.0 mL) was added NIS (764.0 mg, 3.4 mmol), and the resulting mixture was stirred at 110° C. for 12 hours. The reaction mixture was then quenched with sat. Na₂SO₃ (15.0 mL) and sat. NaHCO₃ (15.0 mL), stirred for 10 min, then H₂O (15.0 mL) was added and the mixture was stirred for 5 min. The solid was then collected by filtration, washed with H₂O (50.0 mL) and dried under reduced pressure to afford 6-chloro-3-iodo-1H-pyrazolo[3,4-b]pyridine (580.0 mg, 91% yield) as a yellow solid. LC-MS (ESI⁺) m/z 279.8 (M+H)⁺.

Step b: A mixture of 6-chloro-3-iodo-1H-pyrazolo[3,4-b]pyridine (580.0 mg, 2.1 mmol), DHP (520.0 mg, 6.2 mmol) and CSA (48.0 mg, 207.0 μmol) in DCM (15.0 mL) was stirred at 45° C. for 2 hours. The mixture was then poured into sat. NaHCO₃ (40.0 mL), and extracted with DCM (25.0 mL×3). The organic phases were washed with brine (20.0 mL), dried over anhydrous Na₂SO₄, filtered and concentrated in vacuo to give a residue. The residue was purified by silica gel chromatography (ethyl acetate in petroleum ether, 0% to 13%) to afford 6-chloro-3-iodo-1-(oxan-2-yl)-1H-pyrazolo[3,4-b]pyridine (640.0 mg, 85% yield) as a white solid. LC-MS (ESI⁺) m/z 363.8 (M+H)⁺.

Tert-butyl ((1S)-1'-(3-iodo-1-(tetrahydro-2H-pyran-2-yl)-1H-pyrazolo[3,4-b]pyridin-6-yl)-1,3-dihydrospiro[indene-2,4'-piperidin]-1-yl)carbamate, Intermediate FN

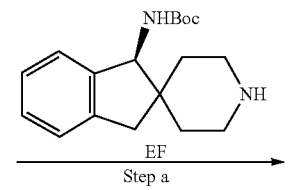

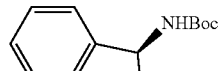

Step a: A mixture of tert-butyl N-[(3S)-1,3-dihydrospiro[indene-2,4'-piperidin]-3-yl]carbamate (520.0 mg, 1.7 mmol, Intermediate EF), 6-chloro-3-iodo-1-(oxan-2-yl)-1H-pyrazolo[3,4-b]pyridine (621.0 mg, 1.7 mmol, Intermediate FM) and TEA (709.0 μL, 5.1 mmol) in DMF (15.0 mL) was stirred at 90° C. for 18 hours. The mixture was then diluted with ethyl acetate (40.0 mL), and washed with H₂O (20.0 mL×3). The organic phase was washed with brine (10.0 mL), dried over anhydrous Na₂SO₄, filtered and concentrated in vacuo to give a residue. The residue was purified by silica gel chromatography (ethyl acetate in petroleum ether=0% to 23%) to afford tert-butyl N-[(3S)-1'-[3-iodo-1-(oxan-2-yl)-1H-pyrazolo[3,4-b]pyridin-6-yl]-1,3-dihydrospiro[indene-2,4'-piperidin]-3-yl]carbamate (290.0 mg, 27% yield) as a yellow solid. LC-MS (ESI⁺) m/z 630.1 (M+H)⁺.

N-[(3R)-1'-(6-bromopyridin-3-yl)-6-fluoro-3H-spiro[1-benzofuran-2,4'-piperidin]-3-yl]-1,1-diphenylmethanimine, Intermediate FO

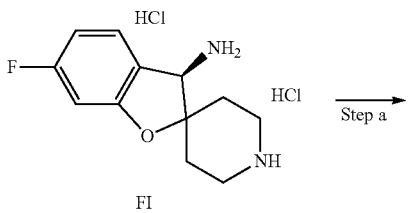

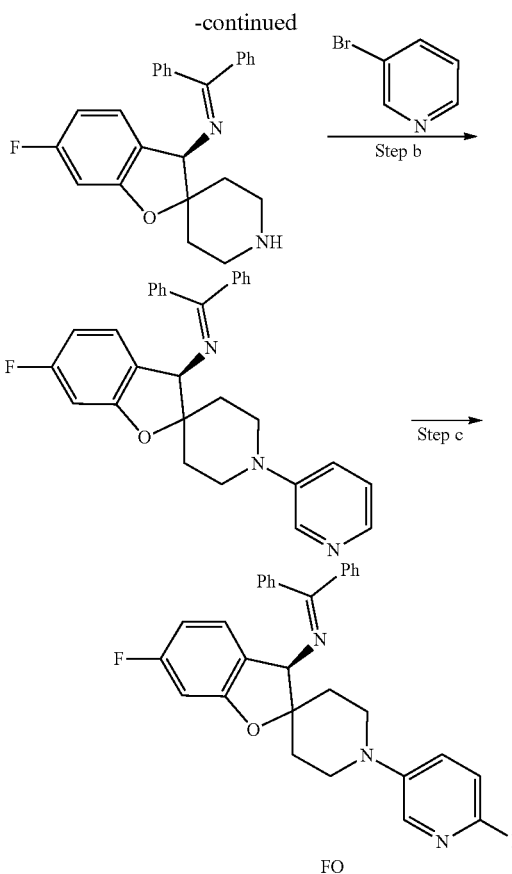

FO

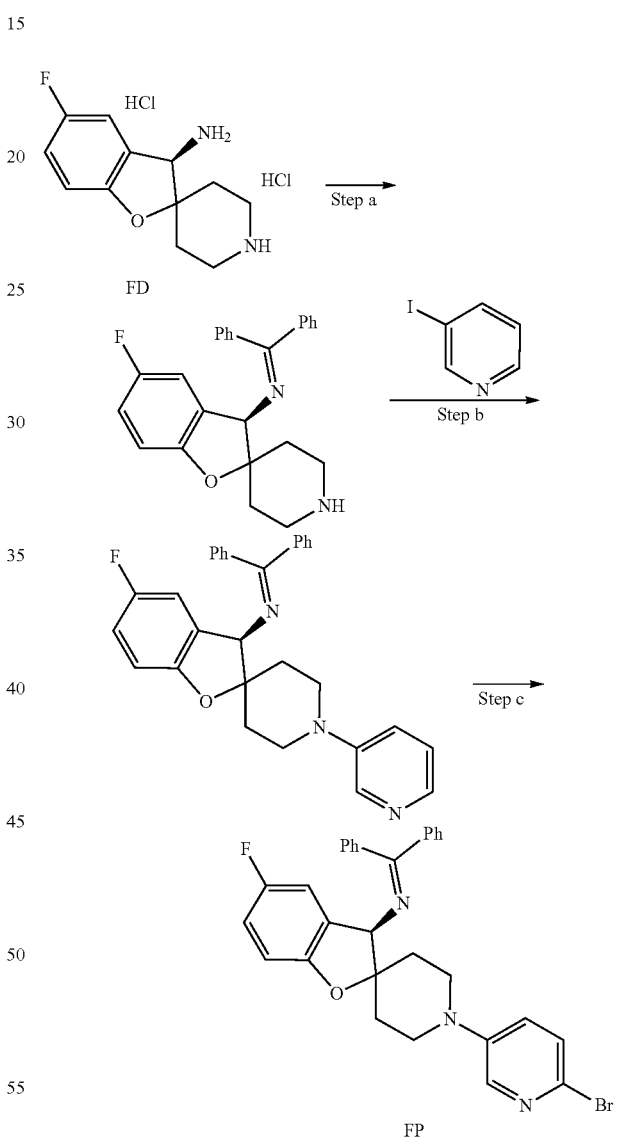

FP

Step a: A mixture of (R)-6-fluoro-3H-spiro[benzofuran-2,4'-piperidin]-3-amine dihydrochloride (600.0 mg, 2.0 mmol, Intermediate FI), diphenylmethanimine (329.0 mg, 1.8 mmol) and TEA (841.0 μL, 6.1 mmol) in MeCN (30.0 mL) was stirred at 80° C. for 12 hours. The reaction mixture was then concentrated under reduced pressure to give a residue, which was purified by silica gel chromatography (dichloromethane:methanol=0% to 7%) to afford (R)—N-(diphenylmethylene)-6-fluoro-3H-spiro[benzofuran-2,4'-piperidin]-3-amine (750.0 mg, 96% yield) as a white solid. LC-MS (ESI+) m/z: 387.1 (M+H)+.

Step b: A mixture of (R)—N-(diphenylmethylene)-6-fluoro-3H-spiro[benzofuran-2,4'-piperidin]-3-amine (750.0 mg, 1.9 mmol), 3-bromopyridine (458.0 mg, 2.9 mmol), Cs$_2$CO$_3$ (1.58 g, 4.9 mmol) and XantPhos-Pd-G4 (186.0 mg, 194.0 μmol) in toluene (35.0 mL) was stirred at 100° C. for 12 hours under N$_2$ atmosphere. The mixture was then concentrated under reduced pressure to give a residue, which was purified by silica gel chromatography (ethyl acetate in petroleum ether=0% to 65%) to afford N-[(3R)-6-fluoro-1'-(pyridin-3-yl)-3H-spiro[1-benzofuran-2,4'-piperidin]-3-yl]-1,1-diphenylmethanimine (230.0 mg, 26% yield) as a yellow solid. LC-MS (ESI+) m/z: 464.1 (M+H)+.

Step c: To a mixture of N-[(3R)-6-fluoro-1'-(pyridin-3-yl)-3H-spiro[1-benzofuran-2,4'-piperidin]-3-yl]-1,1-diphenylmethanimine (230.0 mg, 496.0 μmol) in MeCN (10.0 mL) and DCM (5.0 mL) at 0° C. was added NBS (87.7 mg, 496.0 μmol), and the resulting mixture was stirred at 0° C. for 0.5 hours. The mixture was then concentrated under reduced pressure to give a residue, which was purified by silica gel chromatography (ethyl acetate in petroleum ether=0% to 20%) to afford N-[(3R)-1'-(6-bromopyridin-3-yl)-6-fluoro-3H-spiro[1-benzofuran-2,4'-piperidin]-3-yl]-1,1-diphenylmethanimine (230.0 mg, 85.5% yield) as a white solid. LC-MS (ESI+) m/z: 544.0 (M+H)+;

$^1$HNMR (400 MHz, Methanol-d$_4$): δ 7.96 (d, J=3.2 Hz, 1H), 7.57-7.55 (m, 2H), 7.47-7.39 (m, 3H), 7.35-7.30 (m, 1H), 7.27-7.21 (m, 3H), 7.16-7.12 (m, 2H), 7.04-7.01 (m, 1H), 6.92-6.86 (m, 1H), 6.53-6.46 (m, 2H), 4.67 (s, 1H), 3.46-3.41 (m, 1H), 3.29-3.12 (m, 3H), 2.32-2.28 (m, 1H), 1.98-1.90 (m, 1H), 1.74-1.69 (m, 1H), 1.59-1.54 (m, 1H).

N-[(3R)-1'-(6-bromopyridin-3-yl)-6-fluoro-3H-spiro[1-benzofuran-2,4'-piperidin]-3-yl]-1,1-diphenylmethanimine, Intermediate FP Step a: To a solution of (3R)-5-fluoro-3H-spiro[1-benzofuran-2,4'-piperidin]-3-amine (500.0 mg, 2.2 mmol, Intermediate FD) in MeCN (5.00 mL) was added TEA (678.0 mg, 6.7 mmol), and the reaction mixture was stirred at 95° C. for 1 hour. To the reaction mixture was next added diphenylmethanimine (405.0 mg, 2.24 mmol) and the reaction was stirred for 10 hours at 95° C. The reaction mixture was then concentrated and the residue was purified by silica gel chromatography (DCM/MeOH=30/1 to 8/1) to afford (R)—

403

N-(diphenylmethylene)-5-fluoro-3H-spiro[benzofuran-2,4'-piperidin]-3-amine (600 mg, 69% yield) as a white solid. LC-MS (ESI⁺) m/z: 387.0 (M+H)⁺.

Step b: A mixture of N-[(3R)-5-fluoro-3H-spiro[1-benzofuran-2,4'-piperidin]-3-yl]-1,1-diphenylmethanimine (600.0 mg, 1.5 mmol), Pd$_2$(dba)$_3$ (141.0 mg, 0.15 mmol), t-BuONa (446.0 mg, 4.65 mmol), 3-bromopyridine (489.0 mg, 3.1 mmol) and BINAP (193.0 mg, 0.3 mmol) in toluene (5.00 mL) was stirred at 100° C. for 12 hours under N$_2$ atmosphere. The mixture was then concentrated to give a residue which was purified by silica gel chromatography (ethyl acetate in petroleum ether=0% to 70%) to afford N-[(3R)-5-fluoro-1'-(pyridin-3-yl)-3H-spiro[1-benzofuran-2,4'-piperidin]-3-yl]-1,1-diphenylmethanimine (700.0 mg, 97% yield) as a yellow solid. LC-MS (ESI⁺) m/z: 464.1 (M+H)⁺.

Step c: To a mixture of N-[(3R)-6-fluoro-1'-(pyridin-3-yl)-3H-spiro[1-benzofuran-2,4'-piperidin]-3-yl]-1,1-diphenylmethanimine (300.0 mg, 0.6 mmol) in MeCN (5.00 mL) and DCM (2.50 mL) was added NBS (114.0 mg, 0.6 mmol) at 0° C., and the resulting mixture was stirred at 0° C. for 0.5 hour. The reaction mixture was then concentrated and purified by silica gel chromatography (petroleum ether/EtOAc=30/1 to 1/1) to afford N-[(3R)-1'-(6-bromopyridin-3-yl)-6-fluoro-3H-spiro[1-benzofuran-2,4'-piperidin]-3-yl]-1,1-diphenylmethanimine (330.0 mg, 94% yield) as a yellow solid. LC-MS (ESI⁺) m/z: 544.1 (M+H)⁺.

tert-butyl N-[(3R)-1'-(5-bromopyrazin-2-yl)-6-fluoro-3H-spiro[1-benzofuran-2,4'-piperidin]-3-yl]carbamate, Intermediate FQ

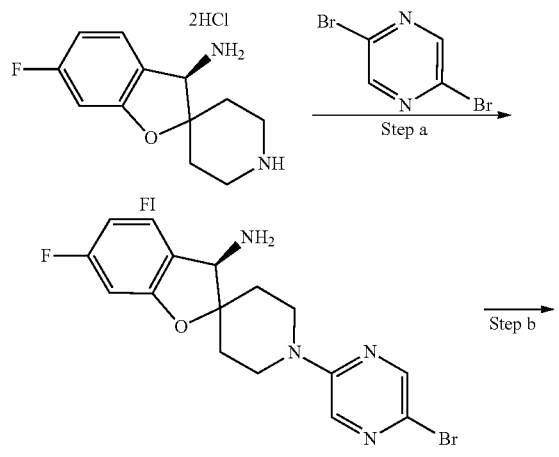

404

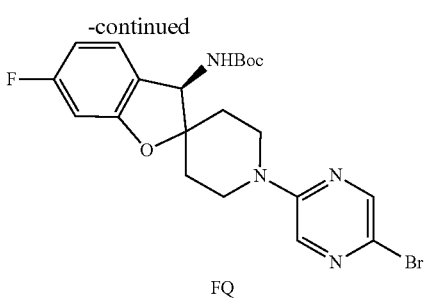

FQ

Step a: A mixture of 2,5-dibromopyrazine (200.0 mg, 0.8 mmol, CAS #23229-25-6), (3R)-6-fluoro-3H-spiro[1-benzofuran-2,4'-piperidin]-3-amine dihydrochloride (272.0 mg, 0.9 mmol, Intermediate FI) and TEA (580 μL, 4.2 mmol) in DMF (10 mL) was stirred at 80° C. for 2 hours. The solution was cooled to rt and used into the next step directly. LC-MS (ESI⁺) m/z: 361.8 (M-NH$_2$)+.

Step b: To the solution of (3R)-1'-(5-bromopyrazin-2-yl)-6-fluoro-3H-spiro[1-benzofuran-2,4'-piperidin]-3-amine (318.0 mg, 0.8 mmol) in DMF (10 mL) was added di-tert-butyl dicarbonate (383 μL, 1.7 mmol) at 15° C., and the reaction mixture was stirred at 15° C. for 12 hours. The reaction mixture was then diluted with water (30 mL), and extracted with EtOAc (50 mL×2). The organic layers were washed with H$_2$O (40 mL), dried over anhydrous Na$_2$SO$_4$, filtered and concentrated. The residue was purified by flash silica gel chromatography (20 g column, EtOAc in petroleum ether from 0% 10%) to give tert-butyl N-[(3R)-1'-(5-bromopyrazin-2-yl)-6-fluoro-3H-spiro[1-benzofuran-2,4'-piperidin]-3-yl]carbamate (260.0 mg, 0.5 mmol, 65% yield over two steps) as a yellow solid. LC-MS (ESI⁺) m/z: 478.9 (M+H)⁺.

tert-butyl N-[(3R)-6-fluoro-1'-(5-sulfanylpyrazin-2-yl)-3H-spiro[1-benzofuran-2,4'-piperidin]-3-yl]carbamate, Intermediate FR

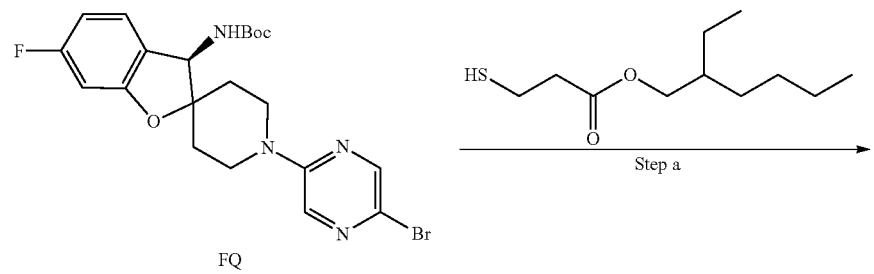

-continued

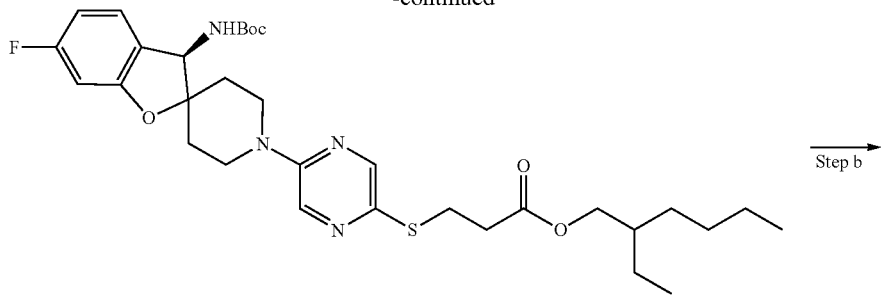

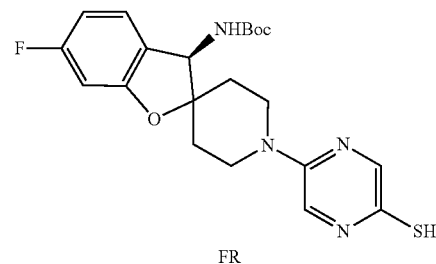

FR

Step a: A mixture of (R)-tert-butyl (1'-(5-bromopyrazin-2-yl)-5-fluoro-3H-spiro[benzofuran-2,4'-piperidin]-3-yl)carbamate (260.0 mg, 0.5 mmol, Intermediate FQ), 2-ethylhexyl 3-sulfanylpropanoate (130.0 mg, 0.6 mmol, CAS #50448-95-8), Pd$_2$(dba)$_3$ (49.6 mg, 0.05 mmol), XantPhos (62.7 mg, 0.11 mmol) and DIPEA (265 µL, 1.6 mmol) in dioxane (10 mL) was stirred at 100° C. for 12 hours under N$_2$ atmosphere. The reaction mixture was then poured into H$_2$O (20 mL) and extracted with EtOAc (40 mL×2). The combined organic layers were washed with brine (20 mL), dried over anhydrous Na$_2$SO$_4$, filtered and concentrated under reduced pressure to give a residue. The residue was purified by silica gel chromatography (ethyl acetate in petroleum ether=0% to 15%) to afford 2-ethylhexyl 3-({5-[(3R)-3-{[(tert-butoxy)carbonyl]amino}-6-fluoro-3H-spiro[1-benzofuran-2,4 (190.0 mg, 0.3 mmol, 57% yield) as a yellow solid. LC-MS (ESI$^+$) m/z: 617.2 (M+H)$^+$.

Step b: To the mixture of 2-ethylhexyl 3-({5-[(3R)-3-{[(tert-butoxy)carbonyl]amino}-6-fluoro-3H-spiro[1-benzofuran-2,4'-piperidin]-1'-yl]pyrazin-2-yl}sulfanyl)propanoate (188.0 mg, 0.3 mmol) in anhydrous THF (1.5 mL) was added t-BuOK (0.9 mL, 0.9 mmol, 1 M in THF) during 10 min at −78° C., and the resulting mixture was stirred at −78° C. for 0.5 hour under N$_2$ atmosphere. The reaction mixture was diluted with DCM (30 mL) and acidified with HCl/EtOAc (2 N, 1 mL) to pH=6 at −78° C. The mixture was then washed with H$_2$O (20 mL) and brine (20 ml). The organic layer were dried over anhydrous Na$_2$SO$_4$, filtered and concentrated to give tert-butyl N-[(3R)-6-fluoro-1'-(5-sulfanylpyrazin-2-yl)-3H-spiro[1-benzofuran-2,4'-piperidin]-3-yl]carbamate (131.0 mg, 100% crude yield) as a red oil.

(1s,4s)-4-(6-sulfanylpyridin-3-yl)-1',3'-dihydrospiro[cyclohexane-1,2'-inden]-3'-one, Intermediate FS

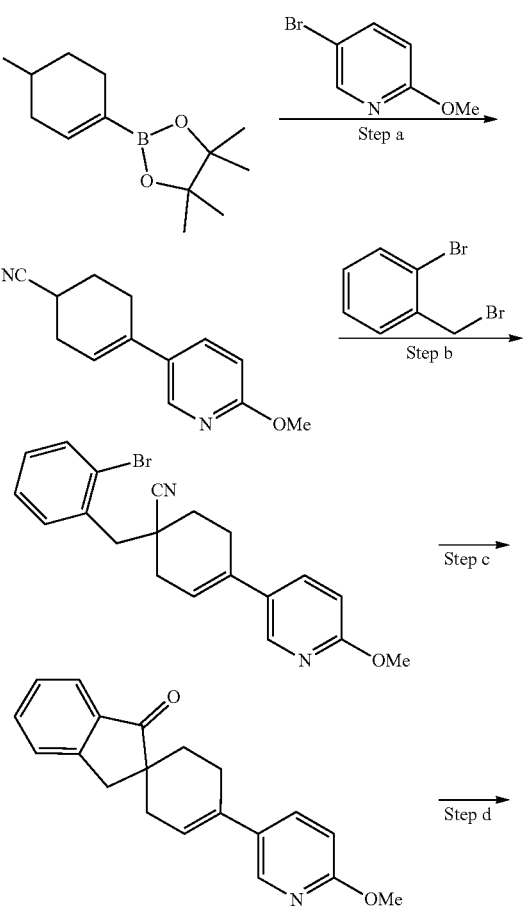

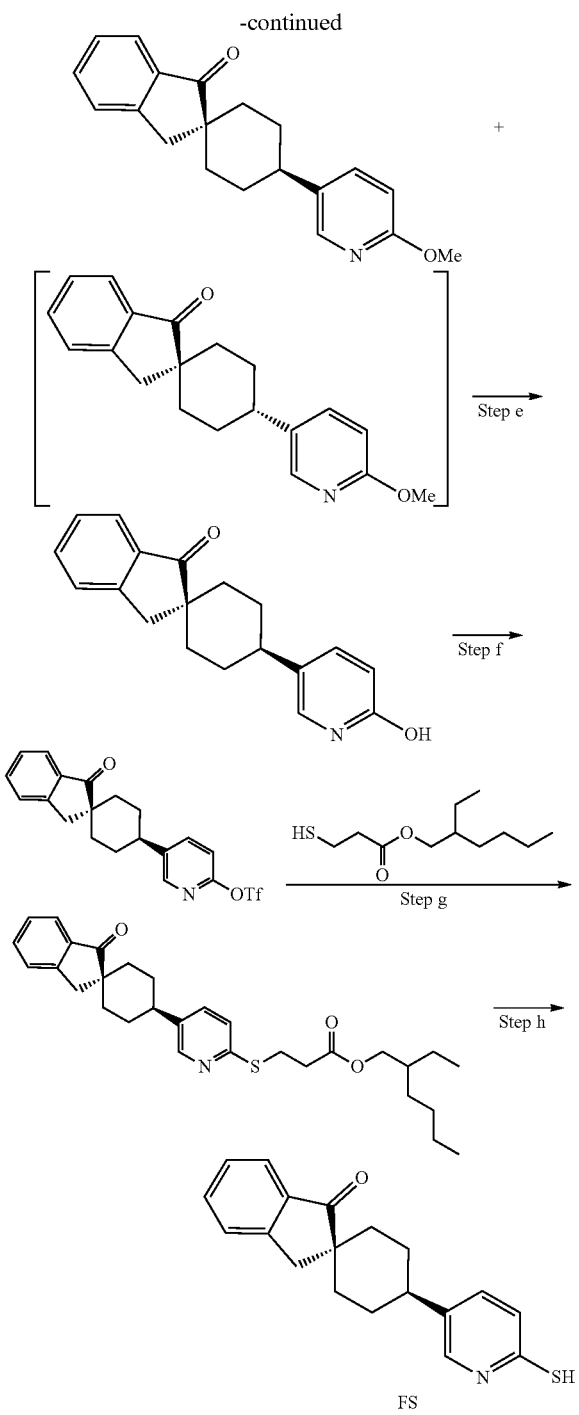

residue. The residue was purified by flash silica gel chromatography (petroleum ether:ethyl acetate=100:0 to 100:30) to afford 4-(6-methoxypyridin-3-yl)cyclohex-3-ene-1-carbonitrile (3.8 g, 17.7 mmol, 92% yield) as a white solid. LC-MS (ESI+) m/z: 215.1 (M+H)+.

Step b: 4-(6-Methoxypyridin-3-yl)cyclohex-3-ene-1-carbonitrile (1.9 g, 8.9 mmol) and 1-bromo-2-(bromomethyl)benzene (2.4 g, 9.7 mmol, CAS #3433-80-5) were dissolved in THF (200 mL). Then LDA (4.9 mL, 9.7 mmol, 2 M in THF) was added dropwise into the mixture at −10° C. The mixture was stirred at 0° C. for 0.5 hour, then the mixture was then warmed to 25° C. for 1 hour. Additional LDA (4.4 mL, 8.9 mmol, 2 M in THF) was added dropwise into the mixture at −10° C. The mixture was stirred at 0° C. for 0.5 hour, then mixture was then warmed to 25° C. for 1 hour. The combined reaction mixture was quenched by addition of sat. NH$_4$C$_1$ (100 mL). The mixture was then extracted with ethyl acetate (200 mL×3). The combined organic layers were washed with brine (100 mL), dried over anhydrous Na$_2$SO$_4$, filtered and concentrated to give a residue. The residue was purified by flash silica gel chromatography (petroleum ether:ethyl acetate=100:0 to 100:20) to afford 1-[(2-bromophenyl)methyl]-4-(6-methoxypyridin-3-yl)cyclohex-3-ene-1-carbonitrile (3.3 g, combined product) as a yellow oil.

Step c: 1-[(2-Bromophenyl)methyl]-4-(6-methoxypyridin-3-yl)cyclohex-3-ene-1-carbonitrile (3.3 g, 8.6 mmol), PdCl$_2$(AmPhos)$_2$ (304.0 mg, 0.4 mmol, CAS #887919-35-9) and TEA (4.8 mL, 34.4 mmol) were placed into DMA (60 mL) and H$_2$O (1.2 mL). The reaction mixture was evacuated and refilled 3 times using N$_2$, and the reaction mixture was stirred at 120° C. for 12 hours. The mixture was concentrated to give a residue, which was purified by flash silica gel chromatography (petroleum ether:ethyl acetate=100:0 to 100:20) to afford 4-(6-methoxypyridin-3-yl)-1', 3'-dihydrospiro[cyclohexane-1,2'-inden]-3-en-3'-one (2.3 g, 88% yield) as a yellow solid. LC-MS (ESI+) m/z: 306.2 (M+H)+.

Step d: 4-(6-Methoxypyridin-3-yl)-1',3'-dihydrospiro[cyclohexane-1,2'-inden]-3-en-3'-one (2.3 g, 7.5 mmol) was dissolved in MeOH (100 mL) and THF (6 mL). Then 10% Pd/C (300.0 mg, wet) was added and the reaction mixture was evacuated and refilled 3 times using H2. The reaction mixture was then stirred at 25° C. for 12 hours under H2 (50 psi). The mixture was then filtered and the filtrate was concentrated to give a residue. The residue was purified by flash silica gel chromatography (80 g, ethyl acetate/petroleum ether=0/100 to 18/100) to (1s,4s)-4-(6-methoxypyridin-3-yl)-1',3'-dihydrospiro[cyclohexane-1,2'-inden]-3'-one (1.02 g, 3.3 mmol, 44% yield) as a yellow solid (LC-MS (ESI+) m/z: 307.9 (M+H)+; $^1$HNMR (400 MHz, CDCl$_3$) δ 8.08 (s, 1H), 7.73 (d, J=7.6 Hz, 1H), 7.65-7.56 (m, 2H), 7.42-7.37 (m, 2H), 6.73 (d, J=8.4 Hz, 1H), 3.93 (s, 3H), 2.99 (s, 2H), 2.61-2.59 (m, 1H), 2.40-2.30 (m, 2H), 1.97 (br d, J=12.4 Hz, 2H), 1.73-1.68 (m, 4H) and (1r,4r)-4-(6-methoxypyridin-3-yl)-1',3'-dihydrospiro[cyclohexane-1,2'-inden]-3'-one (0.7 g, 2.3 mmol, 30% yield) as a yellow solid. LC-MS (ESI+) m/z: 307.9 (M+H)+.

Step e: TMSI (7.1 mL, 49.6 mmol) was added to a mixture of (s,4s)-4-(6-methoxypyridin-3-yl)-1',3'-dihydrospiro[cyclohexane-1,2'-inden]-3'-one (1.02 g, 3.3 mmol) in DCM (70 mL). The mixture was stirred at 50° C. for 12 hours. The mixture was then diluted with DCM (80 mL) and H$_2$O (30 mL) was added. The partitioned layers were separated and the aqueous phase was extracted with DCM (40 mL×2). The combined organic layers were washed with brine (50 mL), dried over anhydrous Na$_2$SO$_4$, filtered and concentrated to give a residue. The residue was triturated with the EtOAc (5

Step a: 4-(4,4,5,5-Tetramethyl-1,3,2-dioxaborolan-2-yl)cyclohex-3-ene-1-carbonitrile (4.5 g, 19.3 mmol, CAS #1310384-20-3), 5-bromo-2-methoxypyridine (4.0 g, 21.2 mmol, CAS #13472-85-0), K$_2$CO$_3$ (5.3 g, 38.6 mmol) and Pd(dppf)Cl$_2$ (1.4 g, 1.9 mmol) were placed into dioxane (300 mL) and H$_2$O (30 mL). The reaction mixture was evacuated and refilled 3 times using N$_2$, and the reaction mixture was stirred at 100° C. for 12 hours. The reaction mixture was then concentrated and H$_2$O (100 mL) was added, and the mixture was extracted with EtOAc (150 mL×3). The combined organic layers were washed with brine (50 mL), dried over anhydrous Na$_2$SO$_4$, filtered and concentrated to give a mL) where precipitate formed, and the solid was collected by filtration. The filter cake was washed with EtOAc (1 mL), and dried to give (1s,4s)-4-(6-hydroxypyridin-3-yl)-1',3'-dihydrospiro[cyclohexane-1,2'-inden]-3'-one (900.0 mg, 3.1 mmol, 93% yield) as a yellow solid. LC-MS (ESI$^+$) m/z: 293.9 (M+H)$^+$.

Step f: (1s,4s)-4-(6-Hydroxypyridin-3-yl)-1',3'-dihydrospiro[cyclohexane-1,2'-inden]-3'-one (800.0 mg, 2.7 mmol) and TEA (5.6 mL, 40.8 mmol) were dissolved in the DCM (35 mL) and Tf$_2$O (3.2 mL, 19.0 mmol) was added. The mixture was stirred at 20° C. for 2 hours. Then the mixture was diluted with DCM (60 mL), washed with H$_2$O (40 mL) and brine (15 mL), dried over anhydrous Na$_2$SO$_4$, filtered and concentrated to give a residue. The residue was purified by flash silica gel chromatography (ethyl acetate/petroleum ether=0/100 to 20/100) to give 5-[(1s,4s)-3'-oxo-1',3'-dihydrospiro[cyclohexane-1,2'-inden]-4-yl]pyridin-2-yl trifluoromethanesulfonate (1.02 g, 2.4 mmol, 89% yield) as a yellow solid. LC-MS (ESI$^+$) m/z: 426.0 (M+H)$^+$.

Step g: 5-[(1s,4s)-3'-Oxo-1',3'-dihydrospiro[cyclohexane-1,2'-inden]-4-yl]pyridin-2-yl trifluoromethanesulfonate (900.0 mg, 2.1 mmol), 2-ethylhexyl 3-sulfanylpropanoate (506.0 mg, 2.3 mmol), XantPhos (244.0 mg, 0.4 mmol), Pd$_2$(dba)$_3$ (193.0 mg, 0.2 mmol), and DIPEA (1.1 mL, 6.3 mol) were added into dioxane (30 mL). The reaction mixture was evacuated and refilled 3 times using N$_2$, and the solution was stirred at 100° C. for 12 hours. The reaction mixture was then diluted with DCM (50 mL), filtered and concentrated to give a residue. The residue was purified by flash column chromatography (40 g column, petroleum ether/EtOAc=100:0 to 100:10) to afford 2-ethylhexyl 3-((5-((1s,4s)-1'-oxo-1',3'-dihydrospiro[cyclohexane-1,2'-inden]-4-yl)pyridin-2-yl)thio)propanoate (1.45 g, 2.9 mmol, combined product) as a yellow oil. LC-MS (ESI$^+$) m/z: 494.2 (M+H)$^+$.

Step h: 2-Ethylhexyl 3-((5-((1s,4s)-1'-oxo-1',3'-dihydrospiro[cyclohexane-1,2'-inden]-4-yl)pyridin-2-yl)thio)propanoate (500.0 mg, 1.0 mmol) was dissolved in THF (6 mL). The reaction mixture was cooled to −78° C. and t-BuOK (3.0 mL, 1 M in THF) was added dropwise over 10 min under N$_2$. The reaction mixture was stirred at −78° C. for 30 min. Then the reaction mixture was diluted with DCM (50 mL) and acidified with HCl/MeOH (2 N) to pH=5-6 at −78° C. The mixture was washed with H$_2$O (30 mL×3) and brine (20 ml). The organic layer was dried over anhydrous Na$_2$SO$_4$, filtered and concentrated to give (1s,4s)-4-(6-sulfanylpyridin-3-yl)-1',3'-dihydrospiro[cyclohexane-1,2'-inden]-3'-one (312.0 mg, 100% crude yield) as a yellow solid.

Tert-butyl N-[(3S)-1'-(1-benzyl-6-oxo-5-sulfanyl-1,6-dihydropyrimidin-2-yl)-1,3-dihydrospiro[indene-2,4'-piperidin]-3-ylcarbamate, Intermediate FT

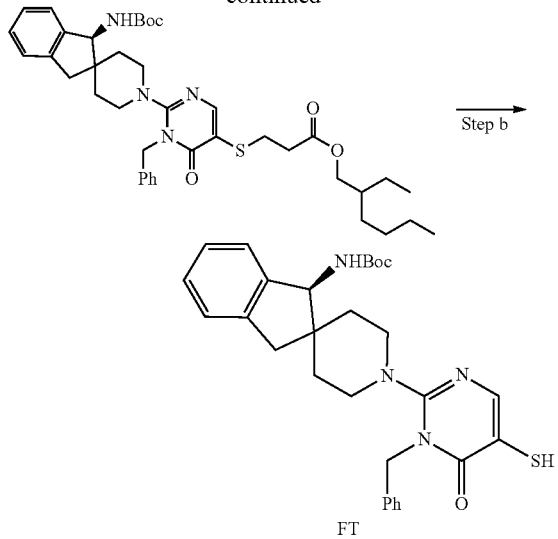

Step a: A mixture of tert-butyl N-[(3S)-1'-(1-benzyl-5-iodo-6-oxo-1,6-dihydropyrimidin-2-yl)-1,3-dihydrospiro[indene-2,4'-piperidin]-3-yl]carbamate (400.0 mg, 0.6 mmol, Intermediate FC), Pd$_2$(dba)$_3$ (59.7 mg, 0.06 mmol), DIPEA (247.0 mg, 1.9 mmol), XantPhos (75.5 mg, 0.1 mmol), and 2-ethylhexyl 3-mercaptopropanoate (283.0 mg, 1.3 mmol) in 1,4-dioxane (10.00 mL) was stirred at 100° C. for 12 hours under N$_2$ atmosphere. The mixture was then concentrated in vacuo to give a residue, which was purified by silica gel chromatography (ethyl acetate in petroleum ether=0% to 85%) to afford 2-ethylhexyl 3-({1-benzyl-2-[(3S)-3-{[(tert-butoxy)carbonyl]amino}-1,3-dihydrospiro[indene-2,4'-piperidin]-1'-yl]-6-oxo-1,6-dihydropyrimidin-5-yl}sulfanyl)propanoate (400.0 mg, 83% yield) as a yellow solid. LC-MS (ESI$^+$) m/z: 703.4 (M+H)$^+$.

Step b: 2-Ethylhexyl 3-({1-benzyl-2-[(3S)-3-{[(tert-butoxy)carbonyl]amino}-1,3-dihydrospiro[indene-2,4'-piperidin]-1'-yl]-6-oxo-1,6-dihydropyrimidin-5-yl}sulfanyl)propanoate (400.0 mg, 0.5 mmol) was dissolved in THF (6.00 mL). The reaction mixture was cooled to −78° C. and t-BuOK (3.03 mL, 1 M in THF) was added dropwise under N$_2$. The reaction mixture was stirred at −78° C. for 60 min. Then the reaction mixture was diluted with DCM (50 mL) and acidified with HCl/MeOH (2 N) to pH=5-6 at −78° C. The mixture was washed with H$_2$O (30 mL×3) and brine (20 ml). The organic layer were dried over anhydrous Na$_2$SO$_4$, filtered and concentrated to give tert-butyl N-[(3S)-1'-(1-benzyl-6-oxo-5-sulfanyl-1,6-dihydropyrimidin-2-yl)-1,3-dihydrospiro[indene-2,4'-piperidin]-3-yl]carbamate (280.0 mg, 95% crude yield) as a yellow solid. LC-MS (ESI$^+$) m/z: 519.1 (M+H)$^+$.

(10R)-5-bromo-8-oxa-1,3,6-triazatricyclo[8.4.0.0$^{2,7}$]tetradeca-2(7),3,5-trien-12-one, Intermediate FU

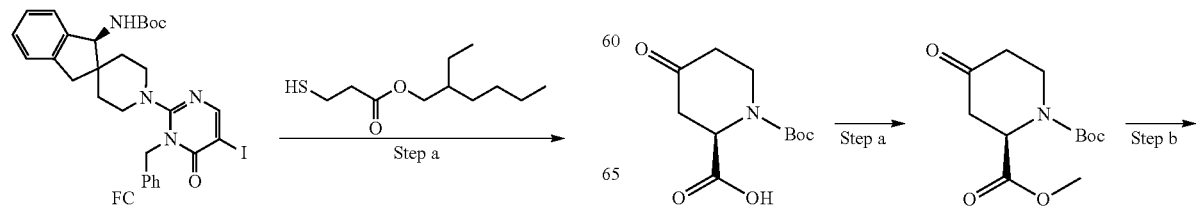

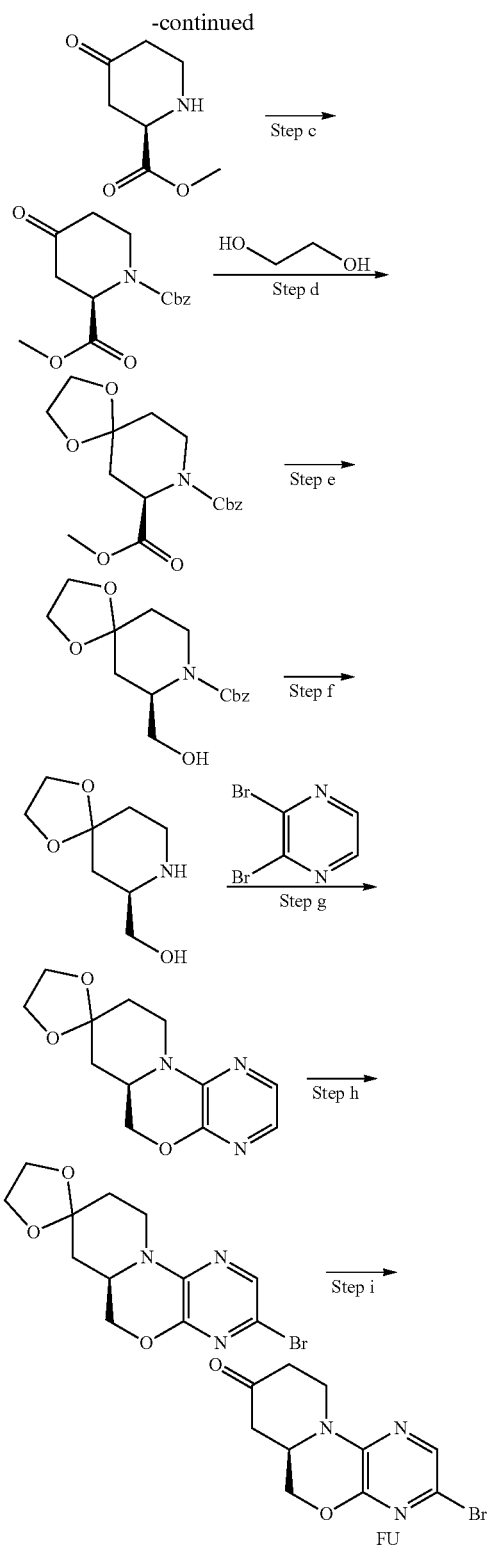

cake was washed with ethyl acetate (500 mL). The filtrate was poured into H₂O (2.00 L) and extracted with ethyl acetate (500 mL×2). The combined organic layers were washed with brine (500 mL×2), dried over Na₂SO₄, filtered and concentrated to give 1-(tert-butyl) 2-methyl (R)-4-oxopiperidine-1,2-dicarboxylate (92.0 g, 88% crude yield) as a yellow oil. ¹HNMR (400 MHz, CDCl₃): δ 5.13-4.85 (m, 1H), 4.11-4.04 (m, 1H), 3.75-3.56 (m, 4H), 2.78 (s, 2H), 2.51 (s, 2H), 1.47 (s, 9H).

Step b: To the stirred solution of 1-(tert-butyl) 2-methyl (R)-4-oxopiperidine-1,2-dicarboxylate (92.0 g, 358 mmol) in DCM (230 mL) was added TFA (354 g, 3.11 mol, 230 mL) at 20° C. and the mixture was stirred at 20° C. for 2 h. The reaction mixture was then concentrated to give methyl (R)-4-oxopiperidine-2-carboxylate (97.0 g, quant. crude yield, TFA) as a yellow oil. ¹HNMR (400 MHz, MeOD): δ 4.21-4.12 (m, 1H), 3.85 (s, 3H), 3.46-3.39 (m, 1H), 3.21-3.08 (m, 1H), 2.45-2.37 (m, 1H), 2.15-2.01 (m, 1H), 1.95-1.76 (m, 2H).

Step c: To the stirred solution of methyl (R)-4-oxopiperidine-2-carboxylate (80.0 g, 295 mmol, TFA) and TEA (149 g, 1.47 mol, 205 mL) in DCM (400 mL) was added CbzCl (75.5 g, 442 mmol, 62.9 mL) at 0° C. Then the reaction was stirred at 15° C. for 12 h. Next, CbzCl (30.0 mL) was added at 0° C. and the reaction mixture was stirred at 15° C. for 2 h. To the reaction mixture was then added H₂O (1.00 L) and the mixture was extracted with DCM (500 mL×3). The combined organic layers were washed with brine (500 mL×3), dried over Na₂SO₄, filtered and concentrated. The residue was purified by column chromatography (petroleum ether/ethyl acetate=1/0~2/1) (petroleum ether/ethyl acetate=2/1, R$_f$=0.60) to give 1-benzyl 2-methyl (R)-4-oxopiperidine-1,2-dicarboxylate (46.0 g, 153 mmol, 50% yield over 3 steps) as a yellow oil. LC-MS (ESI⁺) m/z: 291.9 (M+H)⁺; ¹HNMR (400 MHz, CDCl₃): δ 7.38-7.36 (m, 5H), 5.24-5.02 (m, 3H), 4.17-4.13 (m, 1H), 3.76-3.66 (m, 4H), 2.90-2.74 (m, 2H), 2.55-2.51 (m, 2H)

Step d: A solution of 1-benzyl 2-methyl (R)-4-oxopiperidine-1,2-dicarboxylate (41.0 g, 141 mmol), ethane-1,2-diol (34.9 g, 563 mmol, 31.5 mL) and 4-methylbenzenesulfonic acid; hydrate (2.68 g, 14.1 mmol) in toluene (205 mL) was heated to 110° C. and stirred at 110° C. for 2 h with Dean-Stark trap removal of water. The reaction mixture was poured into saturated NaHCO₃ aqueous (500 mL) and extracted with ethyl acetate (300 mL×2). The combined organic layers were dried over Na₂SO₄, filtered and concentrated to give 8-benzyl 7-methyl (R)-1,4-dioxa-8-azaspiro[4.5]decane-7,8-dicarboxylate (47.2 g, quant. crude yield) as a yellow oil. ¹HNMR (400 MHz, CDCl₃): δ 7.38-7.28 (m, 5H), 5.18-5.11 (m, 2H), 5.06-4.92 (m, 1H), 4.25-4.12 (m, 1H), 4.02-3.87 (m, 4H), 3.75-3.70 (m, 3H), 3.46-3.32 (m, 1H), 2.45-2.36 (m, 2H), 1.89-1.64 (m, 2H).

Step e: To the stirred solution of 8-benzyl 7-methyl (R)-1,4-dioxa-8-azaspiro[4.5]decane-7,8-dicarboxylate (48.0 g, 143 mmol) in THF (480 mL) was added LAH (10.9 g, 286 mmol) in portions at 0° C. under N₂. The reaction mixture was stirred at 20° C. for 2 h. The reaction mixture was then quenched with H₂O (10.9 mL) at 10° C., then 15% NaOH aqueous (10.9 mL) and Na₂SO₄ solid (50.0 g) were added. The resulting mixture was stirred at 20° C. for 0.5 h. The mixture was then filtered and the filter cake was washed with ethyl acetate (500 mL×2), and the filtrate was concentrated to give benzyl (R)-7-(hydroxymethyl)-1,4-dioxa-8-azaspiro[4.5]decane-8-carboxylate (38.2 g, 87% crude yield) as a light yellow oil. ¹HNMR (400 MHz, CDCl₃): δ 7.38-7.29 (m, 5H), 4.70 (s, 2H), 3.99-3.94 (m, 4H), 3.85 (dd, J=11.6, 4.0 Hz, 1H), 3.38 (dd, J=11.2, 2.0 Hz, 1H), 2.90-2.84

Step a: To the stirred solution of (R)-1-(tert-butoxycarbonyl)-4-oxopiperidine-2-carboxylic acid (90.0 g, 370 mmol) in DMF (450 mL) was added Cs₂CO₃ (133 g, 407 mmol) and the mixture was stirred at 20° C. for 10 minutes. Then CH₃I (78.2 g, 551 mmol, 34.3 mL) was added to the mixture dropwise and the reaction mixture was stirred at 20° C. for 2 h. The reaction mixture was filtered and the filter (m, 1H), 2.50-2.43 (m, 1H), 2.31-2.27 (m, 1H), 1.95-1.88 (m, 1H), 1.80 (td, J=12.8, 4.4 Hz, 1H), 1.69-1.63 (m, 2H).

Step f: To the stirred solution of benzyl (R)-7-(hydroxymethyl)-1,4-dioxa-8-azaspiro[4.5]decane-8-carboxylate (41.0 g, 133 mmol) in MeOH (410 mL) was added Pd/C (4.10 g, 10 wt %) under N₂. The suspension was degassed under vacuum and purged with H2 several times. The mixture was stirred under H2 (50 psi) at 15° C. for 14 h. The reaction mixture was then filtered and the filtrate was added Pd/C (5.00 g, 10 wt) under N₂. The suspension was degassed under vacuum and purged with H2 several times. The mixture was again stirred under H2 (50 psi) at 40° C. for 4 h. The reaction mixture was filtered and the filtrate was concentrated. The residue was dissolved in MeOH (400 mL) and added Pd/C (5.00 g, 10 wt %) under N₂. The suspension was degassed under vacuum and purged with H2 several times. The mixture was stirred under H2 (50 psi) at 50° C. for 20 h. Finally, Pd(OH)₂ (5.00 g, 20 wt %) was added under N₂. The suspension was degassed under vacuum and purged with H2 several times. The mixture was stirred under H2 (50 psi) at 50° C. for 20 h. The reaction mixture was filtered and the filtrate was concentrated to give (R)-(1,4-dioxa-8-azaspiro[4.5]decan-7-yl)methanol (25.0 g, quant. crude yield) as a yellow oil. ¹HNMR (400 MHz, MeOD): δ 3.96-3.93 (m, 4H), 3.61-3.59 (m, 2H), 2.89-2.85 (m, 1H), 2.53-2.47 (m, 1H), 2.37-2.32 (m, 1H), 1.81-1.76 (m, 2H), 1.71-1.67 (m, 2H).

Step g: To a solution of (R)-(1,4-dioxa-8-azaspiro[4.5]decan-7-yl)methanol (16.5 g, 95.3 mmol) and CsF (43.4 g, 286 mmol, 10.5 mL) in DMSO (120 mL) was added 2,3-dibromopyrazine (22.7 g, 95.3 mmol). The mixture was stirred at 130° C. for 2.5 h. The reaction mixture was then diluted with H₂O (500 mL) and extracted with ethyl acetate (300 mL×3). The combined organic layers were washed with brine (200 mL×2), dried over Na₂SO₄, filtered and concentrated under reduced pressure to give a residue. The residue was purified by flash silica gel chromatography (petroleum ether/ethyl acetate=50/1-1/2, R$_f$=0.20) to give (R)-6a,7,9,10-tetrahydro-6H-spiro[pyrazino[2,3-b]pyrido[1,2-d][1,4]oxazine-8,2'-[1,3]dioxolane] (7.90 g, 29.5 mmol, 26% yield over 4 steps) as a yellow oil. LC-MS (ESI⁺) m/z: 250.1 (M+H)⁺; ¹HNMR (400 MHz, CDCl₃): δ 7.71 (d, J=2.8 Hz, 1H), 7.45 (d, J=2.8 Hz, 1H), 4.64-4.60 (m, 1H), 4.39 (dd, J=11.2, 2.8 Hz, 1H), 4.14-4.10 (m, 1H), 4.01 (s, 4H), 3.62-3.56 (m, 1H), 3.00-2.93 (m, 1H), 1.85-1.75 (m, 3H), 1.61-1.58 (m, 1H).

Step h: To the stirred solution of (R)-6a,7,9,10-tetrahydro-6H-spiro[pyrazino[2,3-b]pyrido[1,2-d][1,4]oxazine-8,2'-[1,3]dioxolane] (7.90 g, 29.5 mmol) in DCM (79.0 mL) was added NBS (5.25 g, 29.5 mmol). The mixture was stirred at 15° C. for 0.5 h. The reaction mixture was then washed with brine (50.0 mL×2). The organic layer was dried over Na₂SO₄, filtered and concentrated. The residue was triturated with 100 mL of petroleum ether/ethyl acetate (20/1) at 15° C. for 15 mins. The suspension was filtered, the cake was dried under reduced pressure to give (R)-3-bromo-6a,7,9,10-tetrahydro-6H-spiro[pyrazino[2,3-b]pyrido[1,2-d][1,4]oxazine-8,2'-[1,3]dioxolane] (9.40 g, 28.6 mmol, 97% yield) as a yellow solid. LC-MS (ESI⁺) m/z: 328.0 (M+H)⁺; ¹HNMR (400 MHz, CDCl₃): δ 7.80 (s, 1H), 4.55-4.38 (m, 1H), 4.40 (dd, J=11.6, 3.2 Hz, 1H), 4.12 (dd, J=11.2, 7.6 Hz, 1H), 4.02-3.99 (m, 4H), 3.60-3.57 (m, 1H), 3.00-2.92 (m, 1H), 1.84-1.75 (m, 3H), 1.60-1.53 (m, 1H).

Step i: To the stirred solution of give (R)-3-bromo-6a,7,9,10-tetrahydro-6H-spiro[pyrazino[2,3-b]pyrido[1,2-d][1,4]oxazine-8,2'-[1,3]dioxolane] (8.80 g, 26.8 mmol) was added HCOOH (1.29 g, 26.8 mmol, 44.0 mL) at 15° C. The solution was then stirred at 40° C. for 4 h. The reaction mixture was then concentrated. The residue was purified by column chromatography (SiO₂, petroleum ether/ethyl acetate=6/1-2/1, R$_f$=0.30) to give (R)-3-bromo-6a,7,9,10-tetrahydropyrazino[2,3-b]pyrido[1,2-d][1,4]oxazin-8(6H)-one (7.07 g, 24.0 mmol, 90% yield) as a yellow gum. LC-MS (ESI⁺) m/z: 284.0 (M+H)⁺; ¹HNMR (400 MHz, CDCl₃): δ 7.87 (s, 1H), 4.87-4.82 (m, 1H), 4.53 (dd, J=11.6, 3.2 Hz, 1H), 4.22 (dd, J=11.6, 6.0 Hz, 1H), 3.81-3.75 (m, 1H), 3.21-3.18 (m, 1H), 2.60-2.46 (m, 4H).

N-[(3R,7'R)-12'-bromo-3H-9'-oxa-2',11',14'-triazaspiro[1-benzofuran-2,5'-tricyclo[8.4.0.0²,⁷]tetradecane]-1'(10'),11',13'-trien-3-yl]-2-methylpropane-2-sulfinamide, Intermediate FV

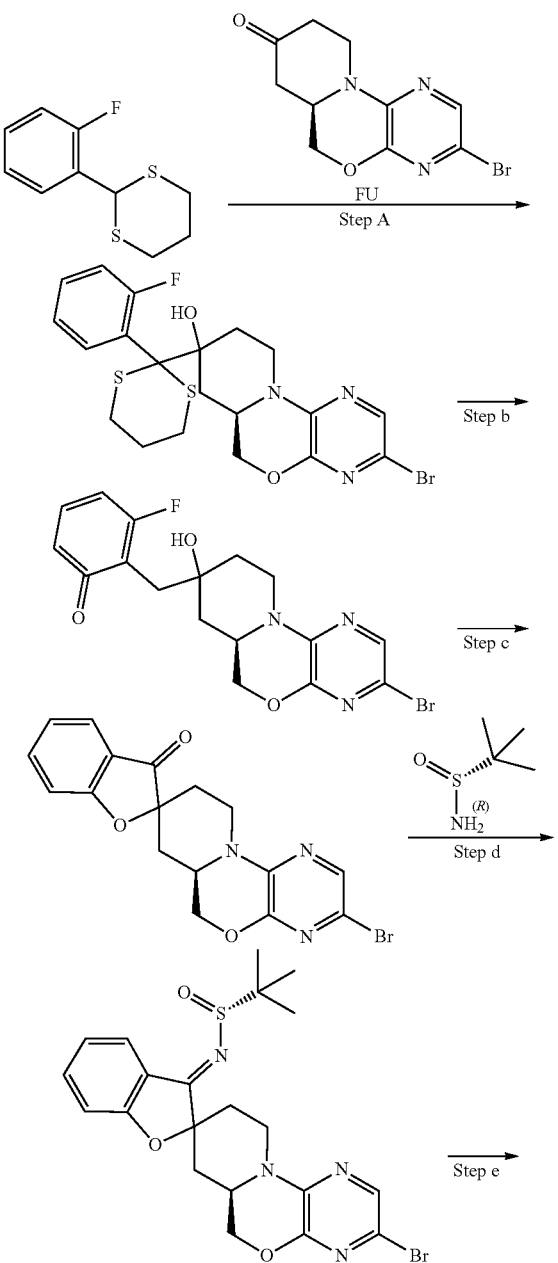

-continued

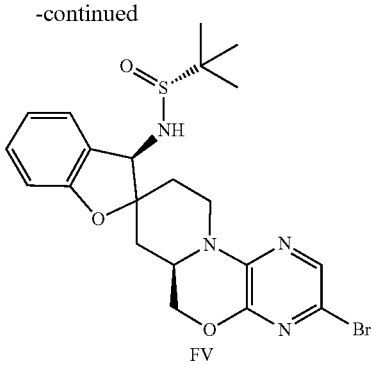

FV

Step a: To a solution of 2-(2-fluorophenyl)-1,3-dithiane (900.0 mg, 4.19 mmol, synthesized via Step a of Intermediate AP) in THF (20.0 mL) was added LDA (2.19 mL, 4.39 mmol, 2 M) at −78° C. under $N_2$. The reaction mixture was stirred at −78° C. for 0.5 hour, then (10R)-5-bromo-8-oxa-1,3,6-triazatricyclo[8.4.0.0$^{2,7}$]tetradeca-2(7),3,5-trien-12-one (600.0 mg, 2.11 mmol, Intermediate FU) in THF (10.0 mL) was added at −78° C. The reaction mixture was then stirred at 10° C. for 11.5 hours under $N_2$. The reaction mixture was then poured into $H_2O$ (100.0 mL) and extracted with EtOAc (100.0 mL×2). The combined layers were concentrated and the residue was triturated with EtOAc: petroleum ether=1:1 to give (10R)-5-bromo-12-[2-(2-fluorophenyl)-1,3-dithian-2-yl]-8-oxa-1,3,6-triazatricyclo [8.4.0.0$^{2,7}$]tetradeca-2(7),3,5-trien-12-ol (700.0 mg, 67.3% yield) as a yellow solid. LC-MS (ESI$^+$) m/z: 497.9 and 499.9 (M+H)$^+$.

Step b: To a solution of (10R)-5-bromo-12-[2-(2-fluorophenyl)-1,3-dithian-2-yl]-8-oxa-1,3,6-triazatricyclo [8.4.0.0$^{2,7}$]tetradeca-2(7),3,5-trien-12-ol (700.0 mg, 1.40 mmol) in DCM/$H_2O$ (30.0 mL/3.0 mL) was added pyridine (0.5 mL), Pyr.HBr$_3$ (668.0 mg, 2.09 mmol) and TBAB (90.2 mg, 280.0 μmol) at 25° C. The reaction mixture was stirred at 25° C. for 12 hours. Then the reaction mixture was poured into $H_2O$ (100.0 mL) and extracted with DCM (100.0 mL×2). The combined organic layers were washed with brine (200.0 mL), dried over anhydrous $Na_2SO_4$, filtered and the filtrate was concentrated under reduced pressure to give a residue. The residue was purified by flash silica gel chromatography (20 g column, ethyl acetate in petroleum ether from 0% to 35%) to give (10R)-5-bromo-12-(2-fluorobenzoyl)-8-oxa-1,3,6-triazatricyclo[8.4.0.0$^2$,]tetradeca-2 (7),3,5-trien-12-ol (530.0 mg, 93% yield) as a yellow oil. LC-MS (ESI$^+$) m/z: 407.9 and 409.9 (M+H)$^+$.

Step c: A solution of (10R)-5-bromo-12-(2-fluorobenzoyl)-8-oxa-1,3,6-triazatricyclo[8.4.0.0$^{2,7}$]tetradeca-2(7),3, 5-trien-12-ol (500.0 mg, 1.22 mmol) and t-BuOK (341.0 mg, 3.05 mmol) in dioxane (15.0 mL) was stirred at 70° C. for 2 hours. The reaction mixture was poured into $H_2O$ (100.0 mL) and extracted with EtOAc (100.0 mL×2). The combined organic layers were washed with brine (200.0 mL), dried over anhydrous $Na_2SO_4$, filtered and concentrated under reduced pressure to give a residue. The residue was purified by flash silica gel chromatography (20 g column, ethyl acetate in petroleum ether from 0% to 25%) to give (7'R)-12'-bromo-3H-9'-oxa-2',11',14'-triazaspiro[1-benzofuran-2,5'-ticyclo[8.4.0.0$^{2,7}$]tetradecane]-(10'),11',1-trien-3-one (210.0 mg, 44% yield) as a white solid. LC-MS (ESI$^+$) m/z: 387.9 and 389.9 (M+H)$^+$.

Step d: To a solution of (7'R)-12'-bromo-3H-9'-oxa-2',11', 14'-triazaspiro[1-benzofuran-2,5'-tricyclo[8.4.0.0$^{2,7}$]tetradecane]-1(10'),11',13'-trien-3-one (210.0 mg, 0.54 mmol) and Ti(OEt)$_4$ (492.0 mg, 2.16 mmol) in 2-Me-THF (15.0 mL) was added (R)-2-methylpropane-2-sulfinamide (130.0 mg, 1.08 mmol). The reaction mixture was stirred at 90° C. for 12 hours under $N_2$. The reaction mixture was cooled to rt and used in the next step without further purification. LC-MS (ESI$^+$) m/z: 491.0 and 493.0 (M+H)$^+$.

Step e: To a solution of N-[(7'R)-12'-bromo-3H-9'-oxa-2',11',14'-triazaspiro[1-benzofuran-2,5'-tricyclo[8.4.0.0$^{2,7}$] tetradecane]-1'(10'),11',13'-trien-3-ylidene]-2-methylpropane-2-sulfinamide (270.0 mg, 0.55 mmol) in 2-Me-THF (15.0 mL) was added LiBH$_4$ (23.7 mg, 1.09 mmol) at −78° C. and the reaction mixture was stirred at −78° C. for 2 hours. The reaction mixture was then poured into $H_2O$ (100.0 mL) and extracted with EtOAc (100.0 mL×2). The combined organic layers were washed with brine (200.0 mL), dried over anhydrous $Na_2SO_4$, filtered and concentrated under reduced pressure to give a residue. The residue was purified by flash silica gel chromatography (4 g, ethyl acetate in petroleum ether from 0% to 50%) to give N-[(3R, 7'R)-12'-bromo-3H-9'-oxa-2',11',14'-triazaspiro[1-benzofuran-2,5'-tricyclo[8.4.0.0$^{2,7}$]tetradecane]-1'(10'),11',13'-trien-3-yl]-2-methylpropane-2-sulfinamide (250.0 mg, 92% yield) as a yellow oil. LC-MS (ESI$^+$) m/z: 493.0 and 495.0 (M+H)$^+$.

(S)—N—((S)-1'-(2-bromothiazole-4-carbonyl)-1,3-dihydrospiro[indene-2,4'-piperidin]-1-yl)-2-methyl-propane-2-sulfinamide, Intermediate FW

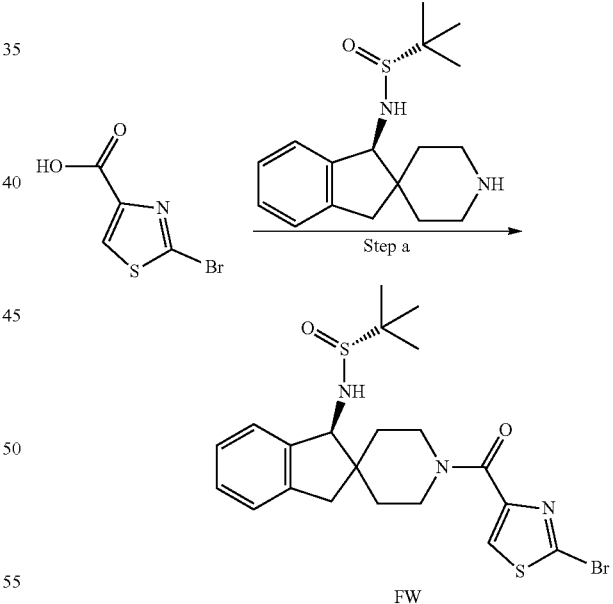

FW

Step a: 2-Bromo-1,3-thiazole-4-carboxylic acid (200.0 mg, 961 μmol), TEA (671 μL, 4.80 mmol), HATU (547.0 mg, 1.44 mmol) and (R)—N—((S)-1,3-dihydrospiro[indene-2,4'-piperidin]-1-yl)-2-methylpropane-2-sulfinamide (352.0 mg, 1.15 μmol, synthesized via Step a of Example 120) were placed into DMF (15 mL). The reaction mixture was evacuated and refilled 3 times using $N_2$, and the reaction mixture was stirred at 25° C. for 1 hour. The mixture was then diluted with EtOAc (100 mL) and the mixture was washed with $H_2O$ (30 mL×5), brine (50 mL), dried over anhydrous Na$_2$SO$_4$, filtered and concentrated to give a residue. The residue was purified by silica gel chromatography (ethyl acetate in petroleum ether=0% to 80%) to afford (S)—N—((S)-1'-(2-bromothiazole-4-carbonyl)-1,3-dihydrospiro[indene-2,4'-piperidin]-1-yl)-2-methylpropane-2-sulfinamide (458 mg,96% yield) as yellow oil. LC-MS (ESI$^+$) m/z: 498.0 (M+H)$^+$.

1-(3-methoxyphenyl)-1H-pyrazole-3-carboxylic acid, Intermediate FX 1-(3-methoxyphenyl)-1H-pyrazole-5-carboxylic acid, Intermediate FY Step c: To the reaction mixture of methyl 1-(3-methoxyphenyl)-1H-pyrazole-5-carboxylate (30 mg, 0.13 mmol) in MeOH (1.00 mL) was added NaOH (51.5 mg, 1.29 mmol) in H$_2$O (1 mL). The reaction mixture was stirred at 60° C. for 1 hour. Then the reaction mixture was concentrated, and quenched with water (10 mL). The mixture was adjusted to pH=5-6 with diluted HCl solution (1.2 M), where precipitate formed. The reaction mixture was extracted with EtOAc (20 mL×2). The organic layers were dried over anhydrous Na$_2$SO$_4$, filtered and concentrated to give 1-(3-methoxyphe-

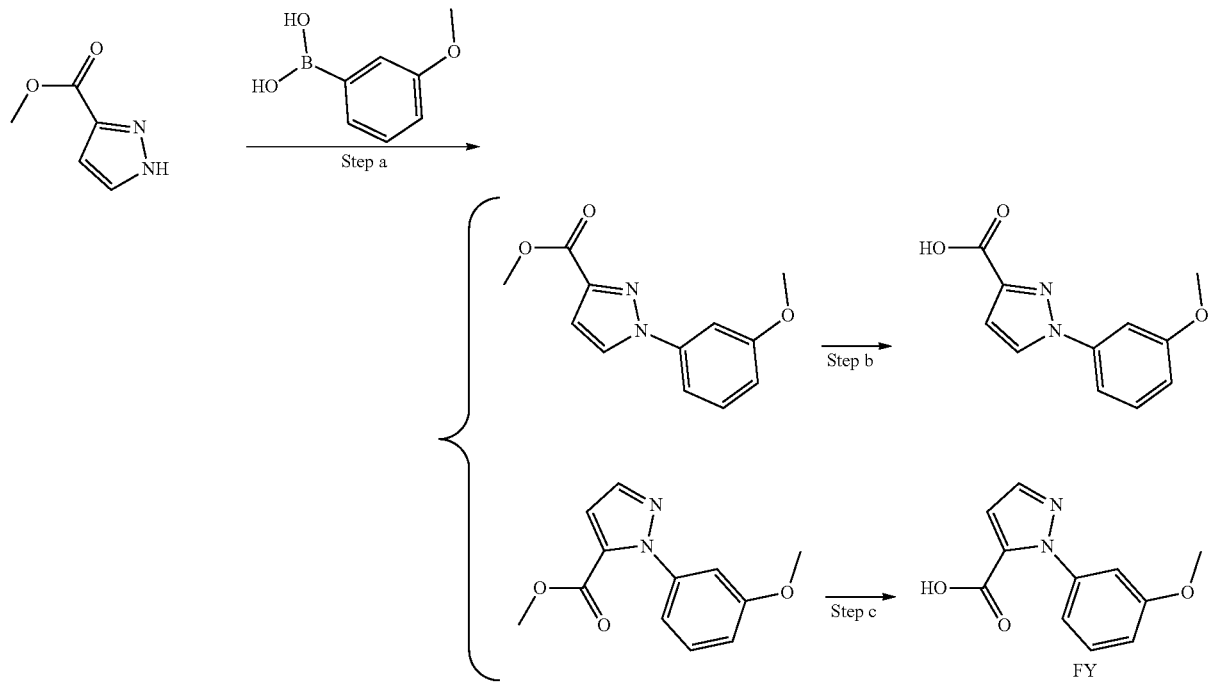

Step a: A mixture of methyl 1H-pyrazole-3-carboxylate (500.0 mg, 3.96 mmol), 3-methoxyphenyl boronic acid (901.0 mg, 5.9 mmol), Cu(OAc)$_2$ (1.43 g, 7.9 mmol) and TEA (2.7 mL, 19.7 mmol) in DCM (15 mL) was stirred at 40° C. for 12 h under 02 atmosphere. The reaction mixture was then filtered. The filtrate was concentrated, and the residue was purified by flash silica gel chromatography (80 g column, EtOAc in petroleum ether from 0% 30%) to give methyl 1-(3-methoxyphenyl)-1H-pyrazole-3-carboxylate (190 mg, 21% yield, the higher polarity) as a yellow oil (LC-MS (ESI$^+$) m/z: 232.9 (M+H)+) and methyl 1-(3-methoxyphenyl)-1H-pyrazole-5-carboxylate (30.0 mg, 3% yield) as a yellow solid (LC-MS (ESI$^+$) m/z: 232.9 (M+H)$^+$).

Step b: To a mixture of methyl 1-(3-methoxyphenyl)-1H-pyrazole-3-carboxylate (190.0 mg, 0.82 mmol) in MeOH (3.00 mL) was added NaOH (327 mg, 8.18 mmol) in H$_2$O (2 mL). The reaction mixture was then stirred at 60° C. for 1 hour. The reaction mixture was then concentrated and quenched with water (10 mL). The mixture was adjusted to pH=5-6 with diluted HCl (1.2 M), where precipitate formed. The solid was collected by filtration, and dried in vacuo to give 1-(3-methoxyphenyl)-1H-pyrazole-3-carboxylic acid (95.0 mg, 53% yield) as an off-white solid. LC-MS (ESI$^+$) m/z: 218.9 (M+H)$^+$.

nyl)-1H-pyrazole-5-carboxylic acid (28.1 mg, 0.13 mmol, quant. crude yield) as a white solid. LC-MS (ESI$^+$) m/z: 218.9 (M+H)$^+$.

1-(2,4-difluorophenyl)-5-methyl-1H-pyrazole-3-carboxylic acid, Intermediate

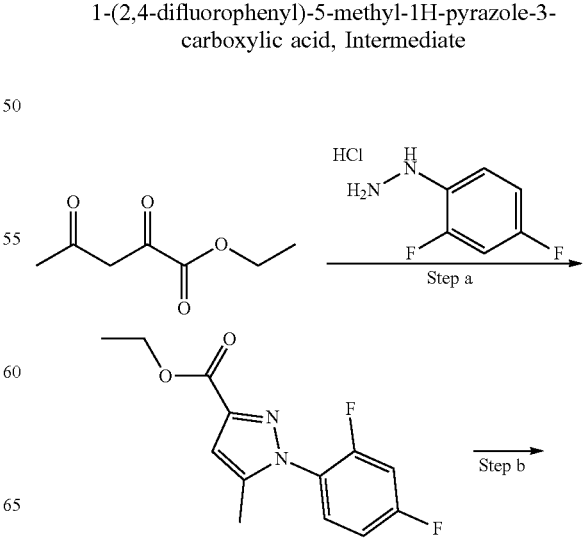

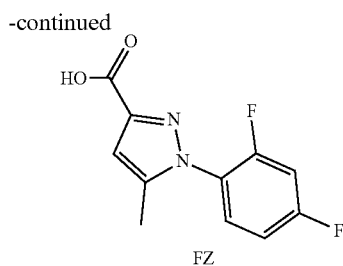

Step a: To a mixture of ethyl 2,4-dioxopentanoate (1.00 g, 6.3 mmol) in EtOH (25.0 mL) was added (2,4-difluorophenyl)hydrazine hydrochloride (1.25 g, 7.0 mmol) and AcOH (2.52 mL, 44.2 mmol), and the resulting mixture was stirred at 60° C. for 12 hours. The mixture was concentrated in vacuo to give a residue, which was dissolved in ethyl acetate (30.0 mL), and washed with sat. NaHCO₃ (20.0 mL×2). The organic phase was washed with brine (10.0 mL), dried over anhydrous Na₂SO₄, filtered and concentrated in vacuo to give a residue, which was purified by silica gel chromatography (ethyl acetate in petroleum ether=0% to 25%) to afford ethyl 1-(2,4-difluorophenyl)-5-methyl-1H-pyrazole-3-carboxylate (1.00 g, 60% yield) as a yellow solid. LC-MS (ESI⁺) m/z 266.9 (M+H)⁺; ¹HNMR (400 MHz, CDCl₃): δ 7.51-7.47 (m, 1H), 7.05-7.00 (m, 2H), 6.76 (s, 1H), 4.46-4.40 (m, 2H), 2.24 (s, 3H), 1.41 (t, J=7.2 Hz, 3H).

Step b: A mixture of ethyl 1-(2,4-difluorophenyl)-5-methyl-1H-pyrazole-3-carboxylate (400.0 mg, 1.5 mmol) and LiOH H₂O (315.0 mg, 7.5 mmol) in MeOH (20.0 mL) and H₂O (8.0 mL) was stirred at 20° C. for 12 hours. The reaction mixture was concentrated in vacuo to give a residue, which was dissolved in H₂O (25.0 mL) and adjusted to pH=4 with 2M HCl. The mixture was then extracted with ethyl acetate (30.0 mL×2), and the organic phases were washed with brine (20.0 mL), dried over anhydrous Na₂SO₄, filtered and concentrated in vacuo to afford 1-(2,4-difluorophenyl)-5-methyl-1H-pyrazole-3-carboxylic acid (310 mg, 86.8% yield) as a yellow solid. LC-MS (ESI⁺) m/z 239.0 (M+H)⁺.

2'-Chloro-3', 6'-dimethyl-3,4'-bipyridine, Intermediate GA

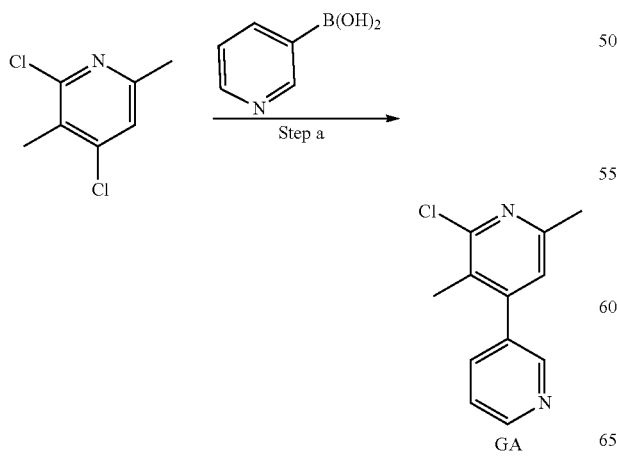

Step a: A mixture of 2, 4-dichloro-3,6-dimethylpyridine (300.0 mg, 1.7 mmol, CAS #83791-90-6), (pyridin-3-yl)boronic acid (271.0 mg, 2.2 mmol, CAS #1692-25-7), Pd(dppf)Cl₂ (124.0 mg, 0.2 mmol), K₂CO₃ (715.0 mg, 5.1 mmol) were added in dioxane (6 mL) and H₂O (2 mL). The reaction mixture was evacuated and refilled 3 times using N₂, and the reaction mixture was stirred at 100° C. for 12 hours. The reaction mixture was poured into H₂O (20 mL) and extracted with EtOAc (40 mL×2). The combined organic layers were washed with brine (20 mL), dried over anhydrous Na₂SO₄, filtered and concentrated under reduced pressure to give a residue. The residue was purified by flash silica gel chromatography (20 g column, EtOAc in petroleum ether from 0% to 50%) to give 2'-chloro-3', 6'-dimethyl-3,4'-bipyridine (270.0 mg, 1.2 mmol, 73% yield) as a brown solid. LC-MS (ESI⁺) m/z: 218.9 (M+H)⁺. ¹HNMR (400 MHz, CD₃OD) δ 9.36 (s, 1H), 9.18 (d, J=5.6 Hz, 1H), 8.98 (d, J=8.0 Hz, 1H), 8.40-8.37 (m, 1H), 8.18 (s, 1H), 2.83 (s, 3H), 2.46 (s, 3H).

EXAMPLES

Method 1, Example 1 & 2: Synthesis of 1-(4-{6-[(3R)-3-amino-1,3-dihydrospiro[indene-2,4'-piperidin]-1'-yl]-1H-pyrazolo[3,4-b]pyrazin-3-yl}-1,2,3,4-tetrahydroquinoxalin-1-yl)ethan-1-one (RTX-1084025) and (1-(4-{6-[(3S)-3-amino-1,3-dihydrospiro[indene-2,4'-piperidin]-1'-yl]-1H-pyrazolo[3,4-b]pyrazin-3-yl}-1,2,3,4-tetrahydroquinoxalin-1-yl)ethan-1-one

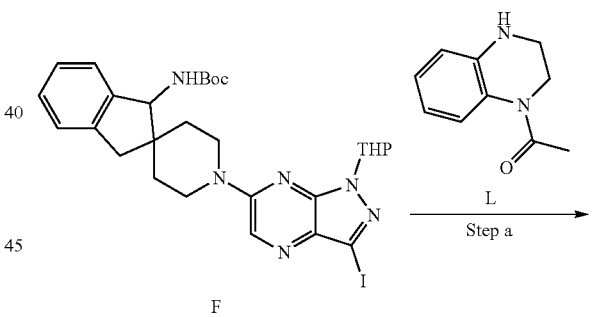

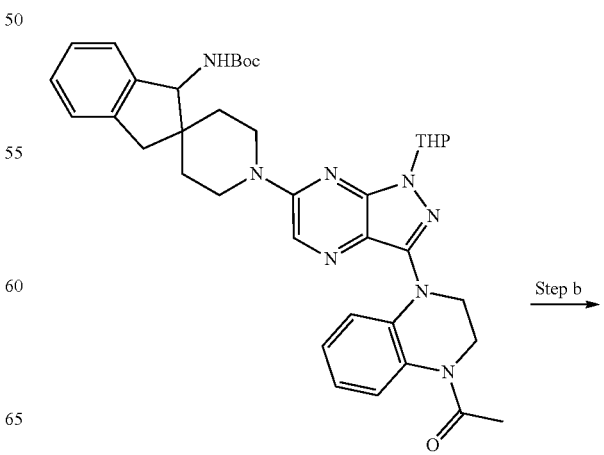

-continued

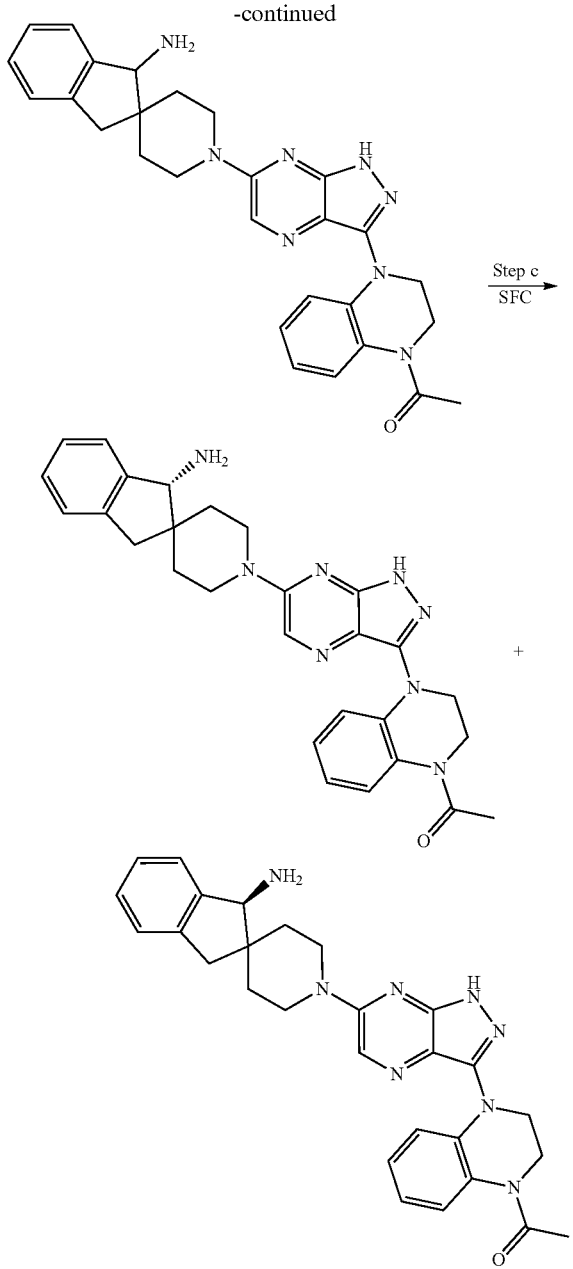

Step a: A mixture of tert-butyl N-{1'-[3-iodo-1-(oxan-2-yl)-1H-pyrazolo[3,4-b]pyrazin-6-yl]-1,3-dihydrospiro[indene-2,4'-piperidin]-3-yl}carbamate (150.0 mg, 237.0 μmol, Intermediate F), 1-(1,2,3,4-tetrahydroquinoxalin-1-yl)ethan-1-one (50.0 mg, 284.0 μmol, Intermediate L), XantPhos-Pd-G4 (22.7 mg, 23.7 μmol) and Cs$_2$CO$_3$ (155.0 mg, 474.0 μmol) in PhMe (10 mL) was stirred at 100° C. under N$_2$ for 12 hours. The reaction mixture was concentrated in vacuo. The residue was purified by silica gel column (EtOAc in Petroleum ether=30~60%) to give tert-butyl N-{1'-[3-(4-acetyl-1,2,3,4-tetrahydroquinoxalin-1-yl)-1-(oxan-2-yl)-1H-pyrazolo[3,4-b]pyrazin-6-yl]-1,3-dihydrospiro[indene-2,4'-piperidin]-3-yl}carbamate (130.0 mg, 81.2% yield) as a yellow solid.

Step b: A solution of tert-butyl N-{1'-[3-(4-acetyl-1,2,3,4-tetrahydroquinoxalin-1-yl)-1-(oxan-2-yl)-1H-pyrazolo[3,4-b]pyrazin-6-yl]-1,3-dihydrospiro[indene-2,4'-piperidin]-3-yl}carbamate (120.0 mg, 176.0 μmol) in TFA (1 mL) and DCM (5 mL) was stirred at 20° C. under N$_2$ for 12 hours. The reaction mixture was then poured into saturated NaHCO$_3$ (50 mL), and extracted with DCM (30 mL×2). The organic layers were dried over anhydrous Na$_2$SO$_4$, filtered and concentrated in vacuo. The residue was purified by silica gel column (MeOH in DCM=0~10%) to give 1-[4-(6-{3-amino-1,3-dihydrospiro[indene-2,4'-piperidin]-1'-yl}-1H-pyrazolo[3,4-b]pyrazin-3-yl)-1,2,3,4-tetrahydroquinoxalin-1-yl]ethan-1-one (85.0 mg, 91% purity, 89% yield) as a yellow solid. LCMS m/z [M+H]$^+$=495.2.

Step c: 1-[4-(6-{3-Amino-1,3-dihydrospiro[indene-2,4'-piperidin]-1'-yl}-1H-pyrazolo[3,4-b]pyrazin-3-yl)-1,2,3,4-tetrahydroquinoxalin-1-yl]ethan-1-one (85.0 mg, 171.0 μmol) was separated by preparative SFC (Column: DAICEL CHIRALPAK AS-H (250 mm*30 mm, 5 um), Mobile phase: A: CO$_2$, B: Ethanol (0.1% NH$_3$.H$_2$O), Gradient: keep 50% of B, Flow rate: 50 mL/min, Column temp: 35° C.) to give 1-(4-{6-[(3R)-3-amino-1,3-dihydrospiro[indene-2,4'-piperidin]-1'-yl]-1H-pyrazolo[3,4-b]pyrazin-3-yl}-1,2,3,4-tetrahydroquinoxalin-1-yl)ethan-1-one (32.0 mg, the faster eluting isomer, 38% yield) as a yellow solid (LCMS m/z [M+H]$^+$=495.0, $^1$HNMR (400 MHz, CDCl$_3$): δ 8.06 (s, 1H), 7.35 (d, J=8.4 Hz, 1H), 7.22-7.30 (m, 1H), 7.12-7.18 (m, 3H), 6.92-7.08 (m, 2H), 6.73-6.83 (m, 1H), 4.18-4.28 (m, 2H), 4.10-4.17 (m, 2H), 3.90-4.07 (m, 3H), 3.15-3.35 (m, 2H), 3.05 (d, J=7.2 Hz, 1H), 2.69 (d, J=7.2 Hz, 1H), 2.24 (s, 3H), 1.70-1.90 (m, 2H), 1.53-1.60 (m, 1H), 1.30-1.40 (m, 1H), SFC ee: 100%) and 1-(4-{6-[(3S)-3-amino-1,3-dihydrospiro[indene-2,4'-piperidin]-1'-yl]-1H-pyrazolo[3,4-b]pyrazin-3-yl}-1,2,3,4-tetrahydroquinoxalin-1-yl)ethan-1-one (35.0 mg, the slower eluting isomer, 41% yield) as a yellow solid (LCMS m/z [M+H]$^+$=495.0, $^1$HNMR (400 MHz, CDCl$_3$): δ 8.06 (s, 1H), 7.35 (d, J=8.4 Hz, 1H), 7.22-7.30 (m, 1H), 7.12-7.18 (m, 3H), 6.92-7.08 (m, 2H), 6.73-6.83 (m, 1H), 4.18-4.28 (m, 2H), 4.10-4.17 (m, 2H), 3.90-4.07 (m, 3H), 3.15-3.35 (m, 2H), 3.05 (d, J=7.2 Hz, 1H), 2.69 (d, J=7.2 Hz, 1H), 2.24 (s, 3H), 1.70-1.90 (m, 2H), 1.53-1.60 (m, 1H), 1.30-1.40 (m, 1H); SFC ee: 98.5%).

Method 1 Table: Compounds Synthesized Via Method 1. With the Cross-Coupling of Various Amines and Iodides in Step a

| Example #$^a$ | Step a Amine | Step a Iodide | LCMS m/z (M + H)$^+$ | $^1$H NMR (400 MHz, DMSO-d6) δ |
|---|---|---|---|---|
| 3 | W | F | 519.2 | 12.52-13.27 (m, 2H), 8.33 (s, 1H), 7.40-7.80 (m, 3H), 7.28-7.38 (m, 1H), 7.10-7.23 (m, 3H), 6.66 (s, 1H), 4.21-4.41 (m, 2H), 3.94-4.04 (m, 2H), 3.88 (s, 1H), 3.18-3.27 (m, 2H), 3.10 (d, J = 15.6 Hz, 1H), 2.94-3.03 (m, 2H), 2.68 (d, J = 15.6 Hz, 1H), 2.05-2.16 (m, 2H), 1.75-1.87 (m, 1H), 1.62-1.75 (m, 1H), 1.48-1.59 (m, 1H), 1.10-1.21 (m, 1H). |

-continued

| Example #a | Step a Amine | Step a Iodide | LCMS m/z (M + H)+ | 1H NMR (400 MHz, DMSO-d6) δ |
|---|---|---|---|---|
| 4 | W | F | 519.1 | 8.37 (s, 1H), 8.13 (d, J = 9.2 Hz, 1H), 7.96 (d, J = 9.2 Hz, 1H), 7.89 (s, 1H), 7.55-7.53 (m, 1H), 7.44-7.42 (m, 3H), 7.03 (s, 1H), 4.57-4.54(m, 1H), 4.44-4.41 (m, 2H), 4.12-4.11 (m, 2H), 3.44-3.42 (m, 2H), 3.39-3.38 (m, 2H), 3.33-3.32 (m, 2H), 2.34-2.32 (m, 2H), 1.96-1.93 (m, 1H), 1.84-1.81 (m, 2H), 1.71-1.68 (m, 1H). |
| 5 | X | F | 533.1 | 8.12 (m, 1H), 7.90 (m,1H), 7.79 (m, 1H), 7.32-7.29 (m, 1H), 7.27-7.24 (m, 1H), 7.18-7.11 (m, 4H), 4.34-4.27 (m, 2H), 3.98 (s, 1H), 3.88-3.84 (m, 2H), 3.82 (s, 3H), 3.29-3.26 (m, 2H), 3.10-3.06 (m, 1H), 2.98-2.94 (m, 2H), 2.85-2.80 (m, 1H), 2.13-2.06 (m, 2H), 1.80-1.68 (m, 2H), 1.55-1.42 (m, 2H). |
| 6 | X | F | 533.2 | 8.12 (m, 1H), 7.90 (m,1H), 7.79 (m, 1H), 7.32-7.29 (m, 1H), 7.27-7.24 (m, 1H), 7.18-7.11 (m, 4H), 4.34-4.27 (m, 2H), 3.98 (s, 1H), 3.88-3.84 (m, 2H), 3.82 (s, 3H), 3.29-3.26 (m, 2H), 3.10-3.06 (m, 1H), 2.98-2.94 (m, 2H), 2.85-2.80 (m, 1H), 2.13-2.06 (m, 2H), 1.80-1.68 (m, 2H), 1.55-1.42 (m, 2H). |
| 7 | 1,2,3,4-tetrahydro-1,5-naphthyridine (CAS# 13993-61-8) | BB | 417.2 | | aStep a was run anywhere from 80-100° C., for 2-12 h. NaOtBu could also be used as the base. Step b was run for 2-12 h; HCl/MeOH could also be used for the deprotection.

Compounds Synthesized in Similar Fashion to Method 1:

Examples 8, 9, 10 & 11: Synthesis of (1S,2S,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine, (1S,2R,5S)-1'-(3-(3,4-dihydro-1,5-naphthyridin-1(2H)-yl)-1H-pyrazolo[3,4-b]pyrazin-6-yl)spiro[bicyclo[[3.1.0]hexane-3,4'-piperidin]-2-amine, (1R,2R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine, and ((1R,2S,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine

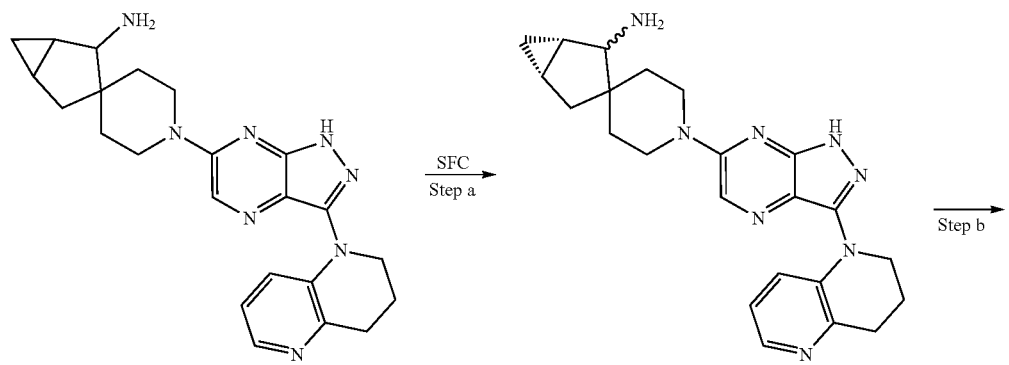

-continued

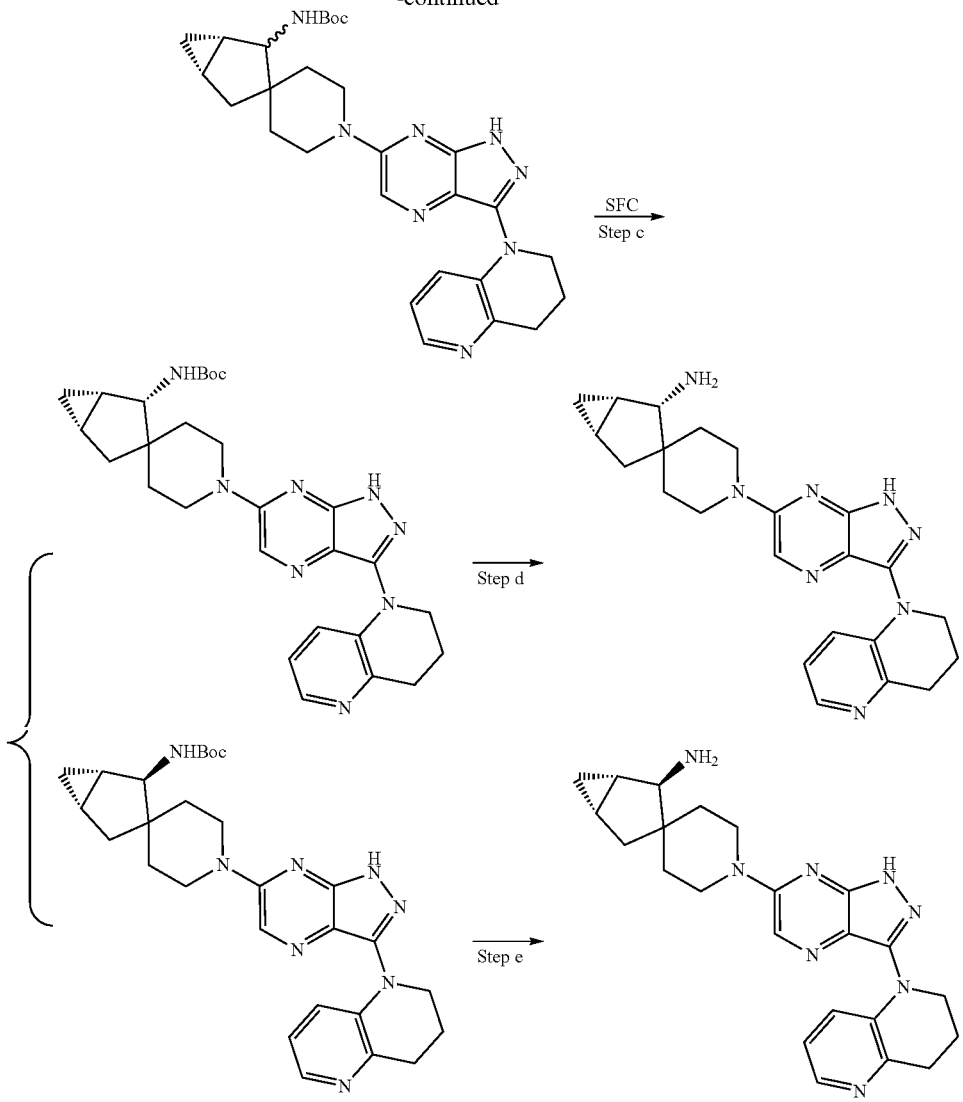

Step a: 1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine (40.0 mg, 96.0 µmol, Example 7) was separated by preparative SFC. Column: DAICEL CHIRALCEL OJ-H (250 mm×30 mm, 5 um). Condition: 0.1% NH₃.H₂O EtOH. Begin B 30%, end B 30%. Flow rate: 50 mL/min. (1 S,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine (16.0 mg, 96 umol, 40% yield) was obtained as a yellow solid and (1R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine (16.0 mg, 96 umol, 40% yield) was obtained as a yellow solid. Absolute stereochemistry of the diastereomers was arbitrarily assigned.

Step b: A solution of (1S,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine (16.0 mg, 38.4 µmol), (Boc)₂O (8.4 mg, 38.4 µmol) and TEA (10.6 µL, 76.8 µmol) in DCM (1.0 mL) was stirred at 15° C. for 15 mins. The reaction mixture was concentrated under reduced pressure. The residue was purified by TLC (Ethyl acetate, 1% NH₃.H₂O). tert-butyl ((1S,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (18.0 mg, 34.8 µmol, 91% yield) was obtained as a yellow solid. LCMS m/z [M+H]⁺=517.2.

Step c: tert-butyl ((1S,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (18 mg, 34.8 µmol) was separated by preparative SFC. Column: DAICEL CHIRALPAK AD-H (250 mm×30 mm, 5 um). Condition: 0.1% NH₃.H₂O EtOH. Begin B 40%, end B 40%. Flow rate: 70 mL/min. tert-butyl ((1S,2S,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (5.00 mg, 9.67 µmol, 100% ee, $R_f$=2.584 min) was obtained as a yellow solid and tert-butyl ((1S,2R,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (10.0 mg, 19.3 µmol, 100% ee, $R_f$=3.266 min) was obtained as a yellow solid. Column: Chiralpak AD-3 100×4.6 mm I.D., 3 um Mobile phase: A: CO₂ B: 40% of ethanol (0.05% DEA) Flow rate: 2.8 mL/min Column temperature: 40° C.

Step d: A solution of ((1S,2S,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (5.0 mg, 9.7 μmol) in HCl/MeOH (2.0 mL, 4N) was stirred at 15° C. for 0.5 hours. The reaction mixture was concentrated under reduced pressure to give the product (1S,4S,5S)-1'-[3-(1,2,3,4-tetrahydro-1,5-naphthyridin-1-yl)-1H-pyrazolo[3,4-b]pyrazin-6-yl]spiro[bicyclo[3.1.0]hexane-3,4'-piperidin]-4-amine hydrochloride (4.3 mg, 9.5 μmol, 95% yield) as a yellow solid. LCMS m/z [M+H]$^+$=417.2. $^1$HNMR (400 MHz, CDCl$_3$): δ 8.31 (s, 1H), 8.03-8.06 (m, 2H), 7.55-7.58 (m, 1H), 4.51-4.56 (m, 1H), 4.36-4.40 (m, 1H), 4.07-4.10 (m, 2H), 3.26-3.30 (m, 3H), 3.15-3.24 (m, 2H), 2.26-2.34 (m, 2H), 2.17-2.22 (m, 1H), 1.94-1.97 (m, 1H), 1.62-1.80 (m, 5H), 1.47-1.52 (m, 1H), 0.88-0.94 (m, 1H), 0.59-0.63 (m, 1H).

Step e: A solution of tert-butyl ((1S,2R,5S)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (10.0 mg, 19.3 μmol) in HCl/MeOH (2 mL, 4N) was stirred at 15° C. for 0.5 hours. The reaction mixture was concentrated under reduced pressure to give the product (1S,4R,5S)-1'-[3-(1,2,3,4-tetrahydro-1,5-naphthyridin-1-yl)-1H-pyrazolo[3,4-b]pyrazin-6-yl]spiro[bicyclo[3.1.0]hexane-3,4'-piperidin]-4-amine (7.2 mg, 17.2 μmol, 76.2% yield) as a yellow solid. LCMS m/z [M+H]$^+$=417.2. $^1$HNMR (400 MHz, CDCl$_3$): δ 8.32 (s, 1H), 8.03-8.06 (m, 2H), 7.55-7.59 (m, 1H), 4.45-4.53 (m, 2H), 4.07-4.10 (m, 2H), 3.65-6.67 (m, 1H), 3.27-3.30 (m, 2H), 3.14-3.21 (m, 2H), 2.28-2.34 (m, 2H), 2.16-2.22 (m, 1H), 2.01-2.05 (m, 1H), 1.79-1.88 (m, 2H), 1.69-1.73 (m, 2H), 1.54-1.64 (m, 2H), 0.80-0.85 (m, 1H), 0.68-0.73 (m, 1H).

Step f: A solution (1R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine (16.0 mg, 38.4 μmol), (Boc)$_2$O (8.8 μL, 38.4 μmol) and TEA (10.6 uL, 76.8 μmol) in DCM (2.0 mL) was stirred at 10° C. for 1 hour. The reaction mixture was concentrated under reduced pressure. The residue was purified by TLC (Ethyl acetate, 1% NH$_3$H$_2$O) to give tert-butyl ((1R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (18.0 mg, 34.8 μmol, 90.9% yield) as a yellow solid. LCMS m/z [M+H]$^+$=517.3.

Step g: tert-butyl ((1R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (18.0 mg, 34.8 μmol) was separated by preparative SFC. Column: Phenomenex-Cellulose-2 (250 mm×30 mm, 5 um). Condition: 0.1% NH$_3$.H$_2$O EtOH. Begin B 40%, end B 40%. Flow rate: 60 mL/min. tert-butyl ((1R,2R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (6.0 mg, 11.6 μmol, 34% yield, SFC e.e. =100.0%, R$_f$=3.660 min) was obtained as a yellow solid and tert-butyl ((1R,2S,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (11.0 mg, 21.2 μmol, 61% yield, SFC e.e. =97.3%, R$_f$=4.290 min) was obtained as a yellow solid. Column: Lux Cellulose-2 150×4.6 mm I.D., 3 um Mobile phase: A: CO$_2$ B: 40% of ethanol (0.05% DEA) Flow rate: 2.8 mL/min Column temperature: 40° C.

Step h: A solution of tert-butyl ((1R,2R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (6.0 mg, 11.6 μmol) in HCl/MeOH (2.0 mL, 4N) was stirred at 10° C. for 1 hour. The reaction mixture was concentrated under reduced pressure to give the product (1R,2R,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine (5.0 mg, 10.2 umol, 88% yield, 2 HCl salt). LCMS m/z [M+H]$^+$=417.1; $^1$HNMR (400 MHz, CDCl$_3$): δ 8.32 (s, 1H), 8.04-8.07 (m, 2H), 7.56-7.59 (m, 1H), 4.52-4.55 (m, 1H), 4.37-4.40 (m, 1H), 4.07-4.10 (m, 2H), 3.26-3.30 (m, 3H), 3.18-3.24 (m, 2H), 2.29-2.34 (m, 2H), 2.18-2.21 (m, 1H), 1.94-1.97 (m, 1H), 1.62-1.80 (m, 5H), 1.48-1.52 (m, 1H), 0.89-0.94 (m, 1H), 0.60-0.63 (m, 1H).

Step i: A solution of tert-butyl ((1R,2S,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-yl)carbamate (11.0 mg, 21.2 μmol) in HCl/MeOH (2.0 mL, 4N) was stirred at 10° C. for 1 hour. The reaction mixture was concentrated under reduced pressure to give the product (1R,2S,5R)-1'-(3-(3,4-dihydro-1,5-naphthyridin-1(2H)-yl)-1H-pyrazolo[3,4-b]pyrazin-6-yl)spiro[bicyclo[3.1.0]hexane-3,4'-piperidin]-2-amine (9.3 mg, 19.0 umol, 90% yield, 2 HCl salt). LCMS m/z [M+H]$^+$=417.1; $^1$HNMR (400 MHz, CDCl$_3$): δ 8.33 (s, 1H), 8.04-8.07 (m, 2H), 7.56-7.59 (m, 1H), 4.45-4.53 (m, 2H), 4.07-4.10 (m, 2H), 3.66-6.67 (m, 1H), 3.28-3.30 (m, 2H), 3.14-3.21 (m, 2H), 2.28-2.34 (m, 2H), 2.16-2.22 (m, 1H), 2.01-2.05 (m, 1H), 1.80-1.89 (m, 2H), 1.69-1.73 (m, 2H), 1.55-1.66 (m, 2H), 0.81-0.86 (m, 1H), 0.70-0.73 (m, 1H).

Method 2, Example 12: Synthesis of 1'-(3-(3,4-dihydro-1,5-naphthyridin-1(2H)-yl)-1H-pyrazolo[3,4-b]pyrazin-6-yl)-1,3-dihydrospiro[indene-2,4'-piperidin]-1-amine

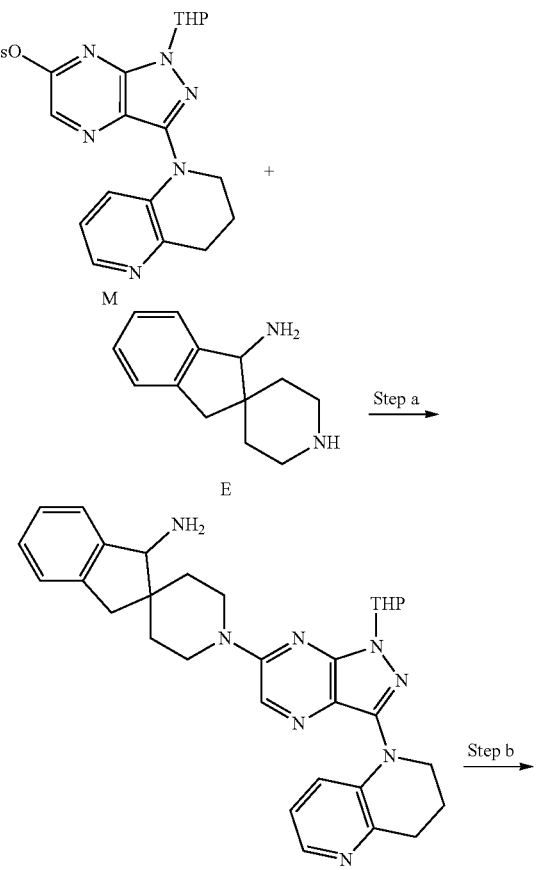

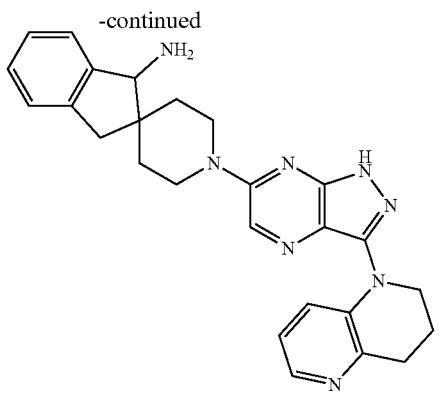

Step a: 1-(Oxan-2-yl)-3-(1,2,3,4-tetrahydro-1,5-naphthyridin-1-yl)-1H-pyrazolo[3,4-b]pyrazin-6-yl 4-methylbenzene-1-sulfonate (531 mg, 1.05 mmol, Intermediate M) and 1,3-dihydrospiro[indene-2,4'-piperidin]-3-amine (214 mg, 1.05 mmol, Intermediate E) were taken up in DMF (25 mL). Diisopropylethylamine (916 µL, 5.25 mmol) was added and the reaction mixture heated at 110° C. for 16 hours. After cooling, the mixture was purified by reversed phase HPLC (0-30% acetonitrile/aq. HCl) to provide 1'-[1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-amine (12.0 mg, 21% yield) after lyophilization. LCMS m/z [M]+=537.6.

Step b: 1'-[1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-amine was taken up in 4M HCl/dioxane (200 µL) and heated at 60° C. for 2 hrs. After cooling, the mixture was purified by reversed phase HPLC (5-10% acetonitrile/aq. HCl) to provide 1'-[1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-amine (6.0 mg, 60% yield). LCMS m/z (M+H)+=453.2; $^1$H-NMR (400 MHz, DMSO-d$_6$) δ 12.57 (br s, 1H), 8.32 (s, 1H), 8.23 (s, 1H), 7.89 (dd, J=1.22, 4.64 Hz, 1H), 7.48 (dd, J=1.22, 8.30 Hz, 1H), 7.27-7.35 (m, 1H), 7.15-7.21 (m, 1H), 6.95 (dd, J=4.52, 8.42 Hz, 1H), 4.31 (br dd, J=7.20, 12.08 Hz, 2H), 3.93-3.99 (m, 2H), 3.90 (s, 1H), 3.17-3.31 (m, 4H), 3.10 (br d, J=15.87 Hz, 1H), 2.93 (br t, J=6.47 Hz, 2H), 2.69 (br d, J=15.87 Hz, 1H), 2.06 (td, J=6.20, 11.78 Hz, 2H), 1.65-1.85 (m, 2H), 1.53 (br d, J=12.94 Hz, 1H), 1.17 (br d, J=13.43 Hz, 1H).

Method 2 Table: Compounds Synthesized Via Method 1, with the Cross-Coupling of Various Amines and Tosylates in Step a

| Example #[a] | Step a Amine | Step a Tosylate | LCMS m/z (M + H)+ | $^1$H NMR (400 MHz, DMSO-d6) δ |
|---|---|---|---|---|
| 13 | N | M | 453.5 | 12.84 (s, 1H), 8.42 (s, 1H), 8.08 (br d, J = 4.88 Hz, 1H), 7.95 (br s, 3H), 7.32-7.42 (m, 2H), 7.22-7.30 (m, 2H), 6.35-6.66 (m, 2H), 4.18-4.28 (m, 2H), 4.14 (br s, 1H), 3.95-4.06 (m, 2H), 3.58 (br t, J = 10.99 Hz, 2H), 3.40-3.49 (m, 1H), 3.11 (br t, J = 6.23 Hz, 2H), 2.92 (br d, J = 17.09 Hz, 1H), 2.53 (s, 2H), 2.04-2.21 (m, 3H), 1.71-1.94 (m, 2H), 1.47-1.56 (m, 1H) |
| 14[b] | N | M | 453.2 | 8.23 (s, 1H), 7.88 (d, J = 20 Hz, 1H), 7.69 (d, J = 10 Hz, 1H), 7.31-7.19 (m, 5H), 4.40-4.28 (m, 1H), 4.26-4.15 (m, 1H), 4.12 (d, J = 4.8 Hz, 1H), 3.95-3.93 (m, 2H), 3.59-3.46 (m, 3H), 3.10-3.07 (m, 2H), 2.91 (d, J = 17.2 Hz, 1H), 2.25-2.14 (m, 3H), 1.94-1.78 (m, 2H), 1.67-1.60 (m, 1H) |
| 15[b] | N | M | 453.2 | 8.16 (s, 1H), 7.77-7.76 (m, 1H), 7.25-7.23 (m, 2H), 7.19-7.17 (m, 1H), 7.12-7.10 (m, 2H), 6.92-6.89 (m, 1H), 4.23-4.14 (m, 2H), 3.86-3.84 (m, 2H), 3.69-3.56 (m, 2H), 3.34-3.23 (m, 2H), 2.96-2.93 (m, 2H), 2.69 (d, J = 17.6 Hz, 1H), 2.13-2.07 (m, 2H), 2.01-1.89 (m, 2H), 1.80-1.70 (m, 1H), 1.63-1.57 (m, 1H) |
| 16 | V | M | 471.2 | 12.58 (br s, 1H), 8.32 (s, 1H), 8.23 (s, 2H), 7.89 (d, J = 3.66 Hz, 1H), 7.48 (d, J = 8.30 Hz, 1H), 7.21-7.28 (m, 1H), 7.16-7.21 (m, 1H), 7.01 (br t, J = 8.54 Hz, 1H), 6.95 (dd, J = 4.39, 8.30 Hz, 1H), 4.31 (br d, J = 13.43 Hz, 2H), 3.95 (br dd, J = 5.49, 10.86 Hz, 3H), 3.28 (q, J = 11.07 Hz, 2H), 3.15 (br d, J = 16.11 Hz, 1H), 2.93 (br t, J = 6.47 Hz, 2H), 2.72 (br d, J = 15.87 Hz, 1H), 2.01-2.10 (m, 2H), 1.66-1.84 (m, 2H), 1.55 (br d, J = 12.94 Hz, 1H), 1.21 (br d, J = 12.70 Hz, 1H) |
| 17 | AD | M | 471.2 | 12.57 (br s, 1H), 8.32 (s, 1H), 8.21 (s, 1H), 7.89 (dd, J = 1.22, 4.39 Hz, 1H), 7.48 (dd, J = 1.22, 8.30 Hz, 1H), 7.33 (dd, J = 5.62, 8.06 Hz, 1H), 6.87-7.08 (m, 3H), 4.30 (br d, J = 13.43 Hz, 2H), 3.85-3.98 (m, 3H), 3.24 (q, J = 11.56 Hz, 3H), 3.10 (br d, J = 16.11 Hz, 1H), 2.93 (t, J = 6.59 Hz, 2H), 2.71 (br d, J = 16.11 Hz, 1H), 2.01-2.10 (m, 2H), 1.64-1.82 (m, 2H), 1.52 (br d, J = 13.18 Hz, 1H), 1.21 (br d, J = 13.67 Hz, 1H) |
| 18 | AR | M | 471.3 | 12.58 (br s, 1H), 8.32 (s, 1H), 8.18 (s, 2H), 7.89 (d, J = 4.15 Hz, 1H), 7.48 (d, J = 8.56 Hz, 1H), 7.23-7.32 (m, 1H), 7.08 (d, J = 7.26 Hz, 1H), 6.89-7.04 (m, 2H), 4.23 (s, 1H), 4.03-4.19 (m, 2H), 3.89-3.97 (m, 2H), |

-continued

| Example #[a] | Step a Amine | Step a Tosylate | LCMS m/z (M + H)+ | 1H NMR (400 MHz, DMSO-d6) δ |
|---|---|---|---|---|
| | | | | 3.38-3.51 (m, 2H), 3.15 (s, 1H), 3.08 (br d, J = 16.08 Hz, 1H), 2.93 (br t, J = 6.35 Hz, 2H), 2.86 (br d, J = 16.08 Hz, 1H), 1.99-2.14 (m, 2H), 1.78-1.91 (m, 1H), 1.53-1.63 (m, 2H), 1.42 (br d, J = 13.48 Hz, 1H) |

[a]Step a was run anywhere from 100-110° C. for 3-16 h. Step b was run anywhere from 60-80° C. for 1-3 h.
[b]Compound was separated via SFC after Step b. Conditions: Column: DAICEL CHIRALPAK. IC (250 mm * 30 mm 10 um); Mobile phase: 0.1% NH3 · H2O, EtOH. Begin B: 55%. End B: 55%. Flow rate: 70 mL/min). Absolute stereochemistry of the enantiomers was arbitrarily assigned.

[a]Step a was run anywhere from 100-110° C. Step b was run anywhere from 60-80° C. for 1-3 h. [b]Compound was separated via SFC after Step b. Conditions: Column: DAICEL CHIRALPAK IC (250 mm*30 mm, 10 um); Mobile phase: 0.1% NH3.H2O, EtOH. Begin B: 55%, End B: 55%. Flow rate: 70 mL/min). Absolute stereochemistry of the enantiomers was arbitrarily assigned.

Compounds Synthesized in Similar Fashion to Method 2:

Examples 19 & 20: Synthesis of (R)-(3-(1-amino-1,3-dihydrospiro[indene-2,4'-piperidin]-1'-yl)-6-(2,3-dichlorophenyl)-5-methylpyrazin-2-yl)methanol and (S)-(3-(1-amino-1,3-dihydrospiro[indene-2,4'-piperidin]-1'-yl)-6-(2,3-dichlorophenyl)-5-methylpyrazin-2-yl)methanol

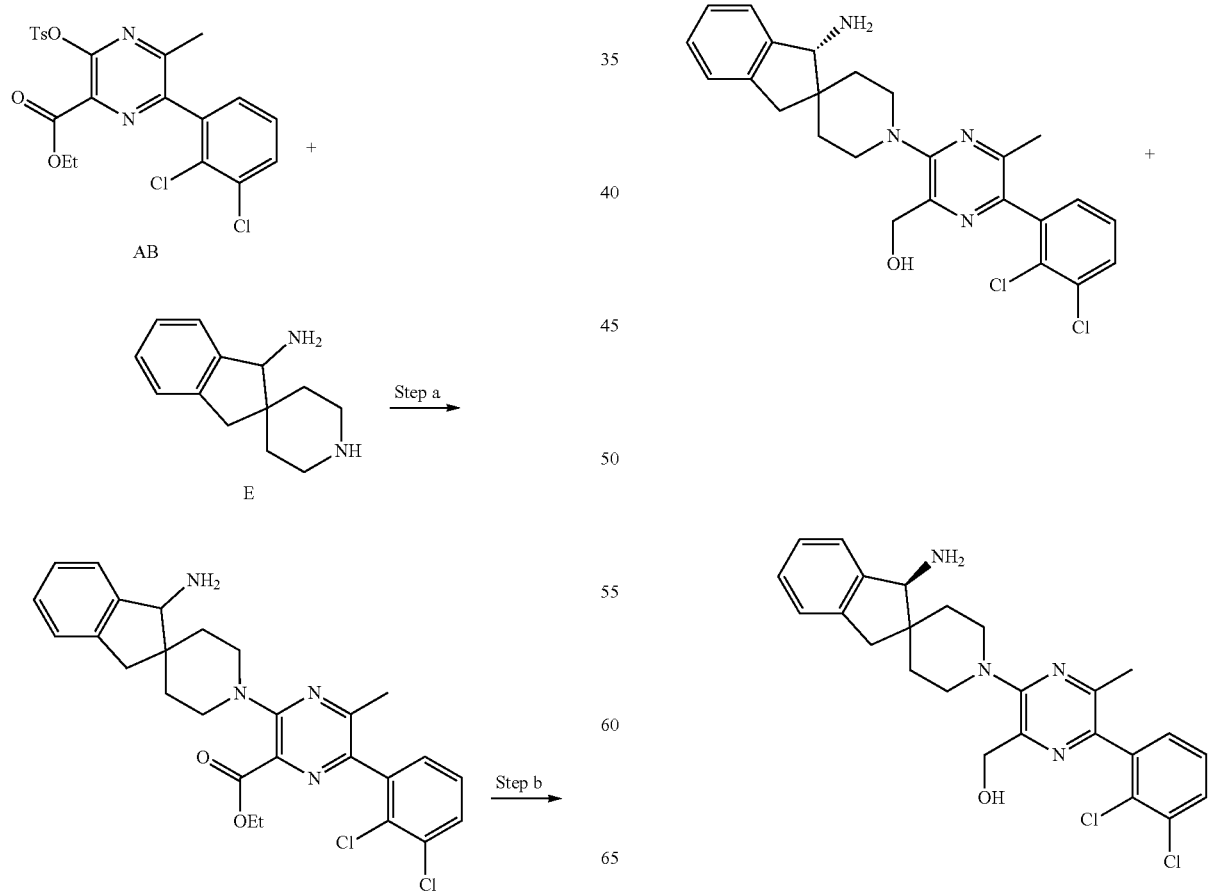

Step a: A solution of ethyl 6-(2,3-dichlorophenyl)-5-methyl-3-[(4-methylbenzenesulfonyl)oxy]pyrazine-2-carboxylate (240.0 mg, 498.0 μmol, Intermediate AB) and 1,3-dihydrospiro[indene-2,4'-piperidin]-1-amine dihydrochloride (164.0 mg, 597.0 μmol, Intermediate E) in DIPEA and NMP (4.0 mL/2.0 mL) was stirred at 90° C. for 12 hours. The solution was poured into H$_2$O (20.0 mL) and extracted with EtOAc (20.0 mL×2). The combined organic layers were washed with brine (20.0 mL), dried over anhydrous Na$_2$SO$_4$, filtered and concentrated under reduced pressure to give a residue. The residue was purified by flash silica gel chromatography (12 g, ethyl acetate in petroleum ether from 0% to 75%) to give ethyl 3-{3-amino-1,3-dihydrospiro[indene-2,4'-piperidin]-1'-yl}-6-(2,3-dichlorophenyl)-5-methylpyrazine-2-carboxylate (350.0 mg, quant. crude yield) as an orange oil. LCMS m/z (M+H)$^+$=511.1/513.1.

Step b: To a solution of ethyl 3-{3-amino-1,3-dihydrospiro[indene-2,4'-piperidin]-1'-yl}-6-(2,3-dichlorophenyl)-5-methylpyrazine-2-carboxylate (300.0 mg, 586.0 μmol) in CH$_2$Cl$_2$ (5.0 mL) was added DIBAL-H (878.0 uL, 878.0 umol, 1M) at 0° C. under N$_2$. The mixture was stirred at 20° C. for 1 hour. To the mixture was added 10% AcOH (30.0 mL) at 0° C. The mixture was then extracted with CH$_2$Cl$_2$ (20.0 mL×2), and the combined organic layers were washed with saturated NaHCO$_3$ (30.0 mL), dried over anhydrous Na$_2$SO$_4$, filtered and concentrated under reduced pressure to give a residue. The residue was purified by prep-HPLC (HCl) to afford (3-{3-amino-1,3-dihydrospiro[indene-2,4'-piperidin]-1'-yl}-6-(2,3-dichlorophenyl)-5-methylpyrazin-2-yl)methanol hydrochloride (40.0 mg, 14% yield) as a yellow solid.

Step c: (3-{3-amino-1,3-dihydrospiro[indene-2,4'-piperidin]-1'-yl}-6-(2,3-dichlorophenyl)-5-methylpyrazin-2-yl)methanol hydrochloride (40.0 mg, 79.0 mmol) was separated by preparative SFC (column: DAICEL CHIRALPAK AS-H (250 mm×30 mm, 5 um), Mobile phase: 0.1% NH$_3$.H$_2$O MeOH (Begin B: 40%, End B: 40%), Flow rate: 55 mL/min) to afford the product of (R)-(3-(1-amino-1,3-dihydrospiro[indene-2,4'-piperidin]-1'-yl)-6-(2,3-dichlorophenyl)-5-methylpyrazin-2-yl)methanol (7.70 mg, 20.8% yield, R$_f$=3.18 min, the faster eluting isomer) as a white solid and (S)-(3-(1-amino-1,3-dihydrospiro[indene-2,4'-piperidin]-1'-yl)-6-(2,3-dichlorophenyl)-5-methylpyrazin-2-yl)methanol (8.50 mg, 22.9% yield, R$_f$=3.41 min, the slower eluting isomer) as a white solid. Absolute stereochemistry of the enantiomers was arbitrarily assigned. Characterization of (R)-(3-(1-amino-1,3-dihydrospiro[indene-2,4'-piperidin]-1'-yl)-6-(2,3-dichlorophenyl)-5-methylpyrazin-2-yl)methanol: LCMS m/z (M+H)$^+$=469.1; $^1$HNMR (400 MHz, CD$_3$OD): 7.52-7.55 (m, 1H), 7.24-7.32 (m, 3H), 7.09-7.13 (m, 3H), 4.59 (s, 2H), 3.91 (s, 1H), 3.57-3.61 (m, 2H), 3.01-3.14 (m, 3H), 2.68-2.73 (m, 1H), 2.16 (s, 3H), 1.83-1.94 (m, 2H), 1.51-1.55 (m, 1H), 1.37-1.41 (m, 1H). SFC: e.e. =96.2%. Characterization of (S)-(3-(1-amino-1,3-dihydrospiro[indene-2,4'-piperidin]-1'-yl)-6-(2,3-dichlorophenyl)-5-methylpyrazin-2-yl)methanol: LCMS m/z (M+H)$^+$=469.1; $^1$HNMR (400 MHz, CD$_3$OD): 7.64-7.66 (m, 1H), 7.38-7.44 (m, 3H), 7.22-7.25 (m, 3H), 4.71 (s, 2H), 4.03 (s, 1H), 3.69-3.73 (m, 2H), 3.13-3.26 (m, 3H), 2.80-2.85 (m, 1H), 2.28 (s, 3H), 1.93-2.07 (m, 2H), 1.63-1.67 (m, 1H), 1.49-1.53 (m, 1H). SFC: e.e. =97.3%, Column: Chiralpak AS-3 100×4.6 mm I.D., 3 μm Mobile phase: A: CO$_2$ B: Methanol (0.1% ethanolamine), Gradient: from 5% to 40% of B in 4.5 min and hold 40% for 2.5 min, then 5% of B for 1 min, Flow rate: 2.8 mL/min, Column temperature: 40° C.

Method 3, Examples 21 & 22: Synthesis of (3R)-1'-[6-amino-5-(2,3-dichlorophenyl)pyrazin-2-yl]-1,3-dihydrospiro[indene-2,4'-piperidin]-3-amine and (3S)-1'-[6-amino-5-(2,3-dichlorophenyl)pyrazin-2-yl]-1,3-dihydrospiro[indene-2,4'-piperidin]-3-amine

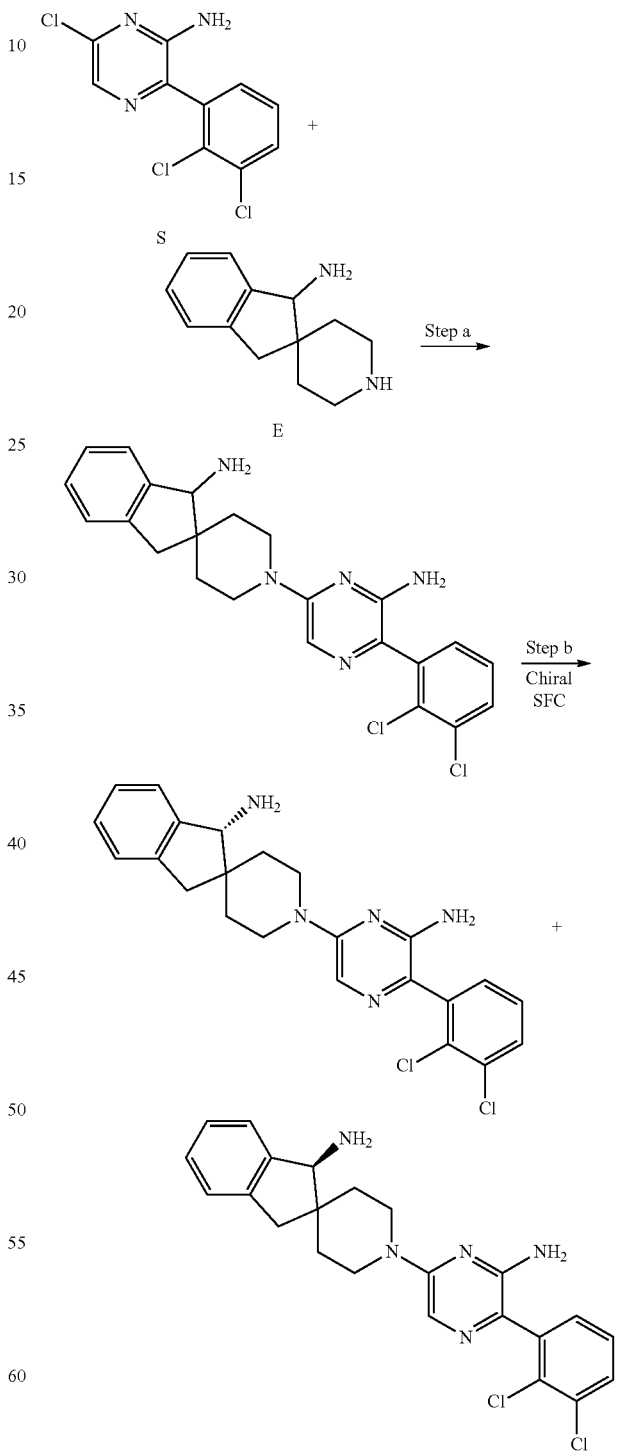

Step a: The mixture of 6-chloro-3-(2,3-dichlorophenyl)pyrazin-2-amine (150 mg, 546 μmol, 1.0 eq, Intermediate S), 1,3-dihydrospiro[indene-2,4'-piperidin]-3-amine dihydrochloride (165 mg, 600 µmol, 1.1 eq, Intermediate E) and Cs$_2$CO$_3$ (886 mg, 2.72 mmol, 5.0 eq) in NMP (1 mL) was stirred at 140° C. for 2 h under N$_2$ atmosphere. The mixture was diluted with saturated NaHCO$_3$ (20 mL), then extracted with EtOAc (20 mL×2). The organic layer was washed with brine (20 mL), dried over anhydrous Na$_2$SO$_4$, filtered and concentrated under reduced pressure. The residue was purified by column chromatography (DCM/MeOH=1:0~20:1) to afford 1'-[6-amino-5-(2,3-dichlorophenyl)pyrazin-2-yl]-1,3-dihydrospiro[indene-2,4'-piperidin]-3-amine (150 mg, 63% yield) as a yellow oil. LCMS m/z [M+H]$^+$=440.1.

Step b: The residue of 1'-[6-amino-5-(2,3-dichlorophenyl) pyrazin-2-yl]-1,3-dihydrospiro[indene-2,4'-piperidin]-3-amine (150 mg, 340 µmol, 1.0 eq) was separated by SFC (Column: DAICEL CHIRALPAK AD (250 mm*30 mm, 10 um). Condition: 0.1% NH$_3$.H$_2$O EtOH. Begin B: 50%. End B: 50%. Flow rate: 70 mL/min.) to afford (3R)-1'-[6-amino-5-(2,3-dichlorophenyl)pyrazin-2-yl]-1,3-dihydrospiro[indene-2,4'-piperidin]-3-amine (31.7 mg, 21% yield, the faster eluting isomer) as a yellow solid and (3S)-1'-[6-amino-5-(2,3-dichlorophenyl)pyrazin-2-yl]-1,3-dihydrospiro[indene-2,4'-piperidin]-3-amine (42.6 mg, 29% yield, the slower eluting isomer) was obtained as a yellow solid. Absolute stereochemistry of the enantiomers was arbitrarily assigned.

Characterization data for (3R)-1'-[6-amino-5-(2,3-dichlorophenyl)pyrazin-2-yl]-1,3-dihydrospiro[indene-2,4'-piperidin]-3-amine: LCMS m/z (M+H)$^+$=439.9; $^1$HNMR (400 MHz, Methanol-d4): δ 7.63-7.59 (m, 1H), 7.48 (s, 1H), 7.41-7.33 (m, 3H), 7.25-7.21 (m, 3H), 4.26-4.22 (m, 2H), 3.99 (s, 1H), 3.25-3.15 (m, 3H), 2.86-2.81 (m, 1H), 1.92-1.76 (m, 2H), 1.62-1.58 (m, 1H), 1.48-1.43 (m, 1H). SFC: e.e. =90.6%, R$_f$=5.279 min. Column: Chiralpak AD-3 100× 4.6 mm I.D., 3 µm Mobile phase: 40% of ethanol (0.1% ethanolamine) in CO$_2$. Flow rate: 2.8 mL/min. Column temperature: 40° C. for (3S)-1'-[6-amino-5-(2,3-dichlorophenyl)pyrazin-2-yl]-1,3-dihydrospiro[indene-2,4'-piperidin]-3-amine: LCMS m/z (M+H)$^+$=439.9; $^1$HNMR (400 MHz, Methanol-d4): δ 7.63-7.60 (m, 1H), 7.48 (s, 1H), 7.43-7.33 (m, 3H), 7.26-7.21 (m, 3H), 4.26-4.22 (m, 2H), 3.99 (s, 1H), 3.25-3.15 (m, 3H), 2.86-2.81 (m, 1H), 1.92-1.76 (m, 2H), 1.62-1.58 (m, 1H), 1.48-1.43 (m, 1H). SFC: e.e. =84.2%, R$_f$=7.362 min. Column: Chiralpak AD-3 100× 4.6 mm I.D., 3 µm Mobile phase: 40% of ethanol (0.1% ethanolamine) in CO$_2$. Flow rate: 2.8 mL/min. Column temperature: 40° C.

Method 3 Table: Compounds Synthesized Via Method 3, with the Coupling of Various Amines and Chlorides in Step a

| Example #[e] | Step a Amine | Step a Chloride | LCMS m/z (M + H)$^+$ | $^1$H NMR (400 MHz, CD3OD) δ ppm |
|---|---|---|---|---|
| 23[a] | T | 6-chloro-1H-pyrazolo[3,4-b]pyrazine (synthesized via Steps a-d of Intermediate A) | 339.0 | (DMSO) 13.06 (br s, 1H), 8.41 (s, 1H), 8.01 (s, 1H), 7.19-7.25 (m, 1H), 7.12-7.16 (m, 1H), 6.96 (br t, J = 8.67 Hz, 1H), 6.68 (br s, 1H), 4.30 (br t, J = 12.21 Hz, 2H), 3.85 (s, 1H), 3.21-3.28 (m, 2H), 3.13 (br d, J = 15.87 Hz, 1H), 2.63 (br d, J = 15.87 Hz, 1H), 2.06 (s, 1H), 1.64-1.83 (m, 2H), 1.55 (br d, J = 12.94Hz, 1H), 1.13 (br d, J = 13.43 Hz, 1H) |
| 24[a] | V | 6-chloro-1H-pyrazolo[3,4-b]pyrazine (synthesized via Steps a-d of Intermediate A) | 339.0 | (DMSO) 13.05 (br s, 1H), 8.41 (s, 1H), 8.01 (br s, 1H), 7.18-7.26 (m, 1H), 7.14 (d, J = 7.32 Hz, 1H), 6.97 (br t, J = 8.67 Hz, 1H), 6.51 (s, 1H), 4.24-4.35 (m, 2H), 3.86 (s, 1H), 3.21-3.27 (m, 1H), 3.13 (br d, J = 15.87 Hz, 1H), 2.63 (br d, J = 15.87 Hz, 1H), 2.53 (s, 1H), 1.78 (dt, J = 4.03, 12.51 Hz, 1H), 1.70 (dt, J = 4.03, 12.63 Hz, 1H), 1.55 (br d, J = 13.18 Hz, 1H), 1.13 (br d, J = 13.92 Hz, 1H) |
| 25[b] | E | AA | 453.2 | 8.28 (s, 1 H) 7.91 (d, J = 3.6 Hz, 1 H) 7.54-7.49 (m, 2 H) 7.41-7.34 (m, 3 H) 7.13 (dd, J = 8.4, 4.8 Hz, 1 H) 4.52 (d, J = 13.6 Hz, 1 H) 4.42-4.38 (m, 2 H) 3.99-3.97 (m, 2 H) 3.44-3.40 (m, 2 H) 3.24-3.22 (m, 2 H) 3.09 (t, J = 6.4 Hz, 2 H) 2.24-2.21 (m, 2 H) 1.93-1.64 (m, 4 H) |
| 26[b] | E | AA | 453.2 | (CDCl3) 1.45 (d, J = 13.6 Hz, 1 H), 1.66 – 1.93 (m, 4 H) 2.21 (t, J = 5.6 Hz, 2 H) 2.78 (d, J = 15.6 Hz, 1 H) 3.08-3.16 (m, 3 H) 3.32 – 3.35 (m, 2 H) 4.03 (s, 1 H) 4.10 (t, J = 5.6 Hz, 2 H) 4.29 – 4.34 (m, 2 H) 6.96 – 6.99 (m, 1 H) 7.25-7.27 (m, 3 H) 7.36 (d, J = 4.4 Hz, 1 H) 7.66 (d, J = 7.6 Hz, 1 H) 8.06 – 8.07 (m, 1 H) 8.16 (s, 1 H) 9.94 (br s, 1 H) |
| 27[c] | AI | AA | 524.2 | 8.26 (s, 1H), 7.87-7.89 (m, 1H), 7.45 (s, 1H), 7.31-7.36 (m, 3H), 6.99-7.04 (m, 1H), 4.41-4.47 (m, |

-continued

| Example #[e] | Step a Amine | Step a Chloride | LCMS m/z (M + H)+ | 1H NMR (400 MHz, CD3OD) δ ppm |
|---|---|---|---|---|
| 28[c] | AI | AA | 524.2 | 2H), 4.01 (s, 1H), 3.94-3.97 (m, 2H), 3.35-3.39<br>8.26 (s, 1H), 7.87-7.89 (m, 1H), 7.45 (s, 1H), 7.31-7.36 (m, 3H), 6.99-7.04 (m, 1H), 4.41-4.47 (m, 2H), 4.01 (s, 1H), 3.94-3.97 (m, 2H), 3.35-3.39 |
| 29[d] | AM | AA | 478.2 | 8.25 (s, 1H), 7.87-7.89 (m, 1H), 7.73 (s, 1H), 7.56-7.61 (m, 1H), 7.42-7.47 (m, 1H), 7.32-7.36 (m, 1H), 7.00-7.03 (m, 1H), 4.41-4.47 (m, 2H), 4.03 |

[a]Hunig's base was used as the amine and the reaction was heated at 100° C. for 5 h. No Step b SFC was performed as amine was chiral.
[b]In Step a, TEA was used as the base and the mixture was heated at 85° C. for 12 h. Before chiral separation, the THP intermediate was deprotected using HCl/MeOH at rt for 0.5 h.
[c]The intermediate after Step A was protected with a BOC group before purification, then deprotected with HCl/MeOH before chiral separation.
[d]CsF was used as the base in Step a, and the reaction was run at 70° C. for 0.5 h. The intermediate of Step a was protected with a BOC group before work up, then deprotected with HCl/MeOH before final purification. No Step b as the amine was chiral.
[e]Absolute stereochemistry of the enantiomers was arbitrarily assigned.

[a]Hunig's base was used as the amine and the reaction was heated at 100° C. for 5 h. No Step b SFC was performed as amine was chiral. [b]In Step a, TEA was used as the base and the mixture was heated at 85° C. for 12 h. Before chiral separation, the THP intermediate was deprotected using HCl/MeOH at rt for 0.5 h. ° The intermediate after Step A was protected with a BOC group before purification, then deprotected with HCl/MeOH before chiral separation. [d]CsF was used as the base in Step a, and the reaction was run at 70° C. for 0.5 h. The intermediate of Step a was protected with a BOC group before work up, then deprotected with HCl/MeOH before final purification. No Step b as the amine was chiral. [e]Absolute stereochemistry of the enantiomers was arbitrarily assigned.

Method 4, Example 30: Synthesis of (S)-1'-(3-(3,4-dihydro-1,5-naphthyridin-1(2H)-yl)-1H-pyrazolo[3,4-b]pyrazin-6-yl)-4-fluoro-1,3-dihydrospiro[indene-2,4'-piperidin]-1-amine

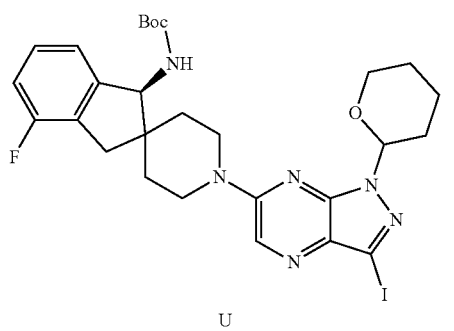

U

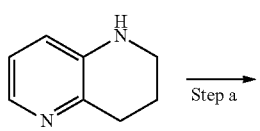

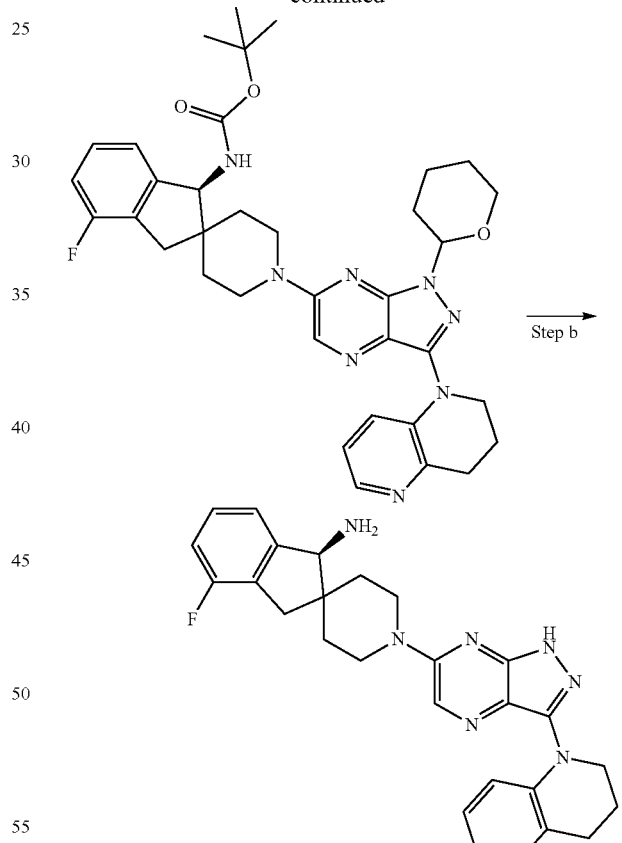

Step a: A round bottom flask was charged with tert-butyl ((1S)-4-fluoro-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (1.3 g, 2.00 mmol, Intermediate U), 1,2,3,4-tetrahydro-1,5-naphthyridine (295 mg, 2.20 mmol), 9-{[5-(diphenylphosphanyl)-9,9-dimethyl-9H-xanthen-4-yl]diphenyl-k-phosphanyl}-8-methyl-8-aza-9-palladatricyclo[8.4.0.0[2,7]]tetradeca-1(14),2(7),3,5,10,12-hexaen-9-yl methanesulfonate (192 mg, 0.2 mmol), and (tert-butoxy)sodium (288 mg, 3.00 mmol). The flask was evacuated and backfilled with N₂ three times. Then toluene (30 mL) was added and the reaction was stirred at 80° C. from 2 h. The reaction was then cooled to rt and diluted with EtOAc and preabsorbed onto silica gel (5 g). The mixture was purified by column chromatography (0-100% EtOAc in heptanes) to give tert-butyl ((1S)-1'-(3-(3,4-dihydro-1,5-naphthyridin-1(2H)-yl)-1-(tetrahydro-2H-pyran-2-yl)-1H-pyrazolo[3,4-b]pyrazin-6-yl)-4-fluoro-1,3-dihydrospiro[indene-2,4'-piperidin]-1-yl)carbamate (1.09 g, 83% yield). LCMS m/z (M+H)⁺=655.7.

Step b: Dissolved t tert-butyl ((1S)-1'-(3-(3,4-dihydro-1,5-naphthyridin-1(2H)-yl)-1-(tetrahydro-2H-pyran-2-yl)-1H-pyrazolo[3,4-b]pyrazin-6-yl)-4-fluoro-1,3-dihydrospiro[indene-2,4'-piperidin]-1-yl)carbamate (1.09 g, 1.66 mmol) in MeOH (15 mL) and added hydrogen chloride (4.15 mL, 16.6 mmol) and stirred at 60° C. for 2 h. The reaction was concentrated, then purified on by prep-HPLC (5-30% B, FA) to give (S)-1'-(3-(3,4-dihydro-1,5-naphthyridin-1(2H)-yl)-1H-pyrazolo[3,4-b]pyrazin-6-yl)-4-fluoro-1,3-dihydrospiro[indene-2,4'-piperidin]-1-amine (465 mg, 60% yield). LCMS m/z (M+H)⁺=471.46; ¹H NMR (400 MHz, DMSO-d6) Shift 12.59 (s, 1H), 8.33 (s, 1H), 8.14 (s, 1H), 7.89 (dd, J=1.52, 4.55 Hz, 1H), 7.49 (dd, J=1.39, 8.46 Hz, 1H), 7.22-7.35 (m, 2H), 7.09 (t, J=8.21 Hz, 1H), 6.96 (dd, J=4.55, 8.34 Hz, 1H), 4.33 (dt, J=4.29, 9.09 Hz, 2H), 4.14 (s, 1H), 3.90-4.00 (m, 2H), 3.17 (br d, J=16.17 Hz, 1H), 2.93 (t, J=6.44 Hz, 2H), 2.85 (br d, J=15.92 Hz, 1H), 2.53 (s, 1H), 2.00-2.13 (m, 2H), 1.66-1.86 (m, 2H), 1.56 (br d, J=13.14 Hz, 1H), 1.34 (br d, J=13.64 Hz, 1H).

Method 4 Table: Compounds Synthesized Via Method 4, with the Cross-Coupling of Various Amines and Iodides in Step a

| Example #[a] | Step a Amine | Step a Iodide | LCMS m/z (M + H)⁺ | ¹H NMR (400 MHz, DMSO-d6 δ ppm |
|---|---|---|---|---|
| 31[b] | 5-methanesulfonyl-1,2,3,4-tetrahydroquinoline (CAS# 343944-90-1) | F | 530.1 | 12.64 (br s, 1H), 8.29 (s, 2H), 7.34 (dd, J = 0.98, 7.57 Hz, 1H), 7.28-7.32 (m, 1H), 7.10-7.22 (m, 5H), 4.22-4.37 (m, 2H), 3.81-3.90 (m, 3H), 3.18-3.24 (m, 7H), 3.09 (br d, J = 15.63 Hz, 2H), 2.66 (br d, J = 15.63 Hz, 1H), 2.02 (td, J = 6.23, 11.96 Hz, 2H), 1.79 (dt, J = 3.91, 12.45 Hz, 1H), 1.68 (dt, J = 3.66,12.45 Hz, 1H), 1.53 (br d, J = 12.94 Hz, 1H), 1.14 (br d, J = 13.18 Hz, 1H) |
| 32[c] | R | C | 562.2 | 8.27 (s, 1H), 7.29-7.37 (m, 1H), 7.14-7.24 (m, 3H), 6.84-6.92 (m, 2H), 6.82 (s, 1H), 4.28 (br d, J = 13.43 Hz, 2H), 3.94-4.00 (m, 2H), 3.91 (br s, 1H), 3.69 (br dd, J = 7.20, 14.04 Hz, 2H), 3.54-3.63 (m, 1H), 3.17-3.32 (m, 4H), 3.03-3.16 (m, 4H), 2.64-2.75 (m, 3H), 1.81-1.92 (m, 2H), 1.70-1.80 (m, 1H), 1.60-1.69 (m, 1H), 1.51 (br d, J = 12.94 Hz, 1H), 1.24 (br d, J = 12.21 Hz, 1H) |
| 33[c] | Q | F | 562.2 | 8.28-8.33 (m, 1H), 7.32-7.39 (m, 1H), 7.17-7.26 (m, 3H), 6.92 (s, 2H), 6.70 (s, 1H), 4.31 (br d, J = 13.18 Hz, 2H), 4.11 (td, J = 7.20, 14.40 Hz, 2H), 3.97-4.05 (m, 3H), 3.94 (ddd, J = 3.66, 6.35, 9.77 Hz, 1H), 3.28-3.33 (m, 2H), 3.25 (br d, J = 9.28 Hz, 1H), 3.16-3.21 (m, 3H), 3.11 (br d, J = 15.87 Hz, 1H), 3.00 (br d, J = 2.20 Hz, 1H), 2.77 (br d, J = 15.87 Hz, 1H), 2.26-2.40 (m, 4H), 1.76 (dt, J = 3.66, 12.45 Hz, 1H), 1.62-1.71 (m, 1H), 1.52 (br d, J = 12.94 Hz, 1H), 1.27 (br d, J = 13.18 Hz, 1H) |
| 34[c] | O | F | 548.2 | 8.26 (br s, 1 H) 7.34 (br d, J = 6.74 Hz, 1H) 7.17-7.26 (m, 3 H) 6.85-6.89 (m, 1H) 6.80-6.85 (m, 1 H) 6.78 (s, 1 H) 4.28 (br d, J = 10.11 Hz, 2 H) 3.96 (br s, 5 H) 3.40-3.49 (m, 1 H) 3.18-3.30 (m, 5 H) 3.09 (br d, J = 16.08 Hz, 1 H) 2.77 (br d, J = 16.08 Hz, 1 H) 2.61-2.70 (m, 2 H) 1.81-1.90 (m, 2 H) 1.69-1.77 (m, 1 H) 1.61-1.68 (m, 1 H) 1.50 (br d, J = 13.23 Hz, 1H) 1.30 (br d, J = 11.41 Hz, 1H) |
| 35[b] | 9 | F | 548.2 | 8.27-8.32 (m, 1H), 7.37 (br d, J = 5.86 Hz, 1H), 7.18-7.28 (m, 3H), 6.86-6.94 (m, 2H), 6.67 (s, 1H), 4.31 (br dd, J = 4.27, 9.40 Hz, 2H), 4.22 (ddd, J = 3.78, 7.02, 10.44 Hz, 1H), 4.11-4.18 (m, 1H), 3.97-4.05 (m, 3H), 3.19-3.32 (m, 4H), 3.11 (br d, J = 15.87 Hz, 1H), 2.80 (br d, J = 15.87 Hz, 1H), 2.29-2.39 (m, 2H), 2.18-2.27 (m, 2H), 1.63-1.80 (m, 2H), 1.51 (br d, J = 12.45 Hz, 1H), 1.31 (br d, J = 12.45 Hz, 1H) |

| Example #ᵃ | Step a Amine | Step a Iodide | LCMS m/z (M + H)⁺ | ¹H NMR (400 MHz, DMSO-d6 δ ppm |
|---|---|---|---|---|
| 36 | 1,2,3,4-tetrahydro-1,5-naphthyridine | Z | 471.2 | 12.57 (br s, 1 H) 8.31 (s, 1 H) 8.20 (s, 1H) 7.86-7.92 (m, 1 H) 7.48 (dd, J = 8.30, 0.78 Hz, 1 H) 7.21 (dd, J = 8.04, 5.45 Hz, 1 H) 7.09 (dd, J = 8.82, 1.82 Hz, 1 H) 6.93-7.00 (m, 2 H) 4.31 (br t, J = 11.93 Hz, 2 H) 3.91-3.97 (m, 2 H) 3.89 (s, 1 H) 3.23 (br dd, J = 21.65, 11.28 Hz, 2 H) 3.08 (br d, J = 15.56 Hz, 1 H) 2.93 (t, J = 6.48 Hz, 2 H) 2.64 (br d, J = 15.30 Hz, 1 H) 2.06 (quin, J = 6.09 Hz, 2 H) 1.81 (td, 1 = 12.58,3.89 Hz, 1 H) 1.67 (td, J = 12.58, 3.89 Hz, 1 H) 1.55 (br d, J = 12.97 Hz, 1 H) 1.14 (br d, J = 12.97 Hz, 1 H |
| 37 | AE | J | 520.2 | (CD3OD) 8.38 (s, 1H), 8.23 (s, 1H), 8.02-8.10 (m, 2H), 7.53-7.55 (m, 2H), 7.41-7.46 (m, 2H), 7.34-7.38 (m, 1H), 4.54-4.57 (m, 1H), 4.41-4.44 (m, 2H), 4.13-4.16 (m, 2H), 3.44-3.52 (m, 2H), 3.38-3.42 (m, 2H), 3.24 (s, 2H), 2.32-2.38 (m, 2H), 1.91-1.99 (m, 1H), 1.81-1.88 (m, 2H), 1.67-1.70 (m, 1H). |
| 38 | 5-methane-sulfonyl-1,2,3,4-tetrahydro-quinoline (CAS# 343944-90-1) | J | 530.5 | 12.64 (br s, 1H), 8.30 (s, 1H), 8.24 (s, 1H), 7.30-7.37 (m, 2H), 7.11-7.22 (m, 5H), 4.30 (dt, J = 3.76, 8.36 Hz, 2H), 3.91 (s, 1H), 3.86 (t, J = 5.83 Hz, 2H), 3.25-3.30 (m, 3H), 3.21 (d, J = 6.22 Hz, 3H), 3.10 (br d, J = 15.82 Hz, 1H), 2.69 (br d, J = 15.82 Hz, 1H), 2.02 (quin, J = 6.09 Hz, 2H), 1.79 (dt, J = 4.15, 12.58 Hz, 1H), 1.69 (dt, J = 3.89, 12.58 Hz, 1H), 1.53 (br d, J = 12.45 Hz, 1H), 1.17 (br d, J = 14.00 Hz, 1H) |
| 39 | AF | J | 543.2 | 12.85 (br s, 1H), 8.35 (s, 1H), 8.25 (s, 1H), 7.29-7.35 (m, 2H), 7.16-7.21 (m, 3H), 7.09-7.13 (m, 1H), 7.05-7.08 (m, 1H), 4.26-4.36 (m, 2H), 4.04 (br t, J = 4.54 Hz, 2H), 3.89 (s, 1H), 3.27 (br d, J = 11.15 Hz, 4H), 3.10 (br d, J = 15.56 Hz, 2H), 2.68 (d, J = 15.82 Hz, 1H), 1.64-1.83 (m, 4H), 1.53 (br d, J = 12.71 Hz, 1H), 1.44 (br d, J = 2.59 Hz, 2H), 1.17 (br d, J = 13.23 Hz, 1H) |
| 40 | X | Z | 551.2 | 12.51 (s, 1H), 8.30 (s, 1H), 8.07 (s, 1H), 7.82 (s, 1H), 7.55 (d, J = 8.56 Hz, 1H), 7.23 (d, J = 8.56 Hz, 1H), 7.19 (dd, J = 5.45, 7.78 Hz, 1H), 7.06 (br d, J = 7.78 Hz, 1H), 6.91-6.97 (m, 1H), 4.25-4.36 (m, 2H), 3.94-4.00 (m, 2H), 3.81-3.87 (m, 4H), 3.14-3.26 (m, 2H), 3.07 (br d, J = 15.56 Hz, 1H), 2.93 (br t, J = 6.48 Hz, 2H), 2.59 (br d, J = 15.30 Hz, 1H), 2.04-2.08 (m, 2H), 1.81 (dt, J = 3.89, 12.58 Hz, 1H), 1.63-1.71 (m, 1H), 1.55 (br d, J = 13.23 Hz, 1H), 1.09 (br d, J = 13.23 Hz, 1H) |
| 41 | 5-methane-sulfonyl-1,2,3,4-tetrahydro-quinoline (CAS# 343944-90-1) | Z | 548.5 | 12.64 (br s, 1H), 8.29 (s, 1H), 8.23 (s, 1H), 7.34 (d, J = 7.52 Hz, 1H), 7.17-7.23 (m, 2H), 7.10-7.16 (m, 1H), 7.08 (br d, J = 8.04 Hz, 1H), 6.91-6.99 (m, 1H), 4.31 (br t, J = 13.35 Hz, 2H), 3.83-3.89 (m, 4H), 3.23 (s, 4H), 3.07 (br d, J = 15.56 Hz, 2H), 2.61 (br d, J = 15.30 Hz, 1H), 2.02 (quin, J = 5.96 Hz, 2H), 1.80 (dt, J = 3.76, 12.51 Hz, 1H), 1.61-1.71 (m, 1H), 1.55 (br d, J = 12.71 Hz, 1H), 1.11 (br d, J = 13.23 Hz, 1H) |
| 42 | X | U | 551.2 | 12.51 (s, 1H), 8.31 (s, 1H), 8.07 (s, 1H), 7.82 (d, J = 0.76 Hz, 1H), 7.55 (d, J = 8.59 Hz, 1H), 7.19-7.28 (m, 2H), 7.13-7.18 (m, 1H), 6.98 (t, J = 8.59 Hz, 1H), 4.30 (dt, J = 3.79, 8.08 Hz, 2H), 3.95-4.00 (m, 2H), 3.90 (s, 1H), 3.84 (s, 3H), 3.24 (br s, 1H), 3.14 (d, J = 15.92 Hz, 1H), 2.93 (t, J = 6.44 Hz, 2H), 2.67 (br d, J = 15.92 Hz, 1H), 2.02-2.12 (m, 2H), 1.65-1.84 |

| Example #[a] | Step a Amine | Step a Iodide | LCMS m/z (M + H)+ | 1H NMR (400 MHz, DMSO-d6 δ ppm |
|---|---|---|---|---|
| 43 | AO | J | 492.2 | (m, 3H), 1.55 (br d, J = 12.13 Hz, 1H), 1.16 (br d, J = 13.14 Hz, 1H) (CD3OD) 8.21 (s, 1H), 7.35-7.34 (m, 1H), 7.21-7.17 (m, 3H), 6.85-6.80 (m, 3H), 4.37 (d, J = 13.6 Hz, 2H), 3.45 (d, J = 4.8 Hz, 2H), 3.94 (s, 1H), 3.46-3.36 (m, 4H), 3.16 (d, J = 15.6 Hz, 1H), 2.96 (s, 3H), 2.81 (d, J = 15.6 Hz, 1H), 1.90-1.76 (m, 2H), 1.61 (d, J = 14.0 Hz, 1H), 2.69 (d, J = 11.2 Hz, 1H). |
| 44 | AQ | J | 483.4 | 12.78 (br s, 1H), 8.37 (s, 1H), 8.23 (s, 1H), 7.30-7.37 (m, 1H), 7.14-7.25 (m, 4H), 5.86 (d, J = 7.83 Hz, 1H), 4.26-4.37 (m, 2H), 3.92 (s, 1H), 3.71-3.80 (m, 2H), 3.30 (s, 3H), 3.26 (br d, J = 13.89 Hz, 2H), 3.11 (d, J = 15.66 Hz, 1H), 2.65-2.76 (m, 1H), 1.93 (quin, J = 5.87 Hz, 2H), 1.80 (dt, J = 4.04, 12.51 Hz, 1H), 1.69 (dt, J = 3.66, 12.44 Hz, 1H), 1.53 (br d, J = 12.63 Hz, 1H), 1.18 (br d, J = 13.89 Hz, 1H) |
| 45[b] | 1,2,3,4-tetrahydro-1,5-naphthyridine | AU | 454.2 | 12.57 (s, 1H), 8.30-8.35 (m, 2H), 7.89 (d, J = 4.15 Hz, 1H), 7.60 (br d, J = 7.26 Hz, 1H), 7.48 (d, J = 8.30 Hz, 1H), 7.16 (dd, J = 4.93, 7.26 Hz, 1H), 6.95 (dd, J = 4.41, 8.30 Hz, 1H), 4.22 (br t, J = 12.84 Hz, 2H), 3.92-3.97 (m, 2H), 3.88 (s, 1H), 3.36 (br s, 2H), 3.08 (br d, J = 16.08 Hz, 1H), 2.93 (t, J = 6.35 Hz, 2H), 2.67 (br d, J = 16.08 Hz, 1H), 2.03-2.09 (m, 2H), 1.74-1.86 (m, 2H), 1.58 (br d, J = 13.23 Hz, 1H), 1.15 (br d, J = 13.48 Hz, 1H) |
| 46[b] | X | AU | 534.3 | 12.51 (s, 1H), 8.33 (br d, J = 4.41 Hz, 1H), 8.31 (s, 1H), 8.07 (s, 1H), 7.82 (s, 1H), 7.60 (d, J = 7.52 Hz, 1H), 7.55 (d, J = 8.56 Hz, 1H), 7.23 (d, J = 8.82 Hz, 1H), 7.16 (dd, J = 5.19, 7.26 Hz, 1H), 4.18-4.27 (m, 2H), 3.95-4.00 (m, 2H), 3.88 (s, 1H), 3.84 (s, 3H), 3.36 (br s, 2H), 3.08 (br d, J = 16.08 Hz, 1H), 2.93 (br t, J = 6.48 Hz, 2H), 2.67 (br d, J = 15.82 Hz, 1H), 2.07 (quin, J = 5.83 Hz, 2H), 1.75-1.86 (m, 2H), 1.58 (br d, J = 13.48 Hz, 1H), 1.15 (br d, J = 13.48 Hz, 1H) |
| 47 | 1,2,3,4-tetrahydro-1,5-naphthyridine | AX | 471.3 | 12.58 (br s, 1H), 8.31 (s, 1H), 8.20 (s, 2H), 7.89 (d, J = 4.15 Hz, 1H), 7.48 (d, J = 8.30 Hz, 1H), 7.22-7.29 (m, 1H), 7.07 (d, J = 7.52 Hz, 1H), 6.93-7.01 (m, 2H), 4.10-4.20 (m, 3H), 4.02-4.09 (m, 2H), 3.91-3.97 (m, 3H), 3.45 (dt, J = 10.89, 13.23 Hz, 3H), 3.05 (br d, J = 16.08 Hz, 1H), 2.93 (t, J = 6.48 Hz, 2H), 2.82 (br d, J = 16.08 Hz, 1H), 2.53 (s, 1H), 2.03-2.10 (m, 2H), 1.81-1.89 (m, 1H), 1.51-1.61 (m, 2H), 1.41 (br d, J = 13.48 Hz, 1H) |
| 48 | X | AX | 551.3 | 12.51 (s, 1H), 8.30 (s, 1H), 8.07 (s, 1H), 7.82 (s, 1H), 7.55 (d, J = 8.56 Hz, 1H), 7.16-7.30 (m, 2H), 7.04 (d, J = 7.26 Hz, 1H), 6.94 (t, J = 8.82 Hz, 1H), 3.95-4.12 (m, 5H), 3.84 (s, 3H), 3.44-3.55 (m, 2H), 3.01 (br d, J = 16.08 Hz, 1H), 2.93 (br t, J = 6.35 Hz, 2H), 2.77 (br d, J = 16.08 Hz, 1H), 2.03-2.10 (m, 2H), 1.82-1.91 (m, 1H), 1.48-1.58 (m, 2H), 1.38-1.46 (m, 1H) |
| 49 | 1,2,3,4-tetrahydro-1,5-naphthyridine | AZ | 454.2 | 12.57 (s, 1H), 8.27-8.40 (m, 2H), 7.87-7.92 (m, 1H), 7.64 (d, J = 7.26 Hz, 1H), 7.48 (d, J = 8.30 Hz, 1H), 7.16 (dd, J = 5.19, 7.26 Hz, 1H), 6.95 (dd, J = 4.67, 8.30 Hz, 1H), 4.26-4.36 (m, 2H), 3.91-3.97 (m, 2H), 3.89 (s, 1H), 3.20-3.29 (m, 3H), 3.12 (d, J = 16.34 Hz, 1H), 2.93 (t, J = 6.48 Hz, 2H), 2.76 (br d, J = 16.08 Hz, 1H), 2.01-2.10 (m, 3H), 1.68-1.83 |

-continued

| Example #ᵃ | Step a Amine | Step a Iodide | LCMS m/z (M + H)⁺ | ¹H NMR (400 MHz, DMSO-d6 δ ppm |
|---|---|---|---|---|
| | | | | (m, 2H), 1.55 (br d, J = 12.97 Hz, 1H), 1.14 (br d, J = 12.97 Hz, 1H) |
| 50 | 1,2,3,4-tetrahydro-1,5-naphthyridine | BD | 454.3 | 12.56 (s, 1H), 8.46 (s, 1H), 8.34 (d, J = 4.67 Hz, 1H), 8.31 (s, 1H), 7.89 (d, J = 4.41 Hz, 1H), 7.48 (d, J = 8.30 Hz, 1H), 7.23 (d, J = 4.93 Hz, 1H), 6.95 (dd, J = 4.67, 8.30 Hz, 1H), 4.27 (br t, J = 12.19 Hz, 2H), 3.90-3.98 (m, 3H), 3.20-3.28 (m, 2H), 3.10 (d, J = 16.60 Hz, 1H), 2.93 (t, J = 6.48 Hz, 2H), 2.68 (br d, J = 16.60 Hz, 1H), 2.03-2.09 (m, 2H), 1.85 (br d, J = 6.22 Hz, 1H), 1.67-1.80 (m, 3H), 1.52 (br d, J = 13.48 Hz, 1H), 1.14 (br d, J = 13.74 Hz, 1H) |
| 51 | BG | J | 521.4 | 12.72 (s, 1H), 8.27 (br s, 3H), 7.51 (d, J = 7.26 Hz, 1H), 7.27-7.39 (m, 3H), 7.18 (d, J = 8.30 Hz, 1H), 6.97 (d, J = 8.56 Hz, 1H), 4.30-4.42 (m, 5H), 3.85-3.95 (m, 2H), 3.20 (br d, J = 16.08 Hz, 1H), 2.99-3.07 (m, 4H), 2.77 (br t, J = 6.35 Hz, 2H), 1.99-2.10 (m, 2H), 1.70-1.83 (m, 2H), 1.53 (br d, J = 12.97 Hz, 2H) |
| 52 | BW | BY | 501.5 | 12.78 (br s, 1H), 8.37 (s, 1H), 8.21 (s, 1H), 7.33 (dd, J = 5.45, 8.04 Hz, 1H), 7.19 (d, J = 7.78 Hz, 1H), 6.96-7.07 (m, 2H), 5.86 (d, J = 7.52 Hz, 1H), 4.30 (br dd, J = 2.33, 12.97 Hz, 2H), 3.88 (s, 1H), 3.72-3.79 (m, 3H), 3.30 (s, 4H), 3.25 (br d, J = 14.00 Hz, 3H), 3.10 (br d, J = 16.08 Hz, 1H), 2.71 (br d, J = 16.08 Hz, 1H), 1.93 (quin, J = 5.90 Hz, 2H), 1.73-1.83 (m, 1H), 1.63-1.72 (m, 2H), 1.53 (br d, J = 12.97 Hz, 1H) |
| 53 | BW | U | 501.5 | 12.78 (br s, 1H), 8.37 (s, 1H), 8.21 (s, 1H), 7.22-7.31 (m, 1H), 7.15-7.21 (m, 2H), 7.01 (t, J = 8.69 Hz, 1H), 5.86 (d, J = 7.78 Hz, 1H), 4.27-4.35 (m, 2H), 3.97 (br s, 1H), 3.73-3.77 (m, 2H), 3.25-3.34 (m, 5H), 3.15 (d, J = 15.82 Hz, 1H), 2.72 (br d, J = 15.82 Hz, 1H), 1.93 (quin, J = 5.90 Hz, 2H), 1.75-1.84 (m, 1H), 1.66-1.74 (m, 1H), 1.56 (br d, J = 12.97 Hz, 1H), 1.21 (br d, J = 12.97 Hz, 1H) |
| 54 | 1,2,3,4-tetrahydro-1,5-naphthyridine | CA | 473.5 | 12.65 (br s, 1H), 8.38 (s, 1H), 8.13 (s, 1H), 7.90 (dd, J = 1.17, 4.54 Hz, 1H), 7.45-7.52 (m, 1H), 7.22 (d, J = 7.26 Hz, 1H), 7.14 (dd, J = 8.56, 10.63 Hz, 1H), 6.96 (dd, J = 4.54, 8.43 Hz, 1H), 6.91 (dt, J = 4.28, 7.84 Hz, 1H), 4.41 (br d, J = 13.48 Hz, 1H), 4.29-4.35 (m, 2H), 3.93-3.99 (m, 2H), 3.41-3.48 (m, 3H), 2.94 (t, J = 6.48 Hz, 2H), 1.97-2.10 (m, 3H), 1.87-1.93 (m, 1H), 1.80-1.86 (m, 2H) |
| 55 | BW | CA | 503.5 | 12.83 (s, 1H), 8.42 (s, 1H), 8.16 (s, 1H), 7.20 (d, J = 7.78 Hz, 1H), 7.15 (d, J = 7.52 Hz, 1H), 7.07 (dd, J = 8.30, 10.89 Hz, 1H), 6.86 (dt, J = 4.41, 7.78 Hz, 1H), 5.86 (d, J = 7.52 Hz, 1H), 4.36 (br d, J = 13.23 Hz, 1H), 4.28 (br d, J = 13.74 Hz, 1H), 4.15 (s, 1H), 3.72-3.78 (m, 3H), 3.43-3.53 (m, 3H), 3.30 (s, 3H), 1.90-2.01 (m, 4H), 1.74-1.88 (m, 4H) |
| 56 | 5-methane-sulfonyl-1,2,3,4-tetrahydro-quinoline (CAS# 343944-90-1) | U | 548.4 | 12.69 (s, 1H), 8.34 (s, 2H), 7.32-7.41 (m, 2H), 7.10-7.25 (m, 2H), 4.28-4.48 (m, 3H), 3.84-3.90 (m, 1H), 3.27-3.37 (m, 2H), 3.15-3.26 (m, 4H), 3.07 (br d, J = 16.17 Hz, 1H), 2.02 (td, J = 6.19, 11.87 Hz, 2H), 1.69-1.86 (m, 3H), 1.49-1.61 (m, 2H), 0.99-1.28 (m, 5H) |
| 57 | BW | CC | 485.5 | 12.83 (s, 1H), 8.43 (s, 1H), 7.35 (d, J = 7.33 Hz, 1H), 7.12-7.24 (m, 2H), 6.89 (dt, J = 0.88, 7.39 Hz, 1H), 6.81 (d, J = 8.08 Hz, 1H), 5.86 (d, J = 7.83 Hz, 1H), 4.26-4.44 (m, 2H), 4.17 (s, 1H), 3.68-3.80 (m, 2H), 3.39-3.53 (m, 2H), |

-continued

| Example #[a] | Step a Amine | Step a Iodide | LCMS m/z (M + H)+ | 1H NMR (400 MHz, DMSO-d6 δ ppm |
|---|---|---|---|---|
| 58 | BW | Z | 501.5 | 3.30 (s, 4H), 1.88-2.04 (m, 3H), 1.67-1.88 (m, 4H)<br>8.35 (s, 1 H), 8.26-8.30 (m, 1 H), 7.23-7.26 (m, 1 H), 7.20 (d, J = 7.78 Hz, 1 H), 7.14 (dd, J = 8.95,1.94 Hz, 1 H), 6.93-7.06 (m, 1 H), 5.85 (d, J = 7.52 Hz, 1 H), 4.32 (br d, J = 13.48 Hz, 2 H), 3.96 (s, 1 H), 3.67-3.77 (m, 2 H), 3.30-3.33 (m, 3 H), 3.16-3.29 (m, 2 H), 3.09 (d, J = 15.82 Hz, 1 H), 2.66-2.75 (m, 1 H), 2.48 (br s, 2 H), 1.88-1.97 (m, 2 H), 1.74-1.84 (m, 1 H), 1.67 (td, J = 12.45, 3.89 Hz, 1 H), 1.55 (br d, J = 12.97 Hz, 1 H), 1.16-1.30 (m, 1 H). |
| 59 | 5-methane-sulfonyl-1,2,3,4-tetrahydro-quinoline (CAS# 343944-90-1) | AX | 548.6 | 12.64 (br s, 1H), 8.29 (s, 1H), 8.18 (s, 1H), 7.34 (dd, J = 1.26, 7.58 Hz, 1H), 7.17-7.26 (m, 2H), 7.10-7.16 (m, 1H), 7.04 (d, J = 7.33 Hz, 1H), 6.95 (t, J = 8.97 Hz, 1H), 3.99-4.13 (m, 3H), 3.82-3.89 (m, 2H), 3.43-3.53 (m, 2H), 3.19-3.24 (m, 5H), 3.02 (d, J = 16.17 Hz, 1H), 2.78 (d, J = 16.17 Hz, 1H), 2.02 (quin, J = 6.13 Hz, 2H), 1.81-1.90 (m, 1H), 1.49-1.59 (m, 2H), 1.41 (br d, J = 13.64 Hz, 1H) |
| 60 | X | CC | 535.1 | (CD3OD) 8.40-8.37 (m, 2H), 8.14-8.12 (m, 2H), 7.77-7.75 (m, 1H), 7.59-7.58 (m, 1H), 7.46-7.42 (m, 1H), 7.11-7.01 (m, 2H), 4.99-4.91 (m, 2H), 4.87-4.86 (m, 1H), 4.84-7.77 (m, 1H), 4.70-4.68 (m, 1H), 4.13-4.11 (m, 2H), 4.02 (s, 3H), 3.58-3.32 (m, 2H), 2.35-2.31 (m, 2H), 2.19-2.15 (m, 2H), 1.95-1.92 (m, 2H). |
| 61 | AE | CC | 522.1 | 12.95 (br, 1H), 8.79 (br, 3H), 8.45 (s, 1H), 8.19 (s, 1H), 7.75-7.73 (d, J = 8.8 Hz, 1H), 7.71-7.68 (d, J = 7.6 Hz, 1H), 7.63-7.60 (d, J = 8.8 Hz, 1H), 7.39-7.34 (m, 2H), 7.04-6.97 (m, 2H), 4.66-4.43 (m, 3H), 4.04-4.01 (m, 2H), 3.42-3.35 (m, 2H), 3.08-3.04 (m, 2H), 2.18-1.84 (m, 6H). |
| 62 | 1,2,3,4-tetrahydro-1,5-naphthyridine | CS | 489.0 | (CD3OD) 8.36 (s, 1H), 8.08-8.05 (m, 2H), 7.61-7.55 (m, 1H), 7.26-7.15 (m, 2H), 4.69 (s, 1H), 4.56-4.40 (m, 2H), 4.12-4.09 (m, 2H), 3.53-3.45 (m, 2H), 3.31-3.26 (m, 4H), 2.34-2.29 (m, 2H), 2.00-1.83 (m, 3H), 1.73-1.68 (m, 1H). |
| 63[d] | (R)-N-[(3S)-1,3-dihydrospiro-[indene-2,4'-piperidin]-3-yl]-2-methyl-propane-2-sulfinamide (synthesized via Step a of Example 120 | CJ | 439.1 | (CD3OD) 8.58 (s, 2H), 7.74-7.72 (d, J = 6.8 Hz, 1H), 7.55-7.36 (m, 4H), 6.95-6.92 (d, J = 6.8 Hz, 1H), 4.45 (s, 1H), 3.96-3.82 (m, 2H), 3.29-3.19 (m, 4H), 2.04-1.68 (m, 4H). |
| 64[d] | CB | BS | 444.0 | (CD3OD) 8.19-8.20 (m, 1H), 8.12-8.13 (m, 1H), 8.00-8.01 (m, 1H), 7.39-7.42 (m, 1H), 7.18-7.23 (m, 1H), 7.02-7.03 (m, 1H), 6.90-6.94 (m, 1H), 6.80-6.82 (m, 1H), 4.33-4.37 (m, 1H), 4.23-4.26 (m, 1H), 4.13 (s, 1H), 3.42-3.49 (m, 2H), 1.95-2.05 (m, 2H), 1.84-1.88 (m, 1H). |
| 176[d] | (2S)-2-phenyl-piperidine (CAS# 70665-05-3) | CZ | 440.1 | (CD3OD) 5 8.15 (s, 1H), 7.86 (s, 1H), 7.50-7.40 (m, 1H), 7.38-7.30 (m, 8H), 4.37 (s, 1H), 4.29 (d, J = 14.0 Hz, 1H), 4.13 (d, J = 13.6 Hz, 1H), 4.00-3.92 (m, 1H), 3.69-3.66 (m, 1H), 3.26-3.20 (m, 2H), 3.14 (s, 2H), 2.36-2.08 (m, 5H), 1.95-1.60 (m, 6H). |

| Example #[a] | Step a Amine | Step a Iodide | LCMS m/z (M + H)+ | 1H NMR (400 MHz, DMSO-d6 δ ppm |
|---|---|---|---|---|
| 196[e] | 1,2,3,4-tetrahydro-1,5-naphthyridine | DW | 427.3 | (MeOD-d4) 8.19 (s, 1H), 8.19-8.15 (m, 2H), 8.13 (d, J = 5.6 Hz, 1H), 7.64-7.60 (m, 1H), 7.55 (d, J = 7.6 Hz, 1H), 7.42-7.35 (m, 3H), 4.49 (s, 1H), 3.93-3.90 (m, 2H), 3.70-3.56 (m, 2H), 3.56-3.37 (m, 2H), 3.25-3.19 (m, 4H), 2.59 (s, 3H), 2.28-2.25 (m, 2H), 2.24-2.05 (m, 2H), 1.89 (d, J = 13.2 Hz, 1H), 1.74 (d, J = 13.6 Hz, 1H). |
| 197[d] | 1,2,3,4-tetrahydro-1,5-naphthyridine | DV | 427.3 | (MeOD-d4) 8.19 (s, 1H), 7.98 (d, J = 5.2 Hz, 1H), 7.55-7.52 (m, 2H), 7.42-7.37 (m, 2H), 7.37-7.35 (m, 1H), 7.20 (d, J = 8.8 Hz, 1H), 4.44-4.42 (m, 2H), 4.32-4.28 (m, 1H), 3.69-3.67 (m, 2H), 3.42-3.36 (m, 2H), 3.26-3.21 (m, 4H), 2.35 (s, 3H), 2.31-2.25 (m, 2H), 1.97-1.96 (m, 1H), 1.87-1.78 (m, 1H), 1.69 (d, J = 13.2 Hz, 1H). |
| 198[d,f] | EF | EE | 438.3 | 8.96-8.95 (m, 1H), 8.43-8.41 (m, 1H), 8.27 (s, 1H), 8.02 (d, J = 0.8 Hz, 1H), 7.96 (d, J = 8.0 Hz, 1H), 7.88 (d, J = 0.8 Hz, 1H), 7.84 (d, J = 6.8 Hz, 1H), 7.64-7.59 (m, 2H), 7.38-7.36 (m, 1H), 7.24-7.19 (m, 3H), 5.94 (s, 2H), 4.00-3.99 (m, 3H), 3.08-2.98 (m, 3H), 2.71 (d, J = 16.0 Hz, 1H), 1.84-1.67 (m, 2H), 1.49 (br d, J = 12.8 Hz, 1H), 1.23 (br d, J = 13.2 Hz, 1H). |
| 199 | pyridin-3-ylmethanamine (CAS# 3731-52-0) | EK | 400.3 | 13.19 (br s, 1 H), 8.76 (br s, 2 H), 8.63 (br s, 1 H), 8.51 (br s, 1 H), 8.20 (br s, 1 H), 7.82-7.78 (m, 2 H), 7.64 (br d, J = 7.6 Hz, 1 H), 7.42 (br s, 1 H), 7.33-7.29 (m, 3 H), 6.65 (br d, J = 7.2 Hz, 1 H), 4.66 (br d, J = 5.6 Hz, 2 H), 4.38 (br s, 1 H), 3.22-3.14 (m, 5 H), 2.95 (br d, J = 16.0 Hz, 1 H), 2.16 (s, 3 H), 2.06-1.90 (m, 2 H) 1.64-1.53 (m, 2 H) |
| 200[g] | piperidine | DS | 434.1 | (MeOD-d4) 8.56 (s, 1H), 7.46 (d, J = 6.5 Hz, 1H), 7.36-7.23 (m, 3H), 4.23 (s, 1H), 3.59-3.48 (m, 5H), 3.47-3.40 (m, 4H), 3.21-3.11 (m, 3H), 2.97 (d, J = 16.1 Hz, 1H), 2.04-1.93 (m, 2H), 1.78-1.59 (m, 8H) |
| 201 | EF | EO | 399.2 | (MeOD-d4) 8.52 (s, 1 H), 8.13-8.10 (m, 1 H), 7.86-7.85 (m, 1 H), 7.59-7.57 (m, 1 H), 7.52-7.51 (m, 1 H), 7.48-7.46 (d, J = 6.8 Hz, 1 H), 7.34-7.28 (m, 4 H), 6.53 (d, J = 2.0 Hz 1 H), 4.32-4.29 (m, 1 H), 3.81 (s, 3 H), 3.50-3.47 (m, 2 H), 3.15-3.11 (m, 2 H), 3.05-3.0 (m, 2 H), 2.05-1.94 (m, 2 H), 1.75-1.67 (m, 2 H) |
| 202[h] | EF | EP | 385.0 | (MeOD-d4) 8.40 (s, 2H), 7.91 (s, 1 H), 7.82 (s, 1 H), 7.53 (s, 1 H), 7.51 (s, 1 H), 7.42-7.32 (m, 3 H), 7.39-7.02 (m, 1 H), 7.05 (s, 1 H), 4.43 (s, 1 H), 3.54-3.50 (d, J = 12.4 Hz, 1 H), 3.46-3.54 (m, 2 H), 3.45-3.41 (d, J = 12.4 Hz, 2 H), 3.12 (s, 2 H), 3.02-2.94 (m, 2 H), 2.06-2.01 (m, 1 H), 1.97-1.90 (m, 1 H), 1.83-1.80 (d, J = 11.6 Hz, 1 H), 1.70-1.66 (d, J = 12.8 Hz, 1H) |
| 203[e,j] | EW | EV | 477.1 (M − NH₂)+ | (CDCl3) 8.59 (d, J = 8.0 Hz, 1H), 8.31 (s, 1H), 8.11 (s, 1H), 7.86-7.84 (m, 1H), 7.64 (t, J = 7.8 Hz, 1H), 7.40 (d, J = 7.2 Hz, 1H), 7.25-7.23 (m, 1H), 7.05 (d, J = 7.6 Hz, 1H), 6.95 (t, J = 7.2 Hz, 1H), 6.85 (d, J = 7.6 Hz, 1H), 6.42 (d, J = 7.6 Hz, 1H), 4.29 (s, 1H), 3.63 (s, 3H), 3.56-3.47 (m, 2H), 3.45-3.41 (m, 2H), 2.67 (s, 3H), 2.25-2.18 (m, 1H), 2.08 (s, 1H), 1.97 (t, J = 5.8 Hz, 1H). |

| Example #[a] | Step a Amine | Step a Iodide | LCMS m/z (M + H)+ | 1H NMR (400 MHz, DMSO-d6 δ ppm |
|---|---|---|---|---|
| 204 | piperidine | FW | 397.1 | (MeOD-d4) 7.54~7.56 (m, 1H), 7.32~7.43 (m, 4H), 4.91~4.93 (m, 4H), 4.48 (s, 1H), 3.50~3.73 (m, 4H), 3.15~3.28 (m, 2H), 1.61~1.97 (m, 10H). |
| 205[k] | 1,2,3,4-tetrahydroquinolin | DQ | 442.1 | (MeOD-d4) 7.83 (s, 1H), 7.51 (m, 1H), 7.42-7.17 (m, 4H), 7.06-6.76 (m, 2H), 6.61 (m, 1H), 6.29 (m, 1H), 4.37 (s, 1H), 3.57 (s, 3H), 3.55-3.44 (m, 4H), 3.24-3.06 (m, 4H), 2.86 (m, 2H), 2.13-1.91 (m, 4H), 1.79-1.64 (m, 2H). |
| 206[k] | EF | FG | 441.1 | 8.60 (s, 3H), 7.60 (d, J = 7.2 Hz, 1H), 7.38-7.30 (m, 4H), 6.90 (d, J = 7.6 Hz, 1H), 6.81-6.77 (m, 1H), 6.49 (t, J = 7.2 Hz, 1H), 6.12 (d, J = 8.0 Hz, 1H), 5.91 (d, J = 7.6 Hz, 1H), 4.40 (d, J = 4.4 Hz, 1H), 3.47 (s, 3H), 3.41-3.38 (m, 2H), 3.18-2.93 (m, 4H), 2.84-2.73 (m, 4H), 1.97-1.91 (m, 4H\ 1.62-1.54 (m, 2H). |
| 207[l] | 1,2,3,4-tetrahydroquinolin | FH | 471.1 | (MeOD-d4) 7.55 (d, J = 7.6 Hz, 1H), 7.47-7.36 (m, 3H), 7.08 (d, J = 7.2 Hz, 1H), 6.99 (t, J = 8.0 Hz, 1H), 6.76 (t, J = 7.2 Hz, 1H), 6.42 (d, J = 8.0 Hz, 1H), 4.49 (s, 1H), 4.08-4.00 (m, 1H), 3.93-3.85 (m, 1H), 3.66-3.55 (m, 4H), 3.23 (s, 2H), 2.92 (t, J = 6.4 Hz, 1H), 2.33 (s, 3H), 2.16-1.92 (m, 4H), 1.90-1.82 (m, 1H), 1.77-1.69 (m, 1H). |
| 208 | piperidine | FL | 438.1 | (MeOD-d4) 7.38-7.35 (m, 1H), 7.21-7.16 (m, 1H), 7.02-6.99 (m, 1H), 4.75 (s, 1H), 4.21-4.14 (m, 1H), 4.14-3.91 (m, 5H), 3.55-3.42 (m, 2H), 2.68 (s, 3H), 2.39-2.31 (m, 1H), 2.18-1.93 (m, 3H), 1.86-1.75 (m, 6H). |
| 209[m] | piperidine | FN | 403.0 | (MeOD-d4) 8.06 (d, J = 9.6 Hz, 1H), 7.42 (d, J = 7.2 Hz, 1H), 7.33-7.22 (m, 3H), 6.76 (d, J = 9.6 Hz, 1H), 4.46-4.37 (m, 1H), 4.33-4.24 (m, 2H), 3.58-3.51 (m, 4H), 3.40-3.28 (m, 2H), 3.11 (s, 2H), 1.83-1.75 (m, 1H), 1.73-1.62 (m, 8H), 1.58-1.50 (m, 1H). |
| 210[n] | 1,2,3,4-tetrahydroquinoline | FC | 428.1 | (MeOD-d4) 7.83 (s, 1H), 7.53 (d, J = 7.2 Hz, 1H), 7.43-7.36 (m, 3H), 6.98 (d, J = 7.2 Hz, 1H), 6.91-6.89 (m, 1H), 6.65 (t, J = 7.2 Hz, 1H), 6.40 (d, J = 8.0 Hz, 1H), 4.48 (s, 1H), 4.34 (br d, J = 13.6 Hz, 1H), 4.19 (br d, J = 14.0 Hz, 1H), 3.60-3.48 (m, 4H), 3.22 (d, J = 4.8 Hz, 2H), 2.84 (t, J = 6.4 Hz, 2H), 2.09-1.72 (m, 6H). |

[a]RuPhos and RuPhos-Pd-G2 or RuPhos with Pd2(dba)3 with Cs2CO3 or NaOtBu as the base, or XantPhos-Pd-G4 with Pd2(dba)3 and Cs2CO3 could also be used as the catalyst system for coupling in Step a. Step a ran from 2-16 h from 80-110° C. Step 2 ran from 2-6 h from 25-60° C. in MeOH or EtOAc.
[b]Compound is racemic.
[c]Compound is a mixture of diastereomers.
[d]Bromide not Iodide was used in Step a.
[e]Chloride not Iodide used in Step a.
[f]TFA was used in Step b for the deprotection.
[g]Step a utilized Cs2CO3 and XantPhos-Pd-G4 in toluene for 100° C. for 12 h. For Step b, TFA and TfOH (10:1) at 100° C. for 16 h was used to accomplish the deprotection.
[h]Step a was run with BrettPhos-Pd-G3 and NaOtBu in tolune at 100° C. for 16 h.
[i]Sphos-G4 with Cs2CO3 in dioxane was used for Step a, which was run at 90° C. for 12 h.
[j]No deprotection Step b required.
[k]RuPhos-Pd-G4, RuPhos. Cs2CO3, and NaI at 120° C. in tolune were used in Step a for 12 h.
[l]CPhos-Pd-G3 was used as the catalyst with tBuON in tolune at 90° C. were used in Step a for 12 h.
[m]tBuXPhos-Pd-G3 with tBuXPhos and tBuONa in tBuOH was used in Step a in tBuOH at 70 C. for 12 h.
[n]TFA and TfOH at 100° C. was used for deprotection in Step b.

[a]RuPhos and RuPhos-Pd-G2 or RuPhos with Pd2(dba)3 with Cs2CO3 or NaOtBu as the base, or XantPhos-Pd-G4 with Pd2(dba)3 and Cs2CO3 could also be used as the catalyst system for coupling in Step a. Step a ran from 2-16 h from 80-110° C. Step 2 ran from 2-6 h from 25-60° C. in MeOH or EtOAc. [b]Compound is racemic. [c]Compound is a mixture of diastereomers. [d]Bromide not Iodide was used in Step a. [e]Chloride not Iodide used in Step a. [f]TFA was used in Step b for the deprotection. [g]Step a utilized Cs2CO3 and XantPhos-Pd-G4 in toluene for 100° C. for 12 h. For Step b, TFA and TfOH (10:1) at 100° C. for 16 h was used to accomplish the deprotection. [h]Step a was run with BrettPhos-Pd-G3 and NaOtBu in tolune at 100° C. for 16 h. [i]Sphos-G4 with Cs2CO3 in dioxane was used for Step a, which was run at 90° C. for 12 h. No deprotection Step b required. RuPhos-Pd-G4, RuPhos, Cs2CO3, and NaI at 120° C. in tolune were used in Step a for 12 h. [l]CPhos-Pd-G3 was used as the catalyst with tBuON in tolune at 90° C. were used in Step a for 12 h. ′′′tBuXPhos-Pd-G3 with tBuXPhos and tBuONa in tBuOH was used in Step a in tBuOH at 70 C for 12 h. ′′TFA and TfOH at 100° C. was used for deprotection in Step b.

Compounds Synthesized in Similar Fashion to Method 4:

Example 65: Synthesis of 1-{6-[(3S)-3-amino-1,3-dihydrospiro[indene-2,4'-piperidin]-1'-yl]-1H-pyrazolo[3,4-b]pyrazin-3-yl}-1,2,3,4-tetrahydroquinolin-6-yl sulfurofluoridate

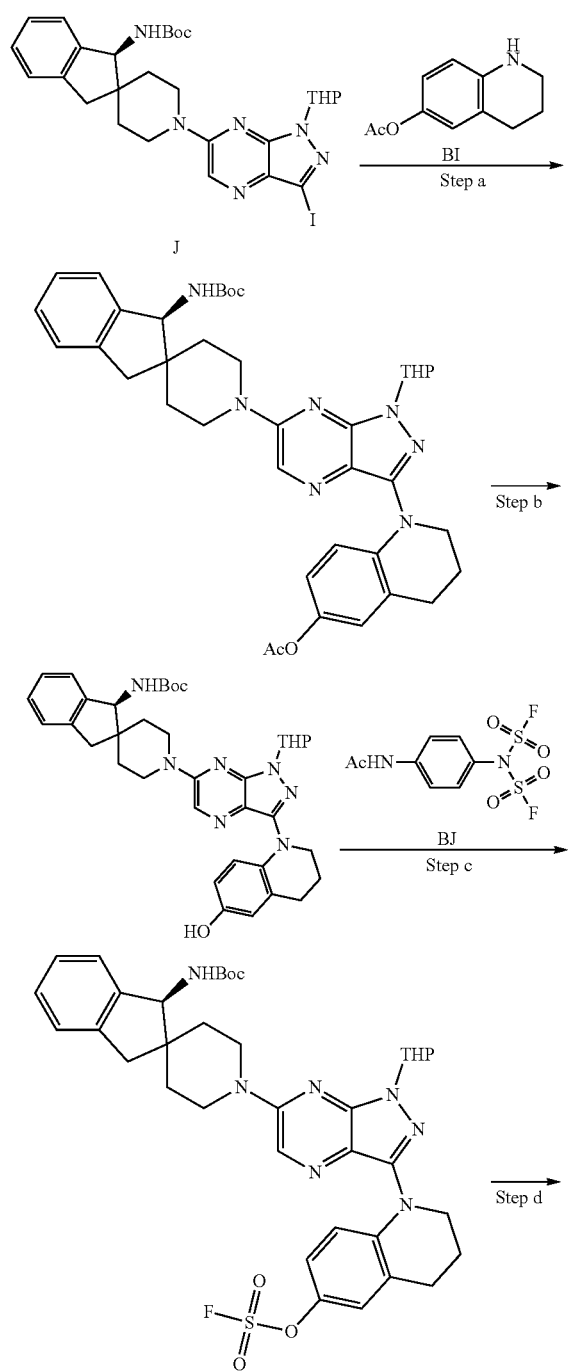

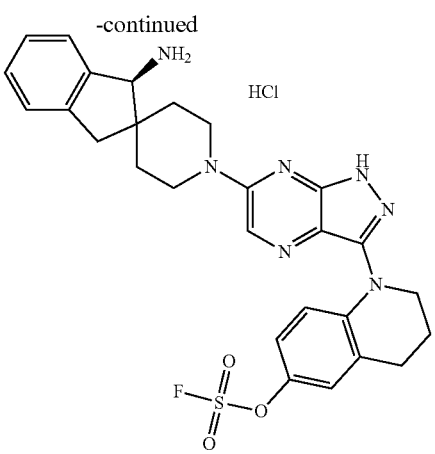

Step a: A solution of tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (400.0 mg, 634.0 μmol, Intermediate J), 1,2,3,4-tetrahydroquinolin-6-yl acetate (240.0 mg, 1.26 mmol, Intermediate BI), XantPhos-Pd-G4 (60.9 mg, 63.4 umol) and $Cs_2CO_3$ (206.0 mg, 634.0 umol) in toluene (15.0 mL) was stirred at 85° C. for 12 hours under $N_2$. The reaction mixture was concentrated under reduced pressure. The mixture was triturated with $H_2O$ (80.0 mL) and extracted with EtOAc (80.0 mL×2). The combined organic layers were washed with brine (50.0 mL), dried over anhydrous $Na_2SO_4$, filtered and concentrated to give the product of 1-{6-[(3S)-3-{[(tert-butoxy)carbonyl]amino}-1,3-dihydrospiro[indene-2,4'-piperidin]-1'-yl]-1-(oxan-2-yl)-1H-pyrazolo[3,4-b]pyrazin-3-yl}-1,2,3,4-tetrahydroquinolin-6-yl acetate (450.0 mg, quant. crude yield) as a brown solid. LCMS m/z $(M+H)^+=694.3$.

Step b: A solution of 1-{6-[(3S)-3-{[(tert-butoxy)carbonyl]amino}-1,3-dihydrospiro[indene-2,4'-piperidin]-1'-yl]-1-(oxan-2-yl)-1H-pyrazolo[3,4-b]pyrazin-3-yl}-1,2,3,4-tetrahydroquinolin-6-yl acetate (450.0 mg, 648.0 μmol) in 2 N NaOH/MeOH (10.0 mL/20.0 mL) was stirred at 20° C. for 0.5 hour. Then the reaction mixture was adjusted pH=5 with 2 N HCl. The reaction mixture was poured into $H_2O$ (80.0 mL) and extracted with EtOAc (80.0 mL×2). The combined organic layers were washed with brine (60.0 mL), dried over anhydrous $Na_2SO_4$, filtered and concentrated to give an orange residue. The residue was purified by flash silica gel chromatography (24 g column, Ethyl acetate in petroleum ether from 0% to 30%) to give tert-butyl N-[(3S)-1'-[3-(6-hydroxy-1,2,3,4-tetrahydroquinolin-1-yl)-1-(oxan-2-yl)-1H-pyrazolo[3,4-b]pyrazin-6-yl]-1,3-dihydrospiro[indene-2,4'-piperidin]-3-yl]carbamate (400.0 mg, 95% yield) as a yellow oil. LCMS m/z $(M+H)^+=652.2$.

Step c: A solution of tert-butyl N-[(3S)-1'-[3-(6-hydroxy-1,2,3,4-tetrahydroquinolin-1-yl)-1-(oxan-2-yl)-1H-pyrazolo[3,4-b]pyrazin-6-yl]-1,3-dihydrospiro[indene-2,4'-piperidin]-3-yl]carbamate (350.0 mg, 536.0 μmol), [(4-acetamidophenyl)(fluorosulfonyl)amino]sulfonyl fluoride (252.0 mg, 804.0 μmol, Intermediate BJ) and DBU (173.0 uL, 1.17 mmol) in THF (9.0 mL) was stirred at 20° C. for 12 hours. The reaction mixture was then poured into $H_2O$ (50.0 mL) and extracted with EtOAc (50.0 mL×2). The combined organic layers were washed with brine (50.0 mL), dried over anhydrous $Na_2SO_4$, filtered and concentrated to give a yellow residue. The residue was purified by flash silica gel chromatography (12 g column, ethyl acetate in petroleum ether from 0% to 20%) to give 1-(6-((S)-1-((tert-butoxycarbonyl)amino)-1,3-dihydrospiro[indene-2,4'-piperidin]-1'-yl)-1-(tetrahydro-2H-pyran-2-yl)-1H-pyrazolo[3,4-b]pyrazin-3-yl)-1,2,3,4-tetrahydroquinolin-6-yl sulfofluoridate (250.0 mg, 64% yield) as a yellow solid. LCMS m/z (M+H)$^+$=734.2.

Step d: A solution of 1-(6-((S)-1-((tert-butoxycarbonyl)amino)-1,3-dihydrospiro[indene-2,4'-piperidin]-1'-yl)-1-(tetrahydro-2H-pyran-2-yl)-1H-pyrazolo[3,4-b]pyrazin-3-yl)-1,2,3,4-tetrahydroquinolin-6-yl sulfurofluoridate (230.0 mg, 313.0 μmol) in HCl/MeOH (20.0 mL, 4 M) was stirred at 20° C. for 0.5 hour. The reaction mixture was concentrated under reduced pressure to give a residue, which was diluted with MeOH (5.0 mL) and purified by prep-HPLC (HCl) to give 1-{6-[(3S)-3-amino-1,3-dihydrospiro[indene-2,4'-piperidin]-1'-yl]-1H-pyrazolo[3,4-b]pyrazin-3-yl}-1,2,3,4-tetrahydroquinolin-6-yl sulfurofluoridate hydrochloride (115.2 mg, 623% yield) as an orange solid. LCMS m/z (M+H)$^+$=550.1; $^1$HNMR (400 MHz, CD$_3$OD): 8.30 (s, 1H), 7.52-7.55 (m, 1H), 7.41-7.44 (m, 2H), 7.36-7.39 (m, 1H), 7.17-7.19 (m, 1H), 6.95-7.00 (m, 2H), 4.52-4.56 (m, 1H), 4.40-4.44 (m, 2H), 3.94-3.98 (m, 2H), 3.39-3.52 (m, 2H), 3.19-3.24 (m, 2H), 2.94-2.98 (m, 2H), 2.12-2.16 (m, 2H), 1.81-1.94 (m, 3H), 1.66-1.70 (m, 1H).

Example 211: Synthesis of {3-[(3S)-3-amino-1,3-dihydrospiro[indene-2,4'-piperidin]-1'-yl]-6-(1,2,3,4-tetrahydro-1,5-naphthyridin-1-yl)pyrazin-2-yl}methanol

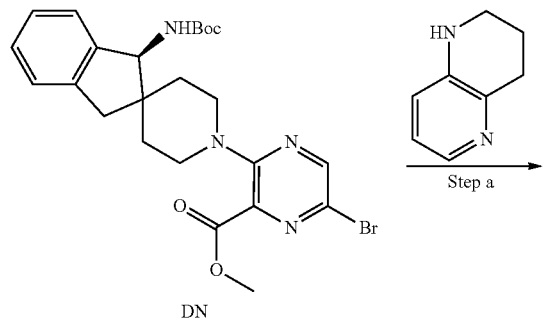

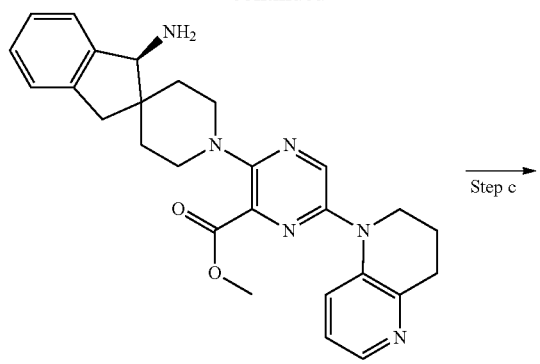

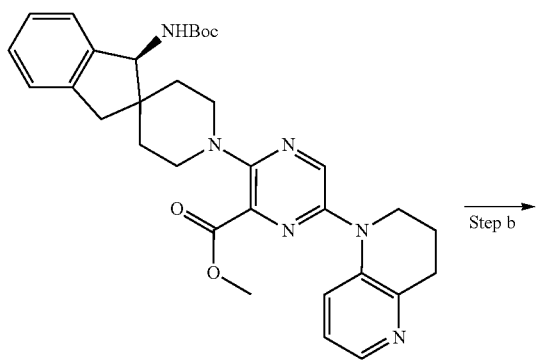

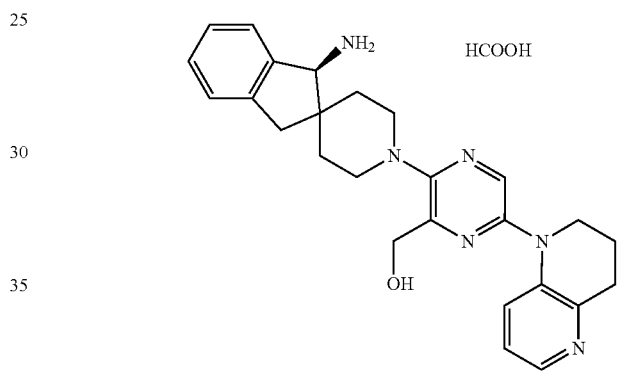

Step c: Methyl 3-[(3S)-3-amino-1,3-dihydrospiro[indene-2,4'-piperidin]-1'-yl]-6-(1,2,3,4-tetrahydro-1,5-naphthyridin-1-yl)pyrazine-2-carboxylate (100 mg, 212 μmol, synthesized via Method 4, using methyl 6-bromo-3-[(3S)-3-{[(tert-butoxy)carbonyl]amino}-1,3-dihydrospiro[indene-2,4'-piperidin]-1'-yl]pyrazine-2-carboxylate, Intermediate DN and 1,2,3,4-tetrahydro-1,5-naphthyridine in the coupling in Step a with Xantphos-Pd-G4 and Cs$_2$CO$_3$ as reactants; and running Step b deprotection at rt for 2 h) and LiBH$_4$ (12.0 mg, 318 μmol) were placed into THF (6 mL) and MeOH (4 mL). The reaction mixture was stirred at 20° C. for 12 hours. The mixture was then concentrated and was purified by prep-HPLC (HCOOH) to afford {3-[(3S)-3-amino-1,3-dihydrospiro[indene-2,4'-piperidin]-1'-yl]-6-(1,2,3,4-tetrahydro-1,5-naphthyridin-1-yl)pyrazin-2-yl}methanol (4.00 mg, 4% yield) as a yellow solid. LC-MS (ESI$^+$) m/z: 443.1 (M+H)$^+$; $^1$HNMR (400 MHz, Methanol-d4) δ 8.68-8.44 (m, 1H), 8.68-8.42 (m, 1H), 8.15 (s, 1H), 8.00 (m, 1H), 7.65 (m, 1H), 7.36-7.26 (m, 3H), 7.19-7.07 (m, 1H), 4.71 (s, 2H), 4.28 (s, 1H), 3.89 (m, 2H), 3.52-3.36 (m, 2H), 3.22-3.08 (m, 4H), 3.05-2.96 (m, 3H), 2.20-2.10 (m, 2H), 2.07-1.92 (m, 2H), 1.74-1.59 (m, 2H).

Example 212: Synthesis of {3-[(3S)-3-amino-1,3-dihydrospiro[indene-2,4'-piperidin]-1'-yl]-6-(1,2,3,4-tetrahydroquinolin-1-yl)pyrazin-2-yl}methanol

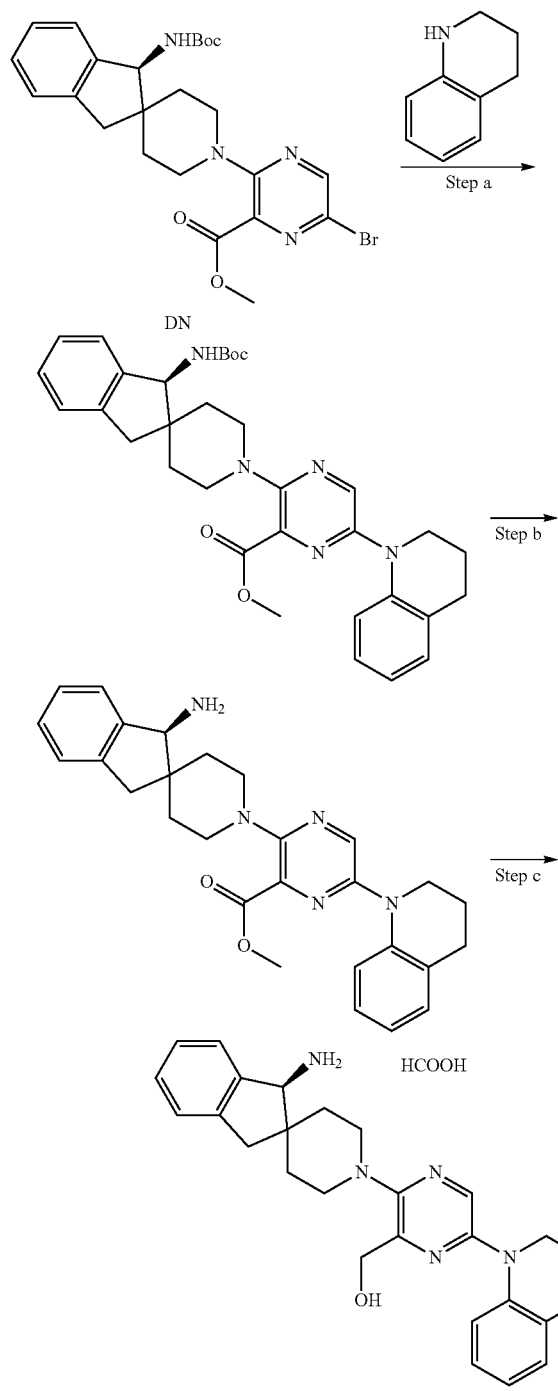

Step c: Methyl-3-[(3S)-3-amino-1,3-dihydrospiro[indene-2,4'-piperidin]-1'-yl]-6-(1,2,3,4-tetrahydroquinolin-1-yl)pyrazine-2-carboxylate (30 mg, 63.8 μmol, synthesized via Method 4, using methyl-6-bromo-3-[(3S)-3-{[(tert-butoxy)carbonyl]amino}-1,3-dihydrospiro[indene-2,4'-piperidin]-1'-yl]pyrazine-2-carboxylate, Intermediate DN and 1,2,3,4-tetrahydroquinoline in the coupling in Step a with Xantphos-Pd-G4 and Cs$_2$CO$_3$ as reactants; and running Step b deprotection at rt for 0.5 h) and LiBH$_4$ (2.79 mg, 127 μmol) were placed into THF (5 mL). The reaction mixture was stirred at 30° C. for 2 hours. The mixture was then concentrated and was purified by prep-HPLC (HCOOH) to afford {3-[(3S)-3-amino-1,3-dihydrospiro[indene-2,4'-piperidin]-1'-yl]-6-(1,2,3,4-tetrahydroquinolin-1-yl)pyrazin-2-yl}methanol (5.30 mg, HCOOH salt, 17% yield) as a yellow solid. LC-MS (ESI$^+$) m/z: 442.1 (M+H)$^+$; $^1$HNMR (400 MHz, Methanol-d4) δ=8.56 (s, 1H), 8.14 (s, 1H), 7.46 (m, 1H), 7.37-7.25 (m, 3H), 7.24-7.13 (m, 2H), 7.12-7.04 (m, 1H), 6.99-6.89 (m, 1H), 4.71 (s, 2H), 4.23 (s, 1H), 3.96-3.86 (m, 2H), 3.30-3.20 (m, 2H), 3.20-3.05 (m, 3H), 3.04-2.91 (m, 1H), 2.83 (m, 2H), 2.08-1.91 (m, 4H), 1.64 (m, 2H).

Example 213: Synthesis of (S)-(3-(1-amino-1,3-dihydrospiro[indene-2,4'-piperidin]-1'-yl)-6-(indolin-1-yl)pyrazin-2-yl) methanol

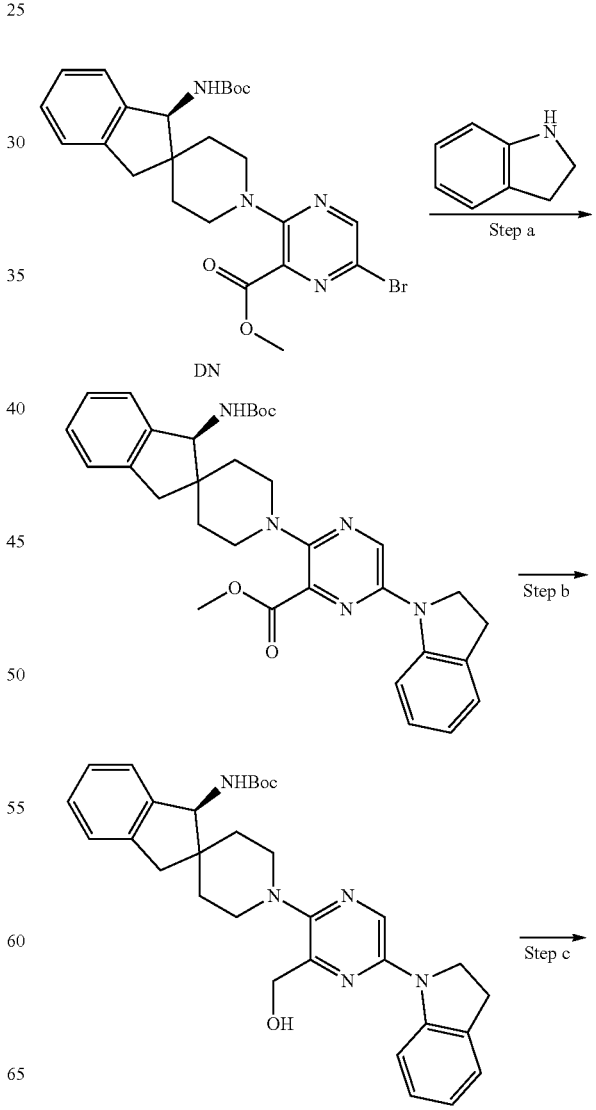

459

-continued

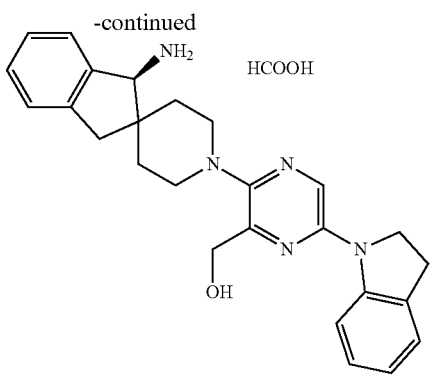

Step b: To a solution of methyl 3-[(3S)-3-{[(tert-butoxy)carbonyl]amino}-1,3-dihydrospiro[indene-2,4'-piperidin]-1'-yl]-6-(2,3-dihydro-1H-indol-1-yl)pyrazine-2-carboxylate (178 mg, 320 µmol, synthesized via Method 4, coupling methyl 6-bromo-3-[(3S)-3-{[(tert-butoxy)carbonyl]amino}-1,3-dihydrospiro[indene-2,4'-piperidin]-1'-yl]pyrazine-2-carboxylate, Intermediate DN, with indoline in Step a using XantPhos-Pd-G4 and Cs$_2$CO$_3$ in PhMe at 100° C. for 12 h) in THF (10 mL) was added DIBAL-H (480 µL, 480 µmol, 1M in toluene) at 0° C. under N$_2$. The solution was stirred for another 2 hours at the same temperature. Then to the reaction mixture was added EtOAc (20 mL) and 10% AcOH (50 mL) slowly, then the solution was extracted with EtOAc (50 mL×3). The combined organic layers were washed with aq. NaHCO$_3$ followed by brine (50 mL×3), dried over anhydrous Na$_2$SO$_4$, filtered and concentrated to give a residue. The residue was purified by flash silica gel chromatography (ethyl acetate/petroleum ether=0/100 to 30/100) to afford tert-butyl N-[(3)-1'-[5-(2,3-dihydro-1H-indol-1-yl)-3-(hydroxymethyl)pyrazin-2-yl]-1,3-dihydrospiro[indene-2,4'-piperidin]-3-yl]carbamate (64.0 mg, 38% yield) as a yellow oil. LC-MS (ESI$^+$) m/z: 528.1 (M+H)$^+$.

Step c: Tert-butyl N-[(3S)-1'-[5-(2,3-dihydro-1H-indol-1-yl)-3-(hydroxymethyl)pyrazin-2-yl]-1,3-dihydrospiro[indene-2,4'-piperidin]-3-yl]carbamate (50.0 mg, 94.7 µmol) was dissolved in EtOAc (1.00 mL). HCl/EtOAc (1.00 mL, 4 N) was then added and the mixture was stirred at 10° C. for 2 h. The reaction mixture was concentrated under reduced pressure. The residue was dissolved with MeOH (5.0 mL) and adjusted to pH=7-8 with solid Na$_2$CO$_3$ and purified by prep-HPLC (HCOOH). (S)-(3-(1-amino-1,3-dihydrospiro[indene-2,4'-piperidin]-1'-yl)-6-(indolin-1-yl)pyrazin-2-yl) methanol formate (31.4 mg, 70% yield) was obtained as a yellow solid. LC-MS (ESI$^+$) m/z: 428.1 (M+H)$^+$; $^1$HNMR (400 MHz, Methanol-d4) δ 8.55 (s, 1H), 8.26 (m, 1H), 7.92 (s, 1H), 7.52 (m, 1H), 7.43-7.28 (m, 3H), 7.25-7.05 (m, 2H), 6.95-6.82 (m, 1H), 4.85-4.73 (m, 2H), 4.39 (s, 1H), 4.10 (m, 2H), 3.31-3.19 (m, 4H), 3.18-3.06 (m, 4H), 2.12-1.81 (m, 2H), 1.80-1.53 (m, 2H).

460

Example 214: Synthesis of (S)-(3-(1-amino-1,3-dihydrospiro[indene-2,4'-piperidin]-1'-yl)-6-(2,3,4,5-tetrahydro-1H-benzo[b]azepin-1-yl)pyrazin-2-yl) methanol

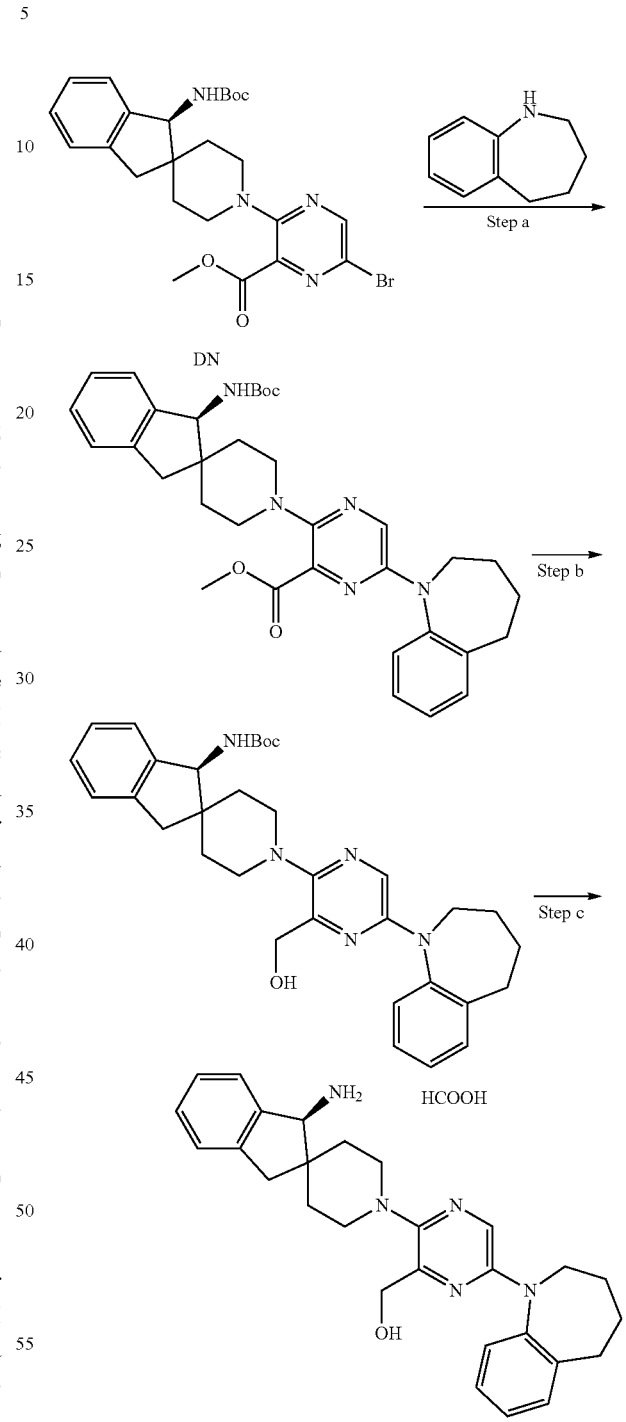

Step a: A solution of methyl 6-bromo-3-[(3S)-3-{[(tert-butoxy)carbonyl]amino}-1,3-dihydrospiro[indene-2,4'-piperidin]-1'-yl]pyrazine-2-carboxylate (800.0 mg, 1.5 mmol), Xantphos-Pd-G4 (147.0 mg, 154 µmol, Intermediate DN), Cs$_2$CO$_3$ (1.00 g, 3.08 mmol) and 2,3,4,5-tetrahydro-1H-benzo[b]azepine (226.0 mg, 1.5 mmol, CAS #1701-57-1) in toluene (25.00 mL) was stirred at 100° C. for 12 hours under N$_2$. The mixture was concentrated and purified by flash silica gel chromatography (petroleum ether:EtOAc=100:0 to 100:20) to afford methyl 3-[(3S)-3-{[(tert-butoxy)carbonyl]amino}-1,3-dihydrospiro[indene-2,4'-piperidin]-1'-yl]-6-(2,3,4,5-tetrahydro-1H-1-benzazepin-1-yl)pyrazine-2-carboxylate (267.0 mg, 30% yield) as a green oil. LC-MS (ESI⁺) m/z: 584.3 (M+H)⁺.

Step b: To a solution of methyl 3-[(3S)-3-{[(tert-butoxy)carbonyl]amino}-1,3-dihydrospiro[indene-2,4'-piperidin]-1'-yl]-6-(2,3,4,5-tetrahydro-1H-1-benzazepin-1-yl)pyrazine-2-carboxylate (265.0 mg, 453 μmol) in THF (10.00 mL) was added DIBAL-H (679 μL, 679 μmol, 1M in toluene) at 0° C. under N₂. The solution was stirred for another 2 hours at the same temperature. To the reaction mixture was added EtOAc (20 mL) and 10% AcOH (50 mL) slowly, then the solution was extracted with EtOAc (50 mL×3). The combined organic layers were washed with aq. NaHCO₃ (50 mL), followed by brine (50 mL×3), dried over anhydrous Na₂SO₄, filtered and concentrated to give a residue. The residue was purified by flash silica gel chromatography (ethyl acetate/petroleum ether=0/100 to 20/100) to afford tert-butyl N-[(3S)-1'-[3-(hydroxymethyl)-5-(2,3,4,5-tetrahydro-1H-1-benzazepin-1-yl)pyrazin-2-yl]-1,3-dihydrospiro[indene-2,4'-piperidin]-3-yl]carbamate (166.0 mg, 66% yield) as a yellow oil. LC-MS (ESI⁺) m/z: 556.2 (M+H)⁺.

Step c: Tert-butyl N-[(3S)-1'-[3-(hydroxymethyl)-5-(2,3,4,5-tetrahydro-1H-1-benzazepin-1-yl)pyrazin-2-yl]-1,3-dihydrospiro[indene-2,4'-piperidin]-3-yl]carbamate (90.0 mg, 161 μmol) was added into HCl/EtOAc (8.00 mL, 4M). The mixture was stirred at 10° C. for 2 hours. The residue was then dissolved with MeOH (5.00 mL) and adjusted to pH=7-8 with solid Na₂CO₃ and purified by prep-HPLC (HCOOH). (S)-(3-(1-amino-1,3-dihydrospiro[indene-2,4'-piperidin]-1'-yl)-6-(2,3,4,5-tetrahydro-1H-benzo[b]azepin-1-yl)pyrazin-2-yl)methanol formate salt (15.4 mg, 19% yield) was obtained as a yellow solid. LC-MS (ESI⁺) m/z: 456.1 (M+H)⁺; ¹H NMR (400 MHz, Methanol-d4) δ=8.56 (s, 1H), 7.47 (m, 1H), 7.41-7.37 (m, 1H), 7.37-7.22 (m, 7H), 4.73 (s, 2H), 4.26 (s, 1H), 4.10-3.67 (m, 2H), 3.18-2.93 (m, 6H), 2.78-2.64 (m, 2H), 2.03-1.82 (m, 4H), 1.81-1.56 (m, 4H).

Method 5, Examples 66 and 67: Synthesis of (3R)-1'-[3-(2-chloro-3-fluoropyridin-4-yl)-1H-pyrazolo[3,4-b]pyrazin-6-yl]-1,3-dihydrospiro[indene-2,4'-piperidin]-3-amine and (3S)-1'-[3-(2-chloro-3-fluoropyridin-4-yl)-1H-pyrazolo[3,4-b]pyrazin-6-yl]-1,3-dihydrospiro[indene-2,4'-piperidin]-3-amine

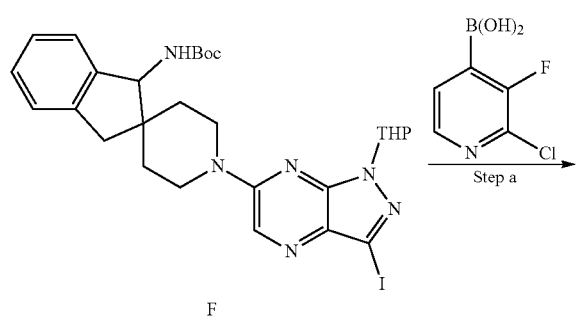

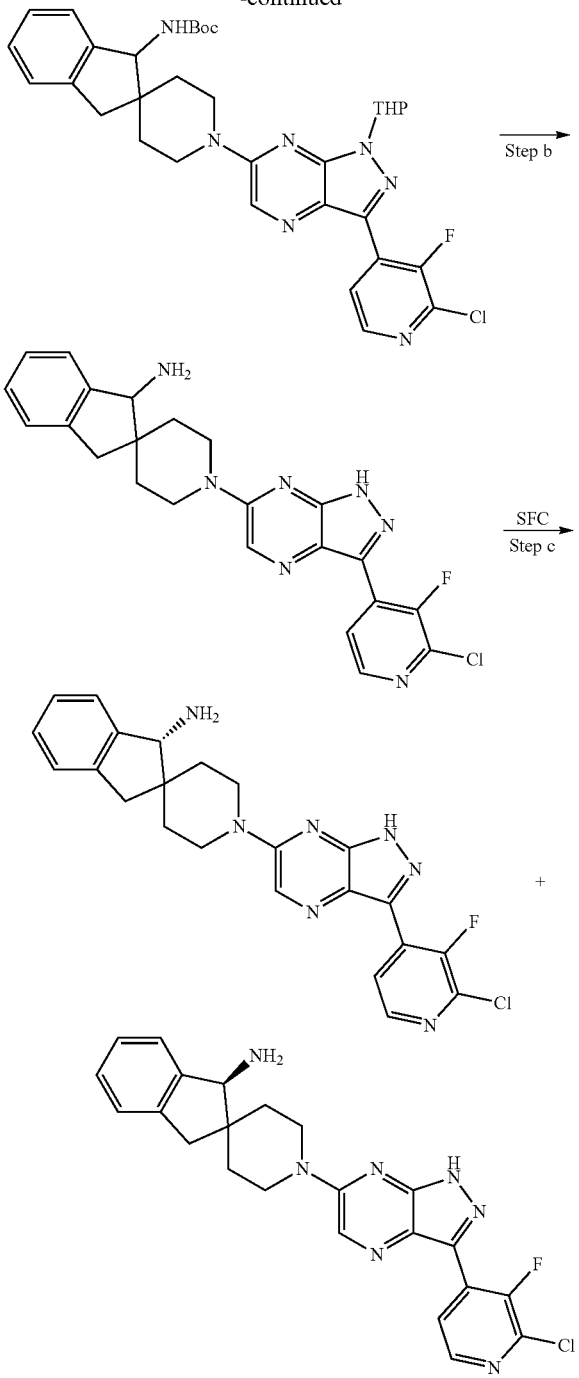

Step a: To a solution of (2-chloro-3-fluoropyridin-4-yl)boronic acid (99.9 mg, 570.0 μmol) tert-butyl N-{1'-[3-iodo-1-(oxan-2-yl)-1H-pyrazolo[3,4-b]pyrazin-6-yl]-1,3-dihydrospiro[indene-2,4'-piperidin]-3-yl}carbamate (300.0 mg, 475.0 μmol, Intermediate F) in dioxane (10.0 mL) and H₂O (1.0 mL) was added Pd(dppf)Cl₂ (34.7 mg, 47.5 μmol) and Cs₂CO₃ (462.0 mg, 1.4 mmol), and the resulting mixture was stirred at 100° C. for 12 hours under N₂. The reaction mixture was then concentrated, diluted with EtOAc (100.0 mL), and washed with H₂O (50.0 mL×2) and brine (50.0 mL). The organic phase was dried over anhydrous Na₂SO₄, filtered and concentrated under reduced pressure to give a residue, which was purified by flash silica gel chromatography (ethyl acetate in petroleum ether=0~30%) to afford tert-butyl (1'-(3-(2-chloro-3-fluoropyridin-4-yl)-1-(tetrahydro-2H-pyran-2-yl)-1H-pyrazolo[3,4-b]pyrazin-6-yl)-1,3-dihydrospiro[indene-2,4'-piperidin]-1-yl)carbamate (135.0 mg, 45% yield) as a yellow solid. LCMS m/z (M+H)$^+$=634.2.

Step b: Tert-butyl N-{1'-[3-(2-chloro-3-fluoropyridin-4-yl)-1-(oxan-2-yl)-1H-pyrazolo[3,4-b]pyrazin-6-yl]-1,3-dihydrospiro[indene-2,4'-piperidin]-3-yl}carbamate (100.0 mg, 0.158 mmol) was dissolved in HCl/MeOH (5.0 mL, 4N) and stirred at 20° C. for 12 hours. The mixture was then concentrated under reduced pressure to give a residue, which was diluted with MeOH (10.0 mL) and adjusted pH=8~9 with solid K$_2$CO$_3$. The mixture was filtered and concentrated under reduced pressure to give a residue, which was purified by flash silica gel chromatography (MeOH in DCM=0~8%) to afford 1'-[3-(2-chloro-3-fluoropyridin-4-yl)-1H-pyrazolo[3,4-b]pyrazin-6-yl]-1,3-dihydrospiro[indene-2,4'-piperidin]-3-amine hydrochloride (40.0 mg, 56% yield) as a yellow solid. LCMS m/z (M+H)$^+$=430.0.

Step c: 1'-[3-(2-chloro-3-fluoropyridin-4-yl)-1H-pyrazolo[3,4-b]pyrazin-6-yl]-1,3-dihydrospiro[indene-2,4'-piperidin]-3-amine (40.0 mg, 88.9 μmol) was separated by preparative chiral SFC (Column: DAICEL CHIRALPAK IC (250 mm×30 mm, 5 um). Condition: 0.1% NH$_3$.H$_2$O EtOH. Begin: 50%, end: 50%. Flow rate: 50 mL/min.) to afford (3R)-1'-[3-(2-chloro-3-fluoropyridin-4-yl)-1H-pyrazolo[3,4-b]pyrazin-6-yl]-1,3-dihydrospiro[indene-2,4'-piperidin]-3-amine (5.70 mg, 12.6 μmol, the faster eluting isomer, Rt=4.410 min, 14% yield, e.e. =100.0%) as a white solid and (3S)-1'-[3-(2-chloro-3-fluoropyridin-4-yl)-1H-pyrazolo[3,4-b]pyrazin-6-yl]-1,3-dihydrospiro[indene-2,4'-piperidin]-3-amine (5.20 mg, 11.5 μmol, the slower eluting isomer, Rt=4.957 min, 13% yield, e.e. =96.7%) as a white solid. Absolute stereochemistry of the enantiomers was arbitrarily assigned. Characterization data for (3R)-1'-[3-(2-chloro-3-fluoropyridin-4-yl)-1H-pyrazolo[3,4-b]pyrazin-6-yl]-1,3-dihydrospiro[indene-2,4'-piperidin]-3-amine: LCMS m/z (M+H)$^+$=450.1; $^1$HNMR (400 MHz, DMSO-d6): 8.52-8.60 (m, 1H), 8.32-8.43 (m, 2H), 7.27-7.33 (m, 1H), 7.10-7.23 (m, 1H), 4.28-4.44 (m, 1H), 3.85 (s, 1H), 3.21-3.27 (m, 2H), 3.10 (d, J=15.6 Hz, 1H), 2.65 (d, J=15.6 Hz, 1H), 1.77-1.87 (m, 1H), 1.64-1.76 (m, 1H), 1.50-1.61 (m, 1H), 1.09-1.19 (m, 1H). SFC: e.e. =100%, Characterization data for (3S)-1'-[3-(2-chloro-3-fluoropyridin-4-yl)-1H-pyrazolo[3,4-b]pyrazin-6-yl]-1,3-dihydrospiro[indene-2,4'-piperidin]-3-amine: LCMS m/z (M+H)$^+$=450.1; $^1$HNMR (400 MHz, DMSO-d6): 8.55-8.59 (m, 1H), 8.34-8.42 (m, 2H), 7.25-7.33 (m, 1H), 7.12-7.24 (m, 1H), 4.28-4.45 (m, 1H), 3.85 (s, 1H), 3.20-3.28 (m, 2H), 3.10 (d, J=15.6 Hz, 1H), 2.65 (d, J=15.6 Hz, 1H), 1.77-1.89 (m, 1H), 1.65-1.76 (m, 1H), 1.50-1.61 (m, 1H), 1.09-1.19 (m, 1H). SFC: e.e. =96.7%.

Method 5 Table: Compounds Synthesized via Method 5, with the Cross-Coupling of tert-butyl (1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (Intermediate F) with various Boronic Acids in Step a

| Example #$^a$ | Step a Boronic Acid | LCMS m/z (M + H)$^+$ | $^1$H NMR (400 MHz, CD3OD) δ ppm |
|---|---|---|---|
| 68 | (quinolin-5-yl)-boronic acid | 448.2 | (CDCl3) 12.46 (br, 1H), 9.12 (d, J = 8.4 Hz, 1H), 8.88-8.85 (m, 1H), 8.25-8.18 (m, 2H), 8.07 (d, J = 8.4 Hz, 1H), 7.79-7.74 (m, 1H), 7.39-7.36 (m, 1H), 7.29-7.27 (m, 1H), 7.17-7.15 (m, 3H), 4.31-4.26 (m, 2H), 3.95 (s, 1H), 3.33-3.23 (m, 2H), 3.07 (d, J = 17.6 Hz, 1H), 2.73-2.68 (m, 1H), 1.90-1.73 (m, 2H), 1.62-1.58 (m, 1H), 1.39-1.35 (m, 1H). |
| 69 | (quinolin-5-yl)-boronic acid | 448.2 | (DMSO) 9.23 (d, J = 8.0 Hz, 1H), 8.98-8.95 (m, 1H), 8.53 (s, 1H), 8.37 (d, J = 6.4 Hz, 1H), 8.10 (d, J = 8.0 Hz, 1H), 7.93-7.89 (m, 1H), 7.61-7.58 (m, 1H), 7.32-7.31 (m, 1H), 7.22-7.14 (m, 3H), 4.42-4.35 (m, 2H), 3.86 (s, 1H), 3.30-3.26 (m, 2H), 3.13 (d, J = 15.6 Hz, 1H), 2.66 (m, J = 15.2 Hz, 1H), 1.90-1.69 (m, 1H), 1.60-1.56 (m, 1H), 1.17-1.14 (m, 1H). |
| 70 | (2,3-dichloro-pyridin-4-yl)-boronic acid (CAS# 951677-39-7) | 466.1 | 8.47-8.42 (m, 2H), 7.84 (d, J = 4.8 Hz, 1H), 7.54 (d, J = 7.6 Hz, 1H), 7.44-7.34 (m, 3H), 4.60-4.38 (m, 3H), 3.53-3.41 (m, 2H), 3.24 (s, 2H), 1.98-1.68 (m, 4H). |
| 71 | (2,3-dichloro-pyridin-4-yl)-boronic acid (CAS# 951677-39-7) | 66.1 | 8.48-8.43 (m, 2H), 7.84 (d, J = 4.4 Hz, 1H), 7.56 (d, J = 7.2 Hz, 1H), 7.45-7.34 (m, 3H), 4.59-4.43 (m, 3H), 3.52-3.41 (m, 2H), 3.25 (d, J = 6.0 Hz, 2H), 2.01-1.67 (m, 4H. |
| 72 | 6-fluoro-5-(4,4,5,5-tetramethyl-1,3,2-dioxaborolan-2-yl)-1H-indole (CAS# 1207623-96-8) | 454.2 | 8.63 (s, 1H), 8.51 (d, J = 7.2 Hz, 1H), 7.54 (d, J = 7.6 Hz, 1H), 7.47-7.34 (m, 5H), 6.62-6.61 (m, 1H), 4.67-4.51 (m, 2H), 4.46 (s, 1H), 3.60-3.49 (m, 2H), 3.26 (s, 2H), 2.02-1.71 (m, 4H). |
| 73 | 6-fluoro-5-(4,4,5,5-tetramethyl-1,3,2-dioxaborolan-2-yl)-1H-indole (CAS# 1207623-96-8) | 454.2 | 8.62 (s, 1H), 8.51 (d, J = 6.8 Hz, 1H), 7.54 (d, J = 7.2 Hz, 1H), 7.47-7.34 (m, 5H), 6.62-6.61 (m, 1H), 4.66-4.46 (m, 3H), 3.60-3.49 (m, 2H), 3.26 (s, 2H), 2.01-1.71 (m, 4H). |

| Example #[a] | Step a Boronic Acid | LCMS m/z (M + H)+ | 1H NMR (400 MHz, CD3OD) δ ppm |
| --- | --- | --- | --- |
| 74 | (3-fluro-pyridin-4-yl)-boronic acid (CAS# 458532-97-3) | 416.1 | 9.15-9.19 (m, 1H), 9.04-9.06 (m, 1H), 8.77-8.79 (m, 1H), 8.59 (s, 1H), 7.53-7.56 (m, 1H), 7.41-7.47 (m, 2H), 7.35-7.39 (m, 1H), 4.58-4.62 (m, 1H), 4.46-4.55 (m, 1H), 4.45 (s, 1H), 3.43-3.54 (m, 2H), 3.25 (s, 2H), 1.82-2.00 (m, 3H), 1.69-1.73 (m, 1H), |
| 75 | (3-fluro-pyridin-4-yl)-boronic acid (CAS# 458532-97-3) | 416.1 | 9.35-9.55 (m, 1H), 9.07-9.08 (m, 1H), 8.79-8.80 (m, 1H), 8.59 (s, 1H), 7.53-7.56 (m, 1H), 7.42-7.46 (m, 2H), 7.34-7.39 (m, 1H), 4.58-4.62 (m, 1H), 4.46-4.55 (m, 1H), 4.45 (s, 1H), 3.43-3.54 (m, 2H), 3.25 (s, 2H), 1.83-2.00 (m, 3H), 1.68-1.72 (m, 1H). |
| 76 | (2,3-dichloro-phenyl) boronic acid | 481.0 | 8.53-8.64 (m, 5H), 7.50-7.51 (m, 1H), 7.36-7.48 (m, 6H), 4.61-4.71 (m, 2H), 4.42-4.44 (m, 1H), 3.49-3.80 (m, 1H), 3.41 (s, 4H), 3.04-3.09 (m, 1H), 1.90-1.95 (m, 2H), 1.69-1.73 (m, 2H). |

[a] Other Suzuki coupling conditions could be utilized such as Pd₂(dba)₃, XPhos (30.2 mg, 63.4 μmol) and K₃PO₄. Step b run anywhere from 1-12 hr at rt. Absolute stereochemistry of the enantiomers was arbitrarily assigned.
[b] tert-butyl (S)-(1'-(7-bromothieno[3,2-d]pyrimidin-4-yl)-1,3-dihydrospiro[indene-2,4'-piperidin]-1-yl)carbamate (Intermediate CW) was used in place of Intermediate F for the cross coupling. The compound was chiral, no Step c was required.

Compounds Synthesized in Similar Fashion to Method 5:

Examples 77 & 78: Synthesis of (R)-1'-(3-(2-amino-3-fluoropyridin-4-yl)-1H-pyrazolo[3,4-b]pyrazin-6-yl)-1,3-dihydrospiro[indene-2,4'-piperidin]-1-amine (S)-1'-(3-(2-amino-3-fluoropyridin-4-yl)-1H-pyrazolo[3,4-b]pyrazin-6-yl)-1,3-dihydrospiro[indene-2,4'-piperidin]-1-amine

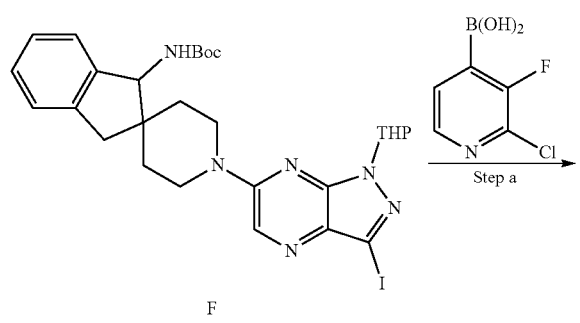

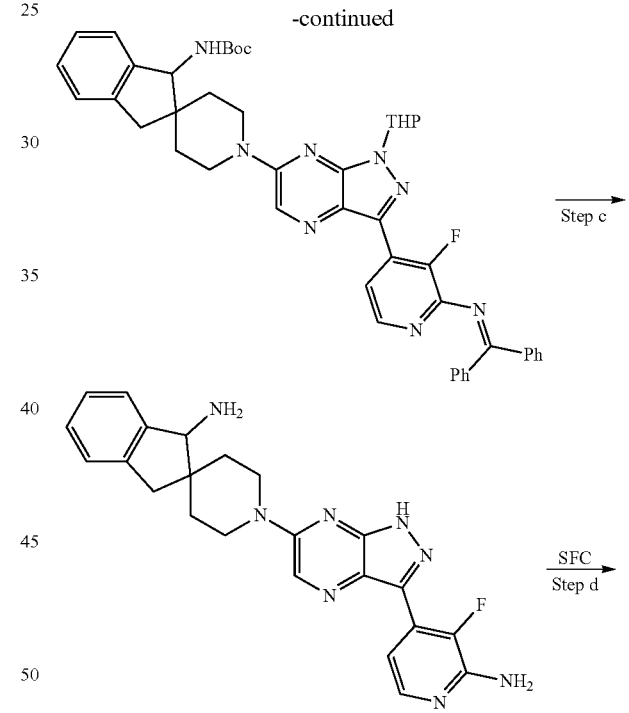

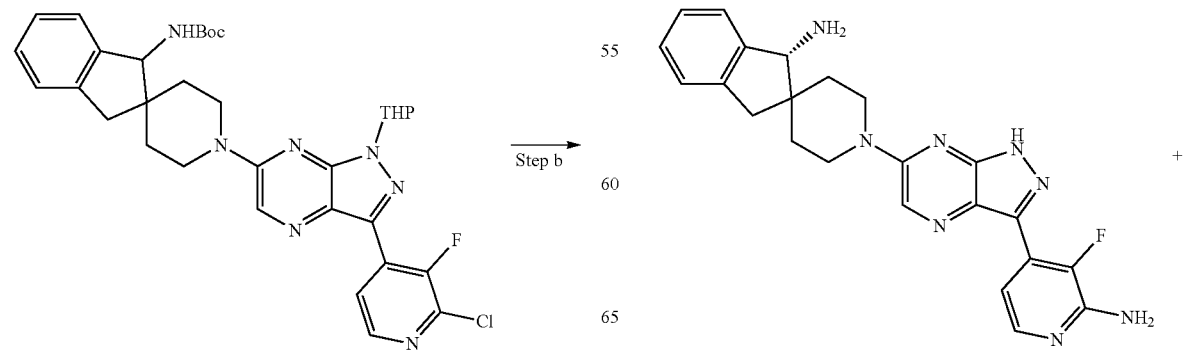

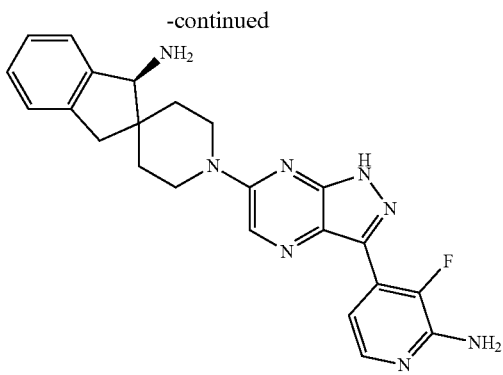

Step a: A mixture of tert-butyl N-{1'-[3-iodo-1-(oxan-2-yl)-1H-pyrazolo[3,4-b]pyrazin-6-yl]-1,3-dihydrospiro[indene-2,4'-piperidin]-3-yl}carbamate (200.0 mg, 317.0 μmol, Intermediate F), (3-chloro-2-fluorophenyl)boronic acid (82.8 mg, 475.0 μmol), Pd(dppf)Cl$_2$ (34.7 mg, 47.5 μmol) and Na$_2$CO$_3$ (67.2 mg, 634.0 μmol) in dioxane (10.0 mL) and H$_2$O (2.0 mL) was stirred at 100° C. for 12 hours. The mixture was concentrated, extracted with EtOAc (50.0 mL×3) and washed with brine (50.0 mL). The organic phase was dried over anhydrous Na$_2$SO$_4$, filtered and concentrated under reduced pressure to give a residue, which was purified by flash silica gel chromatography (ethyl acetate in petroleum ether=0~15%) to afford tert-butyl N-{1'-[3-(2-chloro-3-fluoropyridin-4-yl)-1-(oxan-2-yl)-1H-pyrazolo[3,4-b]pyrazin-6-yl]-1,3-dihydrospiro[indene-2,4'-piperidin]-3-yl}carbamate (70.0 mg, 35% yield) as a yellow solid. LCMS m/z (M+Na)+=656.2.

Step b: The mixture of tert-butyl N-{1'-[3-(2-chloro-3-fluoropyridin-4-yl)-1-(oxan-2-yl)-1H-pyrazolo[3,4-b]pyrazin-6-yl]-1,3-dihydrospiro[indene-2,4'-piperidin]-3-yl}carbamate (130.0 mg, 204.0 μmol), Pd$_2$(dba)$_3$ (18.6 mg, 20.4 μmol), diphenylmethanimine (55.4 mg, 306.0 μmol), Cs$_2$CO$_3$ (199.0 mg, 612.0 μmol) and BINAP (25.4 mg, 40.8 μmol) in toluene (5.0 mL) was evacuated and refilled 3 times using N$_2$, the reaction mixture was stirred at 100° C. for 12 hours. The combined mixture was concentrated, extracted with EtOAc (50.0 mL×2) and washed with brine (50.0 mL). The organic phase was dried over anhydrous Na$_2$SO$_4$, filtered and concentrated under reduced pressure to give a residue, which was purified by flash silica gel chromatography (ethyl acetate in petroleum ether=0~35%) to afford tert-butyl N-[1'-(3-{2-[(diphenylmethylidene)amino]-3-fluoropyridin-4-yl}-1-(oxan-2-yl)-1H-pyrazolo[3,4-b]pyrazin-6-yl)-1,3-dihydrospiro[indene-2,4'-piperidin]-3-yl]carbamate (120.0 mg, 62% yield) as a yellow solid. LCMS m/z (M+H)+=779.4.

Step c: To a solution of tert-butyl (1'-(3-(2-(((diphenylmethylene)amino)-3-fluoropyridin-4-yl)-1-(tetrahydro-2H-pyran-2-yl)-1H-pyrazolo[3,4-b]pyrazin-6-yl)-1,3-dihydrospiro[indene-2,4'-piperidin]-1-yl)carbamate (120.0 mg, 154.0 μmol) in MeOH (2.0 mL) was added HCl/MeOH (2.0 mL, 4N) and the mixture was stirred at 20° C. for 12 hours. The mixture was concentrated to give a residue, which was washed with DCM/petroleum ether (1/2, 5.0 mL×3). The solid was dried under vacuum to give 1'-(3-(2-amino-3-fluoropyridin-4-yl)-1H-pyrazolo[3,4-b]pyrazin-6-yl)-1,3-dihydrospiro[indene-2,4'-piperidin]-1-amine (70.0 mg, quant. crude yield) as a yellow solid. LCMS m/z (M+H)+= 431.1.

Step d: 1'-[3-(2-amino-3-fluoropyridin-4-yl)-1H-pyrazolo[3,4-b]pyrazin-6-yl]-1,3-dihydrospiro[indene-2,4'-piperidin]-3-amine (70.0 mg, 162.0 μmol) was separated by preparative SFC (column: DAICEL CHIRALPAK AS-H (250 mm*30 mm, 5 um), Mobile phase: 0.1% NH$_3$.H$_2$O EtOH (Begin B: 55%, End B: 55%), Flow rate: 50 mL/min) to afford (R)-1'-(3-(2-amino-3-fluoropyridin-4-yl)-1H-pyrazolo[3,4-b]pyrazin-6-yl)-1,3-dihydrospiro[indene-2,4'-piperidin]-1-amine (16.6 mg, Rt=4.631 min, the faster eluting isomer) as a white solid and (S)-1'-(3-(2-amino-3-fluoropyridin-4-yl)-1H-pyrazolo[3,4-b]pyrazin-6-yl)-1,3-dihydrospiro[indene-2,4'-piperidin]-1-amine (13.8 mg, Rt=5.070 min, the slower eluting isomer) as a white solid. Characterization of (R)-1'-(3-(2-amino-3-fluoropyridin-4-yl)-1H-pyrazolo[3,4-b]pyrazin-6-yl)-1,3-dihydrospiro[indene-2,4'-piperidin]-1-amine: LCMS m/z (M+H)+=431.1; $^1$HNMR (400 MHz, Methanol-d4): 8.38 (s, 1H), 7.81 (d, J=5.2 Hz, 1H), 7.33-7.41 (m, 2H), 7.16-7.26 (m, 3H), 4.34-4.49 (m, 2H), 3.95 (s, 1H), 3.33-3.45 (m, 2H), 3.17 (d, J=15.6 Hz, 1H), 2.81 (d, J=15.6 Hz, 1H), 1.74-1.96 (m, 2H), 1.57-1.70 (m, 1H), 1.41-1.51 (m, 1H). SFC: e.e. =98.7%. Characterization of (S)-1'-(3-(2-amino-3-fluoropyridin-4-yl)-1H-pyrazolo[3,4-b]pyrazin-6-yl)-1,3-dihydrospiro[indene-2,4'-piperidin]-1-amine: LCMS m/z (M+H)+=431.1; $^1$HNMR (400 MHz, Methanol-d4): 8.52 (s, 1H), 7.96 (t, J=6.2 Hz, 1H), 7.80 (d, J=6.4 Hz, 1H), 7.53 (d, J=7.2 Hz, 1H), 7.38-7.45 (m, 2H), 7.31-7.38 (m, 1H), 4.52-4.62 (m, 1H), 4.39-4.50 (m, 2H), 3.37-3.55 (m, 2H), 3.23 (s, 2H), 1.90-2.01 (m, 1H), 1.76-1.89 (m, 2H), 1.63-1.74 (m, 1H). SFC: e.e. =97.2%, Column: Chiralpak AS-H 150*4.6 mm I.D., 5 um, Mobile phase: A: CO$_2$ B: ethanol (0.05% DEA), Gradient: hold 5% for 0.5 min, then from 5% to 40% of B in 3.5 min and hold 40% for 2.5 min, then 5% of B for 1.5 min, Flow rate: 3 mL/min, Column temperature: 40° C.

Example 79: Synthesis of (3S)-1'-[3-(2-amino-3-chloropyridin-4-yl)-1H-pyrazolo[3,4-b]pyrazin-6-yl]-1,3-dihydrospiro[indene-2,4'-piperidin]-3-amine

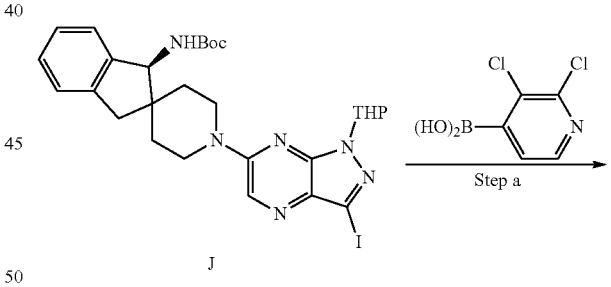

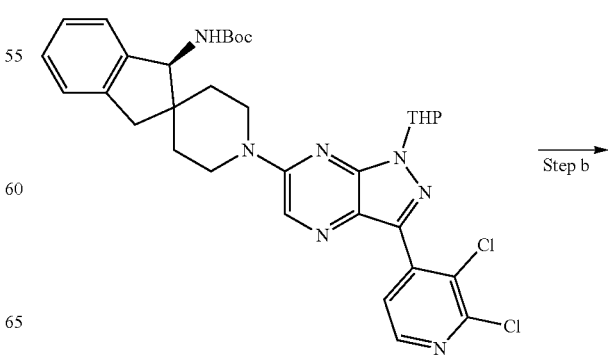

-continued

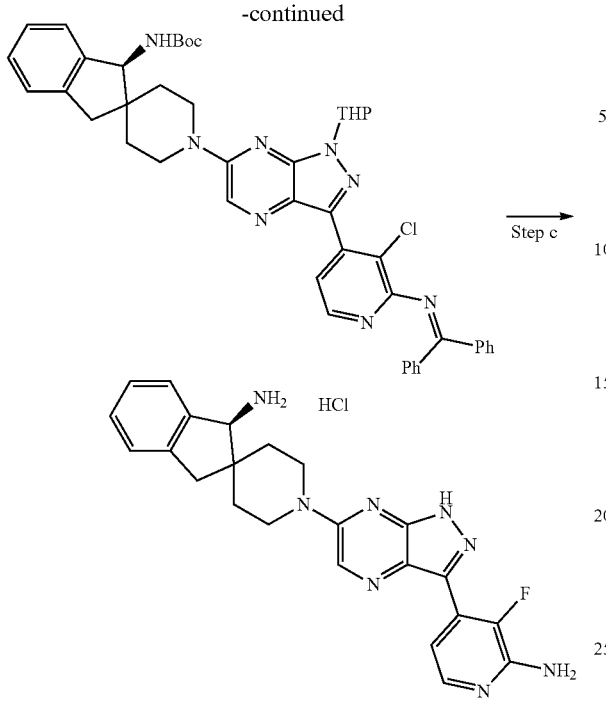

(3S)-1'-[3-(2-amino-3-chloropyridin-4-yl)-1H-pyrazolo[3,4-b]pyrazin-6-yl]-1,3-dihydrospiro[indene-2,4'-piperidin]-3-amine hydrochloride was synthesized as described above for Example 77, coupling tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (Intermediate J) and (2,3-dichloropyridin-4-yl)boronic acid in Step a. No chiral separation was required as the amine was chiral. (3S)-1'-[3-(2-amino-3-chloropyridin-4-yl)-1H-pyrazolo[3,4-b]pyrazin-6-yl]-1,3-dihydrospiro[indene-2,4'-piperidin]-3-amine hydrochloride (29.3 mg, 54% yield) was isolated as a yellow solid. LCMS m/z (M+H)⁺=447.1; ¹HNMR (400 MHz, Methanol-d4): δ 8.50 (s, 1H), 7.99 (d, J=6.8 Hz, 1H), 7.63 (d, J=6.8 Hz, 1H), 7.54 (d, J=7.2 Hz, 1H), 7.46-7.34 (m, 3H), 4.60-4.44 (m, 3H), 3.54-3.41 (m, 2H), 3.24 (s, 2H), 2.04-1.68 (m, 4H). SFC: e.e. =94.0%, $R_t$=5.008 min, Column: Chiralpak AS-H 150×4.6 mm I.D., 5 um Mobile phase: A: CO₂ B: ethanol (0.1% ethanolamine) Gradient: hold 5% for 0.5 min, then from 5% to 40% of B in 3.5 min and hold 40% for 2.5 min, then 5% of B for 1.5 min, Flow rate: 3 mL/min Column temp: 40° C.

Method 6, Examples 80 & 81: Synthesis of (R)-1'-(5-((2-amino-3-chloropyridin-4-yl)thio)pyrazin-2-yl)-1,3-dihydrospiro[indene-2,4'-piperidin]-1-amine and (S)-1'-(5-((2-amino-3-chloropyridin-4-yl)thio)pyrazin-2-yl)-1,3-dihydrospiro[indene-2,4'-piperidin]-1-amine

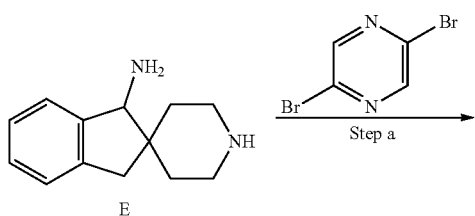

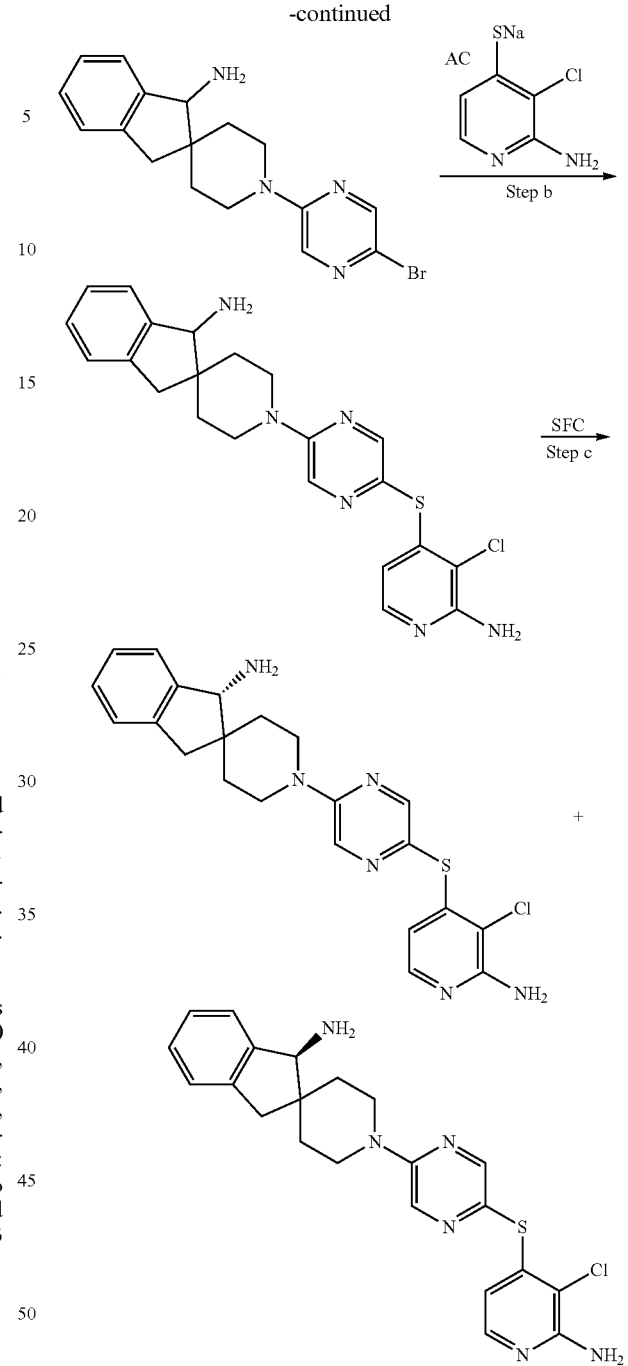

Step a: The compounds of 2,5-dibromopyrazine (500 mg, 2.1 mmol), 1,3-dihydrospiro[indene-2,4'-piperidin]-3-amine dihydrochloride (815 mg, 2.5 mmol, Intermediate E) and TEA (1.5 mL, 10.5 mmol) were added in DMF (20 mL) and the mixture was stirred at 85° C. for 12 h. The mixture was then diluted with ethyl acetate (100 mL). The mixture was washed with H₂O (20 mL×3) and brine (30 mL×3), dried over anhydrous Na₂SO₄, filtered and concentrated to give a residue. The residue was purified by flash silica gel chromatography (DCM:MeOH=100:0 to 100:5) to afford 1'-(5-bromopyrazin-2-yl)-1,3-dihydrospiro[indene-2,4'-piperidin]-3-amine (740 mg, 98% yield) as a yellow oil.

Step b: The compounds of 1'-(5-bromopyrazin-2-yl)-1,3-dihydrospiro[indene-2,4'-piperidin]-3-amine (200 mg, 0.5 mmol), sodium 2-amino-3-chloropyridine-4-thiolate (131 mg, 0.7 mmol, Intermediate AC), Pd$_2$(dba)$_3$ (51 mg, 0.05 mmol), XantPhos (64 mg, 0.1 mmol), DIPEA (0.5 mL, 2.8 mmol) were added in dioxane (10 mL). The reaction mixture was evacuated and refilled 3 times using N$_2$. The reaction mixture was stirred at 110° C. for 12 hours. The mixture was filtered and the filtrate was concentrated to give a residue. The residue was purified by flash silica gel chromatography (petroleum ether:ethyl acetate=100:20 to 100:100 then EtOAc:MeOH=100:5) to afford 1'-{5-[(2-amino-3-chloropyridin-4-yl)sulfanyl]pyrazin-2-yl}-1,3-dihydrospiro[indene-2,4'-piperidin]-3-amine (150 mg, 61% yield) as a yellow solid. LCMS m/z (M+H)$^+$=439.1.

Step c: The compound rac-1'-(5-((2-amino-3-chloropyridin-4-yl)thio)pyrazin-2-yl)-1,3-dihydrospiro[indene-2,4'-piperidin]-1-amine (150 mg, 341 µmol) was separated by Chiral-SFC (Column: DAICEL CHIRALCEL OD (250 mm*30 mm, 10 um)). Mobile phase: 55% of MeOH (0.1% NH$_3$.H$_2$O) in CO$_2$. Flow rate: 70 mL/min.) to afford (R)-1'-(5-((2-amino-3-chloropyridin-4-yl)thio)pyrazin-2-yl)-1,3-dihydrospiro[indene-2,4'-piperidin]-1-amine (43.5 mg, 29% yield, R=1.546 min, the faster eluting isomer) as an off-white solid and (S)-1'-(5-((2-amino-3-chloropyridin-4-yl)thio)pyrazin-2-yl)-1,3-dihydrospiro[indene-2,4'-piperidin]-1-amine (46.5 mg, 31% yield, R=1.982 min, the slower eluting isomer) as an off-white solid. Absolute stereochemistry of the enantiomers was arbitrarily assigned. Characterization of (R)-1'-(5-((2-amino-3-chloropyridin-4-yl)thio)pyrazin-2-yl)-1,3-dihydrospiro[indene-2,4'-piperidin]-1-amine: LCMS m/z (M+H)$^+$=439.1; $^1$HNMR (400 MHz, CD$_3$OD): δ 8.23 (s, 1H), 8.17 (s, 1H), 7.49~7.52 (m, 1H), 7.26~7.28 (m, 1H), 7.09~7.13 (m, 3H), 5.83~5.85 (m, 1H), 4.23~4.27 (m, 2H), 3.88 (s, 1H), 3.24-3.29 (m, 2H), 3.05~3.10 (m, 1H), 2.72~2.77 (m, 1H), 1.65~1.81 (m, 2H), 1.51~1.55 (m, 1H), 1.35~1.39 (m, 1H); SFC: e.e. =93.6%, R$_f$=1.546 min. Characterization of (S)-1'-(5-((2-amino-3-chloropyridin-4-yl)thio)pyrazin-2-yl)-1,3-dihydrospiro[indene-2,4'-piperidin]-1-amine: LCMS m/z (M+H)$^+$=439.1; $^1$HNMR (400 MHz, CD$_3$OD): δ 8.35 (s, 1H), 8.29 (s, 1H), 7.61~7.64 (m, 1H), 7.38~7.40 (m, 1H), 7.21~7.26 (m, 3H), 5.95~5.97 (m, 1H), 4.35~4.38 (m, 2H), 3.98 (s, 1H), 3.37-3.40 (m, 2H), 3.17~3.22 (m, 1H), 2.82~2.87 (m, 1H), 1.77~1.94 (m, 2H), 1.63~1.67 (m, 1H), 1.46~1.50 (m, 1H). SFC: e.e. =98.37%, R$_f$=1.982 min. Column: Chiralcel OD-3 50*4.6 mm I.D., 3 um. Mobile phase: 40% of methanol (0.05% DEA) in CO$_2$. Flow rate: 4 mL/min. Column temp: 40° C.

Example 82: Synthesis of (3R)-1'-{5-[(2,3-dichloropyridin-4-yl)sulfanyl]pyrazin-2-yl}-7-fluoro-3H-spiro[1-benzofuran-2,4'-piperidin-3-amine

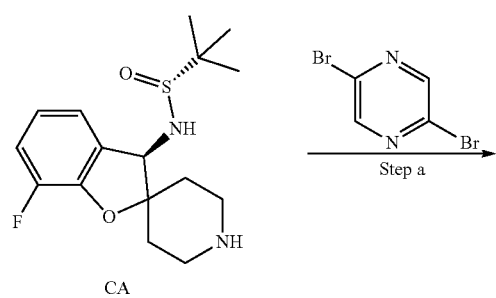

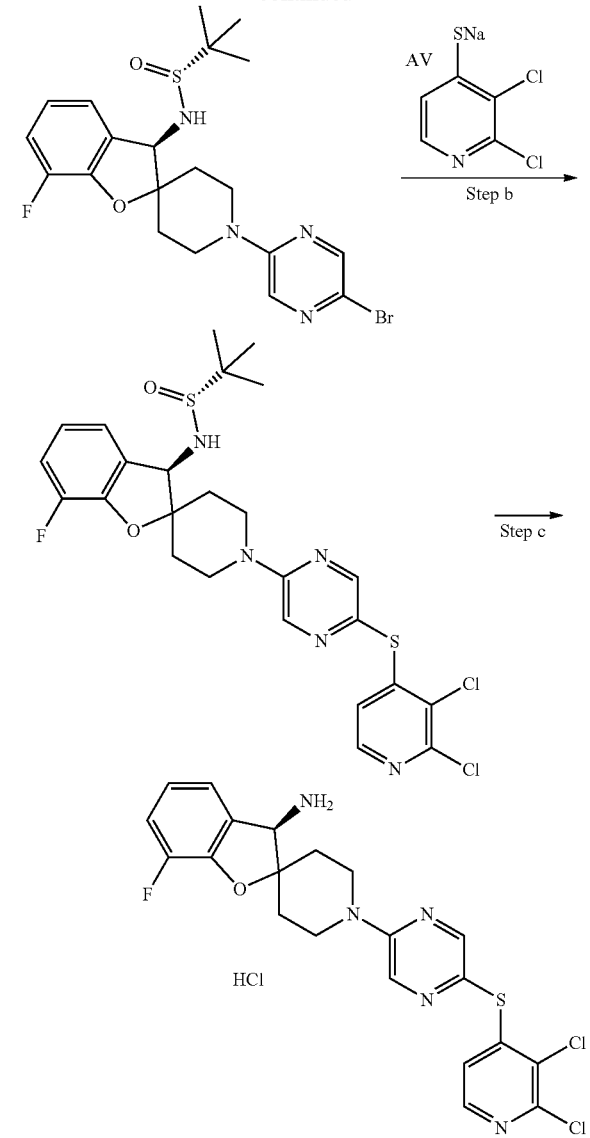

Step a: A mixture of (R)—N-[(3R)-7-fluoro-3H-spiro[1-benzofuran-2,4'-piperidin]-3-yl]-2-methylpropane-2-sulfinamide (150.0 mg, 459 µmol, Intermediate CA), 2,5-dibromopyrazine (130.0 mg, 550 µmol, CAS #23229-25-6) and TEA (316 µL, 2.3 mmol) in DMF (10 mL) was stirred at 80° C. for 12 hours. The mixture was diluted with H$_2$O (25 mL), then extracted with ethyl acetate (30 mL×2). The organic phases were washed with brine (15 mL), dried over anhydrous Na$_2$SO$_4$, filtered and concentrated in vacuo to give a residue. The residue was purified by silica gel chromatography (ethyl acetated in petroleum ether=0% to 60%) to afford (R)—N-[(3R)-1'-(5-bromopyrazin-2-yl)-7-fluoro-3H-spiro[1-benzofuran-2,4'-piperidin]-3-yl]-2-methylpropane-2-sulfinamide (180.0 mg, 81% yield) as a yellow oil. LCMS m/z (M+H)$^+$=482.9, 484.9.

Step b: A mixture of (R)—N-[(3R)-1'-(5-bromopyrazin-2-yl)-7-fluoro-3H-spiro[1-benzofuran-2,4'-piperidin]-3-yl]-2-methylpropane-2-sulfinamide (180.0 mg, 372 µmol), 2,3-dichloro-4-(sodiosulfanyl)pyridine (90.1 mg, 446 µmol, Intermediate AV), Pd$_2$(dba)$_3$ (34.0 mg, 37.2 µmol), XantPhos (43.0 mg, 74.4 µmol) and DIPEA (182 µL, 1.1 mmol)

in 1,4-dioxane (10.0 mL) was stirred at 110° C. for 12 hours under N₂ atmosphere. The reaction mixture was concentrated in vacuo to give a residue. The residue was purified by silica gel chromatography (ethyl acetate in petroleum ether=0% to 80%) to afford (R)—N-[(3R)-1'-{5-[(2,3-dichloropyridin-4-yl)sulfanyl]pyrazin-2-yl}-7-fluoro-3H-spiro[1-benzofuran-2,4'-piperidin]-3-yl]-2-methylpropane-2-sulfinamide (150 mg, 69% yield) as a yellow oil. LCMS m/z (M+H)⁺=582.0.

Step c: A mixture of (R)—N-[(3R)-1'-{5-[(2,3-dichloropyridin-4-yl)sulfanyl]pyrazin-2-yl}-7-fluoro-3H-spiro[1-benzofuran-2,4'-piperidin]-3-yl]-2-methylpropane-2-sulfinamide (140.0 mg, 240 μmol) in HCl/MeOH (4M, 10 mL) was stirred at 25° C. for 0.5 hours. The mixture was concentrated under reduced pressure to give a residue, which was purified by prep-HPLC (HCl) to afford (3R)-1'-{5-[(2,3-dichloropyridin-4-yl)sulfanyl]pyrazin-2-yl}-7-fluoro-3H-spiro[1-benzofuran-2,4'-piperidin]-3-amine hydrochloride (84.1 mg, 68% yield) as a yellow solid. LCMS m/z (M+H)⁺= 477.8; ¹HNMR (400 MHz, Methanol-d4): δ 8.50 (d, J=0.8 Hz, 1H), 8.39 (d, J=0.8 Hz, 1H), 8.04 (d, J=5.6 Hz, 1H),), 7.41 (d, J=7.6 Hz, 1H), 7.30-7.25 (m, 1H), 7.11-7.06 (m, 1H), 6.76 (d, J=5.2 Hz, 1H), 4.79-4.71 (m, 2H), 4.53-4.49 (m, 1H), 3.61-3.48 (m, 2H), 2.26-2.16 (m, 2H), 2.06-1.91 (m, 2H).

Compounds Synthesized in a Similar Fashion to Method 6:

Examples 83 & 84: Synthesis of (S)-1'-(5-((2-amino-3-chloropyridin-4-yl)thio)-6-methylpyrazin-2-yl)-1,3-dihydrospiro[indene-2,4'-piperidin]-1-amine and (S)-1'-(5-((2-amino-3-chloropyridin-4-yl)thio)-3-methylpyrazin-2-yl)-1,3-dihydrospiro[indene-2,4'-piperidin]-1-amine

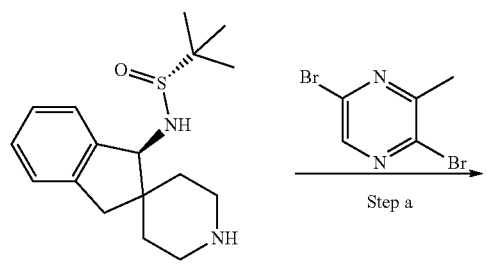

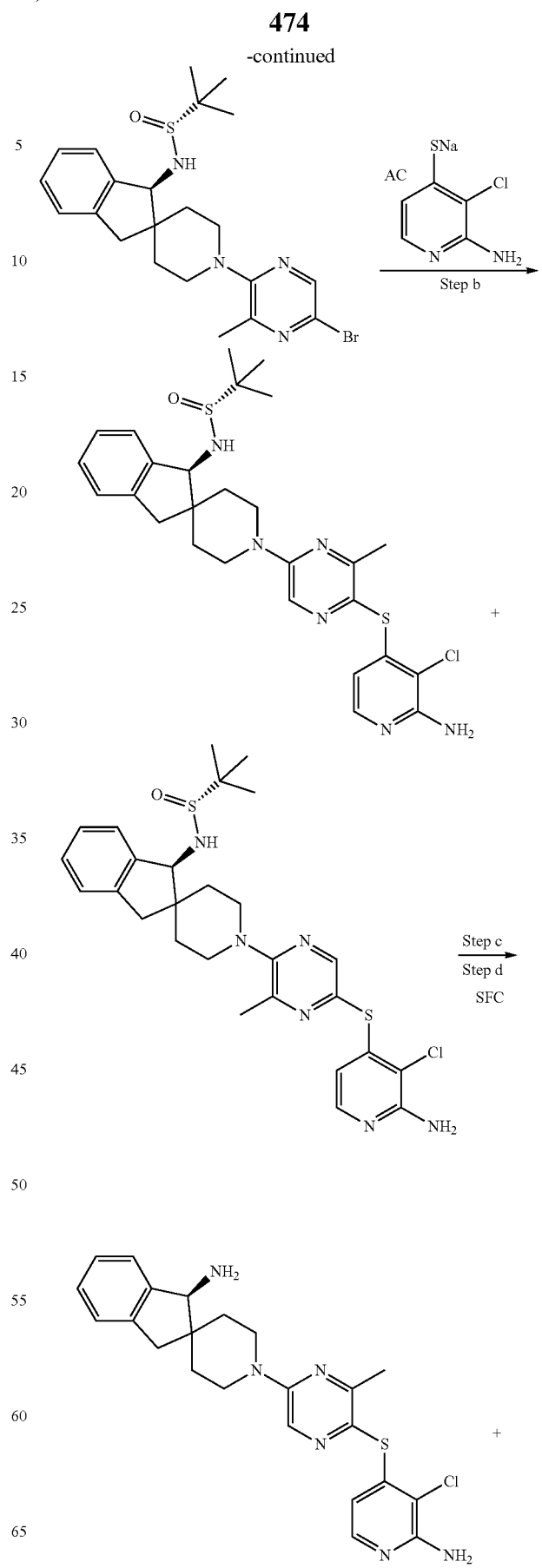

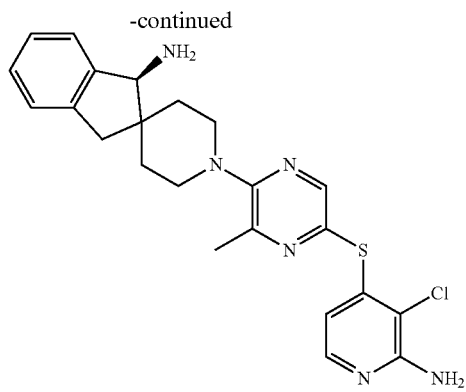

Step a: A mixture of (R)—N-[(3S)-1,3-dihydrospiro[indene-2,4'-piperidin]-3-yl]-2-methylpropane-2-sulfinamide (600 mg, 2.0 mmol, synthesized via Step a of Example 120), 2,5-dibromo-3-methylpyrazine (586 mg, 2.3 mmol, CAS #1260672-37-4) and TEA (1.3 mL, 9.8 mmol) in DMF (15 mL) was stirred at 80° C. for 2 hours. The reaction mixture was diluted with ethyl acetate (40 mL), and washed with $H_2O$ (30 mL×2). The organic phase was washed with brine (10 mL), dried over anhydrous $Na_2SO_4$, filtered and concentrated in vacuo to give a residue. The residue was purified by silica gel chromatography (ethyl acetate in petroleum ether=0% to 70%) to afford (R)—N—((S)-1'-(5-bromo-6-methylpyrazin-2-yl)-1,3-dihydrospiro[indene-2,4'-piperidin]-1-yl)-2-methylpropane-2-sulfinamide and (R)—N—((S)-1'-(5-bromo-3-methylpyrazin-2-yl)-1,3-dihydrospiro[indene-2,4'-piperidin]-1-yl)-2-methylpropane-2-sulfinamide (380 mg, 3:1 ratio of (R)—N—((S)-1'-(5-bromo-6-methylpyrazin-2-yl)-1,3-dihydrospiro[indene-2,4'-piperidin]-1-yl)-2-methylpropane-2-sulfinamide to (R)—N—((S)-1'-(5-bromo-3-methylpyrazin-2-yl)-1,3-dihydrospiro[indene-2,4'-piperidin]-1-yl)-2-methylpropane-2-sulfinamide) as a white solid. LCMS m/z $(M+H)^+$=477.0/479.0.

Step b: A mixture of (R)—N—((S)-1'-(5-bromo-6-methylpyrazin-2-yl)-1,3-dihydrospiro[indene-2,4'-piperidin]-1-yl)-2-methylpropane-2-sulfinamide and (R)—N—((S)-1'-(5-bromo-3-methylpyrazin-2-yl)-1,3-dihydrospiro[indene-2,4'-piperidin]-1-yl)-2-methylpropane-2-sulfinamide (350 mg, 733 μmol), 3-chloro-4-(sodiosulfanyl)pyridin-2-amine (160 mg, 879 μmol, Intermediate AC), $Pd_2(dba)_3$ (67.1 mg, 73.3 μmol), XantPhos (84.4 mg, 146 μmol) and DIPEA (391 μmL, 2.2 mmol) in dioxane (15 mL) was stirred at 110° C. for 12 hours under $N_2$ atmosphere. The reaction mixture was concentrated in vacuo to give a residue, which was purified by silica gel chromatography (Methanol in Dichloromethane=0% to 10%) to afford (R)—N—((S)-1'-(5-((2-amino-3-chloropyridin-4-yl)thio)-6-methylpyrazin-2-yl)-1,3-dihydrospiro[indene-2,4'-piperidin]-1-yl)-2-methylpropane-2-sulfinamide and (R)—N—((S)-1'-(5-((2-amino-3-chloropyridin-4-yl)thio)-3-methylpyrazin-2-yl)-1,3-dihydrospiro[indene-2,4'-piperidin]-1-yl)-2-methylpropane-2-sulfinamide (420 mg) as a brown solid. LCMS m/z $(M+H)^+$=557.0.

Step c: A mixture of (R)—N—((S)-1'-(5-((2-amino-3-chloropyridin-4-yl)thio)-6-methylpyrazin-2-yl)-1,3-dihydrospiro[indene-2,4'-piperidin]-1-yl)-2-methylpropane-2-sulfinamide and (R)—N—((S)-1'-(5-((2-amino-3-chloropyridin-4-yl)thio)-3-methylpyrazin-2-yl)-1,3-dihydrospiro[indene-2,4'-piperidin]-1-yl)-2-methylpropane-2-sulfinamide (350 mg, 628 μmol) in HCl/MeOH (4M, 5 mL) was stirred at 20° C. for 0.5 hours. The mixture was concentrated under reduced pressure to give a residue, which was purified by prep-HPLC ($NH_3.H_2O$) to afford (S)-1'-(5-((2-amino-3-chloropyridin-4-yl)thio)-6-methylpyrazin-2-yl)-1,3-dihydrospiro[indene-2,4'-piperidin]-1-amine and (S)-1'-(5-((2-amino-3-chloropyridin-4-yl)thio)-3-methylpyrazin-2-yl)-1,3-dihydrospiro[indene-2,4'-piperidin]-1-amine (160 mg, mixed) as a yellow solid.

Step d: The mixture of (S)-1'-(5-((2-amino-3-chloropyridin-4-yl)thio)-6-methylpyrazin-2-yl)-1,3-dihydrospiro[indene-2,4'-piperidin]-1-amine and (S)-1'-(5-((2-amino-3-chloropyridin-4-yl)thio)-3-methylpyrazin-2-yl)-1,3-dihydrospiro[indene-2,4'-piperidin]-1-amine (160 mg) was separated by preparative SFC (column: DAICEL CHIRALCEL OJ-H (250 mm×30 mm, 5 um), Mobile phase: 0.1% $NH_3.H_2O$ MeOH (Begin B: 40%, End B: 40%), Flow rate: 60 mL/min) to afford the product of (S)-1'-(5-((2-amino-3-chloropyridin-4-yl)thio)-6-methylpyrazin-2-yl)-1,3-dihydrospiro[indene-2,4'-piperidin]-1-amine (99 mg, 35% yield, $R_f$=5.58 min, the slower eluting isomer) as a white solid and (S)-1'-(5-((2-amino-3-chloropyridin-4-yl)thio)-3-methylpyrazin-2-yl)-1,3-dihydrospiro[indene-2,4'-piperidin]-1-amine (32.9 mg, 12% yield, $R_f$=4.65 min, the faster eluting isomer) as a white solid. Characterization of (S)-1'-(5-((2-amino-3-chloropyridin-4-yl)thio)-6-methylpyrazin-2-yl)-1,3-dihydrospiro[indene-2,4'-piperidin]-1-amine: LCMS m/z $(M+H)^+$=453.0; $^1$HNMR (400 MHz, Methanol-d4): δ 8.03 (s, 1H), 7.49 (d, J=5.6 Hz, 1H), 7.28-7.26 (m, 1H), 7.14-7.09 (m, 3H), 5.71 (d, J=5.2 Hz, 1H), 4.71-4.39 (m, 2H), 4.28-4.23 (m, 2H), 3.86 (s, 1H), 3.07 (d, J=15.6 Hz, 1H), 2.71 (d, J=15.6 Hz, 1H), 2.34 (s, 3H), 1.80-1.64 (m, 2H), 1.54-1.49 (m, 1H), 1.37-1.32 (m, 1H); SFC: e.e.=100%. Characterization of (S)-1'-(5-((2-amino-3-chloropyridin-4-yl)thio)-3-methylpyrazin-2-yl)-1,3-dihydrospiro[indene-2,4'-piperidin]-1-amine: LCMS m/z $(M+H)^+$=453.0; $^1$HNMR (400 MHz, Methanol-d4): δ 8.15 (s, 1H), 7.51 (d, J=5.6 Hz, 1H), 7.29-7.27 (m, 1H), 7.11-7.09 (m, 3H), 5.88 (d, J=5.6 Hz, 1H), 3.88 (s, 1H), 3.63-3.59 (m, 2H), 3.12-3.01 (m, 3H), 2.69 (d, J=15.6 Hz, 1H), 2.46 (s, 3H), 1.94-1.78 (m, 2H), 1.55-1.52 (m, 1H), 1.39-1.36 (m, 1H). SFC: e.e.=95.5%; Chiralcel OJ-3 100×4.6 mm I.D., 3 um; Mobile phase: A: $CO_2$, B: ethanol (0.05% DEA); Gradient: from 5% to 40% of B in 4 min and hold 40% for 2.5 min, then 5% of B for 1.5 Min; Flow rate: 2.8 mL/min; Temperature: 35° C.

Method 7, Examples 85 & 86: Synthesis of (R)-1'-(3-((2-amino-3-chloropyridin-4-yl)thio)-1H-pyrazolo[3,4-b]pyrazin-6-yl)-1,3-dihydrospiro[indene-2,4'-piperidin]-1-amine and (S)-1'-(3-((2-amino-3-chloropyridin-4-yl)thio)-1H-pyrazolo[3,4-b]pyrazin-6-yl)-1,3-dihydrospiro[indene-2,4'-piperidin]-1-amine

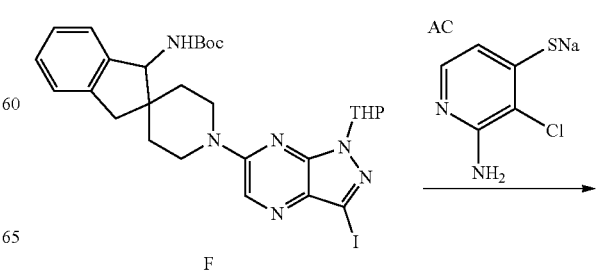

-continued

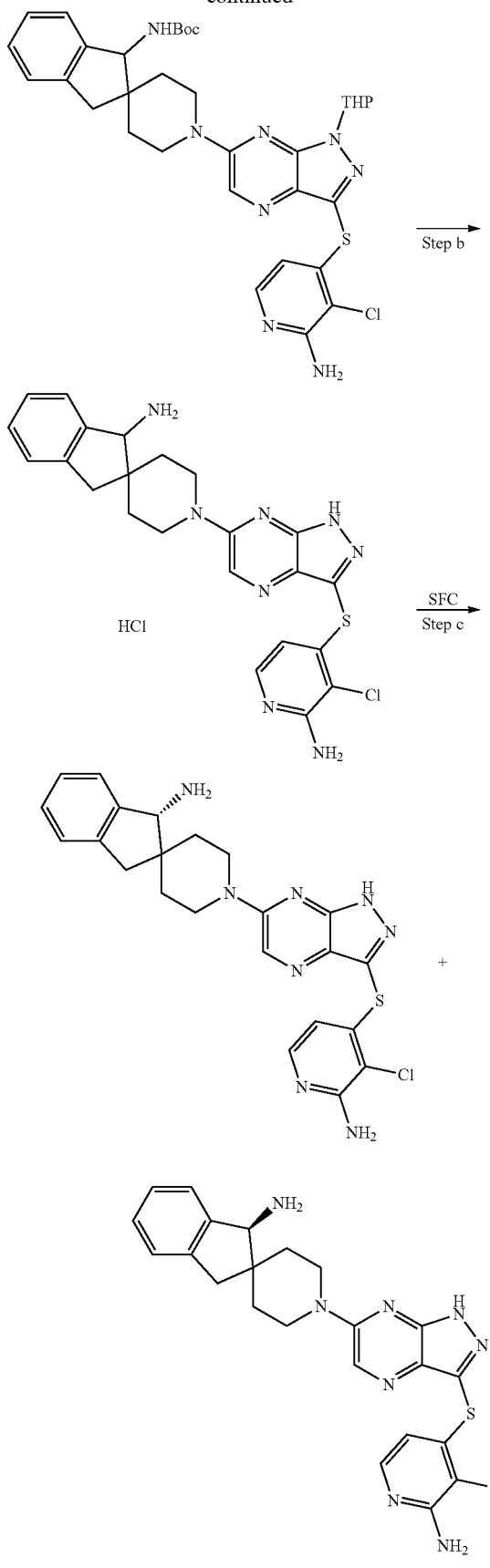

Step a: To a solution of tert-butyl (1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (200 mg, 317 μmol, Intermediate F) and sodium 2-amino-3-chloropyridine-4-thiolate (86.7 mg, 475 μmol, Intermediate AC) in dioxane (5.0 mL) was added Pd$_2$(dba)$_3$ (29 mg, 31.7 μmol), XantPhos (36.6 mg, 63.4 μmol) and Cs$_2$CO$_3$ (206.0 mg, 634.0 μmol). The reaction mixture was purged with N$_2$ for 3 min, and the reaction was stirred at 100° C. for 12 hours. The reaction mixture was concentrated under reduced pressure. The residue was purified by column chromatography (petroleum ether:ethyl acetate=100:0 to 100:70) and then prep-TLC (DCM:MeOH=10:1) to afford the product tert-butyl (1'-(3-((2-amino-3-chloropyridin-4-yl)thio)-1-(tetrahydro-2H-pyran-2-yl)-1H-pyrazolo[3,4-b]pyrazin-6-yl)-1,3-dihydrospiro[indene-2,4'-piperidin]-1-yl)carbamate (120 mg, 57% yield) as a light yellow solid. LCMS m/z (M+H)$^+$=663.1.

Step b: A solution of tert-butyl (1'-(3-((2-amino-3-chloropyridin-4-yl)thio)-1-(tetrahydro-2H-pyran-2-yl)-1H-pyrazolo[3,4-b]pyrazin-6-yl)-1,3-dihydrospiro[indene-2,4'-piperidin]-1-yl)carbamate (120 mg, 180 μmol) in HCl/MeOH (5.0 mL, 4M) was stirred at 15° C. for 1 hour. The reaction mixture was concentrated under reduced pressure to give the product 1'-{3-[(2-amino-3-chloropyridin-4-yl)sulfanyl]-1H-pyrazolo[3,4-b]pyrazin-6-yl}-1,3-dihydrospiro[indene-2,4'-piperidin]-3-amine hydrochloride (85 mg, 92% yield). LCMS m/z (M+H)$^+$=479.1.

Step c: The compound of 1'-(3-((2-amino-3-chloropyridin-4-yl)thio)-1H-pyrazolo[3,4-b]pyrazin-6-yl)-1,3-dihydrospiro[indene-2,4'-piperidin]-1-amine (75 mg, 156 μmol) was separated by SFC to give each enantiomer crude. Conditions for separation: Column: DAICEL CHIRALPAK AS-H (250 mm×30 mm, 5 um). Condition: 0.1% NH$_3$.H$_2$O EtOH. Begin B 50%, end B 50%. Flow rate: 50 mL/min. Each enantiomer was then purified by prep-TLC (Dichloromethane:Methanol=10:1). (R)-1'-(3-((2-amino-3-chloropyridin-4-yl)thio)-1H-pyrazolo[3,4-b]pyrazin-6-yl)-1,3-dihydrospiro[indene-2,4'-piperidin]-1-amine (30.0 mg, 40% yield) was obtained as a white solid. LCMS m/z (M+H)$^+$= 479.1; $^1$HNMR (400 MHz, CDCl$_3$+CD$_3$OD): δ 8.20 (s, 1H), 7.45-7.47 (m, 1H), 7.24-7.27 (m, 1H), 7.14-7.21 (m, 3H), 5.86-5.87 (m, 1H), 4.26-4.29 (m, 2H), 3.92 (s, 1H), 3.23-3.28 (m, 2H), 3.02-3.06 (m, 1H), 2.72-2.75 (m, 1H), 1.68-1.82 (m, 2H), 1.58-1.61 (m, 1H), 1.40-1.43 (m, 1H). SFC: e.e. =96.2%, R$_f$=5.272 min. (S)-1'-(3-((2-amino-3-chloropyridin-4-yl)thio)-1H-pyrazolo[3,4-b]pyrazin-6-yl)-1,3-dihydrospiro[indene-2,4'-piperidin]-1-amine (27.0 mg, 36% yield) was obtained as a white solid. LCMS m/z (M+H)$^+$= 479.1; $^1$HNMR (400 MHz, CDCl$_3$+CD$_3$OD): δ 8.20 (s, 1H), 7.48-7.50 (m, 1H), 7.27-7.28 (m, 1H), 7.17-7.20 (m, 3H), 5.88-5.89 (m, 1H), 4.25-4.28 (m, 2H), 3.94 (s, 1H), 3.22-3.28 (m, 2H), 3.03-3.07 (m, 1H), 2.71-2.75 (m, 1H), 1.69-1.84 (m, 2H), 1.58-1.62 (m, 1H), 1.39-1.43 (m, 1H). SFC: e.e. =97.8%, R$_R$=5.808 min. Column: Chiralpak AS-3 100× 4.6 mm I.D., 3 μm. Mobile phase: A: CO$_2$ B: ethanol (0.05% DEA). Gradient: from 5% to 40% of B in 4.5 min and hold 40% for 2.5 min, then 5% of B for 1 min. Flow rate: 2.8 m/min, Column temperature: 40° C.

Method 7 Table: Compounds Synthesized Via
Method 7. With the Cross-coupling of Sulfur Salts
with various Bromides or Iodides in Step a

| Example #[a] | Step a SNa salt | Step a Iodide or Bromide | LCMS m/z (M + H)+ | $^1$H NMR (400 MHz, CD$_3$OD) δ ppm |
|---|---|---|---|---|
| 87[b] | AC | BF | 453.9 | 7.69 (s, 1H), 7.64~7.67 (m, 1H), 7.52~7.55 (m, 1H), 7.36~7.44 (m, 3H), 6.27~6.29 (m, 1H), 4.30~4.46 (m, 3H), 3.36~3.41 (m, 2H), 3.21 (s, 2H), 1.75-1.93 (m, 3H), 1.60~1.63 (m, 1H). |
| 88[b] | AV | K | 528.0 | (DMSO) 8.09 (s, 1 H) 7.50 (d, J = 5.71 Hz, 1 H) 5.69-5.80 (m, 1 H) 4.55 (s, 2 H) 4.17-4.25 (m, 1 H) 3.83 (d, J = 9.34 Hz, 2 H) 3.61-3.77 (m, 4 H) 3.36 (d, J = 4.41 Hz, 1 H) 2.87-3.07 (m, 2 H) 1.79-1.91 (m, 2H) 1.75 (br s, 1 H) 1.61 (br d, J = 12.97 Hz, 1 H) 1.17 (d, J = 6.48 Hz, 3 H). |
| 89[b] | AW | K | 508.3 | (DMSO) 8.09 (s, 1 H) 7.50 (d, J = 5.71 Hz, 1 H) 5.69-5.80 (m, 1 H) 4.55 (s, 2 H) 4.17-4.25 (m, 1 H) 3.83 (d, J = 9.34 Hz, 2 H) 3.61-3.77 (m, 4 H) 3.36 (d, J = 4.41 Hz, 1 H) 2.87-3.07 (m, 2 H) 1.79-1.91 (m, 2H) 1.75 (br s, 1 H) 1.61 (br d, J = 12.97 Hz, 1 H) 1.17 (d, J = 6.48 Hz, 3 H). |
| 90[b] | AW | J | 478.1 | 8.46 (s, 1H), 8.22-8.24 (d, J = 6.4, 1H), 7.53-7.55 (d, J = 7.2, 1H), 7.34-7.47 (m, 3H), 7.10-7.11 (d, J = 6.4, 1H), 4.56-4.59 (m, 1H), 4.43-4.47 (m, 2H), 3.43-3.54 (m, 2H), 3.24 (s, 2H), 2.83 (s, 3H), 1.81-1.99 (m, 3H), 1.68-1.71 (m, 1H). |
| 91[c] | AV | J | 498.0 | 8.43 (s, 1H), 7.93-7.95 (d, J = 5.2, 1H), 7.51-7.53 (d, J = 7.6, 1H), 7.35-7.46 (m, 3H), 6.62-6.63 (d, J = 5.2, 1H), 4.54-4.57 (m, 1H), 4.43-4.47 (m, 2H), 3.43-3.52 (m, 2H), 3.24 (s, 2H), 1.79-1.96 (m, 3H), 1.67-1.71 (m, 1H). |
| 92 | AV | J | 498.0 | 8.43 (s, 1H), 7.93-7.95 (d, J = 5.6, 1H), 7.51-7.53 (d, J = 7.2, 1H), 7.35-7.46 (m, 3H), 6.62-6.63 (d, J = 5.2, 1H), 4.54-4.58 (m, 1H), 4.43-4.47 (m, 2H), 3.43-3.52 (m, 2H), 3.24 (s, 2H), 1.78-1.96 (m, 3H), 1.67-1.71 (m, 1H). |
| 93[b] | AC | CK | 439.0 | (DMSO) 8.68 (br, 3H), 8.52 (s, 2H), 7.84-7.81 (d, J = 6.8 Hz, 1H), 7.63-7.28 (m, 4H), 6.30-6.28 (d, J = 6.8 Hz, 1H), 4.64-4.53 (m, 2H), 4.36-4.34 (m, 1H), 3.33-2.99 (m, 4H), 1.82-1.52 (m, 4H). |
| 94[b] | AV | CL | 460.0 | 8.48-8.49 (m, 1H), 8.38-8.39 (m, 1H), 8.03-8.04 (d, J = 5.6 Hz, 1H), 7.56-7.58 (m, 1H), 7.42-7.46 (m, 1H), 7.07-7.11 (m, 1H), 7.02-7.04 (m, 1H), 6.74-6.75 (d, J = 5.2 Hz, 1H), 4.67-4.73 (m, 2H), 4.47-4.50 (m, 1H), 3.47-3.59 (m, 2H), 2.11-2.20 (m, 2H), 1.85-1.97 (m, 2H). |
| 95[b] | AJ | CL | 426.0 | 8.44-8.45 (m, 1H), 8.37-8.38 (m, 1H), 7.99-8.00 (d, J = 5.2 Hz, 1H), 7.56-7.58 (m, 1H), 7.42-7.46 (m, 1H), 7.07-7.11 (m, 1H), 7.01-7.04 (m, 1H), 6.92-6.94 (m, 1H), 4.66-4.71 (m, 2H), 4.44-4.48 (m, 1H), 3.45-3.59 (m, 2H), 2.12-2.16 (m, 2H), 1.84-1.97 (m, 2H). |
| 96[b] | CT | CL | 426.0 | 8.39 (s, 1H), 8.32 (s, 1H), 8.19-8.22 (m, 1H), 7.55-7.58 (m, 1H), 7.41-7.47 (m, 2H), 7.27-7.30 (m, 1H), 7.01-7.10 (m, 2H), 4.63-4.76 (m, 2H), 4.41-4.45 (m, 1H), 3.44-3.54 (m, 2H), 2.08-2.15 (m, 2H), 1.86-1.96 (m, 2H). |
| 97[b] | AC | CU | 438.0 | 8.45 (d, J = 2.8 Hz, 1H), 7.73 (d, J = 2.8 Hz, 1H), 7.67-7.63 (m, 2H), 7.55 (d, J = 7.6 Hz, 1H), 7.44-7.42 (m, 3H), 4.45 (s, 3H), 4.00-3.87 (m, 2H), 3.29-3.16 (m, 4H), 2.06-1.69 (m, 4H). |
| 177[b] | AC | CL | 440.9 | 8.50-8.51 (m, 1H), 8.40-8.41 (m, 1H), 7.65-7.67 (m, 1H), 7.56-7.58 (m, 1H), 7.42-7.46 (m, 1H), 7.07-7.11 (m, 1H), 7.01-7.04 (m, 1H), 6.36-6.38 (m, |

-continued

| Example #[a] | Step a SNa salt | Step a Iodide or Bromide | LCMS m/z (M + H)+ | 1H NMR (400 MHz, CD3OD) δ ppm |
|---|---|---|---|---|
| | | | | 1H), 4.68-4.74 (m, 2H), 4.48-4.52 (m, 1H), 3.47-3.60 (m, 2H), 2.11-2.24 (m, 2H), 1.87-1.98 (m, 2H). |
| 215[b] | AC | DT | 467.2 | 7.64 (d, J = 6.8 Hz 1H), 7.54 (d, J = 7.6 Hz, 1H), 7.43-7.38 (m, 2H), 7.36-7.32 (m, 1H), 6.27 (d, J = 6.8 Hz 1H), 4.45 (s, 1H), 3.93 (d, J = 14 Hz, 1H), 3.82 (d, J = 13.6 Hz 1H), 3.34 (d, J = 2.8 Hz 1H), 3.27-3.23 (m, 1H), 3.19 (s, 2 H), 2.55 (d, 6H) 2.09-2.02 (m, 1H), 1.96-1.89, (m, 1H) 1.82 (d, J = 13.2 Hz 1 H), 1.68 (d, J = 13.6 Hz, 1 H) |
| 216[b] | AC | EC | 440.0 | 78.63 (s, 1H), 7.92-7.90 (m, 2H), 7.72 (d, J = 6.80 Hz, 1H), 7.58 (d, J = 7.60 Hz, 1H), 7.44-7.40 (m, 1H), 7.09-7.05 (m, 1H), 7.00 (d, J = 8.40 Hz, 1H), 6.38 (d, J = 7.20 Hz, 1H), 4.70 (s, 1H), 4.24 (d, J = 13.6 Hz, 1H), 4.04 (d, J = 12.4 Hz, 1H), 3.60-3.48 (m, 2H), 2.36-2.30 (m, 1H), 2.14-2.11 (m, 1H), 2.05-2.01 (m, 1H), 1.97-1.93 (m, 1H). |
| 217[b] | AC | DY | 456.2 | 8.61 (d, J = 2.00 Hz, 1H), 7 95-7 91 (m, 2H), 7.73 (d, J = 6.80 Hz, 1H ), 7.56-7.53 (m, 1H), 7.15-7.09 (m, 2H), 6.39 (d, J = 6.80 Hz, 1H), 4.45 (s, 1H), 4.09 (d, J = 13.6 Hz, 1H), 3.98 (d, J = 14 Hz, 1H), 3.45-3.39 (m, 2H), 3.26-3.17 (m, 2H), 2.09-2.04 (m, 1H), 2.03-1.93 (m, 1H), 1.86 (d,J = 12.4 Hz, 1H), 1.72 (d, J = 13.2 Hz, 1H). |
| 218[b] | AC | EA | 456.0 | 8.63 (s, 1H), 7.98-7.93 (m, 2H), 7.74 (d, J = 6.80 Hz, 1H ), 7.40-7.38 (m, 1H), 7.30-7.27 (m, 1H), 7.27-7.16(m, 1H), 6.41 (d, J = 6.80 Hz, 1H), 4.49 (s, 1H), 4.12 (d, J = 13.6 Hz, 1H), 4.01 (d, J = 14Hz, 1H), 3.45-3.38 (m, 2H), 3.23-3.12 (m, 2H), 2.07-1.98 (m, 2H), 1.83 (d, J = 13.2 Hz, 1H), 1.74 (d, J = 12.8 Hz, 1H). |
| 219[b,d] | AC | DU | 452.2 | 8.48 (d, J = 2.8 Hz 1H), 7.90 (d, J = 2.4 Hz, 1H), 7.72 (d J = 7.2 Hz, 1H), 7.53 (d, J = 7.2 Hz 1H), 7.44-7.34 (m, 3H), 6.27 (d, J = 7.2 Hz 1H), 4.46 (s, 1H), 4.11 (d, J = 14 Hz 1H), 3.99 (d, J = 13.6 Hz 1H), 3.44-3.36 (m, 2H), 3.26-3.16 (m, 2 H), 2.49 (s, 3H) 2.08-1.93 (m, 2H), 1.83 (d, J = 12.8 Hz 1H), 1.71 (d, J = 12.8 Hz 1 H). |
| 220[b,e] | AV | DO | 466.0 | 8.54 (s, 2H), 8.10 (m, 1H), 7.50 (m, 1H), 7.41-7.30 (m, 3H), 6.93 (m, 1H). 4.62 (m, 2H), 4.36 (s, 1H), 3.60 (m, 2H), 3.29-3.10 (m, 2H), 2.08-1.86 (m, 2H), 1.83-1.68 (m, 2H) |
| 221[f] | AC | FV | 469.0 | 8.03 (s, 1H), 7.63-7.65 (m, 1H), 7.44-7.46 (m, 1H), 7.19-7.24 (m, 1H), 6.91-6.96 (m, 1H), 6.76-6.79 (m, 1H), 6.06-6.08 (m, 1H), 4.75-4.79 (m, 1H), 4.45-4.51 (m, 2H), 4.19-4.25 (m, 1H), 3.82-3.85 (m, 1H), 3.15-3.22 (m, 1H), 2.54-2.58 (m, 1H), 1.94-2.08 (m, 3H), 1.60-1.67 (m, 1H). |
| 222[f] | AC | FV | 469.0 | 8.09 (s, 1H), 7.68-7.71 (m, 1H), 7.59-7.62 (m, 1H), 7.41-7.46 (m, 1H), 7.08-7.12 (m, 1H), 7.00-7.03 (m, 1H), 6.55-6.57 (m, 1H), 4.76 (s, 1H), 4.67-4.71 (m, 2H), 4.37-4.42 (m, 1H), 4.08-4.15 (m, 1H), 3.35-3.40 (m, 1H), 2.14-2.20 (m, 2H), 1.98-2.02 (m, 2H). |
| 223[b] | AC | FH | 498.1 | 7.69 (d, J = 6.8 Hz, 1H), 7.55 (d, J = 7.2 Hz, 1H), 7.46-7.35 (m, 3H), 6.44 (d, J = 6.8 Hz, 1H), 4.49 (s, 1H), 4.05-4.00 (m, 1H), 3.93-3.87 (m, 1H), 3.61-3.50 (m, 2H), 3.27-3.18 (m, 2H), 2.49 (s, 3H), 2.08-1.92 (m, 2H), 1.86-1.81 (m, 1H), 1.74-1.70 (m, 1H). |

-continued

| Example #[a] | Step a SNa salt | Step a Iodide or Bromide | LCMS m/z (M + H)+ | 1H NMR (400 MHz, CD3OD) δ ppm |
|---|---|---|---|---|
| 224[b,d] | AC | FO | 458.0 | 8.65 (d, J = 2.0 Hz, 1H), 7.95-7.89 (m, 2H), 7.73 (d, J = 7.2 Hz, 1H), 7.61-7.57 (m, 1H), 6.87-6.79 (m, 2H), 6.38 (d, J = 7.2 Hz, 1H), 4.72 (s, 1H), 4.28-4.20 (m, 1H), 4.09-4.00 (m, 1H), 3.60-3.48 (m, 2H), 2.38-2.32(m, 1H), 2.17-1.97 (m, 3H). |
| 225[b,d] | AC | FP | 458.0 | 8.57 (s, 1H), 7.82-7.66 (m, 3H), 7.36-7.30 (m, 1H), 7.21-7.15 (m, 1H), 7.01-6.94 (s, 1H), 4.71 (m, 1H), 4.22-4.11 (m, 1H), 4.03-3.94 (m, 1H), 3.55-3.99 (m, 2H), 2.34-1.94 (m, 4H). |

[a]Step a was run anywhere from 100-120° C. for 12 h. Step b ran anywhere from 1-12 h.
[b]No SFC Step c was required as bromide or iodide utilized in the coupling was chiral.
[c]For compounds separated via SFC, absolute stereochemistry of the enantiomers was arbitrarily assigned.
[d]DIPEA was used as the base in Step a.
[e]HCl/EtOAc (4M) was used for deprotection in Step b.
[f]Step b was ran at 90° C. for 1 h. No SFC Step c required: the diastereomers were separated by prep-HPLC (HCl) and the absolute stereochemistry was arbitrarily assigned.

Method 8, Example 98: Synthesis of (S)-(6-(1-amino-1,3-dihydrospiro[indene-2,4'-piperidin]-1'-yl)-3-(5-(methylsulfonyl)-3,4-dihydrociuinolin-1(2H)-yl)-1H-pyrazolo[3,4-b]pyrazin-5-yl)methanol

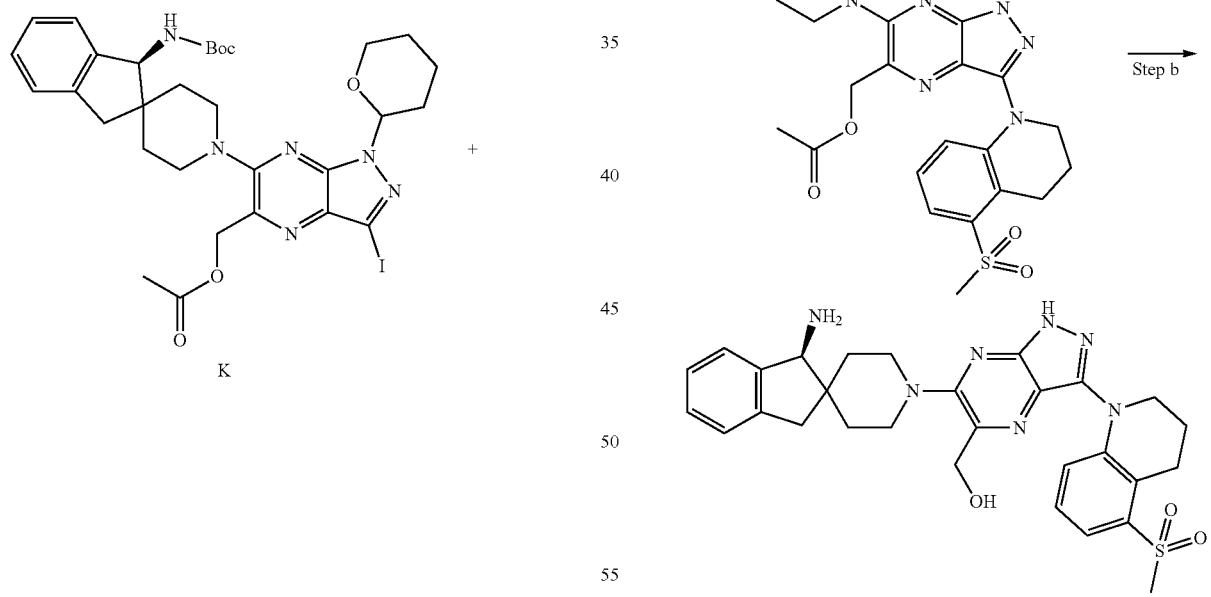

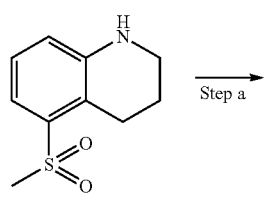

Step a: A resealable reaction vial was charged with {6-[(1S)-1-{[(tert-butoxy)carbonyl]amino}-1,3-dihydrospiro[indene-2,4'-piperidin]-1'-yl]-3-iodo-1-(oxan-2-yl)-1H-pyrazolo[3,4-b]pyrazin-5-yl}methyl acetate (100 mg, 0.14-23 mmol, Intermediate K), 5-methanesulfonyl-1,2,3,4-tetrahydroquinoline (33.0 mg,0.1565 mmol),9-{[5-(diphenylphosphanyl)-9,9-dimethyl-9H-xanthen-4-yl]diphenyl-?5-phosphanyl}-8-methyl-8-aza-9-palladatricyclo[8.4.0.0$^{2,7}$]tetradeca-1(14),2(7),3,5,10,12-hexaen-9-yl methanesulfonate (13.6 mg, 0.01423 mmol), and dicesium(1+) carbonate (92.7 mg, 0.2846 mmol). The vial was evacuated and backfilled with $N_2$ gas 3× then toluene (5 mL) was added and the reaction was stirred at 95° C. for 72 h. The reaction mixture was then pre-absorbed onto silica gel and purified on by column chromatography (10 g column, using 0-100% EA/hep) to give {6-[(3S)-3-{[(tert-butoxy)carbonyl]amino}-1,3-dihydrospiro[indene-2,4'-piperidin]-1'-yl]-3-(5-methanesulfonyl-1,2,3,4-tetrahydroquinolin-1-yl)-1-(oxan-2-yl)-1H-pyrazolo[3,4-b]pyrazin-5-yl}methyl acetate (59.0 mg, 53% yield). LCMS m/z $(M+H)^+$=786.4.

Step b: Dissolved {6-[1(3S)-3-{[(tert-butoxy)carbonyl]amino}-1,3-dihydrospiro[indene-2,4'-piperidin]-1'-yl]-3-(5-methanesulfonyl-1,2,3,4-tetrahydroquinolin-1-yl)-1-(oxan-2-yl)-1H-pyrazolo[3,4-b]pyrazin-5-yl}methylacetate (92 mg, 0.117 mmol) in DCM (3 mL) and added TFA (1 mL) and stirred at rt for 16 h. Toluene was then added and the reaction mixture was concentrated. The residue was then dissolved in THF (5 mL) and lithium(1+) hydroxide (1.17 mL, 1.17 mmol) (1N) was added and the reaction mixture was stirred at rt for 2 hr. The reaction mixture was then concentrated and the residue was dissolved in DMSO with additional formic acid (65.9 μL, 1.75 mmol). The solution was purified by reverse phase prep-HPLC (using 10-40% B (FA) to give {6-[(3S)-3-amino-1,3-dihydrospiro[indene-2,4'-piperidin]-1'-yl]-3-(5-methanesulfonyl-1,2,3,4-tetrahydroquinolin-1-yl)-1H-pyrazolo[3,4-b]pyrazin-5-yl}methanol (18.0 mg, yield). LCMS m/z $(M+H)^+$=560.2; $^1$H NMR (400 MHz, DMSO-d6) δ 12.86-13.16 (m, 1H), 7.33-7.39 (m, 2H), 7.11-7.24 (m, 5H), 4.54 (s, 2H), 4.00 (s, 1H), 3.88-3.93 (m, 2H), 3.73-3.81 (m, 2H), 3.21-3.26 (m, 5H), 3.04-3.17 (m, 3H), 2.71 (br d, J=15.87 Hz, 1H), 2.04 (quin, J=6.04 Hz, 2H), 1.81-1.99 (m, 2H), 1.56 (br d, J=12.70 Hz, 1H), 1.27 (br d, J=12.94 Hz, 1H).

Method 8 Table: Compounds synthesized via Method 8, with the cross-coupling of (6-((S)-1-((tert-butoxycarbonyl)amino)-1,3-dihydrospiro[indene-2,4'-piperidin]-1'-yl)-3-iodo-1-(tetrahydro-2H-pyran-2-yl)-1H-pyrazolo[3,4-b]pyrazin-5-yl)methyl acetate (Intermediate K) with various Amines in Step a

| Example #[a] | Step a Amine | LCMS m/z (M + H)+ | $^1$H NMR (400 MHz, DMSO-d6) δ ppm |
|---|---|---|---|
| 99[b] | 1,2,3,4-tetrahydro-1,5-naphthyridine | 483.2 | 8.27 (s, 1 H) 7.81-7.88 (m, 1 H) 7.45 (d, J = 7.52 Hz, 1 H) 7.30-7.38 (m, 3 H) 7.23-7.29 (m, 1 H) 6.95-7.01 (m, 1 H) 4.55 (s, 2 H) 4.31 (s, 1 H) 3.87-3.93 (m, 2 H) 3.61-3.77 (m, 2 H) 3.05-3.15 (m, 3 H) 2.94-3.02 (m, 1 H) 2.91 (t, J = 6.48 Hz, 2 H) 1.99-2.08 (m, 2 H) 1.78-1.91 (m, 2 H) 1.59 (br d, J = 12.45 Hz, 1 H) 1.51 (br d, J = 12 45 Hz, 1 H). |
| 100 | 1,2,3,4-tetrahydro-1,5-naphthyridine | 483.2 | 12.94 (br s, 1H), 8.16 (s, 1H), 7.91 (dd, J = 1.34, 4.52 Hz, 1H), 7.42-7.49 (m, 2H), 7.24-7.33 (m, 2H), 6.96 (dd, J = 4.64, 8.30 Hz, 1H), 4.56 (s, 2H), 4.26 (s, 1H), 3.95-4.02 (m, 2H), 3.72-3.86 (m, 2H), 3.08-3.19 (m, 3H), 2.85-2.98 (m, 3H), 2.08 (quin, J = 5.98 Hz, 2H), 1.86-1.97 (m, 2H), 1.43-1.59 (m, 2H) |
| 101 | X | 563.3 | 12.87 (br s, 1H), 8.24 (s, 1H), 8.08 (s, 1H), 7.82 (s, 1H), 7.53 (d, J = 8.54 Hz, 1H), 7.32-7.36 (m, 1H), 7.15-7.26 (m, 4H), 5.27 (brs, 1H), 4.56 (s, 2H), 3.99-4.04 (m, 2H), 3.94 (s, 1H), 3.84 (s, 3H), 3.76 (br t, J = 11.35 Hz, 2H), 3.02-3.17 (m, 4H), 2.95 (br t, J = 6.47 Hz, 2H), 2.64-2.70 (m, 1H), 2.04-2.12 (m, 2H), 1.91-1.99 (m, 1H), 1.81-1.90 (m, 1H), 1.56 (br d, J = 12.21 Hz, 1H), 1.22 (br d, J = 12.94 Hz, 1H) |
| 102 | L | 525.2 | 13.01 (br s, 1H), 7.30-7.36 (m, 1H), 7.13-7.25 (m, 3H), 6.96 (br s, 1H), 6.81-6.82 (m, 1H), 6.78 (br t, J = 7.13 Hz, 1H), 5.26 (br s, 1H), 4.55 (br s, 2H), 4.08 (br d, J = 4.93 Hz, 2H), 3.93-3.98 (m, 2H), 3.91 (s, 1H), 3.75 (br t, J = 14.78 Hz, 2H), 3.02-3.17 (m, 3H), 2.65 (br d, J = 15.82 Hz, 1H), 2.23 (s, 3H), 1.91-1.99 (m, 1H), 1.85 (br t, J = 10.76Hz, 1H), 1.56 (br d, J = 12.45 Hz, 1H), 1.16-1.23 (m, 1H) |
| 103 | piperidine | 434.2 | (CDCl3) 7.32-7.38 (m, 1H), 7.18-7.26 (m, 3H), 4.78 (s, 2H), 4.03 (s, 1H), 3.63-3.71 (m, 4H), 3.46-3.57 (m, 2H), 3.04-3.23 (m, 3H), 2.68-2.77 (m, 1H), 1.85-2.07 (m, 2H), 1.71-1.80 (m, 5H), 1.67-1.70 (m, 2H), 1.39-1.46 (m, 1H). |

[a]Step a ran from 12-72 hr at 95-110° C. Step b deprotection could also be achieved using HCl in acetonitrile or other solvents.
[b]In Step a, additional catalyst/base was added after 16 h, and the reaction was run at 100° C. for an additional 16 h. Compound was racemic.

487

Compounds Synthesized in a Similar Fashion to Method 8:

Example 104: Synthesis of (S)-(6-(1-amino-1,3-dihydrospiro[indene-2,4'-piperidin]-1'-yl)-1H-pyrazolo[3,4-b]pyrazin-5-yl)methanol

488

Method 9, Example 105: Synthesis of (3S)-3-amino-1'-[3-(1,2,3,4-tetrahydro-1,5-naphthyridin-1-yl)-1H-pyrazolo[3,4-b]pyrazin-6-yl]-1,3-dihydrospiro[indene-2,4'-piperidine]-4-carbonitrile

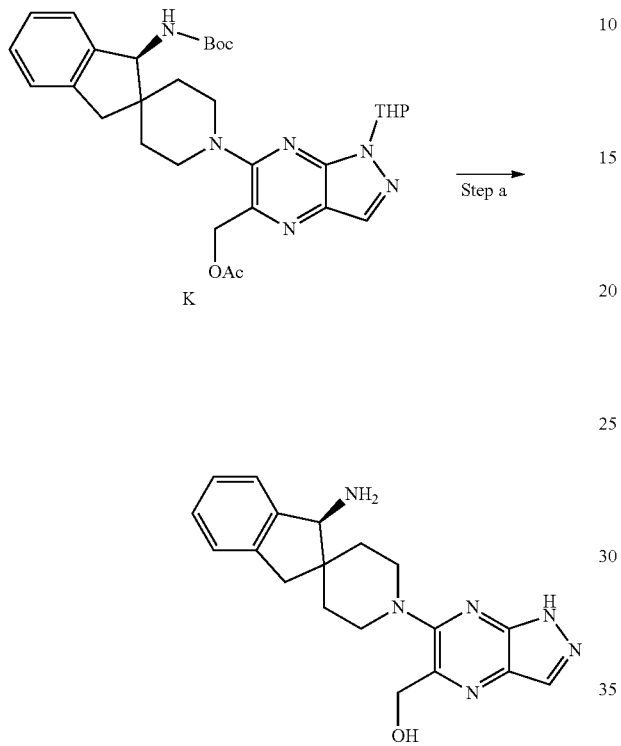

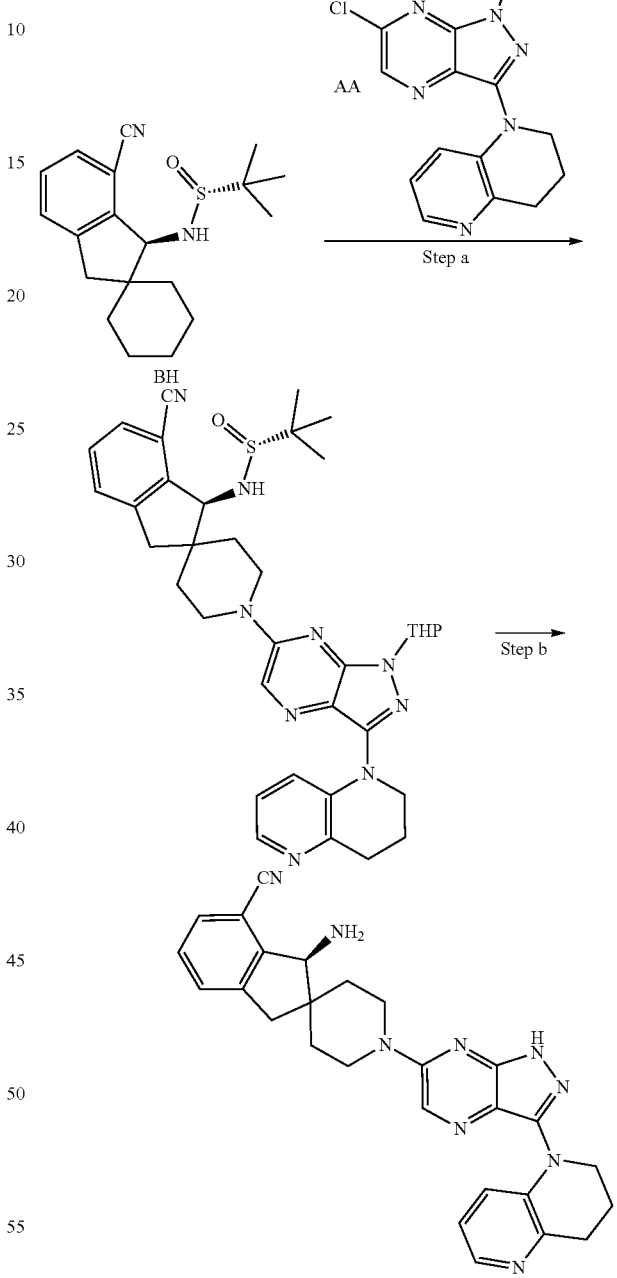

Step a: {6-[(3S)-3-{[(tert-butoxy)carbonyl]amino}-1,3-dihydrospiro[indene-2,4'-piperidin]-1'-yl]-1-(oxan-2-yl)-1H-pyrazolo[3,4-b]pyrazin-5-yl}methyl acetate (98.0 mg, 0.17 mmol, Intermediate K) was dissolved in DCM (2 mL) and TFA (0.5 mL) was added and the reaction mixture was stirred at rt for 16 h to form intermediate (S)-(6-(1-amino-1,3-dihydrospiro[indene-2,4'-piperidin]-1'-yl)-1H-pyrazolo[3,4-b]pyrazin-5-yl)methyl acetate. Then toluene was added and the reaction was concentrated in vacuo, then THF was added and the mixture was concentrated again to remove the TFA. The residue was next redissolved in 2 mL THF and 0.5 mL water then LiOH was added and the reaction mixture was stirred at rt for 3 h. The reaction was then concentrated in vacuo and the residue was redissolved in DMSO with formic acid. The residue was purified on by prep HPLC (5-30% ACN/water/FA) to give (S)-(6-(1-amino-1,3-dihydrospiro[indene-2,4'-piperidin]-1'-yl)-1H-pyrazolo[3,4-b]pyrazin-5-yl)methanol as a yellow solid. LCMS m/z [M+H]$^+$=351.1; 1H NMR (500 MHz, DMSO-d6) ppm: 8.28-8.33 (m, 1H), 8.13-8.19 (m, 1H), 7.37-7.43 (m, 1H), 7.18-7.28 (m, 4H), 4.59-4.63 (m, 2H), 4.06-4.12 (m, 1H), 3.63-3.74 (m, 2H), 3.06-3.14 (m, 2H), 2.75-2.82 (m, 1H), 1.83-1.97 (m, 2H), 1.51-1.60 (m, 2H), 1.33-1.41 (m, 2H).

Step a: A mixture of (R)—N—[(S)-7-cyano-1,3-dihydrospiro[indene-2,4'-piperidin]-1'-yl]-2-methylpropane-2-sulfinamide (153.0 mg, 0.5 mmol, Intermediate BH), 1-[6-chloro-1-(oxan-2-yl)-1H-pyrazolo[3,4-b]pyrazin-3-yl]-1,2,3,4-tetrahydro-1,5-naphthyridine (188.0 mg, 0.5 mmol, Intermediate AA), TEA (640.0 μL, 4.6 mmol) and DMF (4.0 mL) was stirred at 85° C. for 12 hours. The reaction mixture was concentrated and quenched with H$_2$O (30.0 mL). The reaction mixture was extracted with EtOAc (40.0 mL×3).

The combined organic layers were washed with brine (20.0 mL), dried over anhydrous Na$_2$SO$_4$, filtered and concentrated under reduced pressure to give a residue. The residue was purified by prep-TLC (DCM/CH$_3$OH=10/1) to give (3S)-3-amino-1'-[1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidine]-4-carbonitrile (217.0 mg, 71% yield) as a yellow solid. LCMS m/z (M+H)$^+$= 666.2.

Step b: (R)—N-[(3S)-4-cyano-1'-[1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin-3-yl]-2-methylpropane-2-sulfinamide (167.0 mg, 0.3 mmol) was added into HCl/MeOH (20.0 mL, 4 M). The reaction mixture was stirred at 50° C. for 0.5 hour. The combined reaction mixture was concentrated, and the residue was purified by prep-HPLC (basic condition). (3S)-3-amino-1'-[3-(1,2,3,4-tetrahydro-1,5-naphthyridin-1-yl)-1H-pyrazolo[3,4-b]pyrazin-6-yl]-1,3-dihydrospiro[indene-2,4'-piperidine]-4-carbonitrile (88.8 mg, 61% yield) was obtained as a yellow solid. LCMS m/z (M+H)$^+$=478.0; $^1$H NMR (400 MHz, DMSO-d6) δ 12.60 (s, 1H), 8.33 (s, 1H), 7.91 (d, J=1.6 Hz, 1H), 7.64 (d, J=7.6 Hz, 1H), 7.56-7.48 (m, 2H), 7.48-7.41 (m, 1H), 6.97 (t, J=4.4 Hz, 1H), 4.20-4.09 (m, 3H), 3.97-3.94 (m, 2H), 3.44-3.41 (m, 2H), 3.10 (d, J=12.8 Hz, 1H), 2.94 (t, J=6.4 Hz, 2H), 2.86 (d, J=16.4 Hz, 1H), 2.10-2.05 (m, 2H), 1.84-1.43 (m, 4H).

Method 9 Table: Compounds synthesized via Method 9, with the cross-coupling of 1-(6-chloro-1-(tetrahydro-2H-pyran-2-yl)-1H-pyrazolo[3,4-b]pyrazin-3-yl)-1,2,3,4-tetrahydro-1,5-naphthyridine (Intermediate AA) with various Amines in Step a

| Example #[a] | Step a Amine | LCMS m/z (M + H)$^+$ | $^1$H NMR (400 MHz, DMSO-d6) δ ppm |
|---|---|---|---|
| 106 | BL | 484.1 | (CD3OD) 8.26 (s, 1H), 7.87~7.89 (m, 1H), 7.55~7.58 (m, 1H), 7.31~7.34 (m, 1H), 7.00~7.04 (m, 1H), 6.64~6.67 (m, 1H), 4.36~4.40 (m, 2H), 3.94~3.97 (m, 5H), 3.91 (s, 1H), 3.40~3.51 (m, 2H), 3.04~3.11 (m, 3H), 2.77~2.82 (m, 1H), 2.18~2.26 (m, 2H), 1.86~1.98 (m, 2H), 1.68~1.73 (m, 1H), 1.51~1.55 (m, 1H). |
| 107 | BO | 478.1 | 13.03 (br, 1H), 8.89 (s, 3H), 8.44 (s, 1H), 8.15 (d, J = 7.6 Hz, 2H), 7.86-7.80 (m, 3H), 7.63-7.58 (m, 1H), 4.50-4.43 (m, 3H), 4.07-4.04 (m, 2H), 3.37-3.24 (m, 5H), 3.05 (d, J = 16.8 Hz, 1H), 2.20-2.14 (m, 2H), 1.92-1.75 (m, 2H), 1.61-1.53 (m, 2H). |
| 108 | BN | 484.1 | (CD3OD) 8.37 (s, 1H), 8.23 (d, J = 8.8 Hz, 1H), 8.07-8.04 (m, 2H), 7.57 (dd, J = 6.0, 8.4 Hz, 1H), 7.17 (d, J = 8.8 Hz, 1H), 4.60-4.55 (m, 2H), 4.46 (br d, J = 14.0 Hz, 1H), 4.12-4.07 (m, 5H), 3.56-3.34 (m, 4H), 3.28-3.26 (m, 2H), 2.33-2.27 (m, 2H), 2.01-1.76 (m, 4H) |
| 109 | CD | 489.1 | 13.04 (m, 1H), 8.93 (s, 3H), 8.43 (s, 1H), 8.16-8.12 (m, 2H), 7.62-7.57 (m, 1H), 7.46-7.43 (m, 1H), 7.25 (m, 1H), 4.44-4.42 (m, 3H), 4.06-4.03 (m, 2H), 3.22-3.26 (m, 5H), 3.03-2.98 (m, 1H), 2.17-2.14 (m, 2H), 1.86-1.82 (m, 2H), 1.62 (m, 2H). |
| 110 | CP | 457.1 | 8.37 (s, 1H), 8.03~8.07 (m, 2H), 7.54~7.60 (m, 2H), 4.58~4.62 (m, 1H), 4.46~4.50 (m, 1H), 4.23 (s, 1H), 4.08~4.24 (m, 2H), 3.88 (s, 3H), 3.48~3.51 (m, 1H), 3.28~3.32 (m, 3H), 3.18~3.23 (m, 1H), 2.96~3.01 (m, 1H), 2.29~2.36 (m, 2H), 1.98~2.02 (m, 2H), 1.84~1.89 (m, 2H). |
| 111[b] | I | 441.2 | 8.41 (d, J = 1.26 Hz, 1H), 8.24 (s, 1H), 8.12-8.23 (m, 2H), 7.46 (br d, J = 7.58 Hz, 1H), 7.27-7.37 (m, 1H), 7.11-7.23 (m, 3H), 7.05 (dd, J = 4.67, 8.21 Hz, 1H), 4.23-4.35 (m, 2H), 3.88 (s, 1H), 3.83 (dd, J = 5.31, 6.57 Hz, 2H), 3.17-3.24 (m, 2H), 3.08 (d, J = 15.92 Hz, 1H), 2.91 (t, J = 6.82 Hz, 2H), 2.62-2.70 (m, 1H), 1.94-2.03 (m, 2H), 1.75 (dt, J = 4.17, 12.57 Hz, 1H), 1.58-1.68 (m, 1H), 1.51 (br d, J = 12.13 Hz, 1H), 1.14 (br d, J = 13.39 Hz, 1H) |
| 112 | CR | 489.1 | (CD3OD) 8.37 (s, 1H), 8.08-8.05 (m, 2H), 7.61-7.58 (m, 1H), 7.28-7.14 (m, 2H), 4.89 (s, 1H), 4.58-4.41 (m, 2H), 4.12-4.06 (m, 2H), 3.52-3.41 (m, 2H), 3.31-3.28 (m, 4H), 2.34-2.29 (m, 2H), 2.04-1.98 (m, 1H), 1.91-1.85 (m, 2H), 1.72-1.68 (m, 1H). |
| 113 | CV | 468.1 | (CD3OD) 9.68 (br s, 1H), 8.17 (s, 1H), 8.06-8.05 (m, 1H), 7.66 (d, d, J = 7.2 Hz,, 1H), 7.26-7.24 (m, 1H), 7.17-7.15 (m, 1H), 6.98-6.95 (m, 1H), 6.73 (t, J = 7.2 Hz, 1H), 6.45 (d, J = 7.6 Hz, 1H), 4.57-4.44 (m, 2H), 4.25 (s, 1H), 4.11-4.09 (m, 2H), 3.30-3.25 (m, 2H), 3.09 (t, J = 6.4 Hz, 2H), 2.65 (s, 3H), 2.24-2.19 (m, 3H), 1.95-1.77 (m, 2H), 1.47-1.44 (m, 1H). |
| 114[c] | CN | 425.1 | (CDCl3) 11.02 (br, 1H), 7.93-7.96 (m, 1H), 7.59 (s, 1H), 7.49-7.53 (m, 1H), 7.15-7.27 (m, 4H), 6.80-6.85 (m, 1H), 4.35 (d, J = 8.4 Hz, 1H), 4.33 (s, 1H), 4.30 (d, J = 8.8 Hz, 1H), 4.19 (d, J = 8.8 Hz, 1H), 4.04-4.08 (m, 2H), 3.89 (d, J = 8.8 Hz, 1H), 3.38 (d, J = 15.6 Hz, 1H), 3.19 (d, J = 15.6 Hz, 1H), 3.06-3.11 (m, 2H), 2.15-2.23 (m, 1H). |
| 115[c] | CO | 425.1 | (CDCl3) 11.11 (br, 1H), 8.02-8.05 (m, 1H), 7.68 (s, 1H), 7.58-7.62 (m, 1H), 7.25-7.36 (m, 4H), 6.90-6.94 (m, 1H), 4.44 (d, J = 8.4 Hz, 1H), 4.24 (s, 1H), 4.21 (d, J = 8.8 Hz, |

-continued

| Example #[a] | Step a Amine | LCMS m/z (M + H)+ | 1H NMR (400 MHz, DMSO-d6) δ ppm |
|---|---|---|---|
| 226 | EG | 481.3 | 1H), 4.10 (d, J = 8.8 Hz, 1H), 3.96-4.00 (m, 2H), 3.80 (d, J = 8.8 Hz, 1H), 3.29 (d,J = 15.6 Hz, 1H), 3.10 (d, J = 15.6 Hz, 1H), 2.97-3.02 (m, 2H), 2.07-2.14 (m, 1H). (CD3OD) 10.37-10.07 (br, 1H), 8.07-8.05 (m, 1H), 8.03 (s, 1H), 7.71-7.68 (m, 1H), 7.26-7.24 (d, J = 8.0 Hz, 1H), 7.22-7.18 (t, J = 8.0 Hz, 1H), 6.99-6.96 (q, J = 4.0 Hz, 1H), 6.92-6.88 (t, J = 8.0 Hz, 1H), 6.82-6.80 (d, J = 8 Hz, 1H), 4.83 (s, 1H), 4.73 (s, 1H), 4.12-4.09 (t, J = 6 Hz, 2H), 3.89 (s, 1H), 3.11-3.08 (t, J = 6 Hz, 2H), 2.56-2.47 (m, 2H), 2.37-2.32 (m, 1H), 2.24-2.18 (m, 2H), 2.16-2.10 (m, 2H), 2.07-1.97 (m, 2H), 1.91-1.87 (m, 1H). |
| 227 | EX | 479.3 | (CDCl3) 10.03-9.99 (br, 1H), 8.06-8.05 (m, 1H), 7.99 (s, 1H), 7.70-7.61 (m, 1H), 7.36-7.34 (m, 1H), 7.22-7.20 (m, 1H), 7.19-7.16 (m, 1H), 7.12-7.10 (m, 1H), 6.98-6.95 (q, J = 4.0 Hz, 1H), 4.73 (s, 1H), 4.64 (s, 1H), 4.25 (s, 1H), 4.12-4.09 (t, J = 6.0 Hz, 2H), 3.11-3.08 (t, J = 6.0 Hz, 2H), 2.92-2.88 (d, J = 16 Hz, 1H), 2.47-2.44 (d, J = 12 Hz, 1H), 2.34-2.30 (d, J = 16Hz, 1H), 2.24-2.21 (m, 2H), 2.20-2.18 (m, 2H), 2.14-2.08 (m, 2H), 1.98-1.86 (m, 2H), 1.68-1.65 (d, J = 12 Hz, 1H). |

[a]Step a was run anywhere from 70-100° C. for 2-12 hr. Hunigs base could also be used in Step a and CsF could also be used as an additive. Step b run anywhere from 25-50° C.
[b]Instead of Intermediate AA, (Intermediate CE) was used as the coupling partner in Step a. No deprotection Step b was required.
[c]After Step a, the intermediate was protected with Boc2O before purification; absolute configuration of the enantiomer was arbitrarily assigned.

Method 9 Table 2: Compounds Synthesized Via Method 9, with the Cross-couling of(S)-1,3-dihydrosiro[indene-2,4'-piperidin]-1-amine (Intermediate I) with various Chlorides in Step a

| Example #[a] | Step a Chloride | LCMS m/z (M + H)+ | 1H NMR (400 MHz, CD3OD) δ ppm |
|---|---|---|---|
| 178[b] | DA | 527.0 | 7.36-7.39 (m, 2H), 7.20-7.26 (m, 3H), 7.10-1.15 (m, 1H), 6.95-6.97 (m, 1H), 4.01 (s, 1H), 3.54-3.58 (m, 2H), 3.51 (s, 3H), 3.12-3.19 (m, 3H), 2.77-2.82 (m, 1H), 1.92-2.06 (m, 2H), 1.63-1.67 (m, 1H), 1.46-1.50 (m, 1H). |
| 179[c,d] | 2-chloro-quinoxaline (CAS# 1448-87-9) | 330.9 | 9.13 (s, 1H), 8.04-8.02 (m, 1H), 7.96-7.94 (m, 1H), 7.84-7.80 (m, 1H), 7.67-7.62 (m, 1H), 7.57 (d, J = 7.2 Hz, 1H), 7.47-7.36 (m, 3H), 4.67-4.64 (m, 1H), 4.53-4.50 (m, 2H), 3.84-3.74 (m, 2H), 3.30-3.24 (m, 2H), 2.17-2.00 (m, 3H), 1.83 (d, J = 12.8 Hz, 1H). |
| 180[d] | 8-chloro imidazo-[1,2-a]-pyrazine (CAS# 69214-33-1) | 319.9 | (DMSO-d6) 7.97-7.95 (m, 1H), 7.93 (d, J = 4.4 Hz, 1H), 7.61-7.59 (m, 1H), 7.38-7.35 (m, 2H), 7.28-7.21 (m, 3H), 5.28-5.21 (m, 2H), 3.88 (s, 1H), 3.38-3.35 (m, 2H), 3.17 (d, J = 15.6 Hz, 1H), 2.70 (d, J= 15.6 Hz, 1H), 1.91-1.72 (m, 2H), 1.58 (d, J = 12.4 Hz, 1H), 1.18 (d, J = 13.2 Hz, 1H). |
| 181[d] | DC | 335.1 | 8.26 (s, 1H), 8.20 (s, 1H), 7.41-7.34 (m, 1H), 7.30-7.15 (m, 3H), 3.99 (br s, 1H), 3.98 (s, 3H), 3.56 (br d, J = 11.6 Hz, 2H), 3.33 (td, J = 1.6, 3.3 Hz, 2H), 3.22 (d, J = 15.8 Hz, 1H), 2.90-2.81 (m, 1H), 1.98-1.75 (m, 2H), 1.70 (br d, J = 13.3 Hz, 1H), 1.53 (br d, J = 13.1 Hz, 1H) |
| 182[d] | DD | 335.1 | 8.57 (s, 1H), 8.24 (s, 1H), 7.49-7.13 (m, 4H), 4.69-4.56 (m, 2H), 4.20-4.10 (m, 3H), 4.02-3.95 (m, 1H), 3.65-3.47 (m, 2H), 3.33 (td, J = 1.6, 3.3 Hz, 6H), 3.27-3.17 (m, 1H), 2.87 (d, J = 15.8 Hz, 1H), 1.99-1.78 (m, 2H), 1.75-1.66 (m, 1H), 1.53 (br d, J = 13.6 Hz, 1H) |
| 183[c] | DH | 334.0 | 7.99 (s, 1H), 7.87 (d, J = 5.8 Hz, 1H), 7.43-7.35 (m, 3H), 7.28-7.16 (m, 3H), 6.94 (d, J = 5.8 Hz, 1H), 4.81-4.71 (m, 2H), 3.97 (m, 3H), 3.84 (s, 3H), 3.46-3.34 (m, 2H), 3.17 (d, J = 15.8 Hz, 1H), 2.82 (d, J = 15.8 Hz, 1H), 2.00-1.81 (m, 2H), 1.65-1.55 (m, 1H), 1.52- 1.41 (m, 1H) |
| 184[c] | DG | 334.0 | 8.24 (s, 1H), 8.02 (d, J = 5.8 Hz, 1H), 7.45-7.33 (m, 2H), 7.29-7.17 (m, 3H), 4.23 (s, 3H), 4.09-3.98 (m, 1H), 3.41 (br dd, J = 3.5, 12.0 Hz, 2H), 3.27-3.13 (m, 3H), 2.81 (br d, J = 15.8 Hz, 1H), 2.22-1.87 (m, 2H), 1.72 (br s, 1H), 1.54 (br d, J = 12.5 Hz, 1H) |
| 228[d,f] | EJ | 351.2 | (CDCl3) 8.47 (br d, J = 4.4 Hz, 1 H), 7.30-7.28 (m, 1 H), 7.17-7.13 (m, 3 H), 6.93 (s, 1 H), 6.78 (s, 1 H), 4.21-4.13 (m, 2 H), 3.81 (s, 1 H), 3.11-3.01 (m, 3 H), 2.75 (d, J = 4.4 Hz, 3 H), 2.61 (br d, J = 15.6 Hz, 1 H), 2.33 (s, 3 H), 1.79-1.71 (m, 1 H), 1.65-1.60 (m, 1 H), 1.48 (br d, J = 13.6 Hz, 1 H), 1.10-1.05 (m, 1 H) |
| 229[d,g] | DI | 359.1 | (CD3OD) δ 7.83 (s, 1H), 7.73 (s, 1H), 7.56 (d, J = 7.2 Hz, 1H), 7.46-7.36 (m, 3H), 4.66-4.51 (m, 2H), 4.03-3.88 (m, 1H), 3.75-3.57 (m, 2H), 3.31-3.20 (m, 2H), 2.12-1.86 (m, 4H), 1.78-1.72 (m, 1H), 1.10-1.04 (m, 2H), 0.81-0.77 (m, 2H) |
| 230[d,h] | EN | 389.1 | (CD3OD) 9.38 (s, 1H), 7.82 (s, 1 H), 7.31-7.29 (m, 1 H), 7.20-7.15 (m, 3 H), 4.18-4.11 (m, 2 H), 3.86 (s, 1 H), 3.26-3.16 (m, 4 H), 3.09-3.05 (d, J = 15.6 Hz, 1 H), 2.66 (s, 1 H), 1.87-1.80 (m, 1 H), 1.77-1.70 (m, 1 H), 1.56-1.53 (d, J = 13.2 Hz, 1 H), 1.17-1.13 (d, J = 13.2 Hz, 1 H) |
| 231[d,i] | EH | 465.2 | (CDCl3) 2.89 (d, J = 1.2 Hz, 1H), 8.09 (d, J = 1.2 Hz, 1H), 7.73-7.72 (d, J = 4.0 Hz, 1H), 7.36-7.34 (m, 1H), 7.21 -7.18 (m, 2H), 7.15-7.13 (m, 1H), 6.10-6.18 (d, J = 8.0 Hz, 1H), 4.87 (s, 2H), 4.66 (s, 1H), 4.58 (s, 1H), 4.24 (s, 1H), 2.95-2.91 (d, 16 Hz, 1H), 2.47-2.43 (d, 16 Hz, 1H), 2.37-2.33 (d, 16 Hz, 1H), 2.21-2.17 (m, 2H), 2.13-2.04 (m, 2H), 1.94-1.81 (m, 2H), 1.68-1.64 (d, 16 Hz, 1H). |

493

-continued

| Example #[a] | Step a Chloride | LCMS m/z (M + H)+ | 1H NMR (400 MHz, CD3OD) δ ppm |
|---|---|---|---|
| 232[d,j] | EH | 467.2 | (CDCl3) 8.30 (d, J = 0.8 Hz, 1H), 8.14 (8.30 (d, J = 1.2 Hz, 1H), 7.74-7.72 (d, J = 8.0 Hz, 1H), 7.26-7.25 (m, 1H), 7.24-7.20 (t, J = 8.0 Hz, 1H), 6.94-6.90 (t, J = 8.0 Hz, 1H), 6.83-6.81 (d, J = 8.0 Hz, 1H), 6.11-6.09 (d, J = 8.0 Hz, 1H), 4.87 (s, 2H), 4.78 (s, 1H), 4.68 (s, 1H), 3.92 (s, 1H), 2.56-2.47 (m, 2H), 2.33-2.28 (m, 1H), 2.17-2.08 (m, 2H) 2.00-1.99 (m, 2H) 1.91-1.88 (m, 1H) |

[a]Step a was run anywhere from 70-100° C. for 2-12 hr. Hunigs base could also be used in Step a and CsF could also be used as an additive. Step b run anywhere from 25-5F° C.
[b]In Step a, DIPEA was used as the base and it was heated at 120° C. for 12 h. In Step b, TfOH/TFA was used for deprotection which was run at 100° C. for 16 h.
[c]Step 1 was run at 80° C. for 12 in DMF with Cs2CO3 as the base.
[d]No Step 2 deprotection required.
[e]Intermediate I was free based with sodium bicarbonate, then 2 drops of NMP was added and the mixture was heated to 140° C. for 4 h. No deprotection step was required.
[f]DIPEA was used as the base in Step a which was run at 180° C. for 1 h.
[g]The coupling in Step a was achieved using K2CO3 in IPrOh at 120° C. under microwave for 7 hrs. No Step b was required and the product was purfied using silica gel chromoatography (MeOH in DCM from 0-8%) then prep HPLC (HCl) to afford the final product.
[h]Step a was run in NMP at 180° C. with DIPEA for 2 h.
[i]Intermediate EX was used as the amine instead of Intermediate I in Step a.
[j]Intermediate EG was used as the amine instead of Intermediate I in Step a, which was achieved using DIPEA as the base in NMP at 130° C. for 1 h.

Compounds Synthesized in a Similar Fashion to Method 9:

Examples 116 and 117: Synthesis of (R)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile and (S)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile

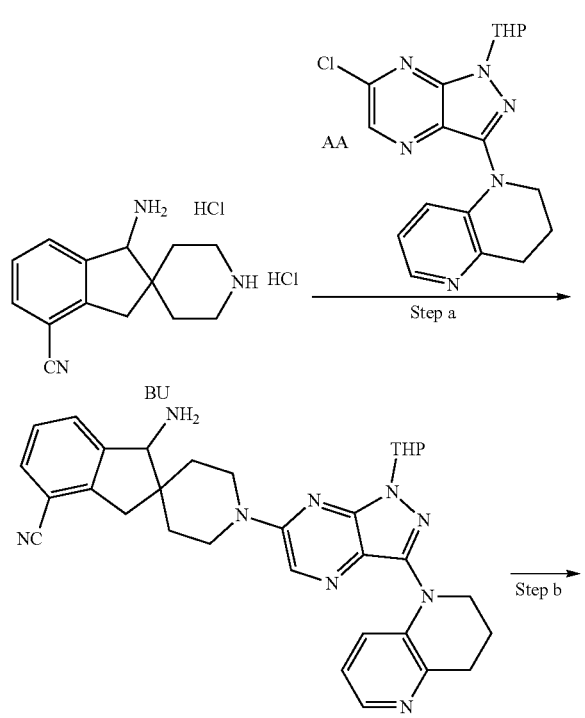

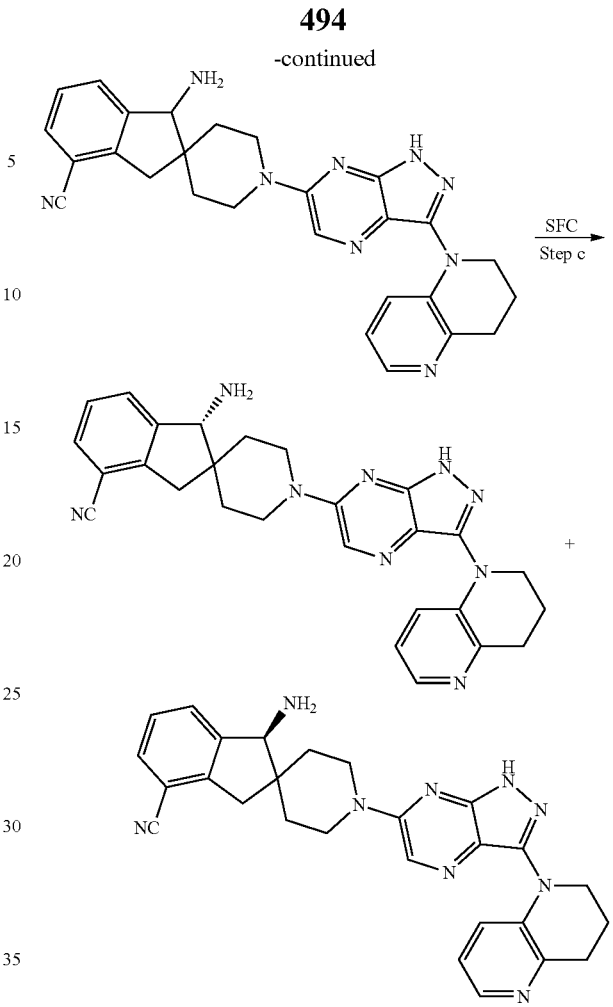

(R)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile and (S)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile was synthesized as described above in Method 9, Example 105, coupling 1-amino-,3-dihydrospiro[indene-2,4'-piperidine]-4-carbonitrile (Intermediate BU) and 1-[6-chloro-1-(oxan-2-yl)-1H-pyrazolo[3,4-b]pyrazin-3-yl]-1,2,3,4-tetrahydro-1,5-naphthyridine (Intermediate AA) in Step a. 3-amino-1'-[3-(1,2,3,4-tetrahydro-1,5-naphthyridin-1-yl)-1H-pyrazolo[3,4-b]pyrazin-6-yl]-1,3-dihydrospiro[indene-2,4'-piperidine]-7-carbonitrile (100.0 mg) was separated by preparative SFC (column: DAICEL CHIRALPAK AD (250 mm*30 mm, 10 um), Mobile phase: 0.1% NH3.H2O IPA (Begin B: 55%, End B: 55%), Flow rate: 70 mL/min) to afford the product of (R)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile (43.7 mg, R=5.24 min, the faster eluting isomer) as a yellow solid and (S)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile (31.0 mg, $R_f$=8.44 min, the slower eluting isomer) as a yellow solid. Absolute stereochemistry of the enantiomers was arbitrarily assigned. (R)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile: LCMS m/z (M+H)+= 478.2; 1HNMR (400 MHz, Methanol-d4): 8.23 (s, 1H), 7.83-7.89 (m, 1H), 7.68 (d, J=7.6 Hz, 1H), 7.57 (d, J=7.6 Hz, 1H), 7.40 (t, J=7.8 Hz, 1H), 7.29-7.34 (m, 1H), 6.96-7.02 (m, 1H), 4.63 (s, 1H), 4.34-4.48 (m, 2H), 4.03 (s, 1H), 3.90-3.97 (m, 2H), 3.34-3.44 (m, 2H), 2.92-3.07 (m, 3H), 2.13-2.25 (m, 2H), 1.78-1.99 (m, 2H), 1.60-1.72 (m, 1H), 1.37-1.49 (m, 1H). SFC: e.e. =90.0%. (S)-1-amino-1'-(3-(3,4-dihydro-1,5-naphthyridin-1(2H)-yl)-1H-pyrazolo[3,4-b]pyrazin-6-yl)-1,3-dihydrospiro[indene-2,4'-piperidine]-4-carbonitrile: LCMS m/z (M+H)$^+$=478.2; $^1$HNMR (400 MHz, Methanol-d4): 8.23 (s, 1H), 7.82-7.90 (m, 1H), 7.68 (d, J=7.6 Hz, 1H), 7.57 (d, J=7.6 Hz, 1H), 7.40 (t, J=7.8 Hz, 1H), 7.28-7.34 (m, 1H), 6.96-7.04 (m, 1H), 4.62 (s, 1H), 4.35-4.47 (m, 2H), 4.04 (s, 1H), 3.89-3.97 (m, 2H), 3.34-3.45 (m, 2H), 2.94-3.08 (m, 3H), 2.13-2.25 (m, 2H), 1.78-1.99 (m, 2H), 1.61-1.71 (m, 1H), 1.38-1.48 (m, 1H). SFC: e.e. =99.5%. Column: Chiralpak AD-3 100×4.6 mm I.D., 3 μm, Mobile phase: 40% of iso-propanol (0.1% ethanolamine) in CO$_2$, Flow rate: 2.8 mL/min, Column temperature: 40° C.

Examples 118 & 119: Synthesis of (S)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine and (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine

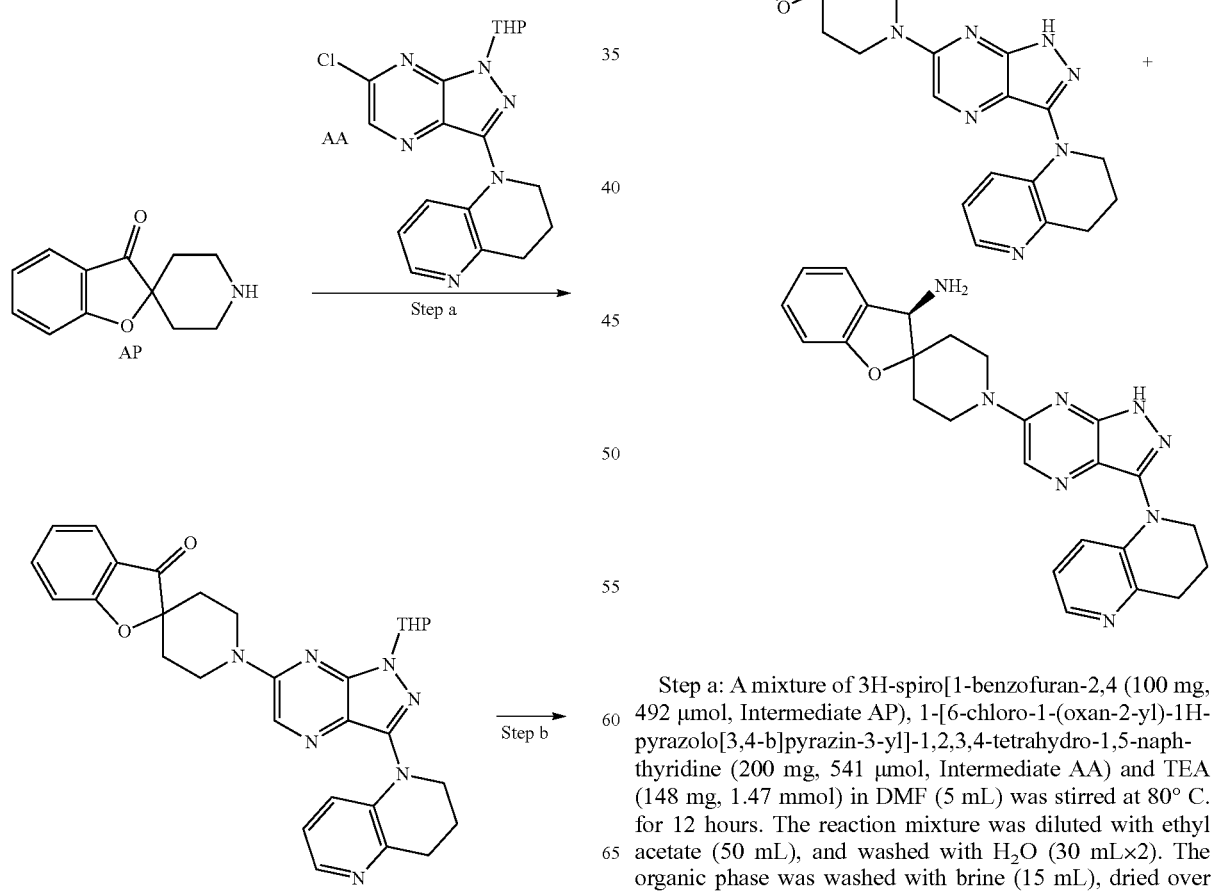

Step a: A mixture of 3H-spiro[1-benzofuran-2,4 (100 mg, 492 μmol, Intermediate AP), 1-[6-chloro-1-(oxan-2-yl)-1H-pyrazolo[3,4-b]pyrazin-3-yl]-1,2,3,4-tetrahydro-1,5-naphthyridine (200 mg, 541 μmol, Intermediate AA) and TEA (148 mg, 1.47 mmol) in DMF (5 mL) was stirred at 80° C. for 12 hours. The reaction mixture was diluted with ethyl acetate (50 mL), and washed with H$_2$O (30 mL×2). The organic phase was washed with brine (15 mL), dried over anhydrous Na$_2$SO$_4$, filtered and concentrated in vacuo to give a residue, which was purified by silica gel chromatography (eluent:petroleum ether:ethyl acetate=1:1) to give 1'-(3-(3,4-dihydro-1,5-naphthyridin-1(2H)-yl)-1-(tetrahydro-2H-pyran-2-yl)-1H-pyrazolo[3,4-b]pyrazin-6-yl)-3H-spiro[benzofuran-2,4'-piperidin]-3-one (250 mg, 95% yield) as a yellow solid. LCMS m/z (M+H)$^+$=538.1.

Step b: A solution of 1'-[1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-one (230 mg, 427 μmol), AcONH$_4$ (640 mg, 8.5 mmol) and NaBH$_3$CN (26.8 mg, 0.42 mmol) in EtOH (15 mL) was stirred at 60° C. for 1 hour. The addition of AcONH$_4$ (640 mg, 8.5 mmol) and NaBH$_3$CN (26.8 mg, 0.42 mmol) at 20° C. was repeated 2 times. The reaction mixture was stirred at 60° C. for another 11 hours. The reaction mixture was poured into H$_2$O (40 mL) and then extracted with EtOAc (40 mL×2). The combined organic layers were washed with brine (30 mL), dried over anhydrous Na$_2$SO$_4$, filtered and concentrated under reduced pressure to give crude product as a yellow solid, which was purified by prep-HPLC (NH$_3$.H$_2$O) to afford 1'-[1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-amine (87.0 mg, 38% yield) as a yellow solid. LCMS m/z (M+H)$^+$=539.1.

Step c: A mixture of 1'-[1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-amine (87 mg, 161 umol) in MeOH (5 mL) was added HCl/MeOH (400 uL, 4M). The mixture was stirred at 20° C. for 2 hours. The mixture was concentrated in vacuo to give a residue, which was purified by prep-HPLC (HCl) to afford 1'-[3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-amine hydrochloride (78.0 mg, 99% yield) as a yellow solid. LC-MS m/z (M+H)$^+$=455.0.

Step d: The product of rac-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3- amine hydrochloride (78 mg, 158 μmol) was separated by SFC (Column: DAICEL CHIRALPAK AY 250 mm×30 mm, 10 um. Condition: 0.1% NH$_3$.H$_2$O ETOH. Begin B: 45%. End B: 45%. Flow-Rate (ml/min): 70) to afford (S)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine (30.7 mg, 43% yield, the faster eluting isomer) as a yellow solid and (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine (39.2 mg, 55% yield, the slower eluting isomer) was obtained as a yellow solids. Characterization of (S)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine: LCMS m/z (M+H)$^+$=455.0; $^1$HNMR (400 MHz, Methanol-d4): δ 8.30 (s, 1H), 7.89-7.88 (m, 1H), 7.42-7.40 (m, 1H), 7.34-7.33 (m, 1H), 7.23-7.22 (m, 1H), 7.15-7.12 (m, 1H), 6.93-6.92 (m, 1H), 6.84-6.82 (m, 1H), 4.51-4.49 (m, 2H), 4.20 (s, 1H), 3.97-3.96 (m, 2H), 3.58-3.48 (m, 2H), 3.08-3.01 (m, 2H), 2.23-2.20 (m, 2H), 2.02-2.00 (m, 2H), 1.88-1.86 (m, 2H). SFC: e.e.=96.4%, R$_f$=4.82 min. Characterization of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine: LCMS m/z (M+H)$^+$=455.0; $^1$HNMR (400 MHz, MeOD-d4): δ 8.22 (s, 1H), 7.82-7.81 (m, 1H), 7.45-7.39 (m, 2H), 7.38-7.31 (m, 1H), 7.03-6.99 (m, 1H), 6.96-6.93 (m, 1H), 6.92-6.89 (m, 1H), 4.85-4.82 (m, 1H), 4.74-4.66 (m, 2H), 3.90-3.87 (m, 2H), 3.48-3.42 (m, 2H), 3.01-2.98 (m, 2H), 2.14-2.12 (m, 2H), 1.96-1.92 (m, 2H), 1.87-1.82 (m, 2H). SFC: e.e.=94.5%, R$_f$=7.86 min, Column: Chiralpak IC-3 150×4.6 mm I.D., 3 um. Mobile phase: 40% of ethanol (0.05% DEA) in CO$_2$; Flow rate: 2.5 mL/min. Column Temperature: 35° C.

Method 10, Example 233: Synthesis of (3S)-1'-[5-(cyclohexylsulfanyl)pyrazin-2-yl]-1,3-dihydrospiro[indene-2,4'-piperidin]-3-amine

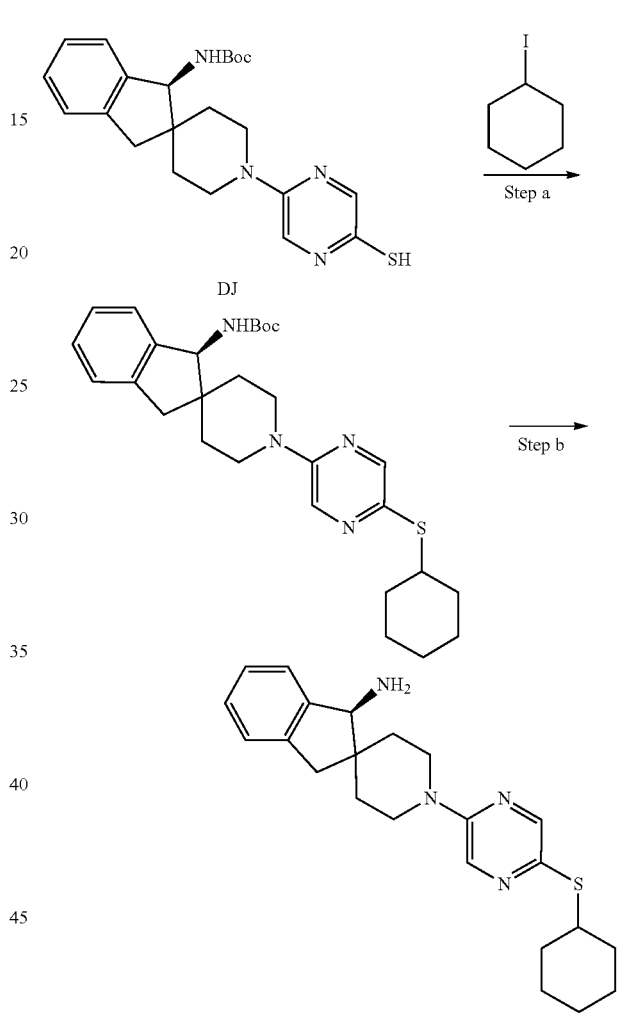

Step a: A mixture of tert-butyl N-[(3S)-1'-(5-sulfanylpyrazin-2-yl)-1,3-dihydrospiro[indene-2,4'-piperidin]-3-yl]carbamate (65.0 mg, 157 μmol, Intermediate DJ), iodocyclohexane (42.8 mg, 204 μmol) and K$_2$CO$_3$ (65.0 mg, 471 μmol) in DMF (2.00 mL) was stirred at 70° C. for 12 hours under N$_2$. The combined reaction mixture was diluted with EtOAc (100 mL), washed with H$_2$O (20 mL×3) and brine (40 mL×2), then dried over anhydrous Na$_2$SO$_4$, filtered and concentrated. The residue was purified by flash silica gel chromatography (12 g column, EtOAc in petroleum ether from 0% 15%) to give tert-butyl N-[(3S)-1'-[5-(cyclohexylsulfanyl)pyrazin-2-yl]-1,3-dihydrospiro[indene-2,4'-piperidin]-3-yl]carbamate (81.0 mg, combined product) as a yellow solid. LC-MS (ESI$^+$) m/z: 517.1 (M+Na)+.

Step b: The mixture of tert-butyl N-[(3S)-1'-[5-(cyclohexylsulfanyl)pyrazin-2-yl]-1,3-dihydrospiro[indene-2,4'-piperidin]-3-yl]carbamate (80.0 mg, 161 μmol) in HCl/MeOH (5.00 mL, 4 M) was stirred at 25° C. for 0.5 hour. The reaction mixture was then concentrated to give a residue. The residue was dissolved in MeOH (5.00 mL), and the reaction mixture was adjusted to pH=8-9 with solid $Na_2CO_3$. The mixture was then filtered, and the filtrate was concentrated to give a residue. The residue was purified by prep-HPLC (basic condition) to give (3S)-1'-[5-(cyclohexylsulfanyl)pyrazin-2-yl]-1,3-dihydrospiro[indene-2,4'-piperidin]-3-amine (23.6 mg,37 yield) a yellow solid. LC-MS (SI) m/z: 395.1 (M+H); $^1$NMR (400 z, $CD_3OD$): δ 8.17 (d, J=1.3 Hz, 1H), 8.09 (d, J=1.3 Hz, 1H), 7.42-7.34 (i, 1H), 7.27-7.17 (m, 3H),4.21 (td, J=3.5, 13.5 Hz, 2H),3.96 (s, 1H), 3.31-3.19 (r 3H),3.16 (d, J=15.8 Hz, 1H), 2.80 (d, J=15.8 Hz, 1H), 2.02-1.73 (m, 6H),1.70-1.56 (m, 2H),1.46-1.29 (m, 6H).

Method 10 Table: Compounds Synthesized Via Method 10. With the Cross-Coupling of Various Thiols with Various Iodides or Bromides in Step a

| Example # | Step a Thiol | Step a Bromide or Iodide | LCMS m/z (M + H)$^+$ | $^1$H NMR (400 MHz, $CD_3OD$) δ ppm |
|---|---|---|---|---|
| 234$^a$ | DJ | 3-bromo-oxolane (CAS# 19311-37-6) | 383.0 | 8.19 (s, 1H), 8.11 (s, 1H), 7.41-7.34 (m, 1H), 7.26-7.16 (m, 3H), 4.21 (br d, J = 13.4 Hz, 2H), 4.12-4.04 (m, 1H), 3.95 (m, 3H), 3.89-3.79 (m, 1H), 3.70 (dd, J = 4.8, 9.1 Hz, 1H), 3.30-3.10 (m, 3H), 2.80 (d, J = 15.6 Hz, 1H), 2.35 (br dd, J = 26.9, 13.3 Hz, 1H), 1.98-1.73 (m, 3H), 1.66-1.57 (m, 1H), 1.48-1.39 (m, 1H) |
| 235$^a$ | DJ | 3-bromo-oxolane (CAS# 19311-37-6) | 383.1 | 8.21-8.16 (m, 1H), 8.12-8.08 (m, 1H), 7.43-7.35 (m, 1H), 7.26-7.16 (m, 3H), 4.21 (br d, J = 13.4 Hz, 2H), 4.08 (dd, J = 6.8, 8.7 Hz, 1H), 4.01-3.90 (m, 3H), 3.88-3.79 (m, 1H), 3.70 (dd, J = 4.8, 9.1 Hz, 1H), 3.37 (s, 2H), 3.31-3.10 (m, 3H), 2.80 (br d, J = 15.6 Hz, 1H), 2.35 (br dd, J = 7.0, 13.4 Hz, 1H), 1.98-1.69 (m, 3H), 1.60 (br d, J = 13.4 Hz, 1H), 1.43 (br d, J = 13.3 Hz, 1H) |
| 236$^b$ | DJ | bromo cyclobutane | 367.0 | 8.16 (d, J = 1.3 Hz, 1H), 8.04 (d, J = 1.3 Hz, 1H), 7.41-7.36 (m, 1H), 7.26-7.19 (m, 3H), 4.25-4.15 (m, 2H), 4.05-3.93 (m 2H) 3.31-3.12 (m, 3H), 2.82 (d, J = 15.8 Hz, 1H), 2.47-2.35 (m, 2H), 2.15-1.72 (m, 6H), 1.60 (br dd, J = 1.9, 13.4 Hz, 1H), 1.45 (br dd, J = 1.5, 13.6 Hz, 1H) |
| 237$^c$ | FT | (bromo-methyl) cyclo-propane | 383.0 | 8.06 (s, 1H), 7.55-7.47 (m, 1H), 7.43-7.29 (m, 3H), 4.72-4.59 (m, 1H), 4.46-4.36 (m, 1H), 4.32-4.22 (m, 1H), 3.62-3.40 (m, 2H), 3.25-3.13 (m, 3H), 3.09-2.94 (m, 1H), 0 1.96-1.83 (m, 4H), 1.72-1.63 (m, 2H),1.53-1.47 (m, 1H), 1.15-1.05 (m, 2H). |
| 238$^d$ | FA | (bromo-methyl) cyclo-propane | 397.1 | 8.52 (s, 1H), 7.93 (s, 1H), 7.50 (m, 1H), 7.42-7.26 (m, 3H), 4.39 (s, 1H), 3.71-3.44 (m, 5H), 3.25-3.04 (m, 4H), 2.72 (m, 2H), 2.10-1.84 (m, 2H), 1.80-1.51 (m, 2H), 0.95 |
| 239$^d$ | FF | (bromo-methyl) cyclo-propane | 387.0 | (m, 1H), 0.62-0.40 (m, 2H), 0.29-0.07 (m, 2H) 8.25 (s, 1H), 8.02 (m, 1H), 7.92 (m, 1H), 7.01 (m, 1H), 6.93-6.79 (m, 1H), 6.67 (m, 1H), 4.28-4.12 (m, 2H), 4.02 (s, 1H), 3.29-3.14 (m, 2H), 2.75 (m, 2H), 1.89-1.73 (m, 2H), 1.71-1.52 (m, 2H), 0.94-0.72 (m, 1H), 0.45-0.22 (m, 2H), 0.10-0.09 (m, 2H) |
| 240$^d$ | FR | (bromo-methyl) cyclo-propane | 387.0 | 8.21 (s, 1H), 8.01 (m, 1H), 7.90 (m, 1H), 7.27 (m, 1H), 6.62-6.40 (m, 2H), 4.34-4.14 (m, 2H), 4.03 (m, 1H), 3.28-3.11 (m, 2H), 2.74 (m, 2H), 1.92-1.75 (m, 2H), 1.73-1.52 (m, 2H), 0.82 (s, 1H), 0.45-0.22 (m, 2H), 0.10-0.15 (m, 2H) |

$^a$The racemic compound from Step b was separated by Chiral-SFC ( DAICEL CHIRALCEL OD-H(250 mm * 30 mm, 5 um). Mobile phase: 30% of EtOH (0.1% NH3 · H2O) in CO2. Flow rate: 70 mL/min. Absolute configuration was arbitrailv assigned.
$^b$Step a ran at 80° C. for 12 h.
$^c$TEA in DMF at rt for 1 h was utilized in Step a. Step b used TFA/TfOH at 100° C. for 1 hr for the deprotection.
$^d$TEA used as the base in Step a. EtAOc was used as a solvent in Step b.

Compounds Synthesized in a Similar Fashion to Method 10:

Example 241: Synthesis of (S)-1'-(5-(cyclopropyl-thio)pyrazin-2-yl)-1,3-dihydrospiro[indene-2,4'-piperidin]-1-amine

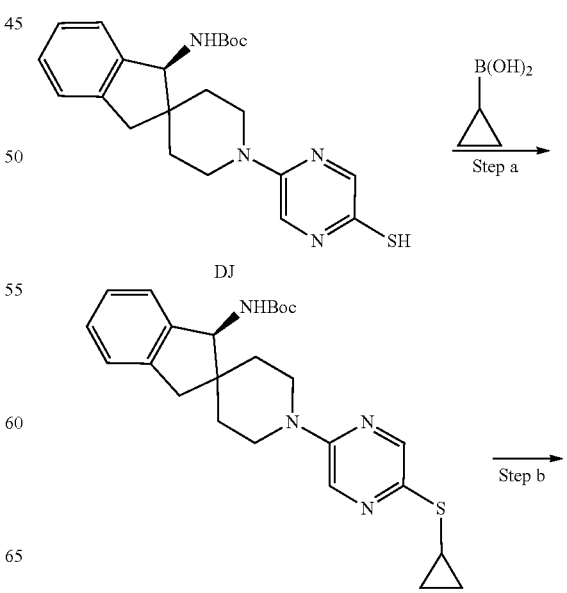

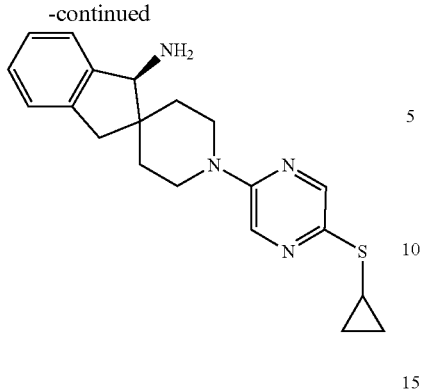

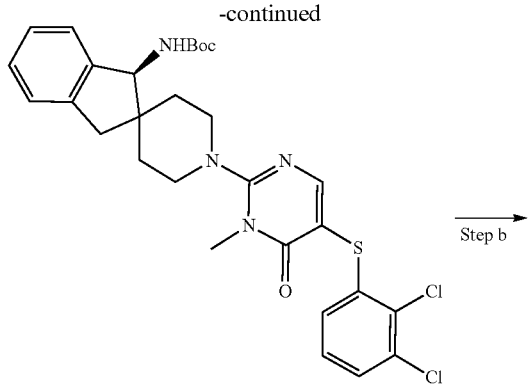

Step a: A mixture of tert-butyl N-[(3S)-1'-(5-sulfanylpyrazin-2-yl)-1,3-dihydrospiro[indene-2,4'-piperidin]-3-yl]carbamate (130.0 mg, 315 μmol, Intermediate DJ), cyclopropylboronic acid (134.0 mg, 1.57 mmol), Cu(OAc)$_2$ (114.0 mg, 630 μmol) and TEA (261 μL, 1.88 mmol) in DCM (10 mL) was stirred at 40° C. for 12 h under O2. The reaction mixture was then filtered and the filtrate was concentrated to give a residue. The residue was purified by flash silica gel chromatography (4 g column, EtOAc in petroleum ether from 0% 20%) to give tert-butyl N-[(3S)-1'-[5-(cyclopropylsulfanyl)pyrazin-2-yl]-1,3-dihydrospiro[indene-2,4'-piperidin]-3-yl]carbamate (42.0 mg, 30% yield) as a white solid. LC-MS (ESI$^+$) m/z: 453.1 (M+H)$^+$.

Step b: A mixture of tert-butyl N-[(3S)-1'-[5-(cyclopropylsulfanyl)pyrazin-2-yl]-1,3-dihydrospiro[indene-2,4'-piperidin]-3-yl]carbamate (40.0 mg, 88.3 μmol) in HCl/MeOH (5.00 mL, 4 M) was stirred at 25° C. for 0.5 hour. The mixture was concentrated to give a residue and the residue was dissolved in MeOH (3 mL). The mixture was adjusted to pH=9-10 with solid Na$_2$CO$_3$. The mixture was then filtered and the filtrate was purified by prep-HPLC (basic condition) to afford (S)-1'-(5-(cyclopropylthio)pyrazin-2-yl)-1,3-dihydrospiro[indene-2,4'-piperidin]-1-amine (13.1 mg, 42% yield) as a yellow solid. LC-MS (ESI$^+$) m/z: 352.9 (M+H)$^+$; $^1$H NMR (400 MHz, CD$_3$OD): δ 8.20 (d, J=1.5 Hz, 1H), 8.13 (d, J=1.5 Hz, 1H), 7.43-7.35 (m, 1H), 7.27-7.17 (m, 3H), 4.19 (m, 2H), 3.97 (s, 1H), 3.30-3.12 (m, 3H), 2.82 (d, J=15.8 Hz, 1H), 2.38-2.28 (m, 1H), 1.97-1.72 (m, 2H), 1.61 (m, 1H), 1.45 (m, 1H), 1.09-1.00 (m, 2H), 0.72-0.63 (m, 2H).

Example 242: Synthesis (S)-2-(1-amino-1,3-dihydrospiro[indene-2,4'-piperidin]-1'-yl)-5-((2,3-dichlorophenyl)thio)-3-methylpyrimidin-4(3H)-one

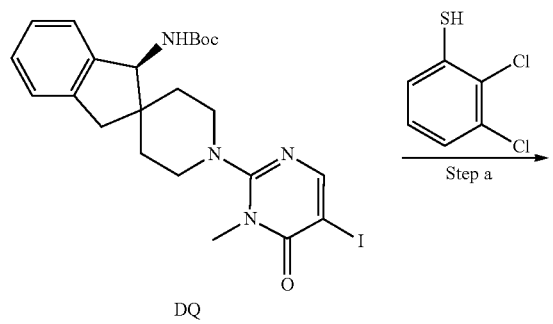

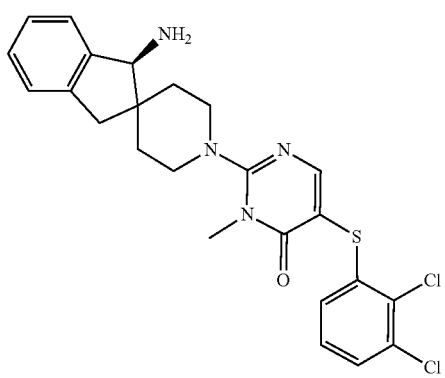

Step a: Tert-butyl (S)-tert-butyl (1'-(5-iodo-1-methyl-6-oxo-1,6-dihydropyrimidin-2-yl)-1,3-dihydrospiro[indene-2,4'-piperidin]-1-yl)carbamate (75.0 mg, 139 μmol, Intermediate DQ), XantPhos (16.0 mg, 27.8 μmol), DIPEA (46.1 μL, 278 μmol), Pd$_2$(dba)$_3$ (12.7 mg, 13.9 μmol) and 2,3-dichlorobenzenethiol (29.7 mg, 166 μmol, CAS #17231-95-7) were placed into dioxane (4.0 mL). The reaction mixture was evacuated and refilled 3 times using N$_2$. The reaction mixture was stirred at 100° C. for 12 hours. The reaction mixture was then concentrated and purified by flash silica gel chromatography (petroleum ether:ethyl acetate=100:0 to 100:60) to afford (S)-tert-butyl (1'-(5-((2,3-dichlorophenyl)thio)-1-methyl-6-oxo-1,6-dihydropyrimidin-2-yl)-1,3-dihydrospiro[indene-2,4'-piperidin]-1-yl)carbamate (90.0 mg, 110% crude yield) as a brown oil. LC-MS (ESI$^+$) m/z: 587.1 (M+H)$^+$.

Step b: A mixture of (S)-tert-butyl (1'-(5-((2,3-dichlorophenyl)thio)-1-methyl-6-oxo-1,6-dihydropyrimidin-2-yl)-1,3-dihydrospiro[indene-2,4'-piperidin]-1-yl)carbamate (88 mg, 149 μmol) in HCl/EtOAc (6.00 mL, 4 M) was stirred at 15° C. for 1 hour. The reaction mixture was concentrated under reduce pressure. The residue was dissolved with MeOH (5.00 mL) and adjusted to pH=7-8 with solid Na$_2$CO$_3$. The mixture was then filtered and the filtrate was purified by prep-HPLC (HCOOH) to afford (S)-2-(1-amino-1,3-dihydrospiro[indene-2,4'-piperidin]-1'-yl)-5-((2,3-dichlorophenyl)thio)-3-methylpyrimidin-4(3H)-one (34.0 mg, 43% yield) as a white solid. LC-MS (ESI$^+$) m/z: 487.0 (M+H)$^+$; $^1$HNMR (400 MHz, Methonol-d$_4$) δ=8.53 (s, 1H), 8.15 (s, 1H), 7.52 (m, 1H), 7.45-7.29 (m, 4H), 7.15 (m, 1H), 6.89 (m, 1H), 4.40 (s, 1H), 3.90-3.62 (m, 2H), 3.56 (s, 3H), 3.39-3.34 (m, 1H), 3.32-3.27 (m, 1H), 3.24-3.06 (m, 2H), 2.15-1.86 (m, 2H), 1.85-1.56 (m, 2H).

Example 243: Synthesis of {3-[(3S)-3-amino-1,3-dihydrospiro[indene-2,4'-piperidin]-1'-yl]-6-[(2,3-dichloropyridin-4-yl)sulfanyl]pyrazin-2-yl}methanol

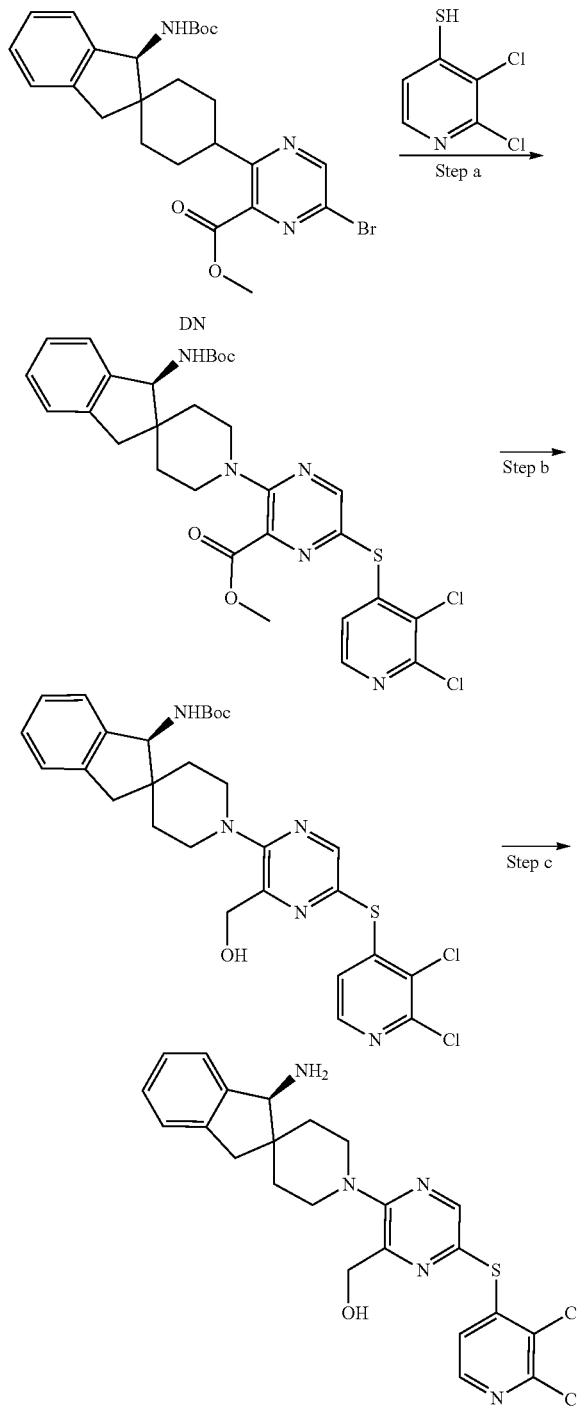

Step a: To a solution of (S)-methyl 6-bromo-3-(1-((tert-butoxycarbonyl)amino)-1,3-dihydrospiro[indene-2,4'-piperidin]-1'-yl)pyrazine-2-carboxylate (3 g, 5.79 mmol, Intermediate DN) and 2,3-dichloropyridine-4-thiol (1.14 g, 6.36 mmol, CAS #1803809-56-4) in dioxane (30 mL) were added Pd$_2$(dba)$_3$ (529 mg, 579 umol), XantPhos (665 mg, 1.15 mmol) and DIPEA (3 mL, 17.3 mmol). The reaction mixture was evacuated and refilled 3 times using N$_2$ and the reaction mixture was stirred at 120° C. for 12 hours. The reaction mixture was then concentrated under reduced pressure to give the residue, which was purified by column chromatography (petroleum ether:ethyl acetate=100:0 to 100:20) to afford methyl (S)-methyl 3-(1-((tert-butoxycarbonyl)amino)-1,3-dihydrospiro[indene-2,4'-piperidin]-1'-yl)-6-((2,3-dichloropyridin-4-yl)thio)pyrazine-2-carboxylate (1.70 g, 48% yield) as a yellow oil. LC-MS (ESI$^+$) m/z: 616.1 (M+H)$^+$.

Step b: To a solution of methyl 3-[(3S)-3-{[(tert-butoxy)carbonyl]amino}-1,3-dihydrospiro[indene-2,4'-piperidin]-1'-yl]-6-[(2,3-dichloropyridin-4-yl)sulfanyl]pyrazine-2-carboxylate (500 mg, 810 μmol) in THF (15 mL) was added DIBAL-H (806 μL, 1.21 mmol, 1.5M in toluene) at −78° C. under N$_2$. The solution was stirred for another 2 hours at the same temperature. Then the reaction was quenched by a solution of 10% aqueous AcOH (50 mL) at −78° C. and extracted with EtOAc (50 mL×3). The combined organic layers were adjusted to pH to 8-9 with saturated aqueous of NaHCO$_3$ and separated. The organic layer was washed with brine (100 mL), dried over anhydrous Na$_2$SO$_4$, filtered and concentrated to give a residue. The residue was purified by flash silica gel chromatography (petroleum ether:ethyl acetate=100:0 to 100:30) to afford tert-butyl N-[(3S)-1'-{5-[(2,3-dichloropyridin-4-yl)sulfanyl]-3-formylpyrazin-2-yl}-1,3-dihydrospiro[indene-2,4'-piperidin]-3-yl]carbamate (260 mg, 55% yield) as a yellow solid. LC-MS (ESI$^+$) m/z: 588.0 (M+H)$^+$.

Step c: Tert-butyl N-[(3S)-1'-{5-[(2,3-dichloropyridin-4-yl)sulfanyl]-3-(hydroxymethyl)pyrazin-2-yl}-1,3-dihydrospiro[indene-2,4'-piperidin]-3-yl]carbamate (120 mg, 203 μmol) was added into HCl/MeOH (10 mL, 2 M). The mixture was stirred at 25° C. for 2 h. The mixture was then adjusted to pH=7-8 with solid Na$_2$CO$_3$. The mixture was filtered and the filtrate was concentrated to give a residue. The residue was dissolved in MeOH (4 mL). Then the mixture was concentrated and was purified by prep-HPLC (FA) to afford {3-[(3S)-3-amino-1,3-dihydrospiro[indene-2,4'-piperidin]-1'-yl]-6-[(2,3-dichloropyridin-4-yl)sulfanyl]pyrazin-2-yl}methanol formate (19.2 mg, 18% yield) as a white solid. LC-MS (ESI$^+$) m/z 488.0 (M+H)$^+$; $^1$HNMR (400 MHz, Methanol-d4) δ 8.43 (s, 1H), 8.50-8.37 (m, 1H), 8.26 (s, 1H), 7.91 (d, J=5.3 Hz, 1H), 7.38 (d, J=7.5 Hz, 1H), 7.31-7.16 (m, 3H), 6.73 (d, J=5.3 Hz, 1H), 4.64-4.58 (m, 2H), 4.56-4.45 (m, 2H), 4.23 (s, 1H), 3.99-3.71 (m, 2H), 3.30-3.22 (m, 2H), 3.15-2.88 (m, 2H), 2.01-1.75 (m, 2H), 1.70-1.44 (m, 2H).

Example 244: Synthesis of (S)-(3-(1-amino-1,3-dihydrospiro[indene-2,4'-piperidin]-1'-yl)-6-((cyclopropylmethyl)thio)pyrazin-2-yl)methanol

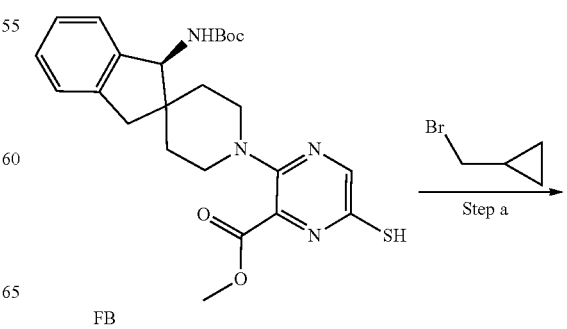

FB

505

-continued

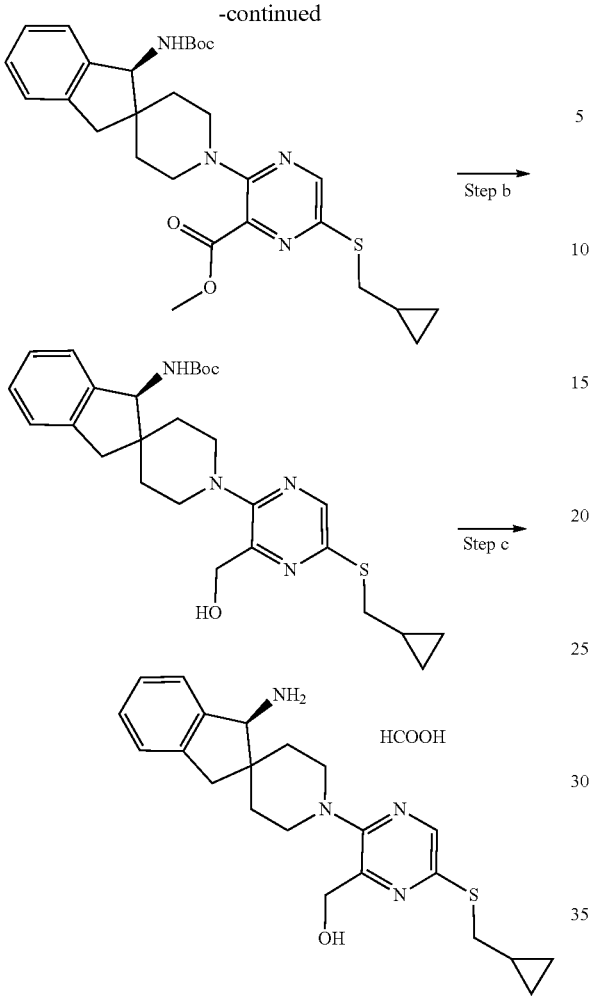

Step a: A mixture of methyl 3-[(3S)-3-{[(tert-butoxy) carbonyl]amino}-1,3-dihydrospiro[indene-2,4'-piperidin]-1'-yl]-6-sulfanylpyrazine-2-carboxylate (179.0 mg, 380.0 µmol, Intermediate FB), (bromomethyl)cyclopropane (153.0 mg, 1.1 mmol) and TEA (260 µL, 1.9 mmol) in DMF (5.0 mL) was stirred at 70° C. for 12 hours under $N_2$. The combined reaction mixture was diluted with EtOAc (100 mL), washed with $H_2O$ (20 mL×3), brine (40 mL×2), dried over anhydrous $Na_2SO_4$, filtered and concentrated. The residue was purified by flash silica gel chromatography (12 g column, EtOAc in petroleum ether from 0% 15%) to give methyl 3-[(3S)-3-{[(tert-butoxy)carbonyl]amino}-1,3-dihydrospiro[indene-2,4'-piperidin]-1'-yl]-6-[(cyclopropylmethyl)sulfanyl]pyrazine-2-carboxylate (230.0 mg, combined product) as a yellow solid. LC-MS (ESI$^+$) m/z: 525.1 (M+H)$^+$.

Step b: To a solution of methyl 3-[(3S)-3-{[(tert-butoxy) carbonyl]amino}-1,3-dihydrospiro[indene-2,4'-piperidin]-1'-yl]-6-[(cyclopropylmethyl)sulfanyl]pyrazine-2-carboxylate (230.0 mg, 438.0 µmol) in THF (15.0 mL) was added DIBAL-H (873.0 µL, 1.3 mmol, 1.5 M in toluene) at −78° C. under $N_2$. The solution was warmed to 20° C. and stirred for 4 hours. The reaction was quenched with a solution of 10% aqueous AcOH (20 mL) at −78° C. and extracted with EtOAc (30 mL×3). The combined organic layer was adjusted pH to 8~9 with saturated aqueous of $NaHCO_3$ and separated. The organic layer was washed with brine (100

506 mL), dried over anhydrous $Na_2SO_4$, filtered and concentrated to give a residue. The residue was purified by flash silica gel chromatography (petroleum ether:ethyl acetate= 100:0 to 100:100) to afford tert-butyl N-[(3S)-1'-{5-[(cyclopropylmethyl)sulfanyl]-3-(hydroxymethyl)pyrazin-2-yl}-1, 3-dihydrospiro[indene-2,4'-piperidin]-3-yl]carbamate (50.0 mg, 23% yield) as a yellow oil. LC-MS (ESI$^+$) m/z: 519.1 (M+Na)+.

Step c: A mixture of tert-butyl N-[(3S)-1'-{5-[(cyclopropylmethyl)sulfanyl]-3-(hydroxymethyl)pyrazin-2-yl}-1,3-dihydrospiro[indene-2,4'-piperidin]-3-yl]carbamate (49.0 mg, 98.6 µmol) was dissolved in EtOAc (0.5 mL). HCl/EtOAc (0.5 mL, 4 M) was then added and the reaction was stirred at 25° C. for 1 hour. The reaction mixture was then diluted with MeCN (5 mL) and adjusted to pH=7-8 with solid $Na_2CO_3$. MeOH (2.00 mL) was added and the mixture was filtered, and the filtrate was concentrated to give a residue. The residue was purified by prep-HPLC (HCOOH) to give (S)-(3-(1-amino-1,3-dihydrospiro[indene-2,4'-piperidin]-1'-yl)-6-((cyclopropylmethyl)thio)pyrazin-2-yl) methanol formate salt (2.1 mg, 5% yield) as a white solid. LC-MS (ESI$^+$) m/z: 397.1 (M+H)$^+$; $^1$HNMR (400 MHz, $CD_3OD$): δ 8.57 (br d, J=2.3 Hz, 1H), 8.10 (s, 1H), 7.47 (d, J=7.5 Hz, 1H), 7.37-7.24 (m, 3H), 4.70 (s, 2H), 4.25 (s, 1H), 3.56-3.40 (m, 2H), 3.20-3.09 (m, 5H), 3.04-2.94 (m, 1H), 2.04-1.90 (m, 2H), 1.64 (m, 2H), 1.18-1.06 (m, 1H), 0.64-0.51 (m, 2H), 0.35-0.25 (m, 2H).

Compounds Synthesized Via Further Methodology:

Example 120: Synthesis of {3-[(3S)-3-amino-1,3-dihydrospiro[indene-2,4'-piperidin]-1'-yl]pyrazin-2-yl}methanol

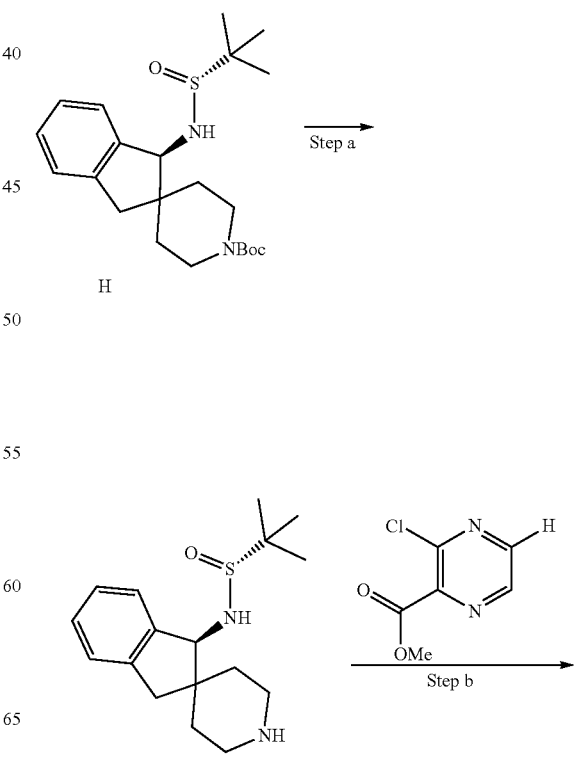

-continued

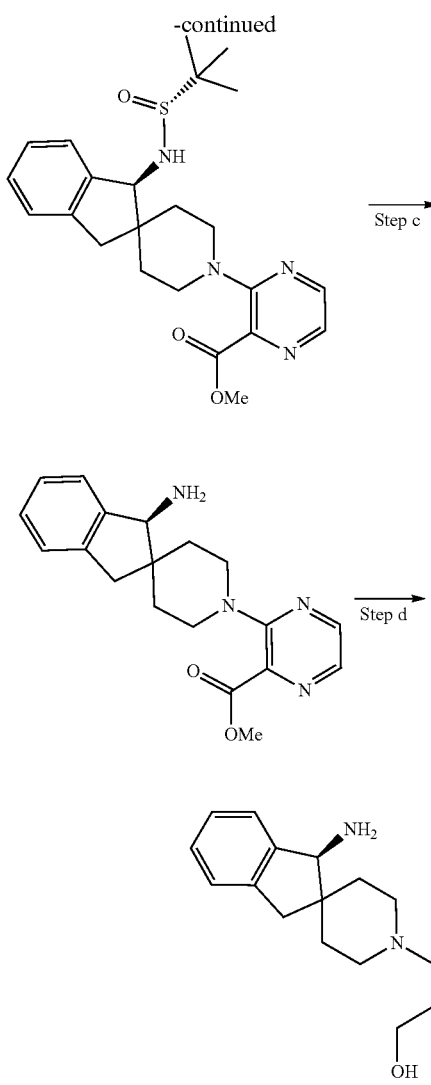

Step a: A solution of tert-butyl (1S)-1-{[(R)-2-methylpropane-2-sulfinyl]amino}-1,3-dihydrospiro[indene-2,4'-piperidine]-1'-carboxylate (1.30 g, 3.19 mmol, Intermediate H) in TFA/DCM (3.0 mL/15.0 mL) was stirred at 20° C. for 0.5 hour. The reaction mixture was concentrated under reduced pressure. The residue was diluted with MeOH (20.0 mL), adjusted pH=9 with solid Na$_2$CO$_3$, filtered and concentrated to give (R)—N-[(3S)-1,3-dihydrospiro[indene-2,4'-piperidin]-3-yl]-2-methylpropane-2-sulfinamide (2.00 g, crude, 50% purity) as a yellow solid. LCMS m/z [M+H]$^+$=307.1.

Step b: A solution of methyl 3-chloropyrazine-2-carboxylate (200.0 mg, 1.15 mmol, CAS #27825-21-4), (R)—N-[(3S)-1,3-dihydrospiro[indene-2,4'-piperidin]-3-yl]-2-methylpropane-2-sulfinamide (772.0 mg, 1.26 mmol, 50% purity) and CsF (522.0 mg, 3.44 mmol) in DMSO (15.0 mL) was stirred at 60° C. for 1 hour. The reaction mixture was poured into H$_2$O (60.0 mL) and extracted with EtOAc (60.0 mL×2). The combined organic layers were washed with brine (40.0 mL), dried over anhydrous Na$_2$SO$_4$, filtered and concentrated under reduced pressure to give an orange residue. The residue was purified by flash silica gel chromatography (12 g column, ethyl acetate in petroleum ether from 0% to 65%) to give methyl 3-[(3S)-3-{[(R)-2-methylpropane-2-sulfinyl]amino}-1,3-dihydrospiro[indene-2,4'-piperidin]-1'-yl]pyrazine-2-carboxylate (450.0 mg, 89% yield) as a yellow oil. LCMS m/z [M+H]$^+$=443.1.

Step c: A solution of methyl 3-[(3S)-3-{[(R)-2-methylpropane-2-sulfinyl]amino}-1,3-dihydrospiro[indene-2,4'-piperidin]-1'-yl]pyrazine-2-carboxylate (450.0 mg, 1.01 mmol) in HCl/MeOH (20.0 mL, 4 M) was stirred at 20° C. for 1 hour. The reaction mixture was concentrated under reduced pressure to give the product of methyl 3-[(3S)-3-amino-1,3-dihydrospiro[indene-2,4'-piperidin]-1'-yl]pyrazine-2-carboxylate hydrochloride (400.0 mg, quant. crude yield) as an orange solid. LCMS m/z [M+H]$^+$=339.1.

Step d: To a solution of methyl 3-[(3S)-3-amino-1,3-dihydrospiro[indene-2,4'-piperidin]-1'-yl]pyrazine-2-carboxylate hydrochloride (350.0 mg, 933.0 μmol) in DCM (20.0 mL) was added DIBAL-H (3.73 mL, 3.73 mmol, 1 M in toluene) at 0° C. under N$_2$. The reaction mixture was stirred at 0° C. for 1 hour. The reaction mixture was quenched with 10% AcOH. The reaction mixture was concentrated under reduced pressure to give a residue, which was purified by prep-HPLC (NH$_3$.H$_2$O) to give {3-[(3S)-3-amino-1,3-dihydrospiro[indene-2,4'-piperidin]-1'-yl]pyrazin-2-yl}methanol (58.2 mg, 20% yield) as a white solid. LCMS m/z [M+H]$^+$=311.1; $^1$HNMR (400 MHz, CD$_3$OD): 8.12-8.18 (m, 2H), 7.39-7.42 (m, 1H), 7.21-7.24 (m, 3H), 4.72 (s, 2H), 4.03 (s, 1H), 3.53-3.57 (m, 2H), 3.11-3.19 (m, 3H), 2.79-2.84 (m, 1H), 1.91-2.05 (m, 2H), 1.61-1.66 (m, 1H), 1.48-1.52 (m, 1H).

Examples 121 & 122: Synthesis of (R)-(3-(1-amino-1,3-dihydrospiro[indene-2,4'-piperidin]-1'-yl)-5-methylpyrazin-2-yl)methanol and (S)-(3-(1-amino-1,3-dihydrospiro[indene-2,4'-piperidin]-1'-yl)-5-methylpyrazin-2-yl)methanol

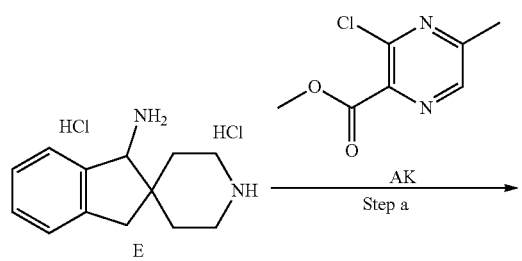

-continued
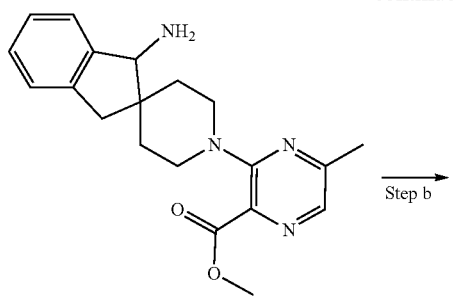
Step b
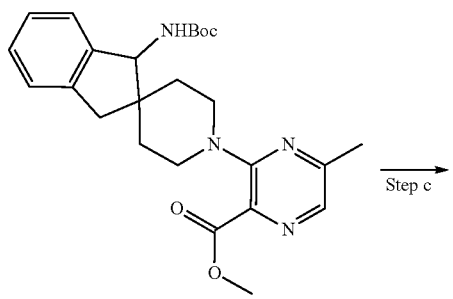
Step c
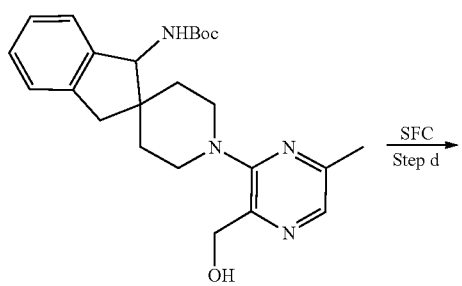
SFC
Step d
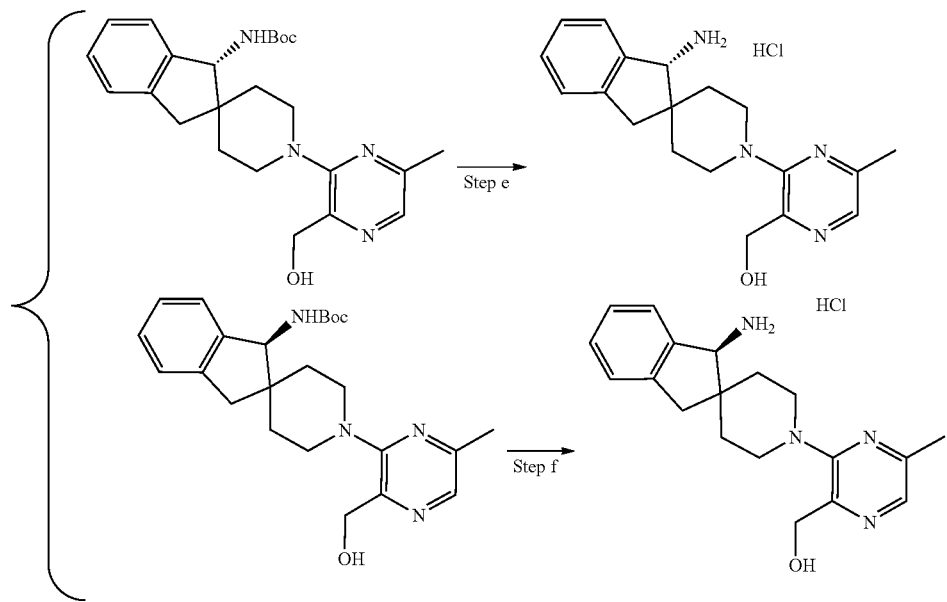

Step a: A mixture of methyl 3-chloro-5-methylpyrazine-2-carboxylate (250 mg, 1.3 mmol, Intermediate AK), 1,3-dihydrospiro[indene-2,4'-piperidin]-3-amine dihydrochloride (473 mg, 1.7 mmol, Intermediate E) and CsF (1.0 g, 6.6 mmol) in DMSO (15 mL) was stirred at 80° C. for 12 hours. The reaction mixture was used directly in the next step without further purification. LCMS m/z (M+H)⁺=352.9.

Step b: A mixture of methyl 3-{3-amino-1,3-dihydrospiro[indene-2,4'-piperidin]-1'-yl}-5-methylpyrazine-2-carboxylate (450 mg, 1.3 mmol, in DMSO from Step a) and (Boc)₂O (548 mg, 2.5 mmol) in aqueous NaOH (2N, 30 mL) was stirred at 20° C. for 12 hours. The reaction mixture was extracted with ethyl acetate (50 mL×2). The organic phases were washed with brine (20 mL), dried over anhydrous Na₂SO₄, filtered and concentrated in vacuo to give a residue. The residue was purified silica gel chromatography (ethyl acetate in petroleum ether=0% to 50%) to afford methyl 3-(3-{[(tert-butoxy)carbonyl]amino}-1,3-dihydrospiro[indene-2,4'-piperidin]-1'-yl)-5-methylpyrazine-2-carboxylate (490 mg, 85% yield) as a yellow solid. LCMS m/z (M+H)⁺=453.2.

Step c: To a mixture of LiAlH₄ (100 mg, 2.6 mmol) in anhydrous THF (10 mL) at 0° C. was added the solution of methyl 3-(3-{[(tert-butoxy)carbonyl]amino}-1,3-dihydrospiro[indene-2,4'-piperidin]-1'-yl)-5-methylpyrazine-2-carboxylate (400 mg, 883 μmol) in THF (10 mL), and the resulting mixture was stirred at this temperature for 2 hours. The reaction mixture was quenched with 15% NaOH (0.1 mL) and filtered. The filtrate was concentrated in vacuo to give a residue, which was purified by prep-HPLC (NH₃.H₂O) to afford tert-butyl N-{1'-[3-(hydroxymethyl)-6-methylpyrazin-2-yl]-1,3-dihydrospiro[indene-2,4'-piperidin]-3-yl}carbamate (80 mg, 21% yield) as a brown solid. LCMS m/z (M+H)⁺=425.1.

Step d: The compound of tert-butyl N-{1'-[3-(hydroxymethyl)-6-methylpyrazin-2-yl]-1,3-dihydrospiro[indene-2,4'-piperidin]-3-yl}carbamate (80 mg, 188 μmol) was separated by preparative SFC (column: DAICEL CHIRALPAK AY-H (250 mm×30 mm, 5 um), Mobile phase: 0.1% NH₃.H₂O EtOH (Begin B: 45%, End B: 45%), Flow rate: 70 mL/min) to afford the product of tert-butyl (R)-(1'-(3-(hydroxymethyl)-6-methylpyrazin-2-yl)-1,3-dihydrospiro[indene-2,4'-piperidin]-1-yl)carbamate (35 mg, 44% yield, Rt=1.79 min, the faster eluting isomer) as a white solid and tert-butyl (S)-(1'-(3-(hydroxymethyl)-6-methylpyrazin-2-yl)-1,3-dihydrospiro[indene-2,4'-piperidin]-1-yl)carbamate (37 mg, 46% yield, $R_R$=4.81 min, the slower eluting isomer) as a white solid. Absolute stereochemistry of the enantiomers was arbitrarily assigned. LCMS m/z (M+H)⁺=425.1. for both enantiomers, SFC: e.e.=100% for both enantiomers, Chiralpak AY 150×4.6 mm I.D., 3 um; Mobile phase: 40% of ethanol (0.05% DEA) in CO₂; Flow rate: 2.5 mL/min; Temperature: 35° C.

Step e: A mixture of tert-butyl N-[(3R)-1'-[3-(hydroxymethyl)-6-methylpyrazin-2-yl]-1,3-dihydrospiro[indene-2,4'-piperidin]-3-yl]carbamate (33 mg, 77.7 μmol) in HCl/MeOH (4 M, 2 mL) was stirred at 15° C. for 2 hours. The reaction mixture was concentrated in vacuo to afford the product of (R)-(3-(1-amino-1,3-dihydrospiro[indene-2,4'-piperidin]-1'-yl)-5-methylpyrazin-2-yl)methanol hydrochloride (23.3 mg, 90% yield) as a yellow solid. LCMS m/z (M+H)⁺=325.0; ¹HNMR (400 MHz, Methanol-d4): δ 7.99 (s, 1H), 7.55 (d, J=7.2 Hz, 1H), 7.45-7.34 (m, 3H), 4.93 (s, 2H), 4.47 (s, 1H), 4.01-3.98 (m, 1H), 3.88-3.84 (m, 1H), 3.49-3.38 (m, 2H), 3.21 (d, J=4.8 Hz, 2H), 2.63 (s, 3H), 2.10-2.03 (m, 1H), 1.97-1.90 (m, 1H), 1.83-1.80 (m, 1H), 1.69-1.65 (m, 1H).

Step f: A mixture of tert-butyl N-[(3S)-1'-[3-(hydroxymethyl)-6-methylpyrazin-2-yl]-1,3-dihydrospiro[indene-2,4'-piperidin]-3-yl]carbamate (37 mg, 87.1 μmol) in HCl/MeOH (4 M, 2 mL) was stirred at 15° C. for 2 hours. The reaction mixture was concentrated in vacuo to afford the product of (S)-(3-(1-amino-1,3-dihydrospiro[indene-2,4'-piperidin]-1'-yl)-5-methylpyrazin-2-yl)methanol hydrochloride (28.7 mg, 91% yield) as a yellow solid. LCMS m/z (M+H)⁺=324.9; ¹HNMR (400 MHz, Methanol-d4): δ 8.00 (s, 1H), 7.55 (d, J=7.6 Hz, 1H), 7.45-7.34 (m, 3H), 4.92 (s, 2H), 4.46 (s, 1H), 4.01-3.97 (m, 1H), 3.86-3.83 (m, 1H), 3.48-3.37 (m, 2H), 3.21 (s, 2H), 2.62 (s, 3H), 2.09-2.02 (m, 1H), 1.96-1.89 (m, 1H), 1.83-1.80 (m, 1H), 1.69-1.65 (m, 1H).

Example 123: Synthesis of {5-amino-3-[(3S)-3-amino-1,3-dihydrospiro[indene-2,4'-piperidin]-1'-yl]pyrazin-2-yl}methanol

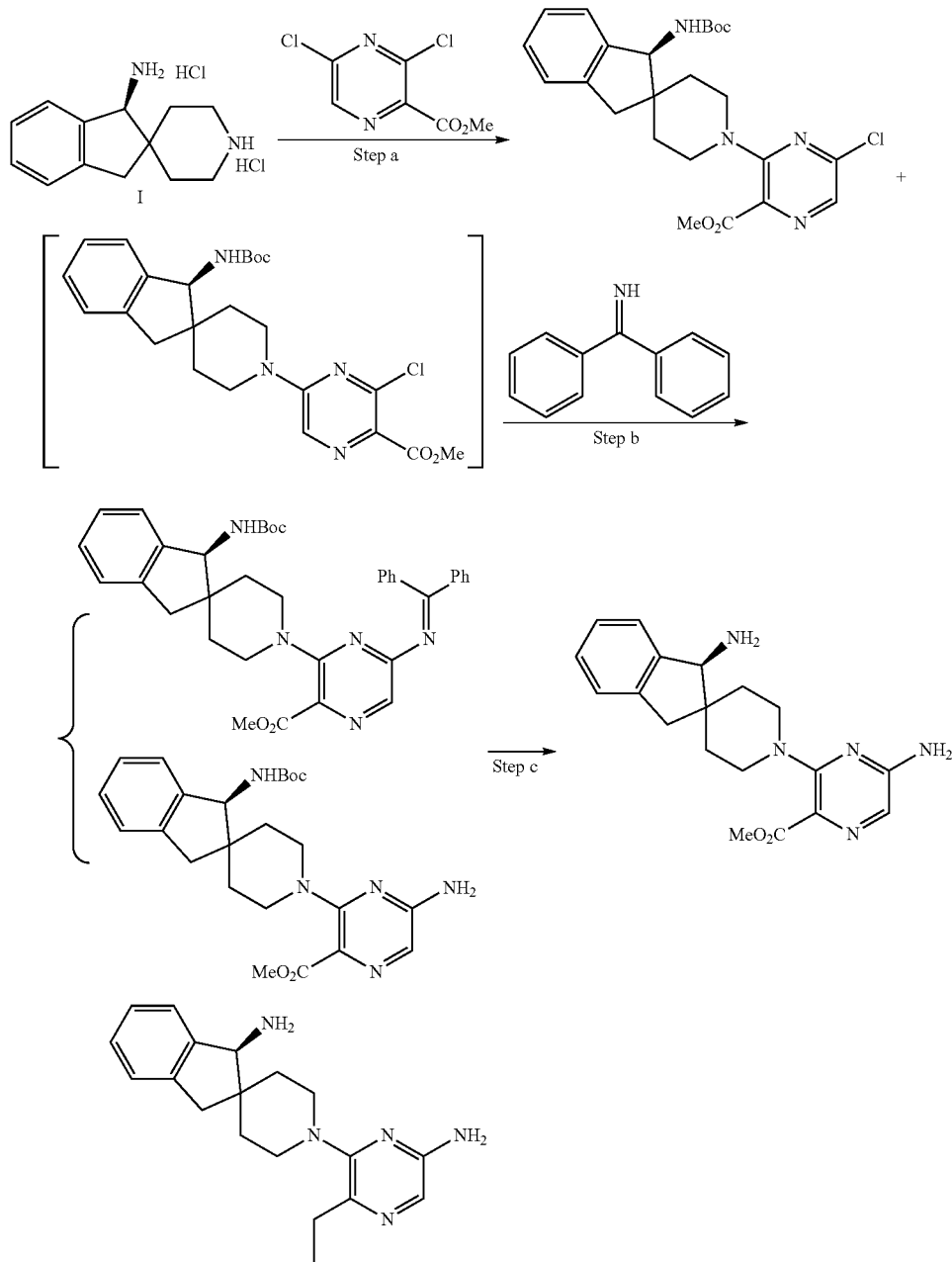

Step a: The mixture of methyl 3,5-dichloropyrazine-2-carboxylate (1.0 g, 4.83 mmol), (3S)-1,3-dihydrospiro[indene-2,4'-piperidin]-3-amine dihydrochloride (1.65 g, 4.83 mmol, Intermediate I) and CsF (3.66 g, 24.1 mmol) in DMF (15 mL) was stirred at 70° C. for 2 hours. Boc$_2$O (1.57 g, 7.24 mmol) and TEA (1 mL) were added to the mixture and the mixture was stirred at 20° C. for 1 hour. The mixture was diluted with H$_2$O (50 mL), extracted with EtOAc (50 mL×2). The organic layer was washed with brine (50 mL), dried over anhydrous Na$_2$SO$_4$, filtered and concentrated under reduced pressure and the residue was purified by column chromatography (petroleum ether/ethyl acetate=1: 0~5:1) to afford methyl 5-[(3S)-3-{[(tert-butoxy)carbonyl]amino}-1,3-dihydrospiro[indene-2,4'-piperidin]-1'-yl]-3-chloropyrazine-2-carboxylate (1.58 g, 69% yield) as a yellow solid and methyl 3-[(3S)-3-{[(tert-butoxy)carbonyl]amino}-1,3-dihydrospiro[indene-2,4'-piperidin]-1'-yl]-5-chloropyrazine-2-carboxylate (320 mg, 14% yield) as a yellow solid. LCMS m/z (M+H)$^+$=473.1 for both isomers.

Step b: The mixture of methyl 3-[(3S)-3-{[(tert-butoxy)carbonyl]amino}-1,3-dihydrospiro[indene-2,4'-piperidin]-1'-yl]-5-chloropyrazine-2-carboxylate (280 mg, 592 μmol), diphenylmethanimine (128 mg, 710 μmol), Cs$_2$CO$_3$ (577 mg, 1.77 mmol), Pd$_2$(dba)$_3$ (27.1 mg, 29.6 μmol) and BINAP (36.8 mg, 59.2 μmol) in PhMe (10 mL) was evacuated and refilled 3 times using $N_2$. The mixture was stirred at 100° C. for 12 hours. The reaction was concentrated under reduced pressure. The residue was diluted with $H_2O$ (20 mL), and extracted with EtOAc (20 mL×2). The organic layer was washed with brine (20 mL), dried over anhydrous $Na_2SO_4$, filtered and concentrated under reduced pressure. The residue was purified by column chromatography (petroleum ether/ethyl acetate=1:0~3:1) to afford the mixture methyl 3-[(3S)-3-{[(tert-butoxy)carbonyl]amino}-1,3-dihydrospiro[indene-2,4'-piperidin]-1'-yl]-5-[(diphenylmethylidene)amino]pyrazine-2-carboxylate (LCMS m/z $(M+H)^+$= 618.2) and methyl 5-amino-3-[(3S)-3-{[(tert-butoxy)carbonyl]amino}-1,3-dihydrospiro[indene-2,4'-piperidin]-1'-yl]pyrazine-2-carboxylate (LCMS m/z $(M+H)^+$=454.2) (260 mg, with the 73% purity as a mixture of both isomers).

Step c: The mixture of methyl 3-[(3S)-3-{[(tert-butoxy)carbonyl]amino}-1,3-dihydrospiro[indene-2,4'-piperidin]-1'-yl]-5-[(diphenylmethylidene)amino]pyrazine-2-carboxylate and methyl 5-amino-3-[(3S)-3-{[(tert-butoxy)carbonyl]amino}-1,3-dihydrospiro[indene-2,4'-piperidin]-1'-yl]pyrazine-2-carboxylate (240 mg, 73% purity) in HCl/MeOH (4M, 10 mL) was stirred at 25° C. for 2 hours. The mixture was concentrated under reduced pressure and the residue was diluted with MeOH. The mixture was adjusted to pH=8 by solid $Na_2CO_3$. The mixture was filtered and the filtrate was concentrated under reduced pressure. The residue was purified by column chromatography (DCM/MeOH=1:0~10:1) to methyl 5-amino-3-[(3S)-3-amino-1,3-dihydrospiro[indene-2,4'-piperidin]-1'-yl]pyrazine-2-carboxylate (70 mg) as a yellow oil. LCMS m/z $(M+H)^+$=354.1

Step d: To a solution of methyl 5-amino-3-[(3S)-3-amino-1,3-dihydrospiro[indene-2,4'-piperidin]-1'-yl]pyrazine-2-carboxylate (130 mg, 367 μmol) in THF (10 mL) was added $LiAlH_4$ (139 mg, 3.66 mmol). The mixture was stirred at 25° C. for 1 hour. Then the mixture was diluted with THF (30 mL). 15% NaOH (0.14 mL) was added and the mixture was filtered. The filtrate was concentrated under reduced pressure and the residue was purified by prep-HPLC ($NH_3.H_2O$) to afford {5-amino-3-[(3S)-3-amino-1,3-dihydrospiro[indene-2,4'-piperidin]-1'-yl]pyrazin-2-yl}methanol (20.2 mg, 17% yield) as a white solid. LCMS m/z $(M+H)^+$=326.2; $^1$HNMR (400 MHz, Methanol_$d_4$): δ 7.47 (s, 1H), 7.41-7.38 (m, 1H), 7.23-7.20 (m, 3H), 4.57 (s, 2H), 3.99 (s, 1H), 3.57-3.53 (m, 2H), 3.14-3.08 (m, 3H), 2.81-2.76 (m, 1H), 1.97-1.89 (m, 2H), 1.60-1.56 (m, 1H), 1.47-1.43 (m, 1H).

Example 124: Synthesis of (S)-1'-(3-(3,4-dihydro-1,5-naphthyridin-1(2H)-yl)-5-methyl-1H-pyrazolo[3,4-b]pyrazin-6-yl)-1,3-dihydrospiro[indene-2,4'-piperidin]-1-amine

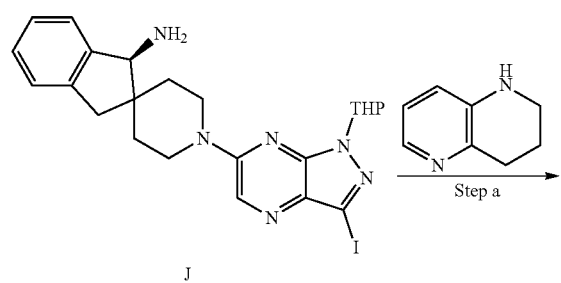

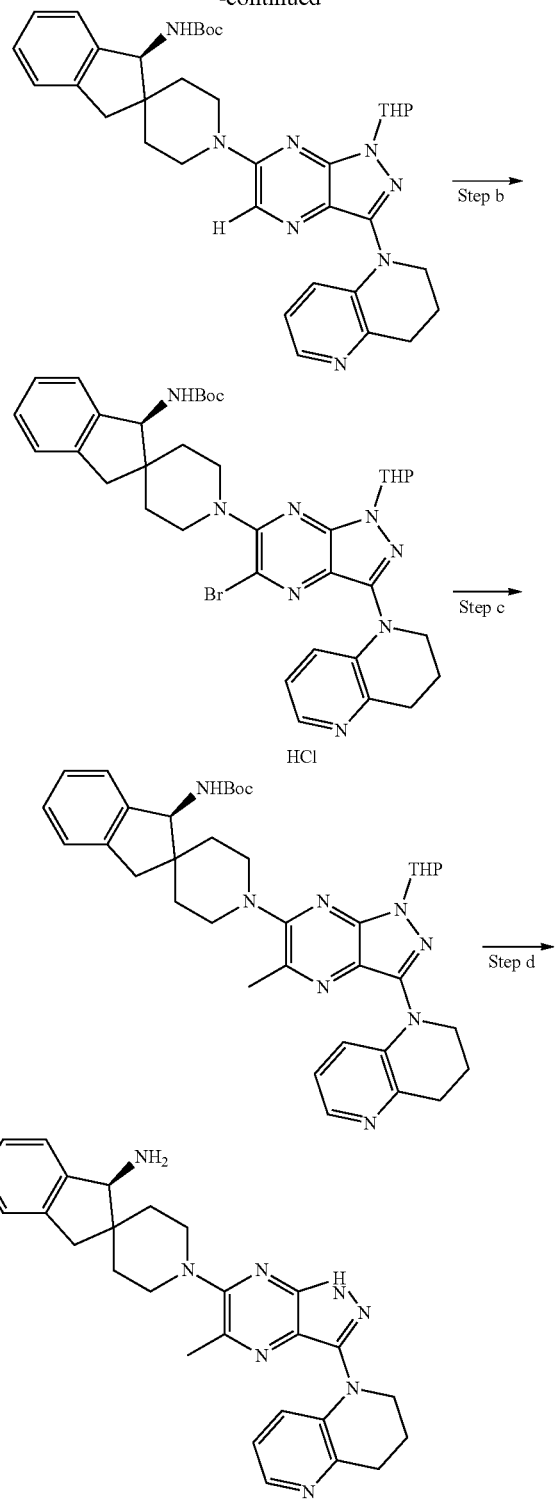

Step a: To a mixture of tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (500 mg, 0.8 mmol, Intermediate J) and 1,2,3,4-tetrahydro-1,5-naphthyridine (136 mg, 1.0 mmol) in toluene (5.0 mL) were added XantPhos-Pd-G4 (60.4 mg, 79.2 μmol) and $Cs_2CO_3$ (514 mg, 1.6 mmol). The reaction mixture was purged with $N_2$ for 3 min and stirred at 100° C. for 12 hours. The reaction mixture was concentrated under reduced pressure to give the residue which was purified by column chromatography (petroleum ether:ethyl acetate=100:0 to 100:80). The product tert-butyl N-[(3S)-1'-[1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (460 mg, 91% yield) was obtained as a yellow solid. LCMS m/z [M+H]$^+$=637.3.

Step b: To a solution of tert-butyl N-[(3S)-1'-[1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (430 mg, 0.7 mmol) in MeCN (2.5 mL) and AcOH (2.5 mL) was added NBS (132 mg, 0.7 mmol). The reaction was stirred at 25° C. for 12 hours. The reaction mixture was concentrated under reduced pressure to give the residue which was purified by column chromatography (petroleum ether:ethyl acetate=100:0 to 100:70). The product of tert-butyl N-[(3S)-1'-[5-bromo-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (400 mg, 83% yield) was obtained as a yellow solid. LCMS m/z [M+H]$^+$=715.1/717.1.

Step c: To a mixture of tert-butyl ((1S)-1'-(5-bromo-3-(3,4-dihydro-1,5-naphthyridin-1(2H)-yl)-1-(tetrahydro-2H-pyran-2-yl)-1H-pyrazolo[3,4-b]pyrazin-6-yl)-1,3-dihydrospiro[indene-2,4'-piperidin]-1-yl)carbamate (400 mg, 0.6 mmol) and trimethyl-1,3,5,2,4,6-trioxatriborinane (76.9 mg, 0.6 mmol) in dioxane (5.0 mL) and H$_2$O (0.5 mL) were added Pd(dppf)Cl$_2$ (40.8 mg, 55.8 μmol) and K$_2$CO$_3$ (153 mg, 1.1 mmol). The reaction mixture was purged with N$_2$ for 3 min and stirred at 100° C. for 12 hours under N$_2$. The reaction mixture was concentrated under reduced pressure to give the residue which was purified by column chromatography (petroleum ether:ethyl acetate=100:0 to 100:70). The product of tert-butyl ((1S)-1'-(3-(3,4-dihydro-1,5-naphthyridin-1(2H)-yl)-5-methyl-1-(tetrahydro-2H-pyran-2-yl)-1H-pyrazolo[3,4-b]pyrazin-6-yl)-1,3-dihydrospiro[indene-2,4'-piperidin]-1-yl)carbamate (240 mg, 66% yield) was obtained as a yellow solid. $^1$HNMR (400 MHz, CDCl$_3$): 8.06-8.07 (m, 1H), 7.82-7.84 (m, 1H), 7.31-7.37 (m, 1H), 7.27-7.26 (m, 3H), 6.99-7.03 (m, 1H), 5.78-5.81 (m, 1H), 5.06-5.10 (m, 1H), 4.70-4.73 (m, 1H), 4.11-4.18 (m, 3H), 3.84-4.00 (m, 2H), 3.74-3.79 (m, 1H), 3.22-3.29 (m, 1H), 3.05-3.11 (m, 3H), 2.81-2.85 (m, 1H), 2.61-2.64 (m, 1H), 2.14-2.25 (m, 4H), 1.90-1.97 (m, 2H), 1.70-1.85 (m, 4H), 1.52 (s, 9H).

Step d: A solution of tert-butyl N-[(3S)-1'-[5-methyl-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (230 mg, 0.4 mmol) in HCl/MeOH (10.0 mL, 4M) was stirred at 25° C. for 12 hours. The reaction mixture was concentrated under reduced pressure. The residue was dissolved in MeOH (8.0 mL) and the solution was purified by reverse phase prep-HPLC (HCl). The product of (S)-1'-(3-(3,4-dihydro-1,5-naphthyridin-1(2H)-yl)-5-methyl-1H-pyrazolo[3,4-b]pyrazin-6-yl)-1,3-dihydrospiro[indene-2,4'-piperidin]-1-amine hydrochloride (145 mg, 82% yield) was obtained as a yellow solid. LCMS m/z [M+H]$^+$=467.2; $^1$HNMR (400 MHz, Methanol-d4): 8.04-8.06 (d, J=5.6, 1H), 7.93-7.96 (d, J=8.4, 1H), 7.54-7.58 (m, 2H), 7.40-7.46 (m, 2H), 7.34-7.38 (m, 1H), 4.48 (s, 1H), 4.08-4.11 (m, 2H), 3.77-3.81 (m, 1H), 3.67-3.71 (m, 1H), 3.24-3.30 (m, 4H), 3.21 (s, 2H), 2.64 (s, 3H), 2.30-2.37 (m, 2H), 2.07-2.14 (m, 1H), 1.95-2.02 (m, 1H), 1.84-1.87 (m, 1H), 1.70-1.73 (m, 1H). SFC: e.e. =98.4%.

Example 125: Synthesis of 6-[(3S)-3-amino-1,3-dihydrospiro[indene-2,4'-piperidin]-1'-yl]-N,5-dimethyl-1H-pyrazolo[3,4-b]pyrazine-3-carboxamide

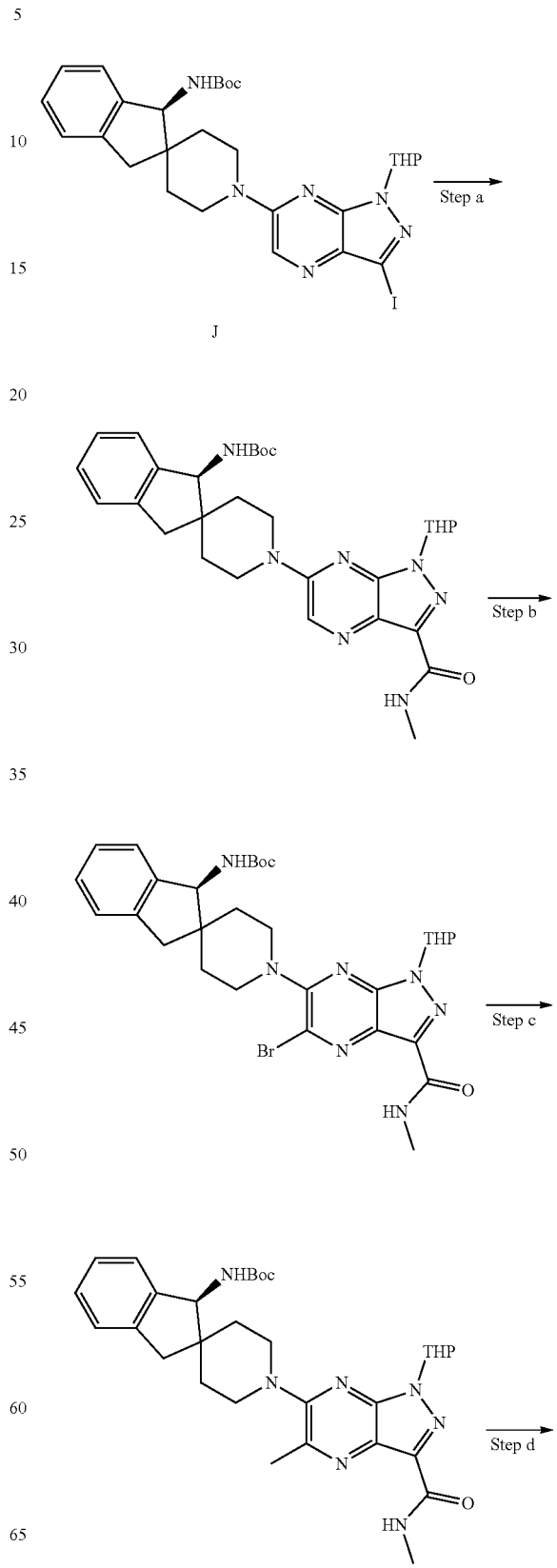

-continued

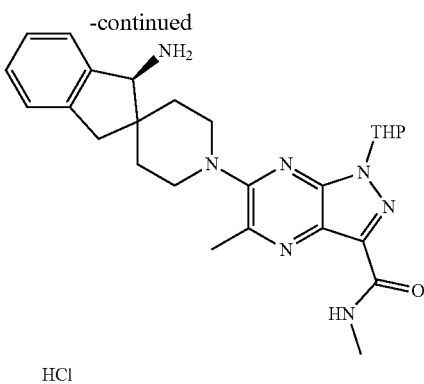

HCl

Step a: A mixture of tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (250 mg, 396 μmol, Intermediate J), methanamine hydrochloride (534 mg, 7.9 mmol), Pd₂(dppf)Cl₂ (28.9 mg, 39.6 μmol) and TEA (1.1 mL, 7.9 mmol) in MeOH (10 mL) was stirred at 80° C. for 12 hours under CO atmosphere (50 psi). The reaction mixture was concentrated in vacuo to give a residue, which was dissolved in ethyl acetate (50 mL), then washed with H₂O (25 mL×2). The organic phase was washed with brine (10 mL), dried over anhydrous Na₂SO₄, filtered and concentrated in vacuo to give a residue, which was purified by silica gel chromatography (ethyl acetate in petroleum ether=0% to 95%) to afford tert-butyl N-[(3S)-1'-[3-(methylcarbamoyl)-1-(oxan-2-yl)-1H-pyrazolo[3,4-b]pyrazin-6-yl]-1,3-dihydrospiro[indene-2,4'-piperidin]-3-yl]carbamate (210 mg, 95% yield) as a brown solid. LCMS m/z [M+H]⁺=562.1.

Step b: A mixture of tert-butyl N-[(3S)-1'-[3-(methylcarbamoyl)-1-(oxan-2-yl)-1H-pyrazolo[3,4-b]pyrazin-6-yl]-1,3-dihydrospiro[indene-2,4'-piperidin]-3-yl]carbamate (210 mg, 373 μmol), NBS (132 mg, 746 μmol) in MeCN (10 mL) and AcOH (1 mL) was stirred at 25° C. for 12 hours. The reaction mixture was concentrated in vacuo to give a residue, which was dissolved in ethyl acetate (20 mL), then washed with sat.NaHCO₃ (15 mL×2). The organic phase was washed with brine (5 mL), dried over anhydrous Na₂SO₄, filtered and concentrated in vacuo to give a residue. The residue was purified by silica gel chromatography (ethyl acetate in petroleum ether=0% to 80%) to afford tert-butyl N-[(3S)-1'-[5-bromo-3-(methylcarbamoyl)-1-(oxan-2-yl)-1H-pyrazolo[3,4-b]pyrazin-6-yl]-1,3-dihydrospiro[indene-2,4'-piperidin]-3-yl]carbamate (100 mg, 42% yield) as a yellow oil. LCMS m/z [M+H]⁺=640.1.

Step c: A mixture of tert-butyl N-[(3S)-1'-[5-bromo-3-(methylcarbamoyl)-1-(oxan-2-yl)-1H-pyrazolo[3,4-b]pyrazin-6-yl]-1,3-dihydrospiro[indene-2,4'-piperidin]-3-yl]carbamate (100 mg, 156 μmol), trimethyl-1,3,5,2,4,6-trioxatriborinane (194 mg, 1.6 mmol), Pd(dppf)Cl₂ (11.4 mg, 15.6 μmol) and K₂CO₃ (43.0 mg, 312 μmol) in 1,4-dioxane (10 mL)/H₂O (1 mL) was stirred at 90° C. for 12 hours under N₂ atmosphere. The reaction mixture was concentrated in vacuo to give a residue, which was purified by silica gel chromatography (ethyl acetate as eluent) to afford tert-butyl N-[(3S)-1'-[5-methyl-3-(methylcarbamoyl)-1-(oxan-2-yl)-1H-pyrazolo[3,4-b]pyrazin-6-yl]-1,3-dihydrospiro[indene-2,4'-piperidin]-3-yl]carbamate (50.0 mg, 56% yield) as a brown oil. LCMS m/z [M+H]⁺=576.2.

Step d: A mixture of tert-butyl N-[(3S)-1'-[5-methyl-3-(methylcarbamoyl)-1-(oxan-2-yl)-1H-pyrazolo[3,4-b]pyrazin-6-yl]-1,3-dihydrospiro[indene-2,4'-piperidin]-3-yl]carbamate (50 mg, 86.8 μmol) in HCl/MeOH (4M, 2 mL) was stirred at 25° C. for 1 hour. The mixture was concentrated under reduced pressure to give a residue, which was purified by prep-HPLC (HCl) to afford 6-[(3S)-3-amino-1,3-dihydrospiro[indene-2,4'-piperidin]-1'-yl]-N,5-dimethyl-1H-pyrazolo[3,4-b]pyrazine-3-carboxamide hydrochloride (15.5 mg, 42% yield) as a yellow solid. LCMS m/z [M+H]⁺=392.1; ¹HNMR (400 MHz, Methanol-d4): δ 7.55 (d, J=7.2 Hz, 1H), 7.45-7.34 (m, 3H), 4.49 (s, 1H), 3.80-3.68 (m, 2H), 3.31-3.21 (m, 4H), 3.07 (s, 3H), 2.74 (s, 3H), 2.14-1.96 (m, 2H), 1.86-1.83 (m, 1H), 1.73-1.70 (m, 1H).

Example 126: Synthesis of (3S)-1'-{3-[(2,3-dichloropyridin-4-yl)oxy]-1H-pyrazolo[3,4-b]pyrazin-6-yl}-1,3-dihydrospiro[indene-2,4'-piperidin]-3-amine

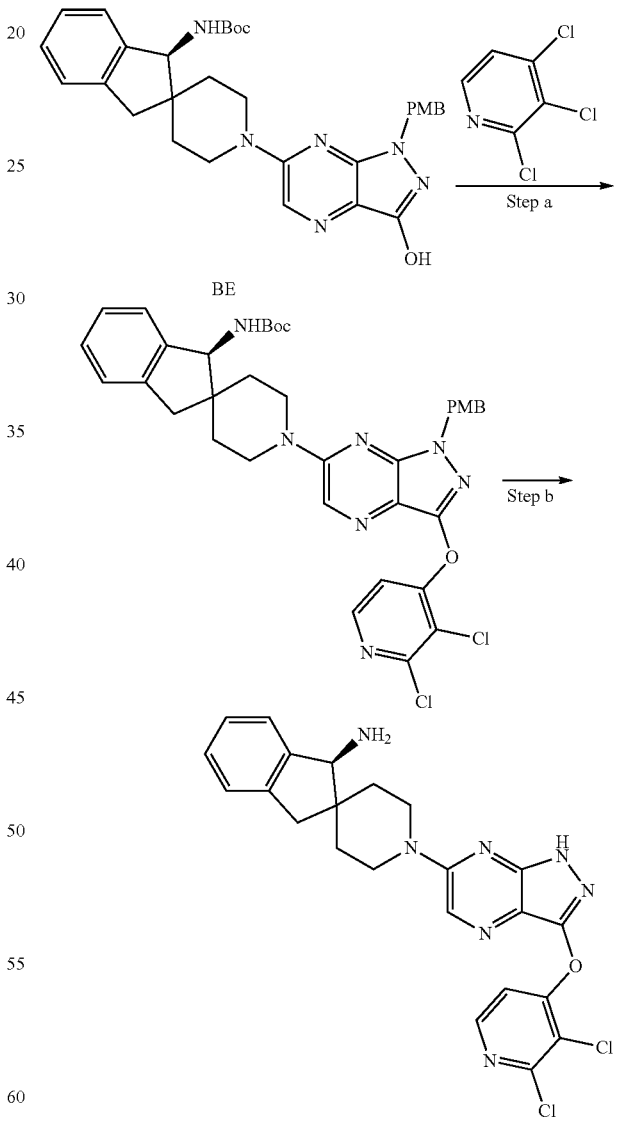

Step a: The mixture of tert-butyl N-[(3S)-1'-{3-hydroxy-1-[(4-methoxyphenyl)methyl]-1H-pyrazolo[3,4-b]pyrazin-6-yl}-1,3-dihydrospiro[indene-2,4'-piperidin]-3-yl]carbamate (2.6 g, 67% purity, 3.12 mmol, Intermediate BE), 2,3,4-trichloropyridine (682 mg, 3.74 mmol) and Cs₂CO₃ (3.05 g, 9.36 mmol) in DMF (30 mL) was stirred at 70° C. for 12 hours. Then the mixture was diluted with H₂O (50 mL), and extracted with EtOAc (50 mL×2). The organic layer was washed with brine (50 mL), dried over anhydrous Na₂SO₄, filtered and concentrated under reduced pressure. The residue was purified by column chromatography (petroleum ether/ethyl acetate=1:0~3:1) to afford tert-butyl N-[(3S)-1'-{3-[(2,3-dichloropyridin-4-yl)oxy]-1-[(4-methoxyphenyl) methyl]-1H-pyrazolo[3,4-b]pyrazin-6-yl}-1,3-dihydrospiro[indene-2,4'-piperidin]-3-yl]carbamate (1.58 g, 72% yield) as a yellow oil. LCMS m/z [M+H]⁺=702.1.

Step b: The mixture of tert-butyl N-[(3S)-1'-{3-[(2,3-dichloropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (100 mg, 142 μmol) in TFA (5 mL) and TfOH (0.5 mL) was stirred at 20° C. for 10 hours. The combined mixture was concentrated under reduced pressure and the residue was diluted with MeOH. The mixture was adjusted to pH=8 by solid Na₂CO₃. The mixture was filtered and the filtrate was purified by prep-HPLC (NH₃.H₂O) to afford (3S)-1'-{3-[(2,3-dichloropyridin-4-yl)oxy]-1H-pyrazolo[3,4-b]pyrazin-6-yl}-1,3-dihydrospiro[indene-2,4'-piperidin]-3-amine (30 mg, 44% yield) as a white solid. LCMS m/z [M+Na]⁺=504.0. ¹HNMR (400 MHz, DMSO-d6+Methanol_d₄): δ 8.37 (s, 1H), 8.22-8.20 (d, J=6.4 Hz, 1H), 7.41-7.39 (m, 1H), 7.28-7.22 (m, 3H), 7.13-7.11 (d, J=6.4 Hz, 1H), 4.44-4.43 (m, 2H), 3.99 (s, 1H), 3.42-3.32 (m, 2H), 3.23-3.19 (m, 1H), 2.87-2.82 (m, 1H), 1.93-1.83 (m, 2H), 1.68-1.64 (m, 1H), 1.49-1.45 (m, 1H).

Example 127: Synthesis of (3S)-1'-{3-[(3-chloro-2-methylpyridin-4-yl)oxy]-1H-pyrazolo[3,4-b]pyrazin-6-yl}-1,3-dihydrospiro[indene-2,4'-piperidin]-3-amine

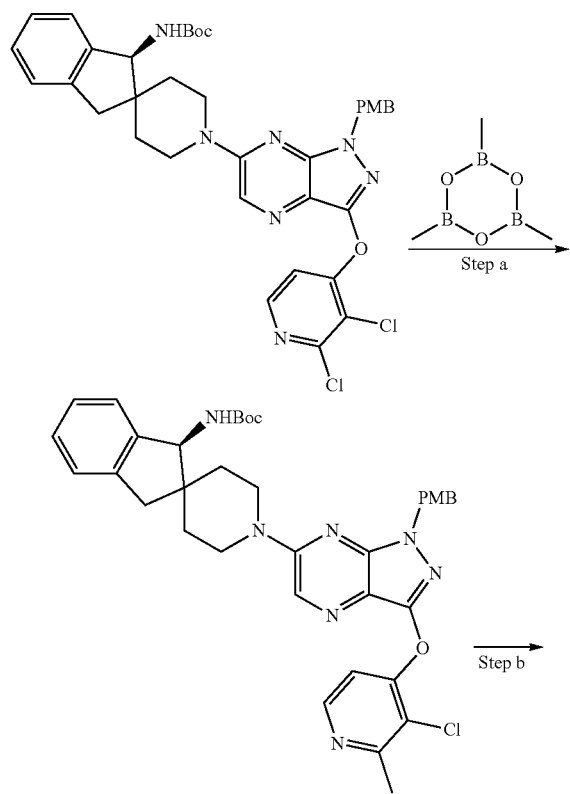

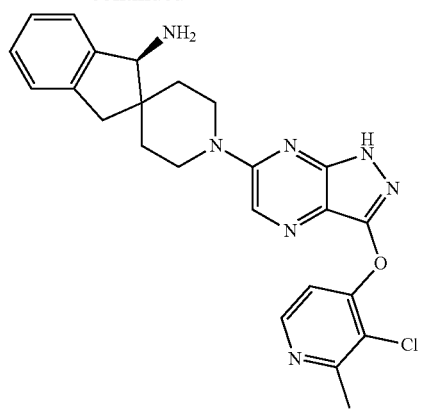

Step a: The mixture of tert-butyl N-[(3S)-1'-{3-[(2,3-dichloropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (100 mg, 142 μmol, synthesized via Step a of Example 126), trimethyl-1,3,5,2,4,6-trioxatriborinane (35.6 mg, 284 μmol), Pd(dppf)Cl₂ (10.3 mg, 14.2 μmol) and K₃PO₄.3H₂O (113 mg, 425 μmol) in H₂O (0.5 ml) and dioxane (5 mL) was evacuated and refilled 3 times using N₂. The mixture was stirred at 100° C. for 12 hours. The reaction mixture was then concentrated under reduced pressure and the residue was purified by column chromatography (petroleum ether/ethyl acetate=1:0~2:1) to afford tert-butyl N-[(3S)-1'-{3-[(3-chloro-2-methylpyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (170 mg, combined product with another identical reaction) as a yellow solid. LCMS m/z [M+H]+=682.2.

Step b: The mixture of tert-butyl N-[(3S)-1'-{3-[(3-chloro-2-methylpyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (150 mg, 219 μmol) in TFA (5 mL) and TfOH (0.5 mL) was stirred at 90° C. for 0.5 hour. The mixture was then concentrated under reduced pressure and the residue was diluted with MeOH. The mixture was adjusted to pH=8 by solid Na₂CO₃. The mixture was filtered and the filtrate was purified by prep-HPLC (NH₃.H₂O) to afford (3S)-1'-{3-[(3-chloro-2-methylpyridin-4-yl)oxy]-1H-pyrazolo[3,4-b]pyrazin-6-yl}-1,3-dihydrospiro[indene-2,4'-piperidin]-3-amine (23.7 mg, 23% yield) as a white solid. LCMS m/z [M+H]⁺=462.1; ¹HNMR (400 MHz, Methanol_d₄): δ 8.29 (s, 1H), 8.21-8.19 (d, J=5.6 Hz, 1H), 7.39-7.36 (m, 1H), 7.26-7.20 (m, 3H), 6.96-6.94 (d, J=5.6 Hz, 1H), 4.44-4.39 (m, 2H), 3.97 (s, 1H), 3.39-3.35 (m, 2H), 3.21-3.16 (m, 1H), 2.85-2.80 (m, 1H), 2.67 (s, 3H), 1.91-1.80 (m, 2H), 1.65-1.61 (m, 1H), 1.48-1.44 (m, 1H).

523

Example 128: Synthesis of (S)-4-((6-(1-amino-1,3-dihydrospiro[indene-2,4'-piperidin]-1'-yl)-1H-pyrazolo[3,4-b]pyrazin-3-yl)oxy)-3-chloro-1-methylpyridin-2(H)-one

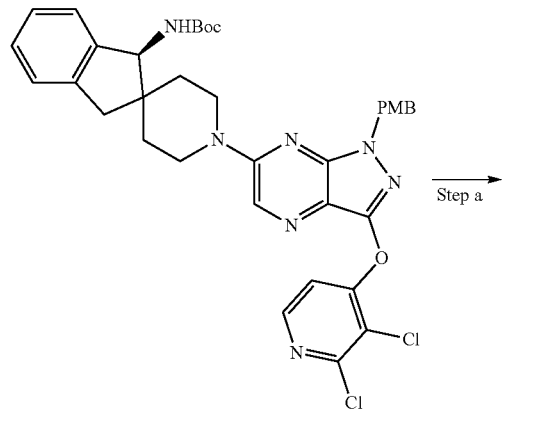

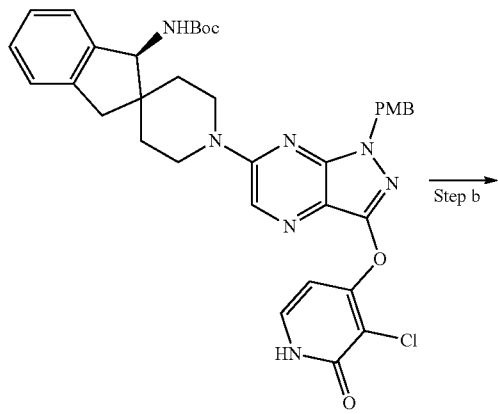

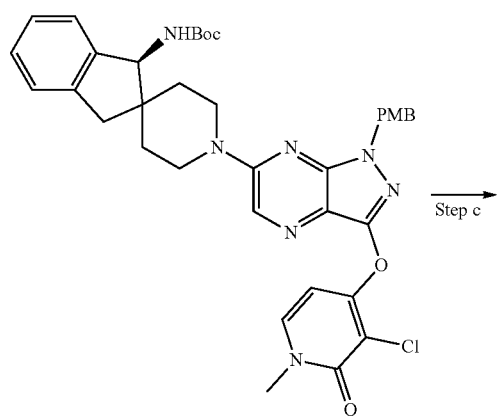

524

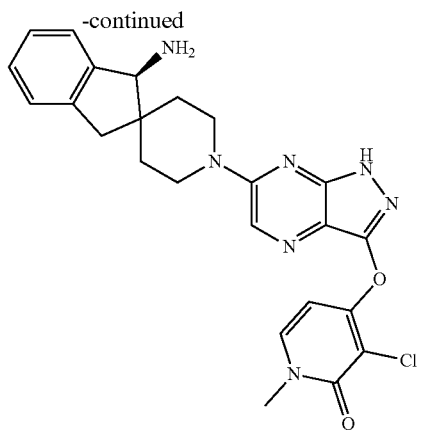

Step a: The mixture of tert-butyl N-[(3S)-1'-{3-[(2,3-dichloropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (450 mg, 499 μmol, synthesized via Step a of Example 126), Pd$_2$(dba)$_3$ (46 mg, 50 μmol), t-BuXPhos (43 mg, 100 μmol) and KOH (83 mg, 1.49 mmol) in dioxane (5 mL) and H$_2$O (5 mL) was stirred at 100° C. for 10 hours under N$_2$. The reaction mixture was then extracted with EtOAc (10 mL×2). The combined organic layers were washed with brine (10 mL), dried over anhydrous Na$_2$SO$_4$, filtered and concentrated under reduced pressure. The residue was purified by column chromatography (petroleum ether/ethyl acetate=1:0~1:2) to afford tert-butyl N-[(3S)-1'-{3-[(3-chloro-2-oxo-1,2-dihydropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (150 mg, 44% yield) as a yellow solid. LCMS m/z [M+H]$^+$=684.1.

Step b: To a mixture of tert-butyl N-[(3S)-1'-{3-[(3-chloro-2-oxo-1,2-dihydropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (140 mg, 204 μmol) and Cs$_2$CO$_3$ (199 mg, 612 μmol) in DMF (5 mL) was added MeI (70.1 μL, 1.12 mmol). The mixture was stirred at 25° C. for 0.5 hour. The combined mixture was diluted with H$_2$O (20 mL), and extracted with EtOAc (20 mL×2). The combined organic layers were washed with brine (20 mL), dried over anhydrous Na$_2$SO$_4$, filtered and concentrated under reduced pressure. The residue was purified by column chromatography (petroleum ether/ethyl acetate=1:1~1:2) to afford tert-butyl N-[(3S)-1'-{3-[(3-chloro-1-methyl-2-oxo-1,2-dihydropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (140 mg) as a yellow oil. LCMS m/z [M+H]$^+$=698.2.

Step c: The mixture of tert-butyl N-[(3S)-1'-{3-[(3-chloro-1-methyl-2-oxo-1,2-dihydropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (130 mg, 186 umol) in TFA (3 mL) and TfOH (0.3 mL) was stirred at 90° C. for 0.5 hour. The mixture was concentrated under reduced pressure and the residue was diluted with MeOH, then adjusted with Na$_2$CO$_3$ to pH=8. The mixture was purified by prep-HPLC (NH$_3$.H$_2$O) to afford (S)-4-((6-(1-amino-1,3-dihydrospiro[indene-2,4'-piperidin]-1'-yl)-1H-pyrazolo[3,4-b]pyrazin-3-yl)oxy)-3-chloro-1-methylpyridin-2(1H)-one (24.2 mg, 27% yield) as a white solid. LCMS m/z [M+H]$^+$=477.9; $^1$HNMR (400 MHz, DMSO-d$_6$+Methanol_d$_4$): δ 8.38 (s, 1H), 7.66-7.63 (d, J=7.6 Hz, 1H), 7.42-7.23 (m, 4H), 6.21-6.18 (d, J=7.6 Hz, 1H), 4.48-4.43 (m, 2H), 3.98 (s, 1H), 3.63 (s, 3H), 3.37-333 (m, 2H), 3.25-3.20 (m, 1H), 2.87-2.82 (m, 1H), 1.90-1.33 (m, 4H).

Example 129: Synthesis of (S)-1'-(5-(((6-amino-2,3-dichloropyridin-4-yl)thio)pyrazin-2-yl)-1,3-dihydrospiro[indene-2,4'-piperidin]-1-amine

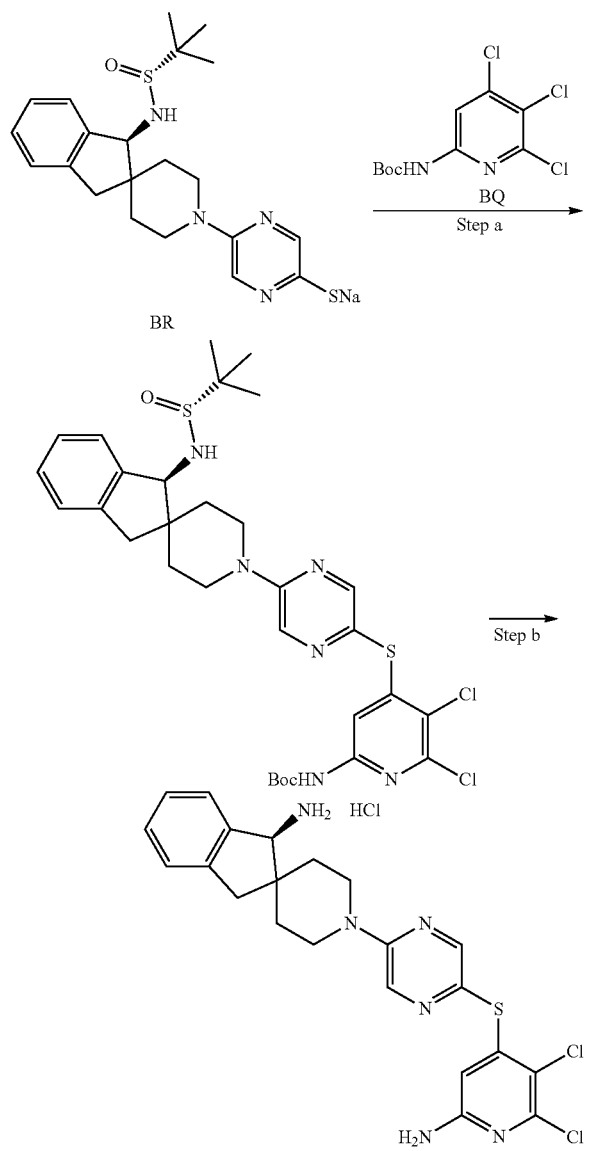

Step a: A mixture of (R)-2-methyl-N-[(3S)-1'-[5-(sodiosulfanyl)pyrazin-2-yl]-1,3-dihydrospiro[indene-2,4'-piperidin]-3-yl]propane-2-sulfinamide (550 mg, 877 µmol, Intermediate BR), tert-butyl N-(4,5,6-trichloropyridin-2-yl)carbamate (866 mg, 877 µmol, Intermediate BQ) and Cs₂CO₃ (570 mg, 1.8 mmol) in DMF (30 mL) was stirred at 70° C. for 12 hours. The reaction mixture was diluted with ethyl acetate (60 mL), washed with H₂O (40 mL×2). The organic phase was washed with brine (15 mL), dried over anhydrous Na₂SO₄, filtered and concentrated in vacuo to give a residue, which was purified by silica gel chromatography (ethyl acetate in petroleum ether=0% to 70%) to afford the product of tert-butyl N-[5,6-dichloro-4-({5-[(3S)-3-{[(R)-2-methylpropane-2-sulfinyl]amino}-1,3-dihydrospiro[indene-2,4'-piperidin]-1'-yl]pyrazin-2-yl}sulfanyl)pyridin-2-yl]carbamate (330 mg, 56% yield) as a yellow solid. LCMS m/z [M+H]⁺=677.1.

Step b: A mixture of tert-butyl N-[5,6-dichloro-4-({5-[(3S)-3-{[(R)-2-methylpropane-2-sulfinyl]amino}-1,3-dihydrospiro[indene-2,4'-piperidin]-1'-yl]pyrazin-2-yl}sulfanyl)pyridin-2-yl]carbamate (300 mg, 442 µmol) in HCl/MeOH (4M, 10 mL) was stirred at 20° C. for 0.5 hour. The mixture was concentrated under reduced pressure to give the crude product, which was triturated with MeOH (3 mL) and filtered to afford (S)-1'-(5-((6-amino-2,3-dichloropyridin-4-yl)thio)pyrazin-2-yl)-1,3-dihydrospiro[indene-2,4'-piperidin]-1-amine hydrochloride (167.5 mg, 74% yield) as a yellow solid. LCMS m/z [M+H]⁺=472.9; ¹HNMR (400 MHz, Methanol-d4): δ 8.43 (d, J=1.6 Hz, 1H), 8.34 (d, J=1.2 Hz, 1H), 7.54 (d, J=7.6 Hz, 1H), 7.44-7.35 (m, 3H), 5.93 (s, 1H), 4.52-4.34 (m, 3H), 3.48-3.36 (m, 2H), 3.24 (s, 2H), 1.97-1.67 (m, 4H).

Example 130: Synthesis of (3S)-1'-{5-[(2,3-dichloropyridin-4-yl)sulfanyl]pyrazin-2-yl}-1,3-dihydrospiro[indene-2,4'-piperidin]-3-amine

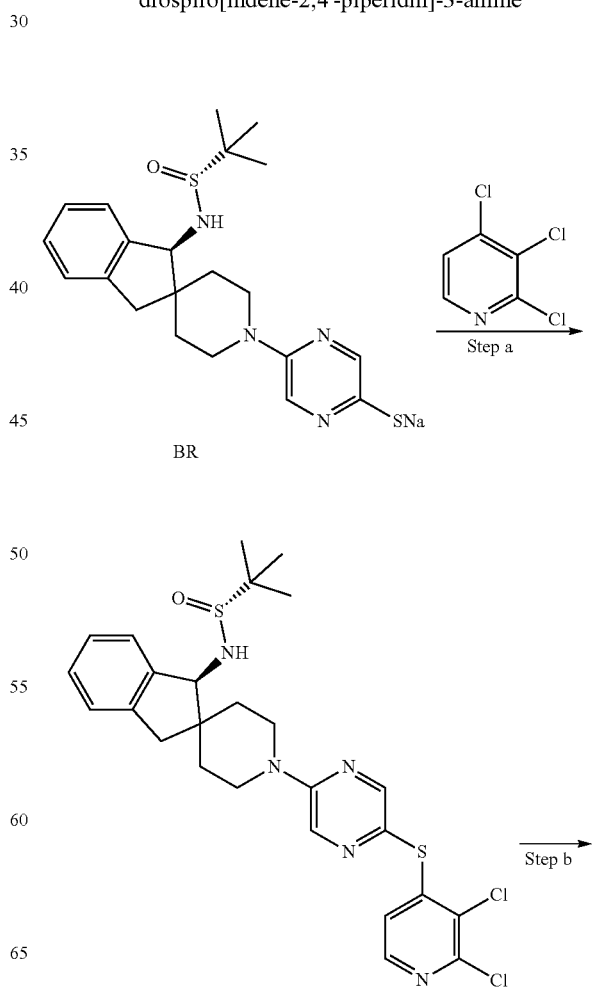

527

-continued

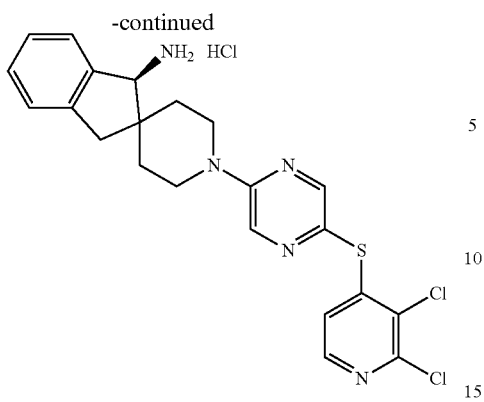

Step a: A mixture of (R)-2-methyl-N-[(3S)-1'-[5-(sodio-sulfanyl)pyrazin-2-yl]-1,3-dihydrospiro[indene-2,4'-piperidin]-3-yl]propane-2-sulfinamide (1.2 g, purity: 70%, Intermediate BR), 2,3,4-trichloropyridine (547 mg, 2.1 mmol) and $Cs_2CO_3$ (1.2 g, 3.8 mmol) in DMF (50 mL) was stirred at 70° C. for 2 hours. The mixture was diluted with ethyl acetate (110 mL), and washed with $H_2O$ (100 mL×2). The combined organic phases were washed with brine (20 mL), dried over anhydrous $Na_2SO_4$, filtered and concentrated in vacuo to give a residue, which was purified by silica gel chromatography (ethyl acetate in petroleum ether=0% to 80%) to afford (R)—N-[(3S)-1'-{5-[(2,3-dichloropyridin-4-yl)sulfanyl]pyrazin-2-yl}-1,3-dihydrospiro[indene-2,4'-piperidin]-3-yl]-2-methylpropane-2-sulfinamide (900 mg, 84% yield) as a white solid. LCMS m/z $[M+H]^+$=562.0/564.0.

Step b: A mixture of (R)—N-[(3S)-1'-{5-[(2,3-dichloropyridin-4-yl)sulfanyl]pyrazin-2-yl}-1,3-dihydrospiro[indene-2,4'-piperidin]-3-yl]-2-methylpropane-2-sulfinamide (80 mg, 142 μmol) in HCl/MeOH (4M, 2 mL) was stirred at 20° C. for 0.5 hours. The mixture was concentrated under reduced pressure to give the crude product. The residue was triturated with MeOH (2 mL), filtered and concentrated in vacuo to afford (3S)-1'-{5-[(2,3-dichloropyridin-4-yl)sulfanyl]pyrazin-2-yl}-1,3-dihydrospiro[indene-2,4'-piperidin]-3-amine hydrochloride (32.1 mg, 46% yield) as a yellow solid. LCMS m/z $[M+H]^+$=457.9; $^1$HNMR (400 MHz, Methanol-d4): δ 8.44 (s, 1H), 8.36 (s, 1H), 8.03 (d, J=5.2 Hz, 1H), 7.54 (d, J=7.2 Hz, 1H), 7.46-7.35 (m, 3H), 6.73 (d, J=5.2 Hz, 1H), 4.53-4.36 (m, 3H), 3.49-3.37 (m, 2H), 3.24 (s, 2H), 1.96-1.67 (m, 4H).

Example 131: Synthesis of 4-({5-[(3S)-3-amino-1,3-dihydrospiro[indene-2,4'-piperidin]-1'-yl]pyrazin-2-yl}sulfanyl)-3-chloro-1,2-dihydropyridin-2-one

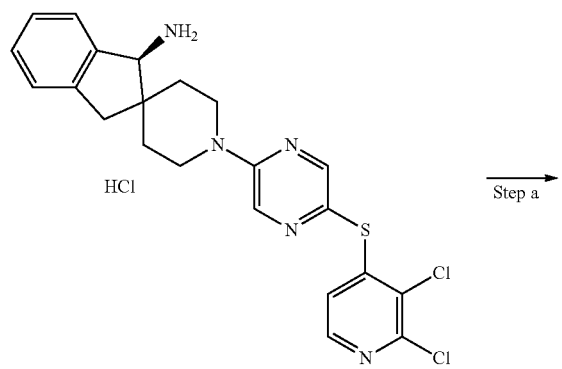

528

-continued

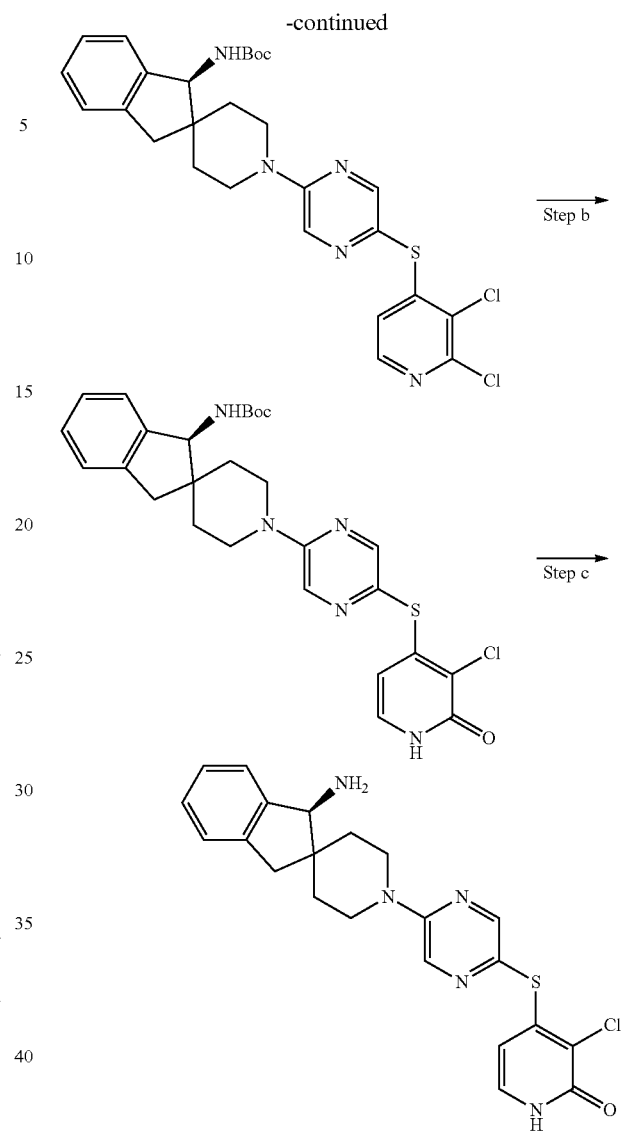

Step a: A mixture of (3S)-1'-{5-[(2,3-dichloropyridin-4-yl)sulfanyl]pyrazin-2-yl}-1,3-dihydrospiro[indene-2,4'-piperidin]-3-amine hydrochloride (700 mg, 1.4 mmol, Example 130), $(Boc)_2O$ (609 mg, 2.8 mmol) and TEA (1.0 mL, 7.1 mmol) in DCM (20 mL) was stirred at 20° C. for 3 hours. The mixture was diluted with $H_2O$ (30 mL), and extracted with dichloromethane (30 mL×3). The combined organic phases were washed with brine (20 mL), dried over anhydrous $Na_2SO_4$, filtered and concentrated in vacuo to give a residue. The residue was purified by silica gel chromatography (ethyl acetate in petroleum ether=0% to 50%) to afford tert-butyl N-[(3S)-1'-{5-[(2,3-dichloropyridin-4-yl)sulfanyl]pyrazin-2-yl}-1,3-dihydrospiro[indene-2,4'-piperidin]-3-yl]carbamate (720 mg, 91% yield) as a white solid. LCMS m/z $[M+H]^+$=558.0/560.0.

Step b: A mixture of tert-butyl N-[(3S)-1'-{5-[(2,3-dichloropyridin-4-yl)sulfanyl]pyrazin-2-yl}-1,3-dihydrospiro[indene-2,4'-piperidin]-3-yl]carbamate (700 mg, 1.3 mmol), KOH (210 mg, 3.8 mmol), t-Bu-XPhos (106 mg, 250 μmol) and $Pd_2(dba)_3$ (114 mg, 125 μmol) in dioxane (10 mL) and $H_2O$ (10 mL) was stirred at 100° C. for 12 hours under $N_2$ atmosphere. The reaction mixture was diluted with $H_2O$ (40 mL), and extracted with ethyl acetate (40 mL×3). The organic phases were washed with brine (30 mL), dried over anhydrous Na₂SO₄, filtered and concentrated in vacuo to give a residue. The residue was purified by silica gel chromatography (ethyl acetate as eluent) to afford tert-butyl N-[(3S)-1'-{5-[(3-chloro-2-oxo-1,2-dihydropyridin-4-yl)sulfanyl]pyrazin-2-yl}-1,3-dihydrospiro[indene-2,4'-piperidin]-3-yl]carbamate (420 mg, 62% yield) as a yellow solid. LCMS m/z [M+H]⁺=540.1.

Step c: A mixture of tert-butyl N-[(3S)-1'-{5-[(3-chloro-2-oxo-1,2-dihydropyridin-4-yl)sulfanyl]pyrazin-2-yl}-1,3-dihydrospiro[indene-2,4'-piperidin]-3-yl]carbamate (110 mg, 203 μmol) in HCl/MeOH (4M, 2 mL) was stirred at 20° C. for 1 hour. The mixture was concentrated under reduced pressure and lyophilized to afford 4-({5-[(3S)-3-amino-1,3-dihydrospiro[indene-2,4'-piperidin]-1'-yl]pyrazin-2-yl}sulfanyl)-3-chloro-1,2-dihydropyridin-2-one hydrochloride (87.4 mg, 90% yield) as a yellow solid. LCMS m/z [M+H]⁺=439.9; ¹HNMR (400 MHz, DMSO-d6): δ 8.58 (s, 3H), 8.53 (s, 1H), 8.36 (s, 1H), 7.60 (d, J=7.6 Hz, 1H), 7.38-7.24 (m, 5H), 5.52 (d, J=6.8 Hz, 1H), 4.42-4.29 (m, 3H), 3.30-3.22 (m, 3H), 3.01 (d, J=16.0 Hz, 1H), 1.87-1.75 (m, 2H), 1.60-1.54 (m, 2H).

Example 132: Synthesis of 4-({5-[(3S)-3-amino-1,3-dihydrospiro[indene-2,4'-piperidin]-1'-yl]pyrazin-2-yl}sulfanyl)-3-chloro-1-methyl-1,2-dihydropyridin-2-one

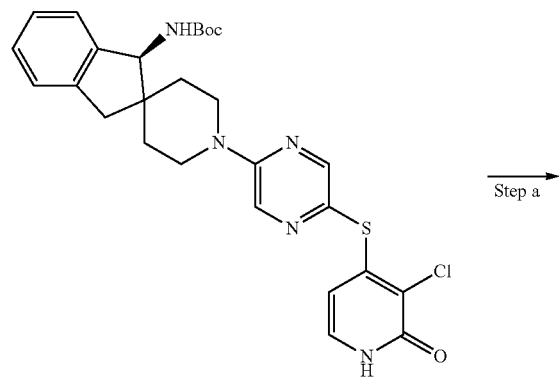

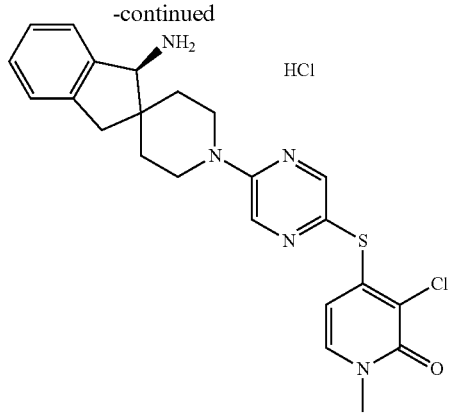

Step a: To a mixture of tert-butyl N-[(3S)-1'-{5-[(3-chloro-2-oxo-1,2-dihydropyridin-4-yl)sulfanyl]pyrazin-2-yl}-1,3-dihydrospiro[indene-2,4'-piperidin]-3-yl]carbamate (250 mg, 462 μmol, synthesized via Steps a-b of Example 131) and Cs₂CO₃ (449 mg, 1.4 mmol) in DMF (20 mL) was added MeI (745 μL, 11.9 mmol), the resulting mixture was stirred at 20° C. for 0.5 hours. The reaction mixture was diluted with ethyl acetate (50 mL), and washed with H₂O (40 mL×2). The organic phase was washed with brine (10 mL), dried over anhydrous Na₂SO₄, filtered and concentrated in vacuo to give a residue. The residue was purified by silica gel chromatography (ethyl acetate as eluent) to afford tert-butyl N-[(3S)-1'-{5-[(3-chloro-1-methyl-2-oxo-1,2-dihydropyridin-4-yl)sulfanyl]pyrazin-2-yl}-1,3-dihydrospiro[indene-2,4'-piperidin]-3-yl]carbamate (250 mg, 98% yield) as a yellow solid. LCMS m/z [M+H]⁺=554.0.

Step b: A mixture of tert-butyl N-[(3S)-1'-{5-[(3-chloro-1-methyl-2-oxo-1,2-dihydropyridin-4-yl)sulfanyl]pyrazin-2-yl}-1,3-dihydrospiro[indene-2,4'-piperidin]-3-yl]carbamate (240 mg, 433 μmol) in HCl/MeOH (4M, 10 mL) was stirred at 20° C. for 0.5 hours. The mixture was concentrated under reduced pressure to give a residue, which was lyophilized to afford 4-({5-[(3S)-3-amino-1,3-dihydrospiro[indene-2,4'-piperidin]-1'-yl]pyrazin-2-yl}sulfanyl)-3-chloro-1-methyl-1,2-dihydropyridin-2-one hydrochloride (161 mg, 76% yield) as a yellow solid. LCMS m/z [M+H]⁺=453.9; ¹HNMR (400 MHz, DMSO-d6): δ 8.62 (s, 3H), 8.53 (s, 1H), 8.35 (s, 1H), 7.61 (d, J=7.2 Hz, 1H), 7.55 (d, J=7.6 Hz, 1H), 7.38-7.28 (m, 3H), 5.59 (d, J=7.2 Hz, 1H), 4.42-4.29 (m, 3H), 3.44 (s, 3H), 3.30-3.22 (m, 3H), 3.01 (d, J=16.0 Hz, 1H), 1.88-1.77 (m, 2H), 1.61-1.54 (m, 2H).

Example 133: Synthesis of (3S)-1'-{5-[(2-amino-3-chloropyridin-4-yl)oxy]pyrazin-2-yl}-1,3-dihydrospiro[indene-2,4'-piperidin]-3-amine

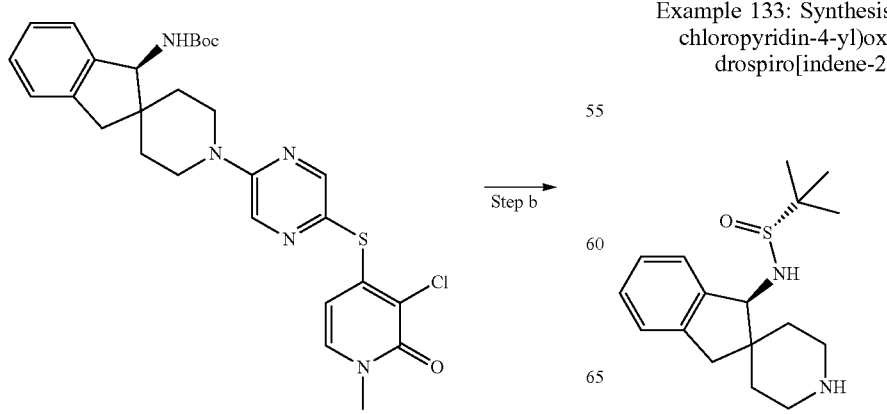

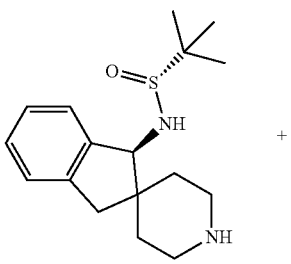

-continued

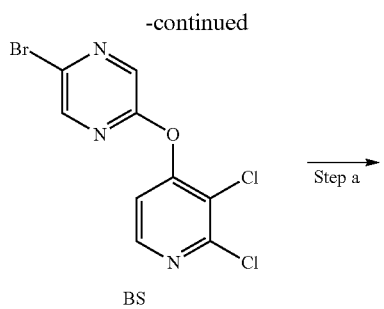

BS

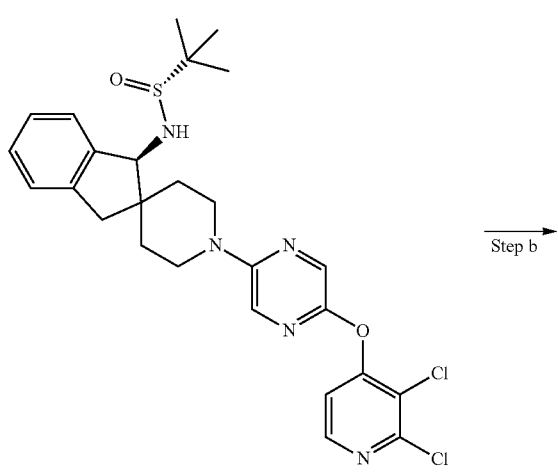

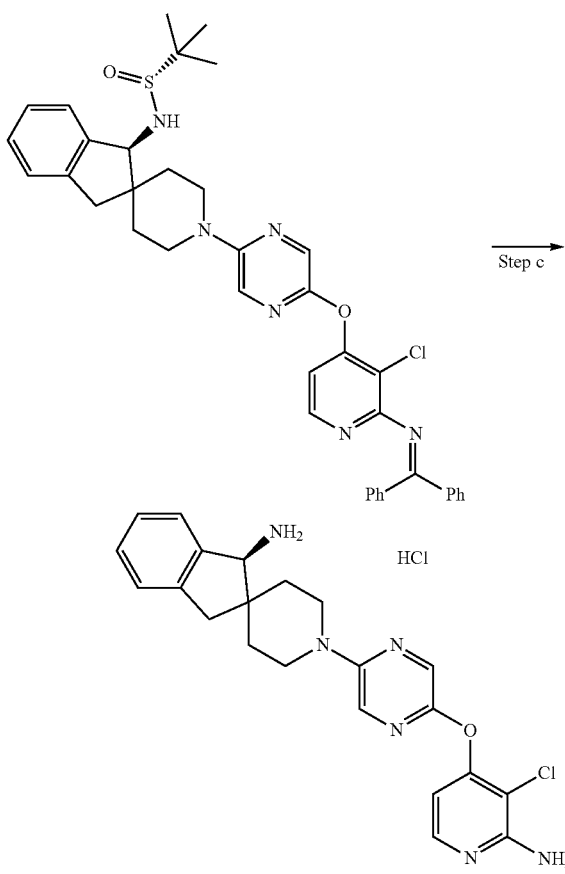

HCl

Step a: To a mixture of 2-bromo-5-[(2,3-dichloropyridin-4-yl)oxy]pyrazine (500 mg, 1.6 mmol, Intermediate BS) and (R)—N-[(3S)-1,3-dihydrospiro[indene-2,4'-piperidin]-3-yl]-2-methylpropane-2-sulfinamide (570 mg, 1.9 mmol, synthesized via Step a of Example 120) in toluene (5.0 mL) were added RuPhos-Pd-G4 (131 mg, 0.2 mmol), RuPhos (144 mg, 0.3 mmol) and $Cs_2CO_3$ (1.0 g, 3.1 mmol). The reaction mixture was purged with $N_2$ for 3 min and stirred at 100° C. for 12 hours under $N_2$. The reaction mixture was concentrated under reduced pressure. The residue was diluted with water (100.0 mL) and extracted ethyl acetate (200.0 mL×2). The combined organic layers were washed with $H_2O$ (100.0 mL) and brine (100.0 mL), dried over anhydrous $Na_2SO_4$, filtered and concentrated under reduced pressure to give a residue. The residue was purified by column chromatography (petroleum ether ethyl acetate=100:0 to 100:60) to give (R)—N-[(3S)-1'-{5-[(2,3-dichloropyridin-4-yl)oxy]pyrazin-2-yl}-1,3-dihydrospiro[indene-2,4'-piperidin]-3-yl]-2-methylpropane-2-sulfinamide (220 mg, 26% yield) as a light yellow solid. LCMS m/z $[M+H]^+$=546.0.

Step b: To a mixture of (R)—N—((S)-1'-(5-((2,3-dichloropyridin-4-yl)oxy)pyrazin-2-yl)-1,3-dihydrospiro[indene-2,4'-piperidin]-1-yl)-2-methylpropane-2-sulfinamide (220 mg, 0.4 mmol) and diphenylmethanimine (134 μL, 0.8 mmol) in toluene (5.0 mL) were added $Pd_2(dba)_3$ (36.7 mg, 40.2 μmol), BINAP (50.0 mg, 80.4 μmol) and $Cs_2CO_3$ (261 mg, 0.8 mmol). The reaction mixture was purged with $N_2$ for 3 min and stirred at 100° C. for 12 hours under $N_2$. The reaction mixture was concentrated under reduced pressure to give a residue. The residue was purified by column chromatography (petroleum ether:ethyl acetate=100:0 to 100:70) to give (R)—N—((S)-1'-(5-((3-chloro-2-((diphenylmethylene)amino)pyridin-4-yl)oxy)pyrazin-2-yl)-1,3-dihydrospiro[indene-2,4'-piperidin]-1-yl)-2-methylpropane-2-sulfinamide (170 mg, 61% yield) as a yellow solid. LCMS m/z $[M+H]^+$=691.1.

Step c: A solution of (R)—N-[(3S)-1'-[5-({3-chloro-2-[(diphenylmethylidene)amino]pyridin-4-yl}oxy)pyrazin-2-yl]-1,3-dihydrospiro[indene-2,4'-piperidin]-3-yl]-2-methylpropane-2-sulfinamide (150 mg, 0.2 mmol) in HCl/MeOH (5.0 mL, 0.5 M) was stirred at 25° C. for 1 hour. The reaction mixture was purified by prep-HPLC (HCl) to give (3S)-1'-{5-[(2-amino-3-chloropyridin-4-yl)oxy]pyrazin-2-yl}-1,3-dihydrospiro[indene-2,4'-piperidin]-3-amine hydrochloride (85.0 mg, 86% yield) as a yellow solid. LCMS m/z $[M+H]^+$= 423.1; $^1$HNMR (400 MHz, Methanol-d4): 8.16-8.17 (m, 1H), 8.05 (s, 1H), 7.86-7.88 (d, J=7.2, 1H), 7.53-7.55 (d, J=7.6, 1H), 7.40-7.45 (m, 2H), 7.34-7.38 (m, 1H), 7.65-7.67 (d, J=7.2, 1H), 4.44 (s, 1H), 4.35-4.39 (m, 1H), 4.21-4.25 (m, 1H), 3.37-3.41 (m, 1H), 3.30-3.32 (m, 1H), 3.17-3.26 (m, 2H), 1.77-1.99 (m, 3H), 1.64-1.67 (m, 1H).

Example 134: Synthesis of (3S)-1'-{5-[(2,3-dichloropyridin-4-yl)oxy]pyrazin-2-yl}-1,3-dihydrospiro[indene-2,4'-piperidin]-3-amine

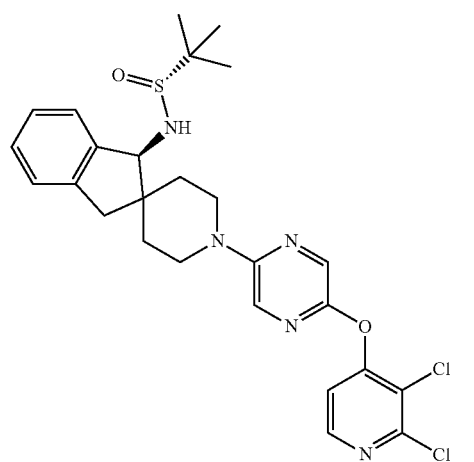

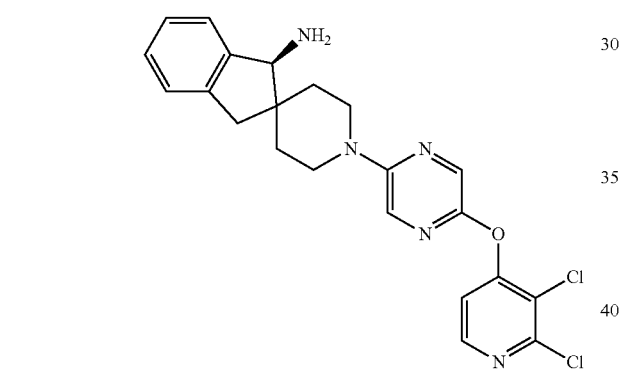

Step a: A solution of (R)—N-[(3S)-1'-{5-[(2,3-dichloropyridin-4-yl)oxy]pyrazin-2-yl}-1,3-dihydrospiro[indene-2,4'-piperidin]-3-yl]-2-methylpropane-2-sulfinamide (90 mg, 0.2 mmol, synthesized via Step a of Example 133) in HCl/MeOH (5.0 mL, 0.5M) was stirred at 25° C. for 0.5 hours. On completion, the reaction mixture was adjusted to pH=8 with solid K$_2$CO$_3$. The reaction was filtered and the filtrate was purified by prep-HPLC (NH$_3$—H$_2$O) to give (3S)-1'-{5-[(2,3-dichloropyridin-4-yl)oxy]pyrazin-2-yl}-1,3-dihydrospiro[indene-2,4'-piperidin]-3-amine (30 mg, 41% yield) as a white solid. LCMS m/z [M+H]$^+$=442.0; $^1$HNMR (400 MHz, CDCl$_3$): 8.08-8.10 (d, J=5.6, 1H), 7.99 (s, 1H), 7.70 (s, 1H), 7.25-7.27 (m, 1H), 7.14-7.17 (m, 3H), 6.77-6.79 (d, J=5.6, 1H), 4.01-4.09 (m, 2H), 3.93 (s, 1H), 3.09-3.19 (m, 2H), 3.00-3.04 (m, 1H), 2.65-2.69 (m, 1H), 1.79-1.86 (m, 1H), 1.69-1.76 (m, 1H), 1.55-1.59 (m, 1H), 1.31-1.35 (m, 1H).

Example 135: Synthesis of 4-({6-[(3S)-3-amino-1,3-dihydrospiro[indene-2,4'-piperidin]-1'-yl]-1H-pyrazolo[3,4-b]pyrazin-3-yl}oxy)-3-chloro-1,2-dihydropyridin-2-one

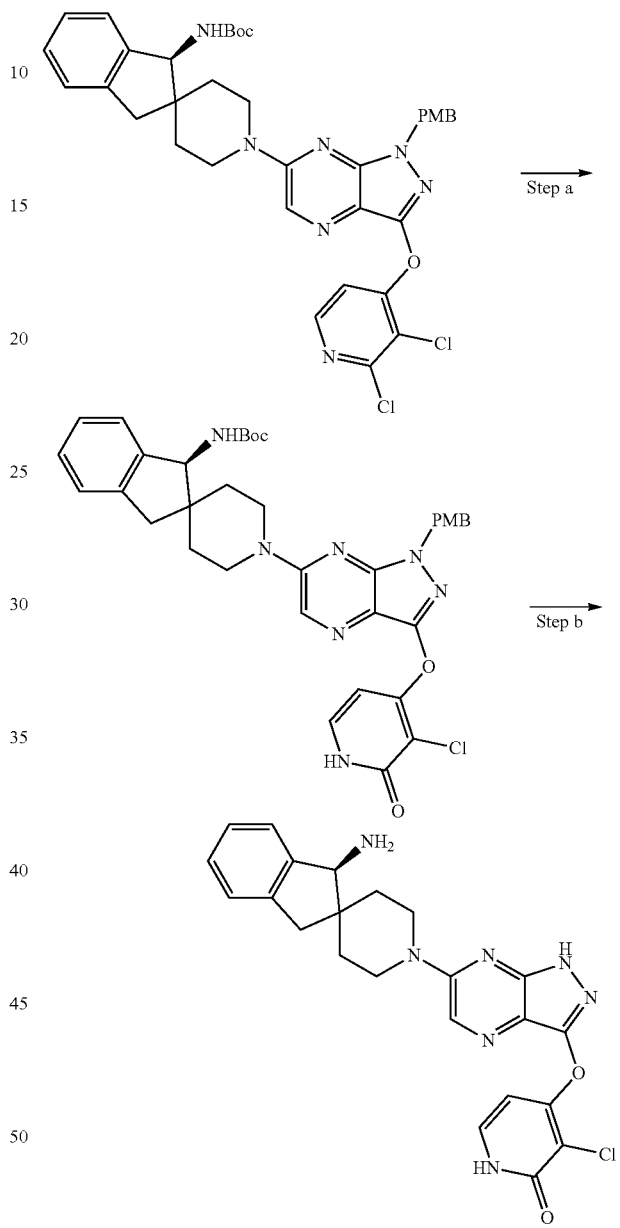

Step a: The mixture of tert-butyl N-[(3S)-1'-{3-[(2,3-dichloropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (250 mg, 355 μmol, synthesized via Step a of Example 126), Pd$_2$(dba)$_3$ (33 mg, 36 μmol), t-BuXPhos (30 mg, 71 μmol) and KOH (59 mg, 1.1 mmol) in dioxane (5 mL) and H$_2$O (5 mL) was stirred at 100° C. for 10 hours under N$_2$. The reaction mixture was then extracted with EtOAc (10 mL×2). The organic layer was washed with brine (10 mL), dried over anhydrous Na$_2$SO$_4$, filtered and concentrated under reduced pressure. The residue was purified by column chromatography (petroleum ether/ethyl acetate=1:0~1:2) to afford tert-butyl N-[(3S)-1'-{3-[(3-chloro-2-oxo-1,2-dihydropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (180 mg, 74% yield) as a yellow solid. LCMS m/z [M+H]$^+$=684.1.

Step b: The mixture of tert-butyl N-[(3S)-1'-{3-[(3-chloro-2-oxo-1,2-dihydropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl]carbamate (160 mg, 233 μmol) in TFA (3 mL) and TfOH (0.5 mL) was stirred at 90° C. for 0.5 hour. The mixture was concentrated under reduced pressure and the residue was diluted with MeOH, adjusted pH=8 with Na$_2$CO$_3$. The mixture was purified by prep-HPLC (NH$_3$.H$_2$O) to afford 4-({6-[(3S)-3-amino-1,3-dihydrospiro[indene-2,4'-piperidin]-1'-yl]-1H-pyrazolo[3,4-b]pyrazin-3-yl}oxy)-3-chloro-1,2-dihydropyridin-2-one (24.2 mg, 22% yield) as a white solid. LCMS m/z [M+H]$^+$= 464.2; $^1$HNMR (400 MHz, DMSO-d$_6$): δ 8.43 (s, 1H), 7.37-7.29 (m, 2H), 7.19-7.16 (m, 3H), 5.98-5.96 (m, 1H), 4.38-4.30 (m, 2H), 3.84 (s, 1H), 3.18-3.08 (m, 3H), 2.67-2.62 (m, 1H), 1.83-1.53 (m, 3H), 1.15-1.11 (m, 1H).

Examples 136 and 137: Synthesis of rel-(R)-1'-(3-((2-amino-3-chloropyridin-4-yl)oxy)-1H-pyrazolo[3,4-b]pyrazin-6-yl)-1,3-dihydrospiro[indene-2,4'-piperidin]-1-amine and rel-(S)-1'-(3-((2-amino-3-chloropyridin-4-yl)oxy)-1H-pyrazolo[3,4-b]pyrazin-6-yl)-1,3-dihydrospiro[indene-2,4'-piperidin]-1-amine

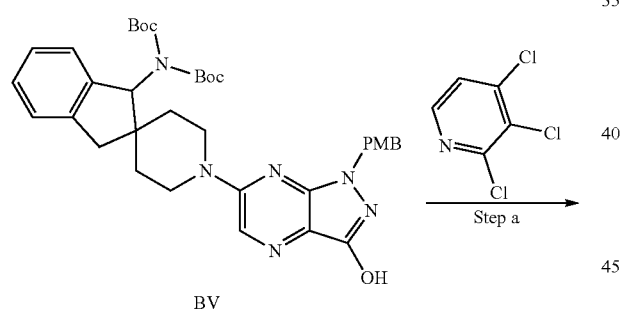

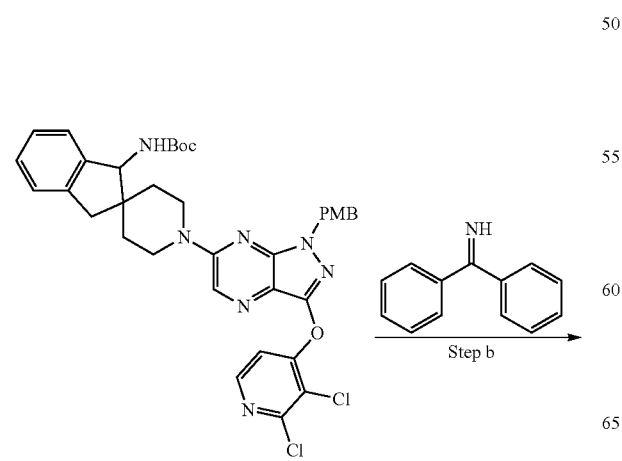

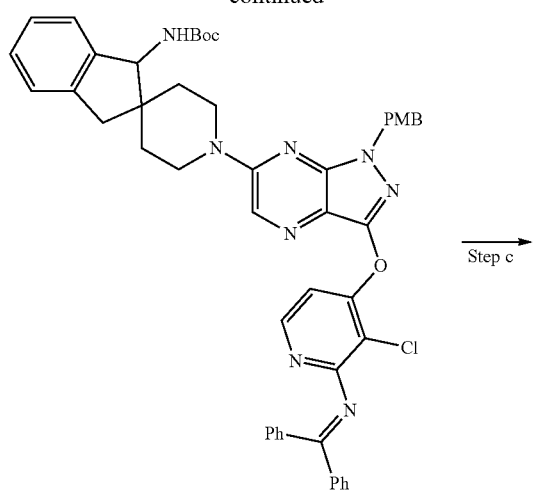

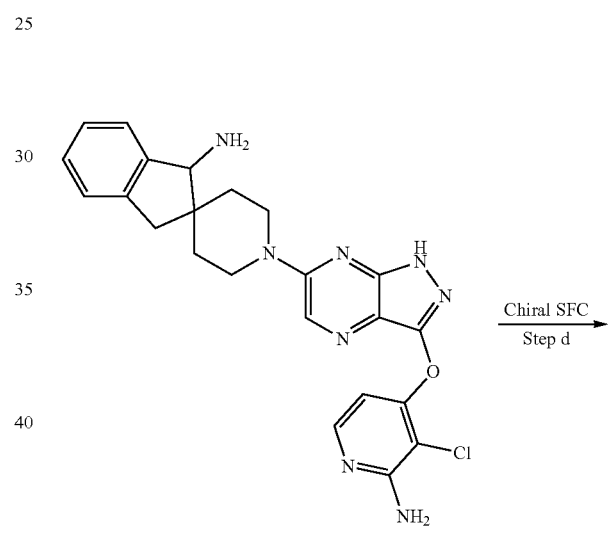

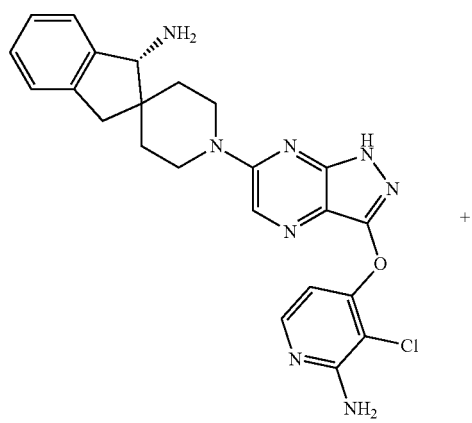

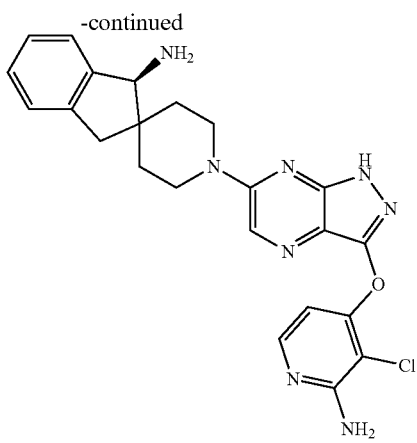

Step a: The mixture of tert-butyl N-[(tert-butoxy)carbonyl]-N-(1'-{3-hydroxy-1-[(4-methoxyphenyl)methyl]-1H-pyrazolo[3,4-b]pyrazin-6-yl}-1,3-dihydrospiro[indene-2,4'-piperidin]-3-yl)carbamate (500 mg, 80% purity, 609 µmol, Intermediate BV), 2,3,4-trichloropyridine (133 mg, 730 µmol) and $Cs_2CO_3$ (593 mg, 1.82 mmol) in DMF (5 mL) was stirred at 100° C. for 24 hours. The mixture was diluted with $H_2O$ (20 mL), and extracted with EtOAc (20 mL×2). The combined organic layers were washed with brine (20 mL), dried over anhydrous $Na_2SO_4$, filtered and concentrated under reduced pressure to afford the residue. The residue was purified by column chromatography (petroleum ether/ethyl acetate=1:0~3:1) to afford tert-butyl N-(1'-{3-[(2,3-dichloropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl)carbamate (160 mg, 37% yield) as a yellow solid. LCMS m/z $[M+H]^+$=702.2.

Step b: The mixture of tert-butyl N-(1'-{3-[(2,3-dichloropyridin-4-yl)oxy]-1-[(4-methoxyphenyl)methyl]-1H-pyrazolo[3,4-b]pyrazin-6-yl}-1,3-dihydrospiro[indene-2,4'-piperidin]-3-yl)carbamate (140 mg, 199 µmol), $Pd_2(dba)_3$ (18.2 mg, 19.9 µmol), diphenyl imine (43.1 mg, 238 µmol), $Cs_2CO_3$ (194 mg, 597 µmol) and BINAP (24.7 mg, 39.8 µmol) in PhMe (10 mL) was evacuated and refilled for 3 times using $N_2$. Then the reaction mixture was stirred at 100° C. for 12 hours. The mixture was concentrated under reduced pressure to afford the residue, which was purified by column chromatography (petroleum ether/ethyl acetate=1:0~3:1) to afford tert-butyl N-{1'-[3-({3-chloro-2-[(diphenylmethylidene)amino]pyridin-4-yl}oxy)-1-[(4-methoxyphenyl)methyl]-1H-pyrazolo[3,4-b]pyrazin-6-yl]-1,3-dihydrospiro[indene-2,4'-piperidin]-3-yl}carbamate (120 mg, 71% yield) as a yellow oil. LCMS m/z $[M+H]^+$=847.2.

Step c: The mixture of tert-butyl N-{1'-[3-({3-chloro-2-[(diphenylmethylidene)amino]pyridin-4-yl}oxy)-1-[(4-methoxyphenyl)methyl]-1H-pyrazolo[3,4-b]pyrazin-6-yl]-1,3-dihydrospiro[indene-2,4'-piperidin]-3-yl}carbamate (110 mg, 129 µmol) in TFA (3 mL) and TfOH (0.3 mL) was stirred at 20° C. for 5 hours. The mixture was concentrated under reduced pressure to afford a residue, which was purified by column chromatography (DCM/MeOH=1:0~10:1) to afford 1'-{3-[(2-amino-3-chloropyridin-4-yl)oxy]-1H-pyrazolo[3,4-b]pyrazin-6-yl}-1,3-dihydrospiro[indene-2,4'-piperidin]-3-amine (35.0 mg, 59% yield) as a yellow oil. LCMS m/z $[M+H]^+$=463.1.

Step d: 1'-{3-[(2-amino-3-chloropyridin-4-yl)oxy]-1H-pyrazolo[3,4-b]pyrazin-6-yl}-1,3-dihydrospiro[indene-2,4'-piperidin]-3-amine (30 mg, 64.8 µmol) was separated by Chiral SFC (Column: DAICEL CHIRALCEL OJ-H (250 mm×30 mm, 5 um). Condition: 0.1% $NH_3.H_2O$ MeOH. Begin B 40%. End B 40%. Flow rate: 50 mL/min). The product of rel-(R)-1'-(3-((2-amino-3-chloropyridin-4-yl)oxy)-1H-pyrazolo[3,4-b]pyrazin-6-yl)-1,3-dihydrospiro[indene-2,4'-piperidin]-1-amine (10 mg, 33% yield, the faster eluting isomer) was obtained as a white solid and the product of rel-(S)-1'-(3-((2-amino-3-chloropyridin-4-yl)oxy)-1H-pyrazolo[3,4-b]pyrazin-6-yl)-1,3-dihydrospiro[indene-2,4'-piperidin]-1-amine (10 mg, 33% yield, the slower eluting isomer) was obtained as a white solid. Absolute stereochemistry of the enantiomers was arbitrarily assigned. Characterization of rel-(R)-1'-(3-((2-amino-3-chloropyridin-4-yl)oxy)-1H-pyrazolo[3,4-b]pyrazin-6-yl)-1,3-dihydrospiro[indene-2,4'-piperidin]-1-amine: LCMS m/z $[M+H]^+$=463.1; $^1HNMR$ (400 MHz, Methanol d4): δ 8.32 (s, 1H), 7.73-7.75 (d, J=6 Hz, 1H), 7.40-7.42 (m, 1H), 7.21-7.29 (m, 3H), 6.27-6.29 (d, J=6 Hz, 1H), 4.42-4.47 (m, 2H), 4.06 (s, 1H), 3.36-3.44 (m, 2H), 3.19-3.23 (m, 1H), 2.90-2.94 (m, 1H), 1.80-1.93 (m, 2H), 1.64-1.67 (m, 1H), 1.52-1.55 (m, 1H). SFC: e.e. =99.5%, $R_f$=4.992 min. Characterization of rel-(S)-1'-(3-((2-amino-3-chloropyridin-4-yl)oxy)-1H-pyrazolo[3,4-b]pyrazin-6-yl)-1,3-dihydrospiro[indene-2,4'-piperidin]-1-amine: LCMS m/z $[M+H]^+$=463.1; $^1HNMR$ (400 MHz, Methanol_$d_4$): δ 8.32 (s, 1H), 7.73-7.75 (d, J=6 Hz, 1H), 7.38-7.40 (m, 1H), 7.21-7.28 (m, 3H), 6.27-6.29 (d, J=6 Hz, 1H), 4.42-4.47 (m, 2H), 4.00 (s, 1H), 3.36-3.44 (m, 2H), 3.18-3.22 (m, 1H), 2.84-2.88 (m, 1H), 1.79-1.94 (m, 2H), 1.63-1.67 (m, 1H), 1.47-1.51 (m, 1H). SFC: e.e. =96.6%, $R_f$=5.265 min. Column: Chiralcel OJ-H 150*4.6 mm I.D., 5 um. Mobile phase: A: $CO_2$ B: methanol (0.05% DEA). Gradient: hold 5% for 0.5 min, then from 5% to 40% of B in 3.5 min and hold 40% for 2.5 min, then 5% of B for 1.5 min. Flow rate: 3 mL/min Column temp: 40° C.

Example 138: Synthesis of (S)—N4-(6-(1-amino-1,3-dihydrospiro[indene-2,4'-piperidin]-1'-yl)-1H-pyrazolo[3,4-b]pyrazin-3-yl)-3-chloropyridine-2,4-diamine

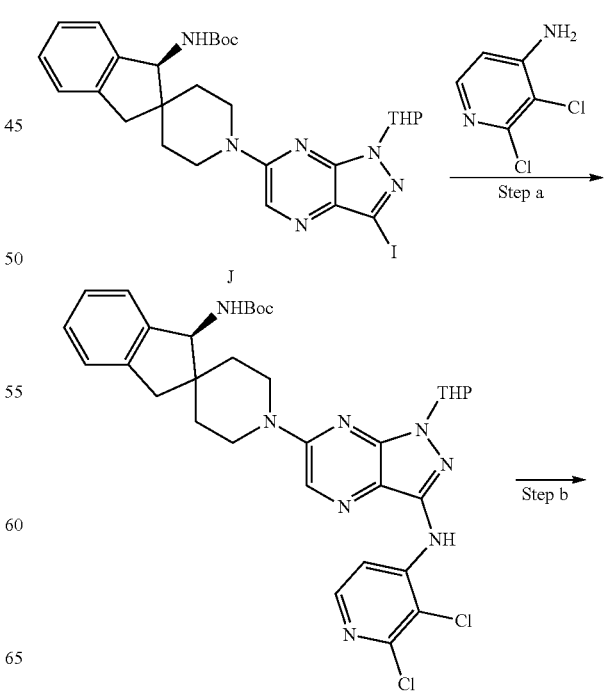

-continued

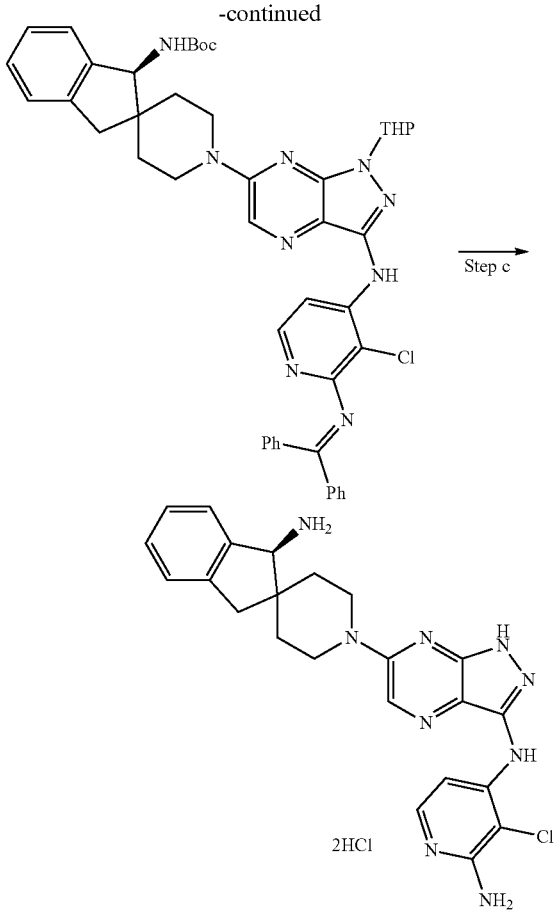

Step a: A mixture of tert-butyl ((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (350.0 mg, 555.0 μmol, from Intermediate J), 2,3-dichloropyridin-4-amine (135.0 mg, 832.0 μmol, CAS #184416-83-9), XantPhos-Pd-G4 (47.6 mg, 55.4 μmol) and $Cs_2CO_3$ (270.0 mg, 832.0 μmol) in PhMe (10 mL) was stirred at 100° C. for 12 hours. The reaction mixture was concentrated and purified by silica gel column (EtOAc in petroleum ether=0~30%) to give tert-butyl N-[(3S)-1'-{3-[(2,3-dichloropyridin-4-yl)amino]-1-(oxan-2-yl)-1H-pyrazolo[3,4-b]pyrazin-6-yl}-1,3-dihydrospiro[indene-2,4'-piperidin]-3-yl]carbamate (200.0 mg, 54% yield) as a yellow solid. LCMS m/z [M+H]$^+$=665.1.

Step b: A mixture of tert-butyl N-[(3S)-1'-{3-[(2,3-dichloropyridin-4-yl)amino]-1-(oxan-2-yl)-1H-pyrazolo[3,4-b]pyrazin-6-yl}-1,3-dihydrospiro[indene-2,4'-piperidin]-3-yl]carbamate (180.0 mg, 270.0 μmol), $Ph_2C$=NH (73.4 mg, 405.0 μmol), $Cs_2CO_3$ (177.0 mg, 540.0 μmol), $Pd_2(dba)_3$ (24.7 mg, 27.0 μmol) and BINAP (33.6 mg, 54.0 μmol) in PhMe (10 mL) was stirred at 100° C. for 12 hours under $N_2$. The reaction mixture was concentrated and purified by silica gel column (EtOAc in petroleum ether=0~30%) to give tert-butyl N-[(3S)-1'-[3-({3-chloro-2-[(diphenylmethylidene)amino]pyridin-4-yl}amino)-1-(oxan-2-yl)-1H-pyrazolo[3,4-b]pyrazin-6-yl]-1,3-dihydrospiro[indene-2,4'-piperidin]-3-yl]carbamate (120.0 mg, 55% yield) as a yellow solid. LCMS m/z (M+H−Ph$_2$C)$^+$=646.2.

Step c: A solution of tert-butyl N-[(3S)-1'-[3-({3-chloro-2-[(diphenylmethylidene)amino]pyridin-4-yl}amino)-1-(oxan-2-yl)-1H-pyrazolo[3,4-b]pyrazin-6-yl]-1,3-dihydrospiro[indene-2,4'-piperidin]-3-yl]carbamate (120.0 mg, 148.0 μmol) in 4M HCl/MeOH (10.0 mL) was stirred at 25° C. for 1 hour. The reaction mixture was concentrated and dissolved in MeOH (5 mL) and purified by prep-HPLC (HCl) to give (S)—N4-(6-(1-amino-1,3-dihydrospiro[indene-2,4'-piperidin]-1'-yl)-1H-pyrazolo[3,4-b]pyrazin-3-yl)-3-chloropyridine-2,4-diamine (23.0 mg) as a yellow solid. (S)—N4-(6-(1-amino-1,3-dihydrospiro[indene-2,4'-piperidin]-1'-yl)-1H-pyrazolo[3,4-b]pyrazin-3-yl)-3-chloropyridine-2,4-diamine (e.e. =70%) was separated by chiral SFC (Column: DAICEL CHIRALPAK AS-H 250 mm*30 mm, 5 um; Mobile phase: A: $CO_2$, B: Ethanol (0.1% $NH_3.H_2O$); Gradient: keep 50% of B; Flow rate: 50 mL/min; Column temp: 35° C.). Some impurity was introduced, so the product was re-purified by prep-HPLC (HCl) again to give (S)—N4-(6-(1-amino-1,3-dihydrospiro[indene-2,4'-piperidin]-1'-yl)-1H-pyrazolo[3,4-b]pyrazin-3-yl)-3-chloropyridine-2,4-diamine dihydrochloride (8.0 mg) as a yellow solid. LCMS m/z [M+H]$^+$=462.1. $^1$HNMR (400 MHz, $CD_3OD$): 8.40 (s, 1H), 7.65 (d, J=7.2 Hz, 1H), 7.55 (d, J=7.2 Hz, 1H), 7.35-7.45 (m, 3H), 7.17 (d, J=7.6 Hz, 1H), 4.40-4.60 (m, 3H), 3.40-3.55 (m, 2H), 3.24 (s, 2H), 1.65-2.00 (m, 4H); SFC: e.e. =98.8%, Rt=3.501 min. Column: AS-3 100× 4.6 mm I.D., 3 um; Mobile phase: A: $CO_2$ B: ethanol (0.05% DEA); Isocratic: 40% B; Flow rate: 2.8 mL/min; Column temp.: 35° C.

Example 139: Synthesis of (S)-1'-(5-((2-amino-3-chloropyridin-4-yl)thio)pyrazin-2-Y)-4-fluoro-1,3-dihydrospiro[indene-2,4'-piperidin]-1-amine

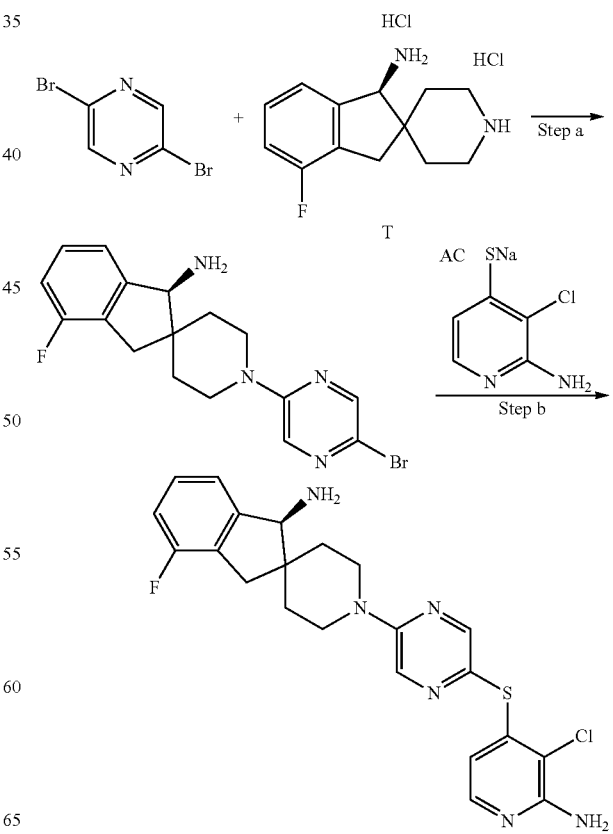

Step a: 2,5-dibromopyrazine (1.02 g, 4.31 mmol), (3S)-7-fluoro-1,3-dihydrospiro[indene-2,4'-piperidin]-3-amine dihydrochloride (1.15 g, 3.92 mmol, Intermediate T) and TEA (2.69 mL, 19.5 mmol) were added in DMF (0.23M, 17 mL). The mixture was stirred at 85° C. for 12 h. EtOAc and brine were added to the reaction mixture, and the solution was extracted with EtOAc(3×). The organic layer was dried over Na$_2$SO$_4$, filtered and concentrated. The residue was purified by column chromatography (0-20% MeOH in DCM with 0.1% NH$_4$OH) to give (S)-1'-(5-bromopyrazin-2-yl)-4-fluoro-1,3-dihydrospiro[indene-2,4'-piperidin]-1-amine (1.36 g, 84% yield). LCMS m/z [M]$^+$=377.3.

Step b: (3S)-1'-(5-bromopyrazin-2-yl)-7-fluoro-1,3-dihydrospiro[indene-2,4'-piperidin]-3-amine (1.36 g, 3.60 mmol), 3-chloro-4-(sodiosulfanyl)pyridin-2-amine (657 mg, 3.60 mmol, Intermediate AC), and Pd-Xantphos-G4 (346 mg, 0.3600 mmol) were placed in a microwave vial and evacuated and backfilled with nitrogen. DIPEA (3.13 mL, 18.0 mmol) and dioxane (15 mL) were added and the reaction was heated to 110° C. in a microwave for 16 h. The reaction was filtered through celite and rinsed with EtOAc and concentrated. The residue was purified by column chromatography (100 g column, 0-20% MeOH in DCM with 0.1% NH$_4$OH). The material was repurifed reverse phase HPLC (5-40% ACN in water with 0.1% formic acid) to give (S)-1'-(5-((2-amino-3-chloropyridin-4-yl)thio)pyrazin-2-yl)-4-fluoro-1,3-dihydrospiro[indene-2,4'-piperidin]-1-amine (173 mg, 10% yield). LCMS m/z [M+H]$^+$=457.3; $^1$H NMR (500 MHz, DMSO-d6) δ ppm 8.46 (d, J=0.78 Hz, 1H), 8.27-8.30 (m, 1H), 8.23-8.27 (m, 1H), 7.65 (d, J=5.19 Hz, 1H), 7.24-7.30 (m, 1H), 7.19-7.24 (m, 1H), 7.00-7.07 (m, 1H), 5.75-5.89 (m, 1H), 4.22-4.35 (m, 2H), 4.03 (s, 1H), 3.21-3.31 (m, 2H), 3.14 (d, J=16.08 Hz, 1H), 2.77 (d, J=15.82 Hz, 1H), 1.74-1.81 (m, 1H), 1.65-1.73 (m, 1H), 1.52-1.59 (m, 1H), 1.26-1.32 (m, 1H).

Example 140: Synthesis of (S)-1'-(5-(difluoromethyl)-3-(3,4-dihydro-1,5-naphthyridin-1(2H)-yl)-1H-pyrazolo[3,4-b]pyrazin-6-yl)-1,3-dihydrospiro[indene-2,4'-piperidin]-1-amine

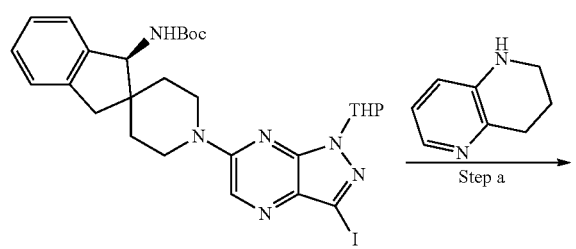

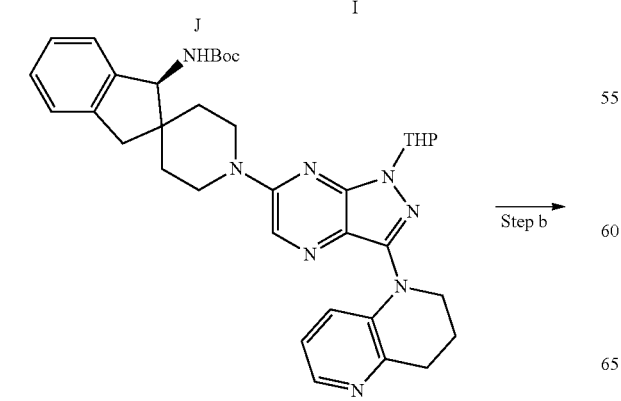

-continued

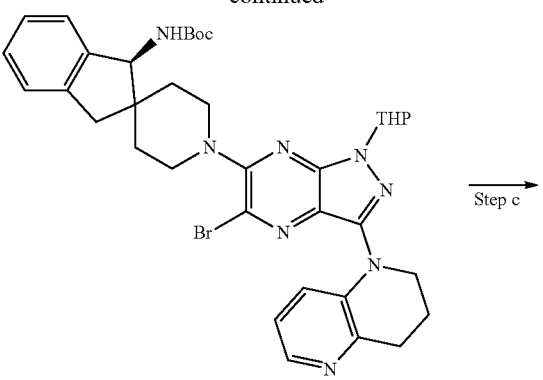

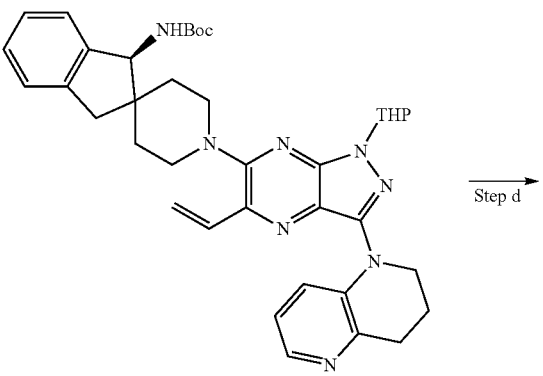

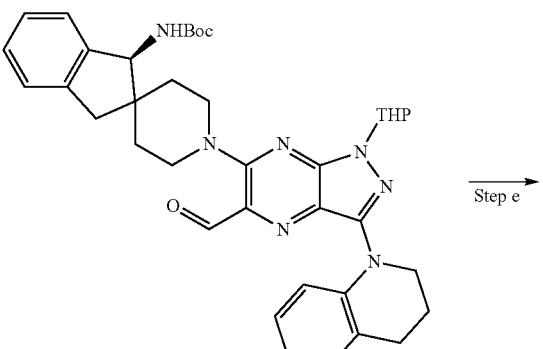

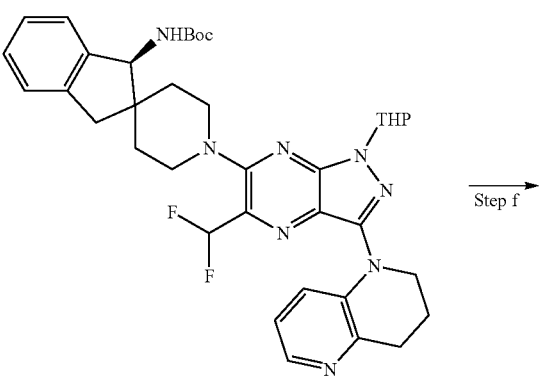

-continued

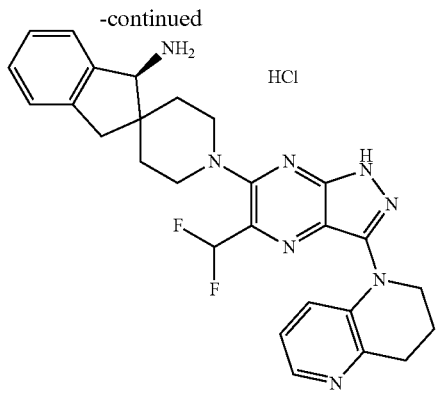

Step a: A solution of tert-butyl ((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate(1.50 g, 2.37 mmol, Intermediate J), 1,2,3,4-tetrahydro-1,5-naphthyridine (381.0 mg, 2.84 mmol), XantPhos-Pd-G4 (227.0 mg, 237.0 umol) and Cs$_2$CO$_3$ (1.54 g, 4.74 mmol) in PhMe (50.0 mL) was stirred at 100° C. for 12 hours under N$_2$. The reaction mixture was poured into H$_2$O (200.0 mL) and extracted with EtOAc (200.0 mL×2). The combined organic layers were washed with brine (200.0 mL), dried over anhydrous Na$_2$SO$_4$, filtered and concentrated under reduced pressure to give a brown residue. The residue was purified by flash silica gel chromatography (40 g column, ethyl acetate in petroleum ether from 0% to 65%) to give tert-butyl ((1S)-1'-(3-(3,4-dihydro-1,5-naphthyridin-1(2H)-yl)-1-(tetrahydro-2H-pyran-2-yl)-1H-pyrazolo[3,4-b]pyrazin-6-yl)-1,3-dihydrospiro[indene-2,4'-piperidin]-1-yl) carbamate (1.20 g, 80% yield) as a yellow oil. LCMS m/z [M+H]$^+$=637.2.

Step b: To a solution of tert-butyl ((1S)-1'-(3-(3,4-dihydro-1,5-naphthyridin-1(2H)-yl)-1-(tetrahydro-2H-pyran-2-yl)-1H-pyrazolo[3,4-b]pyrazin-6-yl)-1,3-dihydrospiro[indene-2,4'-piperidin]-1-yl)carbamate (1.20 g,1.88 mmol) in MeCN/AcOH (30.0 mL/30.0 mL) was added NBS (334.0 mg, 1.88 mmol) in portions at 20° C. The reaction mixture was stirred at 20° C. for 1 hour. The reaction mixture was concentrated under reduced pressure. The residue was triturated with saturated NaHCO$_3$ (150.0 mL) and extracted with EtOAc (150.0 mL×2). The combined organic layers were washed with brine (200.0 mL) and dried over anhydrous Na$_2$SO$_4$, filtered and concentrated under reduced pressure to give a residue. The residue was purified by flash silica gel chromatography (40 g column, ethyl acetate in petroleum ether from 0% to 60%) to give tert-butyl N-[(3S)-1'-[5-bromo-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (1.25 g, 93% yield) as a yellow oil. LCMS m/z [M+H]$^+$=715.1/717.1.

Step c: A solution of tert-butyl N-[(3S)-1'-[5-bromo-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (1.25 g, 1.74 mmol), potassium vinyltrifluoroborate (466.0 mg, 3.48 mmol), Pd(dppf)Cl$_2$ (254.0 mg, 348.0 umol) and K$_3$PO$_4$.3H$_2$O (2.60 g, 5.22 mmol) in i-PrOH/H$_2$O (20.0 mL/2.0 mL) was stirred at 100° C. for 12 hour under N$_2$. The reaction mixture was poured into H$_2$O (200.0 mL) and extracted with EtOAc (200.0 mL×2). The combined organic layers were washed with brine (150.0 mL), dried over anhydrous Na$_2$SO$_4$, filtered and filtrate concentrated under reduced pressure to give a brown residue. The residue was purified by flash silica gel chromatography (40 g column, ethyl acetate in petroleum ether from 0% to 75%) to give tert-butyl N-[(3S)-1'-[5-ethenyl-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (1.00 g, 87% yield) as a yellow solid. LCMS m/z [M+H]$^+$=663.2.

Step d: To a solution of tert-butyl N-[(3S)-1'-[5-ethenyl-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (1.00 g, 1.50 mmol) in acetone/H$_2$O (21.0 mL/7.0 mL) was added K$_2$OsO$_4$.2H$_2$O (55.2 mg, 150.0 umol) and NaIO$_4$ (963.0 mg, 4.50 mmol) at 20° C. The reaction mixture was stirred at 20° C. for 1 hour. The reaction mixture was filtered and filtrate concentrated under reduced pressure to give a residue. The residue was purified by flash silica gel chromatography (40 g column, ethyl acetate in petroleum ether from 0% to 70%) to give tert-butyl N-[(3S)-1'-[5-formyl-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (520.0 mg, 52% yield) as a yellow solid. LCMS m/z [M+H]$^+$=665.2.

Step e: To a solution of tert-butyl N-[(3S)-1'-[5-formyl-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (250.0 mg, 376.0 μmol) in DCM (5.0 mL) was added DAST (303.0 mg, 1.88 mmol) at 0° C. under N$_2$. The reaction mixture was stirred at 0° C. for 1 hour. The reaction mixture was quenched with H$_2$O (30.0 mL) and extracted with DCM (20.0 mL×2). The combined organic layers were washed with brine (20.0 mL), dried over anhydrous Na$_2$SO$_4$, filtered and concentrated under reduced pressure to give a brown residue. The residue was purified by flash silica gel chromatography (12 g column, ethyl acetate in petroleum ether from 0% to 70%) to give tert-butyl N-[(3S)-1'-[5-(difluoromethyl)-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (50.0 mg, 19% yield) as an orange oil. LCMS m/z [M+H]$^+$=687.2.

Step f: A solution of tert-butyl N-[(3S)-1'-[5-(difluoromethyl)-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (50.0 mg, 72.8 μmol) in HCl/MeOH (3.0 mL, 4 M) was stirred at 20° C. for 2 hours. The reaction mixture was concentrated under reduced pressure. The residue was diluted with MeOH (3.0 mL) and purified by prep-HPLC (HCl). The product of (S)-1'-(5-(difluoromethyl)-3-(3,4-dihydro-1,5-naphthyridin-1(2H)-yl)-1H-pyrazolo[3,4-b]pyrazin-6-yl)-1,3-dihydrospiro[indene-2,4'-piperidin]-1-amine hydrochloride (4.30 mg, 11% yield) was obtained as a yellow solid. LCMS m/z [M+H]$^+$=503.1; $^1$HNMR (400 MHz, CD$_3$OD): 8.31-8.34 (m, 1H), 8.10-8.12 (m, 1H), 7.61-7.64 (m, 1H), 7.54-7.57 (m, 1H), 7.36-7.44 (m, 3H), 6.86-7.12 (m, 1H), 4.48 (s, 1H), 4.21-4.25 (m, 2H), 3.71-3.86 (m, 2H), 3.36-3.43 (m, 2H), 3.29-3.31 (m, 2H), 3.21 (s, 2H), 2.31-2.37 (m, 2H), 2.11-2.13 (m, 1H), 2.01-2.10 (m, 1H), 1.83-1.87 (m, 1H), 1.69-1.73 (m, 1H).

545

Examples 141 and Example 142: Synthesis of (R)-1-(6-((S)-1-amino-1,3-dihydrospiro[indene-2,4'-Piperidin]-1'-yl)-3-(3,4-dihydro-1,5-naphthyridin-1(2H)-yl)-1H-pyrazolo[3,4-b]pyrazin-5-yl)ethan-1-ol and (S)-1-(6-((S)-1-amino-1,3-dihydrospiro[indene-2,4'-piperidin]-1'-yl)-3-(3,4-dihydro-1,5-naphthyridin-1(2H)-yl)-1H-pyrazolo[3,4-b]pyrazin-5-yl)ethan-1-ol

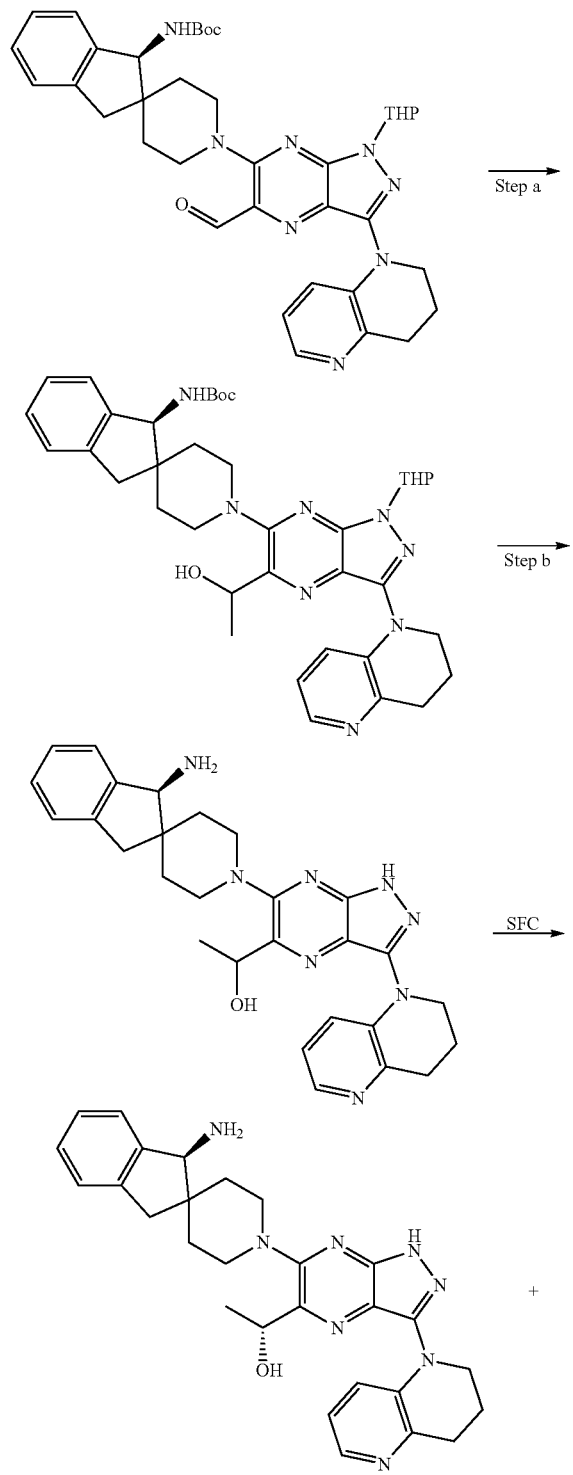

546

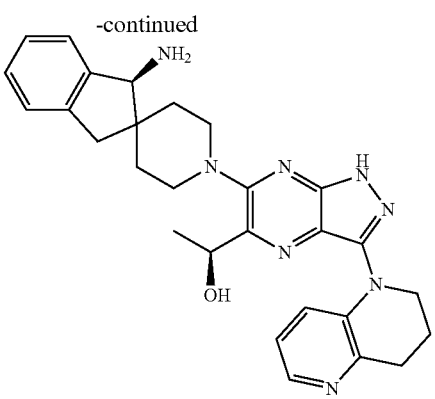

Step a: To a solution of tert-butyl N-[(3S)-1'-[5-formyl-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (260.0 mg, 391.0 μmol, synthesized via Step a-d of Example 140) in THF (10.0 mL) was added MeMgBr (390.0 uL, 1.17 mmol, 3 M in THF) at 20° C. under $N_2$. The reaction mixture was stirred at 20° C. for 3 hours. The reaction mixture was quenched with $H_2O$ (30.0 mL) and extracted with EtOAc (50.0 mL×2). The combined organic layers were washed with brine (50.0 mL), dried over anhydrous $Na_2SO_4$, filtered and filtrate concentrated under reduced pressure to give a brown residue. The residue was purified by flash silica gel chromatography (12 g column, ethyl acetate in petroleum ether from 0% to 85%) to give tert-butyl N-[(3S)-1'-[5-(1-hydroxyethyl)-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (200.0 mg, 75% yield) as a yellow solid. LCMS m/z [M+H]$^+$=681.2.

Step b: A solution of tert-butyl N-[(3S)-1'-[5-(1-hydroxyethyl)-1-(oxan-2-yl)-3-(1,2,3,4-tetrahydro-1,5-naphthyridin-1-yl)-1H-pyrazolo[3,4-b]pyrazin-6-yl]-1,3-dihydrospiro[indene-2,4'-piperidin]-3-yl]carbamate (200.0 mg, 293.0 μmol) in TFA/DCM (5.0 mL/5.0 mL) was stirred at 30° C. for 12 hours. The reaction mixture was concentrated under reduced pressure. The residue was diluted with MeOH (5.0 mL), adjusted to pH=9 with solid $Na_2CO_3$ and purified by prep-HPLC ($NH_3.H_2O$). 1-{6-[(3S)-3-amino-1,3-dihydrospiro[indene-2,4'-piperidin]-1'-yl]-3-(1,2,3,4-tetrahydro-1,5-naphthyridin-1-yl)-1H-pyrazolo[3,4-b]pyrazin-5-yl}ethan-1-ol (40.0 mg, 28% yield) was obtained as a yellow solid. LCMS m/z [M+H]$^+$=497.1.

Step c: 1-{6-[(3S)-3-amino-1,3-dihydrospiro[indene-2,4'-piperidin]-1'-yl]-3-(1,2,3,4-tetrahydro-1,5-naphthyridin-1-yl)-1H-pyrazolo[3,4-b]pyrazin-5-yl}ethan-1-ol (40.0 mg, 80.5 μmol) was separated by preparative SFC (column: DAICEL CHIRALPAK AD (250 mm×30 mm, 10 um), Mobile phase: 0.1% $NH_3.H_2O$ ETOH (Begin B: 40%, End B: 40%), Flow rate: 70 ML/MIN) to afford (R)-1-(6-((S)-1-amino-,3-dihydrospiro[indene-2,4'-piperidin]-1'-yl)-3-(3,4-dihydro-1,5-naphthyridin-1(2H)-yl)-1H-pyrazolo[3,4-b]pyrazin-5-yl)ethan-1-ol (9.6 mg, 24% yield, Rt=3.92 min, the faster eluting isomer) as a yellow solid and (S)-1-(6-((S)-1-amino-1,3-dihydrospiro[indene-2,4'-piperidin]-1'-yl)-3-(3,4-dihydro-1,5-naphthyridin-1(2H)-yl)-1H-pyrazolo[3,4-b]pyrazin-5-yl)ethan-1-ol (10.5 mg, 26% yield, Rt=4.74 min, the slower eluting isomer) as a yellow solid. Absolute stereochemistry of the diastereomers was arbitrarily assigned. Characterization of (R)-1-(6-((S)-1-amino-,3-dihydrospiro[indene-2,4'-piperidin]-1'-yl)-3-(3,4-dihydro- 1,5-naphthyridin-1(2H)-yl)-1H-pyrazolo[3,4-b]pyrazin-5-yl)ethan-1-ol: LCMS m/z [M+H]$^+$=497.1; $^1$HNMR (400 MHz, CD$_3$OD): 7.78-7.80 (m, 1H), 7.40-7.43 (m, 1H), 7.28-7.31 (m, 1H), 7.09-7.13 (m, 3H), 6.92-6.95 (m, 1H), 5.05-5.13 (m, 1H), 3.91-3.99 (s, 3H), 3.65-3.80 (m, 1H), 3.40-3.50 (m, 1H), 3.15-3.20 (m, 1H), 3.00-3.08 (m, 2H), 2.88-2.98 (m, 2H), 2.70-2.75 (m, 1H), 2.08-2.12 (m, 2H), 1.89-2.05 (m, 2H), 1.55-1.60 (m, 1H), 1.38-1.42 (m, 4H); SFC: e.e. =97.6%. Characterization of (S)-1-(6-((S)-1-amino-1,3-dihydrospiro[indene-2,4'-piperidin]-1'-yl)-3-(3,4-dihydro-1,5-naphthyridin-1(2H)-yl)-1H-pyrazolo[3,4-b]pyrazin-5-yl)ethan-1-ol: LCMS m/z [M+H]$^+$=497.1; $^1$HNMR (400 MHz, CD$_3$OD): 7.78-7.80 (m, 1H), 7.40-7.43 (m, 1H), 7.28-7.31 (m, 1H), 7.09-7.13 (m, 3H), 6.92-6.95 (m, 1H), 5.05-5.13 (m, 1H), 3.91-3.99 (s, 3H), 3.65-3.80 (m, 1H), 3.40-3.50 (m, 1H), 3.15-3.20 (m, 1H), 3.00-3.08 (m, 2H), 2.88-2.98 (m, 2H), 2.70-2.75 (m, 1H), 2.08-2.12 (m, 2H), 1.89-2.05 (m, 2H), 1.55-1.60 (m, 1H), 1.38-1.42 (m, 4H). SFC: e.e. =96.4%.

Example 143: Synthesis of (S)-1'-(3-(phenylethynyl)-1H-pyrazolo[3,4-b]pyrazin-6-yl)-1,3-dihydrospiro[indene-2,4'-piperidin]-1-amine

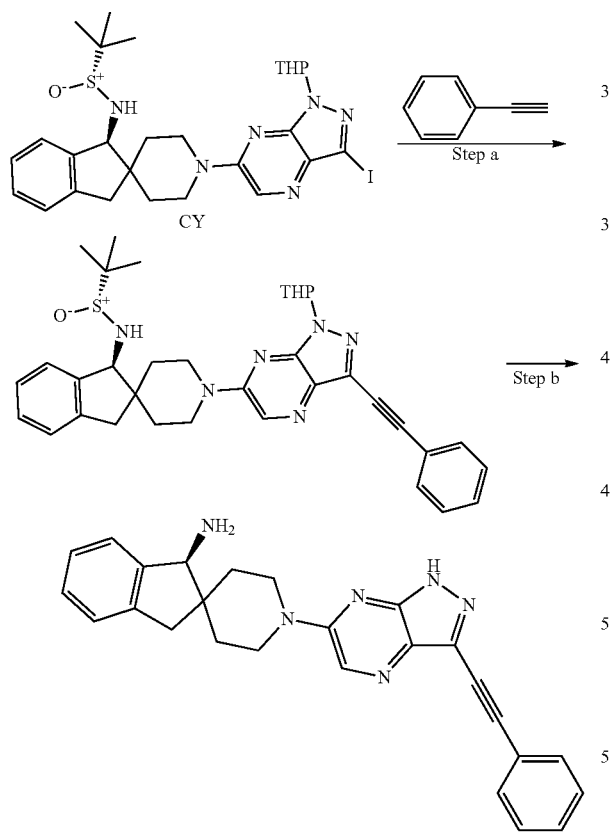

Step a: (R)—N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]-2-methylpropane-2-sulfinamide (250 mg, 0.394 mmol, Intermediate CY), ethynylbenzene (47.5 µL, 0.4332 mmol), ethylbis(propan-2-yl)amine (69.4 µL, 0.3978 mmol), iodocopper (3.74 mg, 0.0197 mmol) and XPhos-Pd-G4 (33.9 mg, 0.0394 mmol) were added to MeCN (5 mL) in a sealed tube. The mixture was bubbled with N$_2$ for 5 min and the reaction was stirred at 80° C. for 20 h. The solvent was removed in vacuo and the crude product was purified by column chromatography (Si-12 g column, 25-100% EA/hep) to afford (R)-2-methyl-N-((1S)-1'-(3-(phenylethynyl)-1-(tetrahydro-2H-pyran-2-yl)-1H-pyrazolo[3,4-b]pyrazin-6-yl)-1,3-dihydrospiro[indene-2,4'-piperidin]-1-yl)propane-2-sulfinamide. LCMS m/z [M+H]$^+$=609.4.

Step b: (R)-2-methyl-N-[(3S)-1'-[1-(oxan-2-yl)-3-(2-phenylethynyl)-1H-pyrazolo[3,4-b]pyrazin-6-yl]-1,3-dihydrospiro[indene-2,4'-piperidin]-3-yl]propane-2-sulfinamide (120 mg, 0.197 mmol) in MeOH (2 mL) was charged with hydrogen chloride (492 µL, 1.97 mmol) and heated to 60° C. for 2 hr. The solvent was removed in vacuo and crude product purified by prep-HPLC (10-40% ACN/water/FA) to afford S)-1'-(3-(phenylethynyl)-1H-pyrazolo[3,4-b]pyrazin-6-yl)-1,3-dihydrospiro[indene-2,4'-piperidin]-1-amine (50 mg, 60% yield) as a white solid. LCMS m/z [M+H]$^+$=421.6; $^1$H NMR (400 MHz, DMSO-d6) Shift 13.35-13.65 (m, 1H), 8.49 (s, 1H), 8.21 (s, 1H), 7.58-7.65 (m, 2H), 7.44-7.49 (m, 3H), 7.31-7.36 (m, 1H), 7.16-7.23 (m, 3H), 4.28-4.39 (m, 2H), 3.93 (s, 1H), 3.30 (br s, 2H), 3.11 (d, J=15.92 Hz, 1H), 2.71 (d, J=15.66 Hz, 1H), 1.76-1.86 (m, 1H), 1.70 (dt, J=3.79, 12.51 Hz, 1H), 1.55 (br d, J=12.63 Hz, 1H), 1.21 (br d, J=12.63 Hz, 1H).

Example 144: Synthesis of (S)-1'-(6-(2-chlorophenyl)-5-methylimidazo[2,1-b][1,3,4]thiadiazol-2-yl)-1,3-dihydrospiro[indene-2,4'-piperidin]-1-amine

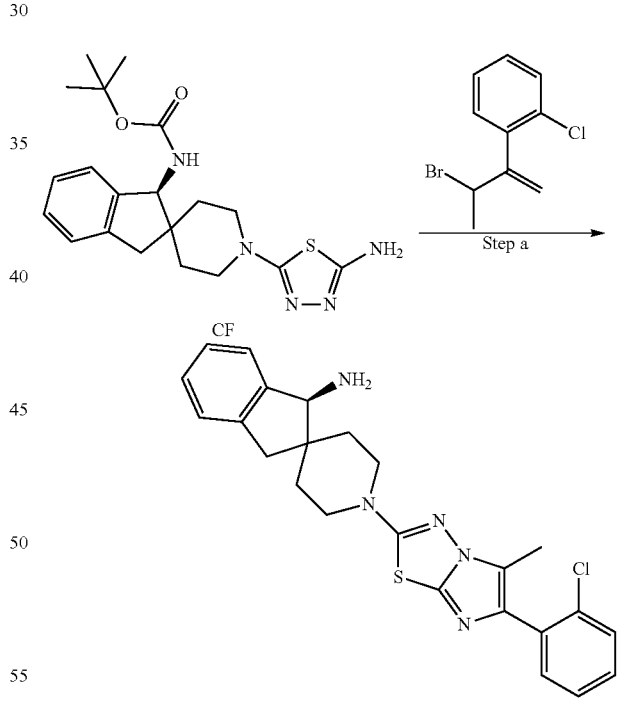

Step a: Dissolved tert-butyl N-[(3S)-1'-(5-amino-1,3,4-thiadiazol-2-yl)-1,3-dihydrospiro[indene-2,4'-piperidin]-3-yl]carbamate (101 mg, 0.252 mmol, Intermediate CF) in 10 mL acetone then added 2-bromo-1-(2-chlorophenyl)propan-1-one (80.8 µL, 0.503 mmol, CAS #75815-22-4) and heated the reaction at reflux for 16 hr. The solvent was then removed and the residue was dissolved in 6N HCl (12 mL) and the reaction was stirred at 100° C. for 1.5 hr. Then an additional equivalent of 2-bromo-1-(2-chlorophenyl)propan-1-one (124 mg, 0.503 mmol) was added and the reaction was stirred at 100° C. for 45 min, then at rt for 48 h. The reaction mixture was concentrated in vacuo and purified by prep HPLC (5-30% B, FA). To give (3S)-1'-[6-(2-chlorophenyl)-5-methylimidazo[2,1-b][1,3,4]thiadiazol-2-yl]-1,3-dihydrospiro[indene-2,4'-piperidin]-3-amine (8.20 mg, 0.0182 mmol). LCMS m/z [M+H]⁺=450.5; ¹H NMR (400 MHz, DMSO-d6) Shift 7.50-7.54 (m, 1H), 7.44-7.48 (m, 1H), 7.35-7.41 (m, 2H), 7.29-7.34 (m, 1H), 7.14-7.21 (m, 3H), 3.90 (s, 1H), 3.69-3.79 (m, 2H), 3.41 (br d, J=3.03 Hz, 2H), 3.07 (d, J=15.66 Hz, 1H), 2.61-2.69 (m, 1H), 2.27 (s, 3H), 1.83-1.92 (m, 1H), 1.77 (dt, J=4.29, 12.63 Hz, 1H), 1.53-1.60 (m, 1H), 1.19 (br d, J=15.41 Hz, 1H).

Example 145: Synthesis of (S)-1'-(5-(2-chlorophenyl)thiazol-2-yl)-1,3-dihydrospiro[indene-2,4'-piperidin]-1-amine

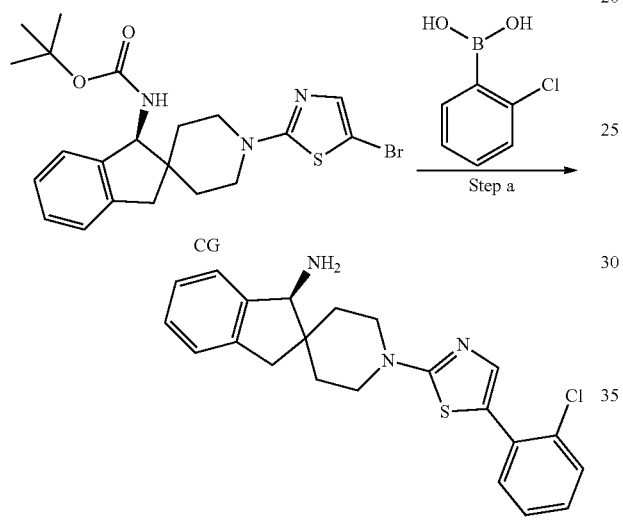

Step a: Dissolved tert-butyl N-[(3S)-1'-(5-bromo-1,3-thiazol-2-yl)-1,3-dihydrospiro[indene-2,4'-piperidin]-3-yl]carbamate (48 mg, 0.103 mmol, Intermediate CG), (2-chlorophenyl)boronic acid (17.7 mg, 0.114 mmol), potassium methaneperoxoate potassium hydride (28.9 mg, 0.207 mmol) and palladium tetrakis (11.9 mg, 0.0103 mmol) in DMF/water (10:1). The reaction mixture was heated in a microwave at 100° C. for 30 min. The reaction was partitioned between water and EtOAc, and the mixture was extracted with EtOAc (2×). The combined organic layer was washed with brine, dried over Na₂SO₄, filtered and concentrated in vacuo. The residue was purified by column chromatography (0-100% EtOAc in heptanes) to give tert-butyl N-[(3S)-1'-[5-(2-chlorophenyl)-1,3-thiazol-2-yl]-1,3-dihydrospiro[indene-2,4'-piperidin]-3-yl]carbamate (29.0 mg, 57% yield). This intermediate was then dissolved in DCM (750 uL) then TFA (200 uL) was added and the reaction mixture was stirred at rt for 15 min. The reaction mixture was concentrated then purified by HPLC (10-40% B (FA)) to give (3S)-1'-[5-(2-chlorophenyl)-1,3-thiazol-2-yl]-1,3-dihydrospiro[indene-2,4'-piperidin]-3-amine (14.9 mg, 37% yield). LCMS m/z [M+H]⁺=396.5; ¹H NMR (500 MHz, DMSO-d6) Shift 7.58 (dd, J=1.53, 7.93 Hz, 1H), 7.50-7.55 (m, 2H), 7.33-7.39 (m, 2H), 7.27-7.31 (m, 1H), 7.19-7.24 (m, 3H), 4.03 (s, 1H), 3.84 (br d, J=13.12 Hz, 2H), 3.24-3.28 (m, 3H), 3.08 (d, J=15.86 Hz, 1H), 2.74 (d, J=15.86 Hz, 1H), 1.80-1.87 (m, 1H), 1.70-1.79 (m, 1H), 1.54 (br dd, J=1.37, 13.27 Hz, 1H), 1.28 (br d, J=12.81 Hz, 1H).

Example 146: Synthesis of (3S)-1'-[5-(1,2,3,4-tetrahydro-1,5-naphthyridin-1-yl)pyrazin-2-yl]-1,3-dihydrospiro[indene-2,4'-piperidin]-3-amine

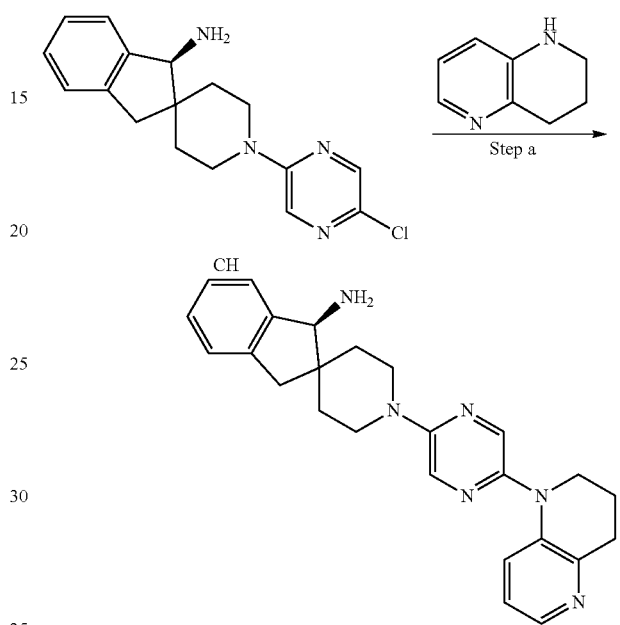

Step a: In a vial, weighed (3S)-1'-(5-chloropyrazin-2-yl)-1,3-dihydrospiro[indene-2,4'-piperidin]-3-amine (52 mg, 0.165 mmol, Intermediate CH), 1,2,3,4-tetrahydro-1,5-naphthyridine (24.3 mg, 0.182 mmol), 9-{[5-(diphenylphosphanyl)-9,9-dimethyl-9H-xanthen-4-yl]diphenyl-λ⁵-phosphanyl}-8-methyl-8-aza-9-palladatricyclo[8.4.0.0²,⁷]tetradeca-1(14),2(7),3,5,10,12-hexaen-9-yl methanesulfonate (15.8 mg, 0.0165 mmol), and (tert-butoxy)sodium (23.7 mg, 0.248 mmol). The reaction mixture was evacuated and backfilled with N₂, then toluene (2 mL) was added and the reaction was stirred at 80° C. for 20 min. The reaction mixture was then concentrated, and the residue was redissolved in DMSO and purified by reverse phase HPLC (5-30% B (FA)) to give (3S)-1'-[5-(1,2,3,4-tetrahydro-1,5-naphthyridin-1-yl)pyrazin-2-yl]-1,3-dihydrospiro[indene-2,4'-piperidin]-3-amine (12.0 mg, 18% yield) as a yellow solid. LCMS m/z (M+H)⁺=413.6; ¹H NMR (500 MHz, DMSO-d6) Shift 8.24 (s, 2H), 8.14 (d, J=1.22 Hz, 1H), 8.07 (d, J=1.22 Hz, 1H), 7.87 (dd, J=1.22, 4.58 Hz, 1H), 7.36-7.41 (m, 1H), 7.17-7.27 (m, 3H), 7.09 (dd, J=1.22, 8.24 Hz, 1H), 6.93 (dd, J=4.58, 8.24 Hz, 1H), 4.12 (dt, J=3.97, 8.39 Hz, 2H), 4.03 (s, 1H), 3.61-3.65 (m, 2H), 3.06-3.14 (m, 3H), 2.89 (t, J=6.41 Hz, 2H), 2.76 (d, J=15.86 Hz, 1H), 1.98-2.04 (m, 2H), 1.79 (dt, J=4.27, 12.51 Hz, 1H), 1.70 (dt, J=4.12, 12.43 Hz, 1H), 1.50 (br d, J=11.90 Hz, 1H), 1.27 (br d, J=12.81 Hz, 1H).

Example 147: Synthesis of (S)-1'-(5-((2,3-dichlorophenyl)thio)pyrazin-2-yl)-1,3-dihydrospiro[indene-2,4'-piperidin]-1-amine

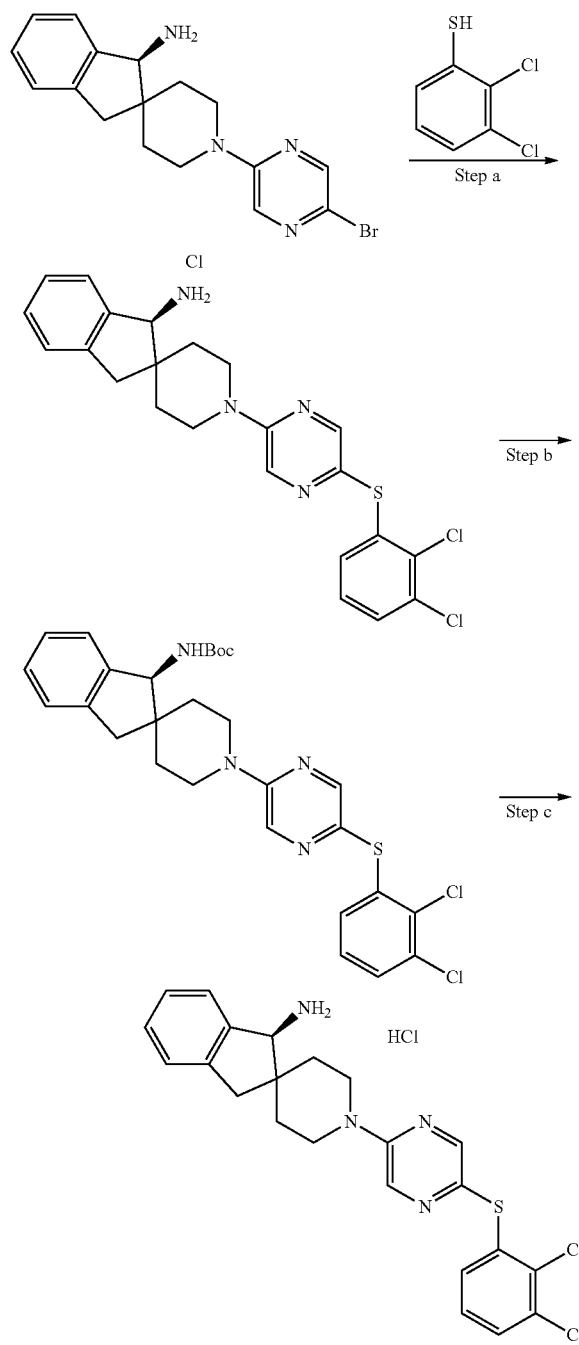

extracted with ethyl acetate (30 mL×3). The combined organic layers were washed with brine (50 mL), dried over anhydrous $Na_2SO_4$, filtered and concentrated to give (S)-1'-(5-((2,3-dichlorophenyl)thio)pyrazin-2-yl)-1,3-dihydrospiro[indene-2,4'-piperidin]-1-amine ((300 mg, quant. crude yield). LCMS m/z (M+53)+=509.

Step b: (S)-1'-(5-((2,3-dichlorophenyl)thio)pyrazin-2-yl)-1,3-dihydrospiro[indene-2,4'-piperidin]-1-amine (254.0 mg, 555 µmol), di-tert-butyl dicarbonate (328 µL, 1.10 mmol) and TEA (228 µL, 1.66 mmol) were dissolved in DCM (10 mL), and the mixture was stirred at rt for 13 hours. The reaction mixture was washed with $H_2O$ (10 mL×2), brine (15 mL), dried over anhydrous $Na_2SO_4$, filtered and concentrated in vacuo to give a residue. The residue was purified by prep-TLC (Petroleum ether:Ethyl acetate=3:1) to afford tert-butyl N-[(3S)-1'-{5-[(2,3-dichlorophenyl)sulfanyl]pyrazin-2-yl}-1,3-dihydrospiro[indene-2,4'-piperidin]-3-yl]carbamate (95.0 mg, 30.7% yield) as a yellow solid. LCMS m/z (M+H)+=456.9.

Step c: The compound of tert-butyl N-[(3S)-1'-{5-[(2,3-dichlorophenyl)sulfanyl]pyrazin-2-yl}-1,3-dihydrospiro[indene-2,4'-piperidin]-3-yl]carbamate (100.0 mg, 179 µmol) was added in HCl/MeOH (5.0 mL, 4M) and the mixture was stirred at 25° C. for 0.5 h. The mixture was then concentrated to give a residue which was purified by prep-HPLC (HCl) to give (3S)-1'-{5-[(2,3-dichlorophenyl)sulfanyl]pyrazin-2-yl}-1,3-dihydrospiro[indene-2,4'-piperidin]-3-amine hydrochloride (35.5 mg, 85% yield) as a yellow solid. LCMS m/z (M+H)+=457.0; $^1$HNMR (400 MHz, DMSO-d6): δ 8.53 (s, 3H), 8.49 (s, 1H), 8.30 (s, 1H), 7.57~7.60 (m, 1H), 7.46~7.49 (m, 1H), 7.23~7.38 (m, 4H), 6.84~6.87 (m, 1H), 4.35~4.39 (m, 2H), 4.25~4.30 (m, 1H), 3.19~3.28 (m, 3H), 2.98~3.03 (m, 1H), 1.73~1.85 (m, 2H), 1.51~1.59 (m, 2H).

Example 148: Synthesis of (S)—N4-(6-(1-amino-1,3-dihydrospiro[indene-2,4'-piperidin]-1'-yl)-1H-pyrazolo[3,4-b]pyrazin-3-yl)-N4-methylpyridine-2,4-diamine

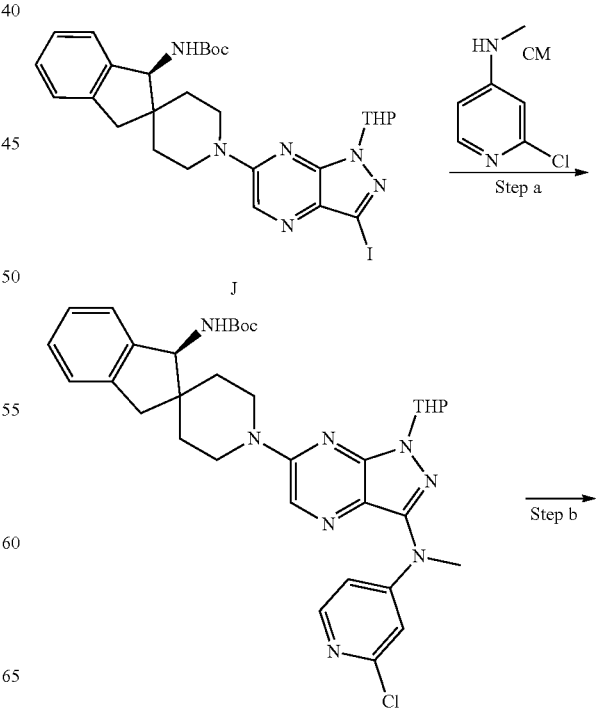

Step a: The compound of (S)-1'-(5-bromopyrazin-2-yl)-1,3-dihydrospiro[indene-2,4'-piperidin]-1-amine (200.0 mg, 556 µmol, Intermediate CI), 2,3-dichlorobenzene-1-thiol (129.0 mg, 722 µmol, CAS #17231-95-7), $Pd_2(dba)_3$ (50.9 mg, 55.6 µmol), XantPhos (64.2 mg, 111 µmol), and DIPEA (485 µL, 2.78 mmol) were added in dioxane (10 mL). The reaction mixture was evacuated and refilled 3 times with $N_2$. The reaction mixture was stirred at 110° C. for 12 hours. Then $H_2O$ (20 mL) was added and the reaction mixture was

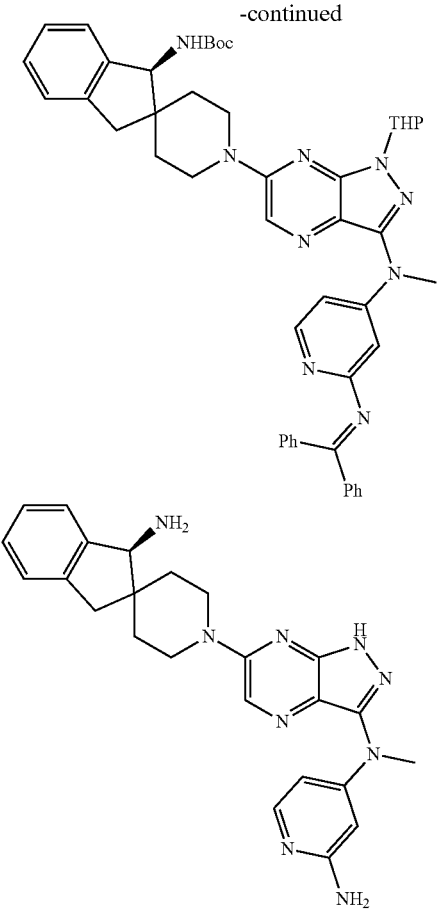

Step a: A solution of tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (300.0 mg, 475.0 μmol, Intermediate J), 2-chloro-N-methylpyridin-4-amine (87.9 mg, 617.0 μmol, Intermediate CM), XantPhos-Pd-G4 (45.6 mg, 47.5 umol) and Cs₂CO₃ (308.0 mg, 950.0 umol) in PhMe (10.0 mL) was stirred at 90° C. for 12 hours under N₂. The reaction mixture was then poured into H₂O (30.0 mL) and extracted with EtOAc (50.0 mL×2). The combined organic layers were washed with brine (50.0 mL), dried over anhydrous Na₂SO₄, filtered and the filtrate was concentrated under reduced pressure to give a brown residue. The residue was purified by flash silica gel chromatography (12 g column, ethyl acetate in petroleum ether from 0% to 35%) to give tert-butyl N-[(3S)-1'-{3-[(2-chloropyridin-4-yl)(methyl)amino]-1-(oxan-2-yl)-1H-pyrazolo[3,4-b]pyrazin-6-yl}-1,3-dihydrospiro[indene-2,4'-piperidin]-3-yl]carbamate (230.0 mg, 75% yield) as a yellow solid. LCMS m/z (M+H)⁺=645.1.

Step b: A solution of tert-butyl N-[(3S)-1'-{3-[(2-chloropyridin-4-yl)(methyl)amino]-1-(oxan-2-yl)-1H-pyrazolo[3,4-b]pyrazin-6-yl}-1,3-dihydrospiro[indene-2,4'-piperidin]-3-yl]carbamate (150.0 mg, 232.0 μmol), diphenylmethanimine (63.0 mg, 348.0 μmol), Pd₂(dba)₃ (21.2 mg, 23.2 umol), XPhos (44.2 mg, 92.8 umol) and t-BuONa (66.8 mg, 696.0 umol) in PhMe (5.0 mL) was stirred at 100° C. for 12 hours under N₂. The reaction mixture was concentrated under reduced pressure. The residue was triturated with EtOAc (10.0 mL), filtered and the filtrate was concentrated to give tert-butyl N-[(3S)-1'-[3-({2-[(diphenylmethylidene)amino]pyridin-4-yl}(methyl)amino)-1-(oxan-2-yl)-1H-pyrazolo[3,4-b]pyrazin-6-yl]-1,3-dihydrospiro[indene-2,4'-piperidin]-3-yl]carbamate (250.0 mg, 137% crude yield) as an orange solid. LCMS m/z (M+H)⁺=790.2.

Step c: A solution of tert-butyl N-[(3S)-1'-[3-({2-[(diphenylmethylidene)amino]pyridin-4-yl}(methyl)amino)-1-(oxan-2-yl)-1H-pyrazolo[3,4-b]pyrazin-6-yl]-1,3-dihydrospiro[indene-2,4'-piperidin]-3-yl]carbamate (250.0 mg, 316.0 μmol) in HCl/MeOH (6.0 mL, 4 M) was stirred at 20° C. for 2 hours. The reaction mixture was poured into H₂O (20.0 mL) and extracted with EtOAc (30.0 mL×2). The aqueous phase was concentrated under reduced pressure. The residue was diluted with MeOH (5.0 mL), purified by prep-HPLC (HCl) and preparative SFC. (S)—N4-(6-(1-amino-1,3-dihydrospiro[indene-2,4'-piperidin]-1'-yl)-1H-pyrazolo[3,4-b]pyrazin-3-yl)-N4-methylpyridine-2,4-diamine (9.7 mg, 35% yield) was obtained as a yellow solid. LCMS m/z (M+H)⁺=442.1; ¹HNMR (400 MHz, CD₃OD): 8.34 (s, 1H), 7.54-7.56 (m, 1H), 7.41-7.43 (m, 1H), 7.26-7.30 (m, 3H), 6.31-6.34 (m, 1H), 6.13-6.14 (m, 1H), 4.41-4.48 (m, 2H), 4.10-4.14 (m, 1H), 3.53 (s, 3H), 3.38-3.45 (m, 2H), 3.19-3.24 (m, 1H), 2.93-2.98 (m, 1H), 1.82-1.92 (m, 2H), 1.55-1.69 (m, 2H). SFC: e.e. =96.9%, R_f=2.23 min. Column: ChiralCel OD-3 150×4.6 mm I.D., 3 um, Mobile phase: 40% of Methanol (0.1% Ethanolamine), Flow rate: 2.5 mL/min Column temperature: 40° C.

Example 149: Synthesis of (3S)-1'-{5-methyl-3-[6-(1-methyl-1H-pyrazol-4-yl)-1,2,3,4-tetrahydro-1,5-naphthyridin-1-yl]-1H-pyrazolo[3,4-b]pyrazin-6-yl}-1,3-dihydrospiro[indene-2,4'-piperidin]-3-amine

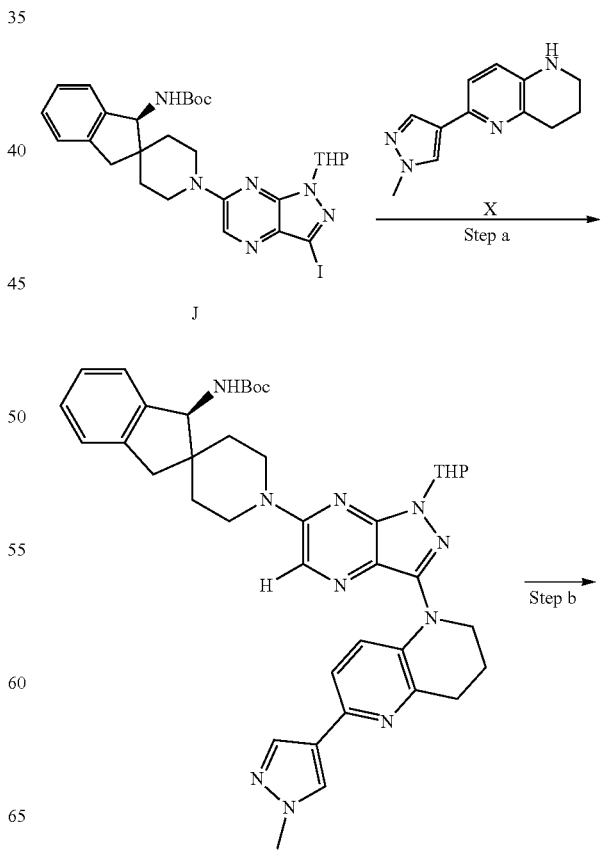

-continued

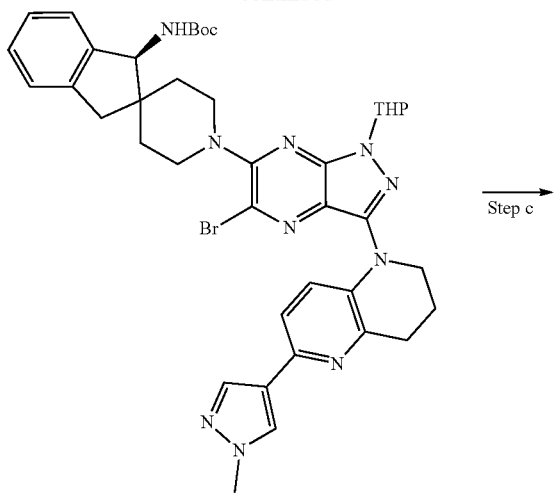

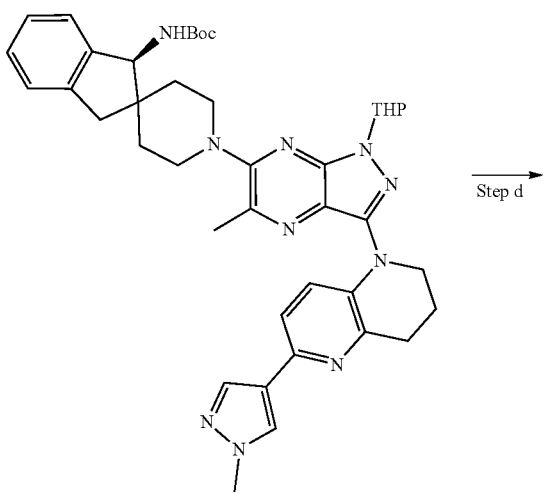

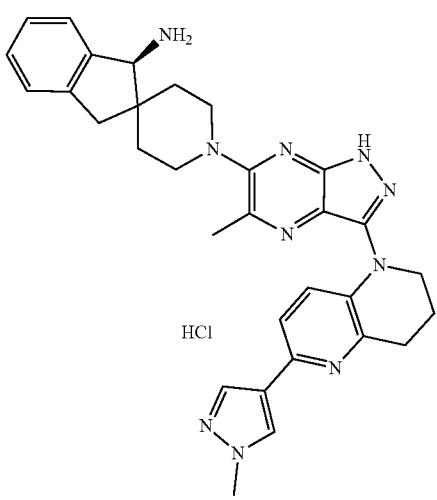

Step a: Tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (300.0 mg, 475.0 μmol, Intermediate J), 6-(1-methyl-1H-pyrazol-4-yl)-1,2,3,4-tetrahydro-1,5-naphthyridine (122.0 mg, 570.0 μmol, Intermediate X), Xantphos-Pd-G4 (45.6 mg, 47.5 μmol, CAS #1599466-81-5) and $Cs_2CO_3$ (462.0 mg, 1.42 mmol) were added in PhMe (16 mL). The reaction mixture was evacuated and refilled 3 times with $N_2$ and stirred at 100° C. for 12 hours. The reaction mixture was concentrated under reduced pressure and purified by flash silica gel chromatography (petroleum ether:ethyl acetate=100:0 to 100:90) to afford tert-butyl N-[(3S)-1'-{3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-1,3-dihydrospiro[indene-2,4'-piperidin]-3-yl]carbamate (320.0 mg, 94% yield) as a yellow solid. LCMS m/z (M+H)$^+$=717.3.

Step b: Tert-butyl N-[(3S)-1'-{3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-1,3-dihydrospiro[indene-2,4'-piperidin]-3-yl]carbamate (320.0 mg, 446.0 μmol) was dissolved in the mixture of ACN (10 mL) and AcOH (10 mL), NBS (79.3 mg, 446.0 μmol) was added, and the reaction mixture was stirred at 25° C. for 2 hours. The reaction mixture was concentrated under reduced pressure and purified by flash silica gel chromatography (petroleum ether:ethyl acetate=100:30 to 0:100) to afford tert-butyl N-[(3S)-1'-{5-bromo-3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-1,3-dihydrospiro[indene-2,4'-piperidin]-3-yl]carbamate (320.0 mg, 90% yield) as a yellow solid. LCMS m/z (M+H)$^+$=797.2.

Step c: tert-butyl N-[(3S)-1'-{5-bromo-3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-1,3-dihydrospiro[indene-2,4'-piperidin]-3-yl]carbamate (220.0 mg, 276.0 μmol), Pd(dppf)Cl$_2$ (20.2 mg, 27.6 μmol), Cs$_2$CO$_3$ (179.0 mg, 552.0 μmol) and MeB(OH)$_2$ (81.4 mg, 1.38 mmol) were added in the mixture of dioxane (16 mL) and H$_2$O (4 mL). The reaction mixture was evacuated and refilled 3 times with N$_2$ and stirred at 100° C. for 12 hours. The reaction mixture was concentrated under reduced pressure and purified by flash silica gel chromatography (petroleum ether:ethyl acetate=100:50 to 100:100) to afford tert-butyl N-[(3S)-1'-{5-methyl-3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-1,3-dihydrospiro[indene-2,4'-piperidin]-3-yl]carbamate (180.0 mg, 90% yield) as a yellow solid. LCMS m/z (M+H)$^+$=731.3.

Step d: Tert-butyl N-[(3S)-1'-{5-methyl-3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-1,3-dihydrospiro[indene-2,4'-piperidin]-3-yl]carbamate (180.0 mg, 246.0 μmol) was added in 4N HCl/MeOH (6 mL), the reaction mixture was stirred at 25° C. for 2 hours. The reaction mixture was concentrated under reduced pressure and purified by prep-HPLC (HCl) to afford (3S)-1'-{5-methyl-3-[6-(1-methyl-1H-pyrazol-4-yl)-1,2,3,4-tetrahydro-1,5-naphthyridin-1-yl]-1H-pyrazolo[3,4-b]pyrazin-6-yl}-1,3-dihydrospiro[indene-2,4'-piperidin]-3-amine hydrochloride (45.4 mg, 34% yield) as a yellow solid. LCMS m/z (M+H)$^+$=547.1. $^1$HNMR (400 MHz, Methanol-d4): δ 8.50 (s, 1H), 7.99 (d, J=6.8 Hz, 1H), 7.63 (d, J=6.8 Hz, 1H), 7.54 (d, J=7.2 Hz, 1H), 7.46-7.34 (m, 3H), 4.60-4.44 (m, 3H), 3.54-3.41 (m, 2H), 3.24 (s, 2H), 2.04-1.68 (m, 4H).

Example 150: Synthesis of (S)-2-((6-((S)-1-amino-1,3-dihydrospiro[indene-2,4'-piperidin]-1'-yl)-1H-pyrazolo[3,4-b]pyrazin-3-yl)(methyl)amino)propanenitrile

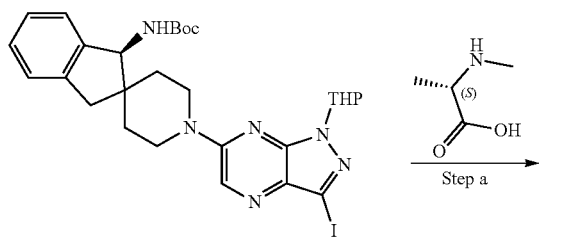

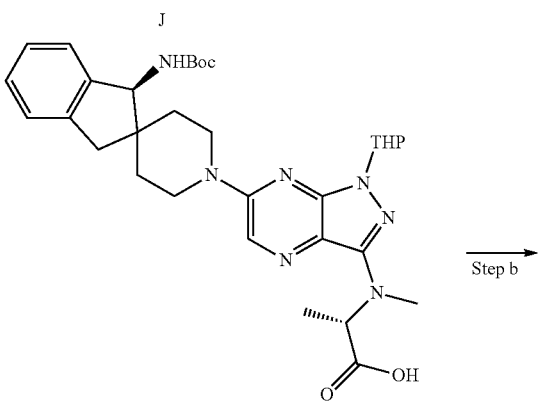

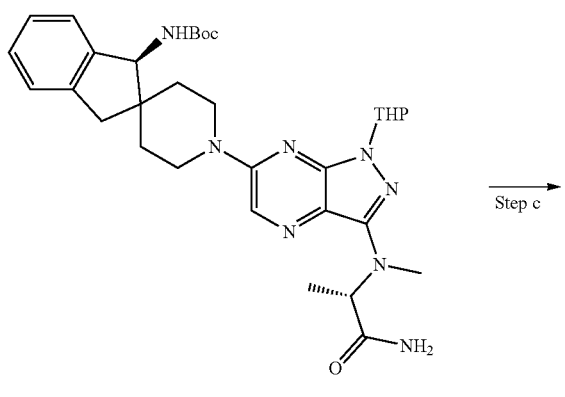

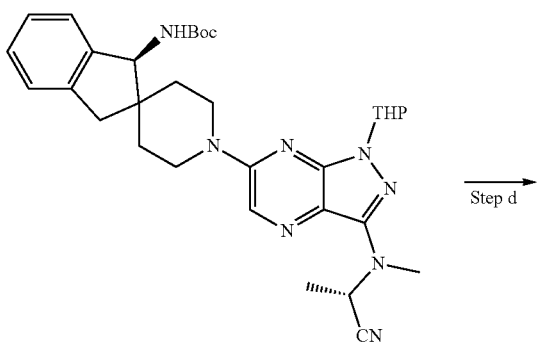

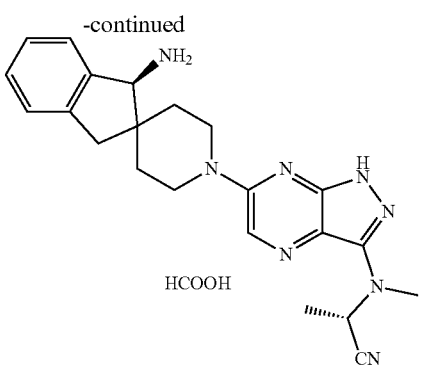

Step a: A mixture of tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (500.0 mg, 792.0 µmol, Intermediate J), (2S)-2-(methylamino)propanoic acid (244.0 mg, 2.4 mmol, CAS #29475-64-7), K₂CO₃ (327.0 mg, 2.40 mmol) and nano-Cu powder (100.0 mg, 1.60 mmol) in NMP (10.0 mL) was stirred under microwave irradiation at 130° C. for 1.5 hours. The reaction mixture was then diluted with H₂O (100.0 mL), adjusted to pH=5-6 with HCl (2N) and extracted with DCM (100.0 mL×3). The combined organic phases were dried over anhydrous Na₂SO₄, filtered and concentrated under reduced pressure to give N-(6-((S)-1-((tert-butoxycarbonyl)amino)-1,3-dihydrospiro[indene-2,4'-piperidin]-1'-yl)-1-(tetrahydro-2H-pyran-2-yl)-1H-pyrazolo[3,4-b]pyrazin-3-yl)-N-methyl-L-alanine (1.00 g, 104% crude yield) as a yellow oil. LCMS m/z (M+H)⁺=606.3.

Step b: A mixture of (2S)-2-({6-[(3S)-3-{[(tert-butoxy)carbonyl]amino}-1,3-dihydrospiro[indene-2,4'-piperidin]-1'-yl]-1-(oxan-2-yl)-1H-pyrazolo[3,4-b]pyrazin-3-yl}(methyl)amino)propanoic acid (1.00 g, crude), ammonium 1H-1,2,3-benzotriazol-1-olate (375.0 mg, 2.5 mmol, CAS #63307-62-0) and EDCI (473.0 mg, 2.5 mmol) in DMF (10.0 mL) was stirred at 20° C. for 12 hours under N₂. The reaction was diluted with H₂O (200.0 mL), and extracted with EtOAc (150.0 mL×3). The combined organic phase were washed with brine (300.0 mL), dried over anhydrous Na₂SO₄, filtered and concentrated under reduced pressure to give a residue. The residue was purified by flash silica gel chromatography (ethyl acetate in petroleum ether=0~90%) to afford tert-butyl ((1S)-1'-(3-(((S)-1-amino-1-oxopropan-2-yl)(methyl)amino)-1-(tetrahydro-2H-pyran-2-yl)-1H-pyrazolo[3,4-b]pyrazin-6-yl)-1,3-dihydrospiro[indene-2,4'-piperidin]-1-yl)carbamate (700.0 mg) as a yellow oil. LCMS m/z (M+H)⁺=605.3.

Step c: To a solution of tert-butyl ((1S)-1'-(3-(((S)-1-amino-1-oxopropan-2-yl)(methyl)amino)-1-(tetrahydro-2H-pyran-2-yl)-1H-pyrazolo[3,4-b]pyrazin-6-yl)-1,3-dihydrospiro[indene-2,4'-piperidin]-1-yl)carbamate (350.0 mg, 578.0 µmol) and Et₃N (158.0 µL, 1.2 mmol) in DCM (10.0 mL) was added TFAA (161.0 µL, 1.2 mmol) dropwise at 0° C. and the mixture was stirred at 25° C. for 12 hours. The reaction mixture was quenched with H₂O (50.0 mL) and extracted with DCM (50.0 mL×2). The combined organic layers were washed with brine (50.0 mL), dried over anhydrous Na₂SO₄, filtered and concentrated under reduced pressure to give a residue. The residue was purified by flash silica gel chromatography (ethyl acetate in petroleum ether=0~30%) to afford tert-butyl N-[(3S)-1'-(3-{[(1S)-1-cyanoethyl](methyl)amino}-1-(oxan-2-yl)-1H-pyrazolo[3, 4-b]pyrazin-6-yl)-1,3-dihydrospiro[indene-2,4'-piperidin]-3-yl]carbamate (100.0 mg, 28% yield) as a yellow oil. LCMS m/z (M+H)⁺=609.1.

Step d: The tert-butyl N-[(3S)-1'-(3-{[(1S)-1-cyanoethyl](methyl)amino}-1-(oxan-2-yl)-1H-pyrazolo[3,4-b]pyrazin-6-yl)-1,3-dihydrospiro[indene-2,4'-piperidin]-3-yl]carbamate (120.0 mg, 204.0 µmol) dissolved in $CH_3CN$ (2.0 mL) and HCl (2.0 mL, 2N) and stirred at 25° C. for 12 hours. The mixture was adjusted pH=8-9 by $NaHCO_3$ (aq.) and extracted with EtOAc (50.0 mL×3). The combined organic layers were dried over anhydrous $Na_2SO_4$, filtered and concentrated under reduced pressure to give a residue. The residue was purified by prep-HPLC ($NH_3.H_2O$) to afford (S)-2-((6-((S)-1-amino-1,3-dihydrospiro[indene-2,4'-piperidin]-1'-yl)-1H-pyrazolo[3,4-b]pyrazin-3-yl)(methyl)amino)propanenitrile (23.4 mg, 28% yield) as a light yellow solid. LCMS m/z (M+H)⁺=403.0; ¹HNMR (400 MHz, $CDCl_3$): δ 9.85 (s, 1H), 8.04 (s, 1H), 7.31-7.38 (m, 1H), 7.19-7.26 (m, 3H), 5.90 (q, J=7.2 Hz, 1H), 4.20-4.33 (m, 2H), 4.01 (s, 1H), 3.24-3.38 (m, 2H), 3.20 (s, 3H), 3.05-3.16 (m, 1H), 2.69-2.81 (m, 1H), 1.75-1.96 (m, 3H), 1.66 (d, J=7.2 Hz, 3H), 1.37-1.46 (m, 1H).

Example 151: Synthesis of (2S)-2-({6-[(3S)-3-amino-1,3-dihydrospiro[indene-2,4'-piperidin]-1'-yl]-1H-pyrazolo[3,4-b]pyrazin-3-yl}(methyl)amino)propanamide

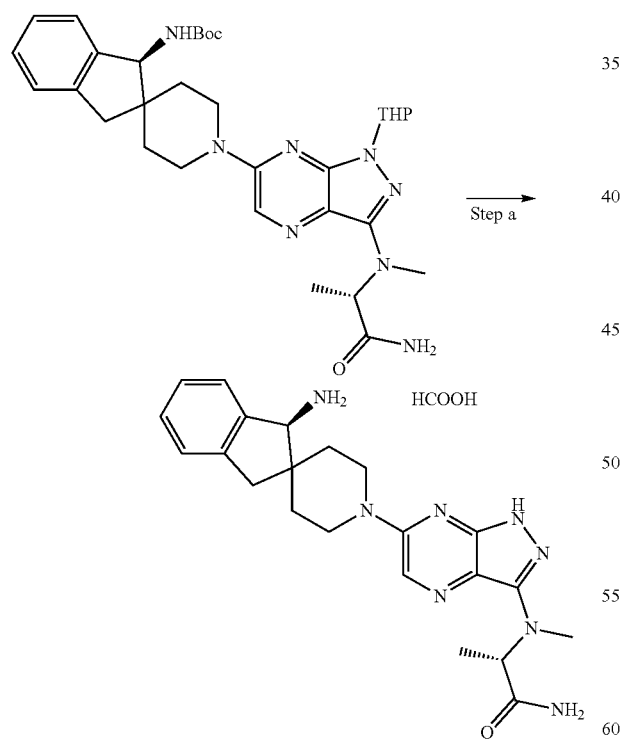

Step a: Tert-butyl N-[(3S)-1'-(3-{[(1S)-1-carbamoylethyl](methyl)amino}-1-(oxan-2-yl)-1H-pyrazolo[3,4-b]pyrazin-6-yl)-1,3-dihydrospiro[indene-2,4'-piperidin]-3-yl]carbamate (200.0 mg, 330.0 µmol, synthesized via Steps a-b of Example 150) was dissolved in EtOAc (5.0 mL) and HCl/ EtOAc (3.0 mL, 4N) and stirred at 25° C. for 12 hours. The mixture was diluted with $H_2O$ (10.0 mL), adjusted pH=8-9 by anhydrous $Na_2CO_3$ and extracted with EtOAc (50.0 mL×3). The combined organic phases were dried over anhydrous $Na_2SO_4$, filtered and concentrated under reduced pressure to give a residue. The residue was purified by prep-HPLC (FA) to afford (2S)-2-({6-[(3S)-3-amino-1,3-dihydrospiro[indene-2,4'-piperidin]-1'-yl]-1H-pyrazolo[3,4-b]pyrazin-3-yl}(methyl)amino)propanamide formate (12.3 mg, 26.3 µmol, 8% yield) as a yellow solid. LCMS m/z (M+H)⁺=421.2; ¹HNMR (400 MHz, DMSO_d6): δ 11.82 (s, 1H), 8.24 (s, 1H), 8.18 (s, 1H), 7.31-7.42 (m, 1H), 7.17-7.27 (m, 3H), 7.02 (s, 1H), 5.23 (q, J=6.9 Hz, 1H), 4.2-4.42 (m, 2H), 4.00 (s, 1H), 3.08-3.20 (m, 3H), 2.97 (s, 3H), 2.75 (m, 1H), 1.62-1.84 (m, 2H), 1.46-1.56 (m, 1H), 1.18-1.31 (m, 4H).

Example 152: Synthesis of (3S)-1'-[5-methyl-3-(piperidin-1-yl)-1H-pyrazolo[3,4-b]pyrazin-6-yl]-1,3-dihydrospiro[indene-2,4'-piperidin]-3-amine

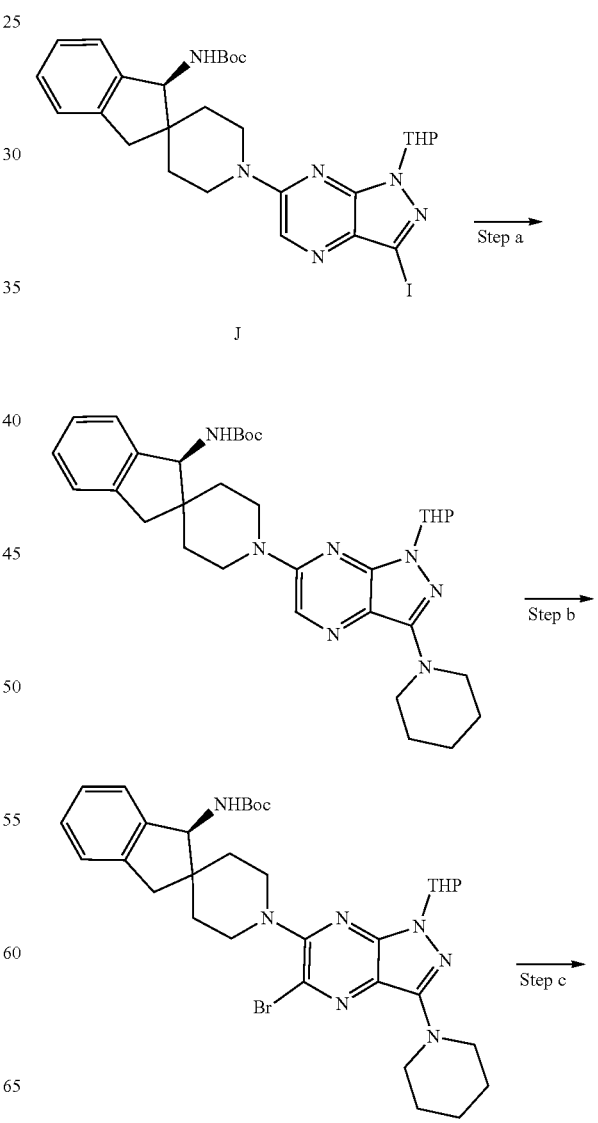

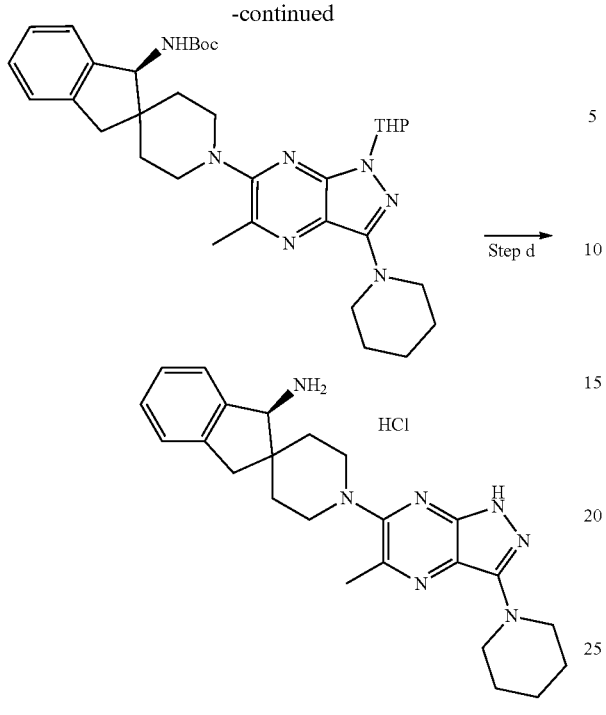

Step a: To a mixture of tert-butyl ((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (500.0 mg, 0.8 mmol, Intermediate J) and piperidine (80.8 mg, 1.0 mmol) in toluene (10.0 mL) were added XantPhos-Pd-G4 (76.1 mg, 79.2 µmol, CAS #1621274-19-8) and Cs₂CO₃ (513.0 mg, 1.6 mmol). The reaction mixture was evacuated and refilled 3 times using N₂. The reaction mixture was stirred at 100° C. for 12 hours. The reaction mixture was concentrated under reduced pressure to give a residue which was purified by column chromatography (petroleum ether:ethyl acetate=100:0 to 100:30) to afford tert-butyl N-[(3S)-1'-[1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (250.0 mg, 54% yield) as a yellow solid. LCMS m/z (M+H)⁺=588.3.

Step b: To a solution of tert-butyl N-[(3S)-1'-[1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (250.0 mg, 0.4 mmol) in MeCN (5.0 mL) and AcOH (3.0 mL) was added NBS (90.6 mg, 0.5 mmol). The reaction mixture was stirred at 25° C. for 12 hours. The reaction mixture was concentrated under reduced pressure to give a residue which was purified by column chromatography (petroleum ether:ethyl acetate=100:0 to 100:30). The product tert-butyl N-[(3S)-1'-[5-bromo-1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (130.0 mg, 46% yield) was obtained as a yellow solid. LCMS m/z (M+H)⁺=666.1.

Step c: To a mixture of tert-butyl N-[(3S)-1'-[5-bromo-1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (130.0 mg, 0.2 mmol) and trimethylboroxine (48.9 mg, 0.4 mmol) in dioxane (5.0 mL) and H₂O (0.5 mL) was added Pd(dppf)Cl₂ (14.2 mg, 19.5 µmol) and K₂CO₃ (53.7 mg, 0.4 mmol). The reaction mixture was purged with N₂ for 3 min and stirred at 100° C. for 12 hours under N₂. The reaction mixture was then concentrated under reduced pressure to give the residue which was purified by column chromatography (petroleum ether:ethyl acetate=100:0 to 100:30). The product tert-butyl N-[(3S)-1'-[5-methyl-1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (80.0 mg, 68% yield) was obtained as a yellow solid. LCMS m/z (M+H)⁺=602.3.

Step d: A solution of tert-butyl N-[(3S)-1'-[5-methyl-1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (75.0 mg, 0.1 mmol) in HCl/MeOH (5.0 mL, 4M) was stirred at 30° C. for 2 hours. The reaction mixture was concentrated under reduce pressure. The residue was dissolved with MeOH (5.0 mL) and purified by prep-HPLC (HCl) to give (3S)-1'-[5-methyl-3-(piperidin-1-yl)-1H-pyrazolo[3,4-b]pyrazin-6-yl]-1,3-dihydrospiro[indene-2,4'-piperidin]-3-amine hydrochloride (40.0 mg, 71% yield) as a yellow solid. LCMS m/z (M+H)⁺=418.1; ¹HNMR (400 MHz, Methanol-d4): 7.54-7.56 (m, 1H), 7.35-7.45 (m, 3H), 7.47 (m, 1H), 3.99-4.03 (m, 1H), 3.85-3.97 (m, 5H), 3.36-3.40 (m, 1H), 3.25-3.32 (m, 1H), 3.21 (s, 2H), 2.66 (s, 3H), 2.03-2.11 (m, 1H), 1.91-1.98 (m, 1H), 1.75-1.87 (m, 7H), 1.68-1.72 (m, 1H).

Example 153: Synthesis of 2-{6-[(3S)-3-amino-1,3-dihydrospiro[indene-2,4'-piperidin]-1'-yl]-5-(hydroxymethyl)-1H-pyrazolo[3,4-b]pyrazin-3-yl}acetonitrile

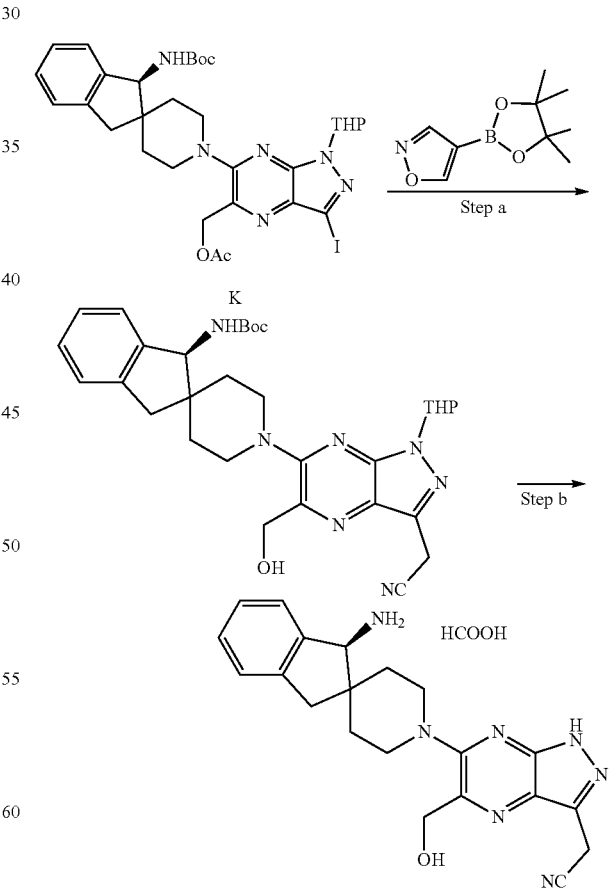

Step a: To the mixture of {6-[(3S)-3-{[(tert-butoxy)carbonyl]amino}-1,3-dihydrospiro[indene-2,4'-piperidin]-1'-yl]-3-iodo-1-(oxan-2-yl)-1H-pyrazolo[3,4-b]pyrazin-5- yl}methyl acetate (300.0 mg, 426.0 µmol, Intermediate K) and 4-(4,4,5,5-tetramethyl-1,3,2-dioxaborolan-2-yl)-1,2-oxazole (83.0 mg, 426.0 µmol, CAS #928664-98-6) in dioxane (8 mL) and H₂O (2 mL) were added Pd(dppf)Cl₂ (31.1 mg, 42.6 µmol) and K₂CO₃ (146.0 mg, 1.0 mmol) under N₂. The mixture was stirred at 100° C. under N₂ for 12 hours. The mixture was concentrated under reduced pressure to give a yellow solid. The residue was purified by flash silica gel chromatography (petroleum ether/EtOAc=I/O to 1/1) to give tert-butyl N-[(3S)-1'-[3-(cyanomethyl)-5-(hydroxymethyl)-1-(oxan-2-yl)-1H-pyrazolo[3,4-b]pyrazin-6-yl]-1,3-dihydrospiro[indene-2,4'-piperidin]-3-yl]carbamate (90.0 mg, 37% yield) as a yellow solid. LCMS m/z (M+H)⁺=574.1.

Step b: To the mixture of tert-butyl N-[(3S)-1'-[3-(cyanomethyl)-5-(hydroxymethyl)-1-(oxan-2-yl)-1H-pyrazolo[3,4-b]pyrazin-6-yl]-1,3-dihydrospiro[indene-2,4'-piperidin]-3-yl]carbamate (60.0 mg, 104.0 µmol) in DCM (1 mL) was added TFA (1 mL). The mixture was stirred at 30° C. for 2 hours. The mixture was adjusted to pH=8 with solid Na₂CO₃ and purified by pre-HPLC (HCOOH) to give 2-{6-[(3S)-3-amino-1,3-dihydrospiro[indene-2,4'-piperidin]-1'-yl]-5-(hydroxymethyl)-1H-pyrazolo[3,4-b]pyrazin-3-yl} acetonitrile formate (15.0 mg, 33% yield) as a white solid. LCMS m/z (M+H)⁺=390.2; ¹H NMR (400 MHz, CD₃OD-d4): 8.54 (s, 1H), 7.53-7.51 (m, 1H), 7.42-7.34 (m, 3H), 4.83 (s, 2H), 4.41 (s, 1H), 4.27 (s, 2H), 3.85-3.73 (m, 2H), 3.31-3.11 (m, 4H), 2.10-1.97 (m, 2H), 1.79-1.68 (m, 2H).

Example 154: Synthesis of 6-[(3S)-3-amino-1,3-dihydrospiro[indene-2,4'-piperidin]-1'-yl]-5-(hydroxymethyl)-1H-pyrazolo[3,4-b]pyrazine-3-carbonitrile

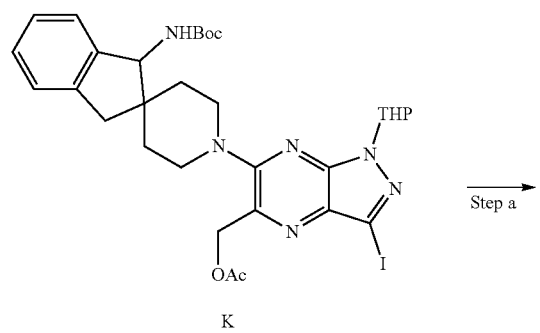

K

Step a

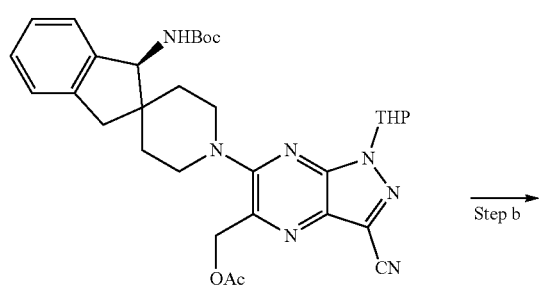

Step b

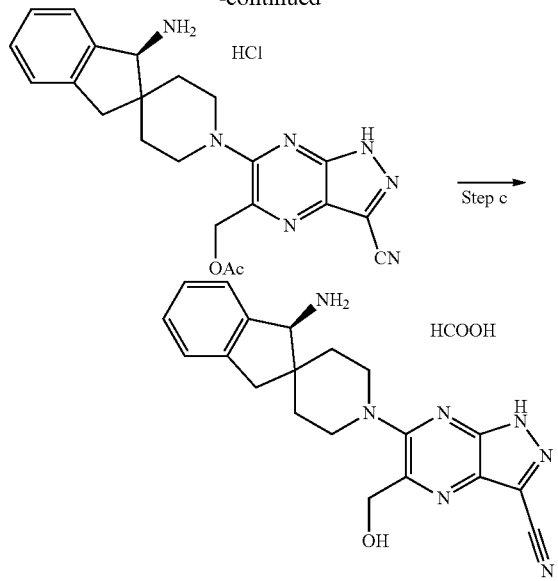

Step a: To the mixture of {6-[(3S)-3-{[(tert-butoxy)carbonyl]amino}-1,3-dihydrospiro[indene-2,4 (300.0 mg, 426.0 µmol, Intermediate K) and Zn(CN)₂ (100.0 mg, 852.0 µmol) in DMF (10 mL) was added [(t-Bu)₃P]2Pd (43.5 mg, 85.2 µmol, CAS #53199-31-8) under N₂. The mixture was stirred at 110° C. under N₂ for 12 hours. The mixture was then poured into water (50 mL) and extracted with EtOAc (50 mL×3). The organic layers were washed with brine (60 mL×3) and dried over anhydrous Na₂SO₄, filtered and concentrated under reduced pressure to give a yellow solid. The residue was purified by flash silica gel chromatography (petroleum ether/EtOAc=I/O to 3/1) to give {6-[(3S)-3-{[(tert-butoxy)carbonyl]amino}-1,3-dihydrospiro[indene-2,4'-piperidin]-1'-yl]-3-cyano-1-(oxan-2-yl)-1H-pyrazolo[3,4-b]pyrazin-5-yl}methyl acetate (250.0 mg, 98% yield) as a yellow solid. LCMS m/z (M+Na)+=624.1.

Step b: A mixture of {6-[(3S)-3-{[(tert-butoxy)carbonyl]amino}-1,3-dihydrospiro[indene-2,4'-piperidin]-1'-yl]-3-cyano-1-(oxan-2-yl)-1H-pyrazolo[3,4-b]pyrazin-5-yl}methyl acetate (150.0 mg, 249.0 µmol) in HCl/EtOAc (2 mL, 4 M) was stirred at 30° C. for 12 hours. The mixture was concentrated under reduced pressure to give {6-[(3S)-3-amino-1,3-dihydrospiro[indene-2,4'-piperidin]-1'-yl]-3-cyano-1H-pyrazolo[3,4-b]pyrazin-5-yl}methyl acetate hydrochloride (113.0 mg, 100% yield) as a brown solid. LCMS m/z (M+Na)+=440.0.

Step c: To the mixture of {6-[(3S)-3-amino-1,3-dihydrospiro[indene-2,4'-piperidin]-1'-yl]-3-cyano-1H-pyrazolo[3,4-b]pyrazin-5-yl}methyl acetate hydrochloride (113.0 mg, 248.0 µmol) in THF (3 mL) and H₂O (1 mL) was added LiOH H₂O (31.2 mg, 744.0 µmol). The mixture was stirred at 30° C. for 12 hours. The mixture was then concentrated under reduced pressure to give a yellow oil. The residue was purified by prep-HPLC (HCOOH) to give 6-[(3S)-3-amino-1,3-dihydrospiro[indene-2,4'-piperidin]-1'-yl]-5-(hydroxymethyl)-1H-pyrazolo[3,4-b]pyrazine-3-carbonitrile formate (35.0 mg, 34% yield) as a white solid. LCMS m/z (M+Na)+=398.0; ¹H NMR (400 MHz, CD₃OD-d4): 8.54 (s, 1H), 7.52-7.50 (m, 1H), 7.40-7.34 (m, 3H), 4.83 (s, 2H), 4.40 (s, 1H), 3.92-3.80 (m, 2H), 3.33-3.11 (m, 4H), 2.10-1.96 (m, 2H), 1.79-1.68 (m, 2H).

Example 155: Synthesis of 6-[(3S)-3-amino-1,3-dihydrospiro[indene-2,4'-piperidin]-1'-yl]-5-(hydroxymethyl)-N-methyl-1H-pyrazolo[3,4-b]pyrazine-3-carboxamide

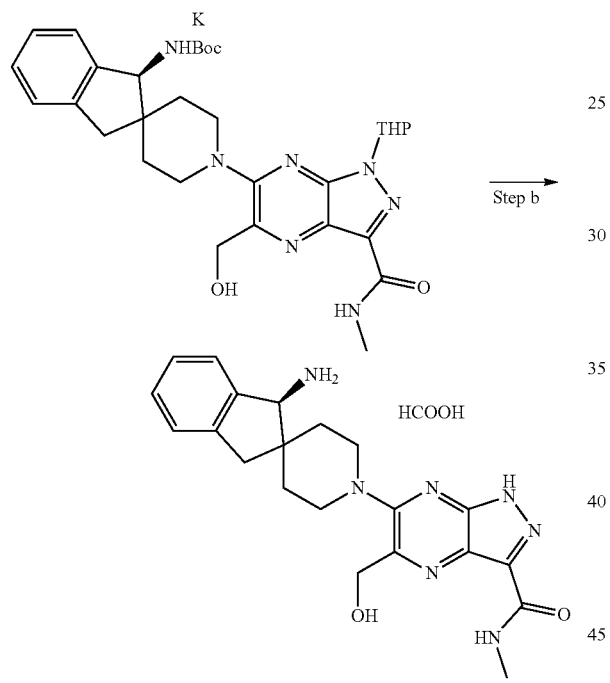

Step a: The mixture of {6-[(3S)-3-{[(tert-butoxy)carbonyl]amino}-1,3-dihydrospiro[indene-2,4'-piperidin]-1'-yl]-3-iodo-1-(oxan-2-yl)-1H-pyrazolo[3,4-b]pyrazin-5-yl}methyl acetate (500.0 mg, 711.0 µmol, Intermediate K), MeNH$_2$ HCl (475.0 mg, 7.1 mmol), Pd(dppf)Cl$_2$ (52.0 mg, 71.1 µmol) and TEA (2 mL) in MeOH (20 mL) was evacuated and refilled 3 times using CO, then stirred at 80° C. for 12 hours under CO (50 psi). The mixture was concentrated under reduced pressure and the residue was purified by column chromatography (DCM/MeOH=1:0~10:1) to afford 170.0 mg of tert-butyl ((1S)-1'-(5-(hydroxymethyl)-3-(methylcarbamoyl)-1-(tetrahydro-2H-pyran-2-yl)-1H-pyrazolo[3,4-b]pyrazin-6-yl)-1,3-dihydrospiro[indene-2,4'-piperidin]-3-yl)carbamate (170.0 mg, 66% purity, 27% yield) as a brown solid. LCMS m/z (M+H)$^+$=592.2.

Step b: The mixture of tert-butyl N-[(3S)-1'-[5-(hydroxymethyl)-3-(methylcarbamoyl)-1-(oxan-2-yl)-1H-pyrazolo[3,4-b]pyrazin-6-yl]-1,3-dihydrospiro[indene-2,4'-piperidin]-3-yl]carbamate (170.0 mg, 66% purity, 189.0 µmol) in HCl/EtOAc (4M, 3 mL) was stirred at 30° C. for 1 hour. The mixture was concentrated under reduced pressure. The residue was diluted with EtOAc (10 mL) and adjusted to pH=8 with K$_2$CO$_3$. The mixture was filtered and the filtrate was concentrated under reduced pressure. The mixture was purified by prep-HPLC (FA) to afford 6-[(3S)-3-amino-1,3-dihydrospiro[indene-2,4'-piperidin]-1'-yl]-5-(hydroxymethyl)-N-methyl-1H-pyrazolo[3,4-b]pyrazine-3-carboxamide; formic acid (17.3 mg, 20% yield) as a yellow solid. LCMS m/z (M+H)$^+$=408.1; $^1$HNMR (400 MHz, CDCl$_3$+MeOD-d4): δ 8.27 (br, 1H), 7.36-7.32 (m, 1H), 7.24-7.20 (m, 3H), 4.76-4.74 (m, 2H), 4.09 (m, 1H), 3.31-3.30 (m, 2H), 3.16-2.83 (m, 7H), 1.62-1.59 (m, 2H), 1.54-1.50 (m, 2H).

Example 156: Synthesis of {6-[(3S)-3-amino-1,3-dihydrospiro[indene-2,4'-piperidin]-1'-yl]-3-methyl-1H-pyrazolo[3,4-b]pyrazin-5-yl}methanol

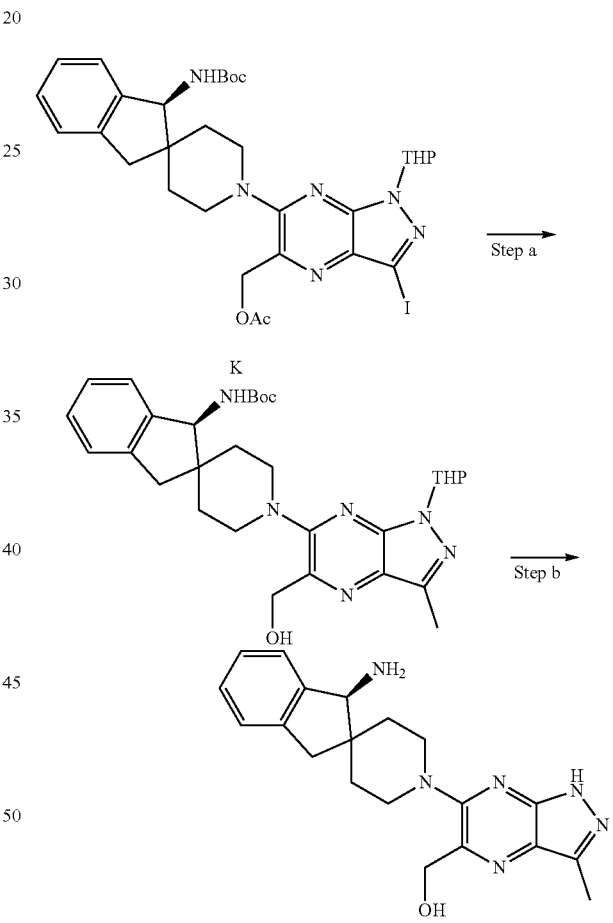

Step a: (6-((S)-1-((tert-butoxycarbonyl)amino)-1,3-dihydrospiro[indene-2,4'-piperidin]-1'-yl)-3-iodo-1-(tetrahydro-2H-pyran-2-yl)-1H-pyrazolo[3,4-b]pyrazin-5-yl)methyl acetate (150 mg, 213 µmol, Intermediate K), K$_3$PO$_4$.3H$_2$O (529 mg, 1.06 mmol), trimethylboroxine (267 mg, 2.13 mmol, CAS #823-96-1) and Pd(PPh$_3$)$_4$ (24.6 mg, 21.3 µmol) were dissolved in PhMe/H$_2$O (10 mL/1 mL). The combined reaction mixture was evacuated and refilled for 3 times using N$_2$. The reaction mixture was stirred at 100° C. for 12 hours. The reaction mixture was diluted with ethyl acetate (30 mL) and H$_2$O (20 mL). The partitioned layers were separated and the aqueous phase was extracted with ethyl acetate (30 mL×3). The combined organic layers were washed with brine (50 mL), dried over anhydrous Na₂SO₄, filtered and concentrated to give a residue. The residue was purified by flash silica gel chromatography (petroleum ether:ethyl acetate=100:0 to 100:40) to afford (6-((S)-1-((tert-butoxycarbonyl)amino)-1,3-dihydrospiro[indene-2,4'-piperidin]-1'-yl)-3-methyl-1-(tetrahydro-2H-pyran-2-yl)-1H-pyrazolo[3,4-b]pyrazin-5-yl)methyl acetate (130 mg, 112% crude yield) as a yellow oil. LCMS m/z (M+H)⁺=591.2.

Step b: {6-[(3S)-3-{[(tert-butoxy)carbonyl]amino}-1,3-dihydrospiro[indene-2,4'-piperidin]-1'-yl]-3-methyl-1-(oxan-2-yl)-1H-pyrazolo[3,4-b]pyrazin-5-yl}methyl acetate (120 mg, 203 µmol) was added into aq. HCl (14 mL, 4 N) and the reaction mixture was stirred at 25° C. for 6 hours. The reaction mixture was adjusted to pH=7~8 with saturated solution of Na₂CO₃. The mixture was purified by prep-HPLC (NH₃.H₂O) to give {6-[(3S)-3-amino-1,3-dihydrospiro[indene-2,4'-piperidin]-1'-yl]-3-methyl-1H-pyrazolo[3,4-b]pyrazin-5-yl}methanol (1.40 mg, 2% yield). LCMS m/z (M+H)⁺=365.1; ¹H NMR (400 MHz, CD₃OD) δ 7.34-7.37 (m, 1H), 7.18-7.20 (m, 3H), 4.76 (s, 3H), 3.65-3.66 (m, 1H), 3.32-3.37 (m, 2H), 3.13-3.26 (m, 3H), 3.04-3.07 (m, H), 2.77 (s, 3H), 1.96-1.97 (m, 2H), 1.48-1.61 (m, 1H), 1.47-1.48 (m, 1H).

Example 157: Synthesis of (3S)-1'-{5-[(2,3-dichloropyridin-4-YL)methyl]pyrazin-2-yl}-1,3-dihydrospiro[indene-2,4'-piperidin]-3-amine

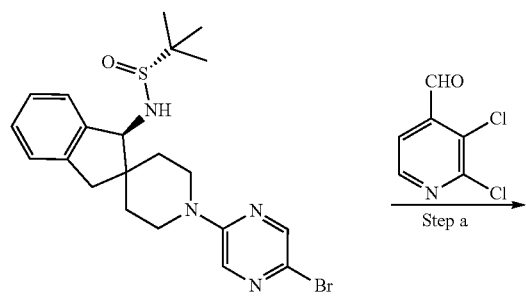

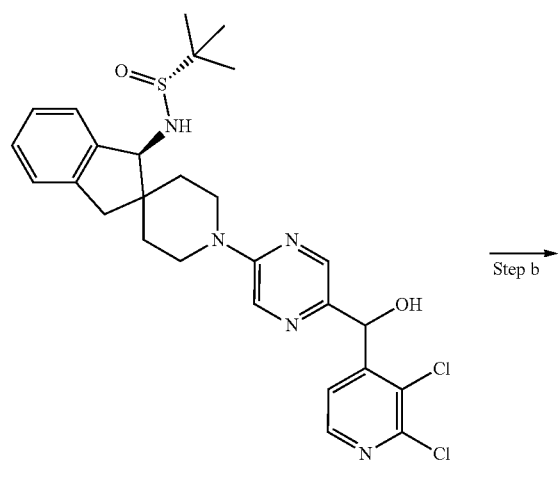

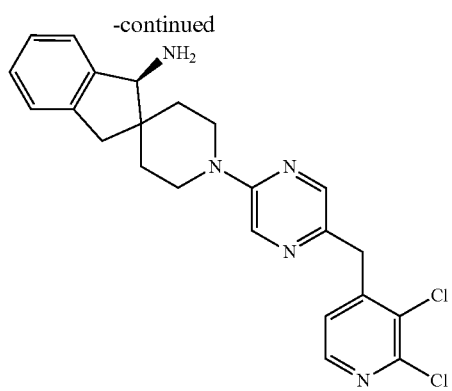

Step a: To the reaction mixture of (R)—N—((S)-1'-(5-bromopyrazin-2-yl)-1,3-dihydrospiro[indene-2,4'-piperidin]-1-yl)-2-methylpropane-2-sulfinamide (400.0 mg, 0.9 mmol, synthesized via Step a of Intermediate BR) in THF (10 mL) was added CuCl (341.0 mg, 3.5 mmol), and the reaction mixture was stirred at 25° C. for 0.5 h. Then n-BuLi (1.38 mL, 3.5 mmol, 2.5 M in THF) was added into the reaction mixture at −78° C. under N₂ atmosphere. The resulting mixture was stirred at −78° C. for 1 hour. Next, 2,3-dichloropyridine-4-carbaldehyde (758.0 mg, 4.3 mmol, CAS #884495-41-4) was added and the resulting mixture was stirred at −78° C. for 1 hour. The reaction mixture was quenched with saturated NH₄Cl (20 mL) and extracted with EtOAc (40 mL×2). The combined organic layers were washed with brine (20 mL), dried over anhydrous Na₂SO₄, filtered and concentrated under reduced pressure to give a residue. The residue was purified by flash silica gel chromatography (20 g column, EtOAc in petroleum ether from 0% to 100%) to give (R)—N-((1S)-1'-(5-((2,3-dichloropyridin-4-yl)(hydroxy)methyl)pyrazin-2-yl)-1,3-dihydrospiro[indene-2,4'-piperidin]-1-yl)-2-methylpropane-2-sulfinamide (155.0 mg, 32% yield) as a yellow oil. LCMS m/z (M+H)⁺=560.0.

Step b: To the reaction mixture of (R)—N-[(3S)-1'-{5-[(2,3-dichloropyridin-4-yl)(hydroxy)methyl]pyrazin-2-yl}-1,3-dihydrospiro[indene-2,4'-piperidin]-3-yl]-2-methylpropane-2-sulfinamide (155.0 mg, 0.3 mmol) in THF (1 mL) was added PBr₃ (74.8 mg, 0.3 mmol) at 25° C. The resulting mixture was stirred at 25° C. for 0.5 hour, and then stirred at 80° C. for 2 hours. The combined reaction mixture was quenched by H₂O (15 mL) at 0° C. and adjusted to pH=10-11 with solid Na₂CO₃. The reaction mixture was extracted with EtOAc (30 mL×3). The combined organic layers were washed with brine (20 mL), dried over anhydrous Na₂SO₄, filtered and concentrated under reduced pressure to give a residue. The residue was purified by prep-HPLC (basic conditions) to give (3S)-1'-{5-[(2,3-dichloropyridin-4-yl)methyl]pyrazin-2-yl}-1,3-dihydrospiro[indene-2,4'-piperidin]-3-amine (3.7 mg, 3% yield) as an off-white solid. LCMS m/z (M+H)⁺=440.0; ¹H NMR (400 MHz, CDCl₃) δ 8.20 (d, J=5.2 Hz, 1H), 8.11 (s, 1H), 8.02 (s, 1H), 7.34-7.33 (m, 1H), 7.24-7.16 (m, 3H), 7.14-7.10 (m, 1H), 4.21-4.11 (m, 4H), 3.99 (s, 1H), 3.24-3.15 (m, 2H), 3.09 (d, J=15.6 Hz, 1H), 2.74 (d, J=16.0 Hz, 1H), 1.90-1.79 (m, 3H), 1.41-1.34 (m, 1H).

Example 158: Synthesis of {6-[(3S)-3-amino-1,3-dihydrospiro[indene-2,4'-piperidin]-1'-yl]-3-methoxy-1H-pyrazolo[3,4-b]pyrazin-5-yl}methanol

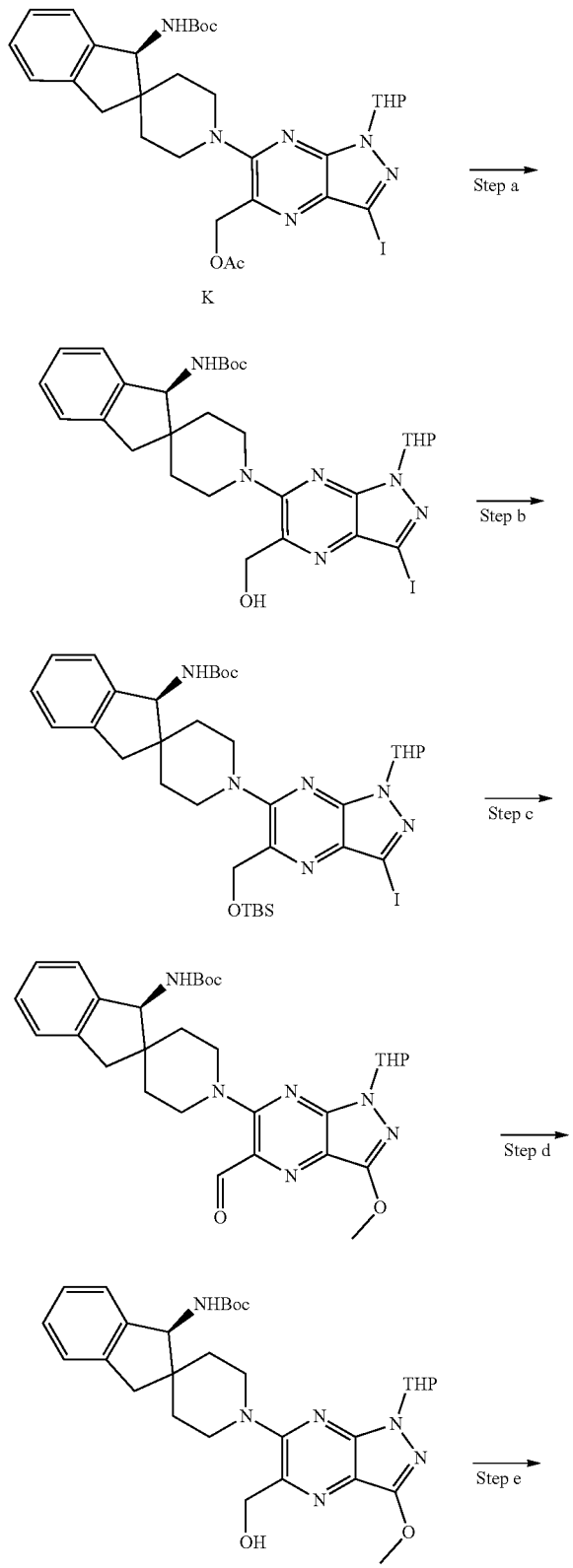

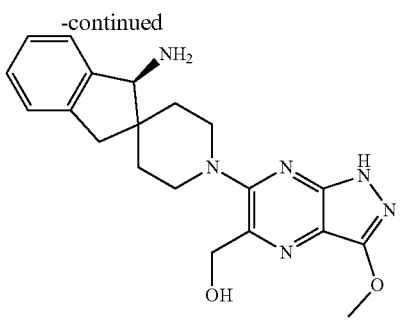

Step a: To the mixture of K$_2$CO$_3$ (146.0 mg, 1.1 mmol) in MeOH (10 mL) was added {6-[(3S)-3-{[(tert-butoxy)carbonyl]amino}-1,3-dihydrospiro[indene-2,4'-piperidin]-1'-yl]-3-iodo-1-(oxan-2-yl)-1H-pyrazolo[3,4-b]pyrazin-5-yl}methyl acetate (250.0 mg, 355.0 μmol, Intermediate K). The mixture was stirred at 20° C. for 12 hours. The mixture was then concentrated under reduced pressure. The residue was purified by column chromatography (petroleum ether/ethyl acetate=1:0~3:1) to afford tert-butyl N-[(3S)-1'-[5-(hydroxymethyl)-3-iodo-1-(oxan-2-yl)-1H-pyrazolo[3,4-b]pyrazin-6-yl]-1,3-dihydrospiro[indene-2,4'-piperidin]-3-yl]carbamate (210.0 mg, 90% yield) as a yellow oil. LCMS m/z (M+H)$^+$=661.1.

Step b: The mixture of tert-butyl N-[(3S)-1'-[5-(hydroxymethyl)-3-iodo-1-(oxan-2-yl)-1H-pyrazolo[3,4-b]pyrazin-6-yl]-1,3-dihydrospiro[indene-2,4'-piperidin]-3-yl]carbamate (190.0 mg, 287.0 μmol) and TBSCl (64.5 mg, 430.0 μmol) in TEA (1 mL) and DCE (5 mL) was stirred at 70° C. for 2 hours. The mixture was diluted with H$_2$O (20 mL), then extracted with EtOAc (20 mL×2). The organic layer was washed with brine (20 mL), dried over anhydrous Na$_2$SO$_4$, filtered and concentrated under reduced pressure. The residue was purified by column chromatography (petroleum ether/ethyl acetate=10:0~10:1) to afford tert-butyl N-[(3S)-1'-(5-{[(tert-butyldimethylsilyl)oxy]methyl}-3-iodo-1-(oxan-2-yl)-1H-pyrazolo[3,4-b]pyrazin-6-yl)-1,3-dihydrospiro[indene-2,4'-piperidin]-3-yl]carbamate (200.0 mg, 90% yield) as a yellow oil. LCMS m/z (M+H)$^+$=775.1.

Step c: The mixture of tert-butyl N-[(3S)-1'-(5-{[(tert-butyldimethylsilyl)oxy]methyl}-3-iodo-1-(oxan-2-yl)-1H-pyrazolo[3,4-b]pyrazin-6-yl)-1,3-dihydrospiro[indene-2,4'-piperidin]-3-yl]carbamate (140.0 mg, 180.0 μmol), Cs$_2$CO$_3$ (117.0 mg, 360.0 μmol), CuI (3.4 mg, 18.0 μmol) and 3,4,7,8-tetramethyl-1,10-phenanthroline (8.5 mg, 36.0 μmol) in MeOH (5 mL) was stirred under microwave irradiation at 100° C. for 2 hours. The TBS group was removed and the hydroxyl group was oxidized to aldehyde in the reaction course. The mixture was concentrated under reduced pressure. The residue was purified by column chromatography (petroleum ether/ethyl acetate=1:0~5:1) to afford tert-butyl N-[(3S)-1'-[5-formyl-3-methoxy-1-(oxan-2-yl)-1H-pyrazolo[3,4-b]pyrazin-6-yl]-1,3-dihydrospiro[indene-2,4'-piperidin]-3-yl]carbamate (40.0 mg, 40% yield) as a yellow oil. LCMS m/z (M+H)$^+$=563.2.

Step d: To the mixture of tert-butyl N-[(3S)-1'-[5-formyl-3-methoxy-1-(oxan-2-yl)-1H-pyrazolo[3,4-b]pyrazin-6-yl]-1,3-dihydrospiro[indene-2,4'-piperidin]-3-yl]carbamate (40.0 mg, 71.0 μmol) in MeOH (5 mL) was added NaBH$_4$ (5.4 mg, 142.0 μmol) at 0° C. under N$_2$ atmosphere. The mixture was stirred at 0° C. for 0.5 hours. The mixture was then quenched with saturated NH$_4$Cl (20 mL), and extracted with EtOAc (20 mL). The organic layer was washed with brine (10 mL), dried over anhydrous Na$_2$SO$_4$, filtered and concentrated under reduced pressure to afford tert-butyl N-[(3S)-1'-[5-(hydroxymethyl)-3-methoxy-1-(oxan-2-yl)-1H-pyrazolo[3,4-b]pyrazin-6-yl]-1,3-dihydrospiro[indene-2,4'-piperidin]-3-yl]carbamate (35.0 mg, 88% yield) as a yellow solid. LCMS m/z (M+H)$^+$=565.2.

Step e: The mixture of tert-butyl N-[(3S)-1'-[5-(hydroxymethyl)-3-methoxy-1-(oxan-2-yl)-1H-pyrazolo[3,4-b]pyrazin-6-yl]-1,3-dihydrospiro[indene-2,4'-piperidin]-3-yl]carbamate (35.0 mg, 61.9 µmol) in DCM (3 mL) and TFA (0.3 mL) was stirred at 30° C. for 12 hours. Then the mixture was concentrated under reduced pressure. The residue was diluted with EtOAc (10 mL), and adjusted pH=7 by $K_2CO_3$. The mixture was filtered and the filtrate was concentrated under reduced pressure. The mixture was then purified by prep-HPLC (NH$_3$.H$_2$O) to afford {6-[(3S)-3-amino-1,3-dihydrospiro[indene-2,4'-piperidin]-1'-yl]-3-methoxy-1H-pyrazolo[3,4-b]pyrazin-5-yl}methanol (6.7 mg, 29% yield) as a white solid. LCMS m/z (M+H)$^+$=381.0; $^1$HNMR (400 MHz, MeOD-d4): δ 7.42-7.39 (m, 1H), 7.26-7.20 (m, 3H), 4.77 (s, 2H), 4.12 (s, 3H), 4.02 (s, 1H), 3.75-3.72 (m, 2H), 3.24-2.79 (m, 4H), 2.05-1.96 (m, 2H), 1.67-1.32 (m, 2H).

Example 159: Synthesis of {6-[(3R)-3-amino-3H-spiro[1-benzofuran-2,4'-piperidin]-1'-yl]-1H-pyrazolo[3,4-b]pyrazin-5-yl}methanol

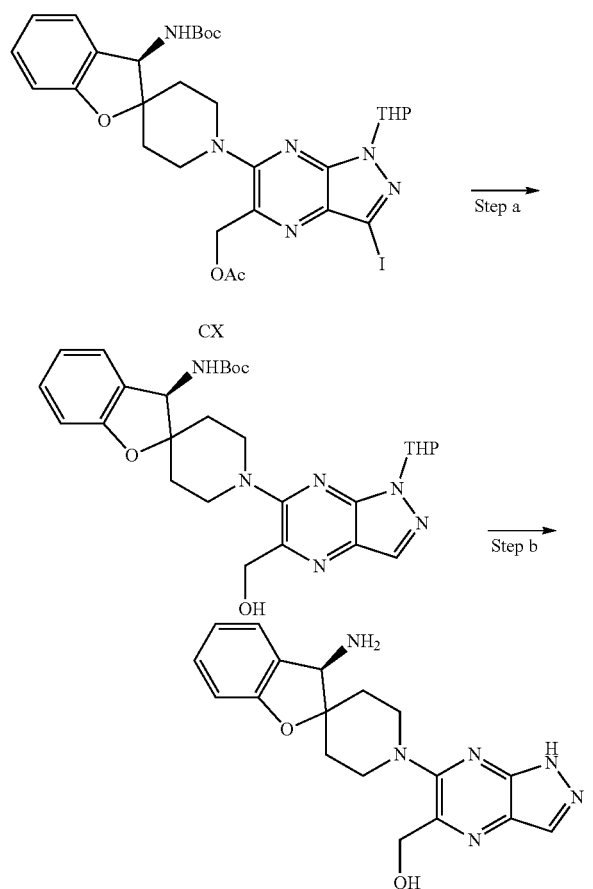

Step a: To a mixture of {6-[(3R)-3-{[(tert-butoxy)carbonyl]amino}-3H-spiro[1-benzofuran-2,4'-piperidin]-1'-yl]-3-iodo-1-(oxan-2-yl)-1H-pyrazolo[3,4-b]pyrazin-5-yl}methyl acetate (200 mg, 0.3 mmol, Intermediate CX) in dioxane (5.0 mL) were added $Cs_2CO_3$ (183 mg, 0.6 mmol), XantPhos-Pd-G4 (21.5 mg, 28.3 µmol) and $Et_3SiH$ (223 µL, 1.4 mmol). The reaction mixture was purged with $N_2$ for 3 min and stirred at 100° C. for 12 hours under $N_2$. The reaction mixture was concentrated under reduced pressure to give a residue which was purified by column chromatography (petroleum ether:ethyl acetate=100:0 to 100:50). tert-butyl N-[(3R)-1'-[5-(hydroxymethyl)-1-(oxan-2-yl)-1H-pyrazolo[3,4-b]pyrazin-6-yl]-3H-spiro[1-benzofuran-2,4'-piperidin]-3-yl]carbamate (100 mg, 66% yield) was obtained as a yellow solid. LCMS m/z (M+H)$^+$=537.2.

Step b: A solution of tert-butyl N-[(3R)-1'-[5-(hydroxymethyl)-1-(oxan-2-yl)-1H-pyrazolo[3,4-b]pyrazin-6-yl]-3H-spiro[1-benzofuran-2,4'-piperidin]-3-yl]carbamate (100 mg, 186 µmol) in THF (3.0 mL) and HCl/H$_2$O (3 mL, 2M) was stirred at 30° C. for 12 hours. The reaction mixture was concentrated under reduced pressure to give a residue. The residue was dissolved with H$_2$O (5.0 mL) and adjusted to pH=8 with solid $K_2CO_3$, then purified by prep. HPLC (NH$_3$.H$_2$O). {6-[(3R)-3-amino-3H-spiro[1-benzofuran-2,4'-piperidin]-1'-yl]-1H-pyrazolo[3,4-b]pyrazin-5-yl}methanol (10.0 mg, 15% yield) was obtained as a white solid. LCMS m/z (M+H)$^+$=353.1; $^1$HNMR (400 MHz, Methanol-d4): 8.13 (s, 1H), 7.40-7.42 (m, 1H), 7.18-7.22 (m, 1H), 6.90-6.94 (m, 1H), 6.80-6.82 (m, 1H), 4.83 (s, 2H), 4.17 (s, 1H), 3.80-3.84 (m, 1H), 3.70-3.74 (m, 1H), 3.42-3.49 (m, 2H), 2.15-2.23 (m, 1H), 2.00-2.08 (m, 2H), 1.80-1.90 (m, 1H).

Example 160: Synthesis of (3S)-1'-[5-methyl-3-(morpholin-4-yl)-1H-pyrazolo[3,4-b]pyrazin-6-yl]-1,3-dihydrospiro[indene-2,4'-piperidin]-3-amine

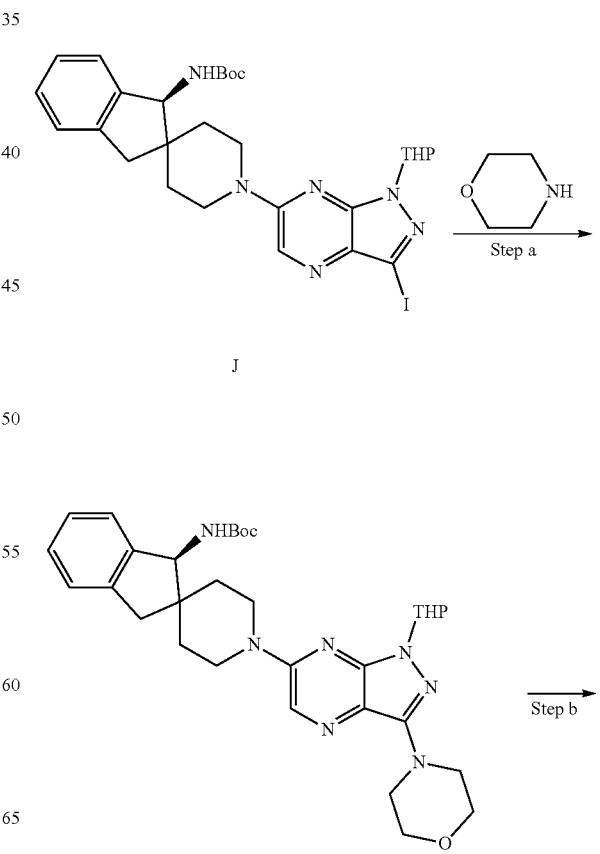

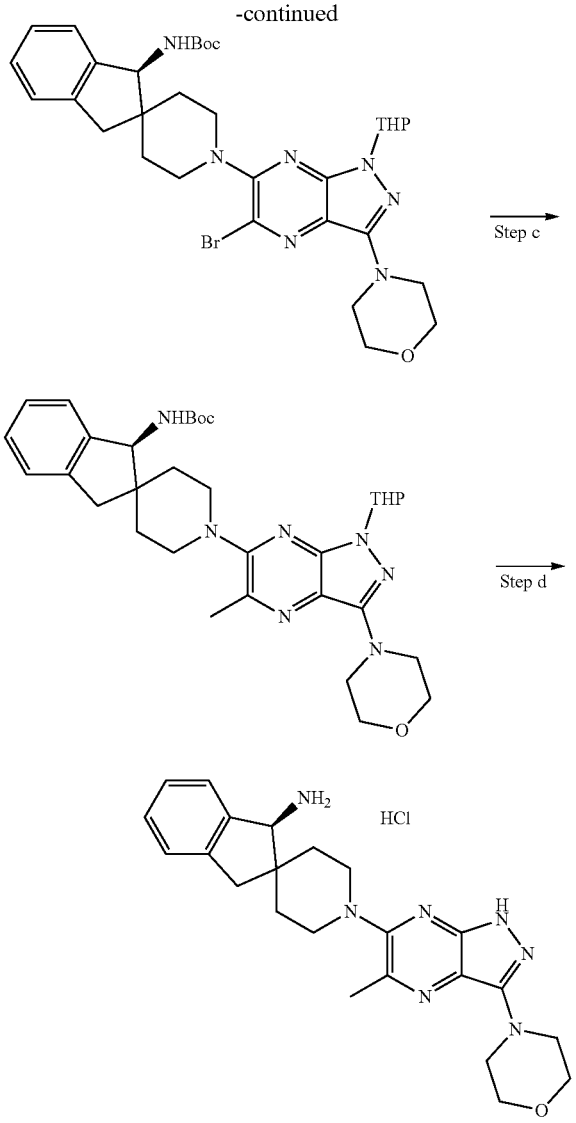

Step a: To the mixture of tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (300.0 mg, 475.0 µmol, Intermediate J) and morpholine (82.7 mg, 950.0 µmol) in toluene (10.0 mL) were added Cs$_2$CO$_3$ (338.0 mg, 1.0 mmol), RuPhos (33.2 mg, 71.2 µmol, CAS #787618-22-8) and RuPhos-Pd-G4 (40.3 mg, 47.5 µmol, CAS #1599466-85-9) under N$_2$. The mixture was stirred at 100° C. under N$_2$ for 12 hours. The mixture was then concentrated under reduced pressure and purified by flash silica gel chromatography (petroleum ether/EtOAc=I/O to 1/1) to give tert-butyl N-[(3S)-1'-[3-(morpholin-4-yl)-1-(oxan-2-yl)-1H-pyrazolo[3,4-b]pyrazin-6-yl]-1,3-dihydrospiro[indene-2,4'-piperidin]-3-yl]carbamate (250.0 mg, 89% yield) as a brown solid. LCMS m/z (ESI$^+$) (M+Na)+=612.2.

Step b: To the mixture of tert-butyl N-[(3S)-1'-[3-(morpholin-4-yl)-1-(oxan-2-yl)-1H-pyrazolo[3,4-b]pyrazin-6-yl]-1,3-dihydrospiro[indene-2,4'-piperidin]-3-yl]carbamate (230.0 mg, 390.0 µmol) in ACN (4.0 mL) and AcOH (4.0 mL) was added NBS (72.8 mg, 409.0 µmol) at −20° C. under N$_2$. The mixture was stirred at −20° C. under N$_2$ for 1 hour. The mixture was concentrated under reduced pressure to give a brown oil. The oil was adjusted to pH=8 with the saturated NaHCO$_3$ and the mixture was extracted with EtOAc (40.0 mL×3). The combined organic layers were washed with brine (50.0 mL) and dried over anhydrous Na$_2$SO$_4$, filtered and concentrated under reduced pressure to give a brown oil. The residue was purified by flash silica gel chromatography (petroleum ether/EtOAc=I/O to 3/1) to give tert-butyl N-[(3S)-1'-[5-bromo-3-(morpholin-4-yl)-1-(oxan-2-yl)-1H-pyrazolo[3,4-b]pyrazin-6-yl]-1,3-dihydrospiro[indene-2,4'-piperidin]-3-yl]carbamate (140.0 mg) as a brown oil. LCMS m/z (M+H)$^+$=668.1, 670.1.

Step c: To the mixture of tert-butyl N-[(3S)-1'-[5-bromo-3-(morpholin-4-yl)-1-(oxan-2-yl)-1H-pyrazolo[3,4-b]pyrazin-6-yl]-1,3-dihydrospiro[indene-2,4'-piperidin]-3-yl]carbamate (120.0 mg, 179.0 µmol) and K$_2$CO$_3$ (61.6 mg, 447.0 µmol) in dioxane (5 mL) and H$_2$O (0.5 mL) were added Pd(dppf)Cl$_2$ (13.0 mg, 17.9 µmol, CAS #72287-26-4) and trimethylboroxine (49.7 µL, 358.0 µmol, CAS #823-96-1) under N$_2$. The mixture was stirred at 90° C. under N$_2$ for 12 hours. The mixture was concentrated under reduced pressure and purified by flash silica gel chromatography (petroleum ether/EtOAc=I/O to 3/1) to give tert-butyl N-[(3S)-1'-[5-methyl-3-(morpholin-4-yl)-1-(oxan-2-yl)-1H-pyrazolo[3,4-b]pyrazin-6-yl]-1,3-dihydrospiro[indene-2,4'-piperidin]-3-yl]carbamate (80.0 mg, 74% yield) as a brown solid. LCMS m/z (M+H)$^+$=604.2.

Step d: A mixture of tert-butyl N-[(3S)-1'-[5-methyl-3-(morpholin-4-yl)-1-(oxan-2-yl)-1H-pyrazolo[3,4-b]pyrazin-6-yl]-1,3-dihydrospiro[indene-2,4'-piperidin]-3-yl]carbamate (80.0 mg, 132.0 µmol) in HCl/EtOAc (4 mL, 4 M) was stirred at 30° C. for 12 hours. The mixture was concentrated under reduced pressure to give a brown solid. The solid in EtOAc (10.0 mL) was stirred at 20° C. for 10 min. The mixture was filtered and filter cake was lyophilized to give (3S)-1'-[5-methyl-3-(morpholin-4-yl)-1H-pyrazolo[3,4-b]pyrazin-6-yl]-1,3-dihydrospiro[indene-2,4'-piperidin]-3-amine hydrochloride (48.0 mg, 80% yield) as a brown solid. LCMS m/z (M+H)$^+$=420.0. $^1$H NMR (400 MHz, CD$_3$OD-d4): 7.54 (d, J=7.2 Hz, 1H), 7.45-7.35 (m, 3H), 4.47 (s, 1H), 3.91-3.87 (m, 5H), 3.82-3.80 (m, 5H), 3.28-7.25 (m, 2H), 3.20 (s, 2H), 2.64 (s, 3H), 2.09-2.03 (m, 2H), 1.96-1.68 (m, 2H).

Example 161: Synthesis of (3R)-1'-[5-methyl-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-amine

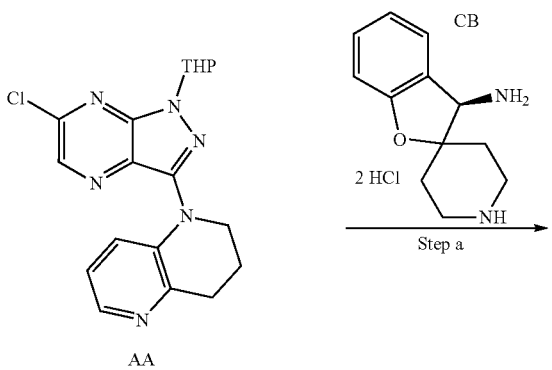

-continued

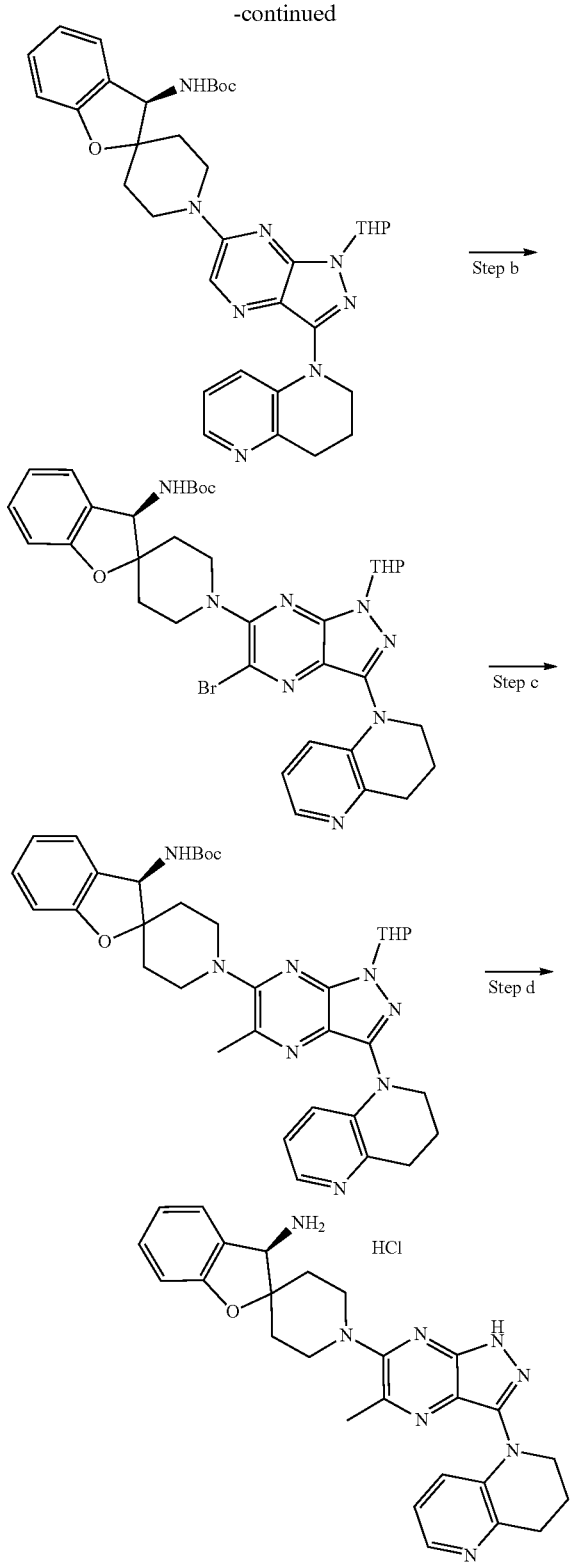

Step a: A solution of (3R)-3H-spiro[1-benzofuran-2,4'-piperidin]-3-amine dihydrochloride (1.10 g, 3.96 mmol, Intermediate CB), 1-[6-chloro-1-(oxan-2-yl)-1H-pyrazolo[3,4-b]pyrazin-3-yl]-1,2,3,4-tetrahydro-1,5-naphthyridine (1.46 g, 3.96 mmol, Intermediate AA) and TEA (3.31 mL, 23.7 mmol) in DMSO (25.0 mL) was stirred at 80° C. for 4 hours. To the mixture was added Boc$_2$O (1.69 g, 7.78 mmol). The reaction mixture was stirred at 20° C. for 0.5 hour. The reaction mixture was then poured into H$_2$O (250.0 mL) and extracted with EtOAc (100.0 mL×2). The combined organic layers were washed with brine (200.0 mL), dried over anhydrous Na$_2$SO$_4$, filtered and the filtrate was concentrated under reduced pressure to give a residue. The residue was purified by flash silica gel chromatography (40 g, ethyl acetate in petroleum ether from 0% to 65%) to give tert-butyl N-[(3R)-1'-[1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-yl]carbamate (1.40 g, 56% yield) as a yellow solid. LCMS m/z (M+H)$^+$=639.1.

Step b: To a solution of tert-butyl N-[(3R)-1'-[1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-yl]carbamate (1.40 g, 2.19 mmol) in MeCN/AcOH (25.0 mL/25.0 mL) was added NBS (389.0 mg, 2.19 mmol). The reaction mixture was stirred at 20° C. for 1 hour. The reaction mixture was then quenched with H$_2$O and concentrated under reduced pressure. The residue was triturated with H$_2$O (200.0 mL) and extracted with EtOAc (150.0 mL×2). The combined organic layers were washed with brine (200.0 mL), dried over anhydrous Na$_2$SO$_4$, filtered and the filtrate was concentrated under reduced pressure to give a residue. The residue was purified by flash silica gel chromatography (40 g, ethyl acetate in petroleum ether from 0% to 35%) to give tert-butyl N-[(3R)-1'-[5-bromo-1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-yl]carbamate (1.25 g, 80% yield) as a yellow solid. LCMS m/z (M+H)$^+$=717.0.

Step c: A solution of tert-butyl N-[(3R)-1'-[5-bromo-1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-yl]carbamate (1.25 g, 1.74 mmol), trimethylboroxine (436.0 mg, 3.48 mmol), Pd(dppf)Cl$_2$ (254.0 mg, 348.0 umol) and K$_2$CO$_3$ (720.0 mg, 5.22 mmol) in dioxane/H$_2$O (50.0 mL/5.0 mL) was stirred at 90° C. for 12 hours under N$_2$. The reaction mixture was poured into H$_2$O (150.0 mL) and extracted with EtOAc (200.0 mL×2). The combined organic layers were washed with brine (200.0 mL), dried over anhydrous Na$_2$SO$_4$, filtered and the filtrate was concentrated under reduced pressure to give a residue. The residue was purified by flash silica gel chromatography (40 g, ethyl acetate in petroleum ether from 0% to 50%) to give tert-butyl N-[(3R)-1'-[5-methyl-1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-yl]carbamate (860.0 mg, 76% yield) as a yellow solid. LC-MS (ESI$^+$) m/z: 653.1 (M+H)$^+$.

Step d: A solution of tert-butyl N-[(3R)-1'-[5-methyl-1-(oxan-2-yl)-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-yl]carbamate (860.0 mg, 1.31 mmol) in HCl/MeOH (30.0 mL, 4 M) was stirred at 20° C. for 1 hour. The reaction mixture was concentrated under reduced pressure to give a solid. The solid was triturated with EtOAc and stirred for 0.5 hour. The mixture was then filtered and the filter cake was lyophilized. (3R)-1'-[5-methyl-3-(1,2,3,4-tetrahydro-1,5-naphthyridin-1-yl)-1H-pyrazolo[3,4-b]pyrazin-6-yl]-3H-spiro[1-benzofuran-2,4'-piperidin]-3-amine hydrochloride (589.3 mg, 89% yield) was obtained as an orange solid. LC-MS (ESI$^+$) m/z: 469.1 (M+H)$^+$. $^1$HNMR (400 MHz, CD$_3$OD): 8.05-8.07 (m, 1H), 7.94-7.97 (m, 1H), 7.57-7.62 (m, 2H), 7.41-7.44 (m, 1H), 7.06-7.11 (m, 1H), 7.00-7.03 (m, 1H), 4.75 (s, 1H), 4.08-4.12 (m, 2H), 3.92-3.94 (m, 1H), 3.74-3.78 (m, 1H), 3.41-3.53 (m, 2H), 3.29-3.32 (m, 2H), 2.67 (s, 3H), 2.33-2.41 (m, 3H), 2.10-2.18 (m, 2H), 1.98-2.06 (m, 1H).

Example 162: Synthesis of (3R)-1'-[5-methyl-3-(piperidin-1-yl)-1H-pyrazolo[3,4-b]pyrazin-6-yl]-3H-spiro[1-benzofuran-2,4'-piperidin]-3-amine

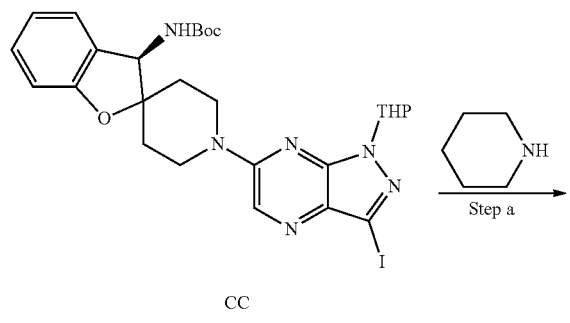

CC

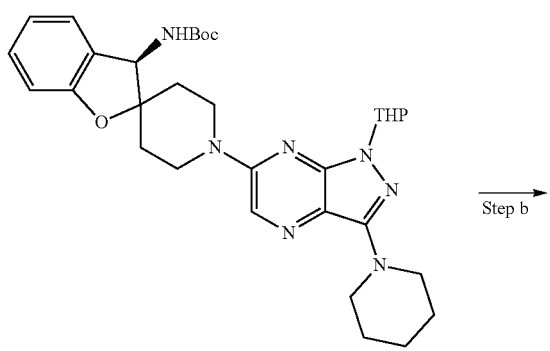

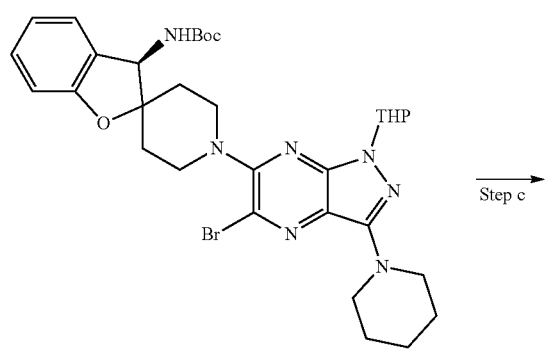

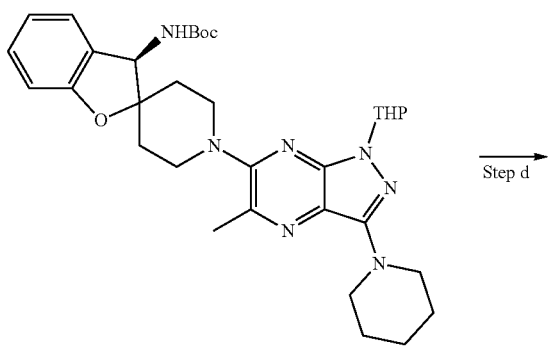

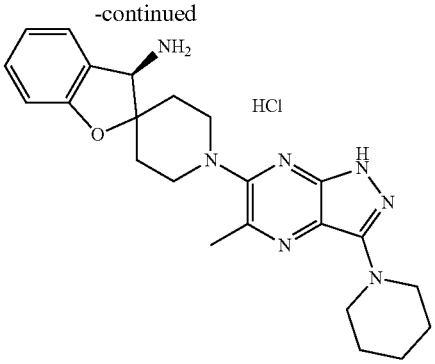

-continued

Step a: A solution of tert-butyl N-[(3R)-1'-[3-iodo-1-(oxan-2-yl)-1H-pyrazolo[3,4-b]pyrazin-6-yl]-3H-spiro[1-benzofuran-2,4'-piperidin]-3-yl]carbamate (702.0 mg, 1.1 mmol, Intermediate CC), piperidine (121.0 mg, 1.4 mmol, CAS #110-89-4), XantPhos-Pd-G4 (105.0 mg, 0.1 mmol, CAS #1621274-19-8) and $Cs_2CO_3$ (716.0 mg, 2.2 mmol) in PhMe (15 mL) was stirred at 110° C. for 12 hours under $N_2$. The reaction mixture was diluted with $H_2O$ (80 mL) and extracted with EtOAc (80 mL×3). The combined organic layers were washed with brine (50 mL), dried over anhydrous $Na_2SO_4$, filtered and concentrated to give a residue. The residue was purified by flash silica gel chromatography (20 g, EtOAc in Petroleum ether from 0% 35%) to give tert-butyl N-[(3R)-1'-[1-(oxan-2-yl)-3-(piperidin-1-yl)-1H-pyrazolo[3,4-b]pyrazin-6-yl]-3H-spiro[1-benzofuran-2,4'-piperidin]-3-yl]carbamate (160.0 mg, 0.3 mmol, 24.6% yield) as a yellow oil. LCMS (ESI$^+$) m/z: 590.2 (M+H)$^+$. (3R)-1'-[5-methyl-3-(piperidin-1-yl)-1H-pyrazolo[3,4-b]pyrazin-6-yl]-3H-spiro[1-benzofuran-2,4'-piperidin]-3-amine hydrochloride was then synthesized via Steps b-d as described in Example 161, where Step b was run at 0° C. instead of 25° C. for 1 hr. (3R)-1'-[5-methyl-3-(piperidin-1-yl)-1H-pyrazolo[3,4-b]pyrazin-6-yl]-3H-spiro[1-benzofuran-2,4'-piperidin]-3-amine hydrochloride (69.0 mg, 90% yield in Step d) was isolated as a brown solid. LC-MS (ESI$^+$) m/z: 420.1 (M+H)$^+$. $^1$HNMR (400 MHz, $CD_3OD$) δ 7.56 (d, J=7.6 Hz, 1H), 7.41 (t, J=7.6 Hz, 1H), 7.06 (t, J=7.6 Hz, 1H), 6.99 (d, J=8.4 Hz, 1H), 4.69 (s, 1H), 4.08 (d, J=12.4 Hz, 1H), 3.92-3.87 (m, 5H), 3.53-3.40 (m, 2H), 2.65 (s, 3H), 2.34-2.28 (m, 1H), 2.14-1.93 (m, 3H), 1.77 (s, 6H).

Example 163: Synthesis of 6-[(3S)-3-amino-1,3-dihydrospiro[indene-2,4'-piperidin]-1'-yl]-5-methyl-1H-pyrazolo[3,4-b]pyrazine-3-carbonitrile

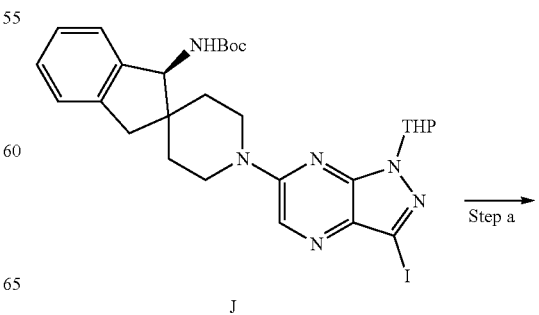

J

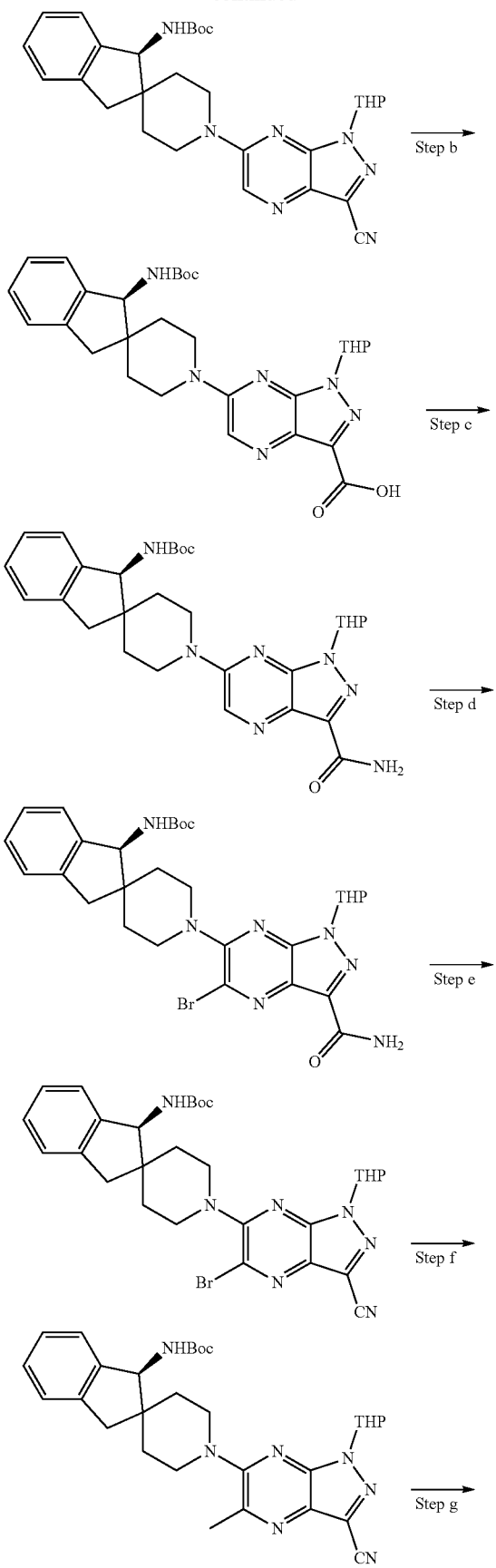

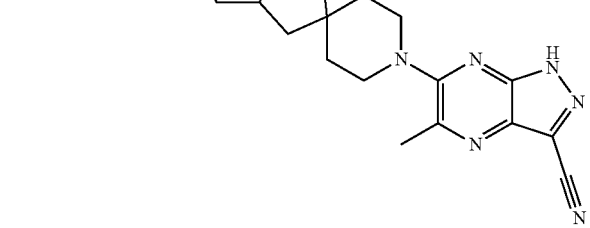

Step a: A mixture of tert-butyl N-[(3S)-1'-[3-iodo-1-(oxan-2-yl)-H-pyrazolo[3,4-b]pyrazin-6-yl]-1,3-dihydrospiro[indene-2,4'-piperidin]-3-yl]carbamate (600.0 mg, 951 μmol, Intermediate J), Zn(CN)$_2$ (272.0 mg, 1.9 mmol) and [(t-Bu$_3$P)$_2$]Pd (48.5 mg, 95.1 μmol) in DMF (30 mL) was stirred at 130° C. for 12 hours under N$_2$ atmosphere. The reaction mixture was diluted with ethyl acetate (45 mL), washed with H$_2$O (35 mL×2) and brine (20 mL), then dried over anhydrous Na$_2$SO$_4$, filtered and concentrated in vacuum to give a residue. The residue was purified by silica gel chromatography (ethyl acetate in petroleum ether=0% to 40%) to afford tert-butyl N-[(3S)-1'-[3-cyano-1-(oxan-2-yl)-1H-pyrazolo[3,4-b]pyrazin-6-yl]-1,3-dihydrospiro[indene-2,4'-piperidin]-3-yl]carbamate (360.0 mg, 72% yield) as a yellow solid. LCMS (ESI$^+$) m/z: 552.1 (M+Na)+.

Step b: A mixture of tert-butyl N-[(3S)-1'-[3-cyano-1-(oxan-2-yl)-1H-pyrazolo[3,4-b]pyrazin-6-yl]-1,3-dihydrospiro[indene-2,4'-piperidin]-3-yl]carbamate (360 mg, 679 μmol) in MeOH (8.0 mL) and aq.NaOH (10%, 8.0 mL) was stirred at 90° C. for 1 hour. The mixture was concentrated in vacuo to give a residue, which was diluted with H$_2$O (20 mL) and adjusted pH=4 with 2N NaOH, then extracted with ethyl acetate (30 mL×3). The combined organic phases were washed with brine (20 mL), dried over anhydrous Na$_2$SO$_4$, filtered and concentrated in vacuo to afford 6-[(3S)-3-{[(tert-butoxy)carbonyl]amino}-1,3-dihydrospiro[indene-2,4'-piperidin]-1'-yl]-1-(oxan-2-yl)-1H-pyrazolo[3,4-b]pyrazine-3-carboxylic acid (360.0 mg, 97% yield) as a yellow solid. LCMS (ESI$^+$) m/z: 549.1 (M+H)$^+$.

Step c: A mixture of 6-[(3S)-3-{[(tert-butoxy)carbonyl]amino}-1,3-dihydrospiro[indene-2,4'-piperidin]-1'-yl]-1-(oxan-2-yl)-1H-pyrazolo[3,4-b]pyrazine-3-carboxylic acid (360.0 mg, 656 μmol), ammonium 1H-1,2,3-benzotriazol-1-olate (149.0 mg, 984 μmol) and EDCI (188 mg, 984 μmol) in DMF (15.0 mL) was stirred at 25° C. for 1 hour. The reaction mixture was diluted with ethyl acetate (40 mL), then washed with H$_2$O (30 mL×3). The combined organic phase was washed with brine (10 mL), dried over anhydrous Na$_2$SO$_4$, filtered and concentrated in vacuo to give a residue. The residue was purified by silica gel chromatography (methanol in petroleum ether=0% to 10%) to afford tert-butyl N-[(3S)-1'-[3-carbamoyl-1-(oxan-2-yl)-1H-pyrazolo[3,4-b]pyrazin-6-yl]-1,3-dihydrospiro[indene-2,4'-piperidin]-3-yl]carbamate (220.0 mg, 61% yield) as a yellow oil. LCMS (ESI$^+$) m/z: 548.1 (M+H)$^+$.

Step d: To a mixture of tert-butyl N-[(3S)-1'-[3-carbamoyl-1-(oxan-2-yl)-1H-pyrazolo[3,4-b]pyrazin-6-yl]-1,3-dihydrospiro[indene-2,4'-piperidin]-3-yl]carbamate (220.0 mg, 401 μmol) in MeCN (10.0 mL) and AcOH (1.0 mL) was added NBS (106.0 mg, 601 μmol), the resulting mixture was stirred at 25° C. for 12 hours. The reaction mixture was concentrated in vacuo to give a residue, which was dissolved in ethyl acetate (25 mL), then washed with sat. NaHCO$_3$ (15 mL×2). The organic phase was washed with brine (10 mL), dried over anhydrous Na$_2$SO$_4$, filtered and concentrated in vacuo to give a residue, which was purified by silica gel chromatography (methanol in dichloromethane=0% to 10%) to afford tert-butyl N-[(3S)-1'-{5-bromo-3-carbamoyl-1H-pyrazolo[3,4-b]pyrazin-6-yl}-1,3-dihydrospiro[indene-2,4'-piperidin]-3-yl]carbamate (210 mg, 97% yield) as a yellow solid. LCMS (ESI$^+$) m/z: 543.0 and 544.0 (M+H)$^+$.

Step e: A mixture of tert-butyl N-[(3S)-1'-{5-bromo-3-carbamoyl-1H-pyrazolo[3,4-b]pyrazin-6-yl}-1,3-dihydrospiro[indene-2,4'-piperidin]-3-yl]carbamate (210.0 mg, 387 μmol), TFAA (108.0 μL, 774 μmol) and TEA (160.0 μL, 1.2 mmol) in DCM (10 mL) was stirred at 25° C. for 12 hours under N$_2$ atmosphere. The reaction mixture was diluted with sat.NaHCO$_3$ (25 mL), then extracted with DCM (30 mL×3). The combined organic phases were washed with brine (20 mL), dried over anhydrous Na$_2$SO$_4$, filtered and concentrated in vacuo to give a residue, which was purified by silica gel chromatography (ethyl acetate in petroleum ether=0% to 35%) to afford tert-butyl N-[(3S)-1'-{5-bromo-3-cyano-1H-pyrazolo[3,4-b]pyrazin-6-yl}-1,3-dihydrospiro[indene-2,4'-piperidin]-3-yl]carbamate (100 mg, 50% yield) as a yellow solid. LCMS (ESI$^+$) m/z: 546.0 (M+Na)+.

Step f: A mixture of tert-butyl N-[(3S)-1'-{5-bromo-3-cyano-1H-pyrazolo[3,4-b]pyrazin-6-yl}-1,3-dihydrospiro[indene-2,4'-piperidin]-3-yl]carbamate (100.0 mg, 190 μmol), trimethyl-1,3,5,2,4,6-trioxatriborinane (71.5 mg, 570 μmol), Pd(dppf)Cl$_2$ (13.9 mg, 19.0 μmol) and K$_2$CO$_3$ (52.4 mg, 380 μmol) in 1,4-dioxane (10.0 mL) and H$_2$O (1.0 mL) was stirred at 90° C. for 12 hours under N$_2$ atmosphere. The reaction mixture was concentrated in vacuo to give a residue, which was purified by silica gel chromatography (ethyl acetate in petroleum ether=0% to 30%) to afford tert-butyl N-[(3S)-1'-{3-cyano-5-methyl-1H-pyrazolo[3,4-b]pyrazin-6-yl}-1,3-dihydrospiro[indene-2,4'-piperidin]-3-yl]carbamate (35.0 mg, 40% yield) as a yellow oil. LCMS (ESI$^+$) m/z: 404.0 (M+H-Boc)+.

Step g: A mixture of tert-butyl N-[(3S)-1'-[3-cyano-5-methyl-1-(oxan-2-yl)-1H-pyrazolo[3,4-b]pyrazin-6-yl]-1,3-dihydrospiro[indene-2,4'-piperidin]-3-yl]carbamate (35.0 mg, 64.3 μmol) in TFA (1.0 mL) was stirred at 25° C. for 2 hours. The reaction mixture was concentrated in vacuo to give a residue, which was dissolved in MeOH (5 mL) and adjusted pH=8 with solid Na$_2$CO$_3$. The mixture was filtered and concentrated in vacuo to give a residue, which was purified by prep-HPLC (NH$_3$.H$_2$O) to afford 6-[(3S)-3-amino-1,3-dihydrospiro[indene-2,4'-piperidin]-1'-yl]-5-methyl-1H-pyrazolo[3,4-b]pyrazine-3-carbonitrile (2.8 mg, 12% yield) as a yellow solid. LCMS (ESI$^+$) m/z: 343.1 (M+H-NH$_2$)+. $^1$HNMR (400 MHz, Methanol-d4): 7.45-7.43 (m, 1H), 7.32-7.24 (m, 3H), 4.15 (s, 1H), 3.74-3.69 (m, 2H), 3.26-3.15 (m, 3H), 2.92 (d, J=16.0 Hz, 1H), 2.70 (s, 3H), 2.07-1.96 (m, 2H), 1.70-1.59 (m, 2H).

Example 164: Synthesis of (3S)-1'-{5-[(2S)-2-phenylpyrrolidin-1-yl]pyrazin-2-yl}-1,3-dihydrospiro[indene-2,4'-piperidin]-3-amine

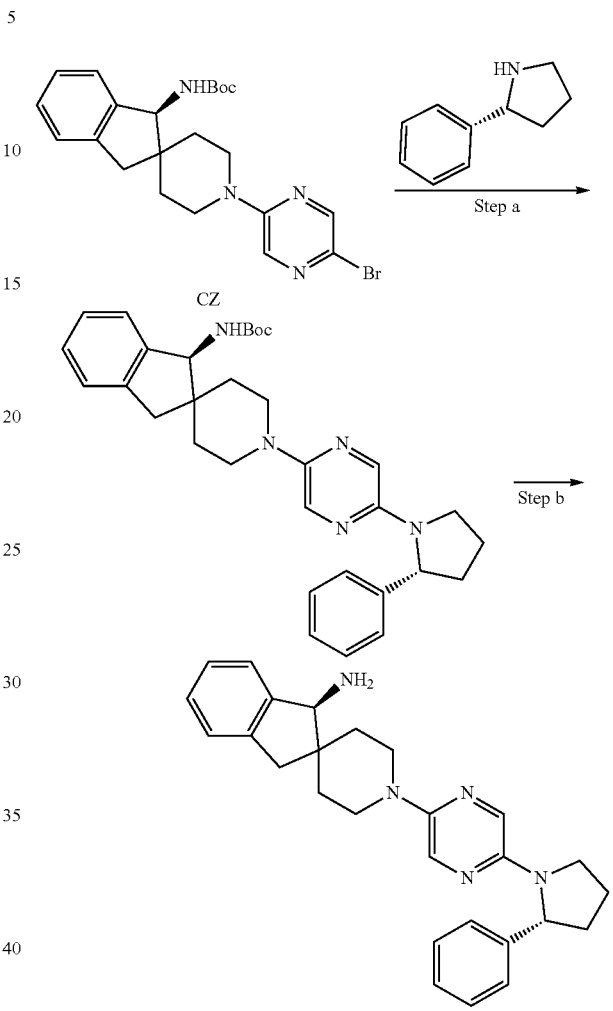

Step a: A mixture of (S)-tert-butyl (1'-(5-bromopyrazin-2-yl)-1,3-dihydrospiro[indene-2,4'-piperidin]-1-yl)carbamate (150.0 mg, 326 μmol, Intermediate CZ), (2R)-2-phenylpyrrolidine (47.9 mg, 326 μmol, CAS #56523-47-8), Cs$_2$CO$_3$ (318.0 mg, 978 μmol), RuPhos-Pd-G4 (27.7 mg, 32.6 μmol) and RuPhos (30.4 mg, 65.2 μmol) in toluene (6.00 mL) was stirred at 100° C. for 12 hours under N$_2$ atmosphere. Then H$_2$O (10 mL) was added and the mixture was extracted with ethyl acetate (15 mL×3). The combined organic layers were washed with brine (30 mL), dried over anhydrous Na$_2$SO$_4$, filtered and concentrated to give a residue. The residue was purified by flash silica gel chromatography (ethyl acetate/petroleum ether=0/100 to 25/100) to afford tert-butyl N-[(3S)-1'-{5-[(2R)-2-phenylpyrrolidin-1-yl]pyrazin-2-yl}-1,3-dihydrospiro[indene-2,4'-piperidin]-3-yl]carbamate (79.0 mg, 46% yield) as a green oil. LCMS (ESI$^+$) m/z: 526.2 (M+H)$^+$.

Step b: The compound of tert-butyl N-[(3S)-1'-{5-[(2R)-2-phenylpyrrolidin-1-yl]pyrazin-2-yl}-1,3-dihydrospiro[indene-2,4'-piperidin]-3-yl]carbamate (79.0 mg, 150 μmol) was added 15 into HCl/dioxane (6.00 mL, 4 M). The mixture was stirred at 25° C. for 0.5 h. The mixture was diluted with H$_2$O (20 mL) and EtOAc (20 mL), then the partitioned layers were separated. The aqueous phase was extracted with EtOAc (20 mL×3). The combined organic layers were washed with brine (30 mL×2), dried over anhydrous Na$_2$SO$_4$, filtered and concentrated to give a residue. The residue was purified by prep-HPLC (NH$_3$.H$_2$O) to afford (3S)-1'-{5-[(2S)-2-phenylpyrrolidin-1-yl]pyrazin-2-yl}-1,3-dihydrospiro[indene-2,4'-piperidin]-3-amine (21.0 mg, 33% yield) as a yellow solid. LCMS (ESI$^+$) m/z: 426.1 (M+H)$^+$. $^1$HNMR (400 MHz, DMSO-d6) δ=7.80 (s, 1H), 7.37 (s, 1H), 7.33-7.25 (m, 3H), 7.21-7.14 (m, 6H), 4.94-4.92 (m, 1H), 3.54-3.47 (m, 3H), 3.46-3.43 (m, 2H), 2.98 (m, 1H), 2.91-2.78 (m, 2H), 2.56 (m, 1H), 2.44-2.31 (m, 1H), 2.00-1.88 (m, 2H), 1.82-1.60 (m, 3H), 1.45 (m, 1H), 1.07 (m, 1H).

Example 165: Synthesis of (3S)-1'-{5-[(2S)-2-phenylpyrrolidin-1-yl]pyrazin-2-yl}-1,3-dihydrospiro[indene-2,4'-piperidin]-3-amine

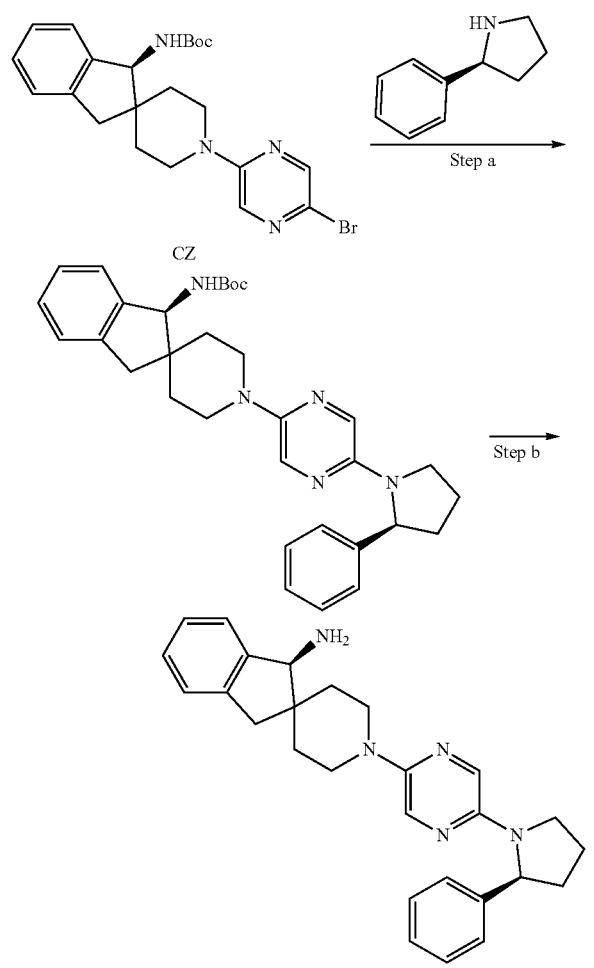

(3S)-1'-{5-[(2S)-2-phenylpyrrolidin-1-yl]pyrazin-2-yl}-1,3-dihydrospiro[indene-2,4'-piperidin]-3-amine was synthesized as described in Example 164, using (2S)-2-phenylpyrrolidine (CAS #59347-91-0) in the coupling in Step 1. Characterization data for (3S)-1'-{5-[(2S)-2-phenylpyrrolidin-1-yl]pyrazin-2-yl}-1,3-dihydrospiro[indene-2,4'-piperidin]-3-amine: LCMS (ESI$^+$) m/z: 426.3 (M+H)$^+$; $^1$HNMR (400 MHz, CD$_3$CN) δ=7.68 (m, 1H), 7.38 (m, 1H), 7.32-7.26 (m, 3H), 7.25-7.14 (m, 6H), 4.93 (m, 1H), 3.86 (s, 1H), 3.85-3.69 (m, 3H), 3.59-3.48 (m, 1H), 3.01 (m, 1H), 2.98-2.84 (m, 2H), 2.41-2.40 (m, 1H), 2.48-2.36 (m, 1H), 2.04-1.96 (m, 2H), 1.88-1.76 (m, 2H), 1.68 (m, 1H), 1.49 (m, 1H), 1.21-1.11 (m, 1H).

Example 166: Synthesis of (S)-1'-(5-((R)-2-phenylpiperidin-1-yl)pyrazin-2-yl)-1,3-dihydrospiro[indene-2,4'-piperidin]-1-amine

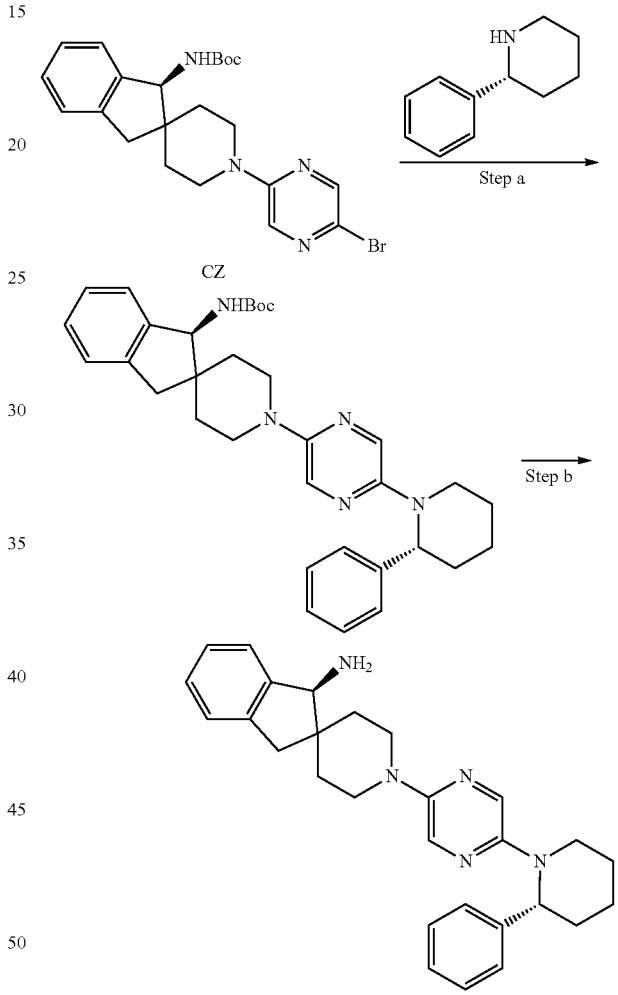

(S)-1'-(5-((R)-2-phenylpiperidin-1-yl)pyrazin-2-yl)-1,3-dihydrospiro[indene-2,4'-piperidin]-1-amine was synthesized as described in Example 164, using (2R)-2-phenylpiperidine (CAS #58613-54-0), in the coupling in Step 1. Characterization data for (S)-1'-(5-((R)-2-phenylpiperidin-1-yl)pyrazin-2-yl)-1,3-dihydrospiro[indene-2,4'-piperidin]-1-amine: LCMS (ESI$^+$) m/z: 440.2 (M+H)$^+$; $^1$HNMR (400 MHz, CD3CN) δ=7.79 (s, 1H), 7.69 (s, 1H), 7.35-7.24 (m, 5H), 7.19 (s, 4H), 5.10-4.98 (m, 1H), 3.94-3.79 (m, 3H), 3.74-3.63 (m, 1H), 3.34 (m, 1H), 3.09-2.93 (m, 3H), 2.65 (m, 1H), 2.07-2.01 (m, 2H), 1.85-1.69 (m, 4H), 1.62-1.50 (m, 3H), 1.21 (m, 1H).

Example 167: Synthesis of of (3S)-1'-[3-(3,6-dihydro-2H-pyran-4-yl)-5-methyl-1H-pyrazolo[3,4-b]pyrazin-6-yl]-1,3-dihydrospiro[indene-2,4'-piperidin]-3-amine

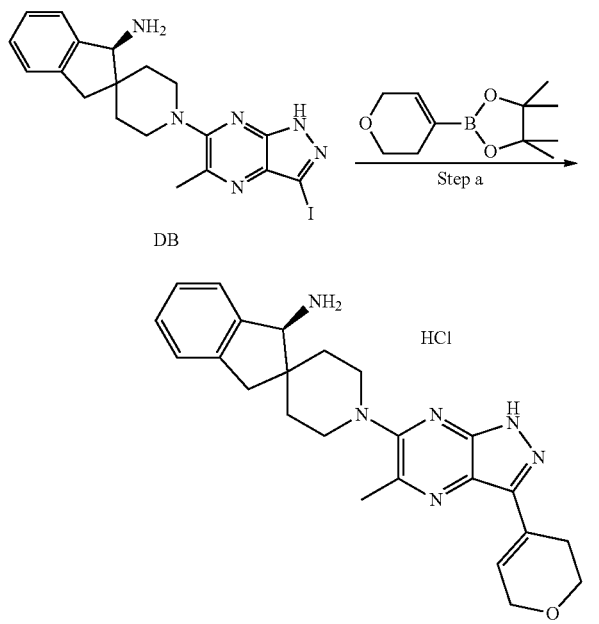

Step a: (3S)-1'-{3-iodo-5-methyl-1H-pyrazolo[3,4-b]pyrazin-6-yl}-1,3-dihydrospiro[indene-2,4'-piperidin]-3-amine (60.0 mg, 130 μmol, Intermediate DB), 2-(3,6-dihydro-2H-pyran-4-yl)-4,4,5,5-tetramethyl-1,3,2-dioxaborolane (32.5 mg, 155.0 μmol), Pd(dppf)Cl$_2$ (9.5 mg, 13.0 μmol) and Cs$_2$CO$_3$ (84.7 mg, 260.0 μmol) were placed into the solvent of dioxane (15 mL) and H$_2$O (1.5 mL). The reaction mixture was evacuated and refilled for 3 times using N$_2$. The reaction mixture was stirred at 90° C. for 12 hours. The reaction mixture was concentrated and H$_2$O (20 mL) was added, then the mixture was extracted with ethyl acetate (20 mL×3). The combined organic layers were washed with brine (50 mL), dried over anhydrous Na$_2$SO$_4$, filtered and concentrated to give a residue. The residue was purified by prep-HPLC (HCl) to afford (3S)-1'-[3-(3,6-dihydro-2H-pyran-4-yl)-5-methyl-1H-pyrazolo[3,4-b]pyrazin-6-yl]-1,3-dihydrospiro[indene-2,4'-piperidin]-3-amine (5.0 mg, 9.2% yield, HCl salt) as a yellow solid. LCMS (ESI$^+$) m/z: 417.1 (M+H)$^+$; $^1$HNMR (400 MHz, CD$_3$OD): δ 7.53~7.56 (m, 1H), 7.30~7.44 (m, 4H), 4.47 (s, 1H), 4.40~4.42 (m, 2H), 3.97~4.00 (m, 2H), 3.63-3.76 (m, 2H), 2.69-2.73 (m, 2H), 2.68 (s, 3H), 1.95-2.63 (m, 2H), 1.81~1.86 (m, 1H), 1.69~1.73 (m, 1H).

Example 168: Synthesis of (3S)-1'-[5-(cyclopentylsulfanyl)pyrazin-2-yl]-1,3-dihydrospiro[indene-2,4'-piperidin]-3-amine

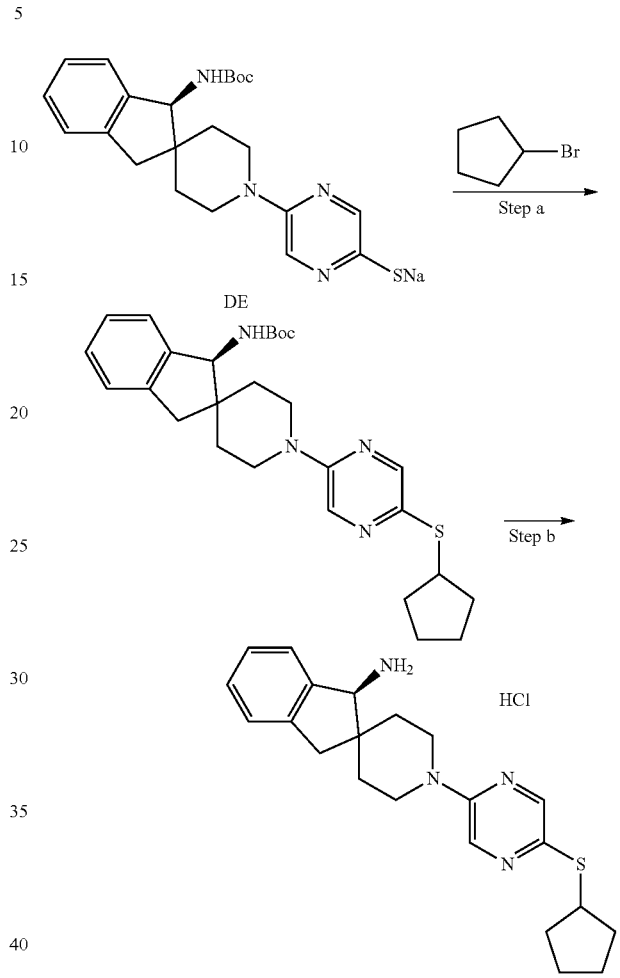

Step a: To the reaction mixture of bromocyclopentane (163.0 mg, 1.1 mmol, CAS #137-43-9) and TEA (228 μL, 1.7 mmol) in DMF (2 mL) was added tert-butyl N-[(3S)-1'-[5-(sodiosulfanyl)pyrazin-2-yl]-1,3-dihydrospiro[indene-2,4'-piperidin]-3-yl]carbamate (120.0 mg, 0.3 mmol, Intermediate DE). The reaction mixture was stirred at 25° C. for 1 hour. The combined reaction mixture was quenched with water (20 mL), then extracted with EtOAc (50 mL×2). The organic layers were washed with water (50 mL×2), dried over anhydrous Na$_2$SO$_4$, filtered and concentrated. The residue was purified by prep-TLC (Petroleum ether/EtOAc=4/1) to give tert-butyl N-[(3S)-1'-[5-(cyclopentylsulfanyl)pyrazin-2-yl]-1,3-dihydrospiro[indene-2,4'-piperidin]-3-yl]carbamate (55.0 mg, 33% yield) as a white solid. LCMS (ESI$^+$) m/z: 481.0 (M+H)$^+$.

Step b: The mixture of tert-butyl N-[(3S)-1'-[5-(cyclopentylsulfanyl)pyrazin-2-yl]-1,3-dihydrospiro[indene-2,4'-piperidin]-3-yl]carbamate (50.0 mg, 0.1 mmol) in HCl/MeOH (2 mL, 4 M) was stirred at 25° C. for 0.5 hour. The combined reaction mixture was concentrated to give a residue. The residue was purified by prep-HPLC (HCl condition) to give (3S)-1'-[5-(cyclopentylsulfanyl)pyrazin-2-yl]-1,3-dihydrospiro[indene-2,4'-piperidin]-3-amine hydrochloride (28.6 mg, 75% yield) as a yellow solid. LCMS (ESI$^+$) m/z:

381.0 (M+H)⁺; ¹H NMR (400 MHz, CD₃OD) δ 8.26 (s, 1H), 8.17 (s, 1H), 7.51 (d, J=7.6 Hz, 1H), 7.41-7.33 (m, 3H), 4.40 (s, 1H), 4.33 (d, J=14 Hz, 1H), 4.19 (d, J=14.4 Hz, 1H), 3.76-3.73 (m, 1H), 3.38-3.33 (m, 2H), 3.19 (s, 2H), 2.05-1.62 (m, 12H).

Example 169: Synthesis of (3S)-1'-{imidazo[1,2-a]pyrazin-6-yl}-1,3-dihydrospiro[indene-2,4'-piperidin]-3-amine

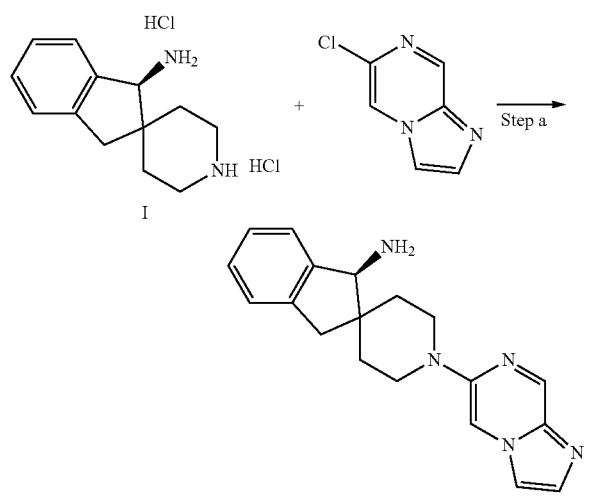

Step a: (3S)-1,3-Dihydrospiro[indene-2,4'-piperidin]-3-amine dihydrochloride (240.0 mg, 872 μmol, Intermediate I) was dissolved in MeOH (2.00 mL). The mixture was then adjusted to pH=9-10 with solid Na₂CO₃, then the mixture was filtered. Next, 6-chloroimidazo[1,2-a]pyrazine (121.0 mg, 792 μmol, CAS #76537-23-0) was added into the filtrate. The mixture was concentrated to give a residue. NMP (2 drops) was added to the residue, then the mixture was stirred at 150° C. for 2 h. On completion, the mixture was cooled to rt and was purified by prep-HPLC (NH₃.H₂O) to afford (3S)-1'-{imidazo[1,2-a]pyrazin-6-yl}-1,3-dihydrospiro[indene-2,4'-piperidin]-3-amine (27.2 mg, 11% yield) as a gray solid. LCMS (ESI⁺) m/z: 320.1 (M+H)⁺; ¹HNMR (400 MHz, Methanol-d4) δ=8.77 (m, 1H), 7.94-7.84 (m, 2H), 7.69 (m, 1H), 7.47-7.36 (m, 1H), 7.23-7.16 (m, 3H), 3.99 (s, 1H), 3.93-3.83 (m, 2H), 3.15-3.11 (m, 4H), 2.79 (m, 1H), 2.10-1.83 (m, 2H), 1.65 (m, 1H), 1.56-1.46 (m, 1H).

Example 170: Synthesis of (3S)-1'-[5-(ethylsulfanyl)pyrazin-2-yl]-1,3-dihydrospiro[indene-2,4'-piperidin]-3-amine

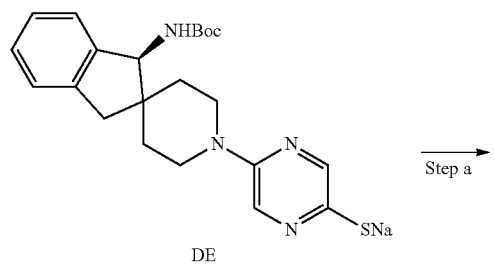

DE

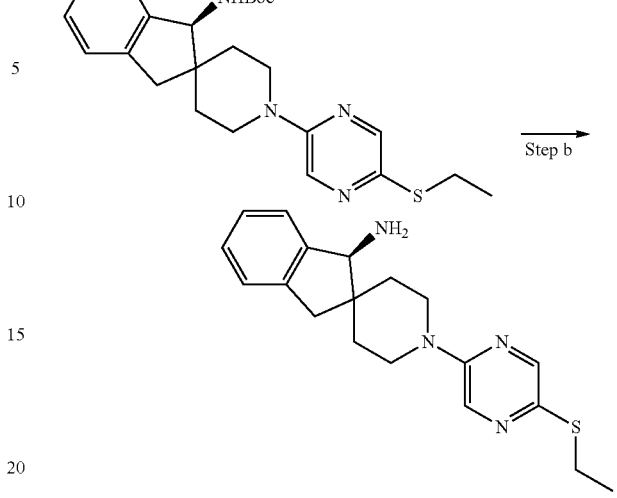

Step a: To the reaction mixture of iodoethane (179.0 mg, 1.2 mmol) and TEA (190 μL, 1.4 mmol) in DMF (2 mL) was added tert-butyl N-[(3S)-1'-[5-(sodiosulfanyl)pyrazin-2-yl]-1,3-dihydrospiro[indene-2,4'-piperidin]-3-yl]carbamate (100.0 mg, 0.2 mmol, Intermediate DE). The reaction mixture was stirred at 25° C. for 0.5 hour. The combined reaction mixture was quenched with water (20 mL), then extracted with EtOAc (50 mL×2). The organic layers were washed with water (50 mL×2), dried over anhydrous Na₂SO₄, filtered and concentrated. The residue was purified by prep-TLC (petroleum ether/EtOAc=4/1) to afford tert-butyl N-[(3S)-1'-[5-(ethylsulfanyl)pyrazin-2-yl]-1,3-dihydrospiro[indene-2,4'-piperidin]-3-yl]carbamate (76.0 mg) as a light yellow solid. LCMS (ESI⁺) m/z: 441.1 (M+H)⁺.

Step b: The mixture of tert-butyl N-[(3S)-1'-[5-(ethylsulfanyl)pyrazin-2-yl]-1,3-dihydrospiro[indene-2,4'-piperidin]-3-yl]carbamate (76.0 mg, 0.172 mmol) in HCl/MeOH (2 mL, 4 M) was stirred at 25° C. for 0.5 hour. The reaction mixture was then concentrated to give a residue. The residue was purified by prep-HPLC (neutral condition) to give (3S)-1'-[5-(ethylsulfanyl)pyrazin-2-yl]-1,3-dihydrospiro[indene-2,4'-piperidin]-3-amine (16.0 mg, 27% yield) as a yellow oil. LCMS (ESI⁺) m/z: 340.9 (M+H)⁺; ¹HNMR (400 MHz, CD₃OD) δ 8.15 (s, 1H), 8.05 (s, 1H), 7.38-7.35 (m, 1H), 7.21-7.18 (m, 3H), 4.19-4.13 (m, 2H), 3.94 (s, 1H), 3.23-3.11 (m, 3H), 2.98 (q, J=7.2 Hz, 2H), 2.78 (d, J=15.6 Hz, 1H), 1.85-1.76 (m, 2H), 1.60-1.44 (m, 2H), 1.26 (t, J=7.2 Hz, 3H).

Example 171: Synthesis of (3S)-1'-[5-(cyclopropylmethoxy)pyrazin-2-yl]-1,3-dihydrospiro[indene-2,4'-piperidin]-3-amine

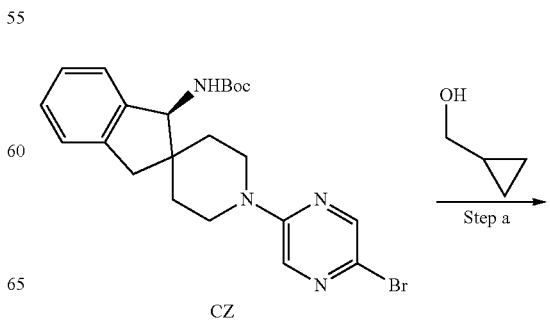

CZ

-continued

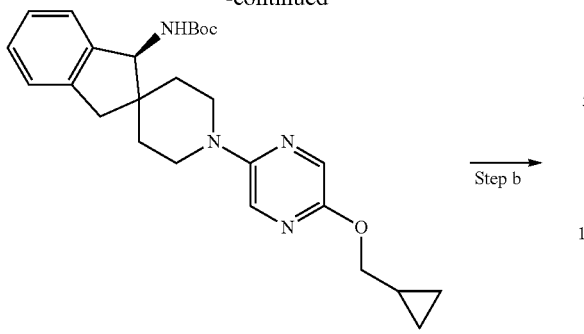

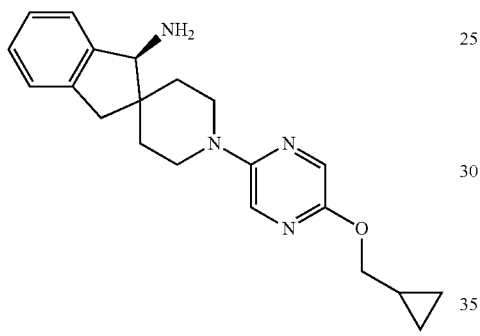

Step a: The mixture of tert-butyl N-[(3S)-1'-(5-bromopyrazin-2-yl)-1,3-dihydrospiro[indene-2,4'-piperidin]-3-yl]carbamate (200.0 mg, 0.4 mmol, Intermediate CZ), Cs$_2$CO$_3$ (285.0 mg, 0.9 mmol), CuI (8.3 mg, 0.04 mmol) and Me$_4$-Phenanthroline (20.5 mg, 0.09 mmol, CAS #1660-93-1) in cyclopropylmethanol (3 mL) was bubbled with N$_2$ for 5 min; then stirred under microwave irradiation at 100° C. for 8 hours. The reaction mixture was then diluted with H$_2$O (20 mL), and extracted with EtOAc (30 mL×2). The organic layers were dried over anhydrous Na$_2$SO$_4$, filtered and concentrated. The residue was purified by flash silica gel chromatography (12 g column, EtOAc in petroleum ether from 0% 15%) to give tert-butyl N-[(3S)-1'-[5-(cyclopropylmethoxy)pyrazin-2-yl]-1,3-dihydrospiro[indene-2,4'-piperidin]-3-yl]carbamate (148.0 mg, 75% yield) as a yellow oil.

Step b: To the reaction mixture of tert-butyl N-[(3S)-1'-[5-(cyclopropylmethoxy)pyrazin-2-yl]-1,3-dihydrospiro[indene-2,4'-piperidin]-3-yl]carbamate (90.0 mg, 0.2 mmol) in DCM (4 mL) was added TFA (0.4 mL). The reaction mixture was stirred at 25° C. for 1 hour. The reaction mixture was then adjusted to pH=8-9 with solid Na$_2$CO$_3$, and filtered. The filtrate was concentrated to give a residue which was purified by prep-HPLC (basic condition) to give (3S)-1'-[5-(cyclopropylmethoxy)pyrazin-2-yl]-1,3-dihydrospiro[indene-2,4'-piperidin]-3-amine (17.8 mg, 25% yield) as a yellow oil. LCMS (ESI$^+$) m/z: 351.1 (M+H)$^+$; $^1$H NMR (400 MHz, CDCl$_3$) δ 7.91 (s, 1H), 7.65 (s, 1H), 7.34 (d, J=5.2 Hz, 1H), 7.24-7.21 (m, 3H), 4.06 (d, J=6.8 Hz, 2H), 4.00 (s, 1H), 3.94-3.89 (m, 2H), 3.12-3.03 (m, 3H), 2.71 (d, J=16.0 Hz, 1H), 1.90-1.80 (m, 2H), 1.61-1.60 (m, 1H), 1.41-1.26 (m, 2H), 0.64-0.60 (m, 2H), 0.37-0.34 (m, 2H).

Examples 172, 173, 174, 175 Syntheses of (1S, 1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine (172), (1R, 1'S)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine (173), (1R, 1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine (174), and (1S,1'S)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine (175)

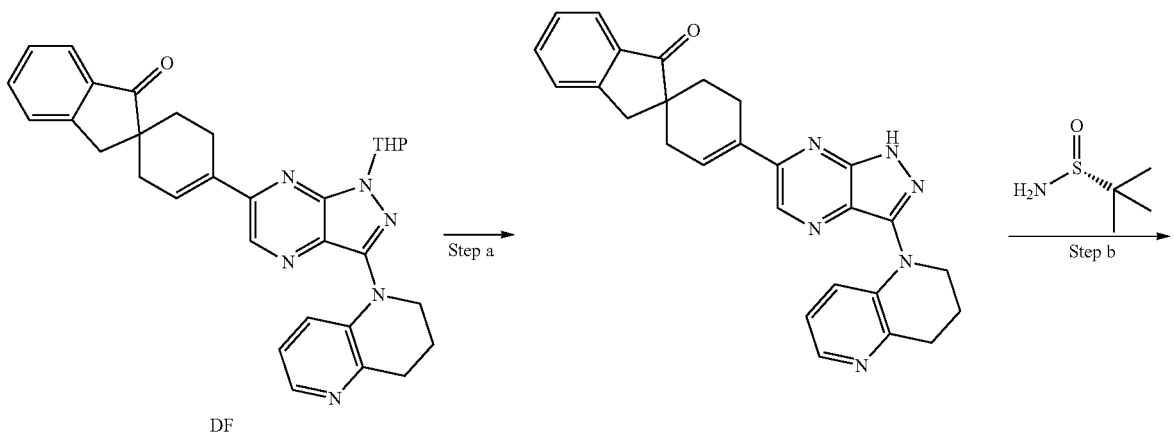

591 592
-continued
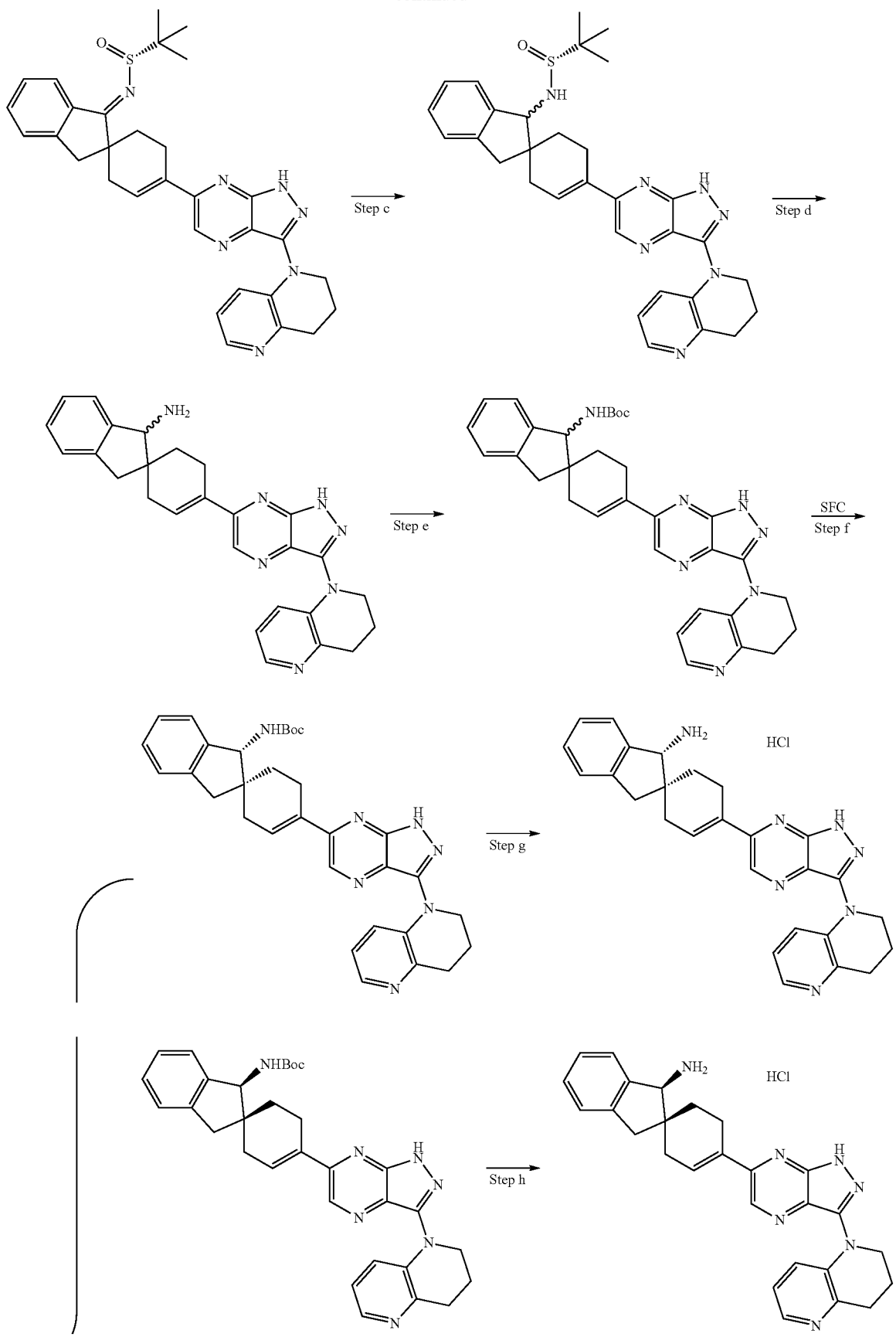

-continued

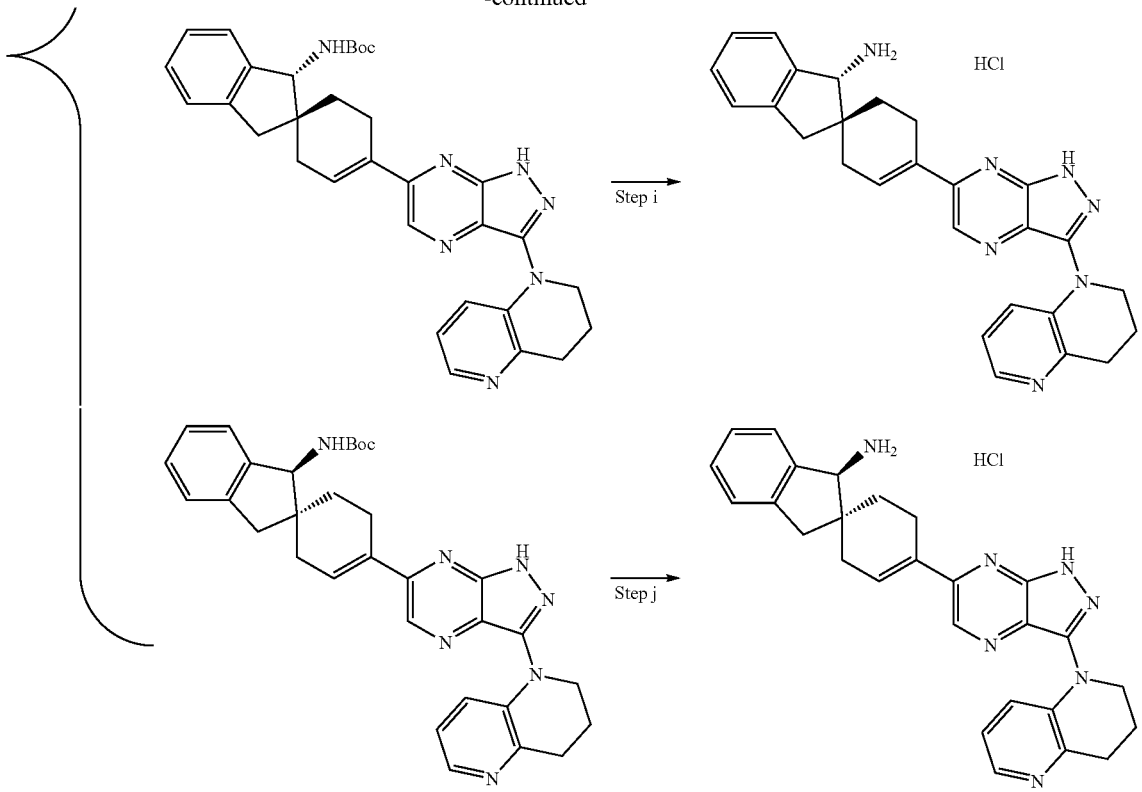

Step a: 4-[1-(Oxan-2-yl)-3-(1,2,3,4-tetrahydro-1,5-naphthyridin-1-yl)-1H-pyrazolo[3,4-b]pyrazin-6-yl]-1 (580.0 mg, 1.1 mmol, Intermediate DF) was added into HCl/MeOH (15.00 mL, 4 M). The mixture was stirred at 25° C. for 1 hour. The mixture was then concentrated to give a residue. The residue was triturated with EtOAC:MeOH=10:1, where a yellow solid was formed, which was collected by filtration. The solid was then dissolved in MeOH (25 mL) and the mixture was adjusted to pH=9-10 with TEA. The mixture was concentrated to give 4-[3-(1,2,3,4-tetrahydro-1,5-naphthyridin-1-yl)-1H-pyrazolo[3,4-b]pyrazin-6-yl]-1 (450.0 mg, 93% crude yield) as a yellow solid. LCMS (ESI+) m/z: 449.0 (M+H)+.

Step b: To a solution of 4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3-en-3'-one (250.0 mg, 557 μmol) and Ti(OEt)$_4$ (1.14 mL, 5.6 mmol) in 2-Me-THF (3.00 mL) was added (R)-2-methylpropane-2-sulfinamide (269.0 mg, 2.2 mmol). The reaction mixture was stirred at 95° C. for 72 hours under N$_2$. The mixture was then diluted with EtOAc (100 mL) and H$_2$O (20 mL) was added, where white solid formed. The mixture was filtered and the partitioned layers of the filtrate were separated. The aqueous phase was extracted with ethyl acetate (50 mL×2). The combined organic layers were washed with H$_2$O (100 mL), brine (100 mL), dried over anhydrous Na$_2$SO$_4$, filtered and concentrated to give (R)-2-methyl-N-{4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3-en-3'-ylidene}propane-2-sulfinamide (300.0 mg, 98% crude yield) as a yellow oil. LCMS (ESI+) m/z: 552.1 (M+H)+.

Step c: (R)-2-methyl-N-{4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3-en-3'-ylidene}propane-2-sulfinamide (300.0 mg, 543 μmol) was dissolved in 2-Me-THF (10.00 mL). Then NaBH$_4$ (40.8 mg, 1.1 mmol) was added at −20° C. and the mixture was allowed to warm to 25° C. and stirred for 2 hours. The reaction was quenched with H$_2$O (5 mL), then the mixture was extracted with ethyl acetate (10 mL×3). The combined organic layers were washed with brine (30 mL), dried over anhydrous Na$_2$SO$_4$, filtered and concentrated to give (R)—N-(4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)-2-methylpropane-2-sulfinamide (300 mg, 100% yield, crude) as a yellow oil. LCMS (ESI+) m/z: 554.1 (M+H)+.

Step d: (R)—N-(4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)-2-methylpropane-2-sulfinamide (300.0 mg, 541 μmol) was added into HCl/MeOH (5 mL, 4M). The mixture was stirred at 25° C. for 0.5 hour. Then the mixture was concentrated to give a residue which was next dissolved in MeOH (5 mL). The mixture was adjusted to pH=9-10 with TEA. The mixture was then concentrated to give 4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine (243 mg, 100% yield, crude) as a yellow solid. LCMS (ESI+) m/z: 450.0 (M+H)+.

Step e: 4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine (243.0 mg, 540 μmol) and TEA (149 μL, 1.08 mmol) were dissolved in DCM (13 ml). Then (Boc)$_2$O (135 μL, 594 μmol) in DCM (2 mL) was added and the mixture was stirred at 25° C. for 2 hours. The mixture was then washed with H$_2$O (10 mL×2), brine (10 mL), dried over anhydrous Na$_2$SO$_4$, filtered and concentrated to give a residue. The residue was purified by pre-HPLC (petroleum ether: ethyl acetate=1:2) to afford tert-butyl (4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (105 mg, 35% yield) as a yellow solid LCMS (ESI+) m/z: 550.1 (M+H)+.

Step f: Tert-butyl (4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (105.0 mg, 191 μmol) was separated by Chiral-SFC (DAICEL CHIRALPAK AD (250 mm×30 mm, 10 u m), mobile phase: 40% of IPA (0.1% NH$_3$H$_2$O) in CO$_2$. Flow rate: 80 mL/min.) to afford tert-butyl ((1R,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate and tert-butyl ((1S,1'S)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate, as well as a mixture of tert-butyl ((1R,1'S)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-3-en-1'-yl)carbamate and tert-butyl ((1S,1'R)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-3-en-1'-yl)carbamate. Absolute stereochemical configuration was assigned randomly for all four isomers.

tert-butyl ((1R,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (12 mg) was further purified by by Chiral-SFC (Column: DAICEL CHIRALPAK AD (250 mm×30 mm, 10 um). Mobile phase: 40% of IPA (0.1% NH$_3$.H$_2$O) in CO$_2$. Flow rate: 70 mL/min.) to afford the product of tert-butyl ((1R,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (10.0 mg, 84% yield) as a yellow solid. LCMS (ESI+) m/z: 550.1 (M+H)+. The product of tert-butyl ((1S,1'S)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (32.0 mg, 31% yield) was obtained as a yellow solid. LC-MS (ESI+) m/z: 550.1 (M+H)+.

The mixture (50 mg) of tert-butyl ((1R,1'S)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-3-en-1'-yl)carbamate and tert-butyl ((1S,1'R)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-3-en-1'-yl)carbamate was separated by Chiral-SFC (Column: DAICEL CHIRALPAK IG (250 mm×30 mm, 10 um), Mobile phase: 55% of EtOH (0.1% NH$_3$.H$_2$O) in CO$_2$. Flow rate: 80 mL/min) to afford of tert-butyl ((1R,1'S)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-3-en-1'-yl)carbamate (42.0 mg, 60% yield. LCMS (ESI+) m/z: 550.1 (M+H)+) and tert-butyl ((1S,1'R)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-3-en-1'-yl)carbamate (8.0 mg, 20% yield, LC-MS (ESI+) m/z: 550.1 (M+H)+) as yellow solids.

Step g: Tert-butyl ((1S,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (10.0 mg, 18.1 μmol) was added into HCl/MeOH (5 mL, 4 M) and the mixture was stirred at 25° C. for 1 hour. The mixture was then concentrated to give a residue. The residue was lyophilized to afford (1S,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine hydrochloride (7.60 mg, HCl salt, 86% yield) as a brown solid. LCMS (ESI+) m/z: 450.1 (M+H)+; $^1$HNMR (400 MHz, CD$_3$OD): δ 8.80 (s, 1H), 7.97-8.06 (m, 2H), 7.42~7.51 (m, 2H), 7.24~7.31 (m, 3H), 6.94 (s, 1H), 4.39 (s, 1H), 4.06-4.10 (m, 2H), 3.14-3.20 (m, 2H), 2.90-3.04 (m, 2H), 2.67-2.86 m, 2H), 2.49-2.60 (m, 1H4), 2.32~2.39 (m, 1H), 2.20~2.27 (m, 2H), 1.77~1.92 (m, 2H). SFC: e.e. =99.6%, R$_R$=4.217 min. Column: Chiralpak AS-3 100×4.6 mm I.D., 3 μm. Mobile phase: A: CO$_2$. B: ethanol (0.05% DEA). Gradient: from 5% to 40% of B in 4 min and hold 40% for 2.5 min, then 5% of B for 1.5 min. Flow rate: 2.8 mL/min. Column temp: 35° C. Absolute stereochemistry was randomly assigned.

Step h: Tert-butyl ((1R,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (42 mg, 76.4 μmol) was added into HCl/MeOH (5 mL, 4 M) and the mixture was stirred at 25° C. for 1 hour. The mixture was then concentrated to give a residue. The residue was lyophilized to afford (1R,1'S)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine hydrochloride (36.4 mg, HCl salt, 98% yield) as a brown solid. LCMS (ESI+) m/z: 450.1 (M+H)+; HNMR (400 MHz, CD$_3$OD): δ 8.89 (s, 1H), 8.09~8.17 (m, 2H), 7.55~7.60 (m, 2H), 7.35~7.41 (m, 3H), 6.96 (s, 1H), 4.49 (s, 1H), 4.18~4.22 (m, 2H), 3.27~3.32 (m, 2H), 3.20~3.25 (m, 1H), 3.09~3.16 (m, 1H), 2.91~2.96 m, 1H), 2.71-2.81 (m, 1H), 2.51~2.57 (m, 1H), 2.31~2.38 (m, 3H), 1.94-2.05 (m, 2H). SFC: e.e. =99.1%, Rt=4.552 min. Column: Chiralpak AS-3 100×4.6 mm I.D., 3 μm. Mobile phase: A: CO$_2$. B: ethanol (0.05% DEA). Gradient: from 5% to 40% of B in 4 min and hold 40% for 2.5 min, then 5% of B for 1.5 min. Flow rate: 2.8 mL/min. Column temp: 35° C. Absolute stereochemistry was randomly assigned.

Step i: Tert-butyl ((1S,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (8 mg, 14.5 μmol) was added into HCl/MeOH (5 mL, 4 M) and the mixture was stirred at 25° C. for 1 hour. The mixture was then concentrated to give a residue. The residue was lyophilized to afford (1R,1'R)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine hydrochloride (6.90 mg, HCl salt, 98% yield) as a brown solid. LC-MS (ESI+) m/z: 450.1 (M+H)+; $^1$HNMR (400 MHz, CD$_3$OD): δ 8.89 (s, 1H), 8.08~8.17 (m, 2H), 7.55~7.60 (m, 2H), 7.35~7.42 (m, 3H), 6.96 (s, 1H), 4.48 (s, 1H), 4.17~4.21 (m, 2H), 3.26~3.32 (m, 2H), 3.19~3.24 (m, 1H), 3.08~3.15 (m, 1H), 2.90~2.95 m, 1H), 2.74-2.81 (m, 1H), 2.51~2.56 (m, 1H), 2.31~2.36 (m, 3H), 1.95-2.06 (m, 2H). SFC: e.e. =100.0%, Rt=4.552 min. Column: Chiralpak AS-3 100×4.6 mm I.D., 3 μm. Mobile phase: A: CO$_2$. B: ethanol (0.05% DEA). Gradient: from 5% to 40% of B in 4 min and hold 40% for 2.5 min, then 5% of B for 1.5 min. Flow rate: 2.8 mL/min. Column temp: 35° C. Absolute stereochemistry was randomly assigned.

Step j: Tert-butyl ((1S,1'S)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-yl)carbamate (32.0 mg, 58.2 μmol) was added into HCl/MeOH (5.00 mL, 4 M) and the mixture was stirred at 25° C. for 1 hour. The mixture was then concentrated to give a residue. The residue was lyophilized to afford (1S,1'S)-4-(3-(3,4-dihydro-1,5-naphthyridin-1(2H)-yl)-1H-pyrazolo[3,4-b]pyrazin-6-yl)-1',3'-dihydrospiro[cyclohex[3]ene-1,2'-inden]-1'-amine hydrochloride (26.9 mg, HCl salt, 95% yield) as a brown solid. LCMS (ESI⁺) m/z: 450.1 (M+H)⁺; ¹HNMR (400 MHz, CD₃OD): δ 8.79 (s, 1H), 7.97~8.05 (m, 2H), 7.42~7.51 (m, 2H), 7.24~7.31 (m, 3H), 6.94 (s, 1H), 4.39 (s, 1H), 4.06-4.10 (m, 2H), 3.16-3.20 (m, 2H), 2.90-3.04 (m, 2H), 2.67-2.86 m, 2H), 2.49-2.55 (m, 1H), 2.32-2.39 (m, 1H), 2.20-2.27 (m, 2H), 1.77-1.92 (m, 2H). SFC: e.e. =98.6%, $R_R$=4.217 min. Column: Chiralpak AS-3 100×4.6 mm I.D., 3 μm. Mobile phase: A: $CO_2$. B: ethanol (0.05% DEA). Gradient: from 5% to 40% of B in 4 min and hold 40% for 2.5 min, then 5% of B for 1.5 min. Flow rate: 2.8 mL/min. Column temp: 35° C. Absolute stereochemistry was randomly assigned.

Example 185: Synthesis of (S)-1'-(5-((tetrahydro-2H-pyran-4-yl)thio)pyrazin-2-yl)-1,3-dihydrospiro[indene-2,4'-piperidin]-1-amine

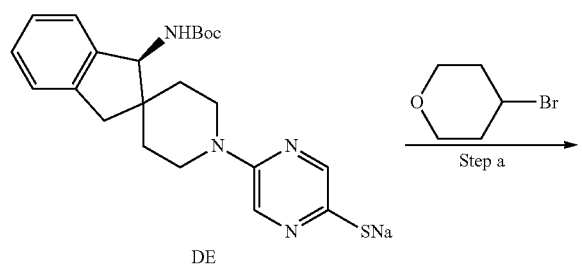

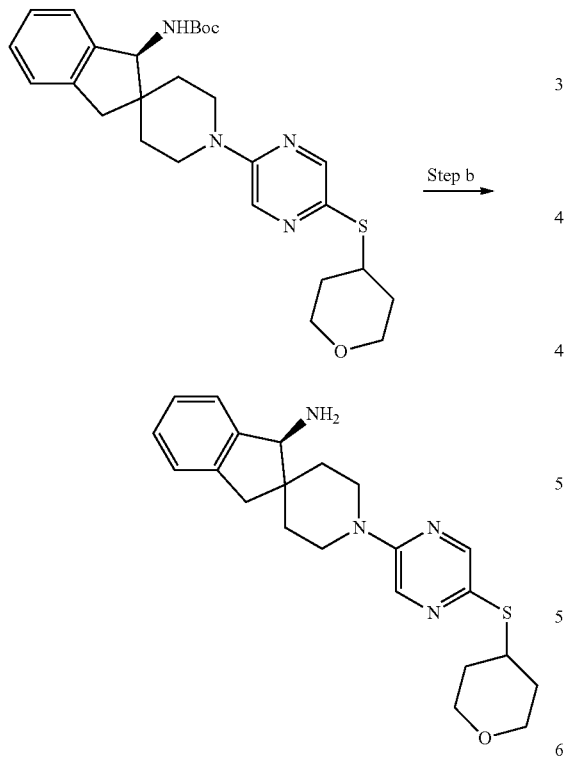

Step a: To the reaction mixture of 4-bromooxane (227.0 mg, 1.4 mmol, CAS #25637-16-5) and TEA (287 μL, 2.1 mmol) in DMF (2.00 mL) was added sodium (S)-5-(1-((tert-butoxycarbonyl)amino)-1,3-dihydrospiro[indene-2,4'-piperidin]-1'-yl)pyrazine-2-thiolate (150.0 mg, 0.3 mmol, Intermediate DE) and the reaction mixture was stirred at 25° C. for 1 hour. The combined reaction mixture was then quenched with water (20 mL), and extracted with EtOAc (50 mL×2). The organic layers were washed with water (50 mL×2), dried over anhydrous Na₂SO₄, filtered and concentrated. The residue was purified by prep-TLC (petroleum ether/EtOAc=4/1) to give (S)-tert-butyl (1'-(5-((tetrahydro-2H-pyran-4-yl)thio)pyrazin-2-yl)-1,3-dihydrospiro[indene-2,4'-piperidin]-1-yl)carbamate (28.0 mg, 20% yield) as a light yellow solid. LCMS (ESI⁺) m/z: 497.1 (M+H)⁺.

Step b: The mixture of (S)-tert-butyl (1'-(5-((tetrahydro-2H-pyran-4-yl)thio)pyrazin-2-yl)-1,3-dihydrospiro[indene-2,4'-piperidin]-1-yl)carbamate (16 mg, 0.03 mmol) in HCl/MeOH (2 mL, 4 M) was stirred at 25° C. for 0.5 hour. The reaction mixture was then concentrated to give a residue. The residue was dissolved in MeOH (5 mL), and the reaction mixture was adjusted to pH=8-9 with solid Na₂CO₃. The mixture was filtered, and the filtrate was concentrated to give a residue. The residue was purified by prep-HPLC (neutral condition) to give (S)-1'-(5-((tetrahydro-2H-pyran-4-yl)thio)pyrazin-2-yl)-1,3-dihydrospiro[indene-2,4'-piperidin]-1-amine (13.2 mg, 0.03 mmol, combined product) as a yellow solid. LCMS (ESI⁺) m/z: 397.1 (M+H)⁺; ¹H NMR (400 MHz, CD₃OD) δ 8.18 (s, 1H), 8.10 (s, 1H), 7.37-7.35 (m, 1H), 7.23-7.18 (m, 3H), 4.22-4.18 (m, 1H), 3.94-3.91 (m, 3H), 3.49-3.42 (m, 3H), 3.22-3.12 (m, 3H), 2.78 (d, J=16.0 Hz, 1H), 1.92-1.44 (m, 8H).

Example 186: Synthesis of (3S)-1'-[3-(4,4-difluoropiperidin-1-yl)-5-methyl-1H-pyrazolo[3,4-b]pyrazin-6-yl]-1,3-dihydrospiro[indene-2,4'-piperidin]-3-amine

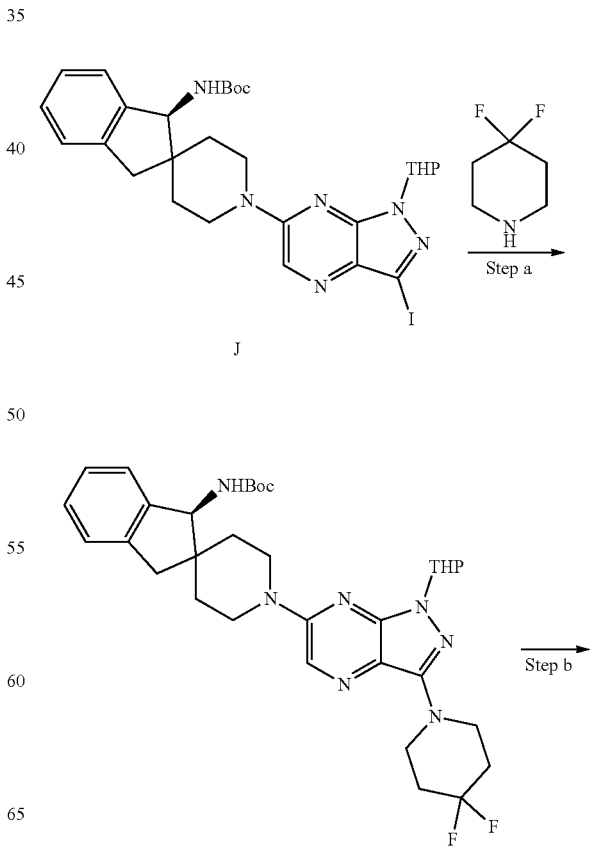

-continued

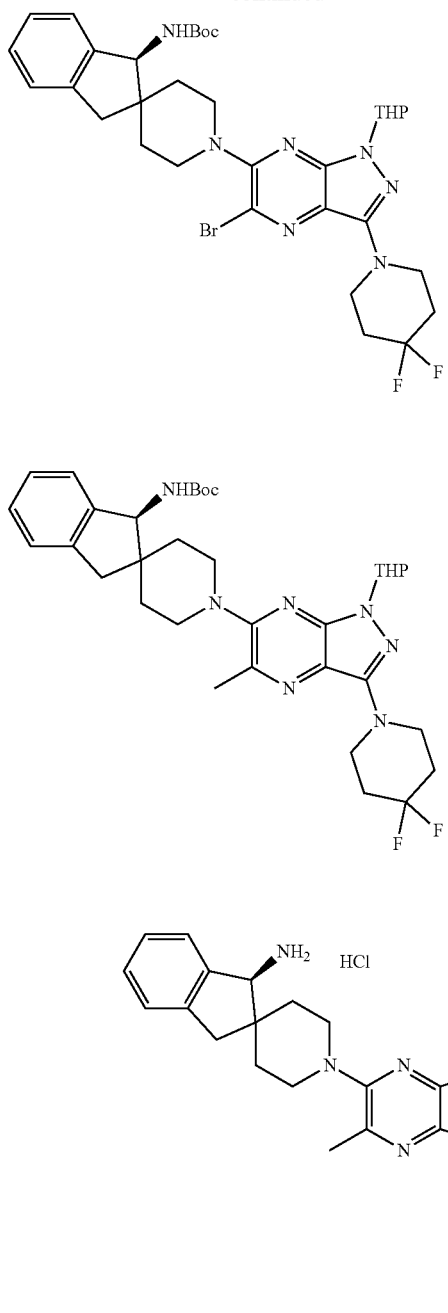

(3S)-1'-[3-(4,4-difluoropiperidin-1-yl)-5-methyl-1H-pyrazolo[3,4-b]pyrazin-6-yl]-1,3-dihydrospiro[indene-2,4'-piperidin]-3-amine was synthesized as described for Example 152, coupling tert-butyl((1S)-1'-(3-iodo-1-(tetrahydro-2H-pyran-2-yl)-1H-pyrazolo[3,4-b]pyrazin-6-yl)-1,3-dihydrospiro[indene-2,4'-piperidin]-1-yl)carbamate (Intermediate J) with 4,4-difluoropiperidine (CAS #21987-29-1) in Step a. Characterization of final compound: LCMS (ESI+) m/z: 454.1 (M+H)+; 1HNMR (400 MHz, Methanol-d4) δ 7.53 (m, 1H), 7.44-7.30 (m, 3H), 4.48-4.41 (m, 1H), 4.01-3.93 (m, 4H), 3.93-3.75 (m, 2H), 3.30-3.21 (m, 2H), 3.19 (s, 2H), 2.68-2.59 (m, 3H), 2.25-1.60 (m, 8H).

Example 187: Synthesis of (3R)-1'-{5-[(2-amino-3-chloropyridin-4-yl)oxy]pyrazin-2-yl}-3H-spiro[1-benzofuran-2,4'-piperidin]-3-amine

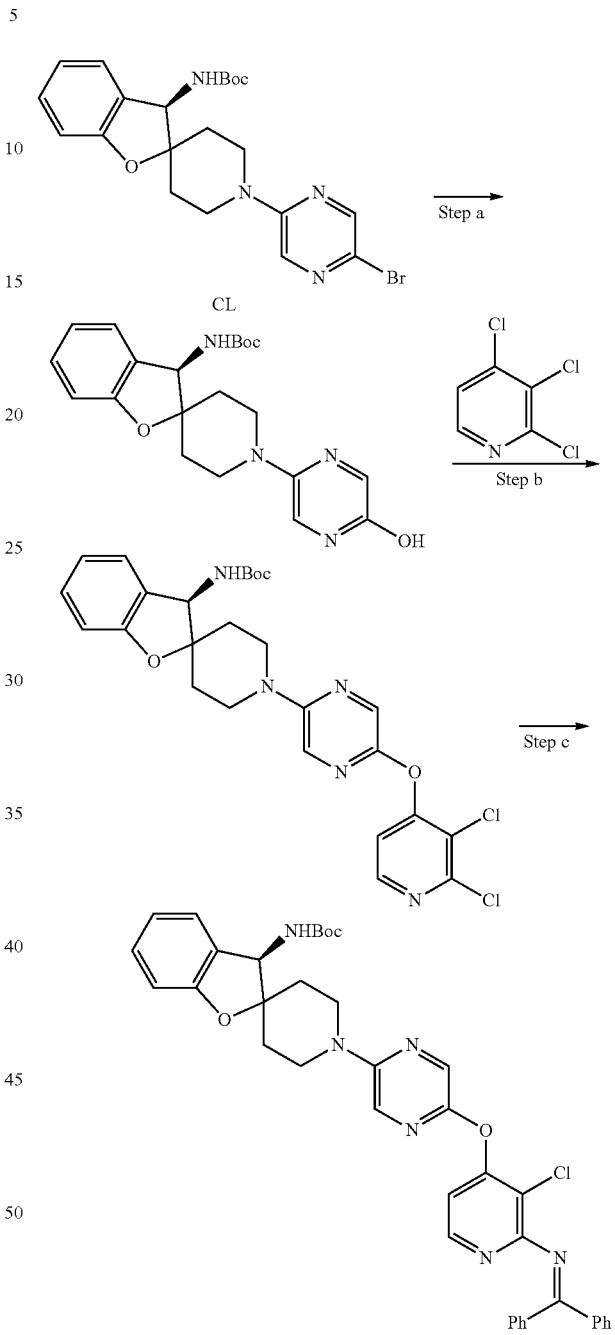

Step a: A mixture of tert-butyl N-[(3R)-1'-(5-bromopyrazin-2-yl)-3H-spiro[1-benzofuran-2,4'-piperidin]-3-yl]carbamate (680.0 mg, 1.5 mmol, Intermediate CL), KOH (247.0 mg, 4.4 mmol), t-BuXPhos (124.0 mg, 294 μmol) and Pd₂(dba)₃ (134.0 mg, 147 μmol) in 1,4-dioxane (8.0 mL) and H₂O (8.0 mL) was stirred at 100° C. for 3 hours under N₂ atmosphere. The reaction mixture was cooled to 0° C., then was acidified to pH=5 with 1 N HCl, and extracted with ethyl acetate (20 mL×3). The organic phases were washed with brine (20 mL), dried over anhydrous Na₂SO₄, filtered and concentrated in vacuo to give a residue, which was purified by silica gel chromatography (Petroleum ether in Ethyl acetate=0% to 90%) to afford tert-butyl N-[(3R)-1'-(5-hydroxypyrazin-2-yl)-3H-spiro[1-benzofuran-2,4'-piperidin]-3-yl]carbamate (210.0 mg, 36% yield) as a yellow solid. LCMS (ESI$^+$) m/z: 399.0 (M+H)$^+$.

Step b: A mixture of tert-butyl N-[(3R)-1'-(5-hydroxypyrazin-2-yl)-3H-spiro[1-benzofuran-2,4'-piperidin]-3-yl]carbamate (200.0 mg, 501 μmol), 2,3,4-trichloropyridine (109.0 mg, 601 μmol, CAS #55934-02-6) and Cs$_2$CO$_3$ (326.0 mg, 1.0 mmol) in DMF (15.0 mL) was stirred at 80° C. for 2.5 hours. The reaction mixture was diluted with ethyl acetate (30 mL), then washed with H$_2$O (20 mL×2). The organic phase was washed with brine (10 mL), dried over anhydrous Na$_2$SO$_4$, filtered and concentrated in vacuo to give a residue. The residue was purified by silica gel chromatography (ethyl acetate in petroleum ether=0% to 40%) to afford tert-butyl N-[(3R)-1'-{5-[(2,3-dichloropyridin-4-yl)oxy]pyrazin-2-yl}-3H-spiro[1-benzofuran-2,4'-piperidin]-3-yl]carbamate (150.0 mg, 55% yield) as a yellow oil. LCMS (ESI$^+$) m/z: 544.0 (M+H)$^+$.

Step c: A mixture of tert-butyl N-[(3R)-1'-{5-[(2,3-dichloropyridin-4-yl)oxy]pyrazin-2-yl}-3H-spiro[1-benzofuran-2,4'-piperidin]-3-yl]carbamate (150.0 mg, 275 μmol), diphenylmethanimine (99.6 mg, 550 μmol), BINAP (34.2 mg, 55.0 μmol), Cs$_2$CO$_3$ (179.0 mg, 550 μmol) and Pd$_2$(dba)$_3$ (25.1 mg, 27.5 μmol) in toluene (15.0 mL) was stirred at 100° C. for 12 hours under N$_2$ atmosphere. The reaction mixture was concentrated in vacuo to give a residue, which was purified by silica gel chromatography (ethyl acetate in petroleum ether=0% to 40%) to afford tert-butyl N-[(3R)-1'-[5-({3-chloro-2-[(diphenylmethylidene)amino]pyridin-4-yl}oxy)pyrazin-2-yl]-3H-spiro[1-benzofuran-2,4'-piperidin]-3-yl]carbamate (120.0 mg, 63% yield) as a yellow oil. LCMS (ESI$^+$) m/z: 689.1 (M+H)$^+$.

Step d: A mixture of tert-butyl N-[(3R)-1'-[5-({3-chloro-2-[(diphenylmethylidene)amino]pyridin-4-yl}oxy)pyrazin-2-yl]-3H-spiro[1-benzofuran-2,4'-piperidin]-3-yl]carbamate (120.0 mg, 174 μmol) in HCl/MeOH (2M, 5.0 mL) was stirred at 25° C. for 3 hours. The reaction mixture was concentrated in vacuo to give a residue, which was dissolved in MeOH (5 mL) and adjusted pH=8 with solid Na$_2$CO$_3$. The mixture was filtered and concentrated in vacuo to give a residue, which was purified by prep-HPLC (NH$_3$.H$_2$O) to afford (3R)-1'-{5-[(2-amino-3-chloropyridin-4-yl)oxy]pyrazin-2-yl}-3H-spiro[1-benzofuran-2,4'-piperidin]-3-amine (39.3 mg, 53% yield) as a white solid. LCMS (ESI$^+$) m/z: 425.1 (M+H)$^+$; $^1$HNMR (400 MHz, Methanol-d4): 8.05 (d, J=1.2 Hz, 1H), 7.96 (d, J=1.2 Hz, 1H), 7.77 (d, J=5.6 Hz, 1H), 7.40 (d, J=7.2 Hz, 1H), 7.20 (t, J=7.6 Hz, 1H), 6.92 (t, J=7.6 Hz, 1H), 6.81 (d, J=8.0 Hz, 1H), 6.22 (d, J=5.6 Hz, 1H), 4.36-4.28 (m, 1H), 4.24-4.18 (m, 1H), 4.12 (s, 1H), 3.49-3.39 (m, 2H), 2.03-1.81 (m, 4H).

Examples 188 & 189: Syntheses of (1s, 1'R, 4S)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-1'-amine and (1s,3'S,4R)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-amine

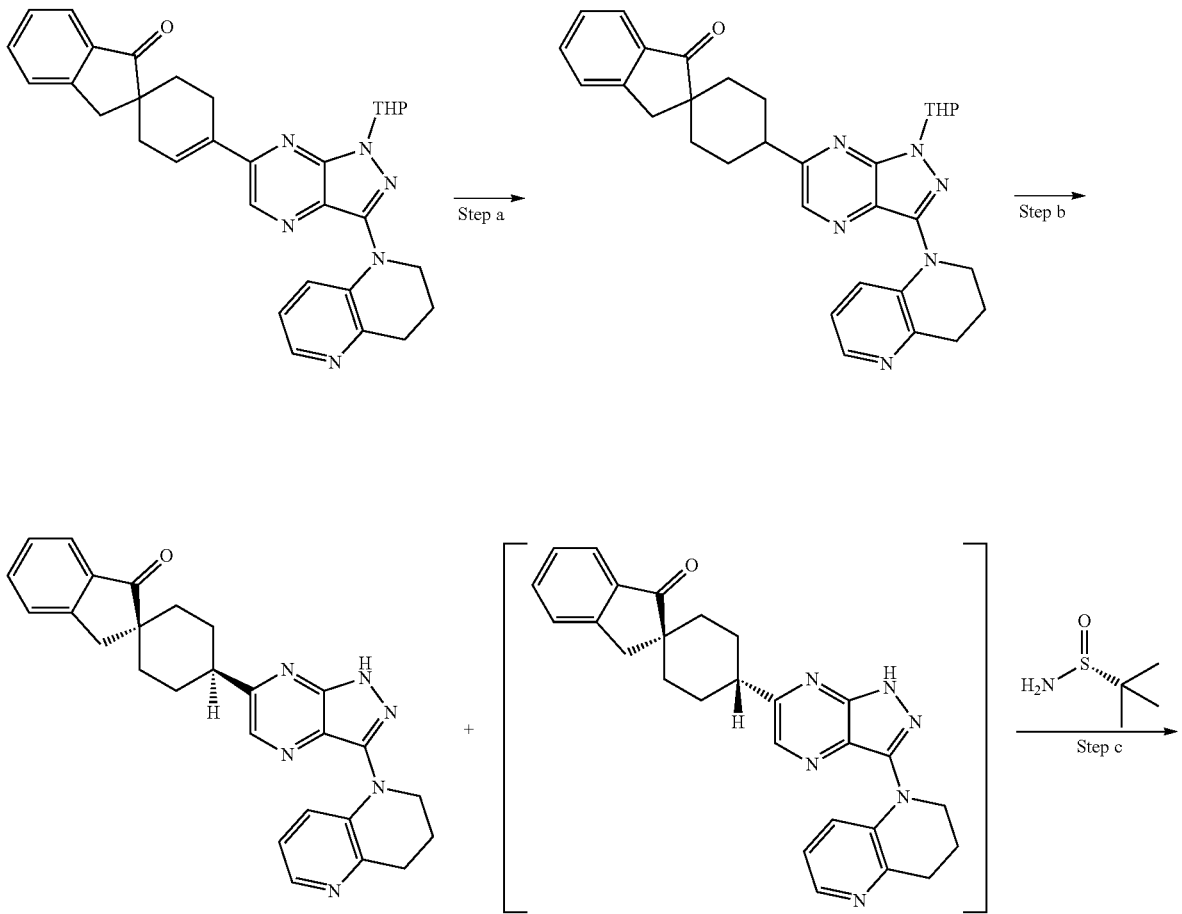

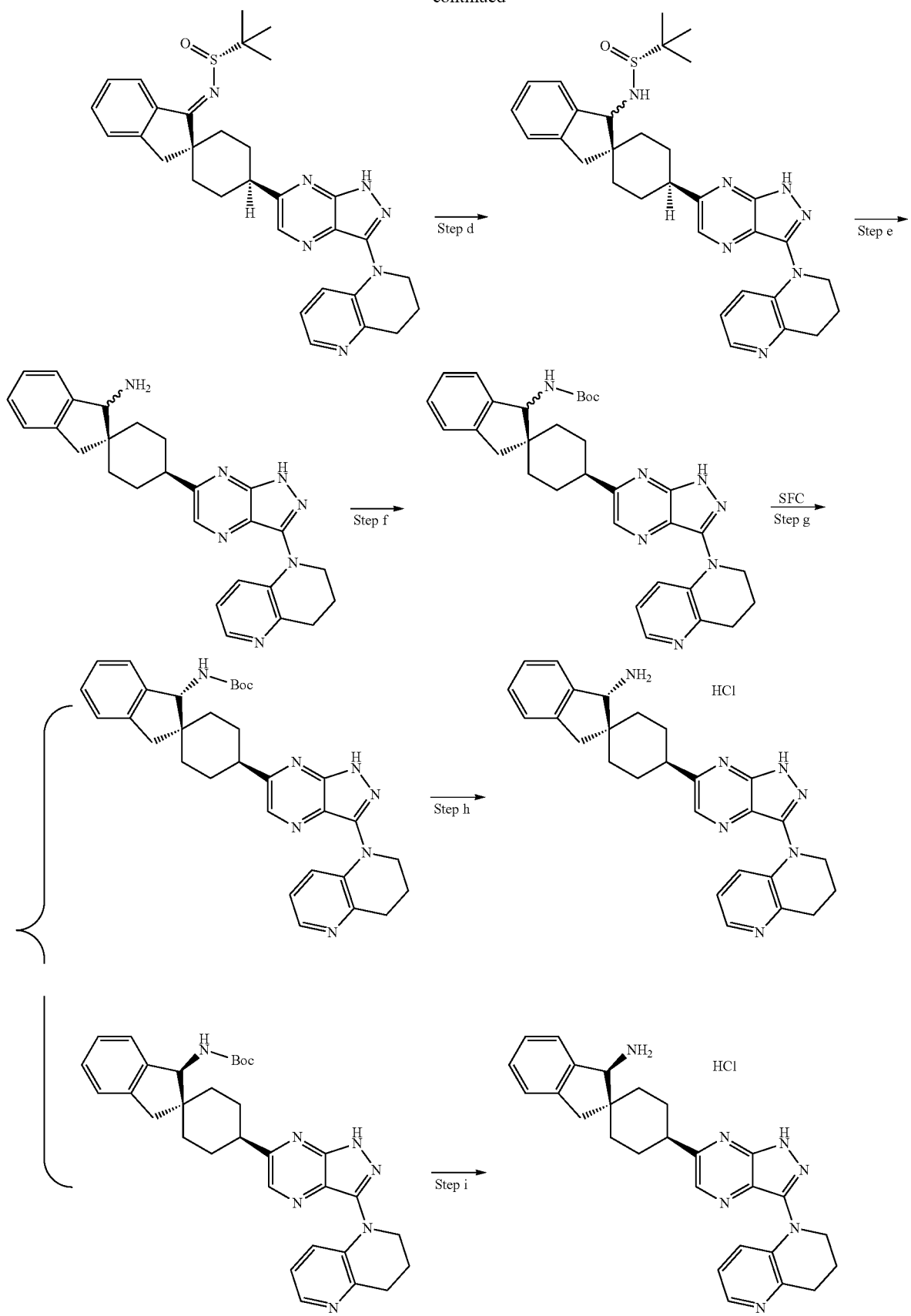

Step a: 4-[I-(Oxan-2-yl)-3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3-en-3'-one (500.0 mg, 938 µmol, Intermediate DF) was dissolved in MeOH (50 mL). Then 10% Pd/C (50 mg, wet) was added and the reaction mixture was evacuated and refilled 3 times using H2 gas. The reaction mixture was stirred at 25° C. for 72 hours under H2 (15 psi). The reaction mixture was then filtered through a pad of celite and washed with MeOH (20 mL). The filtrate was concentrated to give 4-[1-(oxan-2-yl)-3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (501 mg, 100% yield, crude) as a yellow oil. LCMS (ESI$^+$) m/z: 535.0 (M+H)$^+$.

Step b: 4-[I-(Oxan-2-yl)-3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (501.0 mg, 937 µmol) was added into HCl/MeOH (4 mL, 4M). The mixture was stirred at 25° C. for 1 h. The mixture was then concentrated and purified by prep-HPLC (HCl) to give (1s,4s)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (HCl salt) and (1r,4r)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (HCl salt). After lyophilization, (1s,4s)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (HCl salt) was dissolved in MeOH (5 mL). The mixture was adjusted to pH=9-10 with TEA and concentrated to give (1s,4s)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (free base) (50 mg, 12% yield) as a yellow solid. LCMS (ESI$^+$) m/z: 451.0 (M+H)$^+$. $^1$HNMR (400 MHz, CDCl$_3$): δ 10.57 (s, 1H), 8.46 (s, 1H), 8.01~8.03 (m, 1H), 7.66~7.68 (m, 1H), 7.58~7.62 (m, 1H), 7.50~7.55 (m, 1H), 7.28~7.37 (m, 2H), 6.90~6.93 (m, 1H), 4.08~4.12 (m, 2H), 2.97-3.07 (m, 5H), 2.47-2.57 (m, 2H), 2.12-2.19 (m, 2H), 1.99-2.03 (m, 2H), 1.84~1.89 (m, 2H), 1.60~1.68 (m, 2H), 1.50~1.54 (m, 2H). (1r,4r)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (HCl salt) was also dissolved in MeOH (5 mL). The mixture was adjusted to pH=9-10 with TEA and concentrated to give (1r,4r)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one ((80 mg, 19% yield). LCMS (ESI$^+$) m/z: 451.0 (M+H)$^+$. $^1$HNMR (400 MHz, CDCl$_3$): δ 10.27 (s, 1H), 8.39 (s, 1H), 8.02~8.04 (m, 1H), 7.72~7.75 (m, 1H), 7.61~7.64 (m, 1H), 7.53~7.58 (m, 1H), 7.38~7.41 (m, 1H), 7.31~7.35 (m, 1H), 6.90~6.94 (m, 1H), 4.10~4.13 (m, 2H), 2.98~3.10 (m, 5H), 2.12~2.18 (m, 2H), 2.02-2.07 (m, 2H), 1.82~1.98 (m, 4H), 1.55~1.7 (m, 2H).

Step c: To a solution of (1s,4s)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (80 mg, 177 µmol) and Ti(OEt)$_4$ (362 µL, 1.76 mmol, CAS #3087-36-3) in 2-Me-THF (1 mL) was added (R)-2-methylpropane-2-sulfinamide (85.8 mg, 708 µmol, CAS #196929-78-9). The reaction mixture was stirred at 95° C. for 72 h under N$_2$. The mixture was then diluted with EtOAc (30 mL) and H$_2$O (20 mL) was added, where lot of white solid formed. The mixture was filtered and the filtrate was extracted with ethyl acetate (10 mL×2). The combined organic layers were washed with H$_2$O (30 mL), brine (30 mL), dried over anhydrous Na$_2$SO$_4$, filtered and concentrated to give (R)-2-methyl-N-[((1S, 4S)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-ylidene]propane-2-sulfinamide (90.0 mg, 92% yield, crude) as a yellow oil. LCMS (ESI$^+$) m/z: 554.1 (M+H)$^+$.

Step d: (R)-2-methyl-N-[(1s, 4s)-4-[3-(1,2,3,4-tetrahydro-1,5-naphthyridin-1-yl)-1H-pyrazolo[3,4-b]pyrazin-6-yl]-1 (90.0 mg, 162 µmol) was dissolved in 2-MeTHF (10 mL). Then NaBH$_4$ (12.2 mg, 324 µmol) was added at −20° C. The mixture was then warmed to 25° C. and stirred for 2 hours. The reaction was quenched with H$_2$O (10 mL) and the mixture was extracted with ethyl acetate (20 mL×3). The combined organic layers were washed with brine (50 mL), dried over anhydrous Na$_2$SO$_4$, filtered and concentrated to give (R)—N-((1s, 4s)-4-(3-(3,4-dihydro-1,5-naphthyridin-1 (2H)-yl)-1H-pyrazolo[3,4-b]pyrazin-6-yl)-1',3'-dihydrospiro[cyclohexane-1,2'-inden]-1'-yl)-2-methylpropane-2-sulfinamide (90.0 mg, 100% yield, crude) as a yellow oil. LCMS (ESI$^+$) m/z: 578.1 (M+Na)+.

Step e: (R)—N-((1s, 4s)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-1'-yl)-2-methylpropane-2-sulfinamide (90 mg, 161 µmol) was added into HCl/MeOH (5 mL, 4M). The mixture was stirred at 25° C. for 0.5 h. The mixture was then concentrated to give a residue which was dissolved in MeOH (5 mL). The mixture was adjusted to pH=9-10 by with TEA. The mixture was then concentrated to give (s, 4s)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-1'-amine (72.0 mg, 99% yield, crude) as a yellow solid. LCMS (ESI$^+$) m/z: 452.0 (M+H)$^+$.

Step f: (Is, 4s)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-1'-amine (72 mg, 159 µmol) and TEA (43.9 µL, 318 µmol) were dissolved in DCM (8 ml). Then (Boc)$_2$O (39.8 µL, 174 µmol) in DCM (2 mL) was added. The mixture was stirred at 25° C. for 2 hours. The mixture was then washed with H$_2$O (10 mL×2), brine (10 mL), dried over anhydrous Na$_2$SO$_4$, filtered and concentrated to give a residue. The residue was purified by pre-TLC (petroleum ether:ethyl acetate=1:3) to afford tert-butyl N-[(1s, 4s)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (30.0 mg, 34% yield) as a yellow solid. LCMS (ESI$^+$) m/z: 552.1 (M+H)$^+$.

Step g: Tert-butyl N-[(1s, 4s)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (30.0 mg, 54.3 µmol) was separated by Chiral-SFC (Column: DAICEL CHIRALPAK AD (250 mm*30 mm, 10 um). Mobile phase: 45% of EtOH (0.1% NH$_3$.H$_2$O) in CO$_2$. Flow rate: 70 mL/min.) to afford tert-butyl N—[(S, 3'R, 4S)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (5.00 mg, 17% yield, Rt=2.772 min, single peak) as an off-white solid and tert-butyl N-[(1s, 3'S, 4R)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (8.00 mg, 27% yield, Rt=2.928 min, single peak) as an off-white solid. LC-MS (ESI$^+$) m/z: 552.1 (M+H)$^+$. The absolute configuration of the diastereomers was assigned arbitrarily.

Step h: Tert-butyl ((Is, 1'R, 4S)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-1'-yl)carbamate (5.0 mg, 9.06 µmol) was added into HCl/MeOH (5.00 mL, 4 M) and the mixture was stirred at 25° C. for 1 h. The mixture was then concentrated to give a residue. The residue was lyophilized to afford (1s, 1'R, 4S)-4-(3-(3,4-dihydro-1,5-naphthyridin-1(2H)-yl)-1H-pyrazolo[3,4-b]pyrazin-6-yl)-1',3'-dihydrospiro[cyclohexane-1,2'-inden]-1'-amine hydrochloride (4.0 mg, HCl salt, 90% yield) as a yellow solid. LCMS (ESI+) m/z: 452.1 (M+H)+; ¹HNMR (400 MHz, CD₃OD): δ 8.62 (s, 1H), 8.09~8.15 (m, 2H), 7.56~7.59 (m, 2H), 7.27~7.43 (m, 3H), 4.72 (s, 1H), 4.17~4.21 (m, 2H), 3.08~3.27 (m, 4H), 2.71~2.90 (m, 1H), 2.33~2.38 (m, 2H), 1.96-2.11 (m, 6H), 1.75-1.90 (m, 1H), 1.60-1.69 (m, 1H); SFC: e.e. =100%, Rt=4.576 min. Column Chiralcel OD-3 100×4.6 mm I.D., 3 um. Mobile phase: A: CO₂, B: methanol (0.05% DEA). Gradient: from 5% to 40% of B in 4.5 min and hold 40% for 2.5 min, then 5% of B for 1 min. Flow rate: 2.8 mL/min Column temperature: 40° C.

Step i: Tert-butyl N-[(1s,3'S,4R)-4-[3-(1,2,3,4-tetrahydro-1,5-naphthyridin-1-yl)-H-pyrazolo[3,4-b]pyrazin-6-yl]-1',3'-dihydrospiro[cyclohexane-1,2'-inden]-3'-yl]carbamate (8.0 mg, 14.5 μmol) was added into HCl/MeOH (5.00 mL, 4M) and the mixture was stirred at 25° C. for 1 h. The mixture was then concentrated to give a residue. The residue was lyophilized to afford (1s,3'S,4R)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-amine hydrochloride (6.50 mg, HCl salt, 92% yield) as a yellow solid. LCMS (ESI+) m/z: 452.1 (M+H)+; ¹HNMR (400 MHz, CD₃OD): δ 8.62 (s, 1H), 8.09~8.15 (m, 2H), 7.56~7.59 (m, 2H), 7.34~7.43 (m, 3H), 4.72 (s, 1H), 4.17~4.20 (m, 2H), 3.18~3.30 (m, 4H), 2.71~2.83 (m, 1H), 2.31~2.38 (m, 2H), 1.96-2.12 (m, 6H), 1.76-1.80 (m, 1H), 1.62~1.69 (m, 1H); SFC: e.e. =100%, Rt=4.375 min. Column Chiralcel OD-3 100×4.6 mm I.D., 3 um. Mobile phase: A: CO₂, B: methanol (0.05% DEA). Gradient: from 5% to 40% of B in 4.5 min and hold 40% for 2.5 min, then 5% of B for 1 min. Flow rate: 2.8 mL/min Column temperature: 40° C.

Examples 190 and 191: Syntheses of (1r, 3'R, 4R)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-amine and (1r, 3'S, 4S)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-amine

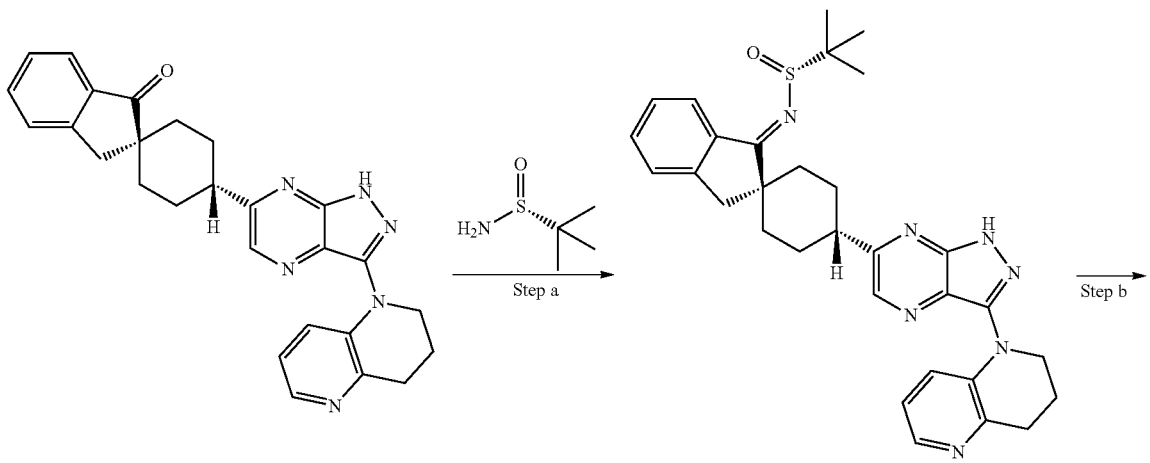

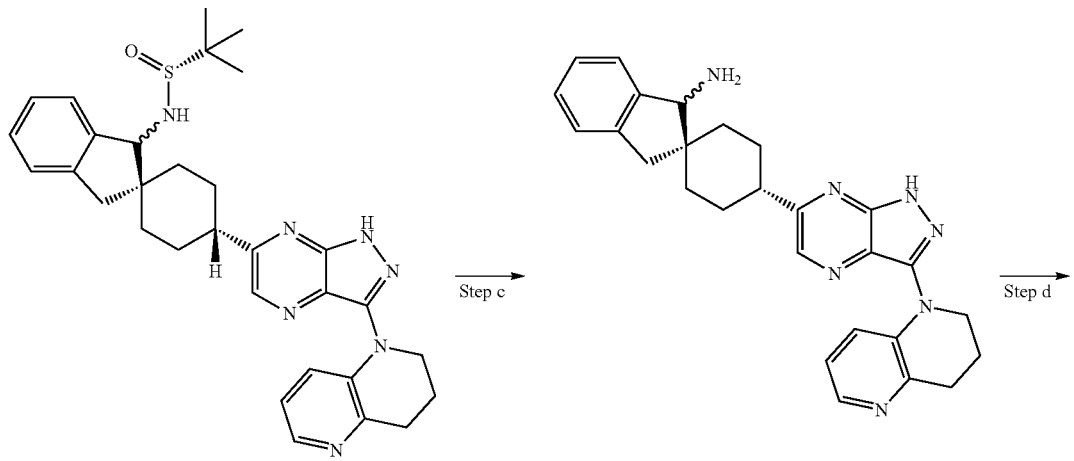

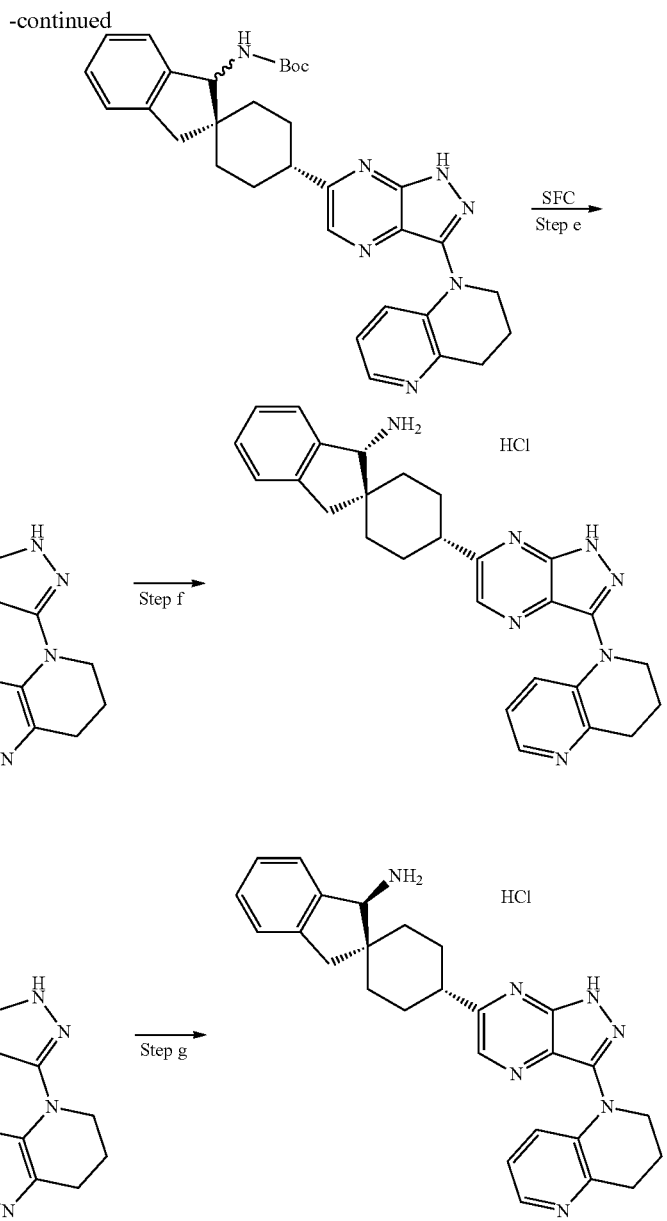

(1r,4r)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-one (90 mg, 199 μmol, synthesized via Steps a and b of Examples 188-189) was brought forward to intermediate tert-butyl N-[(1r, 4r)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate via Steps a-d, which were performed in a similar fashion as described above in Steps c-f for Examples 188-189.

Step e: Tert-butyl N-[(1r, 4r)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (50.0 mg, 90.6 μmol) was separated by Chiral-SFC (Column: DAICEL CHIRALPAK AS (250 mm*50 mm, 10 um). Mobile phase: 30% of EtOH (0.1% NH$_3$.H$_2$O) in CO$_2$. Flow rate: 65 mL/min.) to afford tert-butyl N-[(1r, 3'R, 4R)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (5.00 mg, 10% yield, Rt=3.268 min) was obtained as a yellow solid (LCMS (ESI$^+$) m/z: 552.1 (M+H)+) and tert-butyl N-[(1r,3'S,4S)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (13.0 mg, 26% yield, Rt=3.400 min) as a yellow solid (LCMS (ESI$^+$) m/z: 552.1 (M+H)$^+$).)$^+$. The absolute configuration of the diastereomers was assigned arbitrarily.

Step f: Tert-butyl N-[(1r, 3'R, 4R)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (5.0 mg, 9.06 μmol) was added into HCl/MeOH (5 mL, 4M) and the mixture was stirred at 25° C. for 1 hour. The mixture was then concentrated to give a residue. The residue was lyophilized to afford (1r, 3'R, 4R)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'- amine hydrochloride (3.7 mg, HCl salt, 84% yield) as a yellow solid. LCMS (ESI⁺) m/z: 452.1 (M+H)⁺; ¹HNMR (400 MHz, CD₃OD): δ 8.58 (s, 1H), 8.09~8.15 (m, 2H), 7.58~7.60 (m, 1H), 7.51~7.54 (m, 1H), 7.35~7.42 (m, 3H), 4.38 (s, 1H), 4.17~4.20 (m, 2H), 3.05~3.32 (m, 4H), 2.31~2.38 (m, 2H), 2.09-2.15 (m, 1H), 1.96-2.06 (m, 4H), 1.77-1.86 (m, 4H); SFC: e.e. =99.1%, Rt=5.401 min. Column: Chiralpak AS-3 150×4.6 mm I.D., 3 um. Mobile phase: A: CO₂ B: ethanol (0.05% DEA). Gradient: from 5% to 40% of B in 5 min and hold 40% for 2.5 min, then 5% of B for 2.5 min. Flow rate: 2.5 mL/min. Column temp.: 35° C.

Step g: Tert-butyl N-[(1r, 3'S, 4S)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-yl]carbamate (13.0 mg, 23.5 μmol) was added into HCl/MeOH (5 mL, 4M) and the mixture was stirred at 25° C. for 1 h. The mixture was then concentrated to give a residue. The residue was lyophilized to afford (1r, 3'S, 4S)-4-[3-(1,2,3,4-tetrahydro-1,5-naphthyridin-1-yl)-1H-pyrazolo[3,4-b]pyrazin-6-yl]-1',3'-dihydrospiro[cyclohexane-1,2'-inden]-3'-amine hydrochloride (11.0 mg, HCl salt, 96% yield) as a brown solid. LCMS (ESI⁺) m/z: 452.1 (M+H)⁺; ¹HNMR (400 MHz, CD₃OD): δ 8.58 (s, 1H), 8.09~8.15 (m, 2H), 7.57~7.61 (m, 1H), 7.51~7.54 (m, 1H), 7.35~7.42 (m, 3H), 4.38 (s, 1H), 4.17~4.21 (m, 2H), 3.29~3.33 (m, 4H), 2.31~2.38 (m, 2H), 2.11~2.18 (m, 1H), 1.96~2.06 (m, 4H), 1.78~1.86 (m, 4H); SFC: e.e. =98.7%, Rt=5.817 min. Column: Chiralpak AS-3 150×4.6 mm I.D., 3 um. Mobile phase: A: CO₂ B: ethanol (0.05% DEA). Gradient: from 5% to 40% of B in 5 min and hold 40% for 2.5 min, then 5% of B for 2.5 min. Flow rate: 2.5 mL/min. Column temp.: 35° C.

Examples 192: Syntheses of (3S)-1'-[5-(quinolin-5-yl)-5H-pyrrolo[2,3-b]pyrazin-2-yl]-1,3-dihydrospiro[indene-2,4'-piperidin]-3-amine

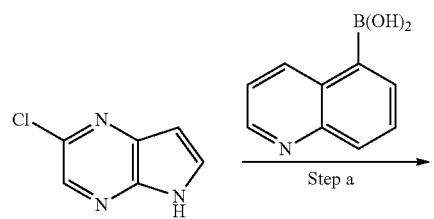

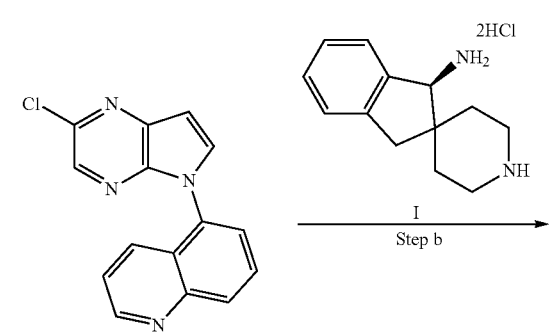

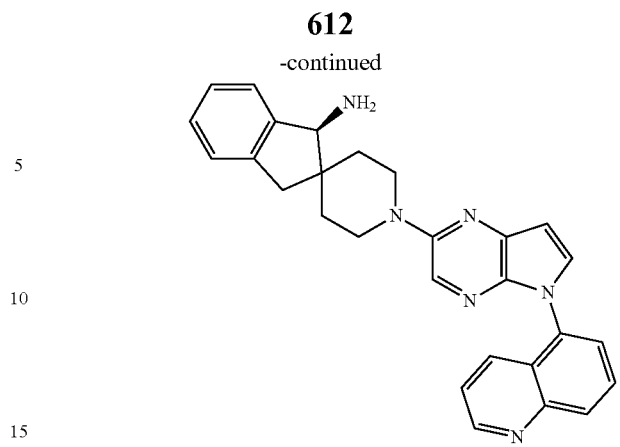

Step a: A mixture of 2-chloro-5H-pyrrolo[2,3-b]pyrazine (200.0 mg, 1.3 mmol, CAS #889447-19-2), (quinolin-5-yl)boronic acid (674.0 mg, 3.9 mmol, CAS #355386-94-6), Cu(OAc)₂ (472.0 mg, 2.6 mmol) and TEA (722 μL, 5.2 mmol) in DCM (6 mL) was stirred at 40° C. for 12 hours under O2 atmosphere. The reaction mixture was filtered and concentrated. The residue was purified by silica gel column (elution: petroleum ether:ethyl acetate=100:0~2:1) to give 5-{2-chloro-5H-pyrrolo[2,3-b]pyrazin-5-yl}quinoline (265.0 mg, 0.9 mmol, 73% yield) as an off-white solid. LC-MS (ESI⁺) m/z: 280.9 (M+H)⁺.

Step b: To a mixture of 5-{2-chloro-5H-pyrrolo[2,3-b]pyrazin-5-yl}quinoline (160.0 mg, 0.6 mmol) and (3S)-1,3-dihydrospiro[indene-2,4'-piperidin]-3-amine dihydrochloride (310.0 mg, 1.1 mmol, Intermediate I, basified by solid Na₂CO₃) was added NMP (4 drops). The mixture was stirred at 140° C. for 7 hours. The reaction mixture was purified by prep-HPLC (basic condition) to give (3S)-1'-[5-(quinolin-5-yl)-5H-pyrrolo[2,3-b]pyrazin-2-yl]-1,3-dihydrospiro[indene-2,4'-piperidin]-3-amine (32.2 mg, 0.07 mmol) as a white solid. LC-MS (ESI⁺) m/z: 447.1 (M+H)⁺; ¹HNMR (400 MHz, CD₃OD) δ 8.93 (s, 1H), 8.21-8.19 (m, 1H), 7.93-7.88 (m, 3H), 7.75-7.70 (m, 2H), 7.37-7.36 (m, 1H), 7.21-7.18 (m, 3H), 6.69 (d, J=3.6 Hz, 1H), 4.13 (d, J=12.8 Hz, 2H), 3.95 (s, 1H), 3.28-3.12 (m, 3H), 2.79 (d, J=15.6 Hz, 1H), 1.94-1.81 (m, 2H), 1.62-1.45 (m, 2H).

Example 193: Synthesis of (3S)-1'-[5-(3,6-dihydro-2H-pyran-4-yl)-3-methyl-5H-pyrrolo[2,3-b]pyrazin-2-yl]-1,3-dihydrospiro[indene-2,4'-piperidin]-3-amine

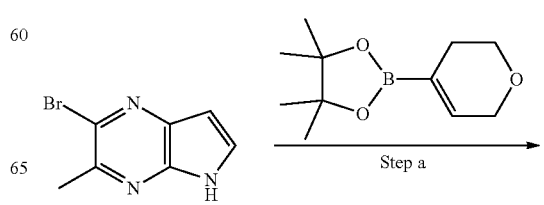

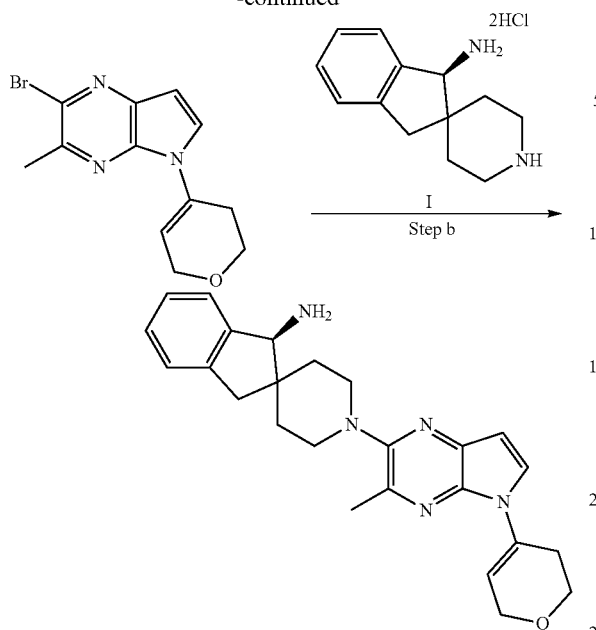

(3S)-1'-[5-(3,6-dihydro-2H-pyran-4-yl)-3-methyl-5H-pyrrolo[2,3-b]pyrazin-2-yl]-1,3-dihydrospiro[indene-2,4'-piperidin]-3-amine was synthesized as described above for Example 192, coupling 2-bromo-3-methyl-5H-pyrrolo[2,3-b]pyrazine (CAS #1260812-97-2) and 2-(3,6-dihydro-2H-pyran-4-yl)-4,4,5,5-tetramethyl-1,3,2-dioxaborolane (CAS #287944-16-5) under the same conditions as Step 1 above for 36 h. Characterization of the final product: LC-MS (ESI$^+$) m/z: 416.1 (M+H)$^+$; $^1$HNMR (400 MHz, CD$_3$OD) δ 7.64 (s, 1H), 7.40-7.38 (m, 1H), 7.23-7.19 (m, 3H), 6.53 (d, J=4.0 Hz, 1H), 6.41-6.40 (m, 1H), 4.37 (s, 2H), 4.02-4.00 (m, 3H), 3.15-3.08 (m, 3H), 2.84-2.78 (m, 3H), 2.62 (s, 3H), 2.04-1.97 (m, 2H), 1.67-1.49 (m, 2H).

Example 194: Synthesis of (3S)-1'-[3-methyl-5-(quinolin-5-yl)-5H-pyrrolo[2,3-b]pyrazin-2-yl]-1,3-dihydrospiro[indene-2,4'-piperidin]-3-amine

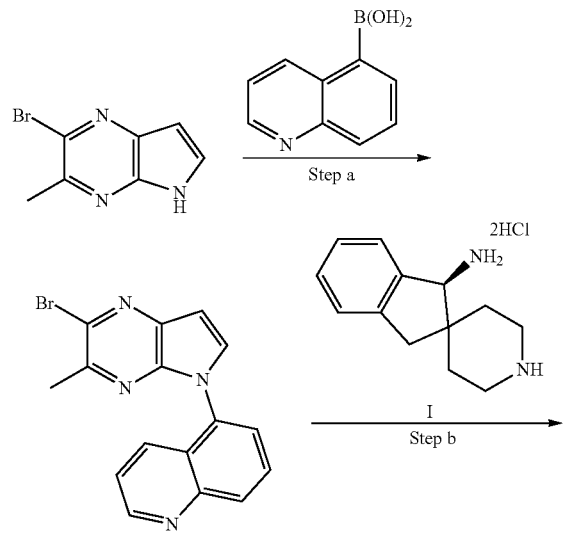

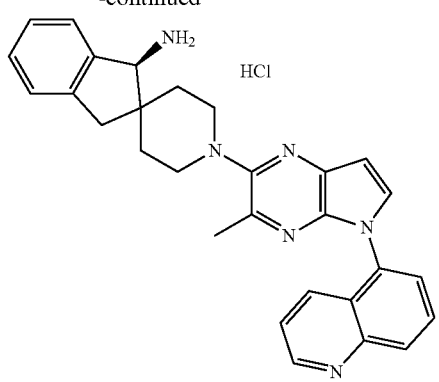

(3S)-1'-[3-methyl-5-(quinolin-5-yl)-5H-pyrrolo[2,3-b]pyrazin-2-yl]-1,3-dihydrospiro[indene-2,4'-piperidin]-3-amine was synthesized as described above for Example 192, coupling 2-bromo-3-methyl-5H-pyrrolo[2,3-b]pyrazine (CAS #1260812-97-2) and (quinolin-5-yl)boronic acid (CAS #355386-94-6) under the same conditions as Step 1 above for 36 h. Characterization of the final product: LC-MS (ESI$^+$) m/z: 461.1 (M+H)$^+$; $^1$H NMR (400 MHz, CD$_3$OD) δ 9.37 (d, J=3.6 Hz, 1H), 8.86 (d, J=6.0 Hz, 1H), 8.50-8.37 (m, 2H), 8.16-8.14 (m, 3H), 7.58 (d, J=7.2 Hz, 1H), 7.43-7.35 (m, 3H), 7.04 (s, 1H), 4.56 (s, 1H), 3.79-3.60 (m, 4H), 3.27-3.23 (m, 2H), 2.64 (s, 3H), 2.33-2.19 (m, 2H), 2.02-1.81 (m, 2H).

Example 195: Synthesis of (3S)-1'-{1-phenyl-1Hpyrazolo[3,4-d]pyrimidin-4-yl}-1,3-dihydrospiro[indene-2,4'-piperidin]-3-amine

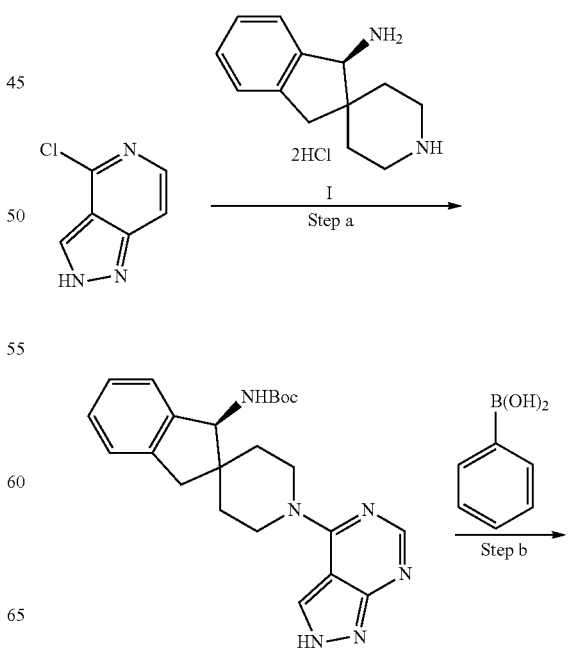

-continued

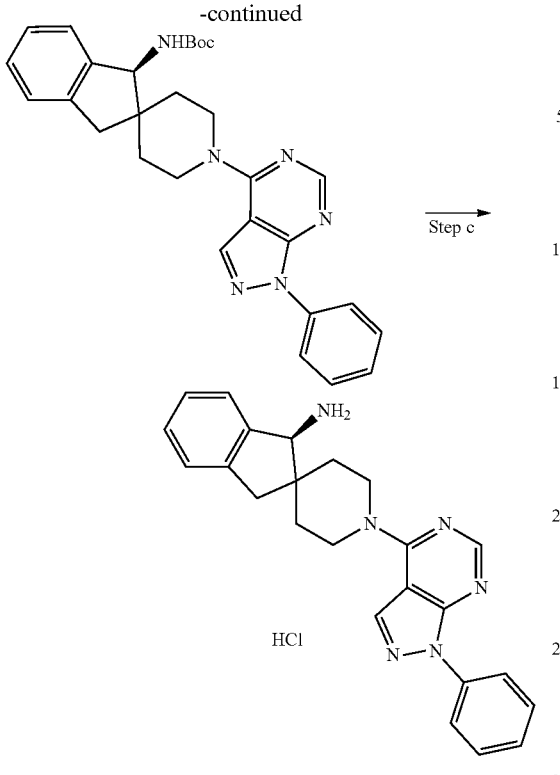

Step a: (3S)-1,3-dihydrospiro[indene-2,4'-piperidin]-3-amine dihydrochloride (200.0 mg, 726.0 µmol, Intermediate I), 4-chloro-2H-pyrazolo[3,4-d]pyrimidine (112.0 mg, 726.0 µmol) and DIPEA (632.0 µL, 3.6 mmol) were added in DMF (6 mL), the reaction mixture was stirred at 80° C. for 2 hours. (Boc)₂O (201.0 µL, 871.0 µmol) was added and the reaction mixture was stirred at 80° C. for 1 hour. The reaction mixture was concentrated under reduced pressure and purified by flash silica gel chromatography (petroleum ether:ethyl acetate=100:0 to 100:70) to afford tert-butyl N-[(3S)-1'-{2H-pyrazolo[3,4-d]pyrimidin-4-yl}-1,3-dihydrospiro[indene-2,4'-piperidin]-3-yl]carbamate (200.0 mg, 66% yield) as a yellow solid. LC-MS (ESI⁺) m/z: 421.1 (M+H)⁺.

Step b: Tert-butyl N-[(3S)-1'-{2H-pyrazolo[3,4-d]pyrimidin-4-yl}-1,3-dihydrospiro[indene-2,4'-piperidin]-3-yl]carbamate (200.0 mg, 475.0 µmol), PhB(OH)₂ (115.0 mg, 950.0 µmol), Cu(OAc)₂ (189.0 mg, 950.0 µmol), and DMAP (173.0 mg, 1.4 mmol) were added in THF (10 mL), and the reaction mixture was evacuated and refilled for 3 times with 02 and stirred at 80° C. for 72 hours under oxygen (balloon). The reaction mixture was then concentrated under reduced pressure and purified by flash silica gel chromatography (petroleum ether:EtOAc=100:0 to 100:80) to afford tert-butyl N-[(3S)-1'-{1-phenyl-1H-pyrazolo[3,4-d]pyrimidin-4-yl}-1,3-dihydrospiro[indene-2,4'-piperidin]-3-yl]carbamate (50.0 mg, 21% yield) as a yellow solid. LC-MS (ESI⁺) m/z: 497.1 (M+H)⁺; ¹HNMR (400 MHz, DMSO-d6): δ 8.60 (br, 1H), 8.38 (br, 1H), 8.18 (d, J=8 Hz, 2H), 7.59-7.54 (m, 2H), 7.37-7.34 (m, 1H), 7.26-7.19 (m, 4H), 4.85 (d, J=9.6 Hz, 1H), 4.42 (br, 2H), 3.64 (br, 2H), 3.15 (d, J=16 Hz, 1H), 2.81 (d, J=15.6 Hz, 1H), 1.72-1.65 (m, 4H), 1.36 (s, 9H).

Step c: Tert-butyl N-[(3S)-1'-{1-phenyl-1H-pyrazolo[3,4-d]pyrimidin-4-yl}-1,3-dihydrospiro[indene-2,4'-piperidin]-3-yl]carbamate (50.0 mg, 100.0 µmol) was added to 4M HCl/MeOH (4 mL), and the reaction mixture was stirred at 25° C. for 2 hours. The reaction mixture was then concentrated under reduced pressure, diluted with EtOAc (10 mL), and filtered to afford (3S)-1'-{1-phenyl-1Hpyrazolo[3,4-d]pyrimidin-4-yl}-1,3-dihydrospiro[indene-2,4'-piperidin]-3-amine hydrochloride (35.0 mg, 81.0% yield) as a white solid. LC-MS (ESI⁺) m/z: 397.1 (M+H)⁺; ¹HNMR (400 MHz, DMSO-d6): δ 8.72 (br, 1H), 8.54 (br, 3H), 8.49 (s, 1H), 8.24 (d, J=7.6 Hz, 2H), 7.67-7.62 (m, 3H), 7.48-7.39 (s, 4H), 4.75 (s, 2H), 7.48 (s, 1H), 4.52-4.50 (m, 2H), 3.38-3.35 (m, 1H), 3.15 (d, J=16 Hz, 1H), 1.95-1.65 (m, 4H).

Example 245: Synthesis of 1-{6-[(3S)-3-amino-6-fluoro-1,3-dihydrospiro[indene-2,4'-piperidin-1'-yl]-5-methyl-1H-pyrazolo[3,4-b]pyrazin-3-yl}-6-methyl-1,2,3,4,5,6-hexahydro-1,6-naphthyridin-5-one

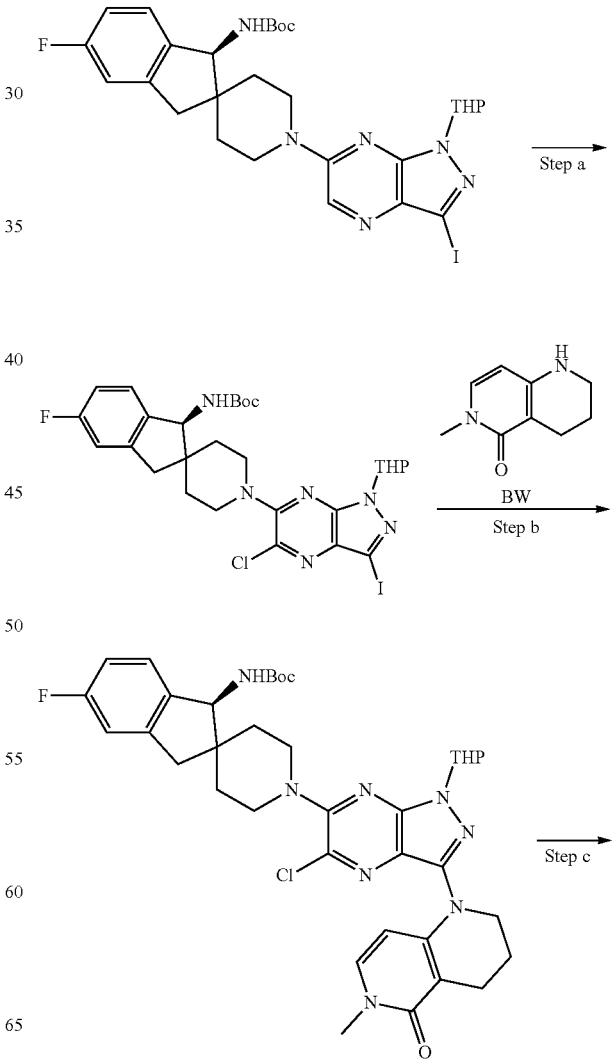

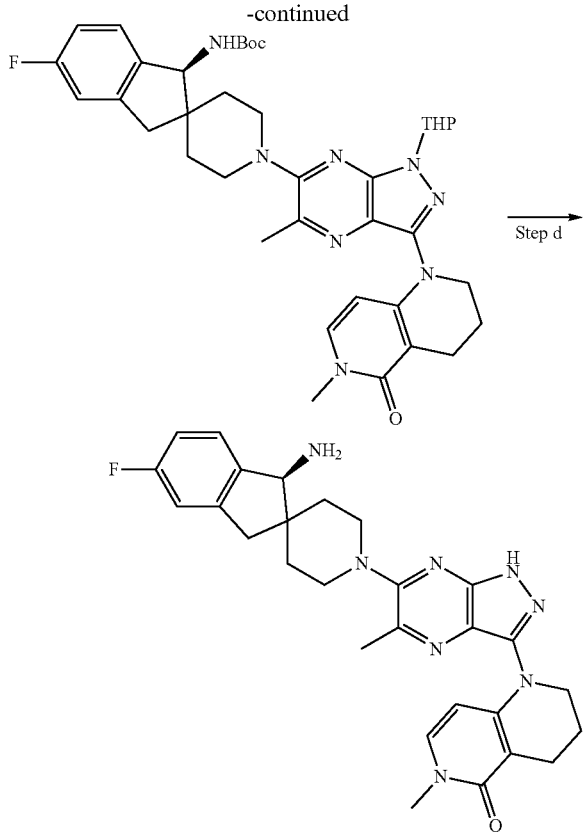

Step a: Tert-butyl N-[(3S)-6-fluoro-1'-[3-iodo-1-(oxan-2-yl)-1H-pyrazolo[3,4-b]pyrazin-6-yl]-1,3-dihydrospiro[indene-2,4'-piperidin]-3-yl]carbamate (500.0 mg, 770 µmol, Intermediate BY) was dissolved in MeCN/AcOH (10 mL/10 mL). Then NCS (123.0 mg, 924 µmol) was added and the mixture was stirred at 70° C. for 2 hours. The mixture was then diluted with EtOAc (100 mL). The mixture was then washed with saturated NaHCO$_3$(50 mL), H$_2$O (30 mL×3) and brine (60 mL), dried over anhydrous Na$_2$SO$_4$, filtered and concentrated to give a residue. The residue was purified by flash silica gel chromatography (petroleum ether:ethyl acetate=100:0 to 100:20) to afford tert-butyl N-[(3S)-1'-[5-chloro-3-iodo-1-(oxan-2-yl)-1H-pyrazolo[3,4-b]pyrazin-6-yl]-6-fluoro-1,3-dihydrospiro[indene-2,4'-piperidin]-3-yl]carbamate (363 mg, 69% yield) as a yellow oil. LC-MS (ESI$^+$) m/z: 683.0 (M+H)$^+$.

Step b: A solution of tert-butyl N-[(3S)-1'-[5-chloro-3-iodo-1-(oxan-2-yl)-1H-pyrazolo[3,4-b]pyrazin-6-yl]-6-fluoro-1,3-dihydrospiro[indene-2,4'-piperidin]-3-yl]carbamate (363.0 mg, 531 µmol), 6-methyl-1,2,3,4,5,6-hexahydro-1,6-naphthyridin-5-one (87.1 mg, 531 µmol, Intermediate BW), Xantphos-Pd-G4 (50.9 mg, 53.1 µmol) and Cs$_2$CO$_3$ (518.0 mg, 1.59 mmol) in toluene (10.0 mL) was stirred at 70° C. for 12 hours under N$_2$. The reaction mixture was diluted with H$_2$O (40 mL) and extracted with EtOAc (40 mL×3). The combined organic layers were washed with brine (50.0 mL), dried over anhydrous Na$_2$SO$_4$, filtered and concentrated to give a residue. The residue was purified by flash silica gel chromatography (EtOAc:MeOH=100:0 to 100:5) to afford tert-butyl N-[(3S)-1'-[5-chloro-3-(6-methyl-5-oxo-1,2,3,4,5,6-hexahydro-1,6-naphthyridin-1-yl)-1-(oxan-2-yl)-1H-pyrazolo[3,4-b]pyrazin-6-yl]-6-fluoro-1,3-dihydrospiro[indene-2,4'-piperidin]-3-yl]carbamate (73.0 mg, 19% yield) as a yellow liquid. LC-MS (ESI$^+$) m/z: 719.2 (M+H)$^+$.

Step c: Tert-butyl N-[(3S)-1'-[5-chloro-3-(6-methyl-5-oxo-1,2,3,4,5,6-hexahydro-1,6-naphthyridin-1-yl)-1-(oxan-2-yl)-1H-pyrazolo[3,4-b]pyrazin-6-yl]-6-fluoro-1,3-dihydrospiro[indene-2,4'-piperidin]-3-yl]carbamate (73.0 mg, 101 µmol), trimethylboroxine (86.5 µL, 3.5M in THF), Pd(dppf)Cl$_2$ (7.39 mg, 10.1 µmol) and K$_2$CO$_3$ (27.9 mg, 202 µmol) were placed into the solvent of dioxane (5.00 mL) and H$_2$O (1.00 mL). The reaction mixture was evacuated and refilled 3 times using N$_2$. The reaction mixture was stirred at 90° C. for 12 hours. The reaction mixture was concentrated and H$_2$O (20 mL) was added, then the solution was extracted with ethyl acetate (30 mL×3). The combined organic layers were washed with brine (50 mL), dried over anhydrous Na$_2$SO$_4$, filtered and concentrated to give a residue. The residue was purified by flash silica gel chromatography (EtOAc:MeOH=100:0 to 100:10) to afford the tert-butyl N-[(3S)-6-fluoro-1'-[5-methyl-3-(6-methyl-5-oxo-1,2,3,4,5,6-hexahydro-1,6-naphthyridin-1-yl)-1-(oxan-2-yl)-1H-pyrazolo[3,4-b]pyrazin-6-yl]-1,3-dihydrospiro[indene-2,4'-piperidin]-3-yl]carbamate (61.0 mg, 87% yield) as a yellow solid. LC-MS (ESI$^+$) m/z: 699.2 (M+H)$^+$.

Step d: Tert-butyl N-[(3S)-6-fluoro-1'-[5-methyl-3-(6-methyl-5-oxo-1,2,3,4,5,6-hexahydro-1,6-naphthyridin-1-yl)-1-(oxan-2-yl)-1H-pyrazolo[3,4-b]pyrazin-6-yl]-1,3-dihydrospiro[indene-2,4'-piperidin]-3-yl]carbamate (61.0 mg, 87.2 µmol) was added into HCl/MeOH (5 mL, 4 M). The reaction mixture was stirred at 25° C. for 0.5 hour. The reaction mixture was concentrated under reduced pressure and purified by prep-HPLC (HCl) to afford 1-{6-[(3S)-3-amino-6-fluoro-1,3-dihydrospiro[indene-2,4'-piperidin]-1'-yl]-5-methyl-H-pyrazolo[3,4-b]pyrazin-3-yl}-6-methyl-1,2,3,4,5,6-hexahydro-1,6-naphthyridin-5-one hydrochloride (23.3 mg, 52% yield) as a yellow solid. LC-MS (ESI$^+$) m/z: 515.2 (M+H)$^+$; $^1$H NMR (400 MHz, METHANOL-d$_4$) δ=7.54-7.57 (m, 1H), 7.37-7.39 (m, 1H), 7.08-7.18 (m, 2H), 6.13-6.15 (m, 1H), 4.46 (s, 1H), 3.88-3.91 (m, 2H), 3.66-3.79 (m, 2H), 3.62 (s, 3H), 3.16-3.26 (m, 4H), 2.75-2.78 (m, 2H), 2.65 (s, 3H), 2.05-2.20 (m, 3H), 1.94-1.99 (m, 1H), 1.85-1.88 (m, 1H), 1.69-1.73 (m, 1H).

Example 246: Synthesis of 1-{6-[(3S)-3-amino-5-fluoro-1,3-dihydrospiro[indene-2,4'-piperidin]-1'-yl]-5-methyl-1H-pyrazolo[3,4-b]pyrazin-3-yl}-6-methyl-1,2,3,4,5,6-hexahydro-1,6-naphthyridin-5-one

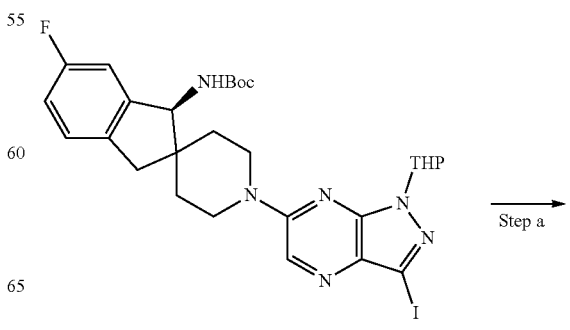

619
-continued

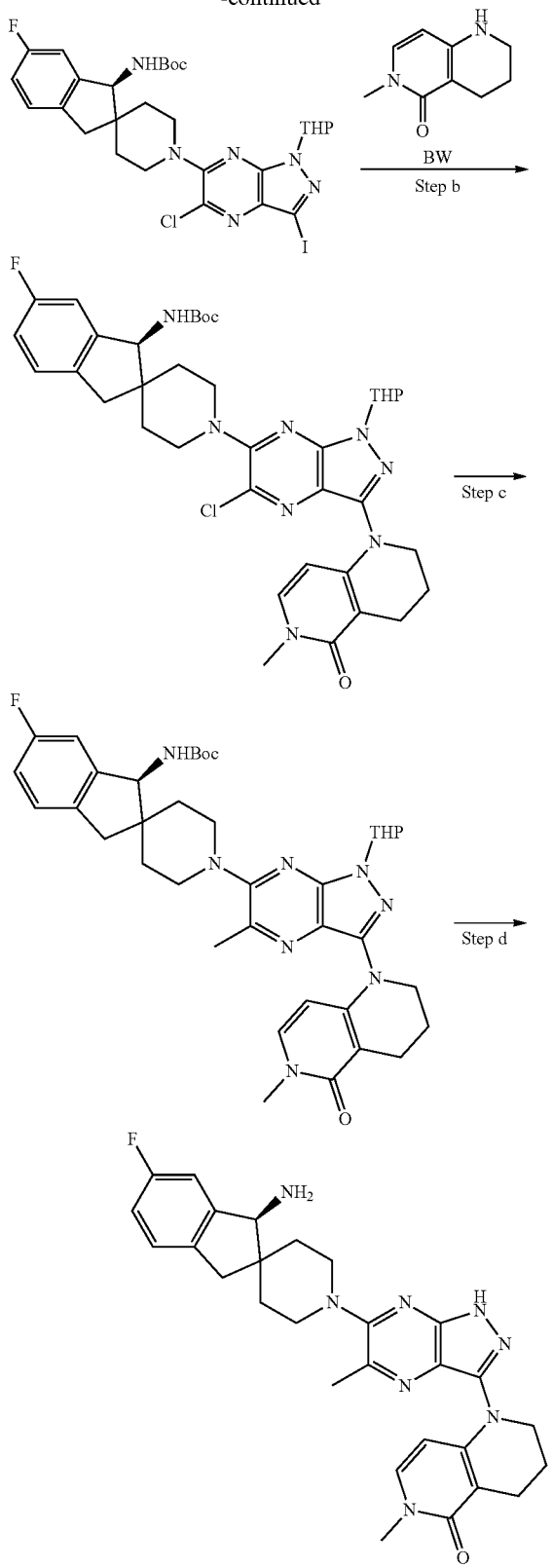

1-{6-[(3S)-3-amino-5-fluoro-1,3-dihydrospiro[indene-2,4'-piperidin]-1'-yl]-5-methyl-1H-pyrazolo[3,4-b]pyrazin-3-yl}-6-methyl-1,2,3,4,5,6-hexahydro-1,6-naphthyridin-5-one hydrochloride was synthesized as described for Example 245 starting with tert-butyl N-[(3S)-5-fluoro-1'-[3-iodo-1-(oxan-2-yl)-1H-pyrazolo[3,4-b]pyrazin-6-yl]-1,3-dihydrospiro[indene-2,4'-piperidin]-3-yl]carbamate (Intermediate Z) in Step a, which was run at 70° C. for 12 hours instead of 2 hrs. Characterization for the final product 1-{6-[(3S)-3-amino-5-fluoro-1,3-dihydrospiro[indene-2,4'-piperidin]-1'-yl]-5-methyl-1H-pyrazolo[3,4-b]pyrazin-3-yl}-6-methyl-1,2,3,4,5,6-hexahydro-1,6-naphthyridin-5-one hydrochloride (59.7 mg, 45% yield, yellow solid): LC-MS (ESI$^+$) m/z: 515.2 (M+H)$^+$; $^1$HNMR (400 MHz, DMSO-d6): δ 13.22 (br, 1H), 8.70 (s, 3H), 7.47-7.49 (m, 1H), 7.34~7.38 (m, 1H), 7.17~7.27 (m, 2H), 5.81~5.83 (m, 1H), 4.43~4.45 (m, 1H), 3.71~3.85 (m, 2H), 3.63~3.66 (m, 2H), 3.41~3.52 (m, 2H), 3.34 (s, 3H), 2.90~3.19 (m, 4H), 2.56 (s, 3H), 1.91~2.08 (m, 4H), 1.59~1.67 (m, 2H).

Example 247: Synthesis of 1-{6-[(3S)-3-amino-1,3-dihydrospiro[indene-2,4'-piperidin]-1'-yl]-5-methyl-1H-pyrazolo[3,4-b]pyrazin-3-yl}-6-methyl-1,2,3,4,5,6-hexahydro-1,6-naphthyridin-5-one

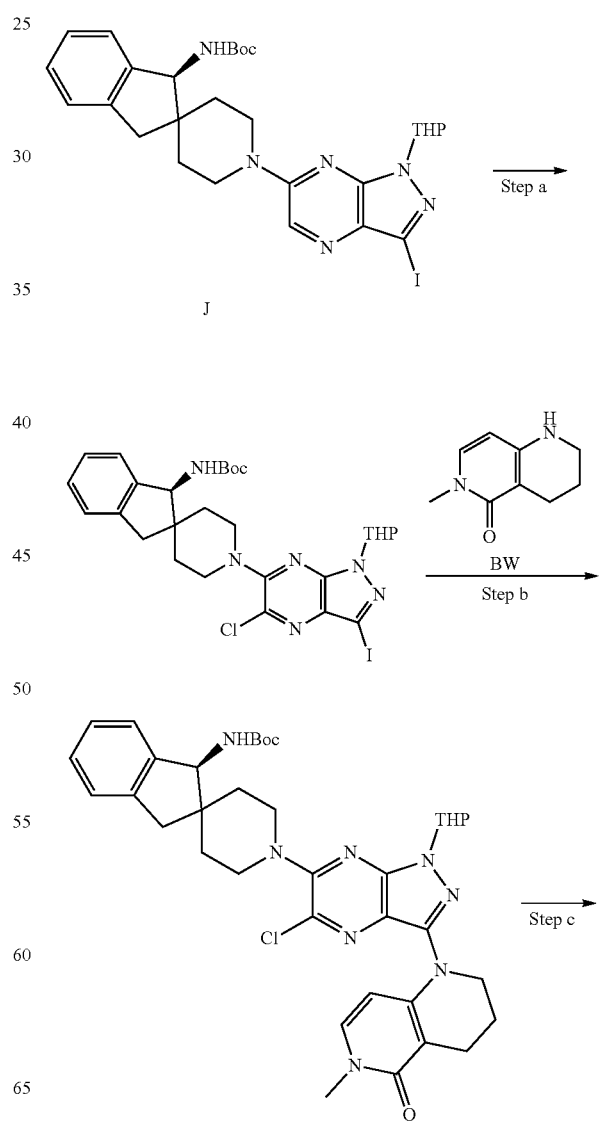

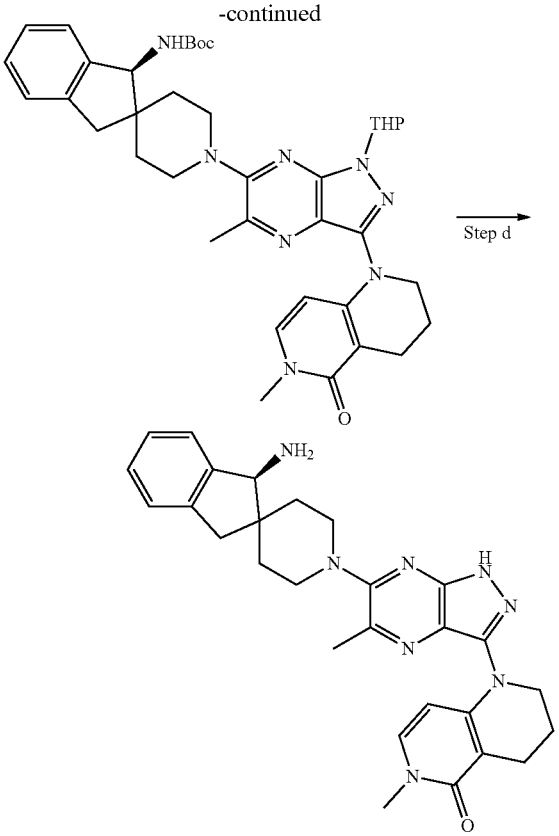
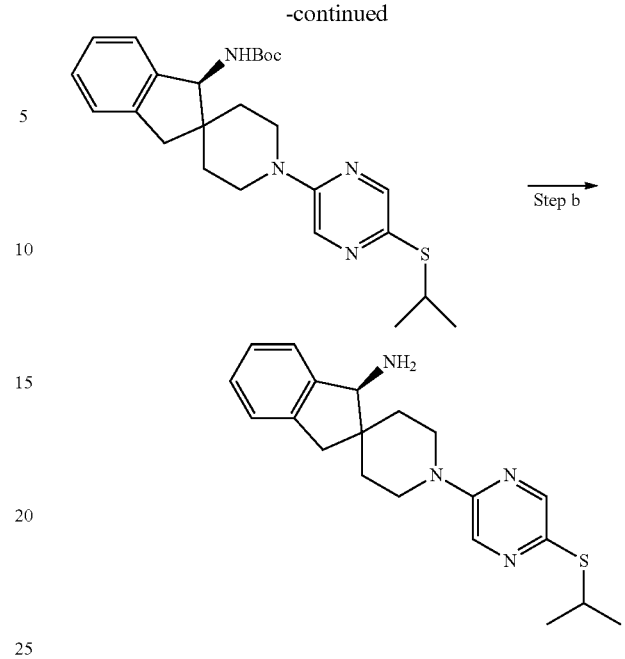

1-{6-[(3S)-3-amino-1,3-dihydrospiro[indene-2,4'-piperidin]-1'-yl]-5-methyl-1H-pyrazolo[3,4-b]pyrazin-3-yl}-6-methyl-1,2,3,4,5,6-hexahydro-1,6-naphthyridin-5-one was synthesized as described for Example 245 starting with tert-butyl N-[(3S)-1'-[3-iodo-1-(oxan-2-yl)-1H-pyrazolo[3,4-b]pyrazin-6-yl]-1,3-dihydrospiro[indene-2,4'-piperidin]-3-yl]carbamate (Intermediate J) in Step a. Characterization for the final product 1-{6-[(3S)-3-amino-1,3-dihydrospiro[indene-2,4'-piperidin]-1'-yl]-5-methyl-1H-pyrazolo[3,4-b]pyrazin-3-yl}-6-methyl-1,2,3,4,5,6-hexahydro-1,6-naphthyridin-5-one (35.0 mg, 69% yield, yellow solid: LC-MS (ESI⁺) m/z: 497.2 (M+H)⁺; ¹HNMR (400 MHz, METHANOL-d4) 7.53-7.55 (m, 1H), 7.31-7.46 (m, 4H), 6.06-6.08 (m, 1H), 4.48 (s, 1H), 3.87-3.90 (m, 2H), 3.67-3.80 (m, 2H), 3.58 (s, 3H), 3.20-3.27 (m, 4H), 2.73-2.77 (m, 2H), 2.65 (s, 3H), 2.05-2.19 (m, 3H), 1.96-2.01 (m, 1H), 1.83-1.86 (m, 1H), 1.70-1.73 (m, 1H).

Example 248: Synthesis of (3S)-1'-[5-(propan-2-ylsulfanyl)pyrazin-2-yl]-1,3-dihydrospiro[indene-2,4'-piperidin]-3-amine

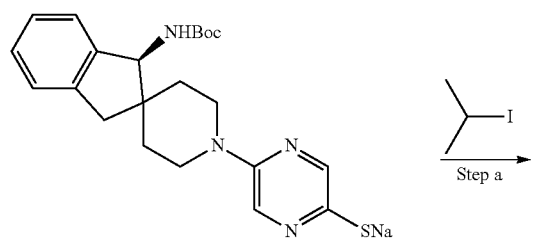

Step a: To a reaction mixture of 2-iodopropane (469.0 mg, 2.8 mmol) and TEA (574 μL, 4.1 mmol) in DMF (8 mL) was added tert-butyl N-[(3S)-1'-[5-(sodiosulfanyl)pyrazin-2-yl]-1,3-dihydrospiro[indene-2,4'-piperidin]-3-yl]carbamate (300.0 mg, 0.7 mmol, Intermediate DE). The reaction mixture was stirred at 25° C. for 1 hour. The reaction mixture was then quenched with water (20 mL), and extracted with EtOAc (50 mL×2). The organic layers were washed with water (50 mL×2), dried over anhydrous Na₂SO₄, filtered and concentrated. The residue was purified by flash silica gel chromatography (40 g column, EtOAc in petroleum ether from 0%-25%) to give tert-butyl N-[(3S)-1'-[5-(propan-2-ylsulfanyl)pyrazin-2-yl]-1,3-dihydrospiro[indene-2,4'-piperidin]-3-yl]carbamate (20.0 mg, 0.04 mmol) as a yellow solid. LC-MS (ESI⁺) m/z: 455.2 (M+H)⁺.

Step b: The mixture of tert-butyl N-[(3S)-1'-[5-(propan-2-ylsulfanyl)pyrazin-2-yl]-1,3-dihydrospiro[indene-2,4'-piperidin]-3-yl]carbamate (20.0 mg, 0.04 mmol) in HCl/MeOH (2 mL, 4 M) was stirred at 25° C. for 0.5 hour. The combined reaction mixture was concentrated to give a residue. The residue was dissolved in MeOH (5 mL), and the reaction mixture was adjusted to pH=8-9 with solid Na₂CO₃. The mixture was filtered, and the filtrate was concentrated to give a residue. The residue was purified by prep-HPLC (basic condition) to give (3S)-1'-[5-(propan-2-ylsulfanyl)pyrazin-2-yl]-1,3-dihydrospiro[indene-2,4'-piperidin]-3-amine (17.9 mg, 0.05 mmol, combined product) was obtained as a yellow solid. LC-MS (ESI⁺) m/z: 354.9 (M+H)⁺; ¹H NMR (400 MHz, CD₃OD) δ 8.17 (d, J=1.6 Hz, 1H), 8.08 (d, J=1.6 Hz, 1H), 7.37-7.35 (m, 1H), 7.23-7.18 (m, 3H), 4.22-4.17 (m, 2H), 3.94 (s, 1H), 3.49-3.46 (m, 1H), 3.24-3.12 (m, 3H), 2.79 (d, J=15.6 Hz, 1H), 1.87-1.75 (m, 2H), 1.60-1.40 (m, 2H), 1.27 (d, J=6.8 Hz, 6H).

Example 249 and 250: Syntheses of (3S)-1'-[5-(cyclopentylsulfanyl)-3-methylpyrazin-2-yl]-1,3-dihydrospiro[indene-2,4'-piperidin]-3-amine and (3S)-1'-[5-(cyclopentylsulfanyl)-6-methylpyrazin-2-yl]-1,3-dihydrospiro[indene-2,4'-piperidin]-3-amine

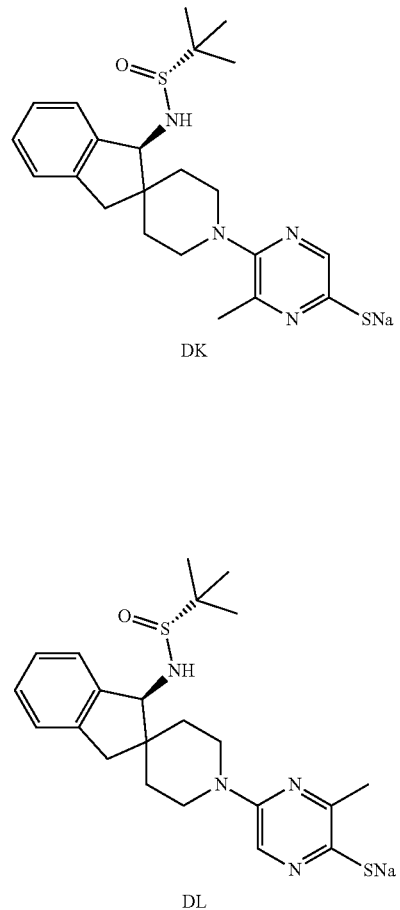
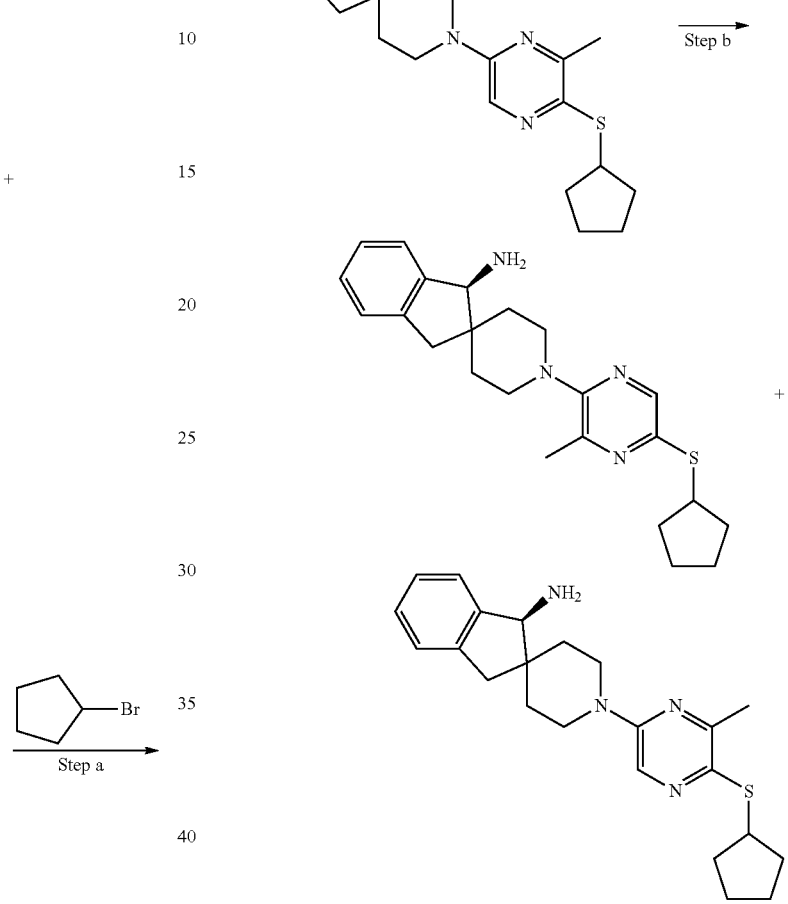

Step a: A mixture of sodium 5-((S)-1-(((R)-tert-butylsulfinyl)amino)-1,3-dihydrospiro[indene-2,4'-piperidin]-1'-yl)-6-methylpyrazine-2-thiolate (Intermediate DK) and sodium 5-((S)-1-(((R)-tert-butylsulfinyl)amino)-1,3-dihydrospiro[indene-2,4'-piperidin]-1'-yl)-3-methylpyrazine-2-thiolate (Intermediate DL) (250.0 mg, 552.0 μmol), bromocyclopentane (163.0 mg, 1.1 mmol) and Cs$_2$CO$_3$ (451.0 mg, 1.4 mmol) in DMF (15.0 mL) was stirred at 70° C. for 3 hours under N$_2$ atmosphere. The mixture was diluted with ethyl acetate (40.0 mL), then washed with H$_2$O (25.0 mL×2). The organic phase was washed with brine (15.0 mL), dried over anhydrous Na$_2$SO$_4$, filtered and concentrated in vacuo to give a residue. The residue was purified by silica gel chromatography (ethyl acetate in petroleum ether=0% to 50%) to afford (R)—N—((S)-1'-(5-(cyclopentylthio)-3-methylpyrazin-2-yl)-1,3-dihydrospiro[indene-2,4'-piperidin]-1-yl)-2-methylpropane-2-sulfinamide and (R)—N—((S)-1'-(5-(cyclopentylthio)-6-methylpyrazin-2-yl)-1,3-dihydrospiro[indene-2,4'-piperidin]-1-yl)-2-methylpropane-2-sulfinamide (230 mg, 84% yield) as a yellow oil. LC-MS (ESI$^+$) m/z 499.1 (M+H)$^+$.

Step b: A mixture of (R)—N—((S)-1'-(5-(cyclopentylthio)-3-methylpyrazin-2-yl)-1,3-dihydrospiro[indene-2,4'- piperidin]-1-yl)-2-methylpropane-2-sulfinamide and (R)—
N—((S)-1'-(5-(cyclopentylthio)-6-methylpyrazin-2-yl)-1,3-
dihydrospiro[indene-2,4'-piperidin]-1-yl)-2-methylpropane-
2-sulfinamide (220.0 mg, 441.0 µmol) in HCl/MeOH (4M, 10 mL) was stirred at 20° C. for 1 hour. The mixture was then concentrated under reduced pressure to give a residue, which was dissolved in MeOH (5.0 mL) and adjusted to pH=8-9 with solid $Na_2CO_3$. The mixture was filtered and concentrated in vacuo to give a residue, which was purified by prep-HPLC ($NH_3.H_2O$) to afford (3S)-1'-[5-(cyclopentylsulfanyl)-3-methylpyrazin-2-yl]-1,3-dihydrospiro[indene-2,4'-piperidin]-3-amine (14.4 mg, 8% yield) as a white solid and (3S)-1'-[5-(cyclopentylsulfanyl)-6-methylpyrazin-2-yl]-1,3-dihydrospiro[indene-2,4'-piperidin]-3-amine (39.2 mg, 23% yield) as a white solid. Characterization of (3S)-1'-[5-(cyclopentylsulfanyl)-3-methylpyrazin-2-yl]-1,3-dihydrospiro[indene-2,4'-piperidin]-3-amine: LC-MS (ESI$^+$) m/z 395.1 (M+H)$^+$; $^1$HNMR (400 MHz, Methanol-d4): δ 8.00 (s, 1H), 7.38 (d, J=4.4 Hz, 1H), 7.25-7.17 (m, 3H), 3.98 (s, 1H), 3.92-3.85 (s, 1H), 3.41 (d, J=12.4 Hz, 2H), 3.13-3.01 (m, 3H), 2.76 (d, J=15.6 Hz, 1H), 2.51 (s, 3H), 2.15-2.09 (m, 2H), 2.03-1.1.79 (m, 4H), 1.71-1.58 (m, 5H), 1.46 (d, J=13.2 Hz, 1H). SFC: e.e.=98.6%, $R_f$=3.007 min, Chiralpak AS-3 100×4.6 mm I.D., 3 um; Mobile phase: A: $CO_2$, B: ethanol (0.05% DEA); Gradient: from 5% to 40% of B in 4.5 min and hold 40% for 2.5 min, then 5% of B for 1 min; Flow rate: 2.8 mL/min; Temperature: 40° C. Characterization of (3S)-1'-[5-(cyclopentylsulfanyl)-6-methylpyrazin-2-yl]-1,3-dihydrospiro[indene-2,4'-piperidin]-3-amine: LC-MS (ESI$^+$) m/z 395.0 (M+H)$^+$; $^1$HNMR (400 MHz, Methanol-d4): δ 7.97 (s, 1H), 7.37 (d, J=4.0 Hz, 1H), 7.25-7.16 (m, 3H), 4.16 (d, J=13.2 Hz, 2H), 3.94 (s, 1H), 3.88-3.82 (s, 1H), 3.21-3.12 (m, 3H), 2.78 (d, J=15.6 Hz, 1H), 2.40 (s, 3H), 2.12-2.02 (m, 2H), 1.91-1.73 (m, 4H), 1.70-1.56 (m, 5H), 1.42 (d, J=13.6 Hz, 1H). SFC: e.e.=97.8%, Rt=3.377 min, same column condions as for other regioisomer.

Example 251: Synthesis of (3S)-1'-[5-(cyclopentyloxy)pyrazin-2-yl]-1,3-dihydrospiro[indene-2,4'-piperidin]-3-amine

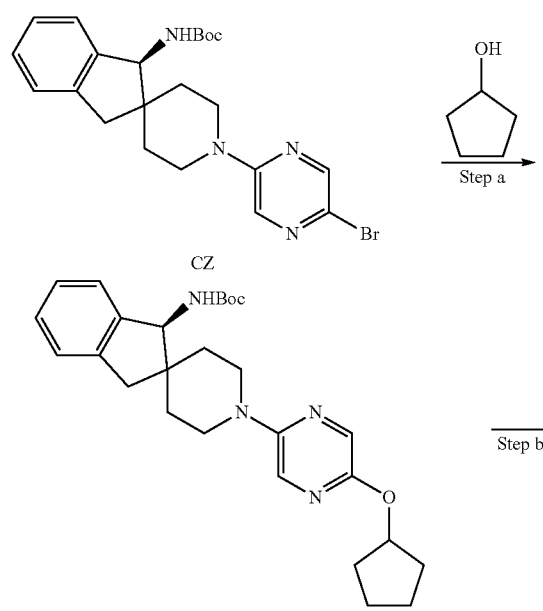

-continued

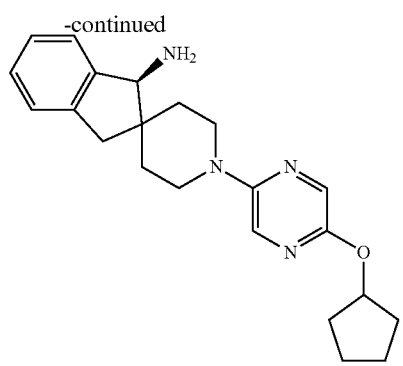

Step a: A mixture of (S)-tert-butyl (1'-(5-bromopyrazin-2-yl)-1,3-dihydrospiro[indene-2,4'-piperidin]-1-yl)carbamate (100.0 mg, 217 µmol, Intermediate CZ), $Cs_2CO_3$ (141.0 mg, 434 µmol), 3,4,7,8-tetramethyl-1,10-phenanthroline (10.2 mg, 43.4 µmol) and CuI (4.1 mg, 21.7 µmol) in cyclopentanol (2 mL) was bubbled with $N_2$ for 5 min, then stirred under microwave irradiation at 130° C. for 2 hours. The reaction mixture was filtered and the filtrate was concentrated to give a residue. The residue was purified by prep-HPLC (basic condition) to afford (S)-tert-butyl (1'-(5-(cyclopentyloxy)pyrazin-2-yl)-1,3-dihydrospiro[indene-2,4'-piperidin]-1-yl)carbamate (20.0 mg, 20% yield) as a white solid. LC-MS (ESI$^+$) m/z: 465.1 (M+H)$^+$.

Step b: The mixture of tert-butyl N-[(3S)-1'-[5-(cyclopentyloxy)pyrazin-2-yl]-1,3-dihydrospiro[indene-2,4'-piperidin]-3-yl]carbamate (20.0 mg, 43.0 µmol) in TFA (0.1 mL) and DCM (1.0 mL) was stirred at 25° C. for 0.5 hour. The mixture was then concentrated to give a residue. The residue was dissolved in MeOH (3 mL) and the mixture was adjusted to pH=9-10 with solid $Na_2CO_3$. The mixture was then filtered and the filtrate was purified by prep-HPLC (basic condition) to afford (3S)-1'-[5-(cyclopentyloxy)pyrazin-2-yl]-1,3-dihydrospiro[indene-2,4'-piperidin]-3-amine (5.30 mg, 34% yield) as a yellow solid. LC-MS (ESI$^+$) m/z: 365.0 (M+H)$^+$; $^1$H NMR (400 MHz, $CD_3OD$): δ 7.66 (s, 2H), 7.32-7.23 (m, 1H), 7.17-7.00 (m, 3H), 5.12 (br t, J=5.3 Hz, 1H), 3.92-3.77 (m, 3H), 3.07-2.93 (m, 3H), 2.67 (d, J=15.6 Hz, 1H), 1.90-1.63 (m, 8H), 1.57-1.29 (m, 4H).

Example 252: Synthesis of (1S)-1'-{6-cyclopentylimidazo[2,1-b][1,3,4]thiadiazol-2-yl}-1,3-dihydrospiro[indene-2,4'-piperidin]-1-amine

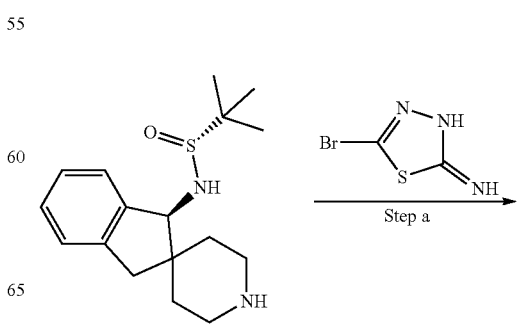

627
-continued

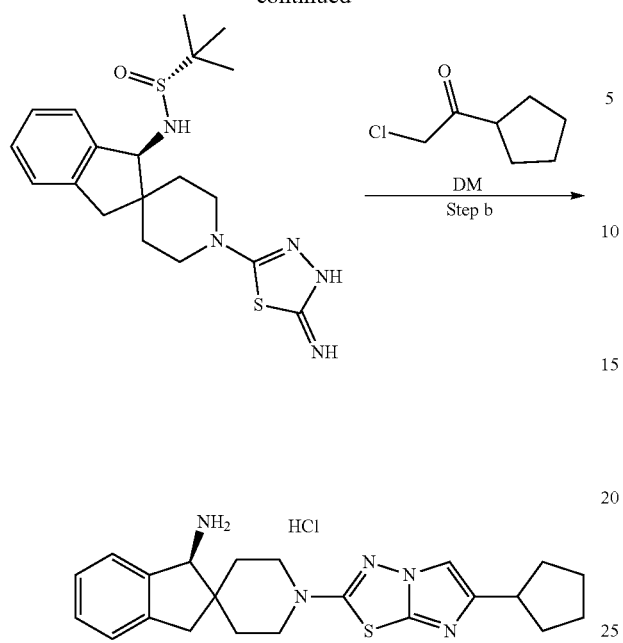

Step a: A mixture of 5-bromo-2,3-dihydro-1,3,4-thiadiazol-2-imine (300.0 mg, 1.7 mmol, CAS #37566-39-5), (R)—N-[(3S)-1,3-dihydrospiro[indene-2,4'-piperidin]-3-yl]-2-methylpropane-2-sulfinamide (781.0 mg, 1.7 mmol, synthesized via Step a of Example 120, 65% purity) and TEA (686.0 μL, 5.0 mmol) in EtOH (25.0 mL) was stirred at 80° C. for 4 hours. The mixture was then concentrated in vacuo to give a residue, which was purified by silica gel chromatography (dichloromethane:methanol=0% to 8%) to afford (R)—N-[(3S)-1'-(5-imino-4,5-dihydro-1,3,4-thiadiazol-2-yl)-1,3-dihydrospiro[indene-2,4'-piperidin]-3-yl]-2-methylpropane-2-sulfinamide (1.1 g, 98% yield, 60% purity) as a brown solid. LC-MS (ESI+) m/z 406.1 (M+H)+.

Step b: A mixture of (R)—N-[(3S)-1'-(5-imino-4,5-dihydro-1,3,4-thiadiazol-2-yl)-1,3-dihydrospiro[indene-2,4'-piperidin]-3-yl]-2-methylpropane-2-sulfinamide (300.0 mg, 443.0 μmol) and 2-chloro-1-cyclopentylethan-1-one (97.3 mg, 664.0 μmol, Intermediate DM) in EtOH (10.0 mL) was stirred at 90° C. for 12 hours under N2 atmosphere. The mixture was concentrated under reduced pressure to give a residue, which was purified by silica gel chromatography (dichloromethane: methanol=0% to 13%) to give the crude product as a white solid. The solid was then re-purified by prep-HPLC (HCl) to afford (1S)-1'-{6-cyclopentylimidazo[2,1-b][1,3,4]thiadiazol-2-yl}-1,3-dihydrospiro[indene-2,4'-piperidin]-1-amine hydrochloride (81.0 mg, 43% yield) as a white solid. LC-MS (ESI+) m/z 394.0 (M+H)+; 1HNMR (400 MHz, Methanol-d4): δ 7.86 (d, J=0.8 Hz, 1H), 7.56 (d, J=7.2 Hz, 1H), 7.45-7.35 (m, 3H), 4.49 (s, 1H), 4.02-3.96 (m, 1H), 3.89-3.82 (m, 1H), 3.62-3.52 (m, 2H), 3.29-3.25 (m, 1H), 3.24-3.19 (m, 2H), 2.24-2.16 (m, 2H), 2.08-1.69 (m, 10H).

628

Example 253: Synthesis of (1S)-1'-{6-cyclopropylimidazo[2,1-b][1,3,4]thiadiazol-2-yl}-1,3-dihydrospiro[indene-2,4'-piperidin]-1-amine

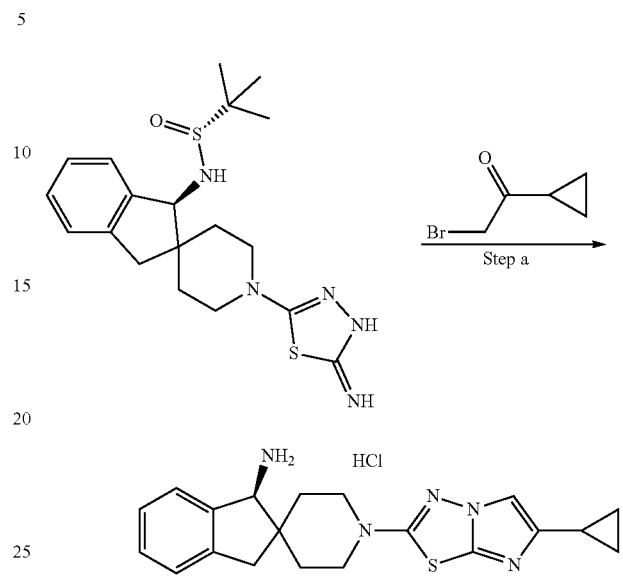

Step a: A mixture of (R)—N-[(3S)-1'-(5-imino-4,5-dihydro-1,3,4-thiadiazol-2-yl)-1,3-dihydrospiro[indene-2,4'-piperidin]-3-yl]-2-methylpropane-2-sulfinamide (200.0 mg, 493.0 μmol, synthesized via Step a of Example 252 and 2-bromo-1-cyclopropylethan-1-one (120.0 mg, 739.0 μmol, CAS #69267-75-0) in EtOH (15.0 mL) was stirred at 90° C. for 18 hours under N2 atmosphere. The mixture was then concentrated under reduced pressure to give a residue, which was purified by silica gel chromatography (dichloromethane:methanol=0% to 13%) to give the crude product as a white solid. The solid was then purified by prep-HPLC (HCl) to afford (1S)-1'-{6-cyclopropylimidazo[2,1-b][1,3,4]thiadiazol-2-yl}-1,3-dihydrospiro[indene-2,4'-piperidin]-1-amine hydrochloride (30.1 mg, 15% yield) as a white solid. LC-MS (ESI+) m/z 366.0 (M+H)+; 1HNMR (400 MHz, Methanol-d4): δ 7.77 (s, 1H), 7.55 (d, J=7.2 Hz, 1H), 7.45-7.34 (m, 3H), 4.49 (s, 1H), 4.01-3.94 (m, 1H), 3.88-3.82 (m, 1H), 3.62-3.51 (m, 2H), 3.26-3.16 (m, 2H), 2.11-1.91 (m, 3H), 1.87-1.81 (m, 1H), 1.74-1.67 (m, 1H), 1.15-1.10 (m, 2H), 0.90-0.86 (m, 2H).

Example 254: Synthesis of (1S)-1'-[5-methyl-3-(pyrrolidin-1-yl)-1H-pyrazolo[3,4-b]pyrazin-6-yl]-1,3-dihydrospiro[indene-2,4'-piperidin]-1-amine

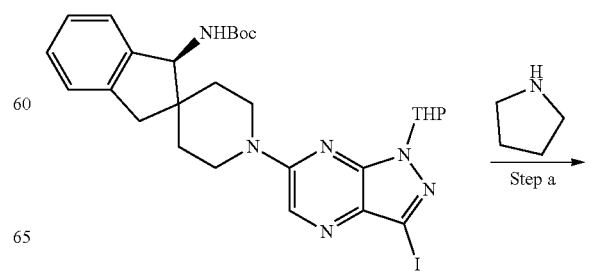

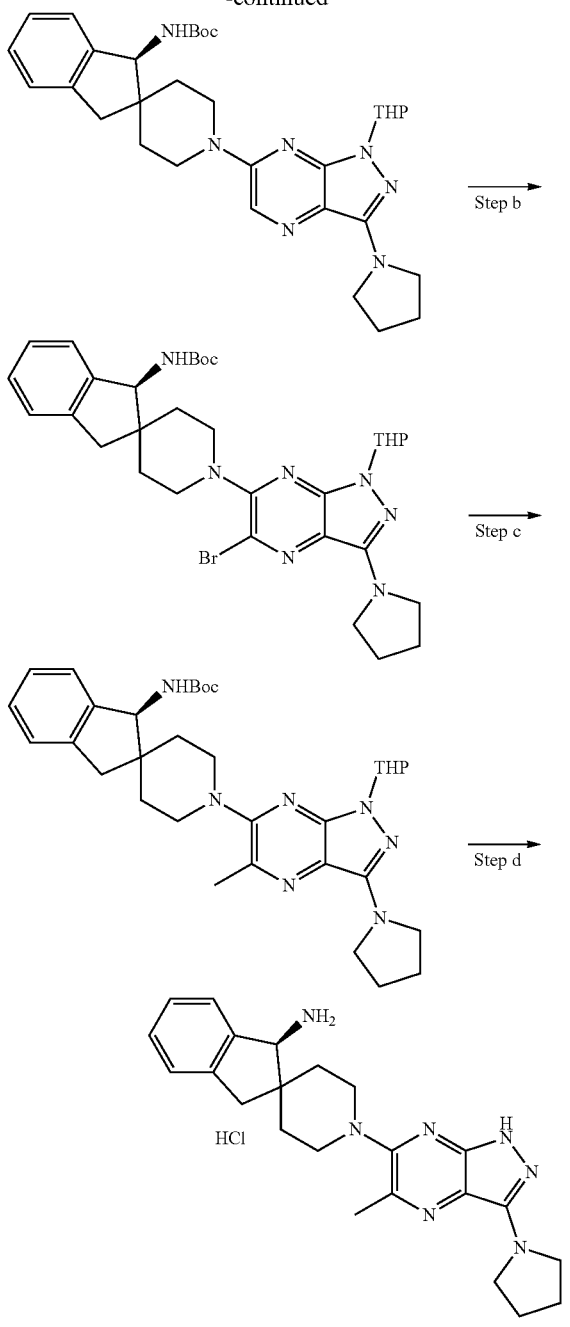

Step a: A mixture of tert-butyl N-[(1S)-1'-[3-iodo-1-(oxan-2-yl)-1H-pyrazolo[3,4-b]pyrazin-6-yl]-1,3-dihydrospiro[indene-2,4'-piperidin]-1-yl]carbamate (350.0 mg, 555.0 µmol, Intermediate J), pyrrolidine (197.0 mg, 2.8 mmol), XantPhos-Pd-G4 (53.3 mg, 55.4 µmol, CAS #1621274-19-8) and Cs₂CO₃ (358.0 mg, 1.1 mmol) in toluene (20.0 mL) was stirred at 90° C. for 12 hours under N₂ atmosphere. The reaction mixture was concentrated in vacuo to give a residue, which was purified by silica gel chromatography (ethyl acetate in petroleum ether=0% to 45%) to afford tert-butyl N—[(S)-1'-[1-(oxan-2-yl)-3-(pyrrolidin-1-yl)-1H-pyrazolo[3,4-b]pyrazin-6-yl]-1,3-dihydrospiro[indene-2,4'-piperidin]-1-yl]carbamate (180.0 mg, 57% yield) as a yellow solid. LC-MS (ESI⁺) m/z 574.3 (M+H)⁺.

Step b: To a mixture of tert-butyl N-[(1S)-1'-[1-(oxan-2-yl)-3-(pyrrolidin-1-yl)-1H-pyrazolo[3,4-b]pyrazin-6-yl]-1,3-dihydrospiro[indene-2,4'-piperidin]-1-yl]carbamate (180.0 mg, 313.0 µmol) in MeCN (5.0 mL) and AcOH (5.0 mL) was added NBS (60.8 mg, 344.0 µmol), and the mixture was stirred at 20° C. for 1 hour. The mixture was then concentrated in vacuo to give a residue, which was dissolved in ethyl acetate (30.0 mL), then washed with sat. NaHCO₃ (20.0 mL) and brine (10.0 mL). The organic phase was dried over anhydrous Na₂SO₄, filtered and concentrated in vacuo to give a residue. The residue was purified by silica gel chromatography (ethyl acetate in petroleum ether=0% to 35%) to afford tert-butyl N-[(1S)-1'-[5-bromo-1-(oxan-2-yl)-3-(pyrrolidin-1-yl)-1H-pyrazolo[3,4-b]pyrazin-6-yl]-1,3-dihydrospiro[indene-2,4'-piperidin]-1-yl]carbamate (130 mg, 64% yield) as a yellow oil. LC-MS (ESI⁺) m/z 654.1 (M+H)⁺.

Step c: A mixture of tert-butyl N-[(1S)-1'-[5-bromo-1-(oxan-2-yl)-3-(pyrrolidin-1-yl)-1H-pyrazolo[3,4-b]pyrazin-6-yl]-1,3-dihydrospiro[indene-2,4'-piperidin]-1-yl]carbamate (130.0 mg, 199.0 µmol), trimethylboroxine (74.9 mg, 597.0 µmol, CAS #823-96-1), K₂CO₃ (54.9 mg, 398.0 µmol) and Pd(dppf)Cl₂ (14.5 mg, 19.9 µmol) in 1,4-dioxane (10.0 mL) and H₂O (3.0 mL) was stirred at 90° C. for 12 hours under N₂ atmosphere. The reaction mixture was then concentrated in vacuo to give a residue. The residue was purified by silica gel chromatography (ethyl acetate in petroleum ether=0% to 40%) to afford tert-butyl N-[(1S)-1'-[5-methyl-1-(oxan-2-yl)-3-(pyrrolidin-1-yl)-1H-pyrazolo[3,4-b]pyrazin-6-yl]-1,3-dihydrospiro[indene-2,4'-piperidin]-1-yl]carbamate (80.0 mg, 69% yield) as a yellow solid. LC-MS (ESI⁺) m/z 588.3 (M+H)⁺.

Step d: A mixture of tert-butyl N-[(1S)-1'-[5-methyl-1-(oxan-2-yl)-3-(pyrrolidin-1-yl)-1H-pyrazolo[3,4-b]pyrazin-6-yl]-1,3-dihydrospiro[indene-2,4'-piperidin]-1-yl]carbamate (80.0 mg, 136.0 µmol) in HCl/MeOH (2M, 3 mL) was stirred at 20° C. for 2 hours. The mixture was then concentrated under reduced pressure to give a residue, which was purified by prep-HPLC (HCl) to afford (1S)-1'-[5-methyl-3-(pyrrolidin-1-yl)-1H-pyrazolo[3,4-b]pyrazin-6-yl]-1,3-dihydrospiro[indene-2,4'-piperidin]-1-amine hydrochloride (36.5 mg, 61% yield) as a red solid. LC-MS (ESI⁺) m/z 404.1 (M+H)⁺; ¹HNMR (400 MHz, Methanol-d4): δ 7.56 (d, J=7.6 Hz, 1H), 7.45-7.35 (m, 3H), 4.48 (s, 1H), 4.09-3.84 (m, 6H), 3.42-3.33 (m, 2H), 3.22 (s, 2H), 2.66 (s, 3H), 2.16-1.68 (m, 8H).

Example 255: Synthesis of (3S)-1'-[5-cyclopropyl-3-(piperidin-1-yl)-1H-pyrazolo[3,4-b]pyrazin-6-yl]-1,3-dihydrospiro[indene-2,4'-piperidin]-3-amine

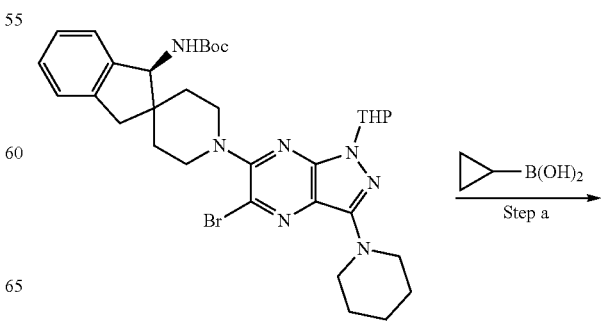

-continued

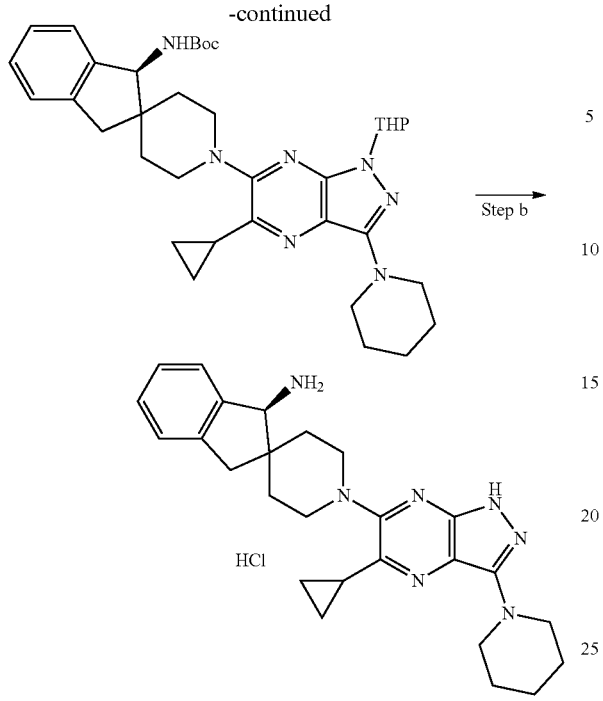

Step a: A mixture of tert-butyl N-[(3S)-1'-[5-bromo-1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (170.0 mg, 255.0 μmol, synthesized via Steps a-b of Example 152), cyclopropylboronic acid (54.7 mg, 637.0 μmol), $K_2CO_3$ (105.0 mg, 764.0 μmol), SPhos (20.8 mg, 50.9 μmol) and $Pd_2(dba)_3$ (23.2 mg, 25.4 μmol) in toluene (20.0 mL) was stirred at 100° C. for 12 hours under $N_2$ atmosphere. The mixture was then concentrated in vacuo to give a residue, which was dissolved in ethyl acetate (30.0 mL) and washed with $H_2O$ (20.0 mL×2). The organic phase was washed with brine (10.0 mL), dried over anhydrous $Na_2SO_4$, filtered and concentrated in vacuo to give a residue. The residue was purified by silica gel chromatography (ethyl acetate in petroleum ether=0% to 25%) to afford tert-butyl N-[(3S)-1'-[5-cyclopropyl-1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (110.0 mg, 69% yield) as a yellow oil. LC-MS (ESI$^+$) m/z 628.4 (M+H)$^+$.

Step b: A mixture of tert-butyl N-[(3S)-1'-[5-cyclopropyl-1-(oxan-2-yl)-3-(piperidin-1-yl)-1H-pyrazolo[3,4-b]pyrazin-6-yl]-1,3-dihydrospiro[indene-2,4'-piperidin]-3-yl]carbamate (110.0 mg, 175.0 μmol) in HCl/MeOH (2M, 5 mL) was stirred at 20° C. for 2 hours. The mixture was concentrated under reduced pressure to give a residue, which was purified by prep-HPLC (HCl) to afford (3S)-1'-[5-cyclopropyl-3-(piperidin-1-yl)-1H-pyrazolo[3,4-b]pyrazin-6-yl]-1,3-dihydrospiro[indene-2,4'-piperidin]-3-amine hydrochloride (73.2 mg, 87% yield) as a yellow solid. LC-MS (ESI$^+$) m/z 444.1 (M+H)$^+$; $^1$HNMR (400 MHz, Methanol-d4): δ 7.56 (d, J=7.2 Hz, 1H), 7.45-7.35 (m, 3H), 4.49 (s, 1H), 4.26-4.14 (m, 2H), 3.93 (s, 4H), 3.46-3.37 (m, 2H), 3.22 (s, 2H), 2.30-2.22 (m, 1H), 2.14-2.07 (m, 1H), 2.02-1.96 (m, 1H), 1.88-1.80 (m, 7H), 1.73-1.70 (m, 1H), 1.21-1.15 (m, 4H).

Example 256: Synthesis of (S)-(5-(1-amino-1,3-dihydrospiro[indene-2,4'-piperidin]-1'-yl)pyrazin-2-yl)(phenyl)methanone

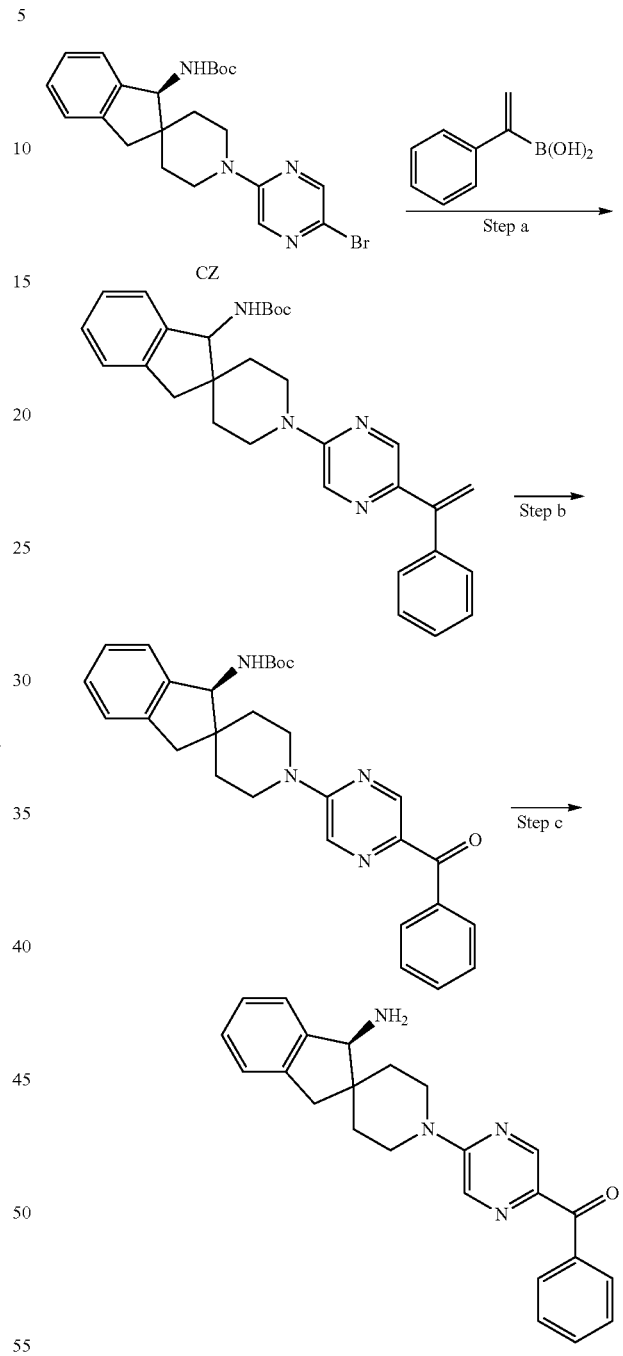

Step a: (S)-tert-butyl (1'-(5-bromopyrazin-2-yl)-1,3-dihydrospiro[indene-2,4'-piperidin]-1-yl)carbamate (100 mg, 217 μmol, Intermediate CZ), (1-phenylethenyl)boronic acid (38.4 mg, 260 μmol), Pd(dppf)Cl$_2$ (15.8 mg, 21.7 μmol) and $Cs_2CO_3$ (141 mg, 434 μmol) were placed into a solution of dioxane (10 mL) and $H_2O$ (1 mL). The reaction mixture was evacuated and refilled 3 times using $N_2$. The reaction mixture was then stirred at 100° C. for 12 hours. The reaction mixture was then concentrated and $H_2O$ (30 mL) was added, and the solution was extracted with EtOAc (50 mL×3). The combined organic layers were washed with brine (50 mL), dried over anhydrous Na₂SO₄, filtered and concentrated to give a residue. The residue was purified by flash silica gel chromatography (petroleum ether:ethyl acetate=100:0 to 100:20) to afford (S)-tert-butyl (1'-(5-(1-phenylvinyl)pyrazin-2-yl)-1,3-dihydrospiro[indene-2,4'-piperidin]-1-yl)carbamate (90.0 mg, 87% yield) as a yellow oil LC-MS (ESI⁺) m/z: 483.1 (M+H)⁺.

Step b: A mixture of tert-butyl N-[(3S)-1'-[5-(1-phenylethenyl)pyrazin-2-yl]-1,3-dihydrospiro[indene-2,4'-piperidin]-3-yl]carbamate (90.0 mg, 186 µmol), K₂OsO₄·2H₂O (92.7 mg, 279 µmol) and NaIO₄ (59.6 mg, 279 µmol) in acetone (10.00 mL) and H₂O (5.00 mL) was stirred at 25° C. for 2 hours. The mixture was then diluted with ethyl ether (30 mL) and H₂O (20 mL). The mixture was filtered and the partitioned layers were separated. The aqueous phase was extracted with ethyl acetate (30 mL×3). The combined organic layers were washed with brine (50 mL), dried over anhydrous Na₂SO₄, filtered and concentrated to give a residue. The residue was purified by flash silica gel chromatography (ethyl acetate/petroleum ether=0/100 to 40/100) to give tert-butyl N-[(3S)-1'-(5-benzoylpyrazin-2-yl)-1,3-dihydrospiro[indene-2,4'-piperidin]-3-yl]carbamate (60.0 mg, 67% yield) as a yellow oil LC-MS (ESI⁺) m/z: 507.1 (M+H)⁺.

Step c: A solution of (S)-tert-butyl (1'-(5-benzoylpyrazin-2-yl)-1,3-dihydrospiro[indene-2,4'-piperidin]-1-yl)carbamate (40 mg, 82.5 µmol) in TFA (0.1 mL and DCM (1 mL) was stirred at 25° C. for 1 hour. The mixture was then adjusted to pH=9-10 with solid Na₂CO₃. The mixture was filtered and the filtrate was concentrated to give a residue. The residue was dissolved in MeCN (3 mL) and was purified by prep. HPLC (basic condition) to give (S)-(5-(1-amino-1,3-dihydrospiro[indene-2,4'-piperidin]-1'-yl)pyrazin-2-yl)(phenyl)methanone (6.50 mg, 16.9 µmol, 21% yield) as a white solid. LC-MS (ESI⁺) m/z 385.1 (M+H)⁺; ¹HNMR (400 MHz, Methanol-d₄) δ=8.74 (s, 1H), 8.30 (s, 1H), 7.97 (d, J=7.8 Hz, 2H), 7.67-7.60 (m, 1H), 7.56-7.48 (m, 2H), 7.42-7.37 (m, 1H), 7.30-7.20 (m, 3H), 4.48 (d, J=13.8 Hz, 2H), 4.01 (s, 1H), 3.48-3.39 (m, 2H), 3.21 (d, J=15.8 Hz, 1H), 2.87 (d, J=15.9 Hz, 1H), 1.97-1.76 (m, 2H), 1.72-1.61 (m, 1H), 1.51 (d, J=13.9 Hz, 1H).

Example 257: Synthesis of (3S)-1'-{5-[(hydroxyimino)(phenyl)methyl]pyrazin-2-yl}-1,3-dihydrospiro[indene-2,4'-piperidin]-3-amine

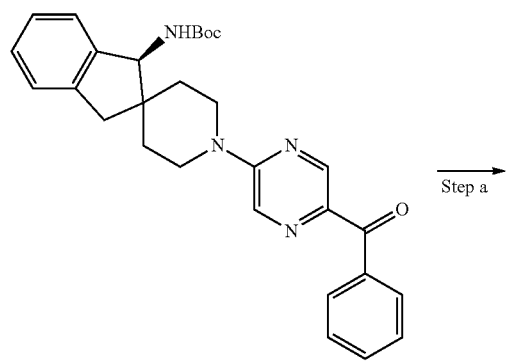

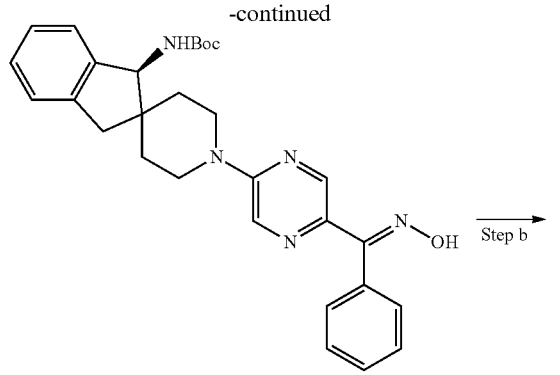

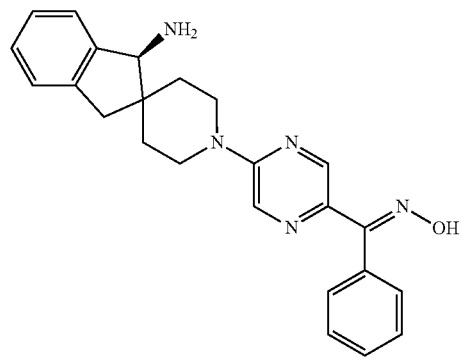

Step a: A mixture of tert-butyl N-[(3S)-1'-(5-benzoylpyrazin-2-yl)-1,3-dihydrospiro[indene-2,4'-piperidin]-3-yl]carbamate (50 mg, 0.1 mmol, synthesized via Steps a and b of Example 256), NH₂OH HCl (70.8 mg, 1.0 mmol), TEA (713 ul, 5.2 mmol) and NH₂OH HCl (286 mg, 4.1 mmol) in MeOH (5.0 mL) and was stirred at 25° C. for 2 h. The mixture was diluted with ethyl ether (30 mL) and H₂O (20 mL). The mixture was then filtered and the partitioned layers were separated. The aqueous phase was extracted with ethyl acetate (30 mL×3). The combined organic layers were washed with brine (50 mL), dried over anhydrous Na₂SO₄, filtered and concentrated to give a residue. The residue was purified by flash silica gel chromatography (ethyl acetate/petroleum ether=0/100 to 80/100) to give (S,E)-tert-butyl (1'-(5-((hydroxyimino)(phenyl)methyl)pyrazin-2-yl)-1,3-dihydrospiro[indene-2,4'-piperidin]-1-yl)carbamate (80 mg, 53% yield) as a yellow oil. LC-MS (ESI⁺) m/z: 500.2 (M+H)⁺.

Step b: A solution of tert-butyl N-[(3S)-1'-{5-[(E)-(hydroxyimino)(phenyl)methyl]pyrazin-2-yl}-1,3-dihydrospiro[indene-2,4'-piperidin]-3-yl]carbamate (80 mg, 160 µmol) in HCl/MeOH (10 ml) was stirred at 25° C. for 1 hour. The mixture was then adjusted to pH=9-10 with solid Na₂CO₃. The mixture was filtered and the filtrate was concentrated to give a residue. The residue was dissolved in HCl/MeOH (10 mL). The mixture was purified by prep. HPLC (basic condition) to give (3S)-1'-{5-[(hydroxyimino)(phenyl)methyl]pyrazin-2-yl}-1,3-dihydrospiro[indene-2,4'-piperidin]-3-amine; formic acid (9.30 mg, 13% yield) as a white solid. LC-MS (ESI⁺) m/z: 385.1. (M+H)⁺; ¹HNMR (400 MHz, Methanol-d4) δ=8.61-8.43 (m, 2H), 8.35-8.26 (m, 1H), 7.57-7.27 (m, 10H), 7.61-7.24 (m, 1H), 4.46-4.26 (m, 3H), 3.44-3.35 (m, 2H), 3.26-3.11 (m, 2H), 1.95-1.78 (m, 2H), 1.76-1.59 (m, 2H), 10.35-1.23 (m, 1H).

Example 258: Synthesis of {3-[(3S)-3-amino-1,3-dihydrospiro[indene-2,4'-piperidin]-1'-yl]-6-[(2-amino-3-chloropyridin-4-yl)sulfanyl]pyridin-2-yl}methanol

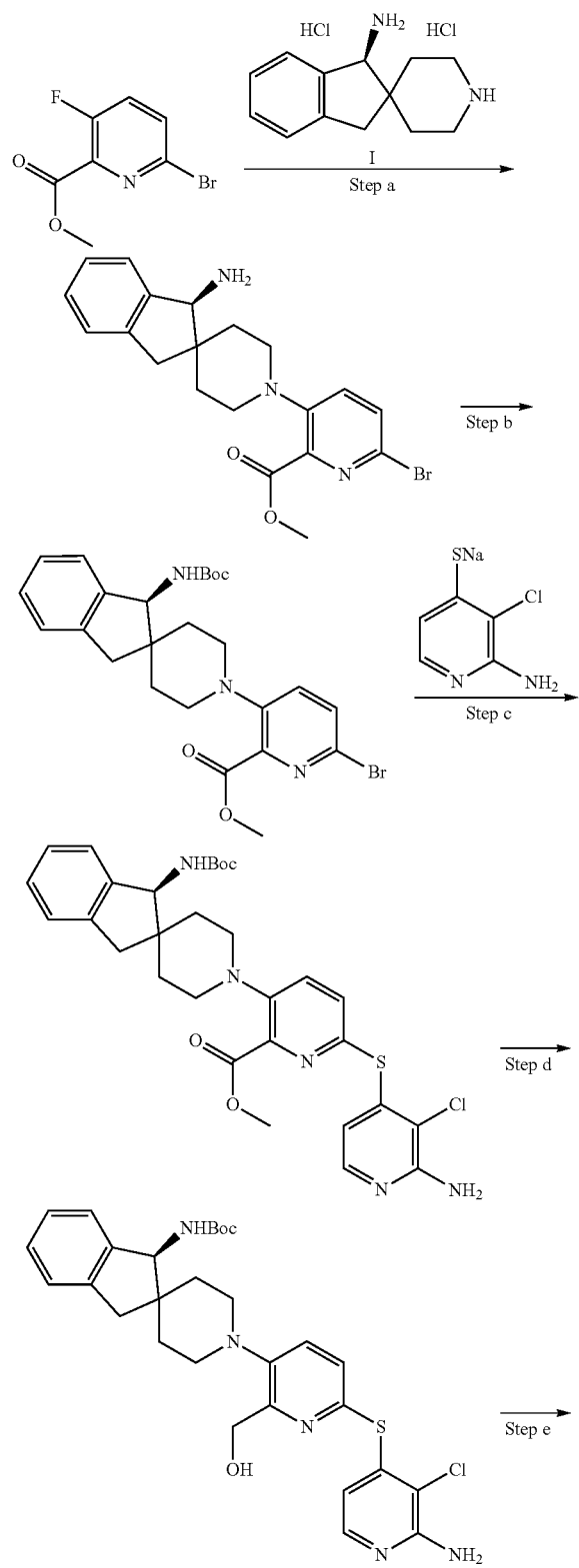

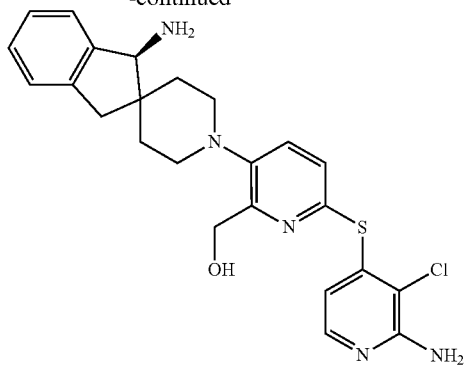

Step a: A mixture of methyl 6-bromo-3-fluoropyridine-2-carboxylate (500.0 mg, 2.1 mmol CAS #1214332-47-4), (3S)-1,3-dihydrospiro[indene-2,4'-piperidin]-3-amine dihydrochloride (586.0 mg, 2.1 mmol, Intermediate I) and TEA (1.46 mL, 10.6 mmol) in DMF (50.0 mL) was stirred at 80° C. for 3 hours. The reaction mixture was used directly without further workup. LC-MS (ESI$^+$) m/z 417.9 (M+H)$^+$.

Step b: To the mixture of methyl 3-[(3S)-3-amino-1,3-dihydrospiro[indene-2,4'-piperidin]-1'-yl]-6-bromopyridine-2-carboxylate (886.0 mg, 2.1 mmol) in DMF (50.0 mL) was added (Boc)$_2$O (722 μL, 3.2 mmol), the mixture was stirred at 20° C. for 2 hours. The mixture was then diluted with ethyl acetate (120.0 mL), and washed with H$_2$O (80.0 mL×2). The organic phase was washed with brine (50.0 mL), dried over anhydrous Na$_2$SO$_4$, filtered and concentrated in vacuo to give a residue, which was purified by silica gel chromatography (ethyl acetate in petroleum ether=0% to 35%) to afford methyl 6-bromo-3-[(3S)-3-{[(tert-butoxy)carbonyl]amino}-1,3-dihydrospiro[indene-2,4'-piperidin]-1'-yl]pyridine-2-carboxylate (700 mg, 64% yield) as a yellow solid. LC-MS (ESI$^+$) m/z 538.0 (M+Na)+.

Step c: A mixture of methyl 6-bromo-3-[(3S)-3-{[(tert-butoxy)carbonyl]amino}-1,3-dihydrospiro[indene-2,4'-piperidin]-1'-yl]pyridine-2-carboxylate (320.0 mg, 619.0 μmol), 3-chloro-4-(sodiosulfanyl)pyridin-2-amine (146.0 mg, 804.0 μmol, Intermediate AC), XantPhos (71.1 mg, 123.0 μmol), DIPEA (352.0 μL, 1.9 mmol) and Pd$_2$(dba)$_3$ (56.6 mg, 61.9 μmol) in 1,4-dioxane (15.0 mL) was stirred at 100° C. for 12 hours under N$_2$ atmosphere. The mixture was then concentrated in vacuo to give a residue, which was purified by silica gel chromatography (ethyl acetate in petroleum ether=0% to 85%) to afford (S)-methyl 6-((2-amino-3-chloropyridin-4-yl)thio)-3-(1-((tert-butoxycarbonyl)amino)-1,3-dihydrospiro[indene-2,4'-piperidin]-1'-yl) picolinate (290.0 mg, 79% yield) as a brown solid. LC-MS (ESI$^+$) m/z 596.1 (M+H)$^+$.

Step d: To a mixture of (S)-methyl 6-((2-amino-3-chloropyridin-4-yl)thio)-3-(1-((tert-butoxycarbonyl)amino)-1,3-dihydrospiro[indene-2,4'-piperidin]-1'-yl)picolinate (290.0 mg, 486.0 μmol) in anhydrous THF (10.0 mL) was added DIBAL-H (2.42 mL, 2.42 mmol) slowly at 0° C., then the resulting mixture was warmed to 15° C. and stirred for 5 hours under N$_2$ atmosphere. The mixture was quenched with 10% AcOH (20.0 mL), then extracted with ethyl acetate (20.0 mL×2). The organic phases were washed with sat. NaHCO$_3$ (20.0 mL) and brine (10.0 mL). The organic phases were dried over anhydrous Na$_2$SO$_4$, filtered and concentrated in vacuo to give a residue, which was purified by silica gel chromatography (methanol in dichloromethane=0% to 8%) to afford tert-butyl N-[(3S)-1'-{6-[(2-amino-3-chloropyridin-4-yl)sulfanyl]-2-(hydroxymethyl)pyridin-3-yl}-1,3-dihydrospiro[indene-2,4'-piperidin]-3-yl]carbamate (50.0 mg, 18% yield) as a yellow solid. LC-MS (ESI$^+$) m/z 568.1 (M+H)$^+$.

Step e: A mixture of tert-butyl N-[(3S)-1'-{6-[(2-amino-3-chloropyridin-4-yl)sulfanyl]-2-(hydroxymethyl)pyridin-3-yl}-1,3-dihydrospiro[indene-2,4'-piperidin]-3-yl]carbamate (50.0 mg, 88.0 μmol) in HCl/EtOAc (4M, 2.0 mL) and EtOAc (2.0 mL) was stirred at 15° C. for 1 hour. The mixture was concentrated under reduced pressure to give a residue, which was dissolved in MeOH (5.0 mL) and adjusted to pH=8.0 with solid Na$_2$CO$_3$. The mixture was filtered and concentrated in vacuo to give a residue, which was purified by prep-HPLC (NH$_3$.H$_2$O) to afford {3-[(3S)-3-amino-1,3-dihydrospiro[indene-2,4'-piperidin]-1'-yl]-6-[(2-amino-3-chloropyridin-4-yl)sulfanyl]pyridin-2-yl}methanol (4.2 mg, 10% yield) as a white solid. LC-MS (ESI$^+$) m/z 490.0 (M+Na)$^+$; $^1$HNMR (400 MHz, Methanol-d4): δ 7.66-7.64 (m, 2H), 7.55 (d, J=8.0 Hz, 1H), 7.43-7.40 (m, 1H), 7.27-7.22 (m, 3H), 6.17 (d, J=5.6 Hz, 1H), 4.78 (s, 2H), 4.05 (s, 1H), 3.21-3.12 (m, 3H), 3.06-2.99 (m, 2H), 2.82 (d, J=16.0 Hz, 1H), 2.08-1.96 (m, 2H), 1.69-1.64 (m, 1H), 1.55-1.51 (m, 1H).

Examples 259 & 260: Syntheses of (1R)-1-{3-[(3S)-3-amino-1,3-dihydrospiro[indene-2,4'-piperidin]-1'-yl]-6-[(2,3-dichloropyridin-4-yl)sulfanyl]pyrazin-2-yl}ethan-1-ol and (1S)-1-{3-[(3S)-3-amino-1,3-dihydrospiro[indene-2,4'-piperidin]-1'-yl]-6-[(2,3-dichloropyridin-4-yl)sulfanyl]pyrazin-2-yl}ethan-1-ol

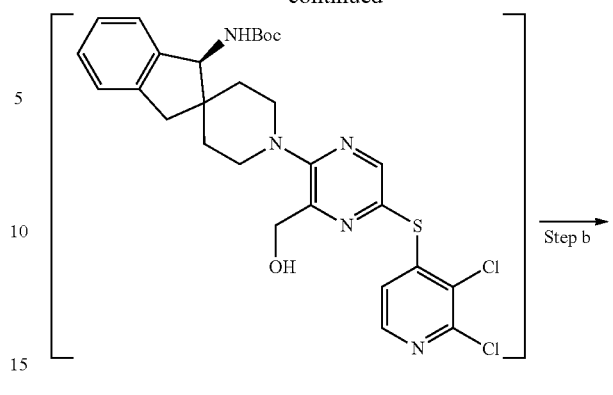

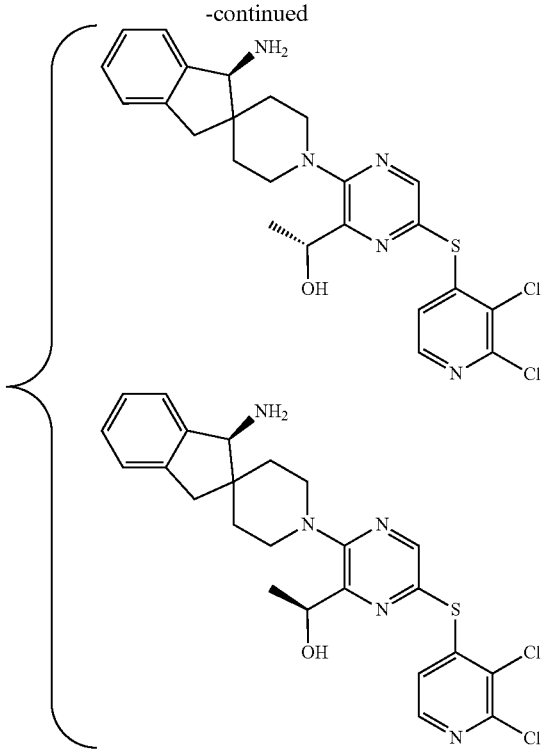

Step a: To a solution of methyl 3-[(3S)-3-{[(tert-butoxy)carbonyl]amino}-1,3-dihydrospiro[indene-2,4'-piperidin]-1'-yl]-6-[(2,3-dichloropyridin-4-yl)sulfanyl]pyrazine-2-carboxylate (500.0 mg, 810 µmol, synthesized via Step a of Example 243) in THF (15.00 mL) was added DIBAL-H (806 µL, 1.21 mmol, 1.5 M in toluene) at −78° C. under N₂. The solution was stirred for 2 hours at the same temperature. The reaction was quenched by a solution of 10% aqueous AcOH (50 mL) at −78° C. and extracted with EtOAc (50 mL×3). The combined organic layer was adjusted pH to 8-9 with saturated aqueous of NaHCO₃ and separated. The organic layer was washed with brine (100 mL), dried over anhydrous Na₂SO₄, filtered and concentrated to give a residue. The residue was purified by flash silica gel chromatography (petroleum ether:ethyl acetate=100:0 to 100:30). The product tert-butyl N-[(3S)-1'-{5-[(2,3-dichloropyridin-4-yl)sulfanyl]-3-formylpyrazin-2-yl}-1,3-dihydrospiro[indene-2,4'-piperidin]-3-yl]carbamate (260.0 mg, 55% yield) was obtained as a yellow solid. LC-MS (ESI⁺) m/z: 586.0 (M+H)⁺. The side product tert-butyl N-[(3S)-1'-{5-[(2,3-dichloropyridin-4-yl)sulfanyl]-3-(hydroxymethyl)pyrazin-2-yl}-1,3-dihydrospiro[indene-2,4'-piperidin]-3-yl]carbamate (120 mg, 25% yield) was also obtained as a yellow oil. LC-MS (ESI⁺) m/z: 588.0 (M+H)⁺.

Step b: To a mixture of tert-butyl N-[(3S)-1'-{5-[(2,3-dichloropyridin-4-yl)sulfanyl]-3-formylpyrazin-2-yl}-1,3-dihydrospiro[indene-2,4'-piperidin]-3-yl]carbamate (200.0 mg, 340 µmol) in THF (3.00 mL) was added MeMgBr (153 µL, 462 µmol, 3M in diethyl ether) slowly at −78° C. The mixture was warmed to 0° C. for 1 hour. Another MeMgBr (153 µL, 462 µmol, 3M in diethyl ether) was added at 0° C. The mixture was stirred at 0° C. for 1 hour. The reaction was then quenched with H₂O (10 mL). The mixture was filtered and the filtrate was extracted with EtOAc (20 mL×3). The combined organic layers were washed with brine (50 mL), dried over anhydrous Na₂SO₄, filtered and concentrated to give a residue. The residue was purified by column chromatography (petroleum ether/ethyl acetate=100:0 to 100:30) to afford tert-butyl N-[(3S)-1'-{5-[(2,3-dichloropyridin-4-yl)sulfanyl]-3-(1-hydroxyethyl)pyrazin-2-yl}-1,3-dihydrospiro[indene-2,4'-piperidin]-3-yl]carbamate (202 mg, 335 µmol, 99% yield) as a yellow solid. LC-MS (ESI⁺) m/z: 602.1 (M+H)⁺.

Step c: Tert-butyl N-[(3S)-1'-{5-[(2,3-dichloropyridin-4-yl)sulfanyl]-3-(1-hydroxyethyl)pyrazin-2-yl}-1,3-dihydrospiro[indene-2,4'-piperidin]-3-yl]carbamate (200.0 mg, 331 µmol) was dissolved in EtOAc (2.00 mL). Then HCl/EtOAc (2.00 mL, 4 M) was added and the mixture was stirred at 25° C. for 1 hour. The yellow solid that precipitated was collected by filtration. The solid was dissolved in MeOH (5.00 mL). The mixture was adjusted to pH=8-9 with solid NaHCO₃. The mixture was filtered and the filtrate was purified by prep-HPLC (HCOOH) to afford 1-{3-[(3S)-3-amino-,3-dihydrospiro[indene-2,4'-piperidin]-1'-yl]-6-[(2,3-dichloropyridin-4-yl)sulfanyl]pyrazin-2-yl}ethan-1-ol; formic acid (100.0 mg, HCOOH salt, 55% yield) as a yellow solid. LC-MS (ESI⁺) m/z: 502.0 (M+H)⁺.

Step d: 1-{3-[(3S)-3-amino-1,3-dihydrospiro[indene-2,4'-piperidin]-1'-yl]-6-[(2,3-dichloropyridin-4-yl)sulfanyl]pyrazin-2-yl}ethan-1-ol (100.0 mg, 199 µmol, HCOOH salt) was basified with solid NaHCO₃ and separated by Chiral-SFC (DAICEL CHIRALPAK AD (250 mm*30 mm, 10 um; mobile phase: 50% of EtOH (0.1% NH₃.H₂O) in CO₂; flow rate: 70 mL/min) to give two diastereomers, which were further purified by a second prep. HPLC (HCOOH condition). The absolute configuration of the diastereomers were arbitrarily assigned. (1R)-1-{3-[(3S)-3-amino-1,3-dihydrospiro[indene-2,4'-piperidin]-1'-yl]-6-[(2,3-dichloropyridin-4-yl)sulfanyl]pyrazin-2-yl}ethan-1-ol; formic acid (26.2 mg, 24% yield) was obtained as a white solid: LC-MS (ESI⁺) m/z: 502.0 (M+H)⁺; ¹HNMR (400 MHz, CD₃OD): δ 8.53 (s, 1H), 8.39 (s, 1H), 8.05 (d, J=5.4 Hz, 1H), 7.52 (d, J=7.4 Hz, 1H), 7.45-7.30 (m, 3H), 6.90 (d, J=5.4 Hz, 1H), 5.10 (q, J=6.4 Hz, 1H), 4.42 (s, 1H), 4.01-3.88 (m, 1H), 3.86-3.77 (m, 1H), 3.42-3.36 (m, 1H), 3.32-3.26 (m, 1H), 3.23-3.10 (m, 2H), 2.09-1.90 (m, 2H), 1.79 (m, 1H), 1.67 (m, 1H), 1.54 (d, J=6.4 Hz, 3H); SFC: e.e. =100%, R$_f$=1.561 min. Column: Chiralpak AD-3 50×4.6 mm I.D., 3 µm. Mobile phase: 40% of ethanol (0.05% DEA) in CO₂. Flow rate: 4 mL/min. Column temperature: 35° C. (1S)-1-{3-[(3S)-3-amino-1,3-dihydrospiro[indene-2,4'-piperidin]-1'-yl]-6-[(2,3-dichloropyridin-4-yl)sulfanyl]pyrazin-2-yl}ethan-1-ol; formic acid (19.8 mg, 18% yield) was obtained as a white solid: LC-MS (ESI⁺) m/z: 502.0 (M+H)⁺; ¹HNMR (400 MHz, CD₃OD): δ 8.55 (s, 1H), 8.39 (s, 1H), 8.05 (d, J=5.4 Hz, 1H), 7.51 (d, J=7.4 Hz, 1H), 7.42-7.29 (m, 3H), 6.90 (d, J=5.4 Hz, 1H), 5.09 (q, J=6.3 Hz, 1H), 4.36 (s, 1H), 4.09-3.97 (m, 1H), 3.80-3.69 (m, 1H), 3.45-3.34 (m, 1H), 3.31-3.22 (m, 1H), 3.21-3.09 (m, 2H), 2.08 (m, 1H), 1.97-1.86 (m, 1H), 1.78-1.64 (m, 2H), 1.53 (d, J=6.4 Hz, 3H. SFC: e.e. =100%, R$_f$=2.320 min with same conditions as stated for other diastereomer.

Example 261: Synthesis of 2-[(3S)-3-amino-1,3-dihydrospiro[indene-2,4'-piperidin]-1'-yl]-5-[(2,3-dichlorophenyl)sulfanyl]-3,4-dihydropyrimidin-4-one

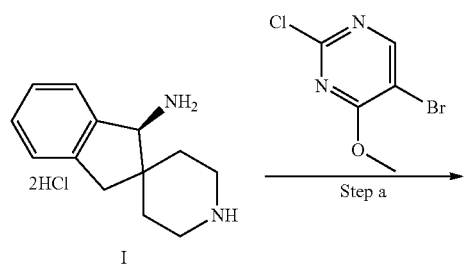

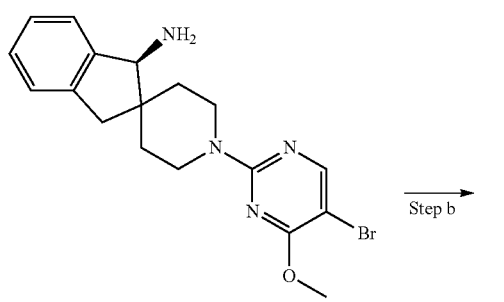

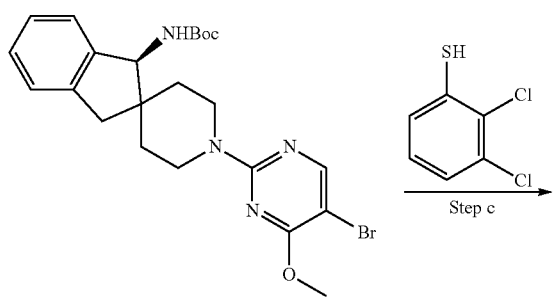

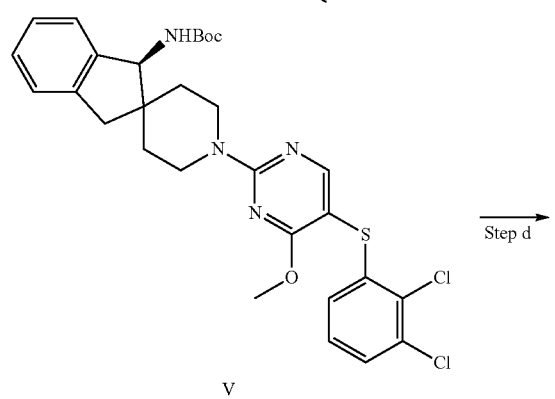

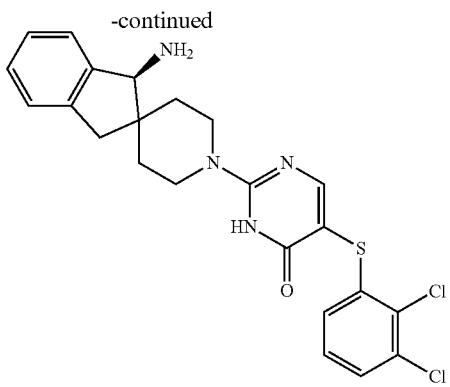

Step a: A mixture of 5-bromo-2-chloro-4-methoxypyrimidine (1.00 g, 4.5 mmol, CAS #57054-92-9), (3S)-1,3-dihydrospiro[indene-2,4'-piperidin]-3-amine dihydrochloride (1.40 g, 4.9 mmol, Intermediate I) and TEA (3.10 mL, 22.3 mmol) in DMF (20.00 mL) was stirred at 50° C. for 1 hour. The mixture was used in next step directly. LC-MS (ESI$^+$) m/z: 388.9, 390.9 (M+H)$^+$.

Step b: To a mixture of (3S)-1'-(5-bromo-4-methoxypyrimidin-2-yl)-1,3-dihydrospiro[indene-2,4'-piperidin]-3-amine (1.70 g, 4.5 mmol) in DMF (20.00 mL) was added (Boc)$_2$O (1.50 mL, 6.7 mmol). The mixture was stirred at 25° C. for 3 hours. The mixture was then diluted with EtOAc (100 mL), washed with H$_2$O (30 mL×3), brine (50 mL), dried over anhydrous Na$_2$SO$_4$, filtered and concentrated to give a residue. The residue was purified by flash silica gel chromatography (petroleum ether:ethyl acetate=100:0 to 100:20) to afford tert-butyl N-[(3S)-1'-(5-bromo-4-methoxypyrimidin-2-yl)-1,3-dihydrospiro[indene-2,4'-piperidin]-3-yl]carbamate (2.20 g, 100% yield) as a white solid. LC-MS (ESI$^+$) m/z: 489.0, 491.0 (M+H)$^+$.

Step c: Tert-butyl N-[(3S)-1'-(5-bromo-4-methoxypyrimidin-2-yl)-1,3-dihydrospiro[indene-2,4'-piperidin]-3-yl]carbamate (300.0 mg, 612 µmol) and 2,3-dichlorobenzene-1-thiol (120.0 mg, 673 µmol) were dissolved in dioxane (20.0 mL). Then XantPhos (70.5 mg, 122 µmol), Pd$_2$(dba)$_3$ (55.9 mg, 61.2 µmol) and DIPEA (318 µL, 1.8 mmol) were added in turn. The mixture was evacuated and refilled 3 times using N$_2$. The reaction mixture was then stirred at 120° C. for 10 hours. The solvent was then removed under reduced pressure to give a black residue, which was purified by column chromatography (petroleum ether/EtOAc=100:0 to 100:60) to afford tert-butyl N-[(3S)-1'-{5-[(2,3-dichlorophenyl)sulfanyl]-4-methoxypyrimidin-2-yl}-1,3-dihydrospiro[indene-2,4'-piperidin]-3-yl]carbamate (260.0 mg, 72% yield) as a yellow solid. LC-MS (ESI$^+$) m/z: 609.1 (M+Na)+.

Step d: Tert-butyl N-[(3S)-1'-{5-[(2,3-dichlorophenyl)sulfanyl]-4-methoxypyrimidin-2-yl}-1,3-dihydrospiro[indene-2,4'-piperidin]-3-yl]carbamate (50.0 mg, 85.0 µmol) was placed into aq. HBr (48%, 20 mL). The reaction mixture was stirred at 100° C. for 6 hours. The mixture was then concentrated to give a residue. The residue was dissolved in MeOH (2.00 mL) and adjusted to pH=7-8 with solid Na$_2$CO$_3$, then purified by prep-HPLC (FA) to afford 2-[(3S)-3-amino-1,3-dihydrospiro[indene-2,4'-piperidin]-1'-yl]-5-[(2,3-dichlorophenyl)sulfanyl]-3,4-dihydropyrimidin-4-one (6.80 mg, 17% yield) as a white solid. LC-MS (ESI$^+$) m/z: 472.9 (M+H)$^+$; $^1$H NMR (400 MHz, Methanol-d4) δ 8.02 (s, 1H), 7.42 (d, J=7.4 Hz, 1H), 7.34-7.17 (m, 4H), 7.05 (t, J=8.0 Hz, 1H), 6.80 (d, J=7.9 Hz, 1H), 4.43-4.28 (m, 2H), 4.16 (d, J=13.9 Hz, 1H), 3.45-3.28 (m, 2H), 3.17-3.03 (m, 2H), 2.12-1.46 (m, 4H).

Example 262: Synthesis of (S)-1'-(5-((2,3-dichlorophenyl)thio)-4-methoxypyrimidin-2-yl)-1,3-dihydrospiro[indene-2,4'-piperidin]-1-amine

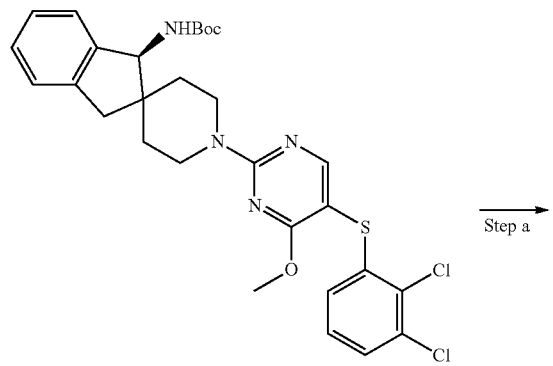

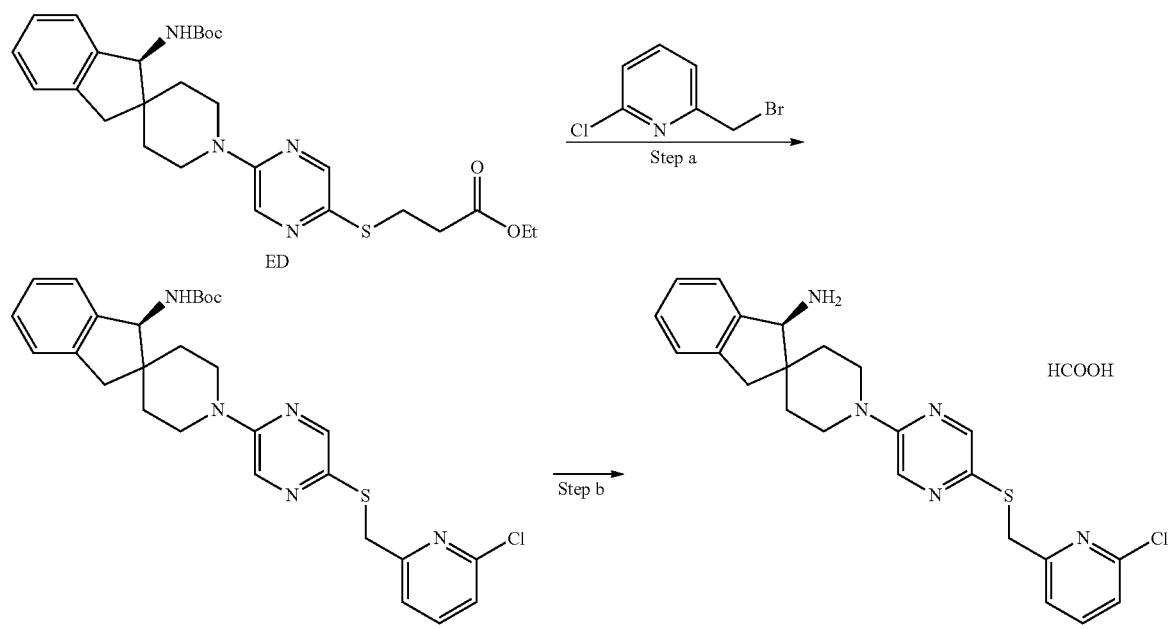

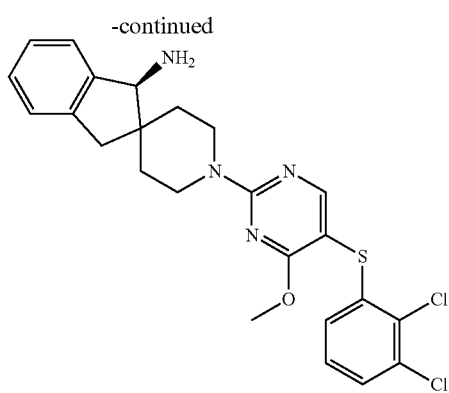

Step a: (S)-tert-butyl (1'-(5-((2,3-dichlorophenyl)thio)-4-methoxypyrimidin-2-yl)-1,3-dihydrospiro[indene-2,4'-piperidin]-1-yl)carbamate (50.0 mg, 85.0 μmol, synthesized via Steps a-c of Example 261) was placed into HCl/EtOAc (10 mL, 4 M). The mixture was then stirred at 25° C. for 2 h. The mixture was then concentrated and was purified by prep-HPLC (FA) to afford (S)-1'-(5-((2,3-dichlorophenyl)thio)-4-methoxypyrimidin-2-yl)-1,3-dihydrospiro[indene-2,4'-piperidin]-1-amine formate (19.4 mg, HCOOH salt 43% yield) as a white solid. LC-MS (ESI$^+$) m/z: 487.0 (M+H)$^+$; $^1$H NMR (400 MHz, Methanol-d4) δ 8.55 (s, 1H), 8.22 (s, 1H), 7.49 (d, J=7.3 Hz, 1H), 7.41-7.26 (m, 4H), 7.12 (t, J=8.0 Hz, 1H), 6.63 (d, J=8.1 Hz, 1H), 4.78-4.65 (m, 2H), 4.31 (s, 1H), 3.97-3.89 (m, 3H), 3.47-3.36 (m, 2H), 3.27-3.18 (m, 1H), 3.16-3.05 (m, 1H), 1.81 (d, J=4.2, 12.4 Hz, 2H), 1.72-1.57 (m, 2H).

Example 263: Synthesis of (S)-1'-(5-(((6-chloropyridin-2-yl)methyl)thio)pyrazin-2-yl)-1,3-dihydrospiro[indene-2,4'-piperidin]-1-amine Step a: To a solution of ethyl (S)-3-((5-(1-((tert-butoxycarbonyl)amino)-1,3-dihydrospiro[indene-2,4'-piperidin]-1'-yl)pyrazin-2-yl)thio)propanoate (190 mg, 371 umol, Intermediate ED) and 2-(bromomethyl)-6-chloropyridine (191 mg, 927 umol, CAS #63763-79-1) in THF (8.00 mL) was added a solution of EtONa (101 mg, 1.48 mmol) in EtOH (1.60 mL) at 0° C. Then the mixture was stirred at 0 to 25° C. for 16 h. The mixture was then poured into water (50.0 mL) and extracted with ethyl acetate (50.0 mL×2). The combined organic layers were washed with brine (50.0 mL×2), dried over Na$_2$SO$_4$, filtered and concentrated to give tert-butyl (S)-(1'-(5-(((6-chloropyridin-2-yl)methyl)thio)pyrazin-2-yl)-1,3-dihydrospiro[indene-2,4'-piperidin]-1-yl)carbamate (335 mg, quant. crude yield) as light yellow oil. LC-MS (ESI$^+$) m/z: 538.3 (M+H)$^+$.

Step b: To a solution of tert-butyl (S)-(1'-(5-(((6-chloropyridin-2-yl)methyl)thio)pyrazin-2-yl)-1,3-dihydrospiro[indene-2,4'-piperidin]-1-yl)carbamate (320 mg, 595 umol) in DCM (12.8 mL) was added TFA (1.97 g, 17.3 mmol, 1.28 mL) at 25° C. The mixture was stirred at 25° C. for 12 h. The mixture was then adjusted the pH to 7~8 with saturated NaHCO₃ solution and extracted with DCM (20.0 mL×3). The organic layer was washed with brine (20.0 mL×2), dried over Na₂SO₄, filtered and concentrated. The residue was purified by prep-HPLC (column: Phenomenex Synergi Max-RP 150*50 mm*10 um; mobile phase: [water (0.225% FA)-ACN]; B %: 16%-46%, 10 min) to give (S)-1'-(5-(((6-chloropyridin-2-yl)methyl)thio)pyrazin-2-yl)-1,3-dihydrospiro[indene-2,4'-piperidin]-1-amine (79.2 mg, 158 umol, 27% yield) as a light yellow solid. LC-MS (ESI⁺) m/z: 438.2 (M+H)⁺; ¹H NMR (400 MHz DMSO-d6): δ 8.30-8.26 (m, 2H), 8.03 (d, J=1.2 Hz, 1H), 7.78 (t, J=7.8 Hz, 1H), 7.38-7.32 (m, 3H), 7.22-7.17 (m, 3H), 4.31 (s, 2H), 4.16-4.12 (m, 2H), 3.91 (s, 1H), 3.16-3.05 (m, 3H), 2.70-2.66 (m, 1H), 1.78-1.62 (m, 2H), 1.49 (br d, J=12.8 Hz, 1H), 1.16 (br d, J=12.8 Hz, 1H).

Example 264: Synthesis of (S)-1'-(5-((cyclopentylmethyl)thio)pyrazin-2-yl)-1,3-dihydrospiro[indene-2,4'-piperidin]-1-amine (S)-1'-(5-((cyclopentylmethyl)thio)pyrazin-2-yl)-1,3-dihydrospiro[indene-2,4'-piperidin]-1-amine was synthesized as described above for Example 263, coupling ethyl (S)-3-((5-(1-((tert-butoxycarbonyl)amino)-1,3-dihydrospiro[indene-2,4'-piperidin]-1'-yl)pyrazin-2-yl)thio)propanoate (Intermediate ED) and (bromomethyl)cyclopentane in Step a.

Characterization of (S)-1'-(5-((cyclopentylmethyl)thio)pyrazin-2-yl)-1,3-dihydrospiro[indene-2,4'-piperidin]-1-amine: LC-MS (ESI⁺) m/z: 395.2 (M+H)⁺; ¹H NMR (400 MHz DMSO-d6): δ 8.34-8.27 (m, 1H), 8.06 (d, J=1.2 Hz, 1H), 7.33-7.31 (m, 1H), 7.21-7.14 (m, 3H), 4.14-4.09 (m, 2H), 3.88 (s, 1H), 3.18-2.99 (m, 5H), 2.65 (br d, J=16.0 Hz, 1H), 2.09-1.98 (m, 1H), 1.80-1.44 (m, 10H), 1.27-1.19 (m, 2H), 1.13 (br d, J=12.4 Hz, 1H).

Example 265: Synthesis of (S)-1'-(5-(phenethylthio)pyrazin-2-yl)-1,3-dihydrospiro[indene-2,4'-piperidin]-1-amine

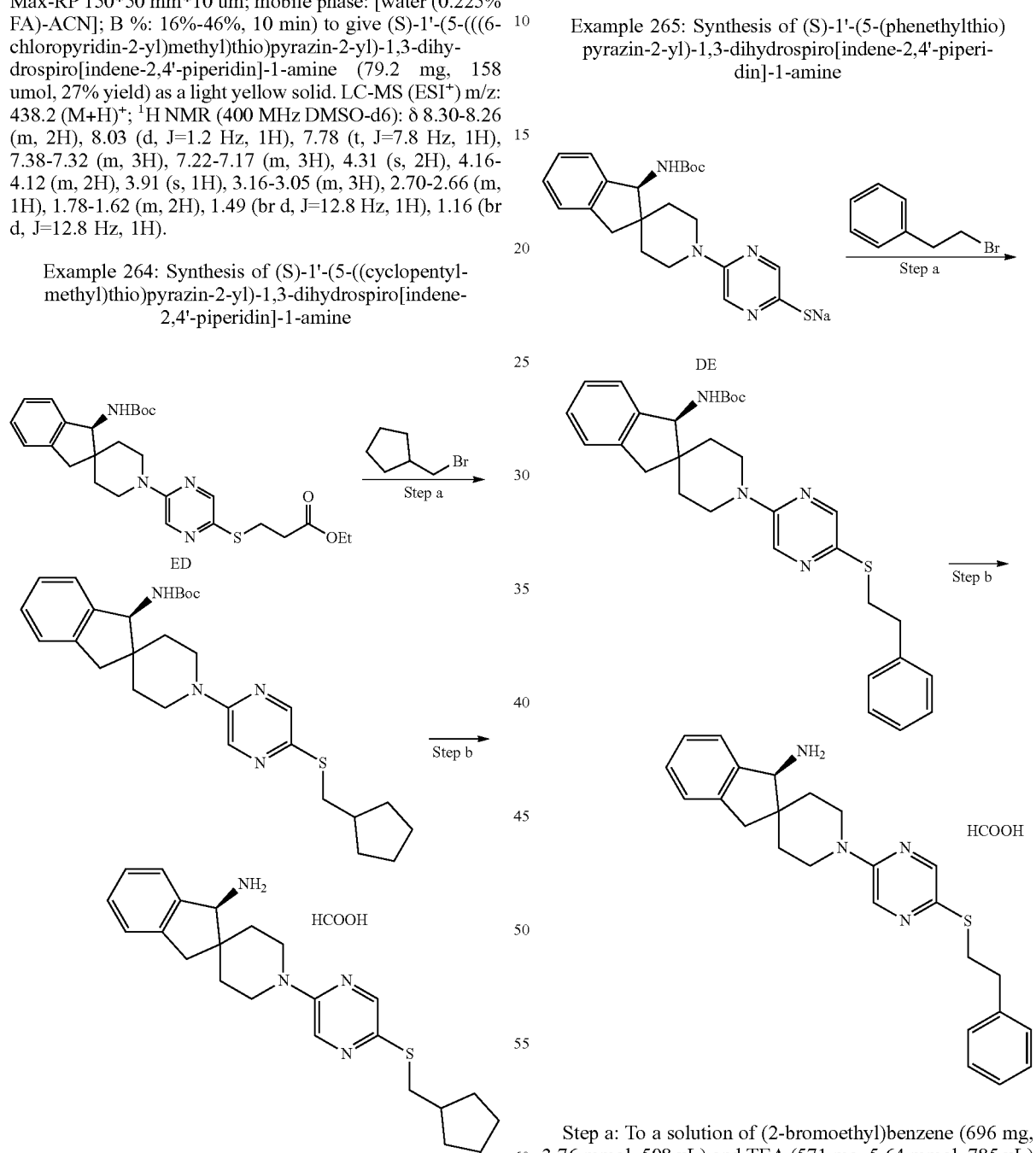

Step a: To a solution of (2-bromoethyl)benzene (696 mg, 3.76 mmol, 508 uL) and TEA (571 mg, 5.64 mmol, 785 uL) in DMF (15.0 mL) was added sodium (S)-5-(1-((tert-butoxycarbonyl)amino)-1,3-dihydrospiro[indene-2,4'-piperidin]-1'-yl)pyrazine-2-thiolate (350 mg, 805 umol, Intermediate DE) at 25° C., and the mixture was stirred at 25° C. for 1 h. The reaction mixture was poured into water (50.0 mL) and extracted with ethyl acetate (50.0 mL×3). The organic layer was washed with brine (50.0 mL×2), dried over Na₂SO₄, filtered and concentrated. The residue was purified by prep-HPLC (column: Phenomenex Synergi C18 150* 25 * 10 um; mobile phase: [water (0.225% FA)-ACN]; B %: 70%-100%, 10 min) to give tert-butyl (S)-(1'-(5-(phenethylthio)pyrazin-2-yl)-1,3-dihydrospiro[indene-2,4'-piperidin]-1-yl)carbamate (130 mg, 30% yield) as a light yellow solid. LC-MS (ESI⁺) m/z: 517.3 (M+H)⁺.

Step b: To a solution of tert-butyl (S)-(1'-(5-(phenethylthio)pyrazin-2-yl)-1,3-dihydrospiro[indene-2,4'-piperidin]-1-yl)carbamate (150 mg, 290 umol) in MeOH (5.00 mL) was added HCl/MeOH (4 M, 2.00 mL) at 25° C., and the mixture was stirred at 25° C. for 12 h. The mixture was then concentrated under vacuum. The residue was dissolved with MeOH (4.00 mL) and pH of the mixture was adjusted to 8~9 with ammonium hydroxide (25~28%). The mixture was purified by prep-HPLC (column: Xtimate C18 150*25 mm*5 um; mobile phase: [water (0.05% ammonia hydroxide v/v)-ACN]; B %: 56%-86%, 10 min) to give a residue. The residue was dissolved with CH₃CN (3.00 mL) and to the mixture was added a solution of HCOOH (78.7 mg, 1.64 mmol) in H₂O (30.0 mL). The mixture was lyophilized to give (S)-1'-(5-(phenethylthio)pyrazin-2-yl)-1,3-dihydrospiro[indene-2,4'-piperidin]-1-amine (57.3 mg, 120 umol, 85% yield) as a light yellow solid. LC-MS (ESI⁺) m/z: 417.2 (M+H)⁺; ¹H NMR (400 MHz DMSO-d6): δ 8.31 (d, J=1.2 Hz, 1H), 8.25 (s, 1H), 8.07 (d, J=1.6 Hz, 1H), 7.35-7.18 (m, 9H), 4.14 (br d, J=13.2 Hz, 2H), 3.94 (s, 1H), 3.27-3.24 (m, 2H), 3.17-3.06 (m, 4H), 2.87 (t, J=7.6 Hz, 2H), 2.69 (d, J=16.0 Hz, 1H), 1.08-1.73 (m, 1H), 1.71-1.63 (m, 1H), 1.50 (br d, J=12.8 Hz, 1H), 1.18 (br d, J=14.4 Hz, 1H).

Example 266: Synthesis of (S)-1'-(5-((cyclopropylmethyl)thio)pyrazin-2-yl)-1,3-dihydrospiro[indene-2,4'-piperidin]-1-amine

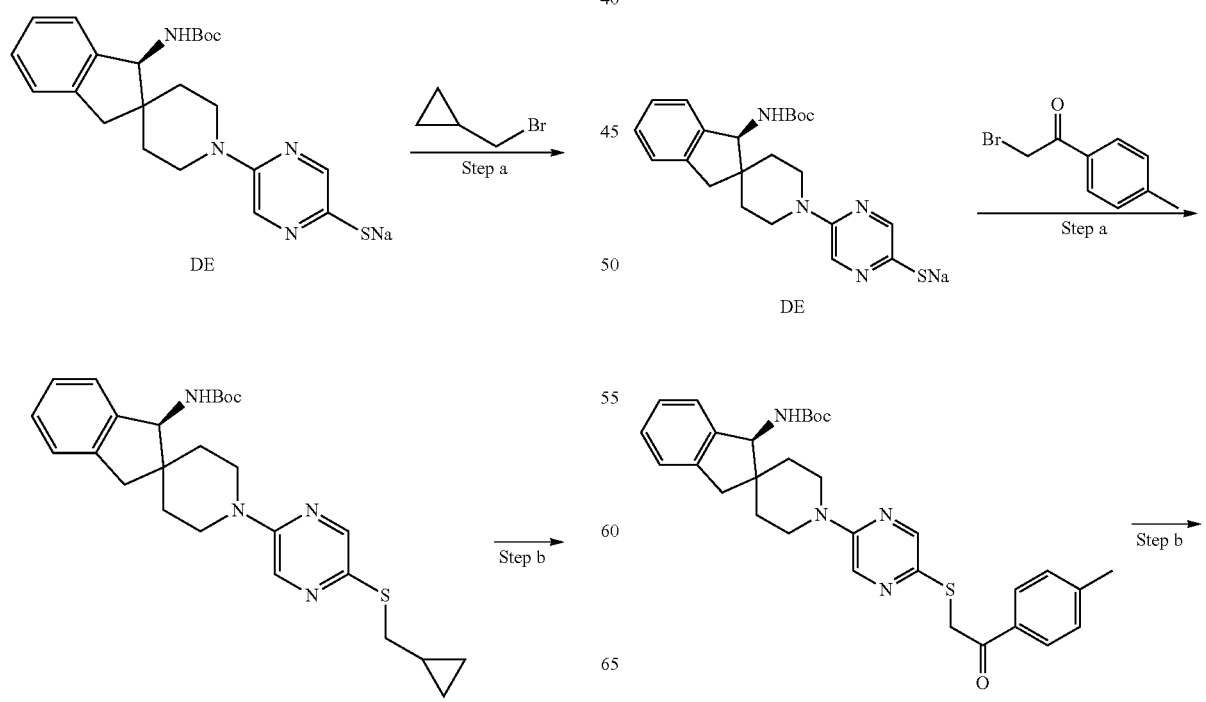

(S)-1'-(5-((cyclopropylmethyl)thio)pyrazin-2-yl)-1,3-dihydrospiro[indene-2,4'-piperidin]-1-amine was synthesized as described for Example 265, coupling sodium (S)-5-(1-((tert-butoxycarbonyl)amino)-1,3-dihydrospiro[indene-2,4'-piperidin]-1'-yl)pyrazine-2-thiolate (Intermediate DE) with (bromomethyl)cyclopropane with TEA as a base in Step a. Characterization of (S)-1'-(5-((cyclopropylmethyl)thio)pyrazin-2-yl)-1,3-dihydrospiro[indene-2,4'-piperidin]-1-amine: LC-MS (ESI⁺) m/z: 350.2 (M−17)⁺; ¹H NMR (400 MHz DMSO-d6): δ 8.28-8.25 (m, 2H), 8.07 (d, J=1.6 Hz, 1H), 7.34-7.33 (m, 1H), 7.22-7.17 (m, 3H), 4.15-4.10 (m, 2H), 3.92 (s, 1H), 3.16-3.05 (m, 4H), 2.95 (d, J=6.8 Hz, 2H), 2.69 (br d, J=10.0 Hz, 1H), 1.80-1.62 (m, 2H), 1.49 (br d, J=3.2 Hz, 1H), 1.17 (br d, J=14.0 Hz, 1H), 1.04-0.97 (m, 1H), 0.51-0.47 (m, 2H), 0.22-0.19 (m, 2H).

Example 267: Synthesis of (S)-2-((5-(1-amino-1,3-dihydrospiro[indene-2,4'-piperidin]-1'-yl)pyrazin-2-yl)thio)-1-(p-tolyl)ethan-1-one

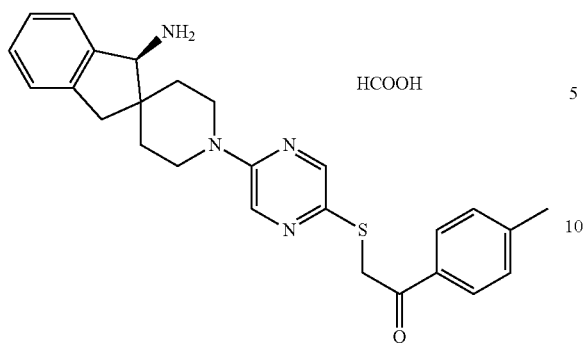

(S)-2-((5-(1-amino-1,3-dihydrospiro[indene-2,4'-piperidin]-1'-yl)pyrazin-2-yl)thio)-1-(p-tolyl)ethan-1-one was synthesized as described for Example 265, coupling sodium (S)-5-(1-((tert-butoxycarbonyl)amino)-1,3-dihydrospiro[indene-2,4'-piperidin]-1'-yl)pyrazine-2-thiolate (Intermediate DE) with 2-bromo-1-(p-tolyl)ethan-1-one (CAS #619-41-0) using TEA as the base in Step a, which was run at rt for 12 h. In Step b, TFA in DCM was used in place of HCl in MeOH for the deprotection. Characterization of (S)-2-((5-(1-amino-1,3-dihydrospiro[indene-2,4'-piperidin]-1'-yl)pyrazin-2-yl)thio)-1-(p-tolyl)ethan-1-one: LC-MS (ESI⁺) m/z: 445.2 (M+H)⁺; ¹H NMR (400 MHz DMSO-d6): δ 8.25-8.22 (m, 2H), 8.06 (d, J=1.2 Hz, 1H), 7.89 (d, J=8.4 Hz, 2H), 7.34 (br d, J=7.6 Hz, 3H), 7.20-7.18 (m, 3H), 4.57 (s, 2H), 4.13 (br d, J=13.6 Hz, 2H), 3.94 (s, 1H), 3.15-3.05 (m, 4H), 2.69 (br d, J=15.6 Hz, 1H), 2.39 (s, 3H), 1.78-1.62 (m, 2H), 1.48 (br d, J=13.6 Hz, 1H), 1.17 (br d, J=13.6 Hz, 1H).

Example 268: Synthesis of (R)-(3-(3-amino-3H-spiro[benzofuran-2,4'-piperidin]-1'-yl)-6-(2,3-dichlorophenyl)-5-methylpyrazin-2-yl)methanol

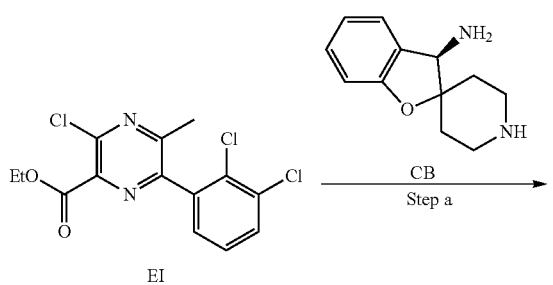

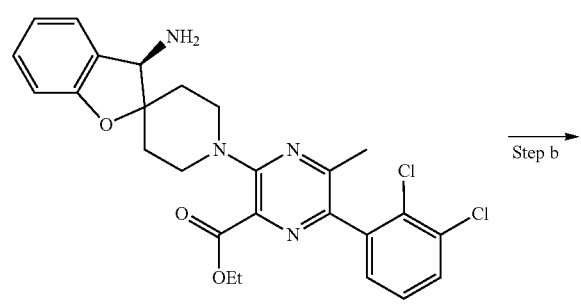

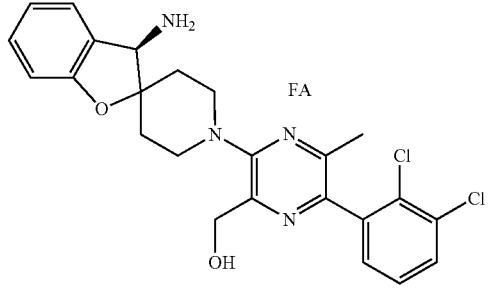

Step a: To a solution of ethyl 3-chloro-6-(2,3-dichlorophenyl)-5-methylpyrazine-2-carboxylate (382 mg, 1.10 mmol, Intermediate EI) and DIPEA (428 mg, 3.31 mmol, 577 uL) in DMF (5.00 mL) was added (R)-3H-spiro[benzofuran-2,4'-piperidin]-3-amine (337 mg, 1.21 mmol, Intermediate CB, 2HCl) at 20° C. The solution was heated to 100° C. and stirred for 15 h. The reaction mixture was diluted with H₂O (20.0 mL), then filtered and the filter cake was dried under reduced pressure to give ethyl (R)-3-(3-amino-3H-spiro[benzofuran-2,4'-piperidin]-1'-yl)-6-(2,3-dichlorophenyl)-5-methylpyrazine-2-carboxylate (498 mg, 88% yield) as a yellow solid. LC-MS (ESI⁺) m/z: 513.4 (M+H)⁺; ¹H NMR (400 MHz MeOD): δ 7.64-7.62 (m, 1H), 7.43-7.39 (m, 2H), 7.37-7.35 (m, 1H), 7.20 (t, J=6.4 Hz, 1H), 6.94-6.70 (m, 1H), 6.82 (d, J=8.0 Hz, 1H), 4.12-4.36 (m, 2H), 4.18 (s, 1H), 4.10-4.93 (m, 2H), 3.55-3.47 (m, 2H), 2.27 (s, 3H), 1.98-1.97 (m, 1H), 1.83-1.82 (m, 3H), 1.39-1.28 (m, 3H).

Step b: To a solution of ethyl (R)-3-(3-amino-3H-spiro[benzofuran-2,4'-piperidin]-1'-yl)-6-(2,3-dichlorophenyl)-5-methylpyrazine-2-carboxylate (498 mg, 970 umol) in DCM (10.0 mL) was added DIBAL-H (1 M, 3.88 mL) at −78° C. under N₂. The solution was stirred at −78° C. for 2 h. The reaction mixture was quenched by addition brine (30.0 mL) at −20° C., and then filtered and the filtrate was extracted with DCM (20.0 mL×3). The combined organic layers were washed with brine (10.0 mL×2), dried over Na₂SO₄ and concentrated under reduced pressure to give a residue, which was purified by pre-HPLC (column: Phenomenex Synergi C18 150*25*10 um; mobile phase: [water (0.225% FA)-ACN]; B %: 30%-60%, 9 min) to give (R)-(3-(3-amino-3H-spiro[benzofuran-2,4'-piperidin]-1'-yl)-6-(2,3-dichlorophenyl)-5-methylpyrazin-2-yl)methanol (30.0 mg, 57.2 umol, 5% yield) as an off-white solid. LC-MS (ESI⁺) m/z: 471.3 (M+H)⁺; ¹H NMR (400 MHz MeOD): δ 8.51 (s, 1H), 7.65-7.63 (m, 1H), 7.47-7.45 (d, J=7.6 Hz, 1H), 7.42-7.41 (d, J=7.6 Hz, 1H), 7.37-7.35 (m, 1H), 7.29 (t, J=5.6 Hz, 1H), 6.97 (t, J=14.4 Hz, 1H), 6.89 (d, J=8.0 Hz, 1H), 4.71 (s, 2H), 4.39 (s, 1H), 3.90 (d, J=13.2 Hz, 1H), 3.75 (d, J=13.6 Hz, 1H), 3.47-3.41 (m, 2H), 2.28 (s, 3H), 2.21 (s, 1H), 2.05-2.01 (m, 2H), 1.89-1.86 (m, 1H).

Example 269: Synthesis of (S)-(3-(1-amino-4-fluoro-1,3-dihydrospiro[indene-2,4'-piperidin]-1'-yl)-6-(2,3-dichlorophenyl)-5-methylpyrazin-2-yl)methanol

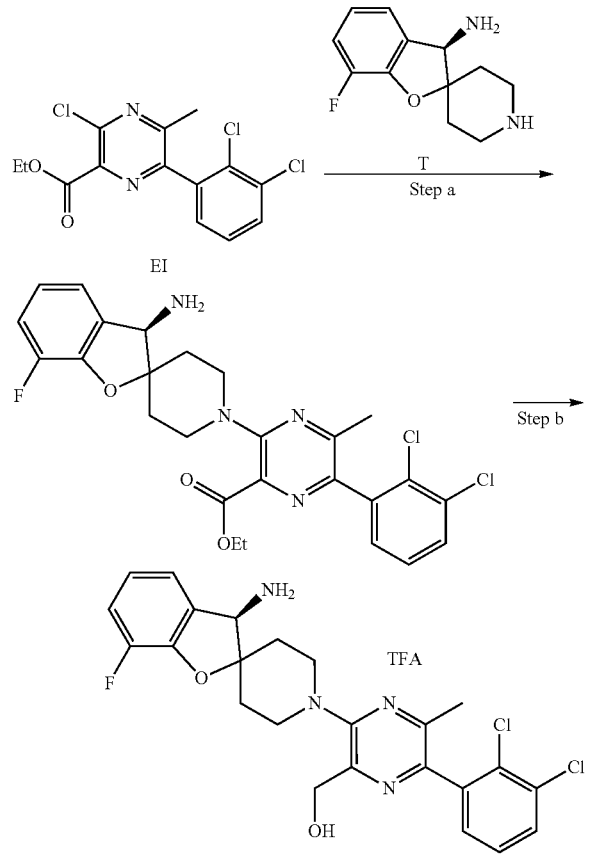

(S)-(3-(1-amino-4-fluoro-1,3-dihydrospiro[indene-2,4'-piperidin]-1'-yl)-6-(2,3-dichlorophenyl)-5-methylpyrazin-2-yl)methanol was synthesized as described above in Example 268, coupling ethyl 3-chloro-6-(2,3-dichlorophenyl)-5-methylpyrazine-2-carboxylate (Intermediate EI) with (S)-4-fluoro-1,3-dihydrospiro[indene-2,4'-piperidin]-1-amine (Intermediate T) in Step a; and allowing Step b to come to rt stirring for 12 hr. (S)-(3-(1-amino-4-fluoro-1,3-dihydrospiro[indene-2,4'-piperidin]-1'-yl)-6-(2,3-dichlorophenyl)-5-methylpyrazin-2-yl)methanol was purified by pre-HPLC (column: Phenomenex Synergi C18 150*25*10 um; mobile phase: [water (0.1% TFA)-ACN]; B %: 30%-60%, 13 min) to give the compound (39.8 mg, 65.5 umol, 7% yield, TFA): LC-MS (ESI$^+$) m/z: 487.1 (M+H)$^+$; $^1$H NMR (400 MHz MeOD): δ 7.64 (dd, J=1.6 Hz, 8.0 Hz, 1H), 7.43 (d, J=7.6 Hz, 1H), 7.41-7.38 (m, 1H), 7.36 (dd, J=1.6 Hz, 7.6 Hz, 2H), 7.16 (t, J=16.4 Hz, 1H), 4.67 (s, 2H), 4.51 (s, 1H), 3.85-3.81 (m, 1H), 3.75-3.72 (m, 1H), 3.26 (d, J=3.2 Hz, 1H), 3.24-3.22 (m, 1H), 3.16 (s, 1H), 3.13-3.12 (m, 1H), 2.27 (s, 3H), 2.08-1.91 (m, 2H), 1.81-1.78 (m, 1H), 1.70-1.67 (m, 1H).

Example 270: Synthesis of (S)-1'-(6-methyl-4-(thiazol-2-yl)pyridin-2-yl)-1,3-dihydrospiro[indene-2,4'-piperidin]-1-amine

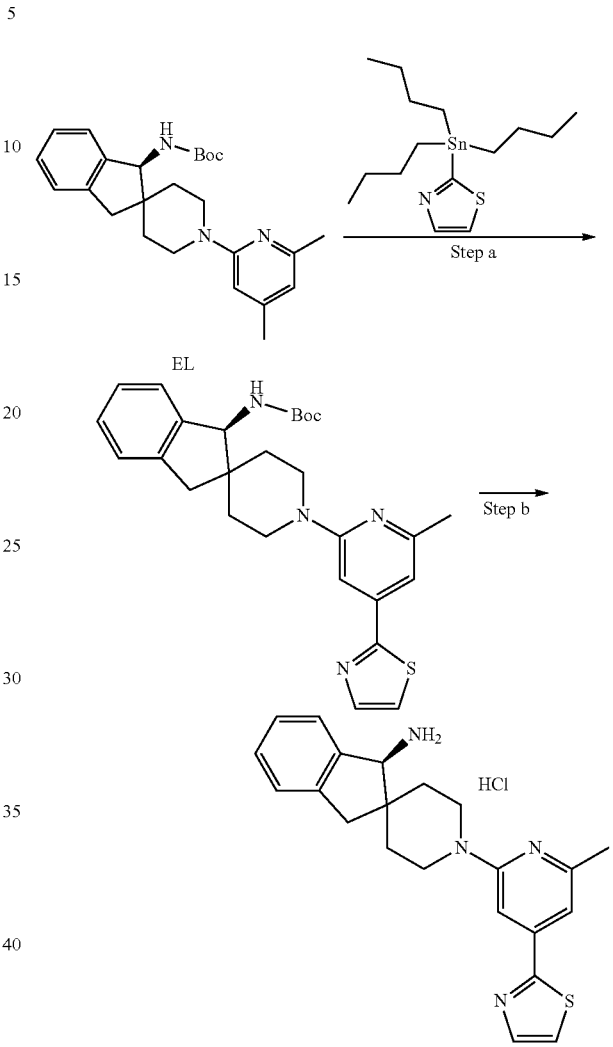

Step a: To a solution of tert-butyl (S)-(1'-(4-iodo-6-methylpyridin-2-yl)-1,3-dihydrospiro[indene-2,4'-piperidin]-1-yl)carbamate (860 mg, 1.66 mmol, Intermediate EL), CsF (755 mg, 4.97 mmol, 183 uL) and Pd(PPh$_3$)$_2$Cl$_2$ (116 mg, 166 umol) in dioxane (20.0 mL) was added 2-(tributylstannyl)thiazole (929 mg, 2.48 mmol, CAS #121359-48-6) under N$_2$, then the mixture was stirred at 100° C. for 3 h. The reaction mixture was poured into water (50.0 mL), then the aqueous phase was extracted with ethyl acetate (50.0 mL×2). The combined organic phase was washed with brine (50.0 mL), dried over Na$_2$SO$_4$, filtered and concentrated in vacuo. The crude product was purified by silica gel chromatography (100-200 mesh silica gel, petroleum ether/ethyl acetate=100/1 to 8/1, Product R$_f$=0.20) to afford tert-butyl (S)-(1'-(6-methyl-4-(thiazol-2-yl)pyridin-2-yl)-1,3-dihydrospiro[indene-2,4'-piperidin]-1-yl)carbamate (580 mg, 1.16 mmol, 70% yield) as a yellow solid. LC-MS (ESI$^+$) m/z: 477.3 (M+H)$^+$.

Step b: To a solution of tert-butyl (S)-(1'-(6-methyl-4-(thiazol-2-yl)pyridin-2-yl)-1,3-dihydrospiro[indene-2,4'-piperidin]-1-yl)carbamate (580 mg, 1.22 mmol) in EtOAc (10.0 mL) was added HCl/EtOAc (4 M, 304 uL), then the mixture was stirred at 25° C. for 1 h. The reaction mixture was concentrated in vacuo to give a crude product, which was diluted with water (20.0 mL). The aqueous phase was extracted ethyl acetate (20.0 mL), then the aqueous phase was lyophilized to afford (S)-1'-(6-methyl-4-(thiazol-2-yl)pyridin-2-yl)-1,3-dihydrospiro[indene-2,4'-piperidin]-1-amine (101.63 mg, 232 umol, 19% yield, HCl) as a yellow solid. LC-MS (ESI+) m/z: 377.2 (M+H)+; 1H NMR (400 MHz DMSO): δ 8.74 (s, 2H), 8.13-8.15 (m, 2H), 7.64 (d, J=7.6 Hz, 1H), 7.51 (s, 1H), 7.28-7.36 (m, 4H), 4.31-4.46 (m, 3H), 3.43-3.49 (m, 2H), 3.25-3.29 (m, 1H), 2.99 (d, J=16.4 Hz, 1H), 2.63 (s, 3H), 1.89-1.99 (m, 2H), 1.59-1.70 (m, 2H).

Example 271: Synthesis of (S)-1'-(3-methyl-5-(methylsulfonyl)phenyl)-1,3-dihydrospiro[indene-2,4'-piperidin]-1-amine

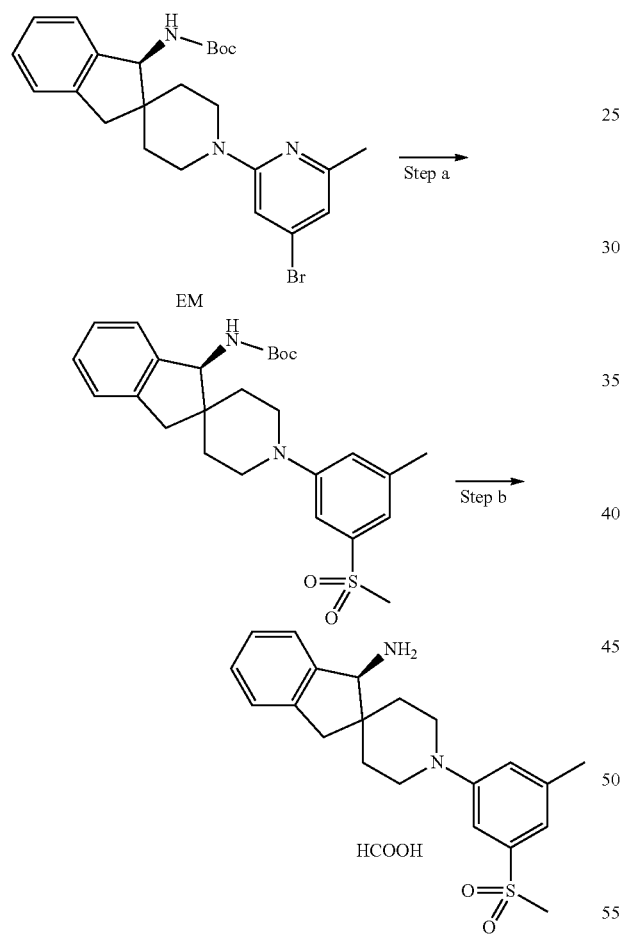

Step a: A mixture of tert-butyl (S)-(1'-(3-bromo-5-methylphenyl)-1,3-dihydrospiro[indene-2,4'-piperidin]-1-yl)carbamate (130 mg, 276 umol, Intermediate EM), MeSO2Na (28.2 mg, 276 umol), L-Proline (6.35 mg, 55.2 umol), K2CO3 (7.62 mg, 55.2 umol) and CuI (5.25 mg, 27.6 umol) in DMSO (4 mL) was irradiated at 140° C. for 2 h under microwave. The reaction mixture was then poured into H2O (40.0 mL), and the aqueous phase was extracted with ethyl acetate (40.0 mL×2). The combined organic phase was washed with brine (40 mL×2), dried with anhydrous Na2SO4, filtered and concentrated in vacuo to give tert-butyl (S)-(1'-(3-methyl-5-(methylsulfonyl)phenyl)-1,3-dihydrospiro[indene-2,4'-piperidin]-1-yl)carbamate (60 mg, 46% yield) as brown oil. LC-MS (ESI+) m/z: 471.2 (M+H)+.

Step b: To a solution of tert-butyl (S)-(1'-(3-methyl-5-(methylsulfonyl)phenyl)-1,3-dihydrospiro[indene-2,4'-piperidin]-1-yl)carbamate (60 mg, 127 umol) in EtOAc (2 mL) was added HCl/EtOAc (4 M, 319 uL) at 25° C. for 1 h. The reaction mixture was concentrated in vacuo to give residue, and then the residue was diluted with water (20.0 mL). The aqueous phase was extracted with ethyl acetate (20.0 mL×2), then the aqueous phase was concentrated in vacuo. The crude product was purified by pre HPLC (column: Phenomenex Synergi C18 150*25*10 um; mobile phase: [water (0.225% FA)-ACN]; B %: 6%-36%, 10 min), and the eluent was concentrated in vacuo to remove ACN. The residual aqueous solution was lyophilized to afford (S)-1'-(3-methyl-5-(methylsulfonyl)phenyl)-1,3-dihydrospiro[indene-2,4'-piperidin]-1-amine (7.40 mg, 17.4 umol, 14% yield, FA) as a yellow solid. LC-MS (ESI+) m/z: 317.2 (M+H)+; 1H NMR (400 MHz MeOD-d4): δ 7.48-7.50 (m, 1H), 7.29-7.37 (m, 4H), 7.19 (s, 1H), 7.14 (s, 1H), 4.35-4.37 (m, 1H), 3.65-3.77 (m, 2H), 3.05-3.16 (m, 7H), 2.40 (s, 3H), 1.84-1.98 (m, 2H), 1.62-1.74 (m, 2H).

Example 272: Synthesis of (S)-1'-(6-((cyclopropylmethyl)thio)pyridin-3-yl)-1,3-dihydrospiro[indene-2,4'-piperidin]-1-amine formate

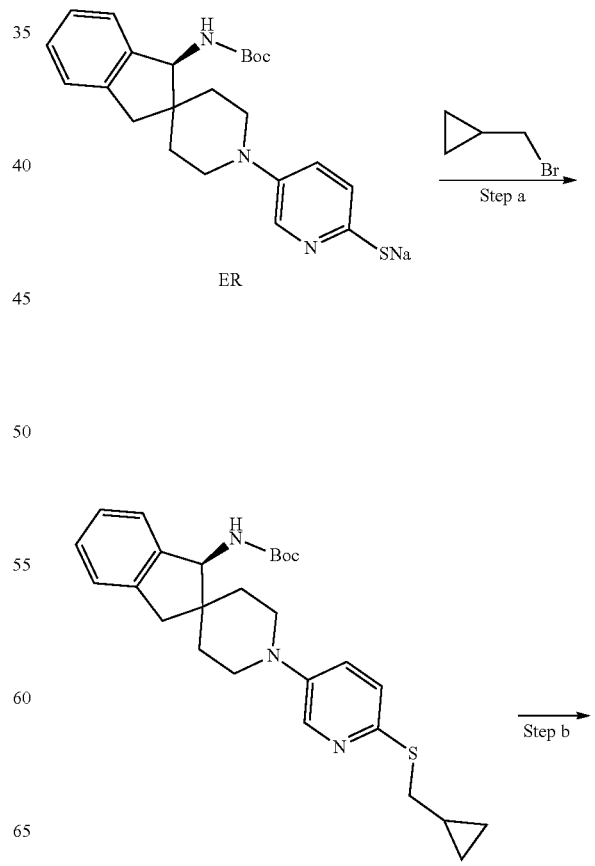

-continued

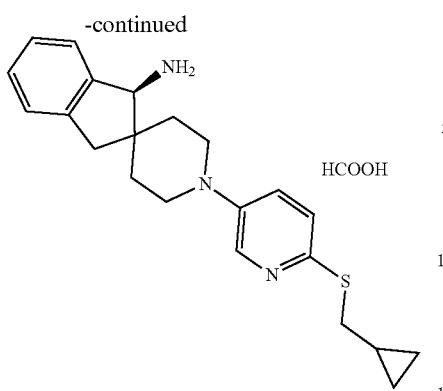

Step a: To a solution of sodium (S)-5-(1-((tert-butoxycarbonyl)amino)-1,3-dihydrospiro[indene-2,4'-piperidin]-1'-yl)pyridine-2-thiolate (423 mg, 977 umol, Intermediate ER) in DMF (10.0 mL) was added TEA (692 mg, 6.84 mmol, 952 uL) and (bromomethyl)cyclopropane (613 mg, 4.54 mmol, 435 uL) at 25° C. and the mixture was stirred at 25° C. for 2 h. The reaction mixture was then poured into water (50.0 mL) and extracted with ethyl acetate (50.0 mL×3). The organic layer was washed with brine (50.0 mL×2), dried over Na$_2$SO$_4$, filtered and concentrated to give tert-butyl (S)-(1'-(6-((cyclopropylmethyl)thio)pyridin-3-yl)-1,3-dihydrospiro[indene-2,4'-piperidin]-1-yl)carbamate (500 mg, quant. crude yield) as a yellow solid. LC-MS (ESI$^+$) m/z: 466.3 (M+H)$^+$.

Step b: To a solution of tert-butyl (S)-(1'-(6-((cyclopropylmethyl)thio)pyridin-3-yl)-1,3-dihydrospiro[indene-2,4'-piperidin]-1-yl)carbamate (500 mg, 1.07 mmol) in DCM (10.0 mL) was added TFA (1.50 mL, 20.2 mmol,) at 25° C., and the mixture was stirred at 25° C. for 16 h The mixture was then adjusted the pH to 7~8 with saturated NaHCO$_3$ solution and extracted with DCM (20.0 mL×3). The organic layer was washed with brine (20.0 mL×2), dried over Na$_2$SO$_4$, filtered and concentrated. The residue was purified by prep-HPLC (column: Phenomenex Synergi C18 150*25*10 um; mobile phase: [water (0.2% FA)-ACN]; B %: 10%-40%, 11 min) to give (S)-1'-(6-((cyclopropylmethyl)thio)pyridin-3-yl)-1,3-dihydrospiro[indene-2,4'-piperidin]-1-amine formate (60.7 mg, 141 umol, 13% yield, FA) as a yellow solid. LC-MS (ESI$^+$) m/z: 366.3 (M+H)$^+$; $^1$H NMR (400 MHz DMSO-d6): δ 8.26 (s, 1H), 8.19 (d, J=3.0 Hz, 1H), 7.38 (t, J=3.6 Hz, 1H), 7.30 (dd, J=3.0, 8.8 Hz, 1H), 7.23-7.19 (m, 3H), 7.13 (d, J=8.8 Hz, 1H), 4.01 (s, 1H), 3.56 (br d, J=12.6 Hz, 2H), 3.06-2.99 (m, 3H), 2.94-2.83 (m, 2H), 2.69 (d, J=16.2 Hz, 1H), 1.91-1.72 (m, 2H), 1.50 (br d, J=13.2 Hz, 1H), 1.27 (br d, J=11.4 Hz, 1H), 1.11-0.99 (m, 1H), 0.53-0.46 (m, 2H), 0.28-0.20 (m, 2H).

Example 273: Synthesis of (R)-1'-(5-((cyclopropylmethyl)thio)pyrazin-2-yl)-3H-spiro[benzofuran-2,4'-piperidin]-3-amine

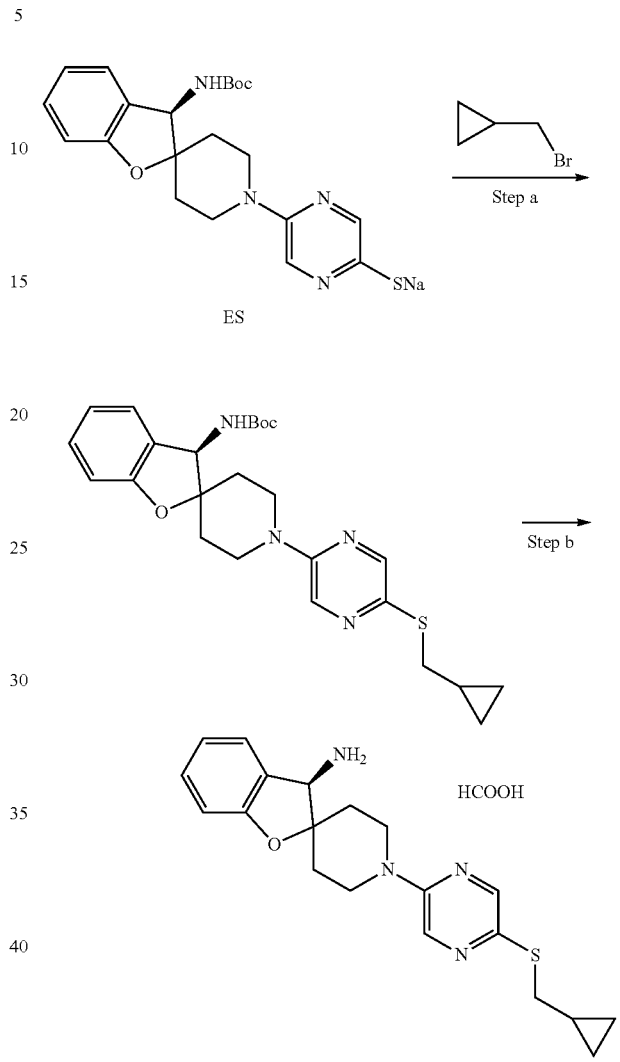

(R)-1'-(5-((cyclopropylmethyl)thio)pyrazin-2-yl)-3H-spiro[benzofuran-2,4'-piperidin]-3-amine was synthesized as described above for Example 272, coupling sodium (R)-5-(3-((tert-butoxycarbonyl)amino)-3H-spiro[benzofuran-2,4'-piperidin]-1'-yl)pyrazine-2-thiolate (Intermediate ES) and (bromomethyl)cyclopropane in Step a. Characterization of (R)-1'-(5-((cyclopropylmethyl)thio)pyrazin-2-yl)-3H-spiro[benzofuran-2,4'-piperidin]-3-amine: LC-MS (ESI$^+$) m/z: 369.2 (M+H)$^+$; $^1$H NMR (400 MHz MeOD-d4): δ 8.45 (s, 1H), 8.21 (d, J=1.4 Hz, 1H), 8.12 (d, J=1.6 Hz, 1H), 7.47 (d, J=7.6 Hz, 1H), 7.35-7.31 (m, 1H), 7.02-6.98 (m, 1H), 6.92 (d, J=8.0 Hz, 1H), 4.43-4.40 (m, 2H), 4.23 (br d, J=13.2 Hz, 1H), 3.45-3.39 (m, 2H), 2.95 (d, J=7.2 Hz, 2H), 2.05-2.01 (m, 2H), 1.85-1.81 (m, 2H), 1.05-1.02 (m, 1H), 0.54-0.51 (m, 2H), 0.21-0.20 (m, 2H).

Example 274: Synthesis of (1'R,2r,3R,5'S)-8'-(5-((cyclopropylmethyl)thio)pyrazin-2-yl)-3H-8'-azaspiro[benzofuran-2,3'-bicyclo[3.2.1]octan]-3-amine

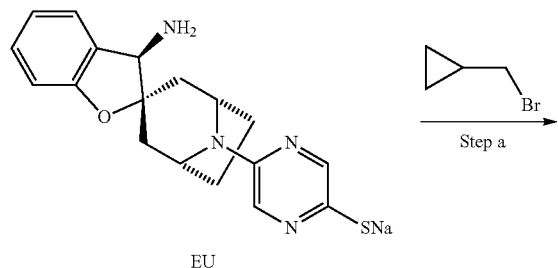

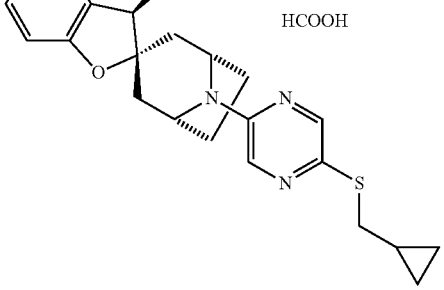

(1'R,2r,3R,5'S)-8'-(5-((cyclopropylmethyl)thio)pyrazin-2-yl)-3H-8'-azaspiro[benzofuran-2,3'-bicyclo[3.2.1]octan]-3-amine was synthesized as described above for Example 272, coupling sodium 5-((1'R,2r,3R,5'S)-3-((tert-butoxycarbonyl)amino)-3H-8'-azaspiro[benzofuran-2,3'-bicyclo[3.2.1]octan]-8'-yl)pyrazine-2-thiolate (Intermediate EU) and (bromomethyl)cyclopropane in Step a. Characterization of (1'R,2r,3R,5'S)-8'-(5-((cyclopropylmethyl)thio)pyrazin-2-yl)-3H-8'-azaspiro[benzofuran-2,3'-bicyclo[3.2.1]octan]-3-amine: LC-MS (ESI$^+$) m/z: 378.1 (M-NH$_2$)*; $^1$H NMR (400 MHz DMSO-d6): δ 8.20-8.19 (m, 2H), 8.09 (s, 1H), 7.24 (d, J=7.2 Hz, 1H), 7.14 (t, J=7.6 Hz, 1H), 6.84 (t, J=7.2 Hz, 1H), 6.77 (d, J=8.0 Hz, 1H), 4.66 (s, 1H), 4.58 (s, 1H), 3.85 (s, 1H), 2.96 (d, J=7.2 Hz, 2H), 2.30 (d, J=7.2 Hz, 2H), 2.26-2.22 (m, 1H), 1.97-1.92 (m, 3H), 1.74 (d, J=14.8 Hz, 1H), 1.62 (d, 15.2 Hz, 1H), 1.04-1.01 (m, 1H), 0.50 (d, J=7.6 Hz, 2H), 0.21 (d, J=4.8 Hz, 2H).

Examples 275, 276, & 277: Syntheses of (1s, 3'S, 4R)-4-{5-[(2,3-dichloropyridin-4-yl)sulfanyl]pyrazin-2-yl}-1',3'-dihydrospiro[cyclohexane-1,2'-inden]-3'-amine, (1s, 3'R, 4S)-4-{5-[(2,3-dichloropyridin-4-yl)sulfanyl]pyrazin-2-yl}-1',3'-dihydrospiro[cyclohexane-1,2'-inden]-3'-amine and (1r, 4r)-4-(5-((2,3-dichloropyridin-4-yl)thio)pyrazin-2-yl)-1',3'-dihydrospiro[cyclohexane-1,2'-inden]-1'-amine

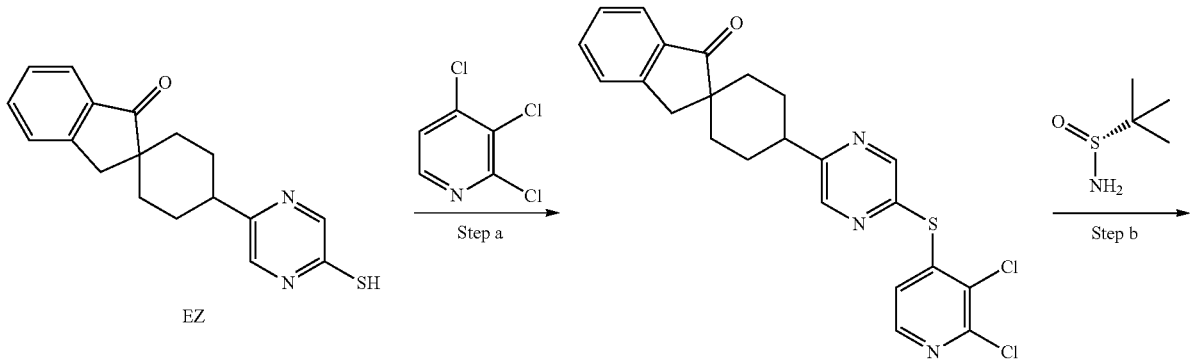

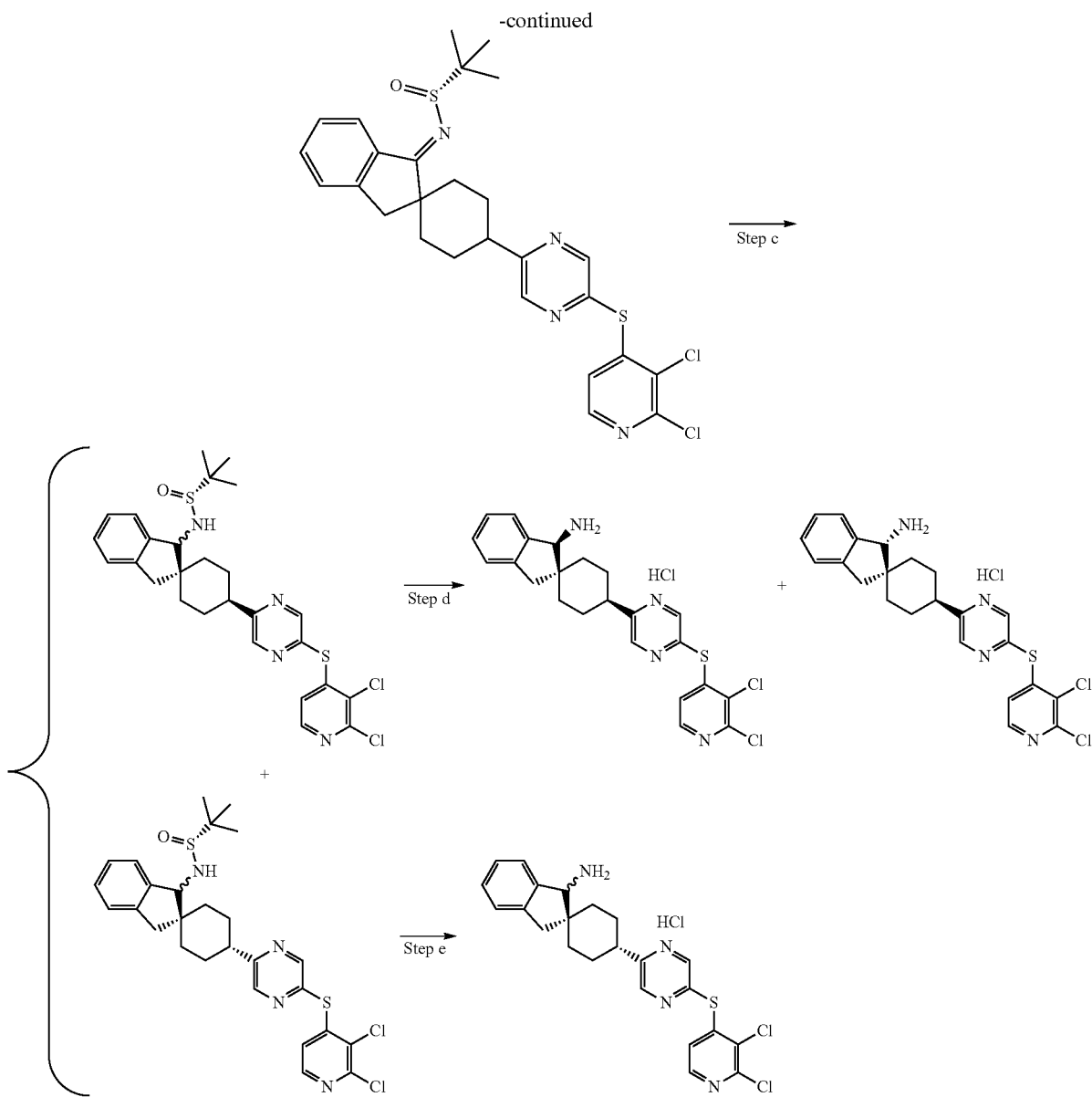

Step a: A mixture of 4-(5-sulfanylpyrazin-2-yl)-1',3'-dihydrospiro[cyclohexane-1,2'-inden]-3'-one (137.0 mg, 441 µmol, Intermediate EZ), 2,3,4-trichloropyridine (120.0 mg, 661 µmol) and TEA (304 µL, 2.20 mmol) in DMF (5.00 mL) was stirred at 70° C. for 12 hour under $N_2$. The reaction mixture was then diluted with EtOAc (100 mL), washed with $H_2O$ (20 mL×3), brine (40 mL×2), dried over anhydrous $Na_2SO_4$, filtered and concentrated to give a residue. The residue was purified by flash silica gel chromatography (12 g column, EtOAc in petroleum ether from 0% 20%) to give 4-{5-[(2,3-dichloropyridin-4-yl)sulfanyl]pyrazin-2-yl}-1',3'-dihydrospiro[cyclohexane-1,2'-inden]-3'-one (200.0 mg, 99% yield) as a colorless oil. LC-MS (ESI$^+$) m/z: 456.0 (M+H)$^+$.

Step b: To a solution of 4-{5-[(2,3-dichloropyridin-4-yl)sulfanyl]pyrazin-2-yl}-1',3'-dihydrospiro[cyclohexane-1,2'-inden]-3'-one (200 mg, 438 µmol) and Ti(OEt)$_4$ (899 µL, 4.37 mmol) in 2-Me-THF (1.00 mL) was added (R)-2-methylpropane-2-sulfinamide (212.0 mg, 1.75 mmol). The reaction mixture was stirred at 95° C. for 48 h under $N_2$. The mixture was then cooled to rt and used in the next step directly. LC-MS (ESI$^+$) m/z: 559.1, 561.0 (M+H)$^+$.

Step c: To the mixture of (R)—N-(4-{5-[(2,3-dichloropyridin-4-yl)sulfanyl]pyrazin-2-yl}-1',3'-dihydrospiro[cyclohexane-1,2'-inden]-3'-ylidene)-2-methylpropane-2-sulfinamide (240 mg, 428 µmol) in 2-Me-THF (5.00 mL) was added NaBH$_4$ (32.3 mg, 856 µmol) at 20° C. The mixture was stirred at 20° C. for 1 hour. The reaction was then quenched with MeOH (1 mL). The mixture was diluted with EtOAc (50 mL) and $H_2O$ (20 mL) and the mixture was stirred at 25° C. for 5 min, where white solid formed. The mixture was filtered and the partitioned layers of the filtrate were separated. The aqueous layer was extracted with ethyl acetate (20 mL×3). The combined organic layers were washed with brine (30 mL), dried over anhydrous $Na_2SO_4$, filtered and concentrated to give a residue. The residue was purified by flash silica gel chromatography (petroleum ether: ethyl acetate=100:0 to 100:60) and prep-TLC (petroleum ether/ethyl acetate=1:1) to afford two products (R)—N-((1s, 4S)-4-(5-((2,3-dichloropyridin-4-yl)thio)pyrazin-2-yl)-1',3'-dihydrospiro[cyclohexane-1,2'-inden]-1'-yl)-2-methylpropane-2-sulfinamide and (R)—N-((1r, 4R)-4-(5-((2,3-dichloropyridin-4-yl)thio)pyrazin-2-yl)-1',3'-dihydrospiro[cyclohexane-1,2'-inden]-1'-yl)-2-methylpropane-2-sulfinamide. The major product (R)—N-((s, 4S)-4-(5-((2,3-dichloropyridin-4-yl)thio)pyrazin-2-yl)-1',3'-dihydrospiro[cyclohexane-1,2'-inden]-1'-yl)-2-methylpropane-2-sulfinamide (40.0 mg, 71.2 μmol) was obtained as a colorless oil, LC-MS (ESI$^+$) m/z: 561.1 (M+H)$^+$. The product (R)—N-((1r, 4R)-4-(5-((2,3-dichloropyridin-4-yl)thio)pyrazin-2-yl)-1',3'-dihydrospiro[cyclohexane-1,2'-inden]-1'-yl)-2-methylpropane-2-sulfinamide (40.0 mg, 16% yield) was obtained as a colorless oil, LC-MS (ESI$^+$) m/z: 560.9 (M+H)$^+$. The absolute configuration of the diastereomers was arbitrarily assigned.

Step d: (R)-2-Methyl-N-[(is, 4s)-4-{5-[(2,3-dichloropyridin-4-yl)sulfanyl]pyrazin-2-yl}-1',3'-dihydrospiro[cyclohexane-1,2'-inden]-3'-yl]propane-2-sulfinamide (40.0 mg, 71.2 μmol) was dissolved in HCl/MeOH (2 mL, 4 M). The mixture was stirred at 25° C. for 1 hour. Then the mixture was concentrated and was purified by prep-HPLC (HCl) to afford two diastereoisomers. The absolute configuration of the diastereomers was arbitrarily assigned. The product (Is, 3'S, 4R)-4-{5-[(2,3-dichloropyridin-4-yl)sulfanyl]pyrazin-2-yl}-1',3'-dihydrospiro[cyclohexane-1,2'-inden]-3'-amine hydrochloride (11.2 mg, 22.6 μmol, HCl salt, 32% yield) was obtained as a white solid. LC-MS (ESI$^+$) m/z: 439.9 (M-NH$_2$)$^+$; $^1$H NMR (400 MHz, CD$_3$OD) δ 8.79 (d, J=1.3 Hz, 1H), 8.68 (d, J=1.3 Hz, 1H), 8.14 (d, J=5.3 Hz, 1H), 7.52 (d, J=7.4 Hz, 1H), 7.46-7.29 (m, 3H), 7.13 (d, J=5.4 Hz, 1H), 4.37 (s, 1H), 3.16 (d, J=6.3 Hz, 2H), 3.05-2.91 (m, 1H), 2.07 (br d, J=3.1 Hz, 1H), 2.02-1.70 (m, 7H). The product (Is, 3'R, 4S)-4-{5-[(2,3-dichloropyridin-4-yl)sulfanyl]pyrazin-2-yl}-1',3'-dihydrospiro[cyclohexane-1,2'-inden]-3'-amine hydrochloride (1.0 mg, HCl salt, 3% yield) as a white solid. LC-MS (ESI$^+$) m/z: 439.9 (M-NH$_2$)$^+$; $^1$H NMR (400 MHz, CD$_3$OD) δ 8.83-8.77 (m, 1H), 8.71-8.59 (m, 1H), 8.18-8.11 (m, 1H), 7.51 (d, J=7.5 Hz, 1H), 7.45-7.31 (m, 3H), 7.13 (d, J=5.3 Hz, 1H), 4.36 (s, 1H), 3.25-3.09 (m, 2H), 3.03-2.88 (m, 1H), 2.14-2.04 (m, 1H), 2.00-1.72 (m, 7H). SFC: e.e. = 100%, Column: Chiralpak AS-3 100×4.6 mm I.D., 3 um. Mobile phase: A: CO$_2$, B: ethanol (0.05% DEA). Gradient: from 5% to 40% of B in 4 min and hold 40% for 2.5 min, then 5% of B for 1.5 min Flow rate: 2.8 mL/min. Column temp.: 35° C. ABPR: 1500 psi.

Step e: (R)-2-methyl-N-[(r,4r)-4-{5-[(2,3-dichloropyridin-4-yl)sulfanyl]pyrazin-2-yl}-1',3'-dihydrospiro[cyclohexane-1,2'-inden]-3'-yl]propane-2-sulfinamide (20.0 mg, 35.6 μmol) was dissolved in HCl/MeOH (2.00 mL, 4 M). The mixture was stirred at 25° C. for 1 hour. The reaction mixture was concentrated and purified by prep-HPLC (HCl) to afford (1r, 4r)-4-(5-((2,3-dichloropyridin-4-yl)thio)pyrazin-2-yl)-1',3'-dihydrospiro[cyclohexane-1,2'-inden]-1'-amine hydrochloride (4.0 mg, 23% yield) as a white solid. The absolute configuration was arbitrarily assigned. LC-MS (ESI$^+$) m/z: 440.0 (M-NH$_2$)$^+$; $^1$H NMR (400 MHz, CD$_3$OD) δ 8.79 (s, 1H), 8.72-8.64 (m, 1H), 8.20-8.09 (m, 1H), 7.60-7.48 (m, 1H), 7.46-7.29 (m, 3H), 7.19-7.08 (m, 1H), 4.69 (s, 0.60H), 4.36 (s, 0.36H), 3.28-3.12 (m, 1H), 3.11-2.92 (m, 1H), 2.79 (d, J=16.3 Hz, 1H), 2.16-1.54 (m, 8H). SFC: Column: Chiralcel OJ-3 100×4.6 mm I.D., 3 um. Mobile phase: A: CO$_2$, B: ethanol (0.05% DEA). Gradient: from 5% to 40% of B in 4 min and hold 40% for 2.5 min, then 5% of B for 1.5 min Flow rate: 2.8 mL/min. Column temp.: 35° C. ABPR: 1500 psi.

Example 278: Synthesis of (3R)-6-fluoro-1'-[5-methyl-3-(piperidin-1-yl)-1H-Pyrazolo[3,4-b]pyrazin-6-yl]-3H-spiro[1-benzofuran-2,4'-piperidin]-3-amine

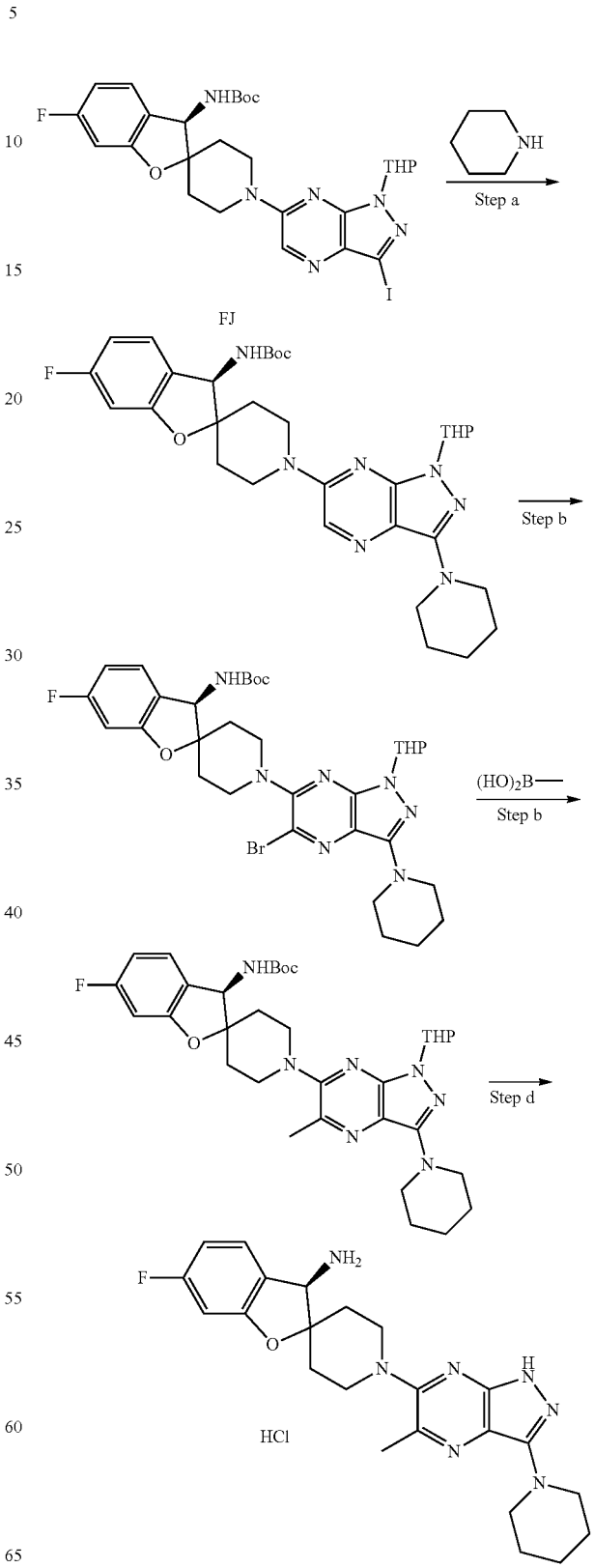

Step a: A mixture of tert-butyl N-[(3R)-6-fluoro-1'-[3-iodo-1-(oxan-2-yl)-1H-pyrazolo[3,4-b]pyrazin-6-yl]-3H-spiro[1-benzofuran-2,4'-piperidin]-3-yl]carbamate (1.3.0 g, 2.0 mmol, Intermediate FJ), piperidine (546.0 μL, 6.0 mmol), Cs₂CO₃ (1.95 g, 6.0 mmol) and XantPhos-Pd-G4 (191.0 mg, 199.0 μmol) in toluene (30.0 mL) was stirred at 100° C. for 12 hours under N₂ atmosphere. The mixture was then concentrated in vacuo to give a residue, which was purified by silica gel chromatography (ethyl acetate in petroleum ether=0% to 35%) to afford tert-butyl N-[(3R)-6-fluoro-1'-[1-(oxan-2-yl)-3-(piperidin-1-yl)-1H-pyrazolo[3,4-b]pyrazin-6-yl]-3H-spiro[1-benzofuran-2,4'-piperidin]-3-yl]carbamate (510.0 mg, 43% yield) as a yellow solid. LC-MS (ESI⁺) m/z: 608.1 (M+H)⁺.

Step b: To a mixture of tert-butyl N-[(3R)-6-fluoro-1'-[1-(oxan-2-yl)-3-(piperidin-1-yl)-1H-pyrazolo[3,4-b]pyrazin-6-yl]-3H-spiro[1-benzofuran-2,4'-piperidin]-3-yl]carbamate (510.0 mg, 839.0 μmol) in MeCN (10.0 mL) and AcOH (10.0 mL) was added NBS (221.0 mg, 1.3 mmol), and the resulting mixture was stirred at 15° C. for 1 hour. The mixture was then concentrated in vacuo to give a residue, which was purified by silica gel chromatography (ethyl acetate in petroleum ether=0% to 25%) to afford tert-butyl N-[(3R)-1'-[5-bromo-1-(oxan-2-yl)-3-(piperidin-1-yl)-1H-pyrazolo[3,4-b]pyrazin-6-yl]-6-fluoro-3H-spiro[1-benzofuran-2,4'-piperidin]-3-yl]carbamate (330.0 mg, 57% yield) as a yellow solid. LC-MS (ESI⁺) m/z: 686.1 (M+H)⁺.

Step c: A mixture of tert-butyl N-[(3R)-1'-[5-bromo-1-(oxan-2-yl)-3-(piperidin-1-yl)-1H-pyrazolo[3,4-b]pyrazin-6-yl]-6-fluoro-3H-spiro[1-benzofuran-2,4'-piperidin]-3-yl]carbamate (330.0 mg, 480.0 μmol), methylboronic acid (143.0 mg, 2.4 mmol), K₂CO₃ (165.0 mg, 1.2 mmol) and Pd(dppf)Cl₂ (35.1 mg, 48.0 μmol) in 1,4-dioxane (15.0 mL) and H₂O (5.0 mL) was stirred at 90° C. for 12 hours under N₂ atmosphere. The mixture was then concentrated in vacuo to give a residue, which was purified by silica gel chromatography (ethyl acetate in petroleum ether=0% to 25%) to afford tert-butyl N-[(3R)-6-fluoro-1'-[5-methyl-1-(oxan-2-yl)-3-(piperidin-1-yl)-1H-pyrazolo[3,4-b]pyrazin-6-yl]-3H-spiro[1-benzofuran-2,4'-piperidin]-3-yl]carbamate (200.0 mg, 67% yield) as a yellow solid. LC-MS (ESI⁺) m/z 622.2 (M+H)⁺.

Step d: A mixture of tert-butyl N-[(3R)-6-fluoro-1'-[5-methyl-1-(oxan-2-yl)-3-(piperidin-1-yl)-1H-pyrazolo[3,4-b]pyrazin-6-yl]-3H-spiro[1-benzofuran-2,4'-piperidin]-3-yl]carbamate (200.0 mg, 321.0 μmol) in HCl/MeOH (4M, 10.0 mL) was stirred at 15° C. for 1 hour. The mixture was then concentrated under reduced pressure to give a residue, which was purified by prep-HPLC (HCl) to afford (3R)-6-fluoro-1'-[5-methyl-3-(piperidin-1-yl)-1H-pyrazolo[3,4-b]pyrazin-6-yl]-3H-spiro[1-benzofuran-2,4'-piperidin]-3-amine hydrochloride (102.1 mg, 67% yield) as a yellow solid. LC-MS (ESI⁺) m/z: 438.1 (M+H)⁺; ¹H NMR (400 MHz, CD₃OD) δ 7.61-7.58 (m, 1H), 6.86-6.79 (m, 2H), 4.73 (s, 1H), 4.24-4.15 (m, 1H), 4.08-3.90 (m, 5H), 3.56-3.43 (m, 2H), 2.68 (s, 3H), 2.40-2.32 (m, 1H), 2.19-1.96 (m, 3H), 1.87-1.74 (m, 6H).

Examples 279 & 280: Syntheses of (1s,3'S,4R)-4-{6-[(2,3-dichloropyridin-4-yl)sulfanyl]pyridin-3-yl}-1',3'-dihydrospiro[cyclohexane-1,2'-inden]-3'-amine and (1s,1'R,4S)-4-(6-((2,3-dichloropyridin-4-yl)thio)pyridin-3-yl)-1',3'-dihydrospiro[cyclohexane-1,2'-inden]-1'-amine

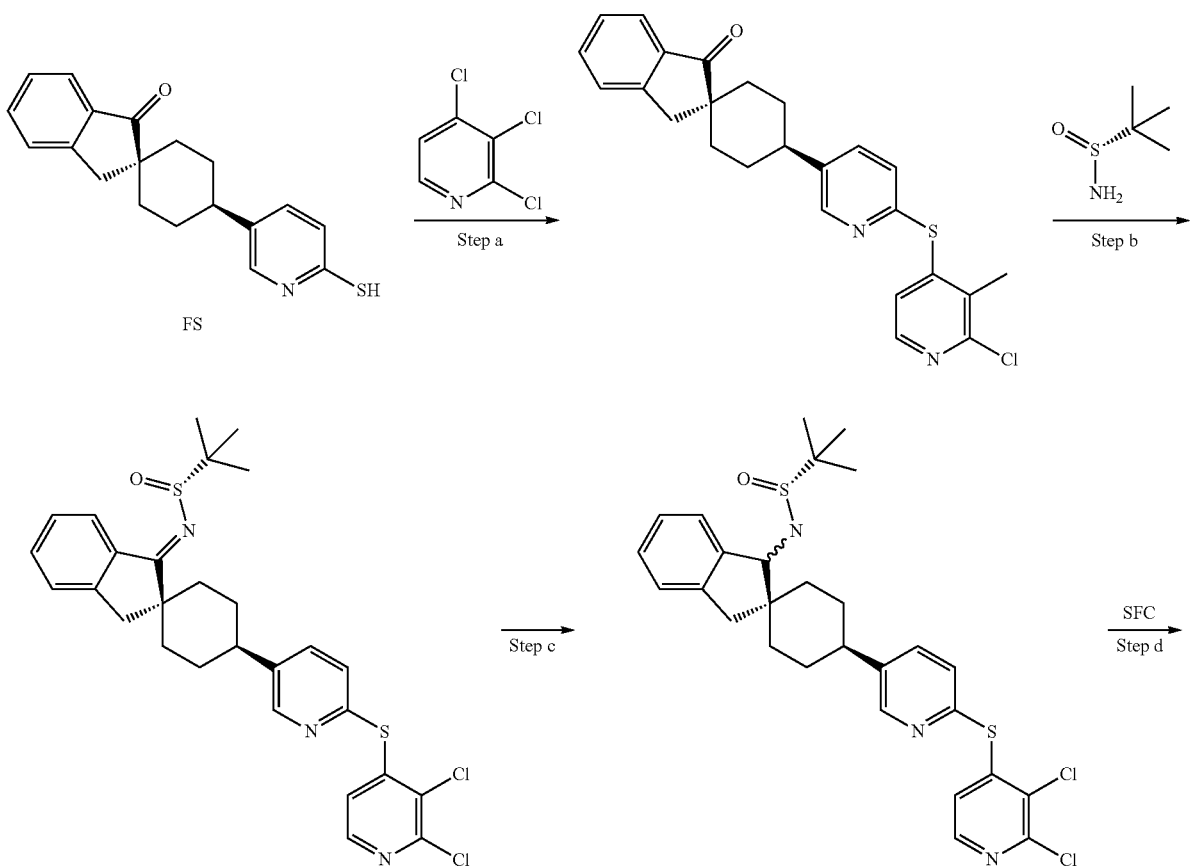

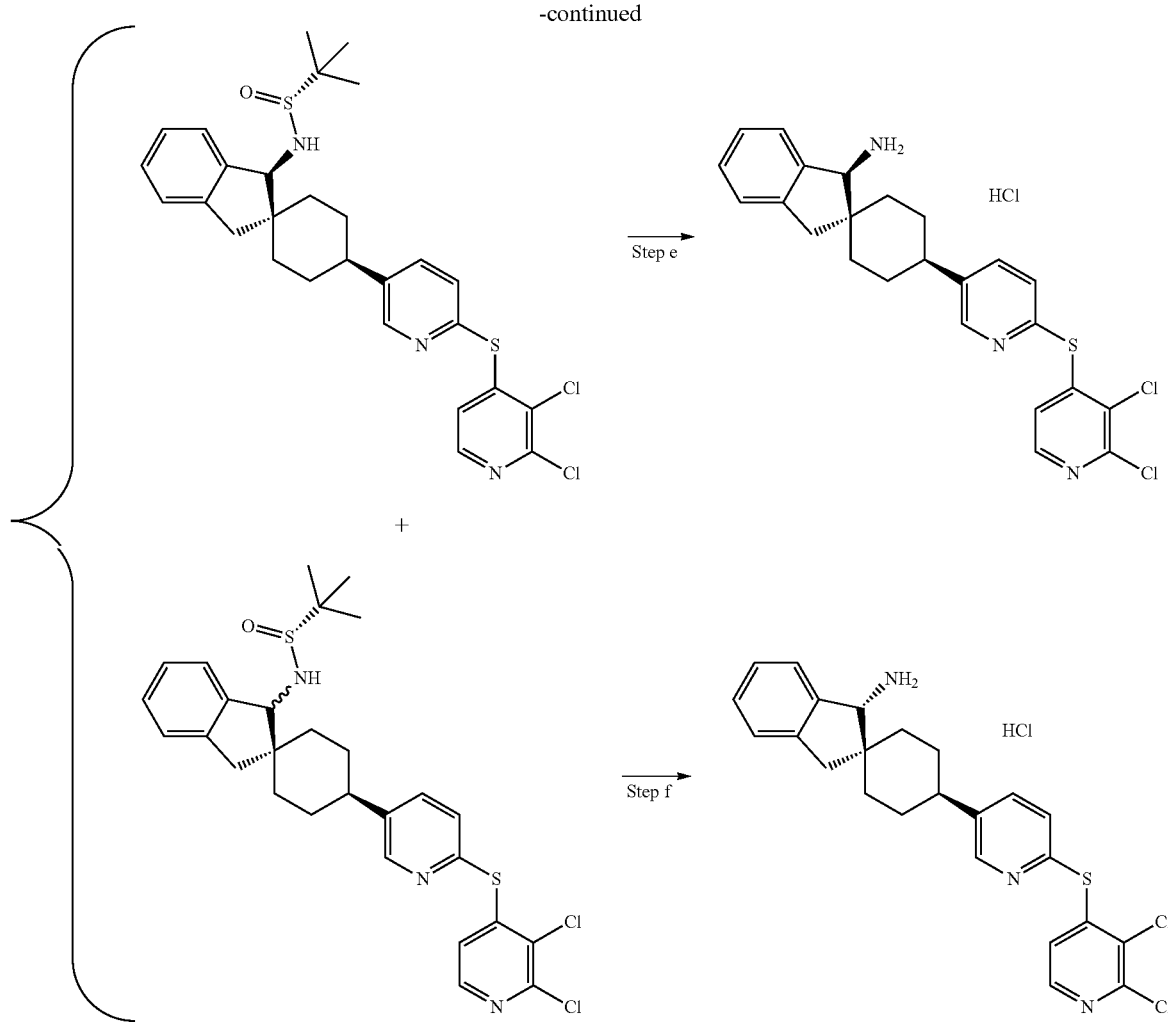

Step a: A mixture of (1s,4s)-4-(6-sulfanylpyridin-3-yl)-1',3'-dihydrospiro[cyclohexane-1,2'-inden]-3'-one (312.0 mg, 1.0 mmol, Intermediate FS), 2,3,4-trichloropyridine (273.0 mg, 1.5 mmol, CAS #55934-02-6) and TEA (693 µL, 5.0 mmol) in DMF (10 mL) was stirred at 70° C. for 14 hours under N₂. The reaction mixture was then diluted with EtOAc (80 mL), washed with H₂O (50 mL×3) and brine (40 mL×2), dried over anhydrous Na₂SO₄, filtered and concentrated. The residue was purified by flash silica gel chromatography (20 g column, EtOAc in petroleum ether from 0% 30%) to give (1s,4s)-4-{6-[(2,3-dichloropyridin-4-yl)sulfanyl]pyridin-3-yl}-1',3'-dihydrospiro[cyclohexane-1,2'-inden]-3'-one (215.0 mg, 0.5 mmol, 47% yield) as a yellow oil. LC-MS (ESI⁺) m/z: 454.9 (M+H)⁺.

Step b: To a solution of (s,4s)-4-{6-[(2,3-dichloropyridin-4-yl)sulfanyl]pyridin-3-yl}-1',3'-dihydrospiro[cyclohexane-1,2'-inden]-3'-one (210.0 mg, 0.5 mmol) and Ti(OEt)₄ (945 µL, 4.6 mmol) in 2-Me-THF (1 mL) was added (R)-2-methylpropane-2-sulfinamide (558.0 mg, 4.6 mmol). The reaction mixture was stirred at 95° C. for 64 hours under N₂. The mixture was then cooled to rt and used in the next step directly.

Step c: To a mixture of (R)-2-methyl-N-[(1s,4s)-4-{6-[(2,3-dichloropyridin-4-yl)sulfanyl]pyridin-3-yl}-1',3'-dihydrospiro[cyclohexane-1,2'-inden]-3'-ylidene]propane-2-sulfinamide (257.0 mg, 0.5 mmol) in 2-Me-THF (5 mL) was added NaBH₄ (34.7 mg, 0.9 mmol) at 20° C., and the mixture was stirred at 20° C. for 1 hour. The reaction was then quenched with MeOH (1 mL) and the mixture was diluted with EtOAc (50 mL) and H₂O (20 mL). The mixture was stirred at 25° C. for 5 min, where precipitat formed. The mixture was filtered and the partitioned layers of the filtrate were separated. The aqueous layer was extracted with ethyl acetate (20 mL×3). The combined organic layers were washed with brine (30 mL), dried over anhydrous Na₂SO₄, filtered and concentrated to give a residue. The residue was purified by flash silica gel chromatography (petroleum ether: ethyl acetate=100:0 to 100:50) to afford (R)-2-methyl-N-[(1s,4s)-4-{6-[(2,3-dichloropyridin-4-yl)sulfanyl]pyridin-3-yl}-1',3'-dihydrospiro[cyclohexane-1,2'-inden]-3'-yl]propane-2-sulfinamide (110.0 mg, 0.2 mmol, 43% yield). LC-MS (ESI⁺) m/z: 560.0 (M+H)⁺.

Step d: (R)-2-Methyl-N-[(s,4s)-4-{6-[(2,3-dichloropyridin-4-yl)sulfanyl]pyridin-3-yl}-1',3'-dihydrospiro[cyclohexane-1,2'-inden]-3'-yl]propane-2-sulfinamide (110.0 mg, 0.2 mmol) was separated by SFC (Column: Chiralpak AD-3 50×4.6 mm I.D., 3 um. Mobile phase: A: CO₂; B: ethanol (0.05% DEA). Isocratic: 40% B. Flow rate: 4 mL/min. Column temp.: 35° C. ABPR: 1500 psi) to give (R)-2-methyl-N-[(1s,3'S,4R)-4-{6-[(2,3-dichloropyridin-4-yl)sulfanyl]pyridin-3-yl}-1',3'-dihydrospiro[cyclohexane-1,2'-inden]-3'-yl]propane-2-sulfinamide (65.0 mg, 0.1 mmol) was as a yellow solid and (R)-2-methyl-N-[(1s,3'R,4S)-4-{6-[(2,3-dichloropyridin-4-yl)sulfanyl]pyridin-3-yl}-1',3'-dihydrospiro[cyclohexane-1,2'-inden]-3'-yl]propane-2-sulfinamide (10.0 mg, 0.02 mmol) as a yellow solid.

Step e: A mixture of (R)-2-methyl-N-[(1s,3'S,4R)-4-{6-[(2,3-dichloropyridin-4-yl)sulfanyl]pyridin-3-yl}-1',3'-dihydrospiro[cyclohexane-1,2'-inden]-3'-yl]propane-2-sulfinamide (65.0 mg, 0.1 mmol) in HCl/MeOH (5 mL, 4 M) was stirred at 25° C. for 15 min. The reaction mixture was then concentrated, and the residue was purified by prep-HPLC (HCl) to give (1s,3'S,4R)-4-{6-[(2,3-dichloropyridin-4-yl)sulfanyl]pyridin-3-yl}-1',3'-dihydrospiro[cyclohexane-1,2'-inden]-3'-amine hydrochloride (25.5 mg, 45% yield) as a white solid. LC-MS (ESI$^+$) m/z: 439.0 (M-NH$_2$)$^+$; $^1$H NMR (400 MHz, CD$_3$OD) δ 8.94 (br s, 1H), 8.49 (br d, J=8.0 Hz, 1H), 8.21 (br d, J=5.2 Hz, 1H), 8.04 (br d, J=8.0 Hz, 1H), 7.58 (d, J=7.2 Hz, 1H), 7.42-7.30 (m, 3H), 7.13 (br d, J=4.8 Hz, 1H), 4.83 (s, 1H), 3.24 (d, J=16.4 Hz, 1H), 3.00 (br s, 1H), 2.73 (d, J=16.0 Hz, 1H), 2.10-1.90 (m, 6H), 1.71-1.61 (m, 2H). SFC: e.e. =99%, R=2.169 min. Column: Chiralpak AD-3 50×4.6 mm I.D., 3 um. Mobile phase: A: CO$_2$, B: ethanol (0.05% DEA). Isocratic: 60% B. Flow rate: 3 mL/min. Column temp.: 35° C.ABPR: 1500 psi.

Step f: A mixture of (R)—N-((1s,1'R,4S)-4-(6-((2,3-dichloropyridin-4-yl)thio)pyridin-3-yl)-1',3'-dihydrospiro[cyclohexane-1,2'-inden]-1'-yl)-2-methylpropane-2-sulfinamide (10.0 mg, 0.02 mmol) in HCl/MeOH (2 mL, 4 M) was stirred at 15° C. for 15 min. The reaction mixture was then concentrated. The residue was purified by prep-HPLC (HCl) to give (1s,1'R,4S)-4-(6-((2,3-dichloropyridin-4-yl)thio)pyridin-3-yl)-1',3'-dihydrospiro[cyclohexane-1,2'-inden]-1'-amine hydrochloride (1.9 mg, 0.004 mmol, 22% yield) as a white solid. LC-MS (ESI$^+$) m/z: 439.0 (M-NH$_2$)$^+$; $^1$HNMR (400 MHz, CD$_3$OD) δ 8.67 (s, 1H), 8.09 (d, J=5.2 Hz, 1H), 7.97 (s, 1H), 7.73 (d, J=8.4 Hz, 1H), 7.56 (d, J=7.2 Hz, 1H), 7.42-7.35 (m, 3H), 6.95 (d, J=5.2 Hz, 1H), 4.76 (s, 1H), 3.24 (d, J=16.4 Hz, 1H), 2.876 (br s, 1H), 2.75 (d, J=16.4 Hz, 1H), 2.08-1.82 (m, 7H), 1.67-1.65 (m, 1H). SFC: e.e. =94%, R$_f$=0.937 min. Column: Chiralpak AD-3 50×4.6 mm I.D., 3 um. Mobile phase: A: CO$_2$. B: ethanol (0.05% DEA). Isocratic: 60% B. Flow rate: 3 mL/min. Column temp.: 35° C. ABPR: 1500 psi.

Examples 281 and 282: Syntheses of (1s, 3'S, 4R)-4-{6-[(cyclopropylmethyl)sulfanyl]pyridin-3-yl}-1',3'-dihydrospiro[cyclohexane-1,2'-inden]-3'-amine and (1s, 3'R, 4S)-4-{6-[(cyclopropylmethyl)sulfanyl]pyridin-3-yl}-1',3'-dihydrospiro[cyclohexane-1,2'-inden]-3'-amine

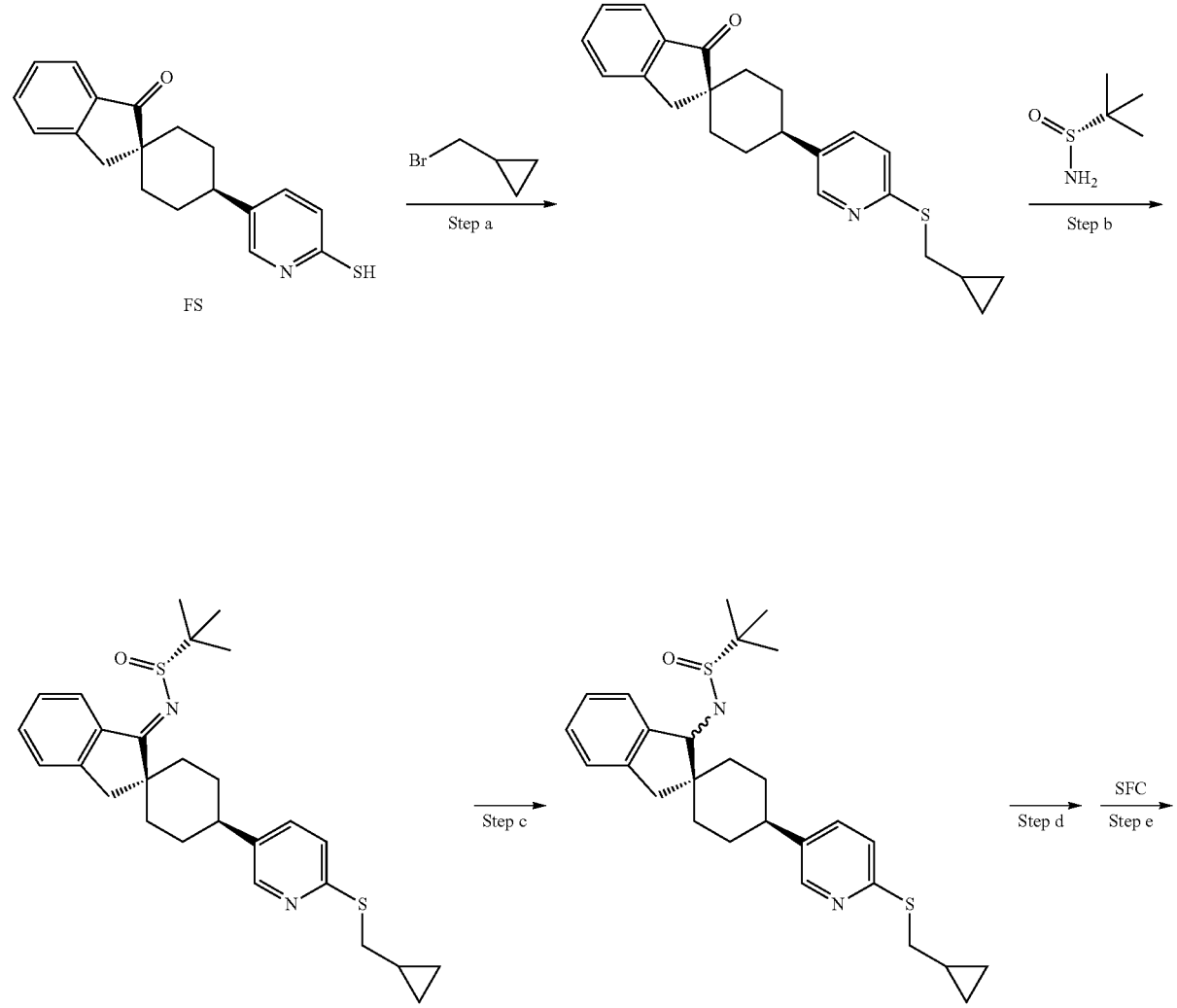

669  670

-continued

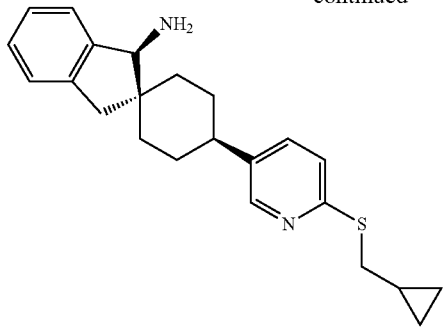 + 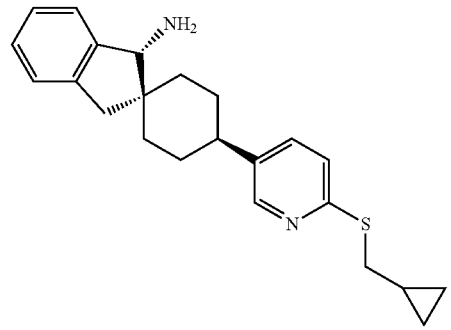

Step a: A mixture of (1s,4s)-4-(6-sulfanylpyridin-3-yl)-1',3'-dihydrospiro[cyclohexane-1,2'-inden]-3'-one (110.0 mg, 355 μmol, Intermediate FS), (bromomethyl)cyclopropane (143.0 mg, 1.1 mmol) and TEA (179.0 mg, 1.7 mmol) in DMF (2.00 mL) was stirred at 70° C. for 12 hour under $N_2$. The reaction mixture was then diluted with EtOAc (100 mL), washed with $H_2O$ (20 mL×3), brine (40 mL×2), dried over anhydrous $Na_2SO_4$, filtered and concentrated. The residue was purified by flash silica gel chromatography (12 g column, EtOAc in petroleum ether from 0% 15%) to give (1s,4s)-4-{6-[(cyclopropylmethyl)sulfanyl]pyridin-3-yl}-1',3'-dihydrospiro[cyclohexane-1,2'-inden]-3'-one (120.0 mg, 93% yield) as a yellow oil. LC-MS (ESI+) m/z: 364.0 (M+H)+.

Step b: To a solution of (1s,4s)-4-{6-[(cyclopropylmethyl)sulfanyl]pyridin-3-yl}-1',3'-dihydrospiro[cyclohexane-1,2'-inden]-3'-one (120.0 mg, 330 μmol) and Ti(OEt)$_4$ (679 μL, 3.30 mmol) in 2-Me-THF (3.00 mL) was added (R)-2-methylpropane-2-sulfinamide (159.0 mg, 1.3 mmol). The reaction mixture was then stirred at 95° C. for 96 h under $N_2$. The mixture was cooled to rt and used directly in the next step. LC-MS (ESI+) m/z: 467.2 (M+H)+.

Step c: To a mixture of (R)-2-methyl-N-[(1s,4s)-4-{6-[(cyclopropylmethyl)sulfanyl]pyridin-3-yl}-1',3'-dihydrospiro[cyclohexane-1,2'-inden]-3'-ylidene]propane-2-sulfinamide (150.0 mg, 321 μmol) in 2-Me-THF (5.00 mL) was added NaBH$_4$ (24.2 mg, 642 μmol) at 20° C. and the reaction was stirred for 2 hours. The reaction was then quenched with MeOH (1.00 mL) and the mixture was diluted with EtOAc (50 mL) and $H_2O$ (20 mL). The mixture was stirred at 25° C. for 5 min, where precipitate formed, and the mixture was filtered. The partitioned layers of the filtrate were separated and the aqueous layer was extracted with ethyl acetate (20 mL×3). The combined organic layers were washed with brine (30 mL), dried over anhydrous $Na_2SO_4$, filtered and concentrated to give a residue. The residue was purified by flash silica gel chromatography (petroleum ether:ethyl acetate=100:0 to 100:30) to afford (R)-2-methyl-N-[(is, 4s)-4-{6-[(cyclopropylmethyl)sulfanyl]pyridin-3-yl}-1',3'-dihydrospiro[cyclohexane-1,2'-inden]-3'-yl]propane-2-sulfinamide (40.0 mg, 27% yield) as a yellow solid. LC-MS (ESI+) m/z: 469.1 (M+H)+.

Step d: (R)-2-Methyl-N-[(1s,4s)-4-{6-[(cyclopropylmethyl)sulfanyl]pyridin-3-yl}-1',3'-dihydrospiro[cyclohexane-1,2'-inden]-3'-yl]propane-2-sulfinamide (40.0 mg, 85.3 μmol) was dissolved in EtOAc (0.5 mL). Then HCl/EtOAc (0.5 mL, 4 M) was added and the mixture was stirred at 20° C. for 1 hour, where yellow solid formed. The yellow solid was collected by filtration to afford (Is, 4s)-4-{6-[(cyclopropylmethyl)sulfanyl]pyridin-3-yl}-1',3'-dihydrospiro[cyclohexane-1,2'-inden]-3'-amine hydrochloride (20.0 mg, HCl salt, 58% yield) as a yellow solid. LC-MS (ESI+) m/z: 365.0 (M+H)+.

Step e: (is, 4s)-4-{6-[(cyclopropylmethyl)sulfanyl]pyridin-3-yl}-1',3'-dihydrospiro[cyclohexane-1,2'-inden]-3'-amine (20.0 mg, 54.8 μmol, HCl salt) was separated by Chiral-SFC (DAICEL CHIRALPAK AS (250 mm*30 mm, 10 um)) Mobile phase: 35% of EtOH (0.1% $NH_3.H_2O$) in $CO_2$, Flow rate: 80 mL/min) to give (Is, 3'S, 4R)-4-{6-[(cyclopropylmethyl)sulfanyl]pyridin-3-yl}-1',3'-dihydrospiro[cyclohexane-1,2'-inden]-3'-amine (3.10 mg, 16% yield) as a yellow solid (LC-MS (ESI+) m/z: 365.1 (M+H)+; $^1$HNMR (400 MHz, Methanol-d4): δ 8.37-8.25 (m, 1H), 7.69-7.53 (m, 1H), 7.41 (br d, J=6.0 Hz, 1H), 7.34-7.09 (m, 4H), 4.25 (s, 1H), 3.28-3.01 (m, 3H), 2.69-2.43 (m, 2H), 2.23-2.04 (m, 1H), 1.94-1.58 (m, 6H), 1.53-1.34 (m, 2H), 1.12 (m, 7.7, 12.0 Hz, 1H), 0.65-0.53 (m, 2H), 0.34-0.25 (m, 2H); SFC: e.e. =100%, R=2.169 min. Column: Chiralpak AS-3 100×4.6 mm I.D., 3 um. Mobile phase: A: $CO_2$, B: ethanol (0.05% DEA). Gradient: from 5% to 40% of B in 4 min and hold 40% for 2.5 min, then 5% of B for 1.5 min Flow rate: 2.8 mL/min. Column temp.: 35° C. ABPR: 1500 psi) and (Is, 3'R, 4S)-4-{6-[(cyclopropylmethyl)sulfanyl]pyridin-3-yl}-1',3'-dihydrospiro[cyclohexane-1,2'-inden]-3'-amine (3.1 mg, 16% yield) as a white solid (LC-MS (ESI+) m/z: 365.1 (M+H)+; $^1$HNMR (400 MHz, Methanol-d4): δ 8.34 (d, J=2.1 Hz, 1H), 7.64 (dd, J=2.3, 8.3 Hz, 1H), 7.57 (d, J=7.5 Hz, 1H), 7.45-7.25 (m, 4H), 4.78 (s, 1H), 3.28-3.04 (m, 3H), 2.79-2.62 (m, 2H), 2.10-1.90 (m, 2H), 1.84-1.54 (m, 4H), 1.52-1.35 (m, 1H), 1.18-1.06 (m, 1H), 0.96-0.86 (m, 1H), 0.64-0.54 (m, 2H), 0.38-0.26 (m, 2H)). The absolute configuration of the diastereomers was assigned arbitrarily.

Examples 283, 284, & 285: Syntheses of (1s, 3'S, 4R)-4-{5-[(cyclopropylmethyl)sulfanyl]pyrazin-2-yl}-1',3'-dihydrospiro[cyclohexane-1,2'-inden]-3'-amine, (1s, 1'R, 4S)-4-(5-((cyclopropylmethyl)thio)pyrazin-2-yl)-1',3'-dihydrospiro[cyclohexane-1,2'-inden]-1'-amine and (1r, 4r)-4-{5-[(cyclopropylmethyl)sulfanyl]pyrazin-2-yl}-1',3'-dihydrospiro[cyclohexane-1,2'-inden]-3'-amine
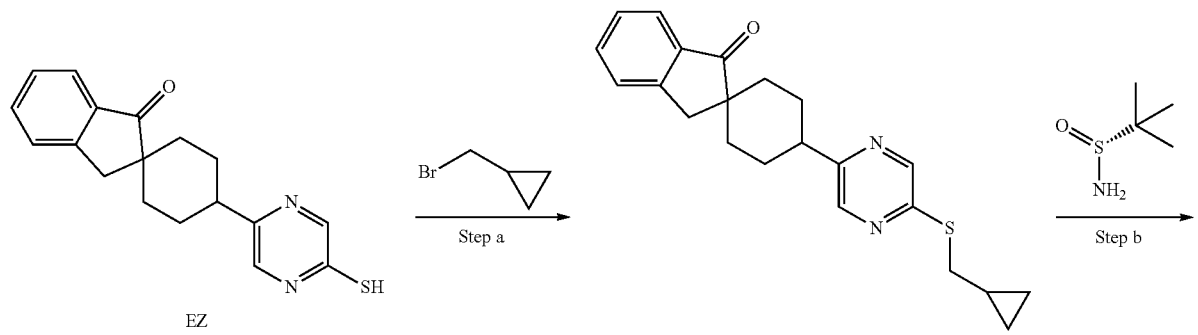
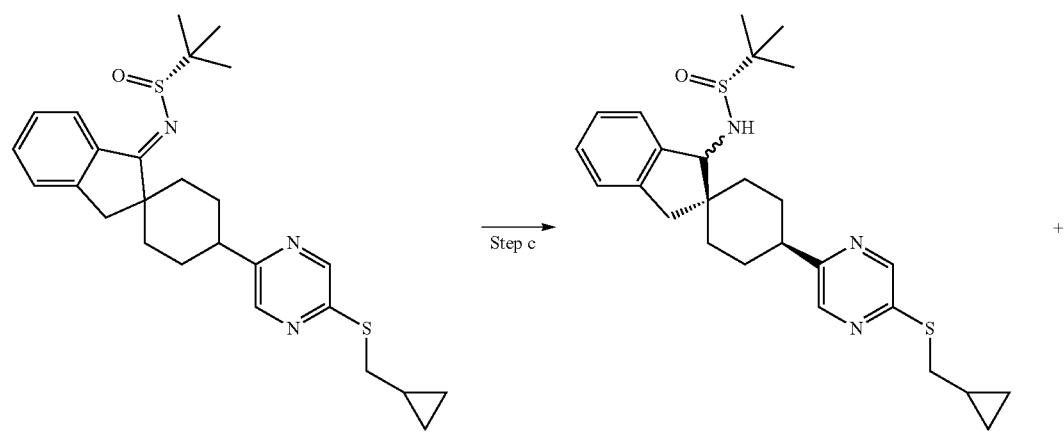
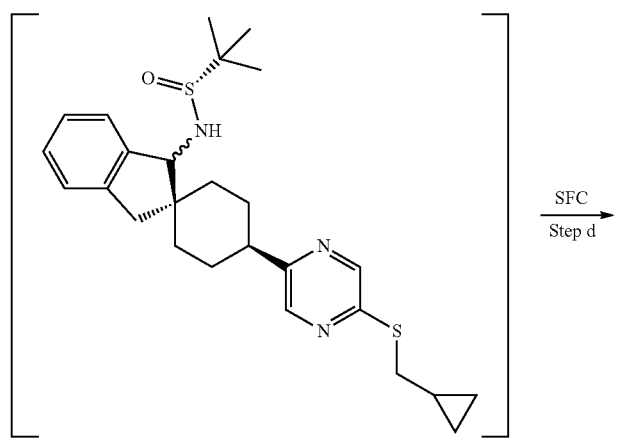

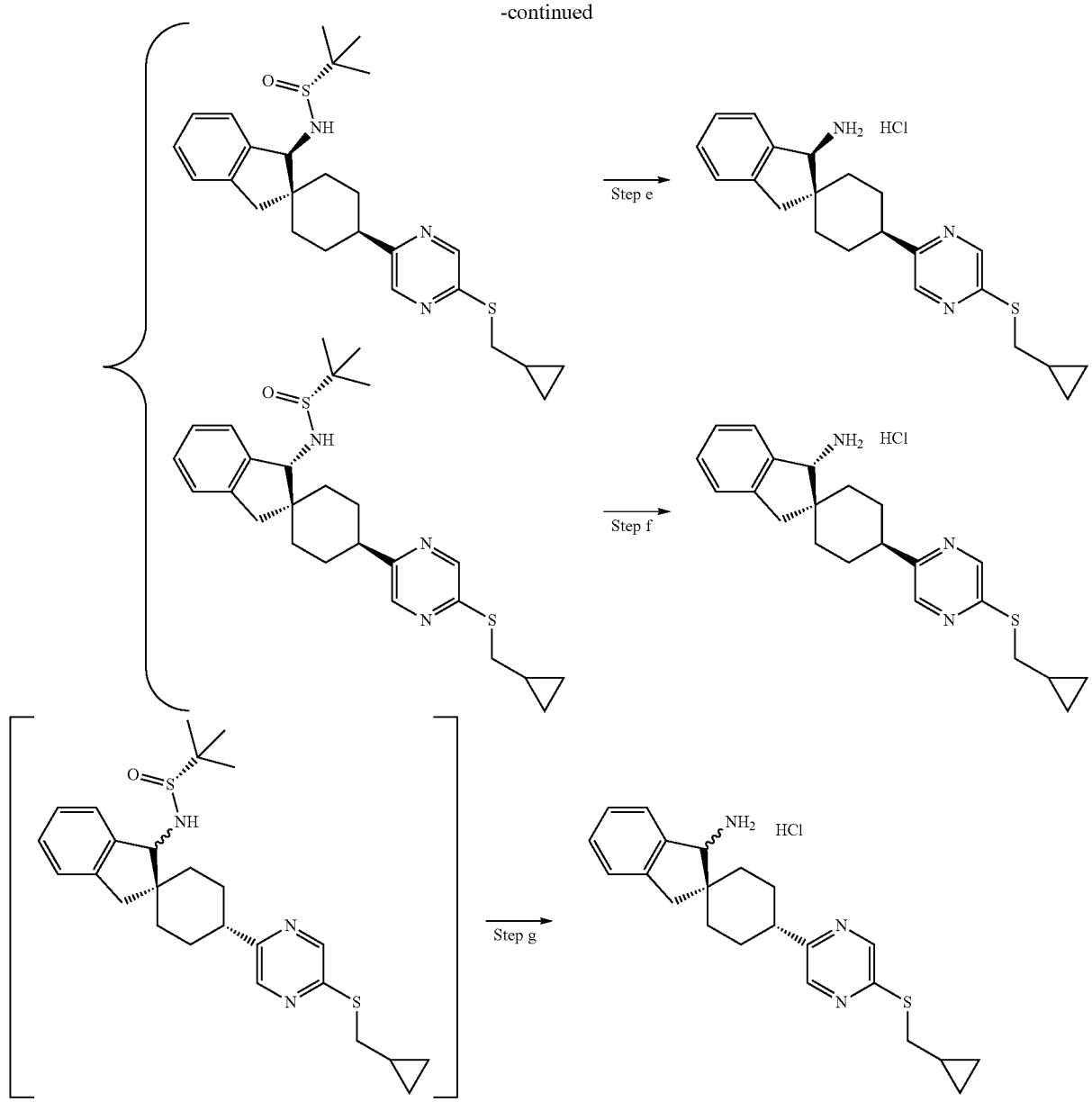

-continued

Step a: A mixture of 4-(5-sulfanylpyrazin-2-yl)-14-(5-mercaptopyrazin-2-yl)spiro[cyclohexane-1,2'-inden]-1'(3'H)-one (137.0 mg, 441 µmol, Intermediate EZ), (bromomethyl)cyclopropane (178.0 mg, 1.32 mmol) and TEA (304 µL, 2.20 mmol) in DMF (2.00 mL) was stirred at 70° C. for 12 hour under $N_2$. The reaction mixture was diluted with EtOAc (50 mL), washed with $H_2O$ (20 mL×3), brine (20 mL×2), dried over anhydrous $Na_2SO_4$, filtered and concentrated to give a residue. The residue was purified by flash silica gel chromatography (EtOAc in petroleum ether from 0%~15%) to give -(5-((cyclopropylmethyl)thio)pyrazin-2-yl)spiro[cyclohexane-1,2'-inden]-1'(3'H)-one (160.0 mg, 438 µmol, 100% yield) as a yellow oil. LC-MS (ESI⁺) m/z: 364.9 (M+H)⁺.

Step b: To a solution of 4-{5-[(cyclopropylmethyl)sulfanyl]pyrazin-2-yl}-1',3'-dihydrospiro[cyclohexane-1,2'-inden]-3'-one (160.0 mg, 438 µmol) and Ti(OEt)₄ (899 µL, 4.37 mmol) in 2-Me-THF (1.00 mL) was added (R)-2-methylpropane-2-sulfinamide (212.0 mg, 1.75 mmol). The reaction mixture was stirred at 95° C. for 48 h under $N_2$. The mixture was then cooled to rt and used in the next step directly. LC-MS (ESI⁺) m/z: 468.2 (M+H)⁺.

Step c: To a mixture of (R)—N-(4-{5-[(cyclopropylmethyl)sulfanyl]pyrazin-2-yl}-1',3'-dihydrospiro[cyclohexane-1,2'-inden]-3'-ylidene)-2-methylpropane-2-sulfinamide (200.0 mg, 427 µmol) in 2-Me-THF (5 mL) was added NaBH₄ (32.2 mg, 854 µmol) at 20° C. The mixture was stirred at 20° C. for 1 hour. The reaction was then quenched with MeOH (1 mL) and the mixture was diluted with EtOAc (50 mL) and $H_2O$ (20 mL). The mixture was stirred at 25° C. for 5 min, where a precipitate formed and the mixture was filtered. The partitioned layers of the filtrate were separated and the aqueous layer was extracted with ethyl acetate (20 mL×3). The combined organic layers were washed with brine (30 mL), dried over anhydrous $Na_2SO_4$, filtered and concentrated to give a residue. The residue was purified by flash silica gel chromatography (petroleum ether:ethyl acetate=100:0 to 100:30) to afford (R)—N-((1S, 4S)-4-(5-((cyclopropylmethyl)thio)pyrazin-2-yl)-1',3'-dihydrospiro[cyclohexane-1,2'-inden]-1'-yl)-2-methylpropane-2-sulfinamide (60.0 mg, 30% yield) as the major product as a colorless oil. LC-MS (ESI⁺) m/z: 470.1 (M+H)⁺. Another product (30.0 mg) was further purified by prep-HPLC (HCOOH) to afford (R)—N-((1r, 4R)-4-(5-((cyclopropylmethyl)thio)pyrazin-2-yl)-1',3'-dihydrospiro[cyclohexane-1,2'-inden]-1'-yl)-2-methylpropane-2-sulfinamide (5.0 mg, 3% yield) as a white solid (5.0 mg, 2.5% yield). LC-MS (ESI⁺) m/z: 470.1 (M+H)⁺. The absolute configuration of the diastereomers was arbitrarily assigned.

Step d: (R)-2-Methyl-N-[(is, 4s)-4-{5-[(cyclopropylmethyl)sulfanyl]pyrazin-2-yl}-1',3'-dihydrospiro[cyclohexane-1,2'-inden]-3'-yl]propane-2-sulfinamide (60.0 mg, 127 µmol) was separated by Chiral-SFC (DAICEL CHIRALCEL OD (250 mm*30 mm, 10 um) Mobile phase: 35% of EtOH (0.1% NH₃H₂O) in CO₂. Flow rate: 70 mL/min) to give (R)-2-methyl-N-[(is, 3'S, 4R)-4-{5-[(cyclopropylmethyl)sulfanyl]pyrazin-2-yl}-1',3'-dihydrospiro[cyclohexane-1,2'-inden]-3'-yl]propane-2-sulfinamide (16.0 mg, 27% yield) as a white solid (LC-MS (ESI⁺) m/z: 470.1 (M+H)+) and (R)-2-methyl-N-[(1s, 3'R, 4S)-4-{5-[(cyclopropylmethyl)sulfanyl]pyrazin-2-yl}-1',3'-dihydrospiro[cyclohexane-1,2'-inden]-3'-yl]propane-2-sulfinamide (9.0 mg, 15% yield) was as a white solid (LC-MS (ESI⁺) m/z: 470.1 (M+H)+).

Step e: (R)-2-Methyl-N-[(s, 3'S, 4R)-4-{5-[(cyclopropylmethyl)sulfanyl]pyrazin-2-yl}-1',3'-dihydrospiro[cyclohexane-1,2'-inden]-3'-yl]propane-2-sulfinamide (16.0 mg, 34.0 µmol) was dissolved in EtOAc (0.25 mL), then HCl/EtOAc (0.25 mL, 4 M) was added. The mixture was stirred at 20° C. for 0.5 hour, where precipitate formed. The solid was collected by filtration and was purified by prep-HPLC (HCl) to afford (Is, 3'S, 4R)-4-{5-[(cyclopropylmethyl)sulfanyl]pyrazin-2-yl}-1',3'-dihydrospiro[cyclohexane-1,2'-inden]-3'-amine hydrochloride (8.4 mg, HCl salt, 62% yield) as a yellow solid. LC-MS (ESI⁺) m/z: 349.1 (M–NH₂)⁺; ¹H NMR (400 MHz, CD₃OD) δ 8.53-8.41 (m, 2H), 7.51 (d, J=7.5 Hz, 1H), 7.44-7.28 (m, 3H), 4.35 (s, 1H), 3.23-3.09 (m, 4H), 2.91-2.76 (m, 1H), 2.08-1.98 (m, 1H), 1.97-1.69 (m, 7H), 1.16 (dt, J=4.7, 7.8 Hz, 1H), 0.69-0.54 (m, 2H), 0.38-0.29 (m, 2H). SFC: e.e. =100%, Rt=2.922 min. Column: Chiralpak AS-3 100×4.6 mm I.D., 3 um. Mobile phase: A: CO₂, B: ethanol (0.05% DEA). Gradient: from 5% to 40% of B in 4 min and hold 40% for 2.5 min, then 5% of B for 1.5 min Flow rate: 2.8 mL/min. Column temp.: 35° C. ABPR: 1500 psi. The absolute configuration of the diastereomer was arbitrarily assigned.

Step f: (R)—N-((1s, 1'R, 4S)-4-(5-((Cyclopropylmethyl)thio)pyrazin-2-yl)-1',3'-dihydrospiro[cyclohexane-1,2'-inden]-1'-yl)-2-methylpropane-2-sulfinamide (9.0 mg, 19.1 µmol) was dissolved in EtOAc (0.25 mL), then HCl/EtOAc (0.25 mL, 4 M) was added and the mixture was stirred at 20° C. for 0.5 hour, where a solid precipitate formed. The yellow solid was collected by filtration to afford (1s, 1'R, 4S)-4-(5-((cyclopropylmethyl)thio)pyrazin-2-yl)-1',3'-dihydrospiro[cyclohexane-1,2'-inden]-1'-amine hydrochloride (6.9 mg, HCl salt, 90% yield) as a yellow solid. LC-MS (ESI⁺) m/z: 349.0 (M-NH₂)⁺; ¹HNMR (400 MHz, CD₃OD) δ 8.56-8.38 (m, 2H), 7.54 (d, J=7.3 Hz, 1H), 7.43-7.28 (m, 3H), 4.69 (s, 1H), 3.26-3.10 (m, 3H), 2.97-2.84 (m, 1H), 2.74 (d, J=16.3 Hz, 1H), 2.09-1.78 (m, 6H), 1.75-1.51 (m, 2H), 1.20-1.07 (m, 1H), 0.64-0.52 (m, 2H), 0.36-0.25 (m, 2H). SFC: e.e. = 100%, Rt=2.827 min. Column: Chiralpak AS-3 100×4.6 mm I.D., 3 um. Mobile phase: A: CO₂, B: ethanol (0.05% DEA). Gradient: from 5% to 40% of B in 4 min and hold 40% for 2.5 min, then 5% of B for 1.5 min Flow rate: 2.8 mL/min. Column temp.: 35° C. ABPR: 1500 psi. The absolute configuration of the diastereomer was arbitrarily assigned.

Step g: (R)-2-Methyl-N-[(1r, 4r)-4-{5-[(cyclopropylmethyl)sulfanyl]pyrazin-2-yl}-1',3'-dihydrospiro[cyclohexane-1,2'-inden]-3'-yl]propane-2-sulfinamide (5.0 mg, 10.6 µmol) was added into HCl/MeOH (1 mL, 4M) and the mixture was stirred at 25° C. for 1 h. The mixture was then concentrated and was purified by prep-HPLC (HCl) to afford (1r, 4r)-4-{5-[(cyclopropylmethyl)sulfanyl]pyrazin-2-yl}-1',3'-dihydrospiro[cyclohexane-1,2'-inden]-3'-amine hydrochloride (2.2 mg, HCl salt, 52% yield) as a white solid as a mixture of diastereomers. LC-MS (ESI⁺) m/z: 348.9 (M-NH₂)⁺; ¹HNMR (400 MHz, CD₃OD) δ 8.56-8.38 (m, 2H), 7.54 (d, J=7.3 Hz, 1H), 7.43-7.28 (m, 3H), 4.69 (s, 1H), 3.26-3.10 (m, 3H), 2.97-2.84 (m, 1H), 2.74 (d, J=16.3 Hz, 1H), 2.09-1.78 (m, 6H), 1.75-1.51 (m, 2H), 1.20-1.07 (m, 1H), 0.64-0.52 (m, 2H), 0.36-0.25 (m, 2H). SFC: R_f=3.453 min and R_f=2.443 min. Column: Chiralcel OJ-3 100×4.6 mm I.D., 3 um. Mobile phase: A: CO₂, B: ethanol (0.05% DEA). Gradient: from 5% to 40% of B in 4 min and hold 40% for 2.5 min, then 5% of B for 1.5 min Flow rate: 2.8 mL/min. Column temp.: 35° C. ABPR: 1500 psi. The absolute configuration of the diastereomer was arbitrarily assigned.

Example 286: Synthesis of (1S)-1'-[2-(2,6-dichlorophenyl)-1,3-thiazole-4-carbonyl]-1,3-dihydrospiro[indene-2,4'-piperidin]-1-amine

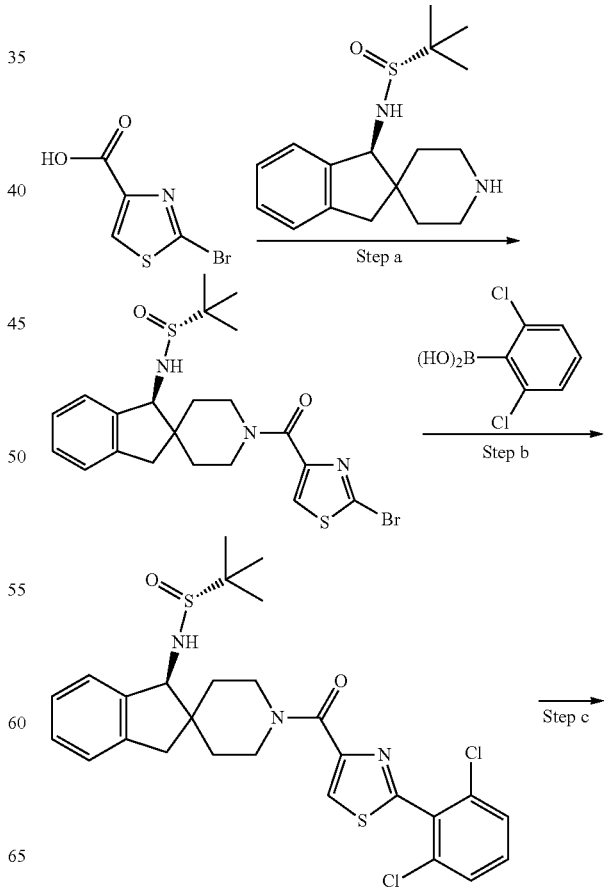

-continued

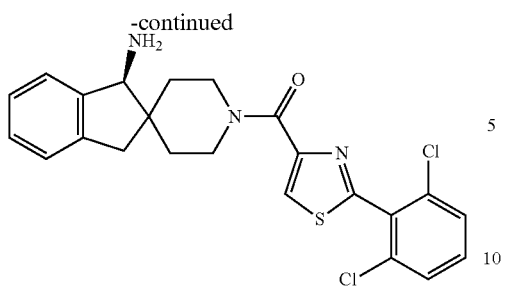

Step a: (R)—N—((S)-1,3-dihydrospiro[indene-2,4'-piperidin]-1-yl)-2-methylpropane-2-sulfinamide (352.0 mg, 1.15 mmol, synthesized via Step a of Example 120), 2-bromo-1,3-thiazole-4-carboxylic acid (200 mg, 961 μmol), HATU (547 mg, 1.44 mmol) and TEA (671 μL, 4.80 mmol) were placed into DMF (10 mL). The reaction mixture was stirred at 25° C. for 12 hour. The mixture was diluted with EtOAc (100 mL) and the mixture was washed with H$_2$O (30 mL×5), brine (50 mL), dried over anhydrous Na$_2$SO$_4$, filtered and concentrated to give a residue. The residue was purified by flash silica gel chromatography (ethyl acetate in petroleum ether=0% to 80%) to afford (R)—N—((S)-1'-(2-bromothiazole-4-carbonyl)-1,3-dihydrospiro[indene-2,4'-piperidin]-1-yl)-2-methylpropane-2-sulfinamide (400 mg, 84% yield) as a yellow oil. LC-MS (ESI$^+$) m/z: 498.0 (M+H)$^+$.

Step b: (S)—N-[(1S)-1'-(2-bromo-1,3-thiazole-4-carbonyl)-1,3-dihydrospiro[indene-2,4'-piperidin]-1-yl]-2-methylpropane-2-sulfinamide (200.0 mg, 402 μmol), bis(tri-tert-butylphosphine)palladium (20.5 mg, 40.2 μmol), DIPEA (114.0 mg, 884 μmol) and (2,6-dichlorophenyl)boronic acid (92.0 mg, 482 μmol) were placed into dioxane/H$_2$O (10/0.6 mL). The reaction mixture was evacuated and refilled 3 times using N$_2$ and the reaction mixture was stirred at 120° C. for 3 hours. The reaction mixture was then concentrated and H$_2$O (30 mL) was added, and the solution was extracted with ethyl acetate (30 mL×3). The combined organic layers were washed with brine (50 mL), dried over anhydrous Na$_2$SO$_4$, filtered and concentrated to give a residue. The residue was purified by flash silica gel chromatography (petroleum ether:ethyl acetate=100:50 to 100:100 then EtOAc:MeOH=100:10) to afford (S)—N-[(1S)-1'-[2-(2,6-dichlorophenyl)-1,3-thiazole-4-carbonyl]-1,3-dihydrospiro[indene-2,4'-piperidin]-1-yl]-2-methylpropane-2-sulfinamide (27.0 mg, 12% yield) as a yellow oil. LC-MS (ESI$^+$) m/z: 584.0 (M+Na)+.

Step c: The mixture of (S)—N-[(1S)-1'-[2-(2,6-dichlorophenyl)-1,3-thiazole-4-carbonyl]-1,3-dihydrospiro[indene-2,4'-piperidin]-1-yl]-2-methylpropane-2-sulfinamide (27.0 mg, 47.9 μmol) in HCl/MeOH (4 mL, 4 M) was stirred at 25° C. for 0.5 hour. The combined reaction mixture was concentrated to give a residue. The residue was dissolved in MeOH (5 mL), and the reaction mixture was adjusted pH=8-9 with solid Na$_2$CO$_3$. The mixture was filtered, and the filtrate was purified by pre-HPLC (basic condition) to afford (1S)-1'-[2-(2,6-dichlorophenyl)-1,3-thiazole-4-carbonyl]-1,3-dihydrospiro[indene-2,4'-piperidin]-1-amine (4.10 mg, 19% yield) as a white solid. LC-MS (ESI$^+$) m/z: 458.0 (M+H)$^+$. $^1$HNMR (400 MHz, CD$_3$OD) δ 8.27 (s, 1H), 7.64-7.49 (m, 3H), 7.37 (s, 1H), 7.26-7.16 (m, 3H), 4.49 (m, 1H), 4.18 (m, 1H), 3.98 (m, 1H), 3.55-3.34 (m, 2H), 3.16 (s, 1H), 2.82 (s, 1H), 2.12-1.77 (m, 2H), 1.76-1.22 (m, 3H).

Example 287: Synthesis of (1S)-1'-[1-(3-methoxyphenyl)-1H-pyrazole-3-carbonyl]-1,3-dihydrospiro[indene-2,4'-piperidin]-1-amine

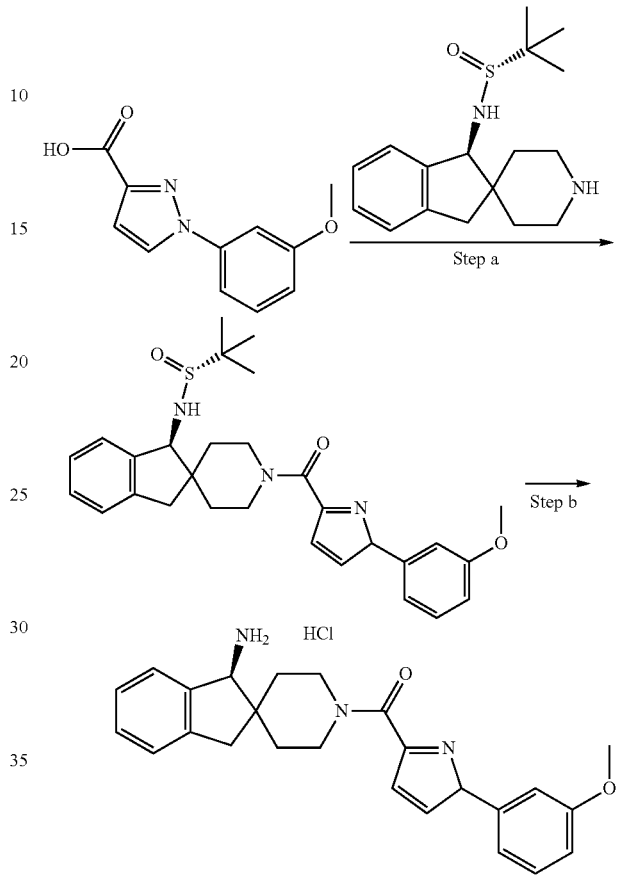

Step a: 1-(3-Methoxyphenyl)-1H-pyrazole-3-carboxylic acid (95.0 mg, 0.44 mmol, Intermediate FX), TEA (303 μL, 2.17 mmol) and HATU (248.0 mg, 0.65 mmol) were placed into DMF (5 mL) and the reaction mixture was stirred at 25° C. for 1 hour. Then (R)—N-[(3S)-1,3-dihydrospiro[indene-2,4'-piperidin]-3-yl]-2-methylpropane-2-sulfinamide (173 mg, 0.57 mmol, synthesized via Step a of Example 120) was added and the resulting mixture was stirred at 25° C. for 12 hours. The mixture was diluted with EtOAc (50 mL). The mixture was washed with H$_2$O (30 mL×2), brine (20 mL), dried over anhydrous Na$_2$SO$_4$, filtered and concentrated to give a residue. The residue was purified by silica gel chromatography (ethyl acetate in petroleum ether=0% to 100% to afford (R)—N-[(3S)-1'-[1-(3-methoxyphenyl)-1H-pyrazole-3-carbonyl]-1,3-dihydrospiro[indene-2,4'-piperidin]-3-yl]-2-methylpropane-2-sulfinamide (126.0 mg, 57% yield) as yellow oil. LC-MS (ESI$^+$) m/z: 507.1 (M+H)$^+$.

Step b: (R)—N-[(3S)-1'-[1-(3-Methoxyphenyl)-1H-pyrazole-3-carbonyl]-1,3-dihydrospiro[indene-2,4'-piperidin]-3-yl]-2-methylpropane-2-sulfinamide (126 mg, 0.2486 mmol) was dissolved in HCl/MeOH (2 mL, 4 M) and stirred at 25° C. for 1 hour. The mixture was then concentrated to give a residue which was purified by prep-HPLC (HCl) to afford (1S)-1'-[1-(3-methoxyphenyl)-1H-pyrazole-3-carbonyl]-1,3-dihydrospiro[indene-2,4'-piperidin]-1-amine hydrochloride (43.2 mg, 34% yield) as a white solid. LC-MS (ESI$^+$)

m/z: 403.1 (M+H)⁺; ¹HNMR (400 MHz, DMSO-d6) δ=8.48-8.51 (m, 4H), 7.62-7.64 (m, 1H), 7.40~7.44 (m, 3H), 7.27~7.38 (m, 3H), 6.92~6.98 (m, 1H), 6.79~6.80 (m, 1H), 4.30~4.60 (m, 3H), 3.86 (s, 3H), 3.22~3.40 (m, 1H), 2.99~3.04 (m, 3H), 1.78~1.89 (m, 2H), 1.54~1.65 (m, 2H).

Example 288: Synthesis of (1S)-1'-[1-(3-methoxyphenyl)-1H-pyrazole-5-carbonyl]-1,3-dihydrospiro[indene-2,4'-piperidin]-1-amine

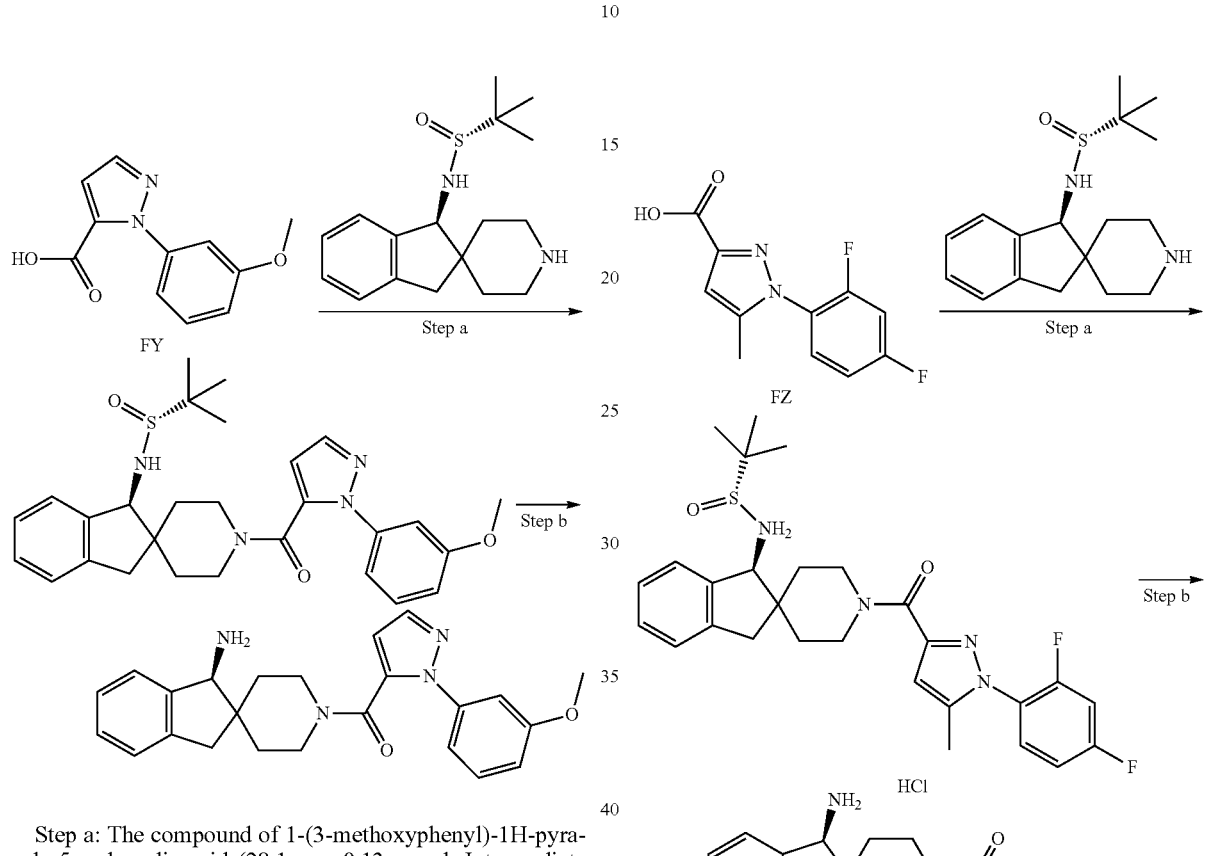

Step a: The compound of 1-(3-methoxyphenyl)-1H-pyrazole-5-carboxylic acid (28.1 mg, 0.13 mmol, Intermediate FY), TEA (90.1 µL, 0.64 mmol) and HATU (73.3 mg, 0.19 mmol) were placed into DMF (2 mL). The reaction mixture was stirred at 25° C. for 1 hour. Then (R)—N-[(3S)-1,3-dihydrospiro[indene-2,4'-piperidin]-3-yl]-2-methylpropane-2-sulfinamide (51.2 mg, 0.1673 mmol, synthesized via Step a of Example 120) was added, and the resulting mixture was stirred at 25° C. for 12 hour. The mixture was then diluted with EtOAc (50 mL). The mixture was washed with H₂O (30 mL×2), brine (20 mL), dried over anhydrous Na₂SO₄, filtered and concentrated to give a residue. The residue was purified by prep-TLC (ethyl acetate:petroleum ether=1:0) to afford (R)—N-[(3S)-1'-[1-(3-methoxyphenyl)-1H-pyrazole-5-carbonyl]-1,3-dihydrospiro[indene-2,4'-piperidin]-3-yl]-2-methylpropane-2-sulfinamide (37.0 mg, 57% yield) as a yellow oil. LC-MS (ESI⁺) m/z: 507.1 (M+H)⁺.

Step b: A solution of tert-butyl N-[(1S)-1'-[1-(3-methoxyphenyl)-1H-pyrazole-5-carbonyl]-1,3-dihydrospiro[indene-2,4'-piperidin]-1-yl]carbamate (37.0 mg, 73.6 µmol) in HCl/MeOH (5 mL, 4 M) was stirred at 25° C. for 1 hour. The reaction mixture was then concentrated under reduced pressure and purified by prep-HPLC (NH₃—H₂O) to afford (1S)-1'-[1-(3-methoxyphenyl)-1H-pyrazole-5-carbonyl]-1,3-dihydrospiro[indene-2,4'-piperidin]-1-amine (14.7 mg, 50% yield) as a white solid. LC-MS (ESI⁺) m/z: 403.2 (M+H)⁺; ¹H NMR (400 MHz, DMSO-d6) δ=7.76-7.78 (m, 1H), 7.41-7.46 (m, 1H), 7.26-7.29 (m, 1H), 7.14~7.18 (m, 3H), 6.99~7.07 (m, 3H), 6.64~6.67 (m, 1H), 4.17~4.24 (m, 1H), 3.72~3.80 (m, 4H), 2.99-3.17 (m, 3H), 2.89-2.96 (m, 1H), 2.52~2.56 (m, 1H), 1.44-1.63 (m, 2H), 1.19~1.32 (m, 1H), 0.82~1.10 (m, 1H).

Example 289: Synthesis of (1S)-1'-[1-(2,4-difluorophenyl)-5-methyl-1H-pyrazole-3-carbonyl]-1,3-dihydrospiro[indene-2,4'-piperidin]-1-amine

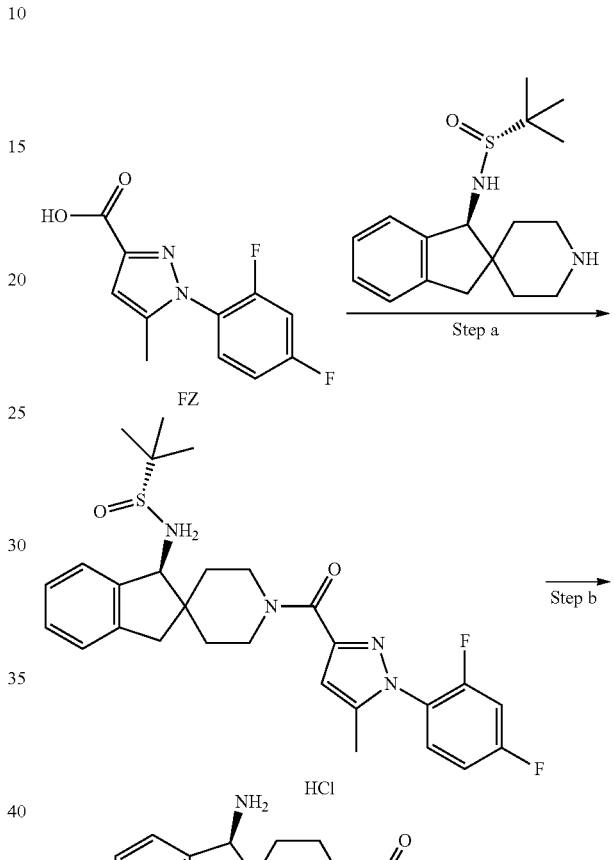

Step a: A mixture of 1-(2,4-difluorophenyl)-5-methyl-1H-pyrazole-3-carboxylic acid (140.0 mg, 587.0 µmol, Intermediate FZ), (R)—N—[(S)-1,3-dihydrospiro[indene-2,4'-piperidin]-1-yl]-2-methylpropane-2-sulfinamide (307.0 mg, 704.0 µmol, synthesized via Step a of Example 120), HATU (334.0 mg, 880.0 µmol) and TEA (242.0 µL, 1.8 mmol) in DMF (10.0 mL) was stirred at 20° C. for 12 hours. The mixture was diluted with ethyl acetate (50.0 mL), and washed with H₂O (30.0 mL×2). The organic phase was washed with brine (15.0 mL), dried over anhydrous Na₂SO₄, filtered and concentrated in vacuo to give a residue. The residue was purified by silica gel chromatography (methanol in dichloromethane=0% to 10%) to afford (R)—N-[(1S)-1'-[1-(2,4-difluorophenyl)-5-methyl-1H-pyrazole-3-carbonyl]-1,3-dihydrospiro[indene-2,4'-piperidin]-1-yl]-2-methylpropane-2-sulfinamide (250 mg, 81% yield) as a white solid. LC-MS (ESI⁺) m/z 527.2 (M+H)⁺.

Step b: A mixture of (R)—N—[(S)-1'-[1-(2,4-difluorophenyl)-5-methyl-1H-pyrazole-3-carbonyl]-1,3-dihydrospiro[indene-2,4'-piperidin]-1-yl]-2-methylpropane-2-sulfinamide (240.0 mg, 455.0 μmol) in HCl/MeOH (4M, 5.0 mL) was stirred at 20° C. for 0.5 hours. The mixture was then concentrated under reduced pressure to give a residue, which was purified by prep-HPLC (HCl) to afford (1S)-1'-[I-(2,4-difluorophenyl)-5-methyl-1H-pyrazole-3-carbonyl]-1,3-dihydrospiro[indene-2,4'-piperidin]-1-amine hydrochloride (151 mg, 73% yield) as a white solid. LC-MS (ESI+) m/z: 406.0 (M-NH$_2$)*; $^1$H NMR (400 MHz, Methanol-d4) δ 7.64-7.17 (m, 7H), 6.60 (d, J=4.0 Hz, 1H), 4.64-4.37 (m, 3H), 3.60-3.50 (m, 1H), 3.28-3.15 (m, 3H), 2.25 (s, 3H), 1.91-1.57 (m, 4H).

Example 290 and 291: Syntheses of (S)-1-((S)-1-amino-1,3-dihydrospiro[indene-2,4'-piperidin]-1'-yl)-2-(4-fluorophenyl)propan-1-one and (R)-1-((S)-1-amino-1,3-dihydrospiro[indene-2,4'-piperidin]-1'-yl)-2-(4-fluorophenyl)propan-1-one

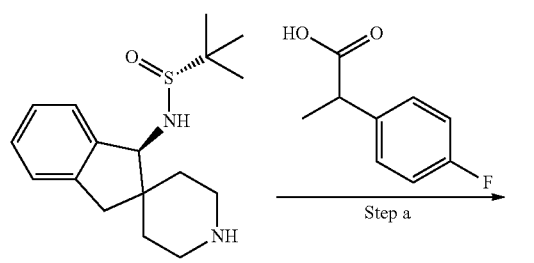

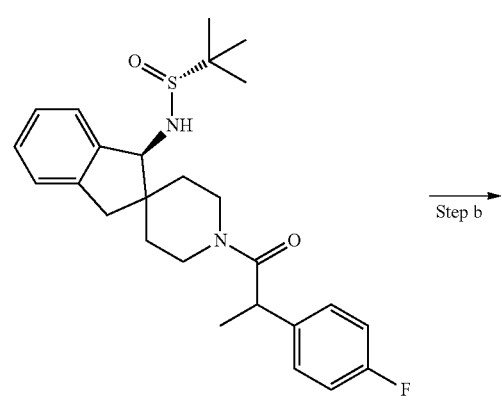

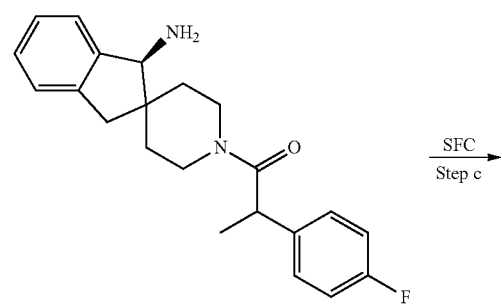

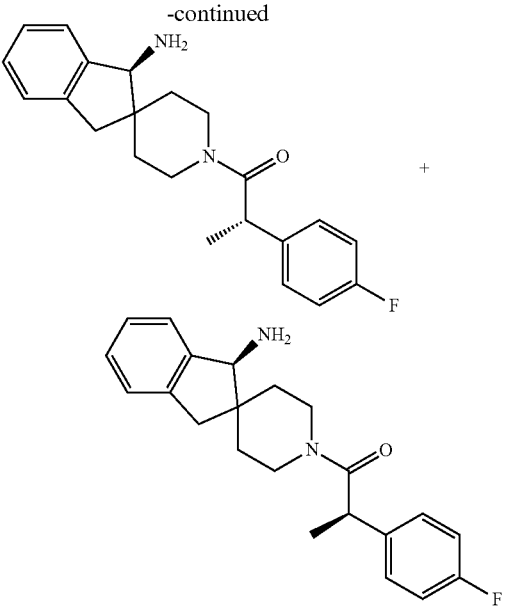

Step a: (R)—N-[(3S)-1,3-dihydrospiro[indene-2,4'-piperidin]-3-yl]-2-methylpropane-2-sulfinamide (652.0 mg, 2.13 mmol, synthesized via Step a of Example 120), 2-(4-fluorophenyl)propanoic acid (300.0 mg, 1.78 mmol), HATU (1.01 g, 2.67 mmol) and TEA (1.24 mL, 8.90 mmol) were placed into DMF (10 mL). The reaction mixture was stirred at 25° C. for 1 hour. The mixture was diluted with EtOAc (100 mL) and the mixture was washed with H$_2$O (30 mL×5), brine (50 mL), dried over anhydrous Na$_2$SO$_4$, filtered and concentrated to give a residue. The residue was purified by flash silica gel chromatography (ethyl acetate in petroleum ether=0% to 75% to afford (R)—N-[(3S)-1'-[2-(4-fluorophenyl)propanoyl]-1,3-dihydrospiro[indene-2,4'-piperidin]-3-yl]-2-methylpropane-2-sulfinamide (370 mg, 46% yield) as yellow oil. LC-MS (ESI+) m/z: 457.1 (M+H)+.

Step b: The mixture of (R)—N-[(3S)-1'-[2-(4-fluorophenyl)propanoyl]-1,3-dihydrospiro[indene-2,4'-piperidin]-3-yl]-2-methylpropane-2-sulfinamide (180.0 mg, 394 μmol) in HCl/MeOH (5 mL, 4 M) was stirred at 25° C. for 0.5 hour. The combined reaction mixture was then concentrated to give a residue. The residue was dissolved in MeOH (5.00 mL), and the reaction mixture was adjusted pH=8-9 with solid Na$_2$CO$_3$. The mixture was filtered, and the filtrate was concentrated to give 1-[(3S)-3-amino-1,3-dihydrospiro[indene-2,4'-piperidin]-1'-yl]-2-(4-fluorophenyl)propan-1-one (110 mg, 80% yield) as a white solid. LC-MS (ESI+) m/z: 336.0 (M-NH$_2$)+.

Step c: 1-((S)-1-amino-1,3-dihydrospiro[indene-2,4'-piperidin]-1'-yl)-2-(4-fluorophenyl)propan-1-one (110 mg, 312 μmol) was separated by Chiral-SFC (DAICEL CHIRALPAK AD (250 mm*30 mm, 10 um)), mobile phase: 45%% NH$_3$.H$_2$O/IPA in CO$_2$, flow rate: 80 mL/min) to give (S)-1-((S)-1-amino-,3-dihydrospiro[indene-2,4'-piperidin]-1'-yl)-2-(4-fluorophenyl)propan-1-one (37.8 mg, 107 μmol, 35% yield, R$_f$=4.004 min) as a white solid (LC-MS (ESI+) m/z: 336.0 (M-NH$_2$)*; $^1$H NMR (400 MHz, Methanol-d4) δ 7.39-7.27 (m, 3H), 7.18 (m, 3H), 7.12-7.03 (m, 2H), 4.44-4.24 (m, 1H), 4.15 (m, 1H), 3.98-3.68 (m, 2H), 3.44-3.34 (m, 1H), 3.16-2.94 (m, 2H), 2.81-2.60 (m, 1H), 1.78-1.63 (m, 1H), 1.51 (s, 1H), 1.40 (m, 5H); SFC: e.e. =100%, R$_f$=3.988 min) and (R)-1-((S)-1-amino-1,3-dihydrospiro[indene-2,4'-piperidin]-1'-yl)-2-(4-fluorophenyl)propan-1-one (40.9 mg, 116 µmol, 38% yield, R$_f$=4.926 min) as a white solid (LC-MS (ESI$^+$) m/z: 336.0 (M–NH$_2$)$^+$; 7.40-7.24 (m, 3H), 7.17 (s, 3H), 7.12-7.01 (m, 2H), 4.45-4.25 (m, 1H), 4.16 (m, 1H), 3.95-3.78 (m, 2H), 3.39-3.33 (m, 1H), 3.11-2.97 (m, 2H), 2.79-2.54 (m, 1H), 1.84-1.20 (m, 7H); SFC: e.e. =99.5%, R$_f$=4.898 min). Column: Chiralpak AD-3 100× 4.6 mm I.D., 3 um. Mobile phase: A: CO$_2$ B: iso-propanol (0.05% DEA). Gradient: from 5% to 40% of B in 4 min and hold 40% for 2.5 min, then 5% of B for 1.5 min. Flow rate: 2.8 mL/min. Column temp.: 35° C. The absolute configuration of the diastereomers was arbitrarily assigned.

Example 292: Synthesis of (3S)-1'-(2-phenoxybenzoyl)-1,3-dihydrospiro[indene-2,4'-piperidin]-3-amine

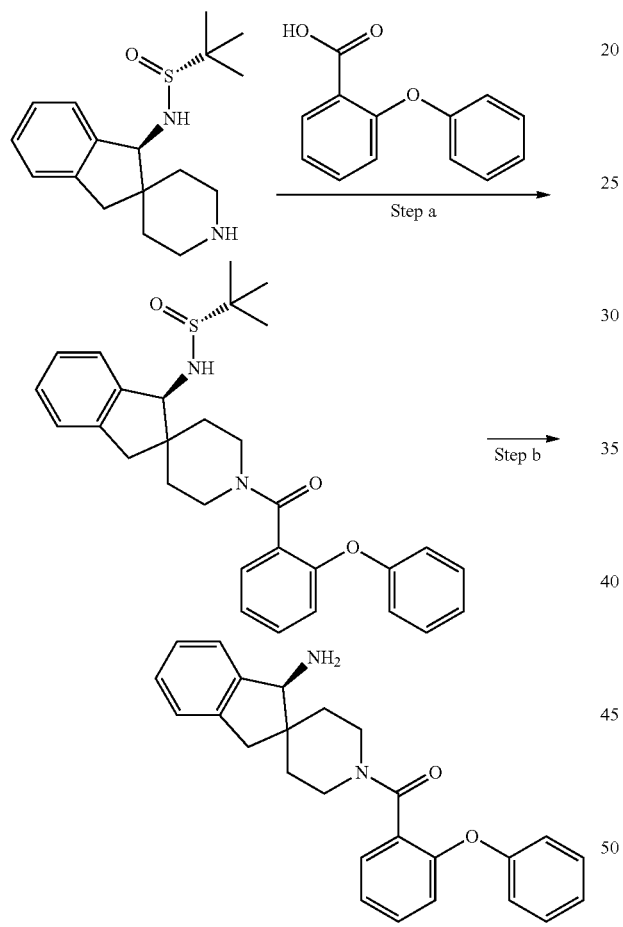

Step a: (R)—N-[(3S)-1,3-dihydrospiro[indene-2,4'-piperidin]-3-yl]-2-methylpropane-2-sulfinamide (171.0 mg, 559 µmol, synthesized via Step a of Example 120), 2-phenoxybenzoic acid (100.0 mg, 466 µmol, CAS #2243-42-7), HATU (265.0 mg, 699 µmol) and TEA (325 µL, 2.3 mmol) were placed into DMF (10.00 mL). The reaction mixture was stirred at 25° C. for 12 hours. The mixture was diluted with EtOAc (100 mL) and was washed with H$_2$O (30 mL×5), brine (50 mL), dried over anhydrous Na$_2$SO$_4$, filtered and concentrated to give a residue. The residue was purified by flash silica gel chromatography (ethyl acetate in petroleum ether=0% to 75% to afford (R)-2-methyl-N-[(3S)-1'-(2-phenoxybenzoyl)-1,3-dihydrospiro[indene-2,4'-piperidin]-3-yl]propane-2-sulfinamide (190.0 mg, 81% yield) as a yellow oil. LC-MS (ESI$^+$) m/z: 525.1 (M+Na)+.

Step b: A mixture of (R)-2-methyl-N-[(3S)-1'-(2-phenoxybenzoyl)-1,3-dihydrospiro[indene-2,4'-piperidin]-3-yl]propane-2-sulfinamide (188.0 mg, 374 µmol) in HCl/MeOH (5.00 mL, 4 M) was stirred at 25° C. for 0.5 hour. The reaction mixture was concentrated to give a residue. The residue was purified by prep-HPLC (HCl) to give (3S)-1'-(2-phenoxybenzoyl)-1,3-dihydrospiro[indene-2,4'-piperidin]-3-amine hydrochloride (63.2 mg, 39% yield) as a white solid. LC-MS (ESI$^+$) m/z: 399.1 (M+H)$^+$; $^1$H NMR (400 MHz, DMSO-d6): δ 8.71-8.38 (m, 3H), 7.64-7.56 (m, 1H), 7.48-7.15 (m, 9H), 7.10-7.00 (m, 2H), 6.90 (br d, J=8.0 Hz, 1H), 4.47-4.02 (m, 2H), 3.54-3.45 (m, 1H), 3.33-3.09 (m, 3H), 3.05-2.83 (m, 1H), 1.94-1.60 (m, 2H), 1.57-1.26 (m, 2H).

Example 293: Synthesis of (S)-1'-(5-methylimidazo[2,1-b][1,3,4]thiadiazol-2-yl)-1,3-dihydrospiro[indene-2,4'-piperidin]-1-amine

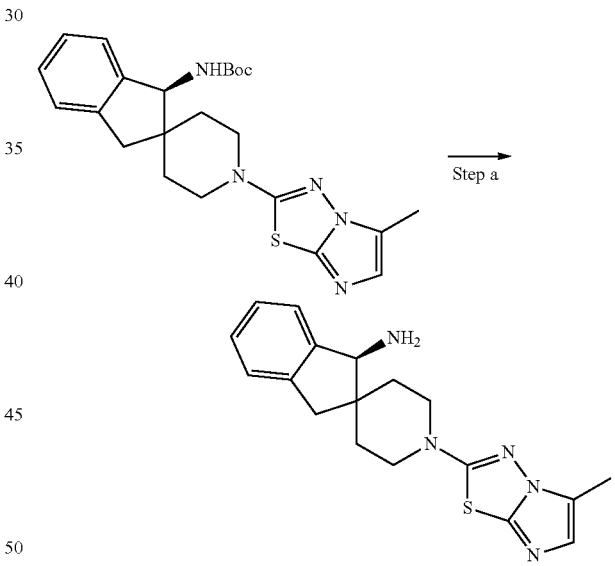

Step a: A mixture of (S)-tert-butyl (1'-(5-methylimidazo[2,1-b][1,3,4]thiadiazol-2-yl)-1,3-dihydrospiro[indene-2,4'-piperidin]-1-yl)carbamate (100.0 mg, 181.0 µmol, synthesized via Steps a-b of Intermediate FH) in HCl/MeOH (4M, 10.0 mL) was stirred at 20° C. for 1 hour. The mixture was concentrated under reduced pressure to give a residue. The residue was purified by prep-HPLC (HCl) to afford (S)-1'-(5-methylimidazo[2,1-b][1,3,4]thiadiazol-2-yl)-1,3-dihydrospiro[indene-2,4'-piperidin]-1-amine hydrochloride (20.6 mg, 30% yield) as a white solid. LC-MS (ESI$^+$) m/z: 339.0 (M+H)$^+$; $^1$H NMR (400 MHz, Methanol-d4): δ 7.55 (d, J=7.6 Hz, 1H), 7.44-7.35 (m, 4H), 4.49 (s, 1H), 4.05-4.00 (m, 1H), 3.91-3.86 (m, 1H), 3.64-3.54 (m, 2H), 3.27-3.18 (m, 2H), 2.49 (d, J=1.2 Hz, 3H), 2.08-1.84 (m, 3H), 1.75-1.69 (m, 1H).

Example 294: Synthesis of (3S)-1'-{3',6'-dimethyl-[3,4'-bipyridin]-2'-yl}-1,3-dihydrospiro[indene-2,4'-piperidin]-3-amine

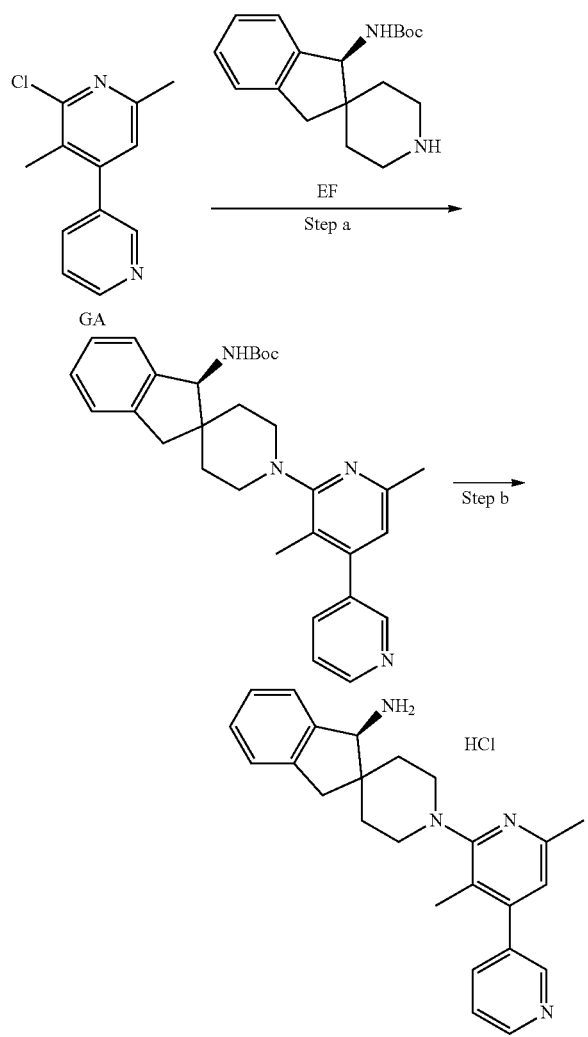

Step a: A mixture of 2'-chloro-3',6'-dimethyl-3,4'-bipyridine (190.0 mg, 0.9 mmol, Intermediate GA), tert-butyl N-[(3S)-1,3-dihydrospiro[indene-2,4'-piperidin]-3-yl]carbamate (338.0 mg, 1.1 mmol, Intermediate EF), RuPhos-Pd-G4 (73.8 mg, 0.08 mmol, CAS #1599466-85-9), RuPhos (81.0 mg, 0.2 mmol, CAS #787618-22-8), Cs$_2$CO$_3$ (852.0 mg, 2.6 mmol) and NaI (194.0 mg, 1.3 mmol) were added in toluene (6 mL). The reaction mixture was evacuated and refilled 3 times using N$_2$, and the reaction mixture was stirred at 120° C. for 12 hours. The reaction mixture was then poured into H$_2$O (40 mL) and extracted with EtOAc (80 mL×2). The combined organic layers were washed with brine (20 mL), dried over anhydrous Na$_2$SO$_4$, filtered and concentrated under reduced pressure to give a residue. The residue was purified by flash silica gel chromatography (10 g, MeOH in DCM from 0% to 10%) to give tert-butyl N-[(3S)-1'-{3',6'-dimethyl-[3,4'-bipyridin]-2'-yl}-1,3-dihydrospiro[indene-2,4'-piperidin]-3-yl]carbamate (134.0 mg, 0.3 mmol, 32% yield) as a brown oil. LC-MS (ESI$^+$) m/z: 485.1 (M+H)$^+$.

Step b: A mixture of tert-butyl N-[(3S)-1'-{3',6'-dimethyl-[3,4'-bipyridin]-2'-yl}-1,3-dihydrospiro[indene-2,4'-piperidin]-3-yl]carbamate (120.0 mg, 0.2 mmol) in HCl/MeOH (5 mL, 4 M) was stirred at 15° C. for 1 hour. The mixture was then concentrated and the residue was purified by prep-HPLC (HCl condition) to give (3S)-1'-{3',6'-dimethyl-[3,4'-bipyridin]-2'-yl}-1,3-dihydrospiro[indene-2,4'-piperidin]-3-amine hydrochloride (44.9 mg, 0.11 mmol, 43% yield) as a yellow solid. LC-MS (ESI$^+$) m/z: 385.1 (M+H)$^+$; $^1$H NMR (400 MHz, CD$_3$OD): δ 9.38 (m, 1H), 9.14 (d, J=5.6 Hz, 1H), 8.98 (d, J=8.0 Hz, 1H), 8.35 (t, J=6.4 Hz, 1H), 7.59-7.54 (m, 1H), 7.42-7.28 (m, 4H), 4.56 (s, 1H), 4.00-3.82 (m, 2H), 3.57-3.47 (m, 2H), 3.25-3.19 (m, 2H), 2.70 (s, 3H), 2.32 (s, 3H), 2.14-1.72 (m, 4H).

SHP2 Allosteric Inhibition Assay.

SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 is monitored using the surrogate substrate DiFMUP in a prompt fluorescence assay format.

More specifically, the phosphatase reactions re performed at room temperature in 96-well black polystyrene plate, flat bottom, low flange, non-binding surface (Corning, Cat #3575) using a final reaction volume of 50 μl and the following assay buffer conditions: 60 mM HEPES, pH 7.2, 75 mM NaCl, 75 mM KCl, 1 mM EDTA 0.005% Brij-35, 5 mM DTT.

The inhibition of SHP2 by compounds of the disclosure (concentrations varying from 0.003-100 μM) is monitored using an assay in which 0.25 nM of SHP2 is incubated with of 0.5 μM of peptide IRS1_pY1172(dPEG8)pY1222 (sequence: H2N-LN(pY)IDLDLV(dPEC8)LST(pY)AS-INFQK-amide). After 30-60 minutes incubation at 25° C., the surrogate substrate DiFMUP (Invitrogen, cat #D6567, 100 M final) is added to the reaction and the conversion of DiFMUP to 6,8-difluoro-7-hydroxyl-4-methylcoumarin (DiFMU) is monitored continuously for 10 minutes with excitation at 355 nm and emission at 460 nm using a microplate reader (PolarStar, BMG). The inhibitor dose response curves are analyzed using normalized IC$_{50}$ regression curve fitting with control based normalization.

Results of the SHP2 allosteric inhibition assay are depicted in the table below. Compounds designated as "A" have an IC$_{50}$ value less than or equal to 50 nM; compounds designated as "B" have an IC$_{50}$ value greater than 50 nM but less than or equal to 1 uM; compounds designated as "C" have an IC$_{50}$ value greater than 1 uM but less than or equal to 10 uM; and compounds designated as "D" have an IC$_{50}$ value greater than 10 uM.

TABLE 2

Results of SHP2 allsosteric inhibition assay.

| Example | SHP2 IC$_{50}$ |
| --- | --- |
| 1 | A |
| 2 | A |
| 3 | A |
| 4 | A |
| 5 | A |
| 6 | A |
| 7 | A |
| 8 | A |

TABLE 2-continued

Results of SHP2 allsosteric inhibition assay.

| Example | SHP2 IC$_{50}$ |
|---|---|
| 9 | A |
| 10 | A |
| 11 | A |
| 12 | A |
| 13 | A |
| 14 | A |
| 15 | B |
| 16 | C |
| 17 | A |
| 18 | A |
| 19 | B |
| 20 | A |
| 21 | A |
| 22 | A |
| 23 | C |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | D |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | B |
| 64 | A |
| 65 | A |
| 66 | B |
| 67 | A |
| 68 | A |
| 69 | A |
| 70 | B |
| 71 | A |
| 72 | A |
| 73 | A |
| 74 | A |
| 75 | A |
| 76 | A |
| 77 | A |
| 78 | A |
| 79 | A |
| 80 | A |
| 80 | A |
| 81 | A |
| 82 | A |
| 84 | A |
| 84 | A |
| 86 | A |
| 87 | A |
| 88 | A |
| 89 | A |
| 90 | B |
| 91 | C |
| 92 | A |
| 93 | A |
| 94 | A |
| 95 | A |
| 96 | A |
| 97 | B |
| 98 | B |
| 99 | A |
| 100 | B |
| 101 | B |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | C |
| 117 | A |
| 118 | A |
| 119 | A |
| 120 | A |
| 121 | A |
| 122 | A |
| 123 | A |
| 124 | A |
| 125 | A |
| 126 | A |
| 127 | B |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | B |
| 151 | A |
| 152 | A |
| 153 | A |
| 154 | A |
| 155 | A |
| 156 | A |
| 157 | A |
| 158 | A |
| 159 | A |
| 160 | A |

TABLE 2-continued

Results of SHP2 allsosteric inhibition assay.

| Example | SHP2 IC$_{50}$ |
|---|---|
| 161 | A |
| 162 | D |
| 163 | C |
| 164 | A |
| 165 | D |
| 166 | A |
| 167 | A |
| 168 | A |
| 169 | C |
| 170 | B |
| 171 | A |
| 172 | C |
| 173 | D |
| 174 | A |
| 175 | C |
| 176 | D |
| 177 | A |
| 178 | D |
| 179 | A |
| 180 | C |
| 181 | C |
| 182 | D |
| 183 | D |
| 184 | B |
| 185 | C |
| 186 | A |
| 187 | A |
| 188 | D |
| 189 | A |
| 190 | A |
| 191 | C |
| 192 | C |
| 193 | A |
| 194 | A |
| 195 | A |
| 196 | A |
| 197 | A |
| 198 | D |
| 199 | A |
| 200 | A |
| 201 | A |
| 202 | A |
| 203 | A |
| 204 | A |
| 205 | B |
| 206 | A |
| 207 | C |
| 208 | C |
| 209 | C |
| 210 | D |
| 211 | B |
| 212 | A |
| 213 | B |
| 214 | A |
| 215 | A |
| 216 | B |
| 217 | A |
| 218 | A |
| 219 | A |
| 220 | A |
| 221 | A |
| 222 | A |
| 223 | A |
| 224 | B |
| 225 | D |
| 226 | A |
| 227 | D |
| 228 | D |
| 229 | A |
| 230 | C |
| 231 | D |
| 232 | A |
| 233 | A |
| 234 | A |
| 235 | D |
| 236 | A |

TABLE 2-continued

Results of SHP2 allsosteric inhibition assay.

| Example | SHP2 IC$_{50}$ |
|---|---|
| 237 | A |
| 238 | A |
| 239 | B |
| 240 | A |
| 241 | A |
| 242 | A |
| 243 | B |
| 244 | A |
| 245 | C |
| 246 | D |
| 247 | C |
| 248 | A |
| 249 | A |
| 250 | A |
| 251 | D |
| 252 | A |
| 253 | A |
| 254 | D |
| 255 | A |
| 256 | A |
| 257 | A |
| 258 | A |
| 259 | A |
| 260 | D |
| 261 | A |
| 262 | B |
| 263 | A |
| 264 | A |
| 265 | A |
| 266 | A |
| 267 | A |
| 268 | A |
| 269 | A |
| 270 | C |
| 271 | A |
| 272 | A |
| 273 | A |
| 274 | C |
| 275 | C |
| 276 | A |
| 277 | B |
| 278 | A |
| 279 | A |
| 280 | A |
| 281 | B |
| 282 | A |
| 283 | D |
| 284 | B |
| 285 | A |
| 286 | A |
| 287 | A |
| 288 | D |
| 289 | A |
| 290 | A |
| 291 | D |
| 292 | D |
| 293 | A |
| 294 | A |

INCORPORATION BY REFERENCE

All publications and patents mentioned herein are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the present disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound selected from the group consisting of:

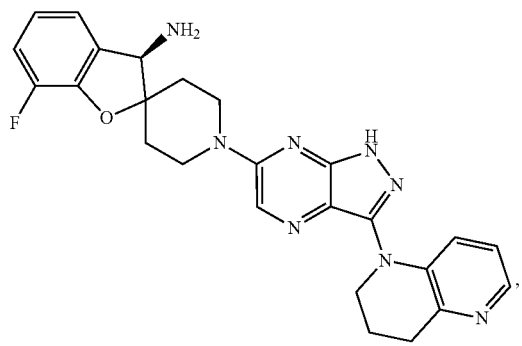

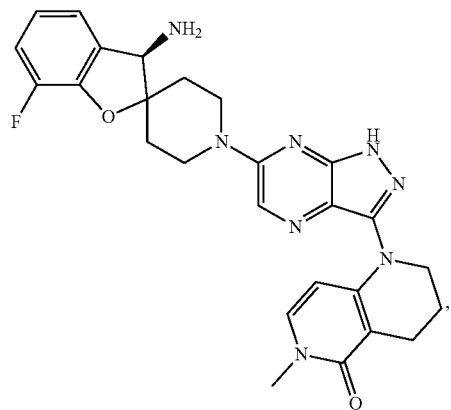

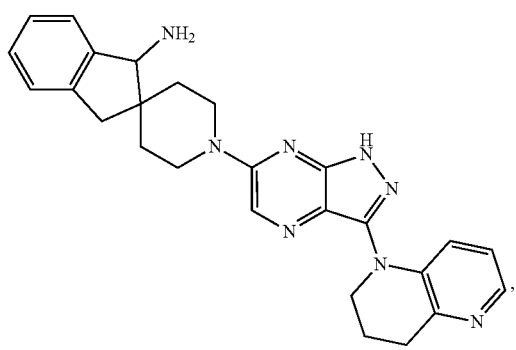

-continued

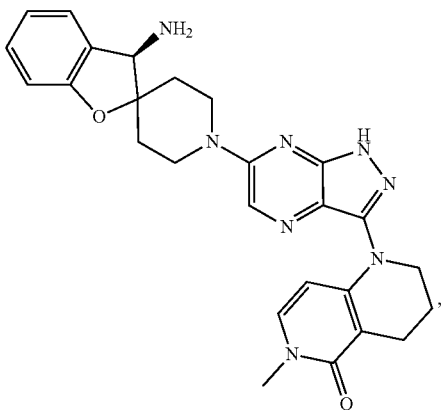

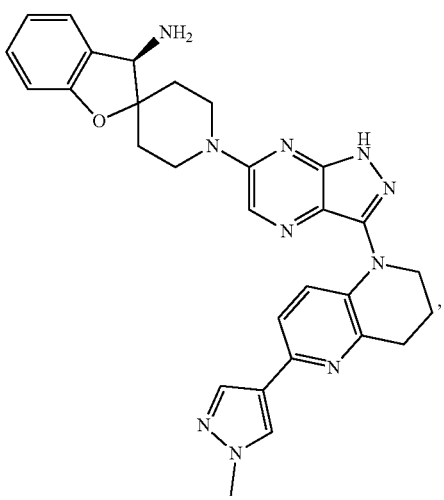

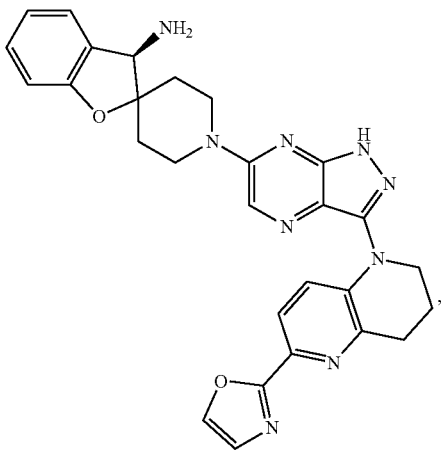

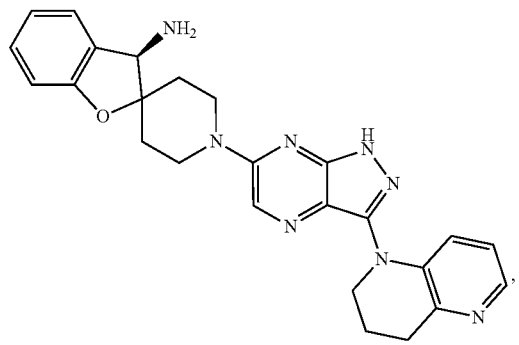

693
-continued
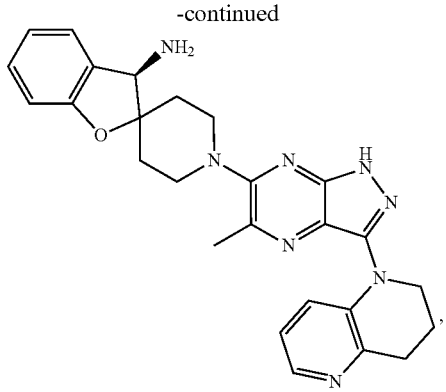
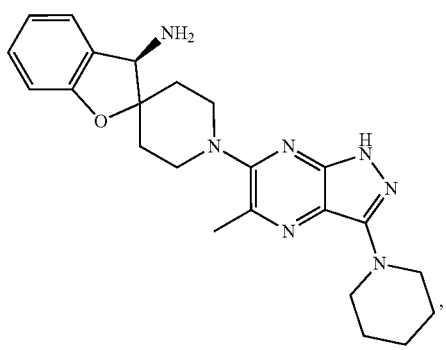
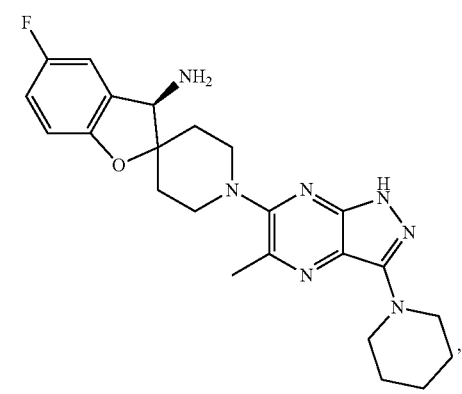
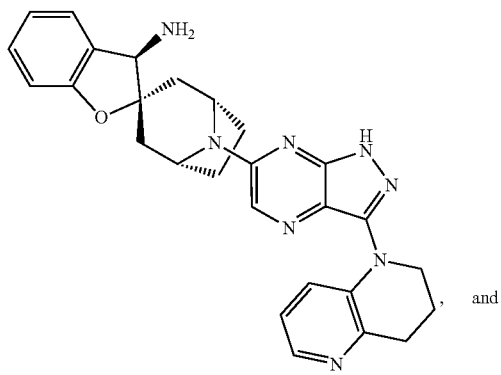
and
694
-continued
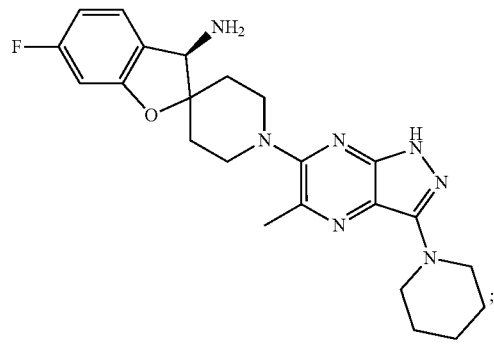
or a pharmaceutically acceptable salt thereof.
2. A pharmaceutical composition comprising a compound of claim 1 and a pharmaceutically acceptable carrier.
3. The compound of claim 1, wherein the compound is selected from the group consisting of:
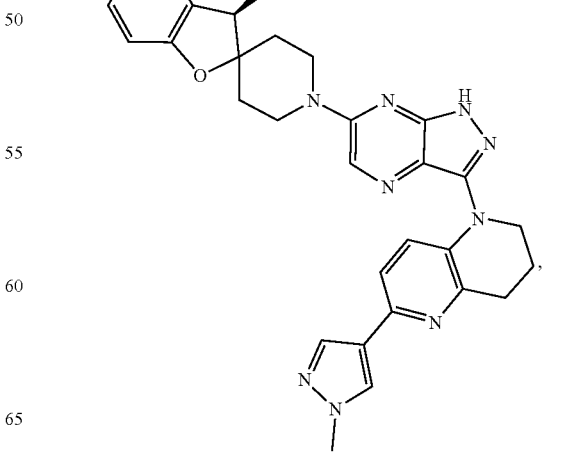

-continued

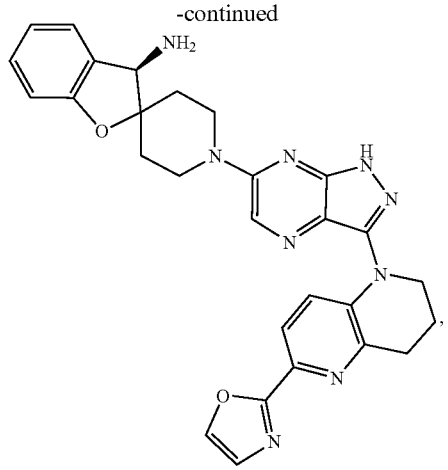

4. A compound represented by:

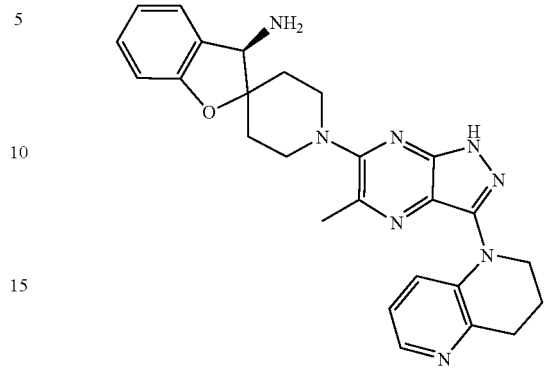

or a pharmaceutically acceptable salt thereof.

5. A pharmaceutical composition comprising a compound of claim 4 and a pharmaceutically acceptable carrier.

6. A compound represented by:

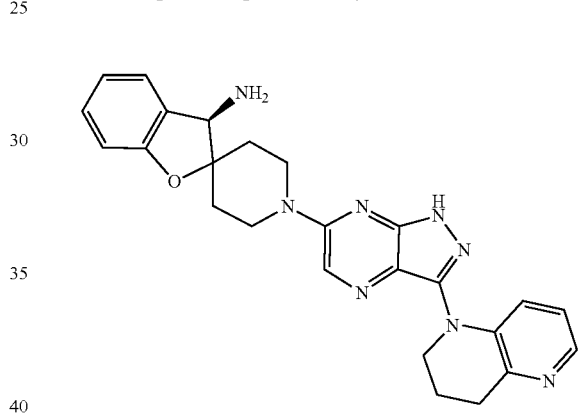

or a pharmaceutically acceptable salt thereof.

7. A pharmaceutical composition comprising a compound of claim 6 and a pharmaceutically acceptable carrier.

* * * * *